US011851422B2

(12) United States Patent
Vandyck et al.

(10) Patent No.: US 11,851,422 B2
(45) Date of Patent: Dec. 26, 2023

(54) ANTI-VIRAL COMPOUNDS

(71) Applicants: Aligos Therapeutics, Inc., South San Francisco, CA (US); Katholieke Universiteit Leuven, Leuven (BE)

(72) Inventors: Koen Vandyck, Paal (BE); Dorothée Alice Marie-Eve Bardiot, Leuven (BE); Pierre Jean-Marie Bernard Raboisson, Wavre (BE); Leonid Beigelman, San Mateo, CA (US); Antitsa Dimitrova Stoycheva, Half Moon Bay, CA (US); Sandro Boland, Leuven (BE); Arnaud Didier Marie Marchand, Leuven (BE)

(73) Assignees: Aligos Therapeutics, Inc.; Katholieke Universiteit Leuven, Leuven (BE)

( * ) Notice: Subject to any disclaimer, the term of this patent is extended or adjusted under 35 U.S.C. 154(b) by 0 days.

(21) Appl. No.: 17/811,008

(22) Filed: Jul. 6, 2022

(65) Prior Publication Data
US 2023/0093249 A1 Mar. 23, 2023

Related U.S. Application Data

(60) Provisional application No. 63/268,052, filed on Feb. 15, 2022, provisional application No. 63/265,479, filed on Dec. 15, 2021, provisional application No. 63/264,212, filed on Nov. 17, 2021, provisional application No. 63/261,480, filed on Sep. 22, 2021, provisional application No. 63/203,135, filed on Jul. 9, 2021.

(51) Int. Cl.
| | | |
|---|---|---|
| C07D 401/12 | (2006.01) |
| C07D 401/14 | (2006.01) |
| C07D 403/12 | (2006.01) |
| C07D 403/14 | (2006.01) |
| C07D 405/14 | (2006.01) |
| C07D 413/12 | (2006.01) |
| C07D 413/14 | (2006.01) |
| C07D 487/04 | (2006.01) |
| C07D 491/04 | (2006.01) |
| C07D 491/107 | (2006.01) |
| C07D 498/04 | (2006.01) |
| A61P 31/14 | (2006.01) |
| A61K 31/403 | (2006.01) |
| A61K 31/422 | (2006.01) |
| A61K 31/4439 | (2006.01) |
| A61K 31/497 | (2006.01) |
| A61K 31/519 | (2006.01) |
| A61K 31/437 | (2006.01) |
| A61K 31/4709 | (2006.01) |
| A61K 31/407 | (2006.01) |
| A61K 31/4155 | (2006.01) |
| A61K 31/538 | (2006.01) |
| A61K 31/5377 | (2006.01) |
| A61K 31/4245 | (2006.01) |
| A61K 31/553 | (2006.01) |
| A61K 31/4192 | (2006.01) |

(52) U.S. Cl.
CPC ......... C07D 403/12 (2013.01); C07D 403/14 (2013.01); C07D 405/14 (2013.01); C07D 413/12 (2013.01); C07D 413/14 (2013.01); C07D 487/04 (2013.01); C07D 491/107 (2013.01); C07D 498/04 (2013.01)

(58) Field of Classification Search
CPC .. C07D 401/12; C07D 401/14; C07D 403/12; C07D 403/14; C07D 405/14; C07D 413/12; C07D 413/14; C07D 487/04; C07D 491/04; C07D 491/107; C07D 498/04; A61P 31/14; A61K 31/403; A61K 31/422; A61K 31/4439; A61K 31/497; A61K 31/519; A61K 31/437; A61K 31/4709; A61K 31/407; A61K 31/4155; A61K 31/538; A61K 31/5377; A61K 31/4245; A61K 31/553; A61K 31/4192
See application file for complete search history.

(56) References Cited

U.S. PATENT DOCUMENTS

| | | |
|---|---|---|
| 4,388,305 A | 6/1983 | Trouet et al. |
| 4,639,456 A | 1/1987 | Trouet et al. |
| 4,970,297 A | 1/1990 | Castelhano et al. |
| 5,147,865 A | 9/1992 | Habich et al. |

(Continued)

FOREIGN PATENT DOCUMENTS

| | | |
|---|---|---|
| AU | 2002318741 | 3/2003 |
| CA | 2851462 | 7/2004 |

(Continued)

OTHER PUBLICATIONS

Abdelnabi et al., "Comparing infectivity and virulence of emerging SARS-CoV-2 variants in Syrian hamsters" EBioMedicine Jun. 2021;68:103403. doi: 10.1016/j.ebiom.2021.103403.

(Continued)

*Primary Examiner* — Brenda L Coleman
(74) *Attorney, Agent, or Firm* — Knobbe Martens Olson & Bear LLP

(57) ABSTRACT

Provided herein are compounds of Formula (I), or pharmaceutically acceptable salts thereof, pharmaceutical compositions that include a compound described herein (including pharmaceutically acceptable salts of a compound described herein) and methods of synthesizing the same. Also provided herein are methods of treating diseases and/or conditions with a compound of Formula (I), or a pharmaceutically acceptable salt thereof.

61 Claims, No Drawings

(56) References Cited

U.S. PATENT DOCUMENTS

| | | |
|---|---|---|
| 5,364,931 A | 11/1994 | Haebich et al. |
| 5,510,333 A | 4/1996 | Angelastro et al. |
| 5,514,694 A | 5/1996 | Powers et al. |
| 5,741,812 A | 4/1998 | Burk et al. |
| 5,756,528 A | 5/1998 | Anthony et al. |
| 5,847,135 A | 12/1998 | Bemis et al. |
| 5,856,309 A | 1/1999 | Konetschny-Rapp et al. |
| 5,874,424 A | 2/1999 | Batchelor et al. |
| 5,955,616 A | 9/1999 | Ohtani et al. |
| 6,159,984 A | 12/2000 | Guzi et al. |
| 6,162,791 A | 12/2000 | Karimian et al. |
| 6,174,887 B1 | 1/2001 | Haruta et al. |
| 9,603,864 B2 | 3/2017 | Blatt et al. |
| 11,124,497 B1 | 9/2021 | Arnold et al. |
| 11,174,231 B1 | 11/2021 | Arnold et al. |
| 2003/0153788 A1 | 8/2003 | Kobayashi et al. |
| 2003/0216325 A1 | 11/2003 | Saksena et al. |
| 2004/0110945 A1 | 6/2004 | Nakayama et al. |
| 2004/0171489 A1 | 9/2004 | Hacker et al. |
| 2006/0111303 A1 | 5/2006 | Hatayama et al. |
| 2007/0032433 A1 | 2/2007 | Saksena et al. |
| 2007/0208001 A1 | 9/2007 | Zhou et al. |
| 2007/0238769 A1 | 10/2007 | Ochi et al. |
| 2013/0109661 A1 | 5/2013 | Hermann et al. |
| 2013/0164694 A1 | 6/2013 | Wang et al. |
| 2013/0178478 A1 | 7/2013 | Hermann et al. |
| 2014/0194386 A1 | 7/2014 | Burns et al. |
| 2014/0374657 A1 | 12/2014 | Matsuyama et al. |
| 2017/0324007 A1 | 11/2017 | Pentlehmer |
| 2021/0355111 A1 | 11/2021 | Arnold et al. |
| 2022/0009903 A1 | 1/2022 | Vandyck et al. |
| 2022/0259145 A1 | 8/2022 | Liu et al. |
| 2022/0396550 A1 | 12/2022 | Ghosh et al. |
| 2022/0402905 A1 | 12/2022 | Soliman et al. |
| 2022/0411401 A1 | 12/2022 | Ghosh et al. |
| 2023/0002413 A1 | 1/2023 | Wu et al. |
| 2023/0031213 A1 | 2/2023 | Wu et al. |
| 2023/0065527 A1 | 3/2023 | Wu et al. |
| 2023/0140238 A1 | 5/2023 | Bardiot et al. |
| 2023/0192713 A1 | 6/2023 | Wu et al. |

FOREIGN PATENT DOCUMENTS

| | | |
|---|---|---|
| CA | 3201360 | 6/2023 |
| CN | 103254129 | 8/2013 |
| CN | 103288832 | 9/2013 |
| CN | 107540726 | 1/2018 |
| CN | 113444144 | 9/2021 |
| CN | 114149415 | 3/2022 |
| CN | 114426568 | 5/2022 |
| DE | 4016994 | 11/1991 |
| EP | 0393445 | 10/1990 |
| EP | 0402646 | 12/1990 |
| EP | 0472077 | 2/1992 |
| EP | 0472078 | 2/1992 |
| EP | 0520336 | 12/1992 |
| EP | 525420 | 2/1993 |
| EP | 0530537 | 3/1993 |
| EP | 0641800 | 3/1995 |
| EP | 0644198 | 3/1995 |
| EP | 1881001 | 3/1995 |
| EP | 0805147 | 11/1997 |
| EP | 1217000 | 6/2002 |
| EP | 1760076 | 3/2007 |
| EP | 1881002 | 1/2008 |
| EP | 2270025 | 1/2011 |
| EP | 3835296 A1 | 6/2021 |
| IN | 2006DE01558 | 1/2008 |
| JP | 63144084 | 6/1988 |
| JP | 06192199 | 7/1994 |
| JP | 04334357 | 11/1995 |
| JP | 07309866 A | 11/1995 |
| JP | 09124571 | 5/1997 |
| JP | 2002145848 | 5/2002 |
| JP | 2005336172 | 12/2005 |
| JP | 2006232707 | 9/2006 |
| JP | 2013032343 | 2/2013 |
| JP | 2015174929 | 10/2015 |
| JP | 7055528 | 4/2022 |
| WO | WO 89/04833 | 6/1989 |
| WO | WO 92/00954 | 1/1992 |
| WO | WO 92/07869 | 5/1992 |
| WO | WO 92/20357 | 11/1992 |
| WO | WO 93/02057 | 2/1993 |
| WO | WO 93/12796 | 7/1993 |
| WO | WO 93/17003 | 9/1993 |
| WO | WO 94/00421 | 1/1994 |
| WO | WO 94/11339 | 5/1994 |
| WO | WO 95/07294 | 3/1995 |
| WO | WO 95/09858 | 4/1995 |
| WO | WO 95/12611 | 5/1995 |
| WO | WO 95/35308 | 12/1995 |
| WO | WO 96/16981 | 6/1996 |
| WO | WO 96/20725 | 7/1996 |
| WO | WO 96/20949 | 7/1996 |
| WO | WO 96/39137 | 12/1996 |
| WO | WO 96/40732 | 12/1996 |
| WO | WO 97/05135 | 2/1997 |
| WO | WO 97/08133 | 3/1997 |
| WO | WO 97/22619 | 6/1997 |
| WO | WO 97/31939 | 9/1997 |
| WO | WO 98/01133 | 1/1998 |
| WO | WO 98/53814 | 12/1998 |
| WO | WO 98/53817 | 12/1998 |
| WO | WO 98/57945 | 12/1998 |
| WO | WO 99/67230 | 12/1999 |
| WO | WO 2000/016627 | 3/2000 |
| WO | WO 2000/051974 | 9/2000 |
| WO | WO 2000/055125 | 9/2000 |
| WO | WO 2000/071572 | 11/2000 |
| WO | WO 2001/012186 | 2/2001 |
| WO | WO 2001/079167 | 10/2001 |
| WO | WO 2002/085899 | 10/2001 |
| WO | WO 2002/053534 | 7/2002 |
| WO | WO 2003/004468 | 1/2003 |
| WO | WO 2003/008380 | 1/2003 |
| WO | WO 2003/029284 | 4/2003 |
| WO | WO 2003/035060 | 5/2003 |
| WO | WO 2003/039529 | 5/2003 |
| WO | WO 2003/062265 | 7/2003 |
| WO | WO 2003/091202 | 11/2003 |
| WO | WO 2004/032846 | 4/2004 |
| WO | WO 2004/046107 | 6/2004 |
| WO | WO 2004/062601 | 7/2004 |
| WO | WO 2005/014532 | 2/2005 |
| WO | WO 2005/061475 | 7/2005 |
| WO | WO 2005/102381 | 11/2005 |
| WO | WO 2006/061714 | 6/2006 |
| WO | WO 2007/022459 | 2/2007 |
| WO | WO 2007/067836 | 6/2007 |
| WO | WO 2007/085895 | 8/2007 |
| WO | WO 2007109080 | 9/2007 |
| WO | WO 2008/074035 | 6/2008 |
| WO | WO 2008/110008 | 9/2008 |
| WO | WO 2008/121065 | 10/2008 |
| WO | WO 2008/141227 | 11/2008 |
| WO | WO 2008/154642 | 12/2008 |
| WO | WO 2009/043889 | 4/2009 |
| WO | WO 2009/103160 | 8/2009 |
| WO | WO 2009/105782 | 8/2009 |
| WO | WO 2010/077836 | 7/2010 |
| WO | WO 2010/126881 | 11/2010 |
| WO | WO 2010/132601 | 11/2010 |
| WO | WO 2011/043994 | 4/2011 |
| WO | WO 2011/047287 | 4/2011 |
| WO | WO 2011/048390 | 4/2011 |
| WO | WO 2011/050160 | 4/2011 |
| WO | WO 2011/082337 | 7/2011 |
| WO | WO 2011/094426 | 8/2011 |
| WO | WO 2011/103932 | 9/2011 |
| WO | WO 2011/103933 | 9/2011 |
| WO | WO 2011/129457 | 10/2011 |
| WO | WO 2012/020747 | 2/2012 |
| WO | WO 2012/058645 | 5/2012 |

(56) References Cited

FOREIGN PATENT DOCUMENTS

| | | |
|---|---|---|
| WO | WO 2012/065963 | 5/2012 |
| WO | WO 2012/083048 | 6/2012 |
| WO | WO 2012/122420 | 9/2012 |
| WO | WO 2012/122422 | 9/2012 |
| WO | WO 2012/123938 | 9/2012 |
| WO | WO 2012/140500 | 10/2012 |
| WO | WO 2012/163724 | 12/2012 |
| WO | WO 2013/003720 | 1/2013 |
| WO | WO 2013/133178 | 9/2013 |
| WO | WO 2013/178816 | 12/2013 |
| WO | WO 2013/188344 | 12/2013 |
| WO | WO 2014/151958 | 9/2014 |
| WO | WO 2014/154682 | 10/2014 |
| WO | WO 2014/188178 | 11/2014 |
| WO | WO 2016/075150 | 5/2016 |
| WO | WO 2016/187712 | 12/2016 |
| WO | WO 2017/091616 | 6/2017 |
| WO | WO 2017/160269 | 9/2017 |
| WO | WO 2017/197377 | 11/2017 |
| WO | WO 2018/020357 | 2/2018 |
| WO | WO 2018/042343 | 3/2018 |
| WO | WO 2018/045084 | 3/2018 |
| WO | WO 2018/064119 | 4/2018 |
| WO | WO 2018/112626 | 6/2018 |
| WO | WO 2018/152633 | 8/2018 |
| WO | WO 2018/167269 | 9/2018 |
| WO | WO 2019/190885 | 10/2019 |
| WO | WO 2019/190999 | 10/2019 |
| WO | WO 2020/006294 | 1/2020 |
| WO | WO 2020/030143 | 2/2020 |
| WO | WO 2020/123675 | 6/2020 |
| WO | WO 2020/136298 | 6/2020 |
| WO | WO 2020/160707 | 8/2020 |
| WO | WO 2020/185830 | 9/2020 |
| WO | WO 2021/146211 | 7/2021 |
| WO | WO 2021/151265 | 8/2021 |
| WO | WO 2021/151387 | 8/2021 |
| WO | WO 2021/207632 | 10/2021 |
| WO | WO 2021/221043 | 11/2021 |
| WO | WO 2021/226546 | 11/2021 |
| WO | WO 2021/231872 | 11/2021 |
| WO | WO 2021/234668 | 11/2021 |
| WO | WO 2021/236771 | 11/2021 |
| WO | WO 2021/250648 | 12/2021 |
| WO | WO 2021/252491 | 12/2021 |
| WO | WO 2021/252644 | 12/2021 |
| WO | WO 2002/008244 | 1/2022 |
| WO | WO 2022/020242 | 1/2022 |
| WO | WO 2022/020711 | 1/2022 |
| WO | WO 2022/040002 | 2/2022 |
| WO | WO 2022/119858 | 6/2022 |
| WO | WO 2022/133069 | 6/2022 |
| WO | WO 2022/187491 | 9/2022 |
| WO | WO 2022/208113 | 10/2022 |
| WO | WO 2022/218442 | 10/2022 |
| WO | WO 2022/266236 | 12/2022 |
| WO | WO 2022/266363 | 12/2022 |
| WO | WO 2022/266368 | 12/2022 |
| WO | WO 2023/030459 | 3/2023 |
| WO | WO 2023/036093 | 3/2023 |
| WO | WO 2023/036140 | 3/2023 |
| WO | WO 2023/043816 | 3/2023 |
| WO | WO 2023/052638 | 4/2023 |
| WO | WO 2023/088418 | 5/2023 |
| WO | WO 2023/122260 | 6/2023 |
| WO | WO 2023/125846 | 7/2023 |
| WO | WO 2023/133174 | 7/2023 |
| WO | WO 2023/149982 | 8/2023 |

OTHER PUBLICATIONS

Arakawa et al., "Synthetic Study of Optically Active 3-Azabicyclo[3.3.0] octane-2,6,8-tricarboxylic Acid" Chemical & Pharmaceutical Bulletin (2003) 51(8), 1015-1020.

Breuning et al., "Enantioselective synthesis of tricyclic amino acid derivatives based on a rigid 4-azatricyclo[5.2.1.0$^{2,6}$]decane skeleton" Beilstein Journal of Organic Chemistry (2009) 5(81):1-5.

De Graff et al., "IBX-mediated oxidation of unactivated cyclic amines: application in highly diastereoselective oxidative Ugi-type and aza-Friedel-Crafts reactions." Organic & Biomolecular Chemistry (2015) 13(40):10108-10112.

Farmer et al., "Inhibitors of hepatitis C virus NS3•4A protease: P2 proline variants." Letters in Drug Design & Discovery (2005) 2(7):497-502.

Gansauer et al., "4-exo Cyclizations by Template Catalysis" Ang. Chem. Int. Ed. (2009) 48(47), 8882-8885, S8882/1-S8882/32.

Good et al., "AT-527 a Double Prodrug of a Guanosine Nucleotide Analog, is a Potent Inhibitor of SARA-CoV-2 In Vitro and a Promising Oral Antiviral for Treatment of COVID-19" Antimicrobial Agents and Chemotherapy (2021) 65(4):e02479-20.

Hoffmann et al., "SARA-CoV-2 Cell Entry Depends on ACE2 and TMPRSS2 and is Blocked by a Clinically Proven Protease Inhibitor" Cell (2020) 181:271-280.

"IUPAC-IUB Commission on Biochemical Nomenclature Abbreviated Nomenclature of Synthetic Polypeptides (Polymerized Amino Acids)* Revised Recommendations (1971)" Biochemistry. (1972) 11(5) :942-944.

Johnson et al., "Synthesis and Characterization of Novel Bi- and Tricyclic α-Amino Acids" Synthetic Communications (2011) 41(18):2769-2793.

Kim et al., "Broad-Spectrum Antivirals against 3C or 3C-Like Proteases of Picornaviruses, Noroviruses, and Coronaviruses" Journal of Virology (2012) 86(21):11754-11762.

Liu et al., "An Improved and Enantioselective Preparation of the Telaprevir Bicyclic [3.3.0] Proline Intermediate and Reuse of Unwanted Enantiomer" Org. Process Res. Dev. (2016) 20(2):320-324.

Mellott et al., "A cysteine protein inhibitor blocks SARS-CoV-2 infection of human and monkey cells" bioRxiv (2020) 2020.2010.2023.347534.

Moody et al., "Stereospecific synthesis of naturally-occurring 4-alkylideneglutamic acids, 4-alkylglumates and 4-alkylprolines" J. Chem. Soc., Perkin Trans. 1 (1997) 23:3519-3530.

Rulíšek et al., "An Experimental and Theoretical Study of Stereoselectivity of Furan-Maleic Anhydride and Furan-Maleimide Diels-Alder Reactions" J. Org. Chem. (2005) 70(16):6295-6302.

Shang et al., "Cell entry mechanisms of SARS-CoV-2" PNAS (2020) 117(21):11727.

Steuten et al., "Challenges for targeting SARS-CoV-2 proteases as a therapeutics strategy for COVID-19" bioRxiv (2020) 2020.2011.2021.392753.

Zhang et al., "a-Ketoamides as Broad-Spectrum Inhibitors of Coronavirus and Enterovirus Replication: Structure-Based Design, Synthesis, and Activity Assessment" JACS (2020) 63:4562-4578 (https://dx.doi.org/10.1021/acs.jmedchem.9b01828).

Znabet et al., "Highly stereoselective synthesis of substituted prolyl peptides using a combination of biocatalytic desymmetrization and multicomponent reactions." Angewandte Chemie International Edition (2010) 49(31):5298-5292.

https://www.cdc.gov/coronavirus/2019-ncov/need-extra-precautions/groups-at-higher-risk.html.

International Search Report and Written Opinion dated Aug. 25, 2022 for PCT Application No. PCT/US2022/036242, filed Jul. 6, 2022.

Alugubelli et al., "A systemic exploration of beceprevir-based main protease inhibitos as SARS-CoV-2 antivirals" European J. of Med. Chem. (2022) 240:114596.

CAS Reg. No. 1040187-41-4, Entry Date Aug. 11, 2008.
CAS Reg. No. 1212645-49-2, Entry Date Mar. 21, 2010.
CAS Reg. No. 1240410-37-0, Entry Date Sep. 9, 2010.

Calaza et al., "Synthesis of [c]-Fused Bicyclic Proline Analogues" Eur. J. Org. Chem. (2015), 2015(8):1633-1658.

Chia et al., "Novel Coronavirus Main Protease Di- and Tripeptide Inhibitors for Treating COVID-19" ACS Med. Chem. Lett. (2002) 13:1388-1389.

Cox et al., "Escaping form Flatland: Substituted Bridged Pyrrolidine Fragments with Inherent Three-Dimensional Character" ACS Med. Chem. Lett. (2020) 11(6):1185-1190.

(56) References Cited

OTHER PUBLICATIONS

Eiden et al., "Synthesis of a 3-Amino-2,3-dihdropyrid-4-one and Related Heterocyclic Anaalogues as Mechanism-Based Inhibitors of BioA, a Pyridoxal Phosphate-Dependent Enzyme" J. Org. Chem. (2017) 82(15):7806-7819.

Gupton et al., "Application of 2-Substituted Vinamidinium Salts to the Synthesis of 2,4-Disubstituted Pyrroles" J. Org. Chem. (1990) 55(15):4735-4740.

Liu et al., "Modular and Stereoselective Synthesis of Tetrasubstituted Helical Alkenes via a Palladium-Catalyzed Domino Reaction" Org. Lett. (2012) 14(14):3648-3651.

Mulamreddy et al., "4-Vinylproline" J. Org. Chem. (2018) 83(21):13580-13586.

Roy et al., "The Hemetsberger-Knittel Synthesis of Substituted 5-,6-, and 7-Azaindoles" Synthesis (2005) 16:2751-2757.

Ahmad et al., "Exploring the Binding Mechanism of PF-07321332 SARS-CoV-2 Protease Inhibitor through Molecular Dynamics and Binding Free Energy Simulations" Int. J. Mol. Sci. (2021) 22(17):91242.

Hartford, B., "To conquer COVID-19, create the perfect pill" Chemical & Engineering News (2021) 99(19):28-31.

Hartford, B., "Pfizer unveils its oral SARS-CoV-2 inhibitor" Chemical & Engineering News (2021), 99(13):7.

Macchiagodena et al., "Virtual Double-System Single-Box for Absolute Dissociation Free Energy Calculations in GROMACS" J. Chem. Inf. Model (2021) 61:5320-5326.

Macchiagodena et al., "Characterization of the non-covalent interaction between the PF-07321332 inhibitor and the SARS-CoV-2 main protease" J. Mol. Graphics & Modelling (2022) 110:108042.

Ngo et al., "Insights into the Binding and Covalent Inhibition Mechanism of PF-07321332 to SARS-CoV-2 Mpro" ChemRxiv (2021) 1-10.

Owen et al., "An oral SARS-CoV $M^{pro}$ inhibitor clinical candidate for the treatment of COVID-19" Science (2021) 374(6575):1586-1593.

Pavan et al., "Supervised Molecular Dynamics (SuMD) Insights into the mechanism of action of SARS-Co-V-2 main protease inhibitor PF-07321332" Journal of Enzyme Inhibition and Medicinal Chemistry (2021) 36(1):1646-1650.

Ramos-Guzman et al., "Computational simulations on the binding and reactivity of a nitrile inhibitor of the SARS-CoV-2 main protease" Chem. Commun. (2021) 57(72):9096-9099 & Supporting Information.

Zhao et al., "Crystal Structure of SARS-CoV-2 main protease in complex with protease inhibitor PF-07321332" Protein & Cell (2021) https://doi.org/10.1007/s13238-021-00883-2.

Znabet et al., "Asymmetric synthesis of synthetic alkaloids by a tandem biocatalysis/Ugi/Pictet-Spengler-type cyclization sequence" Chem. Commun. (2010) 46(41):7706-7708 & Supplemental Information.

ent application,
ANTI-VIRAL COMPOUNDS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application Nos. 63/203,135, filed Jul. 9, 2021, 63/261,480, filed Sep. 22, 2021, 63/264,212, filed Nov. 17, 2021, 63/265,479, filed Dec. 15, 2021 and 63/268,052, filed Feb. 15, 2022, each of which is incorporated by reference in there entireties.

BACKGROUND

Field

The present application relates to the fields of chemistry, biochemistry and medicine. Disclosed herein are compounds of Formula (I), or pharmaceutically acceptable salt thereof, pharmaceutical compositions that include a compound described herein (including pharmaceutically acceptable salts of a compound described herein) and methods of synthesizing the same. Also disclosed herein are methods of treating diseases and/or conditions with a compound of Formula (I), or a pharmaceutically acceptable salt thereof.

Description

A positive-sense single-stranded RNA virus ((+)ssRNA virus) is a virus that uses positive sense, single stranded, RNA as its genetic material. Positive-sense single-stranded RNA viruses can be enveloped or non-enveloped. Coronaviridae, Picornaviridae and Norviruses are each a (+)ssRNA virus. Each of the aforementioned viruses are known to infect mammals, including humans.

SUMMARY

Some embodiments disclosed herein relate to a compound of Formula (I), or a pharmaceutically acceptable salt thereof.

Some embodiments disclosed herein relate to a pharmaceutical composition that can contain an effective amount of a compound of Formula (I), or a pharmaceutically acceptable salt thereof.

Some embodiments described herein relate to a method of treating a coronavirus infection that can include administering to a subject identified as suffering from the coronavirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a coronavirus infection.

Some embodiments disclosed herein relate to a method of inhibiting replication of a coronavirus that can include contacting a cell infected with the coronavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication a coronavirus.

Some embodiments described herein relate to a method of treating a picornavirus infection that can include administering to a subject identified as suffering from the picornavirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a picornavirus infection.

Some embodiments disclosed herein relate to a method of inhibiting replication of a picornavirus that can include contacting a cell infected with the picornavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication a picornavirus.

Some embodiments described herein relate to a method of treating a norovirus infection that can include administering to a subject identified as suffering from the norovirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a norovirus infection.

Some embodiments disclosed herein relate to a method of inhibiting replication of a norovirus that can include contacting a cell infected with the norovirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication a norovirus.

These are other embodiments are described in greater detail below.

DETAILED DESCRIPTION

Coronaviridae viruses are a family of enveloped, positive-stranded, single-stranded, spherical RNA viruses. Coronaviruses are named for the crown-like spikes on their surface. The Coronaviridae family includes two sub-families, Coronavirus and Torovirus. The Coronavirus genus has a helical nucleocapsid, and Torovirus genus has a tubular nucleocapsid. The Coronaviridae family of viruses includes Middle East respiratory syndrome coronavirus (MERS-CoV), SARS and SARS-CoV-2.

Coronavirus disease 2019 (COVID-19) (also referred to as novel coronavirus pneumonia or 2019-nCoV acute respiratory disease) is an infectious disease caused by the virus severe respiratory syndrome coronavirus 2 (SARS-CoV-2) (also referred to as novel coronavirus 2019, or 2019-nCoV). The disease was first identified in December 2019 and spread globally, causing a pandemic. Symptoms of COVID-19 include fever, cough, shortness of breath, fatigue, headache, loss of smell, nasal congestion, sore throat, coughing up sputum, pain in muscles or joints, chills, nausea, vomiting, and diarrhea. In severe cases, symptoms can include difficulty waking, confusion, blueish face or lips, coughing up blood, decreased white blood cell count, and kidney failure. Complications can include pneumonia, viral sepsis, acute respiratory distress syndrome, and kidney failure.

COVID-19 is especially threatening to public health. The virus is highly contagious, and studies currently indicate that it can be spread by asymptomatic carriers or by those who are pre-symptomatic. Likewise, the early stage of the disease is slow-progressing enough that carriers do not often realize they are infected, leading them to expose numerous others to the virus. The combination of COVID-19's ease of transmission, its high rate of hospitalization of victims, and its death rate make the virus a substantial public health risk, especially for countries without a healthcare system equipped to provide supportive care to pandemic-level numbers of patients. There is not yet a vaccine or specific antiviral treatment for COVID-19 and accordingly, there is a pressing need for treatments or cures.

SARS-CoV-2 is not the only coronavirus that causes disease. It is a β-coronavirus, a genus of coronaviruses that includes other human pathogens, including SARS-CoV (the causative agent of SARS), MERS-CoV (the causative agent of MERS), and HCoV-OC43 (a causative agent of the common cold). The infectivity of these viruses, and the severity of the diseases they cause, varies widely. β-coronavirus can also manifest as zoonotic infections, spread to and from humans and animals. Additionally, non-human species such as camels, bats, tigers, non-human primates, and rabbits can be susceptible to β-coronavirus. Accordingly, there is a pressing need for treatments or cures to multiple coronaviruses.

The present disclosure provides molecules useful against coronaviruses, and especially SARS-CoV-2, the causative agent of COVID-19 in humans. Accordingly, the present disclosure fulfills the need in the art for compounds that can be safely and effectively treat or prevent coronavirus infections in humans.

Picornaviruses are a family of positive strand RNA, nonenveloped viruses. A picornavirus has 60 identical subunits (vertices) which contain five protomers. Each protomer is made up of one copy of four proteins, named VP1, VP2, VP3 and VP4. There are several genera of picornaviruses, including, Enterovirus, Aphthovirus, Cardiovirus and Hepatovirus. Enteroviruses known to infect human include, but are not limited to, Rhinovirus A, Rhinovirus B, Rhinovirus C, Coxsackievirus A, Coxsackievirus B and Poliovirus. There is no specific treatment for a picornavirus infection.

Noroviruses are single-stranded positive-sense RNA, non-enveloped viruses belonging to the Caliciviridae family. Noroviruses are often spread by the fecal-oral route, and are a common cause of gastroenteritis. Infected subjects can experience nausea, non-bloody diarrhea, vomiting and/or abdominal pain. Those suffering from a norovirus infection can become severely dehydrated and require medical attention. As with a picornavirus infection, there is no specific treatment for a norovirus infection. Accordingly, there is a need for compounds that effectively treat or prevent a picornavirus and/or a norovirus infection.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) (such as 1, 2 or 3) individually and independently selected from deuterium, alkyl, alkenyl, alkynyl, cycloalkyl, cycloalkenyl, aryl, heteroaryl, heterocyclyl, aryl(alkyl), heteroaryl(alkyl), heterocyclyl(alkyl), hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, C-amido(alkyl), isocyanato, thiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amine and a di-substituted amine.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The length of an alkenyl can vary. For example, the alkenyl can be a $C_{2-4}$ alkenyl, $C_{2-6}$ alkenyl or $C_{2-8}$ alkenyl. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. The length of an alkynyl can vary. For example, the alkynyl can be a $C_{2-4}$ alkynyl, $C_{2-6}$ alkynyl or $C_{2-8}$ alkynyl. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused- or spiro-fashion. Cycloalkyl groups can contain 3 to 10 atoms in the ring(s). 3 to 8 atoms in the ring(s) or 3 to 6 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused- or spiro-fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to a monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The number of atoms in the ring(s) of a heterocyclyl group can vary. For example, the heterocyclyl group can contain 4 to 14 atoms in the ring(s), 5 to 10 atoms in the ring(s) or 5 to 6 atoms in the ring(s). The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl groups may be unsubstituted or substituted. Examples of such "heterocyclyl groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "cycloalkyl(alkyl)" refers to an cycloalkyl group connected, as a substituent, via a lower alkylene group. The lower alkylene and cycloalkyl group of an cycloalkyl(alkyl) may be substituted or unsubstituted. A cycloalkyl(alkyl) group may be unsubstituted or substituted.

As used herein, "aryl(alkyl)" refer to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl), and their benzo-fused analogs.

A "heterocyclyl(alkyl)" refer to a heterocyclic group connected, as a substituent, via a lower alkylene group. The lower alkylene and heterocyclyl of a heterocyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

"Lower alkylene groups" are straight-chained —CH$_2$— tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—) and butylene (—CH$_2$CH$_2$CH$_2$CH$_2$—). A lower alkylene group can be substituted by replacing one or more hydrogen of the lower alkylene group with a substituent(s) listed under the definition of "substituted." Further, when a lower alkylene group is substituted, the lower alkylene can be substituted by replacing both hydrogens on the same carbon with a cycloalkyl group

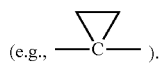

As used herein, "alkoxy" refers to the formula —OR wherein R is an alkyl, an alkenyl, an alkynyl, a cycloalkyl, a cycloalkenyl, an aryl, a heteroaryl, a heterocyclyl, a cycloalkyl(alkyl), an aryl(alkyl), a heteroaryl(alkyl) or a heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzyloxy. In some instances, an alkoxy can be —OR, wherein R is an unsubstituted C$_{1-4}$ alkyl. An alkoxy may be substituted or unsubstituted.

As used herein, "acyl" refers to a hydrogen, an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl(alkyl) connected, as substituents, via a carbonyl group. Examples include formyl, acetyl, propanoyl, benzoyl and acryl. An acyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to a O-alkyl group and O-monocyclic cycloalkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy, 2-fluoroisobutoxy, chloro-substituted cyclopropyl, fluoro-substituted cyclopropyl, chloro-substituted cyclobutyl and fluoro-substituted cyclobutyl. In some instances, a haloalkoxy can be —OR, wherein R is a C$_{1-4}$ alkyl substituted by 1, 2 or 3 halogens. A haloalkoxy may be substituted or unsubstituted.

A "sulfenyl" group refers to an "—SR" group in which R can be hydrogen, an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein each X is a halogen.

A "trihalomethanesulfonamido" group refers to an "X$_3$CS(O)$_2$N(R$_A$)—" group wherein each X is a halogen, and R$_A$ is hydrogen, an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl(alkyl).

The term "amino" as used herein refers to a —NH$_2$ group.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—SCN" group.

An "isothiocyanato" group refers to an "—NCS" group.

A "mercapto" group refers to an "—SH" group.

A "carbonyl" group refers to a —C(=O)— group.

An "S-sulfonamido" group refers to a "—SO$_2$N(R$_A$R$_B$)" group in which R$_A$ and R$_B$ can be independently hydrogen, an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl(alkyl). An S-sulfonamido may be substituted or unsubstituted.

An "N-sulfonamido" group refers to a "RSO$_2$N(R$_A$)—" group in which R and R$_A$ can be independently hydrogen, an alkyl, an alkenyl, an alkynyl, a cycloalkyl, a cycloalkenyl, an aryl, a heteroaryl, a heterocyclyl, an aryl(alkyl), a heteroaryl (alkyl) or a heterocyclyl(alkyl). An N-sulfonamido may be substituted or unsubstituted.

An "O-carbamyl" group refers to a "—OC(=O)N(R$_A$R$_B$)" group in which R$_A$ and R$_B$ can be independently hydrogen, an alkyl, an alkenyl, an alkynyl, a cycloalkyl, a cycloalkenyl, an aryl, a heteroaryl, a heterocyclyl, an aryl (alkyl), a heteroaryl(alkyl) or a heterocyclyl(alkyl). An O-carbamyl may be substituted or unsubstituted.

An "N-carbamyl" group refers to an "ROC(=O)N(R$_A$)—" group in which R and R$_A$ can be independently hydrogen, an alkyl, an alkenyl, an alkynyl, a cycloalkyl, a cycloalkenyl, an aryl, a heteroaryl, a heterocyclyl, an aryl (alkyl), a heteroaryl(alkyl) or a heterocyclyl(alkyl). An N-carbamyl may be substituted or unsubstituted.

An "O-thiocarbamyl" group refers to a "—OC(=S)—N(R$_A$R$_B$)" group in which R$_A$ and R$_B$ can be independently hydrogen, an alkyl, an alkenyl, an alkynyl, a cycloalkyl, a cycloalkenyl, an aryl, a heteroaryl, a heterocyclyl, an aryl (alkyl), a heteroaryl(alkyl) or a heterocyclyl(alkyl). An O-thiocarbamyl may be substituted or unsubstituted.

An "N-thiocarbamyl" group refers to an "ROC(=S)N($R_A$)—" group in which R and $R_A$ can be independently hydrogen, an alkyl, an alkenyl, an alkynyl, a cycloalkyl, a cycloalkenyl, an aryl, a heteroaryl, a heterocyclyl, an aryl (alkyl), a heteroaryl(alkyl) or a heterocyclyl(alkyl). An N-thiocarbamyl may be substituted or unsubstituted.

A "C-amido" group refers to a "—C(=O)N($R_A R_B$)" group in which $R_A$ and $R_B$ can be independently hydrogen, an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl(alkyl). A C-amido may be substituted or unsubstituted.

An "N-amido" group refers to a "RC(=O)N($R_A$)—" group in which R and $R_A$ can be independently hydrogen, an alkyl, an alkenyl, an alkynyl, a cycloalkyl, a cycloalkenyl, an aryl, a heteroaryl, a heterocyclyl, an aryl(alkyl), a heteroaryl (alkyl) or a heterocyclyl(alkyl). An N-amido may be substituted or unsubstituted.

A "mono-substituted amine" refers to a "—$NHR_A$" in which $R_A$ can be independently an alkyl, an alkenyl, an alkynyl, a cycloalkyl, a cycloalkenyl, an aryl, a heteroaryl, a heterocyclyl, an aryl(alkyl), a heteroaryl(alkyl) or a heterocyclyl(alkyl). A mono-substituted amine may be substituted or unsubstituted. In some instances, a mono-substituted amine can be —$NHR_A$, wherein $R_A$ can be an unsubstituted $C_{1-6}$ alkyl or an unsubstituted or a substituted benzyl.

A "di-substituted amine" refers to a "—$NR_A R_B$" in which $R_A$ and $R_B$ can be independently can be independently an alkyl, an alkenyl, an alkynyl, a cycloalkyl, a cycloalkenyl, an aryl, a heteroaryl, a heterocyclyl, an aryl(alkyl), a heteroaryl (alkyl) or a heterocyclyl(alkyl). A mono-substituted amine may be substituted or unsubstituted. In some instances, a mono-substituted amine can be —$NR_A R_B$, wherein $R_A$ and $R_B$ can be independently an unsubstituted $C_{1-6}$ alkyl or an unsubstituted or a substituted benzyl.

A "ketoamide" group refers to a —C(=O)—C(=O)N($R_A R_B$) group in which $R_A$ and $R_B$ can be independently hydrogen, an alkyl, an alkenyl, an alkynyl, a cycloalkyl, a cycloalkenyl, an aryl, a heteroaryl, a heterocyclyl, an aryl (alkyl), a heteroaryl(alkyl) or a heterocyclyl(alkyl). A ketoamide may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof. In addition, the term "comprising" is to be interpreted synonymously with the phrases "having at least" or "including at least". When used in the context of a compound or composition, the term "comprising" means that the compound or composition includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality.

It is understood that, in any compound described herein having one or more chiral centers, if an absolute stereochemistry is not expressly indicated, then each center may independently be of (R)-configuration or (S)-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof:

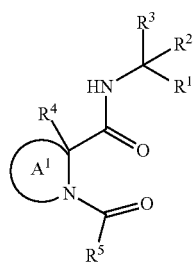

(I)

wherein: Ring $A^1$ can be

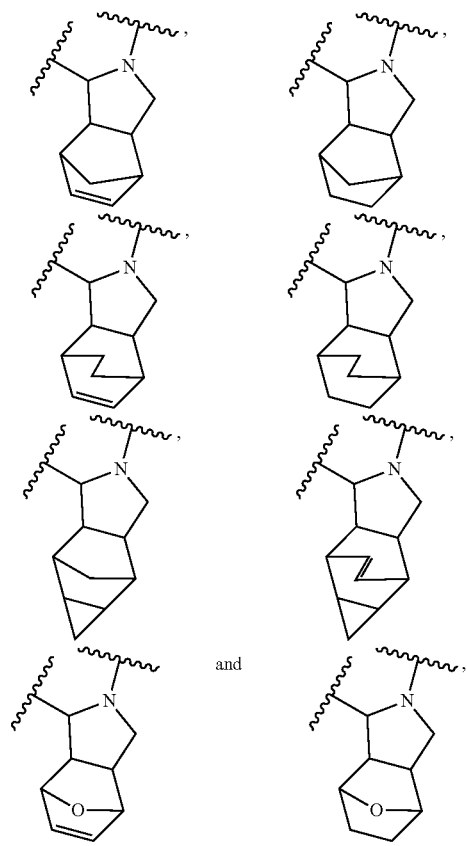

and wherein Ring $A^1$ can be optionally substituted with one or more moieties independently selected from =O, =CH$_2$, deuterium, halogen, hydroxy, an unsubstituted $C_{1-4}$ alkyl, an unsubstituted $C_{1-4}$ haloalkyl, an unsubstituted $C_{2-4}$ alkenyl and an unsubstituted or a substituted $C_{3-6}$ monocyclic cycloalkyl; $R^1$ can be selected from cyano, an unsubstituted or a substituted $C_{2-5}$ alkynyl, an unsubstituted or a substituted acyl, an unsubstituted or a substituted ketoamide, —CH(OH)—(S(=O)$_2$—O—), —CH(OH)((P=O)(OR$^6$)$_2$) and —C(=O)CH$_2$—O—((P=O)(OR$^7$)$_2$); each $R^6$ and each $R^7$ can be independently hydrogen, an unsubstituted $C_{1-6}$ alkyl, an unsubstituted $C_{2-6}$ alkenyl, an unsubstituted $C_{1-6}$ haloalkyl, an unsubstituted or a substituted aryl or an unsubstituted or a substituted aryl($C_{1-4}$ alkyl); $R^2$ can be hydrogen, deuterium or halogen; $R^3$ can be an unsubstituted or a substituted monocyclic nitrogen-containing heterocyclyl ($C_{1-4}$ alkyl), an unsubstituted or a substituted bicyclic nitrogen-containing heterocyclyl($C_{1-4}$ alkyl) or an unsubstituted or a substituted monocyclic nitrogen-containing heteroaryl ($C_{1-4}$ alkyl); $R^4$ can be hydrogen, deuterium or halogen; $R^5$ can be

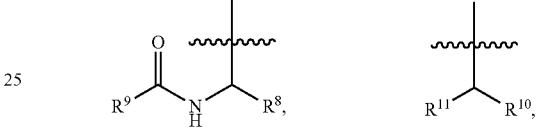

a substituted monocyclic $C_{3-6}$ cycloalkyl or a substituted 4- to 6-membered monocyclic heterocyclyl; $R^8$ and $R^{10}$ can be independently selected from an unsubstituted or a substituted $C_{2-6}$ alkyl, an unsubstituted or a substituted $C_{2-6}$ alkenyl, an unsubstituted or a substituted $C_{2-6}$ alkynyl, an unsubstituted or a substituted monocyclic $C_{3-6}$ cycloalkyl, an unsubstituted or a substituted bicyclic $C_{5-8}$ cycloalkyl, an unsubstituted or a substituted monocyclic 4- to 6-membered heterocyclyl and an unsubstituted monocyclic $C_{3-6}$ cycloalkyl(CH$_2$)—, wherein when the $C_{2-6}$ alkyl is substituted, the $C_{2-6}$ alkyl can be substituted 1, 2, 3 or 4 times with a substituent independently selected from halogen, cyano, an unsubstituted or a substituted monocyclic $C_{3-6}$ cycloalkyl, an unsubstituted $C_{1-4}$ alkoxy and an unsubstituted $C_{1-4}$ haloalkoxy, or the $C_{2-6}$ alkyl is substituted 1 to 13 times with deuterium; wherein when the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl are substituted, the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl can be substituted 1, 2, 3 or 4 times with a substituent independently selected from halogen, an unsubstituted $C_{1-4}$ alkyl, an unsubstituted $C_{2-4}$ alkenyl, an unsubstituted $C_{2-4}$ alkynyl, an unsubstituted $C_{1-4}$ haloalkyl, an unsubstituted or a substituted monocyclic $C_{3-6}$ cycloalkyl and an unsubstituted $C_{1-4}$ alkoxy; $R^9$ can be selected from an unsubstituted or a substituted $C_{1-6}$ alkyl, an unsubstituted or a substituted $C_{1-6}$ haloalkyl, an unsubstituted or a substituted monocyclic $C_{3-6}$ cycloalkyl, an unsubstituted or a substituted bicyclic $C_{5-6}$ cycloalkyl, an unsubstituted or a substituted monocyclic heteroaryl and an unsubstituted or a substituted monocyclic heterocyclyl, wherein the substituted $C_{1-6}$ alkyl is substituted 1 or 2 times with an unsubstituted $C_{1-4}$ alkoxy, wherein the substituted monocyclic $C_{3-6}$ cycloalkyl is substituted 1, 2, 3 or 4 times with a substituent independently selected from halogen, an unsubstituted $C_{1-4}$ alkyl, an unsubstituted $C_{1-4}$ alkoxy, an unsubstituted $C_{1-4}$ haloalkyl and an unsubstituted monocyclic $C_{3-6}$ cycloalkyl, and wherein the substituted $C_{1-6}$ haloalkyl is substituted 1 or 2 times with an unsubstituted $C_{1-4}$ alkoxy; and $R^{11}$ can be an optionally substituted monocyclic 4- to 6-membered heterocyclyl, —(NH)$_m$— an optionally substituted 5- to 6-membered monocyclic heteroaryl, —O— an optionally substituted $C_{1-6}$ alkyl, —O— an optionally substituted $C_{3-8}$ cycloalkyl and —O— an optionally substituted $C_{3-8}$ cycloalkyl($C_{1-4}$ alkyl), wherein m can be 0 or 1.

The substituent $R^1$ can be various moieties. In some embodiments, $R^1$ can be an unsubstituted ketoamide. In some embodiments, $R^1$ can be a substituted ketoamide. The ketoamide can have the structure —C(=O)—C(=O)NR$^{y1}$R$^{z1}$. In some embodiments, $R^1$ can be an acyl, for example, $R^1$ can be —C(=O)H, —C(=O)(an unsubstituted $C_{1-4}$ alkyl), —C(=O)(an unsubstituted to a substituted benzyl), —C(=O)(an unsubstituted to a substituted monocyclic heteroaryl) or —C(=O)(an unsubstituted to a substituted bicyclic heteroaryl). In some embodiments, $R^1$ can be a substituted acyl. The acyl for $R^1$ can have the structure —C(=O)R$^{y2}$. When the acyl is substituted, the possible groups that can be present on the acyl include hydroxy, a substituted or an unsubstituted alkoxy (such as —O-(an unsubstituted $C_{1-4}$ alkyl), —O-(an unsubstituted $C_{3-6}$ cycloalkyl), a substituted or an unsubstituted phenoxy or a substituted or an unsubstituted benzyloxy) or —O—(C=O)-(an unsubstituted $C_{1-6}$ alkyl). In some embodiments, $R^1$ can be an unsubstituted can be —C(=O)—N-sulfonamido.

$R^{y1}$, $R^{y2}$ and $R^{z1}$ can be a variety of groups. In some embodiments, $R^{y1}$, $R^{y2}$ and $R^{z1}$ can be independently selected from hydrogen, $C_{1-8}$ alkyl, $C_{2-8}$ alkenyl, $C_{2-8}$ alkynyl, $C_{3-8}$ cycloalkyl (for example, a monocyclic $C_{3-8}$ cycloalkyl), $C_{3-8}$ cycloalkenyl (such as a monocyclic $C_{3-8}$ cycloalkenyl), aryl (such as phenyl or naphthyl), heteroaryl (including a monocyclic or a bicyclic heteroaryl), heterocyclyl (for example, a monocyclic or a bicyclic heterocyclyl), aryl(alkyl) (such as benzyl), heteroaryl(alkyl) (including a monocyclic heteroaryl(CH$_2$)— and a monocyclic (heteroaryl(CH$_2$CH$_2$)—) or heterocyclyl(alkyl) (such as a monocyclic heterocyclyl(CH$_2$)— and a monocyclic heterocyclyl(CH$_2$CH$_2$)—), wherein each of the aforementioned $R^{y1}$, $R^{y2}$ and $R^{z1}$ groups can be unsubstituted or substituted. In some embodiments, $R^{y1}$, $R^{y2}$ and $R^{z1}$ can be independently selected from H, $C_{1-8}$ alkyl, an unsubstituted $C_{1-4}$ haloalkyl (including —CF$_3$, —CCl$_3$, —CHF$_2$, —C(CH$_3$)F$_2$, —CHCl$_2$, —CH$_2$F, —CH(CH$_3$)F, —CH$_2$CF$_3$, —CH$_2$Cl, —CH$_2$CH$_2$F, —CH$_2$CH$_2$Cl, —CH$_2$CH$_2$CH$_2$F and —CH$_2$CH$_2$CH$_2$Cl), —$C_{1-4}$ alkyl(OH) (including —CH$_2$OH, —CH$_2$CH$_2$OH and —CH(CH$_3$)OH), —$C_{1-4}$ alkyl($C_{1-4}$ alkoxy) (such as —CH$_2$O (an unsubstituted $C_{1-4}$ alkyl) and —CH$_2$CH$_2$O (an unsubstituted $C_{1-4}$ alkyl)), —$C_{1-4}$ alkyl-O-(a monocyclic $C_{3-6}$ cycloalkyl) (such as —CH$_2$O (a monocyclic $C_{3-6}$ cycloalkyl), —CH$_2$CH$_2$O (a monocyclic $C_{3-6}$ cycloalkyl)), —$C_{1-4}$ alkyl-O-(phenyl) (for example, —CH$_2$O (phenyl) and —CH$_2$CH$_2$O (phenyl)), —$C_{1-4}$ alkyl-O-(5- to 6-membered monocyclic heteroaryl) (such as —CH$_2$O (5- to 6-membered monocyclic heteroaryl) and —CH$_2$CH$_2$O (5- to 6-membered monocyclic heteroaryl)), —$C_{1-4}$ alkyl-O-(5- to 6-membered monocyclic heterocyclyl) (for example, —CH$_2$O (5- to 6-membered monocyclic heterocyclyl) and —CH$_2$CH$_2$O (5- to 6-membered monocyclic heterocyclyl)), —$C_{1-4}$ alkyl-O-(a monocyclic $C_{3-6}$ cycloalkyl($C_{1-4}$ alkyl) (such as —$C_{1-4}$ alkyl-O-CH$_2$-(monocyclic $C_{3-6}$ cycloalkyl) and —$C_{1-4}$ alkyl-O-CH$_2$CH$_2$-(monocyclic $C_{3-6}$ cycloalkyl)), —$C_{1-4}$ alkyl-O-(benzyl) (for example, —CH$_2$O (benzyl) and —CH$_2$CH$_2$O (benzyl)), —$C_{1-4}$ alkyl-O-(5- to 6-membered monocyclic heteroaryl($C_{1-4}$ alkyl), —$C_{1-4}$ alkyl-O-(5- to 6-membered monocyclic heterocyclyl($C_{1-4}$ alkyl), —$C_{1-4}$ alkyl-O(C=O) (an unsubstituted $C_{1-6}$ alkyl) (for example, —CH$_2$O(C=O) (an unsubstituted $C_{1-6}$ alkyl)), a monocyclic $C_{3-8}$ cycloalkyl (such as cyclopropyl, cyclobutyl, cyclopentyl, cyclohexyl, cycloheptyl and cyclooctyl), a monocyclic heteroaryl (such as imidazole, 1,3,4-oxadiazole and pyridinyl), a monocyclic heterocyclyl (for example, tetrahydrofuran and tetrahydropyran), a bicyclic heteroaryl (for example, benzothiazole, benzoimidazole and benzooxazole), a bicyclic heterocyclyl, a monocyclic $C_{3-6}$ cycloalkyl(alkyl), aryl(alkyl) (such as benzyl), heteroaryl(alkyl) (for example, a monocyclic heteroaryl-(CH$_2$)—, such as pyridinyl-(CH$_2$)—) and heterocyclyl(alkyl) (for example, a monocyclic heterocyclyl-(CH$_2$)—), wherein each of the aforementioned $R^{y1}$, $R^{y2}$ and $R^{z1}$ groups can be unsubstituted or substituted.

In some embodiments, $R^1$ can be —C(=O)R$^{y2}$, wherein $R^{y2}$ can be —$C_{1-4}$ alkyl(OH) (such as —CH$_2$OH). In some embodiments, $R^1$ can be —C(=O)—C(=O)NR$^{y1}$R$^{z1}$; wherein $R^{y1}$ can be H; and $R^{z1}$ can be any of the moieties listed for $R^{z1}$ in the previous paragraph. In some embodiments, $R^1$ can be —C(=O)—C(=O)NR$^{y1}$R$^{z1}$; wherein $R^{y1}$ can be H; and $R^{z1}$ can be a monocyclic $C_{3-8}$ cycloalkyl (for example, cyclopropyl, cyclobutyl, cyclopentyl, cyclohexyl, cycloheptyl and cyclooctyl).

Prodrug-type and phosphate-containing moieties can be present at $R^1$. In some embodiments, $R^1$ can be —CH(OH)—(S(=O)$_2$—O—). In other embodiments, $R^1$ can be —CH(OH)((P=O)(OR$^6$)$_2$), wherein each $R^6$ can be independently hydrogen, an unsubstituted $C_{1-6}$ alkyl, an unsubstituted $C_{2-6}$ alkenyl, an unsubstituted $C_{1-6}$ haloalkyl, an unsubstituted or a substituted aryl or an unsubstituted or a substituted aryl($C_{1-4}$ alkyl). In still other embodiments, $R^1$ can be —C(=O)CH$_2$—O—((P=O)(OR$^7$)$_2$), wherein each $R^7$ can be independently hydrogen, an unsubstituted $C_{1-6}$ alkyl, an unsubstituted $C_{2-6}$ alkenyl, an unsubstituted $C_{1-6}$ haloalkyl, an unsubstituted or a substituted aryl or an unsubstituted or a substituted aryl($C_{1-4}$ alkyl). Other examples of $R^6$ and $R^7$ groups include methyl, ethyl, n-propyl, isopropyl, n-butyl, iso-butyl, sec-butyl, tert-butyl, pentyl (straight-chained and branched), hexyl (straight-chained and branched), ethenyl, propenyl, butenyl, pentenyl, hexenyl, chloromethyl, fluoromethyl, difluoromethyl, dichloromethyl, trifluoromethyl, trichloromethyl, an unsubstituted or a substituted phenyl and an unsubstituted or a substituted benzyl.

In some embodiments, $R^1$ can be cyano. In other embodiments, $R^1$ can be an unsubstituted $C_{2-5}$ alkynyl. In still other embodiments, $R^1$ can be a substituted $C_{2-5}$ alkynyl. The $C_{2-5}$ alkynyl can have various structures. For example, the $C_{2-5}$ alkynyl can have the structure —(CH$_2$)$_1$—$C_{2-4}$ alkynyl or —(CH$_2$)$_2$—$C_{2-3}$ alkynyl.

As described herein, Ring A1 can be

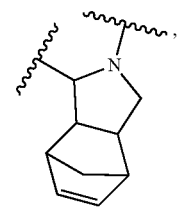 [SMILES: *C1C2C3C=CC(C3)C2CN1*]

wherein Ring A¹ can be optionally substituted. In some embodiments, Ring A¹ can be an unsubstituted

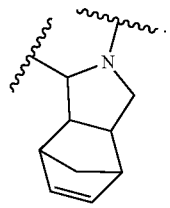 [SMILES: *C1C2C3C=CC(C3)C2CN1*]

In other embodiments, Ring A¹ can be a substituted

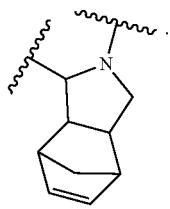 [SMILES: *C1C2C3C=CC(C3)C2CN1*]

In still other embodiments, Ring A¹ can be an unsubstituted

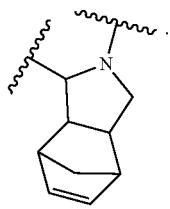 [SMILES: *C1C2C3C=CC(C3)C2CN1*]

In yet still other embodiments, Ring A¹ can be a substituted

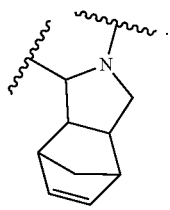

In some embodiments, Ring A¹ can be an unsubstituted

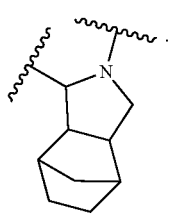 [SMILES: *C1C2C3CCC(C3)C2CN1*]

In other embodiments, Ring A¹ can be a substituted

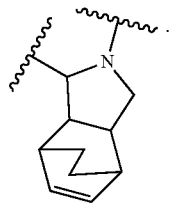 [SMILES: *C1C2C3C=CC(CC3)C2CN1*]

In still other embodiments, Ring A¹ can be an unsubstituted

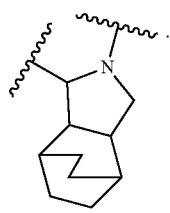 [SMILES: *C1C2C3CCC(CC3)C2CN1*]

In yet still other embodiments, Ring A¹ can be a substituted

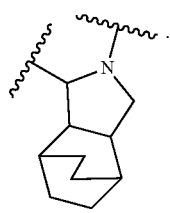 [SMILES: *C1C2C3CCC(CC3)C2CN1*]

In some embodiments, Ring A¹ can be an unsubstituted

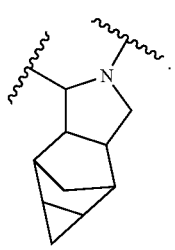 [SMILES: *C1C2C3CC(C4CC43)C2CN1*]

In other embodiments, Ring A¹ can be a substituted

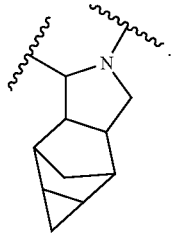 [SMILES: *C1C2C3CC(C4CC43)C2CN1*]

In still other embodiments, Ring A¹ can be an unsubstituted

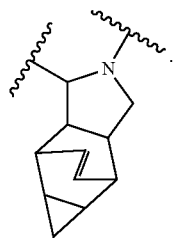 [SMILES: *C1C2C3C=CC(C4CC34)C2CN1*]

In yet still other embodiments, Ring A¹ can be a substituted

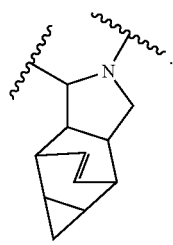 [SMILES: *C1C2C3C=CC(C4CC34)C2CN1*]

In some embodiments, Ring A¹ can be an unsubstituted

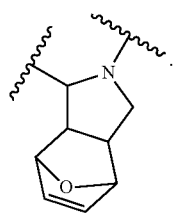 [SMILES: *C1C2C3C=CC(O3)C2CN1*]

In other embodiments, Ring A¹ can be a substituted

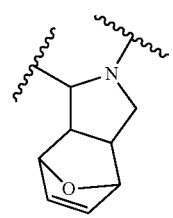 [SMILES: *C1C2C3C=CC(O3)C2CN1*]

In still other embodiments, Ring A¹ can be an unsubstituted

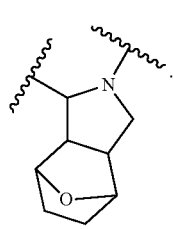 [SMILES: *C1C2C3CCC(O3)C2CN1*]

In yet still other embodiments, Ring A¹ can be a substituted

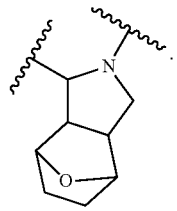

Those skilled in the art understand that the nitrogen shown in each of the ring structures for Ring A¹ corresponds to the ring nitrogen shown in Formula (I), and the carbon adjacent to the ring nitrogen with the

corresponds to the carbon to which R⁴ is attached. For example, those skilled in the art understand that when Ring A¹ is

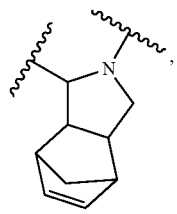 [SMILES: *C1C2C3C=CC(C3)C2CN1*]

then a compound of Formula (I), or a pharmaceutically acceptable salt thereof, can have the following structure:

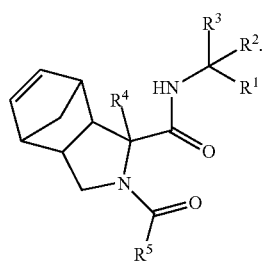

As provided herein, Ring A¹ can be substituted with one or more moieties independently selected from =O, =CH₂, deuterium, halogen, hydroxy, an unsubstituted C$_{1-4}$ alkyl, an unsubstituted C$_{1-4}$ haloalkyl, an unsubstituted C$_{2-4}$ alkenyl and an unsubstituted or a substituted C$_{3-6}$ monocyclic cycloalkyl. Example of suitable substituents that can be present in Ring A¹ include halogen (such as F or Cl), an unsubstituted C$_{1-4}$ alkyl (for example, methyl, ethyl, n-propyl, iso-propyl, n-butyl, iso-butyl, sec-butyl and tert-butyl), an unsubstituted C$_{1-4}$ haloalkyl (including —CF₃, —CCl₃, —CHF₂, —C(CH₃)F₂, —CHCl₂, —CH₂F, —CH(CH₃)F, —CH₂CF₃, —CH₂Cl, —CH₂CH₂F, —CH₂CH₂Cl, —CH₂CH₂CH₂F and —CH₂CH₂CH₂Cl), an unsubstituted C$_{2-4}$ alkenyl (such as ethenyl, propenyl and butenyl) and an unsubstituted or a substituted C$_{3-6}$ monocyclic cycloalkyl (for example, cyclopropyl, cyclobutyl, cyclopentyl and cyclohexyl). When Ring A¹ is substituted by an unsubstituted or a substituted $C_{3-6}$ monocyclic cycloalkyl, the unsubstituted or a substituted $C_{3-6}$ monocyclic cycloalkyl can replace one hydrogen. In some embodiments, an unsubstituted or a substituted $C_{3-6}$ monocyclic cycloalkyl can replace two hydrogens of Ring $A^1$ such that the unsubstituted or a substituted $C_{3-6}$ monocyclic cycloalkyl is connected to Ring $A^1$ in a spiro-fashion. Examples of an unsubstituted or a substituted $C_{3-6}$ monocyclic cycloalkyl replacing two hydrogen of Ring $A^1$ includes the following:

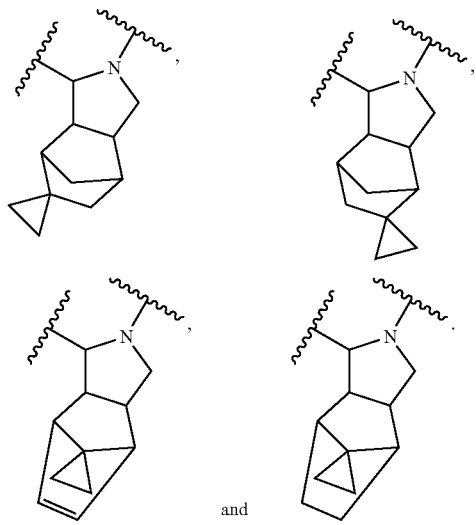

wherein each can be unsubstituted or substituted as described herein. Examples of Ring $A^1$ include, but are not limited to, the following:

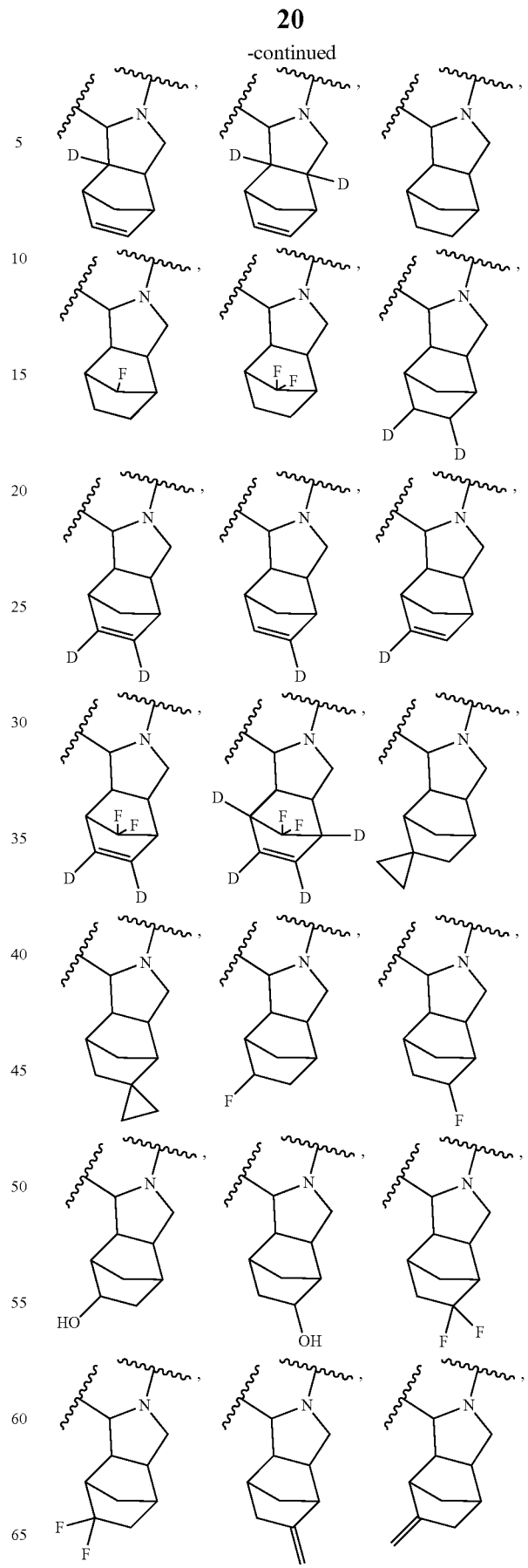

-continued

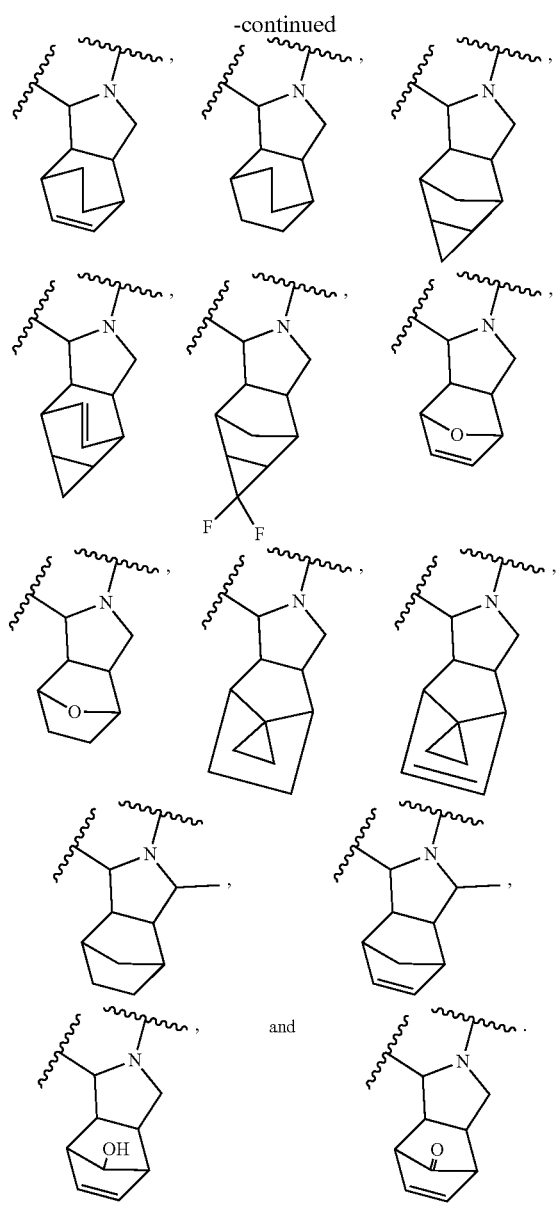

In some embodiments, R⁴ can be hydrogen. In other embodiments, R⁴ can be deuterium. In still other embodiments, R⁴ can be halogen (such as fluoro or chloro).

As provided herein R³ can be a non-hydrogen substituent selected from an unsubstituted or a substituted monocyclic nitrogen-containing heterocyclyl($C_{1-4}$ alkyl) and an unsubstituted or a substituted bicyclic nitrogen-containing heterocyclyl($C_{1-4}$ alkyl). In some embodiments, R³ can be an unsubstituted monocyclic nitrogen-containing heteroaryl ($C_{1-4}$ alkyl). In other embodiments, R³ can be a substituted monocyclic nitrogen-containing heteroaryl($C_{1-4}$ alkyl). In still other embodiments, R³ can be an unsubstituted bicyclic nitrogen-containing heterocyclyl($C_{1-4}$ alkyl). In yet still other embodiments, R³ can be a substituted bicyclic nitrogen-containing heterocyclyl($C_{1-4}$ alkyl). When R³ is a bicyclic nitrogen-containing heterocyclyl($C_{1-4}$ alkyl), the two rings of the bicyclic heterocyclyl can be connected in a fused-fashion (including bridged-fashion) or a spiro-fashion. In some embodiments, R³ can be an unsubstituted monocyclic nitrogen-containing heteroaryl($C_{1-4}$ alkyl). In other embodiments, R³ can be a substituted monocyclic nitrogen-containing heteroaryl($C_{1-4}$ alkyl).

Those skilled in the art understand that when two rings are connected in a spiro-fashion, the two rings are connected by a single ring atom. For example, in the structure

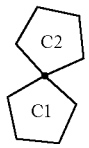

rings C1 and C2 are joined in a spiro-fashion. When two rings described herein are connected in a fused-fashion, the two rings are connected by two or more ring atoms. In some instances, the two rings can be connected by two adjacent ring atoms. As an example, rings D1 and D1 are connected in a fused-fashion by two adjacent ring atoms

In some instances, two rings described herein can be connected by three or more atoms are shared between the two rings. The following structure:

is an example of two rings being connected by three or more ring atoms. When two rings are connected by three or more ring atoms, the three or more ring atoms connecting the two rings would be referred to by those skilled in the art as "bridging" atoms. Further, those skilled in the art would understand based on the disclosure provided herein that two rings connected in a "bridged" fashion is an example of two rings connected in a fused-fashion.

The number of ring atoms for a monocyclic and a bicyclic nitrogen-containing heterocyclyl($C_{1-4}$ alkyl) can vary. Non-limiting examples include an unsubstituted or a substituted 5-membered monocyclic nitrogen-containing heterocyclyl ($C_{1-4}$ alkyl), 6-membered monocyclic nitrogen-containing heterocyclyl($C_{1-4}$ alkyl), an unsubstituted or a substituted 9-membered bicyclic nitrogen-containing heterocyclyl($C_{1-4}$ alkyl) and 10-membered bicyclic nitrogen-containing heterocyclyl($C_{1-4}$ alkyl). Examples of suitable R³ groups include the following: azepan-2-one($C_{1-4}$ alkyl), imidazolidin-2-one($C_{1-4}$ alkyl), tetrahydropyrimidin-2-one($C_{1-4}$ alkyl), pyrrolidin-2-one($C_{1-4}$ alkyl), piperidin-2-one($C_{1-4}$ alkyl), pyrazolidin-3-one($C_{1-4}$ alkyl), oxazolidin-4-one($C_{1-4}$ alkyl), 1,4-oxazepan-3-one($C_{1-4}$ alkyl), morpholin-3-one ($C_{1-4}$ alkyl),

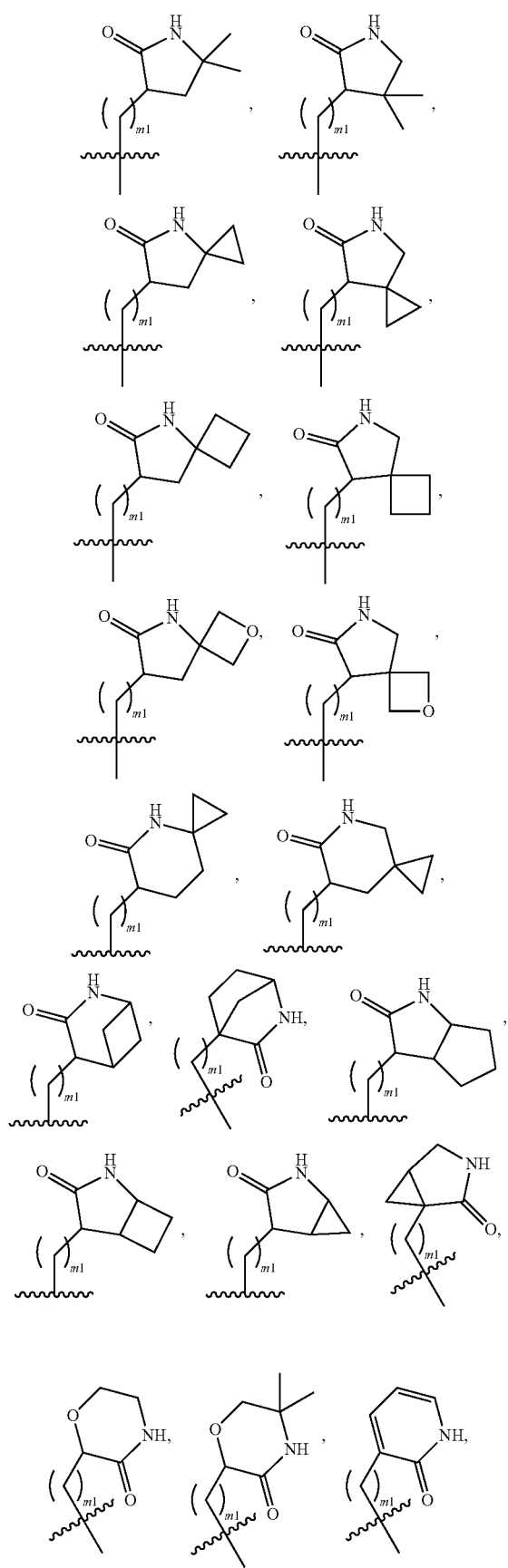
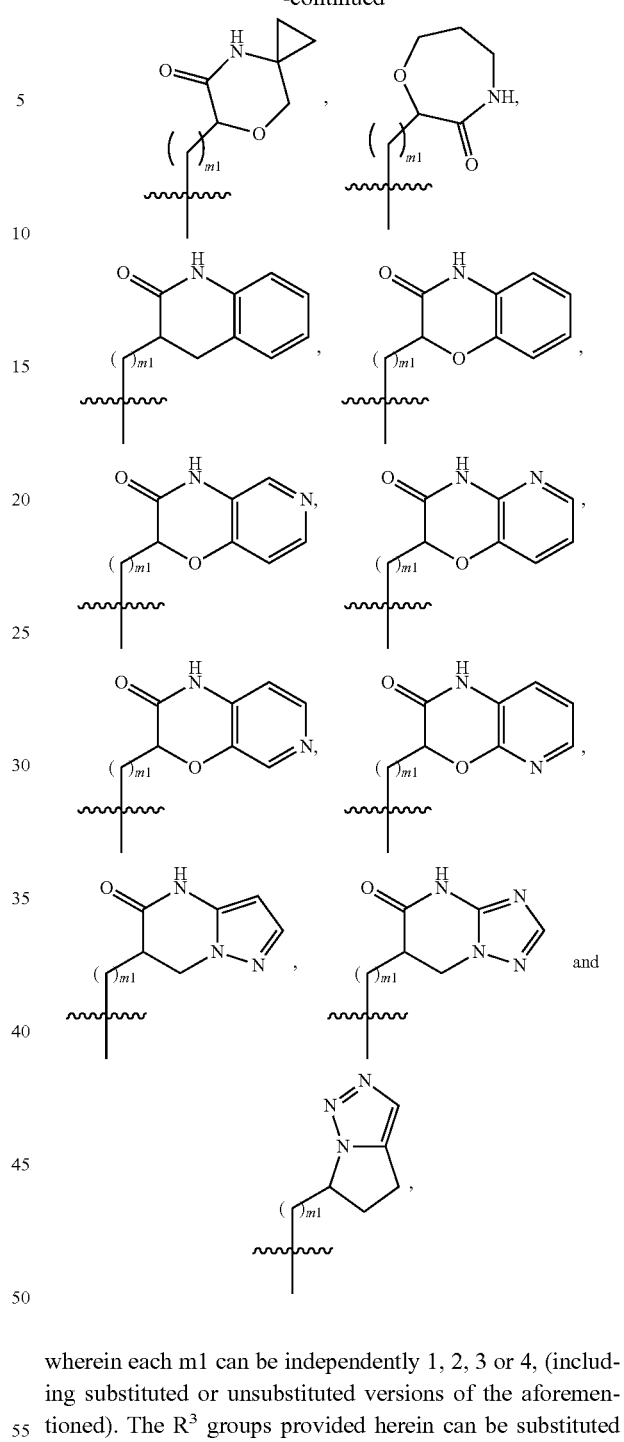

wherein each m1 can be independently 1, 2, 3 or 4, (including substituted or unsubstituted versions of the aforementioned). The R³ groups provided herein can be substituted with one or more moieties independently selected from those listed for "optionally substituted." In some embodiments, a R³ group provided herein can be substituted with one or more moieties selected from deuterium, halogen, hydroxy, an unsubstituted $C_{1-4}$ alkyl, an unsubstituted $C_{2-4}$ alkenyl an unsubstituted $C_{1-4}$ alkoxy, amino, -(an unsubstituted $C_{1-4}$ alkyl)-O—P—(OH)₂ (such as —CH₂—O—P—(OH)₂) and—(an unsubstituted $C_{1-4}$ alkyl)-O—P—(O (an unsubstituted $C_{1-4}$ alkyl))₂ (such as —CH₂—O—P—(OCH₃)₂).

Non-limiting examples of R³ moieties include the following:
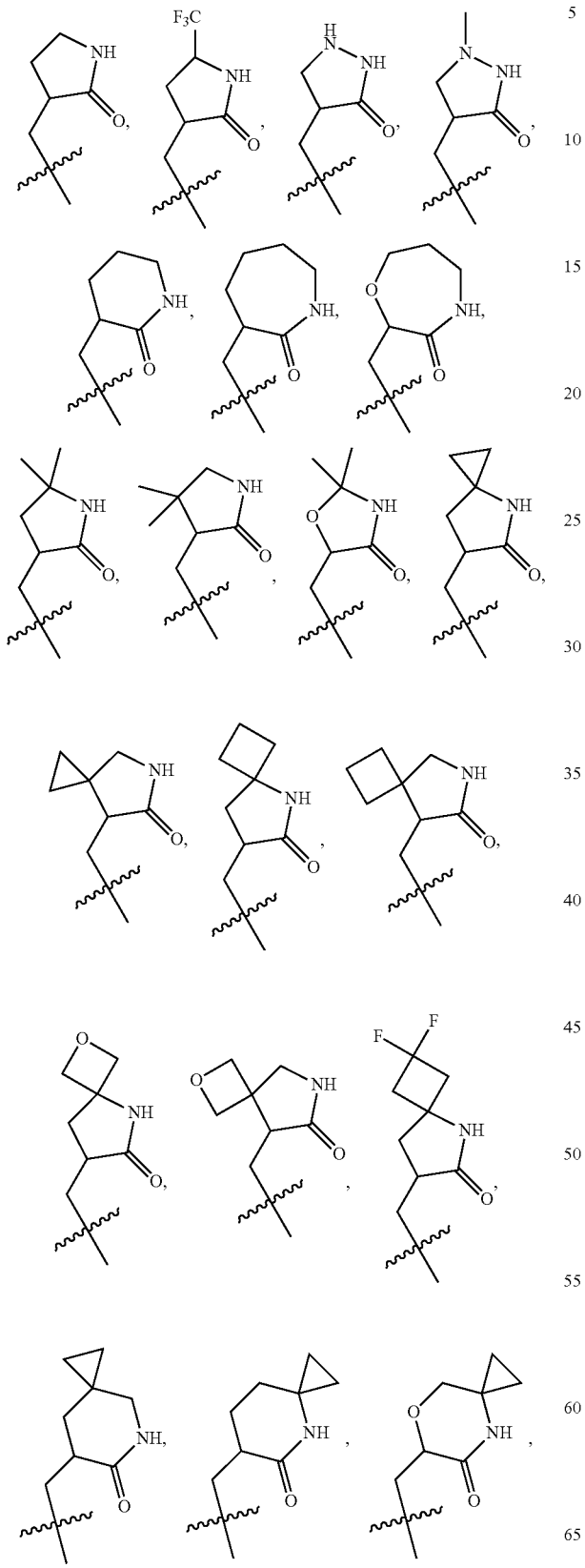
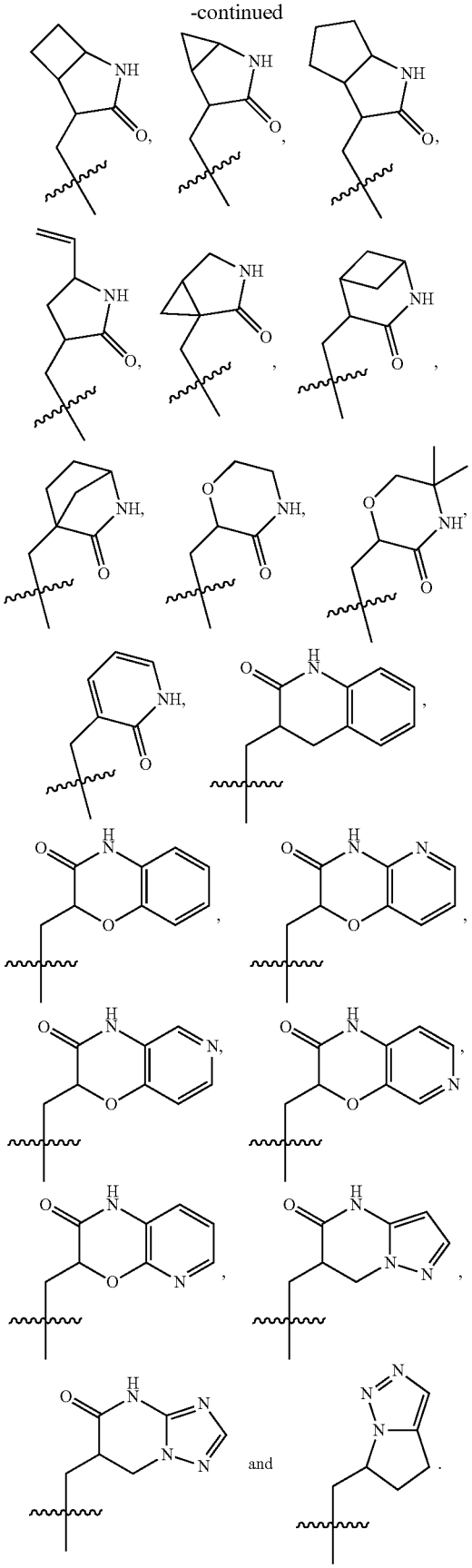

In some embodiments, $R^2$ can be hydrogen. In other embodiments, $R^2$ can be deuterium. In still other embodiments, $R^2$ can be halogen (for example, fluoro or chloro).

As provided herein, $R^5$ can be

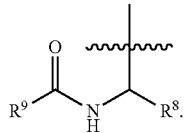

In some embodiments, $R^9$ can be an unsubstituted $C_{1-6}$ haloalkyl. For example, $R^9$ can be —$CF_3$, —$CClF_2$, —$CCl_3$, —$CHF_2$, —$C(CH_3)F_2$, —$CHCl_2$, —$CH_2F$, —$CH(CH_3)F$, —$CH_2CF_3$, —$CH(CH_3)CF_3$, —$CH_2CH_2CF_3$, —$CH_2CH(CH_3)CF_3$, —$CF_2CF_3$, —$CH_2Cl$, —$CH_2CH_2F$, —$CH_2CH_2Cl$, —$CH_2CH_2CH_2F$ and —$CH_2CH_2CH_2Cl$. In some embodiments, $R^9$ can be —$CF_3$. In other embodiments, $R^9$ can be a substituted $C_{1-6}$ haloalkyl where the $C_{1-6}$ haloalkyl can be substituted 1 or 2 times with an unsubstituted $C_{1-4}$ alkoxy. When the $C_{1-6}$ haloalkyl is substituted with 1 or 2 unsubstituted $C_{1-4}$ alkoxys, one or more hydrogens of the $C_{1-6}$ haloalkyl can be replaced with an unsubstituted $C_{1-4}$ alkoxy (such as methoxy, ethoxy, n-propoxy, isopropoxy, n-butoxy, isobutoxy, sec-butoxy and tert-butoxy). Exemplary $C_{1-6}$ haloalkyls substituted with an unsubstituted $C_{1-4}$ alkoxy include —$C(OCH_3)F_2$, —$C(OCH_3)Cl_2$, —$CH(OCH_3)F$, —$C(OCH_3)(CH_3)F$, —$CH(OCH_3)CF_3$, —$C(OCH_3)(CH_3)CF_3$, —$CH_2CH(OCH_3)CF_3$, —$CH_2C(OCH_3)(CH_3)CF_3$, —$CH(OCH_3)Cl$, —$CH_2CH(OCH_3)F$, —$CH_2CH(OCH_3)Cl$, —$CH_2CH_2CH(OCH_3)F$ and —$CH_2CH_2CH(OCH_3)Cl$. In still other embodiments, $R^9$ can be an unsubstituted $C_{1-6}$ alkyl, such as methyl, ethyl, n-propyl, iso-propyl, n-butyl, iso-butyl, sec-butyl, tert-butyl, pentyl (straight-chained or branched) and hexyl (straight-chained or branched). In yet still other embodiments, $R^9$ can be a $C_{1-6}$ alkyl substituted 1 or 2 times with an unsubstituted $C_{1-4}$ alkoxy. When the $C_{1-6}$ alkyl is substituted with an unsubstituted $C_{1-4}$ alkoxy, a hydrogen of the $C_{1-6}$ alkyl can be replaced with an unsubstituted $C_{1-4}$ alkoxy such as those described herein. A non-limiting list of $C_{1-6}$ alkyls substituted 1 or 2 times with an unsubstituted $C_{1-4}$ alkoxy include —$CH_2(OCH_3)$, —$CH(OCH_3)_2$, —$CH(CH_3)(OCH_3)$ and —$C(CH_3)_2(OCH_3)$. In some embodiments, $R^9$ can be an unsubstituted or a substituted monocyclic heteroaryl. A variety of an unsubstituted or a substituted monocyclic heteroaryls can be present for $R^9$. For example, the heteroaryl can be a 5- or 6-membered heteroaryl that includes 1, 2 or 3 heteroatoms selected from nitrogen (N), oxygen (O) and sulfur (S). Exemplary heteroaryls for an unsubstituted or a substituted monocyclic heteroaryl include, but are not limited to, furane, isoxazole, isothiazole pyridine, pyridazine, pyrimidine and pyrazine. In yet still other embodiments, $R^9$ can be an unsubstituted or a substituted monocyclic heterocyclyl. A non-limiting list of monocyclic heterocyclyls for $R^9$ include oxetane, tetrahydrofuran, tetrahydrothiophene, pyrrolidine, tetrahydropyran, tetrahydrothiopyran, piperidine and morpholine. Various substituents can be present on a substituted heteroaryl and/or a substituted heterocyclyl of $R^9$. For example, the heteroaryl can be substituted 1, 2 or 3 times with a moiety selected from halogen, an unsubstituted $C_{1-6}$ alkyl, an unsubstituted $C_{1-6}$ haloalkyl and an unsubstituted $C_{1-6}$ alkoxy. Suitable halogens, unsubstituted $C_{1-6}$ alkyls, unsubstituted $C_{1-6}$ haloalkyls and unsubstituted $C_{1-6}$ alkoxys are described herein.

In some embodiments, $R^9$ can be an unsubstituted monocyclic $C_{3-6}$ cycloalkyl, such as cyclopropyl, cyclobutyl, cyclopentyl and cyclohexyl. In other embodiments, $R^9$ can be a halogen-substituted monocyclic $C_{3-6}$ cycloalkyl. In still other embodiments, $R^9$ can be a monocyclic $C_{3-6}$ cycloalkyl substituted with an unsubstituted $C_{1-4}$ alkyl. In yet still other embodiments, $R^9$ can be a monocyclic $C_{3-6}$ cycloalkyl substituted with an unsubstituted $C_{1-4}$ alkoxy. In some embodiments, $R^9$ can be a monocyclic $C_{3-6}$ cycloalkyl substituted with an unsubstituted $C_{2-4}$ alkenyl. In other embodiments, $R^9$ can be a monocyclic $C_{3-6}$ cycloalkyl substituted with an unsubstituted $C_{1-4}$ haloalkyl. In still other embodiments, $R^9$ can be a monocyclic $C_{3-6}$ cycloalkyl substituted with an unsubstituted monocyclic $C_{3-6}$ cycloalkyl, such as cyclopropyl, cyclobutyl, cyclopentyl or cyclohexyl. In some embodiments, $R^9$ can be an unsubstituted bicyclic $C_{5-6}$ cycloalkyl. In other embodiments, $R^9$ can be a substituted bicyclic $C_{5-6}$ cycloalkyl. The two rings of a bicyclic $C_{5-6}$ cycloalkyl can be connected in a spiro-fashion or a fused-fashion. In some embodiments, $R^9$ can be a halogen-substituted bicyclic $C_{5-6}$ cycloalkyl. In still other embodiments, $R^9$ can be a bicyclic $C_{5-6}$ cycloalkyl substituted with an unsubstituted $C_{1-4}$ alkyl. In yet still other embodiments, $R^9$ can be a bicyclic $C_{5-6}$ cycloalkyl substituted with an unsubstituted $C_{1-4}$ alkoxy. In some embodiments, $R^9$ can be a bicyclic $C_{5-6}$ cycloalkyl substituted with an unsubstituted $C_{2-4}$ alkenyl. In other embodiments, $R^9$ can be a bicyclic $C_{5-6}$ cycloalkyl substituted with an unsubstituted $C_{1-4}$ haloalkyl. In still other embodiments, $R^9$ can be a bicyclic $C_{5-6}$ cycloalkyl substituted with an unsubstituted monocyclic $C_{3-6}$ cycloalkyl (including cyclopropyl, cyclobutyl, cyclopentyl and cyclohexyl). A non-liming list of bicyclic $C_{5-6}$ cycloalkyls include spiro[2.2]pentane, spiro[2.3]hexane, bicyclo[1.1.1]pentane and bicyclo[2.1.1]hexane.

Suitable halogen-substituted monocyclic $C_{3-6}$ cycloalkyls include halogen-substituted cyclopropyl, halogen-substituted cyclobutyl, halogen-substituted cyclopentyl and halogen-substituted cyclohexyl. Additional monocyclic $C_{3-6}$ cycloalkyls include cyclopropyl substituted with an unsubstituted $C_{1-4}$ alkyl, an unsubstituted $C_{1-4}$ alkoxy, an unsubstituted $C_{2-4}$ alkenyl, an unsubstituted $C_{1-4}$ haloalkyl and/or an unsubstituted monocyclic $C_{3-6}$ cycloalkyl, cyclobutyl substituted with an unsubstituted $C_{1-4}$ alkyl, an unsubstituted $C_{1-4}$ alkoxy, an unsubstituted $C_{2-4}$ alkenyl, an unsubstituted $C_{1-4}$ haloalkyl and/or an unsubstituted monocyclic $C_{3-6}$ cycloalkyl, cyclopentyl substituted with an unsubstituted $C_{1-4}$ alkyl, an unsubstituted $C_{1-4}$ alkoxy, an unsubstituted $C_{2-4}$ alkenyl, an unsubstituted $C_{1-4}$ haloalkyl and/or an unsubstituted monocyclic $C_{3-6}$ cycloalkyl and cyclohexyl substituted with an unsubstituted $C_{1-4}$ alkyl, an unsubstituted $C_{1-4}$ alkoxy, an unsubstituted $C_{2-4}$ alkenyl, an unsubstituted $C_{1-4}$ haloalkyl and/or an unsubstituted monocyclic $C_{3-6}$ cycloalkyl. The number halogens on a halogen-substituted monocyclic $C_{3-6}$ cycloalkyl and/or a bicyclic $C_{5-6}$ cycloalkyl, the number of unsubstituted $C_{1-4}$ alkyls on a monocyclic $C_{3-6}$ cycloalkyl and/or a bicyclic $C_{5-6}$ cycloalkyl, the number of unsubstituted $C_{1-4}$ alkoxys on a monocyclic $C_{3-6}$ cycloalkyl and/or a bicyclic $C_{5-6}$ cycloalkyl, the number of unsubstituted $C_{2-4}$ alkenyls on a monocyclic $C_{3-6}$ cycloalkyl and/or a bicyclic $C_{5-6}$ cycloalkyl, the number of unsubstituted $C_{1-4}$ haloalkyls on a monocyclic $C_{3-6}$ cycloalkyl and/or a bicyclic $C_{5-6}$ cycloalkyl and the number of unsubstituted monocyclic $C_{3-6}$ cycloalkyls on a monocyclic $C_{3-6}$ cycloalkyl and/or a bicyclic $C_{5-6}$ cycloalkyl can vary. For example, 1, 2, 3 or 4 halogens can be present on a halogen-substituted monocyclic $C_{3-6}$ cycloalkyl, 1, 2, 3 or 4 unsubstituted $C_{1-4}$ alkyls can be present on a monocyclic $C_{3-6}$ cycloalkyl substituted with an unsubstituted $C_{1-4}$ alkyl, 1, 2, 3 or 4 unsubstituted $C_{1-4}$ alkoxys can be present on a monocyclic $C_{3-6}$ cycloalkyl substituted with an unsubstituted $C_{1-4}$ alkoxy, 1, 2, 3 or 4 unsubstituted $C_{2-4}$ alkenyls can be present on a monocyclic $C_{3-6}$ cycloalkyl substituted with an unsubstituted $C_{2-4}$ alkenyl, 1, 2, 3 or 4 unsubstituted $C_{1-4}$ haloalkyls can be present on a monocyclic $C_{3-6}$ cycloalkyl substituted with an unsubstituted $C_{1-4}$ haloalkyl, 1 or 2 unsubstituted monocyclic $C_{3-6}$ cycloalkyls can be present on a monocyclic $C_{3-6}$ cycloalkyl, 1, 2, 3 or 4 halogens can be present on a halogen-substituted bicyclic $C_{5-6}$ cycloalkyl, 1, 2, 3 or 4 unsubstituted $C_{1-4}$ alkyls can be present on a bicyclic $C_{5-6}$ cycloalkyl substituted with an unsubstituted $C_{1-4}$ alkyl, 1, 2, 3 or 4 unsubstituted $C_{1-4}$ alkoxys can be present on a bicyclic $C_{5-6}$ cycloalkyl substituted with an unsubstituted $C_{2-4}$ alkoxy, 1, 2, 3 or 4 unsubstituted $C_{2-4}$ alkenyls can be present on a bicyclic $C_{5-6}$ cycloalkyl substituted with an unsubstituted $C_{2-4}$ alkenyl, 1, 2, 3 or 4 unsubstituted $C_{1-4}$ haloalkyls can be present on a bicyclic $C_{5-6}$ cycloalkyl substituted with an unsubstituted $C_{1-4}$ haloalkyl and 1 or 2 unsubstituted monocyclic $C_{3-6}$ cycloalkyls can be present on a bicyclic $C_{5-6}$ cycloalkyl. In some embodiments, a monocyclic $C_{3-6}$ cycloalkyl can be substituted with 1 or more substituents (such as 1, 2, 3 or 4 substituents) selected from halogen, an unsubstituted $C_{1-4}$ alkyl, an unsubstituted $C_{1-4}$ alkoxy, an unsubstituted $C_{2-4}$ alkenyl, and an unsubstituted $C_{1-4}$ haloalkyl. In other embodiments, a bicyclic $C_{5-6}$ cycloalkyl can be substituted with 1 or more substituents (such as 1, 2, 3 or 4 substituents) selected from halogen, an unsubstituted $C_{1-4}$ alkyl, an unsubstituted $C_{1-4}$ alkoxy an unsubstituted $C_{2-4}$ alkenyl, and an unsubstituted $C_{1-4}$ haloalkyl. Suitable halogens that can be present on a substituted monocyclic $C_{3-6}$ cycloalkyl include, but are not limited to, fluoro (F) and chloro (Cl). Examples of unsubstituted $C_{1-4}$ haloalkyls include, but are not limited to, —CF$_3$, —CCl$_3$, —CHF$_2$, —C(CH$_3$)F$_2$, —CHCl$_2$, —CH$_2$F, —CH(CH$_3$)F, —CH$_2$CF$_3$, —CH$_2$Cl, —CH$_2$CH$_2$F, —CH$_2$CH$_2$Cl, —CH$_2$CH$_2$CH$_2$F and —CH$_2$CH$_2$CH$_2$Cl.

In some embodiments, $R^5$ can be

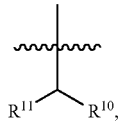

wherein $R^{10}$ can be independently selected from an unsubstituted or a substituted $C_{2-6}$ alkyl, an unsubstituted or a substituted $C_{2-6}$ alkenyl, an unsubstituted or a substituted $C_{2-6}$ alkynyl, an unsubstituted or a substituted monocyclic $C_{3-6}$ cycloalkyl, an unsubstituted or a substituted bicyclic $C_{5-8}$ cycloalkyl and an unsubstituted or a substituted monocyclic 4- to 6-membered heterocyclyl, wherein when the $C_{2-6}$ alkyl is substituted, the $C_{2-6}$ alkyl can be substituted 1, 2, 3 or 4 times with a substituent independently selected from halogen and an unsubstituted $C_{1-4}$ alkoxy; wherein when the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl are substituted, the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl can be substituted 1, 2, 3 or 4 times with a substituent independently selected from halogen, an unsubstituted $C_{1-4}$ alkyl, an unsubstituted $C_{2-4}$ alkenyl, an unsubstituted $C_{2-4}$ alkynyl, an unsubstituted $C_{1-4}$ haloalkyl and an unsubstituted $C_{1-4}$ alkoxy; and $R^{11}$ can be —(NH)$_m$— an optionally substituted 5- to 6-membered monocyclic heteroaryl, wherein m can be 0 or 1. In some embodiments, $R^{11}$ can be an optionally substituted monocyclic 4- to 6-membered heterocyclyl. Examples of heterocyclyls for $R^{11}$ include optionally substituted 4- to 6-membered monocyclic heterocyclyls that include 1, 2 or 3 heteroatoms independently selected from N (nitrogen), O (oxygen) and S (sulfur). A non-limiting list of heterocyclyl for $R^{11}$ include the following: azetidine, pyrrolidine and piperidine. In other embodiments, m can be 0; and $R^{11}$ can be an unsubstituted 5- to 6-membered monocyclic heteroaryl. In other embodiments, m can be 0; and $R^{11}$ can be a substituted 5- to 6-membered monocyclic heteroaryl. In still other embodiment, m can be 1; and $R^{11}$ can be an —(NH)-unsubstituted 5- to 6-membered monocyclic heteroaryl. In other embodiments, m can be 1; and $R^{11}$ can be a —(NH)-substituted 5- to 6-membered monocyclic heteroaryl. An example of a 5- to 6-membered monocyclic heteroaryl that can be present for $R^{11}$ include a 5- to 6-membered monocyclic heteroaryl that includes 1, 2 or 3 heteroatoms independently selected from N (nitrogen), O (oxygen) and S (sulfur). Examples of suitable 5- to 6-membered monocyclic heteroaryls include, but are not limited to, imidazole, pyrazole, oxazole, thiazole, 1,2,3-triazole, 1,2,4-triazole, 1,3,4-oxadiazole and 1,3,4-thiadiazole. In still other embodiments, $R^{11}$ can be —O— an optionally substituted $C_{1-6}$ alkyl. In yet still other embodiments, $R^{11}$ can be —O— an optionally substituted $C_{3-8}$ cycloalkyl. In some embodiments, $R^{11}$ can be —O— an optionally substituted $C_{3-8}$ cycloalkyl($C_{1-4}$ alkyl). The cycloalkyl of —O— an optionally substituted $C_{3-8}$ cycloalkyl and —O— an optionally substituted $C_{3-8}$ cycloalkyl($C_{1-4}$ alkyl) can be a monocyclic $C_{3-6}$ cycloalkyl or a bicyclic $C_{5-8}$ cycloalkyl. The $C_{1-4}$ alkyl of —O— an optionally substituted cycloalkyl($C_{1-4}$ alkyl) can be —CH$_2$—, —CH$_2$CH$_2$—, —CH$_2$CH$_2$CH$_2$— or —CH$_2$CH$_2$CH$_2$CH$_2$—. As described herein, $R^{11}$ can be substituted. Exemplary groups that can be present on $R^{11}$ include halogen, an unsubstituted $C_{1-4}$ alkyl, an unsubstituted $C_{1-4}$ alkoxy and an unsubstituted $C_{1-4}$ haloalkyl.

The $R^8$ and/or $R^{10}$ moieties can be a substituted or an unsubstituted version of a $C_{2-6}$ alkyl, a $C_{2-6}$ alkenyl, a $C_{2-6}$ alkynyl, a monocyclic $C_{3-6}$ cycloalkyl, a bicyclic $C_{5-8}$ cycloalkyl or a monocyclic 4- to 6-membered heterocyclyl. In some embodiments, $R^8$ and/or $R^{10}$ can be an unsubstituted $C_{2-6}$ alkyl. In other embodiments, $R^8$ and/or $R^{10}$ can be a substituted $C_{2-6}$ alkyl. Exemplary $C_{2-6}$ alkyls include methyl, ethyl, n-propyl, isopropyl, n-butyl, isobutyl, sec-butyl, tert-butyl, pentyl (straight-chained and branched) and hexyl (straight-chained and branched). In some embodiments, $R^8$ and/or $R^{10}$ can be an unsubstituted $C_{2-6}$ alkenyl. In other embodiments, $R^8$ and/or $R^{10}$ can be a substituted $C_{2-6}$ alkenyl. In still other embodiments, $R^8$ and/or $R^{10}$ can be an unsubstituted $C_{2-6}$ alkynyl. In yet still other embodiments, $R^8$ and/or $R^{10}$ can be a substituted $C_{2-6}$ alkynyl.

Cyclic moieties, including monocyclic and bicyclic moieties, can also be present for $R^8$ and/or $R^{10}$. In some embodiments, $R^8$ and/or $R^{10}$ can be an unsubstituted monocyclic $C_{3-6}$ cycloalkyl. In some embodiments, $R^8$ and/or $R^{10}$ can be a substituted monocyclic $C_{3-6}$ cycloalkyl. For example, $R^8$ and/or $R^{10}$ can be a substituted or an unsubstituted cyclopropyl, a substituted or an unsubstituted cyclobutyl, a substituted or an unsubstituted cyclopentyl or a substituted or an unsubstituted cyclohexyl. In some embodiments, $R^8$ and/or $R^{10}$ can be an unsubstituted bicyclic $C_{5-8}$ cycloalkyl. In other embodiments, $R^8$ and/or $R^{10}$ can be an unsubstituted bicyclic $C_{5-8}$ cycloalkyl. The two rings of the bicyclic $C_{5-8}$ cycloalkyl can joined in a fused or a spiro-fashion. Examples of rings connected in a fused and a spiro-fashion are provided herein. In some embodiments, $R^8$ and/or $R^{10}$ can be an unsubstituted or a substituted bicyclo [1.1.1]pentyl. In still other embodiments, $R^8$ and/or $R^{10}$ can be an unsubstituted monocyclic 4- to 6-membered heterocyclyl. In yet still other embodiments, $R^8$ and/or $R^{10}$ can be an unsubstituted monocyclic 4- to 6-membered heterocyclyl. The number of heteroatoms present in a monocyclic 4- to 6-membered heterocyclyl for $R^8$ and/or $R^{10}$ can vary. Suitable heteroatoms include, but are not limited to, O (oxygen), S (sulfur) and N (nitrogen). Examples of monocyclic 4- to 6-membered heterocyclyls are oxetane, thietane, azetidine, pyrrolidine, tetrahydrofuran, tetrahydrothiophene, tetrahydropyran, tetrahydrothiopyran and piperidine (including unsubstituted or substituted versions of each of the aforementioned). In some embodiments, $R^8$ and/or $R^{10}$ can be an unsubstituted monocyclic $C_{3-6}$ cycloalkyl($CH_2$)—. Various monocyclic $C_{3-6}$ cycloalkyl are described herein. As examples, $R^8$ and/or $R^{10}$ can be selected from cyclopropyl ($CH_2$)—, cyclobutyl($CH_2$)—, cyclopentyl($CH_2$)— and cyclohexyl($CH_2$)—.

As described herein, $R^8$ and/or $R^{10}$ can be substituted. In some embodiments, when $R^8$ and/or $R^{10}$ is a $C_{2-6}$ alkyl that is substituted, the $C_{2-6}$ alkyl can be substituted 1, 2, 3 or 4 times with a substituent independently selected from halogen, cyano, an unsubstituted or a substituted monocyclic $C_{3-6}$ cycloalkyl, an unsubstituted $C_{1-4}$ alkoxy and an unsubstituted $C_{1-4}$ haloalkoxy. In some embodiments, $R^8$ and/or $R^{10}$ can be a $C_{2-6}$ alkyl that is substituted 1 to 13 times with deuterium. In some embodiments, $R^8$ and/or $R^{10}$ can be a $C_{2-6}$ alkyl that is substituted 1 to 9 times with deuterium, 1 to 6 times with deuterium, 1 to 5 times with deuterium or 1 to 3 times with deuterium. Each halogen can be independently F (fluoro) or $C_1$ (chloro). Exemplary unsubstituted and substituted monocyclic $C_{3-6}$ cycloalkyls that can be present on a substituted $C_{2-6}$ alkyl for $R^8$ and/or $R^{10}$ include cyclopropyl, cyclobutyl, cyclopentyl, cyclohexyl and halogen-substituted monocyclic $C_{3-6}$ cycloalkyls. Suitable unsubstituted $C_{1-4}$ alkoxys that can be substituted on a $C_{2-6}$ alkyl of $R^8$ and/or $R^{10}$ include methoxy, ethoxy, n-propoxy, isopropoxy, n-butoxy, isobutoxy, sec-butoxy and tert-butoxy. Examples of an unsubstituted $C_{1-4}$ haloalkoxy can be substituted on a $C_{2-6}$ alkyl of $R^8$ and/or $R^{10}$ include —$OCl_3$, —$OCF_3$, —$OCH_2Cl$, —$OCH_2F$, —$OCHCl_2$ and —$OCHF_2$. In some embodiments, when $R^8$ and/or $R^{10}$ is a substituted $C_{2-6}$ alkenyl, a substituted $C_{2-6}$ alkynyl, a substituted monocyclic $C_{3-6}$ cycloalkyl, a substituted bicyclic $C_{5-8}$ cycloalkyl or a substituted monocyclic 4- to 6-membered heterocyclyl, each of the aforementioned can be substituted 1, 2, 3 or 4 times with a substituents independently selected from halogen, an unsubstituted $C_{1-4}$ alkyl, an unsubstituted $C_{2-4}$ alkenyl, an unsubstituted $C_{2-4}$ alkynyl, an unsubstituted $C_{1-4}$ haloalkyl, an unsubstituted or a substituted monocyclic $C_{3-6}$ cycloalkyl and an unsubstituted $C_{1-4}$ alkoxy. Examples of unsubstituted $C_{1-4}$ alkyls, an unsubstituted $C_{2-4}$ alkenyl and an unsubstituted $C_{2-4}$ alkynyl that can be substituted on a substituted $C_{2-6}$ alkenyl, a substituted $C_{2-6}$ alkynyl, a substituted monocyclic $C_{3-6}$ cycloalkyl, a substituted bicyclic $C_{5-8}$ cycloalkyl or a substituted monocyclic 4- to 6-membered heterocyclyl include methyl, ethyl, n-propyl, isopropyl, n-butyl, iso-butyl, sec-butyl, tert-butyl, ethenyl, propenyl, butenyl, ethynyl, propynyl and butynyl. Suitable halogens and unsubstituted $C_{1-4}$ alkoxys that can be present on a substituted $C_{2-6}$ alkenyl, a substituted $C_{2-6}$ alkynyl, a substituted monocyclic $C_{3-6}$ cycloalkyl, a substituted bicyclic $C_{5-8}$ cycloalkyl or a substituted monocyclic 4- to 6-membered heterocyclyl are described herein, such as in this paragraph. Non-limiting list of unsubstituted and substituted monocyclic $C_{3-6}$ cycloalkyls include cyclopropyl, cyclobutyl, cyclopentyl, cyclohexyl and halogen-substituted monocyclic $C_{3-6}$ cycloalkyls. Examples of unsubstituted $C_{1-6}$ haloalkyls that can be present on a substituted $C_{2-6}$ alkenyl, a substituted $C_{2-6}$ alkynyl, a substituted monocyclic $C_{3-6}$ cycloalkyl, a substituted bicyclic $C_{5-8}$ cycloalkyl or a substituted monocyclic 4- to 6-membered heterocyclyl include, but are not limited to, —$CF_3$, —$CCl_3$, —$CHF_2$, —$C(CH_3)F_2$, —$CHCl_2$, —$CH_2F$, —$CH(CH_3)F$, —$CH_2CF_3$, —$CH_2Cl$, —$CH_2CH_2F$, —$CH_2CH_2Cl$, —$CH_2CH_2CH_2F$ and —$CH_2CH_2CH_2Cl$.

Exemplary $R^5$ groups include the following:

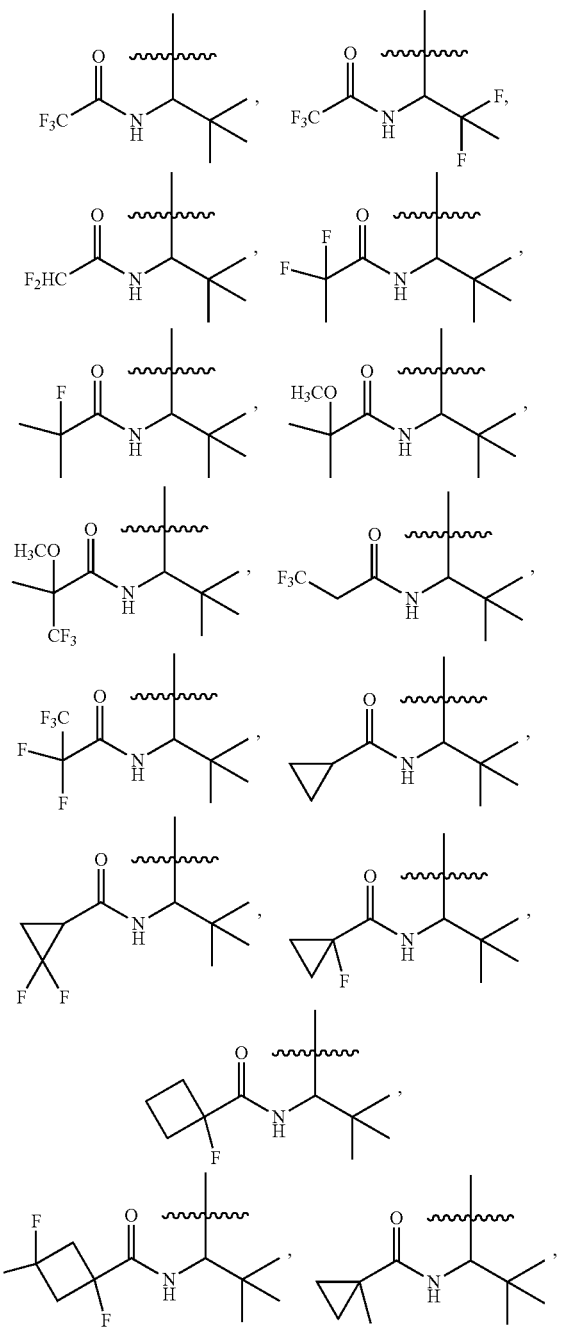

-continued
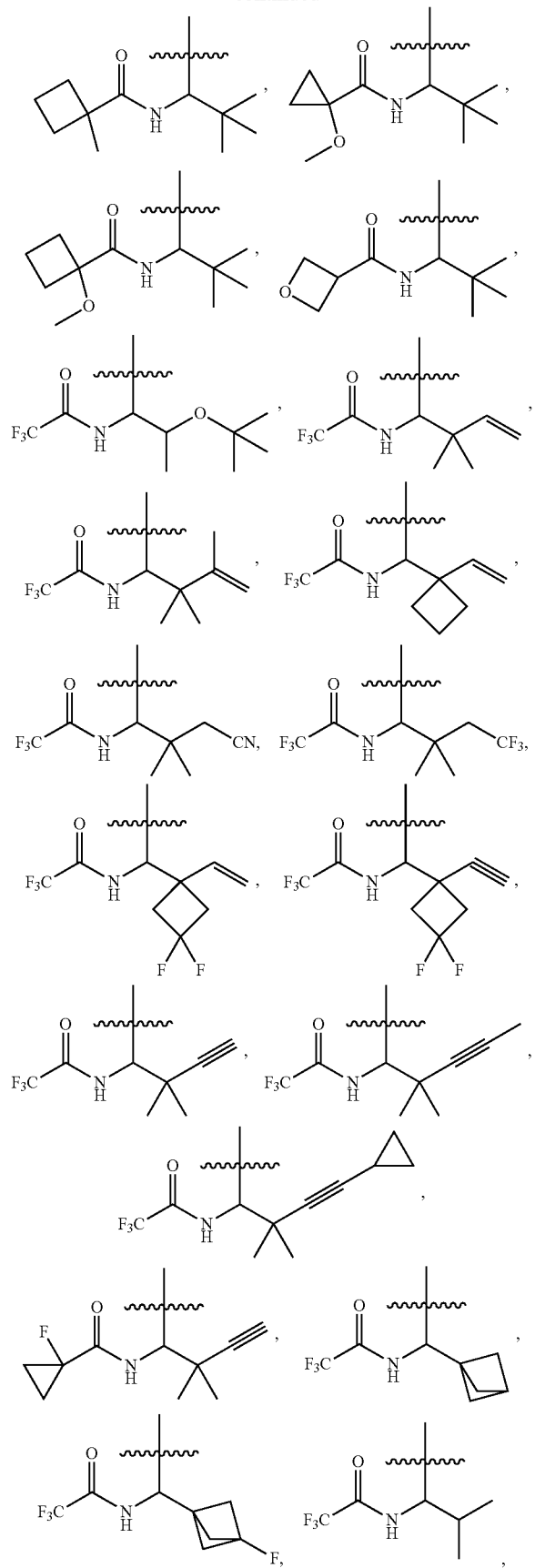
-continued
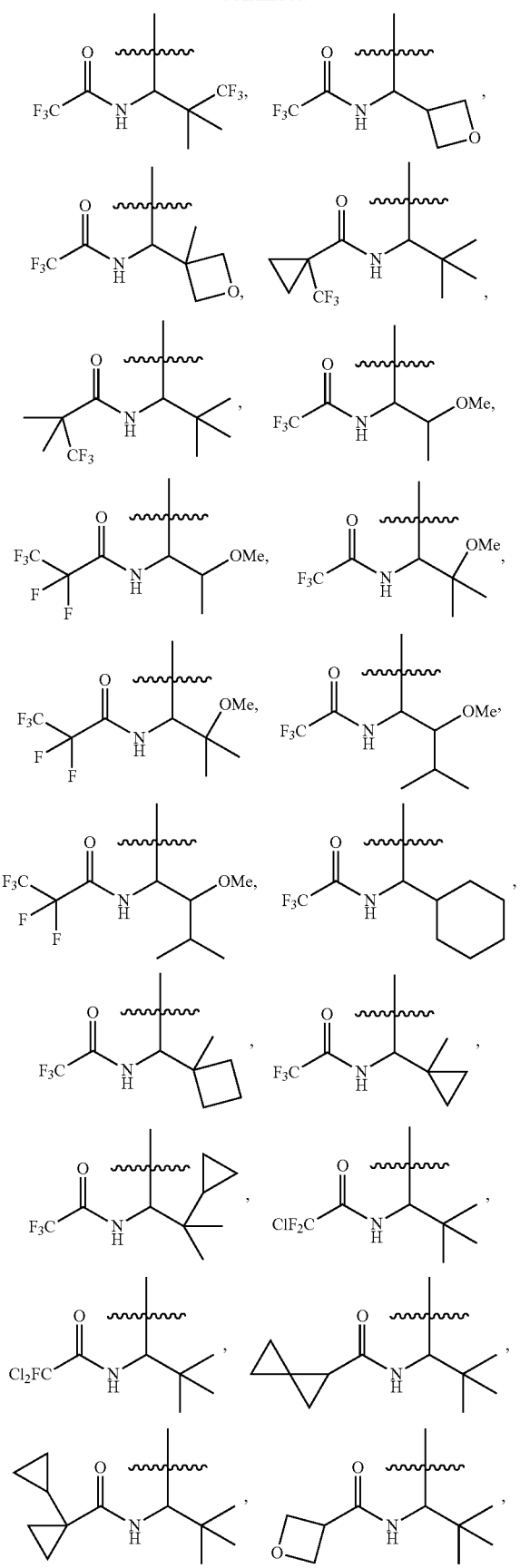

-continued
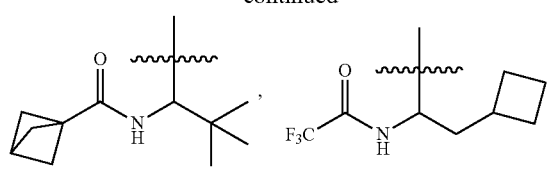
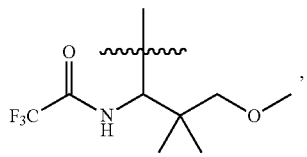
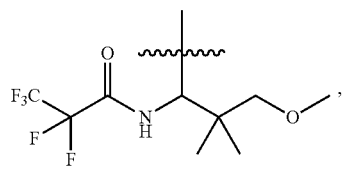
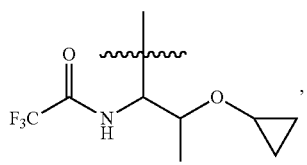
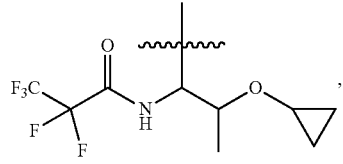
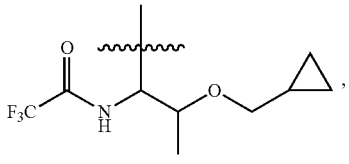
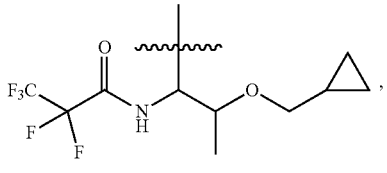
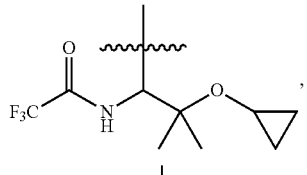
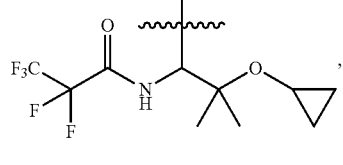
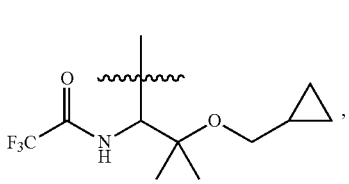
-continued
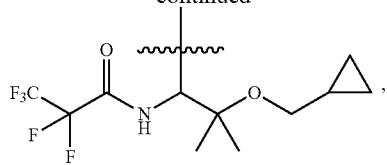
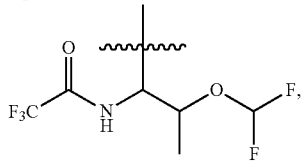
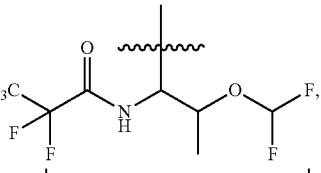
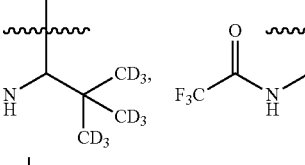
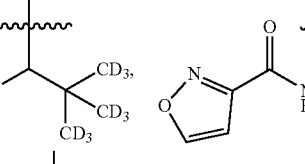
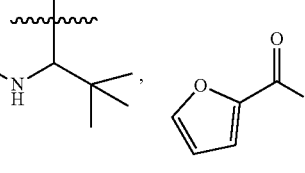
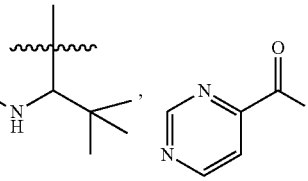
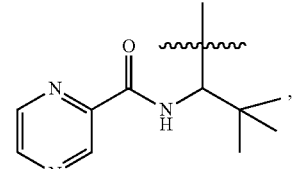
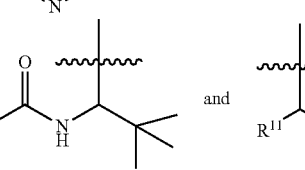
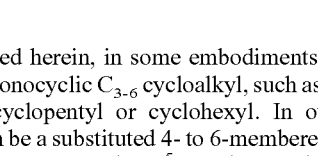
As described herein, in some embodiments, $R^5$ can be a substituted monocyclic $C_{3-6}$ cycloalkyl, such as cyclopropyl, cyclobutyl, cyclopentyl or cyclohexyl. In other embodiments, $R^5$ can be a substituted 4- to 6-membered monocyclic heterocyclyl. For example, $R^5$ can be a substituted 4- to 6-membered monocyclic heterocyclyl that includes 1, 2 or 3 heteroatoms selected from N (nitrogen), O (oxygen) and S (sulfur). The substituted monocyclic $C_{3-6}$ cycloalkyl and/or the substituted 4- to 6-membered monocyclic heterocyclyl can be substituted 1, 2 or 3 times with a moiety selected from deuterium, halogen, an unsubstituted $C_{1-6}$ alkyl, an unsubstituted $C_{1-6}$ haloalkyl and an unsubstituted $C_{1-6}$ alkoxy.

Further, when $R^5$ is a monocyclic $C_{3-6}$ cycloalkyl or a 4- to 6-membered monocyclic heterocyclyl, the monocyclic $C_{3-6}$ cycloalkyl or the 4- to 6-membered monocyclic heterocyclyl can be substituted in a spiro-fashion by an unsubstituted or a substituted bicyclic cycloalkenyl or an unsubstituted or a substituted bicyclic heterocyclyl. The bicyclic cycloalkenyl can be an unsubstituted or a substituted 8- to 10-membered bicyclic cycloalkenyl. An unsubstituted or a substituted bicyclic heterocyclyl can be an unsubstituted or a substituted 8- to 10-membered bicyclic heterocyclyl, for example, an unsubstituted or a substituted 8- to 10-membered bicyclic heterocyclyl that includes 1, 2 or 3 heteroatoms in the rings selected from N (nitrogen), O (oxygen) and S (sulfur). In some embodiments, the bicyclic cycloalkenyl and/or the bicyclic heterocyclyl can be substituted one or more times (such as 1, 2, 3 or 4 times) with a moiety independently selected from halogen, an unsubstituted $C_{1-4}$ alkyl, an unsubstituted $C_{1-6}$ haloalkyl (such as —CF$_3$, —CCl$_3$, —CHF$_2$, —C(CH$_3$)F$_2$, —CHCl$_2$, —CH$_2$F, —CH(CH$_3$)F, —CH$_2$CF$_3$, —CH$_2$Cl, —CH$_2$CH$_2$F, —CH$_2$CH$_2$Cl, —CH$_2$CH$_2$CH$_2$F, —CH$_2$CH$_2$CH$_2$Cl) and an unsubstituted $C_{1-4}$ alkoxy. Examples of $R^5$ as a monocyclic $C_{3-6}$ cycloalkyl or a 4- to 6-membered monocyclic heterocyclyl substituted in a spiro-fashion by an unsubstituted or a substituted bicyclic cycloalkenyl or an unsubstituted or a substituted bicyclic heterocyclyl include the following:

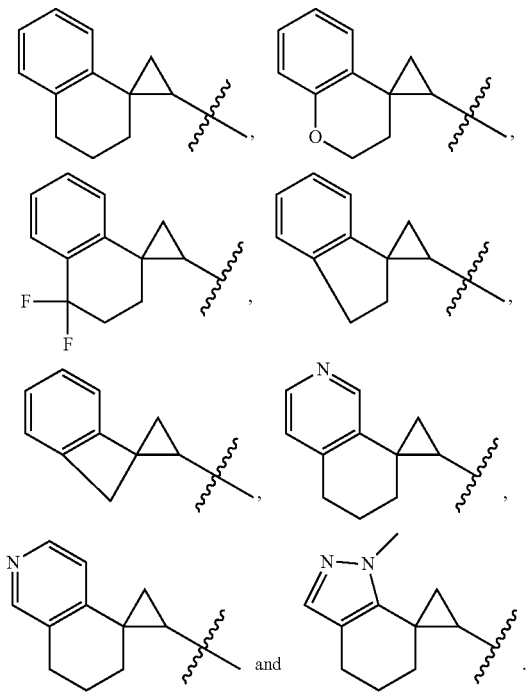

In some embodiments, a compound of Formula (I), or a pharmaceutically acceptable salt thereof, can be where: Ring $A^1$ can be

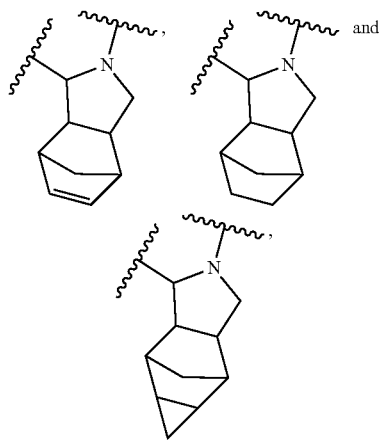

and wherein Ring $A^1$ can be optionally substituted with one or more moieties independently selected from halogen, an unsubstituted $C_{1-4}$ alkyl, an unsubstituted $C_{1-4}$ haloalkyl, an unsubstituted $C_{2-4}$ alkenyl and an unsubstituted or a substituted $C_{3-6}$ monocyclic cycloalkyl; $R^1$ can be selected from cyano, an unsubstituted or a substituted $C_{2-5}$ alkynyl, an unsubstituted or a substituted acyl, an unsubstituted or a substituted ketoamide, —CH(OH)—(S(=O)$_2$—O—), —CH(OH)((P=O)(OR$^6$)$_2$) and —C(=O)CH$_2$—O—((P=O)(OR$^7$)$_2$); each $R^6$ and each $R^7$ can be independently hydrogen, an unsubstituted $C_{1-6}$ alkyl, an unsubstituted $C_{2-6}$ alkenyl, an unsubstituted $C_{1-6}$ haloalkyl, an unsubstituted or a substituted aryl or an unsubstituted or a substituted aryl($C_{1-4}$ alkyl); $R^2$ can be hydrogen, deuterium or halogen; $R^3$ can be an unsubstituted or a substituted monocyclic nitrogen-containing heterocyclyl($C_{1-4}$ alkyl) or an unsubstituted or a substituted bicyclic nitrogen-containing heterocyclyl ($C_{1-4}$ alkyl); $R^4$ can be hydrogen, deuterium or halogen; $R^5$ can be

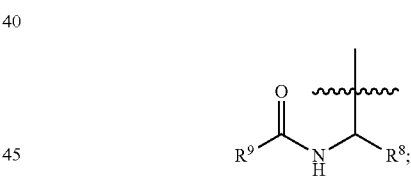

$R^8$ can be selected from an unsubstituted or a substituted $C_{2-6}$ alkyl, an unsubstituted or a substituted $C_{2-6}$ alkenyl, an unsubstituted or a substituted $C_{2-6}$ alkynyl, an unsubstituted or a substituted monocyclic $C_{3-6}$ cycloalkyl, an unsubstituted or a substituted bicyclic $C_{5-8}$ cycloalkyl and an unsubstituted or a substituted monocyclic 4- to 6-membered heterocyclyl, wherein when the $C_{2-6}$ alkyl is substituted, the $C_{2-6}$ alkyl can be substituted 1, 2, 3 or 4 times with a substituent independently selected from halogen and an unsubstituted $C_{1-4}$ alkoxy; wherein when the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl are substituted, the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl can be substituted 1, 2, 3 or 4 times with a substituent independently selected from halogen, an unsubstituted $C_{1-4}$ alkyl and an unsubstituted $C_{1-4}$ alkoxy; and $R^9$ can be selected from an unsubstituted $C_{1-6}$ alkyl, an unsubstituted $C_{1-6}$ haloalkyl and an unsubstituted to a substituted monocyclic C$_{3-6}$ cycloalkyl, wherein the substituted monocyclic C$_{3-6}$ cycloalkyl is substituted 1, 2, 3 or 4 times with a substituent independently selected from halogen, an unsubstituted C$_{1-4}$ alkyl and an unsubstituted C$_{1-4}$ haloalkyl.

In some embodiments, a compound of Formula (I), or a pharmaceutically acceptable salt thereof, can be where: Ring A$^1$ can be

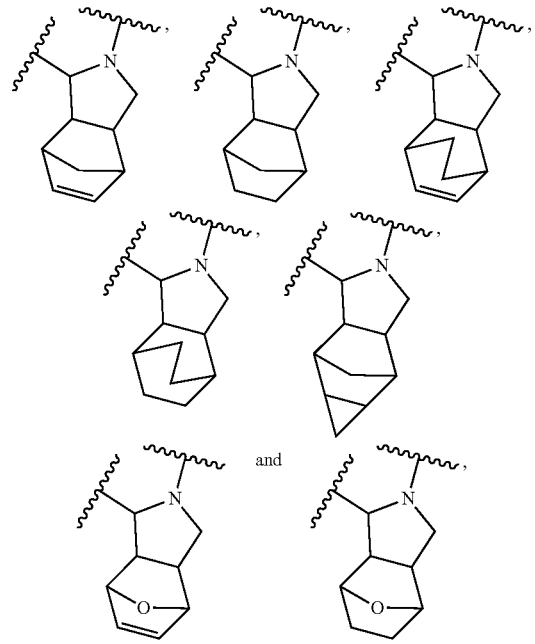

and wherein Ring A$^1$ can be optionally substituted with one or more moieties independently selected from halogen, an unsubstituted C$_{1-4}$ alkyl, an unsubstituted C$_{1-4}$ haloalkyl, an unsubstituted C$_{2-4}$ alkenyl and an unsubstituted or a substituted C$_{3-6}$ monocyclic cycloalkyl; R$^1$ can be selected from cyano, an unsubstituted or a substituted C$_{2-5}$ alkynyl, an unsubstituted or a substituted acyl, an unsubstituted or a substituted ketoamide, —CH(OH)—(S(═O)$_2$—O—), —CH(OH)((P═O)(OR$^6$)$_2$) and —C(═O)CH$_2$—O—((P═O)(OR$^7$)$_2$); each R$^6$ and each R$^7$ can be independently hydrogen, an unsubstituted C$_{1-6}$ alkyl, an unsubstituted C$_{2-6}$ alkenyl, an unsubstituted C$_{1-6}$ haloalkyl, an unsubstituted or a substituted aryl or an unsubstituted or a substituted aryl (C$_{1-4}$ alkyl); R$^2$ can be hydrogen, deuterium or halogen; R$^3$ can be an unsubstituted or a substituted monocyclic nitrogen-containing heterocyclyl(C$_{1-4}$ alkyl) or an unsubstituted or a substituted bicyclic nitrogen-containing heterocyclyl (C$_{1-4}$ alkyl); R$^4$ can be hydrogen, deuterium or halogen; R$^5$ can be

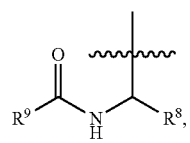

a substituted monocyclic C$_{3-6}$ cycloalkyl or a substituted 4- to 6-membered monocyclic heterocyclyl; R$^8$ can be selected from an unsubstituted or a substituted C$_{2-6}$ alkyl, an unsubstituted or a substituted C$_{2-6}$ alkenyl, an unsubstituted or a substituted C$_{2-6}$ alkynyl, an unsubstituted or a substituted monocyclic C$_{3-6}$ cycloalkyl, an unsubstituted or a substituted bicyclic C$_{5-8}$ cycloalkyl and an unsubstituted or a substituted monocyclic 4- to 6-membered heterocyclyl, wherein when the C$_{2-6}$ alkyl is substituted, the C$_{2-6}$ alkyl can be substituted 1, 2, 3 or 4 times with a substituent independently selected from halogen and an unsubstituted C$_{1-4}$ alkoxy; wherein when the C$_{2-6}$ alkenyl, the C$_{2-6}$ alkynyl, the monocyclic C$_{3-6}$ cycloalkyl, the bicyclic C$_{5-8}$ cycloalkyl and the monocyclic 4- to 6-membered heterocyclyl are substituted, the C$_{2-6}$ alkenyl, the C$_{2-6}$ alkynyl, the monocyclic C$_{3-6}$ cycloalkyl, the bicyclic C$_{5-8}$ cycloalkyl and the monocyclic 4- to 6-membered heterocyclyl can be substituted 1, 2, 3 or 4 times with a substituent independently selected from halogen, an unsubstituted C$_{1-4}$ alkyl, an unsubstituted C$_{1-4}$ haloalkyl and an unsubstituted C$_{1-4}$ alkoxy; and R$^9$ can be selected from an unsubstituted or a substituted C$_{1-6}$ alkyl, an unsubstituted C$_{1-6}$ haloalkyl, an unsubstituted or a substituted monocyclic C$_{3-6}$ cycloalkyl, an unsubstituted or a substituted monocyclic heteroaryl and an unsubstituted or a substituted monocyclic heterocyclyl, wherein the substituted monocyclic C$_{3-6}$ cycloalkyl is substituted 1, 2, 3 or 4 times with a substituent independently selected from halogen, an unsubstituted C$_{1-4}$ alkyl and an unsubstituted C$_{1-4}$ haloalkyl.

In some embodiments, a compound of Formula (I), or a pharmaceutically acceptable salt thereof, can be where: Ring A$^1$ can be

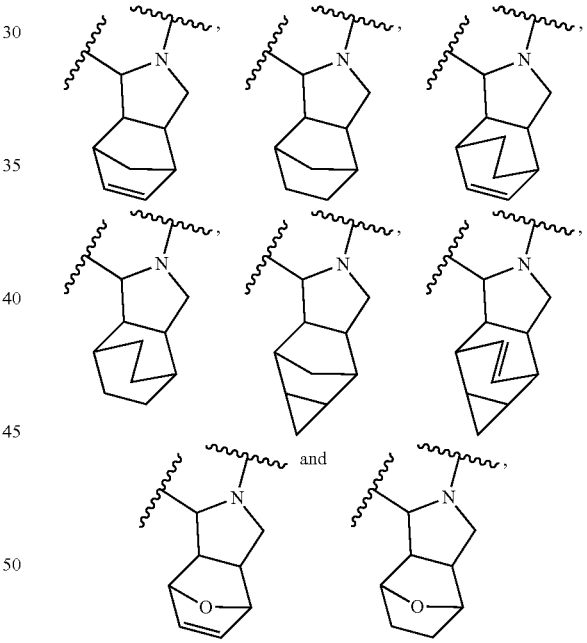

and wherein Ring A$^1$ can be optionally substituted with one or more moieties independently selected from deuterium, halogen, an unsubstituted C$_{1-4}$ alkyl, an unsubstituted C$_{1-4}$ haloalkyl, an unsubstituted C$_{2-4}$ alkenyl and an unsubstituted or a substituted C$_{3-6}$ monocyclic cycloalkyl; R$^1$ can be selected from cyano, an unsubstituted or a substituted C$_{2-5}$ alkynyl, an unsubstituted or a substituted acyl, an unsubstituted or a substituted ketoamide, —CH(OH)—(S(═O)$_2$—O—), —CH(OH)((P═O)(OR$^6$)$_2$) and —C(═O)CH$_2$—O—((P═O)(OR$^7$)$_2$); each R$^6$ and each R$^7$ can be independently hydrogen, an unsubstituted C$_{1-6}$ alkyl, an unsubstituted C$_{2-6}$ alkenyl, an unsubstituted C$_{1-6}$ haloalkyl, an unsubstituted or a substituted aryl or an unsubstituted or a substituted aryl ($C_{1-4}$ alkyl); $R^2$ can be hydrogen, deuterium or halogen; $R^3$ can be an unsubstituted or a substituted monocyclic nitrogen-containing heterocyclyl($C_{1-4}$ alkyl), an unsubstituted or a substituted bicyclic nitrogen-containing heterocyclyl($C_{1-4}$ alkyl), an unsubstituted or a substituted monocyclic nitrogen-containing heteroaryl($C_{1-4}$ alkyl); $R^4$ can be hydrogen, deuterium or halogen; and $R^5$ can be

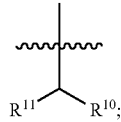

$R^{10}$ can be selected from an unsubstituted or a substituted $C_{2-6}$ alkyl, an unsubstituted or a substituted $C_{2-6}$ alkenyl, an unsubstituted or a substituted $C_{2-6}$ alkynyl, an unsubstituted or a substituted monocyclic $C_{3-6}$ cycloalkyl, an unsubstituted or a substituted bicyclic $C_{5-8}$ cycloalkyl and an unsubstituted or a substituted monocyclic 4- to 6-membered heterocyclyl, wherein when the $C_{2-6}$ alkyl is substituted, the $C_{2-6}$ alkyl can be substituted 1, 2, 3 or 4 times with a substituent independently selected from halogen and an unsubstituted $C_{1-4}$ alkoxy; wherein when the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl are substituted, the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl can be substituted 1, 2, 3 or 4 times with a substituent independently selected from halogen, an unsubstituted $C_{1-4}$ alkyl, an unsubstituted $C_{2-4}$ alkenyl, an unsubstituted $C_{2-4}$ alkynyl, an unsubstituted $C_{1-4}$ haloalkyl and an unsubstituted $C_{1-4}$ alkoxy; and $R^{11}$ can be an optionally substituted monocyclic 4- to 6-membered heterocyclyl, —(NH)$_m$— an optionally substituted 5- to 6-membered monocyclic heteroaryl, —O— an optionally substituted $C_{1-6}$ alkyl, —O— an optionally substituted $C_{3-8}$ cycloalkyl and —O— an optionally substituted $C_{3-8}$ cycloalkyl($C_{1-4}$ alkyl), wherein m can be 0 or 1.

In some embodiments, a compound of Formula (I), or a pharmaceutically acceptable salt thereof, can be where: Ring $A^1$ can be

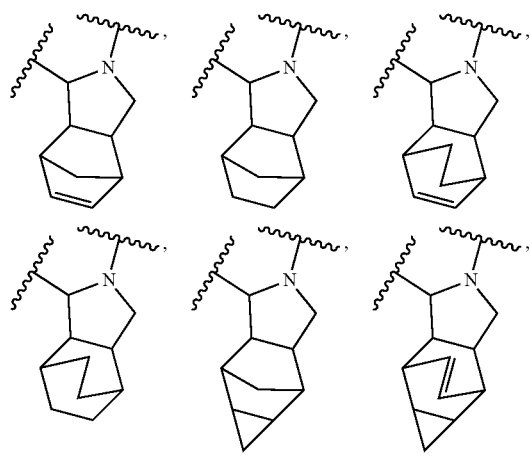

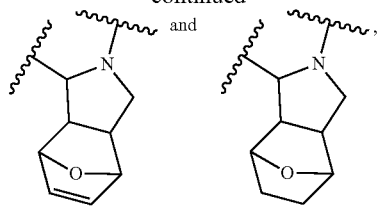

and wherein Ring $A^1$ can be optionally substituted with one or more moieties independently selected from deuterium, halogen, an unsubstituted $C_{1-4}$ alkyl, an unsubstituted $C_{1-4}$ haloalkyl, an unsubstituted $C_{2-4}$ alkenyl and an unsubstituted or a substituted $C_{3-6}$ monocyclic cycloalkyl; $R^1$ can be selected from cyano, an unsubstituted or a substituted $C_{2-5}$ alkynyl, an unsubstituted or a substituted acyl, an unsubstituted or a substituted ketoamide, —CH(OH)—(S(=O)$_2$—O—), —CH(OH)((P=O)(OR$^6$)$_2$) and —C(=O)CH$_2$—O—((P=O)(OR$^7$)$_2$); each $R^6$ and each $R^7$ can be independently hydrogen, an unsubstituted $C_{1-8}$ alkyl, an unsubstituted $C_{2-6}$ alkenyl, an unsubstituted $C_{1-8}$ haloalkyl, an unsubstituted or a substituted aryl or an unsubstituted or a substituted aryl ($C_{1-4}$ alkyl); $R^2$ can be hydrogen, deuterium or halogen; $R^3$ can be an unsubstituted or a substituted monocyclic nitrogen-containing heterocyclyl($C_{1-4}$ alkyl), an unsubstituted or a substituted bicyclic nitrogen-containing heterocyclyl($C_{1-4}$ alkyl) or an unsubstituted or a substituted monocyclic nitrogen-containing heteroaryl($C_{1-4}$ alkyl); $R^4$ can be hydrogen, deuterium or halogen; $R^5$ can be

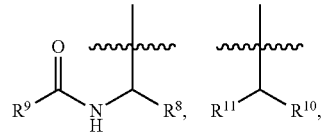

a substituted monocyclic $C_{3-6}$ cycloalkyl or a substituted 4- to 6-membered monocyclic heterocyclyl; $R^8$ and $R^{10}$ can be independently selected from an unsubstituted or a substituted $C_{2-6}$ alkyl, an unsubstituted or a substituted $C_{2-6}$ alkenyl, an unsubstituted or a substituted $C_{2-6}$ alkynyl, an unsubstituted or a substituted monocyclic $C_{3-6}$ cycloalkyl, an unsubstituted or a substituted bicyclic $C_{5-8}$ cycloalkyl and an unsubstituted or a substituted monocyclic 4- to 6-membered heterocyclyl, wherein when the $C_{2-6}$ alkyl is substituted, the $C_{2-6}$ alkyl can be substituted 1, 2, 3 or 4 times with a substituent independently selected from halogen, cyano, an unsubstituted or a substituted monocyclic $C_{3-6}$ cycloalkyl and an unsubstituted $C_{1-4}$ alkoxy; wherein when the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl are substituted, the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl can be substituted 1, 2, 3 or 4 times with a substituent independently selected from halogen, an unsubstituted $C_{1-4}$ alkyl, an unsubstituted $C_{2-4}$ alkenyl, an unsubstituted $C_{2-4}$ alkynyl, an unsubstituted $C_{1-4}$ haloalkyl, an unsubstituted or a substituted monocyclic $C_{3-6}$ cycloalkyl and an unsubstituted $C_{1-4}$ alkoxy; $R^9$ can be selected from an unsubstituted $C_{1-6}$ alkyl, an unsubstituted $C_{1-6}$ haloalkyl, an unsubstituted or a substituted monocyclic $C_{3-6}$ cycloalkyl, an unsubstituted or a substituted bicyclic $C_{5-6}$ cycloalkyl, an unsubstituted or a substituted monocyclic heteroaryl and an unsubstituted or a substituted monocyclic heterocyclyl, wherein the substituted monocyclic $C_{3-6}$ cycloalkyl is substituted 1, 2, 3 or 4 times with a substituent independently selected from halogen, an unsubstituted $C_{1-4}$ alkyl, an unsubstituted $C_{1-4}$ haloalkyl and an unsubstituted monocyclic $C_{3-6}$ cycloalkyl; and $R^{11}$ can be an optionally substituted monocyclic 4- to 6-membered heterocyclyl, —(NH)$_m$— an optionally substituted 5- to 6-membered monocyclic heteroaryl, —O— an optionally substituted $C_{1-6}$ alkyl, —O— an optionally substituted $C_{3-8}$ cycloalkyl and —O— an optionally substituted $C_{3-8}$ cycloalkyl($C_{1-4}$ alkyl), wherein m can be 0 or 1.

In some embodiments, a compound of Formula (I), or a pharmaceutically acceptable salt thereof, can be where: Ring $A^1$ can be

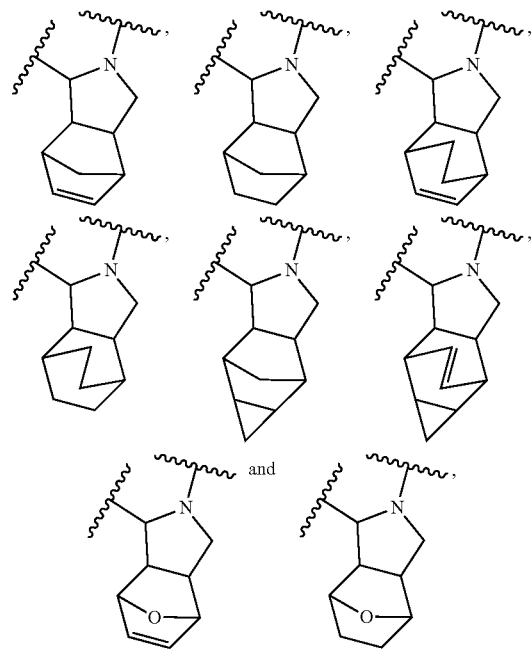

and wherein Ring $A^1$ can be optionally substituted with one or more moieties independently selected from deuterium, halogen, an unsubstituted $C_{1-4}$ alkyl, an unsubstituted $C_{1-4}$ haloalkyl, an unsubstituted $C_{2-4}$ alkenyl and an unsubstituted or a substituted $C_{3-6}$ monocyclic cycloalkyl; $R^1$ can be selected from cyano, an unsubstituted or a substituted $C_{2-5}$ alkynyl, an unsubstituted or a substituted acyl, an unsubstituted or a substituted ketoamide, —CH(OH)—(S(═O)$_2$—O—), —CH(OH)((P═O)(OR$^6$)$_2$) and —C(═O)CH$_2$—O—((P═O)(OR$^7$)$_2$); each $R^6$ and each $R^7$ can be independently hydrogen, an unsubstituted $C_{1-6}$ alkyl, an unsubstituted $C_{2-6}$ alkenyl, an unsubstituted $C_{1-6}$ haloalkyl, an unsubstituted or a substituted aryl or an unsubstituted or a substituted aryl ($C_{1-4}$ alkyl); $R^2$ can be hydrogen, deuterium or halogen; $R^3$ can be an unsubstituted or a substituted monocyclic nitrogen-containing heterocyclyl($C_{1-4}$ alkyl), an unsubstituted or a substituted bicyclic nitrogen-containing heterocyclyl($C_{1-4}$ alkyl) or an unsubstituted or a substituted monocyclic nitrogen-containing heteroaryl($C_{1-4}$ alkyl); $R^4$ can be hydrogen, deuterium or halogen; $R^5$ can be

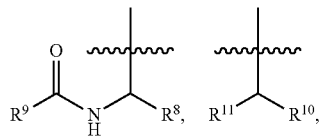

a substituted monocyclic $C_{3-6}$ cycloalkyl or a substituted 4- to 6-membered monocyclic heterocyclyl; $R^8$ and $R^{10}$ can be independently selected from an unsubstituted or a substituted $C_{2-6}$ alkyl, an unsubstituted or a substituted $C_{2-6}$ alkenyl, an unsubstituted or a substituted $C_{2-6}$ alkynyl, an unsubstituted or a substituted monocyclic $C_{3-6}$ cycloalkyl, an unsubstituted or a substituted bicyclic $C_{5-8}$ cycloalkyl, an unsubstituted or a substituted monocyclic 4- to 6-membered heterocyclyl and an unsubstituted monocyclic $C_{3-6}$ cycloalkyl(CH$_2$)—, wherein when the $C_{2-6}$ alkyl is substituted, the $C_{2-6}$ alkyl can be substituted 1, 2, 3 or 4 times with a substituent independently selected from halogen, cyano, an unsubstituted or a substituted monocyclic $C_{3-6}$ cycloalkyl and an unsubstituted $C_{1-4}$ alkoxy; wherein when the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl are substituted, the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl can be substituted 1, 2, 3 or 4 times with a substituent independently selected from halogen, an unsubstituted $C_{1-4}$ alkyl, an unsubstituted $C_{2-4}$ alkenyl, an unsubstituted $C_{2-4}$ alkynyl, an unsubstituted $C_{1-4}$ haloalkyl, an unsubstituted or a substituted monocyclic $C_{3-6}$ cycloalkyl and an unsubstituted $C_{1-4}$ alkoxy; $R^9$ can be selected from an unsubstituted or a substituted $C_{1-6}$ alkyl, an unsubstituted or a substituted $C_{1-6}$ haloalkyl, an unsubstituted or a substituted monocyclic $C_{3-6}$ cycloalkyl, an unsubstituted or a substituted bicyclic $C_{5-6}$ cycloalkyl, an unsubstituted or a substituted monocyclic heteroaryl and an unsubstituted or a substituted monocyclic heterocyclyl, wherein the substituted $C_{1-6}$ alkyl is substituted 1 or 2 times with an unsubstituted $C_{1-4}$ alkoxy, wherein the substituted monocyclic $C_{3-6}$ cycloalkyl is substituted 1, 2, 3 or 4 times with a substituent independently selected from halogen, an unsubstituted $C_{1-4}$ alkyl, an unsubstituted $C_{1-4}$ haloalkyl and an unsubstituted monocyclic $C_{3-6}$ cycloalkyl, and wherein the substituted $C_{1-6}$ haloalkyl is substituted 1 or 2 times with an unsubstituted $C_{1-4}$ alkoxy; and $R^{11}$ can be an optionally substituted monocyclic 4- to 6-membered heterocyclyl, —(NH)$_m$— an optionally substituted 5- to 6-membered monocyclic heteroaryl, —O— an optionally substituted $C_{1-6}$ alkyl, —O— an optionally substituted $C_{3-8}$ cycloalkyl and —O— an optionally substituted $C_{3-8}$ cycloalkyl($C_{1-4}$ alkyl), wherein m can be 0 or 1.

Examples of compounds of Formula (I), include the following:

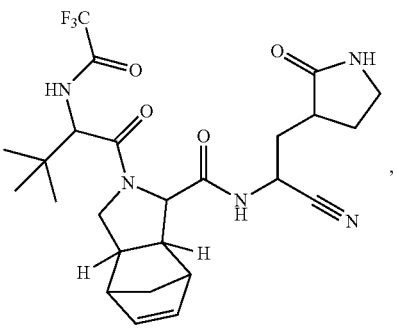

-continued
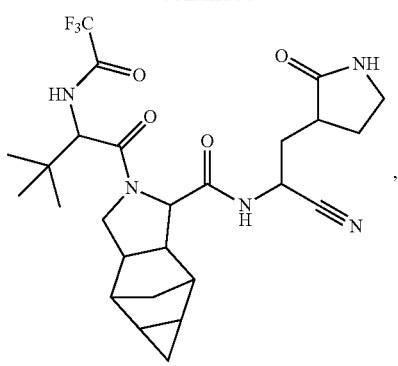
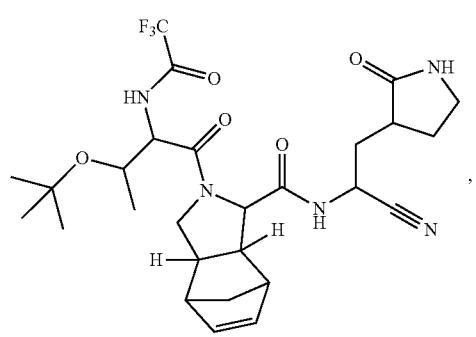
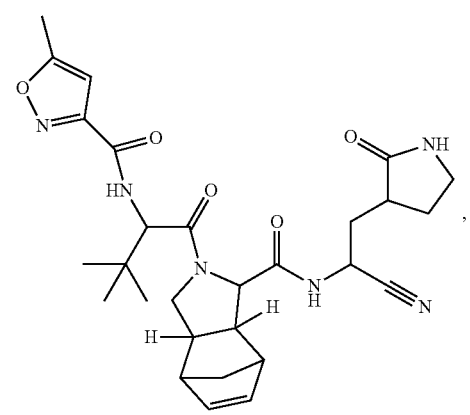
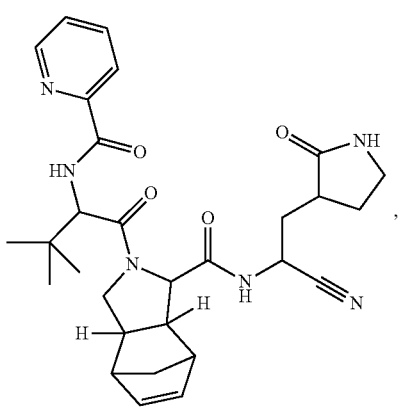
-continued
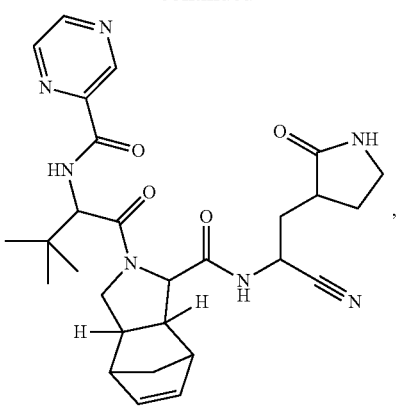
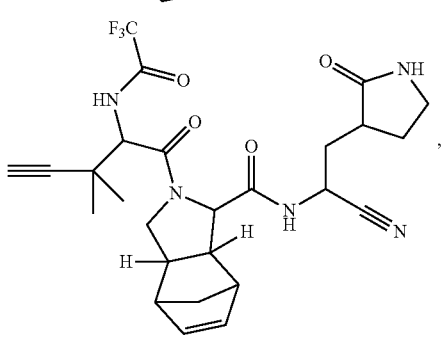
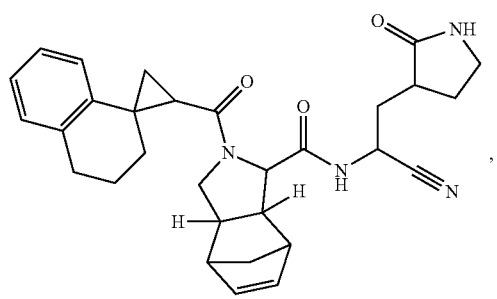
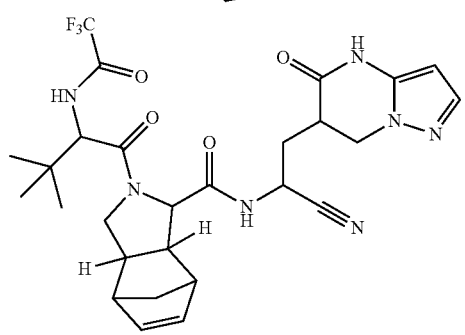
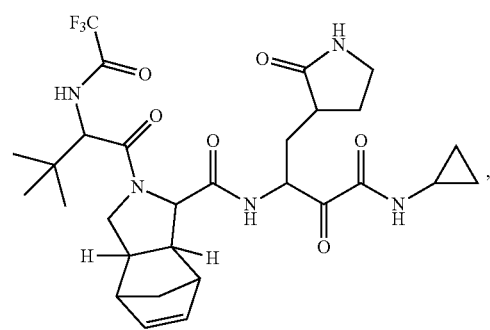

47
-continued
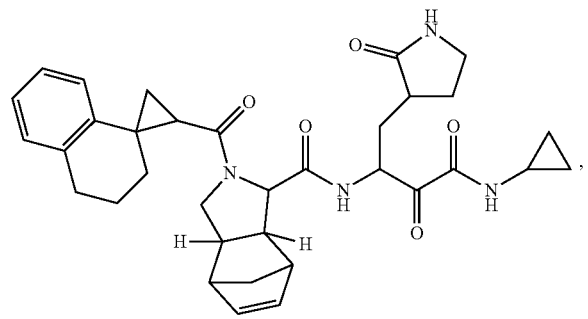
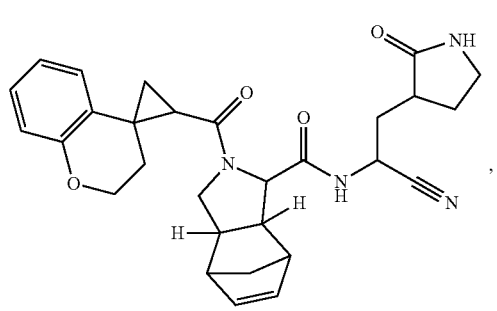
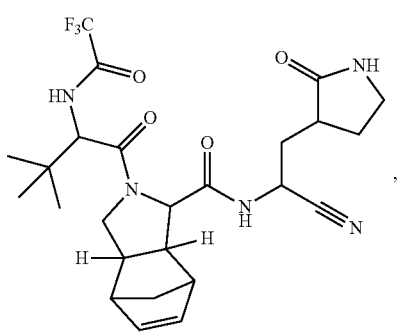
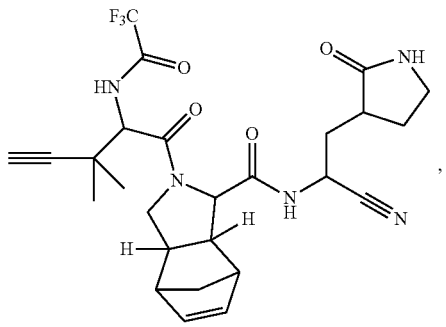
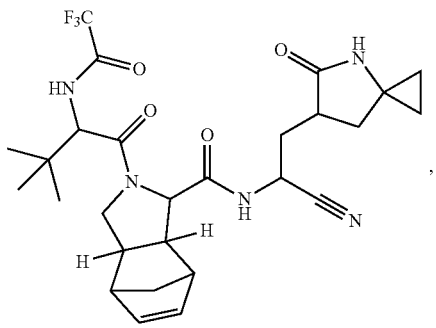
48
-continued
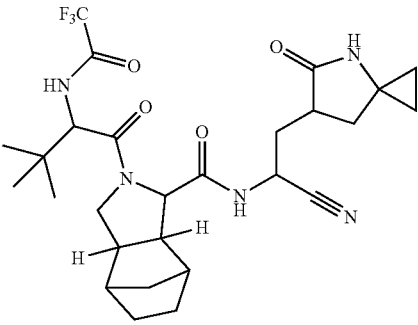
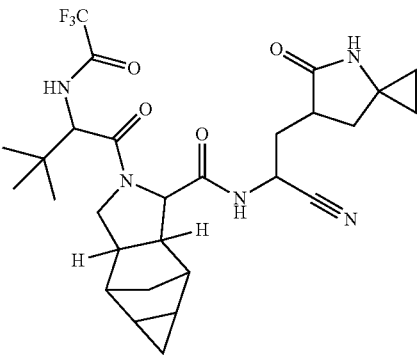
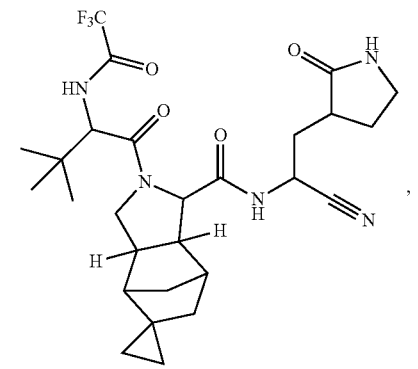
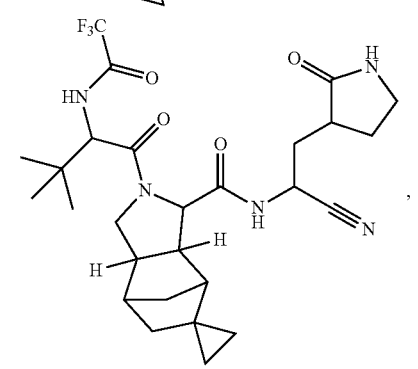
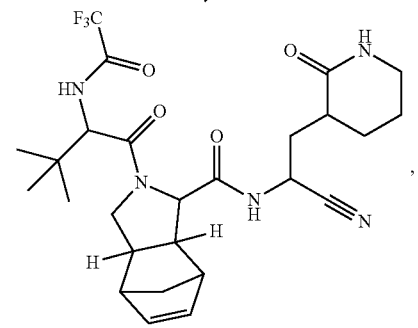

-continued
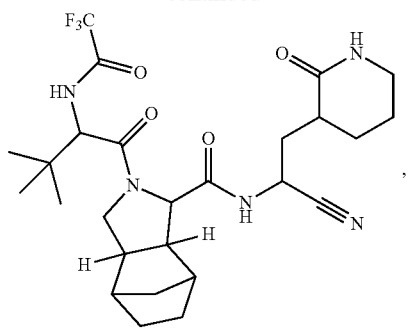
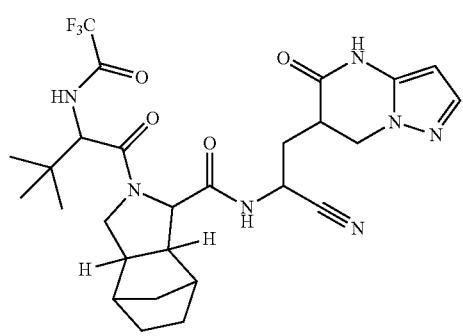
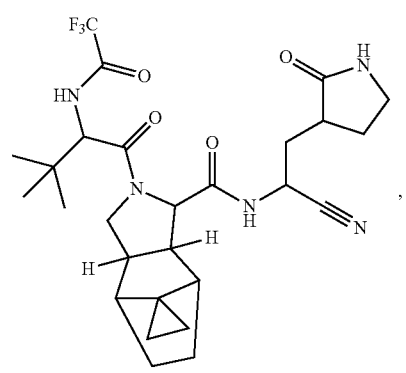
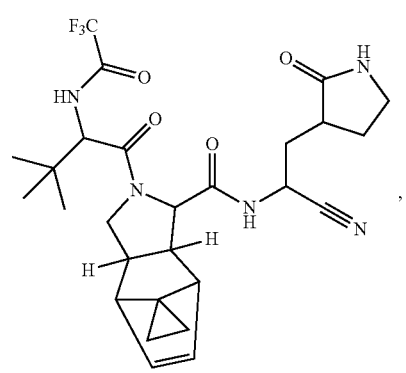
-continued
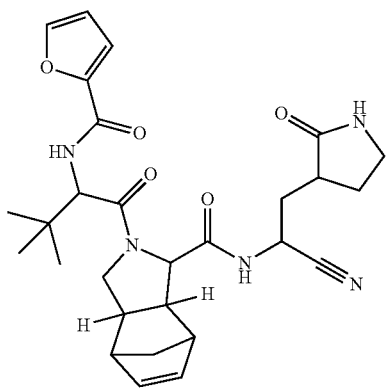
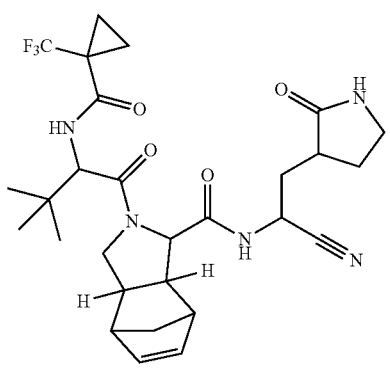
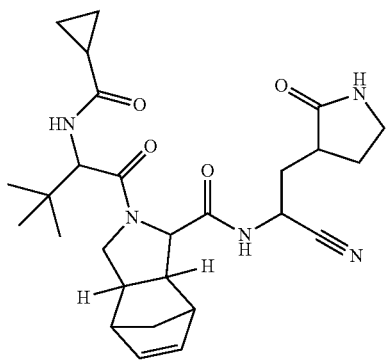
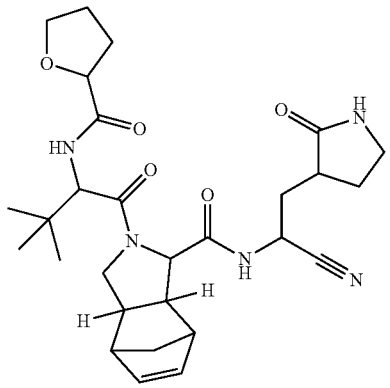

51
-continued
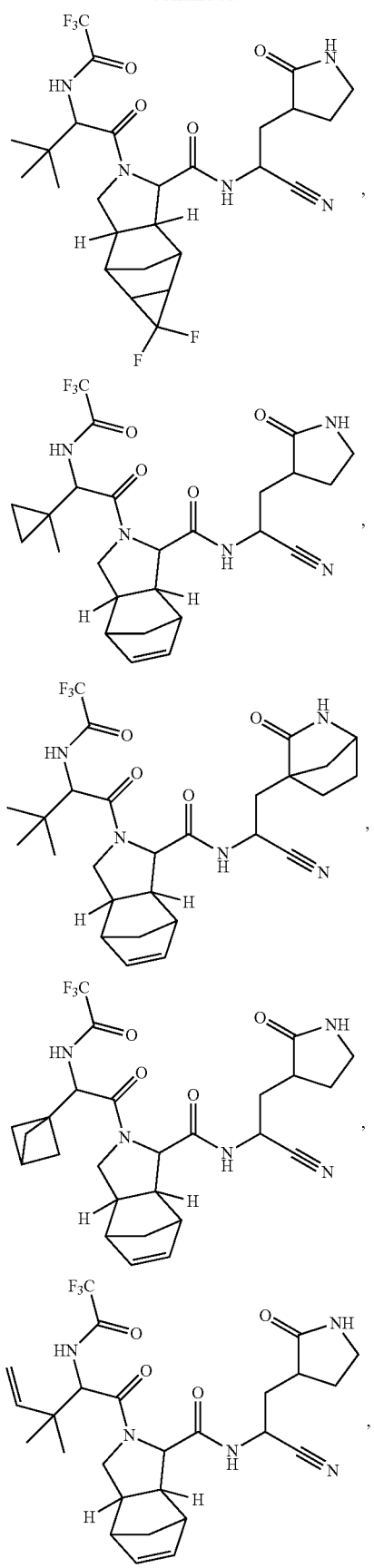
52
-continued
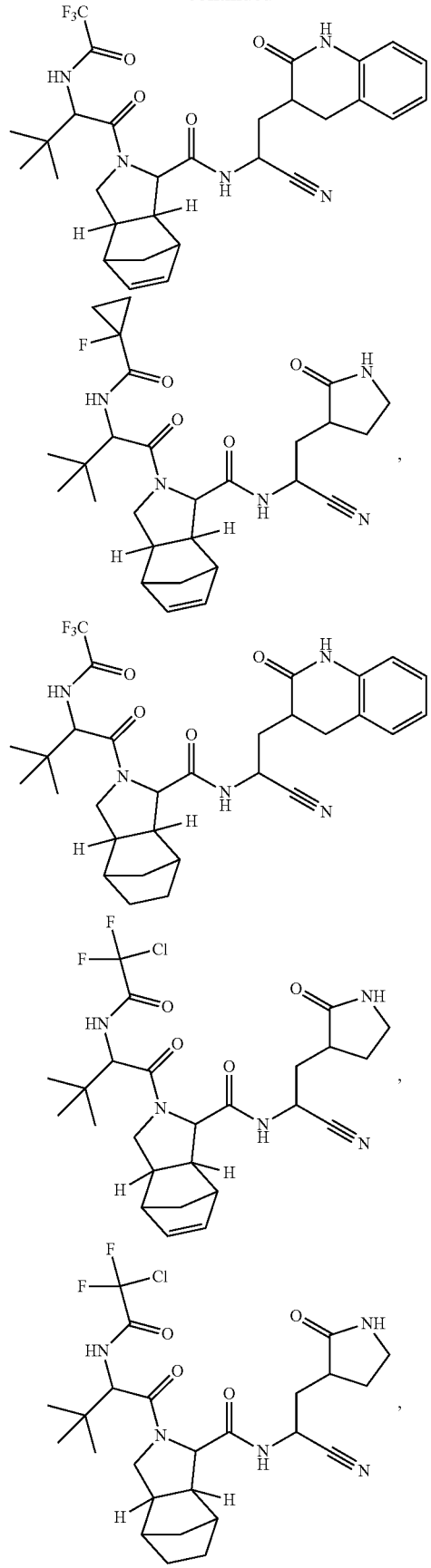

53
-continued
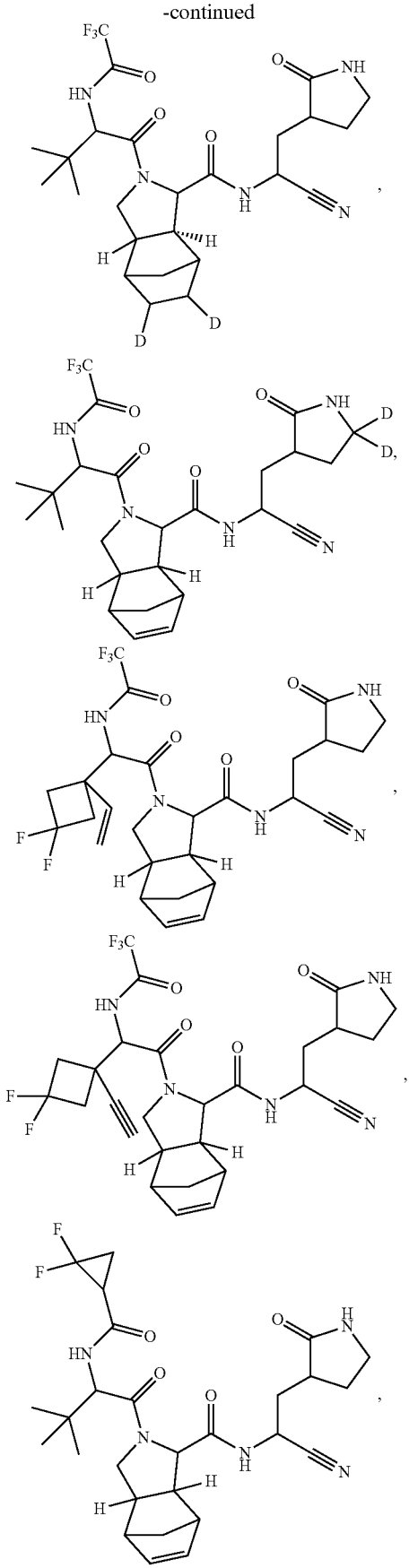
54
-continued
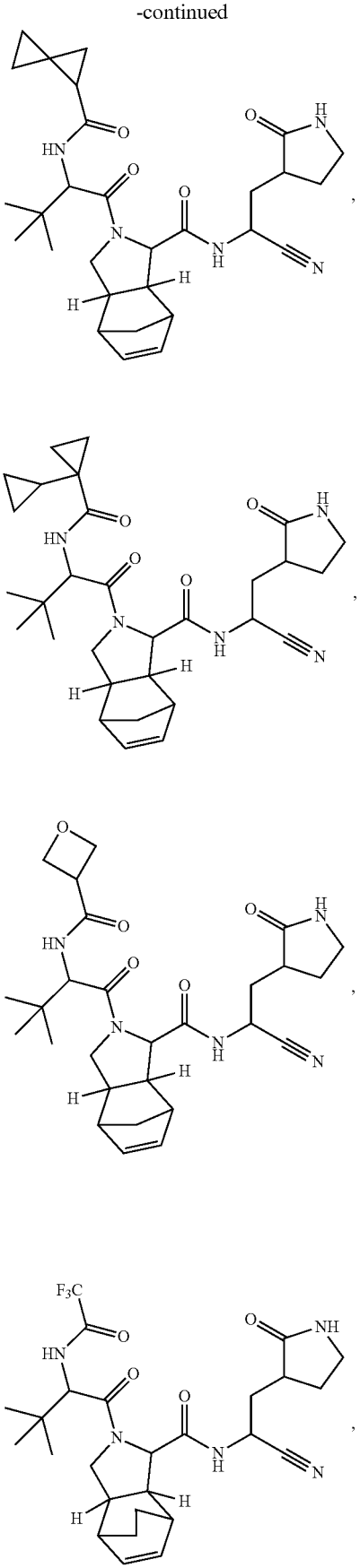

55
-continued
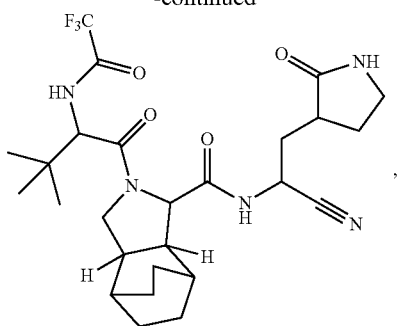
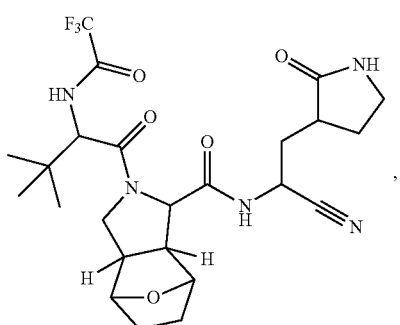
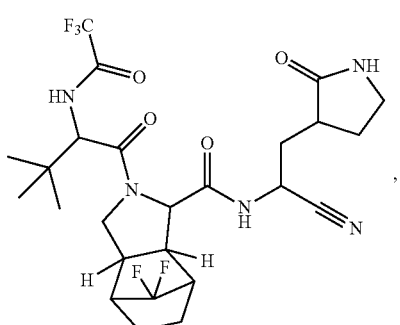
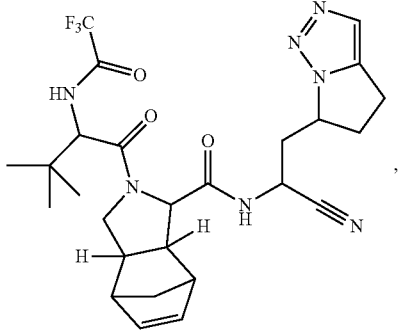
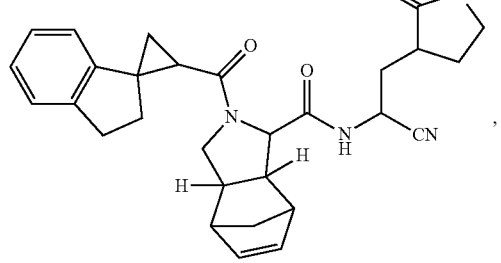
56
-continued
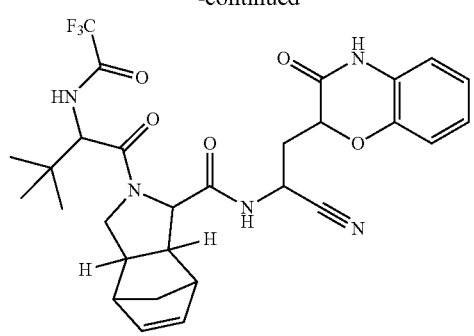
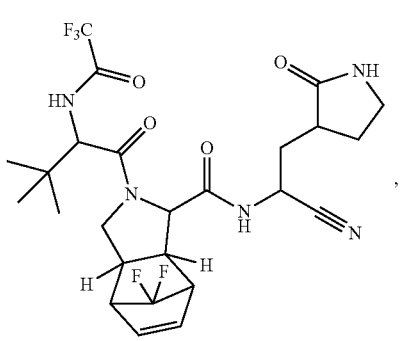
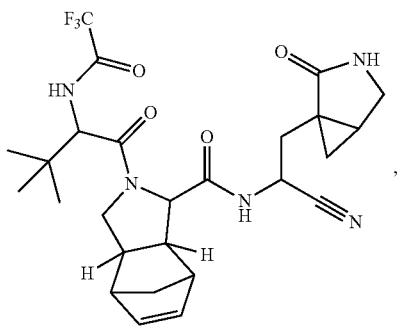
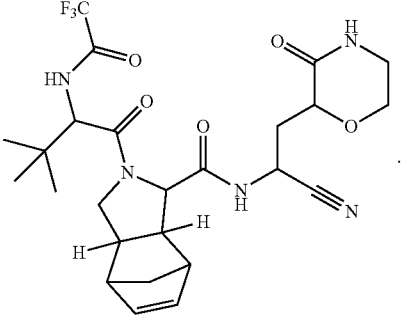
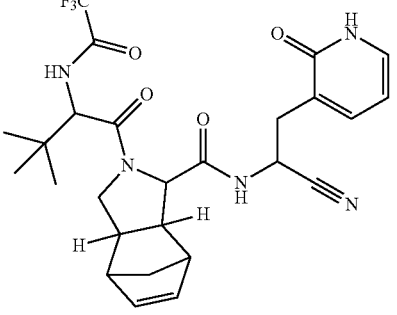

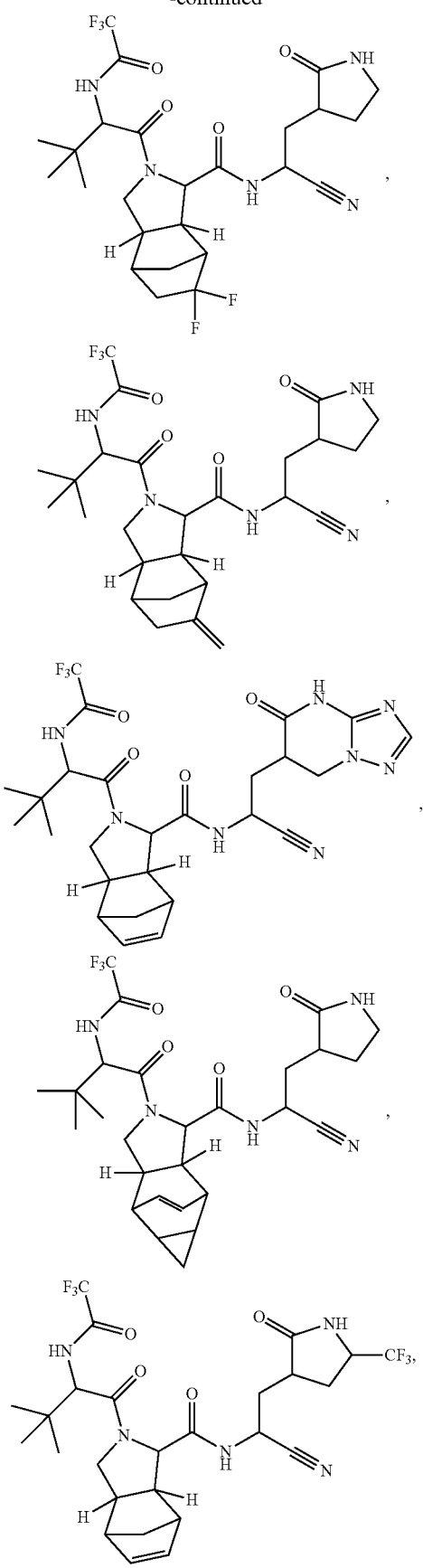
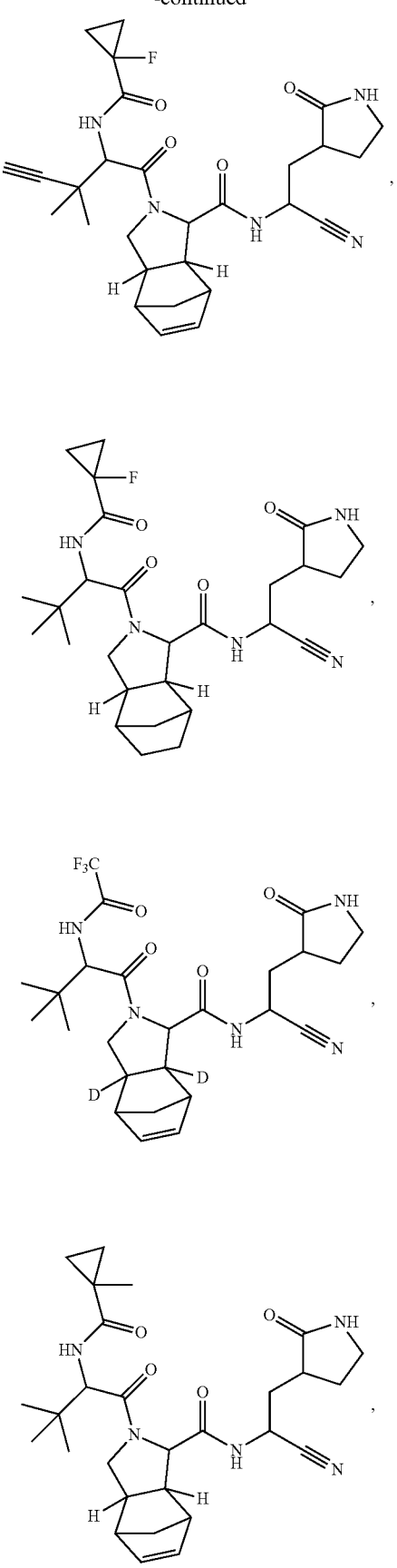

59
-continued
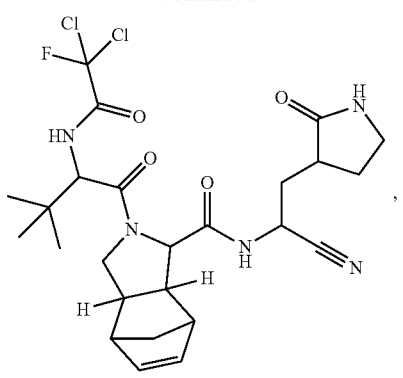
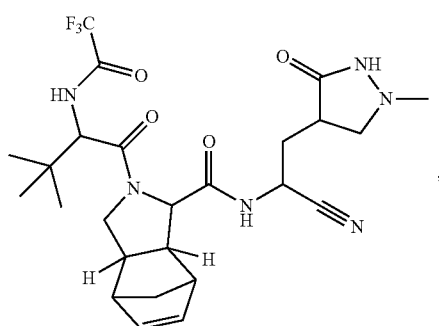
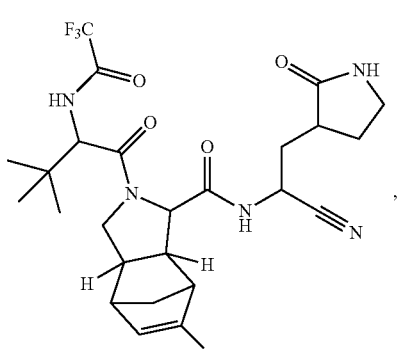
60
-continued
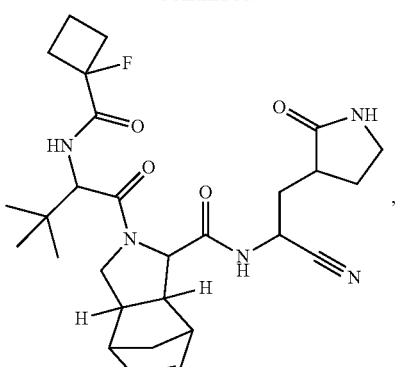
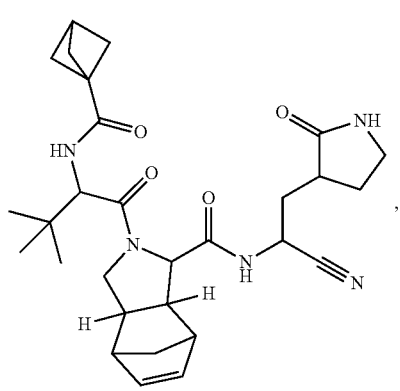
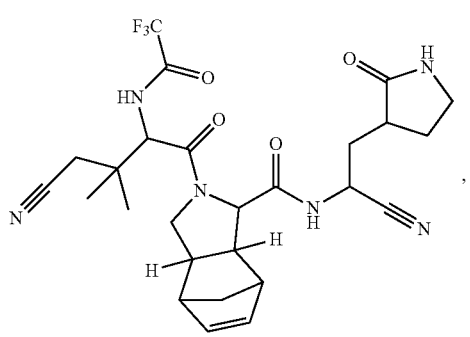

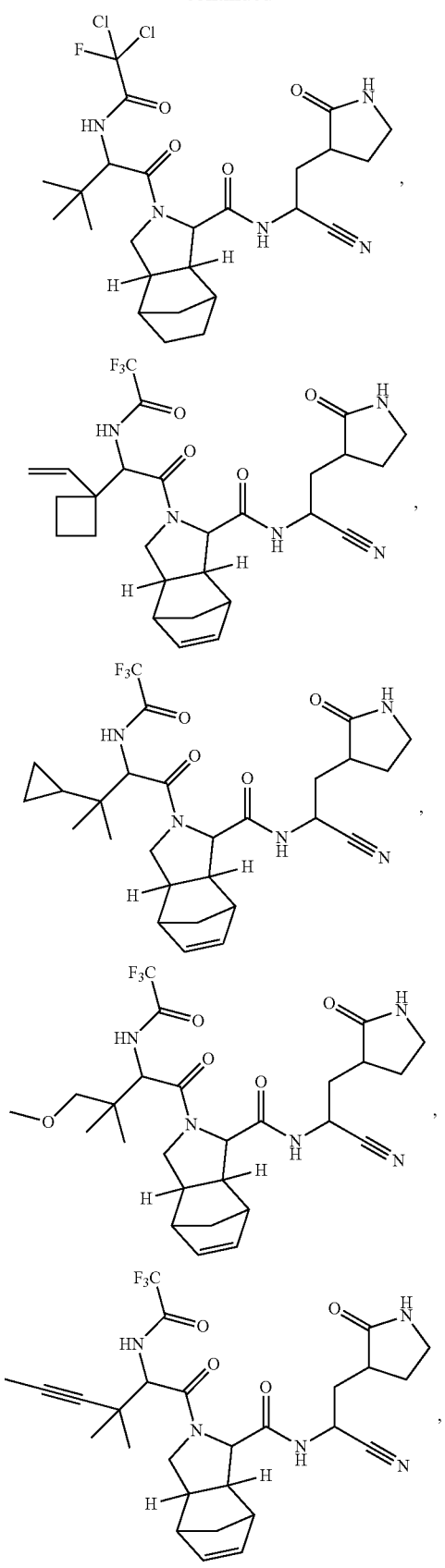
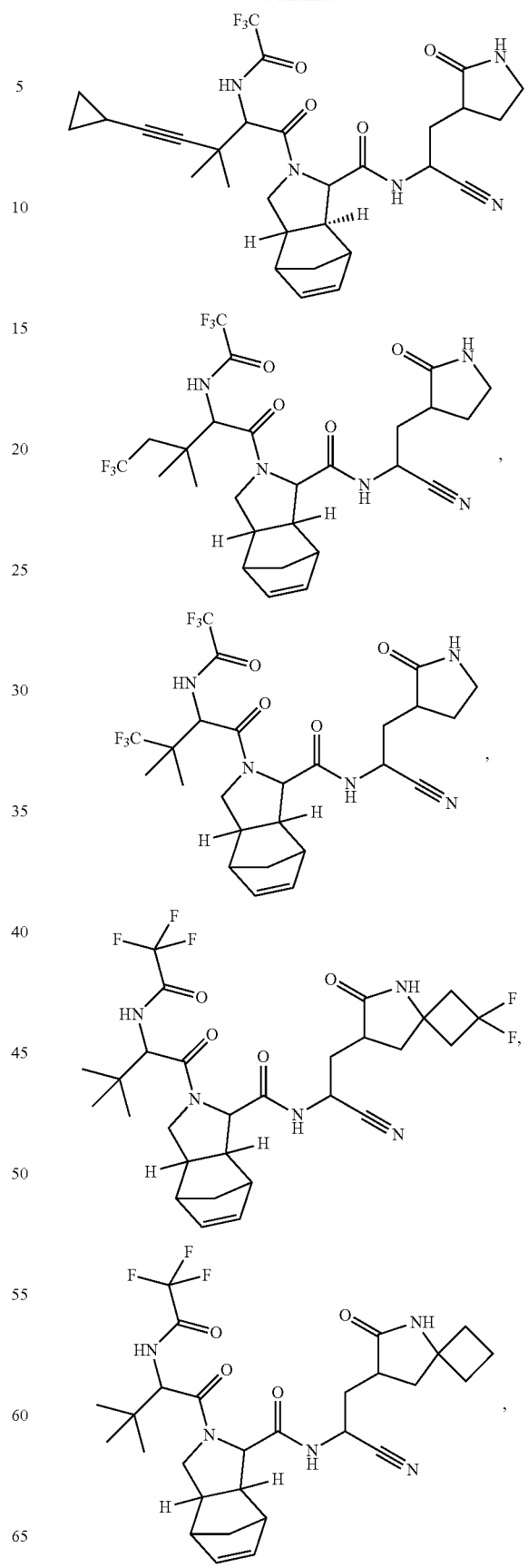

63
-continued
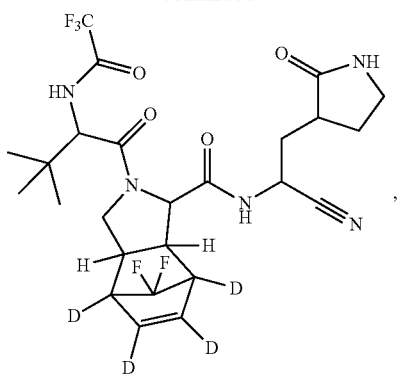
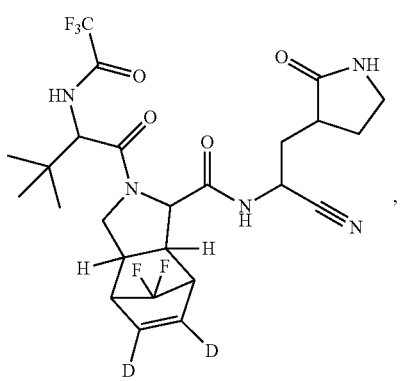
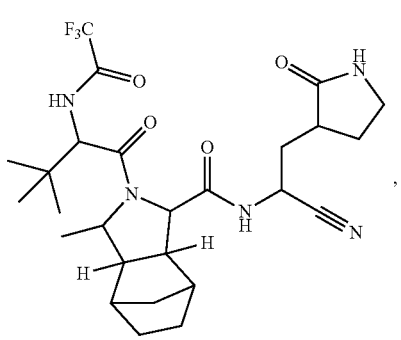
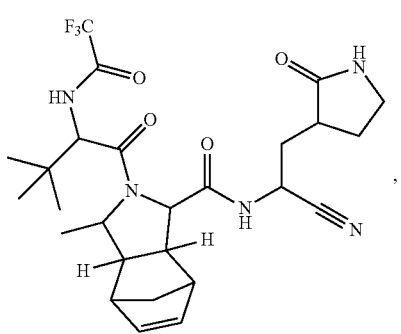
64
-continued
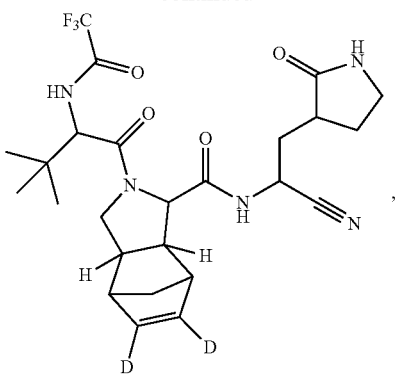
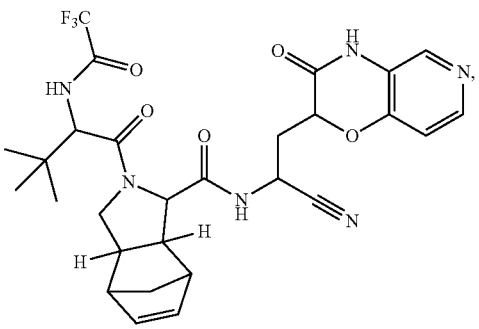
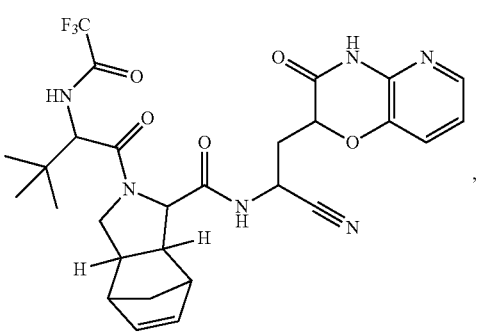
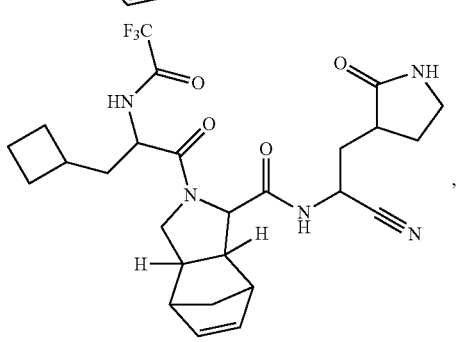
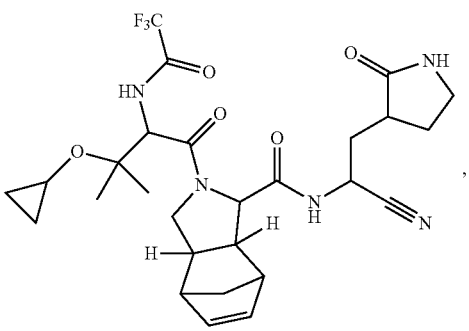

65
-continued
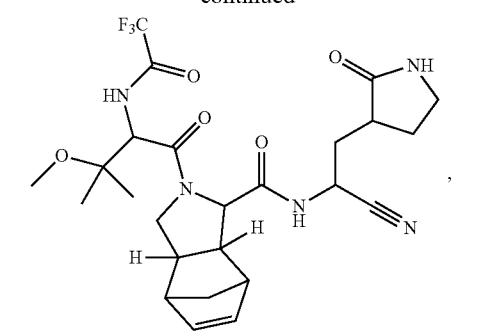
,
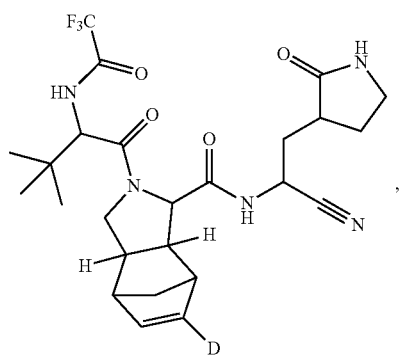
,
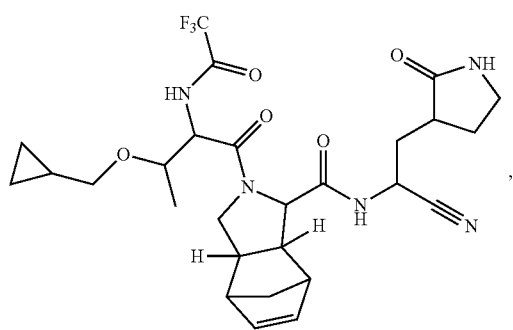
,
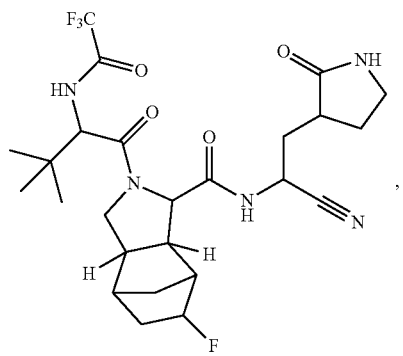
,
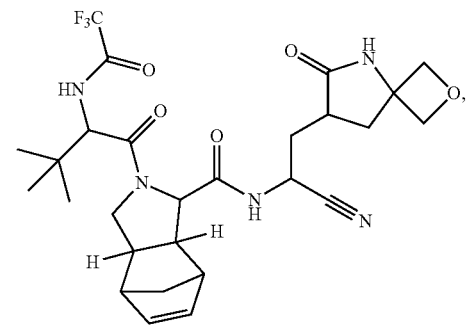
,
66
-continued
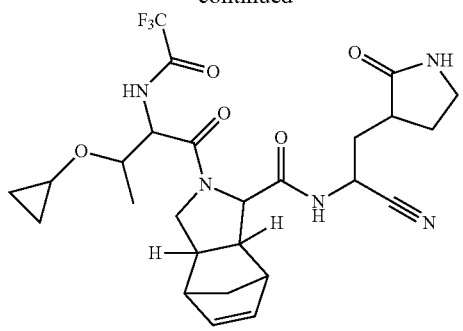
,
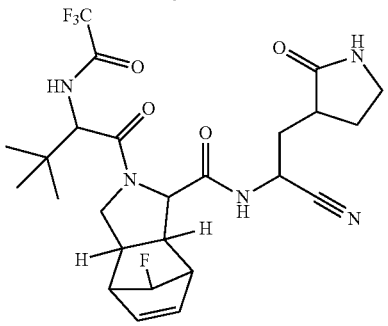
,
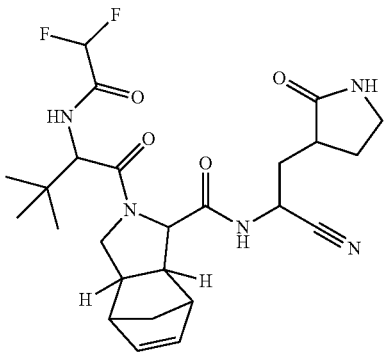
,
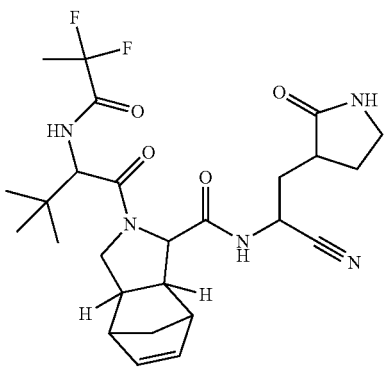
,
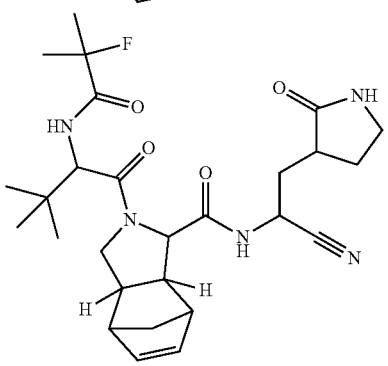
,

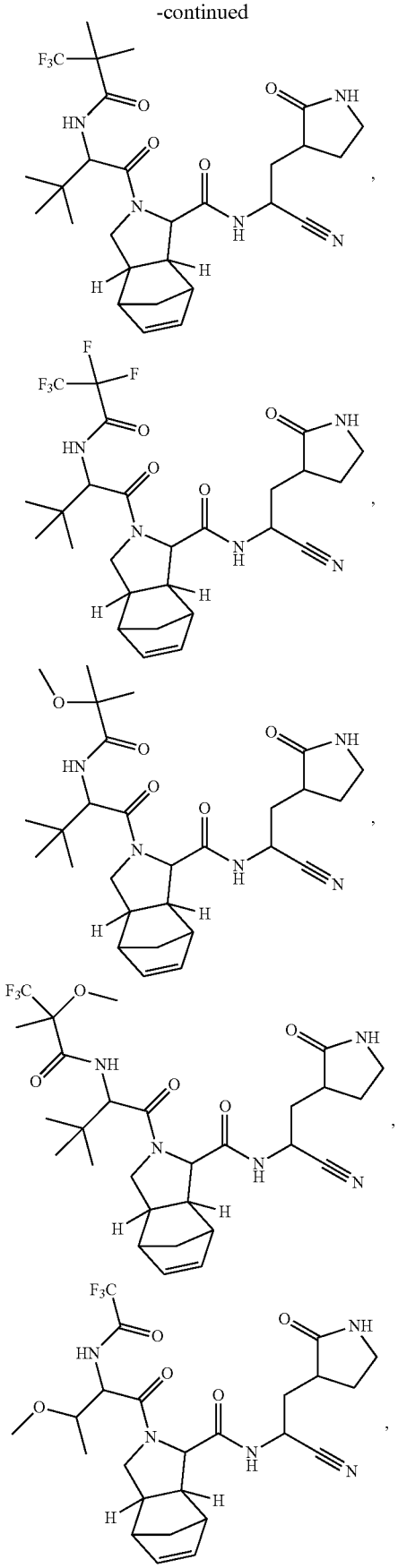
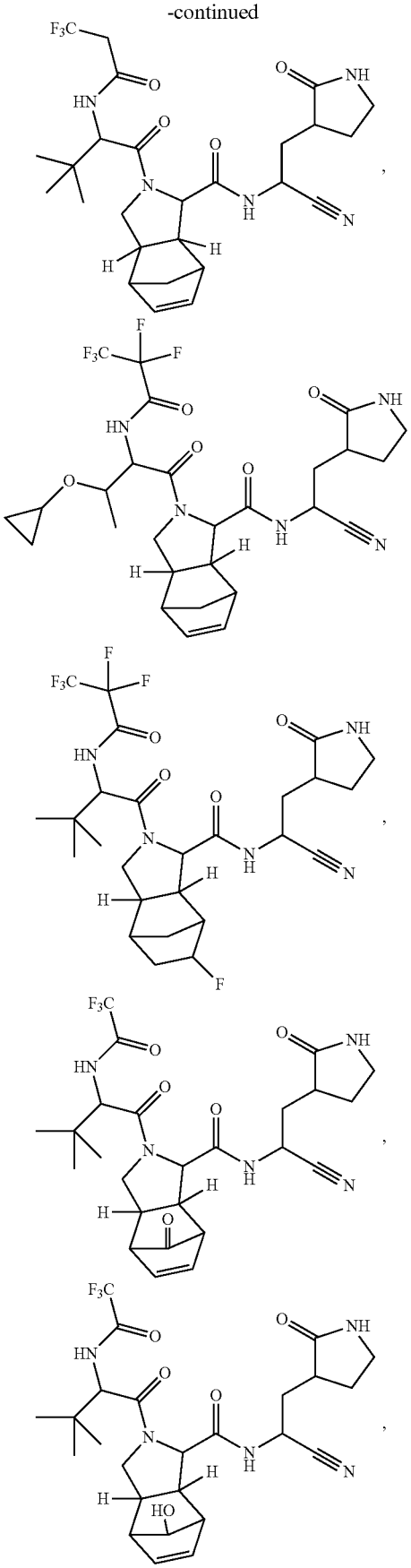

69
-continued
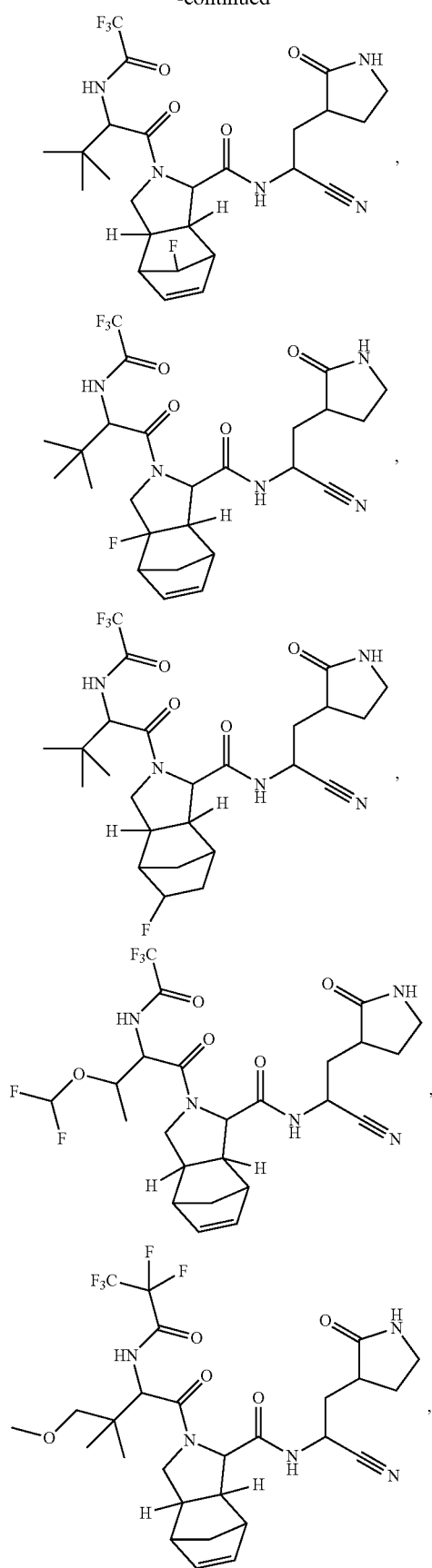
70
-continued
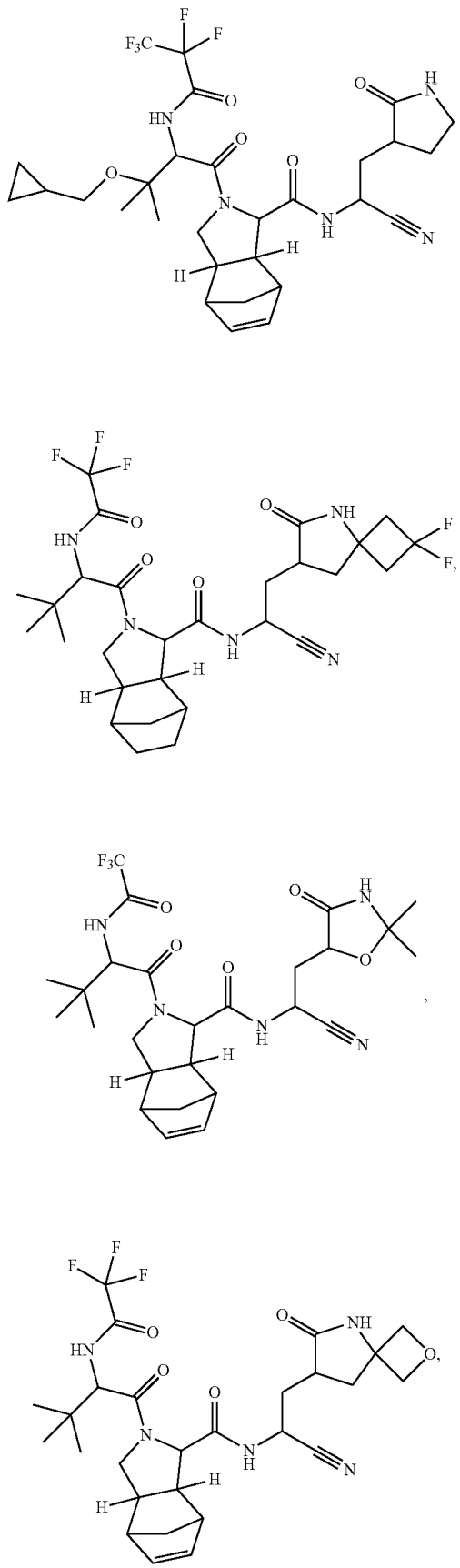

71
-continued
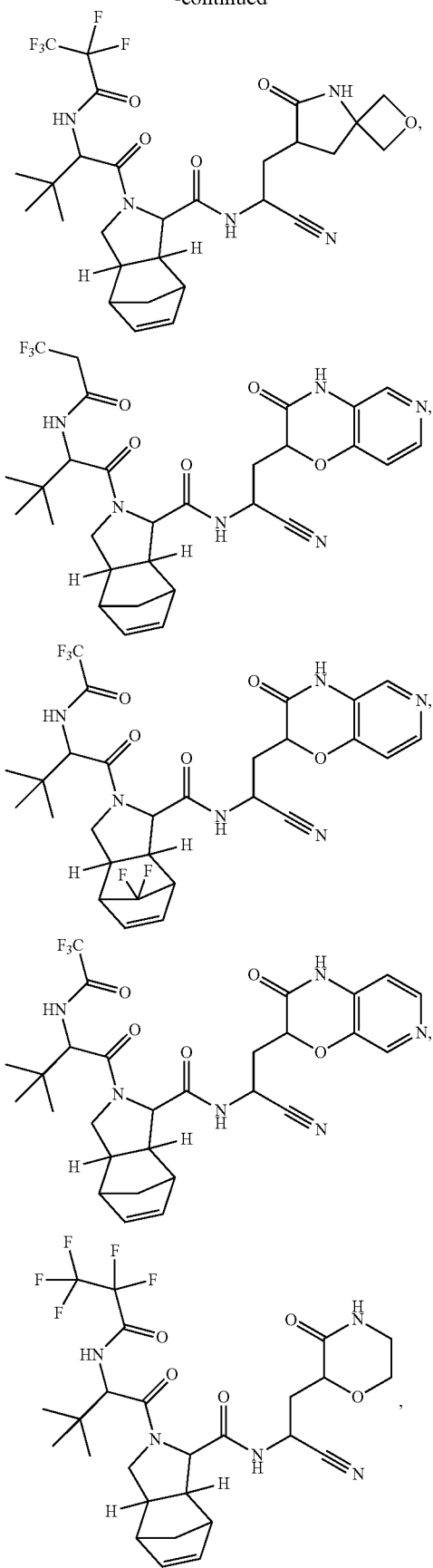
72
-continued
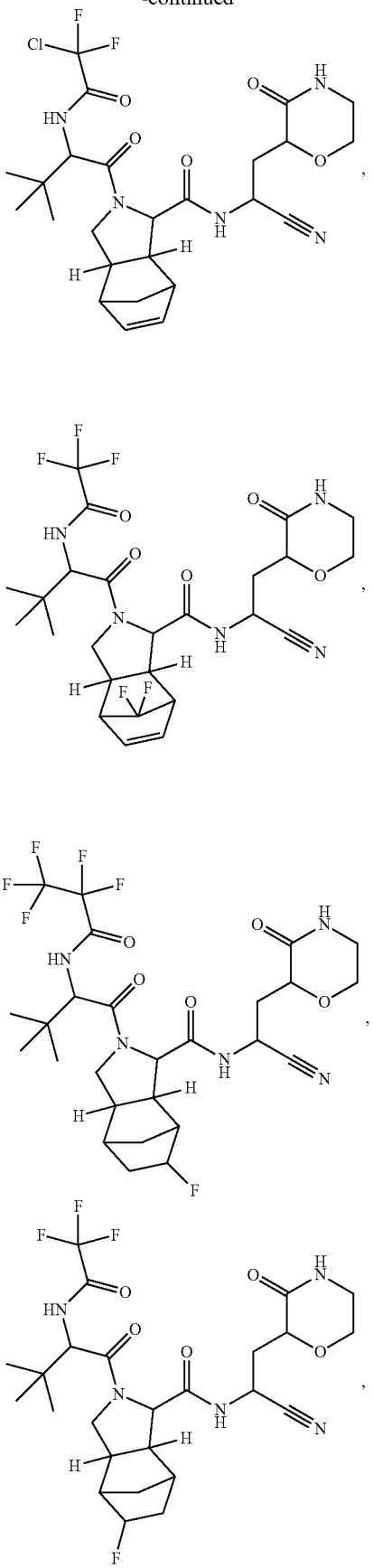

73
-continued
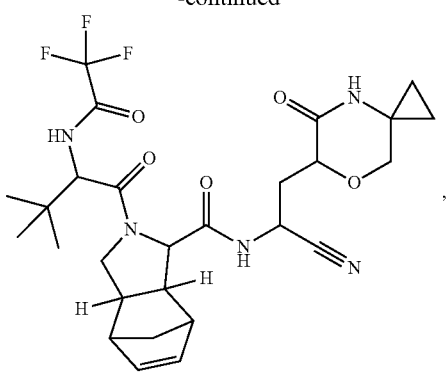
,
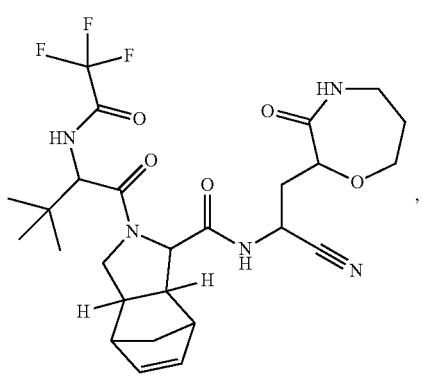
,
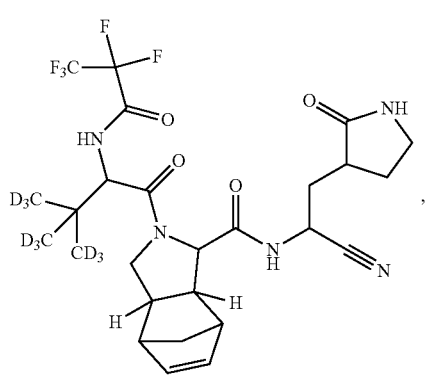
,
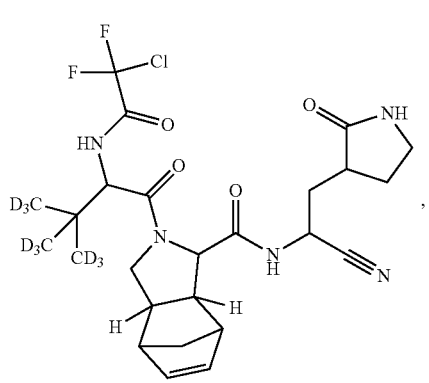
,
74
-continued
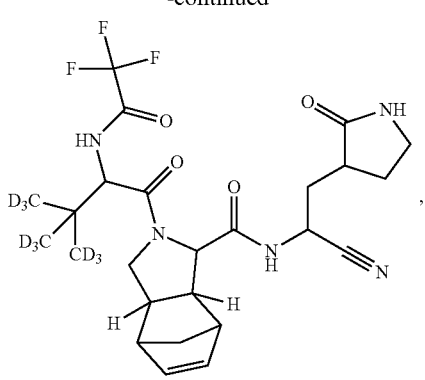
,
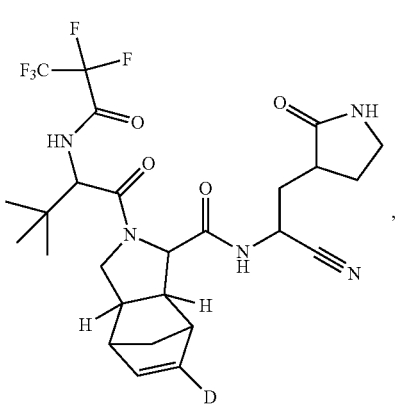
,
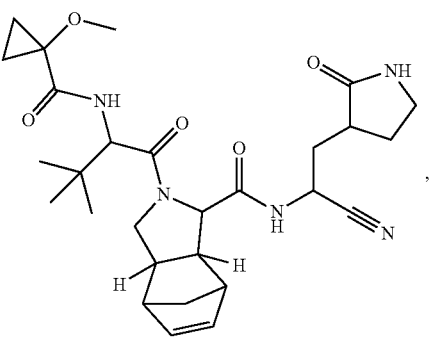
,
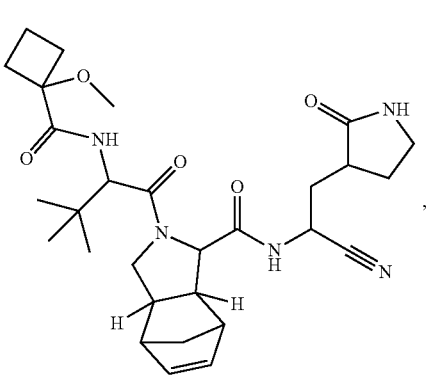
, 75
-continued
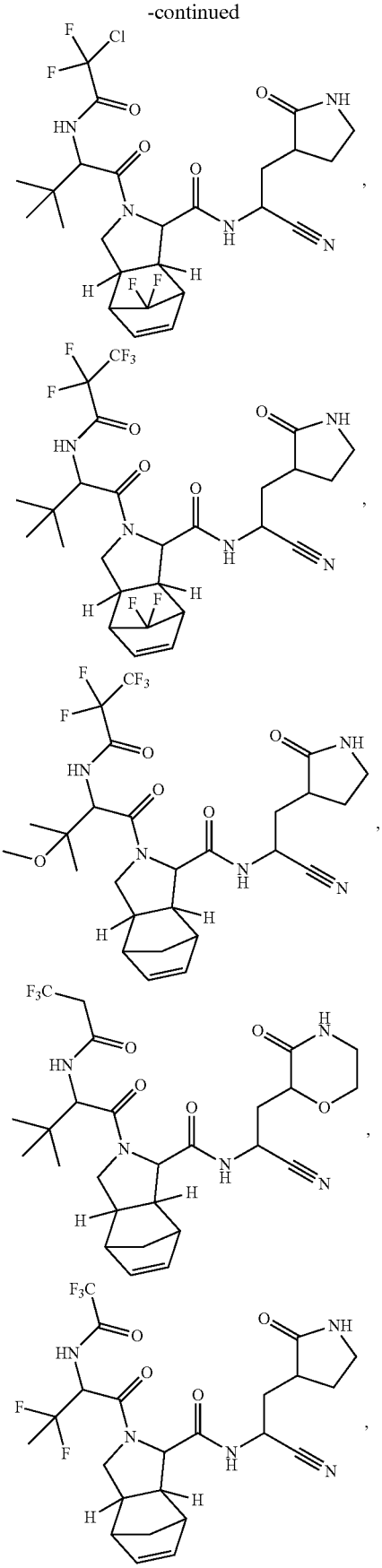
76
-continued
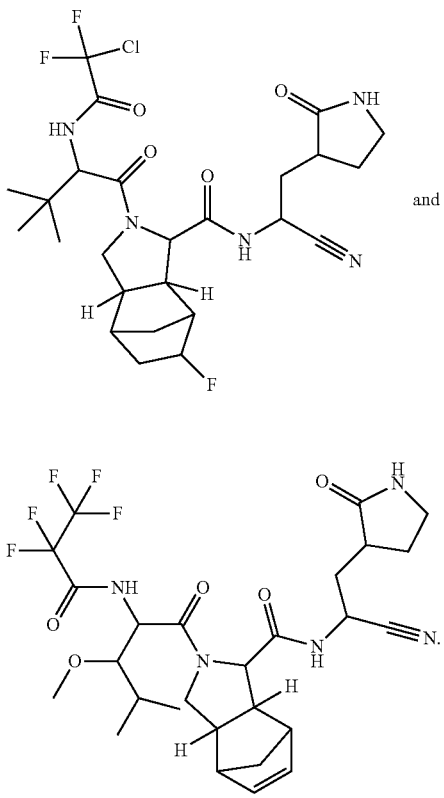
or a pharmaceutically acceptable salt of any of the foregoing.
Additional examples of compounds of Formula (I), include the following:
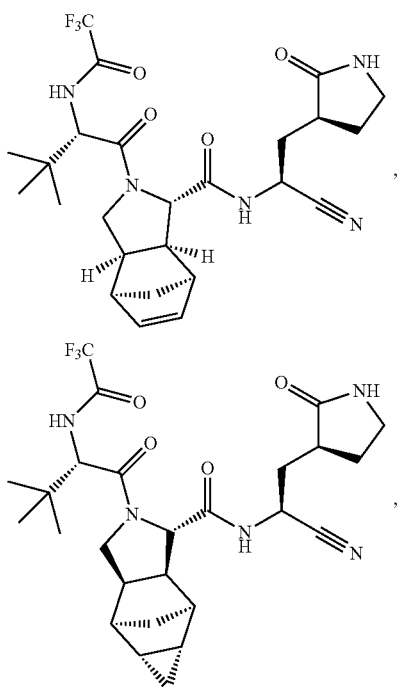

77
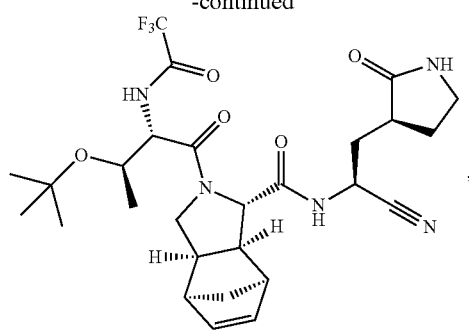
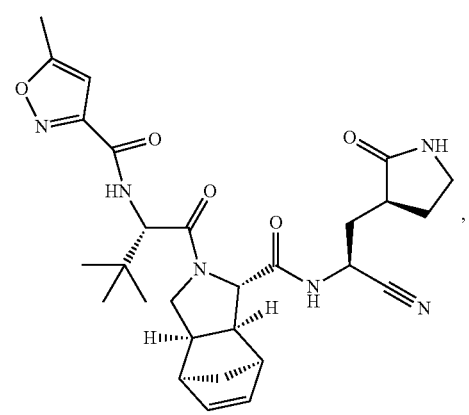
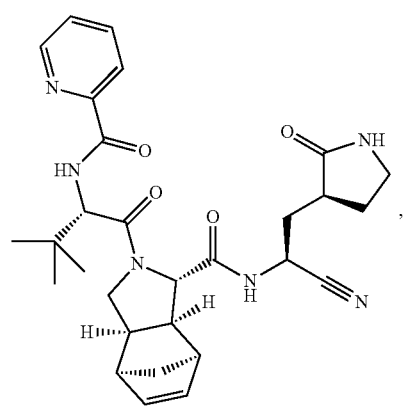
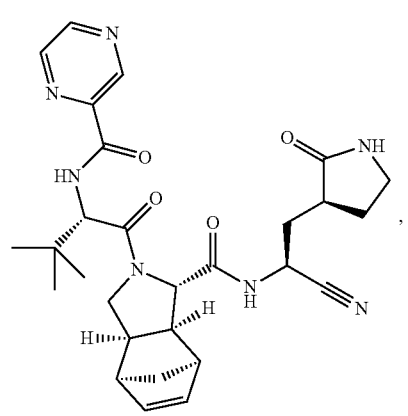
78
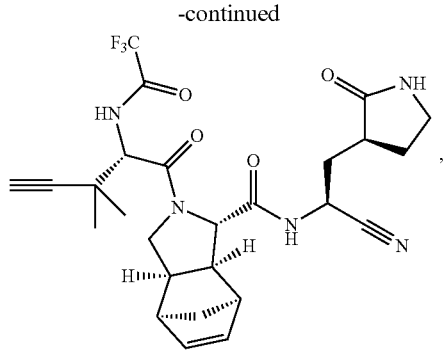
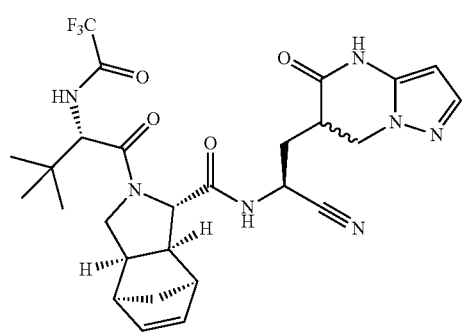
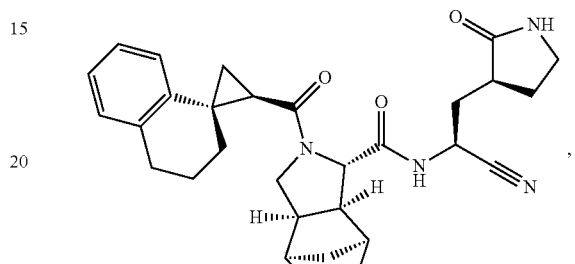
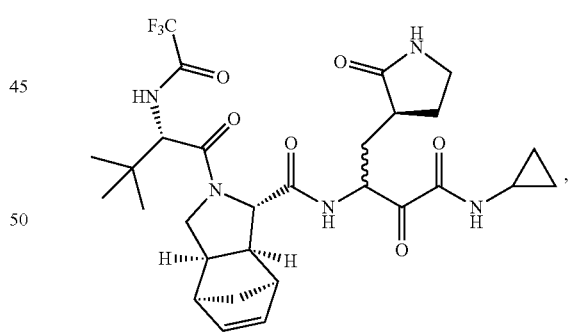
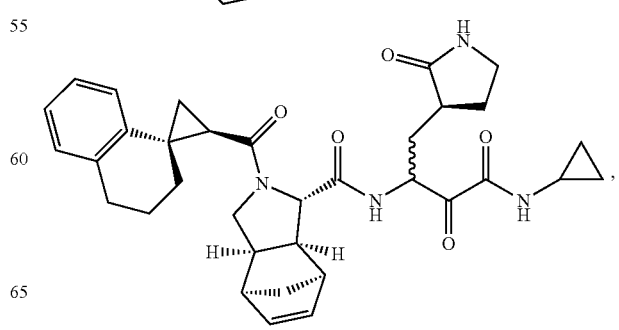

79                                         80
-continued                                -continued
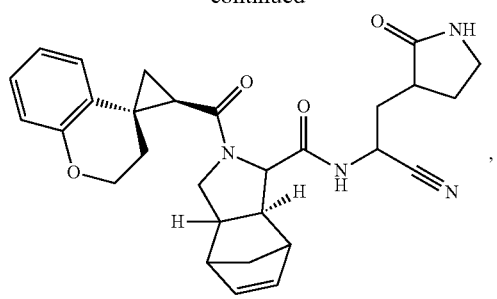
,
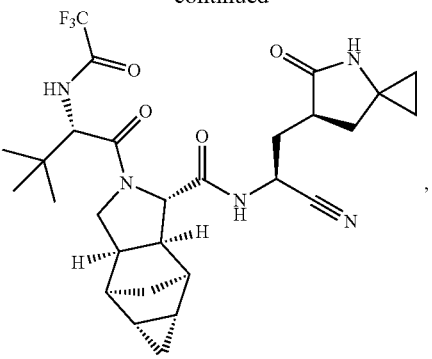
,
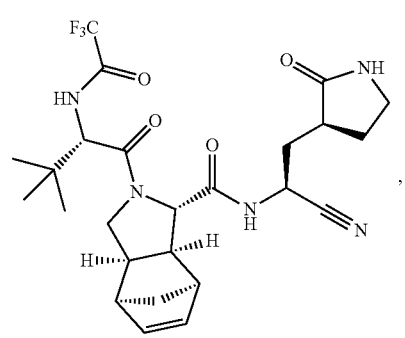
,
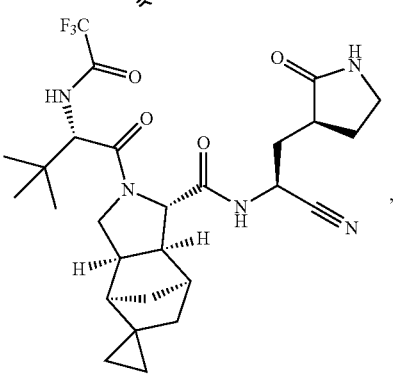
,
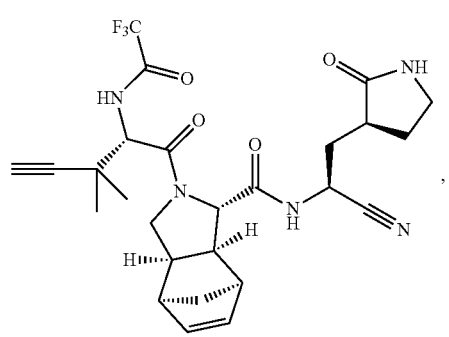
,
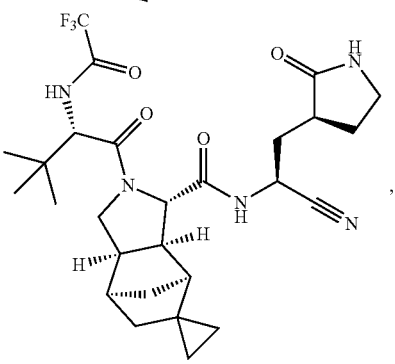
,
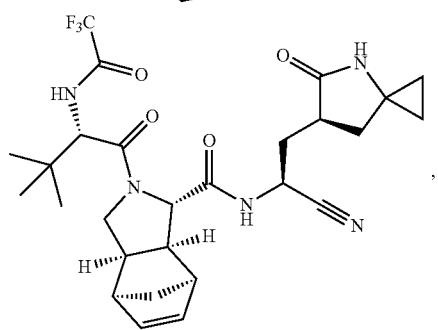
,
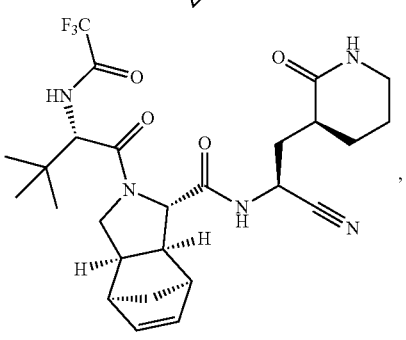
,
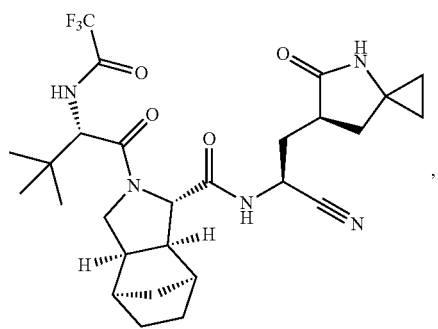
,
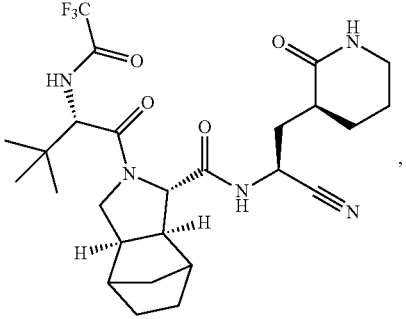
, 81
-continued
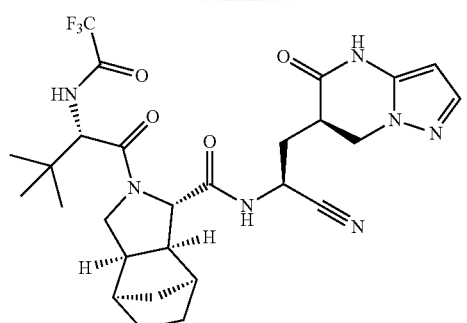
,
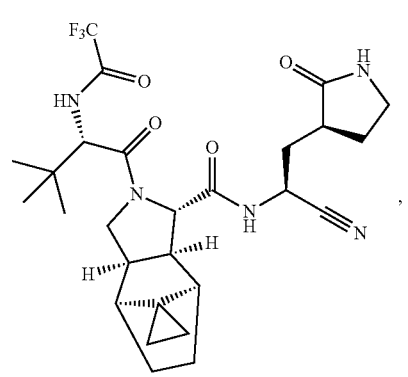
,
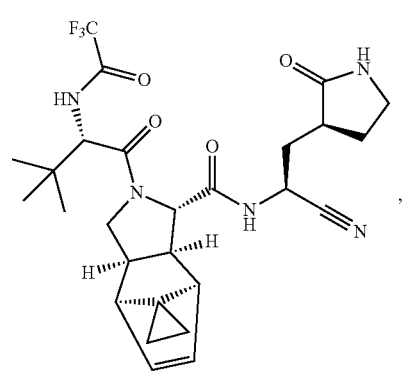
,
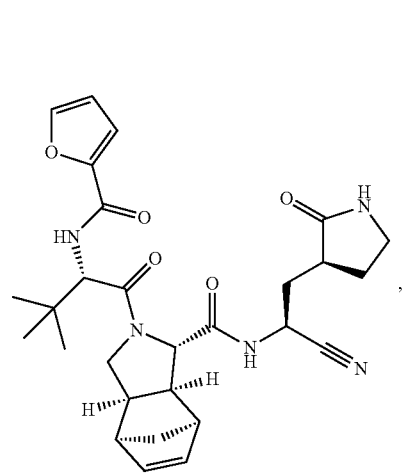
,
82
-continued
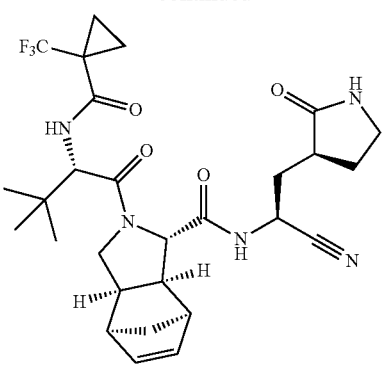
,
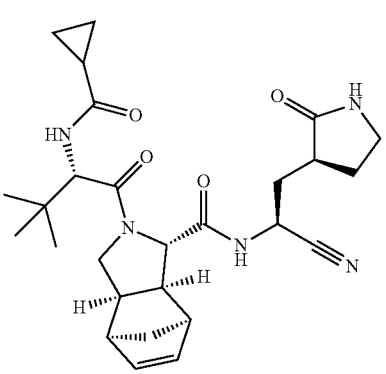
,
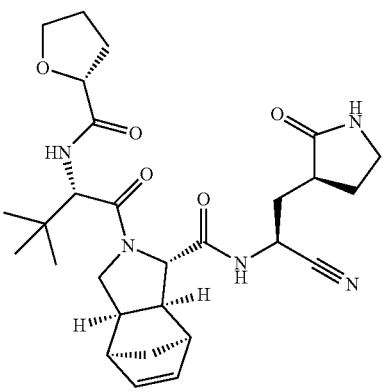
,
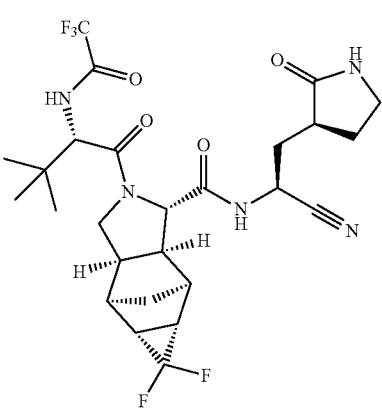
,

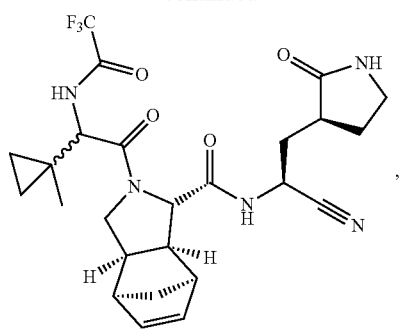,
,
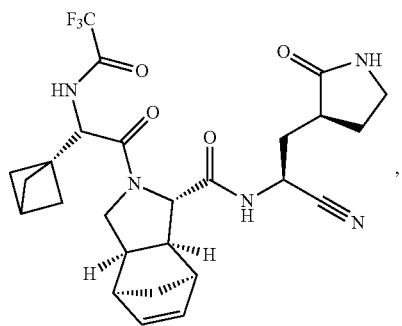,
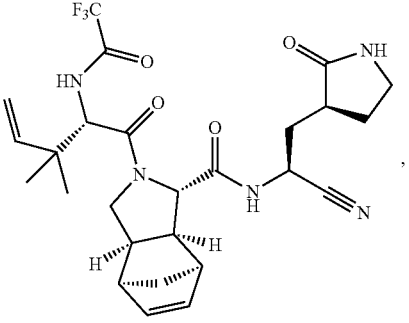,
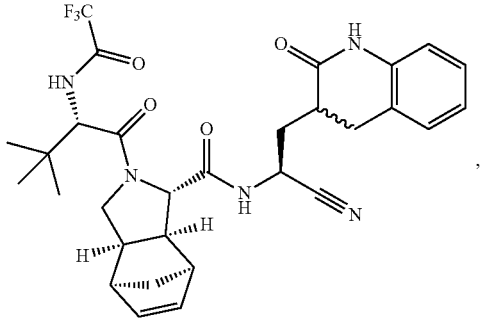,
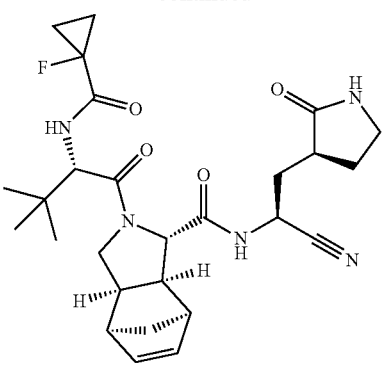,
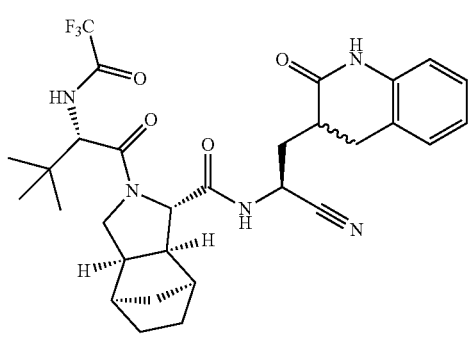,
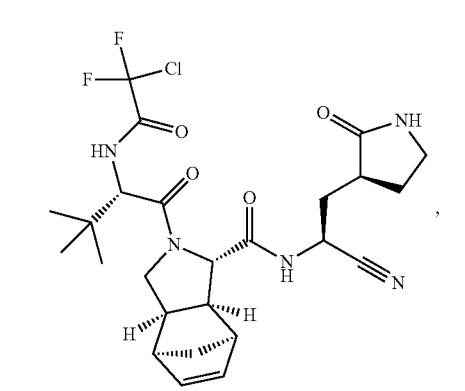,
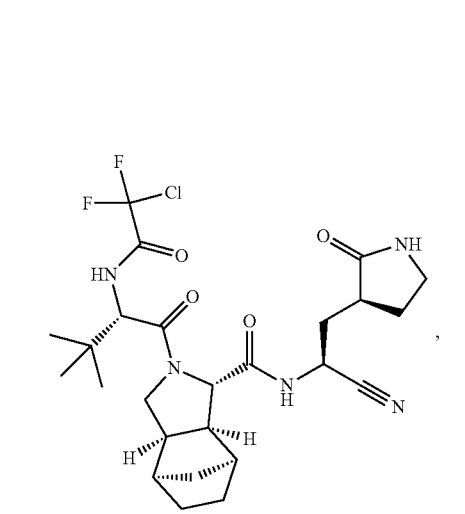, 85
-continued
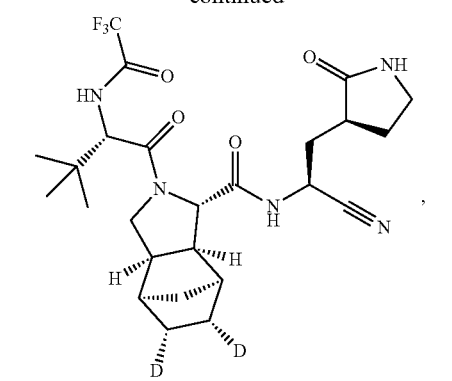
,
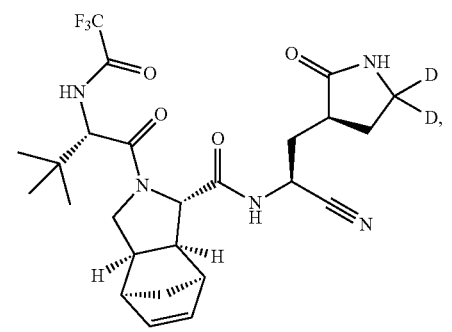
,
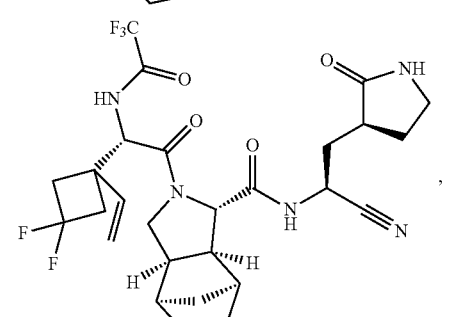
,
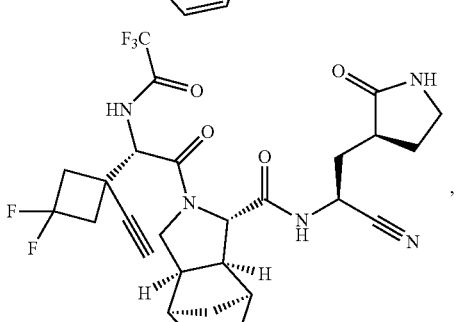
,
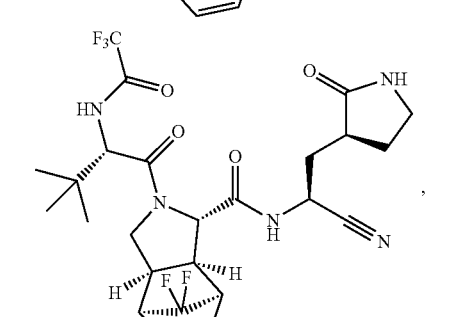
,
86
-continued
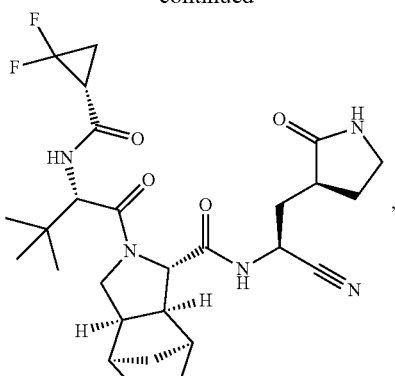
,
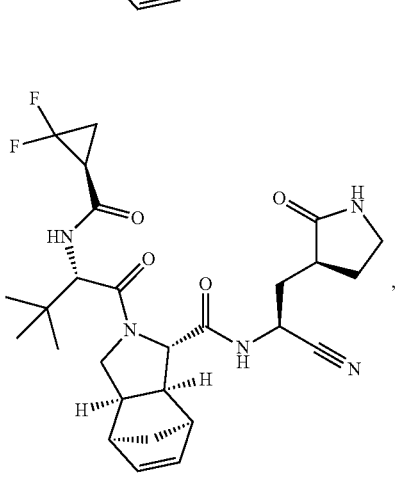
,
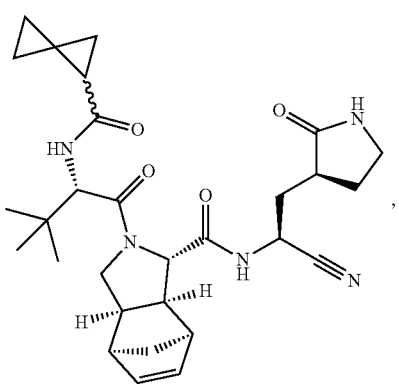
,
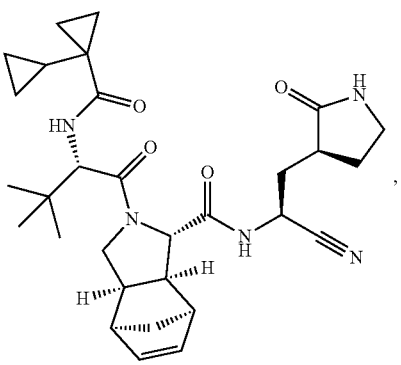
,
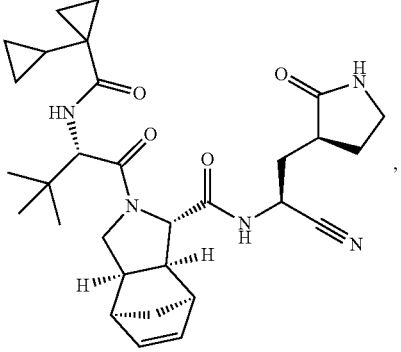
, 87
-continued
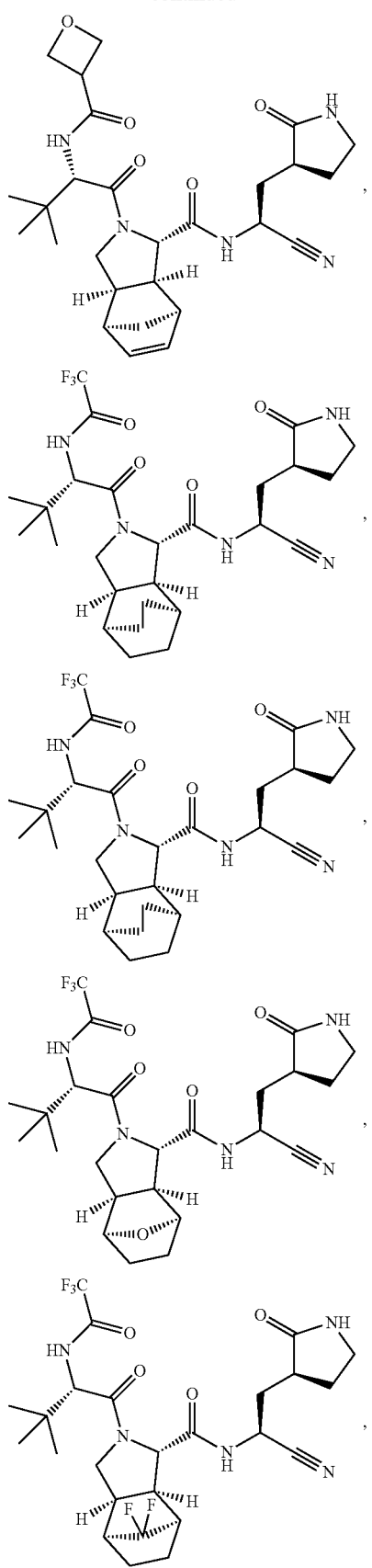
88
-continued
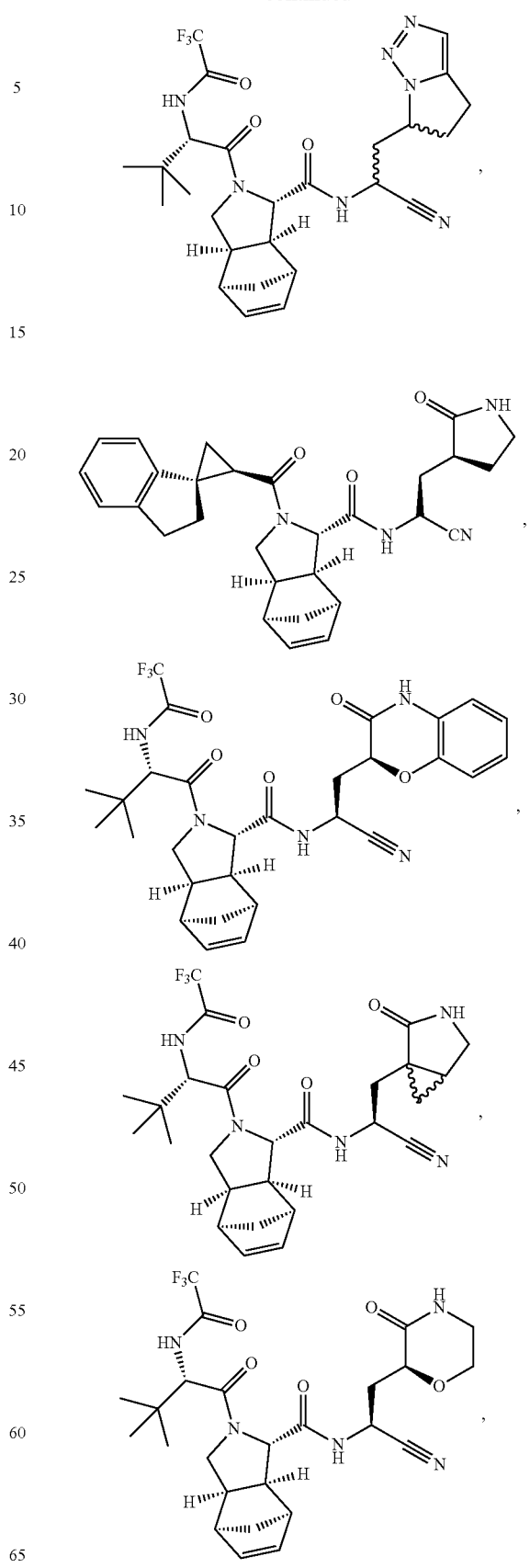

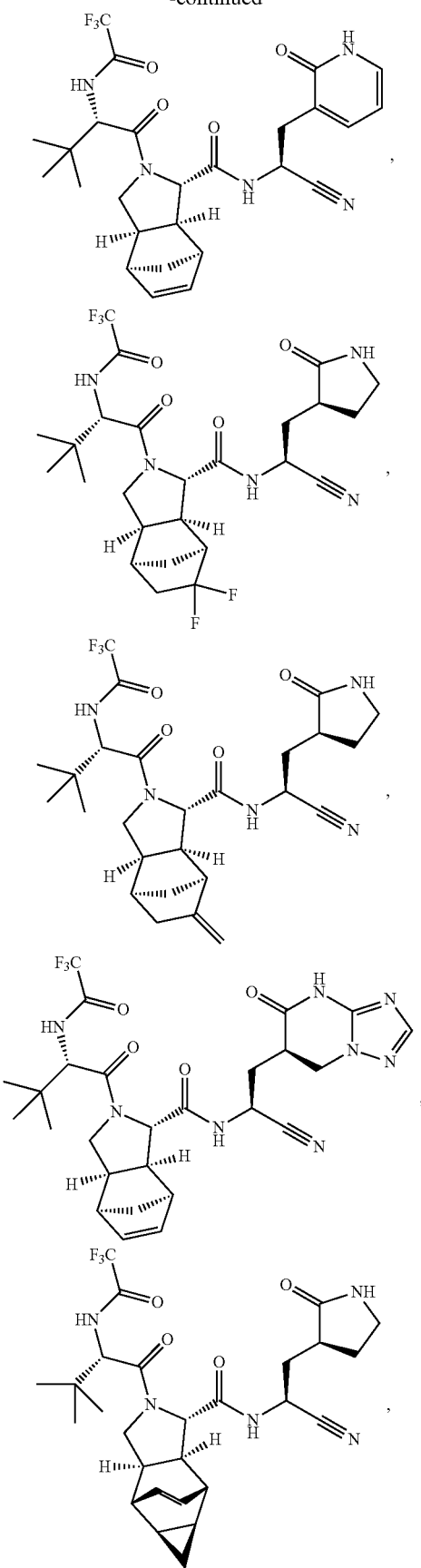
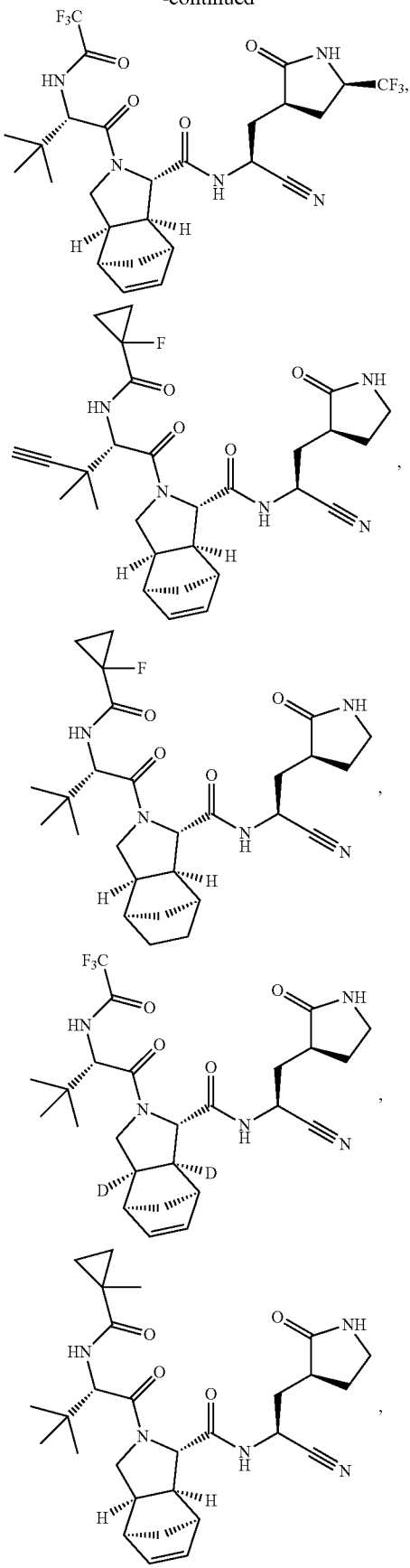

91 92
-continued -continued
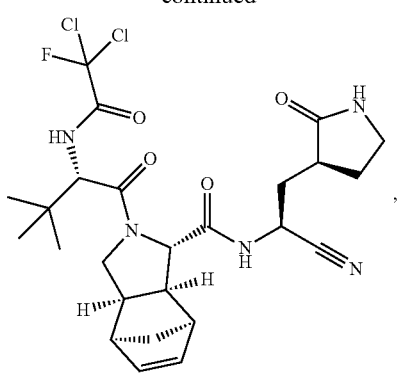
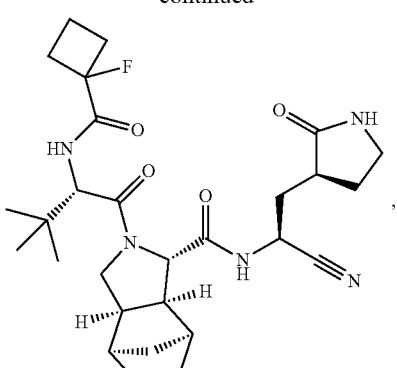
,
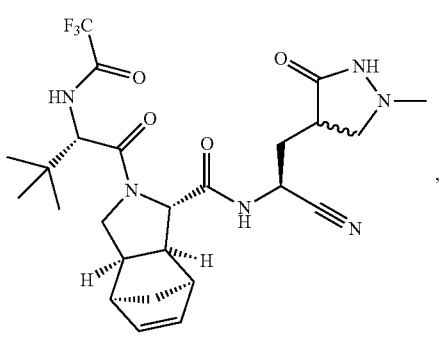
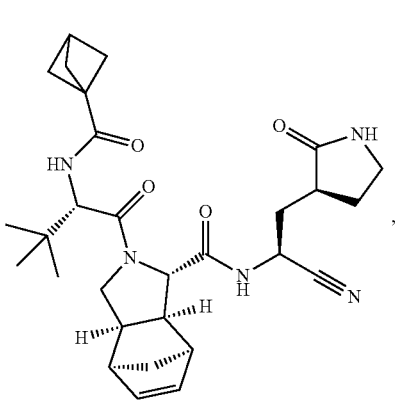
,
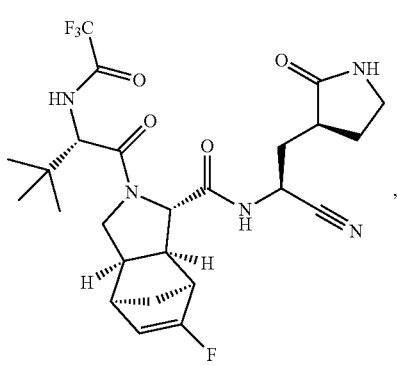
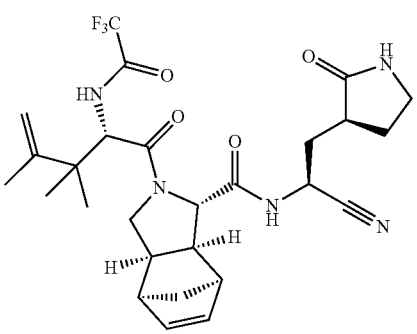
,
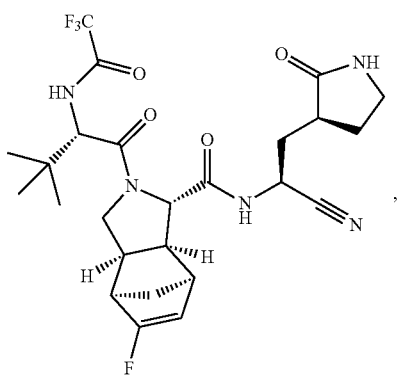
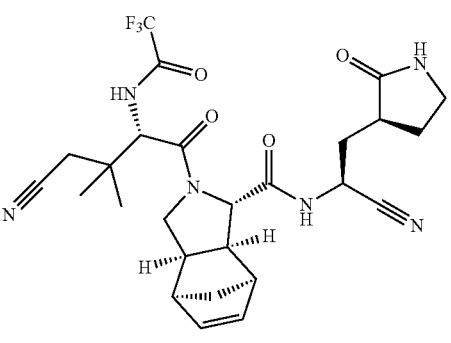
, 93
-continued
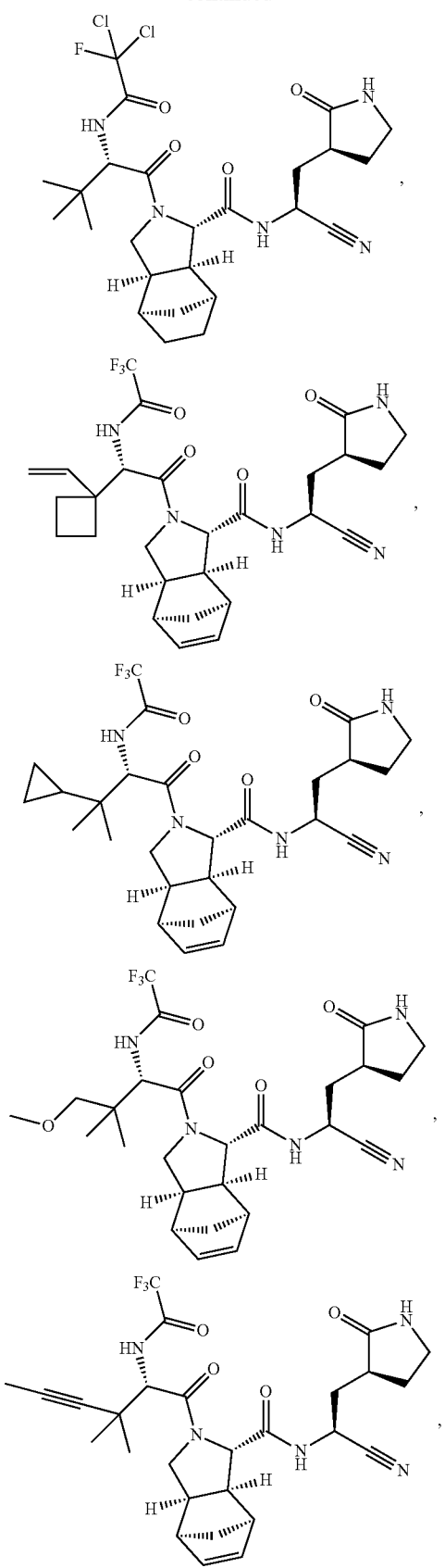
94
-continued
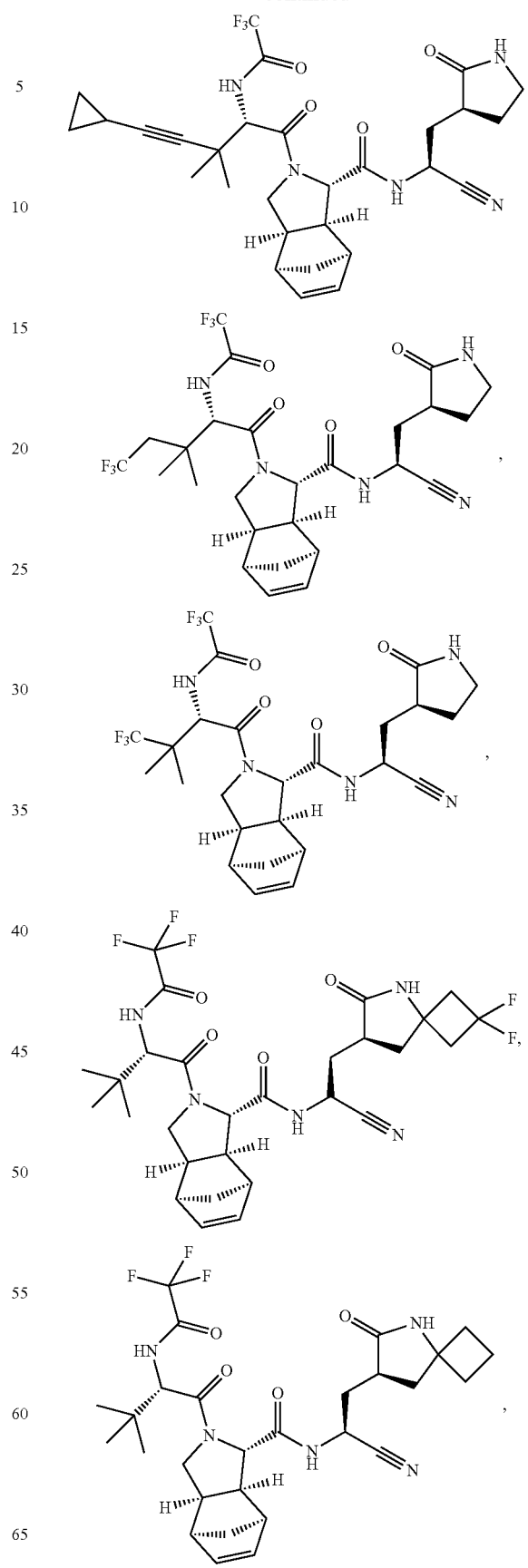

95
-continued
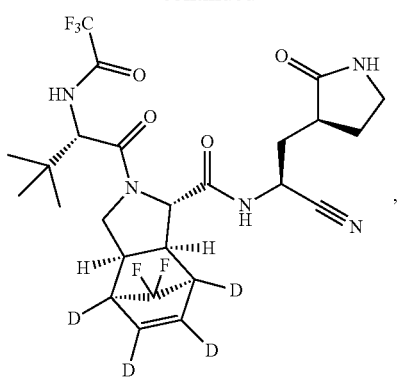
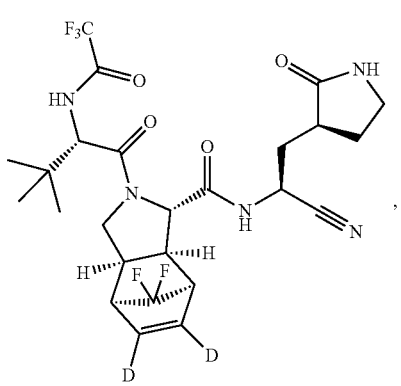
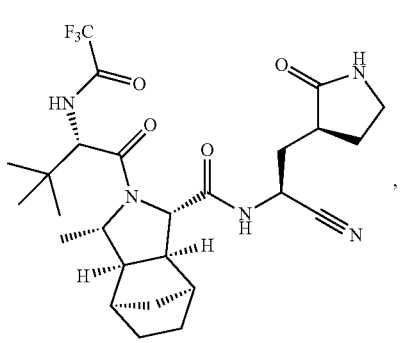
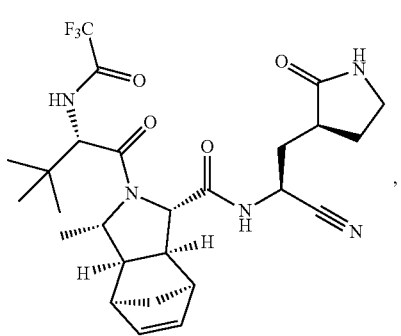
96
-continued
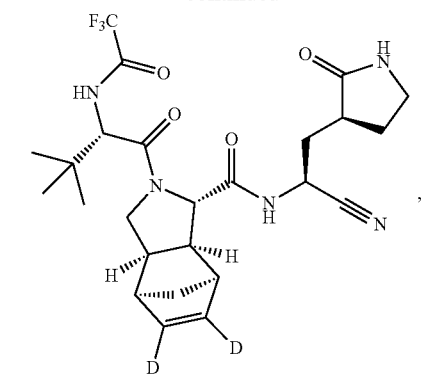
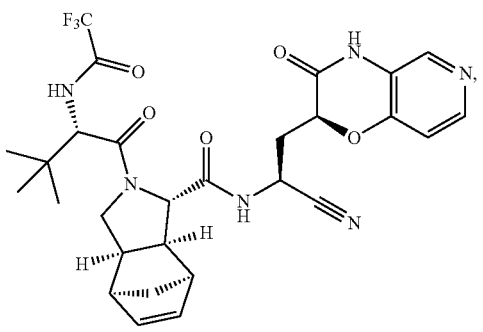
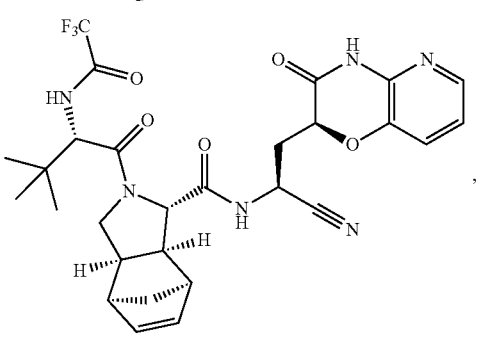
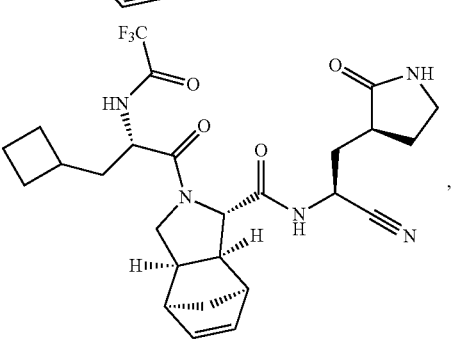
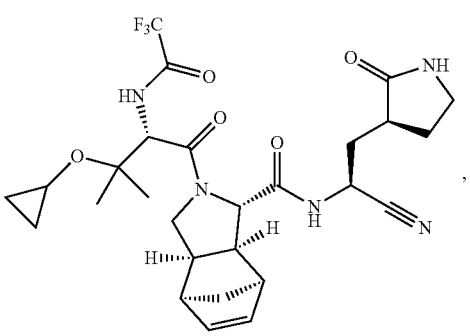

97
-continued
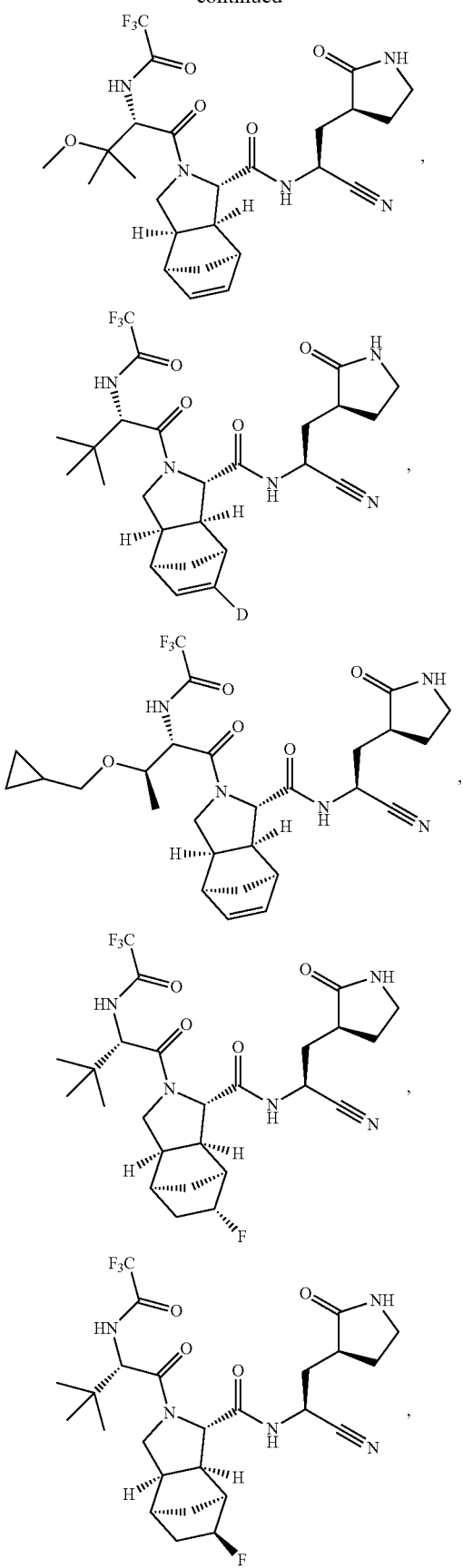
98
-continued
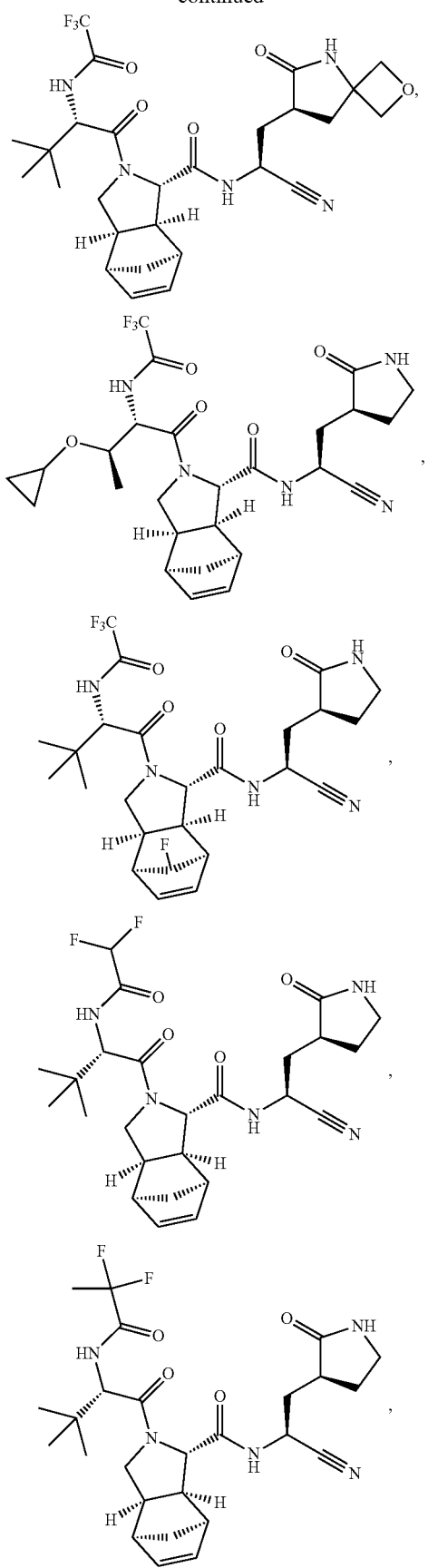

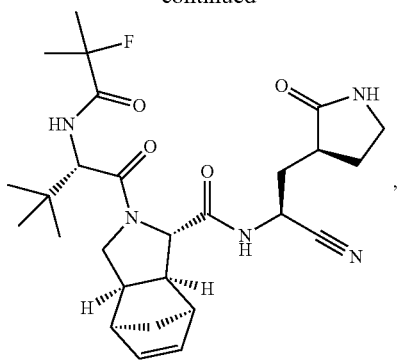
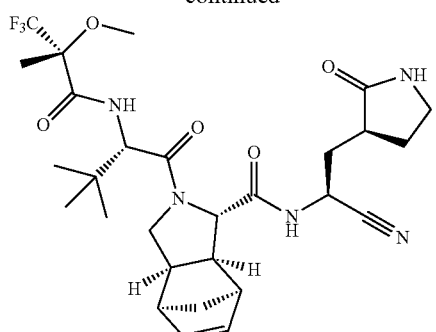
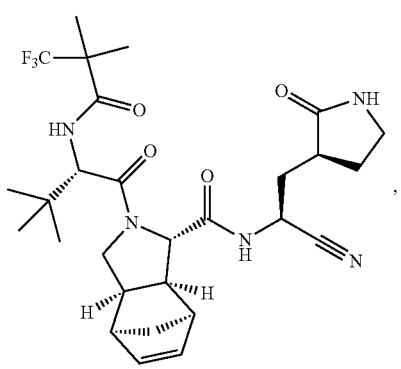
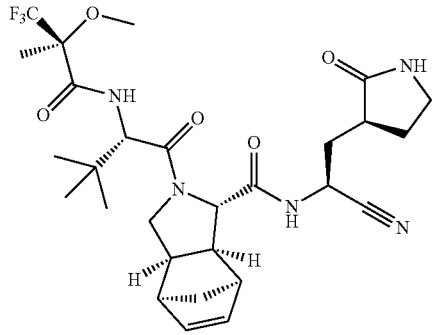
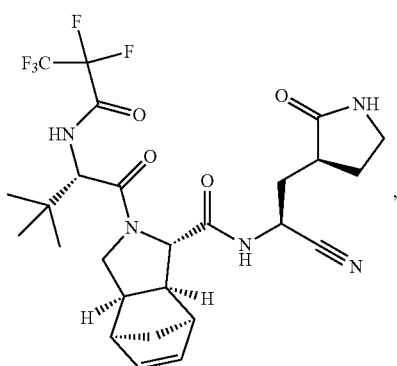
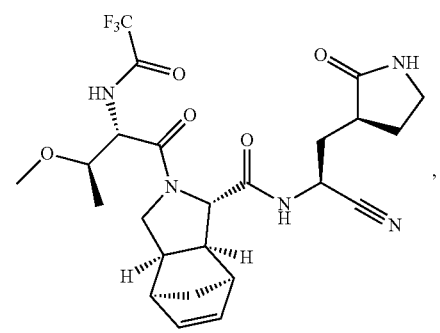
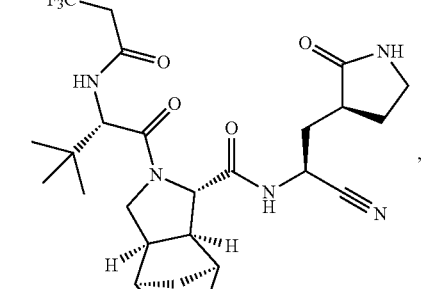
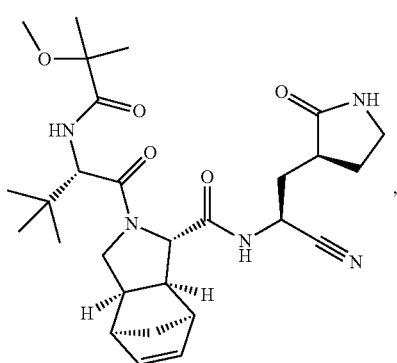
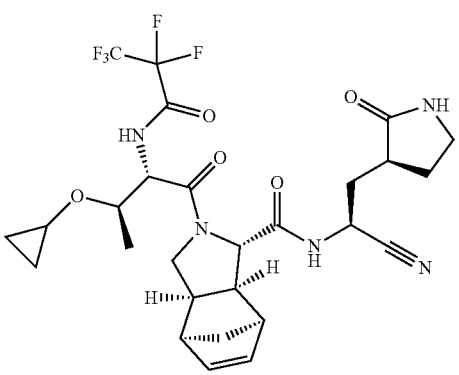

101
-continued
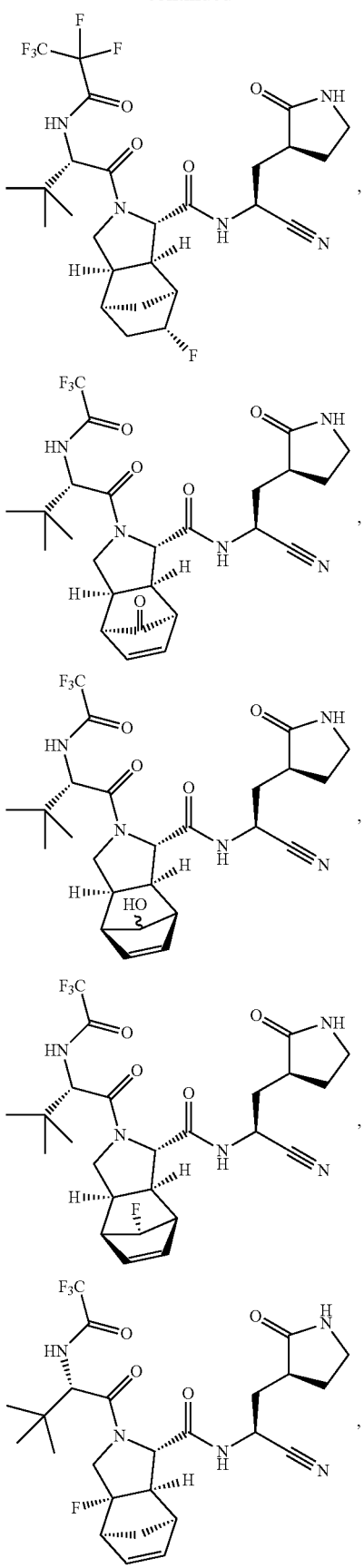
102
-continued
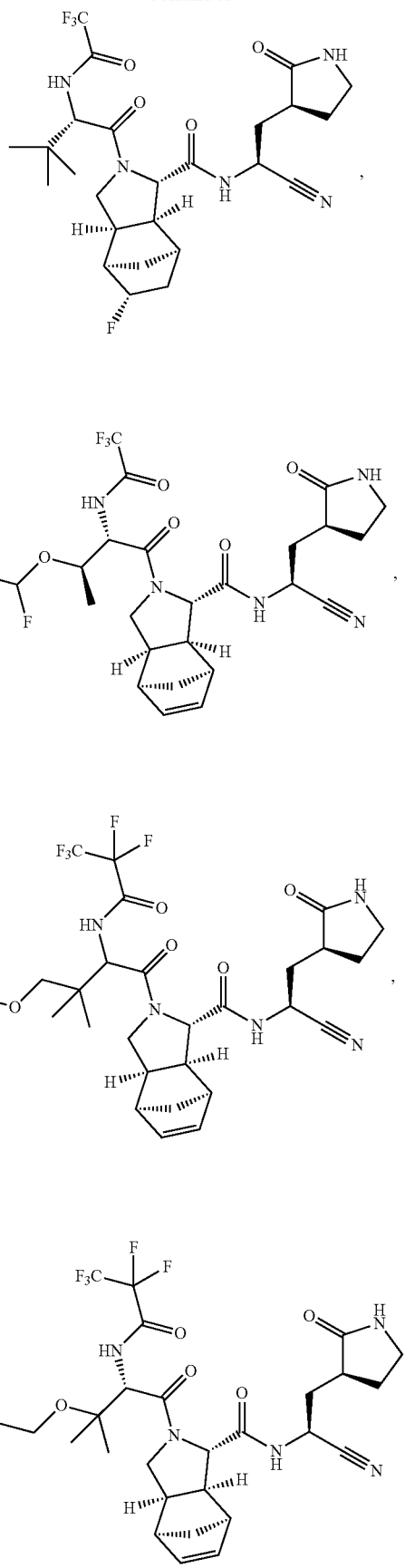

103
-continued
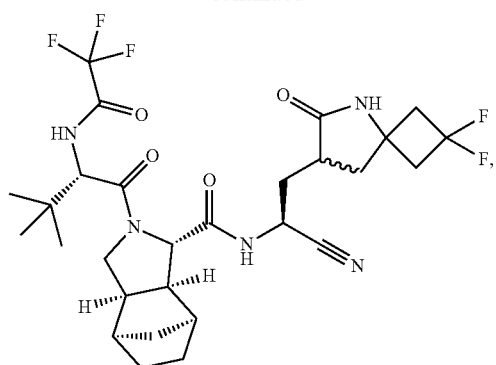
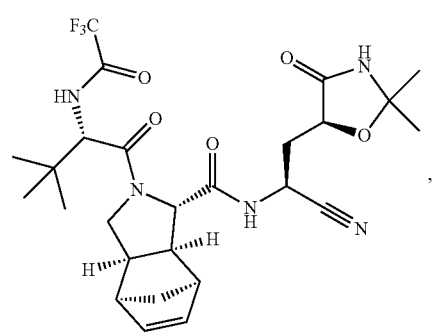
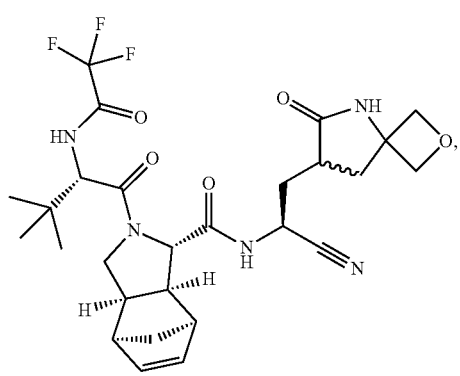
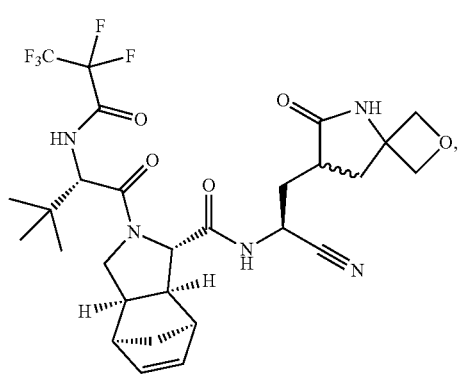
104
-continued
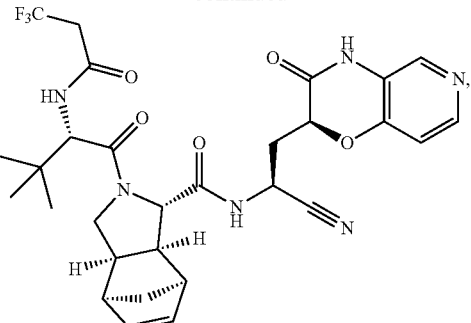
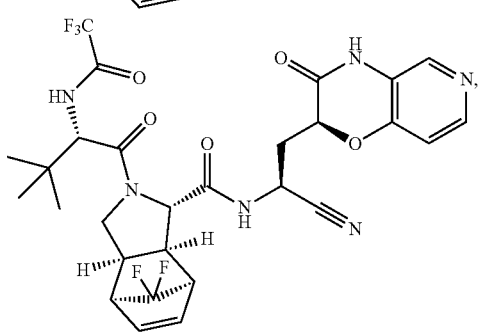
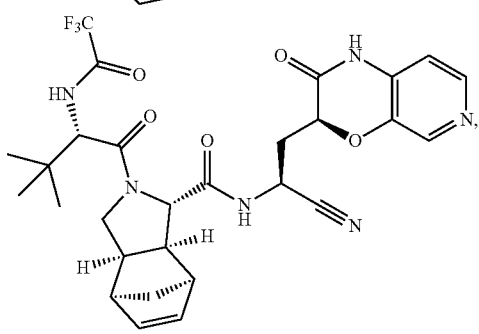
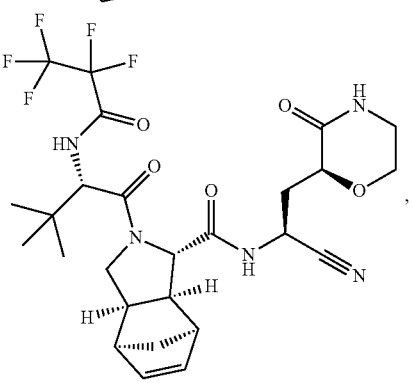
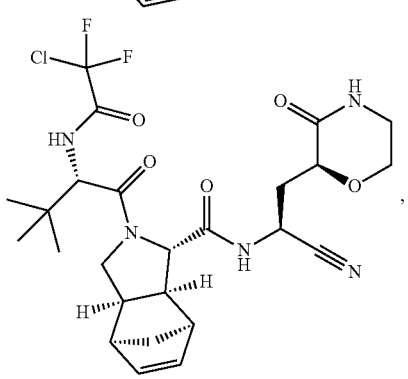

105
-continued
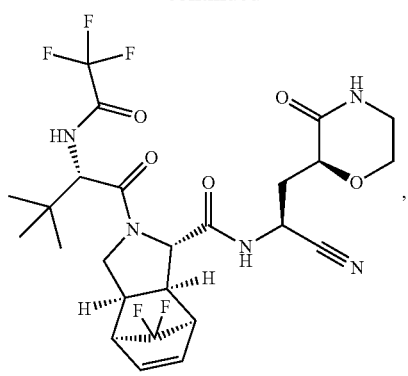
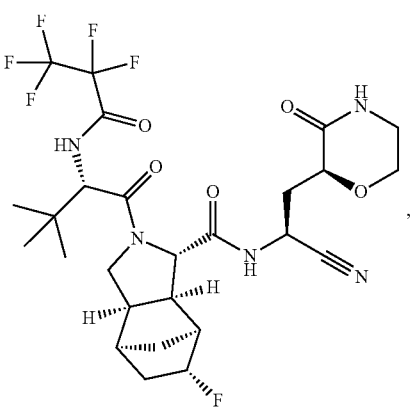
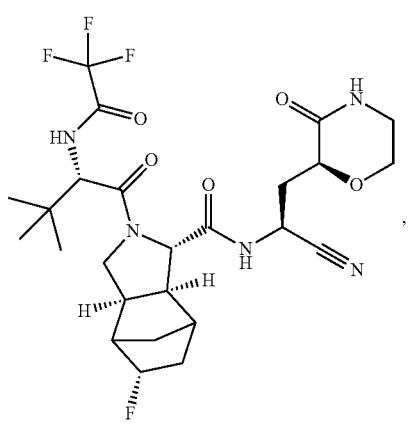
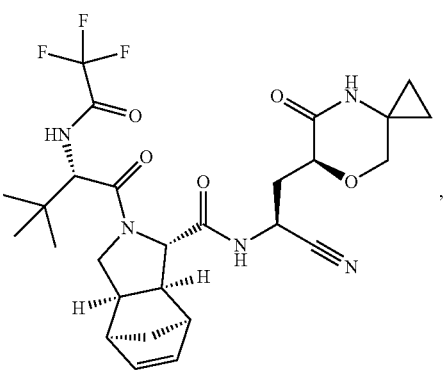
106
-continued
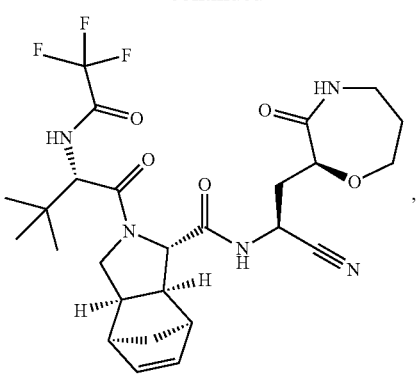
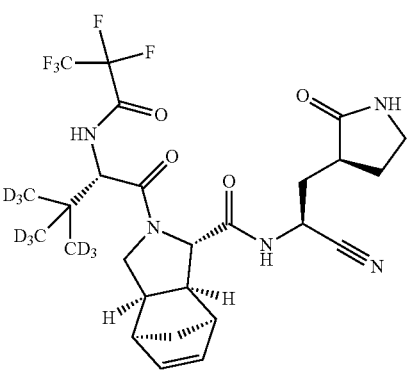
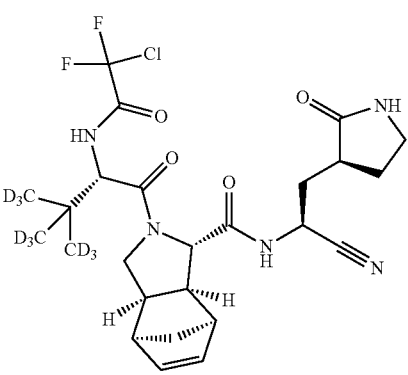
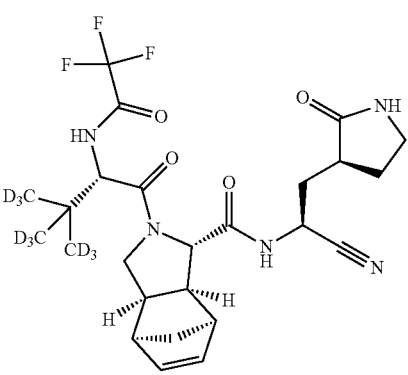

107
-continued
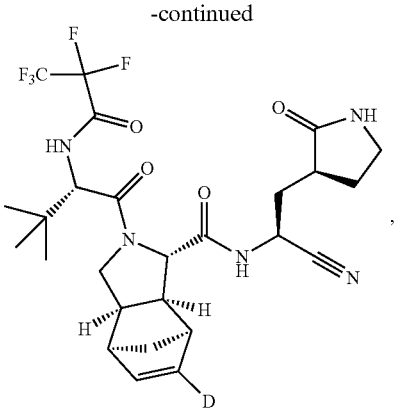
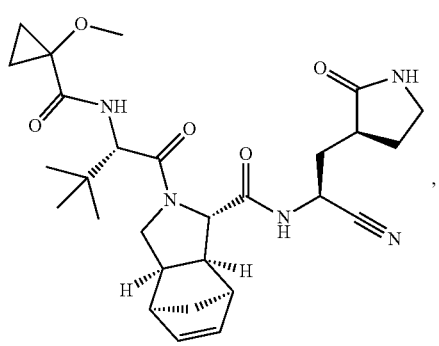
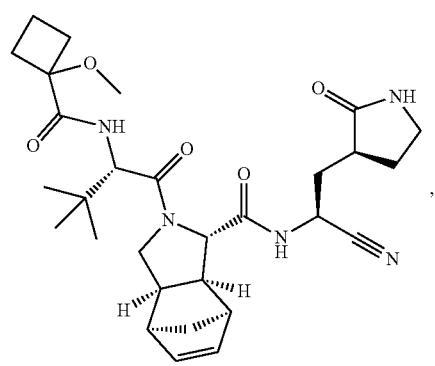
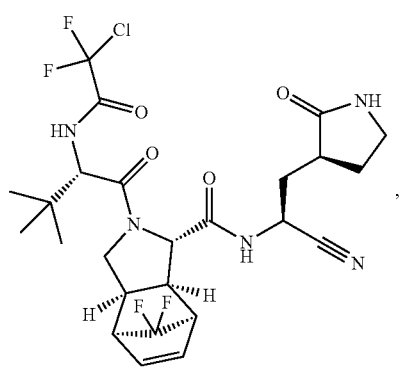
108
-continued
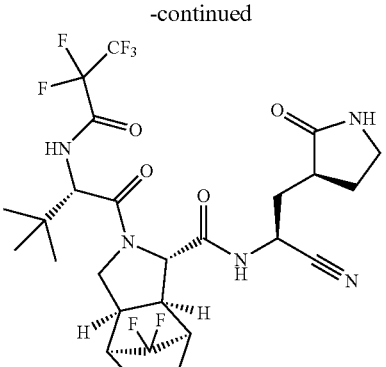
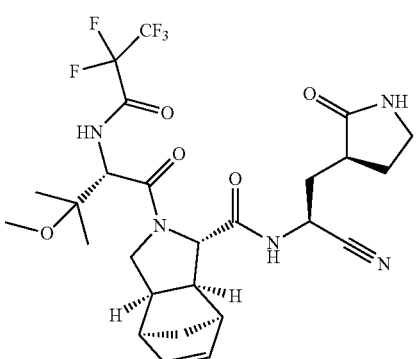
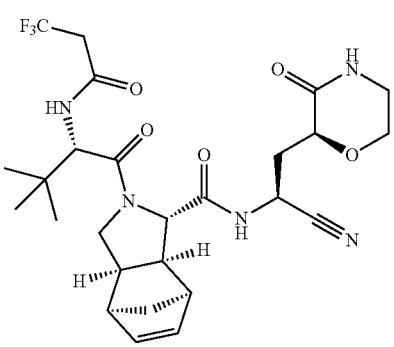
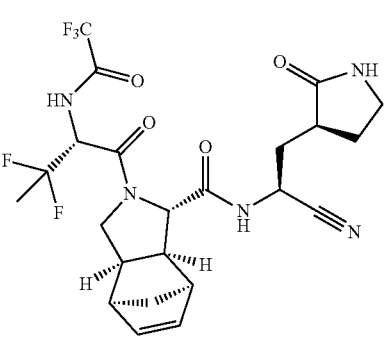

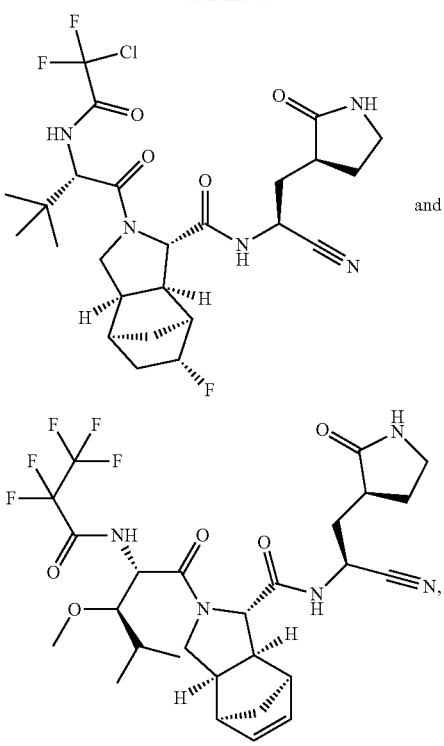
and
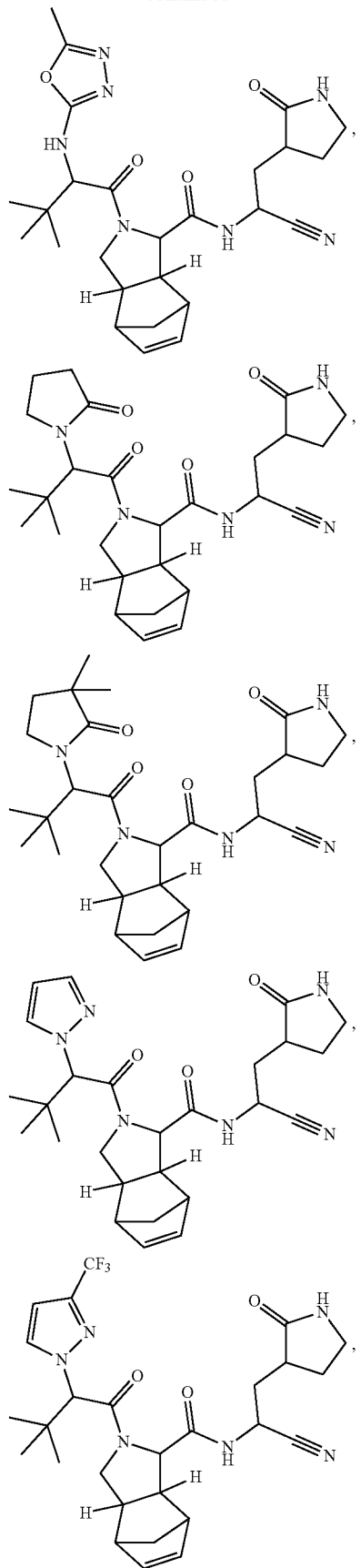
or a pharmaceutically acceptable salt of any of the foregoing.
Further examples of compounds of Formula (I), include the following:
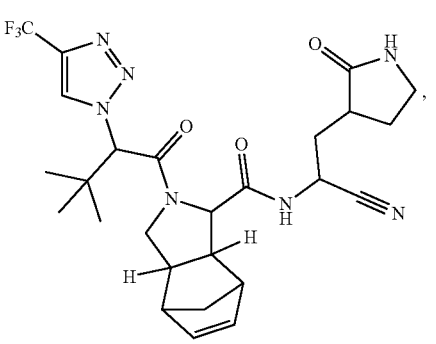
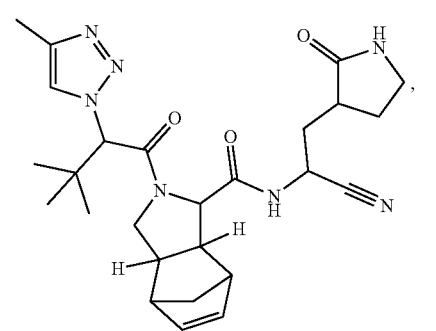

-continued
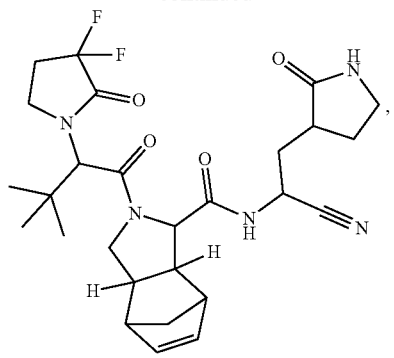
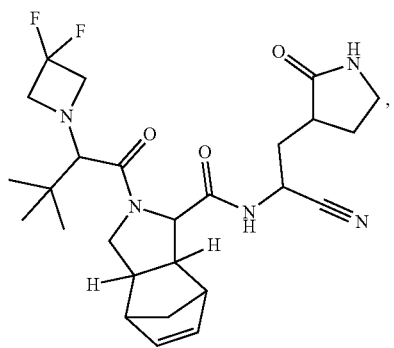
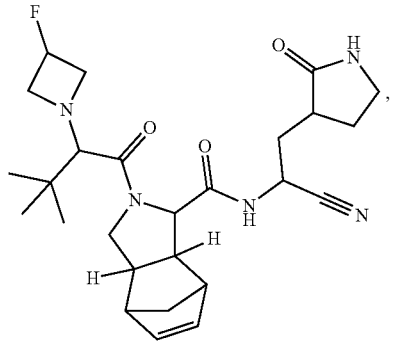

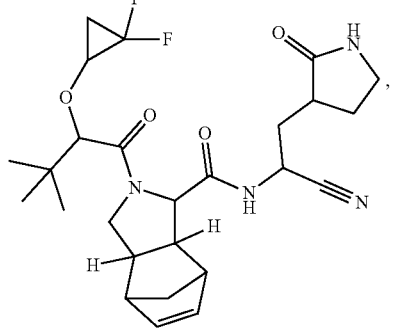
-continued
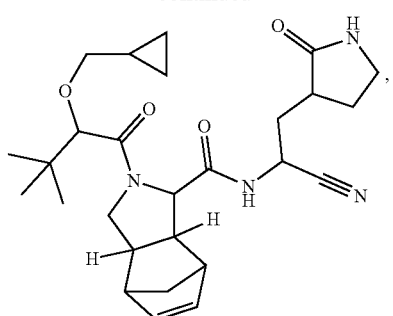
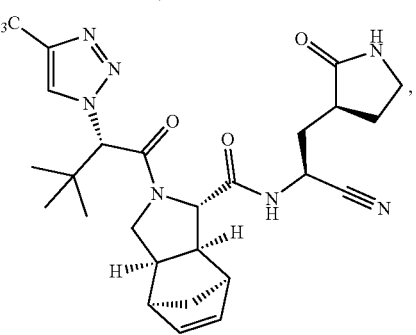
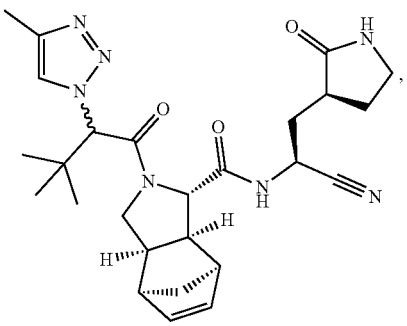
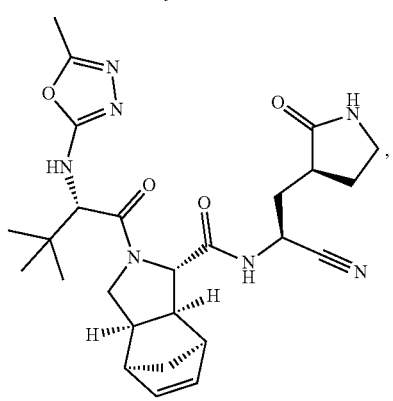
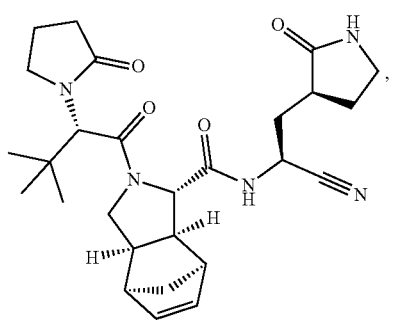

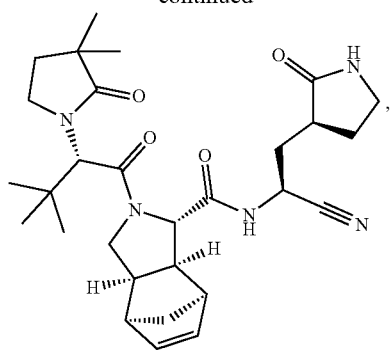
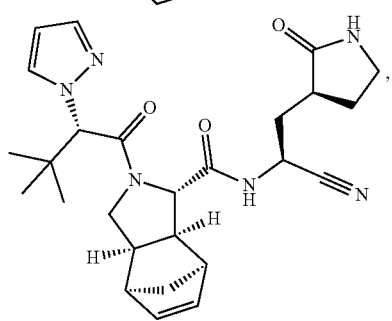
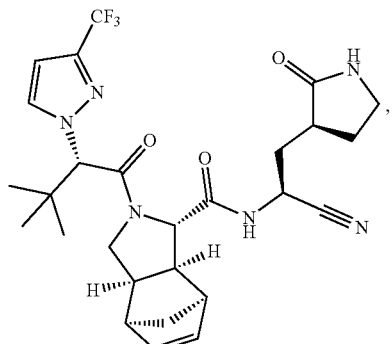
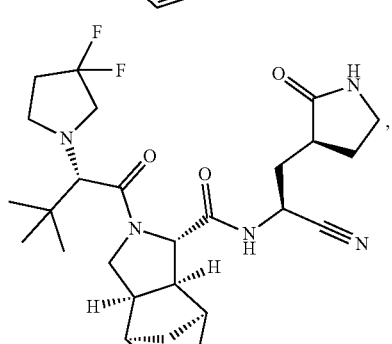
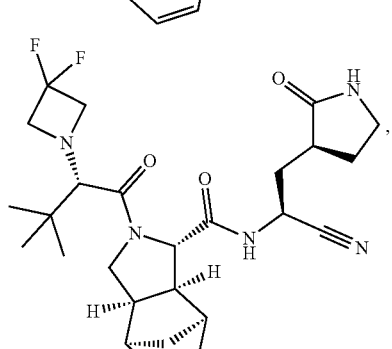
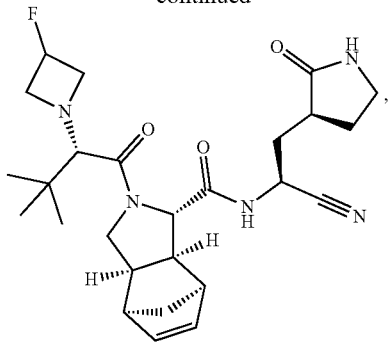
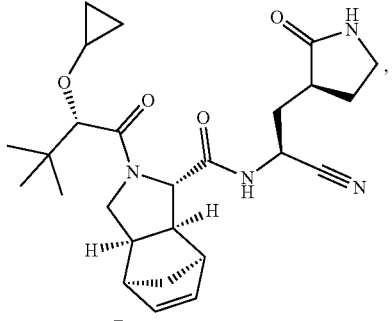
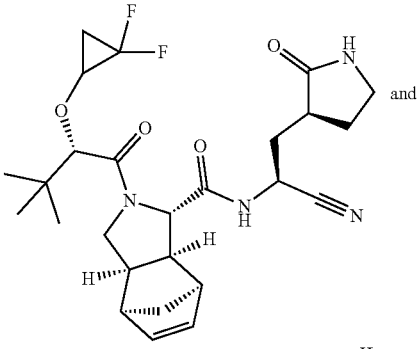
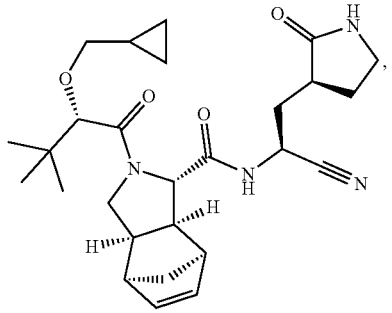
and
or a pharmaceutically acceptable salt of any of the foregoing.
In some embodiments, Ring A¹ can be
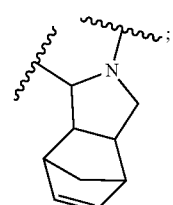

and R⁵ can be

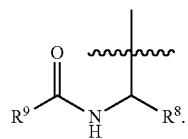

In some embodiments, Ring A¹ can be

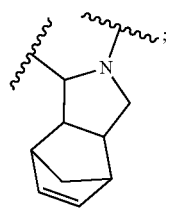 [SMILES: *C1C2C3C=CC(C3)C2CN1*]

R¹ can be cyano; R² can be hydrogen; R³ can be an unsubstituted or a substituted monocyclic nitrogen-containing heterocyclyl(C₁₋₄ alkyl); R⁴ can be hydrogen; and R⁵ can be

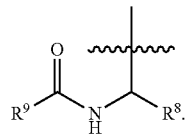

In some embodiments, Ring A¹ can be

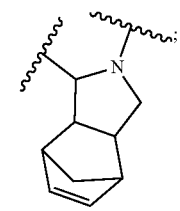 [SMILES: *C1C2C3C=CC(C3)C2CN1*]

R¹ can be cyano; R² can be hydrogen; R³ can be an unsubstituted or a substituted monocyclic nitrogen-containing heterocyclyl(C₁₋₄ alkyl); R⁴ can be hydrogen; R⁵ can be

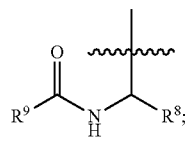

R⁸ can be an unsubstituted C₂₋₆ alkyl; and R⁹ can be, an unsubstituted C₁₋₆ haloalkyl. In some embodiments, Ring A¹ can be

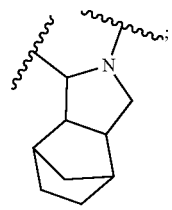 [SMILES: *C1C2C3CCC(C3)C2CN1*]

and R⁵ can be

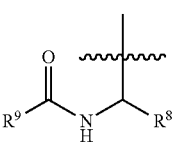

In some embodiments, Ring A¹ can be

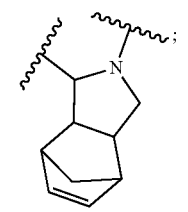

R¹ can be cyano; R² can be hydrogen; R³ can be an unsubstituted or a substituted monocyclic nitrogen-containing heterocyclyl(C₁₋₄ alkyl); R⁴ can be hydrogen; and R⁵ can be

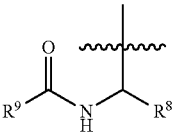

In some embodiments, Ring A¹ can be

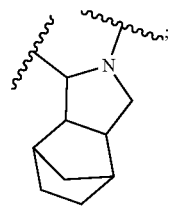 [SMILES: *C1C2C3CCC(C3)C2CN1*]

R¹ can be cyano; R² can be hydrogen; R³ can be an unsubstituted or a substituted monocyclic nitrogen-containing heterocyclyl(C₁₋₄ alkyl); R⁴ can be hydrogen; R⁵ can be

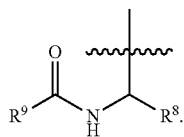

$R^8$ can be an unsubstituted $C_{2-6}$ alkyl; and $R^9$ can be an unsubstituted $C_{1-6}$ haloalkyl. In some embodiments, Ring A1 cannot be

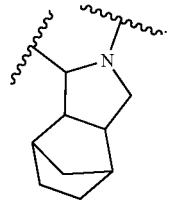 [SMILES: *C1C2C3CCC(C3)C2CN1*]

In some embodiments, Ring $A^1$ cannot be

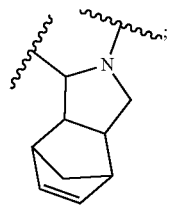 [SMILES: *C1C2C3C=CC(C3)C2CN1*]

Synthesis

Compounds of Formula (I) along with those described herein may be prepared in various ways. General synthetic routes for preparing compounds of Formula (I) are shown and described herein along with some examples of starting materials used to synthesize compounds described herein. Additionally, for the purpose of the general synthetic routes, the structures depicted are appropriately protected, as known by one skilled in the art and the generic structures are meant to include these protecting groups. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

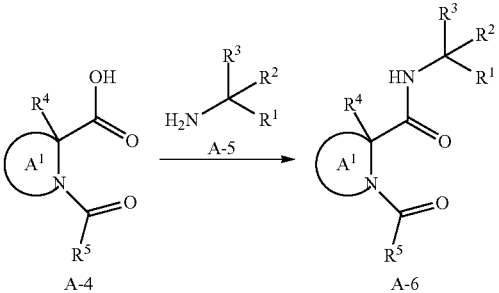

Scheme A describes the synthesis of compounds of general Formula (A-6). An amino ester of general Formula (A-1) (Alk represents alkyl) with an acid of general Formula (A-2), either by activating the carboxylic acid by converting it to an acid chloride, followed by reaction with the amino acid in the presence of a base, or by activation of the acid with a coupling reagent (such as HATU) followed by coupling with the amino ester in the presence of a base (such as DIPEA), resulting in a compound of general Formula (A-3). The ester functionality of general Formula (A-3) can be hydrolyzed, for example, under basic conditions of —OAlk is —OMe, using LiOH in MeOH, providing in a compound of general Formula (A-4). Further coupling of the carboxylic acid of general Formula (A-4) with an amine of general Formula (A-5) can provide a compound of general Formula (A-6). For the purpose of the generic synthesis, $R^1$ may be a latent functionality, converted to a functionality as described herein for $R^1$.

Scheme A1

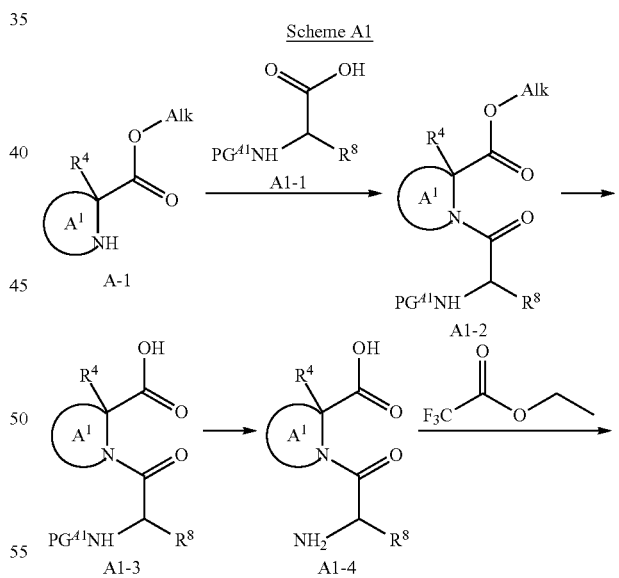

Scheme A

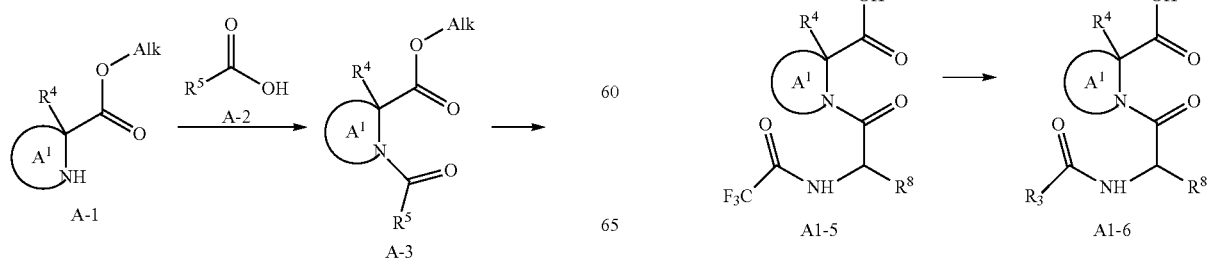

Alternatively, as described in Scheme A1, a sub-group of amino acids of general Formula (A1-5) can be prepared as described in Scheme A1. A protected (PG$^{A1}$) amino acid of general Formula (A1-1) can be coupled with an aminoester of general Formula (A-1) under known amide formation conditions, for example, HATU and iPr$_2$NEt. The ester of a compound of Formula (A1-2) can be deprotected, for example, by using LiOH in THF/H$_2$O, resulting in the acid of general Formula (A1-3). The protecting group PG$^{A1}$ can be removed, for example, by treatment with TFA in case PG$^{A1}$ being Boc, resulting in a compound of general Formula (A1-4). This compound can be converted to a compound of general Formula (A1-5) (for example, by treatment with ethyl 2,2,2-trifluoroacetate in the presence of triethylamine) or alternatively, a compound of general Formula (A1-6) (for example, by treatment of a compound of general Formula (A1-4) with an alkyl trihaloacetate, (such as ethyl 2,2-dichloro-2-fluoroacetate, methyl 2-chloro-2,2-difluoroacetate or ethyl 2-chloro-2,2-difluoroacetate) in the presence of a base like triethylamine (and optionally an additive like and N-methylimidazole), or an alkyl 2,2,3,3,3-pentafluoropropanoate (such as methyl or ethyl 2,2,3,3,3-pentafluoropropanoate) in the presence of a base (for example, triethylamine and an additive, for example, N-methylimidazole)).

General methodology for the synthesis of amino acids of general Formula (A1-1), or precursors that could be converted to an amino acid of general Formula (A1-1) by one skilled in the art, are described in the literature, and include the following examples:

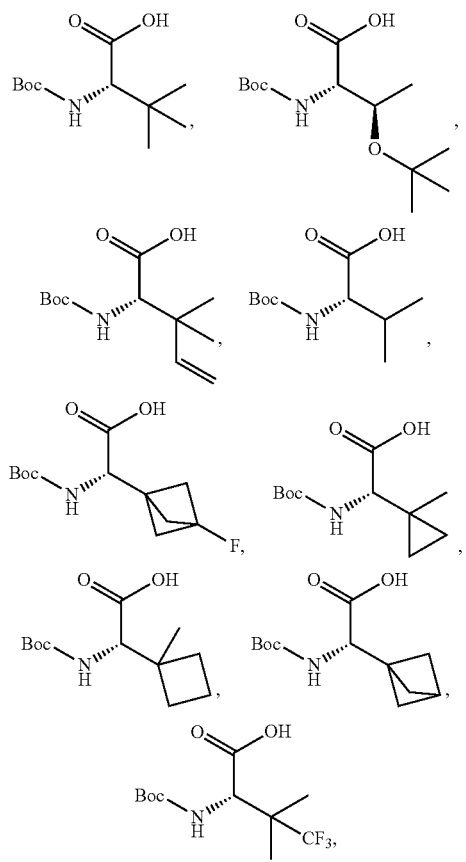

-continued

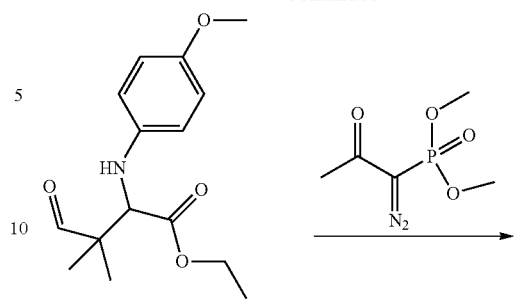

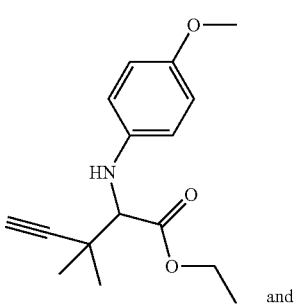

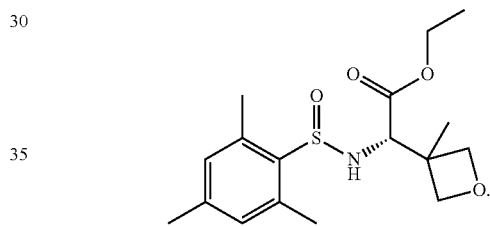

and

Scheme B

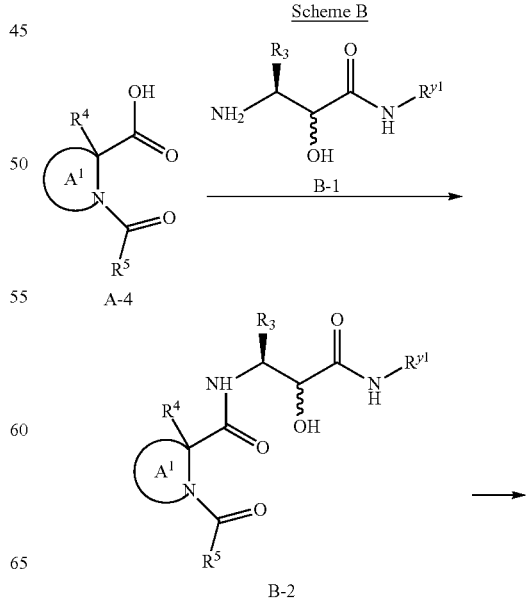

121

-continued

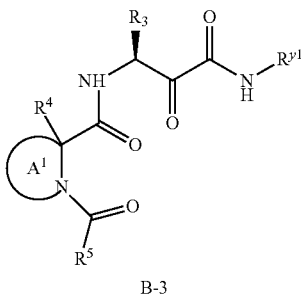

B-3

In Scheme B, a carboxylic acid of general Formula (A-4) can be coupled with an amino acid of general Formula (B-1), for example, under the influence of a coupling reagent (such as T3P) and a base (for example, DIPEA). The obtained compound of general Formula (B-2) can be oxidized, providing in a compound of general Formula (B-3). In Scheme B, $R^{y1}$ can be part of the ketoamide described herein with respect to $R^1$.

Scheme B1

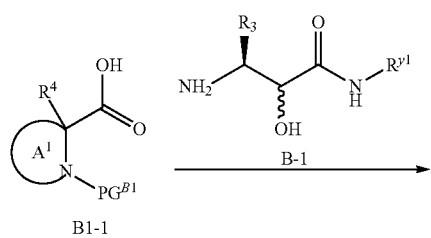

B1-1

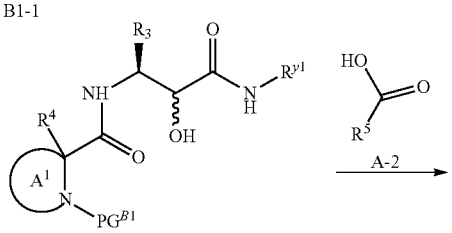

B1-2

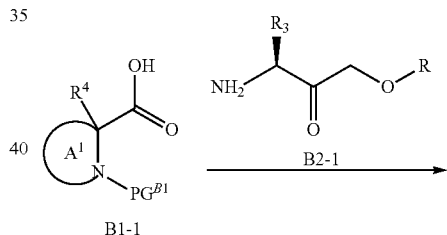

B-2

Alternatively, as depicted in Scheme B1, an amino acid of general Formula (B1-1) (with $PG^{B1}$ a protecting group of the nitrogen, for example, -Boc) can be coupled with a compound of general Formula (B-1), similar as described for the conversion of a compound of general Formula (A-4) to a compound of general Formula (B-2). The protecting group can be removed, for example, by treatment with an acid in case of $PG^{B1}$ being Boc, followed by coupling with a compound of general Formula (A-2), resulting in the formation of a compound of general formula (B-2).

122

Scheme B2

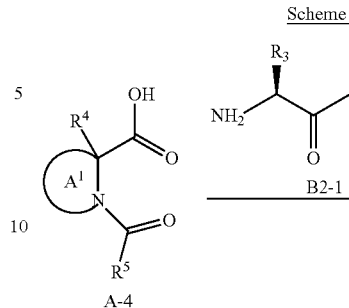

A-4

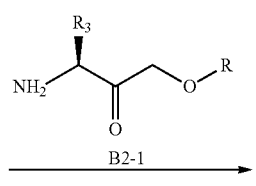

B2-2

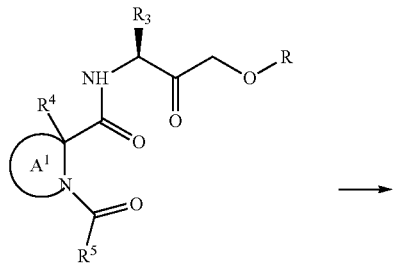

B2-3

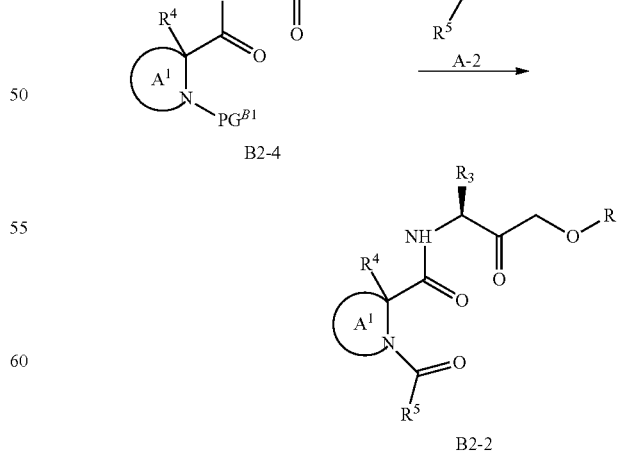

B2-4

B2-2

As described herein, $R^1$ can be a substituted acyl, where the possible groups that can be present on the acyl include hydroxy, a substituted or an unsubstituted alkoxy (for example, —O-(an unsubstituted $C_{1-4}$ alkyl) and —O-(an unsubstituted $C_{3-6}$ cycloalkyl)), an unsubstituted $C_{1-4}$ alkyl (such as a heteroaryl substituted with an unsubstituted $C_{1-4}$ alkyl), a substituted or an unsubstituted phenoxy or a substituted or an unsubstituted benzyloxy). In Scheme B2, R can represent any of the aforementioned moieties that can be present on a substituted acyl for $R^1$. Compounds of general Formulae (B2-2) and (B2-3) can be prepared as described in Scheme B2. An amino-ketone compound of general Formula (B2-1) can be coupled to a carboxylic acid of general Formula (A-4) or (B1-1) under typical amide coupling conditions. A compound of general Formula (B2-2) can be optionally further converted in a hydroxyketone of general Formula (B2-3), for example, in case where R represents a benzyl group, by catalytic hydrogenolysis. The $PG^{B1}$ of a compound of general Formula (B2-4) can be deprotected (for example in the case wherein $PG^{B1}$ is a Boc-group, by treatment with HCl in $Et_2O$). The amine can then be coupled with a carboxylic acid of general Formula (A-2) under typical amide bound formation conditions, to provide a compound of general Formula (B2-2).

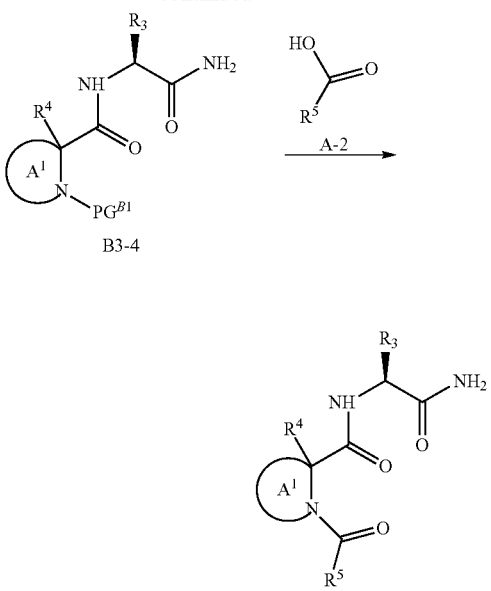

Similar as described in Scheme B2 for a compound of Formula (B2-2), using an amide of general Formula (B3-1) in place of a compound of general Formula (B2-1). a compound of general Formula (B3-2) can be obtained. Conversion of a compound of general Formula (B3-2) to a compound of general Formula B3-3 can, for example, occur under the influence of trifluoroacetic anhydride (TFAA) and pyridine in $CH_2Cl_2$, or by application of the Burgess reagent.

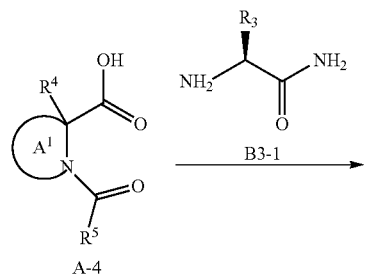

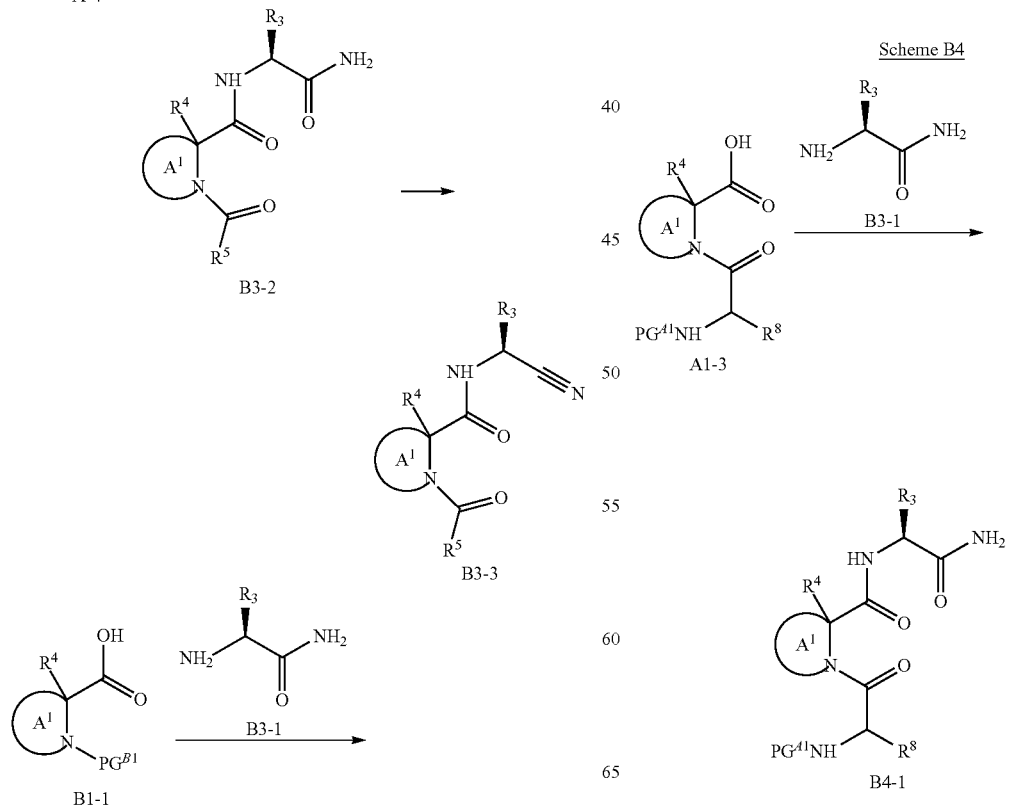

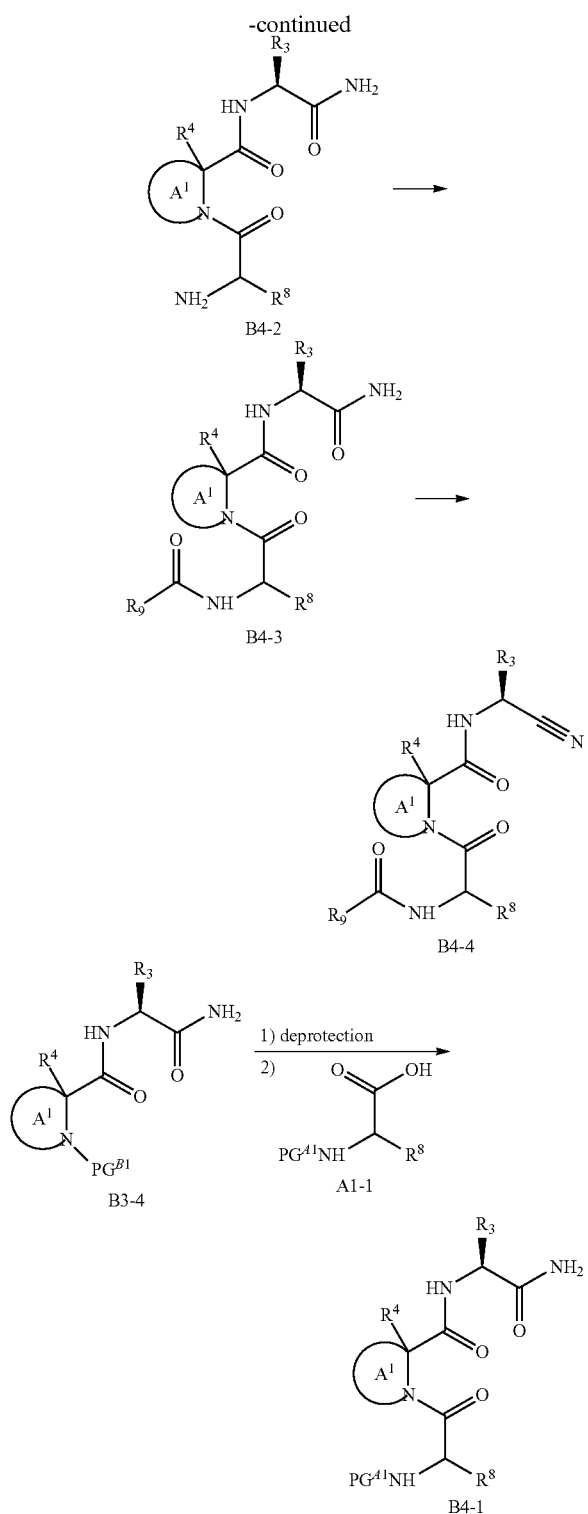

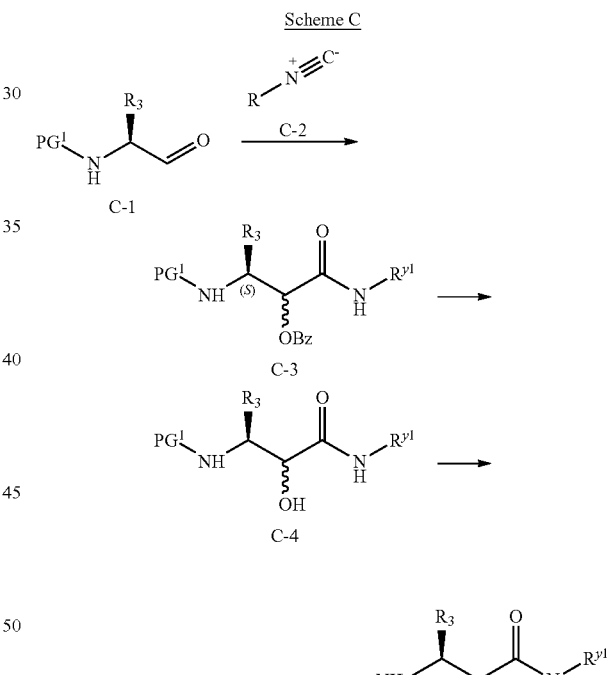

Formula (B4-3) (for example, by treatment with an alkyl trihaloacetate, such as ethyl 2,2-dichloro-2-fluoroacetate, methyl 2-chloro-2,2-difluoroacetate ethyl 2-chloro-2,2-difluoroacetate or ethyl 2,2,2-trifluoroacetate, in the presence of a base (such as triethylamine and optionally an additive, for example, N-methylimidazole), or an alkyl 2,2,3,3,3-pentafluoropropanoate (such as methyl or ethyl 2,2,3,3,3-pentafluoropropanoate) in the presence of a base (for example, triethylamine and an additive, for example, N-methylimidazole); or a carboxylic acid in the presence of a coupling reagent (such as EDC or HATU) and a base (such as NEtO). The compound of general Formula (B4-3) can be converted to a compound of general Formula (B4-4), similar as outlined for the conversion of a compound of general Formula (B3-2) to a compound of general Formula (B3-3). Alternatively, a compound of general Formula (B4-2) can be converted to a compound of general Formula (B4-4) (for example, by treatment with T3P and pyridine in the presence of potassium 2,2,3,3,3-pentafluoropropanoate for —$R_9$ being —$CF_2CF_3$). A compound of general Formula (B4-1) can be obtained by deprotection of $PG^B$ of a compound of general Formula (B3-4), followed by coupling with a compound of general Formula (A1-1).

For the purpose of the generic synthesis the transformations described in Scheme B3 include transformations as described in Scheme B4, where a compound of general Formula (A1-3) can be coupled with amine of general Formula (B3-1), resulting in a compound of general Formula (B4-1), where $PG^{A1}$ can be a protecting group which can be removed (for example, in case $PG^{A1}$ is Boc, by treatment with HCl or TFA). The compound of general Formula (B4-2) can be converted in a compound of general A compound of general Formula (B-1) can be prepared as outlined in Scheme C. An aldehyde of general Formula (C-1) ($PG^1$ can be a nitrogen protecting group, for example—Boc) and an isonitrile of general Formula (C-2), in the presence of a carboxylic acid (for example, benzoic acid), can be condensed in a Passerini-like reaction towards a compound of general Formula (C-3). After hydrolysis, a compound of general Formula (C-4) can be obtained. The $PG^1$ can be removed, for example, by treatment with HCl when $PG^1$ can be Boc.

Scheme C1

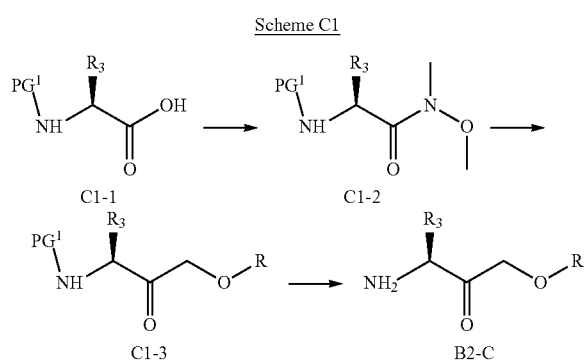

An amino ketone of general Formula (B2-1), can be prepared as outline in Scheme C1. A protected amino acid of general Formula (C1-1) can be converted to its corresponding Weinreb amide under typical amide coupling conditions. Addition of an organometallic reagent to the Weinreb amide, followed by work-up, can result in a ketone of general Formula (C1-3). An example, wherein R can be benzyl, is the formation of an organometallic reagent by mixing Mg, $HgCl_2$ and benzylchloromethyl ether, followed by addition to a Weinreb amide of general Formula (C1-2), followed by work-up with saturated ammonium chloride. The protecting group ($PG^1$) can be removed (for example, when $PG^1$ is Boc, the protecting group can be removed using HCl) resulting in the formation of an amino ketone of general Formula (B2-1). When HCl is used for the deprotection, a compound of general Formula (B2-1) can be obtained as a HCl salt. Examples of a compound of general Formula (C1-1) are (S)-2-((tert-butoxycarbonyl)amino)-3-((S)-2-oxopiperidin-3-yl)propanoic acid and (S)-2-((tert-butoxycarbonyl)amino)-3-((S)-2-oxopyrrolidin-3-yl)propanoic acid.

Scheme D1

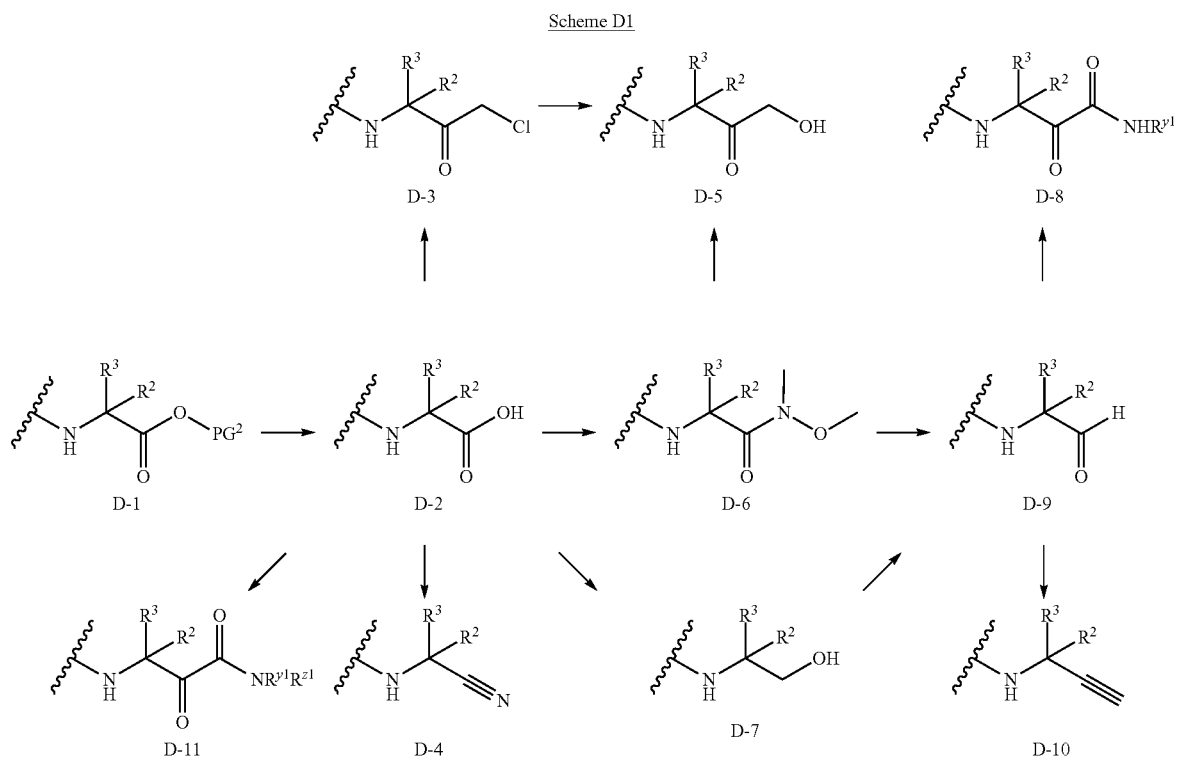

Scheme D2

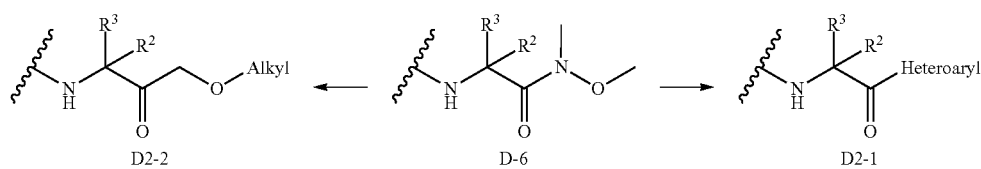

Other conversions for $R^1$ described herein are shown in Schemes D1 and D2. In Schemes D1 and D2, $PG^2$ represents an appropriate protecting group, and $R^{z1}$ and $R^{y1}$ are part of the ketoamide described herein with respect to $R^1$.

Scheme E

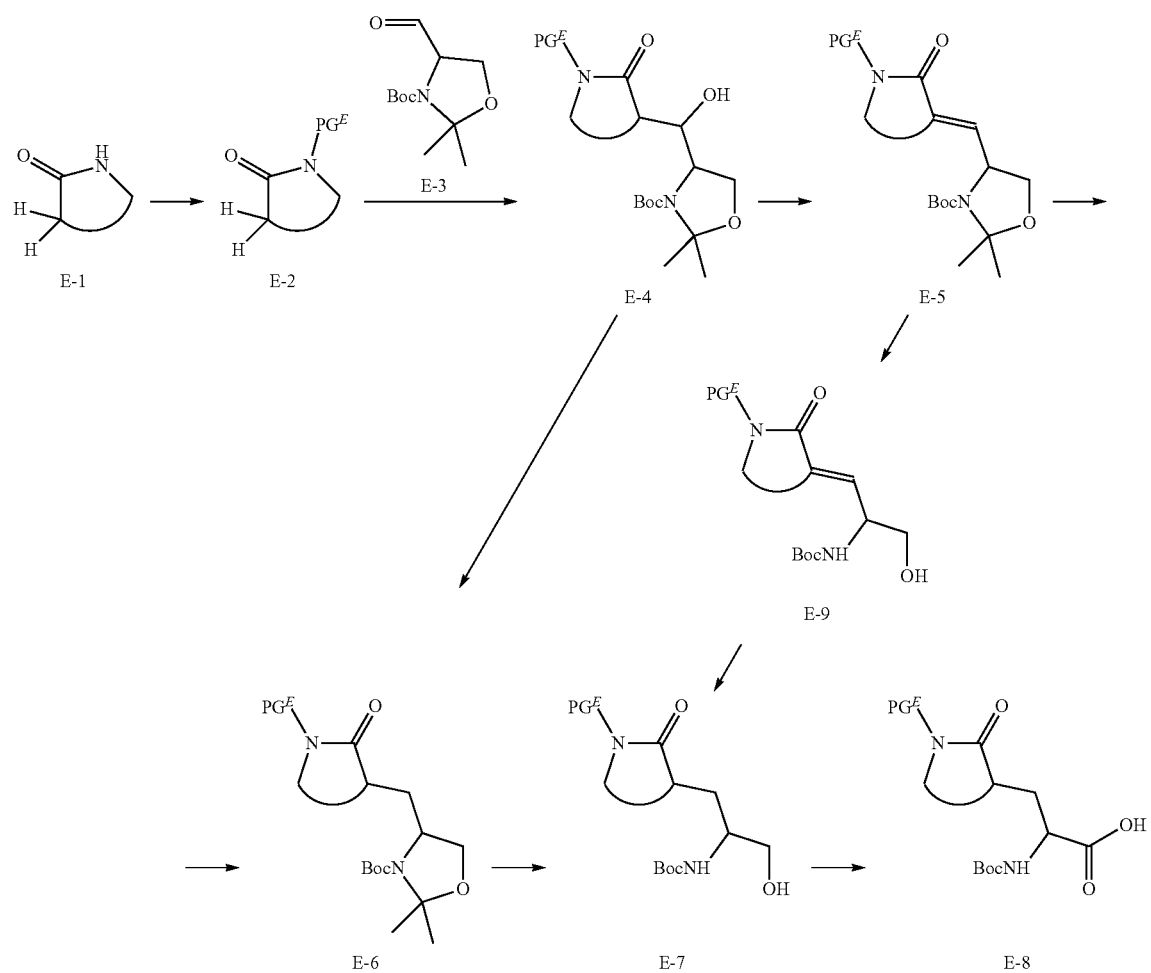

A method for preparing a sub-group of amino acids of general Formula (E-8) are provided in Scheme E. A lactam of general Formula (E-1) can be protected with a suitable protecting group, $PG^E$. An example of such a $PG^E$ group is a Boc-group. For the purpose of the Scheme E, this protecting group can be removed at any relevant stage; and therefore, $PG^E$ present hydrogen for any of compounds of general Formulae (E-4), (E-5), (E-6), (E-7), (E-8) and (E-9). The lactam of general Formula (E-2) can be reacted with an aldehyde of general Formula (E-3) (S or R-garner's aldehyde). The alcohol of general Formula (E-4) can be eliminated to provide an alkene compound of general Formula (E-5) (for example, by sequential conversion of the hydroxy to a corresponding mesylate, followed by elimination under basic conditions). The double bond can be reduced (for example, by hydrogenation, under influence of a homogeneous or a heterogenous catalyst, optionally diastereoselective) to provide a compound of general Formula (E-6). Removal of the acetonide in a compound of general Formula (E-6) to the Boc-protected amino alcohol of general Formula (E-7) can be followed by the oxidation to the carboxylic acid of general Formula (E-8). Alternatively, the acetonide can be deprotected in a compound of general Formula (E-5) to obtain a compound of general Formula (E-9). Reduction of the double bond of a compound of general Formula (E-9) (for example, by hydrogenation under influence of a homogeneous or a heterogenous catalyst, optionally diastereoselective) can be used to obtain a compound of general Formula (E-7). A compound of general Formula (E-4) can be deoxygenated, for example, by a Barton-type deoxygenation, to provide a compound of general Formula (E-6).

Scheme F

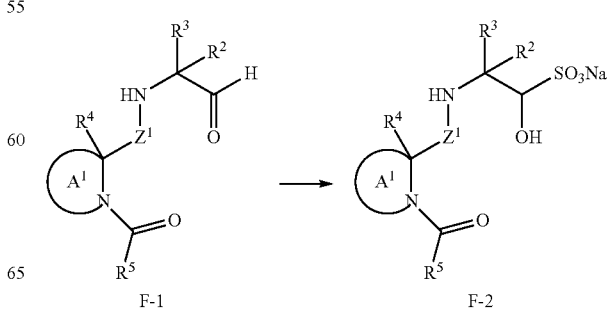

-continued

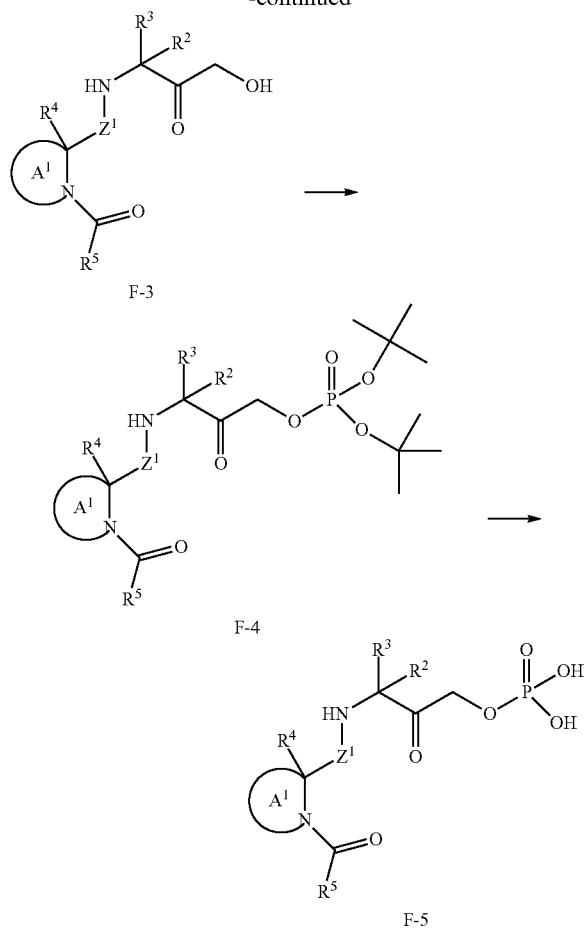

F-3

F-4

F-5

Compounds of Formula (I) can include a prodrug moiety. A method for including a prodrug moiety is depicted in Scheme F. For example an aldehyde of general Formula (F-1) can be transformed into the corresponding bisulfite adduct of general Formula (F-2), by treatment with $NaHSO_3$. A hydroxyketone of general Formula (F-3), can be transformed to the corresponding phosphate of general Formula (F-5), for example, by treatment with di-tert-butyl N,N-dipropan-2-ylphosphoramidite and tetrazole followed by oxidation with $H_2O_2$, that can provide a compound of general Formula (F-4). A compound of general Formula (F-4) can be deprotected (for example by treatment with TFA) to provide a compound of general Formula (F-5).

As shown in Scheme G, the synthesis of an amino ester of general Formula (G2) can be accomplished via a Diels-Alder reaction, such as described in Arakawa et al., Chemical & Pharmaceutical Bulletin (2003) 51(8), 1015-1020 (-$PG_{G1}$ can be -Bz and —$PG_{G2}$ can be —$CH_3$). Also described herein in the synthesis of intermediates, is the use of -$PG_{G1}$ is -Boc and -$PG_{G2}$ is -t-Butyl or Me. A compound of general Formula (G2) can be deprotected using methods known to those skilled in the art and depending on the protecting group used for $PG_{G1}$ and $PG_{G2}$. Alternatively, a compound of general Formula (G2) can be converted to a compound of general Formula (G3), by hydrogenation of the double bond, or to a compound of general Formula (G4), by cyclopropanation of the double bond. The cyclopropanation can, for example, be performed by application of a Simmons-smith cyclopropanation, by treatment with $CH_2N_2$ in the presence of $Pd(OAc)_2$, or other methods described known to those skilled in the art. Alternatively, deuterated intermediates can be used.

Scheme G

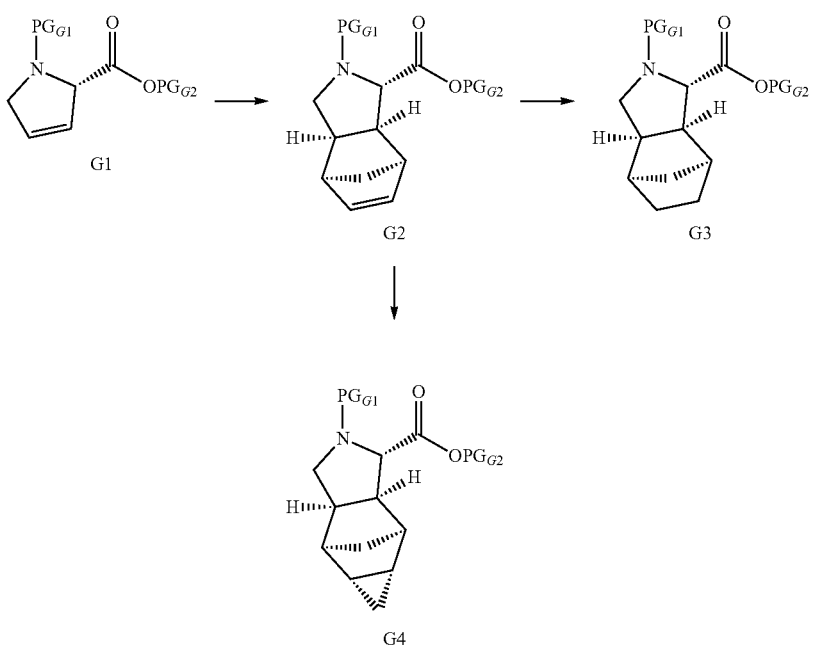

Scheme H

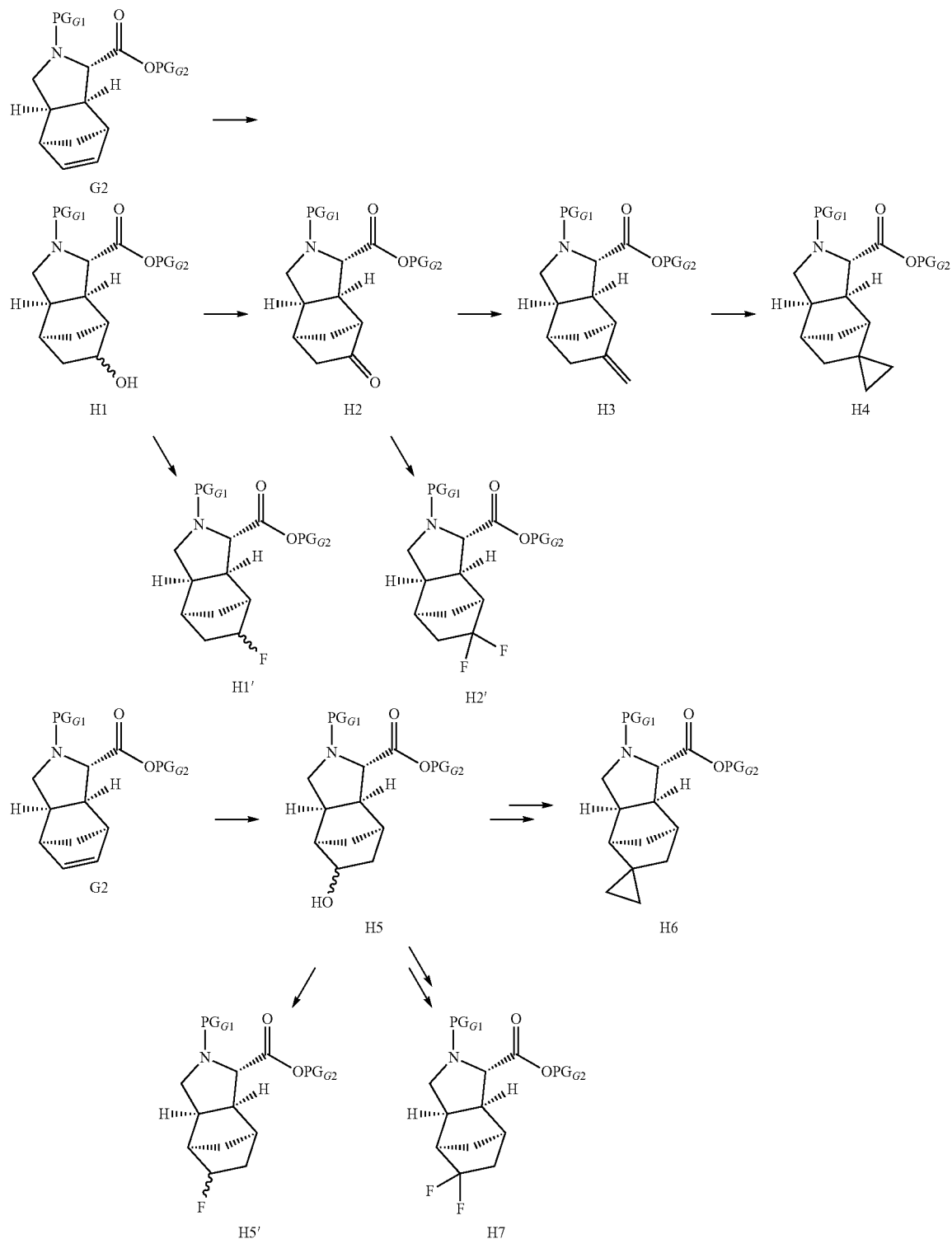

Other intermediates are described in Scheme H. The intermediate of general Formula (G2), can be selectively hydroxylated, for example, by hydrosilylation with trichlorosilane in the presence of a chiral Pd-catalyst, followed by SiCl₃/OH exchange (for example, Breuning et al, Beilstein Journal of Organic Chemistry (2009) 5(81):1-5). Oxidation of the alcohol of general Formula (H1) can provide a ketone of general Formula (H2). The ketone of general Formula (H2) can be converted to an alkene of general Formula (H3), for example, by using a Wittig or a Tebbe reagent. Trans-formation of the double bond towards the cyclopropyl can be done by treatment with $CH_2N_2$ in the presence of $Pd(OAc)_2$, or other methods described in the literature and known to those skilled in the art, and can result in a compound of general Formula (H4). A similar approach can be done with the isomer of a compound of general Formula (H1), a compound of general Formula (H5) can be obtained by using an enantiomeric chiral Pd-catalyst. A compound of general Formula (H5) can then be converted to a compound of general Formula (H6), similar as outlined for the conversion of a compound of general Formula (H1) to a compound of general Formula (H4). Alternatively, the ketone of compound of general Formula (H2) can be converted to a compound of general Formula (H2') by fluorination, for example by application of a DAST reagent. The isomeric compound of general Formula (H7) can be obtained starting from a related isomer. The alcohols of general Formulae (H1) and (H5) can be converted to the related fluoro derivatives of general Formulae (H1') and (H5'), by treatment with a fluorination reagent like DAST (Diethylaminosulfur trifluoride).

Scheme I

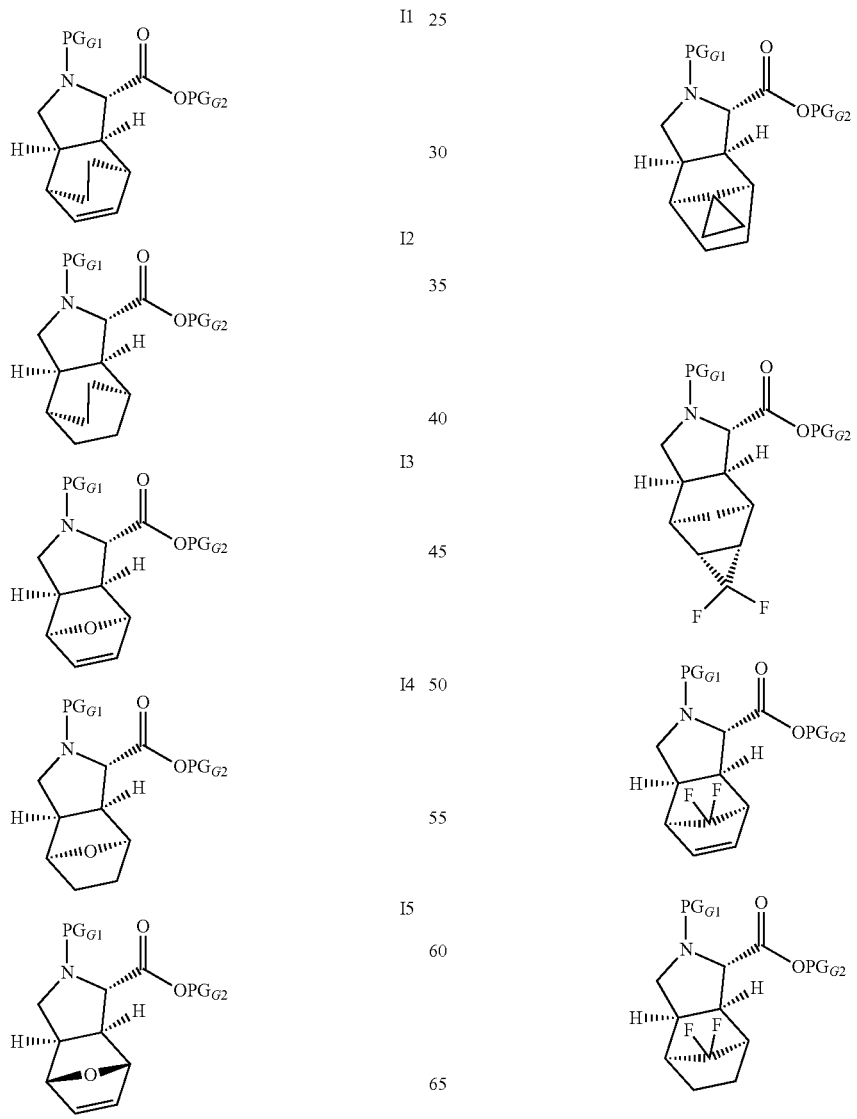

-continued

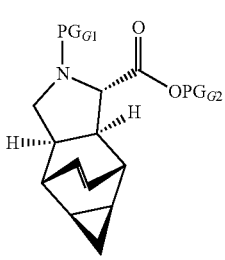

I12

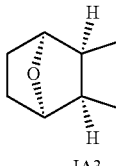

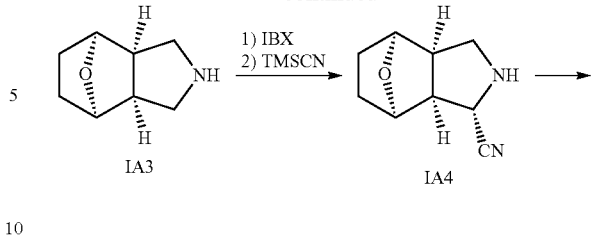

IA3    IA4

Other compounds of general Formulae (I1), (I2) (Johnson et al., Synthetic Communications (2011) 41(18):2769-2793), (I3), (I4), (I5), (I6), (I7), (I8), (I9), (I10), (I11) and (I12) as depicted in Scheme I can be obtained by methods described in literature (for example, de Graaff et al., Org. Biomol. Chem. (2015) 13:10108-10112; and Johnson et al., Synthetic Communications (2011) 41(18):2769-2793) and/or by applying methodologies as described herein. Compounds general Formulae (I1), (I2), (I3), (I4), (I5), (I6), (I7), (I8), (I9), (I10), (I11) and (I12) can be used to obtain compounds of Formula (I), along with pharmaceutically acceptable salts, using similar methods as described herein.

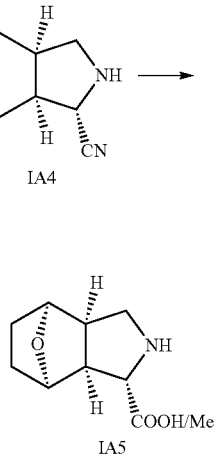

IA5

As an example, as depicted in Scheme IA, a compound of Formula (IA1) (Rulíšek et al., J. Org. Chem. (2005) 70(16): 6295-6302) can be hydrogenated to a compound of Formula (IA2). After reduction of a compound of Formula (IA2), (for example, with LiAlH₄ (Johnson et al., Synthetic Communications (2011) 41(18):2769-2793), can result in a compound of Formula (IA3). A compound of Formula (IA3) can be oxidized using IBX (de Graaff et al., Org. Biomol. Chem. (2015) 13:10108-10112) followed by introduction of nitrile (Liu et al., Org. Process Res. Dev. (2016) 20(2):320-324) to provide a compound of Formula (IA4). The nitrile can next be converted to a carboxylic acid or ester of a compound of Formula (IA5). In the above scheme, racemic material can be obtained upon nitrile introduction from a compound of Formula (IA3) to a compound of Formula (IA4). Alternatively, achiral method can be used to provide enantioenriched compound(s).

Scheme IA

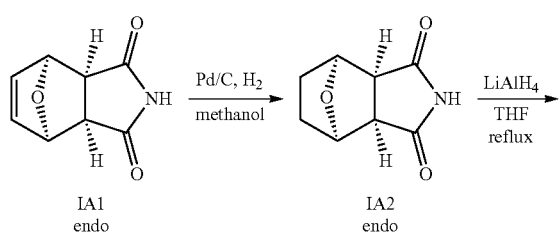

IA1
endo

IA2
endo

Scheme J

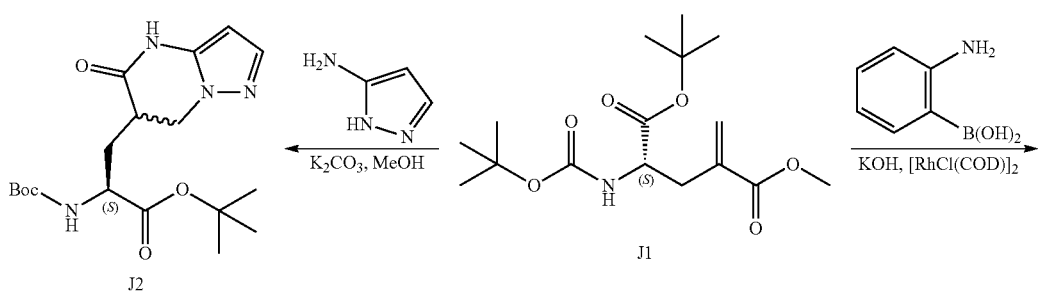

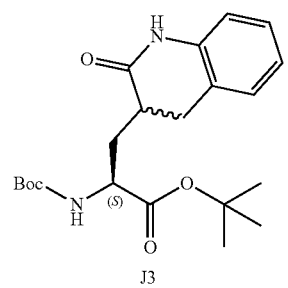

J3

An intermediate, a compound of Formula (J1) (Moody et al., J. Chem. Soc., Perkin Trans. 1 (1997) 23:3519-3530), can be used to prepare amino acids of general Formulae (J2) and (J3) using similar procedures as described for Scheme H.

Pharmaceutical Compositions

Some embodiments described herein relate to a pharmaceutical composition, that can include an effective amount of a compound described herein (e.g., a compound, or a pharmaceutically acceptable salt thereof, as described herein) and a pharmaceutically acceptable carrier, excipient or combination thereof. A pharmaceutical composition described herein is suitable for human and/or veterinary applications.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

Proper formulation is dependent upon the route of administration chosen. Techniques for formulation and administration of the compounds described herein are known to those skilled in the art. Multiple techniques of administering a compound exist in the art including, but not limited to, oral, rectal, topical, aerosol, injection, inhalation and parenteral delivery, including intramuscular, subcutaneous, intravenous, intramedullary injections, intrathecal, direct intraventricular, intraperitoneal, intranasal and intraocular injections. Pharmaceutical compositions will generally be tailored to the specific intended route of administration.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes may be targeted to and taken up selectively by the organ.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. As described herein, compounds used in a pharmaceutical composition may be provided as salts with pharmaceutically compatible counterions.

Methods of Use

Some embodiments described herein relate to a method of treating a coronavirus infection that can include administering to a subject identified as suffering from the coronavirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a coronavirus infection. Still other embodiments described herein relate to the use of a compound, or a pharmaceutically acceptable salt thereof, as described herein or a pharmaceutical composition that includes a compound, or a pharmaceutically acceptable salt thereof, as described herein for treating a coronavirus infection.

Some embodiments disclosed herein relate to a method of treating a coronavirus infection that can include contacting a cell infected with the coronavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a coronavirus infection. Still other embodiments described herein relate to the use of a compound, or a pharmaceutically acceptable salt thereof, as described herein described herein, or a pharmaceutical composition that includes an effective amount of a compound, or a pharmaceutically acceptable salt thereof, as described herein for treating a coronavirus infection.

Some embodiments disclosed herein relate to a method of inhibiting replication of a coronavirus that can include contacting a cell infected with the coronavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for inhibiting replication of a coronavirus. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein, for inhibiting replication of a coronavirus.

In some embodiments, the coronavirus can be an α-coronavirus or a β-coronavirus. A compound described herein may be effective against one or more variants of a coronavirus. Examples of variants include, but are not limited to, alpha-variant (B.1.1.7), beta-variant (B.1.351), gamma variant (P.1) and delta-variant (B.1.617.2). In some embodiments, the coronavirus can be selected from CoV 229E, CoV NL63, CoV OC43, CoV HKU1, Middle East Respiratory Syndrome (MERS)-CoV, Severe Acute Respiratory Syndrome (SARS)-CoV, and SARS-CoV-2.

Some embodiments described herein relate to a method of treating a picornavirus infection that can include administering to a subject identified as suffering from the picornavirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a picornavirus infection. Still other embodiments described herein relate to the use of a compound, or a pharmaceutically acceptable salt thereof, as described herein or a pharmaceutical composition that includes a compound, or a pharmaceutically acceptable salt thereof, as described herein for treating a picornavirus infection.

Some embodiments disclosed herein relate to a method of treating a picornavirus infection that can include contacting a cell infected with the picornavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a picornavirus infection. Still other embodiments described herein relate to the use of a compound, or a pharmaceutically acceptable salt thereof, as described herein described herein, or a pharmaceutical composition that includes an effective amount of a compound, or a pharmaceutically acceptable salt thereof, as described herein for treating a picornavirus infection.

Some embodiments disclosed herein relate to a method of inhibiting replication of a picornavirus that can include contacting a cell infected with the picornavirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for inhibiting replication of a picornavirus. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein, for inhibiting replication of a picornavirus.

In some embodiments, the picornavirus can be a rhinovirus, including rhinovirus A, B and/or C. In some embodiments, a compound described herein, including a compound of Formula (I), or a pharmaceutically acceptable salt thereof, can be used to treat one or serotypes of a rhinovirus.

Some embodiments described herein relate to a method of treating a norovirus infection that can include administering to a subject identified as suffering from the norovirus infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a norovirus infection. Still other embodiments described herein relate to the use of a compound, or a pharmaceutically acceptable salt thereof, as described herein or a pharmaceutical composition that includes a compound, or a pharmaceutically acceptable salt thereof, as described herein for treating a norovirus infection.

Some embodiments disclosed herein relate to a method of treating a norovirus infection that can include contacting a cell infected with the norovirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a norovirus infection. Still other embodiments described herein relate to the use of a compound, or a pharmaceutically acceptable salt thereof, as described herein described herein, or a pharmaceutical composition that includes an effective amount of a compound, or a pharmaceutically acceptable salt thereof, as described herein for treating a norovirus infection.

Some embodiments disclosed herein relate to a method of inhibiting replication of a norovirus that can include contacting a cell infected with the norovirus with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for inhibiting replication of a norovirus. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein, for inhibiting replication of a norovirus.

Some embodiments disclosed herein relate to a method of treating a respiratory condition that is developed because of a coronavirus and/or a picornavirus infection that can include administering to a subject suffering from the respiratory condition and/or contacting a cell infected with the coronavirus and/or the picornavirus in a subject suffering from the respiratory condition with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a respiratory condition due to a coronavirus infection and/or a picornavirus infection with an effective amount of the compound, or a pharmaceutically acceptable salt thereof. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating a respiratory condition due to a coronavirus infection and/or a picornavirus infection.

A subject infected with a coronavirus can be asymptotic. A coronavirus infection can manifest itself via one or more symptoms. Examples of symptoms include, but are not limited to, coughing, sore throat, runny nose, sneezing, headache, fever, shortness of breath, myalgia, abdominal pain, fatigue, difficulty breathing, persistent chest pain or pressure, difficulty waking, loss of smell and taste, muscle or joint pain, chills, nausea or vomiting, nasal congestion, diarrhea, haemoptysis, conjunctival congestion, sputum production, chest tightness and/or palpitations. A coronavirus infection can cause complications. A non-limiting list of complications include, but are not limited to, sinusitis, otitis media, pneumonia, acute respiratory distress syndrome, disseminated intravascular coagulation, pericarditis and/or kidney failure.

As with a coronavirus, a subject infected with a picornavirus can be asymptotic. Alternatively, a subject can exhibit one or more of symptoms. Examples of symptoms of a picornavirus infection include, but are not limited to, aseptic meningitis, rash, conjunctivitis, runny nose a headache a cough a fever a sore throat, chest and/or abdominal pain and paralysis. As provided herein, subjects infected with a norovirus can exhibit one or more the symptoms including, but not limited to, nausea, non-bloody diarrhea, vomiting and abdominal pain. An example of a complication that can be attributed to a norovirus infection is dehydration, including severe dehydration.

Various indicators for determining the effectiveness of a method for treating a coronavirus, picornavirus and/or norovirus infection are also known to those skilled in the art. Examples of suitable indicators include, but are not limited to, a reduction in viral load indicated by reduction in coronavirus (or load) (e.g., reduction <$10^5$ copies/mL in serum), a reduction in plasma viral load, a reduction in viral replication, a reduction in time to seroconversion (virus undetectable in patient serum), an increase in the rate of sustained viral response to therapy a reduction of morbidity or mortality in clinical outcomes, reduction in the need for a ventilator and/or total time on a ventilator, reduction in hospitalization rates and/or reduction in time in an ICU (intensive care unit) and/or hospital.

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, camels, non-human primates, such as monkeys, chimpanzees, and apes, and, in particular, humans. In some embodiments, the subject can be human, for example, a human subject that is 60 years old or older.

The term "effective amount" is used to indicate an amount of an active compound, or pharmaceutical agent, that elicits the biological or medicinal response indicated. For example, an effective amount of compound can be the amount needed to alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In some embodiments, the subject can be asymptomatic, for example, the subject can be infected with coronavirus but does not exhibit any symptoms of the viral infection. In some embodiments, the subject can be have a pre-existing condition, such as asthma, hypertension, immunocompromised subjects (such as subjects with cancer, HIV and/or genetic immune deficiencies, bone marrow transplant subjects, solid organ transplant subjects, subjects who have had stem cells for cancer treatment and/or subjects who use oral or intravenous corticosteroids or other medicines called immunosuppressants), liver disease, subjects at risk for severe illness, chronic kidney disease being treated with dialysis, chronic lung disease, diabetes, hemoglobin disorders, serious heart conditions (for example, heart failure, coronary artery disease, congenital heart disease, cardiomyopathies, and pulmonary hypertension), severe obesity (such as subjects with a body mass index (BMI) of 40 or above) and people who live in a nursing home or long-term care facility. Additional examples and/or further information is provided by the CDC (https://www.cdc.gov/coronavirus/2019-ncov/need-extra-precautions/groups-at-higher-risk-.html).

A compound described herein, including a compound of Formula (I), or a pharmaceutically acceptable salt thereof, can be administered after a subject is infected with a coronavirus. In addition and/or alternatively, a compound described herein, including a compound of Formula (I), or a pharmaceutically acceptable salt thereof, can be administered prophylactically.

Examples of agents that have been used to treat a coronavirus infection include Remdesivir. However, there can be drawbacks associated with compounds being used to treat a coronavirus including, but not limited to, one or more adverse side effects, the need for subcutaneous administration and/or high cost. Potential advantages of a compound of Formula (I), or a pharmaceutically acceptable salt thereof, can be less adverse side effects, delay in the onset of an adverse side effect and/or reduction in the severity of an adverse side effect.

A coronavirus infection can be treated by inhibiting certain mechanisms. In some embodiments, a compound described herein (such as a compound of Formula (I), or a pharmaceutically acceptable salt thereof) can be selective for a coronavirus protease. For example, a compound of Formula (I), or a pharmaceutically acceptable salt thereof, can be selective for a coronavirus protease compared to a host protease, for example, one or more host proteases selected from Cathepsin L, Cathepsin B, Cathepsin D, Cathepsin K, Leukocyte Elastase, Chymotrypsin, Trypsin, Thrombin, Pepsin, Caspase 2, Elastase and Calpain. In some embodiments, the selectivity for a coronavirus protease over a host protease (such as those described herein) can be >2-fold. In some embodiments, the selectivity for a coronavirus protease over a host protease (such as those described herein) can be >10-fold. In some embodiments, the selectivity for a coronavirus protease over a host protease (such as those described herein) can be >100-fold.

Studies have shown that the entry of SARS-CoV-2 into the target cells is a process that can be mediated by multiple proteases including cysteine cathepsins L and/or transmembrane protease serine 2 (TMPRSS2) (Shang et al., PNAS (2020) 117:11727, and Hoffmann et al., Cell (2020) 181:271-280). The cathepsin L inhibitor K117777, which lacks an inhibitory effect on the 3CLpro, can result in potent inhibition of SARS-CoV-2 in VeroE6, A549-ACE2 and/or HeLa-ACE2 (Mellott et al., bioRxiv (2020) 2020.2010.2023.347534). It has also been shown that the potent antiviral effect of K117777 is abolished when TMPRSS2 was expressed in A549-ACE2 (Steuten et al., bioRxiv (2020) 2020.2011.2021.392753). Off target activity of 3CLpro inhibitors, for example, on cathepsin L, may lead to an inaccurate assessment of the 3CLpro component of a compound's cellular potency. As an example, a compound described herein (such as a compound of Formula (I), or a pharmaceutically acceptable salt thereof) can have greater selectivity for a coronavirus protease over a host protease, such as cathepsin L. The selectivity can be determined by those skilled in the art, for example, using $IC_{50}$ and/or Ki values. In some embodiments, a compound described herein does not significantly inhibit cathepsin L (for example, $IC_{50} \geq 10000$ nM or >3.3 µM), but inhibits a coronavirus protease (for example, SARS-Cov-2 3Clpro).

A drawback with anti-viral treatment can be the development of resistance, including cross-resistance. Resistance can be a cause for treatment failure. The term "resistance" as used herein refers to a viral strain displaying a delayed, lessened and/or null response to an anti-viral agent. In some embodiments, a compound, or a pharmaceutically acceptable salt thereof, as described herein can be provided to a subject infected with a coronavirus strain that is resistant to one or more other anti-viral agents. In some embodiments, development of coronavirus resistant strains is delayed when a subject is treated with a compound, or a pharmaceutically acceptable salt thereof, as described herein compared to the development of a coronavirus resistant strain when treated with one or more other anti-viral agents.

Combination Therapies

In some embodiments, a compound, or a pharmaceutically acceptable salt thereof, as described herein can be used in combination with one or more additional agent(s) for treating and/or inhibiting replication a coronavirus. Additional agents include, but are not limited to, an ACE inhibitor, an anticoagulant, an anti-inflammatory, an ARB, an ASO, a Covid-19 convalescent plasma, an entry inhibitor, an $H_2$ pump antagonist, an H-conducting channel, an HIV protease inhibitor, an HMG-CoA reductase inhibitor, an immune globulin, an immunosuppressant, an immunotherapeutic agent, a monoclonal antibody, a neuraminidase inhibitor, a nucleoside inhibitor, a nucleoside analog inhibitor, a polymerase inhibitor, a protease inhibitor, an siRNA, a statin, a tissue plasminogen activator, an antibiotic, an antimicrobial and a vaccine. Examples of additional agents include Ascorbic acid, Anakin, Azithromycin, Baloxavir, Baricitinib, Chloroquine Phosphate, Colchicine, a corticosteroid, Epoprostenol, Famotidine, Favipiravir, an IGIV, an interferon (for example, recombinant interferon alpha 2b, IFN-α and/or PEG-IFN-αX-2a), an IVIG, Ivermectin, γ-globulin, lopinavir, Methylprednisolone, Molnupiravir (MK-4482 or EIDD-2801), Niclosamide, Nitazoxanide, Nitric oxide, Oseltamivir, Peramivir, RANTES, ribavirin, Remdesivir, Ruxolitinib, Sarilumab, Siltuximab, Sirolimus, a statin, Tacrolimus, Tocilizumab, Umifenovir, Zanamivir, Casirivimab, imdevimab, bamlanivimab, etesevimab and AT-527 (Good et al., Antimicrobial Agents and Chemotherapy (2021) 65(4):e02479-20)

In some embodiments, a compound, or a pharmaceutically acceptable salt thereof, as described herein can be administered with one or more additional agent(s) together in a single pharmaceutical composition. In some embodiments, a compound, or a pharmaceutically acceptable salt thereof, can be administered with one or more additional agent(s) as two or more separate pharmaceutical compositions. Further, the order of administration of a compound, or a pharmaceutically acceptable salt thereof, as described herein with one or more additional agent(s) can vary.

EXAMPLES

Additional embodiments are disclosed in further detail in the following examples, which are not in any way intended to limit the scope of the claims.

Compounds

Compounds of Formula (I), along with pharmaceutically acceptable salts thereof, can be prepared in various ways, including those synthetic schemes shown and described herein, are provided below. Those skilled in the art will be able to recognize modifications of the disclosed syntheses and to devise routes based on the disclosures herein; all such modifications and alternate routes are within the scope of the claims.

Synthesis of Intermediates

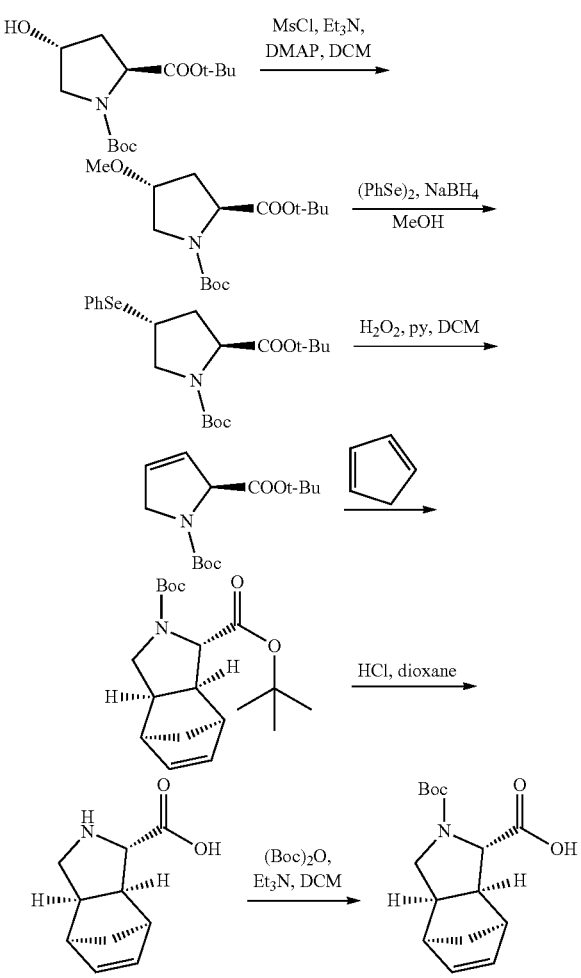

To a solution of 1,2-di-tert-butyl (2S,4R)-4-hydroxypyrrolidine-1,2-dicarboxylate (15 g, 52.2 mmol, 1.0 eq.) in DCM (250 mL) was added triethylamine (9.51 g, 93.9 mmol, 1.8 eq.) and DMAP (1.91 g, 15.7 mmol, 0.3 eq.). MsCl (8.97 g, 78.3 mmol, 1.5 eq.) was added dropwise at 0°

C. The mixture was stirred at room temperature (rt) for 2 h, and the reaction was quenched with water (100 mL). The solution was extracted with DCM (3×150 mL). The organic layers were combined, washed with brine (100 mL), dried over anhydrous sodium sulfate, filtered and concentrated under reduced pressure. The residue was chromatographed on a silica gel column with EA:PE (1:10) to provide 1,2-di-tert-butyl (2S,4R)-4-(methanesulfonyloxy)pyrrolidine-1,2-dicarboxylate (17.8 g, 89%) as a colorless oil. LC-MS (ESI, m/z): 366 [M+H]⁺.

To a solution of 1,2-di-tert-butyl (2S,4R)-4-(methanesulfonyloxy)pyrrolidine-1,2-dicarboxylate (17.8 g, 48.7 mmol, 1.0 eq.) in MeOH (400 mL) was added (phenyldiselanyl)benzene (9.12 g, 29.2 mmol, 0.6 eq.). Sodium borohydride (2.4 g, 63.3 mmol, 1.3 eq.) was added at 0° C. in several portions. The mixture was refluxed overnight and then concentrated under reduced pressure. Water (100 mL) was added, and the mixture was extracted with EA (3×150 mL). The organic layers were combined, washed with brine (100 mL), dried over anhydrous sodium sulfate, filtered and concentrated under reduced pressure. The residue was chromatographed on a silica gel column with EA:PE (1:5) to provide 1,2-di-tert-butyl (2S,4S)-4-(phenylselanyl)pyrrolidine-1,2-dicarboxylate (7.5 g, 32%) as a colorless oil. LC-MS (ESI, m/z): 428 [M+H]⁺.

To a solution of 1,2-di-tert-butyl (2S,4S)-4-(phenylselanyl)pyrrolidine-1,2-dicarboxylate (7.5 g, 17.6 mmol, 1.0 eq.) in DCM (100 mL) was added pyridine (2.4 mL, 30.5 mmol, 1.7 eq.) and 30% aqueous H₂O₂ (5.6 mL, 71.6 mmol, 4.0 eq.). The mixture was stirred at rt for 12 h, and the reaction was quenched with water (20 mL). The solution was extracted with DCM (3×150 mL). The organic layers were combined, washed with 1 M citric acid (80 mL), sat. aq. Na₂SO₃ (100 mL) and brine (100 mL), dried over anhydrous sodium sulfate, filtered and concentrated under reduced pressure. The residue was chromatographed on a silica gel column with EA:PE (1:9) to provide 1,2-di-tert-butyl (2S)-2,5-dihydropyrrole-1,2-dicarboxylate (2.8 g, 53%) as a colorless oil. ¹H NMR (300 MHz, DMSO-d₆) δ 6.02-6.09 (m, 1H), 5.76-5.83 (m, 1H), 4.72-4.78 (m, 1H), 4.05-4.09 (m, 2H), 1.17-1.42 (m, 18H). LC-MS (ESI, m/z): 270 [M+H]⁺.

A solution of 1,2-di-tert-butyl (2S)-2,5-dihydropyrrole-1,2-dicarboxylate (2.8 g, 10.4 mmol, 1.0 eq.) in dicyclopentadiene (60 mL) was stirred at 170° C. for 48 h under nitrogen and then resolved with DCM (200 mL). After removal of the solvent, the residue was chromatographed on a silica gel column with EA:PE (1:9) to provide the product (2.5 g, crude) as a yellow oil. The crude oil was chromatographed on a C18 column with H₂O:MeCN (2:1) to provide di-tert-butyl (1S,3aR,4S,7R,7aS)-1,3,3a,4,7,7a-hexahydro-2H-4,7-methanoisoindole-1,2-dicarboxylate (690 mg, 19%) as a white solid. ¹H NMR (300 MHz, DMSO-d₆) δ 6.14-6.21 (m, 2H), 3.55-3.60 (m, 1H), 3.23-3.27 (m, 1H), 2.95-3.02 (m, 2H), 2.74-2.87 (m, 3H), 1.24-1.48 (m, 20H). LC-MS (ESI, m/z): 270 [M+H]⁺.

To a solution of i-tert-butyl (1S,3aR,4S,7R,7aS)-1,3,3a,4,7,7a-hexahydro-2H-4,7-methanoisoindole-1,2-dicarboxylate (690 mg, 2.1 mmol, 1.0 eq.) in dioxane (10 mL) was added hydrochloric acid (10 mL, 9M). The mixture was stirred at rt overnight and then concentrated under reduced pressure to provide (1S,3aR,4S,7R,7aS)-2,3,3a,4,7,7a-hexahydro-1H-4,7-methanoisoindole-1-carboxylic acid (320 mg, crude) as a black solid. LC-MS (ESI, m/z): 180 [M+H]⁺.

To a solution of (1S,3aR,4S,7R,7aS)-2,3,3a,4,7,7a-hexahydro-1H-4,7-methanoisoindole-1-carboxylic acid (320 mg, 1.79 mmol, 1.0 eq.) in DCM (8 mL) was added di-tert-butyl dicarbonate (429 mg, 1.97 mmol, 1.1 eq.) and triethylamine (542 mg, 5.34 mmol, 3.0 eq.). The mixture was stirred at rt for 3 h and then concentrated under reduced pressure to provide (1S,3aR,4S,7R,7aS)-2-(tert-butoxycarbonyl)-2,3,3a,4,7,7a-hexahydro-1H-4,7-methanoisoindole-1-carboxylic acid (430 mg, crude) as a brown solid. LC-MS (ESI, m/z): 280 [M+H]⁺.

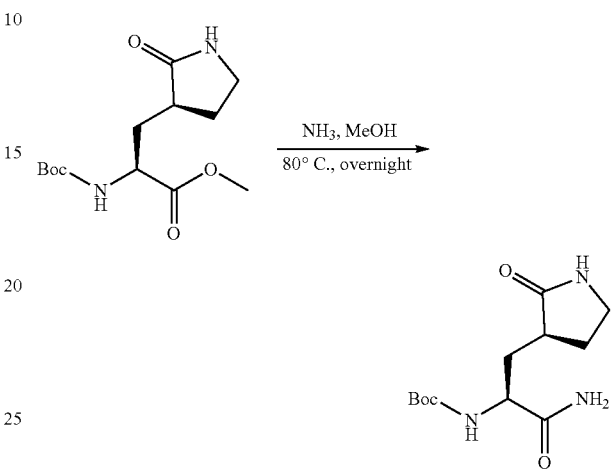

A mixture of methyl (2S)-2-[(tert-butoxycarbonyl)amino]-3-[(3S)-2-oxopyrrolidin-3-yl]propanoate (10.0 g, 34.9 mmol, 1.00 eq.) in ammonia (150 mL, 7 M in MeOH) was stirred overnight at 80° C. and concentrated under reduced pressure to afford tert-butyl N-[(1S)-1-carbamoyl-2-[(3S)-2-oxopyrrolidin-3-yl]ethyl]carbamate (10.0 g, crude) as a light brown solid. ¹H NMR (400 MHz, DMSO-d₆) δ 7.65 (s, 1H), 7.29 (s, 1H), 7.01 (s, 1H), 6.88-6.95 (m, 1H), 3.84-4.15 (m, 1H), 3.09-3.21 (m, 2H), 2.08-2.26 (m, 2H), 1.84-1.96 (m, 1H), 1.60-1.74 (m, 1H), 1.44-1.54 (m, 1H), 1.38 (s, 9H). LC-MS (ESI, m/z): 272 [M+H]⁺.

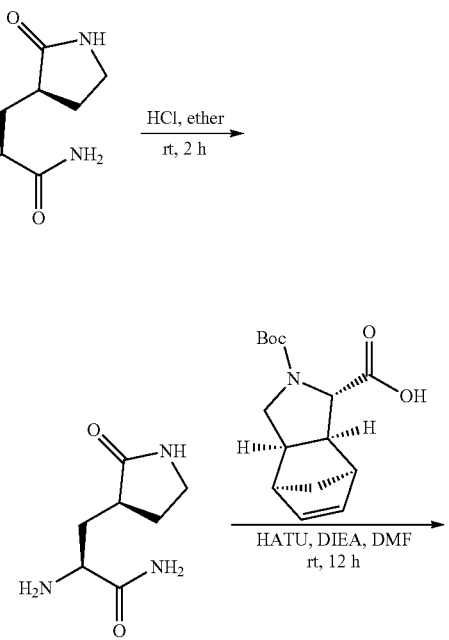

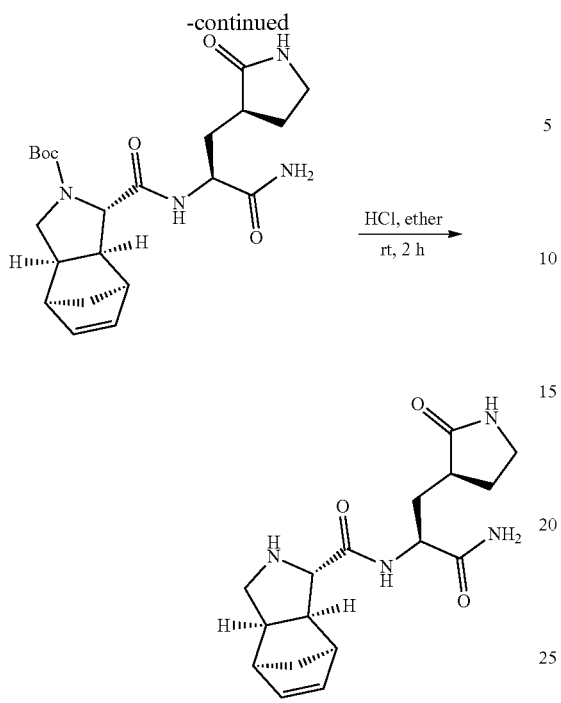

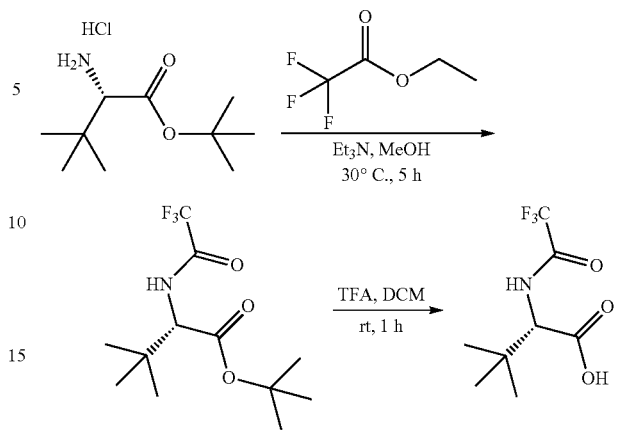

A solution of tert-butyl ((S)-1-amino-1-oxo-3-((S)-2-oxopyrrolidin-3-yl)propan-2-yl)carbamate (710 mg, 2.62 mmol, 1.0 eq.) in hydrochloric acid in ether (12 mL, 2 mol/L) was stirred at rt for 2 h and concentrated under reduced pressure to provide (S)-2-amino-3-((S)-2-oxopyrrolidin-3-yl)propenamide (500 mg, crude) as a white solid. LC-MS (ESI, m/z): 172 [M+H]$^+$.

To a solution of (1S,3aR,4S,7R,7aS)-2-(tert-butoxycarbonyl)-2,3,3a,4,7,7a-hexahydro-1H-4,7-methanoisoindole-1-carboxylic acid (979 mg, 3.5 mmol, 1.2 eq.) in DMF (2 mL) was added N,N,N',N'-Tetramethyl-O-(7-azabenzotriazol-1-yl)uronium hexafluorophosphate (1.44 g, 3.8 mmol, 1.3 eq.) and N,N-diisopropylethylamine (2.64 g, 20.4 mmol, 7.0 eq.). The mixture was stirred at 0° C. for 30 min and then (S)-2-amino-3-((S)-2-oxopyrrolidin-3-yl)propanamide (500 mg, 2.92 mmol, 1.0 eq.) was added. The mixture was stirred at rt for 2 h, and the reaction was quenched with water (5 mL). The mixture was extracted with EA (3×10 mL). The organic layers were combined, washed with brine (3×10 mL), dried over anhydrous sodium sulfate, filtered and concentrated under reduced pressure. The residue was chromatographed on a C18 column with water:MeCN (2:1) to provide tert-butyl (1S,3aR,4S,7R,7aS)-1-(((S)-1-amino-1-oxo-3-((S)-2-oxopyrrolidin-3-yl)propan-2-yl)carbamoyl)-1,3,3a,4,7,7a-hexahydro-2H-4,7-methanoisoindole-2-carboxylate (1.05 g, 75%) as a brown yellow solid. LC-MS (ESI, m/z): 433 [M+H]$^+$.

A solution of tert-butyl (1S,3aR,4S,7R,7aS)-1-(((S)-1-amino-1-oxo-3-((S)-2-oxopyrrolidin-3-yl)propan-2-yl)carbamoyl)-1,3,3a,4,7,7a-hexahydro-2H-4,7-methanoisoindole-2-carboxylate (300 mg, 0.69 mmol, 1.0 eq.) in hydrochloric acid in ether (5 mL, 2 mol/L) was stirred at rt for 2 h and then concentrated under reduced pressure to provide (1S,3aR,4S,7R,7aS)—N—((S)-1-amino-1-oxo-3-((S)-2-oxopyrrolidin-3-yl)propan-2-yl)-2,3,3a,4,7,7a-hexahydro-1H-4,7-methanoisoindole-1-carboxamide (200 mg, crude) as a white solid. LC-MS (ESI, m/z): 333 [M+H]$^+$.

To a stirred mixture of tert-butyl (2S)-2-amino-3,3-dimethylbutanoate hydrochloride (6.00 g, 26.8 mmol, 1.0 eq.) and ethyl 2,2,2-trifluoroacetate (7.62 g, 53.6 mmol, 2.0 eq.) in MeOH (100 mL) was added triethylamine (5.43 g, 53.7 mmol, 2.0 eq.) at 0° C. The mixture was stirred for 5 h at 30° C. and then concentrated under reduced pressure to afford the crude product. The crude product was diluted with DCM (150 mL) and made into a slurry with 100~200 silica gel mesh (15 g), and the slurry was loaded to a column chromatography after removing the DCM. The sample was purified by column chromatography (Column size 6×24 cm, column volume: 600 mL, silica gel size (100~200 mesh) quantity: 330 g) and eluted with MeOH:DCM (0%~10% over 30 min). The collected fractions: 0% MeOH:DCM fractions were chosen as the pure fractions. and those fractions were combined and concentrated under reduced pressure to provide tert-butyl (2S)-3,3-dimethyl-2-(2,2,2-trifluoroacetamido)butanoate (7.20 g, 90%) as a white solid. $^1$H NMR (300 MHz, CDCl$_3$) δ 6.78-6.90 (m, 1H), 4.32-4.38 (m, 1H), 1.50 (s, 9H), 1.01 (s, 9H). LC-MS (ESI, m/z): 282 [M−H]$^−$.

To a mixture of tert-butyl (2S)-3,3-dimethyl-2-(2,2,2-trifluoroacetamido)butanoate (1.03 g, 3.64 mmol, 1.0 eq.) in DCM (5 mL) was added trifluoroacetic acid (5 mL). The mixture was stirred for 1 h at rt and then concentrated under reduced pressure to (2S)-3,3-dimethyl-2-(2,2,2-trifluoroacetamido)butanoic acid (826 mg, crude) as a yellow oil. LC-MS (ESI, m/z): 226 [M−H]$^−$.

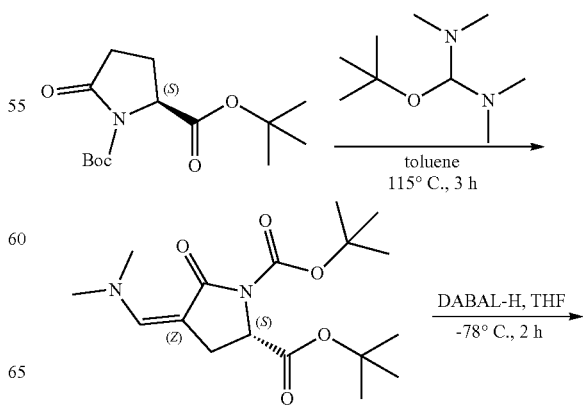

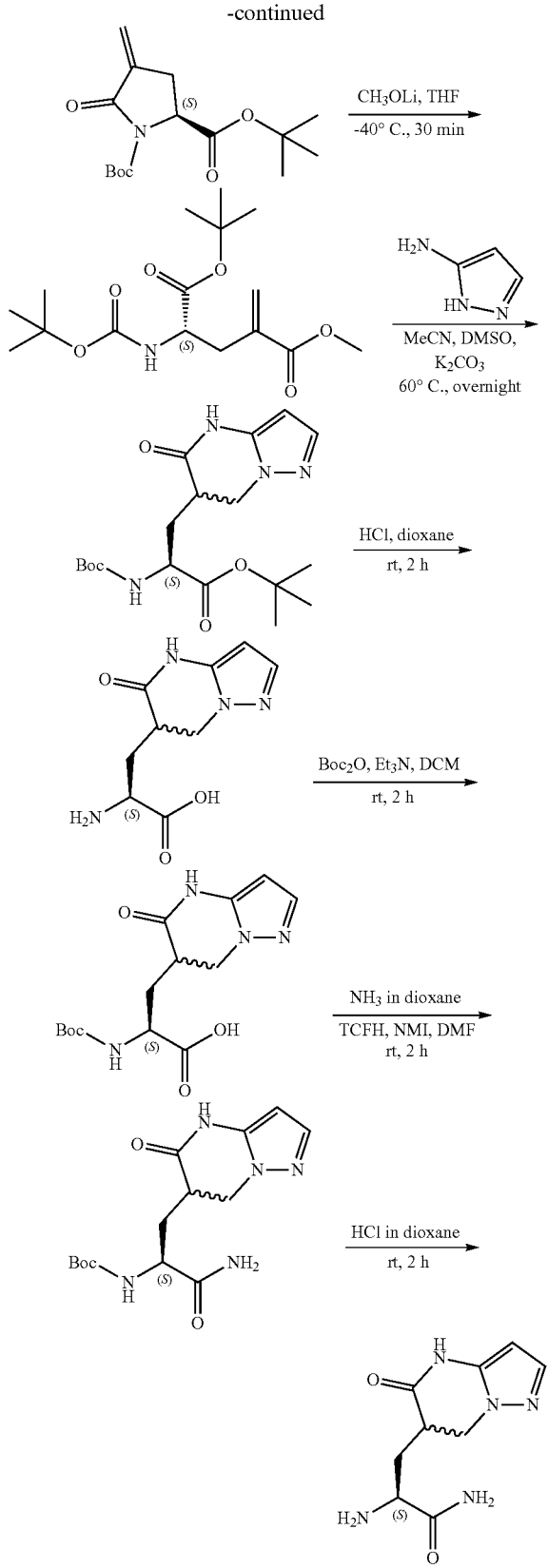

To a solution of 1,2-di-tert-butyl (2S)-5-oxopyrrolidine-1,2-dicarboxylate 1,2-di-tert-butyl (2S)-5-oxopyrrolidine-1,2-dicarboxylate (50 g, 175 mmol, 1.0 eq.) in toluene (500 mL) was added [tert-butoxy(dimethylamino)methyl]dimethylamine (36.7 g, 210 mmol, 1.2 eq.). The mixture was stirred at 115° C. for 3 h under nitrogen and concentrated under reduced pressure to provide di-tert-butyl (S,Z)-4-((dimethylamino)methylene)-5-oxopyrrolidine-1,2-dicarboxylate (46 g, crude) as an orange oil. LC-MS (ESI, m/z): 341 [M+H]+.

To a solution of di-tert-butyl (S,Z)-4-((dimethylamino)methylene)-5-oxopyrrolidine-1,2-dicarboxylate (46 g, 135 mmol, 1.0 eq.) in THF (900 mL) was added DIBAl-H (203 mL, 1M in toluene, 203 mmol, 1.5 eq.) dropwise at −78° C. under $N_2$. The mixture was stirred at −78° C. for 2 h, and was then poured into hydrochloric acid (800 mL, 2 mol/L) slowly at 0° C. The solution was extracted with EA (3×600 mL). The organic layers were combined, dried over anhydrous sodium sulfate, filtered and concentrated under reduced pressure. The residue was chromatographed on a silica gel column with EA:PE (1:5) to provide di-tert-butyl (S)-4-methylene-5-oxopyrrolidine-1,2-dicarboxylate (16 mg, 36%) as a colorless oil. $^1$H NMR (300 MHz, DMSO-$d_6$) δ 5.98-6.00 (m, 1H), 5.58-5.59 (m, 1H), 4.50-4.54 (m, 1H), 3.04-3.34 (m, 1H), 2.57-2.64 (m, 1H), 1.36-1.44 (m, 18H). LC-MS (ESI, m/z): 298 [M+H]+.

To a solution of di-tert-butyl (S)-4-methylene-5-oxopyrrolidine-1,2-dicarboxylate (12 g, 40.4 mmol, 1.0 eq.) in THF (200 mL) was added methoxylithium (22 mL, 2.2M in methanol, 48.4 mmol, 1.2 eq.) at −40° C. under $N_2$. The mixture was stirred at −40° C. for 30 min. The reaction quenched with sat. aq. sodium chloride (100 mL). The solution was extracted with EA (3×100 mL). The organic layers were combined, dried over anhydrous sodium sulfate, filtered and concentrated under reduced pressure. The residue was chromatographed on a silica gel column with EA:PE (1:4) to provide 1-(tert-butyl) 5-methyl (S)-2-((tert-butoxycarbonyl)amino)-4-methylenepentanedioate (12 g, 81%) as a colorless viscous oil. LC-MS (ESI, m/z): 330 [M+H]+.

To a solution of 1-(tert-butyl) 5-methyl (S)-2-((tert-butoxycarbonyl)amino)-4-methylenepentanedioate (7 g, 21 mmol, 1.0 eq.) in MeCN (70 mL) and DMSO (70 mL) was added 2H-pyrazol-3-amine (2.1 g, 25.5 mmol, 1.2 eq.), $K_2CO_3$ (2.94 mg, 21 mmol, 1.0 eq.). The mixture was stirred at 60° C. overnight and then concentrated under reduced pressure. The residue was chromatographed on a C18 column with MeCN:$H_2O$ (3:2) to provide tert-butyl (2S)-2-((tert-butoxycarbonyl)amino)-3-(5-oxo-4,5,6,7-tetrahydropyrazolo[1,5-a]pyrimidin-6-yl)propanoate (1.7 g, 19%) as a brown yellow oil. $^1$H NMR (300 MHz, DMSO-$d_6$) δ 10.76 (s, 1H), 7.18-7.27 (m, 2H), 5.56-5.57 (m, 1H), 4.26-4.36 (m, 1H), 3.89-4.13 (m, 1H), 2.75-2.79 (m, 1H), 2.10-2.25 (m, 1H), 1.61-1.80 (m, 1H), 1.27-1.53 (m, 18H). LC-MS (ESI, m/z): 381 [M+H]+.

To a solution of tert-butyl (2S)-2-((tert-butoxycarbonyl)amino)-3-(5-oxo-4,5,6,7-tetrahydropyrazolo[1,5-a]pyrimidin-6-yl)propanoate (800 mg, 3.55 mmol, 1.0 eq.) in dioxane (8 mL) was added hydrochloric acid (8 mL, 9M). The mixture was stirred at rt for 2 h and then concentrated under reduced pressure to provide (2S)-2-amino-3-(5-oxo-4,5,6,7-tetrahydropyrazolo[1,5-a]pyrimidin-6-yl)propanoic acid (400 mg, crude) as an off-white semi-solid. LC-MS (ESI, m/z): 225 [M+H]+.

To a solution of (2S)-2-amino-3-(5-oxo-4,5,6,7-tetrahydropyrazolo[1,5-a]pyrimidin-6-yl)propanoic acid (400 mg, 1.78 mmol, 1.0 eq.) in DCM (6 mL) was added di-tert-butyl dicarbonate (430 mg, 1.96 mmol, 1.1 eq.) and triethylamine (180 mg, 5.36 mmol, 3.0 eq.). The mixture was stirred for 3 h and then concentrated under reduced pressure to provide (2S)-2-((tert-butoxycarbonyl)amino)-3-(5-oxo-4,5,6,7-tetrahydropyrazolo[1,5-a]pyrimidin-6-yl)propanoic acid (530 mg, crude) as a brown yellow semi-solid. LC-MS (ESI, m/z): 325 [M+H]+.

To a solution of (2S)-2-((tert-butoxycarbonyl)amino)-3-(5-oxo-4,5,6,7-tetrahydropyrazolo[1,5-a]pyrimidin-6-yl)propanoic acid (530 mg, 1.63 mmol, 1.0 eq.) in DMF (8 mL) was added N,N,N,N-tetramethylchloroformamidinium hexafluorophosphate (550 mg, 1.96 mmol, 1.2 eq.), NMI (671 mg, 8.17 mmol, 5.0 eq.) and $NH_3$ in dioxane (40 mL, 10.0 eq., 0.4 mol/L). The mixture was stirred at rt for 2 h and then chromatographed on a C18 column with MeCN:$H_2O$ (1:4) to provide tert-butyl ((2S)-1-amino-1-oxo-3-(5-oxo-4,5,6,7-tetrahydropyrazolo[1,5-a]pyrimidin-6-yl)propan-2-yl)carbamate (280 mg, 48%) as a brown yellow oil. LC-MS (ESI, m/z): 324 [M+H]+.

To a solution of tert-butyl ((2S)-1-amino-1-oxo-3-(5-oxo-4,5,6,7-tetrahydropyrazolo[1,5-a]pyrimidin-6-yl)propan-2-yl)carbamate (280 mg, 0.87 mmol, 1.0 eq.) in hydrochloric acid (4 mL, 2 mol/L in dioxane) was stirred at rt for 2 h and then concentrated under reduced pressure to provide (2S)-2-amino-3-(5-oxo-4,5,6,7-tetrahydropyrazolo[1,5-a]pyrimidin-6-yl)propanamide (180 mg, crude) as an off-white semi-solid. LC-MS (ESI, m/z): 224 [M+H]+.

(S)-3-((R*)-1-(tert-butoxycarbonyl)-5,5-dimethyl-2-oxopyrrolidin-3-yl)-2-((tert-butoxycarbonyl)amino)propanoic acid

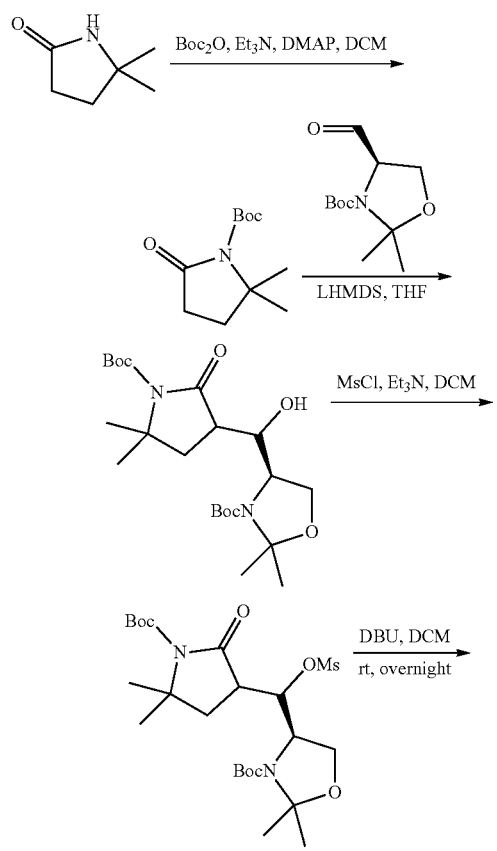

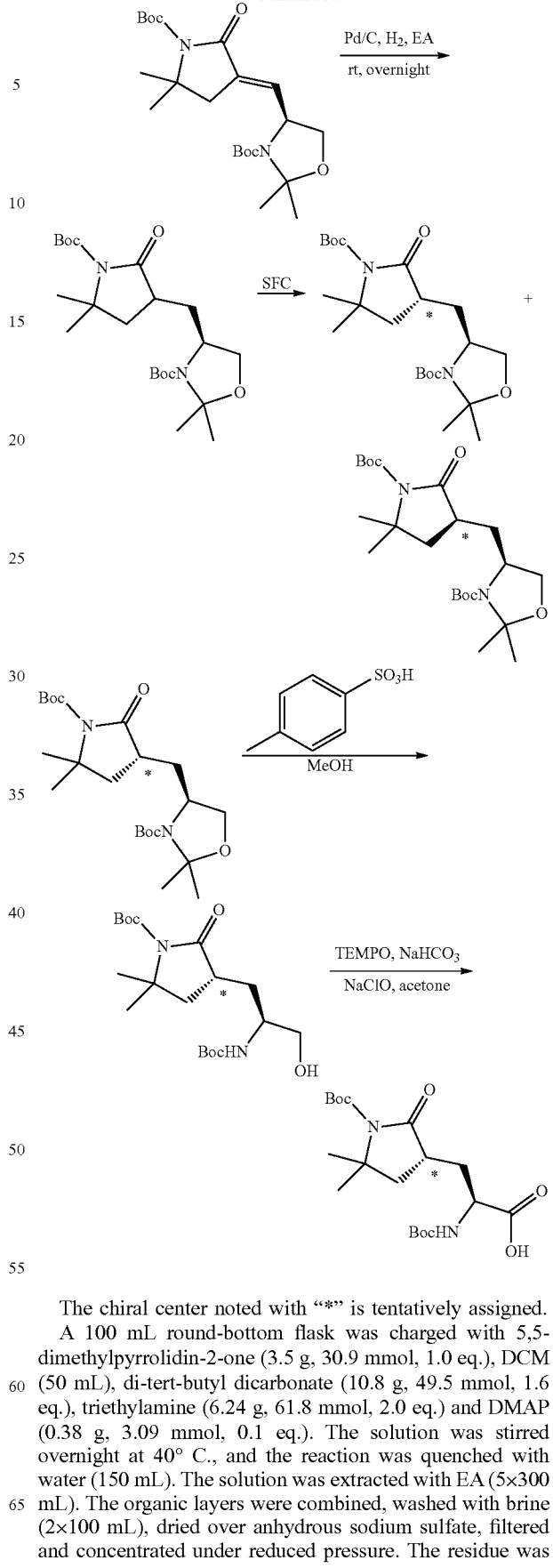

The chiral center noted with "*" is tentatively assigned.

A 100 mL round-bottom flask was charged with 5,5-dimethylpyrrolidin-2-one (3.5 g, 30.9 mmol, 1.0 eq.), DCM (50 mL), di-tert-butyl dicarbonate (10.8 g, 49.5 mmol, 1.6 eq.), triethylamine (6.24 g, 61.8 mmol, 2.0 eq.) and DMAP (0.38 g, 3.09 mmol, 0.1 eq.). The solution was stirred overnight at 40° C., and the reaction was quenched with water (150 mL). The solution was extracted with EA (5×300 mL). The organic layers were combined, washed with brine (2×100 mL), dried over anhydrous sodium sulfate, filtered and concentrated under reduced pressure. The residue was chromatographed on a silica gel column with EA:PE (13:87) to provide tert-butyl 2,2-dimethyl-5-oxopyrrolidine-1-carboxylate (4.0 g, 58%) as a white solid. LC-MS (ESI, m/z): 214 [M+H]+.

A 100 mL round-bottom flask was charged with tert-butyl 2,2-dimethyl-5-oxopyrrolidine-1-carboxylate (3.6 g, 16.9 mmol, 1.00 eq.) and THF (50 mL). The solution was cooled to −78° C. and LiHMDS (20.2 mL, 1M in THF, 20.2 mmol, 1.2 eq.) was added. The mixture was stirred for 1 h at −78° C., and a solution of tert-butyl (4R)-4-formyl-2,2-dimethyl-1,3-oxazolidine-3-carboxylate (5.81 g, 25.3 mmol, 1.5 eq.) in THF (10 mL) was added under Ar. Stirring was continued at −78° C. for 1 h. The reaction was quenched with a sat. ammonium chloride solution (50 mL). The solution was extracted with dichloromethane (3×150 mL). The organic layers were combined, washed with brine (2×50 mL), dried over anhydrous sodium sulfate, filtered and concentrated under reduced pressure. The residue was chromatographed on a silica gel column with EA:PE (1:4) to provide tert-butyl (4R)-4-{[1-(tert-butoxycarbonyl)-5,5-dimethyl-2-oxopyrrolidin-3-yl](hydroxy)methyl}-2,2-dimethyl-1,3-oxazolidine-3-carboxylate (7.2 g, 89%) as a colorless oil. LC-MS (ESI, m/z): 443 [M+H]+.

A 100 mL round-bottom flask was charged with tert-butyl (4R)-4-{[1-(tert-butoxycarbonyl)-5,5-dimethyl-2-oxopyrrolidin-3-yl](hydroxy)methyl}-2,2-dimethyl-1,3-oxazolidine-3-carboxylate (1 g, 2.26 mmol, 1.00 eq.), DCM (10 mL), triethylamine (1.14 g, 11.3 mmol, 5.0 eq.) and MsCl (0.31 g, 4.52 mmol, 2.0 eq.). The mixture was stirred overnight at rt, and the reaction was quenched with water (30 mL). The solution was extracted with dichloromethane (4×50 mL). The organic layers were combined, washed with brine (3×20 mL), dried over anhydrous sodium sulfate, filtered and concentrated under reduced pressure to provide tert-butyl (4R)-4-{[1-(tert-butoxycarbonyl)-5,5-dimethyl-2-oxopyrrolidin-3-yl](methanesulfonyloxy)methyl}-2,2-dimethyl-1,3-oxazolidine-3-carboxylate (960 mg, crude) as a yellow oil. LC-MS (ESI, m/z): 521 [M+H]+.

A 100 mL round-bottom flask was charged with tert-butyl (4R)-4-{[1-(tert-butoxycarbonyl)-5,5-dimethyl-2-oxopyrrolidin-3-yl](methanesulfonyloxy)methyl}-2,2-dimethyl-1,3-oxazolidine-3-carboxylate (900 mg, 1.73 mmol, 1.0 eq.), DCM (20 mL) and DBU (1.32 g, 8.64 mmol, 5.0 eq.). The mixture was stirred overnight at rt, and the reaction was quenched with water (30 mL). The solution was extracted with dichloromethane (3×80 mL). The organic layers were combined, washed with brine (2×30 mL), dried over anhydrous sodium sulfate, filtered and concentrated under reduced pressure. The residue was chromatographed on a silica gel column with EA:PE (1:4) to provide tert-butyl (4S)-4-{[1-(tert-butoxycarbonyl)-5,5-dimethyl-2-oxopyrrolidin-3-ylidene]methyl}-2,2-dimethyl-1,3-oxazolidine-3-carboxylate (635 mg, 82%) as a colorless oil. LC-MS (ESI, m/z): 425 [M+H]+.

A 250 mL round-bottom flask was charged with tert-butyl (4S)-4-{[1-(tert-butoxycarbonyl)-5,5-dimethyl-2-oxopyrrolidin-3-ylidene]methyl}-2,2-dimethyl-1,3-oxazolidine-3-carboxylate (4.4 g, 10.4 mmol, 1.0 eq.), EA (50 mL) and 10% palladium on activated carbon (5.51 g). The contents of the flask were placed under an atmosphere of hydrogen (3 atm). The mixture was stirred overnight at rt. The solids were filtered off. The organic layer was concentrated under reduced pressure to provide tert-butyl (4S)-4-{[1-(tert-butoxycarbonyl)-5,5-dimethyl-2-oxopyrrolidin-3-yl]methyl}-2,2-dimethyl-1,3-oxazolidine-3-carboxylate (4.3 g, 78%) as a colorless oil. LC-MS (ESI, m/z): 427 [M+H]+.

Tert-butyl (4S)-4-((1-(tert-butoxycarbonyl)-5,5-dimethyl-2-oxopyrrolidin-3-yl)methyl)-2,2-dimethyloxazolidine-3-carboxylate (3.6 g) was purified by prep-SFC using the following gradient conditions: Column: Lux 5 um Cellulose-2, 3*25 cm, 5 m; Mobile Phase A: CO2, Mobile Phase B: IPA (0.5% 2M NH3-MeOH); Flow rate: 60 mL/min; Gradient: isocratic 10% B; Column Temperature (° C.): 35; Back Pressure (bar): 100; Wave Length: 220 nm; RT1 (min): 4.81; RT2(min): 6.43; Sample Solvent: MeOH—Preparative; Injection Volume: 1.5 mL; Number Of Runs: 27. Purification resulted in tert-butyl (S)-4-(((S*)-1-(tert-butoxycarbonyl)-5,5-dimethyl-2-oxopyrrolidin-3-yl)methyl)-2,2-dimethyloxazolidine-3-carboxylate (990 mg) as an off-white solid (Lux Celloluse-2 4.6*50 mm, 3 m, 35° C. Co-Solvent: IPA (0.1% DEA), 10% to 50% in 2.0 min, hold 1.0 min at 50%): Rt: 0.969 min), and tert-butyl (S)-4-(((R*)-1-(tert-butoxycarbonyl)-5,5-dimethyl-2-oxopyrrolidin-3-yl)methyl)-2,2-dimethyloxazolidine-3-carboxylate (1.6 g) as an off-white solid Lux Celloluse-2 4.6*50 mm, 3 m, 35° C. Co-Solvent: IPA (0.1% DEA), 10% to 50% in 2.0 min, hold 1.0 min at 50%): Rt: 1.411 min).

A 40 mL vial was charged with tert-butyl (S)-4-(((R*)-1-(tert-butoxycarbonyl)-5,5-dimethyl-2-oxopyrrolidin-3-yl)methyl)-2,2-dimethyloxazolidine-3-carboxylate (1.6 g, 3.75 mmol, 1.0 eq.), para-toluene sulfonate (64.6 mg, 0.375 mmol, 0.1 eq.) and MeOH (20 mL). The mixture was stirred overnight at rt. The reaction was quenched with water (20 mL). The solution was extracted with EA (3×30 mL). The organic layers were combined, washed with brine (50 mL), dried over anhydrous sodium sulfate, filtered and concentrated under reduced pressure to provide tert-butyl(S)-4-((S)-2-((tert-butoxycarbonyl)amino)-3-hydroxypropyl)-2,2-dimethyl-5-oxopyrrolidine-1-carboxylate (1.47 g, crude) as an off-white semi-solid. LC-MS (ESI, m/z): 387 [M+H]+.

To a solution of tert-butyl (S)-4-((R*)-2-((tert-butoxycarbonyl)amino)-3-hydroxypropyl)-2,2-dimethyl-5-oxopyrrolidine-1-carboxylate (1.7 g, 4.40 mmol, 1.0 eq.) in acetone (22 mL) was added 5% sodium bicarbonate solution (22 mL, 13.1 mmol, 3.0 eq.) and 2,2,6,6-Tetramethylpiperidinooxy (0.14 g, 0.88 mmol, 0.2 eq.). Chlorosylsodium (1.15 g, 15.4 mmol, 3.5 eq.) was added dropwise at 0° C. The mixture was stirred at rt overnight, and the reaction was quenched with water (20 mL). The solution was washed with Et2O (2×20 mL). The pH value of the aqueous solution was adjusted to 2 with concentrated hydrochloric acid (1 mol/L). The solution was extracted with EtOAc (3×50 mL). The organic layers were combined, washed with brine (50 mL), dried over anhydrous sodium sulfate, filtered and concentrated under reduced pressure to provide (S)-3-((R*)-1-(tert-butoxycarbonyl)-5,5-dimethyl-2-oxopyrrolidin-3-yl)-2-((tert-butoxycarbonyl)amino)propanoic acid (1.2 g, 61%) as a white solid.

tert-butyl ((S)-1-hydroxy-3-((S*)-5-oxo-4-azaspiro[2.4]heptan-6-yl)propan-2-yl)carbamate

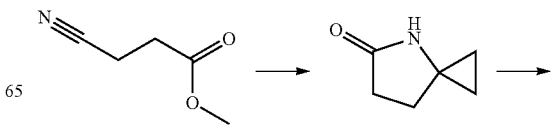

-continued

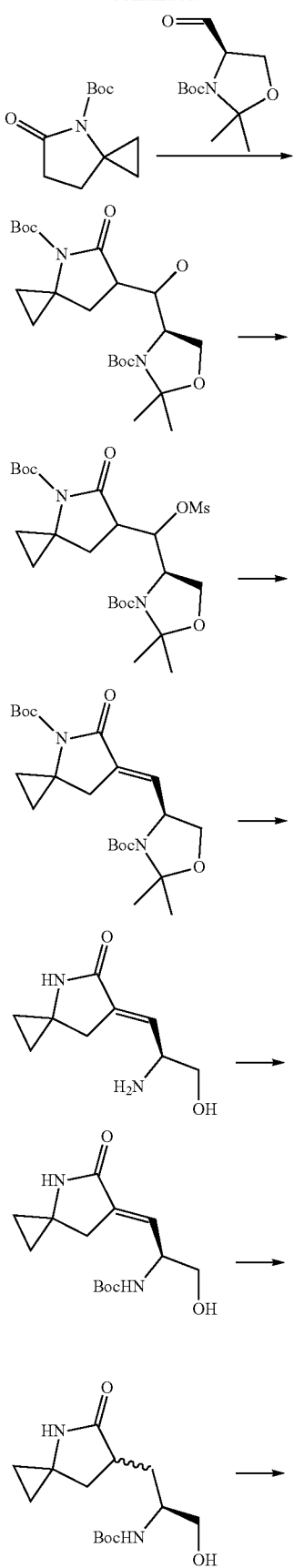

-continued

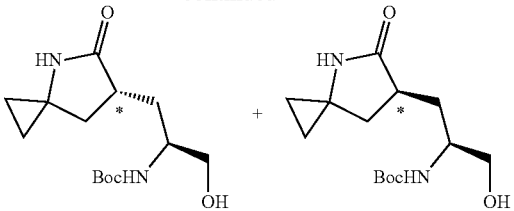 [SMILES: CC(C)(C)OC(=O)N[C@H](CO)C[C@@H]1CC2(CC2)NC1=O ; CC(C)(C)OC(=O)N[C@H](CO)C[C@H]1CC2(CC2)NC1=O]

The absolute configuration of the chiral center noted with "*" is tentatively assigned.

To a solution of methyl 3-cyanopropanoate (10 g, 88.4 mmol, 1.0 eq.) in Et$_2$O (100 mL) was added Ti(O$^i$Pr)$_4$ (5.03 g, 17.7 mmol, 0.2 eq.). EtMgBr (194 mL, 1M in THF, 194 mmol, 2.2 eq.) was then added dropwise under N$_2$. The mixture was stirred at rt for 2 h, and the reaction was quenched with water (20 mL). The mixture was extracted with EA (3×60 mL). The organic layers were combined, washed with brine (50 mL), dried over anhydrous sodium sulfate, filtered and concentrated under reduced pressure. The residue was chromatographed on a silica gel column with PE:MeOH (12:1) to provide 4-azaspiro[2.4]heptan-5-one (8.5 g, 69%) as a colorless oil. LC-MS (ESI, m/z): 112 [M+H]$^+$.

A 250 mL round-bottom flask was charged with 4-azaspiro[2.4]heptan-5-one (8.5 g, 76.5 mmol, 1.0 eq.), DCM (100 mL), di-tert-butyl dicarbonate (26.7 g, 122 mmol, 1.6 eq.), triethylamine (0.77 g, 7.65 mmol, 0.1 eq.) and DMAP (0.93 g, 7.65 mmol, 0.1 eq.). The solution was stirred overnight at 40° C., and the reaction was quenched with water (70 mL). The solution was extracted with DCM (3×100 mL). The organic layers were combined, washed with brine (80 mL), dried over anhydrous sodium sulfate, filtered and concentrated under reduced pressure. The residue was chromatographed on a silica gel column with EA:PE (1:12) to provide tert-butyl 5-oxo-4-azaspiro[2.4]heptane-4-carboxylate (11 g, 58%) as a white solid. LC-MS (ESI, m/z): 212 [M+H]$^+$.

A 500 mL round-bottom flask was charged with tert-butyl 5-oxo-4-azaspiro[2.4]heptane-4-carboxylate (11 g, 52.1 mmol, 1.0 eq.) and THF (150 mL). The solution was cooled to −78° C. and LiHMDS (62.5 mL, 1M in THF, 62.5 mmol, 1.2 eq.) was added. The mixture was stirred for 1 h at −78° C. and a solution of tert-butyl (4R)-4-formyl-2,2-dimethyl-1,3-oxazolidine-3-carboxylate (17.9 g, 78.1 mmol, 1.5 eq.) in THF (50 mL) under Ar was added. Stirring was continued at −78° C. for 1 h. The reaction was quenched with sat. ammonium chloride solution (100 mL). The solution was extracted with EA (3×200 mL). The organic layers were combined, washed with brine (200 mL), dried over anhydrous sodium sulfate, filtered and concentrated under reduced pressure. The residue was chromatographed on a silica gel column with EA:PE (1:8) to provide tert-butyl (4R)-4-((4-(tert-butoxycarbonyl)-5-oxo-4-azaspiro[2.4]heptan-6-yl)(hydroxy)methyl)-2,2-dimethyloxazolidine-3-carboxylate (19.7 g, 69%) as a colorless oil. LC-MS (ESI, m/z): 441 [M+H]$^+$.

A 500 mL round-bottom flask was charged with tert-butyl (4R)-4-((4-(tert-butoxycarbonyl)-5-oxo-4-azaspiro[2.4]heptan-6-yl)(hydroxy)methyl)-2,2-dimethyloxazolidine-3-carboxylate (19.7 g, 44.7 mmol, 1.0 eq.), DCM (250 mL), triethylamine (27.2 g, 268 mmol, 6.0 eq.) and MsCl (20.5 g, 179 mmol, 4.0 eq.). The mixture was stirred overnight at rt, and the reaction was quenched with water (100 mL). The solution was extracted with DCM (4×150 mL). The organic layers were combined, washed with brine (100 mL), dried over anhydrous sodium sulfate, filtered and concentrated under reduced pressure to provide tert-butyl (4R)-4-((4-(tert-butoxycarbonyl)-5-oxo-4-azaspiro[2.4]heptan-6-yl)((methylsulfonyl)oxy)methyl)-2,2-dimethyloxazolidine-3-carboxylate (22 g, crude) as an orange oil. LC-MS (ESI, m/z): 519 [M+H]⁺.

A 500 mL round-bottom flask was charged with tert-butyl (4R)-4-((4-(tert-butoxycarbonyl)-5-oxo-4-azaspiro[2.4]heptan-6-yl)((methylsulfonyl)oxy)methyl)-2,2-dimethyloxazolidine-3-carboxylate (22 g, 42.4 mmol, 1.0 eq.), DCM (200 mL) and DBU (14.2 g, 93.3 mmol, 2.2 eq.). The mixture was stirred overnight at rt, and the reaction was quenched with water (80 mL). The solution was extracted with DCM (3×100 mL). The organic layers were combined, washed with brine (80 mL), dried over anhydrous sodium sulfate, filtered and concentrated under reduced pressure. The residue was chromatographed on a silica gel column with EA:PE (1:12) to provide tert-butyl 6-{[(4S)-3-(tert-butoxycarbonyl)-2,2-dimethyl-1,3-oxazolidin-4-yl]methylidene}-5-oxo-4-azaspiro[2.4]heptane-4-carboxylate (11.3 g, 57%) as a colorless oil. LC-MS (ESI, m/z): 423 [M+H]⁺.

A 250 mL vial was charged with tert-butyl 6-{[(4S)-3-(tert-butoxycarbonyl)-2,2-dimethyl-1,3-oxazolidin-4-yl]methylidene}-5-oxo-4-azaspiro[2.4]heptane-4-carboxylate (11.3 g, 26.7 mmol, 1.0 eq.), 4-methylbenzenesulfonic acid (5.53 g, 32.1 mmol, 1.2 eq.) and MeOH (120 mL). The mixture was stirred overnight at rt, and then concentrated under reduced pressure to provide 6-[(2S)-2-amino-3-hydroxypropylidene]-4-azaspiro[2.4]heptan-5-one (5.8 g, crude) as an orange oil. LC-MS (ESI, m/z): 183 [M+H]⁺.

To a solution of 6-[(2S)-2-amino-3-hydroxypropylidene]-4-azaspiro[2.4]heptan-5-one (5.8 g, 31.829 mmol, 1.00 eq.) in DCM (90 mL) was added triethylamine (25.8 g, 255 mmol, 8.0 eq.) and di-tert-butyl dicarbonate (20.8 g, 95.5 mmol, 3.0 eq.). The mixture was stirred at rt overnight, and the reaction was quenched with water (30 mL). The mixture was extracted with CDCl₃:isopropyl alcohol=3:1 (3×50 mL). The organic layers were combined, dried over anhydrous sodium sulfate, filtered and concentrated under reduced pressure. The residue was chromatographed on a silica gel column with MeOH:DCM (1:25) to provide tert-butyl N-[(2S)-1-hydroxy-3-[(6E)-5-oxo-4-azaspiro[2.4]heptan-6-ylidene]propan-2-yl]carbamate (3.9 g, 39%) as a brown yellow solid. LCMS (ESI, m/z): 283 [M+H]⁺.

To a solution of tert-butyl N-[(2S)-1-hydroxy-3-[5-oxo-4-azaspiro[2.4]heptan-6-ylidene]propan-2-yl]carbamate (3.9 g, 13.8 mmol, 1.0 eq.) in THF (30 mL) and MeOH (90 mL) was added NiCl₂·6H₂O (23 g, 96.7 mmol, 7.0 eq.). NaBH₄ (11 g, 290 mmol, 21.0 eq.) was added in several portions at 0° C. The mixture was stirred at rt overnight, and the reaction was quenched with water (30 mL). The mixture was extracted with CDCl₃:isopropyl alcohol=3:1 (3×60 mL). The organic layers were combined, dried over anhydrous sodium sulfate, filtered and concentrated under reduced pressure. The residue was chromatographed on a C18 column with MeCN:H₂O (4:1) to provide tert-butyl N-[(2S)-1-hydroxy-3-{5-oxo-4-azaspiro[2.4]heptan-6-yl}propan-2-yl]carbamate (1.7 g, 39%) as a brown yellow solid. LCMS (ESI, m/z): 285 [M+H]⁺.

Tert-butyl N-[(2S)-1-hydroxy-3-{5-oxo-4-azaspiro[2.4]heptan-6-yl}propan-2-yl]carbamate (1.7 g) was purified by SFC using the following gradient conditions: Column: NB-Lux Sum i-Cellulose-5, 2.12*25 cm, 5 µm; Mobile Phase A: CO₂, Mobile Phase B: MeOH (0.1% 2M NH₃-MeOH); Flow rate: 100 mL/min; Gradient: isocratic 25% B; Column Temperature (° C.): 35; Back Pressure (bar): 100; Wave Length: 220 nm; RT1 (min): 3.37; RT2(min): 4.02; Sample Solvent: MeOH—Preparative; Injection Volume: 1 mL; Number Of Runs: 40. Purification resulted in 590 mg of first eluding tert-butyl ((S)-1-hydroxy-3-((R*)-5-oxo-4-azaspiro[2.4]heptan-6-yl)propan-2-yl)carbamate as a brown yellow solid and 640 mg of last eluding tert-butyl ((S)-1-hydroxy-3-((S*)-5-oxo-4-azaspiro[2.4]heptan-6-yl)propan-2-yl)carbamate as a brown yellow solid.

(3S)-3-amino-N-cyclopropyl-2-hydroxy-4-((S)-2-oxopyrrolidin-3-yl)butanamide

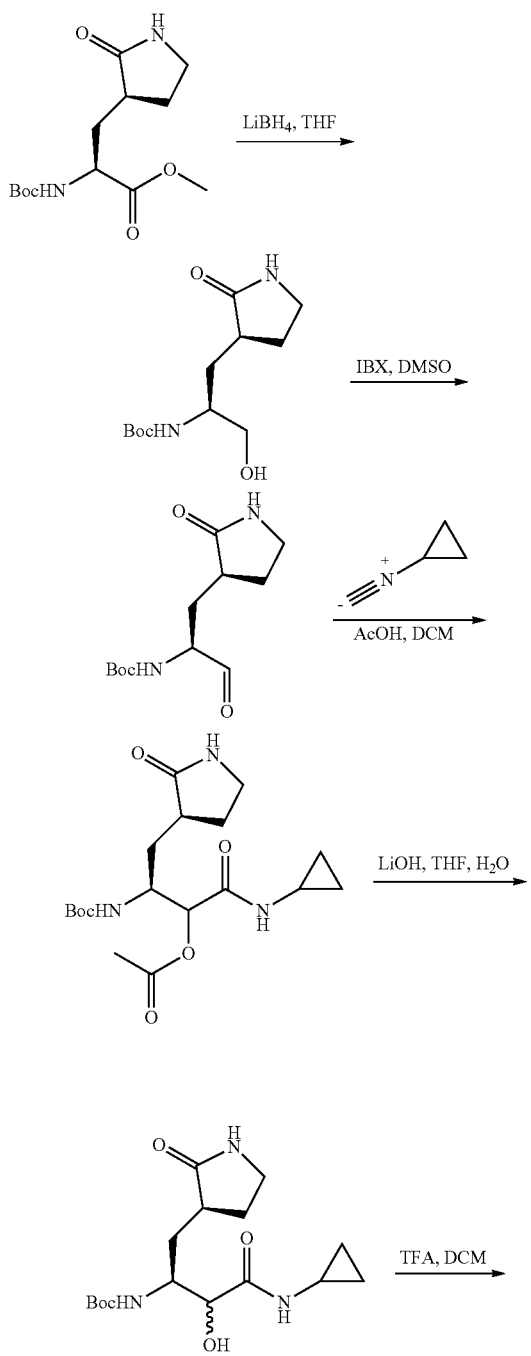

-continued

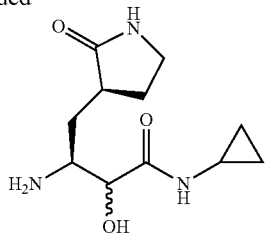

To a stirred mixture of methyl (2S)-2-[(tert-butoxycarbonyl)amino]-3-[(3S)-2-oxopyrrolidin-3-yl]propanoate (3.0 g, 10.5 mmol, 1.0 eq.) in tetrahydrofuran (50 mL) was added lithium borohydride (26.2 mL, 52.4 mmol, 5.0 eq.) dropwise at 0° C. The mixture was stirred for 1 h at 0° C. and then concentrated under reduced pressure. The mixture was diluted with water (20 mL), and then extracted with isopropanol:trichloromethane (1:5, 4×50 mL). The organic layers were combined, dried over anhydrous sodium sulfate, filtered and concentrated under reduced pressure. The residue was purified by silica gel column chromatography, eluted with dichloromethane:methanol (19:1) to afford tert-butyl N-[(2S)-1-hydroxy-3-[(3S)-2-oxopyrrolidin-3-yl]propan-2-yl]carbamate (2.6 g, crude) as a white solid. The crude product was precipitated by the addition of PE:EA (4:1, 40 mL) to afford tert-butyl N-[(2S)-1-hydroxy-3-[(3S)-2-oxopyrrolidin-3-yl]propan-2-yl]carbamate (2.4 g, 79%) as a white solid. LC-MS (ESI, m/z): 259 [M+H]⁺.

To a stirred mixture of tert-butyl N-[(2S)-1-hydroxy-3-[(3S)-2-oxopyrrolidin-3-yl]propan-2-yl]carbamate (2.4 g, 9.29 mmol, 1.0 eq.) in dimethyl sulfoxide (40 mL) was added 2-iodoxybenzoic acid (7.80 g, 27.8 mmol, 3.0 eq.) in portions at rt. The mixture was stirred for 3 h at rt, and then basified to pH=8 with sat. sodium bicarbonate (aq.). The mixture was diluted with water (20 mL) and extracted with EA (4×200 mL). The organic layers were combined, washed with brine (3×100 mL), dried over anhydrous sodium sulfate, filtered and concentrated under reduced pressure to afford tert-butyl N-[(2S)-1-oxo-3-[(3S)-2-oxopyrrolidin-3-yl]propan-2-yl]carbamate (1.5 g, 63%) as a yellow solid. LC-MS (ESI, m/z): 257 [M+H]⁺.

To a stirred mixture of tert-butyl N-[(2S)-1-oxo-3-[(3S)-2-oxopyrrolidin-3-yl]propan-2-yl]carbamate (900 mg, 3.51 mmol, 1.0 eq.) in dichloromethane (10 mL) were added isocyanocyclopropane (471 mg, 7.02 mmol, 2.0 eq.) and acetic acid (633 mg, 10.5 mmol, 3.0 eq.) dropwise at 0° C. The mixture was stirred for 5 h at rt and then concentrated under reduced pressure. The residue was purified by silica gel column chromatography, eluted with dichloromethane:methanol (49:1) to afford (2S)-2-[(tert-butoxycarbonyl)amino]-1-(cyclopropylcarbamoyl)-3-[(3S)-2-oxopyrrolidin-3-yl]propyl acetate (820 mg, 55%) as a yellow solid. LC-MS (ESI, m/z): 384 [M+H]⁺.

To a stirred mixture of (2S)-2-[(tert-butoxycarbonyl)amino]-1-(cyclopropylcarbamoyl)-3-[(3S)-2-oxopyrrolidin-3-yl]propyl acetate (810 mg, 2.11 mmol, 1.0 eq.) in tetrahydrofuran (8 mL) was added lithium hydroxide (253 mg, 10.5 mmol, 5.0 eq., in water 8 mL) at 0° C. The mixture was stirred for 1 h at 0° C. The mixture was acidified to pH=6 with hydrochloric acid (2M). The mixture was extracted with EA (4×60 mL). The organic layers were combined, dried over anhydrous sodium sulfate, filtered and concentrated under reduced pressure to afford tert-butyl N-[(2S)-1-(cyclopropylcarbamoyl)-2-hydroxy-3-[(3S)-2-oxopyrrolidin-3-yl]propan-2-yl]carbamate (680 mg, 94%) as a yellow solid. LCMS (ESI, m/z): 342 [M+H]⁺.

To a stirred mixture of tert-butyl N-[(2S)-1-(cyclopropylcarbamoyl)-1-hydroxy-3-[(3S)-2-oxopyrrolidin-3-yl]propan-2-yl]carbamate (400 mg, 1.17 mmol, 1.0 eq.) in dichloromethane (6 mL) was added trifluoroacetic acid (2 mL) dropwise at rt. The mixture was stirred for 1 h at rt and then concentrated under reduced pressure to afford (3S)-3-amino-N-cyclopropyl-2-hydroxy-4-[(3S)-2-oxopyrrolidin-3-yl]butanamide (290 mg, crude) as a brown solid. LC-MS (ESI, m/z): 242 [M+H]⁺.

tert-butyl (1S,3aR,4S,7R,7aS)-1-(((2S)-4-(cyclopropylamino)-3-hydroxy-4-oxo-1-((S)-2-oxopyrrolidin-3-yl)butan-2-yl)carbamoyl)-1,3,3a,4,7,7a-hexahydro-2H-4,7-methanoisoindole-2-carboxylate

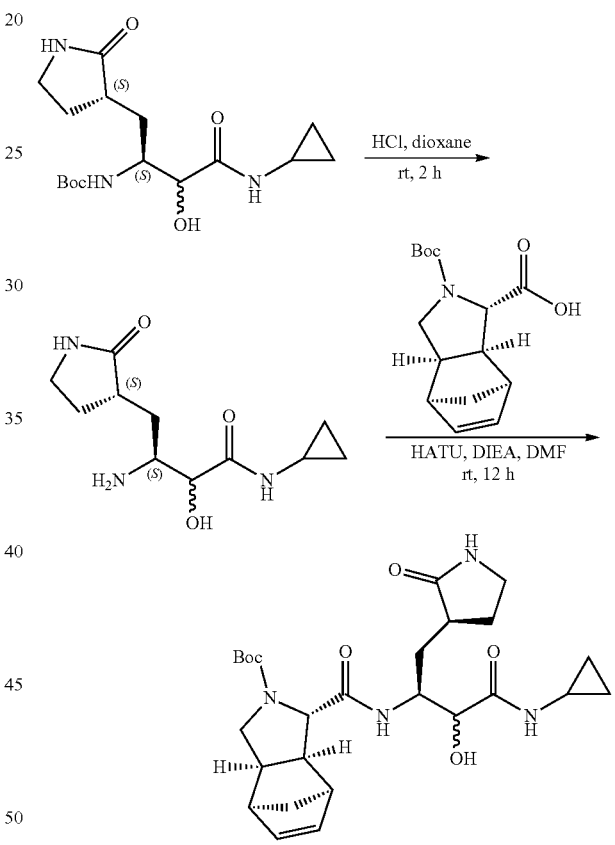

A solution of tert-butyl ((2S)-4-(cyclopropylamino)-3-hydroxy-4-oxo-1-((S)-2-oxopyrrolidin-3-yl)butan-2-yl)carbamate (800 mg, 2.34 mmol, 1.0 eq.) in hydrochloric acid (14 mL, 4 M in dioxane) was stirred at rt for 2 h and then concentrated under reduced pressure to provide (3S)-3-amino-N-cyclopropyl-2-hydroxy-4-((S)-2-oxopyrrolidin-3-yl)butanamide (550 mg, crude) as an off-white solid. LC-MS (ESI, m/z): 242 [M+H]⁺.

To a solution of (1S,3aR,4S,7R,7aS)-2-(tert-butoxycarbonyl)-2,3,3a,4,7,7a-hexahydro-1H-4,7-methanoisoindole-1-carboxylic acid (700 mg, 2.5 mmol, 1.1 eq.) in DMF (8 mL) were added N,N,N',N'-Tetramethyl-O-(7-azabenzotriazol-1-yl)uronium hexafluorophospate (1.13 g, 2.96 mmol, 1.3 eq.) and N,N-diisopropylethylamine (2.06 g, 16 mmol, 7.0 eq.). The mixture was stirred at 0° C. for 30 min and (3S)-3- amino-N-cyclopropyl-2-hydroxy-4-((S)-2-oxopyrrolidin-3-yl)butanamide (550 mg, 2.28 mmol, 1.0 eq.) was added. The mixture was stirred at rt for 2 h, and the reaction was quenched with water (10 mL). The mixture was extracted with EA (3×20 mL). The organic layers were combined, washed with brine (3×10 mL), dried over anhydrous sodium sulfate, filtered and concentrated under reduced pressure. The residue was chromatographed on a silica gel column with MeOH:DCM (1:12) to provide tert-butyl (1S,3aR,4S,7R,7aS)-1-(((2S)-4-(cyclopropylamino)-3-hydroxy-4-oxo-1-((S)-2-oxopyrrolidin-3-yl)butan-2-yl)carbamoyl)-1,3,3a,4,7,7a-hexahydro-2H-4,7-methanoisoindole-2-carboxylate (900 mg, 70%) as a brown yellow solid. LC-MS (ESI, m/z): 503 [M+H]+.

Example 1

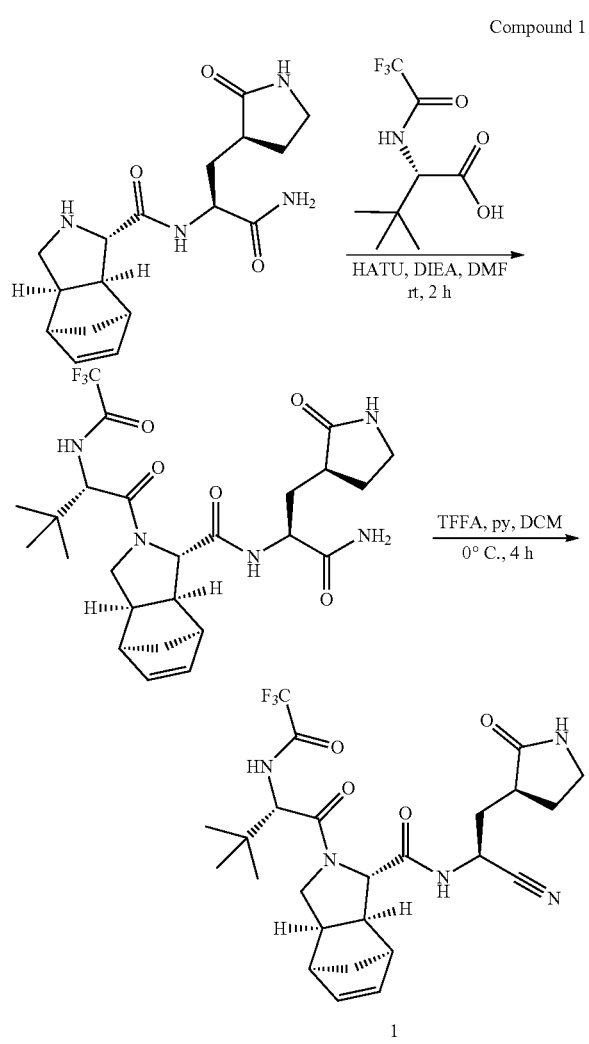

Compound 1

To a solution of tert-butyl (2S)-3,3-dimethyl-2-(2,2,2-trifluoroacetamido)butanoate (118 mg, 0.42 mmol, 1.2 eq.) in DMF (2 mL) was added N,N,N',N'-Tetramethyl-O-(7-azabenzotriazol-1-yl)uronium hexafluorophospate (171 mg, 0.45 mmol, 1.3 eq.) and N,N-diisopropylethylamine (313 mg, 2.42 mmol, 7.0 eq.). The mixture was stirred at 0° C. for 30 min and then (1S,3aR,4S,7R,7aS)—N—((S)-1-amino-1-oxo-3-((S)-2-oxopyrrolidin-3-yl)propan-2-yl)-2,3,3a,4,7,7a-hexahydro-1H-4,7-methanoisoindole-1-carboxamide (115 mg, 0.35 mmol, 1.0 eq.) was added. The mixture was stirred at rt for 2 h, and the reaction was quenched with water (3 mL). The mixture was extracted with EA (3×5 mL). The organic layers were combined, washed with brine (3×5 mL), dried over anhydrous sodium sulfate, filtered and concentrated under reduced pressure. The residue was chromatographed on a C18 column with water:MeCN (2:1) to provide (1S,3aR,4S,7R,7aS)—N—((S)-1-amino-1-oxo-3-((S)-2-oxopyrrolidin-3-yl)propan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (150 mg, yield 72%) as a brown yellow solid. LC-MS (ESI, m/z): 542 [M+H]+.

To a solution of (1S,3aR,4S,7R,7aS)—N—((S)-1-amino-1-oxo-3-((S)-2-oxopyrrolidin-3-yl)propan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (120 mg, 0.22 mmol, 1.0 eq.) in DCM (3 mL) was added TFAA (88.4 mg, 0.42 mmol, 1.9 eq.) and pyridine (61.3 mg, 0.78 mmol, 3.5 eq.). The mixture was stirred at 0° C. for 4 h, and the reaction was quenched with water (4 mL). The mixture was extracted with DCM (3×5 mL). The organic layers were combined, dried over anhydrous sodium sulfate, filtered and concentrated under reduced pressure. The residue was purified by Prep-HPLC (Column: XBridge Shield RP18 OBD Column, 19*150 mm, 5 m; Mobile Phase A: Water (0.05% TFA), Mobile Phase B: ACN; Flow rate: 25 mL/min; Gradient: 30% B to 50% B in 7 min, 50% B; Wave Length: 254 nm; RT1 (min): 5.55;) to provide (1S,3aR,4S,7R,7aS)—N—((S)-1-cyano-2-((S)-2-oxopyrrolidin-3-yl)ethyl)-2-((S)-3,3-dimethyl-2-(2,2,2-trifluoroacetamido)butanoyl)-2,3,3a,4,7,7a-hexahydro-1H-4,7-methanoisoindole-1-carboxamide (1) (53.2 mg, yield 45%) as a white solid. 1H NMR (400 MHz, DMSO-d6, 80° C.) δ 8.66-8.95 (m, 2H), 7.28-7.37 (m, 1H), 5.96-6.23 (m, 2H), 4.87-4.93 (m, 1H), 4.41-4.68 (m, 1H), 3.86-4.17 (m, 1H), 3.58-3.71 (m, 1H), 3.20-3.51 (m, 2H), 2.83-3.06 (m, 4H), 2.59-2.79 (m, 1H), 2.29-2.38 (m, 1H), 2.03-2.28 (m, 2H), 1.61-1.84 (m, 2H), 1.31-1.42 (m, 2H), 0.79-0.90 (m, 9H). LC-MS (ESI, m/z): 524 [M+H]+.

Example 2

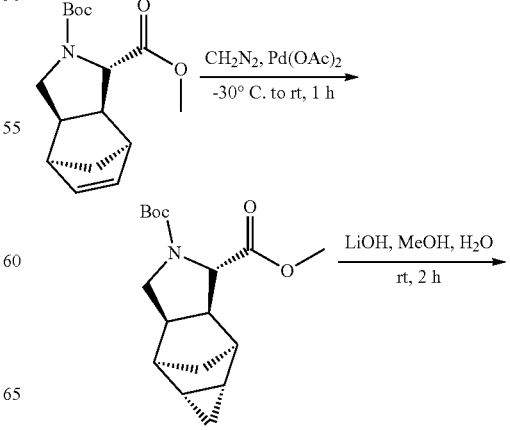

-continued

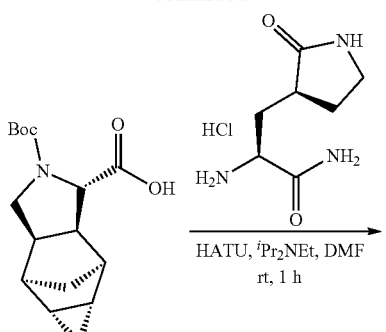

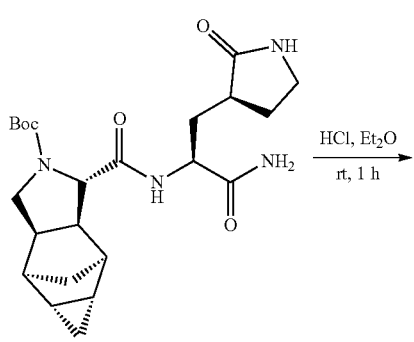

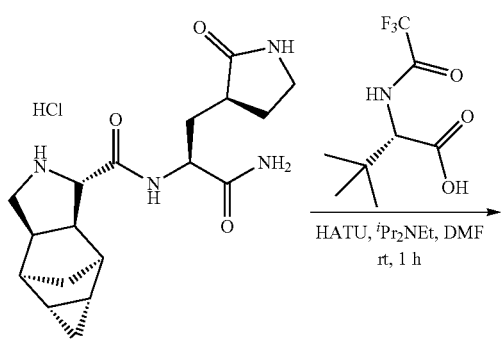

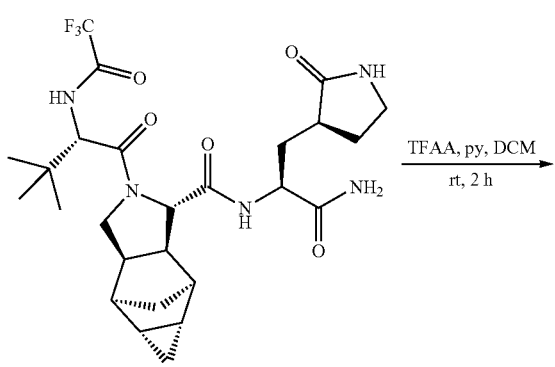

-continued

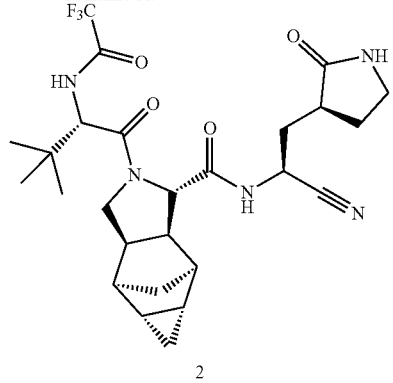

2

To a solution of 4-tert-butyl 3-methyl (1R,2S,3S,6R,7S)-4-azatricyclo[5.2.1.0^{2,6}]dec-8-ene-3,4-dicarboxylate (300 mg, 1.02 mmol, 1.0 eq.) in Et$_2$O (2.5 mL) at −30° C. was added diazomethane (30 mL, 30.0 eq.) and palladium (II) acetate (45.9 mg, 0.205 mmol, 0.2 eq.). The mixture was stirred for 1 h at rt and then filtered. The filter cake was washed with diethyl ether (3×50 mL). The filtrate was concentrated under reduced pressure to afford the crude product. The crude product was chromatographed on a silica gel column with ethyl acetate (EA):petroleum ether (PE) (1:8) to provide 4-tert-butyl 3-methyl (1R,2S,3S,6R,7S,8S,10R)-4-azatetracyclo[5.3.1.0^{2,6}.0^{8,10}]undecane-3,4-dicarboxylate (200 mg, 58%) as a light yellow solid. $^1$H NMR (400 MHz, DMSO-d$_6$) δ 4.25-4.50 (m, 1H), 3.53-3.72 (m, 4H), 3.22-3.30 (m, 1H), 2.52-2.64 (m, 2H), 2.22-2.42 (m, 2H), 1.21-1.47 (m, 9H), 1.03-1.16 (m, 1H), 0.70-0.95 (m, 3H), 0.39-0.54 (m, 1H), −0.09-0.05 (m, 1H). LC-MS (ESI, m/z): 208 [M+H−Boc]$^+$.

To a stirred mixture of 4-tert-butyl 3-methyl (1R,2S,3S,6R,7S,8S,10R)-4-azatetracyclo[5.3.1.0^{2,6}.0^{8,10}]undecane-3,4-dicarboxylate (245 mg, 0.797 mmol, 1.0 eq.) in MeOH (3 mL) and H$_2$O (3 mL) were added lithium hydroxide (95.4 mg, 3.98 mmol, 5.0 eq.). The mixture was stirred for 2 h at rt. The mixture was acidified to pH 4 with hydrochloric acid (1M) and then extracted with ethyl acetate (3×10 mL). The mixture was concentrated under reduced pressure to afford (1R,2S,3S,6R,7S,8S,10R)-4-(tert-butoxycarbonyl)-4-azatetracyclo[5.3.1.0^{2,6}.0^{8,10}]undecane-3-carboxylic acid (200 mg, 85%) as a light yellow solid. $^1$H NMR (400 MHz, DMSO-d$_6$) δ 12.57 (s, 1H), 4.17-4.39 (m, 1H), 3.47-3.76 (m, 1H), 3.12-3.31 (m, 1H), 2.51-2.59 (m, 2H), 2.20-2.44 (m, 2H), 1.27-1.49 (m, 9H), 1.05-1.22 (m, 1H), 0.69-0.93 (m, 3H), 0.40-0.51 (m, 1H), −0.06-0.00 (m, 1H). LC-MS (ESI, m/z): 238 [M+H−56]$^+$.

To a stirred mixture of (1R,2S,3S,6R,7S,8S,10R)-4-(tert-butoxycarbonyl)-4-azatetracyclo[5.3.1.0^{2,6}.0^{8,10}]undecane-3-carboxylic acid (200 mg, 0.682 mmol, 1.0 eq.) in DMF (2 mL) was added o-(7-Azabenzotriazol-1-yl)-N,N,N',N'-tetramethyluronium hexafluorophosphate (311 mg, 0.818 mmol, 1.2 eq.) and N-ethyl-N-isopropylpropan-2-amine (528 mg, 4.09 mmol, 6.0 eq.) at rt. The mixture was stirred for 10 min at 0° C. and then (2S)-2-amino-3-[(3S)-2-oxopyrrolidin-3-yl]propanamide hydrochloride (141 mg, 0.682 mmol, 1.0 eq.) was added. The mixture was stirred for 1 h at rt. The mixture was purified by C18 column with CH$_3$CN:Water (0.05% FA). The compound fraction was concentrated under reduced pressure to provide tert-butyl (1R,2S,3S,6R,7S,8S,10R)-3-{[(1S)-1-carbamoyl-2-[(3S)-2-oxopyrrolidin-3-yl]ethyl]carbamoyl}-4-azatetracyclo

[5.3.1.0^{2,6}.0^{8,10}]undecane-4-carboxylate (200 mg, 55%) as a white solid. LC-MS (ESI, m/z): 447 [M+H]⁺.

To a stirred mixture of tert-butyl (1R,2S,3S,6R,7S,8S,10R)-3-{[(1S)-1-carbamoyl-2-[(3S)-2-oxopyrrolidin-3-yl]ethyl]carbamoyl}-4-azatetracyclo[5.3.1.0^{2,6}.0^{8,10}]undecane-4-carboxylate (200 mg, 0.448 mmol, 1.0 eq.) in DCM (1 mL) was added hydrochloric acid (3 mL, 2M in Et₂O) at rt. The mixture was stirred for 1 h at rt and then concentrated under reduced pressure to afford (2S)-2-[(1R,2S,3S,6R,7S,8S,10R)-4-azatetracyclo[5.3.1.0^{2,6}.0^{8,10}]undecan-3-ylformamido]-3-[(3S)-2-oxopyrrolidin-3-yl]propanamide hydrochloride (200 mg, crude) as a white solid. LC-MS (ESI, m/z): 347 [M+H]⁺.

To a stirred mixture of (2S)-3,3-dimethyl-2-(2,2,2-trifluoroacetamido)butanoic acid (101 mg, 0.446 mmol, 1.1 eq.) in DMF (2 mL) was added o-(7-Azabenzotriazol-1-yl)-N,N,N',N'-tetramethyluronium hexafluorophosphate (184 mg, 0.486 mmol, 1.2 eq.) and N-ethyl-N-isopropylpropan-2-amine (314 mg, 2.43 mmol, 6.0 eq.). The mixture was stirred for 10 min at 0° C., and then (2S)-2-[(1R,2S,3S,6R,7S,8S,10R)-4-azatetracyclo[5.3.1.0^{2,6}.0^{8,10}]undecan-3-ylformamido]-3-[(3S)-2-oxopyrrolidin-3-yl]propanamide hydrochloride (155 mg, 0.405 mmol, 1.0 eq.) was added. The mixture was stirred for 1 h at rt. The mixture was purified by C18 column with CH₃CN:Water (0.05% FA). The compound fraction was concentrated under reduced pressure to provide (2S)-2-{[(1R,2S,3S,6R,7S,8S,10R)-4-[(2S)-3,3-dimethyl-2-(2,2,2-trifluoroacetamido)butanoyl]-4-azatetracyclo[5.3.1.0^{2,6}.0^{8,10}]undecan-3-yl]formamido}-3-[(3S)-2-oxopyrrolidin-3-yl]propanamide (170 mg, 67%) as a white solid. LC-MS (ESI, m/z): 556 [M+H]⁺.

To a stirred mixture of (2S)-2-{[(1R,2S,3S,6R,7S,8S,10R)-4-[(2S)-3,3-dimethyl-2-(2,2,2-trifluoroacetamido)butanoyl]-4-azatetracyclo[5.3.1.0^{2,6}.0^{8,10}]undecan-3-yl]formamido}-3-[(3S)-2-oxopyrrolidin-3-yl]propanamide (100 mg, 0.180 mmol, 1.0 eq.) in DCM (2 mL) was added trifluoroacetic anhydride (75.6 mg, 0.360 mmol, 2.0 eq.) and pyridine (49.8 mg, 0.630 mmol, 3.5 eq.) dropwise at rt. The mixture was stirred for 2 h at rt. The reaction was quenched with water (10 mL). The mixture was extracted with dichloromethane (3×10 mL). The organic layers were combined, washed with brine (2×10 mL), dried over anhydrous sodium sulfate, filtered and concentrated under reduced pressure to afford the crude product. The crude product was purified by Prep-HPLC with the following conditions (Column: Xselect Peptide CSH C18 19*150 mm 5 m, 1; Mobile Phase A: Water (0.1% FA), Mobile Phase B: ACN; Flow rate: 25 mL/min; Gradient: 34% B to 48% B in 10 min, 48% B; Wave Length: 254 nm; RT1 (min): 8.98) to afford (1R,2S,3S,6R,7S,8S,10R)—N-[(1S)-1-cyano-2-[(3S)-2-oxopyrrolidin-3-yl]ethyl]-4-[(2S)-3,3-dimethyl-2-(2,2,2-trifluoroacetamido)butanoyl]-4-azatetracyclo[5.3.1.0^{2,6}.0^{8,10}]undecane-3-carboxamide (9.6 mg, 9%) as a white solid. ¹H NMR (400 MHz, 80° C., DMSO-d₆) δ 8.47-9.13 (m, 2H), 7.33-7.62 (m, 1H), 4.82-4.95 (m, 1H), 4.56-4.75 (m, 2H), 3.90-4.04 (m, 1H), 3.57-3.70 (m, 1H), 3.08-3.20 (m, 2H), 2.59-2.72 (m, 1H), 2.24-2.45 (m, 4H), 2.05-2.20 (m, 2H), 1.60-1.84 (m, 2H), 0.91-1.11 (m, 9H), 0.85-0.91 (m, 1H), 0.75-0.84 (m, 2H), 0.56-0.65 (m, 1H), 0.38-0.51 (m, 1H), −0.30-0.00 (m, 1H).

Example 3

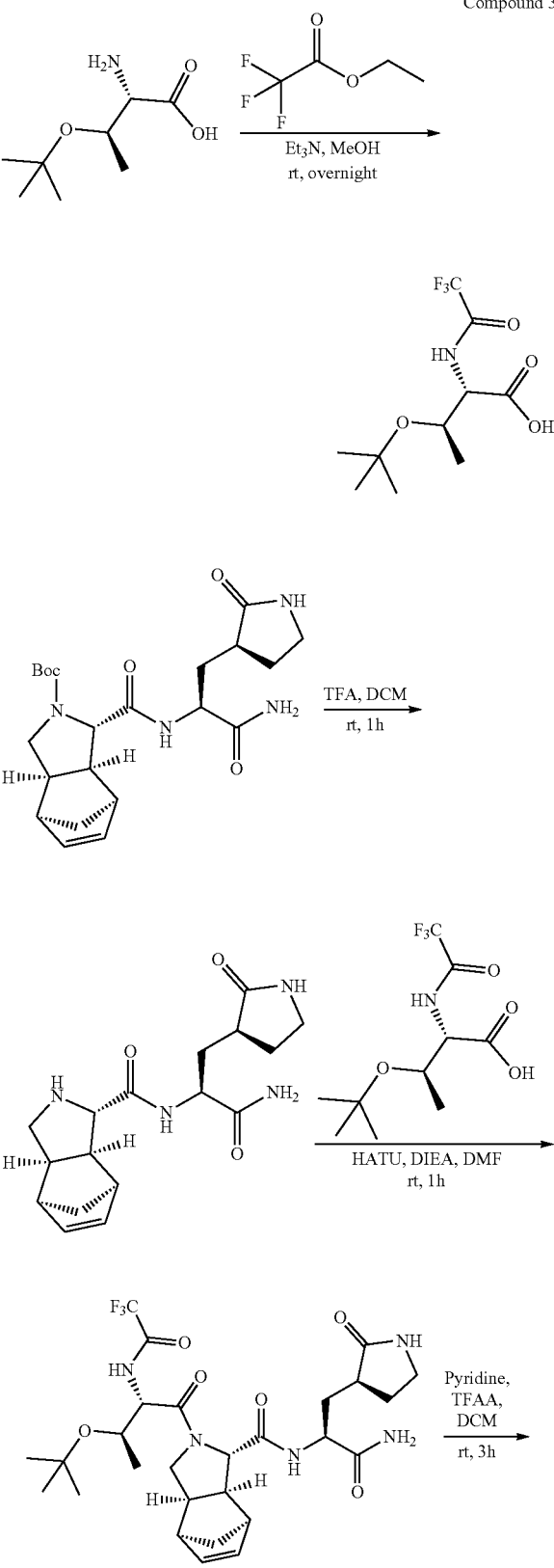

Compound 3

-continued

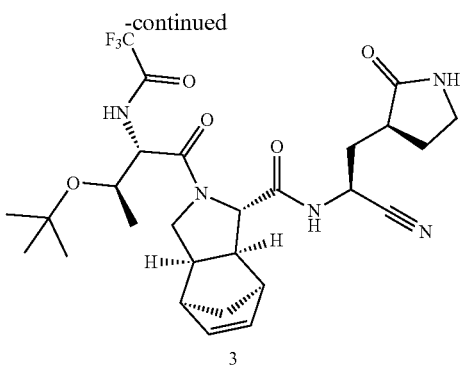

3

To a stirred mixture of (2S,3R)-2-amino-3-(tert-butoxy) butanoic acid (1.00 g, 5.71 mmol, 1.0 eq.) in methanol (15 mL) was added ethyl 2,2,2-trifluoroacetate (0.970 g, 6.84 mmol, 1.2 eq.) and triethylamine (1.73 g, 17.1 mmol, 3.0 eq.). The mixture was stirred for overnight at rt. The reaction was quenched with water (50 mL). The mixture was adjusted to pH 5-6 with hydrochloric acid (1 M) and then extracted with EtOAc (3×50 mL). The organic layers were combined, washed with brine (2×50 mL), dried over anhydrous sodium sulfate, filtered and concentrated under reduced pressure to afford (2S,3R)-3-(tert-butoxy)-2-(2,2,2-trifluoroacetamido)butanoic acid (1.58 g, crude) as a light brown solid. LC-MS (ESI, m/z): 270 [M−H]⁻.

To a stirred mixture of tert-butyl (1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-ene-4-carboxylate (120 mg, 0.277 mmol, 1.0 eq.) in DCM (3 mL) was added trifluoroacetic acid (1 mL). The mixture was stirred for 1 h at rt and then concentrated under reduced pressure to afford (2S)-2-[(1R,2S,3S,6R,7S)-4-azatricyclo[5.2.1.0^{2,6}]dec-8-en-3-ylformamido]-3-[(3S)-2-oxopyrrolidin-3-yl]propanamide (92.0 mg, crude) as a brown oil. LC-MS (ESI, m/z): 333 [M+H]⁺.

To a stirred mixture of (2S)-2-[(1R,2S,3S,6R,7S)-4-azatricyclo[5.2.1.0^{2,6}]dec-8-en-3-ylformamido]-3-[(3S)-2-oxopyrrolidin-3-yl]propanamide (92.0 mg, 0.277 mmol, 1.0 eq.), (2S,3R)-3-(tert-butoxy)-2-(2,2,2-trifluoroacetamido) butanoic acid (75.1 mg, 0.277 mmol, 1.0 eq.) and o-(7-azabenzotriazol-1-yl)-N,N,N',N'-tetramethyluronium hexafluorophosphate (126 mg, 0.332 mmol, 1.2 eq.) in DMF (4 mL) was added N-ethyl-N-isopropylpropan-2-amine (286 mg, 2.21 mmol, 8.0 eq.) at 0° C. The mixture was stirred for 1 h at rt. The reaction was quenched with water (10 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was chromatographed on a silica gel column with MeOH:DCM (1:12) to provide the desired product. The crude product was purified by C18 column with CH₃CN: Water (0.05% TFA), the fraction was concentrated under reduced pressure to provide (2S)-2-{[(1R,2S,3S,6R,7S)-4-[(2S,3R)-3-(tert-butoxy)-2-(2,2,2-trifluoroacetamido)butanoyl]-4-azatricyclo[5.2.1.0^{2,6}]dec-8-en-3-yl]formamido}-3-[(3S)-2-oxopyrrolidin-3-yl]propanamide (61.0 mg, crude) as a light yellow solid. LC-MS (ESI, m/z): 586 [M+H]⁺.

To a stirred mixture of (2S)-2-{[(1R,2S,3S,6R,7S)-4-[(2S,3R)-3-(tert-butoxy)-2-(2,2,2-trifluoroacetamido)butanoyl]-4-azatricyclo[5.2.1.0^{2,6}]dec-8-en-3-yl]formamido}-3-[(3S)-2-oxopyrrolidin-3-yl]propanamide (60.0 mg, 0.102 mmol, 1.0 eq.) in DCM (2 mL) were added pyridine (32.4 mg, 0.408 mmol, 4.0. eq.) and trifluoroacetic anhydride (43.1 mg, 0.204 mmol, 2.0 eq.). The mixture was stirred for 3 h at rt. The reaction was quenched with water (10 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was purified by preparative HPLC (Column: XBridge Prep Phenyl OBD Column, 19*250 mm, 5 m; Mobile Phase A: Water (0.05% TFA), Mobile Phase B: ACN; Flow rate: 25 mL/min; Gradient: 40% B to 56% B in 10 min, 56% B; Wave Length: 254 nm; RT1 (min): 8.22) to provide (1R,2S,3S,6R,7S)-4-[(2S,3R)-3-(tert-butoxy)-2-(2,2,2-trifluoroacetamido)butanoyl]-N-[(1S)-1-cyano-2-[(3S)-2-oxopyrrolidin-3-yl]ethyl]-4-azatricyclo[5.2.1.0^{2,6}] dec-8-ene-3-carboxamide (1.7 mg, 2%). LC-MS (ESI, m/z): 512 [M−56+H]⁺.

Example 4

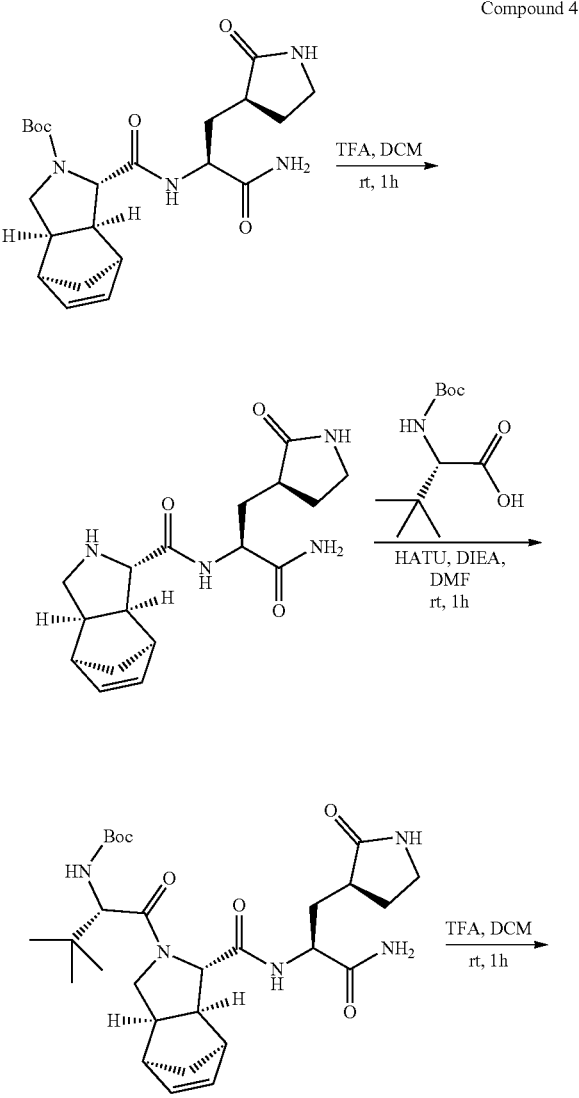

Compound 4

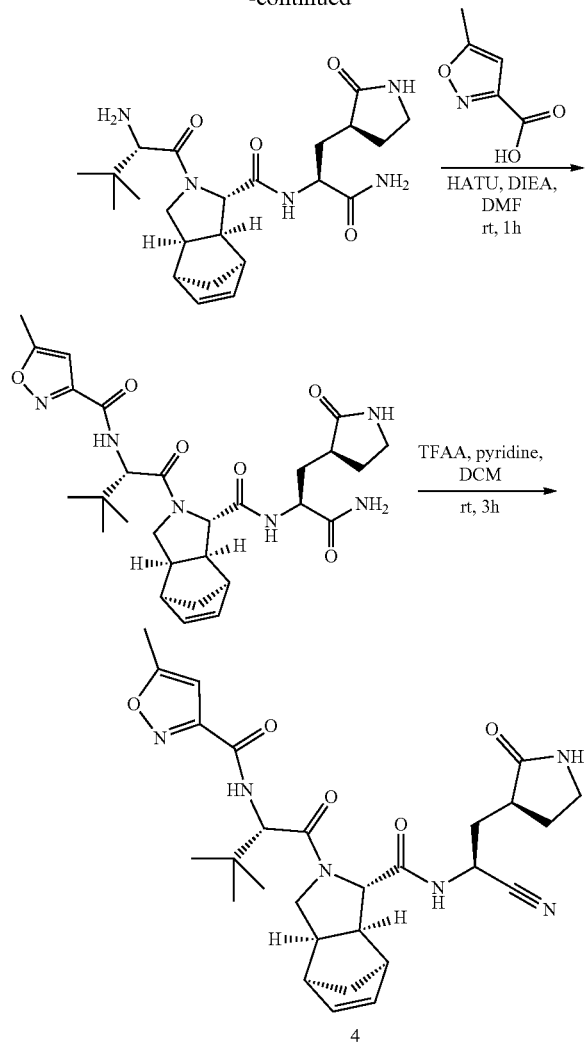

To a stirred mixture of tert-butyl (1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-ene-4-carboxylate (500 mg, 1.15 mmol, 1.0 eq.) in DCM (6 mL) was added trifluoroacetic acid (2 mL). The mixture was stirred for 1 h at rt and then concentrated under reduced pressure to afford (2S)-2-[(1R,2S,3S,6R,7S)-4-azatricyclo[5.2.1.0^{2,6}]dec-8-en-3-ylformamido]-3-[(3S)-2-oxopyrrolidin-3-yl]propanamide (380 mg, crude) as a yellow oil. LC-MS (ESI, m/z): 333 [M+H]$^+$.

To a stirred mixture of (2S)-2-[(1R,2S,3S,6R,7S)-4-azatricyclo[5.2.1.0^{2,6}]dec-8-en-3-ylformamido]-3-[(3S)-2-oxopyrrolidin-3-yl]propanamide (76.0 mg, 0.229 mmol, 1.0 eq.), (2S)-2-[(tert-butoxycarbonyl)amino]-3,3-dimethylbutanoic acid (52.9 mg, 0.229 mmol, 1.0 eq.) and o-(7-azabenzotriazol-1-yl)-N,N,N',N'-tetramethyluronium hexafluorophosphate (104 mg, 0.275 mmol, 1.2 eq.) in DMF (2 mL) were added N-ethyl-N-isopropylpropan-2-amine (236 mg, 1.83 mmol, 8.0 eq.) at 0° C. The mixture was stirred for 1 h at rt. The crude product was purified by C18 column with CH$_3$CN:Water (0.05% TFA). The compound fraction was concentrated under reduced pressure to provide tert-butyl N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxobutan-2-yl]carbamate (105 mg, 78%) as a white solid. LC-MS (ESI, m/z): 546 [M+H]$^+$.

To a stirred mixture of tert-butyl N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxobutan-2-yl]carbamate (100 mg, 0.183 mmol, 1.0 eq.) in DCM (3 mL) was added trifluoroacetic acid (1 mL). The mixture was stirred for 1 h at rt and then concentrated under reduced pressure to afford (2S)-2-{[(1R,2S,3S,6R,7S)-4-[(2S)-2-amino-3,3-dimethylbutanoyl]-4-azatricyclo[5.2.1.0^{2,6}]dec-8-en-3-yl]formamido}-3-[(3S)-2-oxopyrrolidin-3-yl]propanamide (81.0 mg, crude) as a yellow oil. LC-MS (ESI, m/z): 446 [M+H]$^+$.

To a stirred mixture of (2S)-2-{[(1R,2S,3S,6R,7S)-4-[(2S)-2-amino-3,3-dimethylbutanoyl]-4-azatricyclo[5.2.1.0^{2,6}]dec-8-en-3-yl]formamido}-3-[(3S)-2-oxopyrrolidin-3-yl]propanamide (81.5 mg, 0.183 mmol, 1.0 eq.), o-(7-azabenzotriazol-1-yl)-N,N,N',N'-tetramethyluronium hexafluorophosphate (83.5 mg, 0.220 mmol, 1.2 eq.) and 5-methyl-1,2-oxazole-3-carboxylic acid (23.3 mg, 0.183 mmol, 1.0 eq.) in DMF (3 mL) were added N-ethyl-N-isopropylpropan-2-amine (189 mg, 1.46 mmol, 8.0 eq.). The mixture was stirred for 1 h at rt. The crude product was purified by C18 column with CH$_3$CN:Water (0.05% TFA). The compound fraction was concentrated under reduced pressure to provide N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxobutan-2-yl]-5-methyl-1,2-oxazole-3-carboxamide (74 mg, 62%) as a white solid. LC-MS (ESI, m/z): 554 [M+H]$^+$.

To a stirred mixture of N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxobutan-2-yl]-5-methyl-1,2-oxazole-3-carboxamide (70.0 mg, 0.126 mmol, 1.0 eq.) in DCM (2 mL) were added pyridine (39.9 mg, 0.504 mmol, 4.0 eq.) and trifluoroacetic anhydride (53.0 mg, 0.252 mmol, 2.0 eq.). The mixture was stirred for 3 h at rt. The reaction was quenched with water (10 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was purified by prep-HPLC (Column: XBridge Shield RP18 OBD Column, 19*250 mm, 10 m; Mobile Phase A: Water (0.1% FA), Mobile Phase B: ACN; Flow rate: 25 mL/min; Gradient: 35% B to 65% B in 7 min, 65% B; Wave Length: 254 nm; RT1 (min): 5) to provide (1R,2S,3S,6R,7S)—N-[(1S)-1-cyano-2-[(3S)-2-oxopyrrolidin-3-yl]ethyl]-4-[(2S)-3,3-dimethyl-2-[(5-methyl-1,2-oxazol-3-yl)formamido]butanoyl]-4-azatricyclo[5.2.1.0^{2,6}]dec-8-ene-3-carboxamide (7.70 mg, 11%) as a white solid. LC-MS (ESI, m/z): 537 [M+H]$^+$.

Example 5

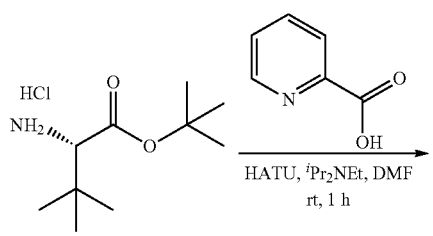

-continued

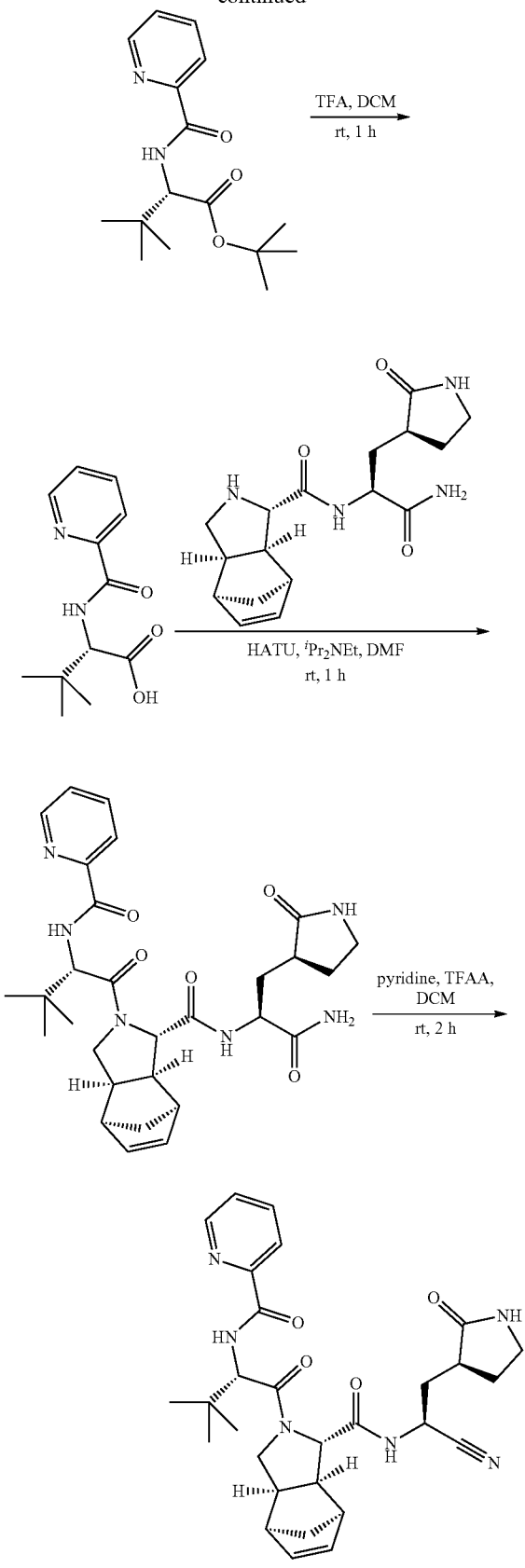

To a solution of picolinic acid (110 mg, 0.894 mmol, 1.0 eq.) in dimethylformamide (2 mL) was added o-(7-azabenzotriazol-1-yl)-N,N,N',N'-tetramethyluronium hexafluorophosphate (408 mg, 1.07 mmol, 1.2 eq.) and N-ethyl-N-isopropylpropan-2-amine (924 mg, 7.15 mmol, 8.0 eq.) 0° C. After 0.5 h, tert-butyl (2S)-2-amino-3,3-dimethylbutanoate hydrochloride (200 mg, 0.894 mmol, 1.0 eq.) was added. The mixture was stirred for 1 h at rt. The reaction was quenched with water (10 mL). The mixture was extracted with ethyl acetate (3×20 mL). The organic layers were combined, washed with brine (2×20 mL), dried over anhydrous sodium sulfate, filtered and concentrated under reduced pressure to afford then crude product. The crude product was purified by silica gel column chromatography to afford tert-butyl (2S)-3,3-dimethyl-2-(pyridin-2-ylformamido)butanoate (88 mg, 33%). $^1$H NMR (400 MHz, DMSO-d$_6$) δ 8.67-8.73 (m, 1H), 8.40-8.50 (m, 1H), 8.00-8.10 (m, 2H), 7.62-7.69 (m, 1H), 4.26-4.33 (m, 1H), 1.44 (s, 9H), 1.00 (s, 9H). LCMS (ESI, m/z): 293 [M+H]$^+$.

To a solution of tert-butyl (2S)-3,3-dimethyl-2-(pyridin-2-ylformamido)butanoate (88.0 mg, 0.291 mmol, 1.0 eq.) in DCM (2 mL) was added trifluoroacetic acid (0.7 mL). The mixture was stirred for 4 h at rt and then concentrated under reduced pressure to afford the crude product. LCMS (ESI, m/z): 237 [M+H]$^+$.

To a solution of (1S,3aR,4S,7R,7aS)—N—((S)-1-amino-1-oxo-3-((S)-2-oxopyrrolidin-3-yl)propan-2-yl)-2,3,3a,4,7,7a-hexahydro-1H-4,7-methanoisoindole-1-carboxamide (100 mg, 0.301 mmol, 1 eq.) in DMF (4 mL) was added (2S)-3,3-dimethyl-2-(pyridin-2-ylformamido)butanoic acid (70.8 mg, 0.301 mmol, 1.0 eq.), o-(7-azabenzotriazol-1-yl)-N,N,N',N'-tetramethyluronium hexafluorophosphate (137.3 mg, 0.361 mmol, 1.2 eq.) and N-ethyl-N-isopropylpropan-2-amine (233 mg, 2.41 mmol, 8.0 eq.) stirred at 0° C. The mixture was stirred for 1 h at rt. The mixture was purified by C18 column with CH$_3$CN:Water (0.05% FA). The compound fraction was concentrated under reduced pressure to afford N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0ˆ{2,6}]dec-8-en-4-yl]-3,3-dimethyl-1-oxobutan-2-yl]pyridine-2-carboxamide (50.0 mg, crude).

To a stirred mixture of N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0ˆ{2,6}]dec-8-en-4-yl]-3,3-dimethyl-1-oxobutan-2-yl]pyridine-2-carboxamide (25.0 mg, 0.045 mmol, 1.0 eq.) in DCM (2 mL) was added trifluoroacetic anhydride (8.81 mg, 0.090 mmol, 2.0 eq.) and pyridine (12.5 mg, 0.158 mmol, 3.5 eq.) dropwise at rt. The mixture was stirred for 2 h at rt. The reaction was quenched with water (10 mL). The mixture was extracted with ethyl acetate (3×10 mL). The organic layers were combined, washed with brine (2×10 mL), dried over anhydrous sodium sulfate, filtered and concentrated under reduced pressure to afford the crude product. The crude product (25 mg) was purified by prep-HPLC with the following conditions (Column: Kinetex EVO C18, 21.2*250 mm, 5 m; Mobile Phase A: Water (0.1% FA), Mobile Phase B: ACN; Flow rate: 25 mL/min; Gradient: 35% B to 62% B in 7 min, 62% B; Wave Length: 254 nm; RT1 (min): 5) to afford (1R,2S,3S,6R,7S)—N-[(1S)-1-cyano-2-[(3S)-2-oxopyrrolidin-3-yl]ethyl]-4-[(2S)-3,3-dimethyl-2-(pyridin-2-ylformamido)butanoyl]-4-azatricyclo[5.2.1.0ˆ{2,6}]dec-8-ene-3-carboxamide (3.2 mg, 12%) as a light yellow solid. LCMS (ESI, m/z): 533 [M+H]$^+$.

Example 6

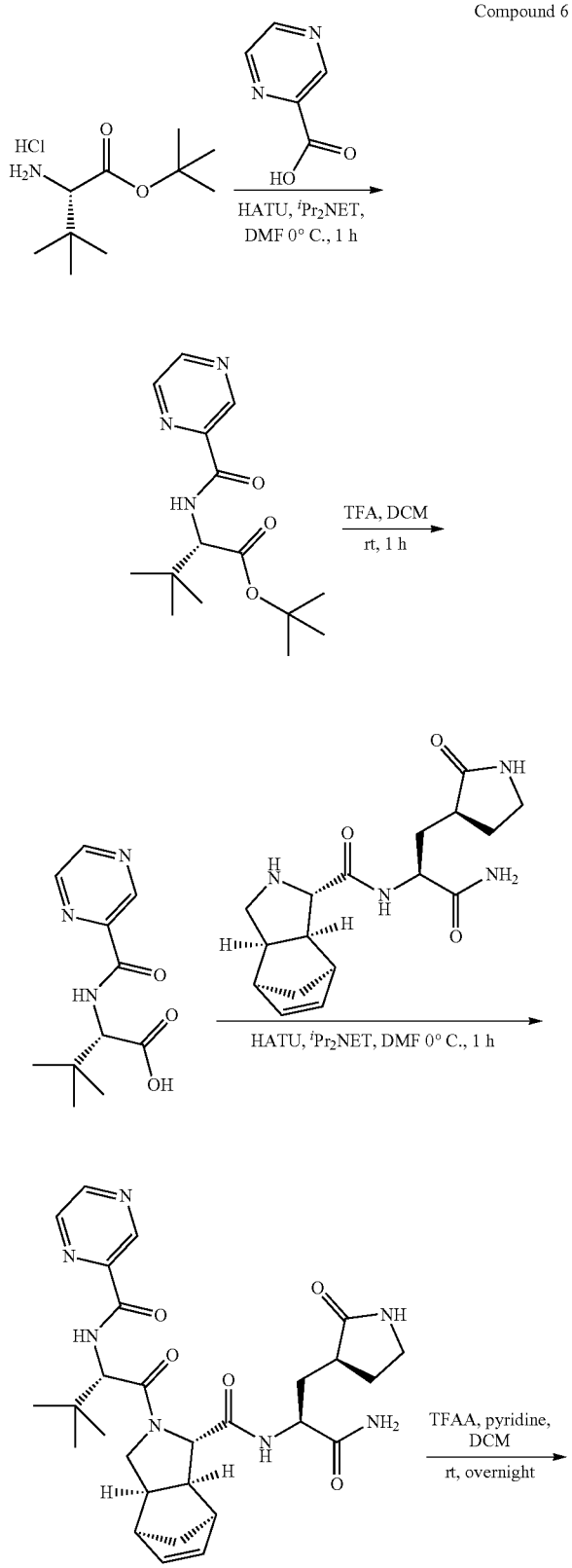

To a mixture of pyrazinoic acid (166 mg, 1.34 mmol, 1.0 eq.), o-(7-azabenzotriazol-1-yl)-N, N, N',N'-tetramethyluronium hexafluorophosphate (612 mg, 1.61 mmol, 1.2 eq.) and N-ethyl-N-isopropylpropan-2-amine (1.04 g, 8.05 mmol, 6.0 eq.) in N,N-dimethylformamide (3 mL) was stirred for 20 min. Tert-butyl (2S)-2-amino-3,3-dimethylbutanoate hydrochloride (300 mg, 1.34 mmol, 1.0 eq.) was added at 0° C. The mixture was stirred for 1 h at rt, and the reaction quenched with water (2 mL). The mixture was extracted with ethyl acetate (3×20 mL). The organic layers were combined, washed with brine (2×20 mL), dried over anhydrous sodium sulfate, filtered and concentrated under reduced pressure to afford the crude product. The crude product was diluted with dichloromethane (10 mL) and made into a slurry with 100~200 silica gel mesh (1 g). The slurry was loaded to a column after removing the dichloromethane. The sample was purified by column chromatography (Column size 4×24 cm, column volume: 200 mL, silica gel size (100~200 mesh) and eluted with EA:PE (0%~40% over 30 min). The collected fractions: 23%-26% EA:PE fractions were chosen as the pure fractions. Those fractions were combined and concentrated under reduced pressure to provide tert-butyl (2S)-3,3-dimethyl-2-(pyrazin-2-ylformamido)butanoate (300 mg, 76%) as a light yellow solid. $^1$H NMR (300 MHz, DMSO-$d_6$) δ 9.21 (br, 1H), 8.91-8.95 (m, 1H), 8.75-8.82 (m, 1H), 8.29-8.33 (m, 1H), 4.31-4.34 (m, 1H), 1.45 (s, 9H), 1.01 (s, 9H). LC-MS (ESI, m/z): 294 [M+H]$^+$.

To a mixture of tert-butyl (2S)-3,3-dimethyl-2-(pyrazin-2-ylformamido)butanoate (87.9 mg, 0.300 mmol, 1.0 eq.) in dichloromethane (1 mL) was added trifluoroacetic acid (0.5 mL). The mixture was stirred for 1 h at rt and then concentrated under reduced pressure to afford (2S)-3,3-dimethyl-2-(pyrazin-2-ylformamido)butanoic acid (80.0 mg, crude) as a yellow oil. LC-MS (ESI, m/z): 238 [M+H]$^+$.

To a mixture of (2S)-3,3-dimethyl-2-(pyrazin-2-ylformamido) butanoic acid (71.1 mg, 0.30 mmol, 1.0 eq.), and (2S)-2-[(1R,2S,3S,6R,7S)-4-azatricyclo[5.2.1.0^{2,6}]dec-8-en-3-ylformamido]-3-[(3S)-2-oxopyrrolidin-3-yl]propanamide (99.6 mg, 0.30 mmol, 1.0 eq.) in DMF (3 mL) was added N-ethyl-N-isopropylpropan-2-amine (348 mg, 2.70 mmol, 9.0 eq.) at 0° C. The mixture was stirred for 1 h at rt. The crude product was purified by C18 column with CH$_3$CN:Water (0.05% NH$_4$HCO$_3$). The compound fraction was concentrated under reduced pressure to provide (1R, 2S,3S,6R,7S)—N-[(1S)-1-cyano-2-[(3S)-2-oxopyrrolidin-3-yl]ethyl]-4-[(2S)-3,3-dimethyl-2-(pyrazin-2-ylformamido)butanoyl]-4-azatricyclo[5.2.1.0^{2,6}]dec-8-ene-3-carboxamide (70.0 mg, 43%) as a yellow solid. LC-MS (ESI, m/z): 552 [M+H]+.

To a mixture of N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxobutan-2-yl]pyrazine-2-carboxamide (55.0 mg, 0.100 mmol, 1.0 eq.) in dichloromethane (1 mL) was added pyridine (31.5 mg, 0.400 mmol, 4.0 eq.) and trifluoroacetic anhydride (41.9 mg, 0.200 mmol, 2.0 eq.). The mixture was stirred for overnight at rt. The reaction was quenched with water (5 mL). The mixture was extracted with ethyl acetate (3×10 mL). The organic layers were combined, washed with brine (2×10 mL), dried over anhydrous sodium sulfate, filtered and concentrated under reduced pressure to afford the crude product. The crude product was purified by prep-HPLC (Column: XBridge Prep C18 OBD Column, 19*150 mm, 5 m; Mobile Phase A: Water (0.1% FA), Mobile Phase B: MeOH—HPLC; Flow rate: 25 mL/min; Gradient: 43% B to 53% B in 12 min, 53% B; Wave Length: 254 nm; RT1 (min): 11) to provide (1R,2S,3S,6R,7S)—N-[(1S)-1-cyano-2-[(3S)-2-oxopyrrolidin-3-yl]ethyl]-4-[(2S)-3,3-dimethyl-2-(pyrazin-2-ylformamido)butanoyl]-4-azatricyclo[5.2.1.0^{2,6}]dec-8-ene-3-carboxamide (3.0 mg, 5%) as an off-white solid. LC-MS (ESI, m/z): 534 [M+H]+.

Example 7

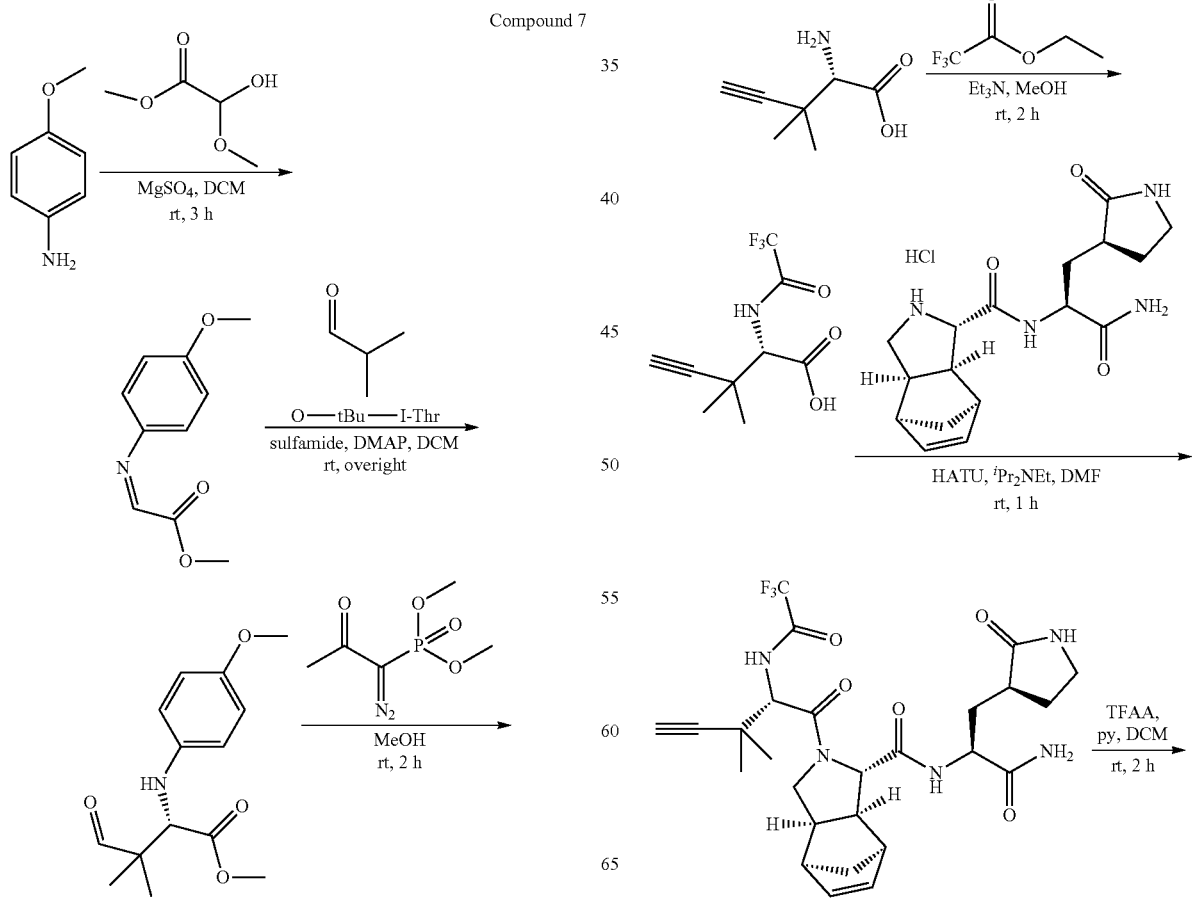

Compound 7

-continued

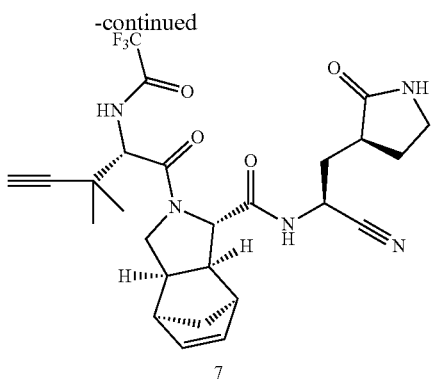

7

To a mixture of 4-methoxyaniline (5.0 g, 36.4 mmol, 1.0 eq.) and magnesium sulfate (24.4 g, 202 mmol, 5.0 eq.) in DCM (100 mL) was added methyl 2-hydroxy-2-methoxyacetate (4.88 g, 40.5 mmol, 1.0 eq.). The mixture was stirred for 3 h at rt and filtered. The filter cake was washed with dichloromethane (3×100 mL). The filtrate was concentrated under reduced pressure to afford methyl (2Z)-2-[(4-methoxyphenyl)imino]acetate (8 g, crude) as a brown yellow oil. $^1$H NMR (400 MHz, CDCl$_3$) δ 7.95 (s, 1H), 7.33-7.43 (m, 2H), 6.85-6.99 (m, 2H), 3.94 (s, 3H), 3.83 (s, 3H). LC-MS (ESI, m/z): 194 [M+H]$^+$.

To a stirred mixture of powdered molecular sieves (5 Å, 4 g), sulfamide (0.20 g, 2.07 mmol, 0.05 eq.) and N,N-dimethylpyridin-4-amine (0.25 g, 2.07 mmol, 0.05 eq.) in DCM (40 mL) was added methyl (2Z)-2-[(4-methoxyphenyl)imino]acetate (8.00 g, 41.4 mmol, 1.0 eq.) and isobutyraldehyde (3.58 g, 49.6 mmol, 1.2 eq.) at rt. The mixture was stirred for overnight at rt. The reaction was quenched with water (150 mL). The mixture was extracted with ethyl acetate (3×150 mL). The organic layers were combined, washed with brine (2×150 mL), dried over anhydrous sodium sulfate, filtered and concentrated under reduced pressure to afford the crude product. The crude product was chromatographed on a silica gel column with EA:PE (1:4) to provide methyl (2S)-2-[(4-methoxyphenyl)amino]-3,3-dimethyl-4-oxobutanoate (4.5 g, 36%) as a light yellow oil. $^1$H NMR (400 MHz, DMSO-d$_6$) δ 9.58 (s, 1H), 6.73 (m, 4H), 5.42 (d, J=8.0 Hz, 1H), 4.44 (d, J=8.0 Hz, 1H), 3.65 (s, 3H), 3.61 (s, 3H), 0.85-1.34 (m, 6H). LC-MS (ESI, m/z): 266 [M+H]$^+$.

To a stirred mixture of methyl (2S)-2-[(4-methoxyphenyl)amino]-3,3-dimethyl-4-oxobutanoate (4.5 g, 16.9 mmol, 1.0 eq.) and potassium carbonate (4.69 g, 33.9 mmol, 2.0 eq.) in MeOH (50 mL) was added dimethyl (1-diazo-2-oxopropyl)phosphonate (4.24 g, 22.0 mmol, 1.3 eq.) dropwise at rt under N$_2$. The mixture was stirred for 2 h at rt. The reaction was quenched with water (200 mL). The mixture was extracted with ethyl acetate (3×200 mL). The organic layers were combined, washed with brine (2×200 mL), dried over anhydrous sodium sulfate, filtered and concentrated under reduced pressure to afford the crude product. The crude product was chromatographed on a silica gel column with EA:PE (1:9) to provide methyl (2S)-2-[(4-methoxyphenyl)amino]-3,3-dimethylpent-4-ynoate (1.70 g, 36%) as a yellow oil. $^1$H NMR (400 MHz, DMSO-d$_6$) δ 6.65-6.76 (m, 4H), 5.05 (d, J=12.0 Hz, 1H), 3.92 (d, J=12.0 Hz, 1H), 3.61-3.64 (m, 6H), 3.09 (s, 1H), 1.34 (s, 3H), 1.29 (s, 3H). LC-MS (ESI, m/z): 262 [M+H]$^+$.

To a stirred mixture of methyl (2S)-2-[(4-methoxyphenyl)amino]-3,3-dimethylpent-4-ynoate (1.14 g, 4.36 mmol, 1.0 eq.) in CH$_3$CN (9 mL) and H$_2$O (3 mL) were added ceric ammonium nitrate (12.0 g, 21.8 mmol, 5.0 eq.) at rt. The mixture was stirred for 2 h at rt. THF (10 mL) was added, followed by trimethylamine and di-tert-butyl dicarbonate (5.48 g, 25.1 mmol, 6.0 eq.). The mixture was stirred for 4 h at rt and then diluted with water (50 mL). The mixture was extracted with ethyl acetate (3×50 mL). The organic layers were combined, washed with brine (2×50 mL), dried over anhydrous sodium sulfate, filtered and concentrated under reduced pressure to afford the crude product. The crude product was chromatographed on a silica gel column with EA:PE (1:9) to provide methyl (2S)-2-[(tert-butoxycarbonyl)amino]-3,3-dimethylpent-4-ynoate (800 mg, 63%) as a yellow oil. $^1$H NMR (400 MHz, DMSO-d$_6$) δ 7.01 (d, J=12.0 Hz, 1H), 4.11 (d, J=12.0 Hz, 1H), 3.65 (s, 3H), 3.06 (s, 1H), 1.39 (s, 9H), 1.21-1.23 (m, 6H). LC-MS (ESI, m/z): 156 [M+H−Boc]$^+$.

To a stirred mixture of methyl (2S)-2-[(tert-butoxycarbonyl)amino]-3,3-dimethylpent-4-ynoate (800 mg, 3.13 mmol, 1.0 eq.) in THF (6 mL) and H$_2$O (2 mL) was added lithium hydroxide (375 mg, 15.6 mmol, 5.0 eq.) at rt. The mixture was stirred for 1 h at 60° C. The mixture was acidified to pH 3 with hydrochloric acid (1M). The aqueous layer was extracted with ethyl acetate (3×20 mL). The mixture was concentrated under reduced pressure to afford (2S)-2-[(tert-butoxycarbonyl)amino]-3,3-dimethylpent-4-ynoic acid (700 mg, 92%) as a light orange solid. $^1$H NMR (400 MHz, DMSO-d$_6$) δ 12.76 (s, 1H), 6.69 (d, J=8.0 Hz, 1H), 4.00 (d, J=8.0 Hz, 1H), 3.03 (s, 1H), 1.40 (s, 9H), 1.17-1.24 (m, 6H). LC-MS (ESI, m/z): 142 [M−100+H]$^+$.

To a stirred mixture of (2S)-2-[(tert-butoxycarbonyl)amino]-3,3-dimethylpent-4-ynoic acid (400 mg, 1.65 mmol, 1.0 eq.) in DCM (3 mL) was added trifluoroacetic acid (1 mL) at rt. The mixture was stirred for 1 h at rt and then concentrated under reduced pressure to afford (2S)-2-amino-3,3-dimethylpent-4-ynoic acid (300 mg, crude) as a brown yellow oil. LC-MS (ESI, m/z): 142 [M+H]$^+$.

To a stirred mixture of (2S)-2-amino-3,3-dimethylpent-4-ynoic acid (234 mg, 1.65 mmol, 1.0 eq.) and triethylamine (670 mg, 6.63 mmol, 4.0 eq.) in MeOH (3 mL) was added ethyl 2,2,2-trifluoroacetate (471 mg, 3.31 mmol, 2.0 eq.). The mixture was stirred for 2 h at rt and then acidified to pH 4 with hydrochloric acid (1M). The mixture was extracted with ethyl acetate (3×20 mL). The combined organic layers were concentrated under reduced pressure to afford (2S)-3,3-dimethyl-2-(2,2,2-trifluoroacetamido)pent-4-ynoic acid (300 mg, 76%) as a light yellow oil. $^1$H NMR (400 MHz, DMSO-d$_6$) δ 13.28 (s, 1H), 9.67 (d, J=8.0 Hz, 1H), 4.45 (d, J=8.0 Hz, 1H), 3.09 (s, 1H), 1.25-1.41 (m, 6H). LC-MS (ESI, m/z): 236 [M−H]$^−$.

To a stirred mixture of (2S)-3,3-dimethyl-2-(2,2,2-trifluoroacetamido)pent-4-ynoic acid (71.3 mg, 0.300 mmol, 1.0 eq.) in DMF (2 mL) was added o-(7-Azabenzotriazol-1-yl)-N,N,N',N'-tetramethyluronium hexafluorophosphate (137 mg, 0.361 mmol, 1.2 eq.) and N-ethyl-N-isopropylpropan-2-amine (232 mg, 1.80 mmol, 6.0 eq.) at rt. The mixture was stirred for 10 min 0° C. and (2S)-2-[(1R,2S,3S,6R,7S)-4-azatricyclo[5.2.1.0^{2,6}]dec-8-en-3-ylformamido]-3-[(3S)-2-oxopyrrolidin-3-yl]propanamide hydrochloride (110 mg, 0.300 mmol, 1.0 eq.) was added. The mixture was stirred for another 1 h at rt. The mixture was purified by C18 column with CH$_3$CN:Water (0.05% FA). The compound fraction was concentrated under reduced pressure to provide (2S)-2-{[(1R,2S,3S,6R,7S)-4-[(2S)-3,3-dimethyl-2-(2,2,2-trifluoroacetamido)pent-4-ynoyl]-4-azatricyclo[5.2.1.0^{2,6}]dec-8-en-3-yl]formamido}-3-[(3S)-2-oxopyrrolidin-3-yl]propanamide (120 mg, 51%) as a light yellow solid. LC-MS (ESI, m/z): 552 [M+H]$^+$.

To a stirred mixture of (2S)-2-{[(1R,2S,3S,6R,7S)-4-[(2S)-3,3-dimethyl-2-(2,2,2-trifluoroacetamido)pent-4-ynoyl]-4-azatricyclo[5.2.1.0^{2,6}]dec-8-en-3-yl]formamido}-3-[(3S)-2-oxopyrrolidin-3-yl]propanamide (120 mg, 0.218 mmol, 1.0 eq.) in DCM (2 mL) was added pyridine (60.2 mg, 0.763 mmol, 3.5 eq.) and trifluoroacetic anhydride (91.3 mg, 0.436 mmol, 2.0 eq.) at rt. The mixture was stirred for 2 h at rt. The reaction was quenched with water (10 mL). The mixture was extracted with ethyl acetate (3×10 mL). The organic layers were combined, washed with brine (2×10 mL), dried over anhydrous sodium sulfate, filtered and concentrated under reduced pressure to afford then crude product. The crude product was purified by prep-HPLC with the following conditions (Column: XBridge Shield RP18 OBD Column, 19*250 mm, 10 m; Mobile Phase A: Water (0.1% FA), Mobile Phase B: ACN; Flow rate: 25 mL/min; Gradient: 40% B to 70% B in 7 min, 70% B; Wave Length: 254 nm; RT1 (min): 5;) to afford (1R,2S,3S,6R,7S)—N-[(1S)-1-cyano-2-[(3S)-2-oxopyrrolidin-3-yl]ethyl]-4-[(2S)-3,3-dimethyl-2-(2,2,2-trifluoroacetamido)pent-4-ynoyl]-4-azatricyclo[5.2.1.0^{2,6}]dec-8-ene-3-carboxamide (14.9 mg, 12%) as a white solid. $^1$H NMR (400 MHz, 80° C., DMSO-$d_6$) δ 8.46-9.16 (m, 2H), 7.27-7.52 (m, 1H), 5.93-6.25 (m, 2H), 4.78-4.93 (m, 1H), 4.62-4.75 (m, 1H), 3.89-4.09 (m, 1H), 3.55-3.76 (m, 1H), 3.33-3.47 (m, 1H), 3.09-3.21 (m, 2H), 2.79-3.02 (m, 4H), 2.65-2.78 (m, 1H), 2.27-2.41 (m, 1H), 1.98-2.25 (m, 2H), 1.61-1.91 (m, 2H), 1.32-1.45 (m, 2H), 1.07-1.31 (m, 6H).

Example 8

Compound 8

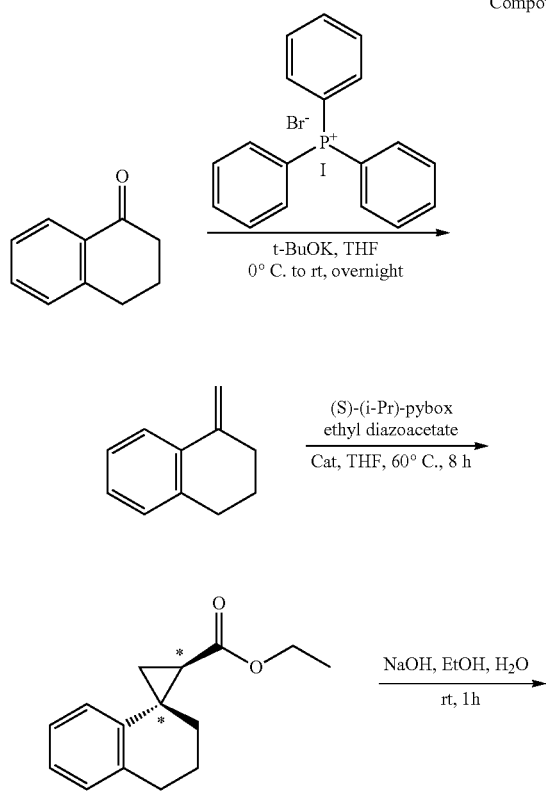

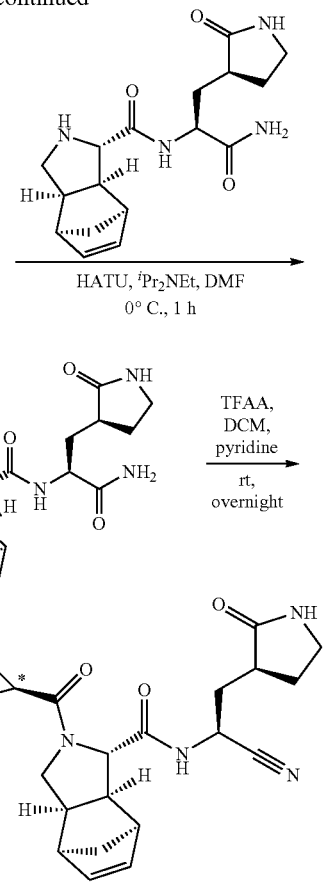

Chiral centers noted with a * are tentatively assigned

To a mixture of methyltriphenylphosphanium bromide (68.4 g, 191 mmol, 1.4 eq.) in tetrahydrofuran (100 mL) was added 1-tetralone (20.0 g, 136 mmol, 1.0 eq.) at 0° C. After stirred for 0.5 h at 0° C., methyltriphenylphosphanium bromide (68.4 g, 191 mmol, 1.4 eq.) was added. The mixture was stirred for overnight at rt, and then filtered. The filtrate was concentrated under reduced pressure to afford the crude product. The crude product was diluted with dichloromethane (100 mL) and made into a slurry with 100~200 silica gel mesh (60 g). The mixture was loaded to a column after removing the dichloromethane. The sample was purified by column chromatography (Column size 6×24 cm, column volume: 600 mL, silica gel size (100~200 mesh) and eluted with PE (0%~10% over 30 min). The collected fractions: 0% PE fractions were chosen as the pure fractions. Those fractions were combined and concentrated under reduced pressure to provide 1-methylidene-3,4-dihydro-2H-naphthalene (12.0 g, 60%) as a light yellow oil. LC-MS (ESI, m/z): 145 [M+H]$^+$.

To a stirred mixture of 1-methylidene-3,4-dihydro-2H-naphthalene (1.00 g, 6.930 mmol, 1.0 eq.), [Ru(p-cymene)Cl$_2$]$_2$ (212 mg, 0.350 mmol, 0.05 eq.) and (S)-(i-Pr)-Pybox (209 mg, 0.690 mmol, 0.1 eq.) in tetrahydrofuran (80 mL) was added ethyl 2-diazoacetate (1.18 g, 10.4 mmol, 1.5 eq.) in portions over 8 h at 60° C. under nitrogen. The reaction was quenched with water (20 mL). The mixture was extracted with ethyl acetate (3×100 mL). The organic layers were combined, washed with brine (2×100 mL), dried over anhydrous sodium sulfate, filtered and concentrated under reduced pressure to afford the crude product. The sample was purified by column chromatography (Column size 6×24 cm, column volume: 600 mL, silica gel size (100~200 mesh) and eluted with EA:PE (0%~10% over 30 min). The collected fractions: 5~8% PE fractions were chosen as pure fractions. Those fractions were combined and concentrated under reduced pressure to provide the crude product. The crude product was purified by TLC (Mobile phase: EA:PE=1:40; $R_f$=0.4; detection: UV) to provide ethyl (1R*,3R*)-3',4'-dihydro-2'H-spiro[cyclopropane-1,1'-naphthalene]-3-carboxylate as a light yellow oil. $^1$H NMR (300 MHz, DMSO-$d_6$) δ 7.01-7.13 (m, 3H), 6.81-6.86 (m, 1H), 4.02-4.19 (m, 2H), 2.80-2.84 (m, 2H), 1.76-1.93 (m, 4H), 1.52-1.71 (m, 2H), 1.34-1.43 (m, 1H), 1.16-1.24 (m, 3H). LC-MS (ESI, m/z): 231 [M+H]$^+$.

To a stirred solution of ethyl (1R,3R)-3',4'-dihydro-2'H-spiro[cyclopropane-1,1'-naphthalene]-3-carboxylate (380 mg, 1.65 mmol, 1.0 eq.) in ethanol (4 mL) were added sodium hydroxide (461 mg, 11.5 mmol, 7.0 eq., in water 4 mL). The mixture was stirred for overnight at rt. The mixture was concentrated under reduced pressure to remove the ethanol. The mixture was adjusted to pH 5 with hydrochloric acid (2 M) and then extracted with ethyl acetate (3×30 mL). The organic layers were combined, washed with brine (2×20 mL), dried over anhydrous sodium sulfate, filtered and concentrated under reduced pressure to provide (1R,3R)-3',4'-dihydro-2'H-spiro[cyclopropane-1,1'-naphthalene]-3-carboxylic acid (240 mg, 71%) as an off-white solid. $^1$H NMR (300 MHz, DMSO-$d_6$) δ 12.24 (br, 1H), 6.89-7.21 (m, 4H), 2.72-2.91 (m, 2H), 1.51-1.89 (m, 6H), 1.26-1.45 (m, 1H). LC-MS (ESI, m/z): 203 [M+H]$^+$.

To a mixture of (1R,3R)-3',4'-dihydro-2'H-spiro[cyclopropane-1,1'-naphthalene]-3-carboxylic acid (71.2 mg, 0.352 mmol, 1.0 eq.) in N,N-dimethylformamide (3 mL) was added o-(7-azabenzotriazol-1-yl)-N,N,N',N'-tetramethyluronium hexafluorophosphate (24.74 mg, 0.065 mmol, 1.2 eq.) and N-ethyl-N-isopropylpropan-2-amine (273 mg, 2.11 mmol, 6.0 eq.) at 0° C. The mixture was stirred for 20 min at 0° C., and then (2S)-2-[(1R,2S,3S,6R,7S)-4-azatricyclo[5.2.1.0^{2,6}]dec-8-en-3-ylformamido]-3-[(3S)-2-oxopyrrolidin-3-yl]propanamide hydrochloride (130 mg, 0.352 mmol, 1.0 eq.) was added at 0° C. The mixture was stirred for 1 h rt. The crude product was purified by C18 column with CH$_3$CN:Water (TFA 0.05%). The compound fraction was concentrated under reduced pressure to provide (2S)-2-{[(1R,2S,3S,6R,7S)-4-{[(1R,3R)-3',4'-dihydro-2'H-spiro[cyclopropane-1,1'-naphthalen]-3-yl]carbonyl}-4-azatricyclo[5.2.1.0^{2,6}]dec-8-en-3-yl]formamido}-3-[(3S)-2-oxopyrrolidin-3-yl]propenamide (70 mg, 43%) as a yellow solid. LC-MS (ESI, m/z): 517 [M+H]+.

To a mixture of (2S)-2-{[(1R,2S,3S,6R,7S)-4-{[(1S,3S)-3',4'-dihydro-2'H-spiro[cyclopropane-1,1'-naphthalen]-3-yl]carbonyl}-4-azatricyclo[5.2.1.0^{2,6}]dec-8-en-3-yl]formamido}-3-[(3S)-2-oxopyrrolidin-3-yl]propanamide (70.0 mg, 0.135 mmol, 1.0 eq.) in dichloromethane (1 mL) was added pyridine (37.5 mg, 0.473 mmol, 3.5 eq.) and trifluoroacetic anhydride (56.9 mg, 0.270 mmol, 2.0 eq.). The mixture was stirred for overnight at rt. The reaction was quenched with water (5 mL). The mixture was extracted with ethyl acetate (3×10 mL). The organic layers were combined, washed with brine (2×10 mL), dried over anhydrous sodium sulfate, filtered and concentrated under reduced pressure to afford the crude product. The crude product was purified by prep-HPLC (Column: XSelect CSH Prep C18 OBD Column, 19*150 mm, 5 m; Mobile Phase A: Water (0.1% FA), Mobile Phase B: ACN; Flow rate: 25 mL/min; Gradient: 41% B to 61% B in 7 min, 61% B; Wave Length: 254 nm; RT1 (min): 5.47) to provide (1R,2S,3S,6R,7S)—N-[(1S)-1-cyano-2-[(3S)-2-oxopyrrolidin-3-yl]ethyl]-4-{[(1R,3R)-3',4'-dihydro-2'H-spiro[cyclopropane-1,1'-naphthalen]-3-yl]carbonyl}-4-azatricyclo[5.2.1.0^{2,6}]dec-8-ene-3-carboxamide (17 mg, 25%) as an white solid. LC-MS (ESI, m/z): 499 [M+H]$^+$.

Example 9

Compound 9

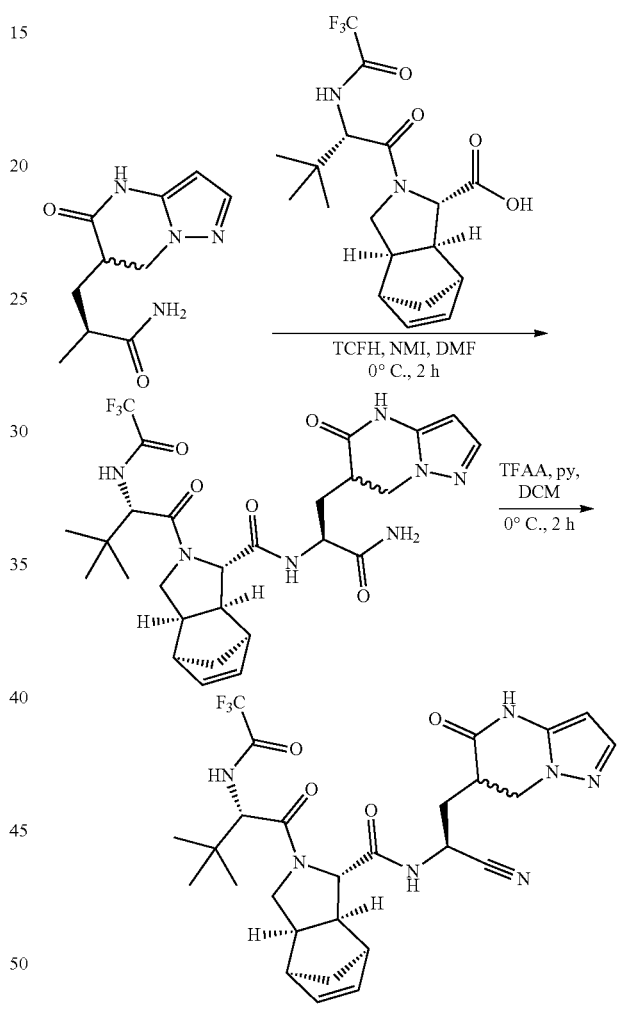

To a solution of (2S)-2-amino-3-(5-oxo-4,5,6,7-tetrahydropyrazolo[1,5-a]pyrimidin-6-yl)propanamide (2S)-2-amino-3-{5-oxo-4H,6H,7H-pyrazolo[1,5-a]pyrimidin-6-yl}propanamide (70 mg, 0.31 mmol, 1.0 eq.) in DMF (2 mL) was added N,N,N,N-tetramethylchloroformamidinium hexafluorophosphate (106 mg, 0.38 mmol, 1.2 eq.), NMI (180 mg, 2.2 mmol, 7.0 eq.) and (2S)-2-amino-3-(5-oxo-4,5,6,7-tetrahydropyrazolo[1,5-a]pyrimidin-6-yl)propanamide (134 mg, 0.35 mmol, 1.1 eq.). The mixture was stirred at 0° C. for 2 h and then chromatographed on a C18 column with MeCN:H$_2$O (3:7) to provide (1S,3aR,4S,7R,7aS)—N-((2S)-1-amino-1-oxo-3-(5-oxo-4,5,6,7-tetrahydropyrazolo[1,5-a]pyrimidin-6-yl)propan-2-yl)-2-((S)-3,3-dimethyl-2-

(2,2,2-trifluoroacetamido)butanoyl)-2,3,3a,4,7,7a-hexahydro-1H-4,7-methanoisoindole-1-carboxamide (75 mg, 36%) as a brown yellow semi-solid. LC-MS (ESI, m/z): 594 [M+H]$^+$.

To a solution of (1S,3aR,4S,7R,7aS)—N-((2S)-1-amino-1-oxo-3-(5-oxo-4,5,6,7-tetrahydropyrazolo[1,5-a]pyrimidin-6-yl)propan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (75 mg, 0.13 mmol, 1.0 eq.) in DCM (2 mL) was added pyridine (70 mg, 0.88 mmol, 7.0 eq.) and TFAA (106 mg, 0.5 mmol, 4.0 eq.) at 0° C. The mixture was stirred at 0° C. for 2 h. The reaction was quenched with water (2 mL). The mixture was extracted with DCM (3×3 mL). The organic layers were combined, dried over anhydrous sodium sulfate, filtered and concentrated under reduced pressure. The residue was purified by prep-HPLC (Column: YMC-Actus Triart C18, 30*150 mm, 5 m; Mobile Phase A: Water (0.1% FA), Mobile Phase B: ACN; Flow rate: 60 mL/min; Gradient: 37% B to 67% B in 7 min, 67% B; Wave Length: 254 nm; RT1 (min): 5.25) to provide (1S,3aR,4S,7R,7aS)—N-((1S)-1-cyano-2-(5-oxo-4,5,6,7-tetrahydropyrazolo[1,5-a]pyrimidin-6-yl)ethyl)-2-((S)-3,3-dimethyl-2-(2,2,2-trifluoroacetamido)butanoyl)-2,3,3a,4,7,7a-hexahydro-1H-4,7-methanoisoindole-1-carboxamide (4.5 mg, 6%) as a white solid. LC-MS (ESI, m/z): 576 [M+H]$^+$.

Example 10

Compound 10

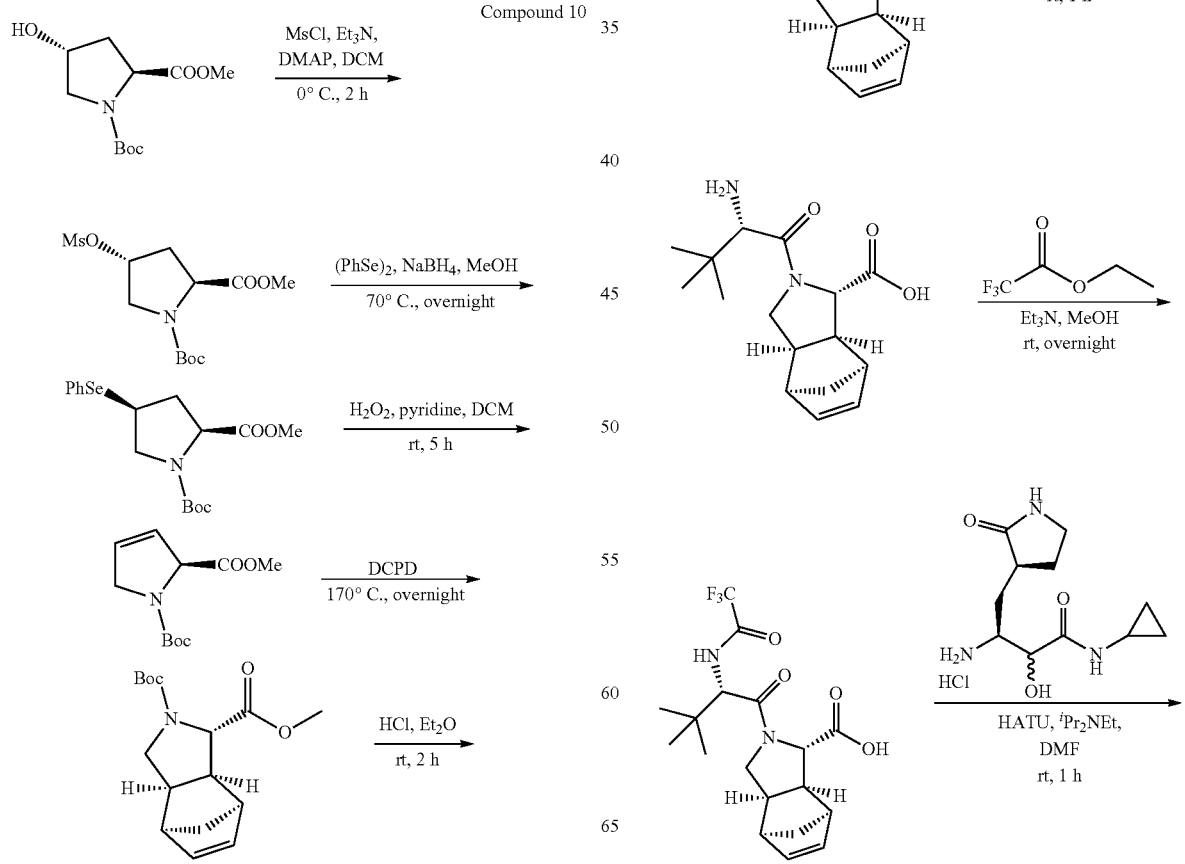
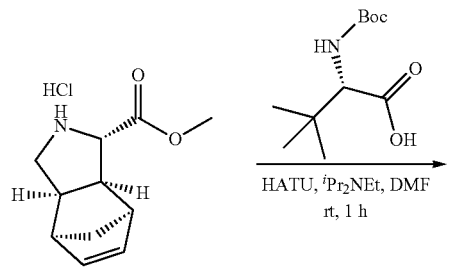
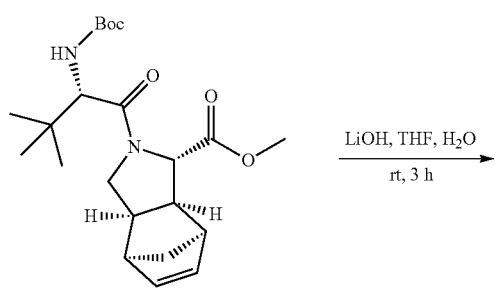
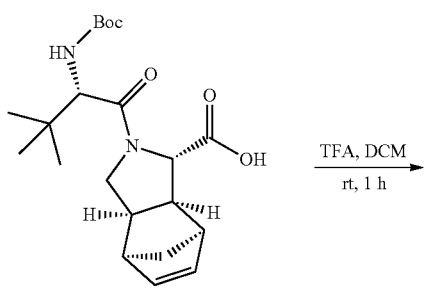
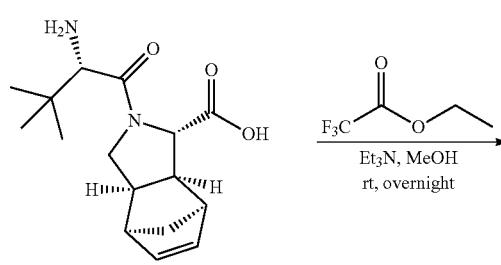
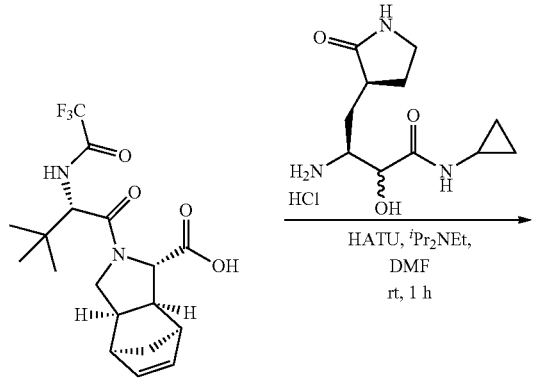

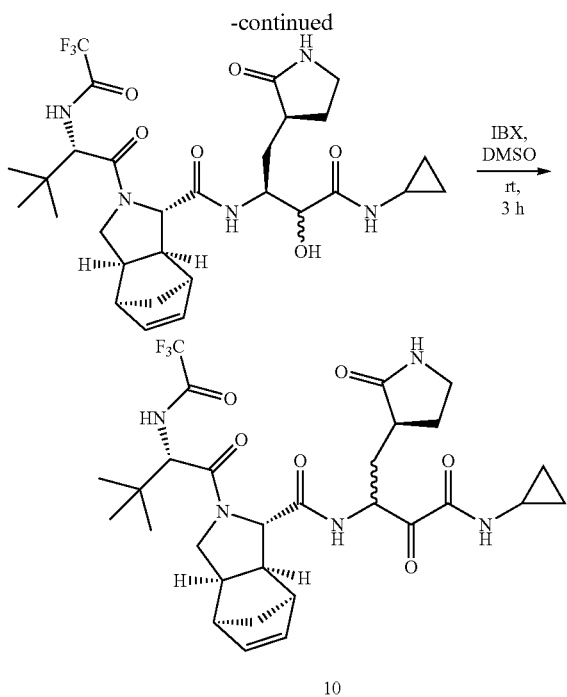

To a mixture of 1-tert-butyl 2-methyl (2S,4R)-4-hydroxypyrrolidine-1,2-dicarboxylate (30.0 g, 122 mmol, 1.0 eq.), triethylamine (22.3 g, 220 mmol, 1.8 eq.) and N,N-dimethylpyridin-4-amine (4.48 g, 36.7 mmol, 0.3 eq.) in DCM (500 mL) was added dropwise methanesulfonyl chloride (21.0 g, 183 mmol, 1.5 eq.) at 0° C. The mixture was stirred for 2 h at 0° C. The reaction was quenched with water (500 mL). The mixture was extracted with DCM (3×500 mL). The organic layers were combined, washed with brine (2×500 mL), dried over anhydrous sodium sulfate, filtered and concentrated under reduced pressure to afford the crude product. The crude product was chromatographed on a silica gel column with EtOAc:PE (1:1) to provide 1-tert-butyl 2-methyl (2S,4R)-4-(methanesulfonyloxy)pyrrolidine-1,2-dicarboxylate (35.0 g, 85%) as a light yellow solid. LC-MS (ESI, m/z): 224 [M+H−Boc]+.

To a mixture of 1-tert-butyl 2-methyl (2S,4R)-4-(methanesulfonyloxy)pyrrolidine-1,2-dicarboxylate (25.0 g, 77.3 mmol, 1.0 eq.) and diphenyl diselenide (24.1 g, 77.3 mmol, 1.0 eq.) in MeOH (600 mL) was added sodium borohydride (3.80 g, 100 mmol, 1.3 eq.) at 0° C. The mixture was stirred overnight at 70° C. and then concentrated under reduced pressure to remove the MeOH. Water (600 mL) was added, and the mixture was extracted with EtOAc (3×600 mL). The organic layers were combined, washed with brine (600 mL), dried over anhydrous sodium sulfate, filtered and concentrated under reduced pressure to afford the crude product. The crude product was chromatographed on a silica gel column with EtOAc:PE (1:8) to provide 1-tert-butyl 2-methyl (2S,4S)-4-(phenylselanyl)pyrrolidine-1,2-dicarboxylate (26.8 g, 84%) as a yellow oil. LC-MS (ESI, m/z): 286 [M−100+H]+.

To a mixture of 1-tert-butyl 2-methyl (2S,4S)-4-(phenylselanyl)pyrrolidine-1,2-dicarboxylate (26.8 g, 69.7 mmol, 1.0 eq.) and pyridine (9.38 g, 118 mmol, 1.7 eq.) in DCM (300 mL) was added hydrogen peroxide (31.6 mL, 279 mmol, 4.0 eq., 30% in water). The mixture was stirred for 5 h at rt. The reaction was quenched with water (500 mL). The mixture was extracted with DCM (3×400 mL). The organic layers were combined, washed with citric acid (500 mL, 1 M), saturated aqueous sodium sulfite (500 mL), washed with brine (500 mL), dried over anhydrous sodium sulfate, filtered and concentrated under reduced pressure to afford the crude product. The crude product was chromatographed on a silica gel column with EtOAc:PE (1:5) to provide 1-tert-butyl 2-methyl (2S)-2,5-dihydropyrrole-1,2-dicarboxylate (10.5 g, 62%) as a yellow oil. 1H NMR (300 MHz, CDCl3) δ 5.91-5.04 (m, 1H), 5.67-5.79 (m, 1H), 4.92-5.09 (m, 1H), 4.17-4.35 (m, 2H), 3.71-3.79 (m, 3H), 1.42-1.52 (m, 9H). LC-MS (ESI, m/z): 128 [M+H−Boc]+.

A mixture of 1-tert-butyl 2-methyl (2S)-2,5-dihydropyrrole-1,2-dicarboxylate (3.68 g, 16.2 mmol, 1.0 eq.) in dicyclopentadiene (40 mL) was stirred overnight at 170° C. The mixture was diluted with DCM (500 mL) and made into a slurry with 100~200 silica gel mesh (50 g). The mixture was loaded to a column. After removed the DCM under reduced pressure, the sample was purified by column chromatography (Column size 6×24 cm, column volume: 600 mL, silica gel size (100~200 mesh) quantity: 330 g) and eluted with EtOAc:PE (0%~50% over 30 min). The collected fractions: 19%-25% EtOAc:PE fractions were chosen as pure fractions. Those fractions were combined and concentrated under reduced pressure to afford the crude product (2.5 g). The crude product was purified by C18 column with CH3CN:Water (0.05% TFA). The compound fraction was concentrated under reduced pressure to provide 4-tert-butyl 3-methyl (1R,2S,3S,6R,7S)-4-azatricyclo[5.2.1.0^{2,6}]dec-8-ene-3,4-dicarboxylate (1.70 g, 32%) as a yellow oil. 1H NMR (300 MHz, CDCl3) δ 6.12-6.30 (m, 2H), 3.78-3.98 (m, 1H), 3.72 (s, 3H), 3.38-3.51 (m, 1H), 3.04-3.21 (m, 2H), 2.77-2.96 (m, 3H), 1.50-1.58 (m, 1H), 1.32-1.46 (m, 10H). LC-MS (ESI, m/z): 194 [M+H−Boc]+.

A mixture of 4-tert-butyl 3-methyl (1R,2S,3S,6R,7S)-4-azatricyclo[5.2.1.0^{2,6}]dec-8-ene-3,4-dicarboxylate (500 mg, 1.70 mmol, 1.0 eq.) in hydrogen chloride (10 mL, 2 M in Et2O) was stirred for 2 h at rt. The mixture was concentrated under reduced pressure to afford methyl (1R,2S,3S,6R,7S)-4-azatricyclo[5.2.1.0^{2,6}]dec-8-ene-3-carboxylate hydrochloride (391 mg, crude) as a yellow oil. LC-MS (ESI, m/z): 194 [M+H]+.

To a mixture of methyl (1R,2S,3S,6R,7S)-4-azatricyclo[5.2.1.0^{2,6}]dec-8-ene-3-carboxylate hydrochloride (391 mg, 1.70 mmol, 1.0 eq.), (2S)-2-[(tert-butoxycarbonyl)amino]-3,3-dimethylbutanoic acid (394 mg, 1.70 mmol, 1.0 eq.) and o-(7-azabenzotriazol-1-yl)-N,N,N',N'-tetramethyluronium hexafluorophosphate (777 mg, 2.04 mmol, 1.2 eq.) in DMF (10 mL) was added N-ethyl-N-isopropylpropan-2-amine (1.32 g, 10.2 mmol, 6.0 eq.) at 0° C. The mixture was stirred for 1 h at rt. The reaction was quenched with water (20 mL). The mixture was extracted with EtOAc (3×20 mL). The organic layers were combined, washed with brine (2×20 mL), dried over anhydrous sodium sulfate, filtered and concentrated under reduced pressure to afford the crude product. The crude product was chromatographed on a silica gel column with EtOAc:PE (8:92) to provide methyl (1R,2S,3S,6R,7S)-4-[(2S)-2-[(tert-butoxycarbonyl)amino]-3,3-dimethylbutanoyl]-4-azatricyclo[5.2.1.0^{2,6}]dec-8-ene-3-carboxylate (490 mg, 69%) as an off-white semi-solid. 1H NMR (300 MHz, CDCl3) δ 6.03-6.27 (m, 2H), 5.11-5.26 (m, 1H), 4.18-4.36 (m, 2H), 3.72-3.78 (m, 3H), 3.54-3.70 (m, 2H), 2.97-3.14 (m, 2H), 2.86-2.94 (m, 2H), 1.49-1.54 (m, 1H), 1.41-1.48 (m, 9H), 1.33-1.39 (m, 1H), 0.92-1.00 (m, 9H). LC-MS (ESI, m/z): 407 [M+H]+.

To a mixture of methyl (1R,2S,3S,6R,7S)-4-[(2S)-2-[(tert-butoxycarbonyl)amino]-3,3-dimethylbutanoyl]-4-azatricyclo[5.2.1.0^{2,6}]dec-8-ene-3-carboxylate (490 mg, 1.205 mmol, 1.0 eq.) in THF (5 mL)/water (5 mL) was added lithium hydroxide (144 mg, 6.03 mmol, 5.0 eq.). The mixture was stirred for 3 h at rt. The mixture was concentrated under reduced pressure to removed then THF and the pH was adjusted to 5 with hydrochloric acid (2 M). The mixture was extracted with EtOAc (3×10 mL). The organic layers were combined, washed with brine (2×10 mL), dried over anhydrous sodium sulfate, filtered and concentrated under reduced pressure to provide (1R,2S,3S,6R,7S)-4-[(2S)-2-[(tert-butoxycarbonyl)amino]-3,3-dimethylbutanoyl]-4-azatricyclo[5.2.1.0^{2,6}]dec-8-ene-3-carboxylic acid (465 mg, 97%) as a white solid. $^1$H NMR (300 MHz, CDCl$_3$) δ 6.04-6.30 (m, 2H), 5.21-5.29 (m, 1H), 4.22-4.32 (m, 2H), 3.52-3.79 (m, 2H), 3.06-3.24 (m, 2H), 2.91-3.04 (m, 2H), 1.51-1.56 (m, 1H), 1.37-1.47 (m, 10H), 0.95-1.00 (m, 9H). LC-MS (ESI, m/z): 393 [M+H]$^+$.

To a mixture of (1R,2S,3S,6R,7S)-4-[(2S)-2-[(tert-butoxycarbonyl)amino]-3,3-dimethylbutanoyl]-4-azatricyclo[5.2.1.0^{2,6}]dec-8-ene-3-carboxylic acid (465 mg, 1.18 mmol, 1.0 eq.) in DCM (15 mL) was added trifluoroacetic acid (5 mL). The mixture was stirred for 1 h at rt and then concentrated under reduced pressure to afford (1R,2S,3S,6R,7S)-4-[(2S)-2-amino-3,3-dimethylbutanoyl]-4-azatricyclo[5.2.1.0^{2,6}]dec-8-ene-3-carboxylic acid (346 mg, crude) as a dark blue semi-solid. LC-MS (ESI, m/z): 293 [M+H]$^+$.

To a mixture of (1R,2S,3S,6R,7S)-4-[(2S)-2-amino-3,3-dimethylbutanoyl]-4-azatricyclo[5.2.1.0^{2,6}]dec-8-ene-3-carboxylic acid (346 mg, 1.18 mmol, 1.0 eq.) in MeOH (10 mL) was added triethylamine (1.44 g, 14.2 mmol, 12.0 eq.) and ethyl 2,2,2-trifluoroacetate (1.01 g, 7.10 mmol, 6.0 eq.). The mixture was stirred overnight at rt and concentrated under reduced pressure to remove then MeOH. The crude product was purified by C18 column with CH$_3$CN: Water (0.05% TFA). The compound fraction was concentrated under reduced pressure to provide (1R,2S,3S,6R,7S)-4-[(2S)-3,3-dimethyl-2-(2,2,2-trifluoroacetamido) butanoyl]-4-azatricyclo[5.2.1.0^{2,6}]dec-8-ene-3-carboxylic acid (310 mg, 65%) as a yellow solid. $^1$H NMR (300 MHz, DMSO-d$_6$) δ 12.22-13.12 (m, 1H), 8.96-9.49 (m, 1H), 5.88-6.24 (m, 2H), 4.24-4.60 (m, 1H), 3.94-4.05 (m, 1H), 3.43-3.58 (m, 2H), 2.67-3.04 (m, 4H), 1.30-1.44 (m, 2H), 0.76-1.05 (m, 9H). LC-MS (ESI, m/z): 389 [M+H]$^+$.

To a mixture of (1R,2S,3S,6R,7S)-4-[(2S)-3,3-dimethyl-2-(2,2,2-trifluoroacetamido)butanoyl]-4-azatricyclo [5.2.1.0^{2,6}]dec-8-ene-3-carboxylic acid (102 mg, 0.263 mmol, 1.0 eq.) and o-(7-azabenzotriazol-1-yl)-N,N,N',N'-tetramethyluronium hexafluorophosphate (120 mg, 0.316 mmol, 1.2 eq.) in DMF (2 mL) was added N-ethyl-N-isopropylpropan-2-amine (204 mg, 1.58 mmol, 6.0 eq.) at 0° C. After stirred for 15 min at 0° C., (3S)-3-amino-N-cyclopropyl-2-hydroxy-4-[(3S)-2-oxopyrrolidin-3-yl]butanamide hydrochloride (73.0 mg, 0.263 mmol, 1.0 eq.) was added. The mixture was stirred for 1 h at rt. The reaction was quenched with water (10 mL). The mixture was extracted with EtOAc (3×10 mL). The organic layers were combined, washed with brine (2×10 mL), dried over anhydrous sodium sulfate, filtered and concentrated under reduced pressure to afford then crude product. The crude product was chromatographed on a silica gel column with MeOH:DCM (7:93) to provide (3S)—N-cyclopropyl-3-{[(1R,2S,3S,6R,7S)-4-[(2S)-3,3-dimethyl-2-(2,2,2-trifluoroacetamido)butanoyl]-4-azatricyclo[5.2.1.0^{2,6}]dec-8-en-3-yl]formamido}-2-hydroxy-4-[(3S)-2-oxopyrrolidin-3-yl]butanamide (120 mg, 68%) as a light yellow solid. LC-MS (ESI, m/z): 612 [M+H]$^+$.

To a mixture of (3S)—N-cyclopropyl-3-{[(1R,2S,3S,6R,7S)-4-[(2S)-3,3-dimethyl-2-(2,2,2-trifluoroacetamido)butanoyl]-4-azatricyclo[5.2.1.0^{2,6}]dec-8-en-3-yl]formamido}-2-hydroxy-4-[(3S)-2-oxopyrrolidin-3-yl]butanamide (120 mg, 0.196 mmol, 1.0 eq.) in DMSO (3 mL) was added 2-iodoxybenzoic acid (165 mg, 0.588 mmol, 3.0 eq.). The mixture was stirred for 3 h at rt. The reaction was quenched with sat. sodium bicarbonate (10 mL). The mixture was extracted with EtOAc (3×20 mL). The organic layers were combined, washed with brine (2×10 mL), dried over anhydrous sodium sulfate, filtered and concentrated under reduced pressure to afford the crude product. The crude product was chromatographed on a silica gel column with MeOH:DCM (4:96) to provide N-cyclopropyl-3-{[(1R,2S,3S,6R,7S)-4-[(2S)-3,3-dimethyl-2-(2,2,2-trifluoroacetamido)butanoyl]-4-azatricyclo[5.2.1.0^{2,6}]dec-8-en-3-yl]formamido}-2-oxo-4-[(3S)-2-oxopyrrolidin-3-yl]butanamide (31.8 mg, 24%) as a white solid. LC-MS (ESI, m/z): 610 [M+H]$^+$.

Example 11

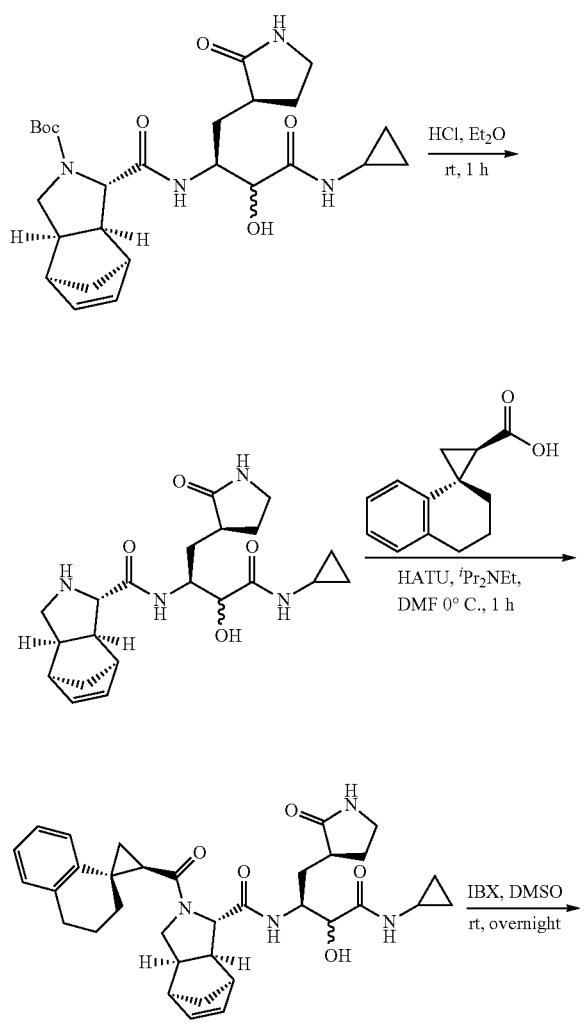

Compound 11

-continued

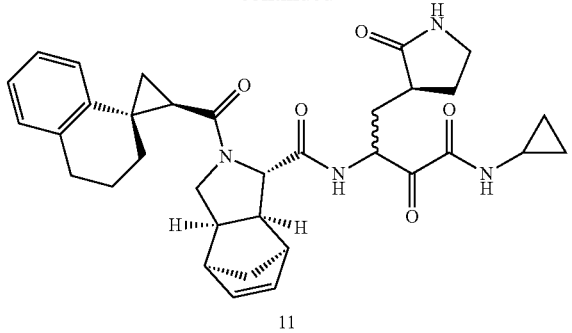

11

A mixture of tert-butyl (1R,2S,3S,6R,7S)-3-{[(2S)-1-(cyclopropylcarbamoyl)-1-hydroxy-3-[(3S)-2-oxopyrrolidin-3-yl]propan-2-yl]carbamoyl}-4-azatricyclo[5.2.1.0^{2,6}]dec-8-ene-4-carboxylate (150 mg, 0.298 mmol, 1.0 eq.) in hydrogen chloride (2 mL, 2 M in Et$_2$O) was stirred for 1 h at rt. The mixture was concentrated under reduced pressure to afford (1S,3aR,4S,7R,7aS)—N-((2S)-4-(cyclopropylamino)-3-hydroxy-4-oxo-1-((S)-2-oxopyrrolidin-3-yl)butan-2-yl)-2,3,3a,4,7,7a-hexahydro-1H-4,7-methanoisoindole-1-carboxamide hydrochloride (130 mg, crude) as a yellow oil. LC-MS (ESI, m/z): 403 [M+H]$^+$.

To a mixture of (1R,3R)-3',4'-dihydro-2'H-spiro[cyclopropane-1,1'-naphthalene]-3-carboxylic acid (76.03 mg, 0.376 mmol, 1.1 eq.) in N,N-dimethylformamide (3 mL) was added o-(7-azabenzotriazol-1-yl)-N,N,N',N'-tetramethyluronium hexafluorophosphate (155 mg, 0.410 mmol, 1.2 eq.) and N-ethyl-N-isopropylpropan-2-amine (265 mg, 2.05 mmol, 6.0 eq.) at 0° C. The mixture was stirred for 20 min at 0° C., and then (1S,3aR,4S,7R,7aS)—N-((2S)-4-(cyclopropylamino)-3-hydroxy-4-oxo-1-((S)-2-oxopyrrolidin-3-yl)butan-2-yl)-2,3,3a,4,7,7a-hexahydro-1H-4,7-methanoisoindole-1-carboxamide hydrochloride (150 mg, 0.342 mmol, 1.0 eq.) was added at 0° C. The mixture was stirred for 1 h at rt. The reaction was quenched with water (10 mL). The mixture was extracted with ethyl acetate (3×20 mL). The residue was purified by TLC (dichloromethane:methanol, 12:1) to afford (1S,3aR,4S,7R,7aS)—N-((2S)-4-(cyclopropylamino)-3-hydroxy-4-oxo-1-((S)-2-oxopyrrolidin-3-yl)butan-2-yl)-2-((1R,2R)-3',4'-dihydro-2'H-spiro[cyclopropane-1,1'-naphthalene]-2-carbonyl)-2,3,3a,4,7,7a-hexahydro-1H-4,7-methanoisoindole-1-carboxamide (80 mg, 40%) as a yellow solid. LC-MS (ESI, m/z): 587 [M+H]$^+$.

To a stirred mixture of (1S,3aR,4S,7R,7aS)—N-((2S)-4-(cyclopropylamino)-3-hydroxy-4-oxo-1-((S)-2-oxopyrrolidin-3-yl)butan-2-yl)-2-((1R,2R)-3',4'-dihydro-2'H-spiro[cyclopropane-1,1'-naphthalene]-2-carbonyl)-2,3,3a,4,7,7a-hexahydro-1H-4,7-methanoisoindole-1-carboxamide (80.0 mg, 0.136 mmol, 1.0 eq.) in DMSO (2 mL) was added 2-iodoxybenzoic acid (114 mg, 0.408 mmol, 3.0 eq.). The mixture was stirred for overnight at rt. The reaction was quenched with sat. sodium bicarbonate (10 mL). The mixture was extracted with EtOAc (3×20 mL). The organic layers were combined, washed with brine (2×10 mL), dried over anhydrous sodium sulfate, filtered and concentrated under reduced pressure to afford the crude product. The crude product was chromatographed on a silica gel column with dichloromethane:methanol (94:6) to provide (1S,3aR,4S,7R,7aS)—N-(4-(cyclopropylamino)-3,4-dioxo-1-((S)-2-oxopyrrolidin-3-yl)butan-2-yl)-2-((1R,2R)-3',4'-dihydro-2'H-spiro[cyclopropane-1,1'-naphthalene]-2-carbonyl)-2,3,3a,4,7,7a-hexahydro-1H-4,7-methanoisoindole-1-carboxamide as a white solid. LC-MS (ESI, m/z): 585 [M+H]$^+$.

Example 12

Compound 12

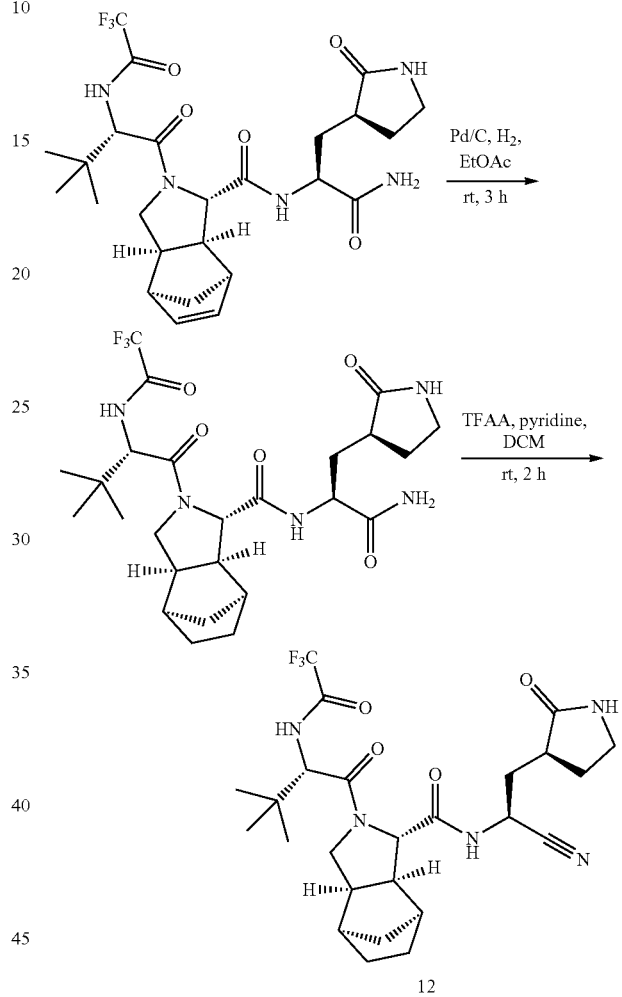

12

To a mixture of (1S,3aR,4S,7R,7aS)—N—((S)-1-amino-1-oxo-3-((S)-2-oxopyrrolidin-3-yl)propan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (95.0 mg, 0.175 mmol, 1.0 eq.) in EtOAc (3 mL) was added 10% palladium on activated carbon (90.0 mg). The mixture was stirred for 3 h at rt under hydrogen. The mixture was filtered through a celite pad. The filtrate was concentrated under reduced pressure to afford (1S,3aR,4R,7S,7aS)—N—((S)-1-amino-1-oxo-3-((S)-2-oxopyrrolidin-3-yl)propan-2-yl)-2-((S)-3,3-dimethyl-2-(2,2,2-trifluoroacetamido)butanoyl)octahydro-1H-4,7-methanoisoindole-1-carboxamide (75.0 mg, crude) as an off-white solid. LC-MS (ESI, m/z): 544 [M+H]$^+$.

To a mixture of (1S,3aR,4R,7S,7aS)—N—((S)-1-amino-1-oxo-3-((S)-2-oxopyrrolidin-3-yl)propan-2-yl)-2-((S)-3,3-dimethyl-2-(2,2,2-trifluoroacetamido)butanoyl)octahydro-1H-4,7-methanoisoindole-1-carboxamide (75.0 mg, 0.138 mmol, 1.0 eq.) in DCM (2 mL) was added pyridine (76 mg, 0.966 mmol, 7.0 eq.) and trifluoroacetic anhydride (116 mg, 0.552 mmol, 4.0 eq.). The mixture was stirred for 2 h at rt. The reaction was quenched with water (5 mL). The mixture was extracted with DCM (3×5 mL). The organic layers were combined, washed with brine (2×5 mL), dried over anhydrous sodium sulfate, filtered and concentrated under reduced pressure to afford the crude product. The crude product was purified by prep-HPLC (Column: XSelect CSH Prep C18 OBD Column, 19×150 mm, 5 m; Mobile Phase A: Water (0.1% FA), Mobile Phase B: ACN; Flow rate: 25 mL/min; Gradient: 36% B to 56% B in 7 min, 56% B; Wave Length: 254 nm; RT: 6.18 min) to provide (1S,3aR,4R,7S,7aS)—N—((S)-1-cyano-2-((S)-2-oxopyrrolidin-3-yl)ethyl)-2-((S)-3,3-dimethyl-2-(2,2,2-trifluoroacetamido)butanoyl) octahydro-1H-4,7-methanoisoindole-1-carboxamide (19.6 mg, 26%) as a white solid. $^1$H NMR (400 MHz, 80° C., DMSO-$d_6$) δ 8.85-9.20 (m, 1H), 8.60-8.84 (m, 1H), 7.35-7.55 (m, 1H), 4.80-4.98 (m, 1H), 4.59-4.75 (m, 1H), 4.30-4.58 (m, 1H), 3.76-3.85 (m, 1H), 3.45-3.75 (m, 1H), 3.10-3.25 (m, 2H), 2.55-2.70 (m, 1H), 2.30-2.54 (m, 3H), 2.05-2.29 (m, 3H), 1.62-1.88 (m, 2H), 1.40-1.60 (m, 2H), 1.05-1.39 (m, 4H), 0.95-1.04 (m, 9H). LC-MS (ESI, m/z): 526 [M+H]$^+$.

Example 13

Compound 13

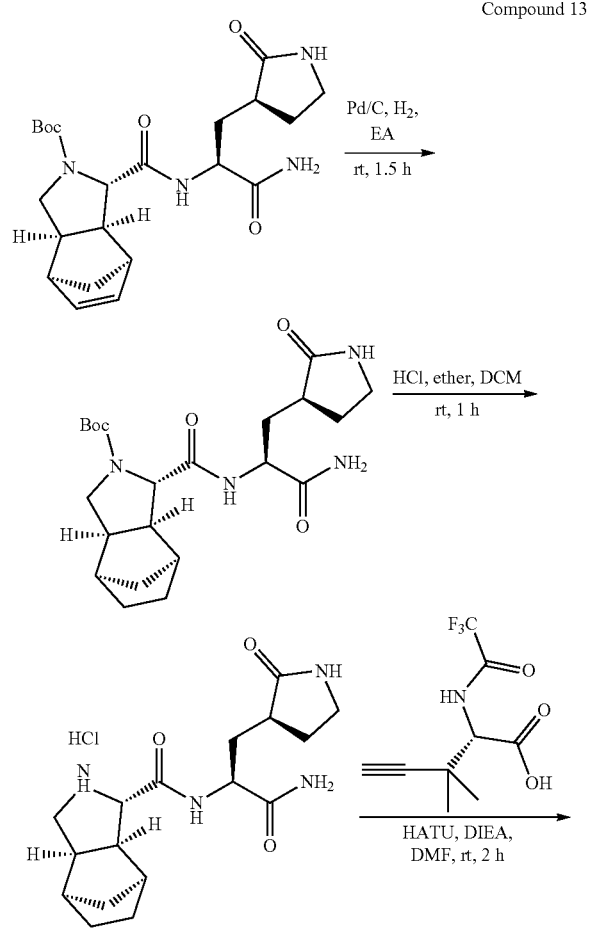

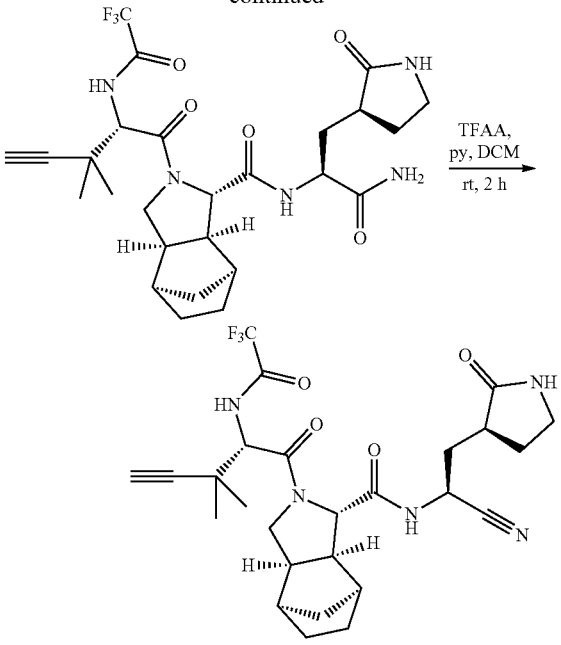

To a stirred mixture of tert-butyl (1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-ene-4-carboxylate (250 mg, 0.578 mmol, 1.0 eq.) in ethyl acetate (3 mL) was added 10% palladium on activated carbon (120 mg) at rt. The mixture was stirred for 1.5 h under hydrogen. The mixture was filtered, and the filter cake was washed with ethyl acetate (3×10 mL). The filtrate was concentrated under reduced pressure to afford tert-butyl (1S,2S,3S,6R,7R)-3-{[(1S)-1-carbamoyl-2-[(3S)-2-oxopyrrolidin-3-yl]ethyl]carbamoyl}-4-azatricyclo[5.2.1.0^{2,6}]decane-4-carboxylate (200 mg, 75%) as a white solid. LC-MS (ESI, m/z): 435 [M+H]$^+$.

To a stirred mixture of tert-butyl (1S,2S,3S,6R,7R)-3-{[(1S)-1-carbamoyl-2-[(3S)-2-oxopyrrolidin-3-yl]ethyl]carbamoyl}-4-azatricyclo[5.2.1.0^{2,6}]decane-4-carboxylate (200 mg, 0.460 mmol, 1.0 eq.) in DCM (2 mL) was added hydrogen chloride (6 mL, 2M in Et$_2$O) at rt. The mixture was stirred for 1 h at rt and then concentrated under reduced pressure to afford (2S)-2-[(1S,2S,3S,6R,7R)-4-azatricyclo[5.2.1.0^{2,6}]decan-3-ylformamido]-3-[(3S)-2-oxopyrrolidin-3-yl]propanamide hydrochloride (180 mg, crude) as a light yellow solid. LC-MS (ESI, m/z): 335 [M+H]$^+$.

To a stirred mixture of (2S)-3,3-dimethyl-2-(2,2,2-trifluoroacetamido)butanoic acid (124 mg, 0.550 mmol, 1.2 eq.) in DMF (2 mL) was added o-(7-Azabenzotriazol-1-yl)-N,N,N',N'-tetramethyluronium hexafluorophosphate (209 mg, 0.550 mmol, 1.2 eq.) and N-ethyl-N-isopropylpropan-2-amine (355 mg, 2.74 mmol, 6.0 eq.) at rt. The mixture was stirred for 10 min at rt, and (2S)-2-[(1S,2S,3S,6R,7R)-4-azatricyclo[5.2.1.0^{2,6}]decan-3-ylformamido]-3-[(3S)-2-oxopyrrolidin-3-yl]propanamide hydrochloride (170 mg, 0.458 mmol, 1.0 eq.) was added. The mixture was stirred for 2 h at rt. The reaction was quenched with water (10 mL). The mixture was extracted with ethyl acetate (3×10 mL). The organic layers were combined, washed with brine (2×10 mL), dried over anhydrous sodium sulfate, filtered and concentrated under reduced pressure to afford the crude product. The crude product was chromatographed on a silica gel column with MeOH:DCM (1:15) to provide (2S)-2-{[(1S,2S,3S,6R,7R)-4-[(2S)-3,3-dimethyl-2-(2,2,2-trifluoro-acetamido)butanoyl]-4-azatricyclo[5.2.1.0^{2,6}]decan-3-yl]formamido}-3-[(3S)-2-oxopyrrolidin-3-yl]propanamide (135 mg, 54%) as a light yellow solid. LC-MS (ESI, m/z): 553 [M+H]+.

To a stirred mixture of (2S)-2-{[(1S,2S,3S,6R,7R)-4-[(2S)-3,3-dimethyl-2-(2,2,2-trifluoroacetamido)pent-4-ynoyl]-4-azatricyclo[5.2.1.0^{2,6}]decan-3-yl]formamido}-3-[(3S)-2-oxopyrrolidin-3-yl]propanamide (135 mg, 0.244 mmol, 1.0 eq.) in DCM (2 mL) was added trifluoroacetic anhydride (102 mg, 0.488 mmol, 2.0 eq.) and pyridine (67.5 mg, 0.854 mmol, 3.5 eq.). The mixture was stirred for 2 h at rt. The reaction was quenched with water (10 mL). The mixture was extracted with dichloromethane (3×10 mL). The organic layers were combined, washed with brine (2×10 mL), dried over anhydrous sodium sulfate, filtered and concentrated under reduced pressure to afford the crude product. The crude product was purified by prep-HPLC with the following conditions (Column: XBridge Prep C18 OBD Column, 19*150 mm, 5 m; Mobile Phase A: Water (0.1% FA), Mobile Phase B: ACN; Flow rate: 25 mL/min; Gradient: 40% B to 70% B in 7 min, 70% B; Wave Length: 254 nm; RT1 (min): 5) to afford (1S,2S,3S,6R,7R)—N-[(1S)-1-cyano-2-[(3S)-2-oxopyrrolidin-3-yl]ethyl]-4-[(2S)-3,3-dimethyl-2-(2,2,2-trifluoroacetamido)pent-4-ynoyl]-4-azatricyclo[5.2.1.0^{2,6}]decane-3-carboxamide (18.8 mg, 14%) as a white solid. LC-MS (ESI, m/z): 536 [M+H]+.

Example 14

Compound 14

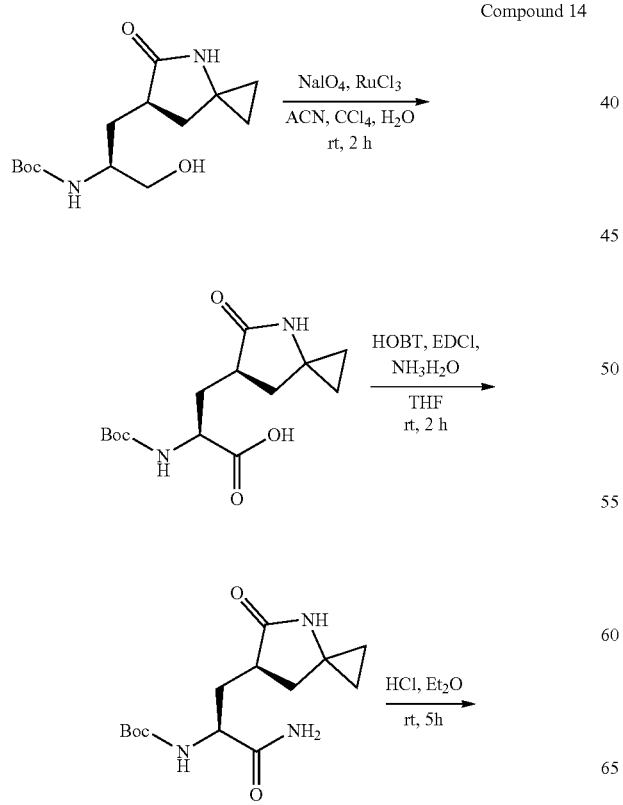

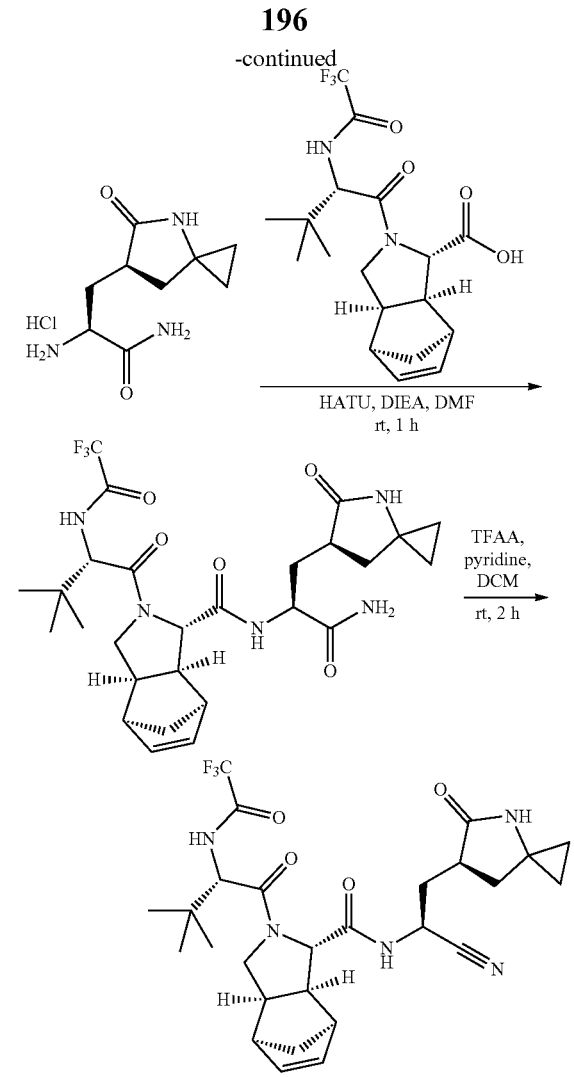

14

To a solution of tert-butyl ((S)-1-hydroxy-3-((R)-5-oxo-4-azaspiro[2.4]heptan-6-yl)propan-2-yl)carbamate (400 mg, 1.41 mmol, 1.0 eq.) in CCl4 (6 mL) and acetonitrile (6 mL) were added sodium periodate (1.52 g, 7.13 mmol, 5.07 eq., in 9 mL water) and trichlororuthenium (35.0 mg, 0.169 mmol, 0.12 eq.) at 0° C. The mixture was stirred for 2 h at rt and then filtered through celite. The filtrate was extracted with DCM (3×50 mL). The organic layers were combined, washed with brine (2×30 mL), dried over anhydrous sodium sulfate, filtered and concentrated under reduced pressure to afford the crude product. The crude product was purified by C18 column with CH3CN:Water (0.05% TFA). The desired fraction was concentrated under reduced pressure to provide (S)-2-((tert-butoxycarbonyl)amino)-3-((R)-5-oxo-4-azaspiro[2.4]heptan-6-yl)propanoic acid (240 mg, 57%) as a white solid. LC-MS (ESI, m/z): 299 [M+H]+.

To a solution of (S)-2-((tert-butoxycarbonyl)amino)-3-((R)-5-oxo-4-azaspiro[2.4]heptan-6-yl)propanoic acid (130 mg, 0.436 mmol, 1.0 eq.) in THF (3 mL) was added 1-hydroxybenzotriazole (177 mg, 1.31 mmol, 3.0 eq.) and 1-(3-dimethylaminopropyl)-3-ethylcarbodiimide hydrochloride (184 mg, 0.959 mmol, 2.2 eq.) stirred at 0° C. After stirred for 1 h, ammonium hydroxide (2.6 mL) was added. The mixture was stirred for 2 h at rt and then concentrated under reduced pressure to afford the crude product. The crude product was purified by C18 column with CH₃CN:Water (0.05% FA). The desired fraction was concentrated under reduced pressure to provide tert-butyl ((S)-1-amino-1-oxo-3-((R)-5-oxo-4-azaspiro[2.4]heptan-6-yl)propan-2-yl)carbamate (80 mg, 61%) as a white solid. $^1$H NMR (400 MHz, CDCl₃) δ 7.11-7.6 (m, 1H), 6.47-6.51 (m, 1H), 6.03 (br, 1H), 5.85 (m, 1H), 4.36-4.42 (m, 1H), 2.78-2.85 (m, 1H), 2.26-2.34 (m, 1H), 2.13-2.21 (m, 1H), 1.89-2.04 (m, 2H), 1.43-1.51 (m, 9H), 0.77-0.98 (m, 2H), 0.67-0.75 (m, 2H). LC-MS (ESI, m/z): 298 [M+H]⁺.

A mixture of tert-butyl ((S)-1-amino-1-oxo-3-((R)-5-oxo-4-azaspiro[2.4]heptan-6-yl)propan-2-yl)carbamate (80.0 mg, 0.269 mmol, 1.0 eq.) in hydrogen chloride (3 mL, 2 M in diethyl ether) was stirred for 5 h at rt and then concentrated under reduced pressure to afford (S)-2-amino-3-((R)-5-oxo-4-azaspiro[2.4]heptan-6-yl)propanamide hydrochloride (60 mg, crude) as a yellow solid. LC-MS (ESI, m/z): 198 [M+H]⁺.

To a mixture of (1R,2S,3S,6R,7S)-4-[(2S)-3,3-dimethyl-2-(2,2,2-trifluoroacetamido)butanoyl]-4-azatricyclo[5.2.1.0^{2,6}]dec-8-ene-3-carboxylic acid (110 mg, 0.283 mmol, 1.1 eq.) in dimethylformamide (2 mL) were added o-(7-azabenzotriazol-1-yl)-N,N,N',N'-tetramethyluronium hexafluorophosphate (117 mg, 0.308 mmol, 1.2 eq.) and N-ethyl-N-isopropylpropan-2-amine (199 mg, 1.54 mmol, 6.0 eq.) at 0° C. After stirred 20 min, (S)-2-amino-3-((R)-5-oxo-4-azaspiro[2.4]heptan-6-yl)propanamide hydrochloride (60.0 mg, 0.257 mmol, 1.0 eq.) was added. The mixture was stirred for 1 h at rt. The reaction was quenched with water (5 mL). The mixture was purified by C18 column with CH₃CN:Water (0.05% TFA). The desired fraction was concentrated under reduced pressure to (1S,3aR,4S,7R,7aS)—N—((S)-1-amino-1-oxo-3-((R)-5-oxo-4-azaspiro[2.4]heptan-6-yl)propan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (65 mg, 44%) as a white solid. LC-MS (ESI, m/z): 568 [M+H]⁺.

To a mixture of (1S,3aR,4S,7R,7aS)—N—((S)-1-amino-1-oxo-3-((R)-5-oxo-4-azaspiro[2.4]heptan-6-yl)propan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (60.0 mg, 0.106 mmol, 1.0 eq.) in DCM (2 mL) were added pyridine (41.8 mg, 0.530 mmol, 5.0 eq.) and trifluoroacetic anhydride (51.1 mg, 0.244 mmol, 2.3 eq.). The mixture was stirred 2 h at rt. The reaction was quenched with water (10 mL). The mixture was extracted with DCM (3×30 mL). The organic layers were combined, washed with brine (2×20 mL), dried over anhydrous sodium sulfate, filtered and concentrated under reduced pressure to afford the crude product. The crude product was purified by prep-HPLC (Column: XBridge Shield RP18 OBD Column, 19*250 mm, 10 m; Mobile Phase A: Water (0.1% FA), Mobile Phase B: ACN; Flow rate: 25 mL/min; Gradient: 40% B to 70% B in 7 min, 70% B; Wave Length: 220 nm; RT1 (min): 5.63;) to provide (1S,3aR,4S,7R,7aS)—N—((S)-1-cyano-2-((R)-5-oxo-4-azaspiro[2.4]heptan-6-yl)ethyl)-2-((S)-3,3-dimethyl-2-(2,2,2-trifluoroacetamido)butanoyl)-2,3,3a,4,7,7a-hexahydro-1H-4,7-methanoisoindole-1-carboxamide (27.5 mg, 47%) as a white solid. $^1$H NMR (400 MHz, 80° C., DMSO-d₆) δ 8.75-8.81 (m, 1H), 8.67-8.69 (m, 1H), 7.50-7.57 (m, 1H), 5.93-6.16 (m, 2H), 4.84-4.89 (m, 1H), 4.44-4.64 (m, 1H), 3.98-4.12 (m, 1H), 3.58-3.66 (m, 1H), 3.37-3.47 (m, 1H), 3.07-3.17 (m, 1H), 2.79-2.93 (m, 2H), 2.63-2.73 (m, 1H), 2.54-2.63 (m, 1H), 2.12-2.29 (m, 1H), 1.74-1.99 (m, 3H), 1.32-1.42 (m, 2H), 0.88-0.94 (m, 9H), 0.71-0.77 (m, 1H), 0.48-0.62 (m, 3H). LC-MS (ESI, m/z): 550 [M+H]⁺.

Example 15

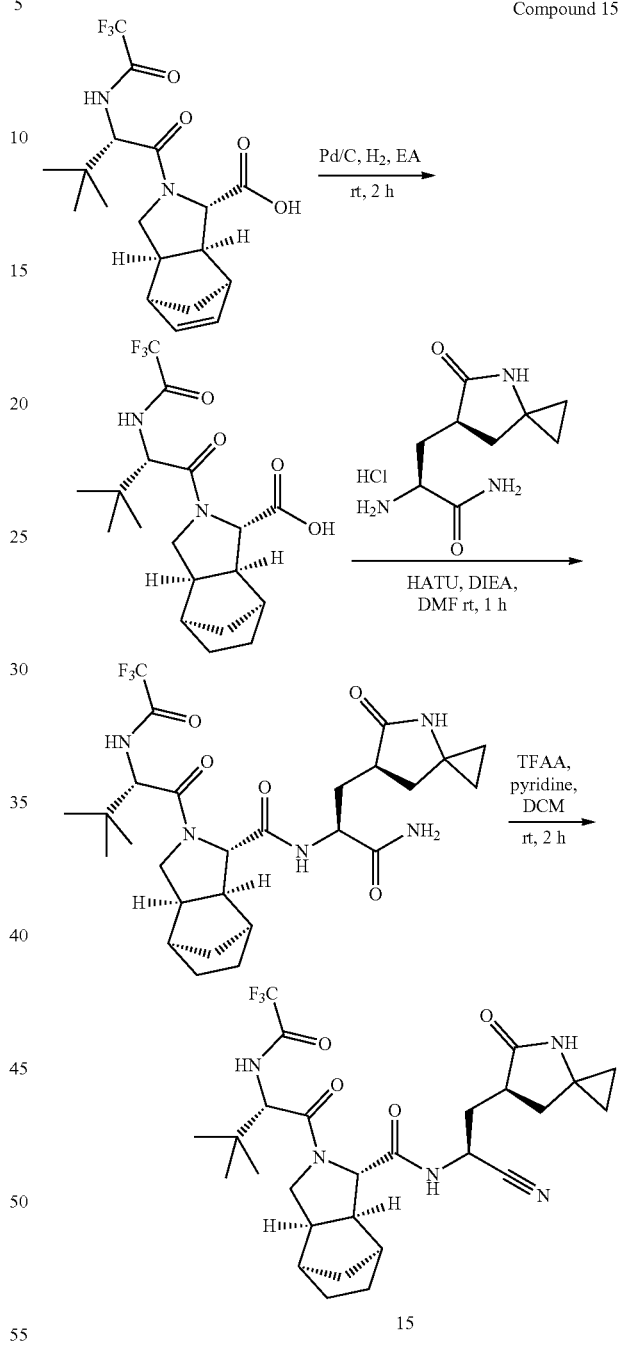

Compound 15

15

To a mixture of (1S,3aR,4S,7R,7aS)-2-((S)-3,3-dimethyl-2-(2,2,2-trifluoroacetamido)butanoyl)-2,3,3a,4,7,7a-hexahydro-1H-4,7-methanoisoindole-1-carboxylic acid (500 mg, 1.29 mmol, 1.0 eq.) in ethyl acetate (10 mL) was added 10% palladium on activated carbon (120 mg). The mixture was stirred for overnight at rt under hydrogen. The mixture was filtered through a celite pad and then washed with ethyl acetate (150 mL). The filtrate was concentrated under reduced pressure to afford (1S,3aR,4R,7S,7aS)-2-((S)-3,3-dimethyl-2-(2,2,2-trifluoroacetamido)butanoyl)octahydro- 1H-4,7-methanoisoindole-1-carboxylic acid (460 mg, crude) as an off white solid. LC-MS (ESI, m/z): 391 [M+H]+.

To a mixture of (1S,3aR,4R,7S,7aS)-2-((S)-3,3-dimethyl-2-(2,2,2-trifluoroacetamido)butanoyl)octahydro-1H-4,7-methanoisoindole-1-carboxylic acid (184 mg, 0.471 mmol, 1.1 eq.) in dimethylformamide (3 mL) was added o-(7-azabenzotriazol-1-yl)-N,N,N',N'-tetramethyluronium hexafluorophosphate (195 mg, 0.514 mmol, 1.2 eq.) and N-ethyl-N-isopropylpropan-2-amine (332 mg, 2.57 mmol, 6.0 eq.) at 0° C. After stirred 20 min, (S)-2-amino-3-((R)-5-oxo-4-azaspiro[2.4]heptan-6-yl)propanamide hydrochloride (100 mg, 0.428 mmol, 1.0 eq.) was added. The mixture was stirred for 1 h at rt. The reaction was quenched with water (5 mL). The mixture was purified by C18 column with CH3CN:Water (0.05% TFA). The desired fraction was concentrated under reduced pressure to provide (1S,3aR,4R,7S,7aS)—N—((S)-1-amino-1-oxo-3-((R)-5-oxo-4-azaspiro[2.4]heptan-6-yl)propan-2-yl)-2-((S)-3,3-dimethyl-2-(2,2,2-trifluoroacetamido)butanoyl)octahydro-1H-4,7-methanoisoindole-1-carboxamide (140 mg, 57%) as a white solid. LC-MS (ESI, m/z): 570 [M+H]+.

To a mixture of (1S,3aR,4R,7S,7aS)—N—((S)-1-amino-1-oxo-3-((R)-5-oxo-4-azaspiro[2.4]heptan-6-yl)propan-2-yl)-2-((S)-3,3-dimethyl-2-(2,2,2-trifluoroacetamido)butanoyl)octahydro-1H-4,7-methanoisoindole-1-carboxamide (140 mg, 0.246 mmol, 1.0 eq.) in DCM (3 mL) was added pyridine (77.8 mg, 0.984 mmol, 4.0 eq.) and trifluoroacetic anhydride (92.9 mg, 0.443 mmol, 1.8 eq.). The mixture was stirred 2 h at rt. The reaction was quenched with water (10 mL). The mixture was extracted with DCM (3×50 mL). The organic layers were combined, washed with brine (2×20 mL), dried over anhydrous sodium sulfate, filtered and concentrated under reduced pressure to afford the crude product. The crude product was chromatographed on a silica gel column with EA:PE (65%-72%) to provide (1S,3aR,4R,7S,7aS)—N—((S)-1-cyano-2-((R)-5-oxo-4-azaspiro[2.4]heptan-6-yl)ethyl)-2-((S)-3,3-dimethyl-2-(2,2,2-trifluoroacetamido)butanoyl)octahydro-1H-4,7-methanoisoindole-1-carboxamide (47.6 mg, 33%) as a white solid. 1H NMR (400 MHz, 80° C., DMSO-d6) δ 8.94-8.98 (m, 1H), 8.57-8.75 (m, 1H), 7.51-7.59 (m, 1H), 4.83-4.90 (m, 1H), 4.56-4.68 (m, 1H), 4.46-4.48 (m, 1H), 3.70-3.79 (m, 1H), 3.57-3.65 (m, 1H), 2.49-2.68 (m, 2H), 2.31-2.42 (m, 2H), 2.12-2.22 (m, 2H), 1.89-2.01 (m, 2H), 1.79-1.86 (m, 1H), 1.35-1.49 (m, 2H), 1.19-1.32 (m, 3H), 1.06-1.14 (m, 1H), 0.93-0.97 (m, 9H), 0.72-0.75 (m, 1H), 0.49-0.62 (m, 3H). LC-MS (ESI, m/z): 552 [M+H]+.

Example 16

Compound 16

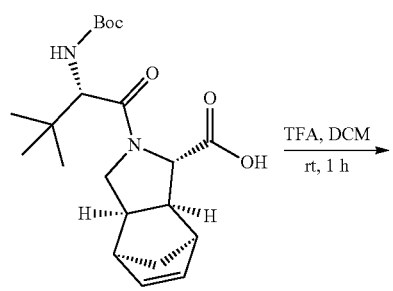

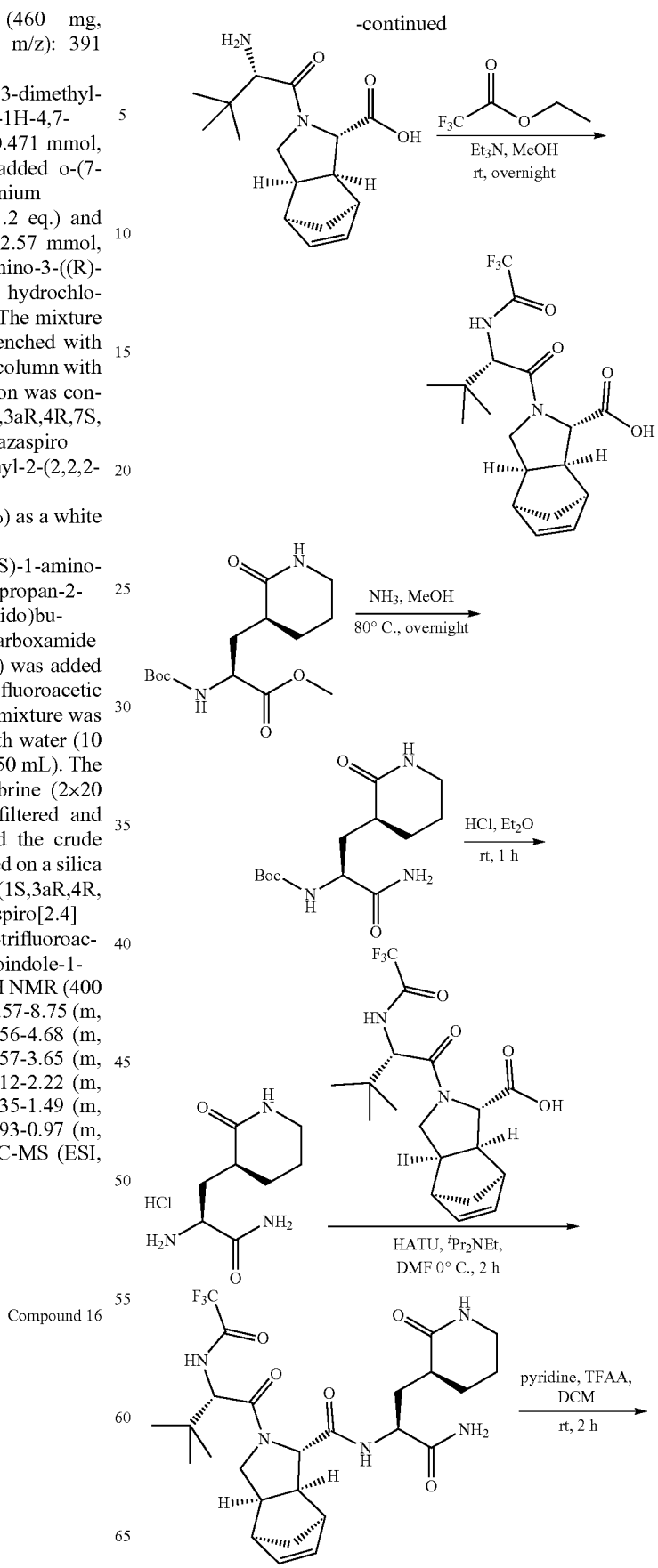

-continued

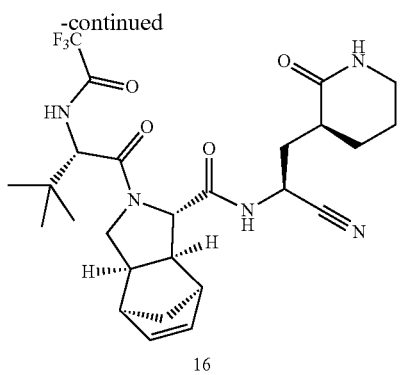

16

To a mixture of (1S,3aR,4S,7R,7aS)-2-((S)-2-((tert-butoxycarbonyl)amino)-3,3-dimethylbutanoyl)-2,3,3a,4,7,7a-hexahydro-1H-4,7-methanoisoindole-1-carboxylic acid (2.00 g, 5.09 mmol, 1.0 eq.) in DCM (30 mL) was added trifluoroacetic acid (10 mL). The mixture was stirred for 1 h at rt and then concentrated under reduced pressure to afford product (1S,3aR,4S,7R,7aS)-2-((S)-2-amino-3,3-dimethylbutanoyl)-2,3,3a,4,7,7a-hexahydro-1H-4,7-methanoisoindole-1-carboxylic acid (1.40 g, crude) as a solid. LC-MS (ESI, m/z): 293 [M+H]+.

To a stirred mixture of (1S,3aR,4S,7R,7aS)-2-((S)-2-amino-3,3-dimethylbutanoyl)-2,3,3a,4,7,7a-hexahydro-1H-4,7-methanoisoindole-1-carboxylic acid (1.49 g, 5.09 mmol, 1.0 eq.) in MeOH (10 mL) was added triethylamine (6.19 g, 61.1 mmol, 12.0 eq.) and ethyl 2,2,2-trifluoroacetate (4.34 g, 30.5 mmol, 6.0 eq.). The mixture was stirred overnight at rt and then concentrated under reduced pressure to remove the MeOH. The crude product was purified by C18 column with CH$_3$CN/Water (0.05% TFA). The desired fraction was concentrated under reduced pressure to provide (1S,3aR,4S,7R,7aS)-2-((S)-3,3-dimethyl-2-(2,2,2-trifluoroacetamido)butanoyl)-2,3,3a,4,7,7a-hexahydro-1H-4,7-methanoisoindole-1-carboxylic acid (1.17 g, 59%) as a yellow solid. LC-MS (ESI, m/z): 389 [M+H]+.

A mixture of methyl (S)-2-((tert-butoxycarbonyl)amino)-3-((S)-2-oxopiperidin-3-yl)propanoate (1.0 g, 3.32 mmol, 1.0 eq.) in ammonia (20 mL, 7 M in MeOH) was stirred overnight at 80° C. The mixture was concentrated under reduced pressure to afford tert-butyl ((S)-1-amino-1-oxo-3-((S)-2-oxopiperidin-3-yl)propan-2-yl)carbamate (1.01 g, crude) as a light brown solid. $^1$H NMR (400 MHz, DMSO-d$_6$) δ 7.36-7.65 (m, 1H), 7.14-7.35 (m, 1H), 6.44-7.12 (m, 2H), 3.74-4.22 (m, 1H), 2.91-3.30 (m, 2H), 1.99-2.40 (m, 2H), 1.45-1.94 (m, 4H), 0.94-1.44 (m, 10H). LC-MS (ESI, m/z): 286 [M+H]+.

A mixture of tert-butyl ((S)-1-amino-1-oxo-3-((S)-2-oxopiperidin-3-yl)propan-2-yl)carbamate (120 mg, 0.421 mmol, 1.0 eq.) in hydrogen chloride (3 mL, 2 M in Et$_2$O) was stirred for 1 h at rt. The mixture was concentrated under reduced pressure to afford (2S)-2-amino-3-[(3S)-2-oxopiperidin-3-yl]propanamide hydrochloride (80.0 mg, crude) as a yellow oil. LC-MS (ESI, m/z): 186 [M+H]+.

To a mixture of (1S,3aR,4S,7R,7aS)-2-((S)-3,3-dimethyl-2-(2,2,2-trifluoroacetamido)butanoyl)-2,3,3a,4,7,7a-hexahydro-1H-4,7-methanoisoindole-1-carboxylic acid (162 mg, 0.420 mmol, 1.0 eq.) in N,N-dimethylformamide (3 mL) was added o-(7-azabenzotriazol-1-yl)-N,N,N',N'-tetramethyluronium hexafluorophosphate (191 mg, 0.504 mmol, 1.2 eq.) and N-ethyl-N-isopropylpropan-2-amine (325 mg, 2.52 mmol, 6.0 eq.) at 0° C. The mixture was stirred for 20 min at 0° C., then (2S)-2-amino-3-[(3S)-2-oxopiperidin-3-yl]propanamide hydrochloride (93.0 mg, 0.420 mmol, 1.0 eq.) was added at 0° C. The mixture was stirred for 2 h at rt. The reaction was quenched with water (30 mL). The mixture was extracted with EtOAc (3×30 mL). The organic layers were combined, washed with brine (2×30 mL), dried over anhydrous sodium sulfate, filtered and concentrated under reduced pressure to afford the crude product. The crude product was chromatographed on a silica gel column with MeOH:DCM (6:94) to provide (1S,3aR,4S,7R,7aS)—N—((S)-1-amino-1-oxo-3-((S)-2-oxopiperidin-3-yl)propan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (160 mg, 68%) as a light yellow solid. LC-MS (ESI, m/z): 556 [M+H]+.

To a mixture of (1S,3aR,4S,7R,7aS)—N—((S)-1-amino-1-oxo-3-((S)-2-oxopiperidin-3-yl)propan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (160 mg, 0.288 mmol, 1.0 eq.) in DCM (3 mL) was added pyridine (91.1 mg, 1.15 mmol, 4.0 eq.) and trifluoroacetic anhydride (120 mg, 0.576 mmol, 2.0 eq.). The mixture was stirred for 2 h at rt. The reaction was quenched with water (5 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was purified by prep-HPLC (Column: XBridge Shield RP18 OBD Column, 19*250 mm, 10 m; Mobile Phase A: Water (0.1% FA), Mobile Phase B: ACN; Flow rate: 25 mL/min; Gradient: 35% B to 55% B in 10 min, 55% B; Wave Length: 254 nm; RT1 (min): 8.15) to provide (1S,3aR,4S,7R,7aS)—N—((S)-1-cyano-2-((S)-2-oxopiperidin-3-yl)ethyl)-2-((S)-3,3-dimethyl-2-(2,2,2-trifluoroacetamido)butanoyl)-2,3,3a,4,7,7a-hexahydro-1H-4,7-methanoisoindole-1-carboxamide (38.5 mg, 25%) as an off-white solid. $^1$H NMR (400 MHz, 80° C., DMSO-d$_6$) δ 8.75-8.95 (m, 1H), 8.60-8.73 (m, 1H), 7.15-7.40 (m, 1H), 5.90-6.30 (m, 2H), 4.65-5.10 (m, 1H), 4.40-4.60 (m, 1H), 3.90-4.25 (m, 1H), 3.55-3.75 (m, 1H), 3.35-3.50 (m, 1H), 3.10-3.20 (m, 2H), 3.00-3.05 (m, 1H), 2.85-3.00 (m, 2H), 2.65-2.80 (m, 1H), 2.20-2.50 (m, 2H), 1.70-1.95 (m, 3H), 1.50-1.70 (m, 1H), 1.30-1.50 (m, 3H), 0.80-1.05 (m, 9H). LC-MS (ESI, m/z): 538 [M+H]+.

Example 17

Compound 17a and 17b

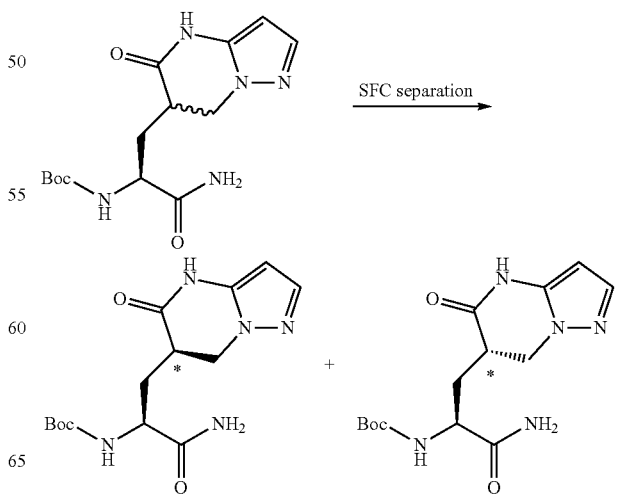

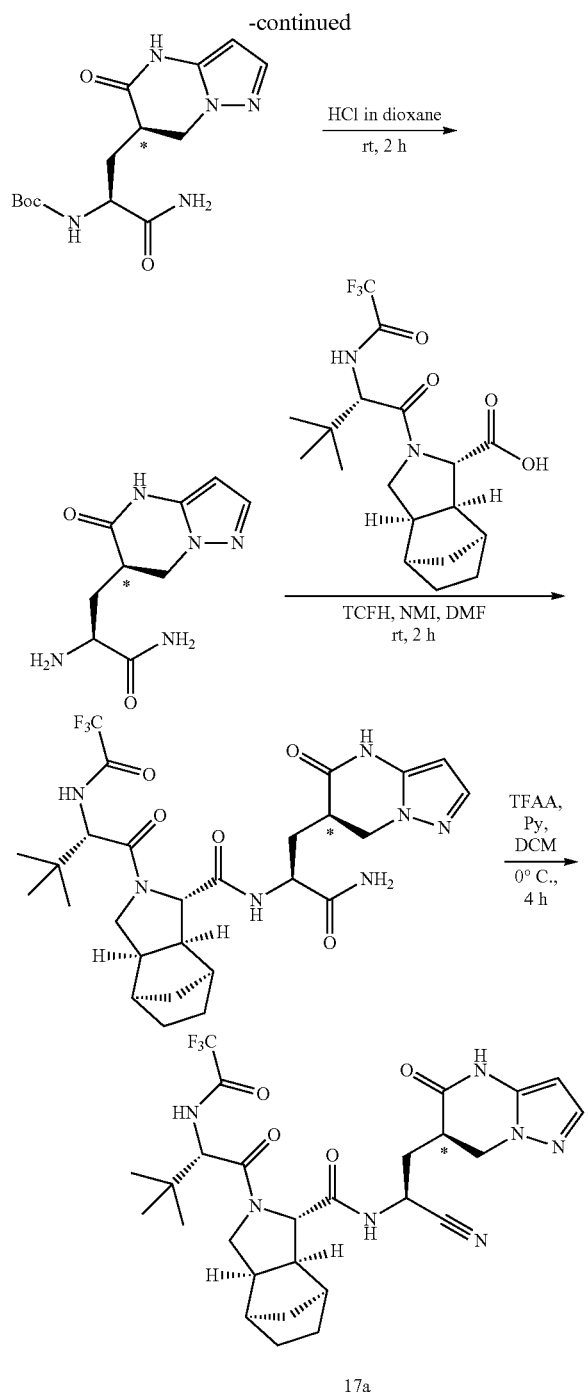

The chiral centers noted with "*" are tentatively assigned

Tert-butyl ((2S)-1-amino-1-oxo-3-(5-oxo-4,5,6,7-tetrahydropyrazolo[1,5-a]pyrimidin-6-yl)propan-2-yl)carbamate (290 mg) was purified by SFC using the following gradient conditions: Column: OptiChiral-C9-5, 3*25 cm, 5 m; Mobile Phase A: CO₂, Mobile Phase B: IPA (0.5% 2M NH₃-MeOH); Flow rate: 100 mL/min; Gradient: isocratic 35% B; Column Temperature (° C.): 35; Back Pressure (bar): 100; Wave Length: 220 nm; RT1 (min): 3.3; RT2 (min): 5.85; Sample Solvent: MeOH—Preparative; Injection Volume: 4.8 mL; Purification resulted in tert-butyl ((2S)-1-amino-1-oxo-3-(5-oxo-4,5,6,7-tetrahydropyrazolo[1,5-a]pyrimidin-6-yl)propan-2-yl)carbamate (210 mg) as an off-white solid, which was purified by SFC using the following gradient conditions: Column: Lux Sum Cellulose-4, 3*25 cm, 5 m; Mobile Phase A: CO₂, Mobile Phase B: IPA (0.5% 2M NH₃-MeOH); Flow rate: 100 mL/min; Gradient: isocratic 40% B; Column Temperature (° C.): 35; Back Pressure (bar): 100; Wave Length: 220 nm; RT1 (min): 2.87; RT2(min): 4.33; Sample Solvent: MeOH-Preparative; Injection Volume: 4.8 mL; Number Of Runs: 4. Purification resulted in a mixture of tert-butyl ((S)-1-amino-1-oxo-3-((R*)-5-oxo-4,5,6,7-tetrahydropyrazolo[1,5-a]pyrimidin-6-yl)propan-2-yl)carbamate (80 mg) as an off-white solid. $^1$H NMR (300 MHz, DMSO-d₆) δ 10.78 (s, 1H), 7.29-7.32 (m, 2H), 6.96-7.06 (m, 2H), 5.59-5.60 (m, 1H), 4.31-4.37 (m, 1H), 3.95-4.03 (m, 2H), 2.69-2.80 (m, 1H), 2.09-2.19 (m, 1H), 1.69-1.77 (m, 1H), 1.24-1.37 (m, 9H). LC-MS (ESI, m/z): 324 [M+H]⁺.

And tert-butyl ((S)-1-amino-1-oxo-3-((S)-5-oxo-4,5,6,7-tetrahydropyrazolo[1,5-a]pyrimidin-6-yl)propan-2-yl)carbamate (90 mg) as an off-white solid. $^1$H NMR (300 MHz, DMSO-d₆) δ 10.76 (s, 1H), 7.29-7.33 (m, 2H), 6.95-7.06 (m, 2H), 5.58-5.59 (m, 1H), 4.40-4.44 (m, 1H), 3.93-4.07 (m, 2H), 2.75-2.81 (m, 1H), 2.21-2.25 (m, 1H), 1.51-1.61 (m, 1H), 1.20-1.24 (m, 9H). LC-MS (ESI, m/z): 324 [M+H]⁺.

A solution of tert-butyl ((S)-1-amino-1-oxo-3-((R*)-5-oxo-4,5,6,7-tetrahydropyrazolo[1,5-a]pyrimidin-6-yl)propan-2-yl)carbamate (70 mg, 0.216 mmol, 1.0 eq.) in hydrochloric acid (2 mL, 4M in dioxane) was stirred at rt for 2 h and then concentrated under reduced pressure to provide (S)-2-amino-3-((R)-5-oxo-4,5,6,7-tetrahydropyrazolo[1,5-a]pyrimidin-6-yl)propanamide (40 mg, crude) as a white solid. LC-MS (ESI, m/z): 224 [M+H]⁺.

To a solution of (S)-2-amino-3-((R*)-5-oxo-4,5,6,7-tetrahydropyrazolo[1,5-a]pyrimidin-6-yl)propanamide (40 mg, 0.18 mmol, 1.0 eq.) in DMF (1 mL) was added (1S,3aR,4R,7S,7aS)-2-((S)-3,3-dimethyl-2-(2,2,2-trifluoroacetamido)butanoyl)octahydro-1H-4,7-methanoisoindole-1-carboxylic acid (77 mg, 0.2 mmol, 1.1 eq.), N,N,N,N-tetramethylchloroformamidinium hexafluorophosphate (66 mg, 0.24 mmol, 1.3 eq.) and NMI (74 mg, 0.9 mmol, 5.0 eq.). The mixture was stirred at rt for 2 h. The residue was chromatographed on a C18 column with water:MeCN (3:1) to provide (1S,3aR,4R,7S,7aS)—N—((S)-1-amino-1-oxo-3-((R)-5-oxo-4,5,6,7-tetrahydropyrazolo[1,5-a]pyrimidin-6-yl)propan-2-yl)-2-((S)-3,3-dimethyl-2-(2,2,2-trifluoroacetamido)butanoyl)octahydro-1H-4,7-methanoisoindole-1-carboxamide (50 mg, 42%) as an off-white solid. LC-MS (ESI, m/z): 596 [M+H]⁺.

To a solution of (1S,3aR,4R,7S,7aS)—N—((S)-1-amino-1-oxo-3-((R*)-5-oxo-4,5,6,7-tetrahydropyrazolo[1,5-a]pyrimidin-6-yl)propan-2-yl)-2-((S)-3,3-dimethyl-2-(2,2,2-trifluoroacetamido)butanoyl)octahydro-1H-4,7-methanoisoindole-1-carboxamide (50 mg, 0.08 mmol, 1.0 eq.) in DCM (3 mL) was added TFAA (35 mg, 0.17 mmol, 2.0 eq.) and pyridine (23 mg, 0.29 mmol, 3.5 eq.). The mixture was stirred at rt for 2 h. The reaction was quenched with water (3 mL). The mixture was extracted with DCM (3×5 mL). The organic layers were combined, dried over anhydrous sodium sulfate, filtered and concentrated under reduced pressure. The residue was purified by prep-HPLC (Column: XBridge Shield RP18 OBD Column, 30*150 mm, 5 m; Mobile Phase A: Water (0.1% FA), Mobile Phase B: ACN; Flow rate: 60 mL/min; Gradient: 37% B to 52% B in 7 min, 52% B; Wave Length: 254 nm; RT1 (min): 5.23) to provide (1S,3aR,4R,7S,7aS)—N—((S)-1-cyano-2-((R*)-5-oxo-4,5,6,7-tetrahydropyrazolo[1,5-a]pyrimidin-6-yl)ethyl)-2-((S)-3,3-dimethyl-2-(2,2,2-trifluoroacetamido)butanoyl)octahydro-1H-4,7-methanoisoindole-1-carboxamide (5.1 mg. 10%) as a white solid. ¹H NMR (400 MHz, DMSO-d₆, 80° C.) δ 10.66 (br, 1H), 8.39-9.09 (m, 2H), 7.24-7.26 (m, 1H), 5.56-5.57 (m, 1H), 4.93-5.10 (m, 1H), 4.61-4.71 (m, 1H), 4.32-4.59 (m, 2H), 3.98-4.06 (m, 1H), 3.78-3.82 (m, 1H), 3.58-3.64 (m, 1H), 2.81-2.92 (m, 1H), 2.58-2.69 (m, 1H), 2.41-2.48 (m, 2H), 2.32-2.36 (m, 1H), 2.21-2.23 (m, 1H), 1.92-2.02 (m, 1H), 1.41-1.55 (m, 2H), 1.18-1.32 (m, 3H), 1.08-1.14 (m, 1H), 0.82-0.95 (m, 9H). LC-MS (ESI, m/z): 578 [M+H]⁺.

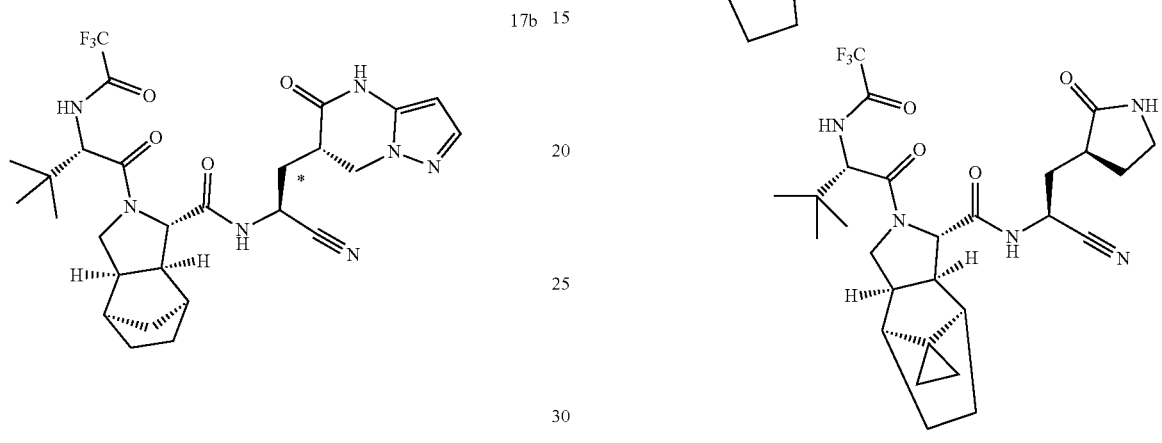

17b

Compound 17b was prepared similarly as described for 17a, using tert-butyl ((S)-1-amino-1-oxo-3-((S*)-5-oxo-4,5,6,7-tetrahydropyrazolo[1,5-a]pyrimidin-6-yl)propan-2-yl)carbamate in place of tert-butyl ((S)-1-amino-1-oxo-3-((R*)-5-oxo-4,5,6,7-tetrahydropyrazolo[1,5-a]pyrimidin-6-yl)propan-2-yl)carbamate. ¹H NMR (400 MHz, DMSO-d₆, 80° C.) δ 10.61 (br, 1H), 8.81-8.95 (m, 1H), 8.67-8.69 (m, 1H), 7.24-7.26 (m, 1H), 5.56-5.58 (m, 1H), 5.09-5.11 (m, 1H), 4.62-4.73 (m, 1H), 4.31-4.52 (m, 2H), 3.91-4.05 (m, 1H), 3.71-3.83 (m, 1H), 3.53-3.66 (m, 1H), 2.81-2.96 (m, 1H), 2.62-2.69 (m, 1H), 2.44-2.51 (m, 2H), 2.32-2.37 (m, 1H), 2.18-2.26 (m, 1H), 1.84-2.05 (m, 1H), 1.38-1.56 (m, 2H), 1.19-1.36 (m, 3H), 1.04-1.17 (m, 1H), 0.82-1.11 (m, 9H). LC-MS (ESI, m/z): 578 [M+H]⁺.

Compound 18

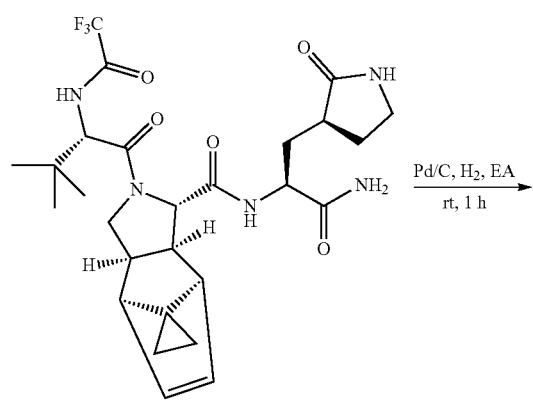

18

To a stirred mixture of (2S)-2-[(1'R,2'S,3'S,6'R,7'S)-4'-[(2S)-3,3-dimethyl-2-(2,2,2-trifluoroacetamido)butanoyl]-4'-azaspiro[cyclopropane-1,10'-tricyclo[5.2.1.0^{2,6}]decan]-8'-en-3'-ylformamido]-3-[(3S)-2-oxopyrrolidin-3-yl]propanamide (250 mg, 0.440 mmol, 1.0 eq.) in EtOAc (4 mL) was added 10% palladium on activated carbon (100 mg). The mixture was stirred for 1 h at rt under hydrogen. The mixture was filtered through a celite pad. The filtrate was concentrated under reduced pressure to provide (2S)-2-[(1'R,2'S,3'S,6'R,7'S)-4'-[(2S)-3,3-dimethyl-2-(2,2,2-trifluoroacetamido)butanoyl]-4'-azaspiro[cyclopropane-1,10'-tricyclo[5.2.1.0^{2,6}]decan]-3'-ylformamido]-3-[(3S)-2-oxopyrrolidin-3-yl]propanamide (235 mg, 91%) as an off-white solid. LC-MS (ESI, m/z): 570 [M+H]⁺.

To a stirred mixture of (2S)-2-[(1'R,2'S,3'S,6'R,7'S)-4'-[(2S)-3,3-dimethyl-2-(2,2,2-trifluoroacetamido)butanoyl]-4'-azaspiro[cyclopropane-1,10'-tricyclo[5.2.1.0^{2,6}]decan]-3'-ylformamido]-3-[(3S)-2-oxopyrrolidin-3-yl]propanamide (230 mg, 0.404 mmol, 1.0 eq.) in DCM (5 mL) was added pyridine (111 mg, 1.41 mmol, 3.5 eq.) and trifluoroacetic anhydride (152 mg, 0.727 mmol, 1.8 eq.). The mixture was stirred for 1 h at rt. The reaction was quenched with water (20 mL). The mixture was extracted with EtOAc (3×20 mL). The organic layers were combined, washed with brine (2×20 mL), dried over anhydrous sodium sulfate, filtered and concentrated under reduced pressure to afford the crude product. The crude product was purified by prep-HPLC (Column: Kinetex EVO C18, 21.2*250 mm, 5 m; Mobile Phase A: Water (0.1% FA), Mobile Phase B: ACN; Flow rate: 25 mL/min; Gradient: 40% B to 63% B in 10 min, 63% B; Wave Length: 254 nm; RT1 (min): 7.45) to provide (1'R,2'S,3'S,6'R,7'S)—N-[(1S)-1-cyano-2-[(3S)-2-oxopyrrolidin-3-yl]ethyl]-4'-[(2S)-3,3-dimethyl-2-(2,2,2-trifluoroacetamido)butanoyl]-4'-azaspiro[cyclopropane-1, 10'-tricyclo[5.2.1.0^{2,6}]decane]-3'-carboxamide (44.3 mg, 19%) as a white solid. $^1$H NMR (400 MHz, 80° C., DMSO-d$_6$) δ 8.91-9.01 (m, 1H), 8.65-8.83 (m, 1H), 7.38-7.53 (m, 1H), 4.81-4.98 (m, 1H), 4.60-4.75 (m, 1H), 4.50-4.58 (m, 1H), 3.79-3.88 (m, 1H), 3.63-3.78 (m, 1H), 3.09-3.23 (m, 2H), 2.72-2.95 (m, 1H), 2.60-2.68 (m, 1H), 2.30-2.41 (m, 1H), 2.09-2.29 (m, 2H), 1.62-1.86 (m, 2H), 1.57-1.61 (m, 1H), 1.31-1.56 (m, 4H), 1.12-1.30 (m, 1H), 0.89-1.09 (m, 9H), 0.50-0.60 (m, 2H), 0.36-0.49 (m, 2H). LC-MS (ESI, m/z): 552 [M+H]$^+$.

Example 19

Compound 19

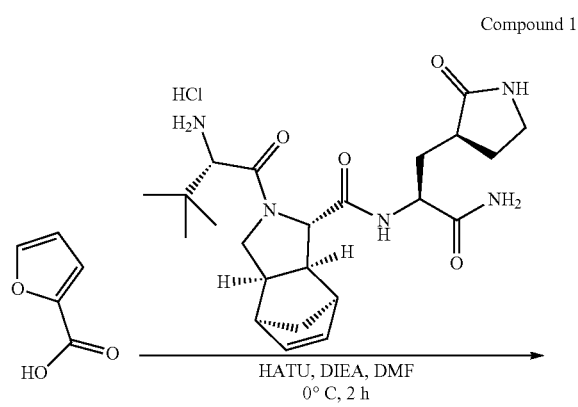

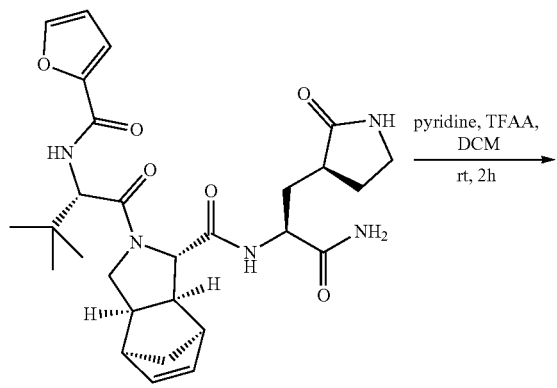

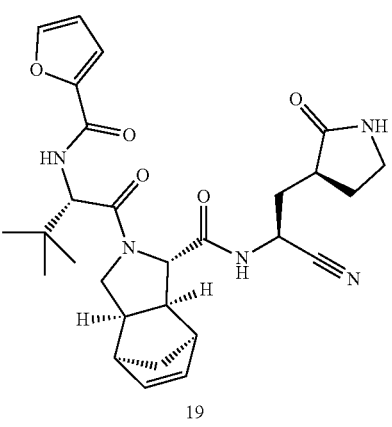

To a mixture of furan-2-carboxylic acid (30.9 mg, 0.276 mmol, 1.0 eq.) in N,N-dimethylformamide (3 mL) was added o-(7-azabenzotriazol-1-yl)-N,N,N',N'-tetramethyluronium hexafluorophosphate (125 mg, 0.331 mmol, 1.2 eq.) and N-ethyl-N-isopropylpropan-2-amine (213 mg, 1.65 mmol, 6.0 eq.) at 0° C. The mixture was stirred for 20 min at 0° C., then (1S,3aR,4S,7R,7aS)—N—((S)-1-amino-1-oxo-3-((S)-2-oxopyrrolidin-3-yl)propan-2-yl)-2-((S)-2-amino-3,3-dimethylbutanoyl)-2,3,3a,4,7,7a-hexahydro-1H-4,7-methanoisoindole-1-carboxamide hydrochloride (133 mg, 0.276 mmol, 1.0 eq.) was added at 0° C. The mixture was stirred for 2 h at rt. The reaction was quenched with water (30 mL). The mixture was extracted with EtOAc (3×30 mL). The organic layers were combined, washed with brine (2×30 mL), dried over anhydrous sodium sulfate, filtered and concentrated under reduced pressure to afford the crude product. The crude product was chromatographed on a silica gel column with MeOH:DCM (7:93) to provide (1S,3aR,4S,7R,7aS)—N—((S)-1-amino-1-oxo-3-((S)-2-oxopyrrolidin-3-yl)propan-2-yl)-2-((S)-2-(furan-2-carboxamido)-3,3-dimethylbutanoyl)-2,3,3a,4,7,7a-hexahydro-1H-4,7-methanoisoindole-1-carboxamide (120 mg, 81%) as a light yellow solid. LC-MS (ESI, m/z): 540 [M+H]$^+$.

To a mixture of (1S,3aR,4S,7R,7aS)—N—((S)-1-amino-1-oxo-3-((S)-2-oxopyrrolidin-3-yl)propan-2-yl)-2-((S)-2-(furan-2-carboxamido)-3,3-dimethylbutanoyl)-2,3,3a,4,7,7a-hexahydro-1H-4,7-methanoisoindole-1-carboxamide (120 mg, 0.222 mmol, 1.0 eq.) in dichloromethane (3 mL) was added pyridine (123 mg, 1.55 mmol, 7.0 eq.) and trifluoroacetic anhydride (140 mg, 0.666 mmol, 3.0 eq.). The mixture was stirred for 2 h at rt. The reaction was quenched with water (5 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was purified by prep-HPLC (Column: XBridge Prep Phenyl OBD Column, 19*250 mm, 5 m; Mobile Phase A: Water (0.1% FA), Mobile Phase B: ACN; Flow rate: 60 mL/min; Gradient: 35% B to 65% B in 7 min, 65% B; Wave Length: 254 nm; RT1 (min): 6) to provide (1S,3aR,4S,7R,7aS)—N—((S)-1-cyano-2-((S)-2-oxopyrrolidin-3-yl)ethyl)-2-((S)-2-(furan-2-carboxamido)-3,3-dimethylbutanoyl)-2,3,3a,4,7,7a-hexahydro-1H-4,7-methanoisoindole-1-carboxamide (17.4 mg, 15%) as an off-white solid. LC-MS (ESI, m/z): 522 [M+H]$^+$.

Example 20

Compound 20

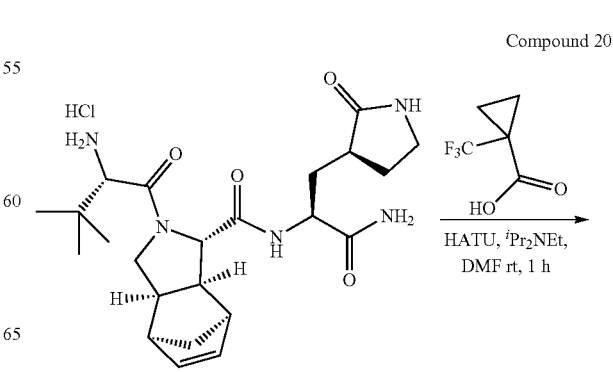

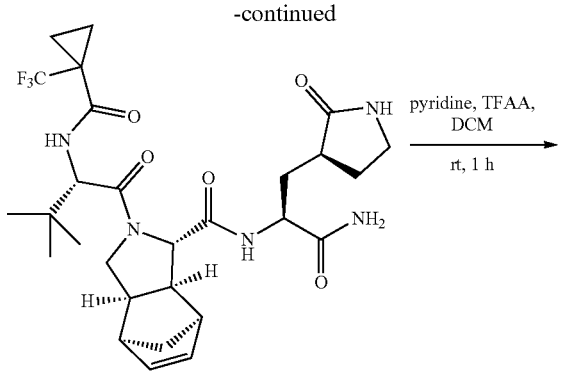

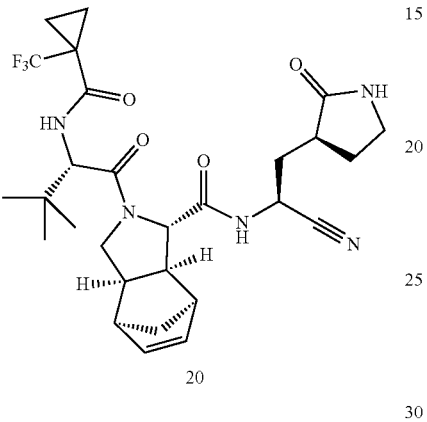

To a mixture of 1-(trifluoromethyl)cyclopropane-1-carboxylic acid (43.0 mg, 0.274 mmol, 1.0 eq.) and o-(7-azabenzotriazol-1-yl)-N,N,N',N'-tetramethyluronium hexafluorophosphate (125 mg, 0.329 mmol, 1.2 eq.) in DMF (3 mL) was added N-ethyl-N-isopropylpropan-2-amine (212 mg, 1.64 mmol, 6.0 eq.) at 0° C. After stirring for 15 min at 0° C., (2S)-2-{[(1R,2S,3S,6R,7S)-4-[(2S)-2-amino-3,3-dimethylbutanoyl]-4-azatricyclo[5.2.1.0^{2,6}]dec-8-en-3-yl]formamido}-3-[(3S)-2-oxopyrrolidin-3-yl]propanamide hydrochloride (132 mg, 0.274 mmol, 1.0 eq.) was added. The mixture was stirred for 1 h at rt. The mixture was purified by C18 column with CH₃CN:Water (0.05% TFA). The desired fraction was concentrated under reduced pressure to provide N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxobutan-2-yl]-1-(trifluoromethyl)cyclopropane-1-carboxamide (130 mg, 78%) as a light yellow solid. LC-MS (ESI, m/z): 582 [M+H]⁺.

To a mixture of N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxobutan-2-yl]-1-(trifluoromethyl)cyclopropane-1-carboxamide (130 mg, 0.224 mmol, 1.0 eq.) in DCM (2 mL) was added pyridine (71.0 mg, 0.896 mmol, 4.0 eq.) and trifluoroacetic anhydride (85.0 mg, 0.403 mmol, 1.8 eq.). The mixture was stirred for 1 h at rt. The reaction was quenched with water (10 mL). The mixture was extracted with DCM (3×10 mL). The organic layers were combined, washed with brine (2×10 mL), dried over anhydrous sodium sulfate, filtered and concentrated under reduced pressure to afford the crude product. The crude product was purified by prep-HPLC (Column: XBridge Shield RP18 OBD Column, 30×150 mm, 5 m; Mobile Phase A: Water (0.1% FA), Mobile Phase B: ACN; Flow rate: 60 mL/min; Gradient: 28% B to 53% B in 10 min, 53% B; Wave Length: 254 nm; RT: 7.47 min) to provide (1R,2S,3S,6R,7S)—N-[(1S)-1-cyano-2-[(3S)-2-oxopyrrolidin-3-yl]ethyl]-4-[(2S)-3,3-dimethyl-2-{[1-(trifluoromethyl)cyclopropyl]formamido}butanoyl]-4-azatricyclo[5.2.1.0^{2,6}]dec-8-ene-3-carboxamide (55.9 mg, 44%) as a white solid. ¹H NMR (400 MHz, 80° C., DMSO-d₆) δ 8.60-8.80 (m, 1H), 7.35-7.55 (m, 1H), 6.58-7.00 (m, 1H), 5.98-6.20 (m, 2H), 4.70-4.98 (m, 1H), 4.46-4.55 (m, 1H), 4.00-4.15 (m, 1H), 3.55-3.65 (m, 1H), 3.35-3.54 (m, 1H), 3.10-3.25 (m, 2H), 3.00-3.09 (m, 1H), 2.80-2.98 (m, 2H), 2.68-2.79 (m, 1H), 2.30-2.42 (m, 1H), 2.08-2.28 (m, 2H), 1.62-1.89 (m, 2H), 1.30-1.48 (m, 3H), 1.10-1.29 (m, 3H), 0.83-0.98 (m, 9H). LC-MS (ESI, m/z): 564 [M+H]⁺.

Example 21

Compound 21

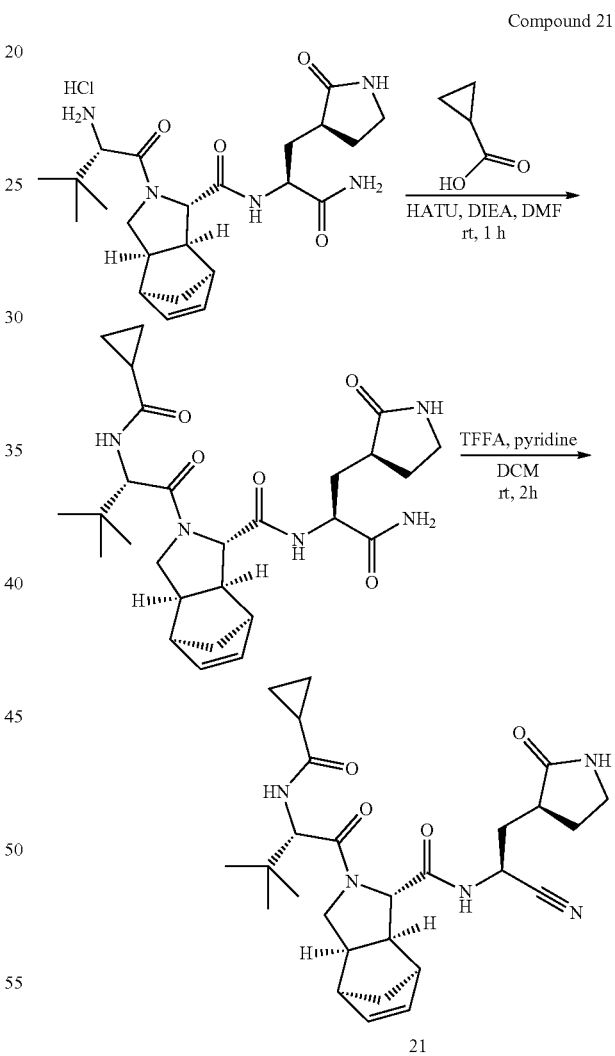

To a stirred mixture of cyclopropanecarboxylic acid (27.5 mg, 0.319 mmol, 1.1 eq.) in DMF (2 mL) was added o-(7-Azabenzotriazol-1-yl)-N,N,N',N'-tetramethyluronium hexafluorophosphate (132 mg, 0.348 mmol, 1.2 eq.) and N-ethyl-N-isopropylpropan-2-amine (225 mg, 1.74 mmol, 6.0 eq.). The mixture was stirred for 10 min at 0° C. (2S)-2-{[(1R,2S,3S,6R,7S)-4-[(2S)-2-amino-3,3-dimethylbutanoyl]-4-azatricyclo[5.2.1.0^{2,6}]dec-8-en-3-yl]formamido}-3-[(3S)-2-oxopyrrolidin-3-yl]propanamide hydrochloride (140 mg, 0.290 mmol, 1.0 eq.) was added. The mixture was stirred for 1 h at rt, and then purified by C18 column with CH₃CN:Water (0.05% FA). The desired fraction was concentrated under reduced pressure to provide N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxobutan-2-yl]cyclopropanecarboxamide (100 mg, 60%) as a white solid. LC-MS (ESI, m/z): 514 [M+H]⁺.

To a stirred mixture of N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxobutan-2-yl]cyclopropanecarboxamide (100 mg, 0.195 mmol, 1.0 eq.) in DCM (2 mL) was added trifluoroacetic anhydride (81.7 mg, 0.390 mmol, 2.0 eq.) and pyridine (53.9 mg, 0.682 mmol, 3.5 eq.). The mixture was stirred for 2 h at rt. The reaction was quenched with water (10 mL). The mixture was extracted with ethyl acetate (3×10 mL). The organic layers were combined, washed with brine (2×10 mL), dried over anhydrous sodium sulfate, filtered and concentrated under reduced pressure to afford the crude product. The crude product was purified by prep-HPLC with the following conditions (Column: XBridge Prep Phenyl OBD Column, 19*250 mm, 5 m; Mobile Phase A: Water (0.1% FA), Mobile Phase B: ACN; Flow rate: 25 mL/min; Gradient: 32% B to 62% B in 7 min, 62% B; Wave Length: 254 nm; RT1 (min): 6) to afford (1R,2S,3S,6R,7S)—N-[(1S)-1-cyano-2-[(3S)-2-oxopyrrolidin-3-yl]ethyl]-4-[(2S)-2-(cyclopropylformamido)-3,3-dimethylbutanoyl]-4-azatricyclo[5.2.1.0^{2,6}]dec-8-ene-3-carboxamide (16.5 mg, 16%) as a white solid. ¹H NMR (400 MHz, 80° C., DMSO-d₆) δ 8.55-8.80 (m, 1H), 7.70-7.85 (m, 1H), 7.30-7.55 (m, 1H), 5.91-6.20 (m, 2H), 4.81-4.98 (m, 1H), 4.40-4.52 (m, 1H), 3.91-4.10 (m, 1H), 3.42-3.62 (m, 2H), 3.08-3.20 (m, 2H), 2.97-3.02 (m, 1H), 2.81-2.95 (m, 2H), 2.63-2.73 (m, 1H), 2.26-2.41 (m, 1H), 2.05-2.22 (m, 2H), 1.60-1.86 (m, 3H), 1.29-1.41 (m, 2H), 0.78-0.96 (m, 9H), 0.66-0.74 (m, 1H), 0.53-0.66 (m, 3H). LC-MS (ESI, m/z): 496 [M+H]⁺.

Example 22

Compound 22

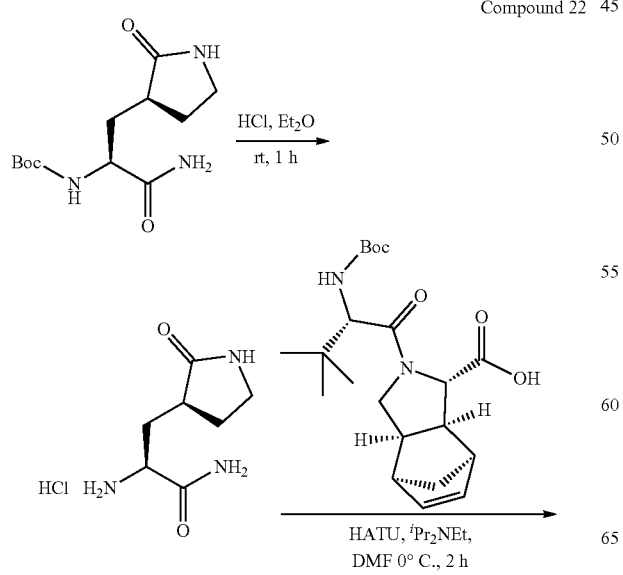

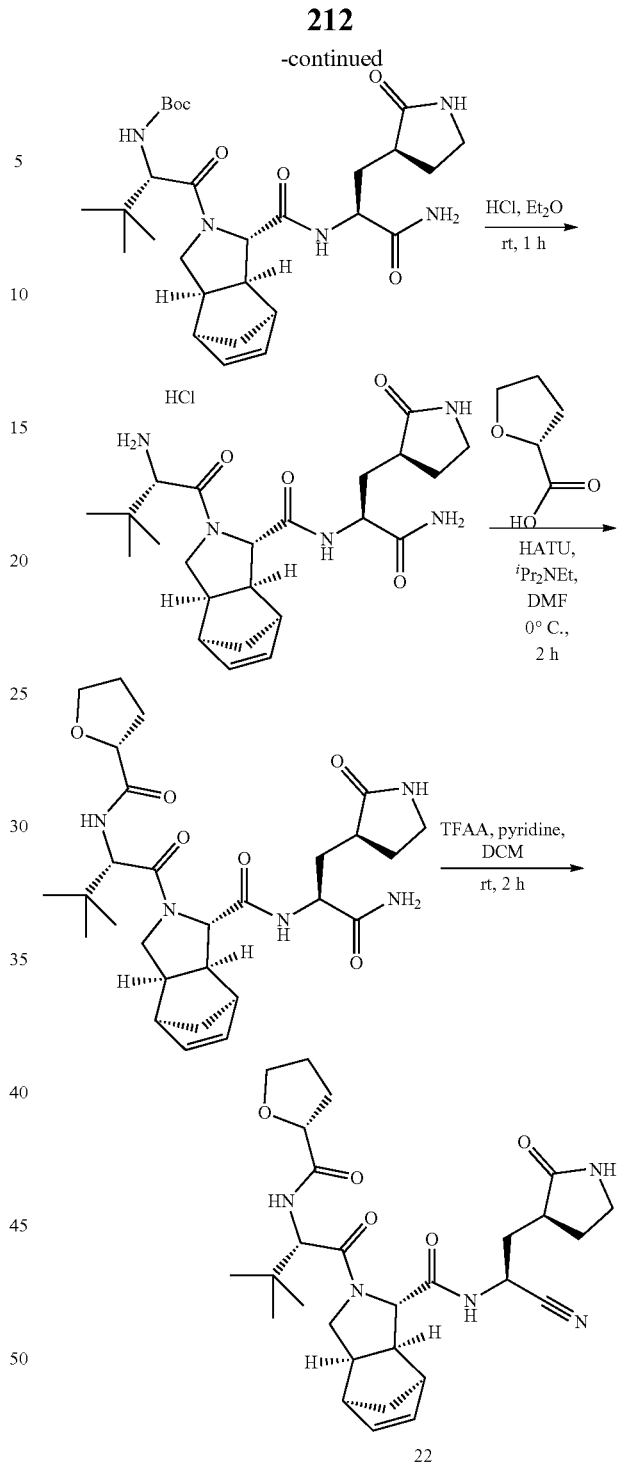

22

A mixture of tert-butyl ((S)-1-amino-1-oxo-3-((S)-2-oxopyrrolidin-3-yl)propan-2-yl)carbamate (1.04 g, 3.83 mmol, 1.0 eq.) in hydrogen chloride (10 mL, 2 M in Et₂O) was stirred for 1 h at rt. The mixture was concentrated under reduced pressure to afford (S)-2-amino-3-((S)-2-oxopyrrolidin-3-yl)propanamide hydrochloride (0.650 g, crude) as a yellow oil. LC-MS (ESI, m/z): 172 [M+H]⁺.

To a mixture of (1S,3aR,4S,7R,7aS)-2-((S)-2-((tert-butoxycarbonyl)amino)-3,3-dimethylbutanoyl)-2,3,3a,4,7,7a-hexahydro-1H-4,7-methanoisoindole-1-carboxylic acid (1.50 g, 3.82 mmol, 1.0 eq.) in N,N-dimethylformamide (15 mL) was added o-(7-azabenzotriazol-1-yl)-N,N,N',N'-tetramethyluronium hexafluorophosphate (1.74 g, 4.58 mmol, 1.2 eq.) and N-ethyl-N-isopropylpropan-2-amine (3.95 g, 30.5 mmol, 8.0 eq.) at 0° C. The mixture was stirred for 20 min at 0° C. (S)-2-amino-3-((S)-2-oxopyrrolidin-3-yl)propanamide hydrochloride (650 mg, 3.82 mmol, 1.0 eq.) was added at 0° C. The mixture was stirred for 2 h at rt. The reaction was quenched with water (50 mL). The mixture was extracted with EtOAc (3×80 mL). The organic layers were combined, washed with brine (2×80 mL), dried over anhydrous sodium sulfate, filtered and concentrated under reduced pressure to afford the crude product. The crude product was chromatographed on a silica gel column with MeOH:DCM (7:93) to provide tert-butyl ((S)-1-((1S,3aR,4S,7R,7aS)-1-(((S)-1-amino-1-oxo-3-((S)-2-oxopyrrolidin-3-yl)propan-2-yl)carbamoyl)-1,3,3a,4,7,7a-hexahydro-2H-4,7-methanoisoindol-2-yl)-3,3-dimethyl-1-oxobutan-2-yl) carbamate (1.46 g, 70%) as a light yellow solid. LC-MS (ESI, m/z): 546 [M+H]$^+$.

A mixture of tert-butyl ((S)-1-((1S,3aR,4S,7R,7aS)-1-(((S)-1-amino-1-oxo-3-((S)-2-oxopyrrolidin-3-yl)propan-2-yl)carbamoyl)-1,3,3a,4,7,7a-hexahydro-2H-4,7-methanoisoindol-2-yl)-3,3-dimethyl-1-oxobutan-2-yl)carbamate (150 mg, 0.275 mmol, 1.0 eq.) in hydrogen chloride (2 mL, 2 M in Et$_2$O) was stirred for 1 h at rt. The mixture was concentrated under reduced pressure to afford (1S,3aR,4S,7R,7aS)—N—((S)-1-amino-1-oxo-3-((S)-2-oxopyrrolidin-3-yl)propan-2-yl)-2-((S)-2-amino-3,3-dimethylbutanoyl)-2,3,3a,4,7,7a-hexahydro-1H-4,7-methanoisoindole-1-carboxamide hydrochloride (133 mg, crude) as a yellow oil. LC-MS (ESI, m/z): 446 [M+H]$^+$.

To a mixture of (R)-tetrahydrofuran-2-carboxylic acid (32.0 mg, 0.276 mmol, 1.0 eq.) in N,N-dimethylformamide (3 mL) was added o-(7-azabenzotriazol-1-yl)-N,N,N',N'-tetramethyluronium hexafluorophosphate (125 mg, 0.331 mmol, 1.2 eq.) and N-ethyl-N-isopropylpropan-2-amine (213 mg, 1.65 mmol, 6.0 eq.) at 0° C. The mixture was stirred for 20 min at 0° C. (1S,3aR,4S,7R,7aS)—N—((S)-1-amino-1-oxo-3-((S)-2-oxopyrrolidin-3-yl)propan-2-yl)-2-((S)-2-amino-3,3-dimethylbutanoyl)-2,3,3a,4,7,7a-hexahydro-1H-4,7-methanoisoindole-1-carboxamide hydrochloride (133 mg, 0.276 mmol, 1.0 eq.) was added at 0° C. The mixture was stirred for 2 h at 0° C. The reaction was quenched with water (30 mL). The mixture was purified by C18 column with CH$_3$CN:Water (0.05% TFA). The desired fraction was concentrated under reduced pressure to provide (1S,3aR,4S,7R,7aS)—N—((S)-1-amino-1-oxo-3-((S)-2-oxopyrrolidin-3-yl)propan-2-yl)-2-((S)-3,3-dimethyl-2-((R)-tetrahydrofuran-2-carboxamido)butanoyl)-2,3,3a,4,7,7a-hexahydro-1H-4,7-methanoisoindole-1-carboxamide (80 mg, 54%) as a light yellow solid. LC-MS (ESI, m/z): 544 [M+H]$^+$.

To a mixture of (1S,3aR,4S,7R,7aS)—N—((S)-1-amino-1-oxo-3-((S)-2-oxopyrrolidin-3-yl)propan-2-yl)-2-((S)-3,3-dimethyl-2-((R)-tetrahydrofuran-2-carboxamido)butanoyl)-2,3,3a,4,7,7a-hexahydro-1H-4,7-methanoisoindole-1-carboxamide (50.0 mg, 0.092 mmol, 1.0 eq.) in DCM (2 mL) was added pyridine (50.9 mg, 0.644 mmol, 7.0 eq.) and trifluoroacetic anhydride (57.9 mg, 0.276 mmol, 3.0 eq.). The mixture was stirred for 2 h at rt. The reaction was quenched with water (5 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was purified by prep-HPLC (Column: XBridge Shield RP18 OBD Column, 19*250 mm, 10 m; Mobile Phase A: Water (0.1% FA), Mobile Phase B: ACN; Flow rate: 25 mL/min; Gradient: 30% B to 47% B in 10 min, 47% B; Wave Length: 254 nm; RT1 (min): 5.97) to provide (1S,3aR,4S,7R,7aS)—N—((S)-1-cyano-2-((S)-2-oxopyrrolidin-3-yl)ethyl)-2-((S)-3,3-dimethyl-2-((R)-tetrahydrofuran-2-carboxamido)butanoyl)-2,3,3a,4,7,7a-hexahydro-1H-4,7-methanoisoindole-1-carboxamide (13.9 mg, 28%) as an off-white solid. $^1$H NMR (400 MHz, 80° C., DMSO-d$_6$) δ 8.60-8.90 (m, 1H), 7.35-7.60 (m, 1H), 6.80-7.20 (m, 1H), 5.80-6.20 (m, 2H), 4.65-5.00 (m, 1H), 4.30-4.50 (m, 1H), 4.15-4.30 (m, 1H), 3.95-4.05 (m, 1H), 3.70-3.90 (m, 2H), 3.50-3.65 (m, 1H), 3.30-3.55 (m, 1H), 3.10-3.25 (m, 2H), 2.90-3.05 (m, 1H), 2.65-2.80 (m, 3H), 2.25-2.45 (m, 1H), 2.05-2.25 (m, 3H), 1.65-1.95 (m, 5H), 1.30-1.50 (m, 2H), 0.65-1.10 (m, 9H). LC-MS (ESI, m/z): 526 [M+H]$^+$.

Example 23

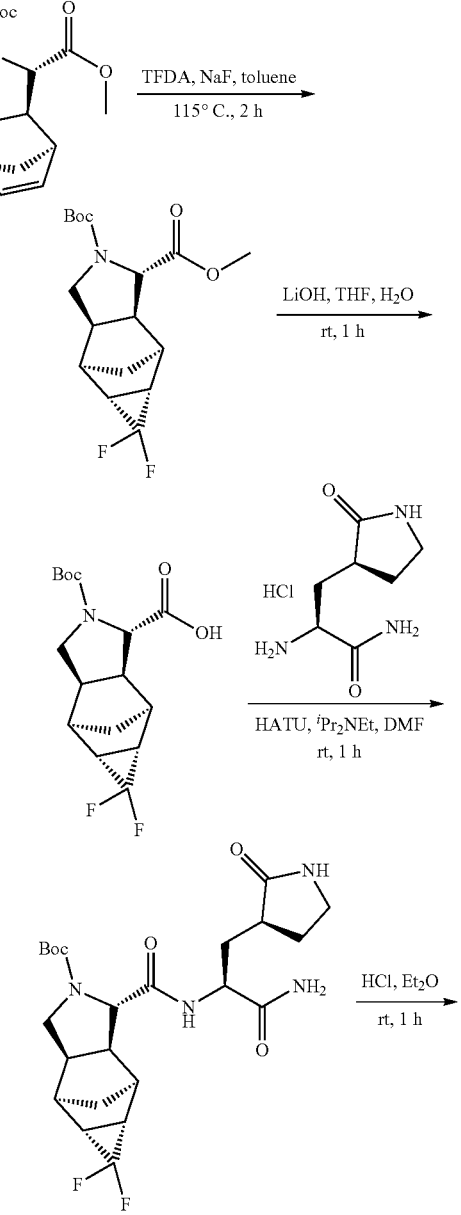

Compound 23

-continued

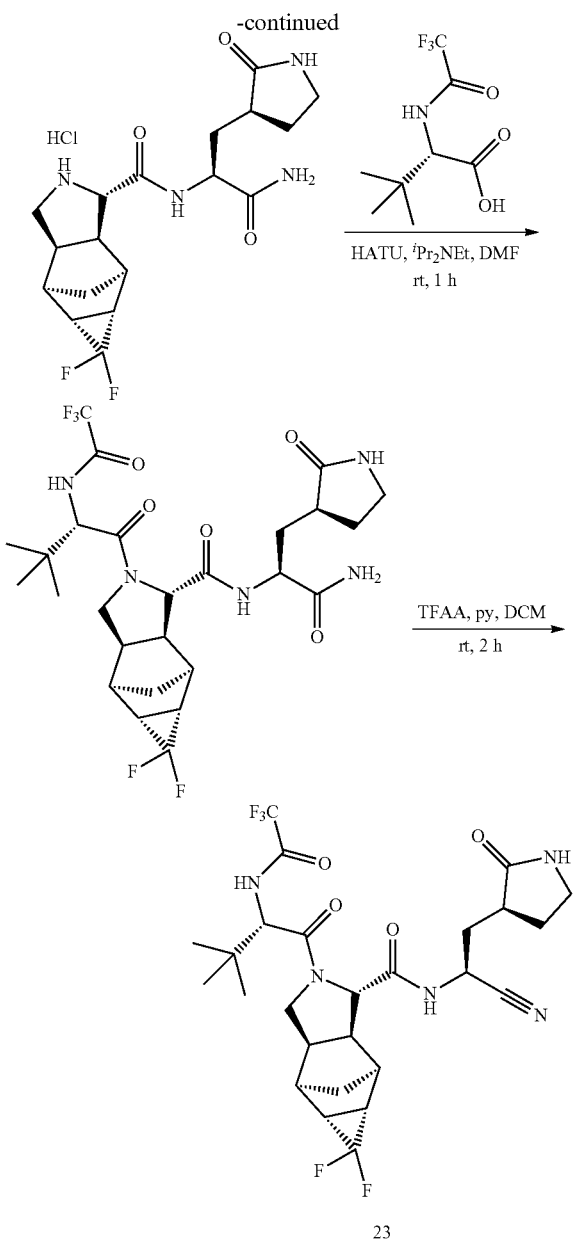

23

To a stirred mixture of 4-tert-butyl 3-methyl (1R,2S,3S, 6R,7S)-4-azatricyclo[5.2.1.0^{2,6}]dec-8-ene-3,4-dicarboxylate (1 g, 3.40 mmol, 1.0 eq.) in toluene (4 mL) was added sodium fluoride (50.0 mg, 1.19 mmol, 0.35 eq.). Trimethylsilyl 2,2-difluoro-2-sulfoacetate (4.27 g, 17.0 mmol, 5.0 eq.) was added slowly for 2 h at 115° C. under nitrogen. The reaction was quenched with water (30 mL). The mixture was extracted with ethyl acetate (3×30 mL)> The organic layers were combined, washed with brine (2×30 mL), dried over anhydrous sodium sulfate, filtered and concentrated under reduced pressure to afford the crude product. The crude product was purified by C18 column with CH₃CN:Water (0.05% FA). The desired fraction was concentrated under reduced pressure to provide 4-tert-butyl 3-methyl (1S,2S,3S,6R,7R,8R,10S)-9,9-difluoro-4-azatetracyclo[5.3.1.0^{2,6}.0^{8,10}]undecane-3,4-dicarboxylate (180 mg, 13%) as a light yellow oil. LC-MS (ESI, m/z): 288 [M−56+H]⁺.

To a stirred mixture of 4-tert-butyl 3-methyl (1S,2S,3S, 6R,7R,8R,10S)-9,9-difluoro-4-azatetracyclo[5.3.1.0^{2, 6}.0^{8,10}]undecane-3,4-dicarboxylate (180 mg, 0.524 mmol, 1.0 eq.) in THF (3 mL) and H₂O (1 mL) was added lithium hydroxide (37.6 mg, 1.57 mmol, 3.0 eq.) at rt. The mixture was stirred for 1 h at rt. The mixture was acidified to pH=4 with hydrochloric acid (2M) and then extracted with ethyl acetate (3×10 mL). The combined organic layers were dried over anhydrous sodium sulfate. After filtration, the filtrate was concentrated under reduced pressure to afford (1S,2S,3S,6R,7R,8R,10S)-4-(tert-butoxycarbonyl)-9, 9-difluoro-4-azatetracyclo[5.3.1.0^{2,6}.0^{8,10}]undecane-3-carboxylic acid (150 mg, crude) as a light yellow oil. LC-MS (ESI, m/z): 328 [M−H]⁻.

To a stirred mixture of (1S,2S,3S,6R,7R,8R,10S)-4-(tert-butoxycarbonyl)-9,9-difluoro-4-azatetracyclo[5.3.1.0^{2, 6}.0^{8,10}]undecane-3-carboxylic acid (150 mg, 0.455 mmol, 1.0 eq.) and o-(7-Azabenzotriazol-1-yl)-N,N,N',N'-tetramethyluronium hexafluorophosphate (207 mg, 0.546 mmol, 1.2 eq.) in DMF (3 mL) was added N-ethyl-N-isopropylpropan-2-amine (353 mg, 2.73 mmol, 6.0 eq.). The mixture was stirred for 10 min at 0° C. (2S)-2-amino-3-[(3S)-2-oxopyrrolidin-3-yl]propanamide hydrochloride (104 mg, 0.501 mmol, 1.1 eq.) was added. The mixture was stirred for 1 h at rt. The mixture was purified by C18 column with CH₃CN:Water (0.05% FA). The desired fraction was concentrated under reduced pressure to provide tert-butyl (1S,2S,3S,6R,7R,8R,10S)-3-{[(1S)-1-carbamoyl-2-[(3S)-2-oxopyrrolidin-3-yl]ethyl]carbamoyl}-9,9-difluoro-4-azatetracyclo[5.3.1.0^{2,6}.0^{8,10}]undecane-4-carboxylate (160 mg, 65%) as a white solid. LC-MS (ESI, m/z): 483 [M+H]⁺.

To a stirred mixture of tert-butyl (1S,2S,3S,6R,7R,8R, 10S)-3-{[(1S)-1-carbamoyl-2-[(3S)-2-oxopyrrolidin-3-yl]ethyl]carbamoyl}-9,9-difluoro-4-azatetracyclo[5.3.1.0^{2, 6}.0^{8,10}]undecane-4-carboxylate (160 mg, 0.332 mmol, 1.0 eq.) in DCM (1 mL) were added hydrogen chloride (5 mL, 2M in Et₂O). The mixture was stirred for 1 h at rt and then concentrated under reduced pressure to afford (2S)-2-{[(1S,2S,3S,6R,7R,8R,10S)-9,9-difluoro-4-azatetracyclo[5.3.1.0^{2,6}.0^{8,10}]undecan-3-yl]formamido}-3-[(3S)-2-oxopyrrolidin-3-yl]propanamide hydrochloride (140 mg, crude) as a white solid. LC-MS (ESI, m/z): 383 [M+H]⁺.

To a stirred mixture of (2S)-3,3-dimethyl-2-(2,2,2-trifluoroacetamido)butanoic acid (83.5 mg, 0.367 mmol, 1.1 eq.) and o-(7-Azabenzotriazol-1-yl)-N,N,N',N'-tetramethyluronium hexafluorophosphate (152 mg, 0.401 mmol, 1.2 eq.) in DMF (2 mL) was added N-ethyl-N-isopropylpropan-2-amine (259 mg, 2.00 mmol, 6.0 eq.). The mixture was stirred for 10 min at 0° C. (2S)-2-{[(1S,2S,3S,6R,7R,8R,10S)-9,9-difluoro-4-azatetracyclo[5.3.1.0^{2,6}.0^{8,10}]undecan-3-yl]formamido}-3-[(3S)-2-oxopyrrolidin-3-yl]propanamide hydrochloride (140 mg, 0.334 mmol, 1.0 eq.) was added. The mixture was stirred for 1 h at rt. The crude product was purified by C18 column with CH₃CN:Water (0.05% FA). The desired fraction was concentrated under reduced pressure to provide (2S)-2-{[(1S,2S,3S,6R,7R,8R,10S)-4-[(2S)-3,3-dimethyl-2-(2,2,2-trifluoroacetamido)butanoyl]-9,9-difluoro-4-azatetracyclo[5.3.1.0^{2,6}.0^{8,10}]undecan-3-yl]formamido}-3-[(3S)-2-oxopyrrolidin-3-yl]propanamide (140 mg, 63%) as a light yellow solid. LC-MS (ESI, m/z): 592 [M+H]⁺.

To a stirred mixture of (2S)-2-{[(1S,2S,3S,6R,7R,8R, 10S)-4-[(2S)-3,3-dimethyl-2-(2,2,2-trifluoroacetamido)butanoyl]-9,9-difluoro-4-azatetracyclo[5.3.1.0^{2,6}.0^{8, 10}]undecan-3-yl]formamido}-3-[(3S)-2-oxopyrrolidin-3-yl]propanamide (140 mg, 0.237 mmol, 1.0 eq.) in DCM (2 mL) was added pyridine (65.5 mg, 0.829 mmol, 3.5 eq.) and trifluoroacetic anhydride (99.4 mg, 0.474 mmol, 2.0 eq.). The mixture was stirred for 2 h at rt. The reaction was quenched with water (10 mL). The mixture was extracted with DCM (3×10 mL). The organic layers were combined, washed with brine (2×10 mL), dried over anhydrous sodium sulfate, filtered and concentrated under reduced pressure to afford the crude product. The crude product was purified by prep-HPLC with the following conditions (Column: XBridge Prep Phenyl OBD Column, 19*250 mm, 5 m; Mobile Phase A: Water (0.1% FA), Mobile Phase B: ACN; Flow rate: 25 mL/min; Gradient: 43% B to 73% B in 7 min, 73% B; Wave Length: 254 nm; RT1 (min): 5;) to afford (1S,2S,3S,6R,7R,8R,10S)—N-[(1S)-1-cyano-2-[(3S)-2-oxopyrrolidin-3-yl]ethyl]-4-[(2S)-3,3-dimethyl-2-(2,2,2-trifluoroacetamido)butanoyl]-9,9-difluoro-4-azatetracyclo [5.3.1.0^{2,6}.0^{8,10}]undecane-3-carboxamide (30.5 mg, 21%) as a white solid. $^1$H NMR (400 MHz, 80° C., DMSO-$d_6$) δ 8.91-9.20 (m, 1H), 8.55-8.87 (m, 1H), 7.35-7.55 (m, 1H), 4.81-4.96 (m, 1H), 4.55-4.73 (m, 2H), 3.91-4.10 (m, 1H), 3.58-3.74 (m, 1H), 3.08-3.20 (m, 2H), 2.73-2.82 (m, 2H), 2.62-2.72 (m, 1H), 2.50-2.60 (m, 1H), 2.26-2.38 (m, 1H), 2.07-2.20 (m, 2H), 1.62-1.87 (m, 3H), 1.45-1.57 (m, 1H), 1.26-1.37 (m, 1H), 1.09-1.23 (m, 1H), 0.84-1.03 (m, 9H). LC-MS (ESI, m/z): 574 [M+H]$^+$.

Example 24

Compound 24

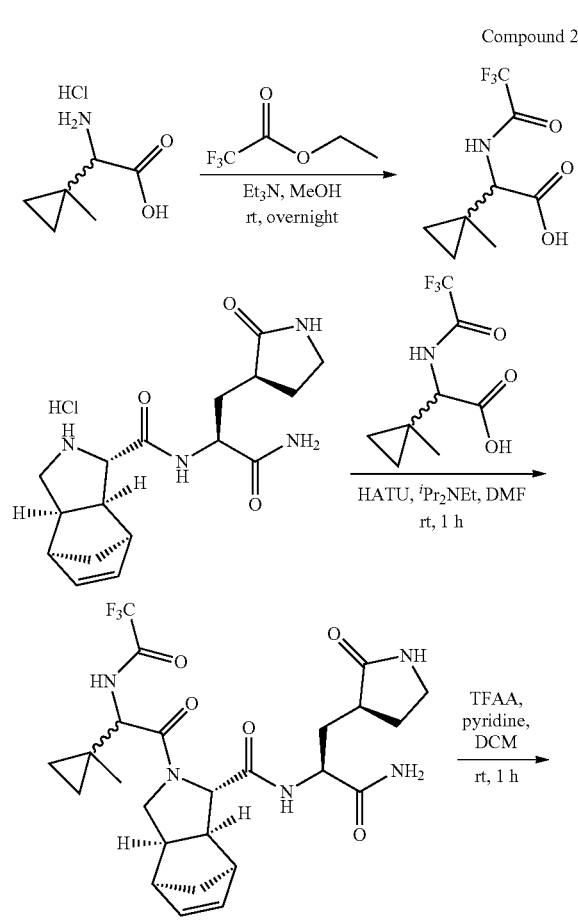

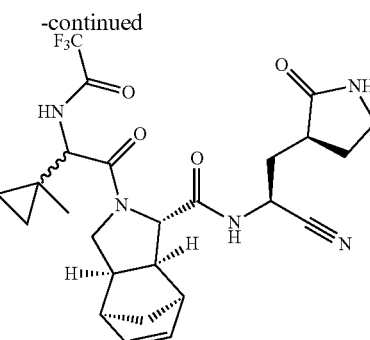

24

To a mixture of amino(1-methylcyclopropyl)acetic acid hydrochloride (300 mg, 1.81 mmol, 1.0 eq.) in MeOH (5 mL) was added triethylamine (733 mg, 7.24 mmol, 4.0 eq.) and ethyl 2,2,2-trifluoroacetate (309 mg, 2.17 mmol, 1.2 eq.). The mixture was stirred overnight at rt. The mixture was concentrated under reduced pressure to afford a residue. The residue was diluted with water (10 mL). The pH was adjusted to 6 with hydrochloric acid (1 M). The mixture was extracted with EtOAc (3×10 mL). The organic layers were combined, washed with brine (2×10 mL), dried over anhydrous sodium sulfate, filtered and concentrated under reduced pressure to provide (1-methylcyclopropyl)(2,2,2-trifluoroacetamido)acetic acid (380 mg, 88%) as a white solid. $^1$H NMR (400 MHz, DMSO-$d_6$) δ 12.95 (br, 1H), 9.76 (d, J=7.3 Hz, 1H), 3.78 (d, J=7.3 Hz, 1H), 1.07 (s, 3H), 0.69-0.77 (m, 1H), 0.49-0.57 (m, 1H), 0.41-0.48 (m, 1H), 0.31-0.38 (m, 1H). LC-MS (ESI, m/z): 226 [M+H]$^+$.

To a mixture of (1-methylcyclopropyl)(2,2,2-trifluoroacetamido)acetic acid (78.0 mg, 0.347 mmol, 1.0 eq.) and o-(7-azabenzotriazol-1-yl)-N,N,N',N'-tetramethyluronium hexafluorophosphate (158 mg, 0.416 mmol, 1.2 eq.) in DMF (3 mL) was added N-ethyl-N-isopropylpropan-2-amine (269 mg, 2.08 mmol, 6.0 eq.) at 0° C. After stirred for 15 min at 0° C., (2S)-2-[(1R,2S,3S,6R,7S)-4-azatricyclo[5.2.1.0^{2, 6}]dec-8-en-3-ylformamido]-3-[(3S)-2-oxopyrrolidin-3-yl] propanamide hydrochloride (128 mg, 0.347 mmol, 1.0 eq.) was added. The mixture was stirred for 1 h at rt. The mixture was purified by C18 column with CH$_3$CN:Water (0.05% TFA). The desired fraction was concentrated under reduced pressure to provide (2S)-2-{[(1R,2S,3S,6R,7S)-4-[2-(1-methylcyclopropyl)-2-(2,2,2-trifluoroacetamido)acetyl]-4-azatricyclo[5.2.1.0^{2,6}]dec-8-en-3-yl]formamido}-3-[(3S)-2-oxopyrrolidin-3-yl]propanamide (110 mg, 50%) as an off-white solid. LC-MS (ESI, m/z): 540 [M+H]$^+$.

To a mixture of (2S)-2-{[(1R,2S,3S,6R,7S)-4-[2-(1-methylcyclopropyl)-2-(2,2,2-trifluoroacetamido)acetyl]-4-azatricyclo[5.2.1.0^{2,6}]dec-8-en-3-yl]formamido}-3-[(3S)-2-oxopyrrolidin-3-yl]propanamide (110 mg, 0.204 mmol, 1.0 eq.) in DCM (2 mL) was added pyridine (65.0 mg, 0.816 mmol, 4.0 eq.) and trifluoroacetic anhydride (77.0 mg, 0.367 mmol, 1.8 eq.). The mixture was stirred for 1 h at rt. The reaction was quenched with water (10 mL). The mixture was extracted with DCM (3×10 mL). The organic layers were combined, washed with brine (2×10 mL), dried over anhydrous sodium sulfate, filtered and concentrated under reduced pressure to afford the crude product. The crude product was purified by prep-HPLC (Column: YMC-Actus Triart C18 ExRS, 20×250 mm, 5 m; Mobile Phase A: Water (0.1% FA), Mobile Phase B: ACN; Flow rate: 25 mL/min; Gradient: 38% B to 59% B in 10 min, 59% B; Wave Length:

254 nm; RT: 7.47 min) to provide (1R,2S,3S,6R,7S)—N-[(1S)-1-cyano-2-[(3S)-2-oxopyrrolidin-3-yl]ethyl]-4-[2-(1-methylcyclopropyl)-2-(2,2,2-trifluoroacetamido)acetyl]-4-azatricyclo[5.2.1.0^{2,6}]dec-8-ene-3-carboxamide (22.1 mg, 20%) as a white solid. $^1$H NMR (400 MHz, 80° C., DMSO-$d_6$) δ 8.85-9.10 (m, 1H), 8.65-8.80 (m, 1H), 7.34-7.55 (m, 1H), 6.12-6.30 (m, 1H), 5.95-6.10 (m, 1H), 4.76-4.95 (m, 1H), 4.35-4.45 (m, 1H), 3.95-4.12 (m, 1H), 3.56-3.70 (m, 1H), 3.30-3.45 (m, 1H), 3.10-3.25 (m, 2H), 2.80-3.05 (m, 3H), 2.63-2.75 (m, 1H), 2.30-2.40 (m, 1H), 1.98-2.28 (m, 2H), 1.60-1.90 (m, 2H), 1.35-1.46 (m, 2H), 0.95-1.10 (m, 3H), 0.63-0.80 (m, 2H), 0.20-0.55 (m, 2H). LC-MS (ESI, m/z): 522 [M+H]$^+$.

Example 25

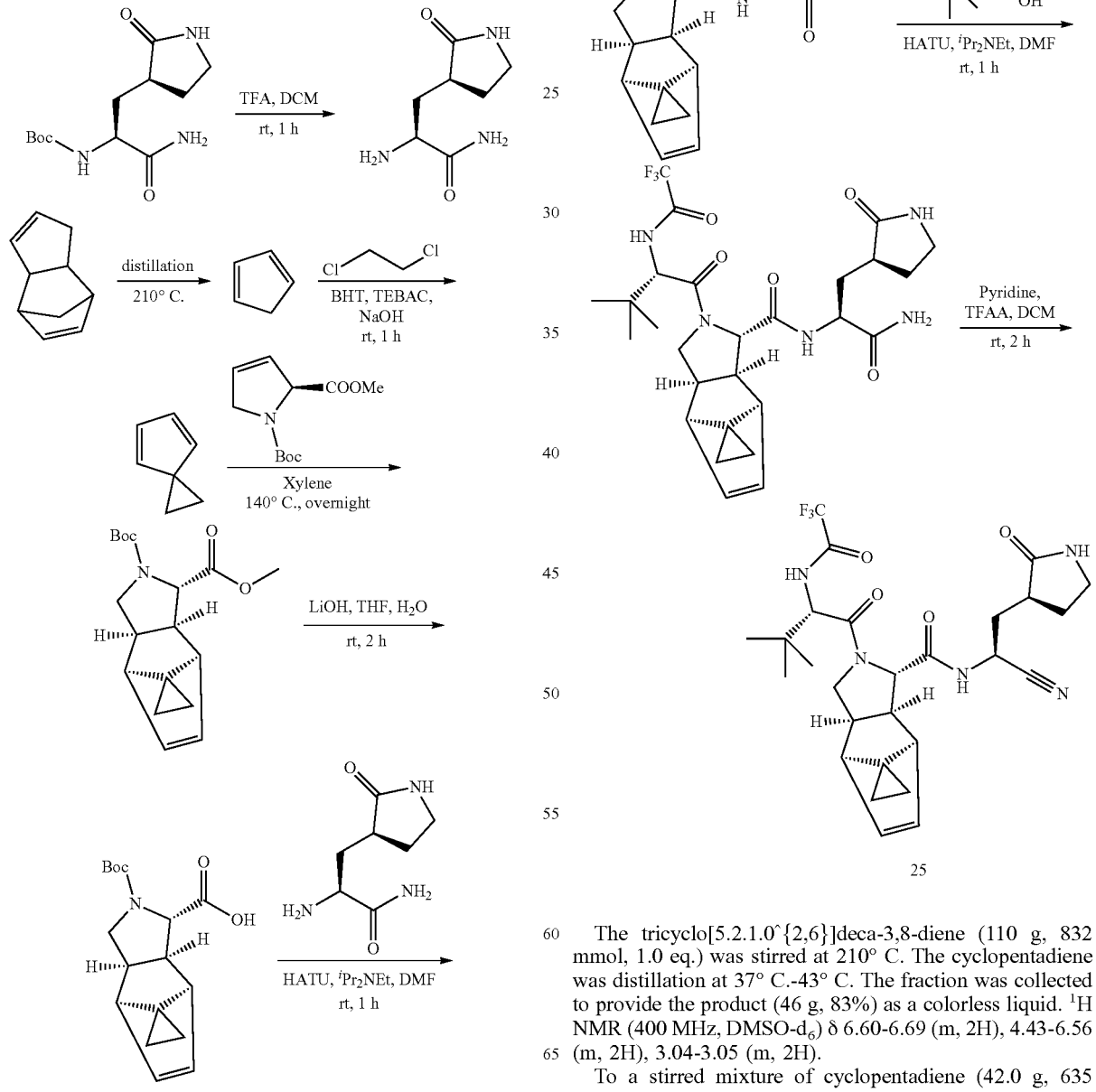

The tricyclo[5.2.1.0^{2,6}]deca-3,8-diene (110 g, 832 mmol, 1.0 eq.) was stirred at 210° C. The cyclopentadiene was distillation at 37° C.-43° C. The fraction was collected to provide the product (46 g, 83%) as a colorless liquid. $^1$H NMR (400 MHz, DMSO-$d_6$) δ 6.60-6.69 (m, 2H), 4.43-6.56 (m, 2H), 3.04-3.05 (m, 2H).

To a stirred mixture of cyclopentadiene (42.0 g, 635 mmol, 1.0 eq.) and ional (0.130 g, 0.572 mmol, 0.0009 eq.)

in ethylene dichloride (62.8 g, 635 mmol, 1.0 eq.). After stirred for 20 min, sodium hydroxide (139 g, 3462 mmol, 5.45 eq.) and benzyltriethylazanium chloride (1.30 g, 5.72 mmol, 0.009 eq.) were added. The mixture was stirred for 1 h at rt. The reaction was quenched with water (50 mL). The mixture was extracted with EtOAc (3×50 mL). The organic layers were combined, washed with brine (2×50 mL), dried over anhydrous sodium sulfate, filtered and concentrated under reduced pressure to afford the crude product. The crude product was stirred at 130° C. Spiro[2.4]hepta-4,6-diene was distillation at 60° C.-65° C. under 0.7 MPa. The desired fraction was collected to provide spiro[2.4]hepta-4,6-diene (10 g, 14%) as a colorless liquid. $^1$H NMR (400 MHz, DMSO-d$_6$) δ 6.47-6.69 (m, 2H), 6.14-6.24 (m, 2H), 1.71-1.72 (m, 4H).

To a stirred mixture of 1-tert-butyl 2-methyl (2R)-2,5-dihydropyrrole-1,2-dicarboxylate (6.00 g, 26.4 mmol, 1.0 eq.) in xylene (6 mL) was added spiro[2.4]hepta-4,6-diene (4.87 g, 52.8 mmol, 1.0 eq.). The mixture was stirred for 2 d at 140° C. and then concentrated under reduced pressure. The crude product was chromatographed on a silica gel column with EA:PE (30:70) to provide the crude product. The crude product was purified by C18 column with CH$_3$CN:Water (0.05% TFA). The desired fraction was concentrated under reduced pressure to provide 4'-tert-butyl 3'-methyl (1'R,2'S,3'S,6'R,7'S)-4'-azaspiro[cyclopropane-1,10'-tricyclo[5.2.1.0^{2,6}]decan]-8'-ene-3',4'-dicarboxylate (1.98 g, 23%) as a yellow oil. $^1$H NMR (400 MHz, DMSO-d$_6$) δ 6.03-6.36 (m, 2H), 3.70-3.89 (m, 1H), 3.55-3.69 (m, 3H), 3.22-3.37 (m, 1H), 2.70-3.10 (m, 3H), 2.33-2.42 (m, 1H), 2.22-2.29 (m, 1H), 1.08-1.53 (m, 9H), 0.22-0.48 (m, 4H). LC-MS (ESI, m/z): 220 [M+H−Boc]$^+$.

To a stirred mixture of 4'-tert-butyl 3'-methyl (1'R,2'S,3'S,6'R,7'S)-4'-azaspiro[cyclopropane-1,10'-tricyclo[5.2.1.0^{2,6}]decan]-8'-ene-3',4'-dicarboxylate (1.00 g, 3.13 mmol, 1.0 eq.) in THF (10 mL) was added lithium hydroxide (300 mg, 12.5 mmol, 4.0 eq., in water 10 mL). The mixture was stirred for 2 h at rt. The pH was adjusted to 6 with hydrochloric acid (2 M). The mixture was extracted with EtOAc (3×30 mL). The organic layers were combined, washed with brine (2×30 mL), dried over anhydrous sodium sulfate, filtered and concentrated under reduced pressure to provide (1'R,2'S,3'S,6'R,7'S)-4'-(tert-butoxycarbonyl)-4'-azaspiro[cyclopropane-1,10'-tricyclo[5.2.1.0^{2,6}]decan]-8'-ene-3'-carboxylic acid (917 mg, 89%) as a light yellow oil. LC-MS (ESI, m/z): 250 [M+H−56]$^+$.

To a stirred mixture of (2S)-2-amino-3-[(3S)-2-oxopyrrolidin-3-yl]propanamide (500 mg, 2.92 mmol, 1.0 eq.) and o-(7-azabenzotriazol-1-yl)-N,N,N',N'-tetramethyluronium hexafluorophosphate (1.33 g, 3.51 mmol, 1.2 eq.) in DMF (10 mL) was added N-ethyl-N-isopropylpropan-2-amine (3.02 g, 23.4 mmol, 8.0 eq.) at 0° C. After stirred for 20 min at 0° C., (2S)-2-amino-3-[(3S)-2-oxopyrrolidin-3-yl]propanamide (500 mg, 2.92 mmol, 1.0 eq.) was added. The mixture was stirred for 1 h at rt. The reaction was quenched with water (30 mL). The mixture was extracted with EtOAc (3×30 mL). The organic layers were combined, washed with brine (2×30 mL), dried over anhydrous sodium sulfate, filtered and concentrated under reduced pressure to afford the crude product. The crude product was chromatographed on a silica gel column with MeOH:DCM (1:11) to provide tert-butyl (1'R,2'S,3'S,6'R,7'S)-3'-{[(1S)-1-carbamoyl-2-[(3S)-2-oxopyrrolidin-3-yl]ethyl]carbamoyl}-4'-azaspiro[cyclopropane-1,10'-tricyclo[5.2.1.0^{2,6}]decan]-8'-ene-4'-carboxylate (758 mg, 55%) as a yellow solid. LC-MS (ESI, m/z): 359 [M−H−Boc]$^+$.

To a stirred mixture of tert-butyl (1'R,2'S,3'S,6'R,7'S)-3'-{[(1S)-1-carbamoyl-2-[(3S)-2-oxopyrrolidin-3-yl]ethyl]carbamoyl}-4'-azaspiro[cyclopropane-1,10'-tricyclo[5.2.1.0^{2,6}]decan]-8'-ene-4'-carboxylate (750 mg, 1.63 mmol, 1.0 eq.) in DCM (10 mL) was added trifluoroacetic acid (3 mL). The mixture was stirred for 1 h at rt and then concentrated under reduced pressure to afford (2S)-2-[(1'R,2'S,3'S,6'R,7'S)-4'-azaspiro[cyclopropane-1,10'-tricyclo[5.2.1.0^{2,6}]decan]-8'-en-3'-ylformamido]-3-[(3S)-2-oxopyrrolidin-3-yl]propanamide (586 mg, crude) as a brown oil. LC-MS (ESI, m/z): 359 [M+H]$^+$.

To a stirred mixture of (2S)-3,3-dimethyl-2-(2,2,2-trifluoroacetamido)butanoic acid (371 mg, 1.63 mmol, 1.0 eq.) and o-(7-azabenzotriazol-1-yl)-N,N,N',N'-tetramethyluronium hexafluorophosphate (746 mg, 1.96 mmol, 1.2 eq.) in DMF (10 mL) was added N-ethyl-N-isopropylpropan-2-amine (1.69 g, 13.1 mmol, 8.0 eq.) at 0° C. After stirred for 20 min at 0° C., (2S)-2-[(1'R,2'S,3'S,6'R,7'S)-4'-azaspiro[cyclopropane-1,10'-tricyclo[5.2.1.0^{2,6}]decan]-8'-en-3'-ylformamido]-3-[(3S)-2-oxopyrrolidin-3-yl]propanamide (586 mg, 1.63 mmol, 1.0 eq.) was added. The mixture was stirred for 1 h at rt. The reaction was quenched with water (15 mL). The mixture was extracted with EtOAc (3×15 mL). The organic layers were combined, washed with brine (2×15 mL), dried over anhydrous sodium sulfate, filtered and concentrated under reduced pressure to afford then crude product. The crude product was chromatographed on a silica gel column with MeOH:DCM (1:13) to provide (2S)-2-[(1'R,2'S,3'S,6'R,7'S)-4'-[(2S)-3,3-dimethyl-2-(2,2,2-trifluoroacetamido)butanoyl]-4'-azaspiro[cyclopropane-1,10'-tricyclo[5.2.1.0^{2,6}]decan]-8'-en-3'-ylformamido]-3-[(3S)-2-oxopyrrolidin-3-yl]propanamide (667 mg, 70%) as a yellow solid. LC-MS (ESI, m/z): 568 [M+H]$^+$.

To a stirred mixture of (2S)-2-[(1'R,2'S,3'S,6'R,7'S)-4'-[(2S)-3,3-dimethyl-2-(2,2,2-trifluoroacetamido)butanoyl]-4'-azaspiro[cyclopropane-1,10'-tricyclo[5.2.1.0^{2,6}]decan]-8'-en-3'-ylformamido]-3-[(3S)-2-oxopyrrolidin-3-yl]propanamide (150 mg, 0.264 mmol, 1.0 eq.) in DCM (4 mL) were added pyridine (73.2 mg, 0.924 mmol, 3.5 eq.) and trifluoroacetic anhydride (99.9 mg, 0.475 mmol, 1.8 eq.). The mixture was stirred for 2 h at rt. The reaction was quenched with water (20 mL). The mixture was extracted with EtOAc (3×20 mL). The organic layers were combined, washed with brine (2×20 mL), dried over anhydrous sodium sulfate, filtered and concentrated under reduced pressure to afford then crude product. The crude product was purified by prep-HPLC (Column: XBridge Shield RP18 OBD Column, 30*150 mm, 5 m; Mobile Phase A: Water (0.1% FA), Mobile Phase B: ACN; Flow rate: 60 mL/min; Gradient: 24% B to 46% B in 10 min, 46% B to 46% B in 11 min, 46% B; Wave Length: 254 nm; RT1 (min): 10.45) to provide (1'R,2'S,3'S,6'R,7'S)—N-[(1S)-1-cyano-2-[(3S)-2-oxopyrrolidin-3-yl]ethyl]-4'-[(2S)-3,3-dimethyl-2-(2,2,2-trifluoroacetamido)butanoyl]-4'-azaspiro[cyclopropane-1,10'-tricyclo[5.2.1.0^{2,6}]decan]-8'-ene-3'-carboxamide (43.4 mg, 29%) as a white solid. $^1$H NMR (400 MHz, 80° C., DMSO-d$_6$) δ 8.75-9.00 (m, 1H), 8.60-8.74 (m, 1H), 7.32-7.59 (m, 1H), 6.00-6.30 (m, 2H), 4.80-5.00 (m, 1H), 4.45-4.70 (m, 1H), 4.00-4.29 (m, 1H), 3.60-3.98 (m, 1H), 3.36-3.53 (m, 1H), 3.10-3.30 (m, 2H), 2.75-3.02 (m, 2H), 2.40-2.48 (m, 1H), 2.25-2.39 (m, 2H), 2.00-2.24 (m, 2H), 1.60-1.90 (m, 2H), 0.83-1.05 (m, 9H), 0.30-0.45 (m, 4H). LC-MS (ESI, m/z): 550 [M+H]$^+$.

Example 26

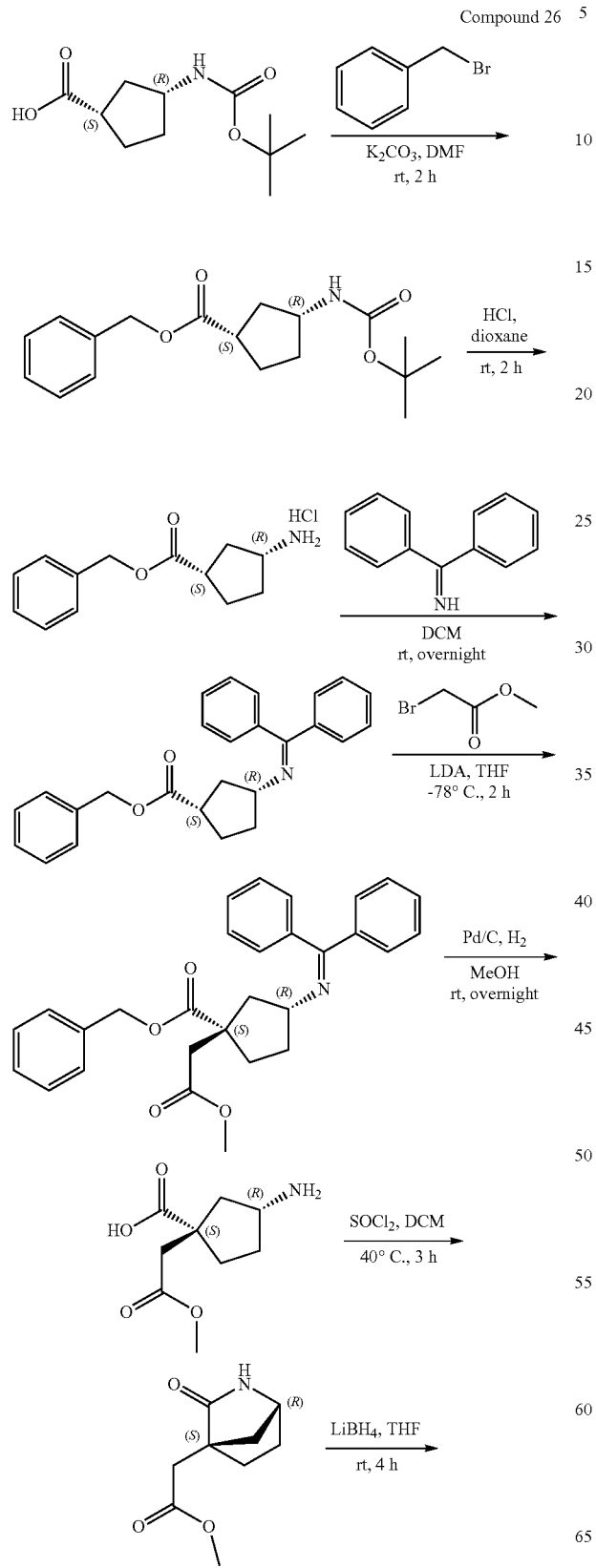

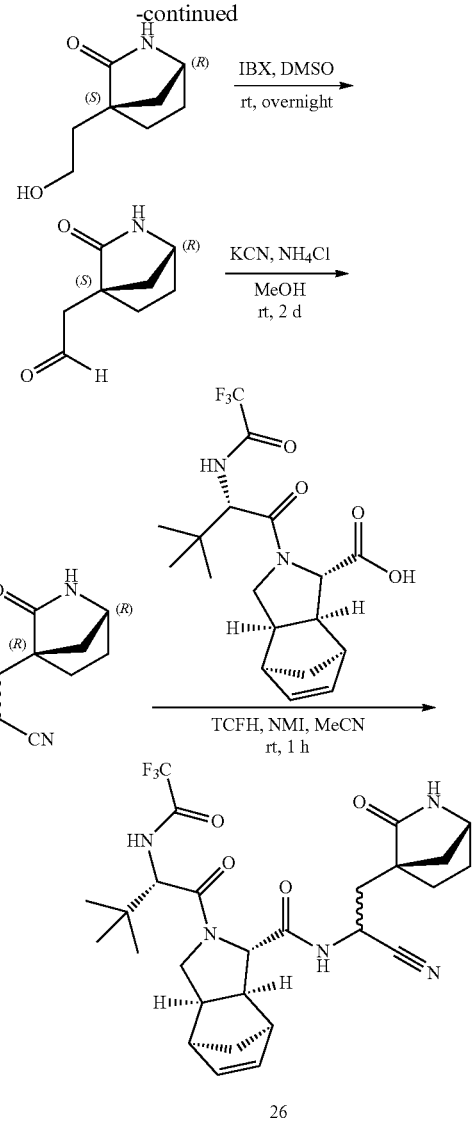

To a mixture of (1S,3R)-3-((tert-butoxycarbonyl)amino) cyclopentane-1-carboxylic acid (35.0 g, 109 mmol, 1.0 eq.) and potassium carbonate (31.7 g, 229 mmol, 1.5 eq.) in DMF (250 mL) was added benzyl bromide (31.3 g, 183 mmol, 1.2 eq.) at rt. The mixture was stirred 2 h at rt. The mixture was filtered through a celite pad and washed with ethyl acetate (3×100 mL). The filtrate was quenched with water (200 mL). The mixture was extracted with ethyl acetate (3×500 mL). The organic layers were combined, washed with brine (2×300 mL), dried over anhydrous sodium sulfate, filtered and concentrated under reduced pressure to afford the crude product. The crude product was chromatographed on a silica gel column with EA:PE (25%-30%) to provide benzyl (1S,3R)-3-((tert-butoxycarbonyl) amino)cyclopentane-1-carboxylate (40.0 g, 85%) as a white solid. LC-MS (ESI, m/z): 320 [M+H]$^+$.

To a mixture of benzyl (1S,3R)-3-((tert-butoxycarbonyl) amino)cyclopentane-1-carboxylate (40.0 g, 125 mmol, 1.0 eq.) in 1,4-dioxane (200 mL) was added hydrogen chloride (400 mL, 4 M in 1,4-dioxane) at rt. The mixture was stirred 2 h at rt and then concentrated under reduced pressure to provide benzyl (1S,3R)-3-aminocyclopentane-1-carboxylate hydrochloride (25.1 g, crude) as a white solid. $^1$H NMR (300 MHz, DMSO-d$_6$) δ 8.26 (br, 3H), 7.31-7.42 (m, 5H), 5.12 (s, 2H), 3.42-3.53 (m, 1H), 2.80-2.95 (m, 1H), 2.23-2.33 (m, 1H), 1.60-1.99 (m, 5H). LC-MS (ESI, m/z): 220 [M+H]$^+$.

To a mixture of benzyl (1S,3R)-3-aminocyclopentane-1-carboxylate hydrochloride (25.1 g, 97.8 mmol, 1.0 eq.) in DCM (400 mL) was added diphenylmethanimine (19.5 g, 108 mmol, 1.1 eq.). The mixture was stirred for overnight at rt. The mixture was filtered through a celite pad and washed with DCM (3×100 mL). The mixture was concentrated under reduced pressure to afford then crude product. The crude product was chromatographed on a silica gel column with EA:PE (11%-13%) to provide benzyl (1S,3R)-3-((diphenylmethylene)amino)cyclopentane-1-carboxylate (33.0 g, crude) as a yellow oil. LC-MS (ESI, m/z): 384 [M+H]$^+$.

To a mixture of benzyl (1S,3R)-3-((diphenylmethylene)amino)cyclopentane-1-carboxylate (33.0 g, 86.2 mmol, 1.0 eq.) in THF (400 mL) was added dropwise lithium diisopropylamide (56.1 mL, 112 mmol, 1.3 eq., 2 M in THF) at −78° C. under nitrogen. After stirred for 1 h at −78° C., methyl 2-bromoacetate (26.4 g, 172 mmol, 2.5 eq.) was added. The mixture was stirred for 1 h at −78° C. The mixture was warmed to 0° C. and stirred for 2 h at 0° C. under nitrogen. The reaction was quenched with water (200 mL). The mixture was extracted with ethyl acetate (3×300 mL). The organic layers were combined, washed with brine (2×200 mL), dried over anhydrous sodium sulfate, filtered and concentrated under reduced pressure to afford the crude product. The crude product was chromatographed on a silica gel column with EA:PE (12%-15%) to provide benzyl (1S,3R)-3-((diphenylmethylene)amino)-1-(2-methoxy-2-oxoethyl)cyclopentane-1-carboxylate (10.7 g, crude) as a yellow oil. LC-MS (ESI, m/z): 456 [M+H]$^+$.

To a mixture of benzyl (1S,3R)-3-((diphenylmethylene)amino)-1-(2-methoxy-2-oxoethyl)cyclopentane-1-carboxylate (10.7 g, 23.5 mmol, 1.0 eq.) in MeOH (150 mL) was added 10% palladium on activated carbon (3.5 g). The mixture was stirred overnight at rt under hydrogen and then filtered. The filter cake was washed with MeOH (3×150 mL). The filtrate was concentrated under reduced pressure to afford (1S,3R)-3-amino-1-(2-methoxy-2-oxoethyl)cyclopentane-1-carboxylic acid (4.5 g, crude) as a yellow solid. LC-MS (ESI, m/z): 202 [M+H]$^+$.

To a mixture of (1S,3R)-3-amino-1-(2-methoxy-2-oxoethyl)cyclopentane-1-carboxylic acid (4.5 g, 22.4 mmol, 1.0 eq.) in DCM (50 mL) was added thionyl chloride (4.26 g, 35.8 mmol, 1.6 eq.). The mixture was stirred 3 h at 40° C. The reaction was quenched with water (20 mL). The mixture was extracted with DCM (3×100 mL). The organic layers were combined, washed with brine (2×50 mL), dried over anhydrous sodium sulfate, filtered and concentrated under reduced pressure to afford the crude product. The crude product was chromatographed on a silica gel column with EA:PE (70%-85%) to provide methyl 2-((1R,4S)-3-oxo-2-azabicyclo[2.2.1]heptan-4-yl)acetate (400 mg, 9%) as a yellow oil. $^1$H NMR (400 MHz, CDCl$_3$) δ 5.99 (br, 1H), 3.89-3.90 (m, 1H), 3.71 (s, 3H), 2.86-2.91 (m, 1H), 2.68-2.72 (m, 1H), 2.05-2.09 (m, 1H), 1.92-1.99 (m, 1H), 1.82-1.88 (m, 1H), 1.65-1.73 (m, 1H), 1.60-1.63 (m, 1H), 1.51-1.59 (m, 1H). LC-MS (ESI, m/z): 184 [M+H]$^+$.

To a mixture of methyl 2-((1R,4S)-3-oxo-2-azabicyclo[2.2.1]heptan-4-yl)acetate (400 mg, 2.18 mmol, 1.0 eq.) in THF (5 mL) was added lithium borohydride (4.4 mL, 8.73 mmol, 4.0 eq., 2 M in THF) at 0° C. The mixture was stirred for 4 h at rt. The reaction was quenched with water (10 mL). The mixture was extracted with ethyl acetate (6×50 mL). The organic layers were combined, washed with brine (2×20 mL), dried over anhydrous sodium sulfate, filtered and concentrated under reduced pressure to afford the crude product. The crude product was chromatographed on a silica gel column with MeOH:DCM (2%-4%) to provide (1R,4S)-4-(2-hydroxyethyl)-2-azabicyclo[2.2.1]heptan-3-one (240 mg, 70%) as a light yellow oil. $^1$H NMR (400 MHz, CDCl$_3$) δ 6.13 (br, 1H), 3.92 (s, 1H), 3.75-3.86 (m, 2H), 3.11 (br, 1H), 2.06-2.14 (m, 1H), 1.92-2.03 (m, 3H), 1.65-1.77 (m, 3H), 1.41-1.44 (m, 1H). LC-MS (ESI, m/z): 156 [M+H]$^+$.

To a mixture of (1R,4S)-4-(2-hydroxyethyl)-2-azabicyclo[2.2.1]heptan-3-one (120 mg, 0.773 mmol, 1.0 eq.) in DMSO (2 mL) was added 2-iodoxybenzoic acid (650 mg, 2.31 mmol, 3.0 eq.). The mixture was stirred for overnight at rt. The reaction was quenched with saturated aqueous sodium bicarbonate (10 mL). The mixture was extracted with ethyl acetate (5×30 mL). The organic layers were combined, washed with brine (2×20 mL), saturated aqueous sodium bicarbonate (2×20 mL), dried over anhydrous sodium sulfate, filtered and concentrated under reduced pressure to afford 2-((1R,4S)-3-oxo-2-azabicyclo[2.2.1]heptan-4-yl)acetaldehyde (80.0 mg, crude) as a yellow oil. LC-MS (ESI, m/z): 154 [M+H]$^+$.

To a solution of 2-((1R,4S)-3-oxo-2-azabicyclo[2.2.1]heptan-4-yl)acetaldehyde (80.0 mg, 0.522 mmol, 1.0 eq.) in CH$_3$OH (2 mL) was added ammonium chloride (83.8 mg, 1.57 mmol, 3.0 eq.). After stirred 2 h at rt, zyankali (44.1 mg, 0.679 mmol, 1.3 eq.) was added. The mixture was stirred for 2 d at rt. The mixture was filtered through a celite pad and washed with CH$_3$OH (3×20 mL) and DCM (3×20 mL). The filtrate was concentrated under reduced pressure to afford 2-amino-3-((1R,4R)-3-oxo-2-azabicyclo[2.2.1]heptan-4-yl)propanenitrile (80.0 mg, crude) as a yellow oil. LC-MS (ESI, m/z): 180 [M+H]$^+$.

To a mixture of 2-amino-3-((1R,4R)-3-oxo-2-azabicyclo[2.2.1]heptan-4-yl)propanenitrile (80.0 mg, 0.446 mmol, 1.0 eq.), (1R,2S,3S,6R,7S)-4-[(2S)-3,3-dimethyl-2-(2,2,2-trifluoroacetamido)butanoyl]-4-azatricyclo[5.2.1.0^{2,6}]dec-8-ene-3-carboxylic acid (191 mg, 0.491 mmol, 1.1 eq.) and N,N,N,N-tetramethylchloroformamidinium hexafluorophosphate (150 mg, 0.535 mmol, 1.2 eq.) in acetonitrile (3 mL) was added 1-methyl-1H-imidazole (367 mg, 4.46 mmol, 10.0 eq.) at 0° C. The mixture was stirred for 1 h at rt. The reaction was quenched with water (10 mL). The mixture was extracted with ethyl acetate (3×30 mL). The organic layers were combined, washed with brine (2×10 mL), dried over anhydrous sodium sulfate, filtered and concentrated under reduced pressure to afford the crude product. The crude product was chromatographed on a silica gel column with EA:PE (78%-85%) to provide the crude product. The crude product was purified by prep-HPLC (Column: XBridge Shield RP18 OBD Column, 19*250 mm, 10 m; Mobile Phase A: Water (10 mmol/L NH$_4$HCO$_3$), Mobile Phase B: ACN; Flow rate: 25 mL/min; Gradient: 35% B to 55% B in 10 min, 55% B; Wave Length: 220 nm; RT1 (min): 8.48;) to provide (1S,3aR,4S,7R,7aS)—N-(1-cyano-2-((1R,4S)-3-oxo-2-azabicyclo[2.2.1]heptan-4-yl)ethyl)-2-((S)-3,3-dimethyl-2-(2,2,2-trifluoroacetamido)butanoyl)-2,3,3a,4,7,7a-hexahydro-1H-4,7-methanoisoindole-1-carboxamide (17.4 mg, 7%) as a white solid. $^1$H NMR (400 MHz, 80° C., DMSO-d$_6$) δ 8.53-8.94 (m, 2H), 7.47 (s, 1H), 5.93-6.16 (m, 2H), 4.71-4.88 (m, 1H), 4.46 (s, 1H), 3.99-4.15 (m, 1H), 3.66-3.77 (m, 1H), 3.56-3.67 (m, 1H), 3.40-3.44 (m, 1H), 2.97-3.02 (m, 1H), 2.78-2.95 (m, 2H), 2.63-2.75 (m, 1H), 2.05-2.29 (m, 2H), 1.60-1.85 (m, 3H), 1.21-1.51 (m, 5H), 0.85-0.96 (m, 9H). LC-MS (ESI, m/z): 550 [M+H]$^+$.

Example 27
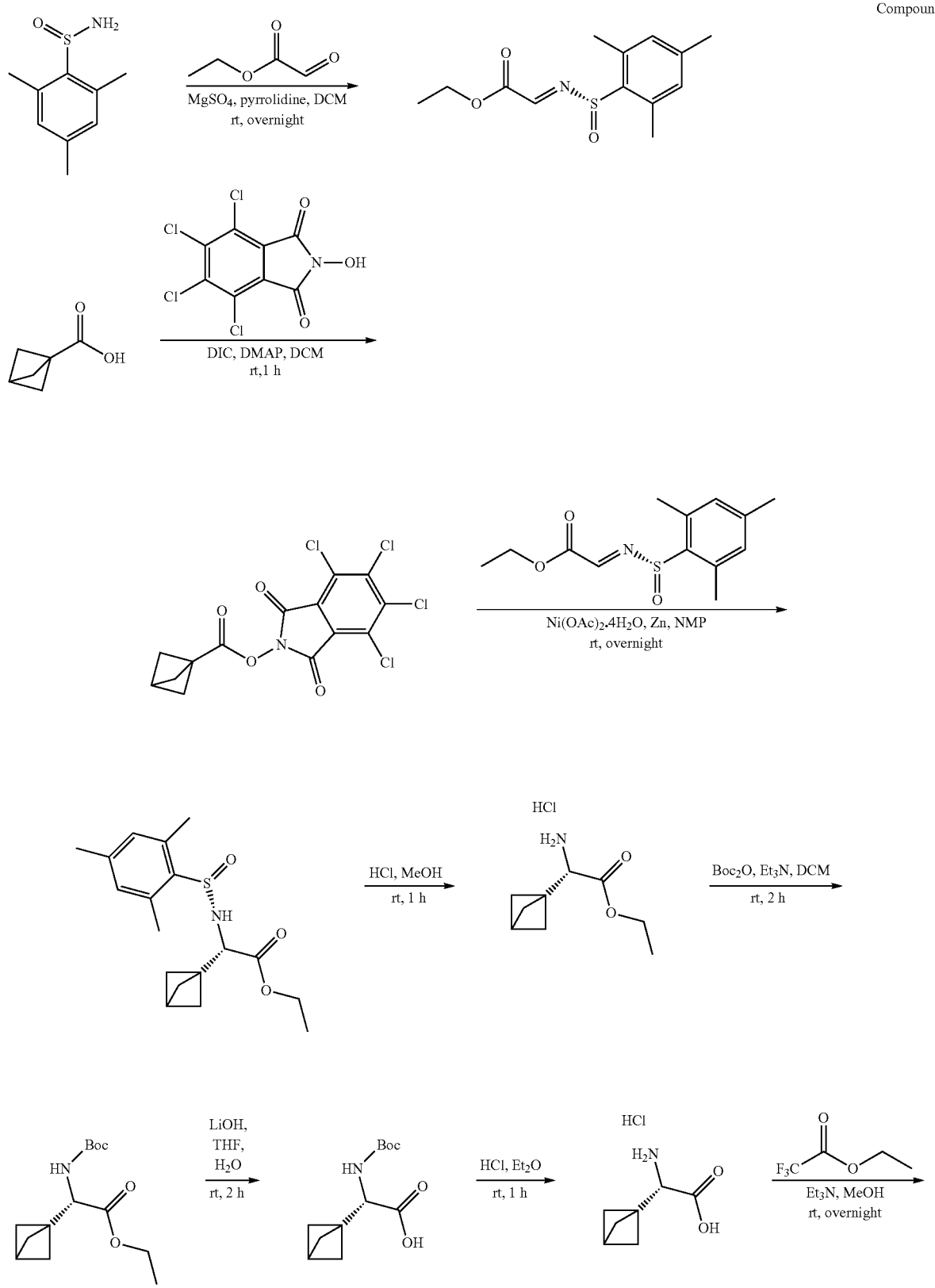
Compound 27

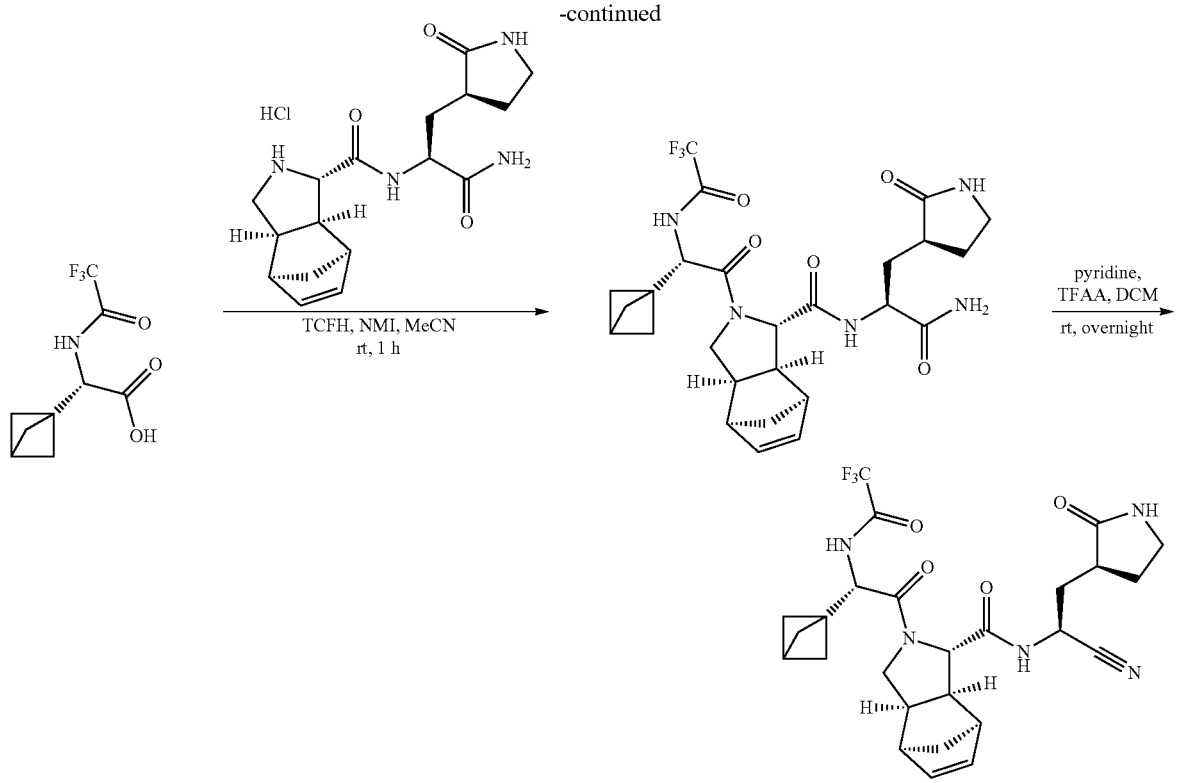

27

To a mixture of (S)-2,4,6-trimethylbenzenesulfinamide (400 mg, 2.18 mmol, 1.0 eq.) and magnesium sulfate (1.31 g, 10.9 mmol, 5.0 eq.) in DCM (12 mL) was added pyrrolidine (16.0 mg, 0.218 mmol, 0.1 eq.) and ethyl glyoxylate (1.34 g, 6.55 mmol, 3.0 eq., 50% in toluene). The mixture was stirred overnight at rt and then filtered. The filtrate was concentrated under reduced pressure to afford ethyl 2-{[(S)-2,4,6-trimethylbenzenesulfinyl]imino}acetate (584 mg, crude) as a light yellow oil. LC-MS (ESI, m/z): 268 [M+H]$^+$.

To a mixture of bicyclo[1.1.1]pentane-1-carboxylic acid (300 mg, 2.68 mmol, 1.0 eq.), 4,5,6,7-tetrachloro-2-hydroxyisoindole-1,3-dione (805 mg, 2.68 mmol, 1.0 eq.) and N,N-dimethylpyridin-4-amine (33.0 mg, 0.268 mmol, 0.1 eq.) in DCM (20 mL) was added N,N'-diisopropylcarbodiimide (371 mg, 2.94 mmol, 1.1 eq.). The mixture was stirred for 1 h at rt. The mixture was chromatographed on a silica gel column with EtOAc:PE (15:85) to provide 4,5,6,7-tetrachloro-1,3-dioxoisoindol-2-yl bicyclo[1.1.1]pentane-1-carboxylate (540 mg, 47%) as a light yellow solid. $^1$H NMR (300 MHz, DMSO-d$_6$) δ 2.60 (s, 1H), 2.30 (m, 6H).

To a mixture of 4,5,6,7-tetrachloro-1,3-dioxoisoindol-2-yl bicyclo[1.1.1]pentane-1-carboxylate (540 mg, 1.38 mmol, 1.0 eq.), ethyl 2-{[(S)-2,4,6-trimethylbenzenesulfinyl]imino}acetate (585 mg, 2.19 mmol, 1.6 eq.) and Nickel(II) acetate tetrahydrate (85.0 mg, 0.342 mmol, 0.25 eq.) in 1-methyl-2-pyrrolidinone (10 mL) was added zinc (268 mg, 4.10 mmol, 3.0 eq.). The mixture was stirred overnight at rt under nitrogen. The reaction was quenched with water (30 mL). The mixture was extracted with EtOAc (3×30 mL). The organic layers were combined, washed with brine (2×30 mL), dried over anhydrous sodium sulfate, filtered and concentrated under reduced pressure to afford the crude product. The crude product was purified by TLC (Mobile phase: EtOAc:PE=1:5; Rf=0.5; detection: UV) to provide ethyl (2S)-2-{bicyclo[1.1.1]pentan-1-yl}-2-{[(S)-2,4,6-trimethylbenzenesulfinyl]amino}acetate (200 mg, 35%) as a light yellow oil. LC-MS (ESI, m/z): 336 [M+H]$^+$.

To a mixture of ethyl (2S)-2-{bicyclo[1.1.1]pentan-1-yl}-2-{[(S)-2,4,6-trimethylbenzenesulfinyl]amino}acetate (200 mg, 0.596 mmol, 1 eq.) in MeOH (2 mL) was added hydrogen chloride (0.60 mL, 2.38 mmol, 4.0 eq., 4 M in EtOH). The mixture was stirred for 1 h at rt and then concentrated under reduced pressure to afford ethyl (2S)-2-amino-2-{bicyclo[1.1.1]pentan-1-yl}acetate hydrochloride (120 mg, crude) as a yellow oil. LC-MS (ESI, m/z): 170 [M+H]$^+$.

To a mixture of ethyl (2S)-2-amino-2-{bicyclo[1.1.1]pentan-1-yl}acetate hydrochloride (120 mg, 0.583 mmol, 1.0 eq.) in DCM (3 mL) was added triethylamine (295 mg, 2.91 mmol, 5.0 eq.) and di-tert-butyl dicarbonate (153 mg, 0.700 mmol, 1.2 eq.). The mixture was stirred for 2 h at rt and then concentrated under reduced pressure to remove the DCM. The residue was purified by C18 column with CH$_3$CN:Water (0.05% TFA). The desired fraction was concentrated under reduced pressure to provide ethyl (2S)-2-{bicyclo[1.1.1]pentan-1-yl}-2-[(tert-butoxycarbonyl)amino]acetate (120 mg, crude) as a yellow oil. LC-MS (ESI, m/z): 214 [M−56+H]$^+$.

To a mixture of ethyl (2S)-2-{bicyclo[1.1.1]pentan-1-yl}-2-[(tert-butoxycarbonyl)amino]acetate (120 mg, 0.446 mmol, 1.0 eq.) in THF (1.5 mL):water (1.5 mL) was added lithium hydroxide (54.0 mg, 2.23 mmol, 5.0 eq.). The mixture was stirred for 2 h at rt and then concentrated under reduced pressure to remove the THF. The pH was adjusted to 6 with hydrochloric acid (1 M). The mixture was extracted with EtOAc (3×3 mL). The organic layers were combined, washed with brine (2×2 mL), dried over anhydrous sodium sulfate, filtered and concentrated under reduced pressure to afford (S)-bicyclo[1.1.1]pentan-1-yl[(tert-butoxycarbonyl) amino]acetic acid (100 mg, crude) as a yellow oil. LC-MS (ESI, m/z): 186 [M−56+H]$^+$.

A mixture of (S)-bicyclo[1.1.1]pentan-1-yl[(tert-butoxycarbonyl)amino]acetic acid (100 mg, 0.414 mmol, 1.0 eq.) in hydrogen chloride (2 mL, 2 M in Et$_2$O) was stirred for 1 h at rt. The mixture was concentrated under reduced pressure to afford (S)-amino(bicyclo[1.1.1]pentan-1-yl)acetic acid hydrochloride (73 mg, crude) as an off-white solid. LC-MS (ESI, m/z): 142 [M+H]$^+$.

To a mixture of (S)-amino(bicyclo[1.1.1]pentan-1-yl)acetic acid hydrochloride (73 mg, 0.411 mmol, 1.0 eq.) in MeOH (2 mL) was added triethylamine (166 mg, 1.64 mmol, 4.0 eq.) and ethyl 2,2,2-trifluoroacetate (117 mg, 0.822 mmol, 2.0 eq.). The mixture was stirred overnight at rt, and then concentrated under reduced pressure to remove the MeOH. The mixture was diluted with water (5 mL) and the pH was adjusted to 6 with hydrochloric acid (1 M). The mixture was extracted with EtOAc (3×5 mL). The organic layers were combined, washed with brine (2×5 mL), dried over anhydrous sodium sulfate, filtered and concentrated under reduced pressure to afford the crude product. The crude product was purified by C18 column with CH$_3$CN: Water (0.05% FA). The desired fraction was concentrated under reduced pressure to provide (S)-bicyclo[1.1.1]pentan-1-yl(2,2,2-trifluoroacetamido)acetic acid (40 mg, 37%) as a yellow oil. $^1$H NMR (400 MHz, Chloroform-d) δ 6.65-6.87 (m, 1H), 4.70-4.77 (m, 1H), 2.61 (s, 1H), 1.79-1.94 (m, 6H). LC-MS (ESI, m/z): 236 [M−H]$^−$.

To a mixture of (2S)-2-[(1R,2S,3S,6R,7S)-4-azatricyclo[5.2.1.0^{2,6}]dec-8-en-3-ylformamido]-3-[(3S)-2-oxopyrrolidin-3-yl]propanamide hydrochloride (62.0 mg, 0.168 mmol, 1.0 eq.), (S)-bicyclo[1.1.1]pentan-1-yl(2,2,2-trifluoroacetamido)acetic acid (40.0 mg, 0.168 mmol, 1.0 eq.) and N,N,N',N'-Tetramethylchloroformamidinium hexafluorophosphate (61.0 mg, 0.218 mmol, 1.3 eq.) in MeCN (2 mL) was added N-methylimidazole (138 mg, 1.68 mmol, 10.0 eq.). The mixture was stirred for 1 h at rt and then purified by C18 column with CH$_3$CN:Water (0.05% FA). The desired fraction was concentrated under reduced pressure to provide (2S)-2-{[(1R,2S,3S,6R,7S)-4-[(2S)-2-{bicyclo[1.1.1]pentan-1-yl}-2-(2,2,2-trifluoroacetamido)acetyl]-4-azatricyclo[5.2.1.0^{2,6}]dec-8-en-3-yl]formamido}-3-[(3S)-2-oxopyrrolidin-3-yl]propanamide (60.0 mg, 54%) as a yellow solid. LC-MS (ESI, m/z): 552 [M+H]$^+$.

To a mixture of (2S)-2-{[(1R,2S,3S,6R,7S)-4-[(2S)-2-{bicyclo[1.1.1]pentan-1-yl}-2-(2,2,2-trifluoroacetamido)acetyl]-4-azatricyclo[5.2.1.0^{2,6}]dec-8-en-3-yl]formamido}-3-[(3S)-2-oxopyrrolidin-3-yl]propanamide (60.0 mg, 0.109 mmol, 1.0 eq.) in DCM (1 mL) were added pyridine (35.0 mg, 0.436 mmol, 4.0 eq.) and trifluoroacetic anhydride (41.0 mg, 0.196 mmol, 1.8 eq.). The mixture was stirred for 1 h at rt. The reaction was quenched with water (5 mL). The mixture was extracted with DCM (3×5 mL). The organic layers were combined, washed with brine (2×5 mL), dried over anhydrous sodium sulfate, filtered and concentrated under reduced pressure to afford the crude product. The crude product was purified by prep-HPLC (Column: XBridge Shield RP18 OBD Column, 19×250 mm, 10 m; Mobile Phase A: Water (0.1% FA), Mobile Phase B: ACN; Flow rate: 25 mL/min; Gradient: 38% B to 68% B in 7 min, 68% B; Wave Length: 220 nm; RT: 5.28 min) to provide (1R,2S,3S,6R,7S)-4-[(2S)-2-{bicyclo[1.1.1]pentan-1-yl}-2-(2,2,2-trifluoroacetamido)acetyl]-N-[(1S)-1-cyano-2-[(3S)-2-oxopyrrolidin-3-yl]ethyl]-4-azatricyclo[5.2.1.0^{2,6}]dec-8-ene-3-carboxamide (6.2 mg, 10%) as a white solid. LC-MS (ESI, m/z): 534 [M+H]$^+$.

Example 28

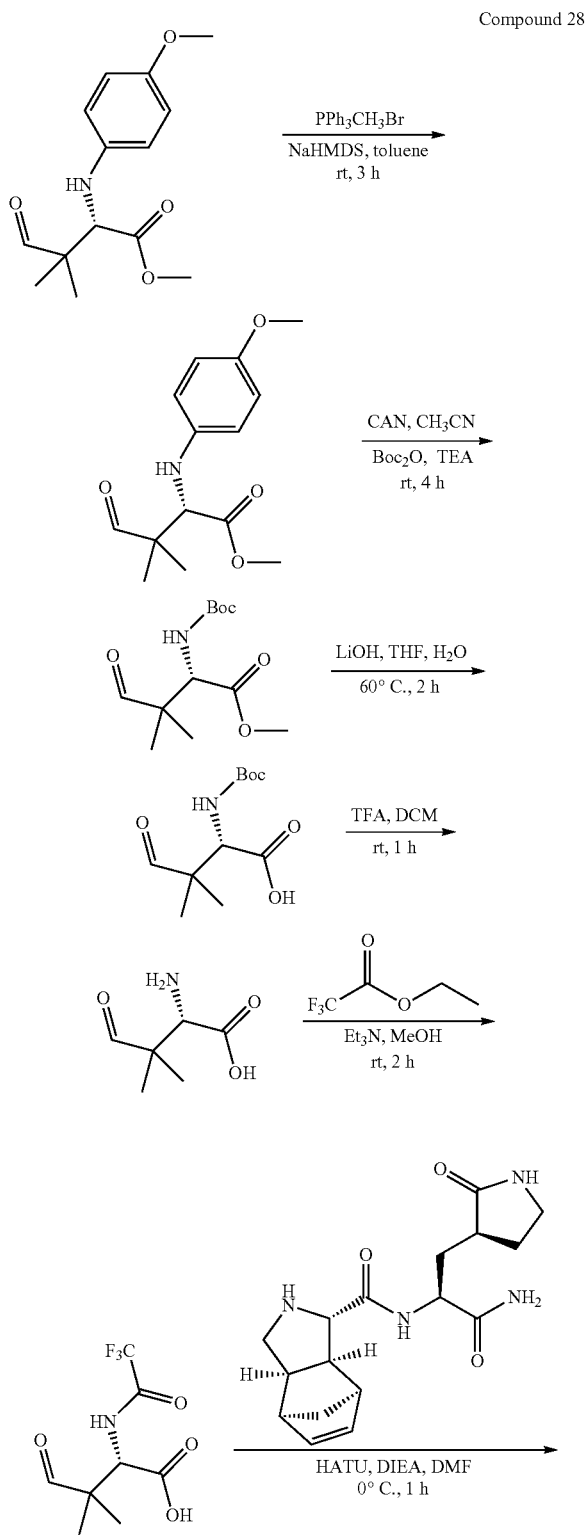

Compound 28

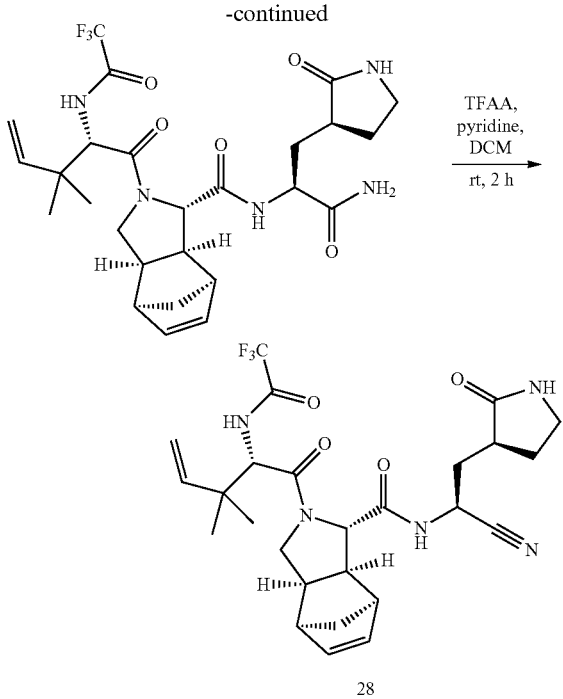

28

To a solution of methyl (S)-2-((4-methoxyphenyl)amino)-3,3-dimethyl-4-oxobutanoate (5.17 g, 18.6 mmol, 1.1 eq.) in toluene was added sodium bis(trimethylsilyl)amide (3.42 g, 18.6 mmol, 1.1 eq.) at 0° C. The mixture was stirred for 30 min at rt. After cooling to 0° C., a solution of methyl (2S)-2-[(4-methoxyphenyl)amino]-3,3-dimethyl-4-oxobutanoate (4.50 g, 16.9 mmol, 1.0 eq.) in toluene (50 mL) was added. The mixture was stirred for 30 min at 0° C. and then poured into ice-cold water (50 mL). The mixture was extracted with ethyl acetate (3×80 mL). The organic phases were combined, washed with brine (50 mL), dried over anhydrous sodium sulfate, filtered and concentrated under reduced pressure to afford the crude product. The crude product was chromatographed on a silica gel column with EA:PE (6:94) to provide the crude product. The crude product was purified by C18 column with CH$_3$CN:Water (0.05% FA). The desired fraction was concentrated under reduced pressure to provide methyl (S)-2-((4-methoxyphenyl)amino)-3,3-dimethylpent-4-enoate (600 mg, crude) as a brown oil. $^1$H NMR (400 MHz, DMSO-d$_6$) δ 6.26-7.33 (m, 4H), 5.64-6.16 (m, 1H), 4.76-5.27 (m, 2H), 3.72-3.87 (m, 1H), 3.37-3.71 (m, 6H), 0.47-1.43 (m, 6H). LC-MS (ESI, m/z): 264 [M+H]$^+$.

To a stirred mixture of methyl (S)-2-((4-methoxyphenyl)amino)-3,3-dimethylpent-4-enoate (0.460 g, 1.75 mmol, 1.0 eq.) in CH$_3$CN (2.4 mL) and H$_2$O (0.8 mL) were added ceric ammonium nitrate (4.80 g, 8.73 mmol, 5.0 eq.) at rt. The mixture was stirred for 2 h at rt and THF (2.5 mL), trimethylamine (basified to pH=8), di-tert-butyl dicarbonate (2.28 g, 10.4 mmol, 6.0 eq.) were added. The mixture was stirred for 2 h at rt. The reaction was quenched with water (30 mL). The mixture was extracted with ethyl acetate (3×50 mL). The organic layers were combined, washed with brine (2×50 mL), dried over anhydrous sodium sulfate, filtered and concentrated under reduced pressure to afford the crude product. The crude product was chromatographed on a silica gel column with EA:PE (10:90) to provide methyl (S)-2-((tert-butoxycarbonyl)amino)-3,3-dimethylpent-4-enoate (195 mg, 43%) as a yellow oil. $^1$H NMR (400 MHz, DMSO-d$_6$) δ 6.75-7.25 (m, 1H), 5.52-6.16 (m, 1H), 4.68-5.20 (m, 2H), 3.80-4.10 (m, 1H), 3.43-3.70 (m, 3H), 1.13-1.73 (m, 9H), 0.64-1.10 (m, 6H). LC-MS (ESI, m/z): 202 [M−56+H]$^+$.

To a stirred mixture of methyl (S)-2-((tert-butoxycarbonyl)amino)-3,3-dimethylpent-4-enoate (195 mg, 0.758 mmol, 1.0 eq.) in THF (3 mL) and H$_2$O (1 mL) was added lithium hydroxide (90.7 mg, 3.79 mmol, 5.0 eq.) at rt. The mixture was stirred for 2 h at 60° C. and then acidified to pH=3 with hydrochloric acid (1M). The mixture was extracted with ethyl acetate (3×20 mL). The organic layers were combined, washed with brine (2×20 mL), dried over anhydrous sodium sulfate, filtered and concentrated under reduced pressure to afford (2S)-2-[(tert-butoxycarbonyl)amino]-3,3-dimethylpent-4-enoic acid (160 mg, 86%, crude) as a light orange solid. LC-MS (ESI, m/z): 188 [M−56+H]$^+$.

To a stirred mixture of (2S)-2-[(tert-butoxycarbonyl)amino]-3,3-dimethylpent-4-enoic acid (160 mg, 0.658 mmol, 1.0 eq.) in DCM (3 mL) was added trifluoroacetic acid (1 mL) at rt. The mixture was stirred for 1 h at rt and then concentrated under reduced pressure to (2S)-2-amino-3,3-dimethylpent-4-enoic acid (200.0 mg, crude) as a brown yellow oil. LC-MS (ESI, m/z): 144 [M+H]$^+$.

To a stirred mixture of (2S)-2-amino-3,3-dimethylpent-4-enoic acid (200 mg, 1.39 mmol, 1.0 eq.) and triethylamine (565 mg, 5.58 mmol, 4.0 eq.) in MeOH (3 mL) was added ethyl 2,2,2-trifluoroacetate (396 mg, 2.79 mmol, 2.0 eq.). The mixture was stirred for 2 h at rt and then acidified to pH=4 with hydrochloric acid (1M). The mixture was extracted with ethyl acetate (3×10 mL). The combined organic layers were concentrated under reduced pressure to afford (2S)-3,3-dimethyl-2-(2,2,2-trifluoroacetamido)pent-4-enoic acid (100 mg, 29%) as a light yellow oil. $^1$H NMR (400 MHz, DMSO-d$_6$) δ 9.19-9.65 (m, 1H), 5.76-6.11 (m, 1H), 4.69-5.29 (m, 2H), 4.13-4.51 (m, 1H), 1.08-1.26 (m, 6H). LC-MS (ESI, m/z): 240 [M+H]$^+$.

To a mixture of (2S)-3,3-dimethyl-2-(2,2,2-trifluoroacetamido)pent-4-enoic acid (107 mg, 0.451 mmol, 1.0 eq.) in N,N-dimethylformamide (2 mL) was added o-(7-azabenzotriazol-1-yl)-N,N,N',N'-tetramethyluronium hexafluorophosphate (205 mg, 0.541 mmol, 1.2 eq.) and N-ethyl-N-isopropylpropan-2-amine (349 mg, 2.70 mmol, 6.0 eq.) at 0° C. The mixture was stirred for 20 min at 0° C., and then (2S)-2-[(1R,2S,3S,6R,7S)-4-azatricyclo[5.2.1.0^{2,6}]dec-8-en-3-yl]formamido]-3-[(3S)-2-oxopyrrolidin-3-yl]propanamide (150 mg, 0.451 mmol, 1.0 eq.) was added at 0° C. The mixture was stirred for 2 h at rt. The reaction was quenched with water (20 mL). The mixture was extracted with EtOAc (3×30 mL). The organic layers were combined, washed with brine (2×30 mL), dried over anhydrous sodium sulfate, filtered and concentrated under reduced pressure to afford the crude product. The mixture was purified by C18 column with CH$_3$CN:Water (0.05% FA). The desired fraction was concentrated under reduced pressure to provide (2S)-2-{[(1R,2S,3S,6R,7S)-4-[(2S)-3,3-dimethyl-2-(2,2,2-trifluoroacetamido)pent-4-enoyl]-4-azatricyclo[5.2.1.0^{2,6}]dec-8-en-3-yl]formamido}-3-[(3S)-2-oxopyrrolidin-3-yl]propanamide (100 mg, 40%) as a light yellow solid. LC-MS (ESI, m/z): 554 [M+H]$^+$.

To a mixture of (2S)-2-{[(1R,2S,3S,6R,7S)-4-[(2S)-3,3-dimethyl-2-(2,2,2-trifluoroacetamido)pent-4-enoyl]-4-azatricyclo[5.2.1.0^{2,6}]dec-8-en-3-yl]formamido}-3-[(3S)-2-oxopyrrolidin-3-yl]propanamide (100 mg, 0.181 mmol, 1.0 eq.) in DCM (2 mL) was added pyridine (57.1 mg, 0.724 mmol, 4.0 eq.) and trifluoroacetic anhydride (68.2 mg, 0.326 mmol, 1.8 eq.). The mixture was stirred for 2 h at rt. The reaction was quenched with water (5 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was purified by prep-HPLC (Column: XBridge Shield RP18 OBD Column, 19*250 mm, 10 m; Mobile Phase A: Water (0.1% FA), Mobile Phase B: ACN; Flow rate: 25 mL/min; Gradient: 30% B to 47% B in 10 min, 47% B; Wave Length: 254 nm; RT1 (min): 5.97) to provide (1R,2S,3S,6R,7S)—N-[(1S)-1-cyano-2-[(3S)-2-oxopyrrolidin-3-yl]ethyl]-4-[(2S)-3,3-dimethyl-2-(2,2,2-trifluoroacetamido)pent-4-enoyl]-4-azatricyclo[5.2.1.0^{2,6}]dec-8-ene-3-carboxamide (9.3 mg, 10%) as an white solid. $^1$H NMR (400 MHz, 80° C., DMSO-d$_6$) δ 8.40-9.00 (m, 2H), 7.30-7.62 (m, 1H), 5.75-6.30 (m, 3H), 4.80-5.10 (m, 3H), 4.45-4.75 (m, 1H), 3.85-4.40 (m, 1H), 3.60-3.80 (m, 1H), 3.30-3.58 (m, 1H), 3.10-3.28 (m, 3H), 2.55-3.00 (m, 3H), 2.00-2.45 (m, 3H), 1.60-1.95 (m, 2H), 1.15-1.50 (m, 2H), 0.80-1.10 (m, 6H). LC-MS (ESI, m/z): 536 [M+H]$^+$.

Example 29

Compound 29

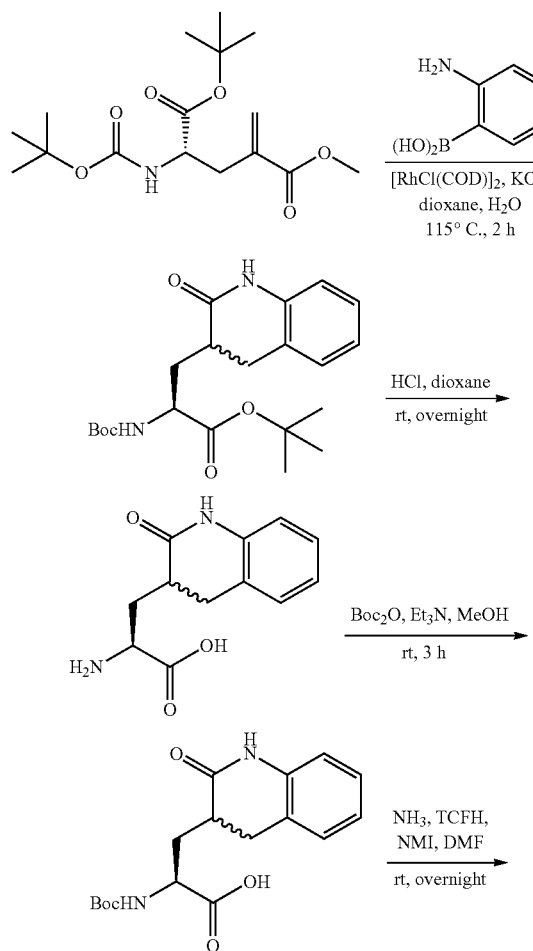

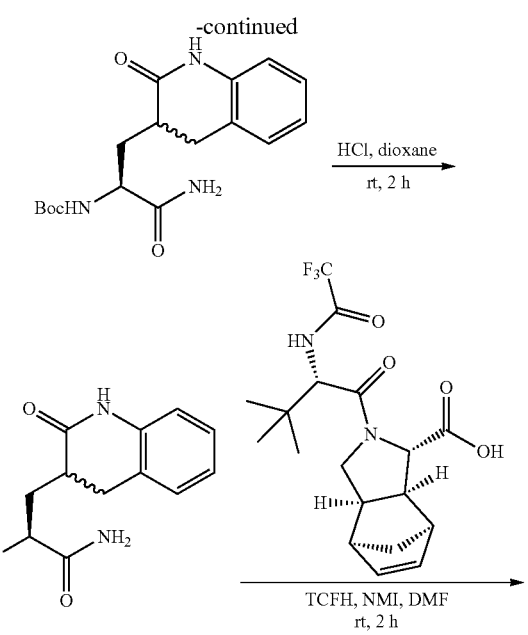

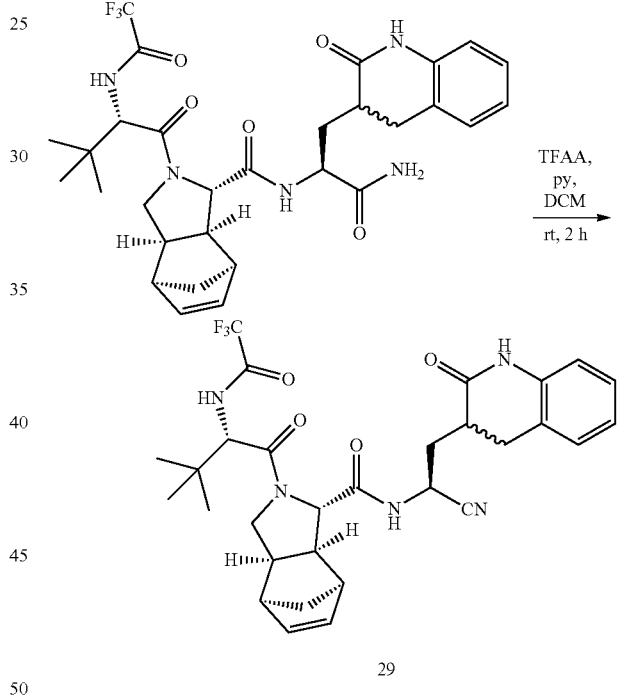

29

To a solution of 1-(tert-butyl) 5-methyl (S)-2-((tert-butoxycarbonyl)amino)-4-methylenepentanedioate (2 g, 6.07 mmol, 1.0 eq.) in dioxane (30 mL) was added 2-aminophenylboronic acid (1.66 g, 12.1 mmol, 2.0 eq.), Chloro(1,5-cyclooctadiene)rhodium(I) dimer (89.8 mg, 0.18 mmol, 0.03 eq.), potassium hydroxide solution (0.6 mL, 1.52 mmol, 0.25 eq.), was stirred at 115° C. for 2 h under N$_2$. The reaction was quenched with water (20 mL). The mixture was extracted with EA (3×30 mL). The organic layers were combined, washed with brine (50 mL), dried over anhydrous sodium sulfate, filtered and concentrated under reduced pressure. The residue was chromatographed on a silica gel column with EA:PE (1:4) to provide tert-butyl (2S)-2-((tert-butoxycarbonyl)amino)-3-(2-oxo-1,2,3,4-tetrahydroquinolin-3-yl)propanoate (1.5 g, 57%) as a white solid. $^1$H NMR (300 MHz, DMSO-d$_6$) δ 10.13 (s, 1H), 7.01-7.24 (m, 3H), 6.82-6.92 (m, 2H), 3.86-4.12 (m, 1H), 2.86-2.95 (m, 1H), 2.59-2.71 (m, 1H), 2.38-2.49 (m, 1H), 2.07-2.18 (m, 1H), 1.54-1.69 (m, 1H), 1.35-1.44 (m, 18H). LC-MS (ESI, m/z): 391 [M+H]$^+$.

To a solution of tert-butyl (2S)-2-((tert-butoxycarbonyl)amino)-3-(2-oxo-1,2,3,4-tetrahydroquinolin-3-yl)propanoate (1.3 g, 3.33 mmol, 1.0 eq.) in dioxane (15 mL) was added hydrochloric acid (15 mL, 9 mol/L in dioxane). The mixture was stirred at rt overnight and then concentrated under reduced pressure to provide (2S)-2-amino-3-(2-oxo-1,2,3,4-tetrahydroquinolin-3-yl)propanoic acid (700 mg, crude) as a white solid. LC-MS (ESI, m/z): 235 [M+H]$^+$.

To a solution of (2S)-2-amino-3-(2-oxo-1,2,3,4-tetrahydroquinolin-3-yl)propanoic acid (700 mg, 2.99 mmol, 1.0 eq.) in MeOH (10 mL) was added di-tert-butyl dicarbonate (717 mg, 3.29 mmol, 1.1 eq.) and triethylamine (907 mg, 8.96 mmol, 3.0 eq.). The mixture was stirred at rt for 3 h and then concentrated under reduced pressure to provide (2S)-2-((tert-butoxycarbonyl)amino)-3-(2-oxo-1,2,3,4-tetrahydroquinolin-3-yl)propanoic acid (800 mg, crude) as an off-white solid. LC-MS (ESI, m/z): 335 [M+H]$^+$.

To a solution of (2S)-2-((tert-butoxycarbonyl)amino)-3-(2-oxo-1,2,3,4-tetrahydroquinolin-3-yl)propanoic acid (800 mg, 2.39 mmol, 1.0 eq.) in DMF (10 mL) was added N,N,N,N-tetramethylchloroformamidinium hexafluorophosphate (4.03 g, 14.4 mmol, 6.0 eq.), NMI (4.91 g, 59.8 mmol, 25.0 eq.), NH$_3$ (120 mL, 0.4 mol/L in dioxane, 47.8 mmol, 20.0 eq.). The mixture was stirred at rt overnight and then chromatographed on a C18 column with MeCN:H$_2$O (1:4) to provide tert-butyl ((2S)-1-amino-1-oxo-3-(2-oxo-1,2,3,4-tetrahydroquinolin-3-yl)propan-2-yl)carbamate (600 mg, 68%) as a brown yellow solid. $^1$H NMR (400 MHz, DMSO-d$_6$) δ 10.12-10.14 (m, 1H), 7.12-7.24 (m, 3H), 6.84-7.01 (m, 4H), 4.01-4.11 (m, 1H), 2.88-3.18 (m, 1H), 2.63-2.72 (m, 1H), 2.41-2.45 (m, 1H), 2.05-2.18 (m, 1H), 1.49-1.67 (m, 1H), 1.36-1.48 (m, 9H). LC-MS (ESI, m/z): 334 [M+H]$^+$.

A solution of tert-butyl ((2S)-1-amino-1-oxo-3-(2-oxo-1,2,3,4-tetrahydroquinolin-3-yl)propan-2-yl)carbamate (150 mg, 0.450 mmol, 1 eq.) in hydrochloric acid (3 mL, 4M in dioxane) was stirred at rt for 2 h and then concentrated under reduced pressure to provide (2S)-2-amino-3-(2-oxo-1,2,3,4-tetrahydroquinolin-3-yl)propenamide (100 mg, crude) as an off-white solid. LC-MS (ESI, m/z): 234 [M+H]$^+$.

To a solution of (2S)-2-amino-3-(2-oxo-1,2,3,4-tetrahydroquinolin-3-yl)propanamide (100 mg, 0.43 mmol, 1.0 eq.) in DMF (3 mL) were added (1S,3aR,4S,7R,7aS)-2-((S)-3,3-dimethyl-2-(2,2,2-trifluoroacetamido)butanoyl)-2,3,3a,4,7,7a-hexahydro-1H-4,7-methanoisoindole-1-carboxylic acid (183 mg, 0.47 mmol, 1.1 eq.), N,N,N,N-tetramethylchloroformamidinium hexafluorophosphate (156 mg, 0.56 mmol, 1.3 eq.) and NMI (176 mg, 2.15 mmol, 5.0 eq.). The mixture was stirred at rt for 2 h and then chromatographed on a C18 column with water:MeCN (3:1) to provide (1S,3aR,4S,7R,7aS)—N-((2S)-1-amino-1-oxo-3-(2-oxo-1,2,3,4-tetrahydroquinolin-3-yl)propan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (200 mg, 70%) as an off-white solid. LC-MS (ESI, m/z): 604 [M+H]$^+$.

To a solution of (1S,3aR,4S,7R,7aS)—N-((2S)-1-amino-1-oxo-3-(2-oxo-1,2,3,4-tetrahydroquinolin-3-yl)propan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (90 mg, 0.15 mmol, 1.0 eq.) in DCM (30 mL) was added pyridine (71 mg, 0.89 mmol, 6.0 eq.) and TFAA (94 mg, 0.45 mmol, 3.0 eq.). The mixture was stirred at rt for 2 h. The reaction was quenched with water (3 mL). The mixture was extracted with DCM (3×5 mL). The organic layers were combined, dried over anhydrous sodium sulfate, filtered and concentrated under reduced pressure. The residue was purified by prep-HPLC (Column: XBridge Shield RP18 OBD Column, 30*150 mm, 5 m; Mobile Phase A: Water (0.1% FA), Mobile Phase B: ACN; Flow rate: 60 mL/min; Gradient: 45% B to 75% B in 7 min, 75% B; Wave Length: 254 nm; RT1 (min): 5.88) to provide (1S,3aR,4S,7R,7aS)—N-((1S)-1-cyano-2-(2-oxo-1,2,3,4-tetrahydroquinolin-3-yl)ethyl)-2-((S)-3,3-dimethyl-2-(2,2,2-trifluoroacetamido)butanoyl)-2,3,3a,4,7,7a-hexahydro-1H-4,7-methanoisoindole-1-carboxamide (24.7 mg, 28%) as a white solid. $^1$H NMR (400 MHz, DMSO-d$_6$, 80° C.) δ 9.86-10.07 (m, 1H), 8.29-8.84 (m, 2H), 6.81-7.24 (m, 4H), 5.98-6.18 (m, 2H), 4.90-5.13 (m, 1H), 4.39-4.52 (m, 1H), 3.98-4.18 (m, 1H), 3.17-3.68 (m, 2H), 3.01-3.03 (m, 1H), 2.88-2.98 (m, 3H), 2.68-2.81 (m, 2H), 2.50-2.52 (m, 1H), 2.29-2.43 (m, 1H), 1.82-1.97 (m, 1H), 1.38-1.47 (m, 2H), 0.51-1.04 (m, 9H). LC-MS (ESI, m/z): 586 [M+H]$^+$.

Example 30

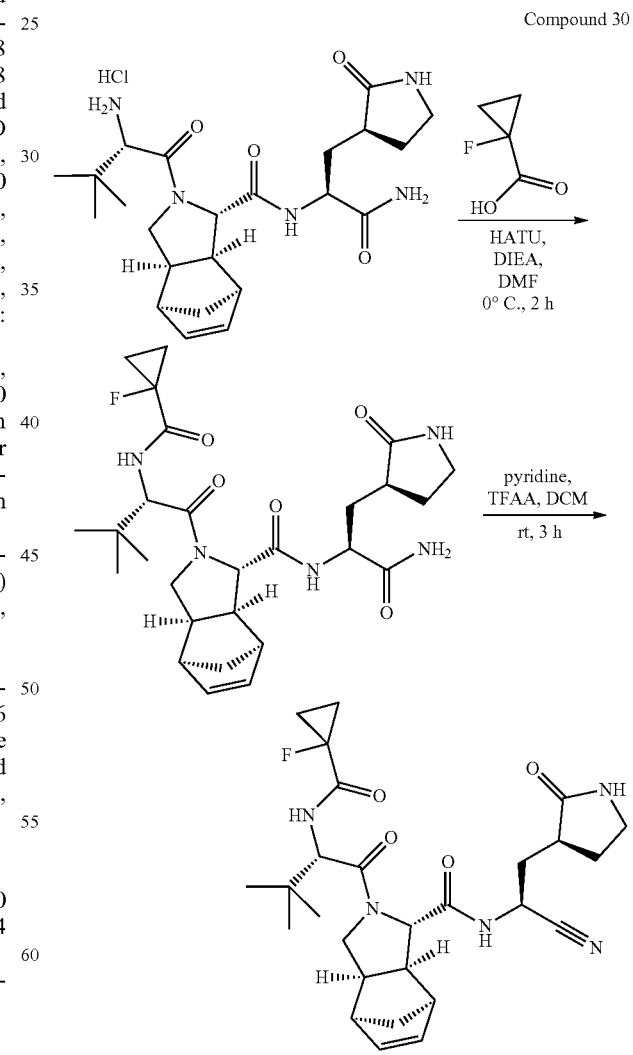

Compound 30

30

To a mixture of 1-fluorocyclopropane-1-carboxylic acid (25.9 mg, 0.249 mmol, 1.0 eq.) in N,N-dimethylformamide (3 mL) was added o-(7-azabenzotriazol-1-yl)-N,N,N',N'-tetramethyluronium hexafluorophosphate (113 mg, 0.299 mmol, 1.2 eq.) and N-ethyl-N-isopropylpropan-2-amine (193 mg, 1.49 mmol, 6.0 eq.) at 0° C. The mixture was stirred for 20 min at 0° C., and then (2S)-2-{[(1R,2S,3S,6R,7S)-4-[(2S)-2-amino-3,3-dimethylbutanoyl]-4-azatricyclo[5.2.1.0^{2,6}]dec-8-en-3-yl]formamido}-3-[(3S)-2-oxopyrrolidin-3-yl]propanamide hydrochloride (120 mg, 0.249 mmol, 1.0 eq.) was added at 0° C. The mixture was stirred for 2 h at rt and then purified by C18 column with $CH_3CN$:Water (0.05% FA). The desired fraction was concentrated under reduced pressure to provide N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxobutan-2-yl]-1-fluorocyclopropane-1-carboxamide (70.0 mg, 52%) as a light yellow solid. LC-MS (ESI, m/z): 532 [M+H]$^+$.

To a mixture of N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxobutan-2-yl]-1-fluorocyclopropane-1-carboxamide (70.0 mg, 0.132 mmol, 1.0 eq.) in DCM (2 mL) was added pyridine (41.7 mg, 0.528 mmol, 4.0 eq.) and trifluoroacetic anhydride (49.8 mg, 0.238 mmol, 1.8 eq.). The mixture was stirred for 3 h at rt. The reaction was quenched with water (5 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was purified by prep-HPLC (Column: XBridge Shield RP18 OBD Column, 19*250 mm, 10 m; Mobile Phase A: Water (0.1% FA), Mobile Phase B: ACN; Flow rate: 25 mL/min; Gradient: 38% B to 68% B in 7 min, 68% B; Wave Length: 254 nm; RT1 (min): 4.48) to provide (1R,2S,3S,6R,7S)—N-[(1S)-1-cyano-2-[(3S)-2-oxopyrrolidin-3-yl]ethyl]-4-[(2S)-2-[(1-fluorocyclopropyl)formamido]-3,3-dimethylbutanoyl]-4-azatricyclo[5.2.1.0^{2,6}]dec-8-ene-3-carboxamide (29.2 mg, 42%) as a white solid. $^1$H NMR (400 MHz, 80° C., DMSO-$d_6$) δ 8.60-8.90 (m, 1H), 7.30-7.60 (m, 1H), 6.90-7.20 (m, 1H), 5.90-6.40 (m, 2H), 4.80-5.00 (m, 1H), 4.40-4.65 (m, 1H), 4.00-4.25 (m, 1H), 3.55-3.80 (m, 1H), 3.35-3.55 (m, 1H), 3.10-3.25 (m, 2H), 2.90-3.00 (m, 2H), 3.70-2.90 (m, 1H), 2.30-2.45 (m, 1H), 2.05-2.30 (m, 2H), 1.60-1.95 (m, 2H), 1.30-1.60 (m, 3H), 1.00-1.30 (m, 4H), 0.70-1.00 (m, 9H). LC-MS (ESI, m/z): 514 [M+H]$^+$.

Example 31

Compound 31

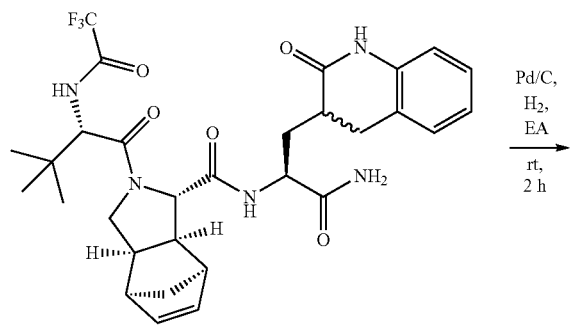

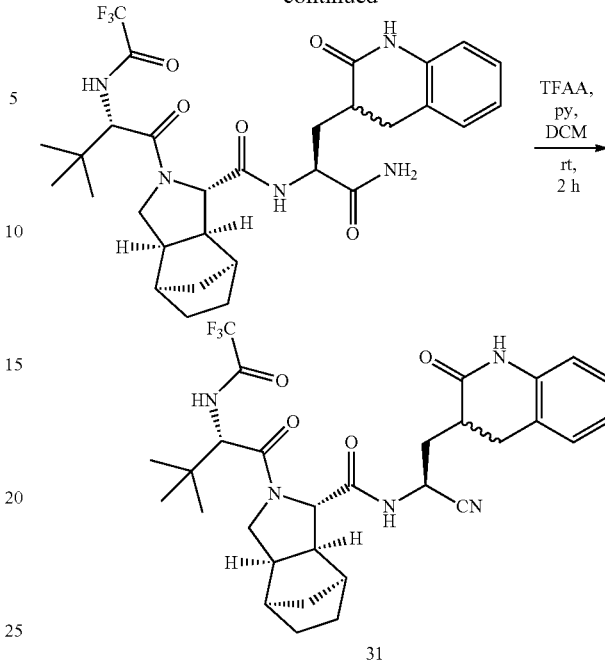

31

A 50 mL round-bottom flask was charged with (1S,3aR,4S,7R,7aS)—N-((2S)-1-amino-1-oxo-3-(2-oxo-1,2,3,4-tetrahydroquinolin-3-yl)propan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (100 mg, 0.17 mmol, 1.0 eq.), ethyl acetate (5 mL), 10% palladium on activated carbon (50 mg). The contents of the flask were placed under an atmosphere of hydrogen (3 atm). The mixture was stirred at rt for 2 h. The solids were filtered out. The organic layer was concentrated under reduced pressure to provide (1S,3aR,4R,7S,7aS)—N-((2S)-1-amino-1-oxo-3-(2-oxo-1,2,3,4-tetrahydroquinolin-3-yl)propan-2-yl)-2-((S)-3,3-dimethyl-2-(2,2,2-trifluoroacetamido)butanoyl)octahydro-1H-4,7-methanoisoindole-1-carboxamide (50 mg, 45%) as a white solid. LC-MS (ESI, m/z): 606 [M+H]$^+$.

To a solution of (1S,3aR,4R,7S,7aS)—N-((2S)-1-amino-1-oxo-3-(2-oxo-1,2,3,4-tetrahydroquinolin-3-yl)propan-2-yl)-2-((S)-3,3-dimethyl-2-(2,2,2-trifluoroacetamido)butanoyl)octahydro-1H-4,7-methanoisoindole-1-carboxamide (45 mg, 0.07 mmol, 1.0 eq.) in DCM (2 mL) was added TFAA (31 mg, 0.15 mmol, 2.0 eq.) and pyridine (24 mg, 0.3 mmol, 4.0 eq.). The mixture was stirred at rt for 2 h. The reaction was quenched with water (3 mL). The mixture was extracted with DCM (3×5 mL). The organic layers were combined, dried over anhydrous sodium sulfate, filtered and concentrated under reduced pressure. The residue was purified by prep-HPLC (Column: XBridge Shield RP18 OBD Column, 19*250 mm, 10 m; Mobile Phase A: Water (0.1% FA), Mobile Phase B: ACN; Flow rate: 25 mL/min; Gradient: 48% B to 78% B in 7 min, 78% B; Wave Length: 254 nm; RT1 (min): 5.67) to provide (1S,3aR,4R,7S,7aS)—N-((1S)-1-cyano-2-(2-oxo-1,2,3,4-tetrahydroquinolin-3-yl)ethyl)-2-((S)-3,3-dimethyl-2-(2,2,2-trifluoroacetamido)butanoyl)octahydro-1H-4,7-methanoisoindole-1-carboxamide (24.1 mg, 55%) as a white solid. $^1$H NMR (400 MHz, DMSO-$d_6$, 80° C.) δ 9.96-10.00 (m, 1H), 8.83-9.01 (m, 1H), 8.64-8.66 (m, 1H), 7.10-7.16 (m, 2H), 6.84-6.90 (m, 2H), 4.93-5.08 (m, 1H), 4.61-4.72 (m, 1H), 4.46-4.56 (m, 1H), 3.75-3.81 (m, 1H), 3.58-3.64 (m, 1H), 2.93-3.07 (m, 1H), 2.51-2.80 (m, 3H), 2.30-2.48 (m, 3H), 2.10-2.22 (m, 1H), 1.82-1.94 (m, 1H), 1.37-1.55 (m, 2H), 1.19-1.34 (m, 3H), 1.03-1.17 (m, 1H), 0.85-0.99 (m, 9H). LC-MS (ESI, m/z): 588 [M+H]⁺.

Example 32

Compound 32

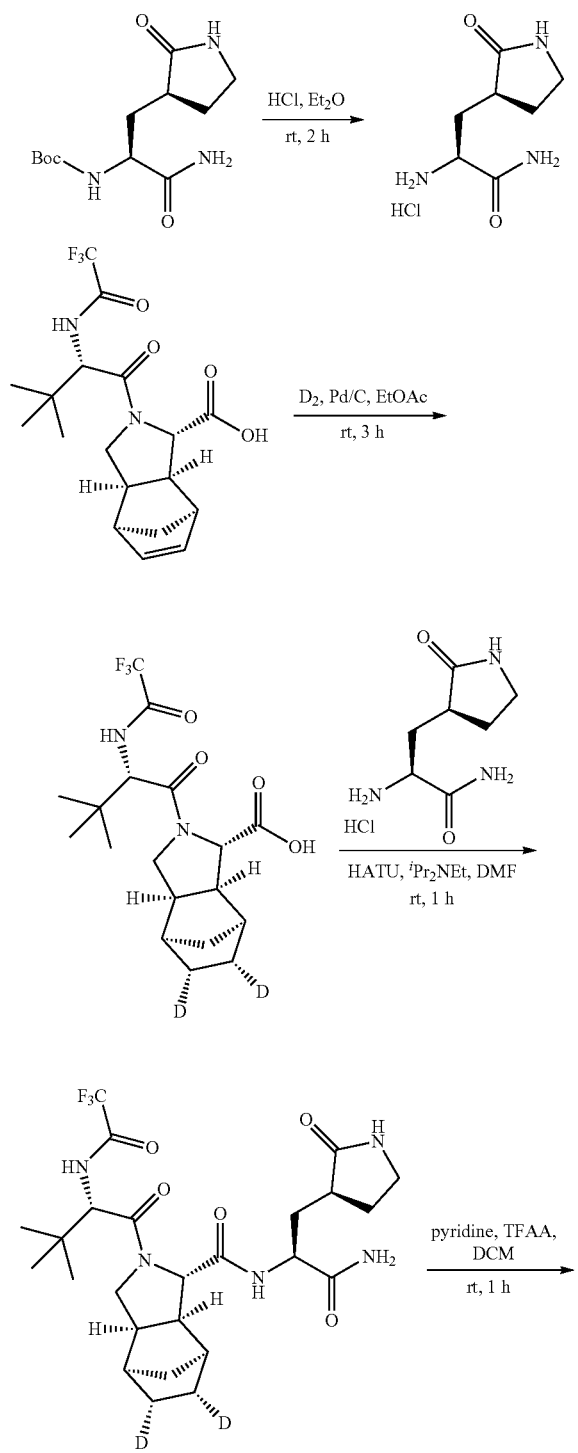

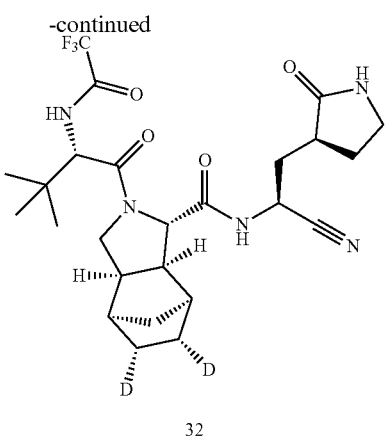

32

To a mixture of (1R,2S,3S,6R,7S)-4-[(2S)-3,3-dimethyl-2-(2,2,2-trifluoroacetamido)butanoyl]-4-azatricyclo[5.2.1.0^{2,6}]dec-8-ene-3-carboxylic acid (200 mg, 0.515 mmol, 1.0 eq.) in EtOAc (5 mL) was added 10% palladium on activated carbon (80 mg). The mixture was stirred for 3 h at rt under deuterium. The mixture was filtered. The filtrate was concentrated under reduced pressure to provide (1S,3aR,4R,5S,6R,7S,7aS)-2-((S)-3,3-dimethyl-2-(2,2,2-trifluoroacetamido)butanoyl)octahydro-1H-4,7-methanoisoindole-1-carboxylic-5,6-d₂ acid (190 mg, 91%) as an off-white solid. ¹H NMR (400 MHz, DMSO-d₆) δ 12.73 (br, 1H), 9.14-9.61 (m, 1H), 4.69-4.84 (m, 1H), 4.41-4.59 (m, 1H), 3.76-3.88 (m, 1H), 3.43-3.67 (m, 1H), 2.53-2.82 (m, 2H), 2.26-2.41 (m, 1H), 2.13-2.24 (m, 1H), 1.35-1.54 (m, 2H), 1.15-1.31 (m, 2H), 0.93-1.06 (m, 9H). LC-MS (ESI, m/z): 393 [M+H]⁺.

To a mixture of (1S,3aR,4R,5S,6R,7S,7aS)-2-((S)-3,3-dimethyl-2-(2,2,2-trifluoroacetamido)butanoyl)octahydro-1H-4,7-methanoisoindole-1-carboxylic-5,6-d₂ acid (144 mg, 0.366 mmol, 1.0 eq.) and o-(7-azabenzotriazol-1-yl)-N,N,N',N'-tetramethyluronium hexafluorophosphate (167 mg, 0.439 mmol, 1.2 eq.) in DMF (3 mL) was added N-ethyl-N-isopropylpropan-2-amine (284 mg, 2.20 mmol, 6.0 eq.) at 0° C. After stirred for 15 min at 0° C., (2S)-2-amino-3-[(3S)-2-oxopyrrolidin-3-yl]propanamide hydrochloride (76.0 mg, 0.366 mmol, 1.0 eq.) was added. The mixture was stirred for 1 h at rt. The mixture was purified by C18 column with CH₃CN:Water (0.05% TFA). The desired fraction was concentrated under reduced pressure to provide (1S,3aR,4R,5S,6R,7S,7aS)—N—((S)-1-amino-1-oxo-3-((S)-2-oxopyrrolidin-3-yl)propan-2-yl)-2-((S)-3,3-dimethyl-2-(2,2,2-trifluoroacetamido)butanoyl)octahydro-1H-4,7-methanoisoindole-5,6-d₂₋₁-carboxamide (160 mg, 75%) as a light yellow solid. LC-MS (ESI, m/z): 546 [M+H]⁺.

To a mixture of (1S,3aR,4R,5S,6R,7S,7aS)—N—((S)-1-amino-1-oxo-3-((S)-2-oxopyrrolidin-3-yl)propan-2-yl)-2-((S)-3,3-dimethyl-2-(2,2,2-trifluoroacetamido)butanoyl)octahydro-1H-4,7-methanoisoindole-5,6-d₂-1-carboxamide (160 mg, 0.293 mmol, 1.0 eq.) in DCM (5 mL) was added pyridine (139 mg, 1.76 mmol, 6.0 eq.) and trifluoroacetic anhydride (136 mg, 0.645 mmol, 2.2 eq.). The mixture was stirred for 1 h at rt. The reaction was quenched with water (20 mL). The mixture was extracted with DCM (3×20 mL). The organic layers were combined, washed with brine (2×20 mL), dried over anhydrous sodium sulfate, filtered and concentrated under reduced pressure to afford then crude product. The crude product was purified by prep-HPLC (Column: XBridge Prep Phenyl OBD Column, 19×250 mm, 5 m; Mobile Phase A: Water (0.05% FA), Mobile Phase B:

ACN; Flow rate: 25 mL/min; Gradient: 42% B to 72% B in 7 min, 72% B; Wave Length: 254 nm; RT: 5 min) to provide (1S,3aR,4R,5S,6R,7S,7aS)—N—((S)-1-cyano-2-((S)-2-oxopyrrolidin-3-yl)ethyl)-2-((S)-3,3-dimethyl-2-(2,2,2-trifluoroacetamido)butanoyl)octahydro-1H-4,7-methanoisoindole-5,6-d²-1-carboxamide (45.4 mg, 28%) as a white solid. ¹H NMR (400 MHz, 80° C., DMSO-d₆) δ 8.85-9.10 (m, 1H), 8.56-8.80 (m, 1H), 7.32-7.60 (m, 1H), 4.80-4.95 (m, 1H), 4.60-4.75 (m, 1H), 4.45-4.58 (m, 1H), 3.75-3.88 (m, 1H), 3.55-3.73 (m, 1H), 3.10-3.22 (m, 2H), 2.50-2.70 (m, 1H), 2.25-2.48 (m, 3H), 2.06-2.24 (m, 3H), 1.60-1.90 (m, 2H), 1.35-1.58 (m, 2H), 1.20-1.34 (m, 1H), 1.05-1.19 (m, 1H), 0.78-1.04 (m, 9H). LC-MS (ESI, m/z): 528 [M+H]⁺.

Example 33

Compound 33

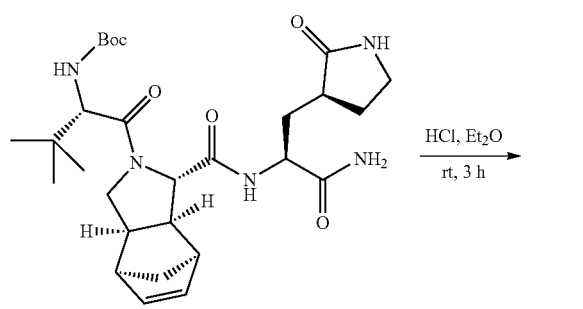

HCl, Et₂O
rt, 3 h

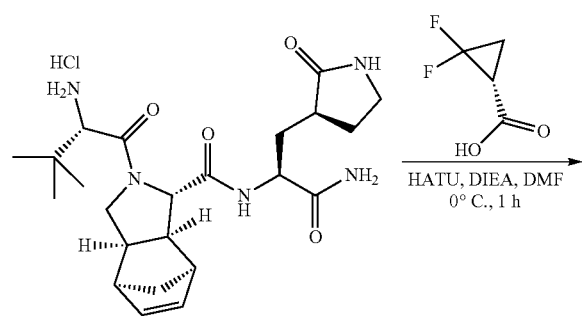

HATU, DIEA, DMF
0° C., 1 h

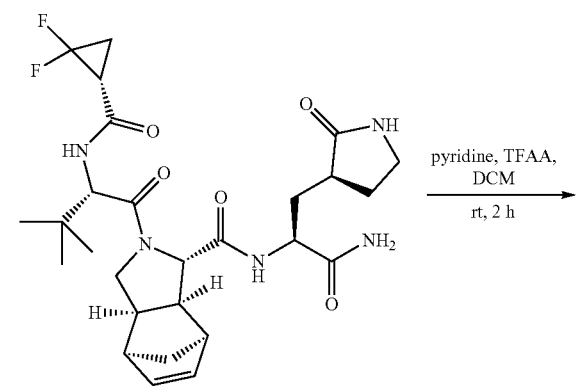

pyridine, TFAA, DCM
rt, 2 h

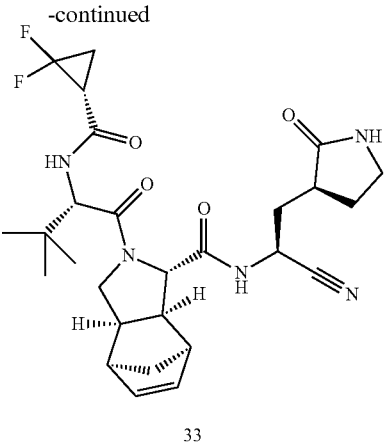

33

To a mixture of (R)-2,2-difluorocyclopropane-1-carboxylic acid (49.1 mg, 0.403 mmol, 1.0 eq.) in N,N-dimethylformamide (3 mL) was added o-(7-azabenzotriazol-1-yl)-N,N,N',N'-tetramethyluronium hexafluorophosphate (183 mg, 0.484 mmol, 1.2 eq.) and N-ethyl-N-isopropylpropan-2-amine (312 mg, 2.41 mmol, 6.0 eq.) at 0° C. The mixture was stirred for 20 min at 0° C., then (2S)-2-{[(1R,2S,3S,6R,7S)-4-[(2S)-2-amino-3,3-dimethylbutanoyl]-4-azatricyclo[5.2.1.0ˆ{2,6}]dec-8-en-3-yl]formamido}-3-[(3S)-2-oxopyrrolidin-3-yl]propanamide hydrochloride (194 mg, 0.403 mmol, 1.0 eq.) was added at 0° C. for 2 h at rt. The mixture was purified by C18 column with CH₃CN:Water (0.05% FA). The desired fraction was concentrated under reduced pressure to provide (1S,3aR,4S,7R,7aS)—N—((S)-1-amino-1-oxo-3-((S)-2-oxopyrrolidin-3-yl)propan-2-yl)-2-((S)-2-((R)-2,2-difluorocyclopropane-1-carboxamido)-3,3-dimethylbutanoyl)-2,3,3a,4,7,7a-hexahydro-1H-4,7-methanoisoindole-1-carboxamide (160 mg, 72%) as a light yellow solid. LC-MS (ESI, m/z): 550 [M+H]⁺.

To a mixture of (1S,3aR,4S,7R,7aS)—N—((S)-1-amino-1-oxo-3-((S)-2-oxopyrrolidin-3-yl)propan-2-yl)-2-((S)-2-((R)-2,2-difluorocyclopropane-1-carboxamido)-3,3-dimethylbutanoyl)-2,3,3a,4,7,7a-hexahydro-1H-4,7-methanoisoindole-1-carboxamide (160 mg, 0.291 mmol, 1.0 eq.) in DCM (2 mL) was added pyridine (92.1 mg, 1.16 mmol, 4.0 eq.) and trifluoroacetic anhydride (110 mg, 0.524 mmol, 1.8 eq.). The mixture was stirred for 2 h at rt. The reaction was quenched with water (5 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was purified by prep-HPLC (Column: XBridge Prep OBD C18 Column, 19*250 mm, 5 m; Mobile Phase A: Water (0.1% FA), Mobile Phase B: ACN; Flow rate: 25 mL/min; Gradient: 38% B to 68% B in 7 min, 68% B; Wave Length: 254 nm; RT1 (min): 4.95) to provide (1S,3aR,4S,7R,7aS)—N—((S)-1-cyano-2-((S)-2-oxopyrrolidin-3-yl)ethyl)-2-((S)-2-((R)-2,2-difluorocyclopropane-1-carboxamido)-3,3-dimethylbutanoyl)-2,3,3a,4,7,7a-hexahydro-1H-4,7-methanoisoindole-1-carboxamide (47.0 mg, 30%) as a white solid. ¹H NMR (400 MHz, 80° C., DMSO-d₆) δ 8.55-8.75 (m, 1H), 8.05-8.30 (m, 1H), 7.30-7.60 (m, 1H), 5.80-6.30 (m, 2H), 4.80-5.00 (m, 1H), 4.40-4.60 (m, 1H), 3.90-4.15 (m, 1H), 3.45-3.75 (m, 2H), 3.05-3.30 (m, 2H), 2.95-3.00 (m, 1H), 2.85-2.95 (m, 3H), 2.60-2.85 (m, 1H), 2.30-2.50 (m, 1H), 2.05-2.30 (m, 2H), 1.80-2.00 (m, 1H), 1.60-1.80 (m, 3H), 1.30-1.50 (m, 2H), 0.80-1.00 (m, 9H). LC-MS (ESI, m/z): 532 [M+H]⁺.

Example 34

Compound 34

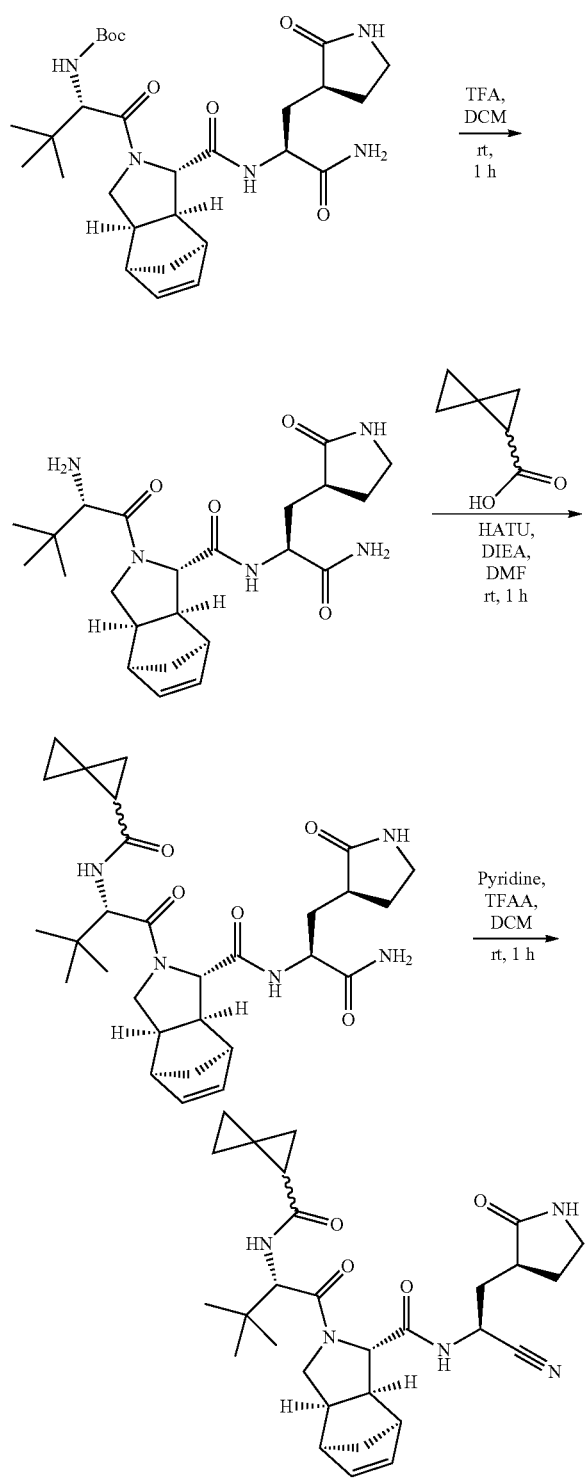

To a stirred mixture of tert-butyl N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxobutan-2-yl]carbamate (220 mg, 0.403 mmol, 1.0 eq.) in DCM (6 mL) were added trifluoroacetic acid (2 mL). The mixture was stirred for 1 h at rt and then concentrated under reduced pressure to afford (2S)-2-{[(1R,2S,3S,6R,7S)-4-[(2S)-2-amino-3,3-dimethylbutanoyl]-4-azatricyclo[5.2.1.0^{2,6}]dec-8-en-3-yl]formamido}-3-[(3S)-2-oxopyrrolidin-3-yl]propanamide (179 mg, crude) as a brown oil. LC-MS (ESI, m/z): 379 [M+H]⁺.

To a stirred mixture of spiro[2.2]pentane-1-carboxylic acid (47.3 mg, 0.422 mmol, 1.05 eq.) and o-(7-azabenzotriazol-1-yl)-N,N,N',N'-tetramethyluronium hexafluorophosphate (183 mg, 0.482 mmol, 1.2 eq.) in DMF (5 mL) were added N-ethyl-N-isopropylpropan-2-amine (415 mg, 3.21 mmol, 8.0 eq.) at 0° C. After stirred for 20 min at 0° C., (2S)-2-{[(1R,2S,3S,6R,7S)-4-[(2S)-2-amino-3,3-dimethylbutanoyl]-4-azatricyclo[5.2.1.0^{2,6}]dec-8-en-3-yl]formamido}-3-[(3S)-2-oxopyrrolidin-3-yl]propanamide (179 mg, 0.402 mmol, 1.0 eq.) was added. The mixture was stirred for 1 h at rt. The crude product was purified by C18 column with CH₃CN:Water (0.05% TFA). The desired fraction was concentrated under reduced pressure to provide N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxobutan-2-yl]spiro[2.2]pentane-1-carboxamide (145 mg, 65%) as a yellow solid. LC-MS (ESI, m/z): 540 [M+H]⁺

To a stirred mixture of N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxobutan-2-yl]spiro[2.2]pentane-1-carboxamide (120 mg, 0.222 mmol, 1.0 eq.) in DCM (4 mL) was added pyridine (66.8 mg, 0.844 mmol, 3.8 eq.) and trifluoroacetic anhydride (38.8 mg, 0.400 mmol, 1.8 eq.). The mixture was stirred for 1 h at rt. The reaction was quenched with water (10 mL). The mixture was extracted with EtOAc (3×10 mL). The organic layers were combined, washed with brine (2×10 mL), dried over anhydrous sodium sulfate, filtered and concentrated under reduced pressure to afford then crude product. The crude product was purified by prep-HPLC (Column: XBridge Prep OBD C18 Column, 19*250 mm, 5 m; Mobile Phase A: Water (0.1% FA), Mobile Phase B: ACN; Flow rate: 25 mL/min; Gradient: 38% B to 68% B in 7 min, 68% B; Wave Length: 254 nm; RT1 (min): 4.78) to provide (1R,2S,3S,6R,7S)—N-[(1S)-1-cyano-2-[(3S)-2-oxopyrrolidin-3-yl]ethyl]-4-[(2S)-3,3-dimethyl-2-{spiro[2.2]pentan-1-ylformamido}butanoyl]-4-azatricyclo[5.2.1.0^{2,6}]dec-8-ene-3-carboxamide (34.8 mg, 29%) as a white solid. ¹H NMR (400 MHz, 80° C., DMSO-d₆) δ 8.50-8.83 (m, 1H), 7.28-7.70 (m, 2H), 5.84-6.25 (m, 2H), 4.65-5.00 (m, 1H), 4.25-4.64 (m, 1H), 3.81-4.24 (m, 1H), 3.40-3.80 (m, 2H), 3.10-3.39 (m, 2H), 2.97-3.05 (m, 1H), 2.80-2.96 (m, 2H), 2.62-2.79 (m, 1H), 2.44-2.23 (m, 1H), 2.00-2.43 (m, 3H), 1.61-1.90 (m, 2H), 1.34-1.50 (m, 2H), 1.00-1.33 (m, 2H), 0.70-0.99 (m, 12H), 0.47-0.69 (m, 1H). LC-MS (ESI, m/z): 522 [M+H]⁺.

Example 35

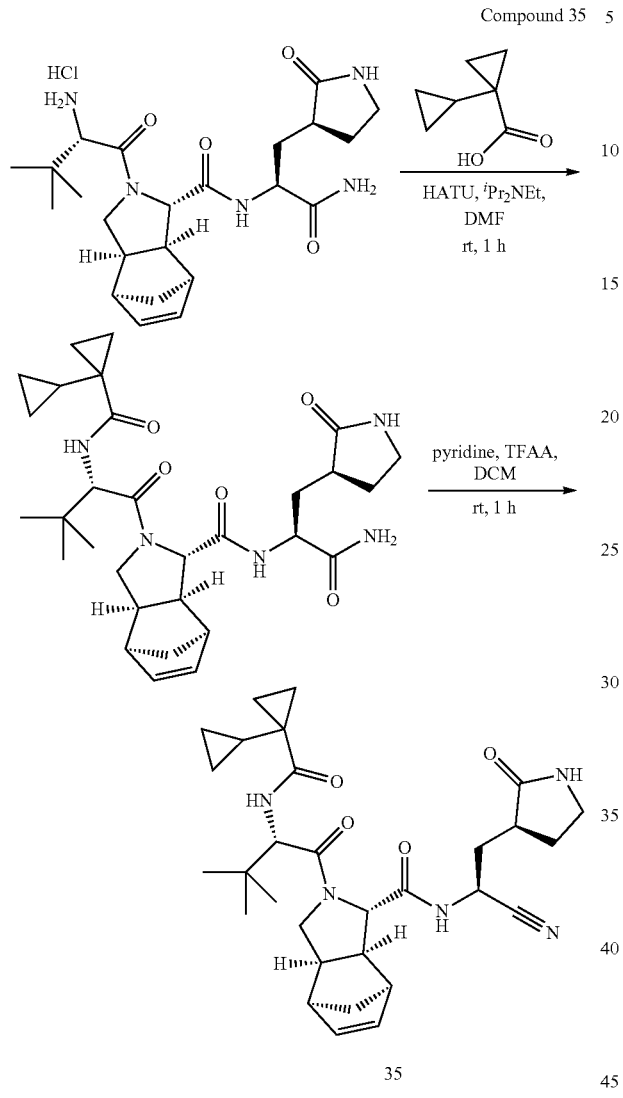

To a mixture of [1,1'-bi(cyclopropane)]-1-carboxylic acid (47.0 mg, 0.367 mmol, 1.0 eq.) and o-(7-azabenzotriazol-1-yl)-N,N,N',N'-tetramethyluronium hexafluorophosphate (168 mg, 0.440 mmol, 1.2 eq.) in DMF (3 mL) was added N-ethyl-N-isopropylpropan-2-amine (285 mg, 2.20 mmol, 6.0 eq.) at 0° C. After stirred for 15 min at 0° C., (2S)-2-{[(1R,2S,3S,6R,7S)-4-[(2S)-2-amino-3,3-dimethylbutanoyl]-4-azatricyclo[5.2.1.0^{2,6}]dec-8-en-3-yl]formamido}-3-[(3S)-2-oxopyrrolidin-3-yl]propanamide hydrochloride (177 mg, 0.367 mmol, 1.0 eq.) was added. The resulting was stirred for 1 h at rt. The mixture was purified by C18 column with CH$_3$CN:Water (0.05% TFA). The desired fraction was concentrated under reduced pressure to provide N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxobutan-2-yl]-[1,1'-bi(cyclopropane)]-1-carboxamide (180 mg, 81%) as an off-white solid. LC-MS (ESI, m/z): 554 [M+H]$^+$.

To a mixture of N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxobutan-2-yl]-[1,1'-bi(cyclopropane)]-1-carboxamide (180 mg, 0.325 mmol, 1.0 eq.) in DCM (5 mL) were added pyridine (103 mg, 1.30 mmol, 4.0 eq.) and trifluoroacetic anhydride (123 mg, 0.585 mmol, 1.8 eq.). The mixture was stirred for 1 h at rt. The reaction was quenched with water (20 mL). The mixture was extracted with DCM (3×20 mL). The organic layers were combined, washed with brine (2×20 mL), dried over anhydrous sodium sulfate, filtered and concentrated under reduced pressure to afford the crude product. The crude product was purified by prep-HPLC (Column: XBridge Prep OBD C18 Column, 19×250 mm, 5 m; Mobile Phase A: Water (0.1% FA), Mobile Phase B: ACN; Flow rate: 25 mL/min; Gradient: 40% B to 70% B in 7 min, 70% B; Wave Length: 254 nm; RT: 5.32 min) to provide (1R,2S,3S,6R,7S)-4-[(2S)-2-{[1,1'-bi(cyclopropane)]-1-ylformamido}-3,3-dimethylbutanoyl]-N-[(1S)-1-cyano-2-[(3S)-2-oxopyrrolidin-3-yl]ethyl]-4-azatricyclo[5.2.1.0^{2,6}]dec-8-ene-3-carboxamide (62.4 mg, 35%) as a white solid. $^1$H NMR (400 MHz, 80° C., DMSO-d$_6$) δ 8.60-8.85 (m, 1H), 7.32-7.60 (m, 1H), 6.84-7.13 (m, 1H), 5.90-6.20 (m, 2H), 4.60-4.98 (m, 1H), 4.40-4.53 (m, 1H), 3.96-4.20 (m, 1H), 3.55-3.77 (m, 1H), 3.38-3.54 (m, 1H), 3.10-3.25 (m, 2H), 3.00-3.05 (m, 1H), 2.78-2.99 (m, 2H), 2.60-2.77 (m, 1H), 2.30-2.42 (m, 1H), 2.05-2.29 (m, 2H), 1.63-1.89 (m, 2H), 1.30-1.45 (m, 2H), 1.15-1.29 (m, 1H), 0.85-1.10 (m, 10H), 0.70-0.84 (m, 1H), 0.32-0.65 (m, 4H), 0.05-0.20 (m, 2H). LC-MS (ESI, m/z): 536 [M+H]$^+$.

Example 36

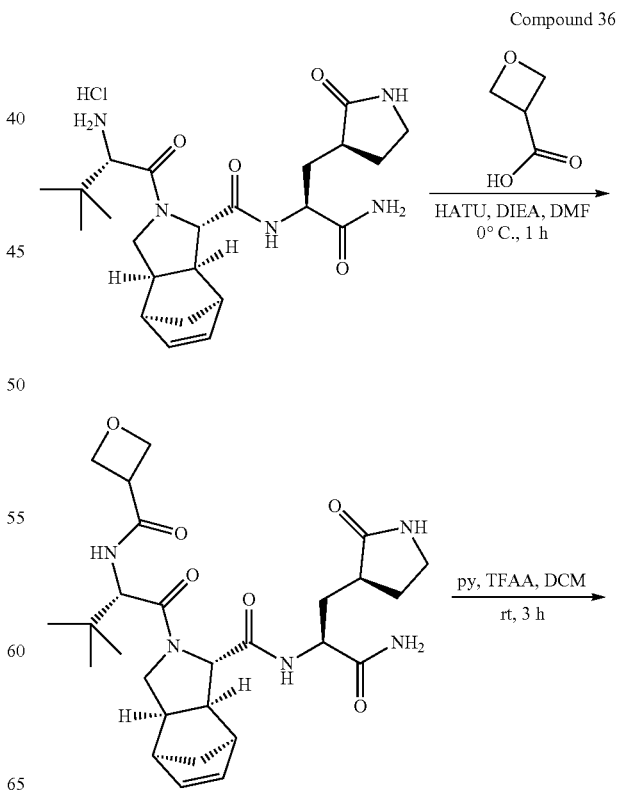

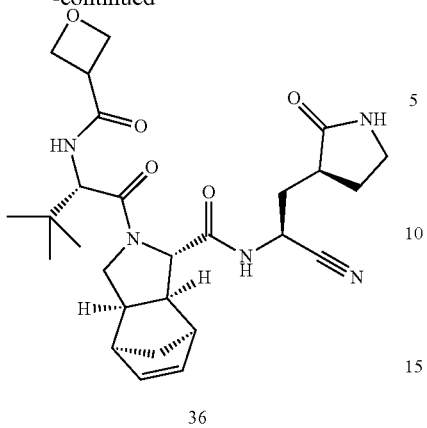

36

To a stirred mixture of oxetane-3-carboxylic acid (40.7 mg, 0.399 mmol, 1.1 eq.), o-(7-azabenzotriazol-1-yl)-N,N,N',N'-tetramethyluronium hexafluorophosphate (165 mg, 0.436 mmol, 1.2 eq.) in DMF (4 mL) was added N-ethyl-N-isopropylpropan-2-amine (281 mg, 2.17 mmol, 6.0 eq.). The mixture was stirred for 10 min at 0° C., and (2S)-2-{[(1R,2S,3S,6R,7S)-4-[(2S)-2-amino-3,3-dimethylbutanoyl]-4-azatricyclo[5.2.1.0^{2,6}]dec-8-en-3-yl]formamido}-3-[(3S)-2-oxopyrrolidin-3-yl]propanamide hydrochloride (175 mg, 0.363 mmol, 1.0 eq.) was added. The mixture was stirred for 1 h at rt. The mixture was purified by C18 column with CH$_3$CN:Water (0.05% FA). The desired fraction was concentrated under reduced pressure to provide N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxobutan-2-yl]oxetane-3-carboxamide (170 mg, 83%) as an off-white solid. LC-MS (ESI, m/z): 530 [M+H]$^+$.

To a stirred mixture of N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxobutan-2-yl]oxetane-3-carboxamide (170 mg, 0.321 mmol, 1.0 eq.) in DCM (3 mL) was added pyridine (101 mg, 1.28 mmol, 4.0 eq.) and trifluoroacetic anhydride (155 mg, 0.738 mmol, 2.3 eq.). The mixture was stirred for 2 h at rt. The reaction was quenched with water (10 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was purified by prep-HPLC with the following conditions (Column: XBridge Prep Phenyl OBD Column, 19*250 mm, 5 m; Mobile Phase A: Water (0.1% FA), Mobile Phase B: ACN; Flow rate: 25 mL/min; Gradient: 30% B to 60% B in 7 min, 60% B; Wave Length: 254 nm; RT1 (min): 6) to afford (1R,2S,3S,6R,7S)—N-[(1S)-1-cyano-2-[(3S)-2-oxopyrrolidin-3-yl]ethyl]-4-[(2S)-3,3-dimethyl-2-(oxetan-3-ylformamido)butanoyl]-4-azatricyclo[5.2.1.0^{2,6}]dec-8-ene-3-carboxamide (54.2 mg, 32%) as a white solid. $^1$H NMR (400 MHz, 80° C., DMSO-d$_6$) δ 8.57-8.65 (m, 1H), 7.58-7.65 (m, 1H), 7.30-7.55 (m, 1H), 6.09-6.14 (m, 1H), 5.90-5.96 (m, 1H), 4.83-4.92 (m, 1H), 4.53-4.75 (m, 3H), 4.44-4.52 (m, 2H), 3.92-4.20 (m, 1H), 3.75-3.92 (m, 1H), 3.58-3.67 (m, 1H), 3.50-3.58 (m, 1H), 3.07-3.21 (m, 2H), 2.97-3.02 (m, 1H), 2.83-2.97 (m, 2H), 2.64-2.83 (m, 1H), 2.26-2.40 (m, 1H), 2.04-2.19 (m, 2H), 1.60-1.81 (m, 2H), 1.33-1.42 (m, 2H), 0.80-0.90 (m, 9H). LC-MS (ESI, m/z): 512 [M+H]$^+$.

Example 37

Compound 37

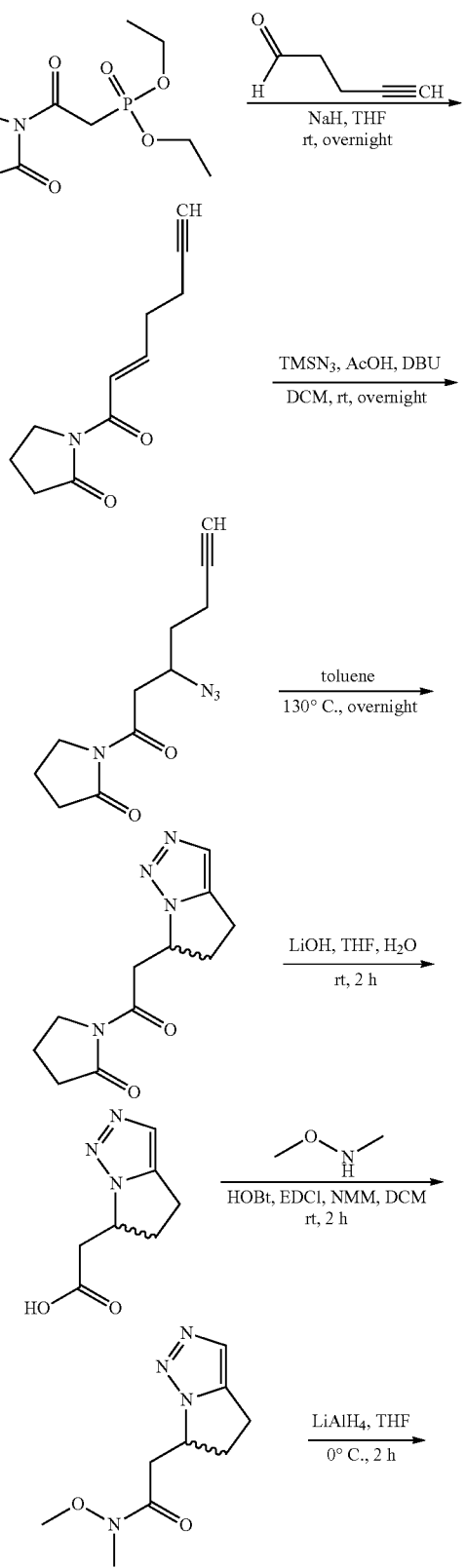

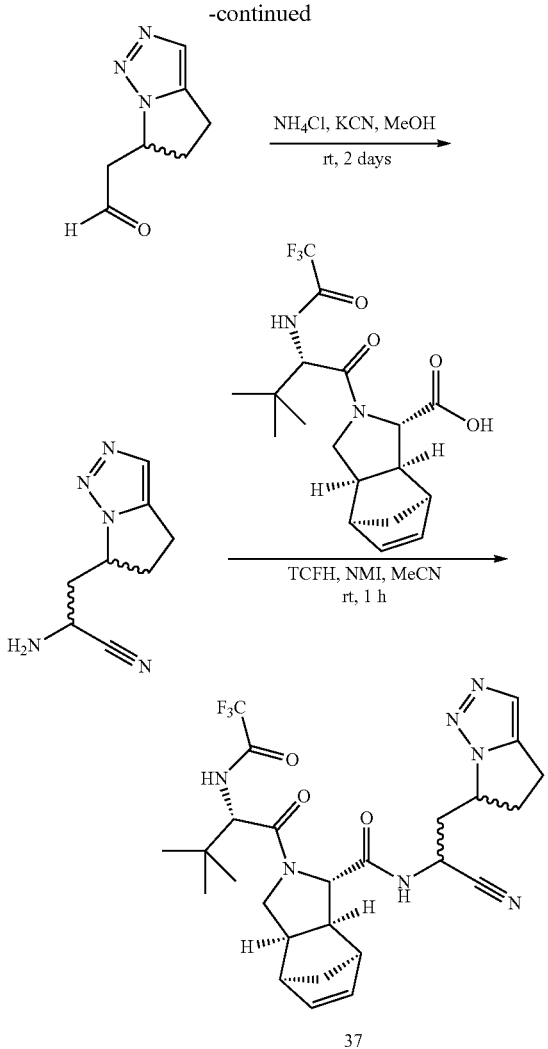

37

To a mixture of diethyl 2-oxo-2-(2-oxopyrrolidin-1-yl) ethylphosphonate (Gansauer et al., Ang. Chem. Int. Ed. (2009) 48(47), 8882-8885, S8882/1-S8882/32; 5.29 g, 20.1 mmol, 1.1 eq.) in THF (50 mL) was added sodium hydride (804 mg, 20.1 mmol, 1.1 eq., 60% in mineral oil) at 0° C. After stirred for 20 min at 0° C., a mixture of pent-4-ynal (1.50 g, 18.3 mmol, 1.0 eq.) in DCM (5 mL) was added. The mixture was stirred overnight at rt. The reaction was quenched with saturated aqueous ammonium chloride (100 mL). The mixture was extracted with DCM (3×100 mL). The organic layers were combined, washed with brine (2×100 mL), dried over anhydrous sodium sulfate, filtered and concentrated under reduced pressure to afford the crude product. The crude product was diluted with DCM (60 mL) and made into a slurry with 100~200 silica gel mesh (3 g). The slurry was loaded onto a column after removing the DCM. The sample was purified by column chromatography (Column size 5×24 cm, column volume: 300 mL, silica gel size (100~200 mesh) quantity: 120 g) and eluted with EtOAc/PE (0%~-50% over 30 min). The collected fractions: 33%-35% EtOAc/PE fractions were chosen as the pure fractions. Those fractions were combined and concentrated under reduced pressure to provide 1-[(2E)-hept-2-en-6-ynoyl]pyrrolidin-2-one (2.00 g, 55%) as a light yellow oil. $^1$H NMR (300 MHz, CDCl$_3$-d) δ 7.28-7.37 (m, 1H), 7.06-7.19 (m, 1H), 3.80-3.91 (m, 2H), 2.57-2.67 (m, 2H), 2.45-2.56 (m, 2H), 2.32-2.42 (m, 2H), 1.95-2.14 (m, 3H). LC-MS (ESI, m/z): 192 [M+H]$^+$.

To a mixture of trimethylsilyl azide (6.02 g, 52.3 mmol, 5.0 eq.) in DCM (50 mL) was added acetic acid (3.14 g, 52.3 mmol, 5.0 eq.). The mixture was stirred for 20 min at rt, and 1-[(2E)-hept-2-en-6-ynoyl]pyrrolidin-2-one (2.00 g, 10.5 mmol, 1.0 eq.) and 1,8-diazabicyclo[5.4.0]undec-7-ene (318 mg, 2.09 mmol, 0.2 eq.) in DCM (50 mL) were added. The mixture was stirred overnight at rt. The reaction quenched with saturated aqueous sodium bicarbonate (100 mL). The mixture was extracted with DCM (3×100 mL). The organic layers were combined, washed with brine (2×100 mL), dried over anhydrous sodium sulfate, filtered and concentrated under reduced pressure to afford the crude product. The crude product was diluted with DCM (60 mL) and made into a slurry with 100~200 silica gel mesh (5 g). The slurry was loaded to a column after removing the DCM. The sample was purified by column chromatography (Column size 5×24 cm, column volume: 300 mL, silica gel size (100~200 mesh) quantity: 120 g) and eluted with EtOAc/PE (0%-50% over 30 min). The collected fractions: 33%-35% EtOAc/PE fractions were chosen as the pure fractions. Those fractions were combined and concentrated under reduced pressure to provide 1-(3-azidohept-6-ynoyl)pyrrolidin-2-one (2.4 g, 96%) as a light yellow oil. $^1$H NMR (300 MHz, CDCl$_3$-d) δ 4.05-4.22 (m, 1H), 3.78-3.96 (m, 2H), 3.15-3.28 (m, 1H), 2.98-3.10 (m, 1H), 2.55-2.66 (m, 2H), 2.31-2.46 (m, 2H), 1.93-2.17 (m, 3H), 1.64-1.85 (m, 2H). LC-MS (ESI, m/z): 235 [M+H]$^+$.

A solution of 1-(3-azidohept-6-ynoyl)pyrrolidin-2-one (2.40 g, 10.2 mmol, 1.0 CDCl$_3$) in toluene (20 mL) was stirred overnight at 130° C. The mixture was concentrated under reduced pressure to afford the crude product. The crude product was diluted with DCM (50 mL) and made into a slurry with 100~200 silica gel mesh (5 g). The slurry was loaded to a column after removing the DCM. The sample was purified by column chromatography (Column size 5×24 cm, column volume: 300 mL, silica gel size (100~200 mesh) quantity: 120 g) and eluted with MeOH:DCM (0%-5% over 20 min). The collected fractions: 2%-3% MeOH:DCM fractions were chosen as the pure fractions. Those fractions were combined and concentrated under reduced pressure to provide 1-(2-{4H,5H,6H-pyrrolo[1,2-c][1,2,3]triazol-6-yl}acetyl)pyrrolidin-2-one (2.20 g, 73%) as a brown semi solid. $^1$H NMR (300 MHz, CDCl$_3$-d) δ 7.38 (s, 1H), 5.00-5.11 (m, 1H), 3.78-3.91 (m, 3H), 3.28-3.40 (m, 1H), 3.04-3.17 (m, 1H), 2.87-2.99 (m, 2H), 2.57-2.64 (m, 2H), 2.44-2.55 (m, 1H), 2.02-2.13 (m, 2H). LC-MS (ESI, m/z): 235 [M+H]$^+$.

To a mixture of 1-(2-{4H,5H,6H-pyrrolo[1,2-c][1,2,3]triazol-6-yl}acetyl)pyrrolidin-2-one (1.00 g, 4.27 mmol, 1.0 eq.) in THF (5 mL):water (5 mL) was added lithium hydroxide (307 mg, 12.8 mmol, 3.0 eq.). The mixture was stirred for 2 h at rt. The mixture was concentrated under reduced pressure to remove the THF and adjusted to pH=6 with HCl (2 M). The mixture was extracted with EtOAc (5×20 mL). The organic layers were combined, washed with brine (2×10 mL), dried over anhydrous sodium sulfate, filtered and concentrated under reduced pressure to afford 4H,5H,6H-pyrrolo[1,2-c][1,2,3]triazol-6-ylacetic acid (600 mg, crude) as a yellow semi-solid. LC-MS (ESI, m/z): 168 [M+H]$^+$.

To a mixture of 4H,5H,6H-pyrrolo[1,2-c][1,2,3]triazol-6-ylacetic acid (600 mg, 3.59 mmol, 1.0 eq.) in DCM (15 mL) were added N,O-dimethylhydroxylamine hydrochloride (350 mg, 3.59 mmol, 1.0 eq.), 1-hydroxybenzotriazole (485 mg, 3.59 mmol, 1.0 eq.), 1-(3-dimethylaminopropyl)-3-ethylcarbodiimide hydrochloride (757 mg, 3.95 mmol, 1.1 eq.) and N-methylmorphline (1.09 g, 10.77 mmol, 3.0 eq.) at rt. The mixture was stirred for 2 h at rt. The reaction was quenched with water (30 mL). The mixture was extracted with DCM (4×30 mL). The organic layers were combined, washed with brine (30 mL), dried over anhydrous sodium sulfate, filtered and concentrated under reduced pressure to afford the crude product. The crude product was diluted with DCM (30 mL) and made into a slurry with 100~200 silica gel mesh (3 g). The slurry was loaded to a column after removing the DCM. The sample was purified by column chromatography (Column size 5×24 cm, column volume: 300 mL, silica gel size (100~200 mesh) quantity: 120 g) and eluted with MeOH:DCM (0%-10% over 20 min). The collected fractions: 3% MeOH:DCM fractions were chosen as the pure fractions. Those fractions were combined and concentrated under reduced pressure to provide N-methoxy-N-methyl-2-{4H,5H,6H-pyrrolo[1,2-c][1,2,3]triazol-6-yl}acetamide (340 mg, 40%) as a yellow oil. $^1$H NMR (300 MHz, CDCl$_3$-d) δ 7.43 (s, 1H), 4.91-5.05 (m, 1H), 3.70 (s, 3H), 3.46-3.56 (m, 1H), 3.22 (s, 3H), 3.08-3.20 (m, 1H), 2.80-2.98 (m, 3H), 2.45-2.59 (m, 1H). LC-MS (ESI, m/z): 211 [M+H]$^+$.

To a mixture of N-methoxy-N-methyl-2-{4H,5H,6H-pyrrolo[1,2-c][1,2,3]triazol-6-yl}acetamide (300 mg, 1.43 mmol, 1.0 eq.) in THF (6 mL) was added dropwise lithium aluminum hydride (0.68 mL, 1.71 mmol, 1.2 eq., 2.5 M in THF) at 0° C. under nitrogen. The mixture was stirred for 2 h at 0° C. The reaction was quenched with saturated aqueous ammonium chloride (20 mL). The mixture was extracted with chloroform:isopropyl alcohol (5/1, 4×20 mL). The organic layers were combined, washed with brine (2×20 mL), dried over anhydrous sodium sulfate, filtered and concentrated under reduced pressure to afford 2-{4H,5H, 6H-pyrrolo[1,2-c][1,2,3]triazol-6-yl}acetaldehyde (216 mg, crude) as a yellow oil. LC-MS (ESI, m/z): 152 [M+H]$^+$.

To a mixture of 2-{4H,5H,6H-pyrrolo[1,2-c][1,2,3]triazol-6-yl}acetaldehyde (216 mg, 1.43 mmol, 1.0 eq.) in MeOH (5 mL) was added ammonium chloride (153 mg, 2.86 mmol, 2.0 eq.). After being stirred for 2 h at rt, potassium cyanide (140 mg, 2.14 mmol, 1.5 eq.) was added. The mixture was stirred for 2 days at rt, and then filtered. The filtrate was concentrated under reduced pressure to remove the MeOH. The residue was diluted with DCM (5 mL) and filtered. The filtrate was concentrated under reduced pressure to provide 2-amino-3-{4H,5H,6H-pyrrolo [1,2-c][1,2,3]triazol-6-yl}propanenitrile (190 mg, crude) as a yellow oil. LC-MS (ESI, m/z): 178 [M+H]$^+$.

To a mixture of (1R,2S,3S,6R,7S)-4-[(2S)-3,3-dimethyl-2-(2,2,2-trifluoroacetamido)butanoyl]-4-azatricyclo [5.2.1.0^{2,6}]dec-8-ene-3-carboxylic acid (416 mg, 1.07 mmol, 1.0 eq.), 2-amino-3-{4H,5H,6H-pyrrolo[1,2-c][1,2,3]triazol-6-yl}propanenitrile (190 mg, 1.07 mmol, 1.0 eq.) and N,N,N',N'-Tetramethylchloroformamidinium hexafluorophosphate (391 mg, 1.39 mmol, 1.3 eq.) in acetonitrile (10 mL) was added N-methylimidazole (880 mg, 10.7 mmol, 10.0 eq.). The mixture was stirred for 1 h at rt. The reaction was quenched with water (30 mL). The mixture was extracted with EtOAc (3×30 mL). The organic layers were combined, washed with brine (2×30 mL), dried over anhydrous sodium sulfate, filtered and concentrated under reduced pressure to remove then EtOAc. The residue was chromatographed on a silica gel column with MeOH:DCM (8/92) to afford the crude product. The crude product was purified by preparative HPLC (Column: Xselect CSH C18 OBD Column 30×150 mm 5 m, n; Mobile Phase A: Water (0.1% FA), Mobile Phase B: ACN; Flow rate: 60 mL/min; Gradient: 25% B to 45% B in 8 min, 45% B; Wave Length: 254/220 nm; RT: 6.7 min) to provide (1R,2S,3S,6R,7S)—N-(1-cyano-2-{4H,5H,6H-pyrrolo[1,2-c][1,2,3]triazol-6-yl}ethyl)-4-[(2S)-3,3-dimethyl-2-(2,2,2-trifluoroacetamido) butanoyl]-4-azatricyclo[5.2.1.0^{2,6}]dec-8-ene-3-carboxamide (56.0 mg, 9%) as a white solid. LC-MS (ESI, m/z): 548 [M+H]$^+$.

Example 38

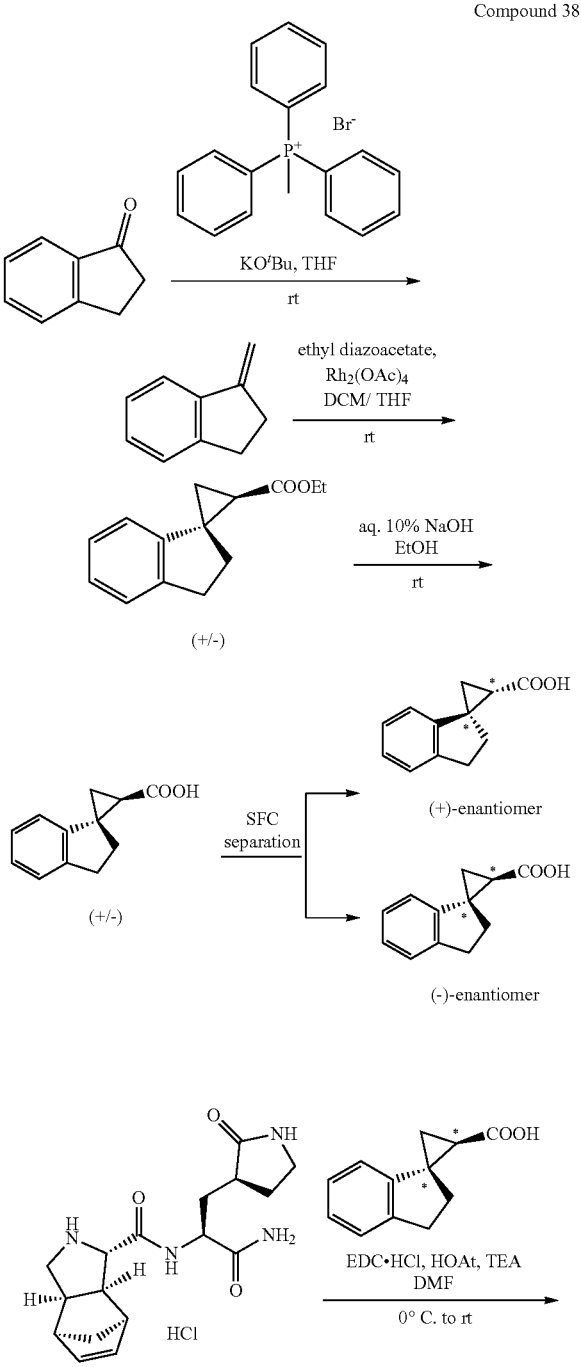

Compound 38

38

The chiral centers noted with "*" are tentatively assigned.

To a suspension of 2,3-dihydro-1H-inden-1-one (4.0 g, 30.3 mmol, 1 eq.) and methyltriphenylphosphonium bromide (16.2 g, 45.4 mmol, 2 eq.) in THF (52 mL) was added dropwise a solution of tBuOK (6.8 g, 60.5 mmol, 2 eq.) in THF (27 mL) over a period of 2 h. The mixture was stirred at rt for 3 h and was concentrated under reduced pressure. The residue was taken up in hexane. The mixture was filtered through a silica-gel plug and rinsed with hexane to get 1-methylene-2,3-dihydro-1H-indene (2.8 g, 71%) as a colorless liquid.

To a solution of 1-methylene-2,3-dihydro-1H-indene (2 g, 15.4 mmol, 1 eq.) and $Rh_2(OAc)_4$ (69 mg, 0.153 mmol, 0.01 eq.) in DCM (6 mL) was added a solution of ethyl diazoacetate (4.05 mL, 38.4 mmol, 2.5 eq.) in THF (4 mL) over a period of 1 h. The mixture was stirred at rt for 1 h and then concentrated under reduced pressure. The residue was purified by flash chromatography on silica gel using a gradient of EA (0 to 2%) in PE and by prep-HPLC (Column: KROMOSIL-C18, 25×150 mm 7 um; Mobile Phase A: 10 mM $NH_4HCO_3$ in water, Mobile Phase B: ACN; Flow rate: 22 mL/min; Isocratic eluent: 70% B) to afford trans ethyl 2',3'-dihydrospiro[cyclopropane-1,1'-indene]-2-carboxylate (650 mg, 19%) as an off-white solid. $^1$H NMR (400 MHz, DMSO-$d_6$) δ 7.18-7.24 (m, 1H), 7.11-7.17 (m, 2H), 6.85-6.92 (m, 1H), 4.10 (q, 2H), 2.85-3.02 (m, 2H), 2.13 (t, 2H), 2.03 (t, 1H), 1.45-1.52 (m, 2H), 1.18 (t, 3H). LC-MS (ESI, m/z): 217 [M+H]$^+$.

250 mg of cis ethyl 2',3'-dihydrospiro[cyclopropane-1,1'-indene]-2-carboxylate was also obtained.

To a solution of trans ethyl 2',3'-dihydrospiro[cyclopropane-1,1'-indene]-2-carboxylate (350 mg, 1.62 mmol, 1 eq.) in EtOH (3.7 mL) was added 10% NaOH aqueous solution (2.7 mL, 6.17 mmol, 4 eq.). The mixture was stirred at rt for 18 h. The mixture was diluted with water (10 mL) and extracted with Et$_2$O (3×5 mL). The aqueous phase was acidified with 1M HCl and extracted with EA (3×10 mL). The organic phases were combined, dried over Na$_2$SO$_4$, filtered and concentrated under reduced pressure to afford trans 2',3'-dihydrospiro[cyclopropane-1,1'-indene]-2-carboxylic acid (300 mg, 98%) as a white solid.

trans 2',3'-Dihydrospiro[cyclopropane-1,1'-indene]-2-carboxylic acid (450 mg) was purified by prep-SFC using the following conditions: Column: Chiralpak AD-H, 4.6*25 cm, 5 m; Mobile Phase A: CO$_2$, Mobile Phase B: MeOH; Flow rate: 60 g/min; Gradient: isocratic 15% B; Column Temperature: 30° C.; Back Pressure: 100 bar. Purification resulted in (1S*,2S*)-2',3'-dihydrospiro[cyclopropane-1,1'-indene]-2-carboxylic acid (210 mg) and (1R*,2R*)-2',3'-dihydrospiro[cyclopropane-1,1'-indene]-2-carboxylic acid (180 mg).

(1S*,2S*)-2',3'-Dihydrospiro[cyclopropane-1,1'-indene]-2-carboxylic acid: $^1$H NMR (400 MHz, DMSO-$d_6$) δ 11.99 (brs, 1H), 7.18-7.25 (m, 1H), 7.10-7.17 (m, 2H), 6.82-6.88 (m, 1H), 2.88-3.20 (m, 2H), 2.08-2.22 (m, 2H), 1.88-1.95 (m, 1H), 1.38-1.48 (m, 2H). $[α]_{25}^{D}$: +444.3° (c 0.1, MeOH). SFC: Chiralpak IG, 4.6*150 mm, 5 m, 30° C., co-Solvent: MeOH, hold 7 min at 10%, Rt: 2.21 min.

(1R*,2R*)-2',3'-Dihydrospiro[cyclopropane-1,1'-indene]-2-carboxylic acid: $^1$H NMR (500 MHz, DMSO-$d_6$) δ 12.10 (brs, 1H), 7.18-7.24 (m, 1H), 7.10-7.17 (m, 2H), 6.82-6.87 (m, 1H), 2.90-3.00 (m, 2H), 2.10-2.22 (m, 2H), 1.90-1.94 (m, 1H), 1.38-1.45 (m, 2H). $[α]_{25}^{D}$: −335.9° (c 0.1, MeOH). SFC: Chiralpak IG, 4.6*150 mm, 5 m, 30° C., co-Solvent: MeOH, hold 7 min at 10%, Rt: 2.89 min.

To a solution of (1S,3aR,4S,7R,7aS)—N—((S)-1-amino-1-oxo-3-((S)-2-oxopyrrolidin-3-yl)propan-2-yl)-2,3,3a,4,7,7a-hexahydro-1H-4,7-methanoisoindole-1-carboxamide hydrochloride (120 mg, 0.325 mmol, 1.0 eq.) in DMF (1.0 mL) cooled at 0° C. were added (1R*,2R*)-2',3'-dihydrospiro[cyclopropane-1,1'-indene]-2-carboxylic acid (61 mg, 0.324 mmol, 1.0 eq.), EDC•HCl (122 mg, 0.637 mmol, 2.0 eq.), HOAt (43 mg, 0.320 mmol, 1.0 eq.) and NEt$_3$ (0.170 mL, 1.28 mmol, 3.0 eq.). The mixture was stirred at rt for 16 h. The mixture was diluted with water (5 mL) and extracted with EA (3×10 mL). The organic phases were combined, dried over Na$_2$SO$_4$, filtered and concentrated under reduced pressure. The residue was purified by flash chromatography on silica gel (12 g column) using a gradient of MeOH (1 to 10%) in DCM to afford (1S,3aR,4S,7R,7aS)—N—((S)-1-amino-1-oxo-3-((S)-2-oxopyrrolidin-3-yl)propan-2-yl)-2-((1R*,2R*)-2',3'-dihydrospiro[cyclopropane-1,1'-indene]-2-carbonyl)-2,3,3a,4,7,7a-hexahydro-1H-4,7-methanoisoindole-1-carboxamide (100 mg, 61%) as a white solid. LC-MS (ESI, m/z): 503 [M+H]$^+$.

To a solution of (1S,3aR,4S,7R,7aS)—N—((S)-1-amino-1-oxo-3-((S)-2-oxopyrrolidin-3-yl)propan-2-yl)-2-((1R*,2R*)-2',3'-dihydrospiro[cyclopropane-1,1'-indene]-2-carbonyl)-2,3,3a,4,7,7a-hexahydro-1H-4,7-methanoisoindole-1-carboxamide (80 mg, 0.159 mmol, 1.0 eq.) in DMF (0.8 mL) were added pyridine (0.038 mL, 0.470 mmol, 3.0 eq.) and TFAA (0.040 mL; 0.318 mmol, 2.0 eq.). The mixture was stirred at rt for 1 h. The mixture was diluted with water (10 mL) and extracted with EA (3×10 mL). The organic phases were combined, washed with brine (2×10 mL), dried over Na$_2$SO$_4$, filtered and concentrated under reduced pressure. The residue was purified by flash chromatography on C18 gel (12 g column) using 0.01% ammonium bicarbonate/ACN and by flash chromatography on silica gel (12 g column) using a gradient of MeOH (1 to 10%) in DCM to afford (1S,3aR,4S,7R,7aS)—N—((S)-1-cyano-2-((S)-2-oxopyrrolidin-3-yl)ethyl)-2-((1R*,2R*)-2',3'-dihydrospiro[cyclopropane-1,1'-indene]-2-carbonyl)-2,3,3a,4,7,7a-hexahydro-1H-4,7-methanoisoindole-1-carboxamide (25 mg, 35%) as a white solid. $^1$H NMR (400 MHz, 360K, DMSO-$d_6$) δ 8.25-8.55 (m, 1H), 7.00-7.42 (m, 4H), 6.70-6.88 (m, 1H), 5.85-6.22 (m, 2H), 4.25-4.95 (m, 1H), 3.98-4.12 (m, 1H), 3.31-3.67 (m, 1H), 3.00-3.22 (m, 4H), 2.70-2.95 (m, 5H), 2.30-2.42 (m, 1H), 1.94-2.22 (m, 4H), 1.68-1.90 (m, 2H), 1.20-1.55 (m, 5H). LCMS (ESI, m/z): 485 [M+H]+.

Example 39

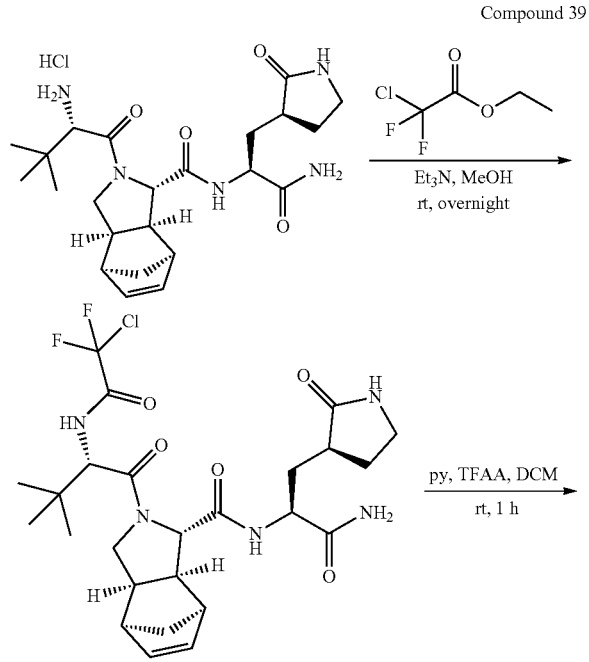

To a mixture of (2S)-2-{[(1R,2S,3S,6R,7S)-4-[(2S)-2-amino-3,3-dimethylbutanoyl]-4-azatricyclo[5.2.1.0^{2,6}]dec-8-en-3-yl]formamido}-3-[(3S)-2-oxopyrrolidin-3-yl]propanamide hydrochloride (177 mg, 0.367 mmol, 1.0 eq.) in MeOH (5 mL) was added triethylamine (446 mg, 4.40 mmol, 12.0 eq.) and ethyl 2-chloro-2,2-difluoroacetate (582 mg, 3.67 mmol, 10.0 eq.). The mixture was stirred overnight at rt, and then concentrated under reduced pressure to remove the MeOH. The mixture was diluted with water (20 mL) and the pH was adjusted to 6 with hydrochloric acid (1 M). The mixture was extracted with EtOAc (3×20 mL). The organic layers were combined, washed with brine (2×20 mL), dried over anhydrous sodium sulfate, filtered and concentrated under reduced pressure to provide (2S)-2-{[(1R,2S,3S,6R,7S)-4-[(2S)-2-(2-chloro-2,2-difluoroacetamido)-3,3-dimethylbutanoyl]-4-azatricyclo[5.2.1.0^{2,6}]dec-8-en-3-yl]formamido}-3-[(3S)-2-oxopyrrolidin-3-yl]propanamide (180 mg, 80%) as a light yellow solid. LC-MS (ESI, m/z): 558 [M+H]+.

To a mixture of (2S)-2-{[(1R,2S,3S,6R,7S)-4-[(2S)-2-(2-chloro-2,2-difluoroacetamido)-3,3-dimethylbutanoyl]-4-azatricyclo[5.2.1.0^{2,6}]dec-8-en-3-yl]formamido}-3-[(3S)-2-oxopyrrolidin-3-yl]propanamide (180 mg, 0.323 mmol, 1.0 eq.) in DCM (3 mL) was added pyridine (102 mg, 1.29 mmol, 4.0 eq.) and trifluoroacetic anhydride (122 mg, 0.581 mmol, 1.8 eq.). The mixture was stirred for 1 h at rt. The reaction was quenched with water (20 mL). The mixture was extracted with DCM (3×20 mL). The organic layers were combined, washed with brine (2×20 mL), dried over anhydrous sodium sulfate, filtered and concentrated under reduced pressure to afford the crude product. The crude product was purified by prep-HPLC (Column: XBridge Shield RP18 OBD Column, 19×250 mm, 10 m; Mobile Phase A: Water (0.1% FA), Mobile Phase B: ACN; Flow rate: 25 mL/min; Gradient: 40% B to 70% B in 7 min, 70% B; Wave Length: 254 nm; RT: 5.4 min;) to provide (1R,2S,3S,6R,7S)-4-[(2S)-2-(2-chloro-2,2-difluoroacetamido)-3,3-dimethylbutanoyl]-N-[(1S)-1-cyano-2-[(3S)-2-oxopyrrolidin-3-yl]ethyl]-4-azatricyclo[5.2.1.0^{2,6}]dec-8-ene-3-carboxamide (41.2 mg, 23%) as a white solid. 1H NMR (400 MHz, 80° C., DMSO-d6) δ 8.65-8.90 (m, 1H), 8.40-8.64 (m, 1H), 7.30-7.62 (m, 1H), 5.95-6.25 (m, 2H), 4.83-5.01 (m, 1H), 4.40-4.75 (m, 1H), 3.95-4.20 (m, 1H), 3.56-3.75 (m, 1H), 3.32-3.55 (m, 1H), 3.06-3.30 (m, 2H), 3.01-3.05 (m, 1H), 2.80-3.00 (m, 2H), 2.60-2.79 (m, 1H), 2.21-2.40 (m, 1H), 2.00-2.20 (m, 2H), 1.60-1.95 (m, 2H), 1.30-1.48 (m, 2H), 0.72-1.10 (m, 9H). LC-MS (ESI, m/z): 540 [M+H]+.

Example 40

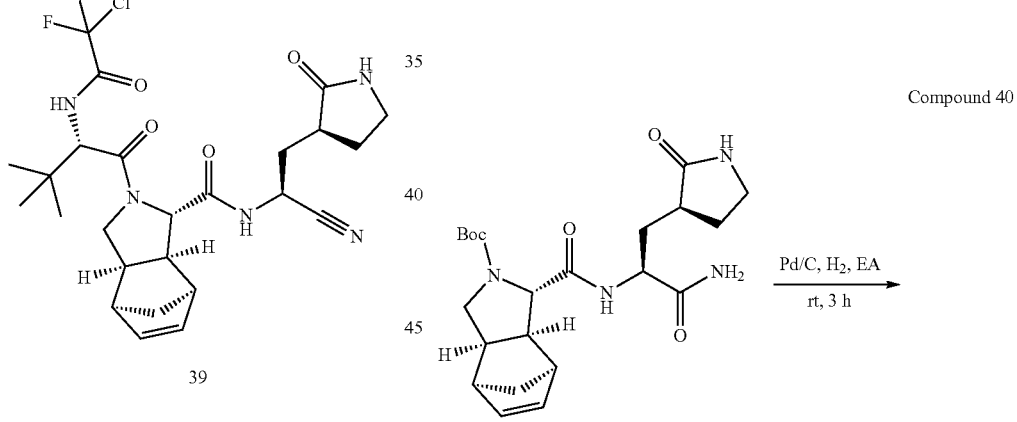

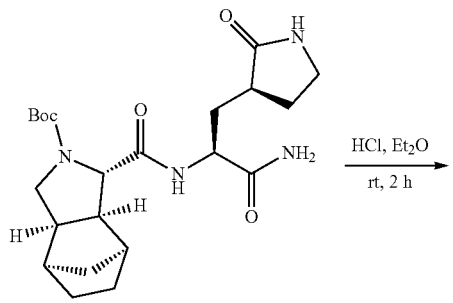

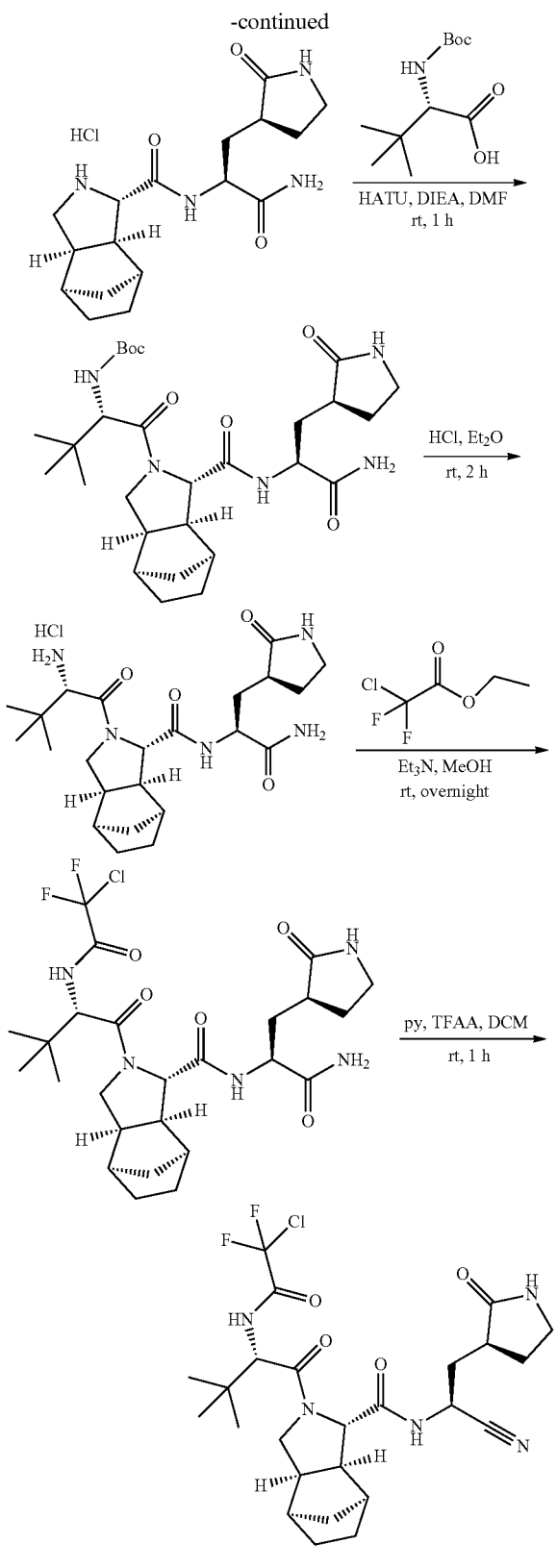

To a mixture of tert-butyl (1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-ene-4-carboxylate (250 mg, 0.578 mmol, 1.0 eq.) in EtOAc (5 mL) was added 10% palladium on activated carbon (120 mg). The mixture was stirred for 3 h at rt under hydrogen and then filtered. The filtrate was concentrated under reduced pressure to provide tert-butyl (1S,2S,3S,6R,7R)-3-{[(1S)-1-carbamoyl-2-[(3S)-2-oxopyrrolidin-3-yl]ethyl]carbamoyl}-4-azatricyclo[5.2.1.0^{2,6}]decane-4-carboxylate (200 mg, 75%) as an off-white solid. LC-MS (ESI, m/z): 435 [M+H]+.

A mixture of tert-butyl (1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-ene-4-carboxylate (200 mg, 0.462 mmol, 1.0 eq.) in hydrogen chloride (5 mL, 2M in Et₂O) was stirred for 2 h at rt. The mixture was concentrated under reduced pressure to afford (2S)-2-[(1S,2S,3S,6R,7R)-4-azatricyclo[5.2.1.0^{2,6}]decan-3-ylformamido]-3-[(3S)-2-oxopyrrolidin-3-yl]propanamide hydrochloride (170 mg, crude) as an off-white solid. LC-MS (ESI, m/z): 335 [M+H]+.

To a mixture of (2S)-2-[(tert-butoxycarbonyl)amino]-3,3-dimethylbutanoic acid (106 mg, 0.458 mmol, 1.0 eq.) and o-(7-azabenzotriazol-1-yl)-N,N,N',N'-tetramethyluronium hexafluorophosphate (209 mg, 0.550 mmol, 1.2 eq.) in DMF (3 mL) was added N-ethyl-N-isopropylpropan-2-amine (355 mg, 2.75 mmol, 6.0 eq.) at 0° C. After stirred for 15 min at 0° C., (2S)-2-[(1S,2S,3S,6R,7R)-4-azatricyclo[5.2.1.0^{2,6}]decan-3-ylformamido]-3-[(3S)-2-oxopyrrolidin-3-yl]propanamide hydrochloride (170 mg, 0.458 mmol, 1.0 eq.) was added. The mixture was stirred for 1 h at rt. The mixture was purified by C18 column with CH₃CN:Water (0.05% TFA). The desired fraction was concentrated under reduced pressure to provide tert-butyl N-[(2S)-1-[(1S,2S,3S,6R,7R)-3-{[(1S)-1-carbamoyl-2-[(3S)-2-oxopyrrolidin-3-yl]ethyl]carbamoyl}-4-azatricyclo[5.2.1.0^{2,6}]decan-4-yl]-3,3-dimethyl-1-oxobutan-2-yl]carbamate (155 mg, 59%) as a light yellow solid. LC-MS (ESI, m/z): 548 [M+H]+.

A mixture of tert-butyl N-[(2S)-1-[(1S,2S,3S,6R,7R)-3-{[(1S)-1-carbamoyl-2-[(3S)-2-oxopyrrolidin-3-yl]ethyl]carbamoyl}-4-azatricyclo[5.2.1.0^{2,6}]decan-4-yl]-3,3-dimethyl-1-oxobutan-2-yl]carbamate (155 mg, 0.283 mmol, 1.0 eq.) in hydrogen chloride (5 mL, 2 M in Et₂O) was stirred for 2 h at rt. The mixture was concentrated under reduced pressure to afford (2S)-2-{[(1S,2S,3S,6R,7R)-4-[(2S)-2-amino-3,3-dimethylbutanoyl]-4-azatricyclo[5.2.1.0^{2,6}]decan-3-yl]formamido}-3-[(3S)-2-oxopyrrolidin-3-yl]propanamide hydrochloride (137 mg, crude) as an off-white solid. LC-MS (ESI, m/z): 448 [M+H]+.

To a mixture of (2S)-2-{[(1S,2S,3S,6R,7R)-4-[(2S)-2-amino-3,3-dimethylbutanoyl]-4-azatricyclo[5.2.1.0^{2,6}]decan-3-yl]formamido}-3-[(3S)-2-oxopyrrolidin-3-yl]propanamide hydrochloride (137 mg, 0.283 mmol, 1.0 eq.) in MeOH (3 mL) was added triethylamine (344 mg, 3.40 mmol, 12.0 eq.) and ethyl 2-chloro-2,2-difluoroacetate (449 mg, 2.83 mmol, 10.0 eq.). The mixture was stirred overnight at rt. The mixture was concentrated under reduced pressure to remove MeOH. The mixture was diluted with water (20 mL) and the pH was adjusted to 6 with hydrochloric acid (1 M). The mixture was extracted with EtOAc (3×20 mL). The organic layers were combined, washed with brine (2×20 mL), dried over anhydrous sodium sulfate, filtered and concentrated under reduced pressure to provide (2S)-2-{[(1S,2S,3S,6R,7R)-4-[(2S)-2-(2-chloro-2,2-difluoroacetamido)-3,3-dimethylbutanoyl]-4-azatricyclo[5.2.1.0^{2,6}]decan-3-yl]formamido}-3-[(3S)-2-oxopyrrolidin-3-yl]propanamide (100 mg, 57%) as a yellow solid. LC-MS (ESI, m/z): 560 [M+H]+.

To a mixture of (2S)-2-{[(1S,2S,3S,6R,7R)-4-[(2S)-2-(2-chloro-2,2-difluoroacetamido)-3,3-dimethylbutanoyl]-4- azatricyclo[5.2.1.0^{2,6}]decan-3-yl]formamido}-3-[(3S)-2-oxopyrrolidin-3-yl]propanamide (100 mg, 0.179 mmol, 1.0 eq.) in DCM (3 mL) was added pyridine (56.0 mg, 0.716 mmol, 4.0 eq.) and trifluoroacetic anhydride (68.0 mg, 0.322 mmol, 1.8 eq.). The mixture was stirred for 1 h at rt. The reaction was quenched with water (10 mL). The mixture was extracted with DCM (3×10 mL). The organic layers were combined, washed with brine (2×10 mL), dried over anhydrous sodium sulfate, filtered and concentrated under reduced pressure to afford the crude product. The crude product was purified by prep-HPLC (Column: XBridge Shield RP18 OBD Column, 19×250 mm, 10 m; Mobile Phase A: Water (0.1% FA), Mobile Phase B: ACN; Flow rate: 25 mL/min; Gradient: 40% B to 70% B in 7 min, 70% B; Wave Length: 254 nm; RT: 5.43 min) to provide (1S,2S,3S,6R,7R)-4-[(2S)-2-(2-chloro-2,2-difluoroacetamido)-3,3-dimethylbutanoyl]-N-[(1S)-1-cyano-2-[(3S)-2-oxopyrrolidin-3-yl]ethyl]-4-azatricyclo[5.2.1.0^{2,6}]decane-3-carboxamide (25.2 mg, 25%) as a white solid. $^1$H NMR (400 MHz, 80° C., DMSO-$d_6$) δ 8.55-8.80 (m, 2H), 7.35-7.60 (m, 1H), 4.80-4.95 (m, 1H), 4.60-4.75 (m, 1H), 4.40-4.55 (m, 1H), 3.75-3.90 (m, 1H), 3.50-3.74 (m, 1H), 3.10-3.40 (m, 2H), 2.60-2.73 (m, 1H), 2.36-2.44 (m, 1H), 2.26-2.35 (m, 2H), 2.17-2.22 (m, 1H), 2.00-2.16 (m, 2H), 1.61-1.89 (m, 2H), 1.40-1.60 (m, 2H), 1.20-1.38 (m, 3H), 1.05-1.19 (m, 1H), 0.76-1.04 (m, 9H). LC-MS (ESI, m/z): 542 [M+H]$^+$.

Example 41

Compound 41

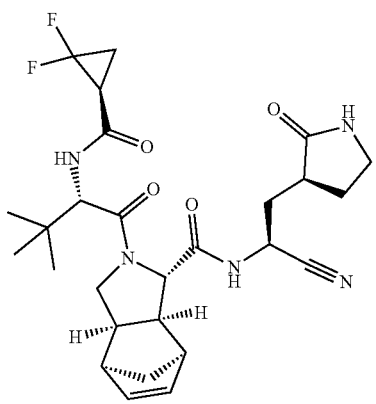

Compound was prepare similarly as described or compound 33, using (S)-2,2-difluorocyclopropane-1-carboxylic acid in place of (R)-2,2-difluorocyclopropane-1-carboxylic acid. $^1$H NMR (400 MHz, 80° C., DMSO-$d_6$) δ 8.55-8.80 (m, 1H), 7.80-8.20 (m, 1H), 7.30-7.60 (m, 1H), 5.85-6.30 (m, 2H), 4.70-5.00 (m, 1H), 4.40-4.60 (m, 1H), 3.90-4.25 (m, 1H), 3.30-3.70 (m, 2H), 3.10-3.25 (m, 2H), 2.95-3.05 (m, 1H), 2.85-2.95 (m, 2H), 2.60-2.85 (m, 2H), 2.30-2.50 (m, 1H), 2.05-2.30 (m, 2H), 1.60-2.00 (m, 4H), 1.30-1.50 (m, 2H), 0.80-1.00 (m, 9H). LC-MS (ESI, m/z): 532 [M+H]$^+$.

Example 42

Compound 42

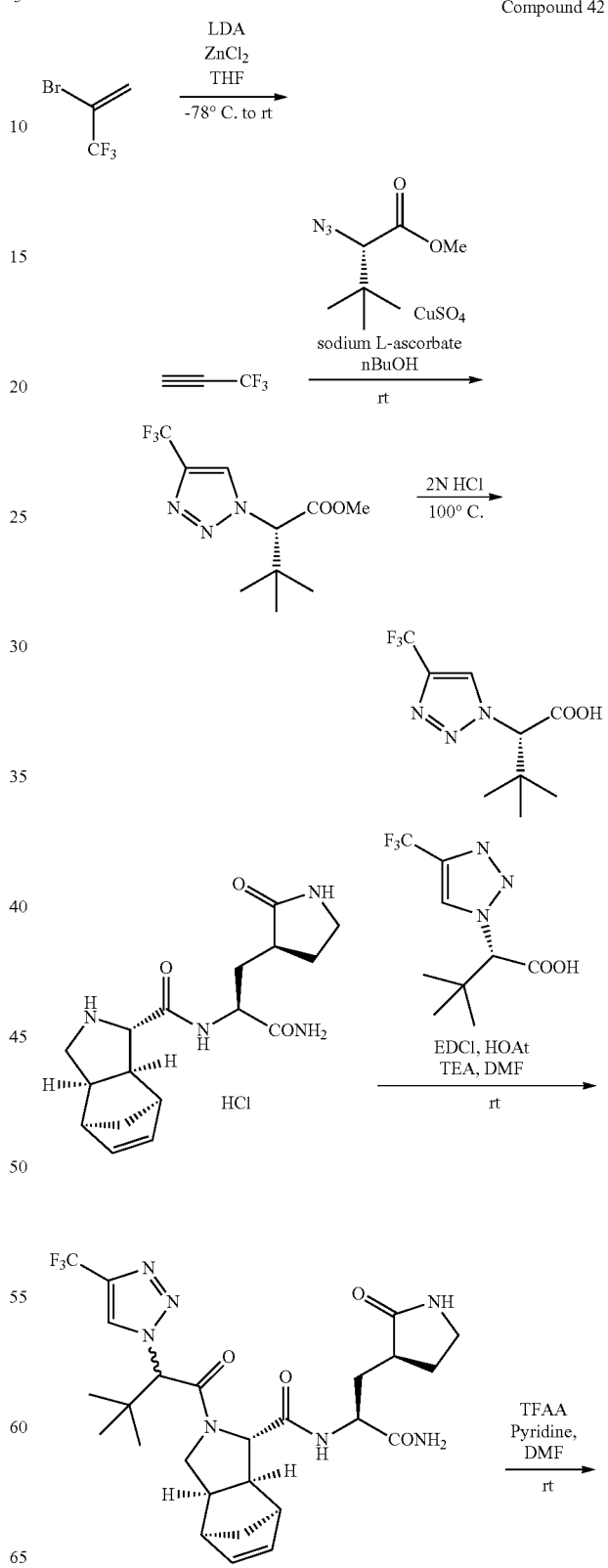

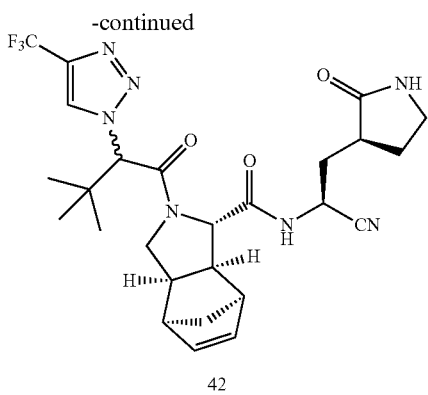

42

To a solution of diisopropylamine (3.0 g, 37.7 mmol, 2.2 eq.) in THF (30 mL) cooled to −78° C. were added 1.6M nBuLi in hexanes (23 mL, 37.7 mmol, 2.2 eq.) and 2-bromo-3,3,3-trifluoroprop-1-ene (3.0 g, 17.1 mmol, 1.0 eq.). The mixture was stirred at −78° C. for 30 min and 0.5M ZnCl₂ in THF (37 mL, 18.5 mmol, 1.1 eq.). The mixture was warmed to rt over 1 h. The solution of 3,3,3-trifluoroprop-1-yne in THF was used as such directly in the next step.

To a mixture of methyl (S)-2-azido-3,3-dimethylbutanoate (1.5 g, 8.77 mmol, 1.0 eq.) and a solution of 3,3,3-trifluoroprop-1-yne in THF (17.1 mmol, 2.0 eq.) in n-BuOH (13.5 mL) and water (1.5 mL) were added copper sulfate (69 mg, 0.043 mmol, 0.05 eq.) and sodium ascorbate (260 mg, 1.31 mmol, 0.15 eq.). The mixture was stirred at rt overnight. Water (50 mL) was added. The resulting precipitate was filtered and washed with water and diethyl ether. The phases of the filtrate were separated. The organic phase was washed with water (3×10 mL) and brine (1×10 mL), dried over Na₂SO₄, filtered and concentrated under reduced pressure. The residue was purified by flash chromatography on silica gel using a gradient of EA (5 to 10%) in hexane to afford methyl (S)-3,3-dimethyl-2-(4-(trifluoromethyl)-1H-1,2,3-triazol-1-yl)butanoate (600 mg, 21%) as a pale yellow liquid. ¹H NMR (500 MHz, CDCl₃) δ 8.41 (s, 1H), 5.37 (s, 1H), 3.83 (s, 3H), 1.03 (s, 9H).

A mixture of (S)-3,3-dimethyl-2-(4-(trifluoromethyl)-1H-1,2,3-triazol-1-yl)butanoate (600 mg, 2.26 mmol, 1.0 eq.) and 2M HCl (4.0 mL, 8.00 mmol) was heated at 100° C. for 48 h. After cooling to rt, the mixture was extracted with EtOAc (2×50 mL). The organic phases were combined, dried over Na₂SO₄, filtered and concentrated under reduced pressure. The residue was triturated with 5% diethyl ether in pentane to afford (S)-3,3-dimethyl-2-(4-(trifluoromethyl)-1H-1,2,3-triazol-1-yl)butanoic acid (0.720 g, 83%) as a white solid.

To a solution of (1S,3aR,4S,7R,7aS)—N—((S)-1-amino-1-oxo-3-((S)-2-oxopyrrolidin-3-yl)propan-2-yl)-2,3,3a,4,7,7a-hexahydro-1H-4,7-methanoisoindole-1-carboxamide hydrochloride (100 mg, 0.271 mmol, 1.0 eq.) in DMF (1.0 mL) cooled at 0° C. were added (S)-3,3-dimethyl-2-(4-(trifluoromethyl)-1H-1,2,3-triazol-1-yl)butanoic acid (82 mg, 0.326 mmol, 1.2 eq.), EDC•HCl (104 mg, 0.543 mmol, 2.0 eq.), HOAt (37 mg, 0.271 mmol, 1.0 eq.) and NEt₃ (0.151 mL, 1.09 mmol, 4.0 eq.). The mixture was stirred at rt for 16 h. The mixture was diluted with water (5 mL) and extracted with EA (3×10 mL). The organic phases were combined, dried over Na₂SO₄, filtered and concentrated under reduced pressure. The residue was purified by flash chromatography on silica gel (12 g column) using a gradient of MeOH (1 to 10%) in DCM to afford (1S,3aR,4S,7R,7aS)—N—((S)-1-amino-1-oxo-3-((S)-2-oxopyrrolidin-3-yl)propan-2-yl)-2-(3,3-dimethyl-2-(4-(trifluoromethyl)-1H-1,2,3-triazol-1-yl)butanoyl)-2,3,3a,4,7,7a-hexahydro-1H-4,7-methanoisoindole-1-carboxamide (100 mg, 60%) as a white solid. LC-MS (ESI, m/z): 566 [M+H]⁺.

To a solution of (1S,3aR,4S,7R,7aS)—N—((S)-1-amino-1-oxo-3-((S)-2-oxopyrrolidin-3-yl)propan-2-yl)-2-(3,3-dimethyl-2-(4-(trifluoromethyl)-1H-1,2,3-triazol-1-yl)butanoyl)-2,3,3a,4,7,7a-hexahydro-1H-4,7-methanoisoindole-1-carboxamide (70 mg, 0.123 mmol, 1.0 eq.) in DMF (0.7 mL) were added pyridine (0.030 mL, 0.371 mmol, 3.0 eq.) and TFAA (0.034 mL; 0.247 mmol, 2.0 eq.). The mixture was stirred at rt for 1 h. The mixture was diluted with water (10 mL) and extracted with EA (3×10 mL). The organic phases were combined, washed with brine (2×10 mL), dried over Na₂SO₄, filtered and concentrated under reduced pressure. The residue was purified by prep-HPLC (Column: X-SELECT-C18, 19×150 mm Sum; Mobile Phase A: 10 mM Ammonium bicarbonate in water, Mobile Phase B: ACN; Flow rate: 17 mL/min; gradient: 20% B to 70% B in 8 min) to afford (1S,3aR,4S,7R,7aS)—N—((S)-1-cyano-2-((S)-2-oxopyrrolidin-3-yl)ethyl)-2-(3,3-dimethyl-2-(4-(trifluoromethyl)-1H-1,2,3-triazol-1-yl)butanoyl)-2,3,3a,4,7,7a-hexahydro-1H-4,7-methanoisoindole-1-carboxamide (33 mg, 47%) as a white solid. ¹H NMR (400 MHz, 362K, DMSO-d₆) δ 8.42-8.76 (m, 2H), 7.34 (m, 1H), 6.16-6.30 (m, 1H), 5.61-5.83 (m, 1H), 5.44 (m, 1H), 4.90-5.01 (m, 1H), 4.01 (m, 1H), 3.75 (m, 1H), 3.40-3.53 (m, 1H), 3.07-3.24 (m, 4H), 2.87 (m, 1H), 2.73-2.85 (m, 1H), 2.37 (m, 1H), 2.03-2.19 (m, 2H), 1.55-1.84 (m, 2H), 1.35-1.44 (m, 2H), 0.94 (s, 9H). LCMS (ESI, m/z): 546 [M−H]⁻.

Example 43

Compound 43

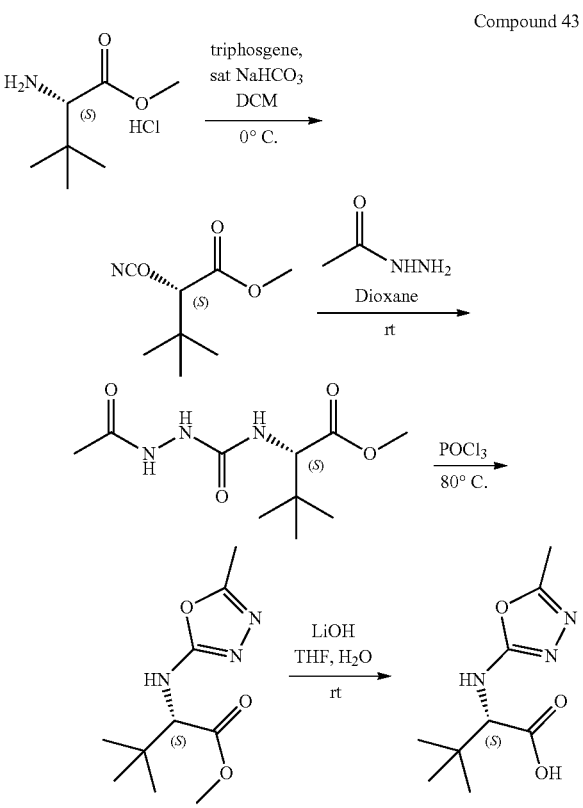

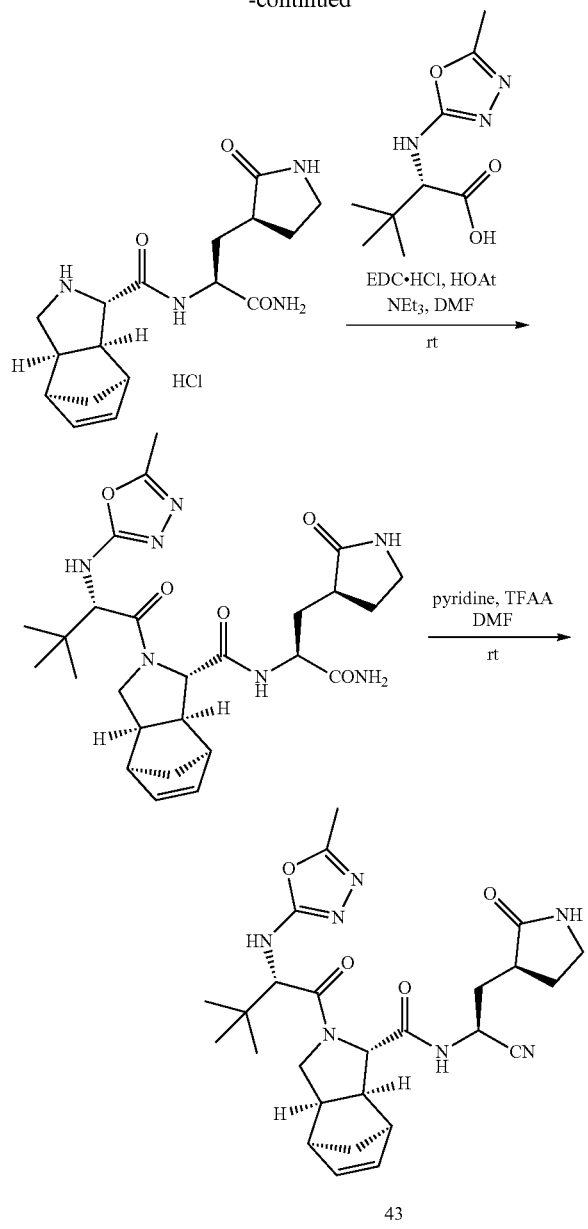

43

To a solution of methyl (S)-2-amino-3,3-dimethylbutanoate hydrochloride (1.0 g, 6.90 mmol, 1.0 eq.) in a mixture of sat. NaHCO₃ (43 mL) and DCM (22 mL) cooled at 0° C. was added triphosgene (818 mg, 2.76 mmol, 0.4 eq.). The mixture was stirred at 0° C. for 2 h. The mixture was diluted with DCM (10 mL) and washed with brine (10 mL). The phases were separated. The organic phase was washed with brine (10 mL), dried over Na₂SO₄, filtered and concentrated under reduced pressure to afford methyl (S)-2-isocyanato-3,3-dimethylbutanoate as a pale yellow liquid, which was used in the next step without further purification.

To a solution of methyl (S)-2-isocyanato-3,3-dimethylbutanoate (6.90 mmol, 1.0 eq.) in dioxane (10 mL) was added acetohydrazide (649 mg, 8.77 mmol, 1.5 eq.). The mixture was stirred at rt for 2 h and then concentrated under reduced pressure. The residue was purified by flash chromatography on silica gel (24 g column) using a gradient of EA (40 to 60%) in PE to afford methyl (S)-2-(2-acetylhydrazine-1-carboxamido)-3,3-dimethylbutanoate (1.0 g, 59% over two steps) as an off-white solid. ¹H NMR (500 MHz, DMSO-d₆) δ 9.56 (s, 1H), 7.86 (s, 1H), 6.54 (d, 1H), 4.02 (d, 1H), 3.63 (s, 3H), 1.80 (s, 3H), 0.90 (s, 9H).

A solution of methyl (S)-2-(2-acetylhydrazine-1-carboxamido)-3,3-dimethylbutanoate (1.0 g, 4.08 mmol, 1.0 eq.) in POCl₃ (4 mL) was heated at 80° C. for 2 h. After cooling to rt, the mixture was poured into ice/water (20 mL), basified with NaHCO₃ until pH=8 and extracted with EA (2×20 mL). The organic phases were combined, dried over Na₂SO₄, filtered and concentrated under reduced pressure. The residue was purified by flash chromatography on silica gel (24 g column) using a gradient of EA (20 to 40%) in PE to afford methyl (S)-3,3-dimethyl-2-((5-methyl-1,3,4-oxadiazol-2-yl)amino)butanoate (800 mg, 90%) as an off-white solid. ¹H NMR (400 MHz, DMSO-d₆) δ 7.78 (d, 1H), 3.91 (d, 1H), 3.63 (s, 3H), 2.29 (s, 3H), 0.98 (s, 9H).

To a solution of methyl (S)-3,3-dimethyl-2-((5-methyl-1,3,4-oxadiazol-2-yl)amino)butanoate (200 mg, 0.881 mmol, 1.0 eq.) in THF (1 mL) and water (1 mL) was added LiOH (42 mg, 1.76 mmol, 2.0 eq.). The mixture was stirred at rt for 2 h. The mixture was diluted with water (5 mL), acidified with sat. citric acid and extracted with EA (2×20 mL). The organic phases were combined, dried over Na₂SO₄, filtered and concentrated under reduced pressure to afford (S)-3,3-dimethyl-2-((5-methyl-1,3,4-oxadiazol-2-yl)amino)butanoic acid (170 mg, 91%) as an off-white solid. LC-MS (ESI, m/z): 214 [M+H]⁺.

To a solution of (1S,3aR,4S,7R,7aS)—N—((S)-1-amino-1-oxo-3-((S)-2-oxopyrrolidin-3-yl)propan-2-yl)-2,3,3a,4,7,7a-hexahydro-1H-4,7-methanoisoindole-1-carboxamide hydrochloride (100 mg, 0.272 mmol, 1.0 eq.) in DMF (1.0 mL) cooled at 0° C. were added (S)-3,3-dimethyl-2-((5-methyl-1,3,4-oxadiazol-2-yl)amino)butanoic acid (70 mg, 0.326 mmol, 1.2 eq.), EDC•HCl (103 mg, 0.544 mmol, 2.0 eq.), HOAt (37 mg, 0.272 mmol, 1.0 eq.) and NEt₃ (0.110 mL, 0.816 mmol, 3.0 eq.). The mixture was stirred at rt for 16 h. The mixture was diluted with water (5 mL) and extracted with EA (2×5 mL). The organic phases were combined, washed with brine (2×5 mL), dried over Na₂SO₄, filtered and concentrated under reduced pressure. The residue was purified by flash chromatography on silica gel (12 g column) using a gradient of MeOH (1 to 10%) in DCM to afford (1S,3aR,4S,7R,7aS)—N—((S)-1-amino-1-oxo-3-((S)-2-oxopyrrolidin-3-yl)propan-2-yl)-2-((S)-3,3-dimethyl-2-((5-methyl-1,3,4-oxadiazol-2-yl)amino)butanoyl)-2,3,3a,4,7,7a-hexahydro-1H-4,7-methanoisoindole-1-carboxamide (70 mg, 49%) as an off-white solid. LC-MS (ESI, m/z): 528 [M+H]⁺.

To a solution of (1S,3aR,4S,7R,7aS)—N—((S)-1-amino-1-oxo-3-((S)-2-oxopyrrolidin-3-yl)propan-2-yl)-2-((S)-3,3-dimethyl-2-((5-methyl-1,3,4-oxadiazol-2-yl)amino)butanoyl)-2,3,3a,4,7,7a-hexahydro-1H-4,7-methanoisoindole-1-carboxamide (70 mg, 0.132 mmol, 1.0 eq.) in DMF (0.7 mL) were added pyridine (0.030 mL, 0.398 mmol, 3.0 eq.) and TFAA (0.030 mL; 0.260 mmol, 2.0 eq.). The mixture was stirred at rt for 30 min. The mixture was diluted with water (5 mL) and extracted with EA (2×10 mL). The organic phases were combined, washed with brine (2×10 mL), dried over Na₂SO₄, filtered and concentrated under reduced pressure. The residue was purified by prep-HPLC (Column: X-SELECT-C18, 19×150 mm 5um; Mobile Phase A: 10 mM Ammonium bicarbonate, Mobile Phase B: ACN; Flow rate: 17 mL/min; gradient: 10% B to 60% B in 8 min) to afford (1S,3aR,4S,7R,7aS)—N—((S)-1-cyano-2-((S)-2-oxopyrrolidin-3-yl)ethyl)-2-((S)-3,3-dimethyl-2-((5-methyl-1,3,4-oxadiazol-2-yl)amino)butanoyl)-2,3,3a,4,7, 7a-hexahydro-1H-4,7-methanoisoindole-1-carboxamide (35 mg, 52%) as a white solid. $^1$H NMR (500 MHz, 363K, DMSO-$d_6$) δ 8.60 (br. s., 1H), 7.32 (s, 1H), 6.93 (br. s., 1H), 6.08 (m, 1H), 5.91 (m, 1H), 4.90 (m, 1H), 4.12 (s, 1H), 3.98 (m, 1H), 3.66 (m, 2H), 3.08-3.20 (m, 3H), 2.88 (m, 2H), 2.71 (m, 1H), 2.36 (m, 1H), 2.28 (s, 3H), 2.15 (m, 2H), 1.69-1.79 (m, 2H), 1.39 (s, 2H), 0.94 (s, 9H). LCMS (ESI, m/z): 508 [M−H]$^-$.

Example 44

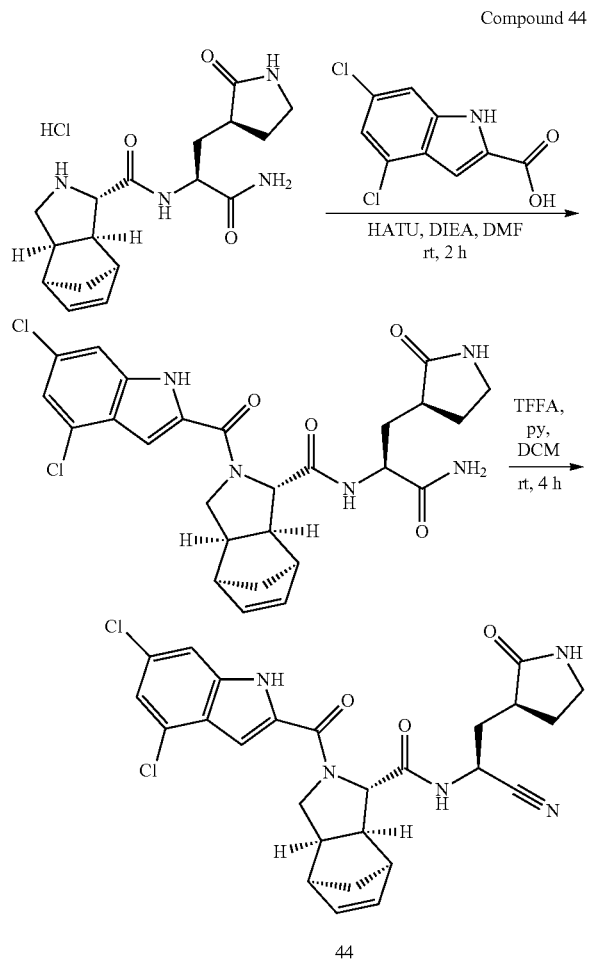

Compound 44

To a solution of 4,6-dichloro-1H-indole-2-carboxylic acid (83 mg, 0.36 mmol, 1.2 eq.) in DMF (2 mL) were added N,N,N',N'-Tetramethyl-O-(7-azabenzotriazol-1-yl)uronium hexafluorophospate (149 mg, 0.39 mmol, 1.3 eq.) and N,N-diisopropylethylamine (272 mg, 2.1 mmol, 7.0 eq.). The mixture was stirred at 0° C. for 30 min and (1S,3aR,4S,7R,7aS)—N—((S)-1-amino-1-oxo-3-((S)-2-oxopyrrolidin-3-yl)propan-2-yl)-2,3,3a,4,7,7a-hexahydro-1H-4,7-methanoisoindole-1-carboxamide (100 mg, 0.30 mmol, 1.0 eq.) was added. The mixture was stirred at rt for 2 h. The reaction was quenched with water (3 mL). The mixture was extracted with EA (3×5 mL). The organic layers were combined, washed with brine (3×5 mL), dried over anhydrous sodium sulfate, filtered and concentrated under reduced pressure. The residue was chromatographed on a C18 column with water:MeCN (2:1) to provide (1S,3aR,4S,7R,7aS)—N—((S)-1-amino-1-oxo-3-((S)-2-oxopyrrolidin-3-yl)propan-2-yl)-2-(4,6-dichloro-1H-indole-2-carbonyl)-2,3,3a,4,7,7a-hexahydro-1H-4,7-methanoisoindole-1-carboxamide (70 mg, 40%) as a brown yellow solid. LC-MS (ESI, m/z): 544 [M+H]$^+$.

To a solution of (1S,3aR,4S,7R,7aS)—N—((S)-1-amino-1-oxo-3-((S)-2-oxopyrrolidin-3-yl)propan-2-yl)-2-(4,6-dichloro-1H-indole-2-carbonyl)-2,3,3a,4,7,7a-hexahydro-1H-4,7-methanoisoindole-1-carboxamide (70 mg, 0.13 mmol, 1.0 eq.) in DCM (1 mL) were added TFAA (37.8 mg, 0.18 mmol, 1.4 eq.) and pyridine (35.6 mg, 0.45 mmol, 3.5 eq.). The mixture was stirred at rt for 4 h. The reaction was quenched with water (2 mL). The mixture was extracted with DCM (3×3 mL). The organic layers were combined, dried over anhydrous sodium sulfate, filtered and concentrated under reduced pressure. The residue was purified by Pre-HPLC (Column: XBridge Shield RP18 OBD Column, 30*150 mm, 5 m; Mobile Phase A: Water (0.1% FA), Mobile Phase B: ACN; Flow rate: 60 mL/min; Gradient: 40% B to 70% B in 7 min, 70% B; Wave Length: 254 nm; RT1 (min): 5.2;) to provide (1S,3aR,4S,7R,7aS)—N—((S)-1-cyano-2-((S)-2-oxopyrrolidin-3-yl)ethyl)-2-(4,6-dichloro-1H-indole-2-carbonyl)-2,3,3a,4,7,7a-hexahydro-1H-4,7-methanoisoindole-1-carboxamide (18.3 mg, 27%) as a white solid. $^1$H NMR (400 MHz, DMSO-$d_6$, 80° C.) δ 11.78 (br, 1H), 8.72-9.00 (m, 1H), 7.44-7.52 (m, 2H), 7.34 (s, 1H), 6.59-6.90 (m, 1H), 6.05-6.25 (m, 2H), 4.80-5.05 (m, 1H), 4.30-4.61 (m, 1H), 3.85-4.05 (m, 1H), 3.63-3.65 (m, 1H), 3.01-3.10 (m, 3H), 2.79-2.96 (m, 3H), 2.01-2.50 (m, 3H), 1.56-1.96 (m, 2H), 1.44 (s, 2H). LC-MS (ESI, m/z): 526 [M+H]$^+$.

Example 45

Compound 45

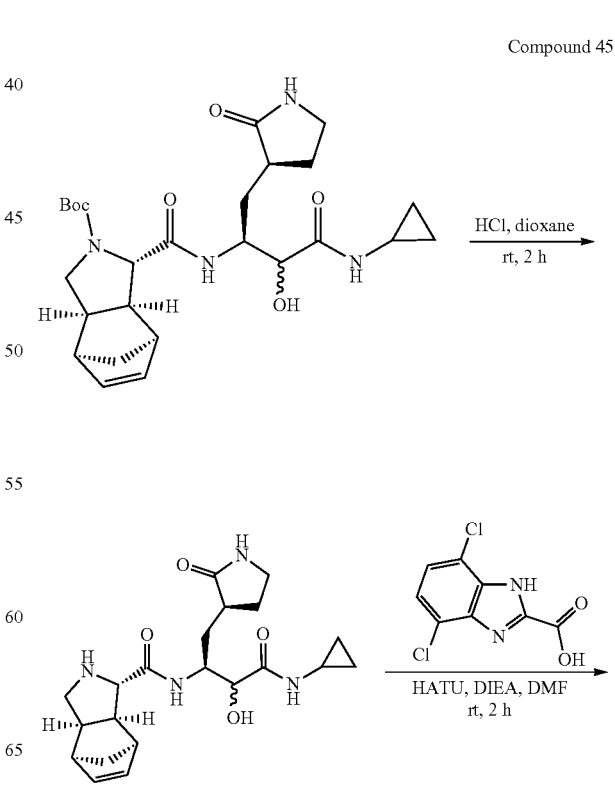

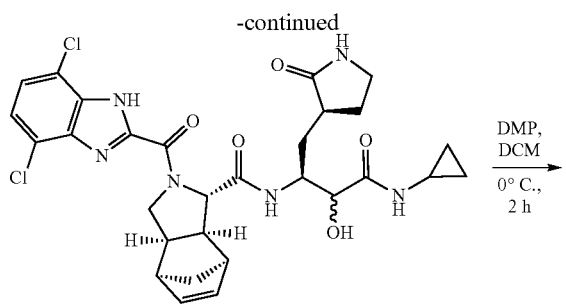

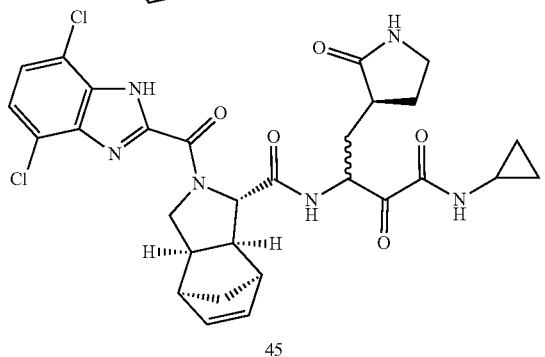

A solution of tert-butyl (1S,3aR,4S,7R,7aS)-1-(((2S)-4-(cyclopropylamino)-3-hydroxy-4-oxo-1-((S)-2-oxopyrrolidin-3-yl)butan-2-yl)carbamoyl)-1,3,3a,4,7,7a-hexahydro-2H-4,7-methanoisoindole-2-carboxylate (400 mg, 0.8 mmol, 1.0 eq.) in hydrochloric acid (8 mL, 4M in dioxane) was stirred at rt for 2 h and then concentrated under reduced pressure to provide (1S,3aR,4S,7R,7aS)—N-((2S)-4-(cyclopropylamino)-3-hydroxy-4-oxo-1-((S)-2-oxopyrrolidin-3-yl)butan-2-yl)-2,3,3a,4,7,7a-hexahydro-1H-4,7-methanoisoindole-1-carboxamide (300 mg, crude) as an off-white solid. LC-MS (ESI, m/z): 403 [M+H]$^+$.

To a solution of 4,7-dichloro-1H-benzo[d]imidazole-2-carboxylic acid (63 mg, 0.27 mmol, 1.1 eq.) in DMF (2 mL) were added N,N,N',N'-Tetramethyl-O-(7-azabenzotriazol-1-yl)uronium hexafluorophospate (123 mg, 0.32 mmol, 1.3 eq.) and N,N-diisopropylethylamine (225 mg, 1.74 mmol, 7.0 eq.). The mixture was stirred at 0° C. for 30 min and (1S,3aR,4S,7R,7aS)—N-((2S)-4-(cyclopropylamino)-3-hydroxy-4-oxo-1-((S)-2-oxopyrrolidin-3-yl)butan-2-yl)-2,3,3a,4,7,7a-hexahydro-1H-4,7-methanoisoindole-1-carboxamide (100 mg, 0.25 mmol, 1.0 eq.) was added. The mixture was stirred at rt for 2 h. The reaction was quenched with water (3 mL). The mixture was extracted with EA (3×5 mL). The organic layers were combined, washed with brine (3×5 mL), dried over anhydrous sodium sulfate, filtered and concentrated under reduced pressure. The residue was chromatographed on a silica gel column with MeOH:DCM (1:12) to provide (1S,3aR,4S,7R,7aS)—N-((2S)-4-(cyclopropylamino)-3-hydroxy-4-oxo-1-((S)-2-oxopyrrolidin-3-yl)butan-2-yl)-2-(4,7-dichloro-1H-benzo[d]imidazole-2-carbonyl)-2,3,3a,4,7,7a-hexahydro-1H-4,7-methanoisoindole-1-carboxamide (80 mg, 47%) as a white solid. LC-MS (ESI, m/z): 615 [M+H]$^+$.

To a solution of (1S,3aR,4S,7R,7aS)—N-((2S)-4-(cyclopropylamino)-3-hydroxy-4-oxo-1-((S)-2-oxopyrrolidin-3-yl)butan-2-yl)-2-(4,7-dichloro-1H-benzo[d]imidazole-2-carbonyl)-2,3,3a,4,7,7a-hexahydro-1H-4,7-methanoisoindole-1-carboxamide (80 mg, 0.13 mmol, 1.0 eq.) in DCM (2 mL) was added DMP (165 mg, 0.39 mmol, 3.0 eq.) at 0° C. under N$_2$. The mixture was stirred at 0° C.

for 2 h. The reaction was quenched with sodium thiosulfate solution (2 mL) and sodium bicarbonate solution (2 mL). The mixture was extracted with DCM (3×5 mL). The organic layers were combined, dried over anhydrous sodium sulfate, filtered and concentrated under reduced pressure. The residue was purified by prep-TLC to provide (1S,3aR,4S,7R,7aS)—N-(4-(cyclopropylamino)-3,4-dioxo-1-((S)-2-oxopyrrolidin-3-yl)butan-2-yl)-2-(4,7-dichloro-1H-benzo[d]imidazole-2-carbonyl)-2,3,3a,4,7,7a-hexahydro-1H-4,7-methanoisoindole-1-carboxamide (30.4 mg, 38%) as a white solid. LC-MS (ESI, m/z): 613 [M+H]$^+$.

Example 46

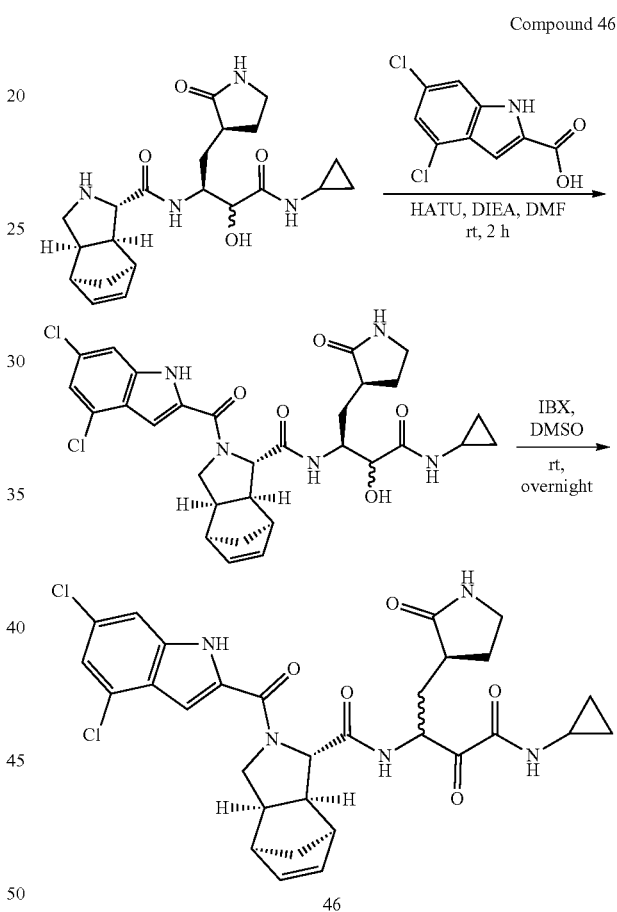

To a solution of 4,6-dichloro-1H-indole-2-carboxylic acid (126 mg, 0.55 mmol, 1.1 eq.) in DMF (3 mL) were added N,N,N',N'-Tetramethyl-O-(7-azabenzotriazol-1-yl)uronium hexafluorophospate (246 mg, 0.65 mmol, 1.3 eq.) and N,N-diisopropylethylamine (450 mg, 3.48 mmol, 7.0 eq.). The mixture was stirred at 0° C. for 30 min and (1S,3aR,4S,7R,7aS)—N-((2S)-4-(cyclopropylamino)-3-hydroxy-4-oxo-1-((S)-2-oxopyrrolidin-3-yl)butan-2-yl)-2,3,3a,4,7,7a-hexahydro-1H-4,7-methanoisoindole-1-carboxamide (200 mg, 0.5 mmol, 1.0 eq.) was added. The mixture was stirred at rt for 2 h. The reaction was quenched with water (3 mL). The mixture was extracted with EA (3×5 mL). The organic layers were combined, washed with brine (3×5 mL), dried over anhydrous sodium sulfate, filtered and concentrated under reduced pressure. The residue was chromatographed on a silica gel column with MeOH:DCM (1:12) to provide (1S, 3aR,4S,7R,7aS)—N-((2S)-4-(cyclopropylamino)-3-hydroxy-4-oxo-1-((S)-2-oxopyrrolidin-3-yl)butan-2-yl)-2-(4, 6-dichloro-1H-indole-2-carbonyl)-2,3,3a,4,7,7a-hexahydro-1H-4,7-methanoisoindole-1-carboxamide (70 mg, 20%) as a white solid. LC-MS (ESI, m/z): 614 [M+H]$^+$.

To a solution of (1S,3aR,4S,7R,7aS)—N-((2S)-4-(cyclopropylamino)-3-hydroxy-4-oxo-1-((S)-2-oxopyrrolidin-3-yl)butan-2-yl)-2-(4,6-dichloro-1H-indole-2-carbonyl)-2,3, 3a,4,7,7a-hexahydro-1H-4,7-methanoisoindole-1-carboxamide (70 mg, 0.11 mmol, 1.0 eq.) in DMSO (3 mL) was added IBX (96 mg, 0.34 mmol, 3.0 eq.). The mixture was stirred at rt overnight. The reaction was quenched with water (3 mL). The mixture was extracted with EA (3×5 mL). The organic layers were combined, dried over anhydrous sodium sulfate, filtered and concentrated under reduced pressure. The residue was purified by prep-TLC to provide (1S,3aR,4S,7R,7aS)—N-(4-(cyclopropylamino)-3,4-dioxo-1-((S)-2-oxopyrrolidin-3-yl)butan-2-yl)-2-(4,6-dichloro-1H-indole-2-carbonyl)-2,3,3a,4,7,7a-hexahydro-1H-4,7-methanoisoindole-1-carboxamide (26.5 mg, 37%) as a white solid. LC-MS (ESI, m/z): 612 [M+H]$^+$.

Example 47

Compound 47

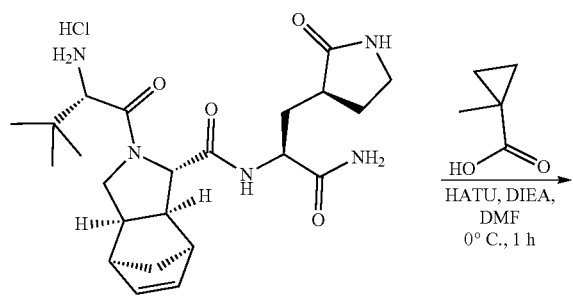

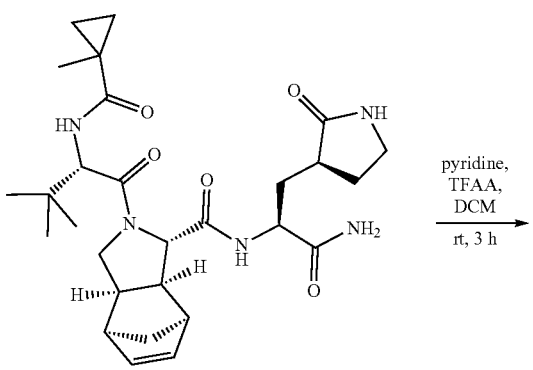

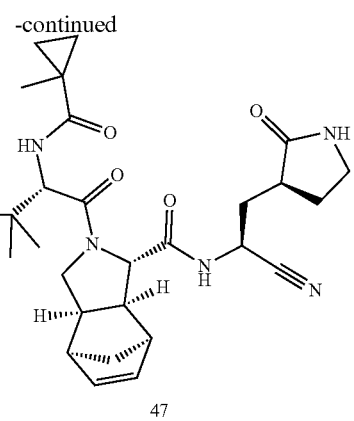

47

To a mixture of 1-methylcyclopropane-1-carboxylic acid (36.3 mg, 0.363 mmol, 1.1 eq.) in N,N-dimethylformamide (3 mL) were added o-(7-azabenzotriazol-1-yl)-N,N,N',N'-tetramethyluronium hexafluorophosphate (163 mg, 0.429 mmol, 1.3 eq.) and N-ethyl-N-isopropylpropan-2-amine (341 mg, 2.64 mmol, 8.0 eq.) at 0° C. The mixture was stirred for 20 min at 0° C., and then (2S)-2-{[(1R,2S,3S, 6R,7S)-4-[(2S)-2-amino-3,3-dimethylbutanoyl]-4-azatricyclo[5.2.1.0^{2,6}]dec-8-en-3-yl]formamido}-3-[(3S)-2-oxopyrrolidin-3-yl]propanamide (140 mg, 0.314 mmol, 1.0 eq.) was added at 0° C. The mixture was stirred for 1 h at rt. The mixture was purified by C18 column with CH$_3$CN: Water (0.05% FA). The desired fraction was concentrated under reduced pressure to provide N-[(2S)-1-[(1R,2S,3S,6R, 7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxobutan-2-yl]-1-methylcyclopropane-1-carboxamide (160 mg, 91%) as a light yellow solid. LC-MS (ESI, m/z): 528 [M+H]$^+$.

To a mixture of N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxobutan-2-yl]-1-methylcyclopropane-1-carboxamide (160 mg, 0.303 mmol, 1.0 eq.) in DCM (2 mL) were added pyridine (95.6 mg, 1.21 mmol, 4.0 eq.) and trifluoroacetic anhydride (114 mg, 0.545 mmol, 1.8 eq.). The mixture was stirred for 3 h at rt. The reaction was quenched with water (5 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was purified by prep-HPLC (Column: XSelect CSH Prep C18 OBD Column, 19*250 mm, 5 m; Mobile Phase A: Water (0.1% FA), Mobile Phase B: ACN; Flow rate: 25 mL/min; Gradient: 37% B to 67% B in 7 min, 67% B; Wave Length: 254 nm; RT1 (min): 5.15) to provide (1R,2S,3S,6R,7S)—N-[(1S)-1-cyano-2-[(3S)-2-oxopyrrolidin-3-yl]ethyl]-4-[(2S)-3,3-dimethyl-2-[(1-methylcyclopropyl)formamido]butanoyl]-4-azatricyclo[5.2.1.0^{2,6}]dec-8-ene-3-carboxamide (27.9 mg, 16%) as a white solid. $^1$H NMR (400 MHz, 80° C., DMSO-d$_6$) δ 8.55-8.85 (m, 1H), 7.30-7.60 (m, 1H), 6.35-6.60 (m, 1H), 5.90-6.30 (m, 2H), 4.60-5.00 (m, 1H), 4.40-4.55 (m, 1H), 3.95-4.20 (m, 1H), 3.55-3.70 (m, 1H), 3.35-3.55 (m, 1H), 3.15-3.30 (m, 1H), 3.05-3.15 (m, 2H), 2.80-3.00 (m, 2H), 2.60-2.80 (m, 1H), 2.25-2.45 (m, 1H), 2.05-2.25 (m, 2H), 1.60-1.95 (m, 2H), 1.35-1.50 (m, 2H), 1.15-1.35 (m, 3H), 0.75-1.10 (m, 11H), 0.40-0.75 (m, 2H). LC-MS (ESI, m/z): 510 [M+H]$^+$.

Example 48

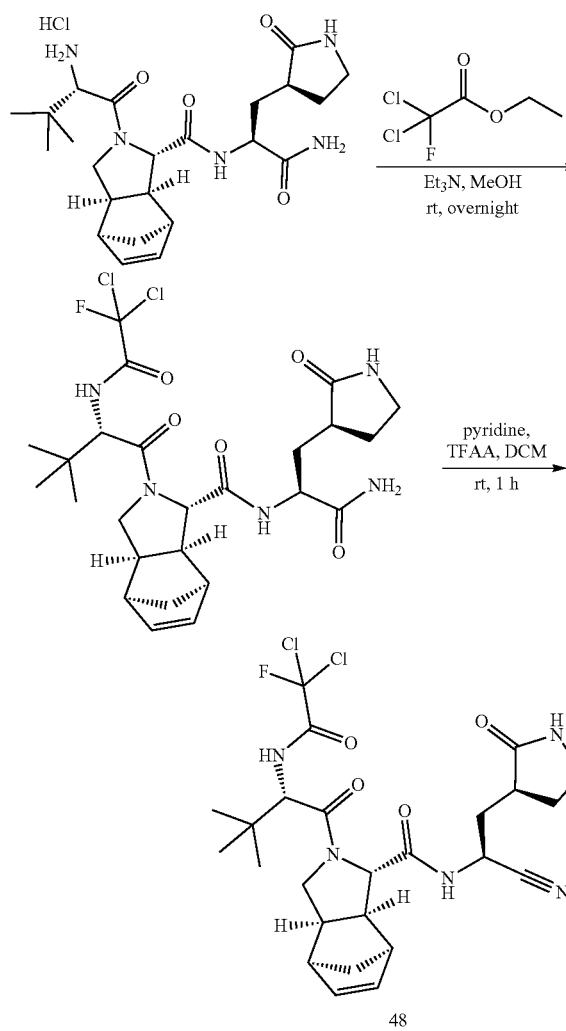

To a mixture of (2S)-2-{[(1R,2S,3S,6R,7S)-4-[(2S)-2-amino-3,3-dimethylbutanoyl]-4-azatricyclo[5.2.1.0^{2,6}]dec-8-en-3-yl]formamido}-3-[(3S)-2-oxopyrrolidin-3-yl]propanamide hydrochloride (177 mg, 0.367 mmol, 1.0 eq.) in MeOH (3 mL) was added triethylamine (446 mg, 4.40 mmol, 12.0 eq.) and ethyl 2,2-dichloro-2-fluoroacetate (643 mg, 3.67 mmol, 10.0 eq.). The mixture was stirred overnight at rt. The mixture was concentrated under reduced pressure to remove MeOH. The mixture was diluted with water (10 mL) and adjusted to pH=6 with hydrochloric acid (1 M). The resulting mixture was extracted with EtOAc (3×10 mL). The organic layers were combined, washed with brine (2×10 mL), dried over anhydrous sodium sulfate, filtered and concentrated under reduced pressure to afford the crude product. The crude product was triturated with Et$_2$O (5 mL) to provide (2S)-2-{[(1R,2S,3S,6R,7S)-4-[(2S)-2-(2,2-dichloro-2-fluoroacetamido)-3,3-dimethylbutanoyl]-4-azatricyclo[5.2.1.0^{2,6}]dec-8-en-3-yl]formamido}-3-[(3S)-2-oxopyrrolidin-3-yl]propanamide (75.0 mg, 33%) as an off-white solid. LC-MS (ESI, m/z): 574[M+H]$^+$.

To a mixture of (2S)-2-{[(1R,2S,3S,6R,7S)-4-[(2S)-2-(2,2-dichloro-2-fluoroacetamido)-3,3-dimethylbutanoyl]-4-azatricyclo[5.2.1.0^{2,6}]dec-8-en-3-yl]formamido}-3-[(3S)-2-oxopyrrolidin-3-yl]propanamide (75.0 mg, 0.131 mmol, 1.0 eq.) in DCM (1 mL) were added pyridine (41.0 mg, 0.524 mmol, 4.0 eq.) and trifluoroacetic anhydride (49.0 mg, 0.236 mmol, 1.8 eq.). The mixture was stirred for 1 h at rt. The reaction was quenched with water (5 mL). The mixture was extracted with DCM (3×5 mL). The organic layers were combined, washed with brine (2×5 mL), dried over anhydrous sodium sulfate, filtered and concentrated under reduced pressure to afford the crude product. The crude product was purified by prep-HPLC (Column: Kinetex EVO C18, 21.2×250 mm, 5 m; Mobile Phase A: Water (0.1% FA), Mobile Phase B: ACN; Flow rate: 25 mL/min; Gradient: 40% B to 70% B in 7 min, 70% B; Wave Length: 254 nm; RT: 5.55 min) to provide (1R,2S,3S,6R,7S)—N-[(1S)-1-cyano-2-[(3S)-2-oxopyrrolidin-3-yl]ethyl]-4-[(2S)-2-(2,2-dichloro-2-fluoroacetamido)-3,3-dimethylbutanoyl]-4-azatricyclo[5.2.1.0^{2,6}]dec-8-ene-3-carboxamide (28.3 mg, 37%) as a white solid. $^1$H NMR (400 MHz, 80° C., DMSO-d$_6$) δ 8.60-8.90 (m, 1H), 7.90-8.20 (m, 1H), 7.30-7.62 (m, 1H), 5.90-6.25 (m, 2H), 4.65-5.00 (m, 1H), 4.40-4.52 (m, 1H), 3.95-4.23 (m, 1H), 3.56-3.75 (m, 1H), 3.35-3.55 (m, 1H), 3.08-3.30 (m, 2H), 2.98-3.05 (m, 1H), 2.78-2.97 (m, 2H), 2.63-2.77 (m, 1H), 2.30-2.45 (m, 1H), 2.05-2.29 (m, 2H), 1.62-1.93 (m, 2H), 1.30-1.50 (m, 2H), 0.73-1.15 (m, 9H). LC-MS (ESI, m/z): 556 [M+H]$^+$.

Example 49

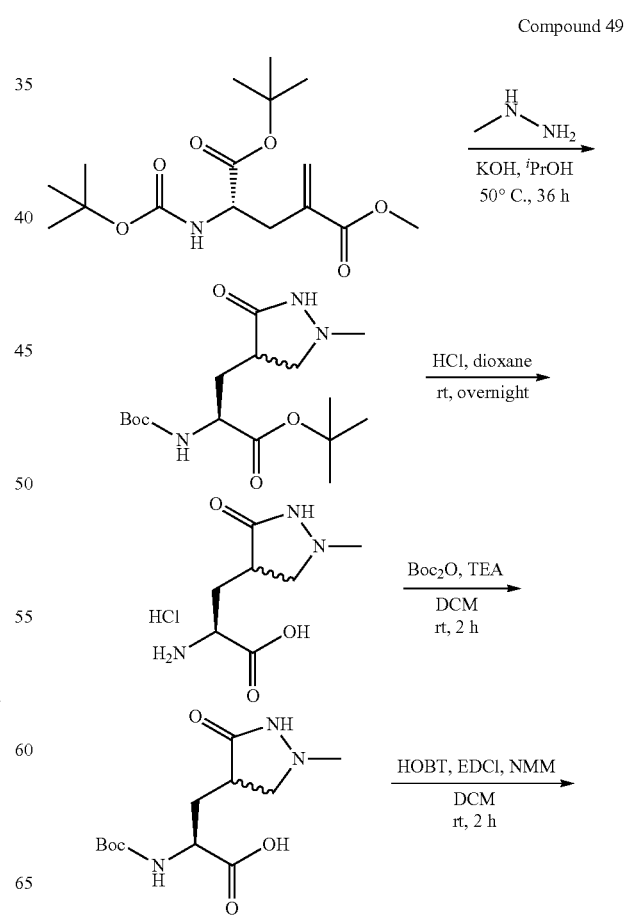

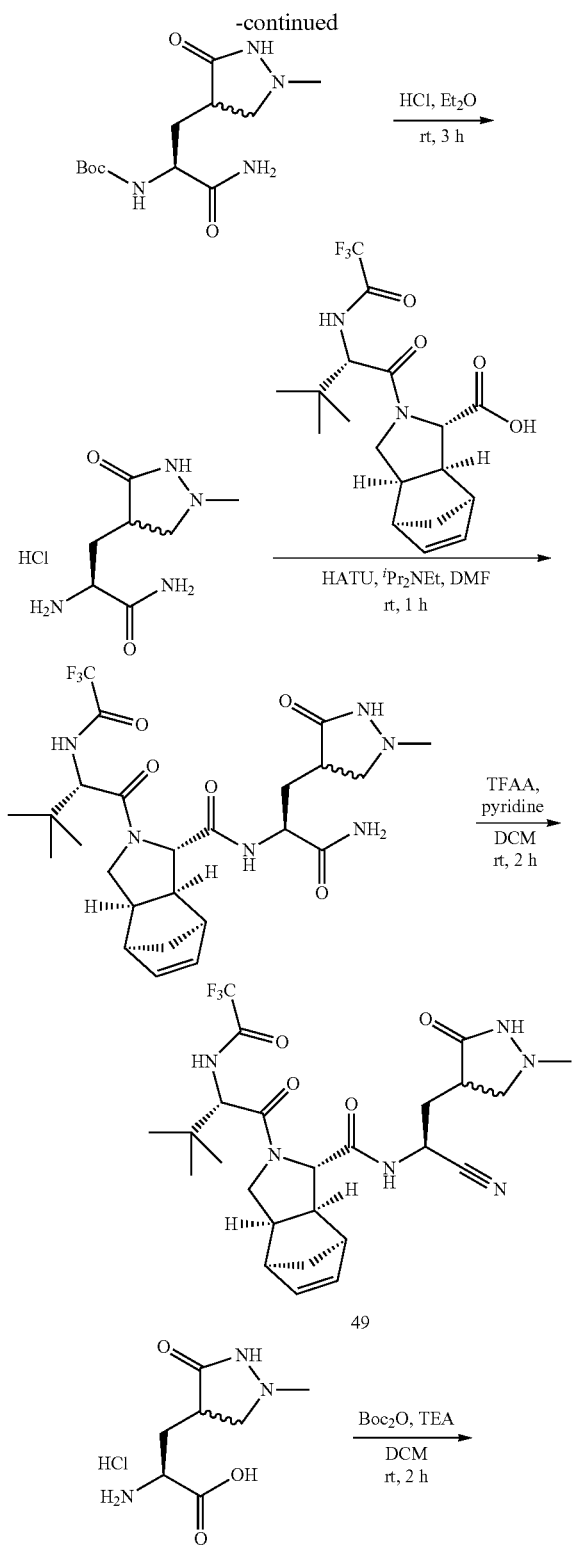

To a mixture of 1-(tert-butyl) 5-methyl (S)-2-((tert-butoxycarbonyl)amino)-4-methylenepentanedioate (5.0 g, 15.2 mmol, 1.0 eq.) in ⁱPrOH (50 mL) were added methyl hydrazine (3.50 g, 75.9 mmol, 5.0 eq.) and potassium hydroxide (42.6 mg, 0.759 mmol, 0.05 eq.) at rt. The mixture was stirred for 36 h at 50° C. and then concentrated under reduced pressure to afford the crude product. The crude product was chromatographed on a silica gel column with EA:PE (90%-100%) to provide the crude product. The crude product was separated by prep-achiral-SFC-HPLC column (Column: GreenSep Basic, 3*15 cm, 5 m; Mobile Phase A: $CO_2$, Mobile Phase B: MeOH (0.1% 2M $NH_3$-MeOH); Flow rate: 75 mL/min; Gradient: isocratic 13% B; Column Temperature (° C.): 35; Back Pressure (bar): 100; Wave Length: 220 nm; RT1 (min): 1.56; RT2(min): 3.85; Sample Solvent: MeOH—HPLC; Injection Volume: 1.5 mL;) to provide tert-butyl (S)-2-((tert-butoxycarbonyl)amino)-3-(-1-methyl-3-oxopyrazolidin-4-yl)propanoate (1.75 g, 33%) as white solid. ¹H NMR (400 MHz, CDCl₃) δ 5.31-5.58 (m, 1H), 4.13-4.25 (m, 1H), 3.40-3.65 (m, 1H), 2.85-2.99 (m, 2H), 2.66-2.67 (m, 3H), 2.02-2.38 (m, 1H), 1.75-1.93 (m, 1H), 1.46-1.51 (m, 18H). LC-MS (ESI, m/z): 344 [M+H]⁺.

To a solution of tert-butyl (S)-2-((tert-butoxycarbonyl)amino)-3-(1-methyl-3-oxopyrazolidin-4-yl)propanoate (800 mg, 2.33 mmol, 1.0 eq.) in 1,4-dioxane (8 mL) was added hydrogen chloride (8 mL, 9 M in $H_2O$). The mixture was stirred for overnight at rt and then concentrated under reduced pressure to afford (S)-2-amino-3-(1-methyl-3-oxopyrazolidin-4-yl)propanoic acid hydrochloride (500 mg, crude) as a yellow solid. LC-MS (ESI, m/z): 188 [M+H]⁺.

To a solution of (S)-2-amino-3-(1-methyl-3-oxopyrazolidin-4-yl)propanoic acid hydrochloride (500 mg, 2.23 mmol, 1.0 eq.) in DCM (10 mL) were added di-tert-butyl dicarbonate (537 mg, 2.46 mmol, 1.1 eq.) and triethylamine (679 mg, 6.71 mmol, 3.0 eq.). The mixture was stirred for 2 h at rt. The reaction was quenched with water (10 mL). The mixture was concentrated under reduced pressure to remove DCM and adjusted to pH=6 with HCl (1 M). The mixture was extracted with CHCl₃:ⁱPrOH (4:1) (3×100 mL). The organic layers were combined, dried over anhydrous sodium sulfate, filtered and concentrated under reduced pressure to afford (S)-2-((tert-butoxycarbonyl)amino)-3-(1-methyl-3-oxopyrazolidin-4-yl)propanoic acid (400 mg, crude) as a yellow solid. LC-MS (ESI, m/z): 288 [M+H]⁺.

To a mixture of (S)-2-((tert-butoxycarbonyl)amino)-3-((R)-1-methyl-3-oxopyrazolidin-4-yl)propanoic acid (400 mg, 1.39 mmol, 1.0 eq.) in DCM (8 mL) was added 1-hydroxybenzotriazole (225 mg, 1.67 mmol, 1.2 eq.), 1-(3-dimethylaminopropyl)-3-ethylcarbodiimide hydrochloride (294 mg, 1.53 mmol, 1.1 eq.), ammonia (0.04 mL, 0.280 mmol, 2.0 eq., 7 M in MeOH) and N-methylmorphline (422 mg, 4.18 mmol, 3.0 eq.) stirred at 0° C. The mixture was stirred for 2 h at rt. The reaction was quenched with water (10 mL). The mixture was extracted with CHCl₃:ⁱPrOH (4:1) (5×100 mL). The organic layers were combined, dried over anhydrous sodium sulfate, filtered and concentrated under reduced pressure to afford the crude product. The crude product was chromatographed on a silica gel column with MeOH:DCM (12%) to provide tert-butyl ((S)-1-amino-3-(1-methyl-3-oxopyrazolidin-4-yl)-1-oxopropan-2-yl)carbamate (110 mg, crude) as a yellow solid. ¹H NMR (400 MHz, CDCl₃) δ 6.87-6.99 (m, 2H), 5.85-5.99 (m, 2H), 4.36-4.42 (m, 1H), 3.38-3.56 (m, 1H), 2.84-3.14 (m, 2H), 2.64-2.68 (m, 3H), 1.94-2.16 (m, 2H), 1.45-1.48 (m, 9H). LC-MS (ESI, m/z): 287[M+H]⁺.

A mixture of tert-butyl ((S)-1-amino-3-(1-methyl-3-oxopyrazolidin-4-yl)-1-oxopropan-2-yl)carbamate (110 mg, 0.384 mmol, 1.0 eq.) in hydrogen chloride (3 mL, 2 M in diethyl ether) was stirred for 3 h at rt and then concentrated under reduced pressure to afford (S)-2-amino-3-((R)-1-methyl-3-oxopyrazolidin-4-yl)propanamide hydrochloride (70 mg, crude) as a yellow solid. LC-MS (ESI, m/z): 187 [M+H]⁺.

To a mixture of (1S,2S,3S,6R,7R)-4-[(2S)-3,3-dimethyl-2-(2,2,2-trifluoroacetamido)butanoyl]-4-azatricyclo[5.2.1.0^{2,6}]decane-3-carboxylic acid (129 mg, 0.330 mmol, 1.1 eq.) in dimethylformamide (3 mL) were added o-(7-azabenzotriazol-1-yl)-N,N,N',N'-tetramethyluronium hexafluorophosphate (137 mg, 0.360 mmol, 1.2 eq.) and N-ethyl-N-isopropylpropan-2-amine (232 mg, 1.80 mmol, 6.0 eq.) at 0° C. After stirred 20 min, (S)-2-amino-3-(1-methyl-3-oxopyrazolidin-4-yl)propanamide hydrochloride (70 mg, 0.300 mmol, 1.0 eq.) was added. The mixture was stirred for 1 h at rt. The reaction was quenched with water (5 mL). The mixture was purified by C18 column with $CH_3CN$/Water (0.05% TFA). The fraction was concentrated under reduced pressure to provide (1S,3aR,4S,7R,7aS)—N—((S)-1-amino-3-(1-methyl-3-oxopyrazolidin-4-yl)-1-oxopropan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (50.0 mg, 29%) as a white solid. LC-MS (ESI, m/z): 557 [M+H]$^+$.

To a mixture of (1S,3aR,4S,7R,7aS)—N—((S)-1-amino-3-(1-methyl-3-oxopyrazolidin-4-yl)-1-oxopropan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (50.0 mg, 0.090 mmol, 1.0 eq.) in DCM (2 mL) were added pyridine (28.4 mg, 0.360 mmol, 4.0 eq.) and trifluoroacetic anhydride (32.1 mg, 0.153 mmol, 1.7 eq.). The mixture was stirred 2 h at rt. The reaction was quenched with water (10 mL). The mixture was extracted with DCM (3×50 mL). The organic layers were combined, washed with brine (2×20 mL), dried over anhydrous sodium sulfate, filtered and concentrated under reduced pressure to afford the crude product. The crude product was purified by prep-HPLC (Column: XSelect CSH Prep C18 OBD Column, 19*250 mm, 5 m; Mobile Phase A: Water (0.1% FA), Mobile Phase B: ACN; Flow rate: 25 mL/min; Gradient: 39% B to 69% B in 7 min, 69% B; Wave Length: 254 nm; RT1 (min): 5.18;) to provide (1S,3aR,4S,7R,7aS)—N—((S)-1-cyano-2-(1-methyl-3-oxopyrazolidin-4-yl)ethyl)-2-((S)-3,3-dimethyl-2-(2,2,2-trifluoroacetamido)butanoyl)-2,3,3a,4,7,7a-hexahydro-1H-4,7-methanoisoindole-1-carboxamide (12.6 mg, 25%) as an off-white solid. LC-MS (ESI, m/z): 539 [M+H]$^+$.

Example 50

Compound 50

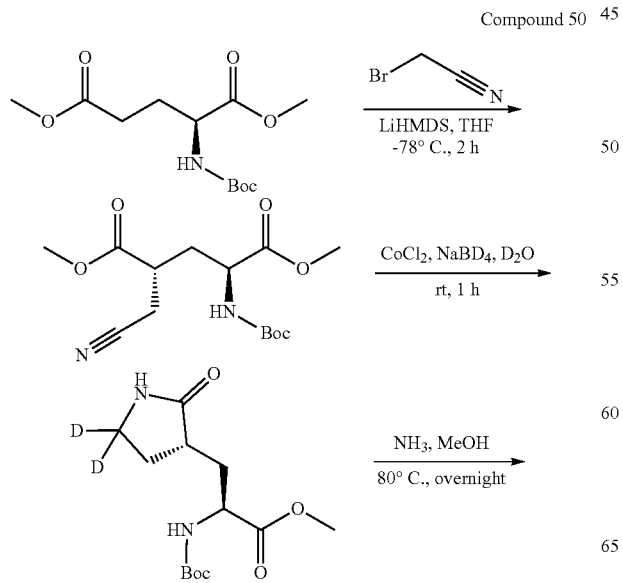

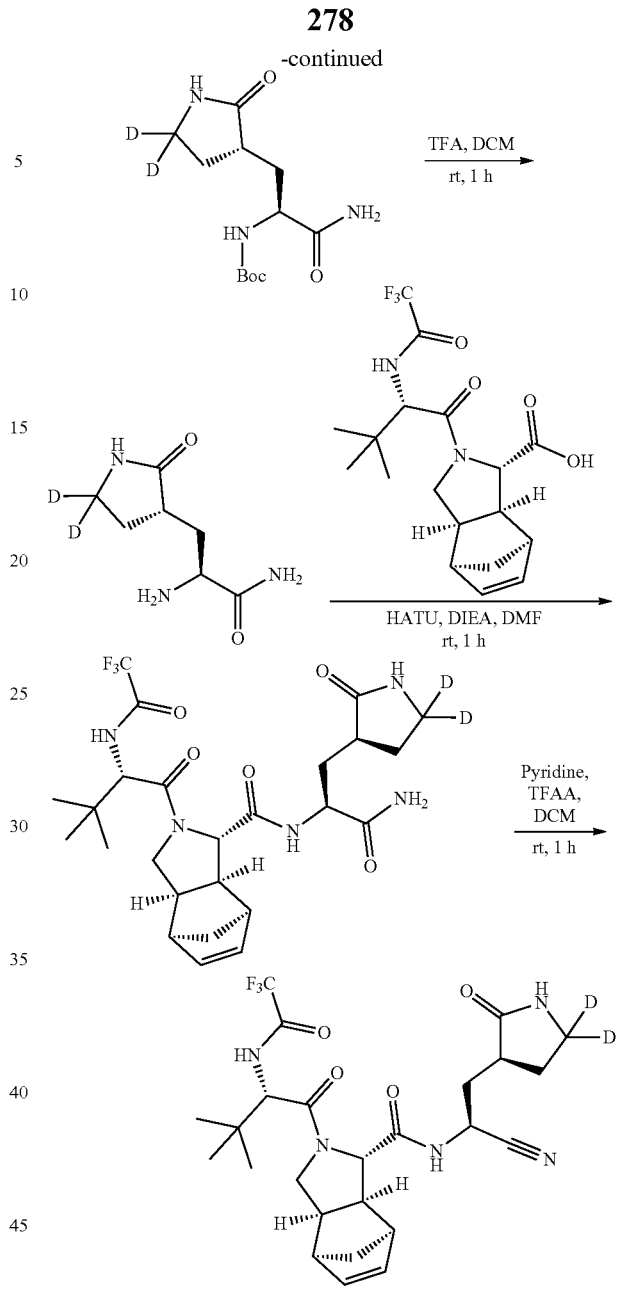

To a mixture of 1,5-dimethyl (2S)-2-[(tert-butoxycarbonyl)amino]pentanedioate (60.0 g, 217 mmol, 1.0 eq.) in THF (500 mL) was added lithium bis(trimethylsilyl)amide (80.2 g, 479 mmol, 2.2 eq.) at −78° C. under nitrogen atmosphere. After stirred for 1 h at −78° C., 2-bromoacetonitrile (28.7 g, 239 mmol, 1.1 eq.) was added. The mixture was stirred for 2 h at −78° C. under nitrogen. The reaction was quenched with methanol (200 mL) and hydrochloric acid (300 mL, 2M). The mixture was extracted with ethyl acetate (3×250 mL). The organic layers were combined, washed with brine (2×250 mL), dried over anhydrous sodium sulfate, filtered and concentrated under reduced pressure to afford the crude product. The crude product was chromatographed on a silica gel column with EA:PE (1:1) to provide 1,5-dimethyl (2S, 4R)-2-[(tert-butoxycarbonyl)amino]-4-(cyanomethyl)pentanedioate (41.4 g, 57%) as a yellow oil. LC-MS (ESI, m/z): 315 [M+H]$^+$.

To a stirred mixture of 1,5-dimethyl (2S,4R)-2-[(tert-butoxycarbonyl)amino]-4-(cyanomethyl)pentanedioate (1.50 g, 4.77 mmol, 1.0 eq.) and cobalt(II) chloride (1.24 g, 9.54 mmol, 2.0 eq.) in D$_2$O (15 mL) was added sodium borodeuteride (2.00 g, 47.7 mmol, 10 eq.). The mixture was stirred for 1 h at rt. The reaction was quenched with water (30 mL). The mixture was extracted with EtOAc (3×30 mL). The organic layers were combined, washed with brine (2×30 mL), dried over anhydrous sodium sulfate, filtered and concentrated under reduced pressure to afford the crude product. The crude product was chromatographed on a silica gel column with MeOH:DCM (1:20) to provide methyl (S)-2-((tert-butoxycarbonyl)amino)-3-((S)-2-oxopyrrolidin-3-yl-5,5-d2)propanoate (190 mg, 13%) as yellow solid. $^1$H NMR (400 MHz, DMSO-d$_6$) δ 7.53-7.73 (m, 1H), 7.28-7.49 (m, 1H), 3.96-4.11 (m, 1H), 3.54-3.71 (m, 3H), 2.20-2.32 (m, 1H), 2.07-2.18 (m, 1H), 1.91-2.06 (m, 1H), 1.50-1.70 (m, 2H), 1.30-1.44 (m, 9H). LC-MS (ESI, m/z): 189 [M−Boc+H]$^+$.

Methyl (S)-2-((tert-butoxycarbonyl)amino)-3-((S)-2-oxopyrrolidin-3-yl-5,5-d2)propanoate (190 mg, 0.659 mmol, 1.0 eq.) was stirred with NH$_3$ in MeOH (10 mL, 7 M NH$_3$ in MeOH). The mixture was stirred overnight at 80° C. and then concentrated under reduced pressure to afford tert-butyl ((S)-1-amino-1-oxo-3-((S)-2-oxopyrrolidin-3-yl-5,5-d2)propan-2-yl)carbamate (140 mg, crude) as a brown oil. LC-MS (ESI, m/z): 274 [M+H]$^+$.

To a stirred mixture of tert-butyl ((S)-1-amino-1-oxo-3-((S)-2-oxopyrrolidin-3-yl-5,5-d2)propan-2-yl)carbamate (140 mg, 0.512 mmol, 1.0 eq.) in DCM (4 mL) was added trifluoroacetic acid (1.5 mL). The mixture was stirred for 1 h at rt and then concentrated under reduced pressure to afford (S)-2-amino-3-((S)-2-oxopyrrolidin-3-yl-5,5-d2)propanamide (88 mg, crude) as a brown oil. LC-MS (ESI, m/z): 174 [M+H]$^+$.

To a stirred mixture of (1R,2S,3S,6R,7S)-4-[(2S)-3,3-dimethyl-2-(2,2,2-trifluoroacetamido)butanoyl]-4-azatricyclo[5.2.1.0^{2,6}]dec-8-ene-3-carboxylic acid (217 mg, 0.559 mmol, 1.1 eq.) and o-(7-azabenzotriazol-1-yl)-N,N,N',N'-tetramethyluronium hexafluorophosphate (231 mg, 0.610 mmol, 1.2 eq.) in DMF (3 mL) was added N-ethyl-N-isopropylpropan-2-amine (525 mg, 4.06 mmol, 8.0 eq.) at 0° C. After stirred for 20 min at 0° C., (S)-2-amino-3-((S)-2-oxopyrrolidin-3-yl-5,5-d2)propanamide (88.0 mg, 0.508 mmol, 1.0 eq.) was added. The mixture was stirred for 1 h at rt. The reaction quenched with water (15 mL). The mixture was extracted with EtOAc (3×15 mL). The organic layers were combined, washed with brine (2×15 mL), dried over anhydrous sodium sulfate, filtered and concentrated under reduced pressure to afford the crude product. The crude product was chromatographed on a silica gel column with MeOH:DCM (9:91) to provide (1S,3aR,4S,7R,7aS)—N—((S)-1-amino-1-oxo-3-((S)-2-oxopyrrolidin-3-yl-5,5-d2)propan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (170 mg, 61%) as a white solid. LC-MS (ESI, m/z): 544 [M+H]$^+$.

To a stirred mixture of (1S,3aR,4S,7R,7aS)—N—((S)-1-amino-1-oxo-3-((S)-2-oxopyrrolidin-3-yl-5,5-d2)propan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (170 mg, 0.313 mmol, 1.0 eq.) in DCM (4 mL) were added pyridine (98.9 mg, 1.25 mmol, 4.0 eq.) and trifluoroacetic anhydride (111 mg, 0.532 mmol, 1.7 eq.). The mixture was stirred for 1 h at rt. The reaction was quenched with water (15 mL). The mixture was extracted with EtOAc (3×15 mL). The organic layers were combined, washed with brine (2×15 mL), dried over anhydrous sodium sulfate, filtered and concentrated under reduced pressure to afford the crude product. The crude product was purified by prep-HPLC (Column: XSelect CSH Prep C18 OBD Column, 19*250 mm, 5 m; Mobile Phase A: Water (0.1% FA), Mobile Phase B: ACN; Flow rate: 25 mL/min; Gradient: 40% B to 75% B in 7 min, 75% B; Wave Length: 254 nm; RT1 (min): 5.42) to provide (1S,3aR,4S,7R,7aS)—N—((S)-1-cyano-2-((S)-2-oxopyrrolidin-3-yl-5,5-d2)ethyl)-2-((S)-3,3-dimethyl-2-(2,2,2-trifluoroacetamido)butanoyl)-2,3,3a,4,7,7a-hexahydro-1H-4,7-methanoisoindole-1-carboxamide (58.6 mg, 35%) as a white solid. $^1$H NMR (400 MHz, 80° C., DMSO-d6) δ 8.73-9.09 (m, 1H), 8.30-8.72 (m, 1H), 7.29-7.62 (m, 1H), 5.91-6.29 (m, 2H), 4.80-5.01 (m, 1H), 4.40-4.75 (m, 1H), 3.92-4.25 (m, 1H), 3.56-3.79 (m, 1H), 3.30-3.55 (m, 1H), 3.00-3.05 (m, 1H), 2.89-2.99 (m, 2H), 2.60-2.88 (m, 1H), 2.30-2.40 (m, 1H), 2.00-2.29 (m, 2H), 1.60-1.93 (m, 2H), 1.19-1.53 (m, 2H), 0.70-1.15 (m, 9H). LC-MS (ESI, m/z): 526 [M+H]$^+$.

Example 51

Compound 51

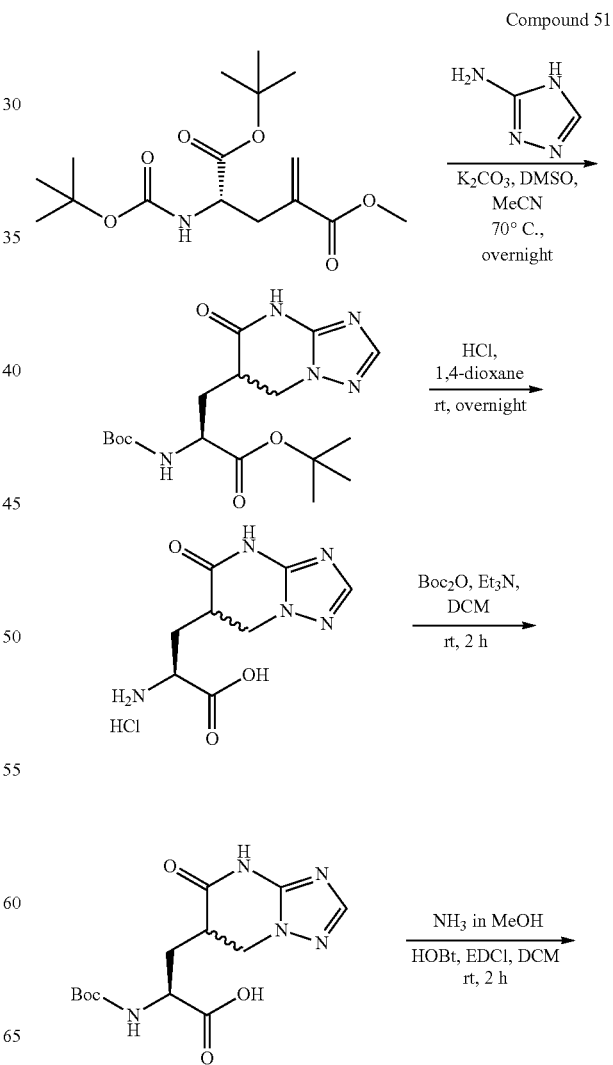

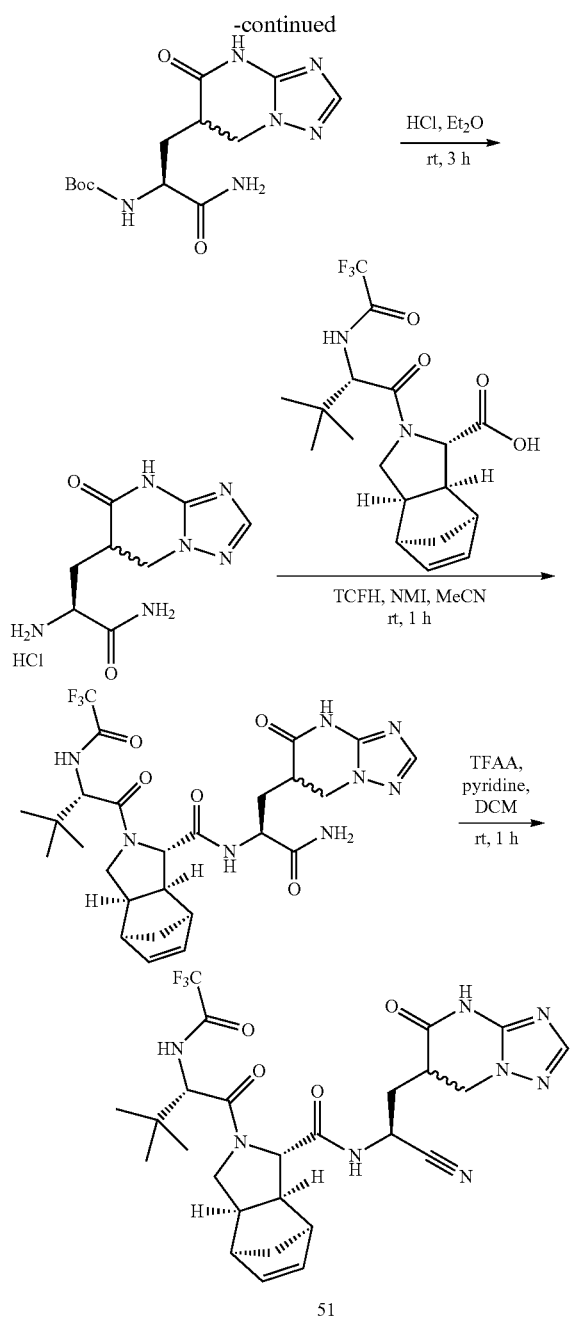

51

To a mixture of 1-tert-butyl 5-methyl (2S)-2-[(tert-butoxycarbonyl)amino]-4-methylidenepentanedioate (1.00 g, 3.04 mmol, 1 eq.) in DMSO (5 mL)/MeCN (5 mL) were added 2-amino-1,3,4-triazole (383 mg, 4.55 mmol, 1.5 eq.) and potassium carbonate (634 mg, 4.55 mmol, 1.5 eq.). The mixture was stirred overnight at 70° C. The reaction was quenched with water (50 mL). The mixture was extracted with EtOAc (3×50 mL). The organic layers were combined, washed with brine (2×50 mL), dried over anhydrous sodium sulfate, filtered and concentrated under reduced pressure to afford the crude product. The crude product was chromatographed on a silica gel column with EtOAc:PE (7:3) to provide tert-butyl (2S)-2-[(tert-butoxycarbonyl)amino]-3-{5-oxo-4H,6H,7H-[1,2,4]triazolo[1,5-a]pyrimidin-6-yl}propanoate (620 mg, 49%) as a white solid. $^1$H NMR (400 MHz, DMSO-d$_6$) δ 11.42-11.53 (m, 1H), 7.67-7.75 (m, 1H), 7.19-7.32 (m, 1H), 4.30-4.42 (m, 1H), 3.88-4.14 (m, 2H), 2.88-3.04 (m, 1H), 2.18-2.29 (m, 1H), 1.52-1.88 (m, 1H), 1.31-1.48 (m, 18H). LC-MS (ESI, m/z): 382 [M+H]$^+$.

To a mixture of tert-butyl (2S)-2-[(tert-butoxycarbonyl)amino]-3-{5-oxo-4H,6H,7H-[1,2,4]triazolo[1,5-a]pyrimidin-6-yl}propanoate (900 mg, 2.36 mmol, 1.0 eq.) in 1,4-dioxane (15 mL) was added hydrochloric acid (15 mL, 9 M). The mixture was stirred overnight at rt. The mixture was concentrated under reduced pressure to afford (2S)-2-amino-3-{5-oxo-4H,6H,7H-[1,2,4]triazolo[1,5-a]pyrimidin-6-yl}propanoic acid hydrochloride (616 mg, crude) as an off-white solid. LC-MS (ESI, m/z): 226 [M+H]$^+$.

To mixture of (2S)-2-amino-3-{5-oxo-4H,6H,7H-[1,2,4]triazolo[1,5-a]pyrimidin-6-yl}propanoic acid hydrochloride (616 mg, 2.35 mmol, 1.0 eq.) in DCM (10 mL) were added triethylamine (1.43 g, 14.1 mmol, 6.0 eq.) and di-tert-butyl dicarbonate (1.03 g, 4.71 mmol, 2.0 eq.). The mixture was stirred for 2 h at rt and then concentrated under reduced pressure to remove DCM. The residue was diluted with water (30 mL) and adjusted to pH=6 with hydrochloric acid (1 M). The mixture was extracted with IPA:chloroform (1:4, 3×30 mL). The organic layers were combined, dried over anhydrous sodium sulfate, filtered and concentrated under reduced pressure to afford (2S)-2-[(tert-butoxycarbonyl)amino]-3-{5-oxo-4H,6H,7H-[1,2,4]triazolo[1,5-a]pyrimidin-6-yl}propanoic acid (768 mg, crude) as an off-white solid. LC-MS (ESI, m/z): 270 [M−56+H]$^+$.

To a mixture of (2S)-2-[(tert-butoxycarbonyl)amino]-3-{5-oxo-4H,6H,7H-[1,2,4]triazolo[1,5-a]pyrimidin-6-yl}propanoic acid (384 mg, 1.18 mmol, 1.0 eq.) in DCM (5 mL) were added 1-hydroxybenzotriazole (191 mg, 1.42 mmol, 1.2 eq.), 1-(3-dimethylaminopropyl)-3-ethylcarbodiimide hydrochloride (249 mg, 1.30 mmol, 1.1 eq.) and ammonia (1.69 mL, 11.8 mmol, 10.0 eq., 7 M in MeOH). The mixture was stirred for 2 h at rt. The reaction was quenched with water (20 mL). The mixture was extracted with IPA:chloroform (1:4, 3×20 mL). The organic layers were combined, washed with brine (2×20 mL), dried over anhydrous sodium sulfate, filtered and concentrated under reduced pressure to afford the crude product. The crude product was chromatographed on a silica gel column with MeOH:DCM (11:89) to provide tert-butyl N-[(1S)-1-carbamoyl-2-{5-oxo-4H,6H,7H-[1,2,4]triazolo[1,5-a]pyrimidin-6-yl}ethyl]carbamate (60.0 mg, 14%) as an off-white solid. $^1$H NMR (400 MHz, DMSO-d$_6$) δ 11.41-11.51 (m, 1H), 7.69-7.75 (m, 1H), 7.29-7.40 (m, 1H), 7.09 (s, 1H), 6.94-7.02 (m, 1H), 4.31-4.50 (m, 1H), 3.94-4.06 (m, 2H), 2.82-2.98 (m, 1H), 2.09-2.34 (m, 1H), 1.53-1.79 (m, 1H), 1.27-1.48 (m, 9H). LC-MS (ESI, m/z): 269 [M−56+H]$^+$.

A mixture of tert-butyl N-[(1S)-1-carbamoyl-2-{5-oxo-4H,6H,7H-[1,2,4]triazolo[1,5-a]pyrimidin-6-yl}ethyl]carbamate (60.0 mg, 0.185 mmol, 1.0 eq.) in hydrogen chloride (3 mL, 2 M in Et$_2$O) was stirred for 1 h at rt. The mixture was concentrated under reduced pressure to afford (2S)-2-amino-3-{5-oxo-4H,6H,7H-[1,2,4]triazolo[1,5-a]pyrimidin-6-yl}propanamide hydrochloride (48.0 mg, crude) as a white solid. LC-MS (ESI, m/z): 225 [M+H]$^+$.

To a mixture of (2S)-2-amino-3-{5-oxo-4H,6H,7H-[1,2,4]triazolo[1,5-a]pyrimidin-6-yl}propanamide hydrochloride (48.0 mg, 0.184 mmol, 1.0 eq.), (1R,2S,3S,6R,7S)-4-[(2S)-3,3-dimethyl-2-(2,2,2-trifluoroacetamido)butanoyl]-4-azatricyclo[5.2.1.0^{2,6}]dec-8-ene-3-carboxylic acid (72.0 mg, 0.184 mmol, 1.0 eq.) and N,N,N',N'-Tetramethylchloroformamidinium hexafluorophosphate (67.0 mg, 0.239 mmol, 1.3 eq.) in MeCN (3 mL) was added N-methylimidazole (151 mg, 1.84 mmol, 10.0 eq.). The mixture was stirred for 1 h at rt. The crude product was purified by C18 column with CH₃CN/Water (0.05% TFA). The desired fraction was concentrated under reduced pressure to provide (2S)-2-{[(1R,2S,3S,6R,7S)-4-[(2S)-3,3-dimethyl-2-(2,2,2-trifluoroacetamido)butanoyl]-4-azatricyclo[5.2.1.0^{2,6}]dec-8-en-3-yl]formamido}-3-{5-oxo-4H,6H,7H-[1,2,4]triazolo[1,5-a]pyrimidin-6-yl}propanamide (80.0 mg, 68%) as an off-white solid.

To a mixture of (2S)-2-{[(1R,2S,3S,6R,7S)-4-[(2S)-3,3-dimethyl-2-(2,2,2-trifluoroacetamido)butanoyl]-4-azatricyclo[5.2.1.0^{2,6}]dec-8-en-3-yl]formamido}-3-{5-oxo-4H,6H,7H-[1,2,4]triazolo[1,5-a]pyrimidin-6-yl}propanamide (80.0 mg, 0.135 mmol, 1.0 eq.) in DCM (2 mL) were added pyridine (43.0 mg, 0.540 mmol, 4.0 eq.) and trifluoroacetic anhydride (42.0 mg, 0.203 mmol, 1.5 eq.). The mixture was stirred for 1 h at rt. The mixture was quenched with water (10 mL). The mixture was extracted with DCM (3×10 mL). The organic layers were combined, washed with brine (2×10 mL), dried over anhydrous sodium sulfate, filtered and concentrated under reduced pressure to afford the crude product. The crude product was purified by prep-HPLC (Column: XBridge Prep Phenyl OBD Column, 19×250 mm, 5 m; Mobile Phase A: Water (0.1% FA), Mobile Phase B: ACN; Flow rate: 25 mL/min; Gradient: 37% B to 67% B in 7 min, 67% B; Wave Length: 254 nm; RT: 5 min) to provide (1R,2S,3S,6R,7S)—N-[(1S)-1-cyano-2-{5-oxo-4H,6H,7H-[1,2,4]triazolo[1,5-a]pyrimidin-6-yl}ethyl]-4-[(2S)-3,3-dimethyl-2-(2,2,2-trifluoroacetamido)butanoyl]-4-azatricyclo[5.2.1.0^{2,6}]dec-8-ene-3-carboxamide (23.5 mg, 30%) as a white solid. LC-MS (ESI, m/z): 577[M+H]⁺.

Example 52

Compound 52

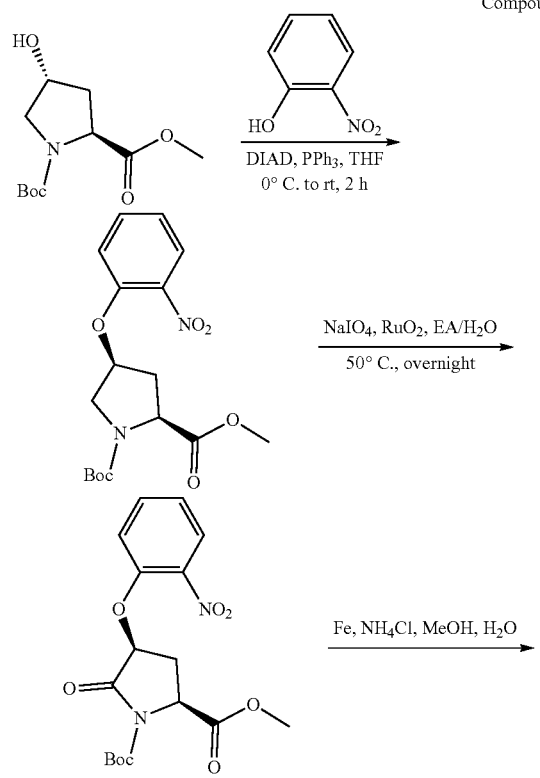

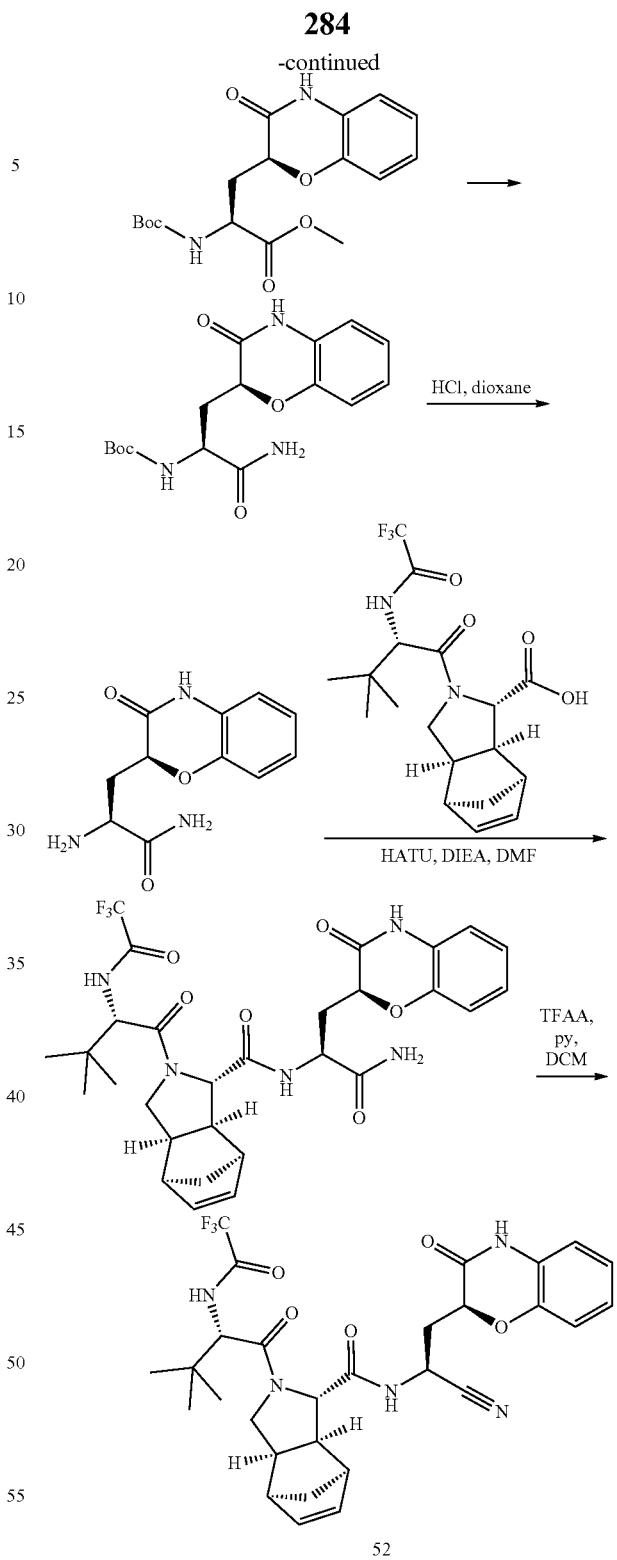

Compound 52 was prepared according to the synthetic scheme described above. To a solution of 1-(tert-butyl) 2-methyl (2S,4R)-4-hydroxypyrrolidine-1,2-dicarboxylate (20.0 g, 81.5 mmol, 1.0 eq.), o-nitrophenol (11.3 g, 81.5 mmol, 1.0 eq.) and triphenylphosphine (25.7 g, 97.8 mmol, 1.2 eq.) in THF (300 mL) was added diisopropyl azodicarboxylate (19.8 g, 97.9 mmol, 1.2 eq.) stirred at 0° C. under nitrogen. The mixture was stirred for 2 h at rt. The reaction was quenched with water (200 mL). The mixture was extracted with ethyl acetate (3×300 mL). The organic layers were combined, washed with brine (2×100 mL), dried over anhydrous sodium sulfate, filtered and concentrated under reduced pressure to afford the crude product. The crude product was chromatographed on a silica gel column with EA:PE (45:100) to provide 1-(tert-butyl) 2-methyl (2S,4S)-4-(2-nitrophenoxy)pyrrolidine-1,2-dicarboxylate (23 g, 76%) as a light yellow solid. $^1$H NMR (400 MHz, Chloroform-d) δ 7.83-7.87 (m, 1H), 7.49-7.57 (m, 1H), 7.05-7.11 (m, 1H), 6.94-6.97 (m, 1H), 4.97-5.03 (m, 1H), 4.47-4.65 (m, 1H), 3.71-3.89 (m, 5H), 2.47-2.65 (m, 2H), 1.41-1.52 (m, 9H). LCMS (ESI, m/z): 367 [M+H]$^+$.

A solution of sodium periodate (21.0 g, 98.3 mmol, 7.2 eq.) and ruthenium(IV) oxide (1.03 g, 6.82 mmol, 0.5 eq.) in H$_2$O (150 mL) was stirred for 5 min at rt under nitrogen. Then 1-(tert-butyl) 2-methyl (2S,4S)-4-(2-nitrophenoxy)pyrrolidine-1,2-dicarboxylate (5.00 g, 13.6 mmol, 1.0 eq.) in ethyl acetate (150 mL) was added. The mixture was stirred for overnight at 50° C. The mixture was diluted with ethyl acetate (200 mL) and filtered through a celite pad. The filtrate was washed with saturated aqueous sodium bisulfite (100 mL). The organic layer was washed with brine (100 mL), dried over anhydrous sodium sulfate, filtered and concentrated under reduced pressure to afford the crude product. The crude product was chromatographed on a silica gel column with EA:PE (46:100) to provide the crude product. The crude product was purified by prep-HPLC (Column: XSelect CSH Prep C18 OBD Column, 5 um, 19*150 mm; Mobile Phase A: Water (10 mmol/L NH$_4$HCO$_3$), Mobile Phase B: ACN; Flow rate: 25 mL/min; Gradient: 25% B to 70% B in 7 min; 254 nm; Rt: 5.30 min) to provide 1-(tert-butyl) 2-methyl (2S,4S)-4-(2-nitrophenoxy)-5-oxopyrrolidine-1,2-dicarboxylate (650 mg, 12%) as white solid. $^1$H NMR (400 MHz, Chloroform-d) δ 7.83-7.86 (m, 1H), 7.54-7.64 (m, 2H), 7.12-7.17 (m, 1H), 4.90-4.94 (m, 1H), 4.67-4.71 (m, 1H), 3.87 (s, 3H), 2.78-2.87 (m, 1H), 2.45-2.54 (m, 1H), 1.49-1.59 (m, 9H). LCMS (ESI, m/z): 381 [M+H]$^+$.

To a solution of 1-(tert-butyl) 2-methyl (2S,4S)-4-(2-nitrophenoxy)-5-oxopyrrolidine-1,2-dicarboxylate (650 mg, 1.71 mmol, 1.0 eq.) in methanol (8 mL) and H$_2$O (2 mL) was added iron (477 mg, 8.55 mmol, 5.0 eq.) and ammonium chloride (219 mg, 4.10 mmol, 2.4 eq.). The mixture was stirred for 24 h at 70° C. The mixture was filtered through a celite pad and washed with methanol (3×50 mL). The filtrate was dried over anhydrous sodium sulfate, filtered and concentrated under reduced pressure to afford methyl (S)-2-((tert-butoxycarbonyl)amino)-3-((S)-3-oxo-3,4-dihydro-2H-benzo[b][1,4]oxazin-2-yl)propanoate (500 mg, crude) as a yellow solid. $^1$H NMR (400 MHz, DMSO-d$_6$) δ 10.72-10.77 (m, 1H), 7.25-7.49 (m, 1H), 6.70-7.00 (m, 4H), 4.44-4.74 (m, 1H), 4.03-4.30 (m, 1H), 3.51-3.70 (m, 3H), 1.98-2.22 (m, 2H), 1.25-1.57 (m, 9H). LCMS (ESI, m/z): 351 [M+H]$^+$.

A mixture of methyl (S)-2-((tert-butoxycarbonyl)amino)-3-((S)-3-oxo-3,4-dihydro-2H-benzo[b][1,4]oxazin-2-yl)propanoate (500 mg, 1.43 mmol, 1.0 eq.) in ammonia (8 mL, 7 M in methanol) was stirred for overnight at 70° C. The mixture was concentrated under reduced pressure to afford tert-butyl ((S)-1-amino-1-oxo-3-((S)-3-oxo-3,4-dihydro-2H-benzo[b][1,4]oxazin-2-yl)propan-2-yl)carbamate (460 mg, crude) as a red solid. LCMS (ESI, m/z): 336 [M+H]$^+$.

To a mixture of tert-butyl ((S)-1-amino-1-oxo-3-((S)-3-oxo-3,4-dihydro-2H-benzo[b][1,4]oxazin-2-yl)propan-2-yl) carbamate (300 mg, 0.895 mmol, 1.0 eq.) in 1,4-dioxane (4 mL) was added hydrogen chloride (6 mL, 4 M in 1,4-dioxane). The mixture was stirred for 3 h at rt and then concentrated under reduced pressure to afford (S)-2-amino-3-((S)-3-oxo-3,4-dihydro-2H-benzo[b][1,4]oxazin-2-yl) propanamide hydrochloride (250 mg, crude) as a yellow solid. LCMS (ESI, m/z): 236 [M+H]$^+$.

To a mixture of (1S,3aR,4S,7R,7aS)-2-((S)-3,3-dimethyl-2-(2,2,2-trifluoroacetamido)butanoyl)-2,3,3a,4,7,7a-hexahydro-1H-4,7-methanoisoindole-1-carboxylic acid (357 mg, 0.920 mmol, 1.0 eq.) in dimethylformamide (10 mL) was added o-(7-azabenzotriazol-1-yl)-N,N,N',N'-tetramethyluronium hexafluorophosphate (385 mg, 1.01 mmol, 1.1 eq.) and N-ethyl-N-isopropylpropan-2-amine (714 mg, 5.52 mmol, 6.0 eq.) at 0° C. After stirred 20 min, (S)-2-amino-3-((S)-3-oxo-3,4-dihydro-2H-benzo[b][1,4]oxazin-2-yl) propanamide hydrochloride (250 mg, 0.920 mmol, 1.0 eq.) was added. The mixture was stirred for 1 h at rt and then purified by C18 column with CH$_3$CN/Water (0.05% TFA). The desired fraction was concentrated under reduced pressure to provide (1S,3aR,4S,7R,7aS)—N—((S)-1-amino-1-oxo-3-((S)-3-oxo-3,4-dihydro-2H-benzo[b][1,4]oxazin-2-yl)propan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (430 mg, 77%) as a yellow solid. LCMS (ESI, m/z): 606 [M+H]$^+$.

To a mixture of (1S,3aR,4S,7R,7aS)—N—((S)-1-amino-1-oxo-3-((S)-3-oxo-3,4-dihydro-2H-benzo[b][1,4]oxazin-2-yl)propan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (250 mg, 0.413 mmol, 1.0 eq.) in DCM (3 mL) was added pyridine (131 mg, 1.65 mmol, 4.0 eq.) and trifluoroacetic anhydride (130 mg, 0.619 mmol, 1.5 eq.). The mixture was stirred 1 h at rt. The reaction was quenched with water (10 mL). The mixture was extracted with DCM (3×50 mL). The organic layers were combined, washed with brine (2×20 mL), dried over anhydrous sodium sulfate, filtered and concentrated under reduced pressure to afford the crude product. The crude product was purified by prep-HPLC (Column: XBridge Shield RP18 OBD Column, 30*150 mm, 5 m; Mobile Phase A: Water (0.1% FA), Mobile Phase B: ACN; Flow rate: 60 mL/min; Gradient: 38% B to 58% B in 7 min, 58% B; Wave Length: 254 nm; RT1 (min): 6.4;) to provide (1S,3aR,4S,7R,7aS)—N—((S)-1-cyano-2-((S)-3-oxo-3,4-dihydro-2H-benzo[b][1,4]oxazin-2-yl)ethyl)-2-((S)-3,3-dimethyl-2-(2,2,2-trifluoroacetamido)butanoyl)-2,3,3a,4,7,7a-hexahydro-1H-4,7-methanoisoindole-1-carboxamide (101.6 mg, 42%) as a white solid. $^1$H NMR (400 MHz, 80° C., DMSO-d$_6$) δ 10.55-10.56 (m, 1H), 8.70-8.93 (m, 2H), 6.86-6.99 (m, 4H), 5.95-6.16 (m, 2H), 5.04-5.06 (m, 1H), 0.4.44-4.82 (m, 2H), 4.01-4.16 (m, 1H), 3.62-3.70 (m, 1H), 3.40-3.49 (m, 1H), 2.95-3.05 (m, 2H), 2.82-2.94 (m, 2H), 2.75-2.80 (m, 1H), 2.20-2.39 (m, 1H), 1.31-1.46 (m, 2H), 0.74-0.96 (m, 9H). LCMS (ESI, m/z): 588 [M+H]$^+$.

Example 53

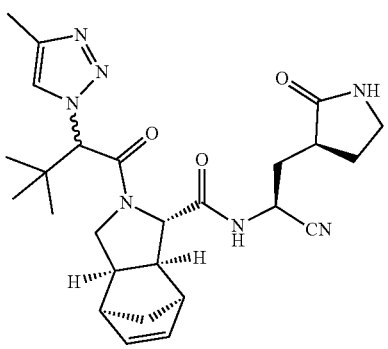

Compound 53

Compound 53 was prepared similarly as described for Compound 42 using methyl (S)-3,3-dimethyl-2-(4-methyl-1H-1,2,3-triazol-1-yl)butanoate in place of methyl (S)-3,3-dimethyl-2-(4-(trifluoromethyl)-1H-1,2,3-triazol-1-yl)butanoate. $^1$H NMR (500 MHz, 365K, DMSO-d$_6$) δ 8.62-8.78 (m, 1H), 7.74 (m, 1H), 7.36 (br. s., 1H), 6.21 (m, 1H), 5.83 (m, 1H), 5.51 (m, 1H), 5.20 (s, 1H), 4.92 (m, 1H), 3.97 (m, 1H), 3.74 (m, 1H), 3.07-3.24 (m, 4H), 2.89-3.09 (m, 1H), 2.83 (m, 1H), 2.73 (m, 1H), 2.33-2.42 (m, 1H), 2.10-2.29 (m, 4H), 1.67-1.88 (m, 2H), 1.31-1.35 (m, 2H), 0.91-0.95 (s, 9H). LCMS (ESI, m/z): 492 [M−H]$^-$.

Methyl (S)-3,3-dimethyl-2-(4-methyl-1H-1,2,3-triazol-1-yl)butanoate: To a solution of 4-methylbenzenesulfonohydrazide (1.57 g, 8.46 mmol, 1.0 eq.) in DMSO (4.0 mL) was added 1,1-dimethoxypropan-2-one (1.0 g, 8.46 mmol, 1.0 eq.). The mixture was stirred at rt for 1 h and then diluted with water (100 mL). The mixture was stirred vigorously for 10 min. The precipitate was filtered and dried under high vacuum to afford N'-(1,1-dimethoxypropan-2-ylidene)-4-methylbenzenesulfonohydrazide (800 mg, 41%) as a white solid.

A solution of N'-(1,1-dimethoxypropan-2-ylidene)-4-methylbenzenesulfonohydrazide (0.800 g, 2.89 mmol, 1.0 eq.), methyl (S)-2-amino-3,3-dimethylbutanoate (0.400 g, 2.79 mmol, 1.0 eq.) and NEt$_3$ (0.428 mL, 3.07 mmol, 1.1 eq.) in MeOH (16 mL) was heated at 75° C. for 18 h. After cooling to rt, the mixture was diluted with water (80 mL) and extracted with EA (3×100 mL). The organic phases were combined, dried over Na$_2$SO$_4$, filtered and concentrated under reduced pressure. The residue was purified by flash chromatography on silica gel using 15% EA in PE as eluent to afford methyl (S)-3,3-dimethyl-2-(4-methyl-1H-1,2,3-triazol-1-yl)butanoate (0.500 g, 84%) as a colourless solid. $^1$H NMR (400 MHz, CDCl$_3$) δ ppm 7.78 (s, 1H), 5.25 (s, 1H), 3.78 (s, 3H), 2.37 (s, 3H), 1.02 (s, 9H).

Example 54

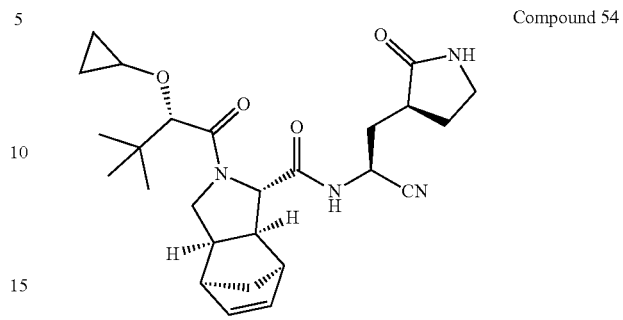

Compound 54

Compound 54 was prepared similarly as described for Compound 42 using (S)-2-cyclopropoxy-3,3-dimethylbutanoic acid in place of (S)-3,3-dimethyl-2-(4-(trifluoromethyl)-1H-1,2,3-triazol-1-yl)butanoic acid. $^1$H NMR (500 MHz, 362K, DMSO-d6) δ 8.63 (d, 1H), 7.33 (m, 1H), 6.17 (m, 1H), 6.10 (m, 1H), 4.90 (m, 1H), 4.07 (m, 1H), 3.72 (s, 1H), 3.62 (m, 1H), 3.49 (m, 1H), 3.12 (m, 2H), 3.07 (m, 2H), 2.93-3.00 (m, 2H), 2.70 (m, 1H), 2.40 (m, 1H), 2.12-2.18 (m, 2H), 1.68-1.77 (m, 2H), 1.43 (m, 2H), 0.82 (s, 9H), 0.33-0.57 (m, 4H). LCMS (ESI, m/z): 467 [M−H]$^-$.

(S)-2-Cyclopropoxy-3,3-dimethylbutanoic acid: A mixture of methyl (S)-2-hydroxy-3,3-dimethylbutanoate (2.0 g, 13.7 mmol, 1.0 eq.), chloro-1,5-cyclooctadiene iridium(I) dimer (453 mg, 0.674 mmol, 0.05 eq.), sodium carbonate (870 mg, 8.21 mmol, 0.6 eq.) and vinyl acetate (5 mL, 54.8 mmol, 4.0 eq.) in toluene (20 mL) was heated at 100° C. for 3 h. The mixture was concentrated under reduced pressure. The residue was purified by flash chromatography on silica gel using a gradient of EA (5 to 10%) in PE to afford methyl (S)-3,3-dimethyl-2-(vinyloxy)butanoate (900 mg, 40%) as a pale yellow liquid.

To a solution of methyl (S)-3,3-dimethyl-2-(vinyloxy)butanoate (1.0 g, 5.81 mmol, 1.0 eq.) in DCM (10 mL) cooled at 0° C. were added 1M diethyl zinc solution in THF (14.53 mL, 14.53 mmol, 2.5 eq.) followed by diiodomethane (2.3 mL, 29.1 mmol, 5.0 eq.). The mixture was stirred at rt for 16 h. The reaction was quenched by the addition of cold water (20 mL). The mixture was extracted with DCM (3×20 mL). The organic phases were combined, washed with water (10 mL), dried over Na$_2$SO$_4$, filtered and concentrated under reduced pressure. The residue was purified by flash chromatography on silica gel using a gradient of EA (15 to 20%) in PE to afford methyl (S)-2-cyclopropoxy-3,3-dimethylbutanoate (700 mg, 65%) as a pale yellow liquid.

To a solution of methyl (S)-2-cyclopropoxy-3,3-dimethylbutanoate (400 mg, 2.15 mmol, 1.0 eq.) in THF (1.3 mL), MeOH (1.3 mL) and water (1.3 mL) cooled at 0° C. was added LiOH (180 mg, 4.30 mmol, 1.5 eq.). The mixture was stirred at rt for 16 h and then concentrated under reduced pressure. The residues were taken up with water, acidified with sat. citric acid solution and extracted with 10% MeOH/DCM (3×10 mL). The organic phases were combined, dried over Na$_2$SO$_4$, filtered and concentrated under reduced pressure to afford (S)-2-cyclopropoxy-3,3-dimethylbutanoic acid (70 mg, 97%) as a pale yellow liquid. $^1$H NMR (400 MHz, DMSO-d$_6$) δ 12.59 (br. s., 1H), 3.46 (s, 1H), 3.26 (m, 1H), 0.87 (s, 9H), 0.57 (m, 1H), 0.31-0.50 (m, 3H).

Example 55

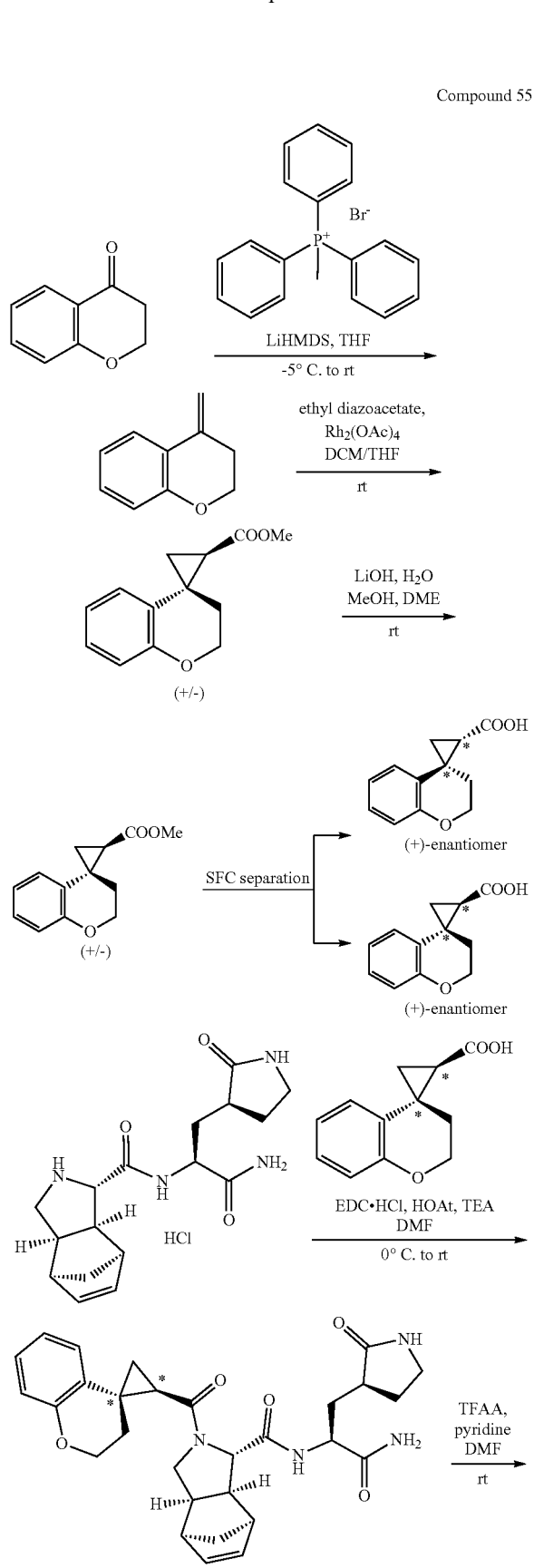

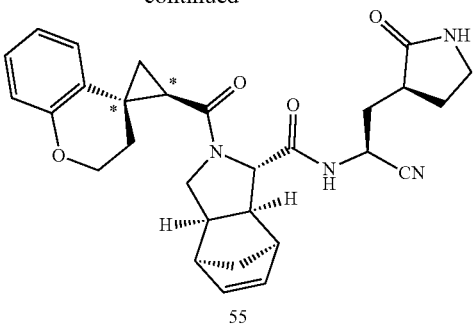

Compound 55

The chiral centers noted with "*" are tentatively assigned.

To a suspension of methyltriphenylphosphonium bromide (14.5 g, 40.5 mmol, 1.2 eq.) in THF (50 mL) cooled at 0° C. was added 1M LiHMDS in THF (40.5 mL, 40.5 mmol, 1.2 eq.). The mixture was stirred at rt for 1 h. After cooling to −5° C., a solution of chroman-4-one (5.0 g, 33.8 mmol, 1.0 eq.) in THF (10 mL) added dropwise. The mixture was stirred at rt for 1.5 h. The reaction mass was quenched with addition of sat. NH$_4$Cl (100 mL). The aqueous phase was extracted with EA (3×50 mL). The organic phases were combined, washed with brine, dried over Na$_2$SO$_4$, filtered and concentrated under reduced pressure. The residue was purified by flash chromatography on silica gel using a gradient of EA (20 to 25%) in PE to afford 4-methylenechromane (3.1 g, 63%) as a colourless liquid.

To a solution of 4-methylenechromane (2.1 g, 14.4 mmol, 1.0 eq.), Rh$_2$(OAc)$_4$ (64 mg, 0.142 mmol, 0.01 eq.) in DCM (8.8 mL) was added a solution of ethyl diazoacetate (3.8 mL, 35.9 mmol, 2.5 eq.) in THF (4.2 mL) over a period of 1 h. The mixture was stirred at rt for 1 h and then concentrated under reduced pressure. The residue was purified by flash chromatography on silica gel using a gradient of EA (3 to 5%) in PE and by prep-HPLC (Column: X-SELECT-C18 19×250 mm, 5um; Mobile Phase A: 10 mM NH$_4$HCO$_3$ in water, Mobile Phase B: ACN; Flow rate: 17 mL/min; gradient: 20% B to 70% B in 8 min) to afford trans ethyl spiro[chromane-4,1'-cyclopropane]-2'-carboxylate (800 mg, 24%) as a colourless liquid. $^1$H NMR (400 MHz, CDCl$_3$) δ 7.07-7.14 (m, 1H), 6.81-6.89 (m, 2H), 6.75-6.78 (m, 1H), 4.20-4.28 (m, 1H), 3.98-4.15 (m, 3H), 1.98-2.12 (m, 3H), 1.65-1.72 (m, 1H), 1.44 (t, 1H), 1.18 (t, 3H). LC-MS (ESI, m/z): 233 [M+H]$^+$. (cis ethyl spiro[chromane-4,1'-cyclopropane]-2'-carboxylate (500 mg) was also obtained.)

To a solution of trans ethyl spiro[chromane-4,1'-cyclopropane]-2'-carboxylate (800 mg, 3.44 mmol, 1.0 eq.) in MeOH (3.5 mL), DME (3.5 mL) and water (1.4 mL) cooled at 0° C. was added LiOH (289 mg, 6.89 mmol, 2.0 eq.). The mixture was stirred at rt for 16 h. 10% citric acid (15 mL) was added. The mixture was extracted with EA (4×20 mL). The organic phases were combined, dried over Na$_2$SO$_4$, filtered and concentrated under reduced pressure to afford trans spiro[chromane-4,1'-cyclopropane]-2'-carboxylic acid (690 mg, 98%) as a white solid.

trans Spiro[chromane-4,1'-cyclopropane]-2'-carboxylic acid (690 mg) was purified by prep-SFC using the following conditions: Column: Chiralcel OJ-H, 30*250 mm, 5m; Mobile Phase A: CO$_2$, Mobile Phase B: MeOH; Flow rate: 90 g/min; Gradient: isocratic 20% B; Column Temperature: 30° C.; Back Pressure: 100 bar. Purification resulted in (2'S*,4R*)-spiro[chromane-4,1'-cyclopropane]-2'-carboxylic acid (270 mg) and (2'R*,4S*)-spiro[chromane-4,1'-cyclopropane]-2'-carboxylic acid (280 mg).

(2'S*,4R*)-Spiro[chromane-4,1'-cyclopropane]-2'-carboxylic acid: $^1$H NMR (400 MHz, DMSO-d$_6$) δ 12.41 (br. s., 1H), 7.05-7.12 (m, 1H), 6.82-6.87 (m, 2H), 6.76 (d, 1H), 4.28-4.30 (m, 1H), 4.00-4.08 (m, 1H), 1.98-2.08 (m, 3H), 1.60-1.65 (m, 1H), 1.39 (t, 1H). [α]$_{25}^D$: +311.7° (c 0.1, MeOH). SFC: Chiralcel OJ-H, 4.6*250 mm, 3 m, 30° C., co-Solvent: MeOH, hold 5 min at 20%, Rt: 1.29 min.

(2'R*,4S*)-Spiro[chromane-4,1'-cyclopropane]-2'-carboxylic acid: $^1$H NMR (400 MHz, DMSO-d$_6$) δ 12.38 (br. s., 1H), 7.05-7.12 (m, 1H), 6.82-6.87 (m, 2H), 6.76 (d, 1H), 4.28-4.30 (m, 1H), 4.00-4.08 (m, 1H), 1.98-2.08 (m, 3H), 1.60-1.65 (m, 1H), 1.39 (t, 1H). [α]$^{25}_D$: −321.8° (c 0.1, MeOH). SFC: Chiralcel OJ-H, 4.6*250 mm, 3 m, 30° C., co-Solvent: MeOH, hold 5 min at 20%, Rt: 1.76 min.

To a solution of (1S,3aR,4S,7R,7aS)—N—((S)-1-amino-1-oxo-3-((S)-2-oxopyrrolidin-3-yl)propan-2-yl)-2,3,3a,4,7,7a-hexahydro-1H-4,7-methanoisoindole-1-carboxamide hydrochloride (120 mg, 0.325 mmol, 1.0 eq.) in DMF (1.2 mL) cooled at 0° C. were added (2'R*,4S*)-spiro[chromane-4,1'-cyclopropane]-2'-carboxylic acid (65 mg, 0.318 mmol, 1.0 eq.), EDC•HCl (122 mg, 0.637 mmol, 2.0 eq.), HOAt (43 mg, 0.320 mmol, 1.0 eq.) and NEt$_3$ (0.170 mL, 1.28 mmol, 3.0 eq.). The mixture was stirred at rt for 16 h. The mixture was diluted with water (5 mL) and extracted with EA (3×5 mL). The organic phases were combined, dried over Na$_2$SO$_4$, filtered and concentrated under reduced pressure. The residue was purified by flash chromatography on silica gel using a gradient of MeOH (1 to 10%) in DCM to afford (1S,3aR,4S,7R,7aS)—N—((S)-1-amino-1-oxo-3-((S)-2-oxopyrrolidin-3-yl)propan-2-yl)-2-((2'R*,4S*)-spiro[chromane-4,1'-cyclopropane]-2'-carbonyl)-2,3,3a,4,7,7a-hexahydro-1H-4,7-methanoisoindole-1-carboxamide (110 mg, 65%) as an off-white solid. LC-MS (ESI, m/z): 519 [M+H]$^+$.

To a solution of (1S,3aR,4S,7R,7aS)—N—((S)-1-amino-1-oxo-3-((S)-2-oxopyrrolidin-3-yl)propan-2-yl)-2-((2'R*,4S*)-spiro[chromane-4,1'-cyclopropane]-2'-carbonyl)-2,3,3a,4,7,7a-hexahydro-1H-4,7-methanoisoindole-1-carboxamide (90 mg, 0.174 mmol, 1.0 eq.) in DMF (0.9 mL) were added pyridine (0.042 mL, 0.521 mmol, 3.0 eq.) and TFAA (0.040 mL; 0.390 mmol, 2.2 eq.). The mixture was stirred at rt for 1 h. The mixture was diluted with water (10 mL) and extracted with EA (3×10 mL). The organic phases were combined, washed with brine (2×10 mL), dried over Na$_2$SO$_4$, filtered and concentrated under reduced pressure. The residue was purified by flash chromatography on silica gel using a gradient of MeOH (1 to 10%) in DCM and by flash chromatography on C18 gel using a gradient of ACN (30 to 40%) in water to afford (1S,3aR,4S,7R,7aS)—N—((S)-1-cyano-2-((S)-2-oxopyrrolidin-3-yl)ethyl)-2-((2'R*,4S*)-spiro[chromane-4,1'-cyclopropane]-2'-carbonyl)-2,3,3a,4,7,7a-hexahydro-1H-4,7-methanoisoindole-1-carboxamide (30 mg, 34%) as a white solid. $^1$H NMR (500 MHz, 365K, DMSO-d$_6$) δ 8.52 (br. s., 1H), 7.29-7.46 (m, 1H), 6.95-7.10 (m, 1H), 6.62-6.88 (m, 3H), 6.25-6.00 (m, 2H), 4.35-4.92 (m, 1H), 4.17 (m, 1H), 3.91-4.12 (m, 2H), 3.75 (m, 1H), 3.10-3.40 (m, 4H), 2.70-2.95 (m, 3H), 2.38 (m, 1H), 1.90-2.22 (m, 4H), 1.68-1.86 (m, 3H), 1.40 (m, 4H). LCMS (ESI, m/z): 501 [M+H]$^+$.

Example 56

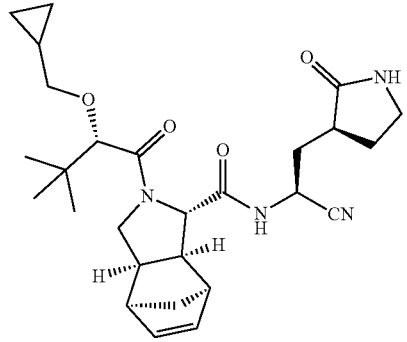

Compound 56

Compound 56 was prepared similarly as described for Compound 42 using (S)-2-(cyclopropylmethoxy)-3,3-dimethylbutanoic acid in place of (S)-3,3-dimethyl-2-(4-(trifluoromethyl)-1H-1,2,3-triazol-1-yl)butanoic acid. $^1$H NMR (500 MHz, 363K, DMSO-d6) δ 8.63 (br. s., 1H), 7.34-7.50 (m, 1H), 6.05-6.18 (m, 2H), 4.91 (m, 1H), 4.00-4.12 (m, 1H), 3.67 (s, 1H), 3.59 (m, 1H), 3.47 (m, 1H), 3.05-3.25 (m, 5H), 2.90-3.00 (m, 2H), 2.71 (m, 1H), 2.40 (m, 1H), 2.17 (m, 2H), 1.68-1.84 (m, 2H), 1.43 (m, 2H), 1.00 (m, 1H), 0.90 (m, 9H), 0.40-0.50 (m, 2H), 0.10-0.22 (m, 2H). LCMS (ESI, m/z): 483 [M+H]$^+$.

(S)-2-(Cyclopropylmethoxy)-3,3-dimethylbutanoic acid: To a solution of methyl (S)-2-hydroxy-3,3-dimethylbutanoate (100 mg, 0.684 mmol, 1.0 eq.) and (bromomethyl)cyclopropane (0.140 mL, 1.37 mmol, 2.0 eq.) in DMF (1 mL) cooled at 0° C. was added portion wise NaH (30 mg, 0.750 mmol, 1.1 eq.). The mixture was stirred at 0° C. for 6 h. The reaction was quenched by addition of cold water (5 mL). The mixture was extracted with Et$_2$O (3×10 mL). The organic phases were combined, washed with water and brine, dried over Na$_2$SO$_4$, filtered and concentrated under reduced pressure. The residue was purified by flash chromatography on silica gel using a gradient of Et$_2$O (5 to 10%) in pentane to afford methyl (S)-2-(cyclopropylmethoxy)-3,3-dimethylbutanoate (30 mg, 22%) as a colourless liquid.

To a solution of methyl (S)-2-(cyclopropylmethoxy)-3,3-dimethylbutanoate (350 mg 1.75 mmol, 1.0 eq.) in THF (1.5 mL), MeOH (1.5 mL), and water (0.4 mL) cooled at 0° C. was added LiOH (221 mg, 5.25 mmol, 3.0 eq.). The mixture stirred at rt for 8 h. The mixture was diluted with EA (3 mL) and water (2 mL), and then acidified with 1N HCl. The phases were separated. The aqueous phase was extracted with EA (2×5 mL). The organic phase was washed with water and brine, dried over Na$_2$SO$_4$, filtered and concentrated under reduced pressure to afford (S)-2-(cyclopropylmethoxy)-3,3-dimethylbutanoic acid (100 mg, 36%) as an off-white solid. $^1$H NMR (500 MHz, DMSO-d$_6$) δ 12.43 (br. s., 1H), 3.45 (s, 1H), 3.26-3.35 (m, 1H), 3.09-3.15 (m, 1H), 0.95-1.02 (m, 1H), 0.92 (s, 9H), 0.40-0.50 (m, 2H), 0.12-0.22 (m, 2H).

Example 57
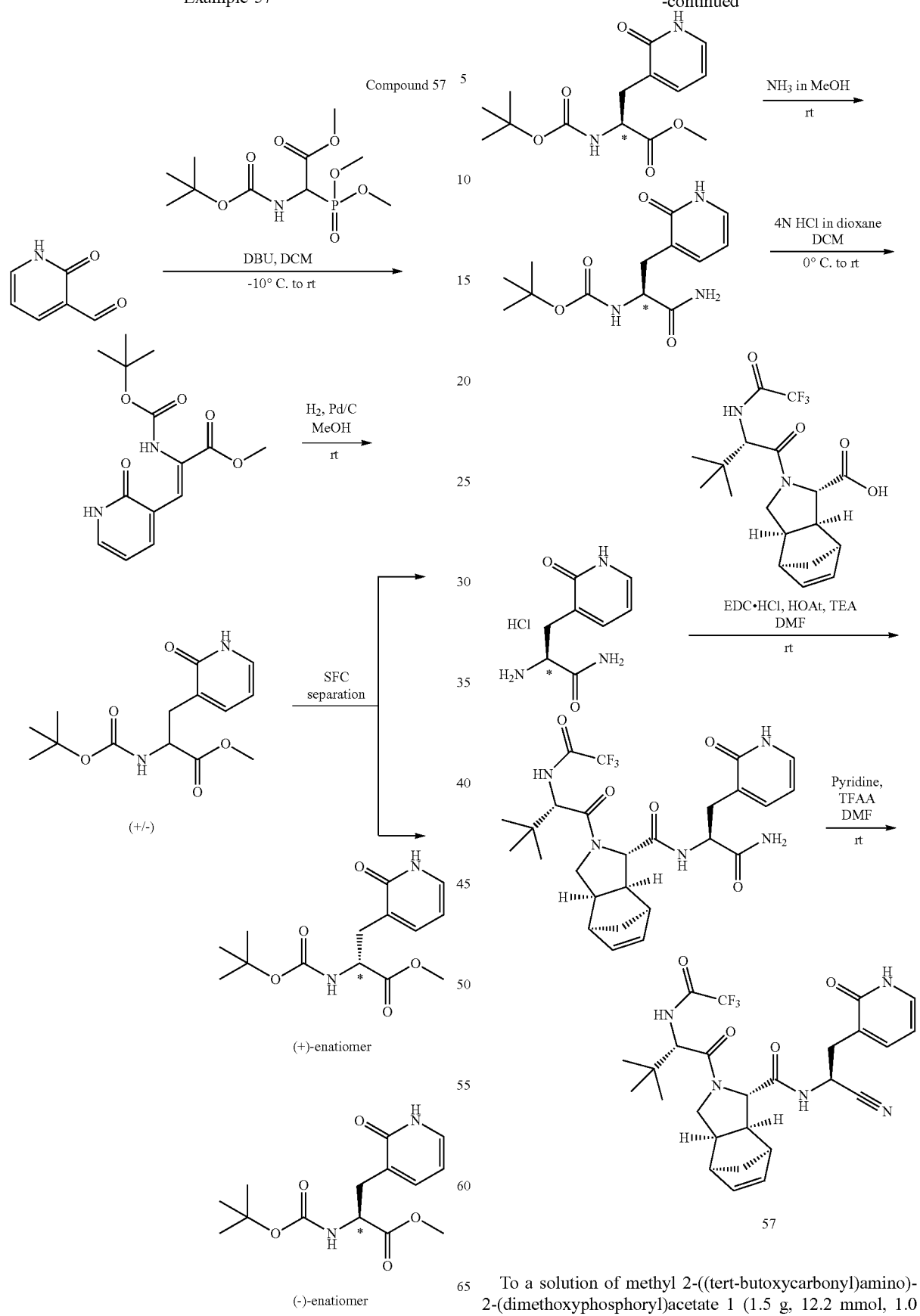
To a solution of methyl 2-((tert-butoxycarbonyl)amino)-2-(dimethoxyphosphoryl)acetate 1 (1.5 g, 12.2 mmol, 1.0 eq.) in DCM (20 mL) cooled at −10° C. was added DBU (2.2 mL, 14.6 mmol, 1.2 eq.). The mixture was stirred at −10° C. for 30 min. 2-Oxo-1,2-dihydropyridine-3-carbaldehyde (4.34 g, 14.6 mmol, 1.2 eq.) was added, and the mixture was stirred at rt for 16 h. The mixture was diluted with water (20 mL) and extracted with EA (2×20 mL). The organic phases were combined, washed with brine (2×20 mL), dried over $Na_2SO_4$, filtered and concentrated under reduced pressure. The residue was purified by flash chromatography on silica gel using a gradient of MeOH (1 to 10%) in DCM to afford methyl 2-((tert-butoxycarbonyl)amino)-3-(2-oxo-1,2-dihydropyridin-3-yl)acrylate (1.5 g, 42%) as an off-white solid.

To a solution of methyl 2-((tert-butoxycarbonyl)amino)-3-(2-oxo-1,2-dihydropyridin-3-yl)acrylate (1.5 g, 5.10 mmol, 1.0 eq.) in MeOH (15 mL) was added 10% Pd/C (1.0 g). The mixture was stirred for 3 h under hydrogen bladder pressure and then filtered through celite bed. The filtrate was concentrated under reduced pressure. The residue was purified by flash chromatography on silica gel using a gradient of MeOH (1 to 10%) in DCM to afford methyl 2-((tert-butoxycarbonyl)amino)-3-(2-oxo-1,2-dihydropyridin-3-yl)propanoate (1.4 g, 91%) as a white solid.

Methyl 2-((tert-butoxycarbonyl)amino)-3-(2-oxo-1,2-dihydropyridin-3-yl)propanoate (1.2 g) was purified by prep-SFC using the following conditions: Column: Chiralpak-IG, 25*200 mm, 5 m; Mobile Phase A: $CO_2$, Mobile Phase B: MeOH; Flow rate: 100 g/min; Gradient: isocratic 15% B; Column Temperature: 30° C.; Back Pressure: 110 bar. Purification resulted in methyl (R*)-2-((tert-butoxycarbonyl)amino)-3-(2-oxo-1,2-dihydropyridin-3-yl)propanoate (500 mg) and methyl (S*)-2-((tert-butoxycarbonyl)amino)-3-(2-oxo-1,2-dihydropyridin-3-yl)propanoate (480 mg).

Methyl (R*)-2-((tert-butoxycarbonyl)amino)-3-(2-oxo-1,2-dihydropyridin-3-yl)propanoate: $^1$H NMR (500 MHz, DMSO-$d_6$) δ 11.64 (s, 1H), 7.22-7.31 (m, 3H), 6.12 (t, 1H), 4.24-4.29 (m, 1H), 3.58 (s, 3H), 2.87 (dd, 1H), 2.54-2.60 (m, 1H), 1.20-1.37 (m, 9H). $[α]_{25}^D$: +70.2° (c 0.1, MeOH). SFC: Chiralpak-IG, 4.6*150 mm, 3 m, 30° C., co-Solvent: 0.5% DEA in MeOH, hold 12 min at 20%, Rt: 1.74 min.

Methyl (S*)-2-((tert-butoxycarbonyl)amino)-3-(2-oxo-1,2-dihydropyridin-3-yl)propanoate: $^1$H NMR (400 MHz, DMSO-$d_6$) δ 11.63 (s, 1H), 7.22-7.31 (m, 3H), 6.12 (t, 1H), 4.24-4.29 (m, 1H), 3.58 (s, 3H), 2.87 (dd, 1H), 2.58 (dd, 1H), 1.23-1.33 (m, 9H). $[α]^{25}_D$: −97.9° (c 0.1, MeOH). SFC: Chiralpak-IG, 4.6*150 mm, 3 m, 30° C., co-Solvent: 0.5% DEA in MeOH, hold 12 min at 20%, Rt: 3.73 min.

A solution of methyl (S*)-2-((tert-butoxycarbonyl)amino)-3-(2-oxo-1,2-dihydropyridin-3-yl)propanoate (300 mg, 1.01 mmol, 1.0 eq.) in 7M $NH_3$ in MeOH (10 mL) was stirred at rt for 32 h in a sealed tube. The mixture was concentrated under reduced pressure. The residue was purified by flash chromatography on silica gel using a gradient of MeOH (1 to 10%) in DCM to afford tert-butyl (S*)-(1-amino-1-oxo-3-(2-oxo-1,2-dihydropyridin-3-yl)propan-2-yl)carbamate (260 mg, 91%) as a white solid.

To a solution of tert-butyl (S*)-(1-amino-1-oxo-3-(2-oxo-1,2-dihydropyridin-3-yl)propan-2-yl)carbamate (260 mg, 0.925 mmol, 1.0 eq.) in DCM (3 mL) cooled at 0° C. was added 4N HCl in dioxane (0.920 mL, 3.70 mmol, 4.0 eq.). The mixture was stirred at rt for 2 h and then concentrated under reduced pressure to afford (S*)-2-amino-3-(2-oxo-1,2-dihydropyridin-3-yl)propanamide hydrochloride (150 mg, 89%) as a white solid.

To a solution of (1S,3aR,4S,7R,7aS)-2-((S)-3,3-dimethyl-2-(2,2,2-trifluoroacetamido)butanoyl)-2,3,3a,4,7,7a-hexahydro-1H-4,7-methanoisoindole-1-carboxylic acid (150 mg, 0.386 mmol, 1.0 eq.) in DMF (1.5 mL) cooled at 0° C. were added (S*)-2-amino-3-(2-oxo-1,2-dihydropyridin-3-yl)propanamide hydrochloride (100 mg, 0.463 mmol, 1.2 eq.), EDC•HCl (147 mg, 0.772 mmol, 2.0 eq.), HOAt (52 mg, 0.386 mmol, 1.0 eq.) and $NEt_3$ (0.16 mL, 1.15 mmol, 3.0 eq.). The mixture was stirred at rt for 16 h. The mixture was diluted with water (10 mL) and extracted with EA (2×10 mL). The organic phases were combined, washed with brine (2×10 mL), dried over $Na_2SO_4$, filtered and concentrated under reduced pressure. The residue was purified by flash chromatography on C18 gel using 0.01% FA in ACN to afford (1S,3aR,4S,7R,7aS)—N—((S*)-1-amino-1-oxo-3-(2-oxo-1,2-dihydropyridin-3-yl)propan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (150 mg, 70%) as a white solid. LC-MS (ESI, m/z): 552 $[M+H]^+$.

To a solution of (1S,3aR,4S,7R,7aS)—N—((S*)-1-amino-1-oxo-3-(2-oxo-1,2-dihydropyridin-3-yl)propan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (150 mg, 0.272 mmol, 1.0 eq.) in DMF (1.5 mL) were added pyridine (0.060 mL, 0.816 mmol, 3.0 eq.) and TFAA (0.070 mL, 0.544 mmol, 2.0 eq.). The mixture was stirred at rt for 1 h. The mixture was diluted with water (5 mL) and extracted with EA (2×5 mL). The organic phases were combined, washed with brine (2×5 mL), dried over $Na_2SO_4$, filtered and concentrated under reduced pressure. The residue was purified by prep-HPLC (Column: KROMOSIL-C18, 25×150 mm, 7 um; Mobile Phase A: 10 mM Ammonium bicarbonate in water, Mobile Phase B: ACN; Flow rate: 22 mL/min; gradient: 20% B to 70% B in 8 min) to afford (1S,3aR,4S,7R,7aS)—N—((S*)-1-cyano-2-(2-oxo-1,2-dihydropyridin-3-yl)ethyl)-2-((S)-3,3-dimethyl-2-(2,2,2-trifluoroacetamido)butanoyl)-2,3,3a,4,7,7a-hexahydro-1H-4,7-methanoisoindole-1-carboxamide (60 mg, 41%) as a white solid. $^1$H NMR (400 MHz, 363K, DMSO-$d_6$) δ 10.5 (br. s., 1H), 8.73 (br. s., 1H), 7.38 (d, 1H), 7.30 (d, 1H), 6.14 (t, 1H), 5.99 (m, 2H), 4.97 (m, 1H), 4.46 (m, 1H), 4.01-4.10 (m, 1H), 3.65 (m, 1H), 3.43 (m, 1H), 2.82-3.10 (m, 6H), 2.65 (m, 1H), 1.37 (m, 2H), 0.94 (s, 9H). LCMS (ESI, m/z): 532 $[M−H]^−$.

Example 58

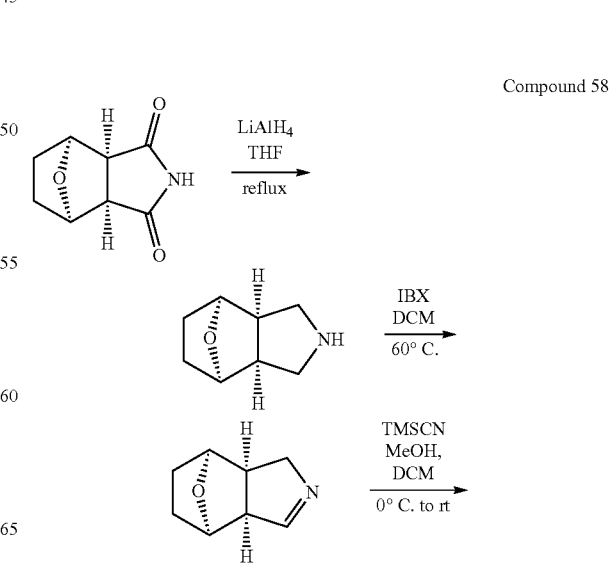

Compound 58

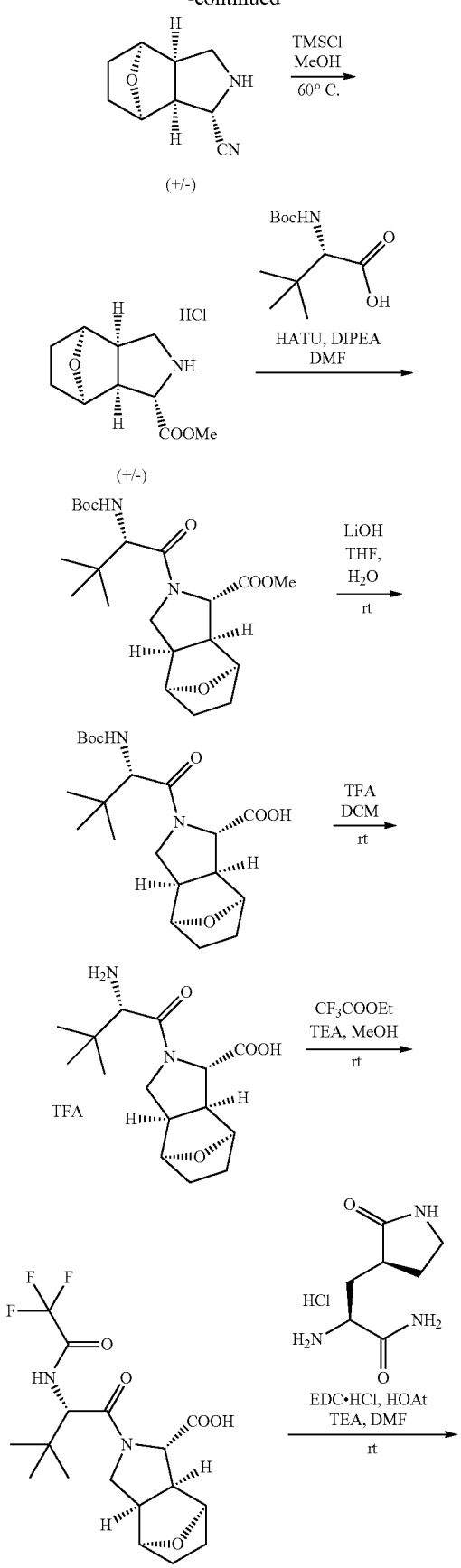

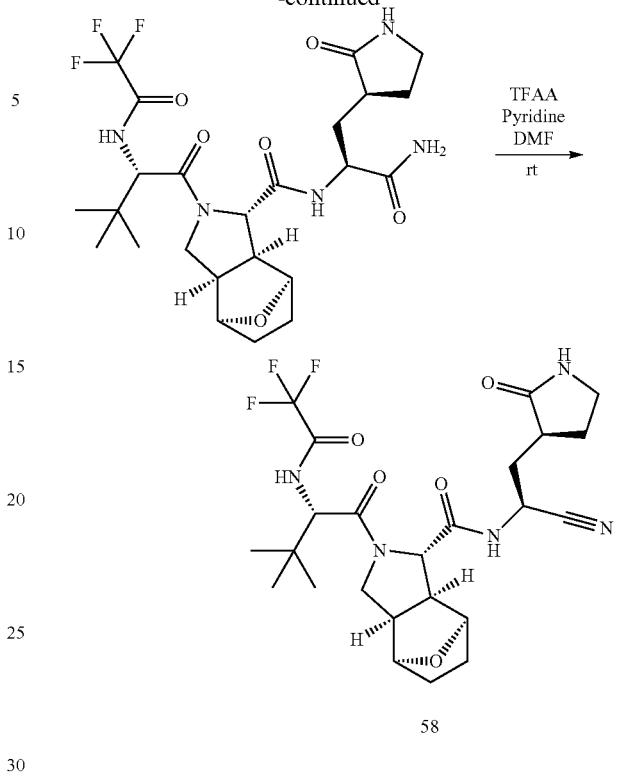

58

To a solution of (3aR,4R,7S,7aS)-hexahydro-1H-4,7-epoxyisoindole-1,3(2H)-dione (260 mg, 1.55 mmol, 1.0 eq.) in THF (5 mL) cooled at 0° C. was added 2M LiAlH$_4$ in THF (3.1 mL, 6.20 mmol, 4 eq.). The mixture was stirred at reflux for 16 h. After cooling to rt, the reaction was quenched with sat. Na$_2$SO$_4$ (10 mL). The mixture was filtered through celite, and the solids were washed with THF (10 mL). The filtrate was concentrated under reduced pressure to afford quantitatively (3aR,4S,7R,7aS)-octahydro-1H-4,7-epoxyisoindole as a pale yellow viscous liquid.

To a solution of (3aR,4S,7R,7aS)-octahydro-1H-4,7-epoxyisoindole (1.8 g, 12.9 mmol, 1.0 eq.) in DCM (20 mL) was added IBX (3.6 g, 12.9 mmol, 1.0 eq.). The mixture was stirred in sealed tube at 60° C. for 1 h. After cooling to rt, the mixture was washed with sat. sodium dithionate (10 mL). The phases were separated. The organic phase was washed with sat. sodium carbonate (70 mL) and brine (30 mL). The aqueous phases were extracted with DCM (3×50 mL). The organic phases were combined, dried over Na$_2$SO$_4$, filtered and concentrated under reduced pressure. The residue was purified by flash chromatography on silica gel using a gradient of MeOH (2 to 5%) in DCM to afford (3aS,4R,7S,7aR)-3a,4,5,6,7,7a-hexahydro-1H-4,7-epoxyisoindole (1.2 g, 68%) as a pale yellow oil.

To a solution of (3aS,4R,7S,7aR)-3a,4,5,6,7,7a-hexahydro-1H-4,7-epoxyisoindole (1.2 g, 8.75 mmol, 1.0 eq.) in DCM (12 mL) and MeOH (1.2 mL) cooled at 0° C. was added TMSCN (2.7 mL, 21.9 mmol, 2.5 eq.). The mixture was stirred at rt for 16 h and then concentrated under reduced pressure. The residue was purified by flash chromatography on silica gel using a gradient of MeOH (1 to 3%) in DCM to afford (+/−)-(1S,3aR,4S,7R,7aS)-octahydro-1H-4,7-epoxyisoindole-1-carbonitrile (800 mg, 56%) as an off-white solid.

To a solution of (+/−)-((1S,3aR,4S,7R,7aS)-octahydro-1H-4,7-epoxyisoindole-1-carbonitrile (300 mg, 1.82 mmol, 1.0 eq.) in MeOH (3 mL) cooled at 0° C. was added TMSCl (0.600 mL, 5.48 mmol, 3.0 eq.). The mixture was stirred at 60° C. for 6 h. The mixture was concentrated under reduced pressure to afford quantitatively (+/−)-methyl (1S,3aR,4S,7R,7aS)-octahydro-1H-4,7-epoxyisoindole-1-carboxylate hydrochloride as a pale yellow solid.

To a solution of (+/−)-methyl (1S,3aR,4S,7R,7aS)-octahydro-1H-4,7-epoxyisoindole-1-carboxylate hydrochloride (360 mg, 1.82 mmol, 1.0 eq.) in DMF (3.6 mL) cooled at 0° C. were added (S)-2-((tert-butoxycarbonyl)amino)-3,3-dimethylbutanoic acid (506 mg, 2.19 mmol, 1.2 eq.), HATU (1.05 g, 2.73 mmol, 1.5 eq.) and DIPEA (1.0 mL, 5.46 mmol, 3.0 eq.). The mixture was stirred at rt for 5 h. The mixture was diluted with water (5 mL) and extracted with EtOAc (2×10 mL). The organic phases were combined, washed with brine (2×20 mL), dried over $Na_2SO_4$, filtered and concentrated under reduced pressure. The residue was purified by flash chromatography on silica gel using a gradient of EA (30 to 60%) in PE to afford methyl (1S,3aR,4S,7R,7aS)-2-((S)-2-((tert-butoxycarbonyl)amino)-3,3-dimethylbutanoyl)octahydro-1H-4,7-epoxyisoindole-1-carboxylate (350 mg, 50%) as a colourless viscous liquid.

To a solution of methyl (1S,3aR,4S,7R,7aS)-2-((S)-2-((tert-butoxycarbonyl)amino)-3,3-dimethylbutanoyl)octahydro-1H-4,7-epoxyisoindole-1-carboxylate (350 mg, 0.853 mmol, 1.0 eq.) in THF (3 mL) and water (3 mL) cooled at 0° C. was added LiOH (53 mg, 1.28 mmol, 1.5 eq.). The mixture was stirred at rt for 2 h and then concentrated under reduced pressure. The residue was taken up with 1N HCl and extracted with EA (2×20 mL). The organic phases were combined, dried over $Na_2SO_4$, filtered and concentrated under reduced pressure to afford (1S,3aR,4S,7R,7aS)-2-((S)-2-((tert-butoxycarbonyl)amino)-3,3-dimethylbutanoyl)octahydro-1H-4,7-epoxyisoindole-1-carboxylic acid (280 mg, 82%) as an off-white solid.

To a solution of (1S,3aR,4S,7R,7aS)-2-((S)-2-((tert-butoxycarbonyl)amino)-3,3-dimethylbutanoyl)octahydro-1H-4,7-epoxyisoindole-1-carboxylic acid (250 mg, 0.631 mmol, 1.0 eq.) in DCM (3 mL) cooled at 0° C. was added TFA (0.350 mL, 3.15 mmol, 5.0 eq.). The mixture was at rt stirred for 2 h and then concentrated under reduced pressure to afford (1S,3aR,4S,7R,7aS)-2-((S)-2-amino-3,3-dimethylbutanoyl)octahydro-1H-4,7-epoxyisoindole-1-carboxylic under its acid trifluoroacetic acid salt (250 mg) as an oil.

To a solution of (1S,3aR,4S,7R,7aS)-2-((S)-2-amino-3,3-dimethylbutanoyl)octahydro-1H-4,7-epoxyisoindole-1-carboxylic acid under its trifluoroacetic acid salt (250 mg, 0.844 mmol, 1.0 eq.) in MeOH (2.5 mL) were added ethyl 2,2,2-trifluoroacetate (0.300 mL, 4.22 mmol, 5.0 eq.) and $NEt_3$ (0.600 mL, 4.22 mmol, 5.0 eq.). The mixture was stirred at rt for 32 h and then concentrated under reduced pressure. The residue was purified by flash chromatography on C18 gel using 0.01% TFA in ACN to afford (1S,3aR,4S,7R,7aS)-2-((S)-3,3-dimethyl-2-(2,2,2-trifluoroacetamido)butanoyl)octahydro-1H-4,7-epoxyisoindole-1-carboxylic acid (90 mg, 36% over 2 steps) as a white solid.

To a solution of (1S,3aR,4S,7R,7aS)-2-((S)-3,3-dimethyl-2-(2,2,2-trifluoroacetamido)butanoyl)octahydro-1H-4,7-epoxyisoindole-1-carboxylic acid (90 mg, 0.229 mmol, 1.0 eq.) in DMF (1 mL) at 0° C. were added (S)-2-amino-3-((S)-2-oxopyrrolidin-3-yl)propanamide hydrochloride (60 mg, 0.276 mmol, 1.2 eq.), EDC•HCl (88 mg, 0.646 mmol, 2.8 eq.), HOAt (31 mg, 0.228 mmol, 1.0 eq.) and TEA (0.1 mL, 0.717 mmol, 3.1 eq.). The mixture was stirred at rt for 16 h. The mixture was diluted with water (10 mL) and extracted with EA (2×10 mL). The organic phases were combined, washed with brine (2×10 mL), dried over $Na_2SO_4$, filtered and concentrated under reduced pressure. The residue was purified by flash chromatography on C18 gel using 0.01% FA in ACN to afford (1S,3aR,4S,7R,7aS)—N—((S)-1-amino-1-oxo-3-((S)-2-oxopyrrolidin-3-yl)propan-2-yl)-2-((S)-3,3-dimethyl-2-(2,2,2-trifluoroacetamido)butanoyl)octahydro-1H-4,7-epoxyisoindole-1-carboxamide (75 mg, 60%) as a white solid.

To a stirred solution of (1S,3aR,4S,7R,7aS)—N—((S)-1-amino-1-oxo-3-((S)-2-oxopyrrolidin-3-yl)propan-2-yl)-2-((S)-3,3-dimethyl-2-(2,2,2-trifluoroacetamido)butanoyl)octahydro-1H-4,7-epoxyisoindole-1-carboxamide (70 mg, 0.128 mmol, 1.0 eq.) in DMF (0.7 mL) were added pyridine (0.036 mL, 0.256 mmol, 3.0 eq.) and TFAA (0.03 mL, 0.384 mmol, 2.0 eq.). The mixture was stirred at rt for 2 h. The mixture was diluted with water (5 mL) and extracted with EA (2×5 mL). The organic phases were combined, washed with brine (2×5 mL), dried over $Na_2SO_4$, filtered and concentrated under reduced pressure. The residue was purified by prep-HPLC (Column: X-SELECT-C18, 19×250 mm, 5um; Mobile Phase A: 10 mM Ammonium bicarbonate in water, Mobile Phase B: ACN; Flow rate: 17 mL/min; gradient: 10% B to 60% B in 8 min) to afford (1S,3aR,4S,7R,7aS)—N—((S)-1-cyano-2-((S)-2-oxopyrrolidin-3-yl)ethyl)-2-((S)-3,3-dimethyl-2-(2,2,2-trifluoroacetamido)butanoyl)octahydro-1H-4,7-epoxyisoindole-1-carboxamide (25 mg, 40%) as a white solid. $^1$H NMR (500 MHz, 363K, DMSO-$d_6$) δ 8.60-8.90 (m, 2H), 7.30-7.40 (m, 1H), 4.89 (m, 1H), 4.46-4.66 (m, 4H), 3.55-3.85 (m, 2H), 3.08-3.16 (m, 2H), 2.70-2.81 (m, 1H), 2.59 (m, 1H), 2.35 (m, 1H), 2.05-2.22 (m, 2H), 1.69-1.82 (m, 2H), 1.31-1.61 (m, 4H), 0.97 (m, 9H). LCMS (ESI, m/z): 528 [M+H]$^+$.

Example 58-1

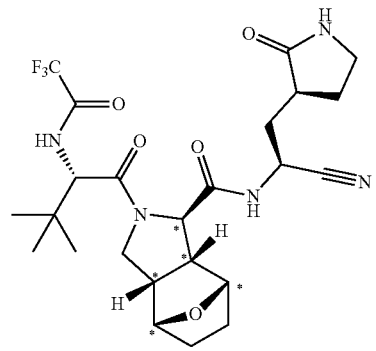

Compound 58a

Compound 58a was prepared similarly as described for Compound 59a using 2-(tert-butyl) 1-methyl (1R*,3aS*,4R*,7S*,7aR*)-octahydro-2H-4,7-epoxyisoindole-1,2-dicarboxylate in place of 2-(tert-butyl) 1-methyl (1R*,3aS*,4R*,7S*,7aR*)-1,3,3a,4,7,7a-hexahydro-2H-4,7-ethanoisoindole-1,2-dicarboxylate. $^1$H NMR (400 MHz, 363K, DMSO-$d_6$) δ 8.90 (br. s., 1H), 8.51-8.74 (m, 1H), 7.40 (br. s., 1H), 4.81-4.97 (m, 1H), 4.68 (d, 1H), 4.33-4.59 (m, 3H), 3.76 (m, 1H), 3.51-3.58 (m, 1H), 3.18 (m, 2H), 2.80 (m, 1H), 2.60 (m, 1H), 2.33 (m, 1H), 2.23 (m, 1H), 2.10 (m, 1H), 1.67-1.88 (m, 2H), 1.21-1.58 (m, 4H), 0.89-1.10 (m, 9H). LCMS (ESI, m/z): 528 [M+H]$^+$.

2-(tert-Butyl) 1-methyl (1R*,3aS*,4R*,7S*,7aR*)-octahydro-2H-4,7-epoxyisoindole-1,2-dicarboxylate: To a solution of (+/−)-methyl (1S,3aR,4S,7R,7aS)-octahydro-1H-4,7- epoxyisoindole-1-carboxylate hydrochloride (800 mg, 1.82 mmol, 1.0 eq.) in THF (8 mL) and water (8 mL) cooled at 0° C. were added NaHCO₃ (1.7 g, 20.3 mmol, 5.0 eq.) and Boc₂O (1.3 g, 6.09 mmol, 1.5 eq.). The mixture was stirred at rt for 16 h. The mixture was diluted with water and extracted with EA (3×10 mL). The organic phases were combined, washed with brine (2×20 mL), dried over Na₂SO₄, filtered and concentrated under reduced pressure. The residue was purified by flash chromatography on silica gel using a gradient of EA (15 to 20%) in PE to afford (+/−)-2-(tert-butyl) 1-methyl (1S,3aR,4S,7R,7aS)-octahydro-2H-4,7-epoxyisoindole-1,2-dicarboxylate (800 mg, 66%).

(+/−)-2-(tert-Butyl) 1-methyl (1S,3aR,4S,7R,7aS)-octahydro-2H-4,7-epoxyisoindole-1,2-dicarboxylate (1.7 g) was purified by prep-SFC using the following conditions: Column: Chiralpak IG, 30*250 mm, 5 m; Mobile Phase A: CO₂, Mobile Phase B: 0.5% DEA in MeOH; Flow rate: 90 g/min; Gradient: isocratic 10% B; Column Temperature: 30° C.; Back Pressure: 100 bar. Purification resulted in 2-(tert-butyl) 1-methyl (1R*,3aS*,4R*,7S*,7aR*)-octahydro-2H-4,7-epoxyisoindole-1,2-dicarboxylate (700 mg) and 2-(tert-butyl) 1-methyl (1S*,3aR*,4S*,7R*,7aS*)-octahydro-2H-4,7-epoxyisoindole-1,2-dicarboxylate (600 mg).

2-(tert-Butyl) 1-methyl (1R*,3aS*,4R*,7S*,7aR*)-octahydro-2H-4,7-epoxyisoindole-1,2-dicarboxylate: ¹H NMR (400 MHz, CDCl₃) δ 4.66 (m, 1H), 4.55 (m, 1H), 4.16-4.31 (m, 1H), 3.73 (s, 3H), 3.38-3.54 (m, 2H), 2.79 (m, 2H), 1.61-1.69 (m, 4H), 1.47 (m, 9H). [α]²⁵_D: +30.2° (c 0.16, CHCl₃). SFC: CHIRALPAK IG, 4.6*150 mm, 3 m, Mobile Phase A: CO₂, Mobile Phase B: MeOH; Flow rate: 3 g/min; Gradient: isocratic 10% B; Column Temperature: 30° C.; Back Pressure: 100 bar, Rt: 1.29 min.

2-(tert-Butyl) 1-methyl (1S*,3aR*,4S*,7R*,7aS*)-octahydro-2H-4,7-epoxyisoindole-1,2-dicarboxylate: ¹H NMR (400 MHz, CDCl₃) δ 4.66 (m, 1H), 4.55 (m, 1H), 4.16-4.31 (m, 1H), 3.73 (s, 3H), 3.38-3.54 (m, 2H), 2.79 (m, 2H), 1.61-1.69 (m, 4H), 1.47 (m, 9H). [α]²⁵_D: −41.3° (c 0.16, CHCl₃). SFC: CHIRALPAK IG, 4.6*150 mm, 3 m, Mobile Phase A: CO₂, Mobile Phase B: MeOH; Flow rate: 3 g/min; Gradient: isocratic 10% B; Column Temperature: 30° C.; Back Pressure: 100 bar, Rt: 1.65 min.

Example 58-2

Compound 58b

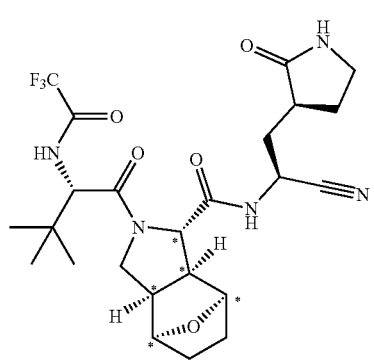

Compound 58b was prepared similarly as described for Compound 59a using 2-(tert-butyl) 1-methyl (1S*,3aR*, 4S*,7R*,7aS*)-octahydro-2H-4,7-epoxyisoindole-1,2-dicarboxylate in place of 2-(tert-butyl) 1-methyl (1R*,3aS*, 4R*,7S*,7aR*)-1,3,3a,4,7,7a-hexahydro-2H-4,7-ethanoisoindole-1,2-dicarboxylate. ¹H NMR (400 MHz, 363K, DMSO-d₆) δ 8.91 (br. s., 1H), 8.50-8.74 (m, 1H), 7.37 (br. s., 1H), 4.91 (m, 1H), 4.67 (m, 1H), 4.57 (m, 1H), 4.30-4.54 (m, 2H), 3.71-3.83 (m, 1H), 3.55-3.70 (m, 1H), 3.06-3.37 (m, 2H), 2.83 (m, 1H), 2.58 (m, 1H), 2.34 (m, 1H), 2.08-2.24 (m, 2H), 1.62-1.87 (m, 2H), 1.22-1.59 (m, 4H), 0.89-1.06 (m, 9H). LCMS (ESI, m/z): 528 [M+H]⁺.

Example 59

Compound 59

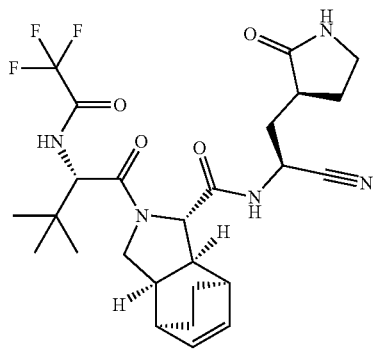

Compound 59 was prepared similarly as described for Compound 58 using (+/−)-methyl (1S,3aR,4S,7R,7aS)-2,3, 3a,4,7,7a-hexahydro-1H-4,7-ethanoisoindole-1-carboxylate hydrochloride in place of (+/−)-methyl (1S,3aR,4S,7R,7aS)-octahydro-1H-4,7-epoxyisoindole-1-carboxylate hydrochloride. ¹H NMR (500 MHz, 363K, DMSO-d6) δ 8.40-8.79 (m, 2H), 7.32-7.44 (m, 1H), 6.09-6.23 (m, 2H), 4.91 (m, 1H), 4.51-4.70 (m, 1H), 3.99-4.10 (m, 1H), 3.80 (m, 1H), 3.30-3.60 (m, 1H), 3.06-3.21 (m, 2H), 2.80 (m, 1H), 2.57-2.69 (m, 2H), 2.00-2.45 (m, 4H), 1.68-1.80 (m, 2H), 1.40-1.51 (m, 2H), 1.06-1.20 (m, 2H), 0.88-1.00 (m, 9H). LCMS (ESI, m/z): 538 [M+H]⁺.

(+/−)-Methyl (1S,3aR,4S,7R,7aS)-2,3,3a,4,7,7a-hexahydro-1H-4,7-ethanoisoindole-1-carboxylate hydrochloride: To a solution of (3aR,4S,7R,7aS)-2,3,3a,4,7,7a-hexahydro-1H-4,7-ethanoisoindole (1.1 g, 7.37 mmol, 1.0 eq.) in DCM (35 mL) was added IBX (2.06 g, 7.37 mmol, 1.0 eq.). The mixture was stirred in sealed tube at 60° C. for 1 h. After cooling to rt, the mixture was washed with sat. sodium dithionate (40 mL). The phases were separated. The organic phase was washed with sat. sodium carbonate (70 mL) and brine (30 mL). The aqueous phases were extracted with DCM (3×100 mL). The organic phases were combined, dried over Na₂SO₄, filtered and concentrated under reduced pressure. The residue was purified by flash chromatography on silica gel using a gradient of MeOH (1 to 5%) in DCM to afford (3aS,4R,7S,7aR)-3a,4,7,7a-tetrahydro-1H-4,7-ethanoisoindole (780 mg, 71%) as a white oil.

To a solution of (3aS,4R,7S,7aR)-3a,4,7,7a-tetrahydro-1H-4,7-ethanoisoindole (780 mg, 5.31 mmol, 1.0 eq.) in DCM (8 mL) and MeOH (0.6 mL) cooled at 0° C. was added TMSCN (1.8 mL, 13.3 mmol, 2.5 eq.). The mixture was stirred at 0-10° C. for 4 h. The mixture was concentrated under reduced pressure. The residue was purified by flash chromatography on silica gel using a gradient of MeOH (1 to 5%) in DCM to afford (+/−)-(1S,3aR,4S,7R,7aS)-2,3,3a, 4,7,7a-hexahydro-1H-4,7-ethanoisoindole-1-carbonitrile (550 mg, 59%) as a brown oil.

303
A solution of (+/−)-(1S,3aR,4S,7R,7aS)-2,3,3a,4,7,7a-hexahydro-1H-4,7-ethanoisoindole-1-carbonitrile (550 mg, 3.16 mmol, 1.0 eq.) in 4N HCl in MeOH (5.5 mL) was stirred for 6 h at 60° C. The mixture was concentrated under reduced pressure to afford (+/−)-methyl (1S,3aR,4S,7R,7aS)-2,3,3a,4,7,7a-hexahydro-1H-4,7-ethanoisoindole-1-carboxylate hydrochloride (580 mg, 88%) as a yellow oil.
Example 59-1
Compound 59a
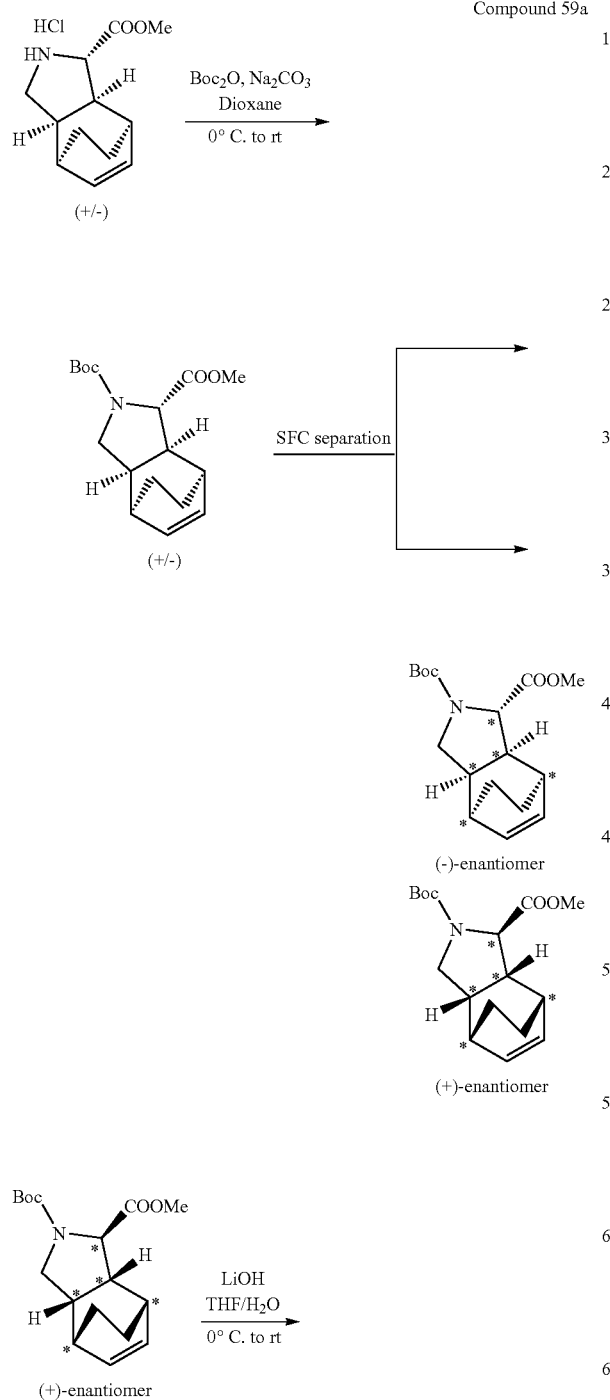
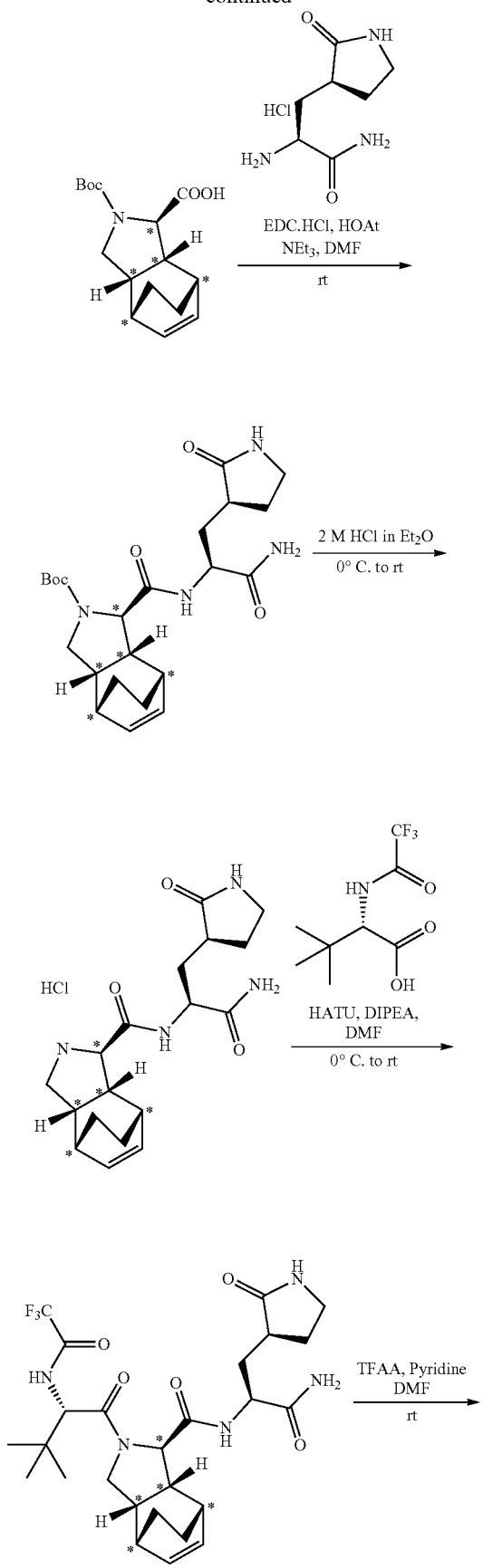

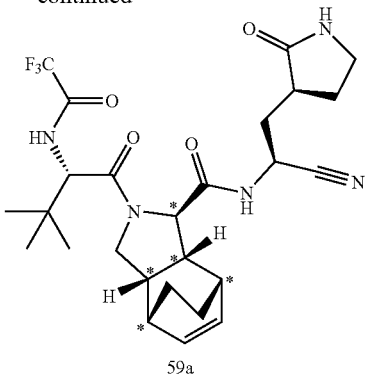

59a

The chiral centers noted with "*" are tentatively assigned.

To a solution of (+/−)-methyl (1S,3aR,4S,7R,7aS)-2,3,3a, 4,7,7a-hexahydro-1H-4,7-ethanoisoindole-1-carboxylate hydrochloride (1 g, 4.10 mmol, 1.0 eq.) in dioxane (15 mL) cooled at 0° C. were added Na$_2$CO$_3$ (870 mg, 8.21 mmol, 2.0 eq.) and Boc$_2$O (1.8 g, 8.21 mmol, 2.0 eq.). The mixture was stirred at rt for 24 h. After cooling to 0° C., Na$_2$CO$_3$ (870 mg, 8.21 mmol, 2.0 eq.) and Boc$_2$O (1.8 g, 8.21 mmol, 2.0 eq.) were added. The mixture was stirred at rt for 24 h. The mixture was diluted with EA (50 mL) and washed with water. The phases were separated. The aqueous phase was extracted twice with EA. The organic phases were combined, washed with brine, dried over Na$_2$SO$_4$, filtered and concentrated under reduced pressure. The residue was purified by flash chromatography on silica gel using a gradient of EA (0 to 30%) in PE to afford (+/−)-2-(tert-butyl) 1-methyl (1S,3aR,4S,7R,7aS)-1,3,3a,4,7,7a-hexahydro-2H-4,7-ethanoisoindole-1,2-dicarboxylate (1.1 g, 74%) as a brown oil.

(+/−)-2-(tert-Butyl) 1-methyl (1S,3aR,4S,7R,7aS)-1,3,3a,4,7,7a-hexahydro-2H-4,7-ethanoisoindole-1,2-dicarboxylate (900 mg) was purified by prep-SFC using the following conditions: Column: Lux Cellulose-2, 30*250 mm, 5 m; Mobile Phase A: CO$_2$, Mobile Phase B: MeOH; Flow rate: 60 g/min; Gradient: isocratic 10% B; Column Temperature: 30° C.; Back Pressure: 100 bar. Purification resulted in 2-(tert-butyl) 1-methyl (1S*,3aR*,4S*,7R*,7aS*)-1,3,3a,4,7,7a-hexahydro-2H-4,7-ethanoisoindole-1,2-dicarboxylate (370 mg) and 2-(tert-butyl) 1-methyl (1R*,3aS*,4R*,7S*,7aR*)-1,3,3a,4,7,7a-hexahydro-2H-4,7-ethanoisoindole-1,2-dicarboxylate (370 mg).

2-(tert-Butyl) 1-methyl (1S*,3aR*,4S*,7R*,7aS*)-1,3,3a,4,7,7a-hexahydro-2H-4,7-ethanoisoindole-1,2-dicarboxylate: $^1$H NMR (400 MHz, CDCl$_3$) δ 6.22-6.33 (m, 2H), 3.87-4.02 (m, 1H), 3.71 (s, 3H), 3.52-3.70 (m, 1H), 3.14-3.28 (m, 1H), 2.78 (m, 1H), 2.59 (m, 1H), 2.40-2.52 (m, 2H), 1.32-1.50 (m, 11H), 1.18-1.30 (m, 2H). $[α]^{25}_D$: −29.1° (c 0.1, CHCl$_3$). SFC: Lux Cellulose-2, 4.6*150 mm, 3 m, Mobile Phase A: CO$_2$, Mobile Phase B: 0.5% DEA in MeOH; Flow rate: 3 g/min; Gradient: isocratic 15% B; Column Temperature: 30° C.; Back Pressure: 100 bar, Rt: 0.98 min.

2-(tert-Butyl) 1-methyl (1R*,3aS*,4R*,7S*,7aR*)-1,3,3a,4,7,7a-hexahydro-2H-4,7-ethanoisoindole-1,2-dicarboxylate: $^1$H NMR (400 MHz, CDCl$_3$) δ 6.22-6.33 (m, 2H), 3.87-4.02 (m, 1H), 3.71 (s, 3H), 3.52-3.70 (m, 1H), 3.14-3.28 (m, 1H), 2.78 (m, 1H), 2.59 (m, 1H), 2.40-2.52 (m, 2H), 1.32-1.50 (m, 11H), 1.18-1.30 (m, 2H). $[α]^{25}_D$: +21.6° (c 0.1, CHCl$_3$). SFC: Lux Cellulose-2, 4.6*150 mm, 3 m, Mobile Phase A: CO$_2$, Mobile Phase B: 0.5% DEA in MeOH; Flow rate: 3 g/min; Gradient: isocratic 15% B; Column Temperature: 30° C.; Back Pressure: 100 bar, Rt: 1.12 min.

To a solution of 2-(tert-butyl) 1-methyl (1R*,3aS*,4R*,7S*,7aR*)-1,3,3a,4,7,7a-hexahydro-2H-4,7-ethanoisoindole-1,2-dicarboxylate (100 mg, 0.325 mmol, 1.0 eq.) in THF (1 mL) and water (1 mL) cooled at 0° C. was added LiOH (21 mg, 0.500 mmol, 1.5 eq.). The mixture was stirred for 2 h at rt and then partially concentrated under reduced pressure to remove THF. The residue was acidified by addition of 1N HCl until pH=2. The mixture was extracted with EA (3×10 mL). The organic phases were combined, dried over Na$_2$SO$_4$, filtered and concentrated under reduced pressure to afford (1R*,3aS*,4R*,7S*,7aR*)-2-(tert-butoxycarbonyl)-2,3,3a,4,7,7a-hexahydro-1H-4,7-ethanoisoindole-1-carboxylic acid (82 mg, 86%) as an oil.

To a solution of (1R*,3aS*,4R*,7S*,7aR*)-2-(tert-butoxycarbonyl)-2,3,3a,4,7,7a-hexahydro-1H-4,7-ethanoisoindole-1-carboxylic acid (160 mg, 0.546 mmol, 1.0 eq.) in DMF (1.6 mL) cooled at 0° C. were added (S)-2-amino-3-((S)-2-oxopyrrolidin-3-yl)propanamide hydrochloride (141 mg, 0.655 mmol, 1.2 eq.), EDC•HCl (208 mg, 1.09 mmol, 2.0 eq.), HOAt (74 mg, 0.546 mmol, 1.0 eq.) and NEt$_3$ (0.380 mL, 2.73 mmol, 5.0 eq.). The mixture was stirred at rt for 16 h. The mixture was diluted with water (10 mL) and extracted with EA (2×10 mL). The organic phases were combined, washed with brine (2×10 mL), dried over Na$_2$SO$_4$, filtered and concentrated under reduced pressure. The residue was purified by flash chromatography on C18 using 0.01% FA in ACN to afford tert-butyl (1R*,3aS*,4R*,7S*,7aR*)-1-(((S)-1-amino-1-oxo-3-((S)-2-oxopyrrolidin-3-yl)propan-2-yl)carbamoyl)-1,3,3a,4,7,7a-hexahydro-2H-4,7-ethanoisoindole-2-carboxylate (180 mg, 74%) as a white solid. LC-MS (ESI, m/z): 447 [M+H]$^+$.

A solution of tert-butyl (1R*,3aS*,4R*,7S*,7aR*)-1-(((S)-1-amino-1-oxo-3-((S)-2-oxopyrrolidin-3-yl)propan-2-yl)carbamoyl)-1,3,3a,4,7,7a-hexahydro-2H-4,7-ethanoisoindole-2-carboxylate (170 mg, 0.381 mmol, 1.0 eq.) in 2M HCl in ether (20 mL) was stirred at rt for 5 h. The mixture was concentrated under reduced pressure to afford quantitatively (1R*,3aS*,4R*,7S*,7aR*)—N—((S)-1-amino-1-oxo-3-((S)-2-oxopyrrolidin-3-yl)propan-2-yl)-2,3,3a,4,7,7a-hexahydro-1H-4,7-ethanoisoindole-1-carboxamide hydrochloride as a white solid.

To a solution of (1R*,3aS*,4R*,7S*,7aR*)—N—((S)-1-amino-1-oxo-3-((S)-2-oxopyrrolidin-3-yl)propan-2-yl)-2,3,3a,4,7,7a-hexahydro-1H-4,7-ethanoisoindole-1-carboxamide hydrochloride (170 mg, 0.445 mmol, 1.0 eq.) in DMF (1.7 mL) cooled at 0° C. were added (S)-3,3-dimethyl-2-(2,2,2-trifluoroacetamido)butanoic acid (121 mg, 0.533 mmol, 1.2 eq.), HATU (253 mg, 0.667 mmol, 1.5 eq.) and DIPEA (0.380 mL, 2.18 mmol, 5.0 eq.). The mixture was stirred at rt for 2 h. The mixture was diluted with water (5 mL) and extracted with EA (3×10 mL). The organic phases were combined, washed with brine (2×20 mL), dried over Na$_2$SO$_4$, filtered and concentrated under reduced pressure. The residue was purified by flash chromatography on C18 using 0.01% FA in ACN to afford (1R*,3aS*,4R*,7S*,7aR*)—N—((S)-1-amino-1-oxo-3-((S)-2-oxopyrrolidin-3-yl)propan-2-yl)-2-((S)-3,3-dimethyl-2-(2,2,2-trifluoroacetamido)butanoyl)-2,3,3a,4,7,7a-hexahydro-1H-4,7-ethanoisoindole-1-carboxamide (125 mg, 55%) as an off-white solid.

To a solution of (1R*,3aS*,4R*,7S*,7aR*)—N—((S)-1-amino-1-oxo-3-((S)-2-oxopyrrolidin-3-yl)propan-2-yl)-2-((S)-3,3-dimethyl-2-(2,2,2-trifluoroacetamido)butanoyl)-2,3,3a,4,7,7a-hexahydro-1H-4,7-ethanoisoindole-1- carboxamide (100 mg, 0.180 mmol, 1.0 eq.) in DMF (1 mL) were added pyridine (0.043 mL, 0.540 mmol, 3.0 eq.) and TFAA (0.050 mL, 0.360 mmol, 2.0 eq.). The mixture was stirred at rt for 2 h. The mixture was diluted with water (5 mL) and extracted with EA (3×5 mL). The organic phases were combined, washed with brine (2×5 mL), dried over Na₂SO₄, filtered and concentrated under reduced pressure. The residue was purified by prep-HPLC (Column: X-SELECT-C18 Column, 19*250 mm, 5 m; Mobile Phase A: 10 mM NH₄HCO₃ in water, Mobile Phase B: ACN; Flow rate: 17 mL/min; Gradient: 10% B to 60% B in 8 min) to afford (1R*,3aS*,4R*,7S*,7aR*)—N—((S)-1-cyano-2-((S)-2-oxopyrrolidin-3-yl)ethyl)-2-((S)-3,3-dimethyl-2-(2,2,2-trifluoroacetamido)butanoyl)-2,3,3a,4,7,7a-hexahydro-1H-4,7-ethanoisoindole-1-carboxamide (45 mg, 40%) as a white solid. ¹H NMR (400 MHz, 363K, DMSO-d₆) δ 8.52-8.87 (m, 2H), 7.39 (s, 1H), 6.02-6.22 (m, 2H), 4.91 (dd, 1H), 4.52 (s, 1H), 4.08-4.31 (m, 1H), 3.79 (t, 1H), 3.49 (d, 1H), 3.11-3.37 (m, 2H), 2.78 (m, 1H), 2.51-2.61 (m, 2H), 2.04-2.36 (m, 4H), 1.82 (m, 1H), 1.72 (m, 1H), 1.44 (d, 2H), 1.13 (m, 2H), 0.96 (s, 9H). LCMS (ESI, m/z): 536 [M−H]⁻.

Example 59-2

Compound 59b

Compound 59b was prepared similarly as described for Compound 59a using 2-(tert-butyl) 1-methyl (1S*,3aR*,4S*,7R*,7aS*)-1,3,3a,4,7,7a-hexahydro-2H-4,7-ethanoisoindole-1,2-dicarboxylate in place of 2-(tert-butyl) 1-methyl (1R*,3aS*,4R*,7S*,7aR*)-1,3,3a,4,7,7a-hexahydro-2H-4,7-ethanoisoindole-1,2-dicarboxylate. ¹H NMR (400 MHz, 363K, DMSO-d6) δ 8.56-8.85 (m, 2H), 7.30-7.48 (m, 1H), 6.06-6.26 (m, 2H), 4.90 (m, 1H), 4.50-4.72 (m, 1H), 3.98-4.10 (m, 1H), 3.80 (m, 1H), 3.28-3.57 (m, 1H), 3.08-3.20 (m, 2H), 2.82 (m, 1H), 2.53-2.62 (m, 2H), 2.25-2.45 (m, 2H), 2.10-2.20 (m, 2H), 1.65-1.90 (m, 2H), 1.41-1.52 (m, 2H), 1.07-1.23 (m, 2H), 0.85-1.02 (m, 9H). LCMS (ESI, m/z): 536 [M−H]⁻.

Example 60

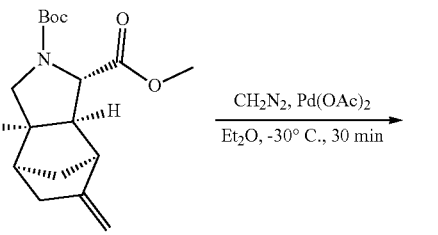

Compound 60

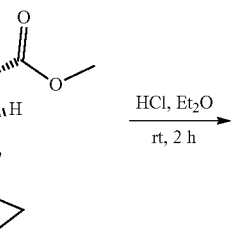

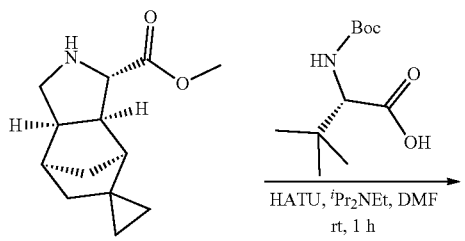

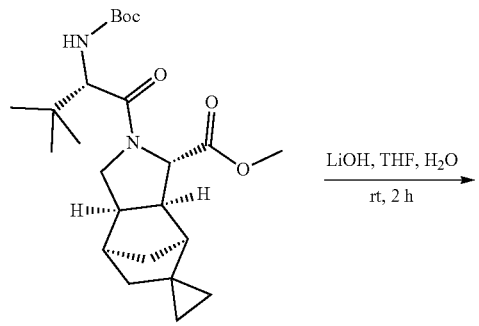

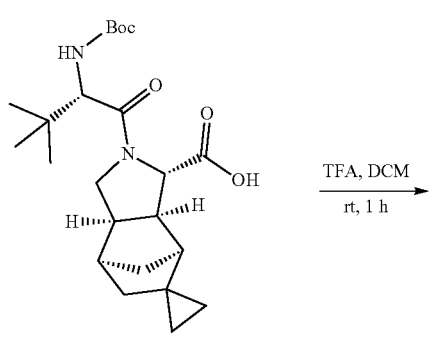

-continued

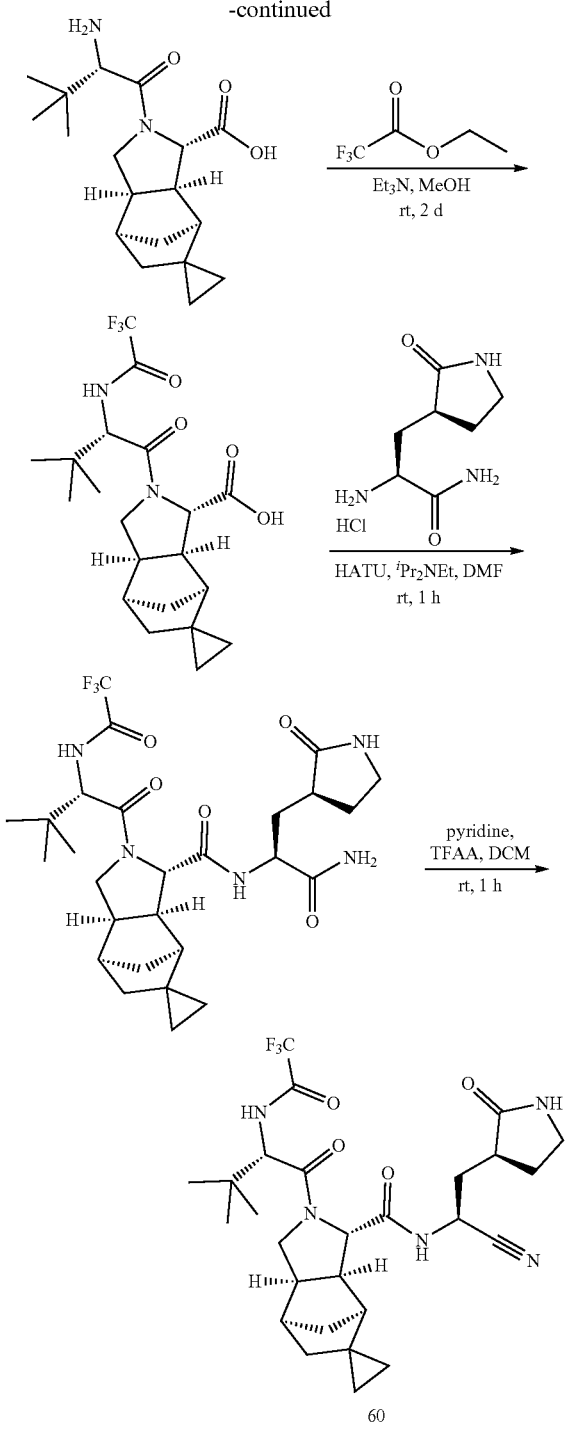

To a mixture of 4-tert-butyl 3-methyl (1S,2S,3S,6R,7S)-9-methylidene-4-azatricyclo[5.2.1.0^{2,6}]decane-3,4-dicarboxylate (400 mg, 1.30 mmol, 1.0 eq.) and diazomethane (15 mL, excess in Et₂O) in Et₂O (4 mL) was added palladium(II) acetate (88.0 mg, 0.390 mmol, 0.3 eq.) at −30° C. The mixture was stirred for 30 min at −30° C. The mixture raised naturally to rt, filtered and concentrated under reduced pressure to afford the crude product (This process was repeated for 5 times until the starting materials was completely converted). The crude product was chromatographed on a silica gel column with EtOAc:PE (1:9) to provide 4'-tert-butyl 5'-methyl (1'S,2'R,5'S,6'S,7'S)-4'-azaspiro[cyclopropane-1,8'-tricyclo[5.2.1.0^{2,6}]decane]-4',5'-dicarboxylate (350 mg, crude) as a yellow oil. LC-MS (ESI, m/z): 222 [M−100+H]⁺.

A solution of 4'-tert-butyl 5'-methyl (1'S,2'R,5'S,6'S,7'S)-4'-azaspiro[cyclopropane-1,8'-tricyclo[5.2.1.0^{2,6}]decane]-4',5'-dicarboxylate (350 mg, 1.09 mmol, 1.0 eq.) in hydrogen chloride (10 mL, 2 M in Et₂O) was stirred for 2 h at rt. The mixture was concentrated under reduced pressure to afford methyl (1'S,2'R,5'S,6'S,7'S)-4'-azaspiro[cyclopropane-1,8'-tricyclo[5.2.1.0^{2,6}]decane]-5'-carboxylate hydrochloride (280 mg, crude) as a yellow solid. LC-MS (ESI, m/z): 222 [M+H]⁺.

To a mixture of (2S)-2-[(tert-butoxycarbonyl)amino]-3,3-dimethylbutanoic acid (251 mg, 1.09 mmol, 1.0 eq.) and o-(7-azabenzotriazol-1-yl)-N,N,N',N'-tetramethyluronium hexafluorophosphate (496 mg, 1.30 mmol, 1.2 eq.) in DMF (5 mL) was added N-ethyl-N-isopropylpropan-2-amine (842 mg, 6.52 mmol, 6.0 eq.) at 0° C. After stirred for 15 min at 0° C., methyl (1'S,2'R,5'S,6'S,7'S)-4'-azaspiro[cyclopropane-1,8'-tricyclo[5.2.1.0^{2,6}]decane]-5'-carboxylate hydrochloride (280 mg, 1.09 mmol, 1.0 eq.) was added. The mixture was stirred for 1 h at rt. The reaction was quenched with water (30 mL). The mixture was extracted with EtOAc (3×30 mL). The organic layers were combined, washed with brine (2×30 mL), dried over anhydrous sodium sulfate, filtered and concentrated under reduced pressure to afford the crude product. The crude product was chromatographed on a silica gel column with EtOAc:PE (14:86) to provide methyl (1'S,2'R,5'S,6'S,7'S)-4'-[(2S)-2-[(tert-butoxycarbonyl)amino]-3,3-dimethylbutanoyl]-4'-azaspiro[cyclopropane-1,8'-tricyclo[5.2.1.0^{2,6}]decane]-5'-carboxylate (300 mg, 57%) as a yellow oil. LC-MS (ESI, m/z): 435 [M+H]⁺.

To a mixture of methyl (1'S,2'R,5'S,6'S,7'S)-4'-[(2S)-2-[(tert-butoxycarbonyl)amino]-3,3-dimethylbutanoyl]-4'-azaspiro[cyclopropane-1,8'-tricyclo[5.2.1.0^{2,6}]decane]-5'-carboxylate (300 mg, 0.690 mmol, 1.0 eq.) in THF (3 mL)/water (3 mL) was added lithium hydroxide (83.0 mg, 3.45 mmol, 5.0 eq.). The mixture was stirred for 2 h at rt. The mixture was concentrated under reduced pressure to remove THF and adjusted to pH=6 with hydrochloric acid (1 M). The mixture was extracted with EtOAc (3×10 mL). The organic layers were combined, washed with brine (2×10 mL), dried over anhydrous sodium sulfate, filtered and concentrated under reduced pressure to afford (1'S,2'R,5'S,6'S,7'S)-4'-[(2S)-2-[(tert-butoxycarbonyl)amino]-3,3-dimethylbutanoyl]-4'-azaspiro[cyclopropane-1,8'-tricyclo[5.2.1.0^{2,6}]decane]-5'-carboxylic acid (280 mg, crude) as a light yellow solid. LC-MS (ESI, m/z): 421 [M+H]⁺.

To a solution of (1'S,2'R,5'S,6'S,7'S)-4'-[(2S)-2-[(tert-butoxycarbonyl)amino]-3,3-dimethylbutanoyl]-4'-azaspiro[cyclopropane-1,8'-tricyclo[5.2.1.0^{2,6}]decane]-5'-carboxylic acid (280 mg, 0.667 mmol, 1.0 eq.) in DCM (6 mL) was added trifluoroacetic acid (2 mL). The mixture was stirred for 1 h at rt and then concentrated under reduced pressure to afford (1'S,2'R,5'S,6'S,7'S)-4'-[(2S)-2-amino-3,3-dimethylbutanoyl]-4'-azaspiro[cyclopropane-1,8'-tricyclo[5.2.1.0^{2,6}]decane]-5'-carboxylic acid (213 mg, crude) as a brown semi-solid. LC-MS (ESI, m/z): 321 [M+H]⁺.

To a mixture of (1'S,2'R,5'S,6'S,7'S)-4'-[(2S)-2-amino-3,3-dimethylbutanoyl]-4'-azaspiro[cyclopropane-1,8'-tricyclo[5.2.1.0^{2,6}]decane]-5'-carboxylic acid (213 mg, 0.667 mmol, 1.0 eq.) in MeOH (5 mL) was added triethylamine (807 mg, 7.97 mmol, 12.0 eq.) and ethyl 2,2,2-trifluoroacetate (945 mg, 6.67 mmol, 10.0 eq.). The mixture was stirred for 2 days at rt. The mixture was concentrated under reduced pressure to remove MeOH. The mixture was diluted with water (30 mL) and adjusted to pH=6 with hydrochloric acid (1 M). The mixture was extracted with EtOAc (3×30 mL). The organic layers were combined, washed with brine (2×20 mL), dried over anhydrous sodium sulfate, filtered and concentrated under reduced pressure to provide (1'S,2'R,5'S,6'S,7'S)-4'-[(2S)-3,3-dimethyl-2-(2,2,2-trifluoroacetamido)butanoyl]-4'-azaspiro[cyclopropane-1,8'-tricyclo[5.2.1.0^{2,6}]decane]-5'-carboxylic acid (240 mg, 75%) as a light yellow solid. LC-MS (ESI, m/z): 417 [M+H]$^+$.

A mixture of tert-butyl N-[(1S)-1-carbamoyl-2-[(3S)-2-oxopyrrolidin-3-yl]ethyl]carbamate (150 mg, 0.553 mmol, 1.0 eq.) in hydrogen chloride (10 mL, 2 M in Et$_2$O) was stirred for 2 h at rt. The mixture was concentrated under reduced pressure to afford (2S)-2-amino-3-[(3S)-2-oxopyrrolidin-3-yl]propanamide hydrochloride (115 mg, crude) as an off-white solid. LC-MS (ESI, m/z): 172 [M+H]$^+$.

To a mixture of (1'S,2'R,5'S,6'S,7'S)-4'-[(2S)-3,3-dimethyl-2-(2,2,2-trifluoroacetamido)butanoyl]-4'-azaspiro[cyclopropane-1,8'-tricyclo[5.2.1.0^{2,6}]decane]-5'-carboxylic acid (221 mg, 0.530 mmol, 1.0 eq.) and o-(7-azabenzotriazol-1-yl)-N,N,N',N'-tetramethyluronium hexafluorophosphate (241 mg, 0.635 mmol, 1.2 eq.) in DMF (5 mL) was added N-ethyl-N-isopropylpropan-2-amine (411 mg, 3.18 mmol, 6.0 eq.) at 0° C. After stirred for 15 min at 0° C., (2S)-2-amino-3-[(3S)-2-oxopyrrolidin-3-yl]propanamide hydrochloride (110 mg, 0.530 mmol, 1.0 eq.) was added. The mixture was stirred for 1 h at rt. The mixture was purified by C18 column with CH$_3$CN/Water (0.05% FA). The desired fraction was concentrated under reduced pressure to provide (2S)-2-[(1'S,2'R,5'S,6'S,7'S)-4'-[(2S)-3,3-dimethyl-2-(2,2,2-trifluoroacetamido)butanoyl]-4'-azaspiro[cyclopropane-1,8'-tricyclo[5.2.1.0^{2,6}]decan]-5'-ylformamido]-3-[(3S)-2-oxopyrrolidin-3-yl]propanamide (180 mg, 52%) as a yellow solid. LC-MS (ESI, m/z): 570 [M+H]$^+$.

To a mixture of (2S)-2-[(1'S,2'R,5'S,6'S,7'S)-4'-[(2S)-3,3-dimethyl-2-(2,2,2-trifluoroacetamido)butanoyl]-4'-azaspiro[cyclopropane-1,8'-tricyclo[5.2.1.0^{2,6}]decan]-5'-ylformamido]-3-[(3S)-2-oxopyrrolidin-3-yl]propanamide (180 mg, 0.316 mmol, 1.0 eq.) in DCM (3 mL) was added pyridine (87.0 mg, 1.11 mmol, 3.5 eq.) and trifluoroacetic anhydride (100 mg, 0.474 mmol, 1.5 eq.). The mixture was stirred for 1 h at rt. The reaction was quenched with water (5 mL). The mixture was extracted with DCM (3×5 mL). The organic layers were combined, washed with brine (2×5 mL), dried over anhydrous sodium sulfate, filtered and concentrated under reduced pressure to afford the crude product. The crude product was purified by prep-HPLC (Column: XBridge Shield RP18 OBD Column, 30×150 mm, 5 m; Mobile Phase A: Water (0.1% FA), Mobile Phase B: ACN; Flow rate: 60 mL/min; Gradient: 34% B to 64% B in 7 min, 64% B; Wave Length: 254 nm; RT1 (min): 5.33) to provide (1'S,2'R,5'S,6'S,7'S)—N-[(1S)-1-cyano-2-[(3S)-2-oxopyrrolidin-3-yl]ethyl]-4'-[(2S)-3,3-dimethyl-2-(2,2,2-trifluoroacetamido)butanoyl]-4'-azaspiro[cyclopropane-1,8'-tricyclo[5.2.1.0^{2,6}]decane]-5'-carboxamide (61.3 mg, 34%) as an off-white solid. $^1$H NMR (400 MHz, 80° C., DMSO-d$_6$) δ 8.90-9.18 (m, 1H), 8.60-8.89 (m, 1H), 7.30-7.65 (m, 1H), 4.82-5.02 (m, 2H), 4.63-4.81 (m, 1H), 3.82-3.95 (m, 1H), 3.61-3.81 (m, 1H), 3.10-3.39 (m, 2H), 2.63-2.85 (m, 1H), 2.30-2.50 (m, 3H), 2.05-2.25 (m, 2H), 1.68-1.90 (m, 3H), 1.60-1.67 (m, 1H), 1.50-1.59 (m, 1H), 1.25-1.42 (m, 2H), 0.95-1.05 (m, 9H), 0.70-0.90 (m, 1H), 0.70-0.90 (m, 2H), −0.15--0.03 (m, 1H). LC-MS (ESI, m/z): 552 [M+H]$^+$.

Example 61

Compound 61

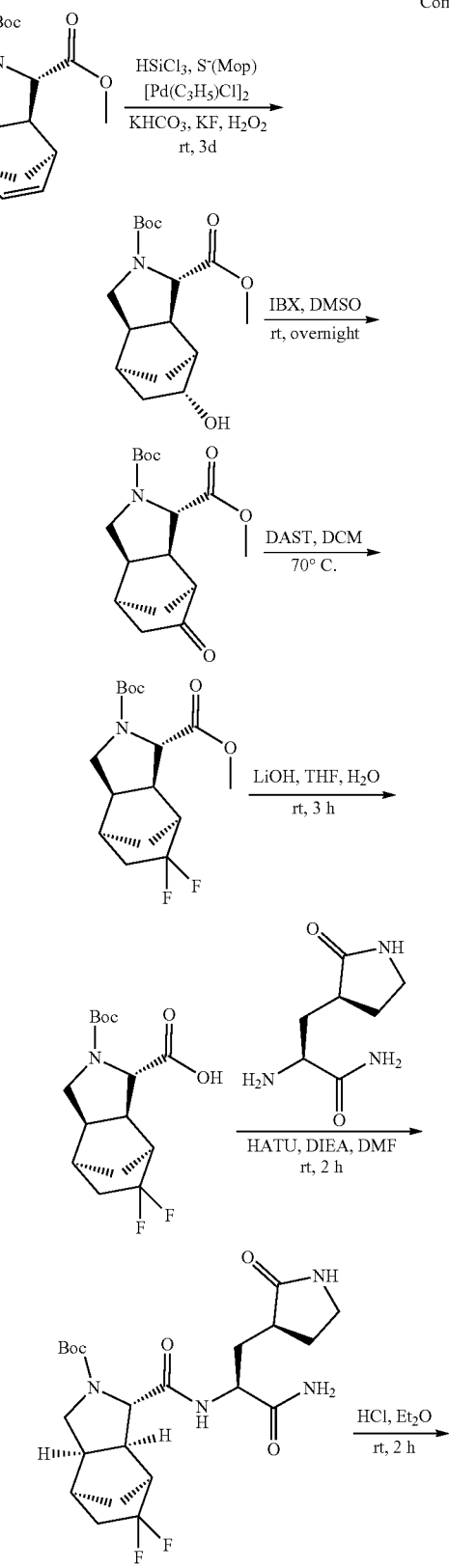

-continued

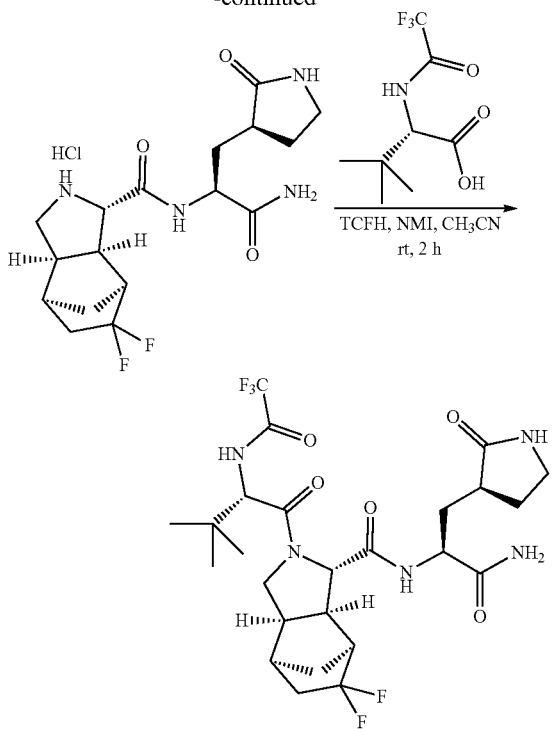

The 4-tert-butyl 3-methyl (1R,2S,3S,6R,7S)-4-azatricyclo[5.2.1.0^{2,6}]dec-8-ene-3,4-dicarboxylate (4.00 g, 13.6 mmol, 1.0 eq.) was dissolved in toluene (8 mL) under nitrogen and cooled to 0° C. (S)-MOP (S)-(−)-2-Diphenylphosphino-2′-methoxy-1,1′-binaphthyl (15.9 mg, 0.034 mmol, 0.0025 eq.), [Pd(C3H5)Cl]2 allylpalladium chloride dimer (3.00 mg, 0.008 mmol, 0.0006 eq.) and trichlorosilane (5.87 g, 43.5 mmol, 3.2 eq.) were added consecutively. The mixture was warmed to rt and then stirred for 3 d. The mixture was concentrated under reduced pressure. The residue was re-dissolved in THF (36 mL) and MeOH (36 mL). The mixture was poured into a suspension of potassium fluoride (6.26 g, 108 mmol, 8.0 eq.) and KHCO₃ (13.6 g, 136 mmol, 10.0 eq.) in THF (36 mL) and MeOH (36 mL) at 0° C. Then H₂O₂ (20 mL) was added. The mixture was stirred for 1 d at rt. The mixture was extracted with EtOAc (3×100 mL). The organic layers were combined, washed with brine (2×50 mL), dried over anhydrous sodium sulfate, filtered and concentrated under reduced pressure to afford the crude product. The crude product was chromatographed on a silica gel column with EA:PE (40:60) to provide 4-tert-butyl 3-methyl (1S,2R,3S,6R,7S)-9-hydroxy-4-azatricyclo [5.2.1.0^{2,6}]decane-3,4-dicarboxylate (2.00 g, 47%) as a yellow oil. LC-MS (ESI, m/z): 256 [M−56+H]⁺.

To a stirred mixture of 4-tert-butyl 3-methyl (1S,2R,3S,6R,7S)-9-hydroxy-4-azatricyclo[5.2.1.0^{2,6}]decane-3,4-dicarboxylate (2.00 g, 6.43 mmol, 1.0 eq.) in DMSO (20 mL) was added 2-iodoxybenzoic acid (5.29 g, 18.9 mmol, 3.0 eq.). The mixture was stirred for overnight at rt. The reaction was quenched with sat. sodium bicarbonate (50 mL). The mixture was extracted with EtOAc (3×80 mL). The organic layers were combined, washed with brine (2×50 mL), dried over anhydrous sodium sulfate, filtered and concentrated under reduced pressure to afford the crude product. The crude product was chromatographed on a silica gel column with EA:PE (50:50) to provide 4-tert-butyl 3-methyl (1S,2R,3S,6R,7S)-9-oxo-4-azatricyclo[5.2.1.0^{2, 6}]decane-3,4-dicarboxylate (1.5 g, 78%) as a white oil. LC-MS (ESI, m/z): 310 [M+H]⁺.

A mixture of 4-tert-butyl 3-methyl (1S,2R,3S,6R,7S)-9-oxo-4-azatricyclo[5.2.1.0^{2,6}]decane-3,4-dicarboxylate (1.00 g, 3.23 mmol, 1.0 eq.) in diethylaminosulfur trifluoride (20 mL) was stirred for 6 h at 70° C. The mixture was diluted with dichloromethane (50 mL). The reaction was quenched with sat. sodium bicarbonate (100 mL) at 0° C. The mixture was extracted with dichloromethane (3×100 mL). The organic layers were combined, washed with brine (2×60 mL), dried over anhydrous sodium sulfate, filtered and concentrated under reduced pressure. The residue was purified by silica gel column chromatography with PE:EA (7:3) to afford 4-tert-butyl 3-methyl (1S,2R,3S,6R,7S)-9,9-difluoro-4-azatricyclo[5.2.1.0^{2,6}]decane-3,4-dicarboxylate (300 mg, 28%) as a yellow oil. LC-MS (ESI, m/z): 310 [M+H]⁺.

To a stirred mixture of 4-tert-butyl 3-methyl (1S,2R,3S,6R,7S)-9,9-difluoro-4-azatricyclo[5.2.1.0^{2,6}]decane-3,4-dicarboxylate (300 mg, 0.905 mmol, 1.0 eq.) in THF (3 mL) and H₂O (3 mL) was added lithium hydroxide (108 mg, 4.52 mmol, 5.0 eq.) at rt. The mixture was stirred for 2 h and acidified to pH=3 with hydrochloric acid (1M in H₂O). The aqueous layer was extracted with ethyl acetate (3×30 mL). The organic layers were combined, washed with brine (2×20 mL), dried over anhydrous sodium sulfate, filtered and concentrated under reduced pressure to afford (1S,2R,3S,6R,7S)-4-(tert-butoxycarbonyl)-9,9-difluoro-4-azatricyclo [5.2.1.0^{2,6}]decane-3-carboxylic acid (270 mg, crude) as a light yellow solid. LC-MS (ESI, m/z): 318 [M+H]⁺.

To a mixture of (1S,2R,3S,6R,7S)-4-(tert-butoxycarbonyl)-9,9-difluoro-4-azatricyclo[5.2.1.0^{2,6}]decane-3-carboxylic acid (270 mg, 0.851 mmol, 1.0 eq.) in N,N-dimethylformamide (3 mL) was added o-(7-azabenzotriazol-1-yl)-N,N,N',N'-tetramethyluronium hexafluorophosphate (387 mg, 1.02 mmol, 1.2 eq.) and N-ethyl-N-isopropylpropan-2-amine (658 mg, 5.10 mmol, 6.0 eq.) at 0° C. The mixture was stirred for 20 min at 0° C., and then (2S)-2-amino-3-[(3S)-2-oxopyrrolidin-3-yl]propanamide (145 mg, 0.851 mmol, 1.0 eq.) was added at 0° C. The mixture was purified by C18 column with CH₃CN/Water (0.05% TFA). The desired fraction was concentrated under reduced pressure to provide tert-butyl (1S,2R,3S,6R,7S)-3-{[(1S)-1-carbamoyl-2-[(3S)-2-oxopyrrolidin-3-yl]ethyl]carbamoyl}-9,9-difluoro-4-azatricyclo[5.2.1.0^{2,6}]decane-4-carboxylate (200 mg, 50%) as a light yellow solid. LC-MS (ESI, m/z): 471 [M+H]⁺.

A mixture of tert-butyl (1S,2R,3S,6R,7S)-3-{[(1S)-1-carbamoyl-2-[(3S)-2-oxopyrrolidin-3-yl]ethyl]carbamoyl}-9,9-difluoro-4-azatricyclo[5.2.1.0^{2,6}]decane-4-carboxylate (200 mg, 0.425 mmol, 1.0 eq.) in hydrogen chloride (1 mL, 2 M in Et₂O) was stirred for 1 h at rt. The mixture was concentrated under reduced pressure to afford (2S)-2-{[(1S,2R,3S,6R,7S)-9,9-difluoro-4-azatricyclo[5.2.1.0^{2,6}]decan-3-yl]formamido}-3-[(3S)-2-oxopyrrolidin-3-yl]propanamide hydrochloride (160 mg, crude) as a yellow solid. LC-MS (ESI, m/z): 371 [M+H]⁺.

To a mixture of (2S)-3,3-dimethyl-2-(2,2,2-trifluoroacetamido)butanoic acid (154 mg, 0.680 mmol, 1.6 eq.) in MeCN (2 mL) was added N,N,N',N'-tetramethylchloroformamidinium hexafluorophosphate (238 mg, 0.850 mmol, 2.0 eq.) and N-methylimidazole (522 mg, 6.37 mmol, 15 eq.) at rt. The mixture was stirred for 20 min, and then (2S)-2-{[(1S,2R,3S,6R,7S)-9,9-difluoro-4-azatricyclo [5.2.1.0^{2,6}]decan-3-yl]formamido}-3-[(3S)-2-oxopyrrolidin-3-yl]propanamide hydrochloride (160 mg, 0.425 mmol, 1.0 eq.) was added at rt. The mixture was purified by C18 column with CH₃CN/Water (0.05% FA). The desired fraction was concentrated under reduced pressure to provide (2S)-2-{[(1S,2R,3S,6R,7S)-4-[(2S)-3,3-dimethyl-2-(2,2,2-trifluoroacetamido)butanoyl]-9,9-difluoro-4-azatricyclo[5.2.1.0^{2,6}]decan-3-yl]formamido}-3-[(3S)-2-oxopyrrolidin-3-yl]propanamide (105 mg, 42%) as a light yellow solid. LC-MS (ESI, m/z): 580 [M+H]⁺.

To a mixture of (2S)-2-{[(1S,2R,3S,6R,7S)-4-[(2S)-3,3-dimethyl-2-(2,2,2-trifluoroacetamido)butanoyl]-9,9-difluoro-4-azatricyclo[5.2.1.0^{2,6}]decan-3-yl]formamido}-3-[(3S)-2-oxopyrrolidin-3-yl]propanamide (100 mg, 0.173 mmol, 1.0 eq.) in DCM (1 mL) was added pyridine (47.7 mg, 0.605 mmol, 3.5 eq.) and trifluoroacetic anhydride (54.3 mg, 0.259 mmol, 1.5 eq.). The mixture was stirred for 2 h at rt. The reaction was quenched with water (5 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was purified by prep-HPLC (Column: Xselect CSH C18 OBD Column 30*150 mm 5 m, n; Mobile Phase A: Water (0.1% FA), Mobile Phase B: ACN; Flow rate: 60 mL/min; Gradient: 30% B to 60% B in 8 min, 60% B; Wave Length: 254/220 nm; RT1 (min): 6) to provide (1S,2R,3S,6R,7S)—N-[(1S)-1-cyano-2-[(3S)-2-oxopyrrolidin-3-yl]ethyl]-4-[(2S)-3,3-dimethyl-2-(2,2,2-trifluoroacetamido)butanoyl]-9,9-difluoro-4-azatricyclo[5.2.1.0^{2,6}]decane-3-carboxamide (4.7 mg, 4%) as an off-white solid. ¹H NMR (400 MHz, 80° C., DMSO-d₆) δ 8.95-9.30 (m, 1H), 8.60-8.95 (m, 1H), 7.30-7.65 (m, 1H), 4.80-5.10 (m, 1H), 4.45-4.80 (m, 2H), 3.60-4.00 (m, 2H), 3.10-3.20 (m, 2H), 2.80-2.95 (m, 1H), 2.55-2.80 (m, 2H), 2.40-2.50 (m, 1H), 2.30-2.40 (m, 1H), 2.05-2.25 (m, 2H), 1.55-1.95 (m, 6H), 0.80-1.40 (m, 9H). LC-MS (ESI, m/z): 562 [M+H]⁺.

Example 62

Compound 62

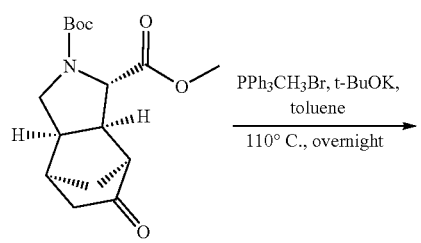

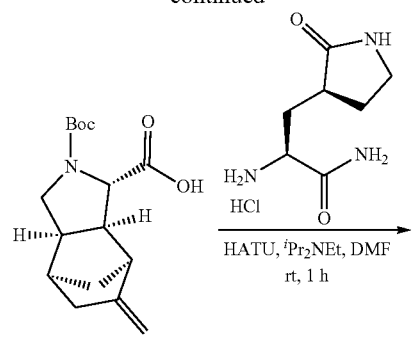

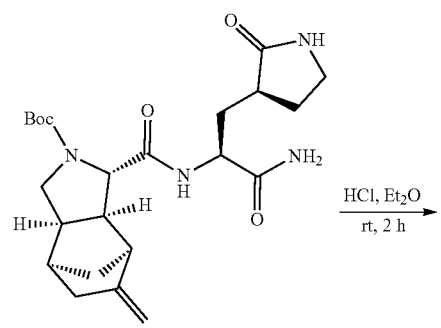

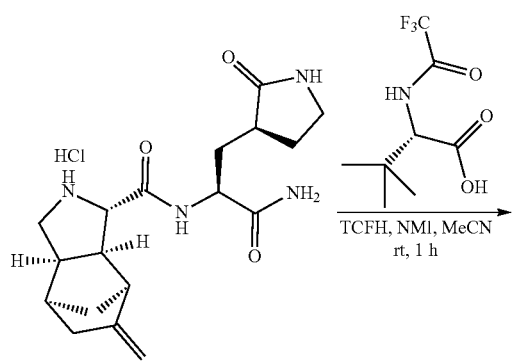

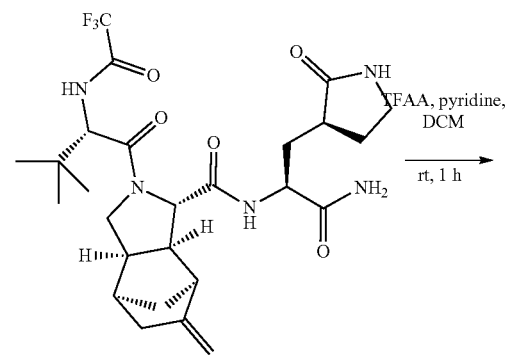

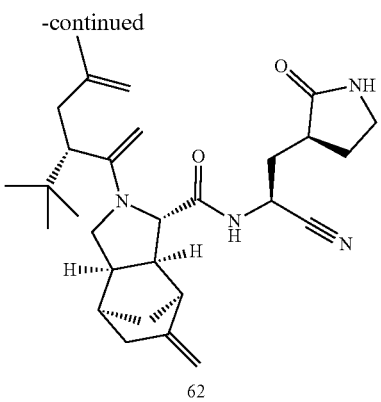

62

To a mixture of bromo(methyl)triphenyl-λ⁵-phosphane (2.96 g, 8.27 mmol, 1.6 eq.) in toluene (48 mL) was added potassium tert-butoxide (928 mg, 8.27 mmol, 1.6 eq.). After stirred for 2 h at 110° C., 4-tert-butyl 3-methyl (1S,2R,3S,6R,7S)-9-oxo-4-azatricyclo[5.2.1.0ˆ{2,6}]decane-3,4-dicarboxylate (1.60 g, 5.17 mmol, 1.0 eq.) was added. The mixture was stirred overnight at 110° C. The reaction was quenched with ice-water (50 mL). The mixture was extracted with EtOAc (3×50 mL). The organic layers were combined, washed with brine (2×50 mL), dried over anhydrous sodium sulfate, filtered and concentrated under reduced pressure to afford the crude product. The crude product was chromatographed on a silica gel column with EA:PE (15:85) to provide 4-tert-butyl 3-methyl (1S,2S,3S,6R,7S)-9-methylidene-4-azatricyclo[5.2.1.0ˆ{2,6}]decane-3,4-dicarboxylate (480 mg, 29%) as a light yellow oil. ¹H NMR (400 MHz, Chloroform-d) δ 4.89-4.96 (m, 1H), 4.71-4.80 (m, 1H), 4.17-4.33 (m, 1H), 3.72 (s, 3H), 3.52-3.66 (m, 1H), 3.35-3.44 (m, 1H), 2.56-2.85 (m, 3H), 2.33-2.42 (m, 1H), 1.98-2.22 (m, 2H), 1.62-1.71 (m, 1H), 1.52-1.60 (m, 1H), 1.36-1.50 (m, 9H). LC-MS (ESI, m/z): 208[M−100+H]⁺.

To a mixture of 4-tert-butyl 3-methyl (1S,2S,3S,6R,7S)-9-methylidene-4-azatricyclo[5.2.1.0ˆ{2,6}]decane-3,4-dicarboxylate (220 mg, 0.716 mmol, 1.0 eq.) in tetrahydrofuran (2 mL)/water (2 mL) was added lithium hydroxide (86.0 mg, 3.58 mmol, 5.0 eq.). The mixture was stirred for 3 h at rt. The reaction was quenched with water (5 mL) and extracted with EtOAc (5 mL). The aqueous phase was adjusted to pH=6 with HCl (1M). The mixture was extracted with EtOAc (3×5 mL). The organic layers were combined, washed with brine (2×5 mL), dried over anhydrous sodium sulfate, filtered and concentrated under reduced pressure to afford (1S,2S,3S,6R,7S)-4-(tert-butoxycarbonyl)-9-methylidene-4-azatricyclo[5.2.1.0ˆ{2,6}]decane-3-carboxylic acid (170 mg, 76%, crude) as a yellow oil. LC-MS (ESI, m/z): 194 [M−Boc+H]⁺.

To a mixture of (1S,2S,3S,6R,7S)-4-(tert-butoxycarbonyl)-9-methylidene-4-azatricyclo[5.2.1.0ˆ{2,6}]decane-3-carboxylic acid (201 mg, 0.684 mmol, 1.0 eq.) and o-(7-azabenzotriazol-1-yl)-N,N,N',N'-tetramethyluronium hexafluorophosphate (312 mg, 0.821 mmol, 1.2 eq.) in DMF (5 mL) was added N-ethyl-N-isopropylpropan-2-amine (530 mg, 4.10 mmol, 6.0 eq.) at 0° C. After stirred for 15 min at 0° C., (2S)-2-amino-3-[(3S)-2-oxopyrrolidin-3-yl]propanamide hydrochloride (142 mg, 0.684 mmol, 1.0 eq.) was added. The mixture was stirred for 1 h at rt. The mixture was purified by C18 column with CH₃CN/Water (0.05% TFA). The desired fraction was concentrated under reduced pressure to provide tert-butyl (1S,2S,3S,6R,7S)-3-{[(1S)-1-carbamoyl-2-[(3S)-2-oxopyrrolidin-3-yl]ethyl]carbamoyl}-9-methylidene-4-azatricyclo[5.2.1.0ˆ{2,6}]decane-4-carboxylate (180 mg, 50%) as a light yellow solid. LC-MS (ESI, m/z): 447 [M+H]⁺.

A mixture of tert-butyl (1S,2S,3S,6R,7S)-3-{[(1S)-1-carbamoyl-2-[(3S)-2-oxopyrrolidin-3-yl]ethyl]carbamoyl}-9-methylidene-4-azatricyclo[5.2.1.0ˆ{2,6}]decane-4-carboxylate (160 mg, 0.358 mmol, 1.0 eq.) in hydrogen chloride (5 mL, 2 M in Et₂O) was stirred for 2 h at rt. The mixture was concentrated under reduced pressure to afford (2S)-2-{[(1S,2S,3S,6R,7S)-9-methylidene-4-azatricyclo[5.2.1.0ˆ{2,6}]decan-3-yl]formamido}-3-[(3S)-2-oxopyrrolidin-3-yl]propanamide hydrochloride (137 mg, crude) as an off-white solid. LC-MS (ESI, m/z): 540 [M+H]⁺.

To a mixture of (2S)-2-{[(1S,2S,3S,6R,7S)-9-methylidene-4-azatricyclo[5.2.1.0ˆ{2,6}]decan-3-yl]formamido}-3-[(3S)-2-oxopyrrolidin-3-yl]propanamide hydrochloride (137 mg, 0.358 mmol, 1.0 eq.), (2S)-3,3-dimethyl-2-(2,2,2-trifluoroacetamido)butanoic acid (81.0 mg, 0.358 mmol, 1.0 eq.) and N,N,N',N'-tetramethylchloroformamidinium hexafluorophosphate (130 mg, 0.465 mmol, 1.3 eq.) in MeCN (3 mL) was added N-methylimidazole (294 mg, 3.58 mmol, 10.0 eq.) at rt. The mixture was stirred for 1 h at rt. The mixture was purified by C18 column with CH₃CN/Water (0.05% TFA). The desired fraction was concentrated under reduced pressure to afford (2S)-2-{[(1S,2S,3S,6R,7S)-4-[(2S)-3,3-dimethyl-2-(2,2,2-trifluoroacetamido)butanoyl]-9-methylidene-4-azatricyclo[5.2.1.0ˆ{2,6}]decan-3-yl]formamido}-3-[(3S)-2-oxopyrrolidin-3-yl]propanamide (160 mg, crude) as a yellow solid. LC-MS (ESI, m/z): 556 [M+H]⁺.

To a mixture of (2S)-2-{[(1S,2S,3S,6R,7S)-4-[(2S)-3,3-dimethyl-2-(2,2,2-trifluoroacetamido)butanoyl]-9-methylidene-4-azatricyclo[5.2.1.0ˆ{2,6}]decan-3-yl]formamido}-3-[(3S)-2-oxopyrrolidin-3-yl]propanamide (160 mg, 0.288 mmol, 1.0 eq.) in DCM (3 mL) was added pyridine (80.0 mg, 1.01 mmol, 3.5 eq.) and trifluoroacetic anhydride (91.0 mg, 0.432 mmol, 1.5 eq.). The mixture was stirred for 1 h at rt. The reaction was quenched with water (5 mL). The mixture was extracted with DCM (3×5 mL). The organic layers were combined, washed with brine (2×5 mL), dried over anhydrous sodium sulfate, filtered and concentrated under reduced pressure to afford the crude product. The crude product was purified by prep-HPLC (Column: XBridge Shield RP18 OBD Column, 30×150 mm, 5 m; Mobile Phase A: Water (0.1% FA), Mobile Phase B: ACN; Flow rate: 60 mL/min; Gradient: 32% B to 62% B in 7 min, 62% B; Wave Length: 254 nm; RT: 5.07 min) to provide (1S,2S,3S,6R,7S)—N-[(1S)-1-cyano-2-[(3S)-2-oxopyrrolidin-3-yl]ethyl]-4-[(2S)-3,3-dimethyl-2-(2,2,2-trifluoroacetamido)butanoyl]-9-methylidene-4-azatricyclo[5.2.1.0ˆ{2,6}]decane-3-carboxamide (30.2 mg, 19%) as a white solid. ¹H NMR (400 MHz, 80° C., DMSO-d₆) δ 8.48-9.05 (m, 2H), 7.35-7.55 (m, 1H), 4.81-5.10 (m, 1H), 4.75-4.80 (m, 1H), 4.53-4.74 (m, 1H), 4.40-4.52 (m, 1H), 4.20-4.39 (m, 1H), 3.45-3.90 (m, 2H), 3.10-3.43 (m, 2H), 2.65-2.95 (m, 2H), 2.50-2.64 (m, 1H), 2.28-2.45 (m, 2H), 1.82-2.26 (m, 4H), 1.25-1.81 (m, 4H), 0.80-1.15 (m, 9H). LC-MS (ESI, m/z): 538 [M+H]⁺.

Example 63

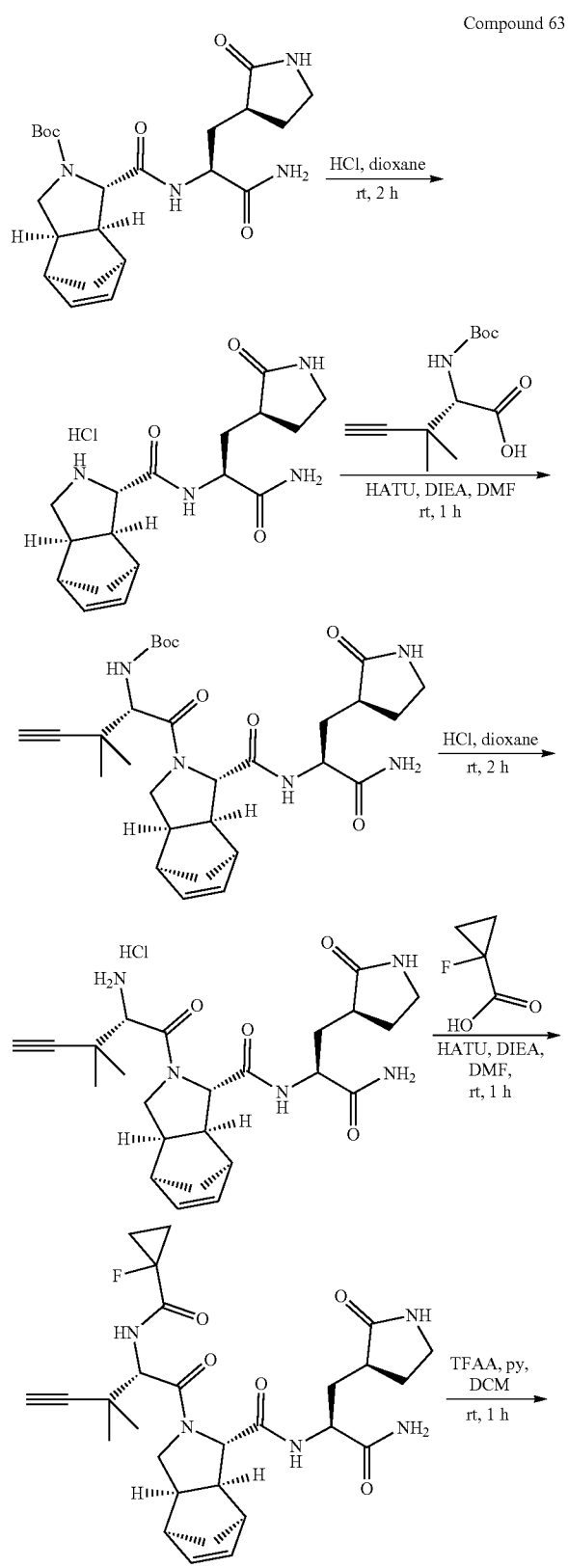

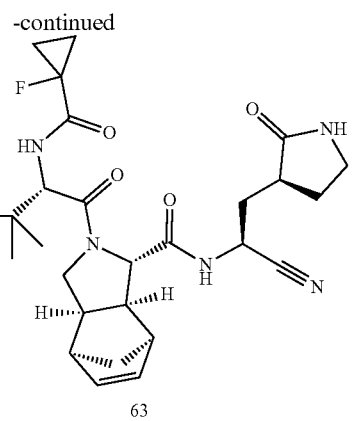

Compound 63

To a stirred mixture of tert-butyl (1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-ene-4-carboxylate (250 mg, 0.578 mmol, 1.0 eq.) in DCM (1 mL) was added hydrogen chloride (3 mL, 4M in 1,4-dioxane). The mixture was stirred for 2 h at rt, and then concentrated under reduced pressure to afford (2S)-2-[(1R,2S,3S,6R,7S)-4-azatricyclo[5.2.1.0^{2,6}]dec-8-en-3-ylformamido]-3-[(3S)-2-oxopyrrolidin-3-yl]propanamide hydrochloride (220 mg, crude) as an off-white solid. LC-MS (ESI, m/z): 333 [M+H]$^+$.

To a stirred mixture of (2S)-2-[(1R,2S,3S,6R,7S)-4-azatricyclo[5.2.1.0^{2,6}]dec-8-en-3-ylformamido]-3-[(3S)-2-oxopyrrolidin-3-yl]propanamide hydrochloride (220 mg, 0.596 mmol, 1.0 eq.) and (2S)-2-[(tert-butoxycarbonyl)amino]-3,3-dimethylpent-4-ynoic acid (143 mg, 0.596 mmol, 1.0 eq.) in DMF (3 mL) was added o-(7-Azabenzotriazol-1-yl)-N,N,N',N'-tetramethyluronium hexafluorophosphate (272 mg, 0.715 mmol, 1.2 eq.) and N-ethyl-N-isopropylpropan-2-amine (462 mg, 3.57 mmol, 6.0 eq.) at rt. The mixture was stirred for 1 h at rt. The crude product was purified by C18 column with CH$_3$CN/Water (0.05% FA). The desired fraction was concentrated under reduced pressure to provide tert-butyl N-[(2S)-1-[(1R,2S,3S,6R,7S)-3-{[(1S)-1-cyano-2-[(3S)-2-oxopyrrolidin-3-yl]ethyl]carbamoyl}-4-azatricyclo[5.2.1.0^{2,6}]dec-8-en-4-yl]-3,3-dimethyl-1-oxopent-4-yn-2-yl]carbamate (260 mg, 77%) as a light yellow solid. LC-MS (ESI, m/z): 556 [M+H]$^+$.

To a stirred mixture of tert-butyl N-[(2S)-1-[(1R,2S,3S,6R,7S)-3-{[(1S)-1-cyano-2-[(3S)-2-oxopyrrolidin-3-yl]ethyl]carbamoyl}-4-azatricyclo[5.2.1.0^{2,6}]dec-8-en-4-yl]-3,3-dimethyl-1-oxopent-4-yn-2-yl]carbamate (260 mg, 0.484 mmol, 1.0 eq.) in DCM (1 mL) was added hydrogen chloride (3 mL, 4M in dioxane). The mixture was stirred for 2 h at rt and then concentrated under reduced pressure to afford (2S)-2-{[(1R,2S,3S,6R,7S)-4-[(2S)-2-amino-3,3-dimethylpent-4-ynoyl]-4-azatricyclo[5.2.1.0^{2,6}]dec-8-en-3-yl]formamido}-3-[(3S)-2-oxopyrrolidin-3-yl]propanamide hydrochloride (240 mg, crude) as an off-white solid. LC-MS (ESI, m/z): 456 [M+H]$^+$.

To a stirred mixture of (2S)-2-{[(1R,2S,3S,6R,7S)-4-[(2S)-2-amino-3,3-dimethylpent-4-ynoyl]-4-azatricyclo[5.2.1.0^{2,6}]dec-8-en-3-yl]formamido}-3-[(3S)-2-oxopyrrolidin-3-yl]propanamide hydrochloride (240 mg, 0.488 mmol, 1.0 eq.) and 1-fluorocyclopropane-1-carboxylic acid (50.7 mg, 0.488 mmol, 1.0 eq.) in DMF (3 mL) was added o-(7-Azabenzotriazol-1-yl)-N,N,N',N'-tetramethyluronium hexafluorophosphate (222 mg, 0.586 mmol, 1.2 eq.) and N-ethyl-N-isopropylpropan-2-amine (378 mg, 2.92 mmol, 6.0 eq.) at rt. The mixture was stirred for 1 h at rt. The crude product was purified by C18 column with CH₃CN/Water (0.05% FA). The desired fraction was concentrated under reduced pressure to provide N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxopent-4-yn-2-yl]-1-fluorocyclopropane-1-carboxamide (170 mg, 61%). LC-MS (ESI, m/z): 542 [M+H]⁺.

To a stirred mixture of N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxopent-4-yn-2-yl]-1-fluorocyclopropane-1-carboxamide (170 mg, 0.314 mmol, 1.0 eq.) in DCM (2 mL) were added pyridine (99.3 mg, 1.25 mmol, 4.0 eq.) and trifluoroacetic anhydride (118 mg, 0.565 mmol, 1.8 eq.) at rt. The mixture was stirred for 1 h at rt. The reaction was quenched with water (20 mL). The mixture was extracted with DCM (3×20 mL). The organic layers were combined, washed with brine (2×20 mL), dried over anhydrous sodium sulfate, filtered and concentrated under reduced pressure to afford the crude product. The crude product was purified by prep-HPLC with the following conditions (Column: Xselect CSH F-Phenyl OBD column, 19*250 mm, 5 m; Mobile Phase A: Water (0.1% FA), Mobile Phase B: ACN; Flow rate: 25 mL/min; Gradient: 33% B to 63% B in 7 min, 63% B; Wave Length: 254 nm; RT1 (min): 4.95) to afford (1R,2S,3S,6R,7S)—N-[(1S)-1-cyano-2-[(3S)-2-oxopyrrolidin-3-yl]ethyl]-4-[(2S)-2-[(1-fluorocyclopropyl)formamido]-3,3-dimethylpent-4-ynoyl]-4-azatricyclo[5.2.1.0^{2,6}]dec-8-ene-3-carboxamide (60 mg, 36%) as a white solid. ¹H NMR (400 MHz, DMSO-d₆, 80° C.) δ 8.50-8.90 (m, 1H), 7.30-7.60 (m, 1H), 6.80-7.20 (m, 1H), 5.92-6.24 (m, 2H), 4.68-4.95 (m, 1H), 4.54-4.65 (m, 1H), 3.94-4.32 (m, 1H), 3.57-3.71 (m, 1H), 3.33-3.52 (m, 1H), 3.06-3.21 (m, 2H), 2.67-3.02 (m, 5H), 2.25-2.45 (m, 1H), 2.06-2.24 (m, 2H), 1.58-1.87 (m, 2H), 1.01-1.45 (m, 12H). LC-MS (ESI, m/z): 524 [M+H]⁺.

Example 64

Compound 64

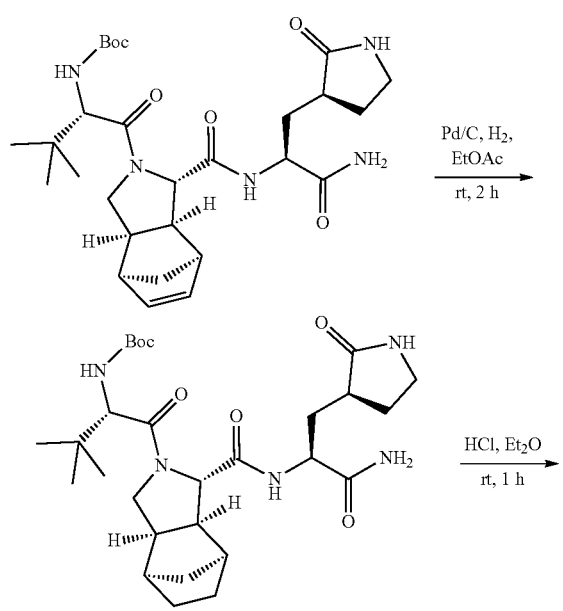

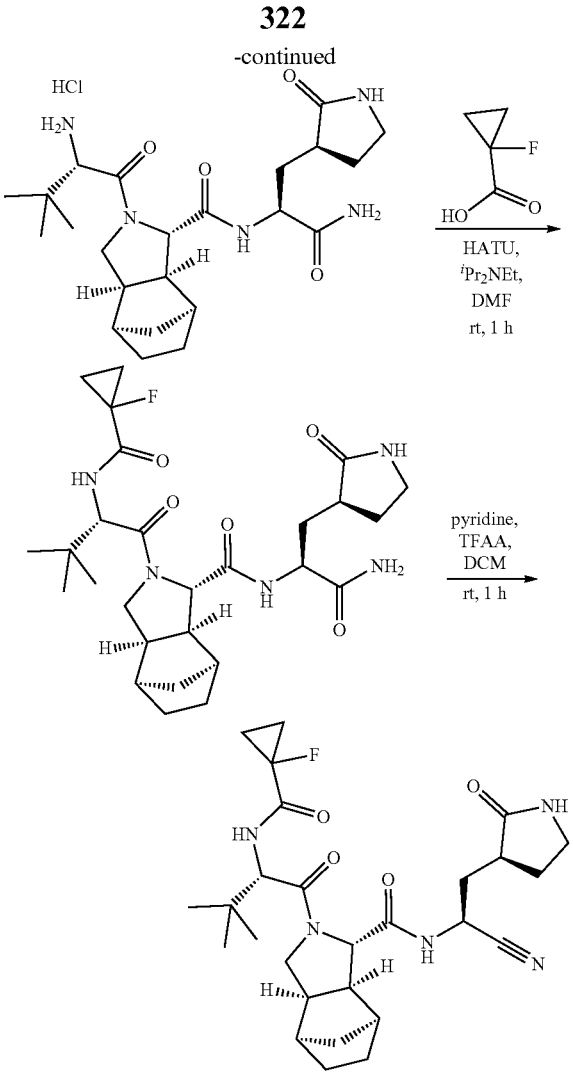

64

To a mixture of tert-butyl N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-3,3-dimethyl-1-oxobutan-2-yl]carbamate (600 mg, 1.10 mmol, 1.0 eq.) in EtOAc (20 mL) was added 10% Palladium on activated carbon (300 mg). The mixture was stirred for 2 h at rt under hydrogen. The mixture was filtered through a celite pad. The filtrate was concentrated under reduced pressure to provide tert-butyl N-[(2S)-1-[(1S,2S,3S,6R,7R)-3-{[(1S)-1-carbamoyl-2-[(3S)-2-oxopyrrolidin-3-yl]ethyl]carbamoyl}-4-azatricyclo[5.2.1.0^{2,6}]decan-4-yl]-3,3-dimethyl-1-oxobutan-2-yl]carbamate (590 mg, crude) as an off-white solid. LC-MS (ESI, m/z): 548 [M+H]⁺.

A mixture of tert-butyl N-[(2S)-1-[(1S,2S,3S,6R,7R)-3-{[(1S)-1-carbamoyl-2-[(3S)-2-oxopyrrolidin-3-yl]ethyl]carbamoyl}-4-azatricyclo[5.2.1.0^{2,6}]decan-4-yl]-3,3-dimethyl-1-oxobutan-2-yl]carbamate (590 mg, 1.08 mmol, 1.0 eq.) in hydrogen chloride (20 mL, 2 M in Et₂O) was stirred for 1 h at rt. The mixture was concentrated under reduced pressure to afford (2S)-2-{[(1S,2S,3S,6R,7R)-4-[(2S)-2-amino-3,3-dimethylbutanoyl]-4-azatricyclo[5.2.1.0^{2,6}]decan-3-yl]formamido}-3-[(3S)-2-oxopyrrolidin-3-yl]propanamide hydrochloride (520 mg, crude) as an off-white solid. LC-MS (ESI, m/z): 448 [M+H]⁺.

To a mixture of 1-fluorocyclopropane-1-carboxylic acid (112 mg, 1.07 mmol, 1.0 eq.) and o-(7-azabenzotriazol-1-yl)-N,N,N',N'-tetramethyluronium hexafluorophosphate (490 mg, 1.29 mmol, 1.2 eq.) in DMF (10 mL) was added N-ethyl-N-isopropylpropan-2-amine (833 mg, 6.44 mmol, 6.0 eq.) at 0° C. After stirred for 15 min at 0° C., (2S)-2-{[(1S,2S,3S,6R,7R)-4-[(2S)-2-amino-3,3-dimethylbutanoyl]-4-azatricyclo[5.2.1.0^{2,6}]decan-3-yl]formamido}-3-[(3S)-2-oxopyrrolidin-3-yl]propanamide hydrochloride (520 mg, 1.07 mmol, 1.0 eq.) was added. The mixture was stirred for 1 h at rt. The mixture was purified by C18 column with CH$_3$CN/Water (0.05% TFA). The desired fraction was concentrated under reduced pressure to provide N-[(2S)-1-[(1S,2S,3S,6R,7R)-3-{[(1S)-1-carbamoyl-2-[(3S)-2-oxopyrrolidin-3-yl]ethyl]carbamoyl}-4-azatricyclo[5.2.1.0^{2,6}]decan-4-yl]-3,3-dimethyl-1-oxobutan-2-yl]-1-fluorocyclopropane-1-carboxamide (500 mg, 84%) as a light yellow solid. $^1$H NMR (400 MHz, DMSO-d$_6$) δ 8.16-8.26 (m, 1H), 7.60 (s, 1H), 7.27-7.37 (m, 2H), 6.94-7.08 (m, 1H), 4.70-4.78 (m, 1H), 4.54-4.62 (m, 1H), 4.19-4.33 (m, 1H), 3.75-3.86 (m, 1H), 3.57-3.67 (m, 1H), 3.01-3.19 (m, 2H), 2.53-2.63 (m, 1H), 2.42-2.49 (m, 1H), 2.25-2.39 (m, 2H), 2.08-2.21 (m, 2H), 1.92-1.99 (m, 1H), 1.59-1.70 (m, 1H), 1.44-1.53 (m, 2H), 1.33-1.42 (m, 3H), 1.20-1.30 (m, 4H), 1.06-1.15 (m, 2H), 0.93-1.01 (m, 9H). LC-MS (ESI, m/z): 534[M+H]$^+$.

To a mixture of N-[(2S)-1-[(1S,2S,3S,6R,7R)-3-{[(1S)-1-carbamoyl-2-[(3S)-2-oxopyrrolidin-3-yl]ethyl]carbamoyl}-4-azatricyclo[5.2.1.0^{2,6}]decan-4-yl]-3,3-dimethyl-1-oxobutan-2-yl]-1-fluorocyclopropane-1-carboxamide (500 mg, 0.937 mmol, 1.0 eq.) in DCM (10 mL) were added pyridine (259 mg, 3.28 mmol, 3.5 eq.) and trifluoroacetic anhydride (295 mg, 1.40 mmol, 1.5 eq.). The mixture was stirred for 1 h at rt. The reaction was quenched with water (30 mL). The mixture was extracted with DCM (3×30 mL). The organic layers were combined, washed with brine (2×30 mL), dried over anhydrous sodium sulfate, filtered and concentrated under reduced pressure to afford the crude product. The crude product was purified by prep-HPLC (Column: XBridge Prep OBD C18 Column, 30×150 mm, 5 m; Mobile Phase A: Water (0.1% FA), Mobile Phase B: ACN; Flow rate: 60 mL/min; Gradient: 30% B to 60% B in 7 min, 60% B; Wave Length: 254 nm; RT1 (min): 6) to provide (1S,2S,3S,6R,7R)—N-[(1S)-1-cyano-2-[(3S)-2-oxopyrrolidin-3-yl]ethyl]-4-[(2S)-2-[(1-fluorocyclopropyl)formamido]-3,3-dimethylbutanoyl]-4-azatricyclo[5.2.1.0^{2,6}]decane-3-carboxamide (217.4 mg, 44%) a white solid. $^1$H NMR (400 MHz, 80° C., DMSO-d$_6$) δ 8.60-8.88 (m, 1H), 7.32-7.60 (m, 1H), 6.72-7.26 (m, 1H), 4.80-5.00 (m, 1H), 4.62-4.79 (m, 1H), 4.21-4.60 (m, 1H), 3.75-3.95 (m, 1H), 3.30-3.70 (m, 1H), 3.05-3.25 (m, 2H), 2.55-2.74 (m, 1H), 2.38-2.45 (m, 1H), 2.26-2.37 (m, 2H), 1.98-2.25 (m, 3H), 1.65-1.90 (m, 2H), 1.40-1.58 (m, 2H), 1.20-1.39 (m, 6H), 1.05-1.19 (m, 2H), 0.75-1.04 (m, 9H). LC-MS (ESI, m/z): 516 [M+H]$^+$.

Example 65

Compound 65

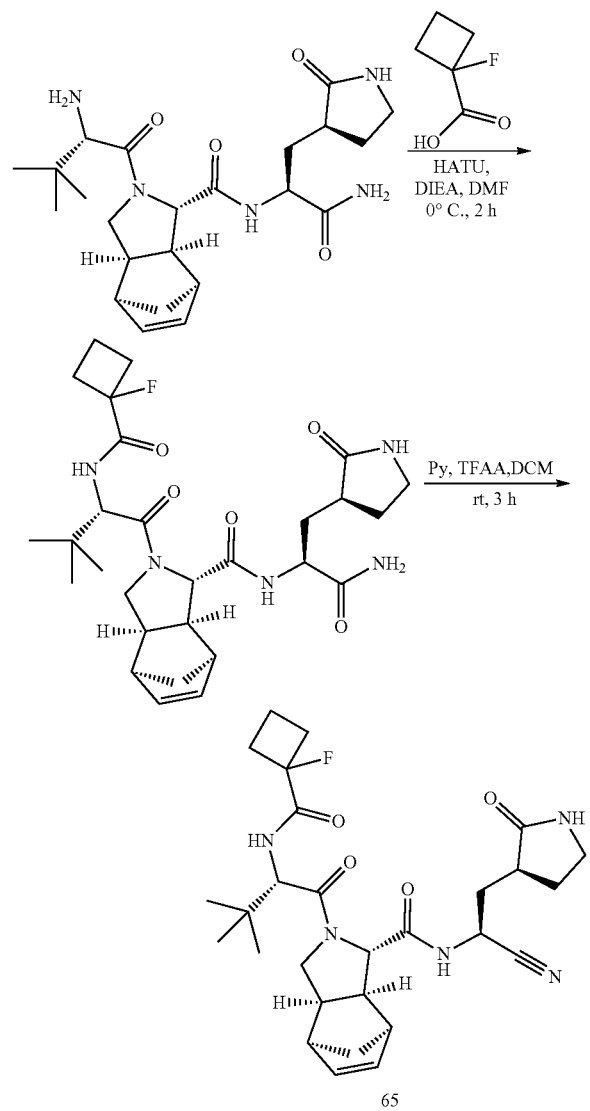

To a mixture of 1-fluorocyclobutane-1-carboxylic acid (66.0 mg, 0.555 mmol, 1.2 eq.) and o-(7-azabenzotriazol-1-yl)-N,N,N',N'-tetramethyluronium hexafluorophosphate (349 mg, 0.916 mmol, 2.0 eq.) in DMF (5 mL) was added N-ethyl-N-isopropylpropan-2-amine (593 mg, 4.58 mmol, 10.0 eq.) at 0° C. After stirred for 20 minutes at 0° C., (2S)-2-{[(1R,2S,3S,6R,7S)-4-[(2S)-2-amino-3,3-dimethylbutanoyl]-4-azatricyclo[5.2.1.0^{2,6}]dec-8-en-3-yl]formamido}-3-[(3S)-2-oxopyrrolidin-3-yl]propanamide (200 mg, 0.458 mmol, 1.0 eq.) were added. The mixture was stirred for 2 h at rt. The mixture was filtered. The filtrate was purified by reverse phase chromatography (Column: Agela C18 Column, 120 g; Mobile Phase A: Water (10 mM NH$_4$HCO$_3$), Mobile Phase B: ACN; Flow rate: 50 mL/min; Gradient: 0% B to 60% B in 30 min; Wavelength: 210 nm). The collected fraction was concentrated under reduced pressure to afford (1S,3aR,4S,7R,7aS)—N—((S)-1-amino-1-oxo-3-((S)-2-oxopyrrolidin-3-yl)propan-2-yl)-2-((S)-2-(1- fluorocyclobutane-1-carboxamido)-3,3-dimethylbutanoyl)-2,3,3a,4,7,7a-hexahydro-1H-4,7-methanoisoindole-1-carboxamide (210 mg, 84%) as a light yellow solid. LC-MS (ESI, m/z): 546 [M+H]$^+$.

To a solution of (1S,3aR,4S,7R,7aS)—N—((S)-1-amino-1-oxo-3-((S)-2-oxopyrrolidin-3-yl)propan-2-yl)-2-((S)-2-(1-fluorocyclobutane-1-carboxamido)-3,3-dimethylbutanoyl)-2,3,3a,4,7,7a-hexahydro-1H-4,7-methanoisoindole-1-carboxamide (210 mg, 0.385 mmol, 1.0 eq.) in DCM (10 mL) were added pyridine (124 mg, 1.56 mmol, 4.0 eq.) and trifluoroacetic anhydride (147 mg, 0.700 mmol, 1.8 eq.) at rt. The mixture was stirred for 3 h at rt. The mixture was diluted with water (50 mL) and extracted with DCM (3×100 mL). The organic layers were washed with brine (2×50 mL), dried over anhydrous sodium sulfate and filtered. The filtrate was concentrated under reduced pressure. The crude product was purified by reverse phase chromatography (Column: Agela C18 Column, 120 g; Mobile Phase A: Water (10 mM NH$_4$HCO$_3$), Mobile Phase B: ACN; Flow rate: 50 mL/min; Gradient: 0% B to 100% B in 50 min; Wave Length: 210 nm), and then re-purified by prep-HPLC (Column: XBridge Shield RP$_{18}$ OBD Column, 30*150 mm, 5 m; Mobile Phase A: Water (0.1% FA), Mobile Phase B: ACN; Flow rate: 60 mL/min; Gradient: 28% B to 58% B in 7 min, 58% B; Wave Length: 254 nm; RT (min): 5.18) to afford (1S,3aR,4S,7R,7aS)—N—((S)-1-cyano-2-((S)-2-oxopyrrolidin-3-yl)ethyl)-2-((S)-2-(1-fluorocyclobutane-1-carboxamido)-3,3-dimethylbutanoyl)-2,3,3a,4,7,7a-hexahydro-1H-4,7-methanoisoindole-1-carboxamide (73.4 mg, 36% yield) as a white solid. $^1$H NMR (400 MHz, 80° C., DMSO-d6) δ 8.62-8.85 (m, 1H), 7.39-7.59 (m, 1H), 6.80-6.83 (m, 1H), 6.00-6.05 (m, 1H), 5.90-5.96 (m, 1H), 4.90-4.91 (m, 1H), 4.40-4.50 (m, 1H), 4.00-4.15 (m, 1H), 3.64-3.70 (m, 1H), 3.40-3.52 (m, 1H), 2.93-3.20 (m, 5H), 2.70-2.80 (m, 1H), 2.49-2.60 (m, 1H), 2.22-2.48 (m, 4H), 2.05-2.20 (m, 2H), 1.80-1.95 (m, 1H), 1.60-1.80 (m, 3H), 1.30-1.50 (m, 2H), 0.90 (s, 9H). LC-MS (ESI, m/z): 528 [M+H]$^+$.

Example 66

Compound 66

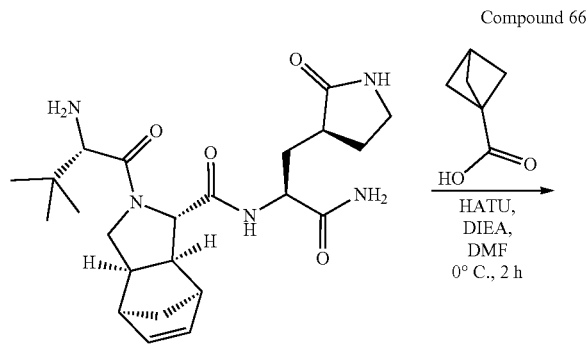

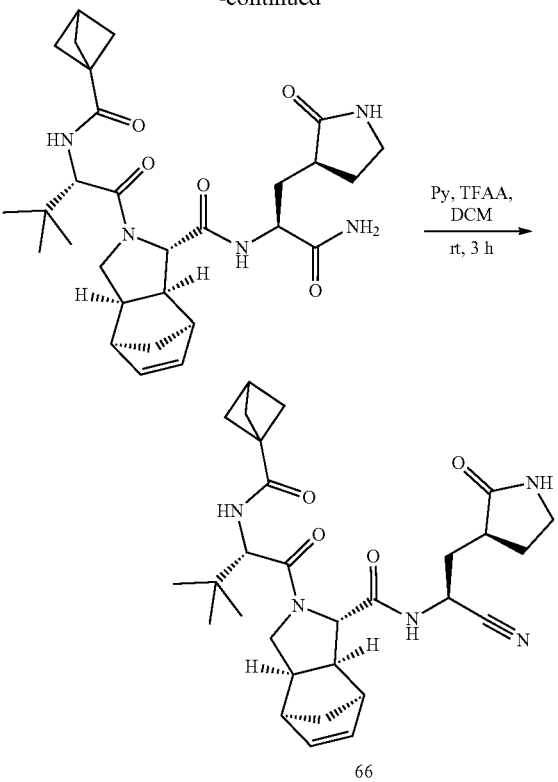

66

To a mixture of bicyclo[1.1.1]pentane-1-carboxylic acid (62 mg, 0.555 mmol, 1.2 eq.) and o-(7-azabenzotriazol-1-yl)-N,N,N',N'-tetramethyluronium hexafluorophosphate (349 mg, 0.916 mmol, 2 eq.) in DMF (5 mL) was added N-ethyl-N-isopropylpropan-2-amine (593 mg, 4.58 mmol, 10.0 eq.) at 0° C. After stirred for 20 minutes at 0° C., (2S)-2-{[(1R,2S,3S,6R,7S)-4-[(2S)-2-amino-3,3-dimethylbutanoyl]-4-azatricyclo[5.2.1.0^{2,6}]dec-8-en-3-yl]formamido}-3-[(3S)-2-oxopyrrolidin-3-yl]propanamide (200 mg, 0.458 mmol, 1.0 eq.) was added. The mixture was stirred for 2 h at rt, and then filtered. The filtrate was purified by reverse phase chromatography (Column: Agela C18 Column, 120 g; Mobile Phase A: Water (10 mM NH$_4$HCO$_3$), Mobile Phase B: ACN; Flow rate: 50 mL/min; Gradient: 0% B to 50% B in 25 min; Wavelength: 210 nm). The collected fraction was concentrated under reduced pressure to afford (1S,3aR,4S,7R,7aS)—N—((S)-1-amino-1-oxo-3-((S)-2-oxopyrrolidin-3-yl)propan-2-yl)-2-((S)-2-(bicyclo[1.1.1]pentane-1-carboxamido)-3,3-dimethylbutanoyl)-2,3,3a,4,7,7a-hexahydro-1H-4,7-methanoisoindole-1-carboxamide (210 mg, 85% yield for two steps) as a light yellow solid. LC-MS (ESI, m/z): 540 [M+H]$^+$.

To a solution of (1S,3aR,4S,7R,7aS)—N—((S)-1-amino-1-oxo-3-((S)-2-oxopyrrolidin-3-yl)propan-2-yl)-2-((S)-2-(bicyclo[1.1.1]pentane-1-carboxamido)-3,3-dimethylbutanoyl)-2,3,3a,4,7,7a-hexahydro-1H-4,7-methanoisoindole-1-carboxamide (210 mg, 0.389 mmol, 1.0 eq.) in DCM (10 mL) were added pyridine (124 mg, 1.56 mmol, 4.0 eq.) and trifluoroacetic anhydride (147 mg, 0.700 mmol, 1.8 eq.) at rt. The mixture was stirred for 3 h at rt. The mixture was diluted with water (50 mL) and extracted with DCM (3×100 mL). The organic layers were washed with brine (2×50 mL), dried over anhydrous sodium sulfate and filtered. The filtrate was concentrated under reduced pressure. The crude product was purified by reverse phase chromatography (Column: Agela C18 Column, 120 g; Mobile Phase A: Water (10 mM NH₄HCO₃), Mobile Phase B: ACN; Flow rate: 50 mL/min; Gradient: 0% B to 100% B in 50 min; Wave Length: 210 nm), then re-purified by preparative HPLC (Column: XBridge Shield RP$_{18}$ OBD Column, 30*150 mm, 5 m; Mobile Phase A: Water (0.1% FA), Mobile Phase B: ACN; Flow rate: 60 mL/min; Gradient: 28% B to 48% B in 7 min, 48% B; Wave Length: 254 nm; RT (min): 4.75) to afford (1S,3aR,4S,7R,7aS)-2-((S)-2-(bicyclo[1.1.1]pentane-1-carboxamido)-3,3-dimethylbutanoyl)-N—((S)-1-cyano-2-((S)-2-oxopyrrolidin-3-yl)ethyl)-2,3,3a,4,7,7a-hexahydro-1H-4,7-methanoisoindole-1-carboxamide (89.2 mg, 44% yield) as a white solid. $^1$H NMR (400 MHz, 80° C., DMSO-d₆) δ 8.61-8.78 (m, 1H), 7.38-7.41 (m, 1H), 6.75 (d, J=9.6 Hz, 1H), 5.96-6.00 (m, 2H), 4.90-4.91 (m, 1H), 4.44 (d, J=8.8 Hz, 1H), 3.98-4.10 (m, 1H), 3.40-3.61 (m, 2H), 3.06-3.30 (m, 2H), 2.90-3.05 (m, 1H), 2.80-2.90 (m, 2H), 2.70-2.80 (m, 1H), 2.40-2.49 (m, 2H), 2.00-2.20 (m, 2H), 1.98 (s, 6H), 1.60-1.80 (m, 2H), 1.30-1.38 (m, 2H), 0.81-0.88 (s, 9H). LC-MS (ESI, m/z): 522 [M+H]⁺.

Example 67

Compound 67

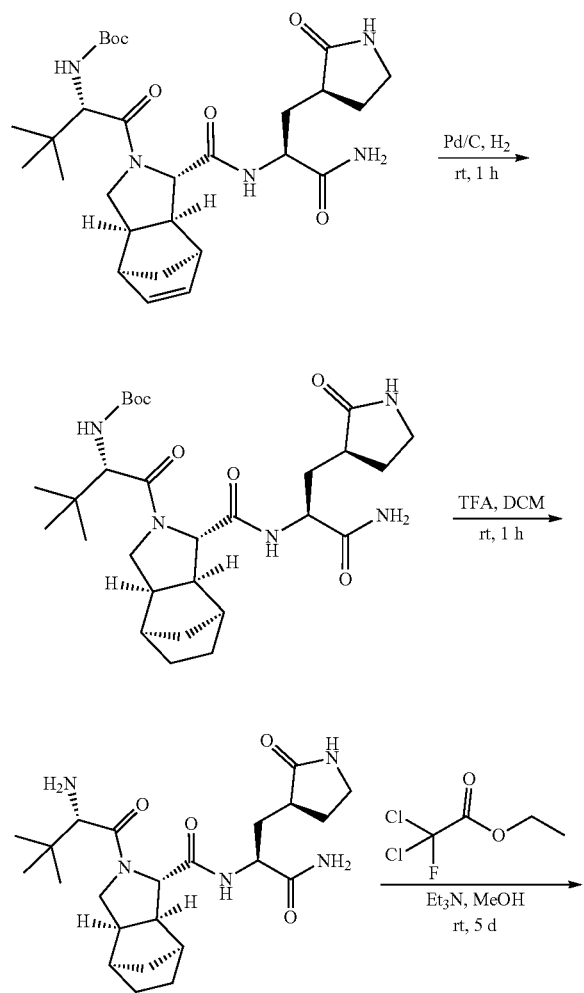

To a stirred mixture of tert-butyl N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0ˆ{2,6}]dec-8-en-4-yl]-3,3-dimethyl-1-oxobutan-2-yl]carbamate (500 mg, 0.916 mmol, 1.0 eq.) and 10% palladium on activated carbon (250 mg) in EtOAc (5 mL). The mixture was stirred for 1 h at rt under hydrogen. The mixture was filtered through a celite pad. The filtrate was concentrated under reduced pressure to provide tert-butyl N-[(2S)-1-[(1S,2S,3S,6R,7R)-3-{[(1S)-1-carbamoyl-2-[(3S)-2-oxopyrrolidin-3-yl]ethyl]carbamoyl}-4-azatricyclo[5.2.1.0ˆ{2,6}]decan-4-yl]-3,3-dimethyl-1-oxobutan-2-yl]carbamate (480 mg, crude) as an off-white solid. LC-MS (ESI, m/z): 548 [M+H]⁺.

To a stirred mixture of tert-butyl N-[(2S)-1-[(1S,2S,3S,6R,7R)-3-{[(1S)-1-carbamoyl-2-[(3S)-2-oxopyrrolidin-3-yl]ethyl]carbamoyl}-4-azatricyclo[5.2.1.0ˆ{2,6}]decan-4-yl]-3,3-dimethyl-1-oxobutan-2-yl]carbamate (480 mg, 0.876 mmol, 1.0 eq.) in DCM (15 mL) was added trifluoroacetic acid (5 mL). The mixture was stirred for 1 h at rt and then concentrated under reduced pressure to afford (2S)-2-{[(1S,2S,3S,6R,7R)-4-[(2S)-2-amino-3,3-dimethylbutanoyl]-4-azatricyclo[5.2.1.0ˆ{2,6}]decan-3-yl]formamido}-3-[(3S)-2-oxopyrrolidin-3-yl]propanamide (390 mg, crude) as a brown oil. LC-MS (ESI, m/z): 448 [M+H]⁺.

To a stirred mixture of (2S)-2-{[(1S,2S,3S,6R,7R)-4-[(2S)-2-amino-3,3-dimethylbutanoyl]-4-azatricyclo[5.2.1.0ˆ{2,6}]decan-3-yl]formamido}-3-[(3S)-2-oxopyrrolidin-3-yl]propanamide (480 mg, 1.07 mmol, 1.0 eq.) and ethyl 2,2-dichloro-2-fluoroacetate (938 mg, 5.36 mmol, 5.0 eq.) in methanol (5 mL) was added triethylamine (1.41 g, 13.9 mmol, 13.0 eq.). The mixture was stirred for 5 d at rt and then concentrated under reduced pressure to remove methanol. The mixture was diluted with water (20 mL) and adjusted to pH=6 with hydrochloric acid (1M). The mixture was extracted with EtOAc (3×80 mL). The organic layers were combined, washed with brine (2×50 mL), dried over anhydrous sodium sulfate, filtered and concentrated under reduced pressure to afford (2S)-2-{[(1S,2S,3S,6R,7R)-4-[(2S)-2-(2,2-dichloro-2-fluoroacetamido)-3,3-dimethylbutanoyl]-4-azatricyclo[5.2.1.0^{2,6}]decan-3-yl]formamido}-3-[(3S)-2-oxopyrrolidin-3-yl]propanamide (220 mg, 35%, crude) as an off-white solid. LC-MS (ESI, m/z): 576 [M+H]+.

To a stirred mixture of (2S)-2-{[(1S,2S,3S,6R,7R)-4-[(2S)-2-(2,2-dichloro-2-fluoroacetamido)-3,3-dimethylbutanoyl]-4-azatricyclo[5.2.1.0^{2,6}]decan-3-yl]formamido}-3-[(3S)-2-oxopyrrolidin-3-yl]propanamide (220 mg, 0.382 mmol, 1.0 eq.) in DCM (3 mL) was added pyridine (120 mg, 1.52 mmol, 4.0 eq.) and trifluoroacetic anhydride (136 mg, 0.649 mmol, 1.7 eq.). The mixture was stirred for 1 h at rt. The reaction quenched with water (15 mL). The mixture was extracted with EtOAc (3×15 mL). The organic layers were combined, washed with brine (2×15 mL), dried over anhydrous sodium sulfate, filtered and concentrated under reduced pressure to afford the crude product. The crude product was purified by prep-HPLC (Column: XBridge Shield RP18 OBD Column, 19*250 mm, 10 m; Mobile Phase A: Water (0.1% FA), Mobile Phase B: ACN; Flow rate: 25 mL/min; Gradient: 40% B to 70% B in 7 min, 70% B; Wave Length: 254 nm; RT1 (min): 6.02) to provide (1S,2S,3S,6R,7R)—N-[(1S)-1-cyano-2-[(3S)-2-oxopyrrolidin-3-yl]ethyl]-4-[(2S)-2-(2,2-dichloro-2-fluoroacetamido)-3,3-dimethylbutanoyl]-4-azatricyclo[5.2.1.0^{2,6}]decane-3-carboxamide (57.9 mg, 26%) as a white solid. $^1$H NMR (400 MHz, 80° C., DMSO-$d_6$) δ 8.69-8.89 (m, 1H), 8.08-8.30 (m, 1H), 7.34-7.80 (m, 1H), 4.80-5.00 (m, 1H), 4.60-4.76 (m, 1H), 4.45-4.59 (m, 1H), 3.78-3.90 (m, 1H), 3.52-3.72 (m, 1H), 3.05-3.25 (m, 2H), 2.60-2.73 (m, 1H), 2.30-2.48 (m, 3H), 2.08-2.29 (m, 3H), 1.61-1.92 (m, 2H), 1.38-1.45 (m, 1H), 1.46-1.60 (m, 1H), 1.18-1.32 (m, 3H), 1.08-1.15 (m, 1H), 0.70-1.15 (m, 9H). LC-MS (ESI, m/z): 558 [M+H]+.

Example 68

Compound 68

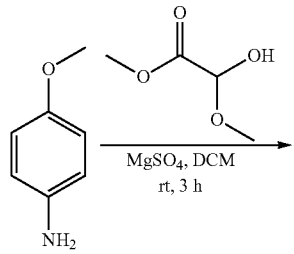

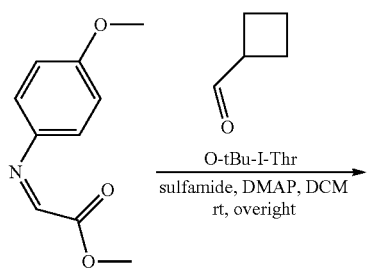

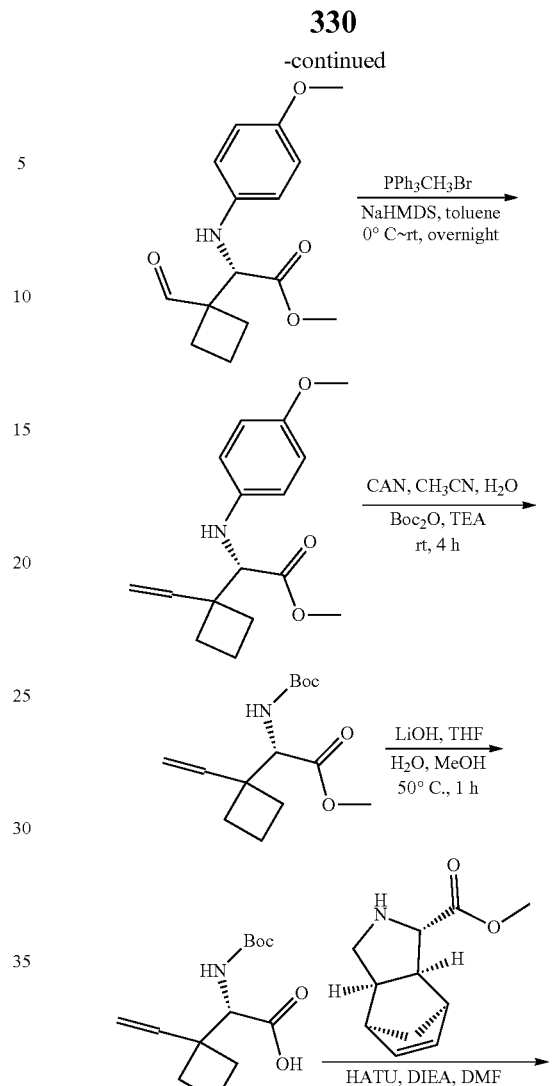

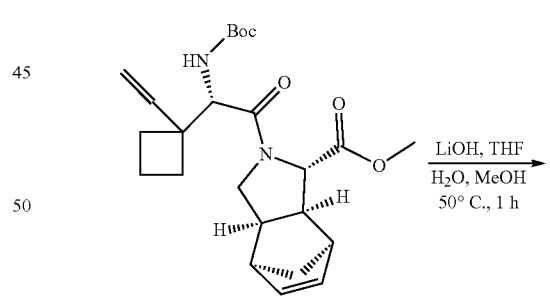

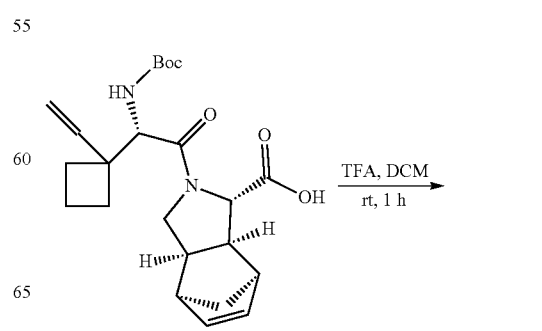

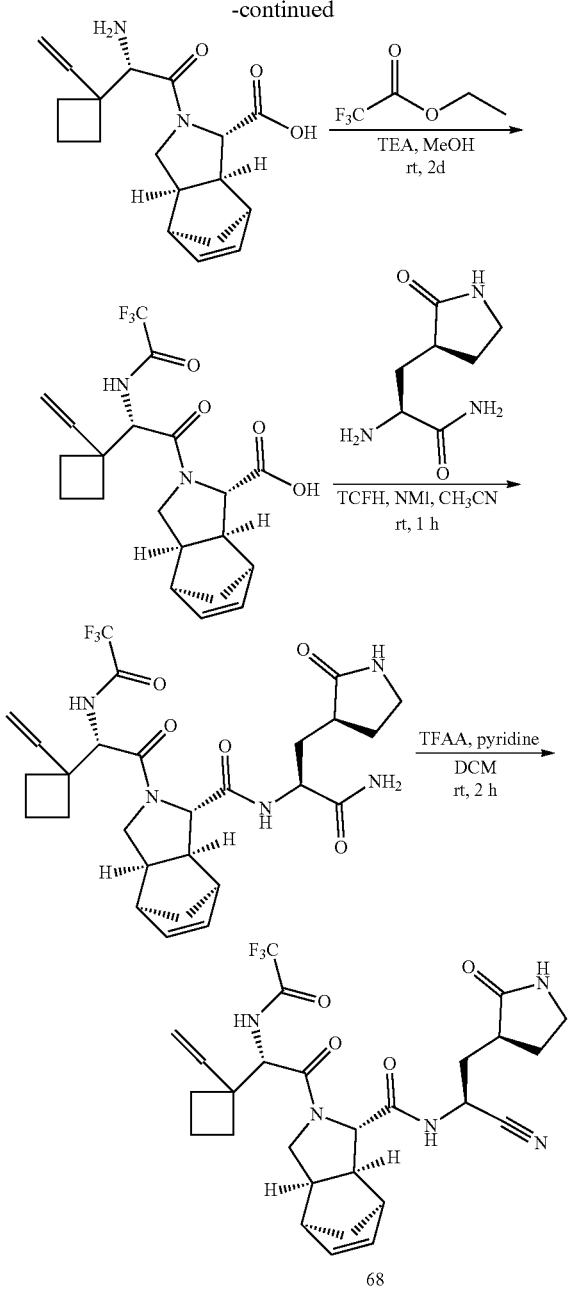

68

To a solution of 4-methoxyaniline (7.00 g, 56.8 mmol, 1.0 eq.) in DCM (100 mL) was added methyl 2-hydroxy-2-methoxyacetate (6.83 g, 56.8 mmol, 1.0 eq.) and magnesium sulfate (34.2 g, 284 mmol, 5.0 eq.). The mixture was stirred for 3 h at rt. The mixture was filtered through a celite pad and washed with DCM (3×100 mL). The filtrate was concentrated under reduced pressure to afford methyl (Z)-2-((4-methoxyphenyl)imino)acetate (11.0 g, crude) as a yellow oil. LC-MS (ESI, m/z): 194 [M+H]$^+$.

To a mixture of powdered molecular sieves (5 Å, 5.5 g), 2-amino-3-(tert-butoxy)butanoic acid (499 mg, 2.85 mmol, 0.05 eq.), sulfamide (274 mg, 2.85 mmol, 0.05 eq.) and N,N-dimethylpyridin-4-amine (348 mg, 2.85 mmol, 0.05 eq.) in DCM (60 mL) were added methyl (Z)-2-((4-methoxyphenyl)imino)acetate (11.0 g, 56.9 mmol, 1.0 eq.) and cyclobutyral (7.66 g, 91.1 mmol, 1.6 eq.) at rt. The mixture was stirred overnight at rt. The reaction was quenched with water (50 mL). The mixture was extracted with DCM (3×150 mL). The organic layers were combined, washed with brine (2×100 mL), dried over anhydrous sodium sulfate, filtered and concentrated under reduced pressure to afford the crude product. The crude product was chromatographed on a silica gel column with EA:PE (16:100) to provide methyl (S)-2-(1-formylcyclobutyl)-2-((4-methoxyphenyl)amino)acetate (2.6 g, crude) as a red oil. LC-MS (ESI, m/z): 278 [M+H]$^+$.

To a stirred mixture of methyltriphenylphosphanium bromide (4.69 g, 13.1 mmol, 1.4 eq.) in toluene (30 mL) was added sodium bis(trimethylsilyl)amide (6.55 mL, 13.1 mmol, 1.4 eq., 2 M in THF) at 0° C. under nitrogen. The mixture was stirred for 1 h at 0° C., and then methyl (S)-2-(1-formylcyclobutyl)-2-((4-methoxyphenyl)amino) acetate (2.6 g, 9.38 mmol, 1.0 eq.) was added. The mixture was stirred for 1 h at 0° C. The reaction was quenched with water (20 mL). The mixture was extracted with EtOAc (3×100 mL). The organic layers were combined, washed with brine (2×50 mL), dried over anhydrous sodium sulfate, filtered and concentrated under reduced pressure to afford the crude product. The crude product was chromatographed on a silica gel column with EA:PE (11:100) to provide methyl (S)-2-((4-methoxyphenyl)amino)-2-(1-vinylcyclobutyl)acetate (820 mg, 31%) as a yellow oil. LC-MS (ESI, m/z): 276 [M+H]$^+$.

To a stirred mixture of methyl (S)-2-((4-methoxyphenyl)amino)-2-(1-vinylcyclobutyl)acetate (820 mg, 2.98 mmol, 1.0 eq.) in CH$_3$CN (20 mL) and H$_2$O (5 mL) were added ceric ammonium nitrate (8.19 g, 14.9 mmol, 5.0 eq.). The mixture was stirred for 2 h at rt. THF (5 mL) was added, and the mixture was basified to pH=8 with triethylamine. Di-tert-butyl dicarbonate (3.90 g, 17.9 mmol, 6.0 eq.) was added. The mixture was stirred for 2 h at rt. The reaction was quenched with H$_2$O (30 mL). The mixture was extracted with EA (3×100 mL). The organic layers were combined, washed with brine (2×30 mL), dried over anhydrous sodium sulfate, filtered and concentrated under reduced pressure to afford the crude product. The crude product was chromatographed on a silica gel column with EA:PE (6:100) to provide methyl (S)-2-((tert-butoxycarbonyl)amino)-2-(1-vinylcyclobutyl)acetate (470 mg, crude) as a yellow oil. $^1$H NMR (400 MHz, Chloroform-d) δ 5.72-5.80 (m, 1H), 5.35-5.52 (m, 2H), 4.45-4.50 (m, 1H), 3.72 (s, 3H), 2.25-2.45 (m, 1H), 2.10-2.21 (m, 2H), 1.75-2.00 (m, 3H), 1.47 (s, 9H). LC-MS (ESI, m/z): 270 [M+H]$^+$.

To a mixture of methyl (S)-2-((tert-butoxycarbonyl)amino)-2-(1-vinylcyclobutyl)acetate (470 mg, 1.75 mmol, 1.0 eq.) in THF (3 mL), H$_2$O (2 mL) and MeOH (1 mL) was added lithium hydroxide (209 mg, 8.73 mmol, 5.0 eq.). The mixture was stirred for 1 h at 50° C. and then concentrated under reduced pressure to remove MeOH. The mixture was adjusted to pH=5 with HCl (1 M). The mixture was extracted with EA (3×80 mL). The organic layers were combined, dried over anhydrous sodium sulfate, filtered and concentrated under reduced pressure to provide (S)-2-((tert-butoxycarbonyl)amino)-2-(1-vinylcyclobutyl)acetic acid (420 mg, crude) as an off-white solid. LC-MS (ESI, m/z): 256 [M+H]$^+$.

To a mixture of (S)-2-((tert-butoxycarbonyl)amino)-2-(1-vinylcyclobutyl)acetic acid (467 mg, 1.83 mmol, 1.0 eq.) and o-(7-azabenzotriazol-1-yl)-N,N,N',N'-tetramethyluronium hexafluorophosphate (834 mg, 2.19 mmol, 1.2 eq.) in dimethylformamide (5 mL) was added N-ethyl-N-isopropylpropan-2-amine (1.42 g, 11.0 mmol, 6.0 eq.) at 0° C. After stirred 20 mins, methyl (1R,2S,3S,6R,7S)-4-azatricyclo

[5.2.1.0^{2,6}]dec-8-ene-3-carboxylate hydrochloride (420 mg, 1.83 mmol, 1.0 eq.) was added. The mixture was stirred for 1 h at rt. The reaction was quenched with water (5 mL). The crude product was purified by C18 column with CH$_3$CN/Water (0.05% FA). The desired fraction was concentrated under reduced pressure to provide methyl (1S,3aR,4S,7R,7aS)-2-((S)-2-((tert-butoxycarbonyl)amino)-2-(1-vinylcyclobutyl)acetyl)-2,3,3a,4,7,7a-hexahydro-1H-4,7-methanoisoindole-1-carboxylate (430 mg, 54%) as a white solid. LC-MS (ESI, m/z): 431 [M+H]$^+$.

To a mixture of methyl (1S,3aR,4S,7R,7aS)-2-((S)-2-((tert-butoxycarbonyl)amino)-2-(1-vinylcyclobutyl)acetyl)-2,3,3a,4,7,7a-hexahydro-1H-4,7-methanoisoindole-1-carboxylate (430 mg, 1.00 mmol, 1.0 eq.) in THF (3 mL), MeOH (1 mL) and H$_2$O (2 mL) was added lithium hydroxide (120 mg, 4.99 mmol, 5.0 eq.). The mixture was stirred for 1 h at 50° C. The mixture was concentrated under reduced pressure to remove MeOH. The mixture was adjusted to pH=5 with HCl (1 M). The mixture was extracted with EA (3×80 mL). The organic layers were combined, dried over anhydrous sodium sulfate, filtered and concentrated under reduced pressure to provide (1S,3aR,4S,7R,7aS)-2-((S)-2-((tert-butoxycarbonyl)amino)-2-(1-vinylcyclobutyl)acetyl)-2,3,3a,4,7,7a-hexahydro-1H-4,7-methanoisoindole-1-carboxylic acid (310 mg, 71%) as a white solid. LC-MS (ESI, m/z): 417 [M+H]$^+$.

To a solution of (1S,3aR,4S,7R,7aS)-2-((S)-2-((tert-butoxycarbonyl)amino)-2-(1-vinylcyclobutyl)acetyl)-2,3,3a,4,7,7a-hexahydro-1H-4,7-methanoisoindole-1-carboxylic acid (310 mg, 0.744 mmol, 1.0 eq.) in DCM (3 mL) was added trifluoroacetic acid (1 mL) stirred at rt. The mixture was stirred for 1 h at rt and then concentrated under reduced pressure to afford (1S,3aR,4S,7R,7aS)-2-((S)-2-amino-2-(1-vinylcyclobutyl)acetyl)-2,3,3a,4,7,7a-hexahydro-1H-4,7-methanoisoindole-1-carboxylic acid (280 mg, crude) as a brown semi-solid. LC-MS (ESI, m/z): 317 [M+H]$^+$.

To a solution of (1S,3aR,4S,7R,7aS)-2-((S)-2-amino-2-(1-vinylcyclobutyl)acetyl)-2,3,3a,4,7,7a-hexahydro-1H-4,7-methanoisoindole-1-carboxylic acid (280 mg, 0.885 mmol, 1.0 eq.) in MeOH (3 mL) was added triethylamine (1.07 g, 10.6 mmol, 12.0 eq.) and ethyl 2,2,2-trifluoroacetate (1.26 g, 8.85 mmol, 10.0 eq.). The mixture was stirred for 2 d at rt. The reaction was quenched with water (10 mL). The mixture was concentrated under reduced pressure to remove MeOH. The mixture was adjusted to pH=4 with HCl (1 M), and then extracted with EtOAc (3×100 mL). The organic layers were combined, washed with brine (2×30 mL), dried over anhydrous sodium sulfate, filtered and concentrated under reduced pressure to afford (1S,3aR,4S,7R,7aS)-2-((S)-2-(2,2,2-trifluoroacetamido)-2-(1-vinylcyclobutyl)acetyl)-2,3,3a,4,7,7a-hexahydro-1H-4,7-methanoisoindole-1-carboxylic acid (260 mg, crude) as a yellow solid. LC-MS (ESI, m/z): 413 [M+H]$^+$.

To a mixture of (1R,2S,3S,6R,7S)-4-[(2S)-2-(1-ethenylcyclobutyl)-2-(2,2,2-trifluoroacetamido)acetyl]-4-azatricyclo[5.2.1.0^{2,6}]dec-8-ene-3-carboxylic acid (260 mg, 0.630 mmol, 1.00 eq.) in CH$_3$CN (5 mL,) was added N,N,N,N-tetramethylchloroformamidinium hexafluorophosphate (212 mg, 0.756 mmol, 1.2 eq.) and 1-methyl-1H-imidazole (311 mg, 3.78 mmol, 6.0 eq.) at 0° C. After stirred 20 mins, (S)-2-amino-3-((S)-2-oxopyrrolidin-3-yl)propanamide (108 mg, 0.630 mmol, 1.0 eq.) was added. The mixture was stirred for 1 h at rt. The crude product was purified by C18 column with CH$_3$CN/Water (0.05% TFA). The desired fraction was concentrated under reduced pressure to provide (1S,3aR,4S,7R,7aS)—N—((S)-1-amino-1-oxo-3-((S)-2-oxopyrrolidin-3-yl)propan-2-yl)-2-((S)-2-(2,2,2-trifluoroacetamido)-2-(1-vinylcyclobutyl)acetyl)-2,3,3a,4,7,7a-hexahydro-1H-4,7-methanoisoindole-1-carboxamide (130 mg, 36%) as a white solid. LC-MS (ESI, m/z): 566 [M+H]+.

To a mixture of (1S,3aR,4S,7R,7aS)—N—((S)-1-amino-1-oxo-3-((S)-2-oxopyrrolidin-3-yl)propan-2-yl)-2-((S)-2-(2,2,2-trifluoroacetamido)-2-(1-vinylcyclobutyl)acetyl)-2,3,3a,4,7,7a-hexahydro-1H-4,7-methanoisoindole-1-carboxamide (130 mg, 0.230 mmol, 1.0 eq.) in DCM (3 mL) was added pyridine (90.9 mg, 1.15 mmol, 5.0 eq.) and trifluoroacetic anhydride (86.9 mg, 0.414 mmol, 1.8 eq.). The mixture was stirred 2 h at rt. The reaction was quenched with water (5 mL). The mixture was extracted with DCM (3×30 mL). The organic layers were combined, washed with brine (2×10 mL), dried over anhydrous sodium sulfate, filtered and concentrated under reduced pressure to afford the crude product. The crude product was purified by prep-HPLC (Column: Xselect CSH C18 OBD Column 30*150 mm 5 m, n; Mobile Phase A: Water (0.1% FA), Mobile Phase B:ACN; Flow rate: 60 mL/min; Gradient: 30% B to 60% B in 8 min, 60% B; Wave Length: 254/220 nm; RT1 (min): 6;) to provide (1S,3aR,4S,7R,7aS)—N—((S)-1-cyano-2-((S)-2-oxopyrrolidin-3-yl)ethyl)-2-((S)-2-(2,2,2-trifluoroacetamido)-2-(1-vinylcyclobutyl)acetyl)-2,3,3a,4,7,7a-hexahydro-1H-4,7-methanoisoindole-1-carboxamide (46.2 mg, 36%) as a white solid. $^1$H NMR (400 MHz, 80° C., DMSO-d6) δ 8.94-9.00 (m, 1H), 8.60-8.77 (m, 1H), 7.38-7.52 (m, 1H), 5.99-6.18 (m, 2H), 5.83-5.98 (m, 1H), 5.15-5.20 (m, 2H), 4.79-4.92 (m, 1H), 4.52-4.69 (m, 1H), 3.88-4.02 (m, 1H), 3.56-3.64 (m, 1H), 3.27-3.34 (m, 1H), 3.00-3.21 (m, 3H), 2.84-2.97 (m, 2H), 2.66-2.79 (m, 1H), 2.24-2.40 (m, 2H), 1.97-2.21 (m, 3H), 1.56-1.66 (m, 3H), 1.68-1.89 (m, 3H), 1.31-1.43 (m, 2H). LC-MS (ESI, m/z): 548 [M+H]$^+$.

Example 69

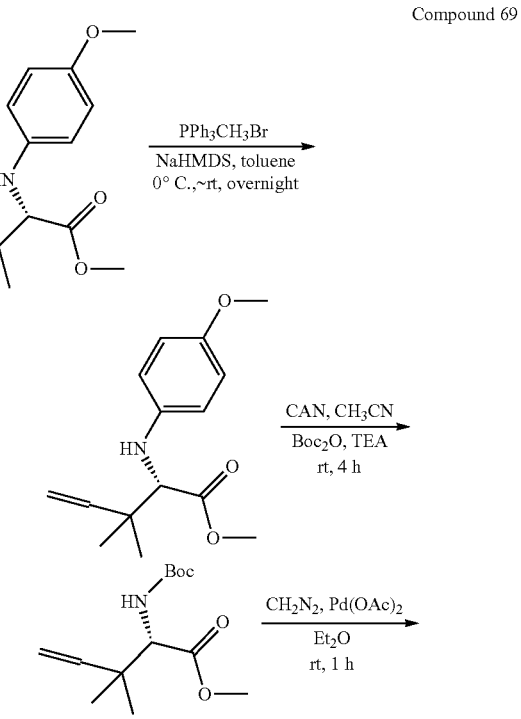

Compound 69

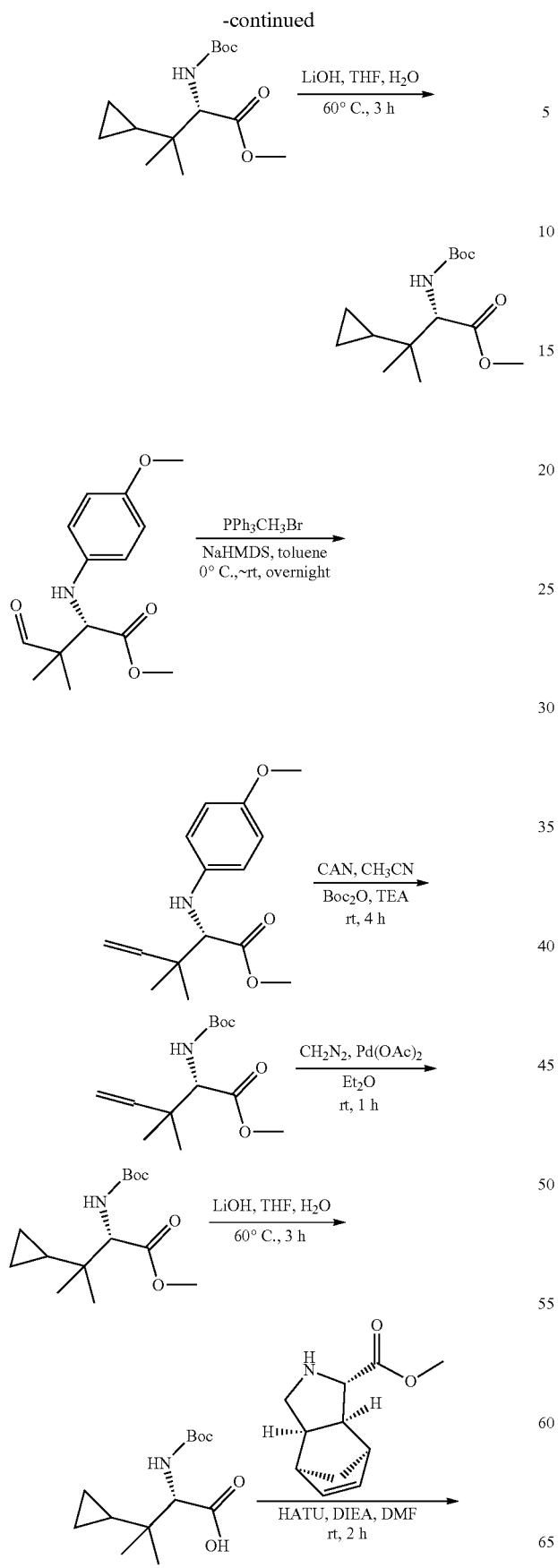
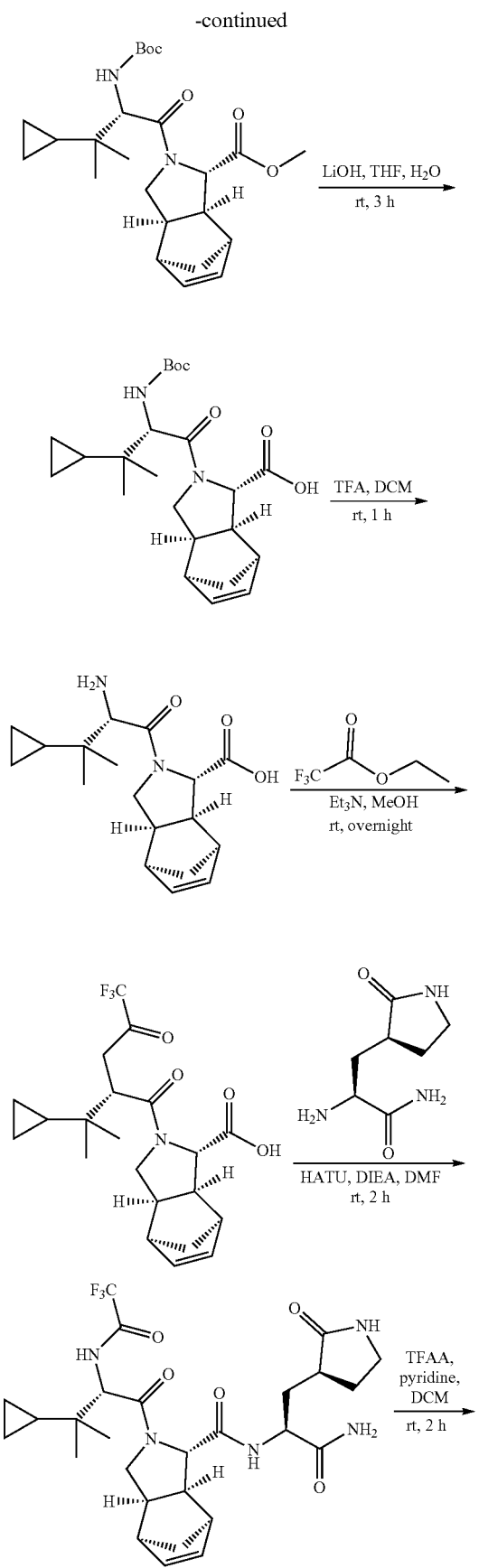

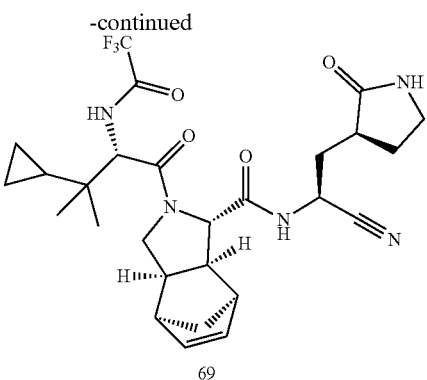

69

To a solution of methyltriphenylphosphanium bromide (13.2 g, 37.2 mmol, 1.1 eq.) in toluene (100 mL) was added sodium bis(trimethylsilyl)amide (6.80 g, 37.2 mmol, 1.1 eq.) at 0° C. The mixture was warmed to rt and stirred for 30 min. After cooling to 0° C., a solution of methyl (2S)-2-[(4-methoxyphenyl)amino]-3,3-dimethyl-4-oxobutanoate (9.00 g, 33.9 mmol, 1.0 eq.) in toluene was added. The mixture was stirred overnight and poured into ice-cold water (100 mL). The mixture was extracted with ethyl acetate (3×200 mL). The organic phases were combined, washed with brine (100 mL), dried over anhydrous sodium sulfate, filtered and concentrated under reduced pressure to afford the crude product. The crude product was chromatographed on a silica gel column with EA:PE (12:88) to provide methyl (2S)-2-[(4-methoxyphenyl)amino]-3,3-dimethylpent-4-enoate (5.00 g, 56%) as a brown oil. LC-MS (ESI, m/z): 264 [M+H]$^+$.

To a stirred mixture of methyl (2S)-2-[(4-methoxyphenyl)amino]-3,3-dimethylpent-4-enoate (5.00 g, 18.9 mmol, 1.0 eq.) in CH$_3$CN (45 mL) and H$_2$O (15 mL) were added ceric ammonium nitrate (52.2 g, 94.9 mmol, 5.0 eq.) at rt. The mixture was stirred for 2 h at rt. The mixture was added THF (10 mL) and basified to pH=8 with triethylamine. Di-tert-butyl dicarbonate (24.8 g, 113 mmol, 6.0 eq.) was added. The mixture was stirred for 2 h at rt. The reaction was quenched with water. The mixture was extracted with EA (3×100 mL). The organic layers were combined, washed with brine (2×80 mL), dried over anhydrous sodium sulfate, filtered and concentrated under reduced pressure to afford the crude product. The crude product was chromatographed on a silica gel column with EA:PE (1:9) to provide methyl (2S)-2-[(tert-butoxycarbonyl)amino]-3,3-dimethylpent-4-enoate (3.2 g, crude) as a yellow oil. LC-MS (ESI, m/z): 158 [M−100+H]$^+$.

To a solution of methyl (2S)-2-[(tert-butoxycarbonyl)amino]-3,3-dimethylpent-4-enoate (1.80 g, 7.00 mmol, 1.0 eq.) in Et$_2$O (20 mL) at −30° C. was added diazomethane (54.0 g, 210 mmol, 30.0 eq.) and palladium(II) acetate (0.235 g, 1.05 mmol, 0.15 eq.). The mixture was stirred for 1 h at rt and then filtered. The filter cake was washed with diethyl ether (3×80 mL). The filtrate was concentrated under reduced pressure to afford the crude product. The crude product was chromatographed on a silica gel column with EA:PE (13:87) to provide methyl (2S)-2-[(tert-butoxycarbonyl)amino]-3-cyclopropyl-3-methylbutanoate (0.800 g, 42%) as a light yellow oil. LC-MS (ESI, m/z): 272 [M+H]$^+$.

To a stirred mixture of methyl (2S)-2-[(tert-butoxycarbonyl)amino]-3-cyclopropyl-3-methylbutanoate (800 mg, 2.95 mmol, 1.0 eq.) in THF (18 mL) and H$_2$O (18 mL) was added lithium hydroxide (338 mg, 14.7 mmol, 5.0 eq.) at rt. The mixture was stirred for 3 h at 60° C. The mixture was acidified to pH=3 with hydrochloric acid (2M). The aqueous layer was extracted with EA (3×100 mL). The organic layers were combined, washed with brine (2×80 mL), dried over anhydrous sodium sulfate, filtered and concentrated under reduced pressure to afford (2S)-2-[(tert-butoxycarbonyl)amino]-3-cyclopropyl-3-methylbutanoic acid (500 mg, crude) as a light yellow solid. LC-MS (ESI, m/z): 258 [M+H]$^+$.

To a mixture of (2S)-2-[(tert-butoxycarbonyl)amino]-3-cyclopropyl-3-methylbutanoic acid (500 mg, 1.94 mmol, 1.0 eq.) in N,N-dimethylformamide (5 mL) was added o-(7-azabenzotriazol-1-yl)-N,N,N',N'-tetramethyluronium hexafluorophosphate (886 mg, 2.33 mmol, 1.2 eq.) and N-ethyl-N-isopropylpropan-2-amine (1.50 g, 11.6 mmol, 6.0 eq.) at 0° C. The mixture was stirred for 20 min at 0° C., and then methyl (1R,2S,3S,6R,7S)-4-azatricyclo[5.2.1.0^{2,6}]dec-8-ene-3-carboxylate (375 mg, 1.94 mmol, 1.00 eq.) was added at 0° C. The mixture was stirred for 2 h at rt. The mixture was purified by C18 column with CH$_3$CN/Water (0.05% FA). The desired fraction was concentrated under reduced pressure to provide methyl (1R,2S,3S,6R,7S)-4-[(2S)-2-[(tert-butoxycarbonyl)amino]-3-cyclopropyl-3-methylbutanoyl]-4-azatricyclo[5.2.1.0^{2,6}]dec-8-ene-3-carboxylate (450 mg, 53%) as a light yellow solid. LC-MS (ESI, m/z): 433 [M+H]$^+$.

To a stirred mixture of methyl (1R,2S,3S,6R,7S)-4-[(2S)-2-[(tert-butoxycarbonyl)amino]-3-cyclopropyl-3-methylbutanoyl]-4-azatricyclo[5.2.1.0^{2,6}]dec-8-ene-3-carboxylate (450 mg, 1.04 mmol, 1.0 eq.) in THF (5 mL) and H$_2$O (5 mL) was added lithium hydroxide (119 mg, 5.20 mmol, 5.0 eq.) at rt. The mixture was stirred for 3 h at rt and then acidified to pH=3 with hydrochloric acid (1M). The aqueous layer was extracted with EA (3×50 mL). The organic layers were combined, washed with brine (2×30 mL) and dried over anhydrous sodium sulfate. The mixture was concentrated under reduced pressure to afford (1R,2S,3S,6R,7S)-4-[(2S)-2-[(tert-butoxycarbonyl)amino]-3-cyclopropyl-3-methylbutanoyl]-4-azatricyclo[5.2.1.0^{2,6}]dec-8-ene-3-carboxylic acid (400 mg, crude) as a light orange solid. LC-MS (ESI, m/z): 419 [M+H]$^+$.

To a stirred mixture of (1R,2S,3S,6R,7S)-4-[(2S)-2-[(tert-butoxycarbonyl)amino]-3-cyclopropyl-3-methylbutanoyl]-4-azatricyclo[5.2.1.0^{2,6}]dec-8-ene-3-carboxylic acid (400 mg, 0.956 mmol, 1.0 eq.) in DCM (5 mL) was added trifluoroacetic acid (1.7 mL) at rt. The mixture was stirred for 1 h at rt and then concentrated under reduced pressure to provide (1R,2S,3S,6R,7S)-4-[(2S)-2-amino-3-cyclopropyl-3-methylbutanoyl]-4-azatricyclo[5.2.1.0^{2,6}]dec-8-ene-3-carboxylic acid (338 mg, crude) as a brown yellow oil. LC-MS (ESI, m/z): 319 [M+H]$^+$.

To a stirred mixture of (1R,2S,3S,6R,7S)-4-[(2S)-2-amino-3-cyclopropyl-3-methylbutanoyl]-4-azatricyclo[5.2.1.0^{2,6}]dec-8-ene-3-carboxylic acid (0.338 g, 1.06 mmol, 1.0 eq.) and triethylamine (1.28 g, 12.7 mmol, 12 eq.) in MeOH (4 mL) was added ethyl 2,2,2-trifluoroacetate (1.50 g, 10.6 mmol, 10 eq.). The mixture was stirred overnight at rt and then acidified to pH=4 with hydrochloric acid (1M). The mixture was extracted with EA (3×20 mL). The combined organic layers were concentrated under reduced pressure to afford (1R,2S,3S,6R,7S)-4-[(2S)-3-cyclopropyl-3-methyl-2-(2,2,2-trifluoroacetamido)butanoyl]-4-azatricyclo[5.2.1.0^{2,6}]dec-8-ene-3-carboxylic acid (0.33 g, 75%) as a light yellow oil. LC-MS (ESI, m/z): 415 [M+H]$^+$.

To a mixture of (1R,2S,3S,6R,7S)-4-[(2S)-3-cyclopropyl-3-methyl-2-(2,2,2-trifluoroacetamido)butanoyl]-4-azatricyclo[5.2.1.0^{2,6}]dec-8-ene-3-carboxylic acid (285 mg, 0.688 mmol, 1.0 eq.) in N,N-dimethylformamide (3 mL) was added o-(7-azabenzotriazol-1-yl)-N,N,N',N'-tetramethyluronium hexafluorophosphate (313 mg, 0.825 mmol, 1.2 eq.) and N-ethyl-N-isopropylpropan-2-amine (531 mg, 4.12 mmol, 6.0 eq.) at 0° C. The mixture was stirred for 20 min at 0° C., and then (2S)-2-amino-3-[(3S)-2-oxopyrrolidin-3-yl]propanamide (117 mg, 0.688 mmol, 1.0 eq.) was added at 0° C. The mixture was stirred for 2 h at rt. The mixture was purified by C18 column with CH$_3$CN/Water (0.05% FA). The desired fraction was concentrated under reduced pressure to provide (2S)-2-{[(1R,2S,3S,6R,7S)-4-[(2S)-3-cyclopropyl-3-methyl-2-(2,2,2-trifluoroacetamido)butanoyl]-4-azatricyclo[5.2.1.0ˆ{2,6}]dec-8-en-3-yl]formamido}-3-[(3S)-2-oxopyrrolidin-3-yl]propanamide (160 mg, 40%) as a light yellow solid. LC-MS (ESI, m/z): 568 [M+H]$^+$.

To a mixture of (2S)-2-{[(1R,2S,3S,6R,7S)-4-[(2S)-3-cyclopropyl-3-methyl-2-(2,2,2-trifluoroacetamido)butanoyl]-4-azatricyclo[5.2.1.0ˆ{2,6}]dec-8-en-3-yl]formamido}-3-[(3S)-2-oxopyrrolidin-3-yl]propanamide (160 mg, 0.282 mmol, 1.0 eq.) in DCM (2 mL) was added pyridine (77.9 mg, 0.987 mmol, 3.5 eq.) and trifluoroacetic anhydride (94.7 mg, 0.451 mmol, 1.6 eq.). The mixture was stirred for 2 h at rt. The reaction was quenched with water (5 mL). The mixture was extracted with EtOAc (3×20 mL). The organic layers were combined, washed with brine (2×10 mL), dried over anhydrous sodium sulfate, filtered and concentrated under reduced pressure to afford the crude product. The crude product was purified by prep-HPLC (Column: Kinetex EVO C18 Column, 30*150, 5um; Mobile Phase A: Water (0.1% FA), Mobile Phase B: ACN; Flow rate: 60 mL/min; Gradient: 39% B to 59% B in 7 min, 59% B; Wave Length: 254 nm; RT1 (min): 5) to provide (1R,2S,3S,6R,7S)—N-[(1S)-1-cyano-2-[(3S)-2-oxopyrrolidin-3-yl]ethyl]-4-[(2S)-3-cyclopropyl-3-methyl-2-(2,2,2-trifluoroacetamido)butanoyl]-4-azatricyclo[5.2.1.0ˆ{2,6}]dec-8-ene-3-carboxamide (79.8 mg, 51%) as a white solid. $^1$H NMR (400 MHz, 80° C., DMSO-d$_6$) δ 8.10-9.15 (m, 2H), 7.30-7.65 (m, 1H), 5.95-6.30 (m, 2H), 4.80-5.00 (m, 1H), 4.55-4.75 (m, 1H), 3.85-4.30 (m, 1H), 3.60-3.80 (m, 1H), 3.35-3.60 (m, 1H), 3.10-3.30 (m, 2H), 3.00-3.05 (m, 1H), 2.80-3.00 (m, 2H), 2.65-2.80 (m, 1H), 2.25-2.45 (m, 1H), 2.00-2.25 (m, 2H), 1.60-1.95 (m, 2H), 1.30-1.50 (m, 2H), 0.60-0.98 (m, 7H), 0.20-0.35 (m, 3H), 0.05-0.20 (m, 1H). LC-MS (ESI, m/z): 550 [M+H]$^+$.

Example 70

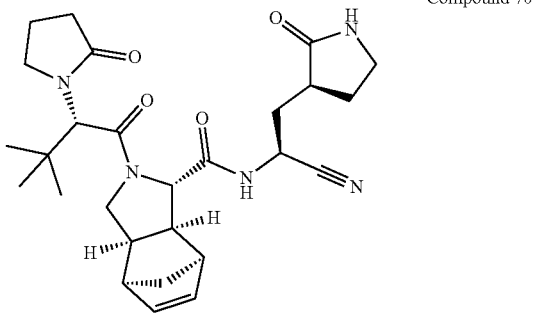

Compound 70

Compound 70 was prepared similarly as described for Compound 42 using (S)-3,3-dimethyl-2-(2-oxopyrrolidin-1-yl)butanoic acid in place of methyl (S)-3,3-dimethyl-2-(4-(trifluoromethyl)-1H-1,2,3-triazol-1-yl) butanoic acid. $^1$H NMR (500 MHz, 363K, DMSO-d$_6$) δ 8.54 (d, 1H), 7.30-7.44 (m, 1H), 5.97-6.12 (m, 2H), 4.77-4.94 (m, 1H), 4.21-4.55 (m, 1H), 3.95-4.06 (m, 1H), 3.62 (m, 1H), 3.41-3.56 (m, 1H), 3.25-3.40 (m, 2H), 3.07-3.24 (m, 2H), 3.09 (m, 1H), 2.85-2.95 (m, 2H), 2.68-2.82 (m, 1H), 2.29-2.41 (m, 2H), 2.05-2.24 (m, 3H), 1.65-1.98 (m, 4H), 1.39 (m, 2H), 0.94 (s, 9H). LCMS (ESI, m/z): 496 [M+H]$^+$.

(S)-3,3-Dimethyl-2-(2-oxopyrrolidin-1-yl)butanoic acid: To a suspension of methyl (S)-2-amino-3,3-dimethylbutanoate hydrochloride (1 g, 5.52 mmol, 1.0 eq.) in DCM (30 mL) cooled at 0° C. were added pyridine (0.91 mL, 11.0 mmol, 2.0 eq.) and 4-bromobutanoyl chloride (0.76 mL, 6.62 mmol, 1.2 eq.). The mixture was stirred at rt for 16 h and then washed with water. The phases were separated. The aqueous phase was extracted with DCM (3×10 mL). The organic phases were combined, washed with brine (15 mL), dried over Na$_2$SO$_4$, filtered and concentrated under reduced pressure. The residue was purified by flash chromatography on silica gel using a gradient of EA (10 to 15%) in hexane to afford methyl (S)-2-(4-bromobutanamido)-3,3-dimethylbutanoate (1.1 g, 68%) as a yellow liquid.

To a solution of methyl (S)-2-(4-bromobutanamido)-3,3-dimethylbutanoate (500 mg, 1.70 mmol, 1.0 eq.) in DMF (5 mL) cooled at 0° C. was added NaH (68 mg, 2.83 mmol, 1.7 eq.). The mixture was stirred at rt for 16 h. The reaction was quenched by addition of sat. NH$_4$Cl. The mixture was extracted with EA (3×10 mL). The organic phases were combined, washed with cold water (3×10 mL) and brine (10 mL), dried over Na$_2$SO$_4$, filtered and concentrated under reduced pressure. The residue was purified by flash chromatography on silica gel using a gradient of EA (10 to 15%) in hexane to afford methyl (S)-3,3-dimethyl-2-(2-oxopyrrolidin-1-yl)butanoate (250 mg, 69%) as a yellow liquid.

To a solution of methyl (S)-3,3-dimethyl-2-(2-oxopyrrolidin-1-yl)butanoate (400 mg, 1.86 mmol, 1.0 eq.) in THF (2 mL) and water (2 mL) cooled at 0° C. was added LiOH (197 mg, 4.67 mmol, 2.5 eq.). The mixture was stirred at rt for 16 h and then partially concentrated under reduced pressure to remove THF. The residue was diluted with water (5 mL) and extracted with Et$_2$O (2×10 mL). The aqueous layer was acidified with 2N HCl and extracted with 10% iPrOH in DCM (5×10 mL). The organic phases were combined, dried over Na$_2$SO$_4$, filtered and concentrated under reduced pressure. The residue was triturated with 5% Et$_2$O in pentane to furnish (S)-3,3-dimethyl-2-(2-oxopyrrolidin-1-yl)butanoic acid (250 mg, 67%) as a white solid. $^1$H NMR (500 MHz, 363K, DMSO-d$_6$) δ 12.76 (s, 1H), 4.42 (s, 1H), 3.64 (m, 1H), 3.51 (m, 1H), 2.19-2.27 (m, 2H), 1.90 (m, 2H), 1.00 (s, 9H).

Example 71

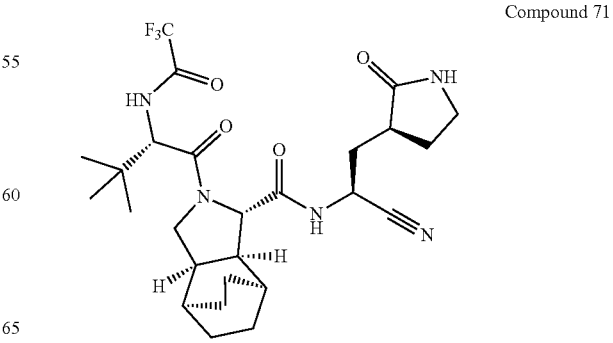

Compound 71

Compound 71 was prepared similarly as described for Compound 58 using (+/−)-methyl (1S,3aR,4R,7S,7aS)-octahydro-1H-4,7-ethanoisoindole-1-carboxylate hydrochloride in place of (+/−)-methyl (1S,3aR,4S,7R,7aS)-octahydro-1H-4,7-epoxyisoindole-1-carboxylate hydrochloride. $^1$H NMR (400 MHz, 363K, DMSO-d$_6$) δ 8.50-8.98 (m, 2H), 7.32-7.46 (m, 1H), 4.91 (m, 1H), 4.59-4.77 (m, 1H), 4.27-4.54 (m, 1H), 3.57-3.94 (m, 2H), 3.05-3.22 (m, 2H), 2.10-2.44 (m, 4H), 1.65-1.85 (m, 3H), 1.22-1.62 (m, 10H), 0.90-1.09 (m, 9H). LCMS (ESI, m/z): 540 [M+H]$^+$.

(+/−)-Methyl (1S,3aR,4R,7S,7aS)-octahydro-1H-4,7-ethanoisoindole-1-carboxylate hydrochloride: A mixture of (3aR,4S,7R,7aS)-2,3,3a,4,7,7a-hexahydro-1H-4,7-ethanoisoindole (7 g, 46.9 mmol, 1.0 eq.) and 10% Pd/C (700 mg) in MeOH (150 mL) was stirred at rt under H$_2$ pressure (60 psi) for 16 h. The mixture was filtered through celite, and the solids were washed with MeOH (50 mL). The filtrate was concentrated under reduced pressure to afford (3aR,4R,7S,7aS)-octahydro-1H-4,7-ethanoisoindole (6.1 g, 86%) as a colorless oil.

To a solution of (3aR,4R,7S,7aS)-octahydro-1H-4,7-ethanoisoindole (500 mg, 3.31 mmol, 1.0 eq.) in DCM (15 mL) was added IBX (926 mg, 3.31 mmol, 1.0 eq.). The mixture was stirred in sealed tube at 60° C. for 1 h. After cooling to rt, the mixture was washed with sat. sodium dithionate (10 mL). The phases were separated. The organic phase was washed with sat. sodium carbonate (10 mL) and brine (10 mL). The aqueous phases were extracted with DCM (3×30 mL). The organic phases were combined, dried over Na$_2$SO$_4$, filtered and concentrated under reduced pressure. The residue was purified by flash chromatography on silica gel using a gradient of MeOH (2 to 3%) in DCM to afford (3aS,4S,7R,7aR)-3a,4,5,6,7,7a-hexahydro-1H-4,7-ethanoisoindole (335 mg, 68%) as an off-white solid.

To a solution of (3aS,4S,7R,7aR)-3a,4,5,6,7,7a-hexahydro-1H-4,7-ethanoisoindole (330 mg, 2.21 mmol, 1.0 eq.) in DCM (3.3 mL) and MeOH (0.3 mL) cooled at 0° C. was added TMSCN (0.7 mL, 5.53 mmol, 2.5 eq.). The mixture was stirred at 0-10° C. for 4 h. The mixture was concentrated under reduced pressure. The residue was purified by flash chromatography on silica gel using a gradient of EA (15 to 20%) in PE to afford (+/−)-(1S,3aR,4R,7S,7aS)-octahydro-1H-4,7-ethanoisoindole-1-carbonitrile (330 mg, 85%) as a white oil.

A solution of (+/−)-(1S,3aR,4R,7S,7aS)-octahydro-1H-4,7-ethanoisoindole-1-carbonitrile (330 mg, 1.87 mmol, 1.0 eq.) in 4N HCl in MeOH (6.6 mL) was stirred for 6 h at 60° C. The mixture was concentrated under reduced pressure to afford (+/−)-methyl (1S,3aR,4R,7S,7aS)-octahydro-1H-4,7-ethanoisoindole-1-carboxylate hydrochloride (400 mg, 87%) as a white oil.

Example 71-1

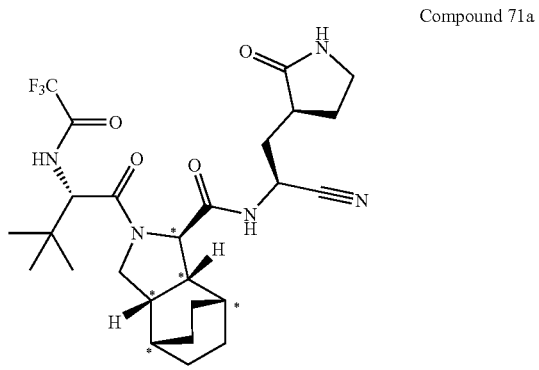 [SMILES: CC(C)(C)[C@H](NC(=O)C(F)(F)F)C(=O)N1C[C@H]2[C@H]3CC[C@H](CC3)[C@H]2[C@@H]1C(=O)N[C@H](C#N)C[C@@H]1CCNC1=O]

Compound 71a

Compound 71a was prepared similarly as described for Compound 59a using 2-(tert-butyl) 1-methyl (1R*,3aS*,4S*,7R*,7aR*)-octahydro-2H-4,7-ethanoisoindole-1,2-dicarboxylate in place of 2-(tert-butyl) 1-methyl (1R*,3aS*,4R*,7S*,7aR*)-1,3,3a,4,7,7a-hexahydro-2H-4,7-ethanoisoindole-1,2-dicarboxylate. $^1$H NMR (500 MHz, 363K, DMSO-d$_6$) δ 8.53-8.91 (m, 2H), 7.36 (s, 1H), 4.92 (m, 1H), 4.65 (s, 1H), 4.25-4.54 (m, 1H), 3.71-3.94 (m, 2H), 3.17 (m, 2H), 2.45 (m, 1H), 2.17-2.38 (m, 2H), 1.99-2.13 (m, 1H), 1.66-1.87 (m, 3H), 1.20-1.64 (m, 10H), 0.90-1.08 (s, 9H). LCMS (ESI, m/z): 538 [M−H]$^-$.

2-(tert-Butyl) 1-methyl (1R*,3aS*,4S*,7R*,7aR*)-octahydro-2H-4,7-ethanoisoindole-1,2-dicarboxylate: To a solution of (+/−)-methyl (1S,3aR,4R,7S,7aS)-octahydro-1H-4,7-ethanoisoindole-1-carboxylate hydrochloride (1.8 g, 7.33 mmol, 1.0 eq.) in dioxane (36 mL) cooled at 0° C. were added Na$_2$CO$_3$ (3.1 g, 29.3 mmol, 4.0 eq.) and Boc$_2$O (6.4 g, 29.3 mmol, 4.0 eq.). The mixture was stirred at rt for 16 h. The mixture was diluted with EA (100 mL) and washed with water. The phases were separated. The organic phase was washed with brine, dried over Na$_2$SO$_4$, filtered and concentrated under reduced pressure. The residue was purified by flash chromatography on silica gel using a gradient of EA (10 to 20%) in PE to afford (+/−)-2-(tert-butyl) 1-methyl (1S,3aR,4R,7S,7aS)-octahydro-2H-4,7-ethanoisoindole-1,2-dicarboxylate (2.0 g, 95%) as a colourless oil.

(+/−)-2-(tert-Butyl) 1-methyl (1S,3aR,4R,7S,7aS)-octahydro-2H-4,7-ethanoisoindole-1,2-dicarboxylate (2.0 g) was purified by prep-SFC using the following conditions: Column: Chiralpak IG, 30*250 mm, 5 m; Mobile Phase A: CO$_2$, Mobile Phase B: hexane/iPrOH (1/1); Flow rate: 90 g/min; Gradient: isocratic 10% B; Column Temperature: 30° C.; Back Pressure: 100 bar. Purification resulted in 2-(tert-butyl) 1-methyl (1R*,3aS*,4S*,7R*,7aR*)-octahydro-2H-4,7-ethanoisoindole-1,2-dicarboxylate (400 mg) and 2-(tert-butyl) 1-methyl (1S*,3aR*,4R*,7S*,7aS*)-octahydro-2H-4,7-ethanoisoindole-1,2-dicarboxylate (350 mg).

2-(tert-Butyl) 1-methyl (1R*,3aS*,4S*,7R*,7aR*)-octahydro-2H-4,7-ethanoisoindole-1,2-dicarboxylate: $^1$H NMR (400 MHz, CDCl$_3$) δ 4.21-4.35 (m, 1H), 3.72 (s, 3H), 3.48-3.70 (m, 2H), 2.37 (m, 2H), 1.30-1.75 (m, 19H). [α]$^{25}_D$: +30.1° (c 0.1, CHCl$_3$). SFC: CHIRALPAK IG, 4.6*150 mm, 5 m, Mobile Phase A: CO$_2$, Mobile Phase B: hexane/iPrOH (1/1); Flow rate: 3 g/min; Gradient: isocratic 10% B; Column Temperature: 30° C.; Back Pressure: 100 bar, Rt: 2.02 min.

2-(tert-Butyl) 1-methyl (1S*,3aR*,4R*,7S*,7aS*)-octahydro-2H-4,7-ethanoisoindole-1,2-dicarboxylate: $^1$H NMR (400 MHz, CDCl$_3$) δ 4.21-4.35 (m, 1H), 3.72 (s, 3H), 3.48-3.70 (m, 2H), 2.37 (m, 2H), 1.30-1.75 (m, 19H). [α]$^{25}_D$: −33.1° (c 0.1, CHCl$_3$). SFC: CHIRALPAK IG, 4.6*150 mm, 5 m, Mobile Phase A: CO$_2$, Mobile Phase B: hexane/iPrOH (1/1); Flow rate: 3 g/min; Gradient: isocratic 10% B; Column Temperature: 30° C.; Back Pressure: 100 bar, Rt: 2.43 min.

Example 71-2

Compound 71b

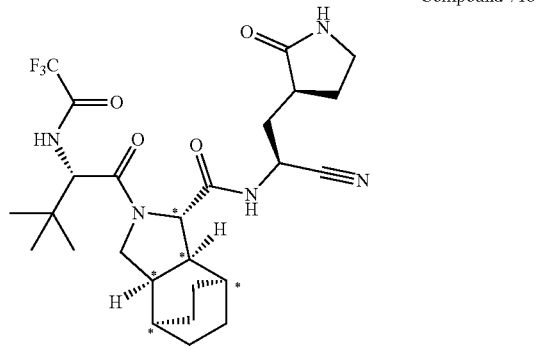

Compound 71b was prepared similarly as described for Compound 59a using 2-(tert-butyl) 1-methyl (1S*,3aR*,4R*,7S*,7aS*)-octahydro-2H-4,7-ethanoisoindole-1,2-dicarboxylate in place of 2-(tert-butyl) 1-methyl (1R*,3aS*,4R*,7S*,7aR*)-1,3,3a,4,7,7a-hexahydro-2H-4,7-ethanoisoindole-1,2-dicarboxylate. $^1$H NMR (500 MHz, 363K, DMSO-d$_6$) δ 8.65-8.98 (m, 2H), 7.37-7.50 (m, 1H), 4.92 (m, 1H), 4.62-4.72 (m, 1H), 4.28-4.52 (m, 1H), 3.90 (m, 1H), 3.80-3.85 (m, 1H), 3.06-3.20 (m, 2H), 2.33-2.43 (m, 1H), 2.22-2.13 (m, 3H), 1.67-1.81 (m, 3H), 1.22-1.64 (m, 10H), 0.95-1.05 (m, 9H). LCMS (ESI, m/z): 540 [M+H]$^+$.

Example 72

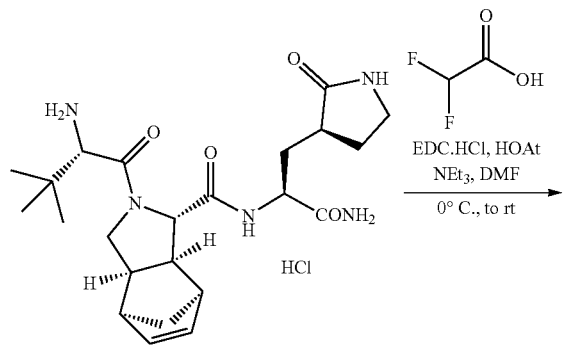

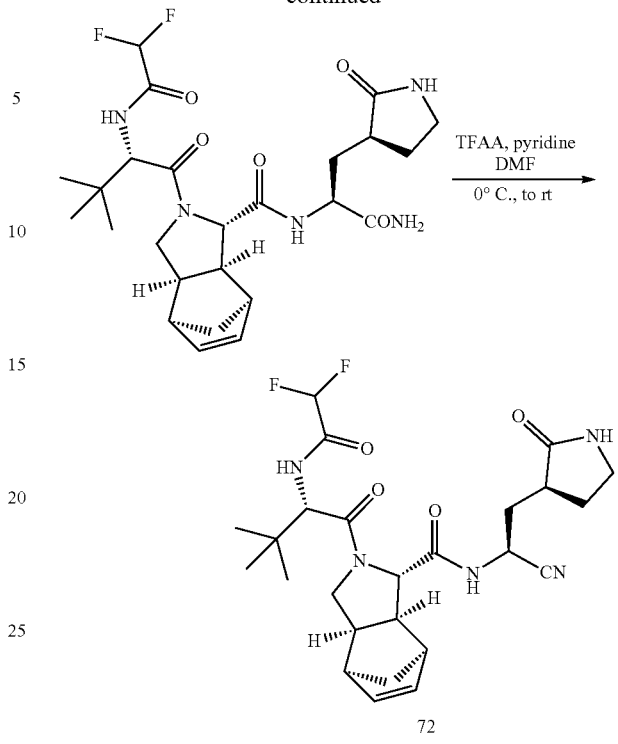

72

To a solution of (1S,3aR,4S,7R,7aS)—N—((S)-1-amino-1-oxo-3-((S)-2-oxopyrrolidin-3-yl)propan-2-yl)-2-((S)-2-amino-3,3-dimethylbutanoyl)-2,3,3a,4,7,7a-hexahydro-1H-4,7-methanoisoindole-1-carboxamide hydrochloride (120 mg, 0.249 mmol, 1.0 eq.) in DMF (1.2 mL) cooled at 0° C. were added 2,2-difluoroacetic acid (60 mg, 0.625 mmol, 1.0 eq.), EDC•HCl (96 mg, 0.501 mmol, 2.0 eq.), HOAt (35 mg, 0.257 mmol, 1.0 eq.) and NEt$_3$ (0.172 mL, 1.25 mmol, 5.0 eq.). The mixture was stirred at rt for 16 h. The mixture was diluted with water (10 mL) and extracted with 10% MeOH in DCM (3×10 mL). The organic phases were combined, dried over Na$_2$SO$_4$, filtered and concentrated under reduced pressure. The residue was purified by flash chromatography on silica gel using a gradient of MeOH (1 to 10%) in DCM to afford (1S,3aR,4S,7R,7aS)—N—((S)-1-amino-1-oxo-3-((S)-2-oxopyrrolidin-3-yl)propan-2-yl)-2-((S)-2-(2,2-difluoroacetamido)-3,3-dimethylbutanoyl)-2,3,3a,4,7,7a-hexahydro-1H-4,7-methanoisoindole-1-carboxamide (65 mg, 50%) as an off-white solid. LC-MS (ESI, m/z): 524 [M+H]$^+$.

To a solution of (1S,3aR,4S,7R,7aS)—N—((S)-1-amino-1-oxo-3-((S)-2-oxopyrrolidin-3-yl)propan-2-yl)-2-((S)-2-(2,2-difluoroacetamido)-3,3-dimethylbutanoyl)-2,3,3a,4,7,7a-hexahydro-1H-4,7-methanoisoindole-1-carboxamide (65 mg, 0.124 mmol, 1.0 eq.) in DMF (0.7 mL) cooled at 0° C. were added pyridine (0.030 mL, 0.372 mmol, 3.0 eq.) and TFAA (0.035 mL; 0.248 mmol, 2.0 eq.). The mixture was stirred at rt for 1 h. The mixture was diluted with water (10 mL) and extracted with EA (3×10 mL). The organic phases were combined, washed with brine (2×10 mL), dried over Na$_2$SO$_4$, filtered and concentrated under reduced pressure. The residue was purified by prep-HPLC (Column: X-SELECT-C18 Column, 19*250 mm, 5 m; Mobile Phase A: 10 mM NH$_4$HCO$_3$ in water, Mobile Phase B: ACN; Flow rate: 17 mL/min; Gradient: 10% B to 60% B in 8 min) to afford (1S,3aR,4S,7R,7aS)—N—((S)-1-cyano-2-((S)-2-oxopyrrolidin-3-yl)ethyl)-2-((S)-2-(2,2-difluoroacetamido)-3,3-dimethylbutanoyl)-2,3,3a,4,7,7a-hexahydro-1H-4,7-methanoisoindole-1-carboxamide (26 mg, 42%) as a white solid. $^1$H NMR (400 MHz, 363K, DMSO-d$_6$) δ 8.57-8.85 (m, 1H), 7.93-8.38 (m, 1H), 7.28-7.45 (m, 1H), 6.10-6.45 (m, 1H), 5.94-6.06 (m, 2H), 4.62-4.96 (m, 1H), 4.48 (d, 1H), 3.96-4.15 (m, 1H), 3.66 (m, 1H), 3.37-3.51 (m, 1H), 3.03-3.22 (m, 3H), 2.89-2.95 (m, 2H), 2.73 (m, 1H), 2.37 (m, 1H), 2.14 (m, 2H), 1.64-1.83 (m, 2H), 1.32-1.45 (m, 2H), 0.83-0.97 (s, 9H). LCMS (ESI, m/z): 506 [M+H]$^+$.

Example 73

Compound 73

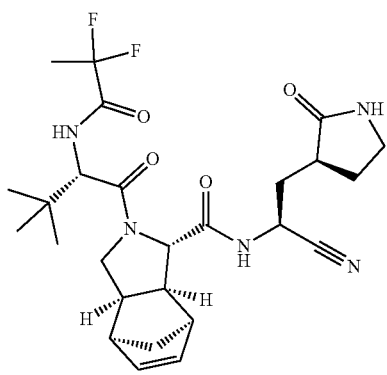

Compound 73 was prepared similarly as described for Compound 72 using 2,2-difluoropropanoic acid in place of 2,2-difluoroacetic acid. $^1$H NMR (400 MHz, 363K, DMSO-d$_6$) δ 8.58-8.82 (m, 1H), 6.95-7.50 (m, 2H), 5.92-6.18 (m, 2H), 4.69-4.95 (m, 1H), 4.46 (d, 1H), 3.97-4.13 (m, 1H), 3.65 (m, 1H), 3.36-3.49 (m, 1H), 3.02-3.25 (m, 3H), 2.90-3.00 (m, 2H), 2.74 (m, 1H), 2.34 (m, 1H), 2.15 (m, 2H), 1.63-1.85 (m, 5H), 1.31-1.45 (m, 2H), 0.80-0.99 (m, 9H). LCMS (ESI, m/z): 520 [M+H]$^+$.

Example 74

Compound 74

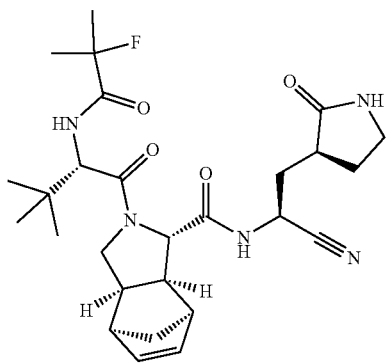

Compound 74 was prepared similarly as described for Compound 72 using 2-fluoro-2-methylpropanoic acid in place of 2,2-difluoroacetic acid. $^1$H NMR (400 MHz, 363K, DMSO-d$_6$) δ 8.54-8.81 (m, 1H), 7.28-7.47 (m, 1H), 6.57-6.90 (m, 1H), 5.92-6.20 (m, 2H), 4.68-4.95 (m, 1H), 4.44 (d, 1H), 3.98-4.12 (m, 1H), 3.63 (m, 1H), 3.35-3.55 (m, 1H), 3.02-3.25 (m, 3H), 2.98-2.88 (m, 2H), 2.74 (m, 1H), 2.34 (m, 1H), 2.14 (m, 2H), 1.64-1.88 (m, 2H), 1.32-1.58 (m, 8H), 0.83-0.96 (m, 9H). LCMS (ESI, m/z): 516 [M+H]$^+$.

Example 75

Compound 75

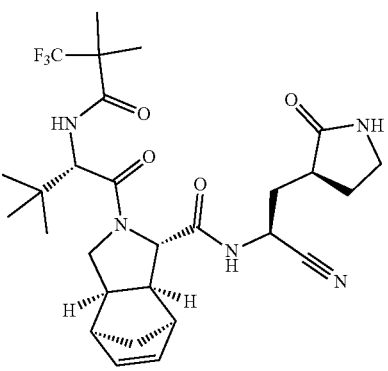

Compound 75 was prepared similarly as described for Compound 72 using 3,3,3-trifluoro-2,2-dimethylpropanoic acid in place of 2,2-difluoroacetic acid. $^1$H NMR (400 MHz, 363K, DMSO-d$_6$) δ 8.56-8.79 (m, 1H), 7.29-7.47 (m, 1H), 6.39-6.78 (m, 1H), 5.84-6.23 (m, 2H), 4.68-4.95 (m, 1H), 4.52 (d, 1H), 4.00-4.13 (m, 1H), 3.61 (m, 1H), 3.36-3.51 (m, 1H), 3.03-3.22 (m, 3H), 2.90-3.00 (m, 2H), 2.74 (m, 1H), 2.33 (m, 1H), 2.15 (m, 2H), 1.62-1.90 (m, 2H), 1.21-1.46 (m, 8H), 0.78-0.98 (m, 9H). LCMS (ESI, m/z): 566 [M+H]$^+$.

Example 76

Compound 76

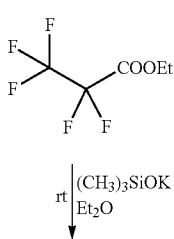

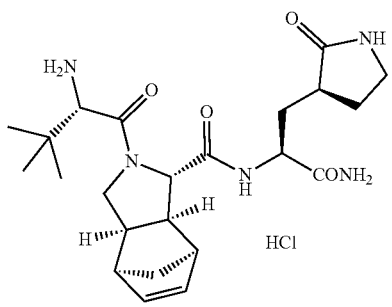

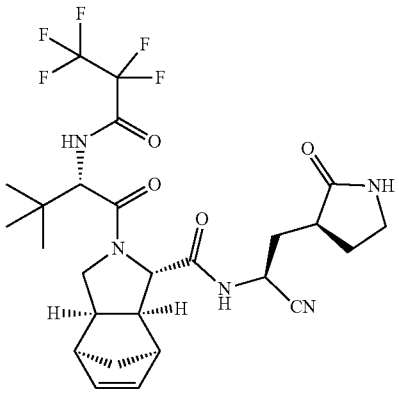

76

To a suspension of potassium trimethylsilanolate (67 mg, 0.522 mmol, 1.0 eq.) in Et₂O (1 mL) cooled at 0° C. was added dropwise a solution of ethyl 2,2,3,3,3-pentafluoropropanoate (100 mg, 0.521 mmol, 1.0 eq.) in Et₂O (1 mL). The mixture stirred at rt for 16 h and then concentrated under reduced pressure. The residue was triturated with Et₂O. The solid was filtered and dried under reduced pressure to afford potassium 2,2,3,3,3-pentafluoropropanoate (85 mg, 80%) as an off-white solid.

To a mixture of (1S,3aR,4S,7R,7aS)—N—((S)-1-amino-1-oxo-3-((S)-2-oxopyrrolidin-3-yl)propan-2-yl)-2-((S)-2-amino-3,3-dimethylbutanoyl)-2,3,3a,4,7,7a-hexahydro-1H-4,7-methanoisoindole-1-carboxamide hydrochloride (60 mg, 0.124 mmol, 1.0 eq.), potassium 2,2,3,3,3-pentafluoropropanoate (25 mg, 0.195 mmol, 1.6 eq.) and 50% T3P in EA (0.390 g, 1.25 mmol, 10.0 eq.) cooled at 0° C. was added pyridine (0.050 mL, 0.620 mmol, 5.0 eq.). The mixture was stirred at rt for 16 h. The mixture was diluted with water (10 mL) and extracted with EA (3×10 mL). The organic phases were combined, washed with brine (2×10 mL), dried over Na₂SO₄, filtered and concentrated under reduced pressure. The residue was purified by flash chromatography on silica gel using a gradient of MeOH (1 to 10%) in DCM and by prep-HPLC (Column: YMC-TRIART-C18, 25*150 mm, 10 m; Mobile Phase A: 10 mM NH₄HCO₃ in water, Mobile Phase B: ACN; Flow rate: 22 mL/min; Gradient: 20% B to 80% B in 8 min) to afford (1S,3aR,4S,7R,7aS)—N—((S)-1-cyano-2-((S)-2-oxopyrrolidin-3-yl)ethyl)-2-((S)-3,3-dimethyl-2-(2,2,3,3,3-pentafluoropropanamido) butanoyl)-2,3,3a,4,7,7a-hexahydro-1H-4,7-methanoisoindole-1-carboxamide (30 mg, 40%) as an off-white solid. ¹H NMR (400 MHz, 363K, DMSO-d₆) δ 8.49-8.83 (m, 2H), 7.29-7.46 (m, 1H), 5.91-6.22 (m, 2H), 4.60-4.97 (m, 1H), 4.55 (s, 1H), 4.00-4.16 (m, 1H), 3.65 (m, 1H), 3.36-3.51 (m, 1H), 3.03-3.23 (m, 3H), 2.88-2.96 (m, 2H), 2.72 (m, 1H), 2.37 (m, 1H), 2.15 (m, 2H), 1.64-1.94 (m, 2H), 1.35-1.46 (m, 2H), 0.82-1.00 (m, 9H). LCMS (ESI, m/z): 574 [M+H]⁺.

Example 77

Compound 77

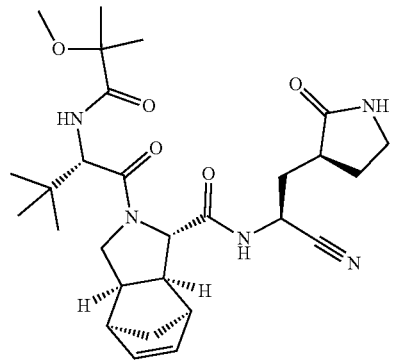

Compound 77 was prepared similarly as described for Compound 72 using 2-methoxy-2-methylpropanoic acid in place of 2,2-difluoroacetic acid. ¹H NMR (400 MHz, 363K, DMSO-d₆) δ 8.57-8.80 (m, 1H), 7.29-7.47 (m, 1H), 6.78-7.01 (m, 1H), 5.86-6.20 (m, 2H), 4.70-4.96 (m, 1H), 4.41 (d, 1H), 3.98-4.12 (m, 1H), 3.62 (m, 1H), 3.33-3.54 (m, 1H), 3.05-3.23 (m, 6H), 2.86-2.94 (m, 2H), 2.73 (m, 1H), 2.33 (m, 1H), 2.15 (m, 2H), 1.64-1.84 (m, 2H), 1.17-1.43 (m, 8H), 0.80-0.96 (m, 9H). LCMS (ESI, m/z): 528 [M+H]⁺.

Example 78

Compound 78

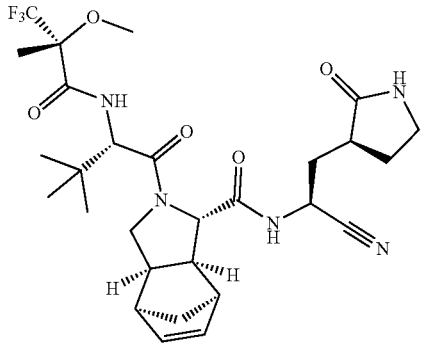

Compound 78 was prepared similarly as described for Compound 72 using (R)-3,3,3-trifluoro-2-methoxy-2-methylpropanoic acid in place of 2,2-difluoroacetic acid. ¹H NMR (400 MHz, 363K, DMSO-d₆) δ 8.56-8.74 (m, 1H), 7.30-7.46 (m, 1H), 6.94-7.20 (m, 1H), 5.87-6.22 (m, 2H), 4.75-4.98 (m, 1H), 4.44 (m, 1H), 3.97-4.13 (m, 1H), 3.62 (m, 1H), 3.36-3.54 (m, 1H), 3.29-3.33 (m, 3H), 3.02-3.25 (m, 3H), 2.87-2.97 (m, 2H), 2.75 (m, 1H), 2.32 (m, 1H), 2.15 (m, 2H), 1.62-1.93 (m, 2H), 1.33-1.58 (m, 5H), 0.78-0.93 (m, 9H). LCMS (ESI, m/z): 580 [M−H]⁻.

Example 79

Compound 79

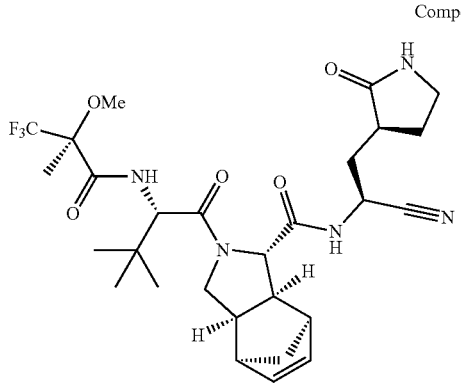

Compound 79 was prepared similarly as described for Compound 72 using (S)-3,3,3-trifluoro-2-methoxy-2-methylpropanoic acid in place of 2,2-difluoroacetic acid. ¹H NMR (500 MHz, 362K, DMSO-d₆) δ 8.64 (br. s., 1H), 7.36 (s, 1H), 6.95-7.21 (m, 1H), 5.84-6.22 (m, 2H), 4.55-4.93 (m, 1H), 4.46 (m, 1H), 4.01-4.13 (m, 1H), 3.62 (m, 1H), 3.47 (m, 1H), 3.37-3.44 (m, 3H), 3.05-3.21 (m, 3H), 2.87-2.94 (m, 2H), 2.73 (m, 1H), 2.34 (m, 1H), 2.14 (m, 2H), 1.65-1.87 (m, 2H), 1.50-1.57 (m, 3H), 1.37 (m, 2H), 0.83-0.95 (m, 9H). LCMS (ESI, m/z): 580 [M−H]⁻.

Example 80

Compound 80

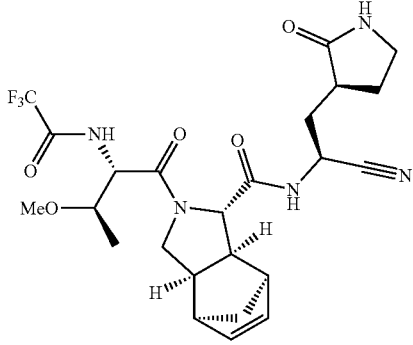

Compound 80 was prepared similarly as described for Compound 3 using O-methyl-L-threonine in place of (2S, 3R)-2-amino-3-(tert-butoxy)butanoic acid. ¹H NMR (500 MHz, 362K, DMSO-d₆) δ 8.98-9.26 (br. s., 1H), 8.44-8.70 (m, 1H), 7.27-7.49 (m, 1H), 5.92-6.22 (m, 2H), 4.75-4.95 (m, 1H), 4.20-4.46 (m, 1H), 3.90-4.02 (m, 1H), 3.54-3.74 (m, 2H), 3.33-3.52 (m, 1H), 3.15-3.30 (m, 3H), 3.04-3.14 (m, 3H), 2.88-2.97 (m, 2H), 2.74 (m, 1H), 2.34 (m, 1H), 2.14 (m, 2H), 1.62-1.89 (m, 2H), 1.30-1.45 (m, 2H), 0.94-1.12 (m, 3H). LCMS (ESI, m/z): 524 [M−H]⁻.

Example 81

Compound 81

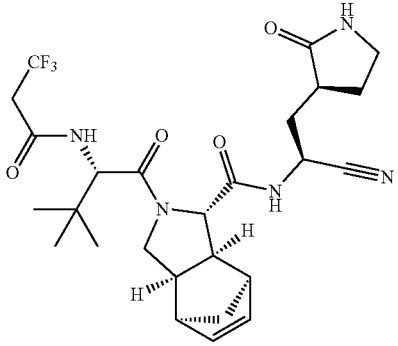

Compound 81 was prepared similarly as described for Compound 72 using 3,3,3-trifluoropropanoic acid in place of 2,2-difluoroacetic acid. ¹H NMR (400 MHz, 363K, DMSO-d₆) 8.60-8.74 (m, 1H), 7.80-8.10 (m, 1H), 7.34-7.46 (m, 1H), 5.93-6.18 (m, 2H), 4.67-4.94 (m, 1H), 4.15-4.48 (m, 1H), 3.97-4.11 (m, 1H), 3.64 (m, 1H), 3.49 (m, 1H), 3.34 (m, 2H), 3.05-3.23 (m, 3H), 2.87-2.96 (m, 2H), 2.72 (m, 1H), 2.37 (m, 1H), 2.14 (m, 2H), 1.64-1.89 (m, 2H), 1.35-1.45 (m, 2H), 0.83-0.97 (m, 9H). LCMS (ESI, m/z): 538 [M+H]⁺.

Example 82

Compound 82

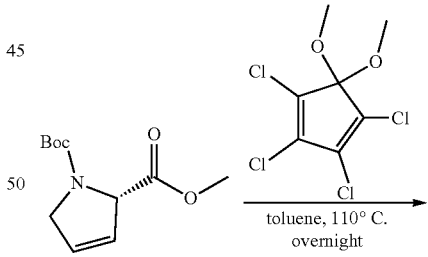

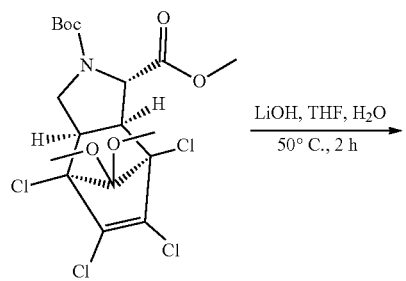

-continued
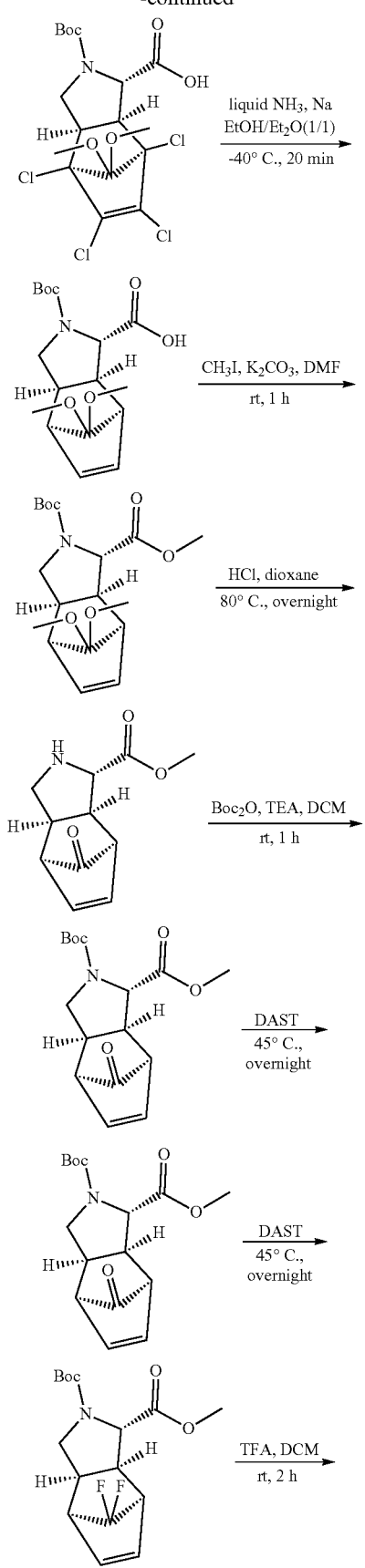
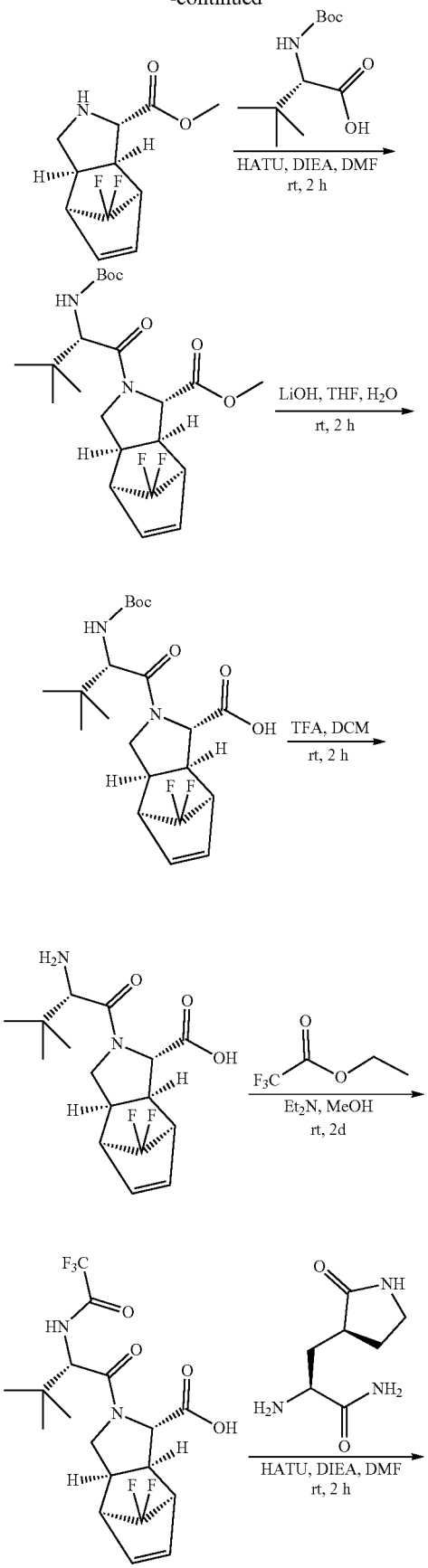

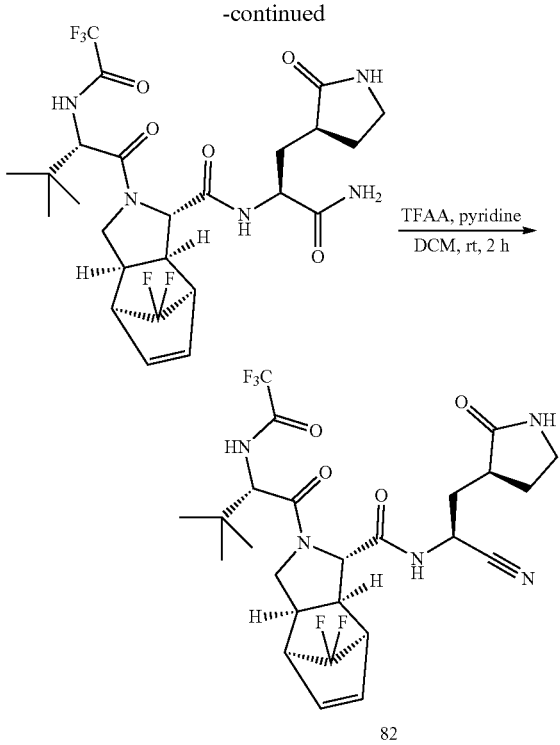

A mixture of 1,2,3,4-tetrachloro-5,5-dimethoxycyclopenta-1,3-diene (17.4 g, 66.0 mmol, 1.5 eq.) and 1-tert-butyl 2-methyl (2S)-2,5-dihydropyrrole-1,2-dicarboxylate (10.0 g, 44.0 mmol, 1.0 eq.) in toluene (10 mL) was stirred overnight at 110° C. under nitrogen and then concentrated under reduced pressure. The residue was chromatographed on a silica gel column with EA:PE (17:100) to provide the crude product. The crude product was purified by C18 column with $CH_3CN$/Water (0.05% TFA). The desired fraction was concentrated under reduced pressure to provide 4-tert-butyl 3-methyl (1S,2S,3S,6R,7R)-1,7,8,9-tetrachloro-10,10-dimethoxy-4-azatricyclo[5.2.1.0^{2,6}]dec-8-ene-3,4-dicarboxylate (7.5 g, 31%) as a yellow solid. $^1H$ NMR (400 MHz, DMSO-$d_6$) δ 4.02-4.23 (m, 1H), 3.65-3.77 (m, 3H), 3.51-3.58 (m, 3H), 3.45-3.49 (m, 3H), 3.31-3.44 (m, 4H), 1.23-1.47 (m, 9H). LC-MS (ESI, m/z): 392 [M−Boc+H]$^+$.

To a stirred solution of 4-tert-butyl 3-methyl (1S,2S,3S,6R,7R)-1,7,8,9-tetrachloro-10,10-dimethoxy-4-azatricyclo[5.2.1.0^{2,6}]dec-8-ene-3,4-dicarboxylate (7.50 g, 15.2 mmol, 1.0 eq.) in THF (40 mL)/water (40 mL) was added lithium hydroxide (1.46 g, 61.0 mmol, 4.0 eq.). The mixture was stirred for 2 h at 50° C. and then concentrated under reduced pressure to removed tetrahydrofuran. The mixture was adjusted to pH=6 with hydrochloric acid (2M) and extracted with EtOAc (3×100 mL). The organic layers were combined, washed with brine (2×100 mL), dried over anhydrous sodium sulfate, filtered and concentrated under reduced pressure to afford (1S,2S,3S,6R,7R)-4-(tert-butoxycarbonyl)-1,7,8,9-tetrachloro-10,10-dimethoxy-4-azatricyclo[5.2.1.0^{2,6}]dec-8-ene-3-carboxylic acid (6.3 g, 86%, crude) as an off-white solid. $^1H$ NMR (400 MHz, DMSO-$d_6$) δ 3.99-4.08 (m, 1H), 3.50-3.58 (m, 3H), 3.43-3.47 (m, 3H), 3.22-3.42 (m, 4H), 1.25-1.48 (m, 9H). LC-MS (ESI, m/z): 378 [M−Boc+H]$^+$.

To a stirred solution of sodium (6×1.68 g, 438 mmol, 35.0 eq.) in liquid $NH_3$ (6×34 mL) was added (1S,2S,3S,6R,7R)-4-(tert-butoxycarbonyl)-1,7,8,9-tetrachloro-10,10-dimethoxy-4-azatricyclo[5.2.1.0^{2,6}]dec-8-ene-3-carboxylic acid (6×1.00 g, 12.5 mmol, 1.0 eq.) in EtOH/ether (6×16 mL, 1:1 ratio) dropwise under nitrogen at −40° C. for 20 min. The mixture was stirred for 20 min at −40° C. and then $NH_4Cl$(s) (6×2 g) was added. The mixture was warmed to rt in 2 h and then diluted with water (6×50 mL). The mixture was extracted with EtOAc (300 mL). The aqueous phase was adjusted to pH=6 with hydrochloric acid (2M). The mixture was extracted with EtOAc (3×300 mL). The organic layers were combined, washed with brine (2×200 mL), dried over anhydrous sodium sulfate, filtered and concentrated under reduced pressure to afford (1R,2R,3S,6S,7S)-4-(tert-butoxycarbonyl)-10,10-dimethoxy-4-azatricyclo[5.2.1.0^{2,6}]dec-8-ene-3-carboxylic acid (3.4 g, crude) as a brown oil. LC-MS (ESI, m/z): 240 [M−Boc+H]$^+$.

To a stirred mixture of (1R,2R,3S,6S,7S)-4-(tert-butoxycarbonyl)-10,10-dimethoxy-4-azatricyclo[5.2.1.0^{2,6}]dec-8-ene-3-carboxylic acid (3.40 g, 10.0 mmol, 1.0 eq.) and potassium carbonate (2.22 g, 16.0 mmol, 1.6 eq.) in DMF (30 mL) was added iodomethane (1.49 g, 10.5 mmol, 1.05 eq.). The mixture was stirred for 1 h at rt. The reaction was quenched with water (100 mL). The mixture was extracted with EtOAc (3×100 mL). The organic layers were combined, washed with brine (2×100 mL), dried over anhydrous sodium sulfate, filtered and concentrated under reduced pressure to afford the crude product. The crude product was chromatographed on a silica gel column with EA:PE (31:100) to provide 4-tert-butyl 3-methyl (1R,2R,3S,6S,7S)-10,10-dimethoxy-4-azatricyclo[5.2.1.0^{2,6}]dec-8-ene-3,4-dicarboxylate (1.62 g, 41%) as a yellow oil. $^1H$ NMR (400 MHz, DMSO-$d_6$) δ 6.07-6.23 (m, 2H), 3.70-3.86 (m, 1H), 3.60-3.69 (m, 3H), 3.26-3.33 (m, 1H), 3.08-3.12 (m, 3H), 3.01-3.07 (m, 2H), 2.97-3.00 (m, 3H), 2.78-2.96 (m, 3H), 1.23-1.44 (m, 9H). LC-MS (ESI, m/z): 254 [M−Boc+H]$^+$.

To a stirred mixture of 4-tert-butyl 3-methyl (1R,2R,3S,6S,7S)-10,10-dimethoxy-4-azatricyclo[5.2.1.0^{2,6}]dec-8-ene-3,4-dicarboxylate (1.62 g, 4.58 mmol, 1.0 eq.) in dioxane (3 mL) was added hydrogen chloride (20 mL, 4M in dioxane). The mixture was stirred for overnight at 80° C. and then concentrated under reduced pressure to afford methyl (1R,2R,3S,6S,7S)-10-oxo-4-azatricyclo[5.2.1.0^{2,6}]dec-8-ene-3-carboxylate (949 mg, crude) as an off-white solid. LC-MS (ESI, m/z): 208 [M+H]$^+$.

To a stirred mixture of methyl (1R,2R,3S,6S,7S)-10-oxo-4-azatricyclo[5.2.1.0^{2,6}]dec-8-ene-3-carboxylate (949 mg, 4.57 mmol, 1.0 eq.) in DCM (10 mL) was added triethylamine (1.39 g, 13.7 mmol, 3.0 eq.) and di-tert-butyl dicarbonate (1.30 g, 5.95 mmol, 1.3 eq.). The mixture was stirred for 1 h at rt. The reaction was quenched with water (50 mL). The mixture was extracted with DCM (3×50 mL). The organic layers were combined, washed with brine (2×50 mL), dried over anhydrous sodium sulfate, filtered and concentrated under reduced pressure to afford the crude product. The crude product was chromatographed on a silica gel column with EA:PE (29:100) to provide 4-tert-butyl 3-methyl (1R,2R,3S,6S,7S)-10-oxo-4-azatricyclo[5.2.1.0^{2,6}]dec-8-ene-3,4-dicarboxylate (800 mg, 56%) as an off-white solid. $^1H$ NMR (400 MHz, DMSO-$d_6$) δ 6.46-6.71 (m, 2H), 3.80-4.00 (m, 1H), 3.57-3.75 (m, 3H), 3.38-3.48 (m, 1H), 2.95-3.27 (m, 5H), 1.11-1.49 (m, 9H). LC-MS (ESI, m/z): 208 [M−Boc+H]$^+$.

A mixture of 2-(tert-butyl) 1-methyl (1S,3aS,4S,7R,7aR)-8-oxo-1,3,3a,4,7,7a-hexahydro-2H-4,7-methanoisoindole-1,2-dicarboxylate (500 mg, 1.63 mmol, 1.0 eq.) in diethylaminosulfur trifluoride (10 mL) was stirred for overnight at 45° C. The mixture was diluted with dichloromethane (30 mL). The reaction was quenched with sat. sodium bicarbonate (50 mL) at 0° C. The mixture was extracted with dichloromethane (3×80 mL). The organic layers were combined, washed with brine (2×30 mL), dried over anhydrous sodium sulfate, filtered and concentrated under reduced pressure. The residue was purified by silica gel column chromatography with PE:EA (7:3) to afford 2-(tert-butyl) 1-methyl (1S,3aS,4S,7R,7aR)-8,8-difluoro-1,3,3a,4,7,7a-hexahydro-2H-4,7-methanoisoindole-1,2-dicarboxylate (350 mg, 65%) as a yellow oil. LC-MS (ESI, m/z): 230 [M−Boc+H]$^+$.

To a stirred mixture of 2-(tert-butyl) 1-methyl (1S,3aS,4S,7R,7aR)-8,8-difluoro-1,3,3a,4,7,7a-hexahydro-2H-4,7-methanoisoindole-1,2-dicarboxylate (350 mg, 1.06 mmol, 1.0 eq.) in dichloromethane (4 mL) was added trifluoroacetic acid (1.3 mL) at rt. The mixture was stirred for 2 h at rt and then concentrated under reduced pressure to provide methyl (1S,3aS,4S,7R,7aR)-8,8-difluoro-2,3,3a,4,7,7a-hexahydro-1H-4,7-methanoisoindole-1-carboxylate (243 mg, crude) as a yellow oil. LC-MS (ESI, m/z): 230 [M+H]$^+$.

To a mixture of (2S)-2-[(tert-butoxycarbonyl)amino]-3,3-dimethylbutanoic acid (246 mg, 1.06 mmol, 1.0 eq.) in N,N-dimethylformamide (3 mL) were added o-(7-azabenzotriazol-1-yl)-N,N,N',N'-tetramethyluronium hexafluorophosphate (485 mg, 1.28 mmol, 1.2 eq.) and N-ethyl-N-isopropylpropan-2-amine (825 mg, 6.38 mmol, 6.0 eq.) at 0° C. The mixture was stirred for 20 min at 0° C., and then methyl (1S,3aS,4S,7R,7aR)-8,8-difluoro-2,3,3a,4,7,7a-hexahydro-1H-4,7-methanoisoindole-1-carboxylate (243 mg, 1.06 mmol, 1.0 eq.) was added at 0° C. The mixture was stirred for 2 h at rt. The mixture was purified by C18 column with CH$_3$CN/Water (0.05% TFA). The desired fraction was concentrated under reduced pressure to provide methyl (1S,3aS,4S,7R,7aR)-2-((S)-2-((tert-butoxycarbonyl)amino)-3,3-dimethylbutanoyl)-8,8-difluoro-2,3,3a,4,7,7a-hexahydro-1H-4,7-methanoisoindole-1-carboxylate (300 mg, 63%) as a yellow solid. $^1$H NMR (400 MHz, DMSO-d$_6$) δ 6.58-6.72 (m, 1H), 6.02-6.35 (m, 2H), 4.19-4.31 (m, 1H), 4.05-4.13 (m, 1H), 3.70-3.87 (m, 1H), 3.61-3.69 (m, 3H), 3.43-3.59 (m, 1H), 3.19-3.36 (m, 2H), 2.93-3.16 (m, 2H), 1.30-1.49 (m, 9H), 0.77-1.00 (m, 9H). LC-MS (ESI, m/z): 443 [M+H]$^+$.

To a stirred methyl (1S,3aS,4S,7R,7aR)-2-((S)-2-((tert-butoxycarbonyl)amino)-3,3-dimethylbutanoyl)-8,8-difluoro-2,3,3a,4,7,7a-hexahydro-1H-4,7-methanoisoindole-1-carboxylate (300 mg, 0.680 mmol, 1.0 eq.) in tetrahydrofuran (3 mL) and water (3 mL) was added lithium hydroxide (81.2 mg, 3.39 mmol, 5.0 eq.) at rt. The mixture was stirred for 2 h at rt. The mixture was acidified to pH=3 with hydrochloric acid (2M) and then extracted with ethyl acetate (3×30 mL). The organic layers were combined, washed with brine (2×20 mL), dried over anhydrous sodium sulfate and concentrated under reduced pressure to afford (1S,3aS,4S,7R,7aR)-2-((S)-2-((tert-butoxycarbonyl)amino)-3,3-dimethylbutanoyl)-8,8-difluoro-2,3,3a,4,7,7a-hexahydro-1H-4,7-methanoisoindole-1-carboxylic acid (265 mg, crude) as an orange solid. $^1$H NMR (400 MHz, DMSO-d$_6$) δ 12.51-13.00 (m, 1H), 6.43-6.78 (m, 1H), 5.93-6.33 (m, 2H), 4.10-4.19 (m, 1H), 3.65-3.89 (m, 1H), 3.48-3.60 (m, 1H), 3.15-3.44 (m, 3H), 2.90-3.13 (m, 2H), 1.22-1.60 (m, 9H), 0.61-1.04 (m, 9H). LC-MS (ESI, m/z): 429 [M+H]$^+$.

To a stirred mixture of (1S,3aS,4S,7R,7aR)-2-((S)-2-((tert-butoxycarbonyl)amino)-3,3-dimethylbutanoyl)-8,8-difluoro-2,3,3a,4,7,7a-hexahydro-1H-4,7-methanoisoindole-1-carboxylic acid (265 mg, 0.618 mmol, 1.0 eq.) in dichloromethane (3 mL) was added trifluoroacetic acid (1 mL) at rt. The mixture was stirred for 2 h at rt and then concentrated under reduced pressure to afford (1S,3aS,4S,7R,7aR)-2-((S)-2-amino-3,3-dimethylbutanoyl)-8,8-difluoro-2,3,3a,4,7,7a-hexahydro-1H-4,7-methanoisoindole-1-carboxylic acid (203 mg, crude) as a yellow oil. LC-MS (ESI, m/z): 329[M+H]$^+$.

To a stirred mixture of (1S,3aS,4S,7R,7aR)-2-((S)-2-amino-3,3-dimethylbutanoyl)-8,8-difluoro-2,3,3a,4,7,7a-hexahydro-1H-4,7-methanoisoindole-1-carboxylic acid (203 mg, 0.618 mmol, 1.0 eq.) and trimethylamine (750 mg, 7.41 mmol, 12 eq.) in MeOH (2 mL) was added ethyl 2,2,2-trifluoroacetate (878 mg, 6.18 mmol, 10 eq.). The mixture was stirred for 2 days at rt and then acidified to pH=4 with hydrochloric acid (2M). The mixture was extracted with ethyl acetate (3×50 mL). The organic layers were combined, washed with brine (2×20 mL) and dried over anhydrous sodium sulfate. The combined organic layers were concentrated under reduced pressure to afford (1S,3aS,4S,7R,7aR)-2-((S)-3,3-dimethyl-2-(2,2,2-trifluoroacetamido)butanoyl)-8,8-difluoro-2,3,3a,4,7,7a-hexahydro-1H-4,7-methanoisoindole-1-carboxylic acid (250 mg, crude) as a light yellow oil. LC-MS (ESI, m/z): 425 [M+H]$^+$.

To a mixture of (1S,3aS,4S,7R,7aR)-2-((S)-3,3-dimethyl-2-(2,2,2-trifluoroacetamido)butanoyl)-8,8-difluoro-2,3,3a,4,7,7a-hexahydro-1H-4,7-methanoisoindole-1-carboxylic acid (250 mg, 0.590 mmol, 1.0 eq.) in N,N-dimethylformamide (2 mL) were added o-(7-azabenzotriazol-1-yl)-N,N,N',N'-tetramethyluronium hexafluorophosphate (269 mg, 0.708 mmol, 1.2 eq.) and N-ethyl-N-isopropylpropan-2-amine (457 mg, 3.54 mmol, 6.0 eq.) at 0° C. The mixture was stirred for 20 min at 0° C., and then (2S)-2-amino-3-[(3S)-2-oxopyrrolidin-3-yl]propanamide (101 mg, 0.590 mmol, 1.0 eq.) was added at 0° C. The mixture was stirred for 2 h at rt and then purified by C18 column with CH$_3$CN/Water (0.05% TFA). The desired fraction was concentrated under reduced pressure to provide (1S,3aS,4S,7R,7aR)—N—((S)-1-amino-1-oxo-3-((S)-2-oxopyrrolidin-3-yl)propan-2-yl)-2-((S)-3,3-dimethyl-2-(2,2,2-trifluoroacetamido)butanoyl)-8,8-difluoro-2,3,3a,4,7,7a-hexahydro-1H-4,7-methanoisoindole-1-carboxamide (170 mg, 50%) as a yellow solid. LC-MS (ESI, m/z): 578 [M+H]$^+$.

To a mixture of (1S,3aS,4S,7R,7aR)—N—((S)-1-amino-1-oxo-3-((S)-2-oxopyrrolidin-3-yl)propan-2-yl)-2-((S)-3,3-dimethyl-2-(2,2,2-trifluoroacetamido)butanoyl)-8,8-difluoro-2,3,3a,4,7,7a-hexahydro-1H-4,7-methanoisoindole-1-carboxamide (170 mg, 0.294 mmol, 1.0 eq.) in dichloromethane (2 mL) were added pyridine (92.4 mg, 1.17 mmol, 4.0 eq.) and trifluoroacetic anhydride (92.6 mg, 0.441 mmol, 1.5 eq.). The mixture was stirred for 2 h at rt. The reaction was quenched with water (20 mL). The mixture was extracted with ethyl acetate (3×50 mL). The organic layers were combined, washed with brine (2×20 mL), dried over anhydrous sodium sulfate, filtered and concentrated under reduced pressure to afford the crude product. The crude product was purified by prep-HPLC (Column: XBridge Prep OBD C18 Column, 30*150 mm, 5 m; Mobile Phase A: Water (0.1% FA), Mobile Phase B: ACN; Flow rate: 60 mL/min; Gradient: 30% B to 60% B in 7 min, 60% B; Wave Length: 254 nm; RT1 (min): 6) to provide (1S,3aS,4S,7R,7aR)—N—((S)-1-cyano-2-((S)-2-oxopyrrolidin-3-yl)ethyl)-2-((S)-3,3-dimethyl-2-(2,2,2-trifluoroacetamido)butanoyl)-8,8-difluoro-2,3,3a,4,7,7a-hexahydro-1H-4,7-methanoisoindole-1-carboxamide (49.1 mg, 28%) as a white solid. $^1$H NMR (400 MHz, 80° C., DMSO-d$_6$) δ 8.30-9.20 (m, 2H), 7.30-7.70 (m, 1H), 6.00-6.40 (m, 2H), 4.60-5.05 (m, 1H), 4.30-4.55 (m, 1H), 4.10-4.28 (m, 1H), 3.65-3.90 (m, 1H), 3.40-3.65 (m, 1H), 3.25-3.40 (m, 1H), 3.05-3.20

(m, 4H), 2.80-2.95 (m, 1H), 2.25-2.45 (m, 1H), 2.05-2.25 (m, 2H), 1.60-2.00 (m, 2H), 0.80-1.10 (m, 9H). LC-MS (ESI, m/z): 560 [M+H]$^+$.

Example 83

Compounds 83, 83a, and 83b

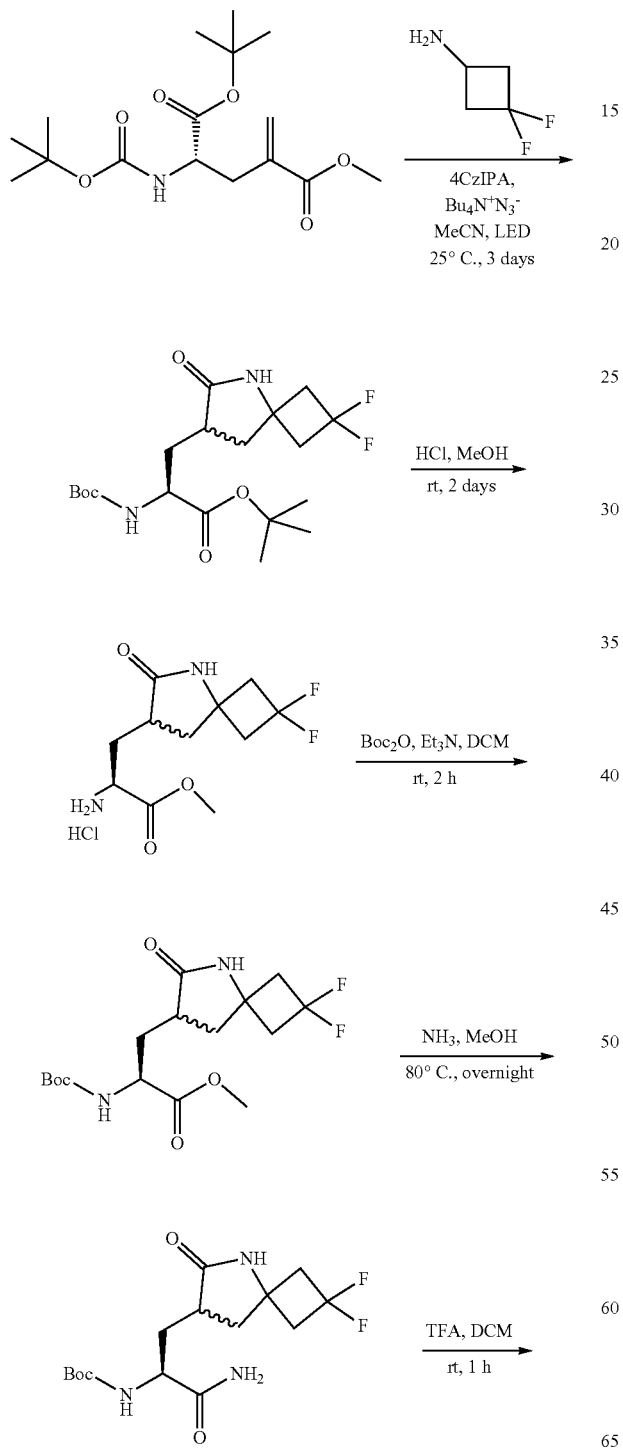

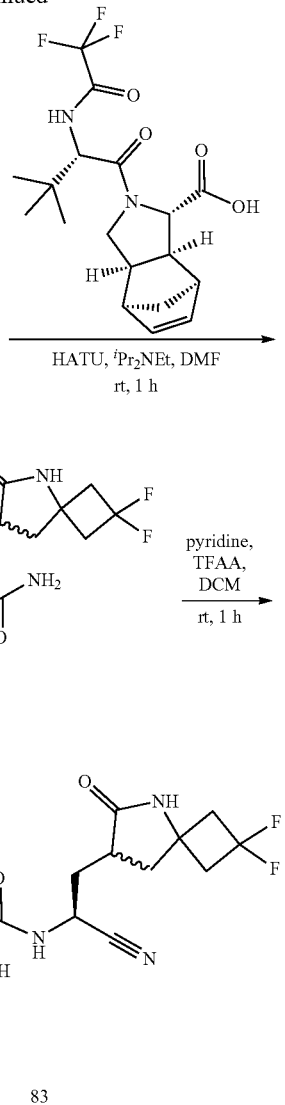

To a mixture of 1-tert-butyl 5-methyl (2S)-2-[(tert-butoxycarbonyl)amino]-4-methylidenepentanedioate (1.00 g, 3.03 mmol, 1.0 eq.), 2,4,5,6-Tetra-9H-carbazol-9-yl-1,3-benzenedicarbonitrile (24.0 mg, 0.030 mmol, 0.01 eq.) and tetrabutylammonium azide (86.0 mg, 0.303 mmol, 0.1 eq.) in acetonitrile (20 mL) was added 3,3-difluorocyclobutan-1-amine (325 mg, 3.03 mmol, 1.0 eq.) under nitrogen. The mixture was stirred for 3 days at 25° C. under nitrogen with a 450 nm LED lamp. The mixture was concentrated under reduced pressure to afford the crude product. The crude product was chromatographed on a silica gel column with MeOH:DCM (3:97) to provide tert-butyl (2S)-2-[(tert-butoxycarbonyl)amino]-3-{2,2-difluoro-6-oxo-5-azaspiro[3.4]octan-7-yl}propanoate (830 mg, 60%) as a brown solid. $^1$H NMR (400 MHz, DMSO-d$_6$) δ 8.13-8.23 (m, 1H), 7.17-7.31 (m, 1H), 3.76-4.09 (m, 1H), 2.82-3.01 (m, 1H), 2.59-2.81 (m, 3H), 2.31-2.45 (m, 2H), 1.94-2.08 (m, 1H), 1.80-1.93 (m, 1H), 1.48-1.60 (m, 1H), 1.29-1.47 (m, 18H). LC-MS (ESI, m/z): 405 [M+H]$^+$.

A mixture of tert-butyl (2S)-2-[(tert-butoxycarbonyl)amino]-3-{2,2-difluoro-6-oxo-5-azaspiro[3.4]octan-7-yl}propanoate (800 mg, 1.98 mmol, 1.0 eq.) in hydrochloric acid (10 mL, 9 M)/methanol (10 mL) was stirred for 2 days at rt. The mixture was concentrated under reduced pressure to afford methyl (2S)-2-amino-3-{2,2-difluoro-6-oxo-5-azaspiro[3.4]octan-7-yl}propanoate hydrochloride (590 mg, crude) as a brown solid. LC-MS (ESI, m/z): 263 [M+H]$^+$.

To a mixture of methyl (2S)-2-amino-3-{2,2-difluoro-6-oxo-5-azaspiro[3.4]octan-7-yl}propanoate hydrochloride (590 mg, 1.98 mmol, 1.0 eq.) in DCM (10 mL) were added triethylamine (600 mg, 5.92 mmol, 3.0 eq.) and di-tert-butyl dicarbonate (517 mg, 2.37 mmol, 1.2 eq.). The mixture was stirred for 2 h at rt. The reaction was quenched with water (30 mL). The mixture was extracted with DCM (3×30 mL). The organic layers were combined, washed with brine (2×20 mL), dried over anhydrous sodium sulfate, filtered and concentrated under reduced pressure to provide methyl (2S)-2-[(tert-butoxycarbonyl)amino]-3-{2,2-difluoro-6-oxo-5-azaspiro[3.4]octan-7-yl}propanoate (720 mg, crude) as a brown oil. $^1$H NMR (400 MHz, DMSO-d$_6$) δ 8.23 (s, 1H), 7.23-7.45 (m, 1H), 4.00-4.31 (m, 1H), 3.55-3.69 (m, 3H), 2.59-3.05 (m, 4H), 2.27-2.47 (m, 2H), 1.94-2.17 (m, 1H), 1.77-1.89 (m, 1H), 1.52-1.62 (m, 1H), 1.32-1.40 (m, 9H). LC-MS (ESI, m/z): 363[M+H]$^+$.

A mixture of methyl (2S)-2-[(tert-butoxycarbonyl)amino]-3-{2,2-difluoro-6-oxo-5-azaspiro[3.4]octan-7-yl}propanoate (720 mg, 1.99 mmol, 1.0 eq.) in ammonia (10 mL, 7 M in MeOH) was stirred overnight at 80° C. The mixture was concentrated under reduced pressure to afford the crude product. The crude product was chromatographed on a silica gel column with MeOH:DCM (1:9) to provide tert-butyl N-[(1S)-1-carbamoyl-2-{2,2-difluoro-6-oxo-5-azaspiro[3.4]octan-7-yl}ethyl]carbamate (260 mg, 35%) as a light yellow solid. LC-MS (ESI, m/z): 348 [M+H]$^+$.

To a solution of tert-butyl N-[(1S)-1-carbamoyl-2-{2,2-difluoro-6-oxo-5-azaspiro[3.4]octan-7-yl}ethyl]carbamate (230 mg, 0.662 mmol, 1.0 eq.) in DCM (10 mL) was added trifluoroacetic acid (3 mL). The mixture was stirred for 1 h at rt and then concentrated under reduced pressure to afford (2S)-2-amino-3-{2,2-difluoro-6-oxo-5-azaspiro[3.4]octan-7-yl}propanamide (164 mg, crude) as a brown oil. LC-MS (ESI, m/z): 248 [M+H]$^+$.

To a mixture of (1R,2S,3S,6R,7S)-4-[(2S)-3,3-dimethyl-2-(2,2,2-trifluoroacetamido)butanoyl]-4-azatricyclo[5.2.1.0ˆ{2,6}]dec-8-ene-3-carboxylic acid (258 mg, 0.663 mmol, 1.0 eq.) and o-(7-azabenzotriazol-1-yl)-N,N,N',N'-tetramethyluronium hexafluorophosphate (303 mg, 0.796 mmol, 1.2 eq.) in DMF (5 mL) was added N-ethyl-N-isopropylpropan-2-amine (514 mg, 3.98 mmol, 6.0 eq.) at 0° C. After stirred for 15 min at 0° C., (2S)-2-amino-3-{2,2-difluoro-6-oxo-5-azaspiro[3.4]octan-7-yl}propanamide (164 mg, 0.663 mmol, 1.0 eq.) was added. The mixture was stirred for 1 h at rt. The mixture was purified by C18 column with CH$_3$CN/Water (0.05% FA). The desired fraction was concentrated under reduced pressure to provide (2S)-3-{2,2-difluoro-6-oxo-5-azaspiro[3.4]octan-7-yl}-2-{[(1R,2S,3S,6R,7S)-4-[(2S)-3,3-dimethyl-2-(2,2,2-trifluoroacetamido)butanoyl]-4-azatricyclo[5.2.1.0ˆ{2,6}]dec-8-en-3-yl]formamido}propanamide (350 mg, 82%) as an off-white solid. LC-MS (ESI, m/z): 618 [M+H]$^+$.

To a mixture of (2S)-3-{2,2-difluoro-6-oxo-5-azaspiro[3.4]octan-7-yl}-2-{[(1R,2S,3S,6R,7S)-4-[(2S)-3,3-dimethyl-2-(2,2,2-trifluoroacetamido)butanoyl]-4-azatricyclo[5.2.1.0ˆ{2,6}]dec-8-en-3-yl]formamido}propanamide (350 mg, 0.567 mmol, 1.0 eq.) in DCM (5 mL) were added pyridine (157 mg, 1.98 mmol, 3.5 eq.) and trifluoroacetic anhydride (178 mg, 0.850 mmol, 1.5 eq.). The mixture was stirred for 1 h at rt. The reaction was quenched with water (20 mL). The mixture was extracted with DCM (3×20 mL). The organic layers were combined, washed with brine (2×20 mL), dried over anhydrous sodium sulfate, filtered and concentrated under reduced pressure to afford the crude product. The crude product was purified by prep-HPLC (Column: XSelect CSH Prep C18 OBD Column, 19×250 mm, 5 m; Mobile Phase A: Water (0.1% FA), Mobile Phase B: ACN; Flow rate: 25 mL/min; Gradient: 46% B to 70% B in 7 min, 70% B; Wave Length: 254 nm; RT: 6.45 min) to provide (1R,2S,3S,6R,7S)—N-[(1S)-1-cyano-2-{2,2-difluoro-6-oxo-5-azaspiro[3.4]octan-7-yl}ethyl]-4-[(2S)-3,3-dimethyl-2-(2,2,2-trifluoroacetamido)butanoyl]-4-azatricyclo[5.2.1.0ˆ{2,6}]dec-8-ene-3-carboxamide (129.9 mg, 38%) as a white solid. $^1$H NMR (400 MHz, 80° C., DMSO-d$_6$) δ 8.75-9.00 (m, 1H), 8.35-8.74 (m, 1H), 7.95-8.23 (m, 1H), 5.94-6.26 (m, 2H), 4.82-5.00 (m, 1H), 4.40-4.68 (m, 1H), 3.95-4.22 (m, 1H), 3.55-3.75 (m, 1H), 3.32-3.53 (m, 1H), 3.05-3.28 (m, 1H), 2.75-2.98 (m, 3H), 2.48-2.74 (m, 5H), 2.08-2.46 (m, 2H), 1.86-2.02 (m, 1H), 1.68-1.85 (m, 1H), 1.30-1.50 (m, 2H), 0.80-1.05 (m, 9H). LC-MS (ESI, m/z): 600 [M+H]$^+$.

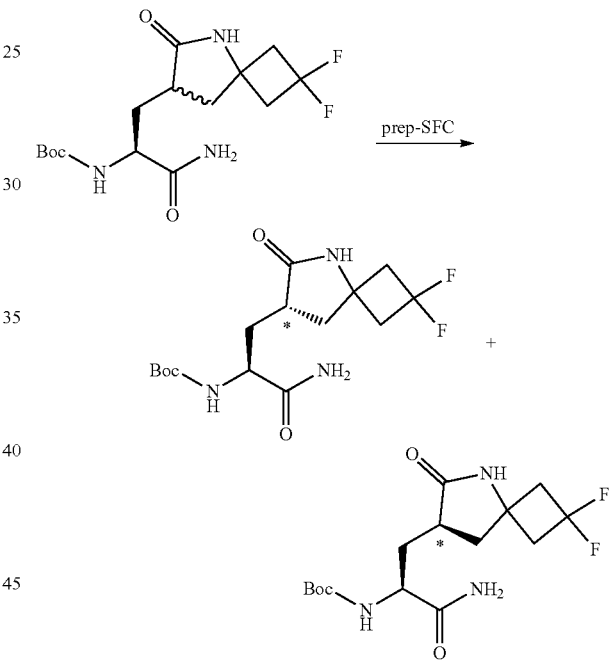

Tert-butyl N-[(1S)-1-carbamoyl-2-{2,2-difluoro-6-oxo-5-azaspiro[3.4]octan-7-yl}ethyl]carbamate (650 mg, 1.87 mmol, 1.0 eq.) was separated by prep-SFC-HPLC column (Column: Lux Sum Celluloes-3, 5×25 cm, 5 m; Mobile Phase A: CO$_2$, Mobile Phase B: MeOH (0.1% 2M NH$_3$-MeOH); Flow rate: 100 mL/min; Gradient: isocratic 20% B; Column Temperature (° C.): 35; Back Pressure (bar): 100; Wave Length: 220 nm; RT1 (min): 5.3; RT2(min): 6.07; Sample Solvent: MeOH (0.1% 2M NH$_3$-MeOH); Injection Volume: 2 mL;) to offered the 1$^{st}$ peak (isomer 1, (tert-butyl N-[(1S)-1-carbamoyl-2-[(7*S)-2,2-difluoro-6-oxo-5-azaspiro[3.4]octan-7-yl]ethyl]carbamate (270 mg, 41%), de>99%) as a white solid. $^1$H NMR (400 MHz, DMSO-d$_6$) δ 8.16 (s, 1H), 7.25-7.40 (m, 1H), 7.03 (s, 1H), 6.82-6.93 (m, 1H), 3.84-4.04 (m, 1H), 2.82-3.02 (m, 1H), 2.58-2.80 (m, 3H), 2.31-2.48 (m, 2H), 2.01-2.12 (m, 1H), 1.80-1.94 (m, 1H), 1.32-1.51 (m, 10H). LC-MS (ESI, m/z): 348 [M+H]$^+$, and 2$^{nd}$ peak (isomer 2 (tert-butyl N-[(1S)-1-carbamoyl-2-

[(7*R)-2,2-difluoro-6-oxo-5-azaspiro[3.4]octan-7-yl]ethyl] carbamate (100 mg, 14%), de>98%) as an off-white solid. $^1$H NMR (400 MHz, DMSO-$d_6$) δ 8.18 (s, 1H), 7.14-7.38 (m, 1H), 6.97-7.12 (m, 1H), 6.86-6.95 (m, 1H), 3.86-3.97 (m, 1H), 2.83-3.02 (m, 1H), 2.62-2.78 (m, 3H), 2.29-2.44 (m, 2H), 1.83-1.96 (m, 2H), 1.45-1.58 (m, 1H), 1.39 (s, 9H). LC-MS (ESI, m/z): 348 [M+H]$^+$. Isomer 1 was converted into compound 83a (LC-MS (ESI, m/z): 600 [M+H]$^+$.) and isomer 2 was converted into compound 83b (LC-MS (ESI, m/z): 600 [M+H]$^+$), similar as described for the isomeric mixture compound 83.

Example 84

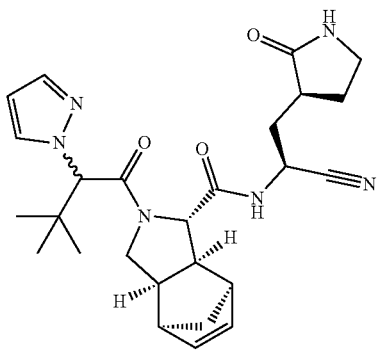

Compound 84

Compound 84 was prepared similarly as described for Compound 42 using 3,3-dimethyl-2-(1H-pyrazol-1-yl)butanoic acid in place of (S)-3,3-dimethyl-2-(4-(trifluoromethyl)-1H-1,2,3-triazol-1-yl)butanoic acid. $^1$H NMR (500 MHz, 363K, DMSO-d6) δ 8.28-8.75 (m, 1H), 7.55-7.79 (m, 1H), 7.24-7.52 (m, 2H), 6.07-6.32 (m, 2H), 5.32-5.85 (m, 1H), 4.60-4.98 (m, 2H), 3.90-4.24 (m, 1H), 3.71 (m, 1H), 3.26-3.43 (m, 1H), 3.01-3.26 (m, 3H), 2.70-3.00 (m, 3H), 2.32-2.44 (m, 1H), 2.07-2.30 (m, 2H), 1.64-1.95 (m, 2H), 1.20-1.46 (m, 2H), 0.86-1.01 (m, 9H). LCMS (ESI, m/z): 479 [M+H]$^+$.

3,3-Dimethyl-2-(1H-pyrazol-1-yl)butanoic acid: To a solution of (R)-2-amino-3,3-dimethylbutanoic acid (10 g, 76.3 mmol, 1.0 eq.) in water (100 mL) cooled at 0° C. were added 47% HBr (55 mL) and a solution of NaNO$_2$ (6.2 g, 91.5 mmol, 1.2 eq.) in water (100 mL). The mixture was stirred at rt for 16 h, and then extracted with EA (3×50 mL). The organic phases were combined, washed with brine (50 mL), dried over Na$_2$SO$_4$, filtered and concentrated under reduced pressure. The residue was purified by flash chromatography on silica gel using a gradient of EA (15 to 50%) in PE to afford (R)-2-bromo-3,3-dimethylbutanoic acid (6 g, 41%) as an off-white solid.

To a solution of (R)-2-bromo-3,3-dimethylbutanoic acid (3.0 g, 15.5 mmol, 1.0 eq.) in methanol (30 mL) cooled at 0° C. was added conc. H$_2$SO$_4$ (0.3 mL). The mixture was refluxed for 18 h. After cooling to rt, the mixture was diluted with water (20 mL) and extracted with EA (3×20 mL). The organic phases were combined, washed with water, dried over Na$_2$SO$_4$, filtered and concentrated under reduced pressure. The residue was purified by flash chromatography on silica gel using a gradient of EA (20 to 30%) in PE to afford methyl (R)-2-bromo-3,3-dimethylbutanoate (1.4 g, 44%) as a colourless oil.

To a solution of potassium salt of pyrazole (0.500 g, 4.71 mmol, 1.0 eq.) in dioxane (5 mL) were added methyl (R)-2-bromo-3,3-dimethylbutanoate (1.4 g, 7.07 mmol, 1.5 eq.) and 15-crown-5 (1.5 g, 7.07 mmol, 1.5 eq.). The mixture was irradiated at 100° C. for 3 h in a microwave oven. After cooling to rt, the mixture was concentrated under reduced pressure. The residue was purified by flash chromatography on C18 using 0.01% TFA in ACN to afford 3,3-dimethyl-2-(1H-pyrazol-1-yl)butanoic acid (70 mg, 9%) as an off-white solid.

Example 85

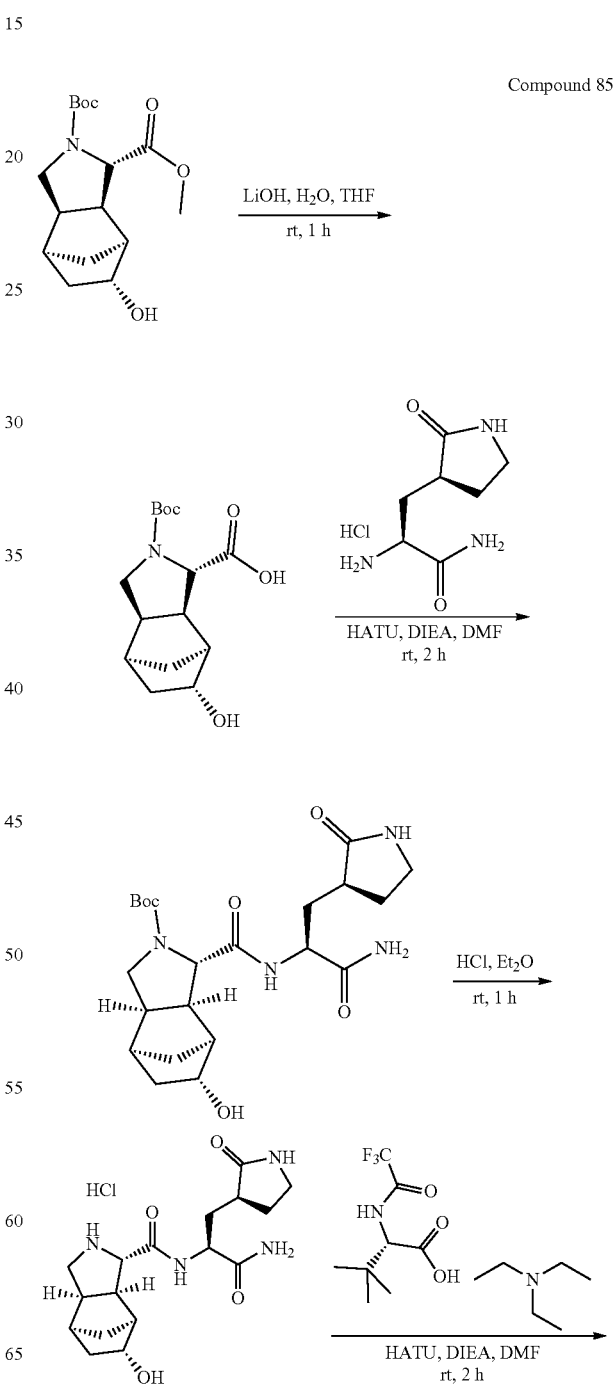

Compound 85

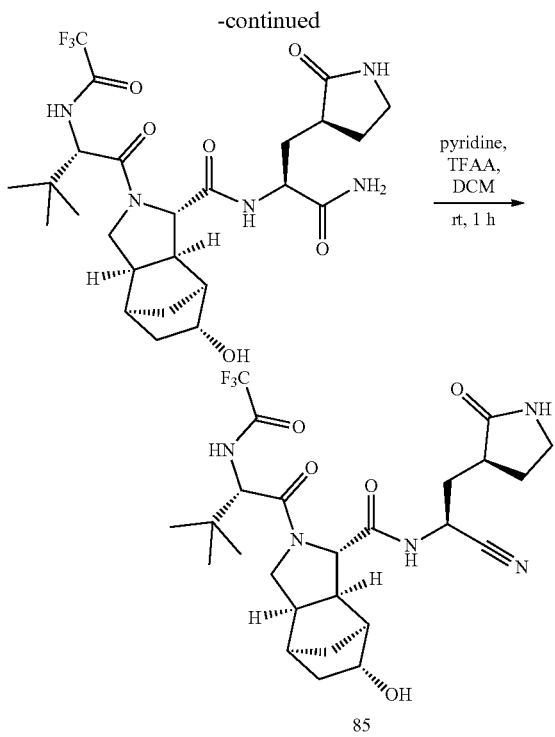

85

To a mixture of 4-tert-butyl 3-methyl (1S,2R,3S,6R,7S,9R)-9-hydroxy-4-azatricyclo[5.2.1.0^{2,6}]decane-3,4-dicarboxylate (200 mg, 0.642 mmol, 1.0 eq.) in tetrahydrofuran (2 mL)/water (2 mL) was added lithiumol (76.9 mg, 3.21 mmol, 5.0 eq.). The mixture was stirred for 1 h at rt and then acidified to pH=4 with hydrochloric acid (1M in H$_2$O). The mixture was extracted with EA (3×30 mL). The organic layers were combined, washed with brine (2×20 mL), dried over anhydrous sodium sulfate, filtered and concentrated under reduced pressure to afford (1S,2R,3S,6R,7S,9R)-4-(tert-butoxycarbonyl)-9-hydroxy-4-azatricyclo[5.2.1.0^{2,6}]decane-3-carboxylic acid) (190 mg, crude) as a white oil. LC-MS (ESI, m/z): 298 [M+H]$^+$.

A mixture of tert-butyl N-[(1S)-1-carbamoyl-2-[(3S)-2-oxopyrrolidin-3-yl]ethyl]carbamate (173 mg, 0.638 mmol, 1.0 eq.) in hydrogen chloride (3 mL, 2 M in Et$_2$O) was stirred for 1 h at rt. The mixture was concentrated under reduced pressure to afford methyl (2S)-2-amino-3-[(3S)-2-oxopyrrolidin-3-yl]propanamide hydrochloride (131 mg, crude) as a yellow solid. LC-MS (ESI, m/z): 172 [M−Boc+H]$^+$.

To a mixture of (1S,2R,3S,6R,7S,9R)-4-(tert-butoxycarbonyl)-9-hydroxy-4-azatricyclo[5.2.1.0^{2,6}]decane-3-carboxylic acid (189 mg, 0.636 mmol, 1.0 eq.) in N,N-dimethylformamide (2 mL) were added o-(7-azabenzotriazol-1-yl)-N,N,N',N'-tetramethyluronium hexafluorophosphate (290 mg, 0.763 mmol, 1.2 eq.) and N-ethyl-N-isopropylpropan-2-amine (493 mg, 3.82 mmol, 6.0 eq.) at 0° C. The mixture was stirred for 20 min at 0° C., and then (2S)-2-amino-3-[(3S)-2-oxopyrrolidin-3-yl]propanamide hydrochloride (132 mg, 0.636 mmol, 1.0 eq.) was added at 0° C. The mixture was stirred for 2 h at rt. The reaction was quenched with water (20 mL). The mixture was extracted with EtOAc (3×30 mL). The organic layers were combined, washed with brine (2×30 mL), dried over anhydrous sodium sulfate, filtered and concentrated under reduced pressure to afford the crude product. The mixture was purified by C18 column with CH$_3$CN/Water (0.05% TFA). The desired fraction was concentrated under reduced pressure to provide tert-butyl (1S,2R,3S,6R,7S,9R)-3-{[(1S)-1-carbamoyl-2-[(3S)-2-oxopyrrolidin-3-yl]ethyl]carbamoyl}-9-hydroxy-4-azatricyclo[5.2.1.0^{2,6}]decane-4-carboxylate (190 mg, 66%) as a light yellow solid. LC-MS (ESI, m/z): 451 [M+H]$^+$.

A mixture of tert-butyl (1S,2R,3S,6R,7S,9R)-3-{[(1S)-1-carbamoyl-2-[(3S)-2-oxopyrrolidin-3-yl]ethyl]carbamoyl}-9-hydroxy-4-azatricyclo[5.2.1.0^{2,6}]decane-4-carboxylate (190 mg, 0.422 mmol, 1.0 eq.) in hydrogen chloride (4 mL, 2 M in Et$_2$O) was stirred for 1 h at rt. The mixture was concentrated under reduced pressure to afford methyl (2S)-2-{[(1S,2R,3S,6R,7S,9R)-9-hydroxy-4-azatricyclo[5.2.1.0^{2,6}]decan-3-yl]formamido}-3-[(3S)-2-oxopyrrolidin-3-yl]propanamide hydrochloride (155 mg, crude) as a yellow solid. LC-MS (ESI, m/z): 351 [M+H]$^+$.

To a mixture of (2S)-3,3-dimethyl-2-(2,2,2-trifluoroacetamido)butanoic acid triethylamine (138 mg, 0.400 mmol, 1.0 eq.) in N,N-dimethylformamide (2 mL) were added o-(7-azabenzotriazol-1-yl)-N,N,N',N'-tetramethyluronium hexafluorophosphate (182 mg, 0.480 mmol, 1.2 eq.) and N-ethyl-N-isopropylpropan-2-amine (309 mg, 2.40 mmol, 6.0 eq.) at 0° C. The mixture was stirred for 20 min at 0° C., and then (2S)-2-{[(1S,2R,3S,6R,7S,9R)-9-hydroxy-4-azatricyclo[5.2.1.0^{2,6}]decan-3-yl]formamido}-3-[(3S)-2-oxopyrrolidin-3-yl]propanamide hydrochloride (155 mg, 0.400 mmol, 1.0 eq.) was added at 0° C. The mixture was stirred for 2 h at rt. The reaction was quenched with water (20 mL). The mixture was extracted with EtOAc (3×30 mL). The organic layers were combined, washed with brine (2×30 mL), dried over anhydrous sodium sulfate, filtered and concentrated under reduced pressure to afford the crude product. The mixture was purified by C18 column with CH$_3$CN/Water (0.05% TFA). The desired fraction was concentrated under reduced pressure to provide (2S)-2-{[(1S,2R,3S,6R,7S,9R)-4-[(2S)-3,3-dimethyl-2-(2,2,2-trifluoroacetamido)butanoyl]-9-hydroxy-4-azatricyclo[5.2.1.0^{2,6}]decan-3-yl]formamido}-3-[(3S)-2-oxopyrrolidin-3-yl]propanamide (60 mg, 27%) as a light yellow solid. LC-MS (ESI, m/z): 560 [M+H]$^+$.

To a mixture of (2S)-2-{[(1S,2R,3S,6R,7S,9R)-4-[(2S)-3,3-dimethyl-2-(2,2,2-trifluoroacetamido)butanoyl]-9-hydroxy-4-azatricyclo[5.2.1.0^{2,6}]decan-3-yl]formamido}-3-[(3S)-2-oxopyrrolidin-3-yl]propanamide (60 mg, 0.107 mmol, 1.0 eq.) in DCM (1 mL) were added pyridine (33.9 mg, 0.429 mmol, 4.0 eq.) and trifluoroacetic anhydride (33.8 mg, 0.161 mmol, 1.50 eq.). The mixture was stirred for 2 h at rt. The reaction was quenched with water (5 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was purified by prep-HPLC (Column: XBridge Prep Phenyl OBD Column, 19*250 mm, 5 m; Mobile Phase A: Water (0.1% FA), Mobile Phase B: ACN; Flow rate: 25 mL/min; Gradient: 33% B to 63% B in 7 min, 63% B; Wave Length: 254 nm; RT1 (min): 5) to provide (1S,2R,3S,6R,7S,9R)—N-[(1S)-1-cyano-2-[(3S)-2-oxopyrrolidin-3-yl]ethyl]-4-[(2S)-3,3-dimethyl-2-(2,2,2-trifluoroacetamido)butanoyl]-9-hydroxy-4-azatricyclo[5.2.1.0^{2,6}]decane-3-carboxamide (4 mg, 10%) as an white solid. $^1$H NMR (400 MHz, 80° C., DMSO-d$_6$) δ 8.80-9.10 (m, 1H), 8.60-8.80 (m, 1H), 7.25-7.50 (m, 1H), 4.70-4.90 (m, 1H), 4.50-4.65 (m, 1H), 4.40-4.50 (m, 1H), 4.38-4.00 (m, 1H), 3.60-3.80 (m, 1H), 3.50-3.60 (m, 1H), 3.30-3.50 (m, 1H), 3.00-3.28 (m, 2H), 2.45-2.65 (m, 1H), 2.30-2.40 (m, 1H), 2.20-2.30 (m, 1H), 2.15-2.20 (m, 1H), 1.98-2.15 (m, 3H), 1.58-1.85 (m, 4H), 1.15-1.35 (m, 1H), 0.75-1.10 (m, 10H). LC-MS (ESI, m/z): 542 [M+H]⁺.

Example 86

Compound 86

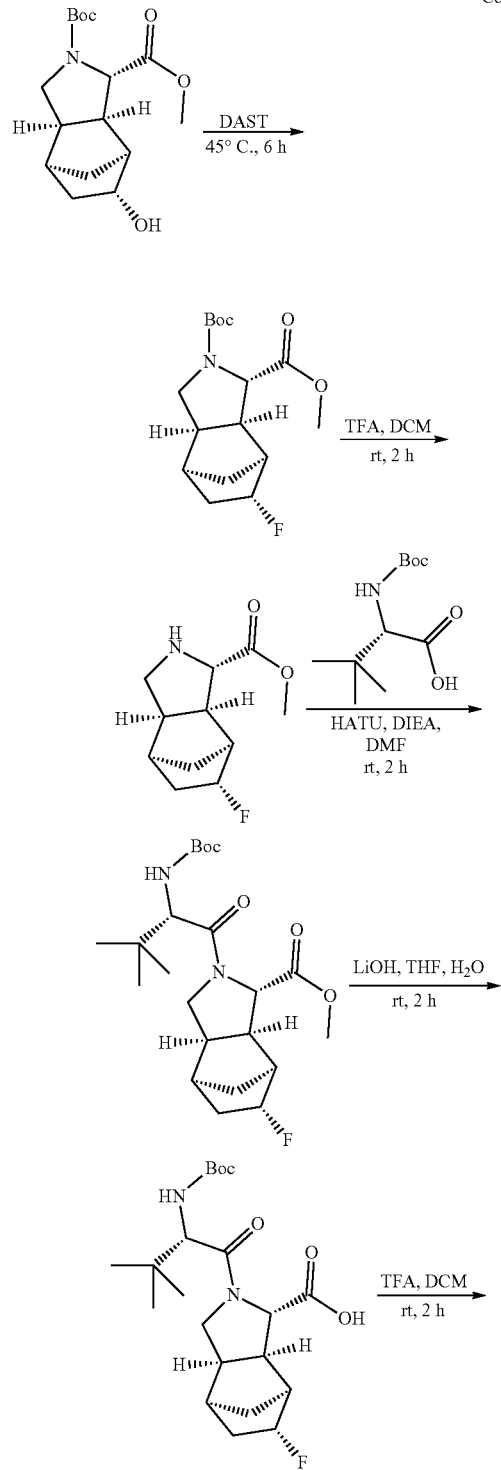

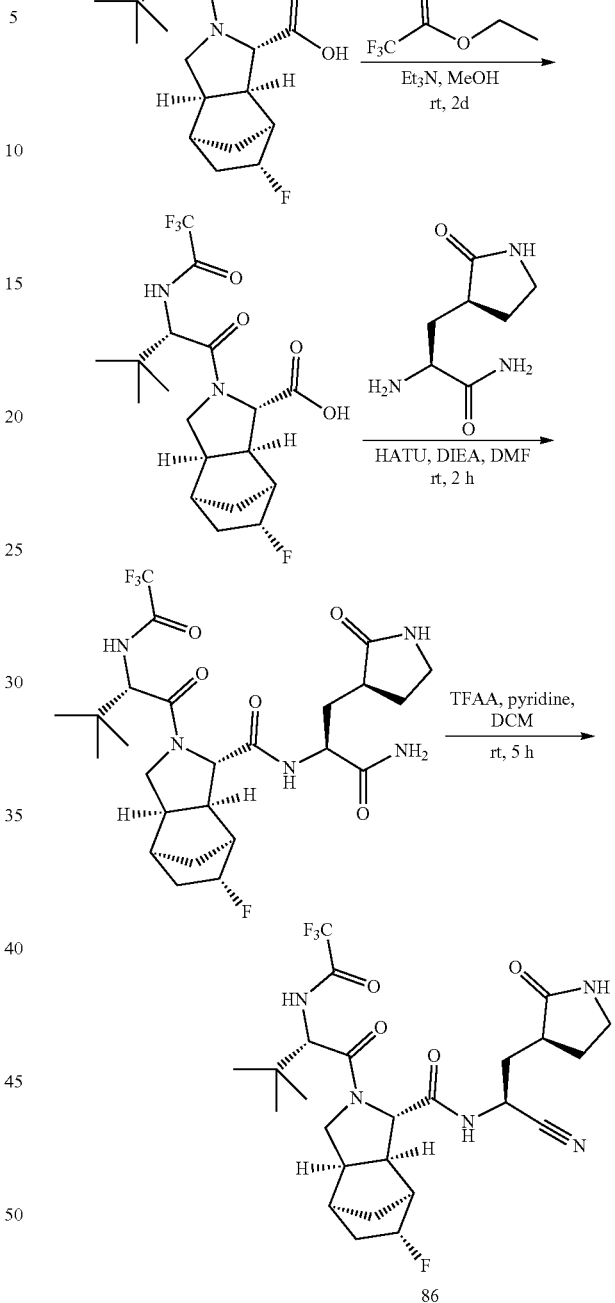

A mixture of 4-tert-butyl 3-methyl (1S,2R,3S,6R,7S,9R)-9-hydroxy-4-azatricyclo[5.2.1.0^{2,6}]decane-3,4-dicarboxylate (500 mg, 1.60 mmol, 1.0 eq.) in diethylaminosulfur trifluoride (10 mL) was stirred for 6 h at 45° C. The mixture was diluted with dichloromethane (80 mL), and the reaction quenched with sat. sodium bicarbonate (50 mL) at 0° C. The mixture was extracted with dichloromethane (3×80 mL). The organic layers were combined, washed with brine (2×50 mL), dried over anhydrous sodium sulfate, filtered and concentrated under reduced pressure. The residue was purified by silica gel column chromatography with PE:EA (7:3) to afford 4-tert-butyl 3-methyl (1S,2R,3S,6R,7S,9R)-9- fluoro-4-azatricyclo[5.2.1.0^{2,6}]decane-3,4-dicarboxylate (210 mg, 42%) as a yellow oil. LC-MS (ESI, m/z): 258 [M−56+H]⁺.

To a stirred mixture of 4-tert-butyl 3-methyl (1S,2R,3S,6R,7S,9R)-9-fluoro-4-azatricyclo[5.2.1.0^{2,6}]decane-3,4-dicarboxylate (210 mg, 0.670 mmol, 1.0 eq.) in dichloromethane (3 mL) was added trifluoroacetic acid (1 mL) at rt. The mixture was stirred for 2 h at rt and then concentrated under reduced pressure to provide product methyl (1S,2R,3S,6R,7S,9R)-9-fluoro-4-azatricyclo[5.2.1.0^{2,6}]decane-3-carboxylate (155 mg, crude) as a yellow oil. LC-MS (ESI, m/z): 213 [M+H]⁺.

To a mixture of (2S)-2-[(tert-butoxycarbonyl)amino]-3,3-dimethylbutanoic acid (155 mg, 0.671 mmol, 1.0 eq.) in N,N-dimethylformamide (2 mL) was added o-(7-azabenzotriazol-1-yl)-N,N,N',N'-tetramethyluronium hexafluorophosphate (305 mg, 0.805 mmol, 1.2 eq.) and N-ethyl-N-isopropylpropan-2-amine (520 mg, 4.026 mmol, 6.0 eq.) at 0° C. The mixture was stirred for 20 min at 0° C., and then methyl (1S,2R,3S,6R,7S,9R)-9-fluoro-4-azatricyclo[5.2.1.0^{2,6}]decane-3-carboxylate (143 mg, 0.671 mmol, 1.0 eq.) was added at 0° C. The mixture was stirred for 2 h at rt and then purified by a C18 column with CH₃CN/Water (0.05% TFA). The desired fraction was concentrated under reduced pressure to provide methyl (1S,2R,3S,6R,7S,9R)-4-[(2S)-2-[(tert-butoxycarbonyl)amino]-3,3-dimethylbutanoyl]-9-fluoro-4-azatricyclo[5.2.1.0^{2,6}]decane-3-carboxylate (190 mg, 66%) as a yellow solid. LC-MS (ESI, m/z): 427 [M+H]⁺.

To a stirred methyl (1S,2R,3S,6R,7S,9R)-4-[(2S)-2-[(tert-butoxycarbonyl)amino]-3,3-dimethylbutanoyl]-9-fluoro-4-azatricyclo[5.2.1.0^{2,6}]decane-3-carboxylate (190 mg, 0.445 mmol, 1.0 eq.) in tetrahydrofuran (2 mL) and water (2 mL) was added lithium hydroxide (53.3 mg, 2.22 mmol, 5.0 eq.) at rt. The mixture was stirred for 2 h and acidified to pH=3 with hydrochloric acid (2M). The mixture was extracted with EA (3×50 mL). The organic layers were combined, washed with brine (2×20 mL) and dried over anhydrous sodium sulfate. The mixture was concentrated under reduced pressure to afford (1S,2R,3S,6R,7S,9R)-4-[(2S)-2-[(tert-butoxycarbonyl)amino]-3,3-dimethylbutanoyl]-9-fluoro-4-azatricyclo[5.2.1.0^{2,6}]decane-3-carboxylic acid (180 mg, crude) as an orange solid. LC-MS (ESI, m/z): 413 [M+H]⁺.

To a stirred mixture of (1S,2R,3S,6R,7S,9S)-4-[(2S)-2-[(tert-butoxycarbonyl)amino]-3,3-dimethylbutanoyl]-9-fluoro-4-azatricyclo[5.2.1.0^{2,6}]decane-3-carboxylic acid (160 mg, 0.388 mmol, 1.0 eq.) in dichloromethane (2 mL) was added trifluoroacetic acid (0.6 mL) at rt. The mixture was stirred for 2 h at rt and then concentrated under reduced pressure to (1S,2R,3S,6R,7S,9S)-4-[(2S)-2-amino-3,3-dimethylbutanoyl]-9-fluoro-4-azatricyclo[5.2.1.0^{2,6}]decane-3-carboxylic acid (121 mg, crude) as a yellow oil. LC-MS (ESI, m/z): 313 [M+H]⁺.

To a stirred mixture of (1S,2R,3S,6R,7S,9R)-4-[(2S)-2-amino-3,3-dimethylbutanoyl]-9-fluoro-4-azatricyclo[5.2.1.0^{2,6}]decane-3-carboxylic acid (121 mg, 0.387 mmol, 1.0 eq.) and trimethylamine (470 mg, 4.64 mmol, 12.0 eq.) in MeOH (1 mL) was added ethyl 2,2,2-trifluoroacetate (550 mg, 3.870 mmol, 10.0 eq.). The mixture was stirred for 2 days at rt. The reaction was quenched with water (10 mL). The mixture was concentrated under reduced pressure to remove MeOH and then acidified to pH=4 with hydrochloric acid (2M). The mixture was extracted with EA (3×50 mL). The organic layers were combined, washed with brine (2×20 mL) and dried over anhydrous sodium sulfate. The combined organic layers were concentrated under reduced pressure to afford (1S,2R,3S,6R,7S,9R)-4-[(2S)-3,3-dimethyl-2-(2,2,2-trifluoroacetamido)butanoyl]-9-fluoro-4-azatricyclo[5.2.1.0^{2,6}]decane-3-carboxylic acid (160 mg, crude) as a light yellow oil. LC-MS (ESI, m/z): 409 [M+H]⁺.

To a mixture of (1S,2R,3S,6R,7S,9R)-4-[(2S)-3,3-dimethyl-2-(2,2,2-trifluoroacetamido)butanoyl]-9-fluoro-4-azatricyclo[5.2.1.0^{2,6}]decane-3-carboxylic acid (160 mg, 0.392 mmol, 1.0 eq.) in N,N-dimethylformamide (2 mL) was added o-(7-azabenzotriazol-1-yl)-N,N,N',N'-tetramethyluronium hexafluorophosphate (178 mg, 0.470 mmol, 1.2 eq.) and N-ethyl-N-isopropylpropan-2-amine (303 mg, 2.35 mmol, 6.0 eq.) at 0° C. The mixture was stirred for 20 min at 0° C., and then (2S)-2-amino-3-[(3S)-2-oxopyrrolidin-3-yl]propanamide (67.0 mg, 0.392 mmol, 1.0 eq.) was added at 0° C. The mixture was stirred for 2 h at rt. The mixture was purified by C18 column with CH₃CN/Water (0.05% TFA). The desired fractions were concentrated under reduced pressure to provide (2S)-2-{[(1S,2R,3S,6R,7S,9R)-4-[(2S)-3,3-dimethyl-2-(2,2,2-trifluoroacetamido)butanoyl]-9-fluoro-4-azatricyclo[5.2.1.0^{2,6}]decan-3-yl]formamido}-3-[(3S)-2-oxopyrrolidin-3-yl]propanamide (130 mg, 59%) as a yellow solid. LC-MS (ESI, m/z): 562 [M+H]⁺.

To a mixture of (2S)-2-{[(1S,2R,3S,6R,7S,9R)-4-[(2S)-3,3-dimethyl-2-(2,2,2-trifluoroacetamido)butanoyl]-9-fluoro-4-azatricyclo[5.2.1.0^{2,6}]decan-3-yl]formamido}-3-[(3S)-2-oxopyrrolidin-3-yl]propanamide (130 mg, 0.231 mmol, 1.0 eq.) in DCM (1 mL) was added pyridine (109 mg, 1.38 mmol, 6.0 eq.) and trifluoroacetic anhydride (58.0 mg, 0.508 mmol, 2.2 eq.). The mixture was stirred for 5 h at rt. The reaction was quenched with water (10 mL). The mixture was extracted with dichloromethane (3×50 mL). The organic layers were combined, washed with brine (2×20 mL), dried over anhydrous sodium sulfate, filtered and concentrated under reduced pressure to afford the crude product. The crude product was purified by prep-HPLC (Column: XSelect CSH Prep C18 OBD Column, 19*150 mm, 5 m; Mobile Phase A: Water (0.1% FA), Mobile Phase B: ACN; Flow rate: 25 mL/min; Gradient: 30% B to 60% B in 7 min, 60% B; Wave Length: 254 nm; RT1 (min): 6.12) to provide (1S,2R,3S,6R,7S,9R)—N-[(1S)-1-cyano-2-[(3S)-2-oxopyrrolidin-3-yl]ethyl]-4-[(2S)-3,3-dimethyl-2-(2,2,2-trifluoroacetamido)butanoyl]-9-fluoro-4-azatricyclo[5.2.1.0^{2,6}] decane-3-carboxamide (50 mg, 39%) as a white solid. ¹H NMR (400 MHz, 80° C., DMSO-d₆) δ 8.95-9.25 (m, 1H), 8.55-8.95 (m, 1H), 7.30-7.60 (m, 1H), 4.80-5.05 (m, 1H), 4.55-4.80 (m, 2H), 4.15-4.55 (m, 1H), 3.45-4.05 (m, 2H), 3.10-3.35 (m, 2H), 2.60-2.90 (m, 2H), 2.50-2.60 (m, 1H), 2.25-2.45 (m, 2H), 2.05-2.25 (m, 2H), 1.85-2.05 (m, 1H), 1.60-1.85 (m, 3H), 1.20-1.55 (m, 2H), 0.90-1.10 (m, 9H). LC-MS (ESI, m/z): 544 [M+H]⁺.

Example 87

Compound 87

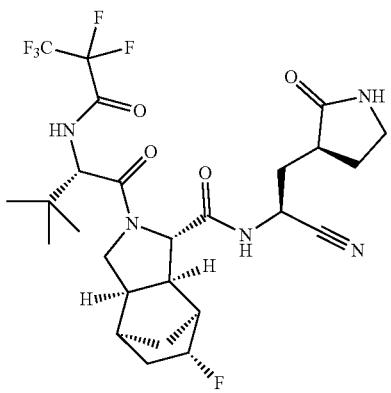

To a mixture of (1S,3aR,4S,6R,7S,7aR)-2-((S)-3,3-dimethyl-2-(2,2,3,3,3-pentafluoropropanamido)butanoyl)-6-fluorooctahydro-1H-4,7-methanoisoindole-1-carboxylic acid (130 mg, 0.284 mmol, 1.0 eq.) in N,N-dimethylformamide (2 mL) were added o-(7-azabenzotriazol-1-yl)-N,N,N',N'-tetramethyluronium hexafluorophosphate (129 mg, 0.340 mmol, 1.2 eq.) and N-ethyl-N-isopropylpropan-2-amine (219 mg, 1.70 mmol, 6.0 eq.) at 0° C. The mixture was stirred for 20 min at 0° C., and then (S)-2-amino-3-((S)-2-oxopyrrolidin-3-yl)propanamide (50 mg, 0.284 mmol, 1.0 eq.) was added at 0° C. The mixture was stirred for 2 h at rt. The mixture was purified by C18 column with CH$_3$CN/Water (0.05% TFA). The desired fraction was concentrated under reduced pressure to provide (1S,3aR,4S,6R,7S,7aR)—N—((S)-1-amino-1-oxo-3-((S)-2-oxopyrrolidin-3-yl)propan-2-yl)-2-((S)-3,3-dimethyl-2-(2,2,3,3,3-pentafluoropropanamido)butanoyl)-6-fluorooctahydro-1H-4,7-methanoisoindole-1-carboxamide (90 mg, 52%) as a yellow solid. LC-MS (ESI, m/z): 612 [M+H]$^+$.

To a mixture of (1S,3aR,4S,6R,7S,7aR)—N—((S)-1-amino-1-oxo-3-((S)-2-oxopyrrolidin-3-yl)propan-2-yl)-2-((S)-3,3-dimethyl-2-(2,2,3,3,3-pentafluoropropanamido)butanoyl)-6-fluorooctahydro-1H-4,7-methanoisoindole-1-carboxamide (90 mg, 0.147 mmol, 1.0 eq.) in DCM (1 mL) were added pyridine (46.5 mg, 0.588 mmol, 4.0 eq.) and trifluoroacetic anhydride (55.7 mg, 0.265 mmol, 1.8 eq.). The mixture was stirred for 4 h at rt. The reaction was quenched with water (10 mL). The mixture was extracted with dichloromethane (3×30 mL). The organic layers were combined, washed with brine (2×10 mL), dried over anhydrous sodium sulfate, filtered and concentrated under reduced pressure to afford the crude product. The crude product was purified by preparative HPLC (Column: Xselect CSH F-Phenyl OBD column, 19*250 mm, 5 m; Mobile Phase A: Water (0.1% FA), Mobile Phase B: ACN; Flow rate: 25 mL/min; Gradient: 35% B to 65% B in 7 min, 65% B; Wave Length: 220 nm; RT1 (min): 6.22) to provide the desired product (1S,3aR,4S,6R,7S,7aR)—N—((S)-1-cyano-2-((S)-2-oxopyrrolidin-3-yl)ethyl)-2-((S)-3,3-dimethyl-2-(2,2,3,3,3-pentafluoropropanamido)butanoyl)-6-fluorooctahydro-1H-4,7-methanoisoindole-1-carboxamide (21.0 mg, 23%) as a white solid. $^1$H NMR (400 MHz, 80° C., DMSO-d6) δ 8.55-9.12 (m, 2H), 7.20-7.70 (m, 1H), 4.80-5.10 (m, 1H), 4.65-4.80 (m, 1H), 4.50-4.65 (m, 1H), 4.25-4.50 (m, 1H), 3.50-3.80 (m, 2H), 3.10-3.30 (m, 2H), 2.50-2.75 (m, 3H), 2.25-2.40 (m, 2H), 2.00-2.25 (m, 2H), 1.20-2.00 (m, 6H), 0.75-1.20 (m, 9H). LC-MS (ESI, m/z): 594 [M+H]$^+$.

Example 88

Compound 88

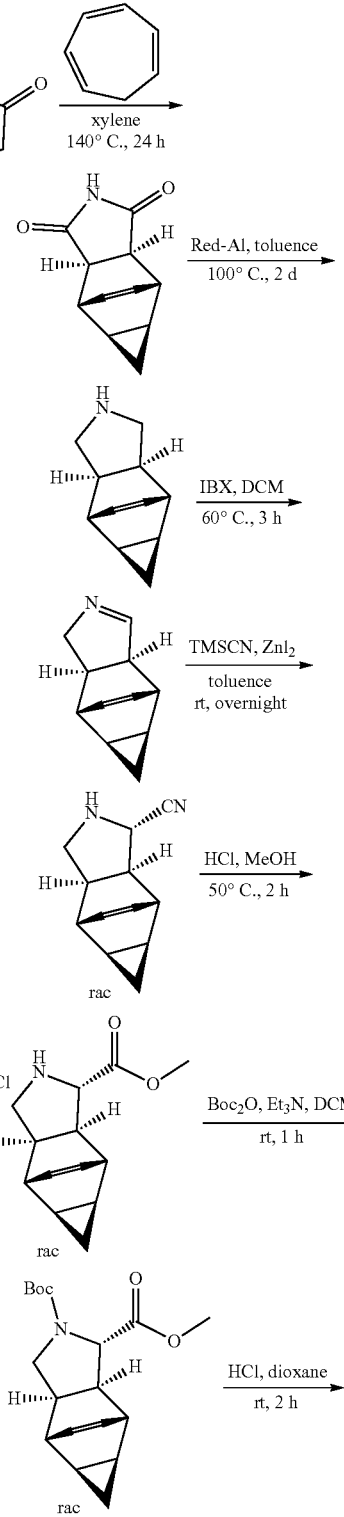

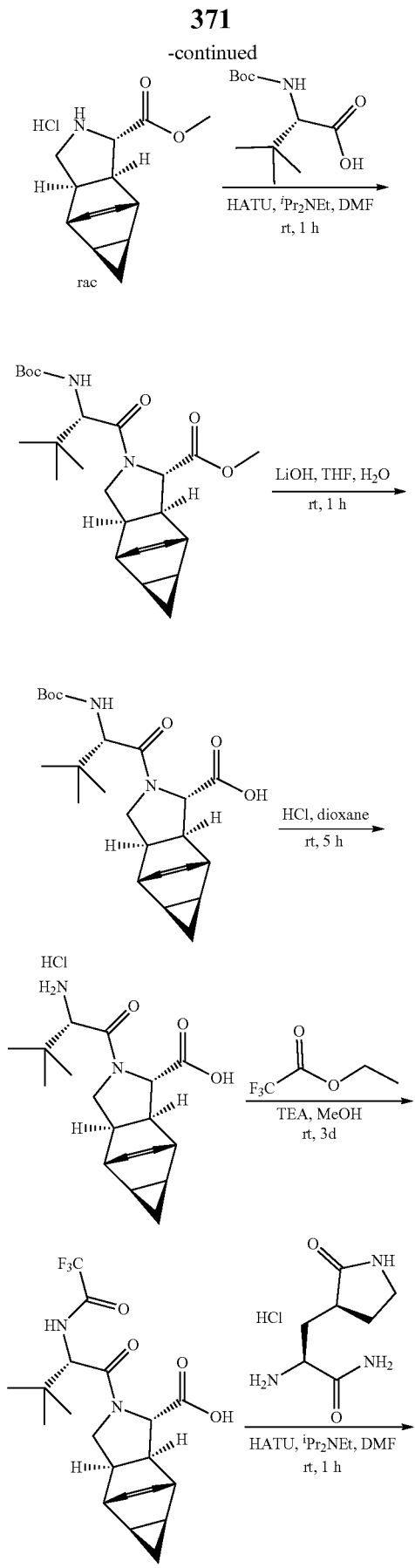

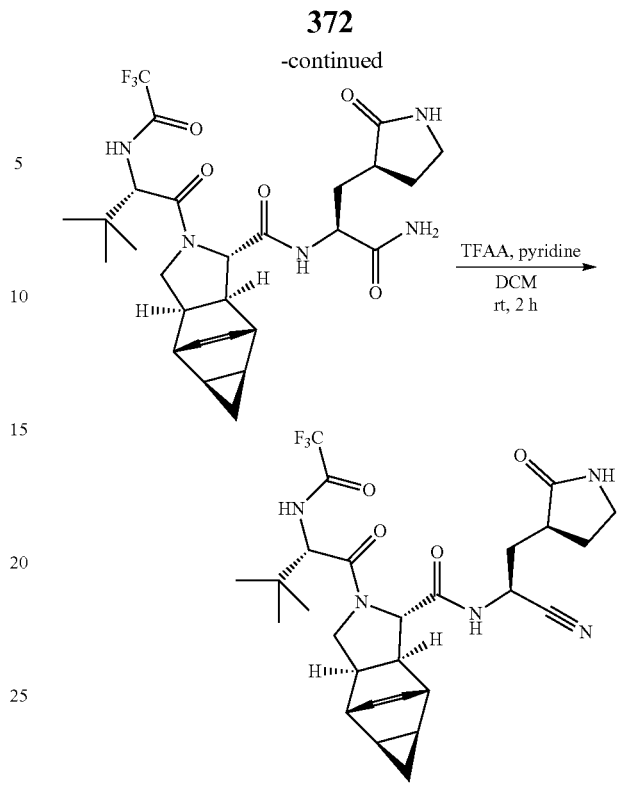

To a solution of cyclohepta-1,3,5-triene (3.13 g, 34.0 mmol, 1.1 eq.) in xylene (15 mL, 81.0 mmol, 2.6 eq.) was added 1H-pyrrole-2,5-dione (3.0 g, 30.9 mmol, 1.0 eq.). The mixture was stirred for 24 h at 140° C. and then cooled to rt. The cream-colored mixture was filtered, and the filter cake was washed with DCM (2×30 mL). The filter cake was combined to provide (3aR,4R,4aR,5aS,6S,6aS)-4,4a,5,5a,6,6a-hexahydro-4,6-ethenocyclopropa[f]isoindole-1,3(2H,3aH)-dione (5.0 g, 85%) as an off-white solid. $^1$H NMR (400 MHz, DMSO-d$_6$) δ 10.94 (s, 1H), 5.72-5.76 (m, 2H), 3.14-3.18 (m, 2H), 2.96-2.97 (m, 2H), 1.07-1.11 (m, 2H), 0.21-0.25 (m, 1H), 0.01-0.06 (m, 1H). LC-MS (ESI, m/z): 190 [M+H]$^+$.

A solution of (3aR,4R,4aR,5aS,6S,6aS)-4,4a,5,5a,6,6a-hexahydro-4,6-ethenocyclopropa[f]isoindole-1,3(2H,3aH)-dione (5.00 g, 26.4 mmol, 1.0 eq.) in toluene was stirred at 0° C., and then sodium bis(2-methoxyethoxy) aluminum hydride (38.4 g, 133 mmol, 5.0 eq., 70% in toluene) was added dropwise. The mixture was stirred for 20 min at 0° C. The solution was stirred for 2 days at 100° C. and then cooled to rt. A sodium hydroxide aqueous solution (100 mL, 30%) was added dropwise at 0° C. The mixture was extracted with EA (3×150 mL). The organic layers were combined, dried over anhydrous sodium sulfate, filtered and concentrated under reduced pressure to afford (3aR,4R,4aR,5aS,6S,6aS)-1,2,3,3a,4,4a,5,5a,6,6a-decahydro-4,6-ethenocyclopropa[f]isoindole (3.5 g, crude) as a red oil. LC-MS (ESI, m/z): 162 [M+H]$^+$.

To a solution of (3aR,4R,4aR,5aS,6S,6aS)-1,2,3,3a,4,4a,5,5a,6,6a-decahydro-4,6-ethenocyclopropa[f]isoindole (3.50 g, 21.7 mmol, 1.0 eq.) in DCM (60 mL) was added 2-Iodoxybenzoic acid (6.69 g, 23.9 mmol, 1.1 eq.). The mixture was stirred for 3 h at 60° C. The reaction was quenched with aqueous sodium thiosulfate (30 mL). The mixture was extracted with DCM (3×100 mL). The organic layers were combined, washed with saturated sodium bicarbonatebrine aqueous (2×50 mL), dried over anhydrous sodium sulfate, filtered and concentrated under reduced pressure to afford the crude product. The crude product was chromatographed on a silica gel column with EA:PE (60%-70%) to provide rac-(3aS,4S,4aS,5aR,6R,6aR)-1,3a,4,4a,5, 5a,6,6a-octahydro-4,6-ethenocyclopropa[f]isoindole (1.7 g, crude) as an off-white solid. $^1$H NMR (400 MHz, Chloroform-d) δ 7.32-7.33 (m, 1H), 5.71-5.73 (m, 2H), 3.83-3.91 (m, 1H), 3.31-3.38 (m, 1H), 3.13-3.17 (m, 1H), 3.00-3.04 (m, 1H), 2.85-2.89 (m, 1H), 2.52-2.59 (m, 1H), 0.92-1.03 (m, 2H), 0.16-0.29 (m, 2H). LC-MS (ESI, m/z): 160 [M+H]$^+$.

To a solution of rac-(3aS,4S,4aS,5aR,6R,6aR)-1,3a,4,4a, 5,5a,6,6a-octahydro-4,6-ethenocyclopropa[f]isoindole (1.7 g, 10.7 mmol, 1.0 eq.) in toluene (40 mL) was added zinc iodide (409 mg, 1.28 mmol, 0.12 eq.) and trimethylsilyl cyanide (4.77 g, 48.0 mmol, 4.5 eq.). The mixture was stirred overnight at rt. The reaction was quenched with water (30 mL). The mixture was extracted with EA (3×100 mL). The organic layers were combined, washed with brine (2×50 mL), dried over anhydrous sodium sulfate, filtered and concentrated under reduced pressure to afford the crude product. The crude product was chromatographed on a silica gel column with EA:PE (60%-80%) to provide rac-(3aR, 4R,4aR,5aS,6S,6aS)-1,2,3,3a,4,4a,5,5a,6,6a-decahydro-4,6-ethenocyclopropa[f]isoindole-1-carbonitrile (1.1 g, 49%) as a light yellow oil. LC-MS (ESI, m/z): 187 [M+H]$^+$.

A mixture rac-(3aR,4R,4aR,5aS,6S,6aS)-1,2,3,3a,4,4a,5, 5a,6,6a-decahydro-4,6-ethenocyclopropa[f]isoindole-1-carbonitrile (800 mg, 4.30 mmol, 1.0 eq.) in hydrogen chloride (7.5 mL, 4 M in MeOH) was stirred for 2 h at 50° C. The mixture was concentrated under reduced pressure to afford methyl rac-(3aR,4R,4aR,5aS,6S,6aS)-1,2,3,3a,4,4a,5,5a,6, 6a-decahydro-4,6-ethenocyclopropa[f]isoindole-1-carboxylate hydrochloride (800 mg, crude) as a yellow solid. LC-MS (ESI, m/z): 220 [M+H]$^+$.

To a solution of methyl rac-(3aR,4R,4aR,5aS,6S,6aS)-1, 2,3,3a,4,4a,5,5a,6,6a-decahydro-4,6-ethenocyclopropa[f] isoindole-1-carboxylate hydrochloride (800 mg, 3.65 mmol, 1.0 eq.) in DCM (10 mL) was added triethylamine (1.11 g, 10.9 mmol, 3.0 eq.) and di-tert-butyl dicarbonate (1.04 g, 4.74 mmol, 1.3 eq.). The mixture was stirred for 1 h at rt. The reaction was quenched with H$_2$O (20 mL). The mixture was extracted with EA (3×50 mL). The organic layers were combined, washed with brine (2×30 mL), dried over anhydrous sodium sulfate, filtered and concentrated under reduced pressure to afford the crude product. The crude product was chromatographed on a silica gel column with EA:PE (10%-15%) to provide rac-2-(tert-butyl) 1-methyl (3aR,4R,4aR,5aS,6S,6aS)-3,3a,4,4a,5,5a,6,6a-octahydro-4, 6-ethenocyclopropa[f]isoindole-1,2(1H)-dicarboxylate (830 mg, 71%) as a colorless oil. $^1$H NMR (400 MHz, CD$_3$OD-d$_4$) δ 5.81-5.89 (m, 2H), 3.92-3.98 (m, 1H), 3.74-3.75 (m, 3H), 3.52-3.58 (m, 1H), 3.20-3.29 (m, 1H), 3.02-3.06 (m, 1H), 2.88-2.92 (m, 1H), 2.55-2.66 (m, 2H), 1.38-1.46 (m, 9H), 0.94-0.99 (m, 2H), 0.13-0.21 (m, 2H). LC-MS (ESI, m/z): 320 [M+H]$^+$.

To a mixture of rac-2-(tert-butyl) 1-methyl (3aR,4R,4aR, 5aS,6S,6aS)-3,3a,4,4a,5,5a,6,6a-octahydro-4,6-ethenocyclopropa[f]isoindole-1,2(1H)-dicarboxylate (400 mg, 1.25 mmol, 1.0 eq.) in 1,4-dioxane (4 mL) was added hydrogen chloride (4 mL, 4 M in 1,4-dioxane) stirred at rt. The mixture was stirred for 2 h at rt and then concentrated under reduced pressure to afford rac-methyl (1S,3aR,4R,4aR,5aS,6S,6aS)-1,2,3,3a,4,4a,5,5a,6,6a-decahydro-4,6-ethenocyclopropa[f] isoindole-1-carboxylate hydrochloride (300 mg, crude) as a light yellow solid. LC-MS (ESI, m/z): 220 [M+H]$^+$.

To a mixture of (S)-2-((tert-butoxycarbonyl)amino)-3,3-dimethylbutanoic acid (271 mg, 1.17 mmol, 1.0 eq.) and o-(7-azabenzotriazol-1-yl)-N,N,N',N'-te-tramethyluronium hexafluorophosphate (535 mg, 1.41 mmol, 1.2 eq.) in dimethylformamide (5 mL) was added N-ethyl-N-isopropylpropan-2-amine (910 mg, 7.04 mmol, 6.0 eq.) at 0° C. After stirring for 20 min, rac-methyl (1S,3aR,4R,4aR,5aS,6S, 6aS)-1,2,3,3a,4,4a,5,5a,6,6a-decahydro-4,6-ethenocyclopropa[f]isoindole-1-carboxylate hydrochloride (300 mg, 1.17 mmol, 1.0 eq.) was added. The mixture was stirred for 1 h at rt. The reaction was quenched with water (20 mL). The mixture was extracted with EA (3×50 mL). The organic layers were combined, washed with brine (2×20 mL), dried over anhydrous sodium sulfate, filtered and concentrated under reduced pressure to afford the crude product. The crude was chromatographed on a silica gel column with EA:PE (11%-13%) to provide methyl (3aR,4R,4aR,5aS,6S, 6aS)-2-((S)-2-((tert-butoxycarbonyl)amino)-3,3-dimethylbutanoyl)-1,2,3,3a,4,4a,5,5a,6,6a-decahydro-4,6-ethenocyclopropa[f]isoindole-1-carboxylate (350 mg, 62%, white solid) as a diastereomeric mixture. LC-MS (ESI, m/z): 433 [M+H]$^+$.

To the diastereomeric mixture with methyl (3aR,4R,4aR, 5aS,6S,6aS)-2-((S)-2-((tert-butoxycarbonyl)amino)-3,3-dimethylbutanoyl)-1,2,3,3a,4,4a,5,5a,6,6a-decahydro-4,6-ethenocyclopropa[f]isoindole-1-carboxylate (350 mg, 0.809 mmol, 1.0 eq.) in THF (4 mL) and H$_2$O (2 mL) was added lithium hydroxide (96.9 mg, 4.05 mmol, 5.0 eq.). The mixture was stirred for 1 h at rt and then concentrated under reduced pressure to remove THF. The mixture was acidified to pH=5 with hydrochloric acid (1 M). The mixture was extracted with EA (3×50 mL). The organic layers were combined, dried over anhydrous sodium sulfate, filtered and concentrated under reduced pressure to provide (3aR,4R, 4aR,5aS,6S,6aS)-2-((S)-2-((tert-butoxycarbonyl)amino)-3, 3-dimethylbutanoyl)-1,2,3,3a,4,4a,5,5a,6,6a-decahydro-4,6-ethenocyclopropa[f]isoindole-1-carboxylic acid (320 mg, 94%, white solid) as a as a diastereomeric mixture. LC-MS (ESI, m/z): 419 [M+H]$^+$.

To the diastereomeric mixture with (3aR,4R,4aR,5aS,6S, 6aS)-2-((S)-2-((tert-butoxycarbonyl)amino)-3,3-dimethylbutanoyl)-1,2,3,3a,4,4a,5,5a,6,6a-decahydro-4,6-ethenocyclopropa[f]isoindole-1-carboxylic acid (320 mg, 0.772 mmol, 1.0 eq.) in dioxane (3 mL) was added hydrogen chloride (3 mL, 4 M in 1,4-dioxane) stirred at rt. The mixture was stirred for 5 h at rt. The mixture was concentrated under reduced pressure to afford (3aR,4R,4aR,5aS)-2-((S)-2-amino-3,3-dimethylbutanoyl)-1,2,3,3a,4,4a,5,5a,6,6a-decahydro-4,6-ethenocyclopropa[f]isoindole-1-carboxylic acid hydrochloride (240 mg, crude, yellow solid) as a diastereomeric mixture. LC-MS (ESI, m/z): 319 [M+H]$^+$.

To the diastereomeric mixture containing (3aR,4R,4aR, 5aS)-2-((S)-2-amino-3,3-dimethylbutanoyl)-1,2,3,3a,4,4a,5, 5a,6,6a-decahydro-4,6-ethenocyclopropa[f]isoindole-1-carboxylic acid hydrochloride (240 mg, 0.759 mmol, 1.0 eq.) in MeOH (2.5 mL) was added triethylamine (921 mg, 9.11 mmol, 12.0 eq.) and ethyl 2,2,2-trifluoroacetate (1.08 g, 7.59 mmol, 10.0 eq.). The mixture was stirred for 3 days at rt. The reaction was quenched with water (50 mL) and then concentrated under reduced pressure to remove MeOH. The mixture was acidified to pH=4 with hydrochloric acid (1 M). The mixture was extracted with EA (3×100 mL). The organic layers were combined, washed with brine (2×30 mL), dried over anhydrous sodium sulfate, filtered and concentrated under reduced pressure to afford (3aR,4R,4aR, 5aS,6S,6aS)-2-((S)-3,3-dimethyl-2-(2,2,2-trifluoroacetamido)butanoyl)-1,2,3,3a,4,4a,5,5a,6,6a-decahydro-4,6- ethenocyclopropa[f]isoindole-1-carboxylic acid (260 mg, crude, yellow solid) as a diastereomeric mixture. LC-MS (ESI, m/z): 415 [M+H]⁺.

To a mixture of the diastereomeric mixture with (3aR,4R,4aR,5aS,6S,6aS)-2-((S)-3,3-dimethyl-2-(2,2,2-trifluoro-acetamido)butanoyl)-1,2,3,3a,4,4a,5,5a,6,6a-decahydro-4,6-ethenocyclopropa[f]isoindole-1-carboxylic acid (260 mg, 0.627 mmol, 1.0 eq.) and o-(7-azabenzotriazol-1-yl)-N,N,N',N'-te-tramethyluronium hexafluorophosphate (286 mg, 0.752 mmol, 1.2 eq.) in dimethylformamide (3 mL) was added N-ethyl-N-isopropylpropan-2-amine (487 mg, 3.76 mmol, 6.0 eq.) at 0° C. After stirring for 20 min, (S)-2-amino-3-((S)-2-oxopyrrolidin-3-yl)propanamide hydrochloride (143 mg, 0.690 mmol, 1.1 eq.) was added. The mixture was stirred for 1 h at rt and then purified by C18 column with CH₃CN/Water (0.05% FA). The desired fraction was concentrated under reduced pressure to provide (1S,3aR,4R,4aR,5aS,6S,6aS)—N—((S)-1-amino-1-oxo-3-((S)-2-oxopyrrolidin-3-yl)propan-2-yl)-2-((S)-3,3-dimethyl-2-(2,2,2-trifluoroacetamido)butanoyl)-1,2,3,3a,4,4a,5,5a,6,6a-decahydro-4,6-ethenocyclopropa[f]isoindole-1-carboxamide (150 mg, 42%, white solid) as a diastereomeric mixture. LC-MS (ESI, m/z): 568 [M+H]⁺.

To a mixture of the diastereomeric mixture with (1S,3aR,4R,4aR,5aS,6S,6aS)—N—((S)-1-amino-1-oxo-3-((S)-2-oxopyrrolidin-3-yl)propan-2-yl)-2-((S)-3,3-dimethyl-2-(2,2,2-trifluoroacetamido)butanoyl)-1,2,3,3a,4,4a,5,5a,6,6a-decahydro-4,6-ethenocyclopropa[f]isoindole-1-carboxamide (150 mg, 0.264 mmol, 1 eq.) in DCM (1.5 mL) was added pyridine (105 mg, 1.32 mmol, 5.0 eq.) and trifluoroacetic anhydride (99.9 mg, 0.475 mmol, 1.8 eq.). The mixture was stirred 2 h at rt. The reaction was quenched with water (20 mL). The mixture was extracted with DCM (3×30 mL). The organic layers were combined, washed with brine (2×10 mL), dried over anhydrous sodium sulfate, filtered and concentrated under reduced pressure to afford the crude product. The crude product was purified by prep-HPLC (Column: XBridge Prep Phenyl OBD Column, 19*250 mm, 5 m; Mobile Phase A: Water (0.1% FA), Mobile Phase B: ACN; Flow rate: 25 mL/min; Gradient: 37% B to 67% B in 7 min, 67% B; Wave Length: 254 nm; RT1 (min): 6) to provide (3aR,4R,4aR,5aS,6S,6aS)—N—((S)-1-cyano-2-((S)-2-oxopyrrolidin-3-yl)ethyl)-2-((S)-3,3-dimethyl-2-(2,2,2-trifluoroacetamido)butanoyl)-1,2,3,3a,4,4a,5,5a,6,6a-decahydro-4,6-ethenocyclopropa[f]isoindole-1-carboxamide (46.4 mg, 31%, white solid) as a diastereomeric mixture. ¹H NMR (400 MHz, 80° C., DMSO-d₆) δ 8.75-9.10 (m, 1H), 8.43-8.73 (m, 1H), 7.32-7.52 (m, 1H), 5.45-5.77 (m, 2H), 4.84-4.93 (m, 1H), 4.20-4.65 (m, 1H), 3.94-4.07 (m, 1H), 3.70-3.80 (m, 1H), 3.32-3.61 (m, 1H), 3.01-3.23 (m, 3H), 2.76-2.95 (m, 1H), 2.58-2.67 (m, 1H), 2.24-2.43 (m, 2H), 1.97-2.23 (m, 2H), 1.62-1.88 (m, 2H), 0.84-1.02 (m, 11H), 0.07-0.15 (m, 1H), 0.00-0.02 (m, 1H). LC-MS (ESI, m/z): 550 [M+H]⁺.

Example 89

Compound 89

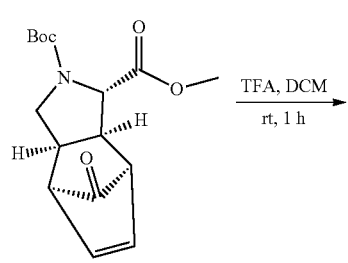

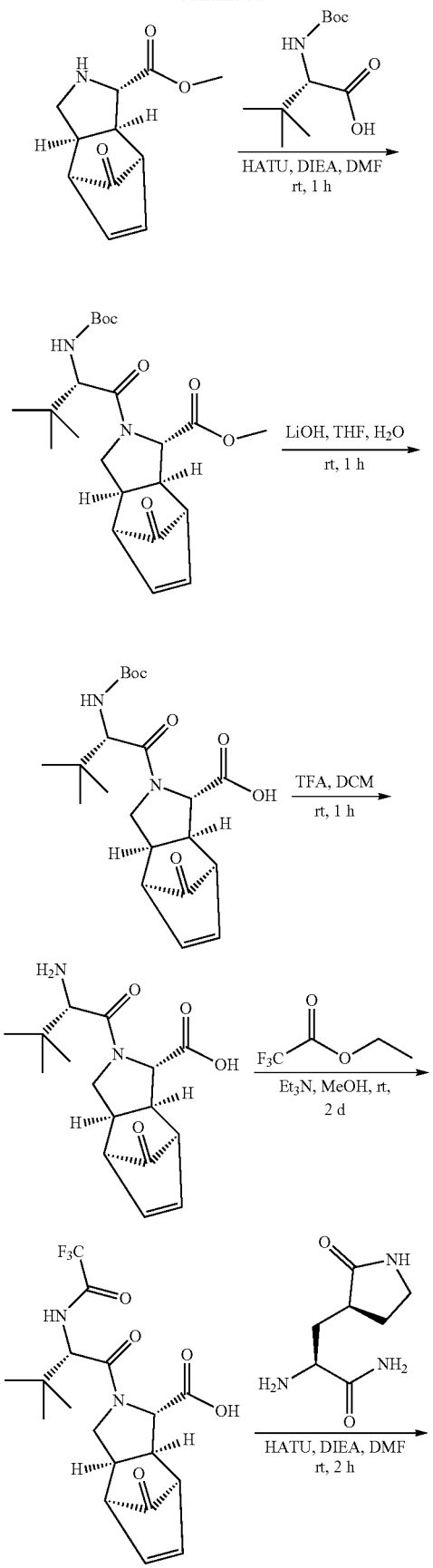

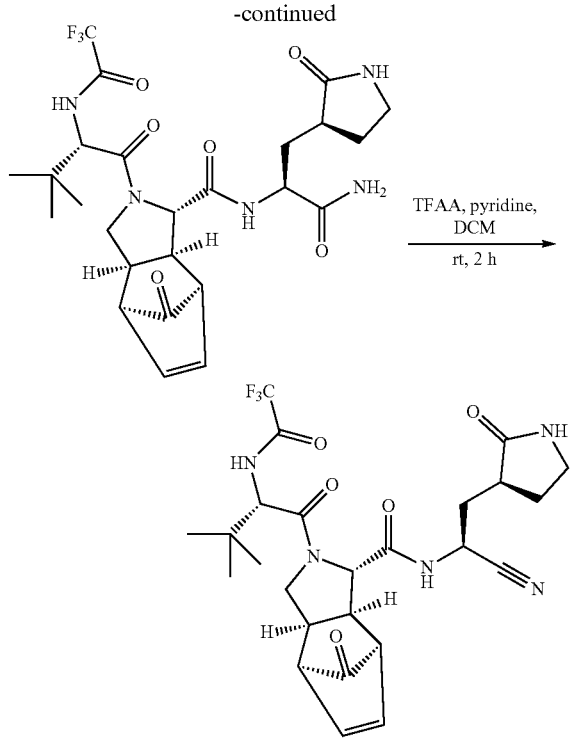

To a stirred mixture of 4-tert-butyl 3-methyl (1R,2R,3S,6S,7S)-10-oxo-4-azatricyclo[5.2.1.0^{2,6}]dec-8-ene-3,4-dicarboxylate (400 mg, 1.30 mmol, 1.0 eq.) in DCM (15 mL) was added trifluoroacetic acid (5 mL) at rt. The mixture was stirred for 1 h at rt and then concentrated under reduced pressure to provide methyl (1R,2R,3S,6S,7S)-10-oxo-4-azatricyclo[5.2.1.0^{2,6}]dec-8-ene-3-carboxylate (269 mg, crude) as a brown oil. LC-MS (ESI, m/z): 208 [M+H]$^+$.

To a stirred mixture of (2S)-2-[(tert-butoxycarbonyl)amino]-3,3-dimethylbutanoic acid (301 mg, 1.30 mmol, 1.0 eq.) and o-(7-azabenzotriazol-1-yl)-N,N,N',N'-te-tramethyluronium hexafluorophosphate (644 mg, 1.69 mol, 1.3 eq.) in DMF (4 mL) was added N-ethyl-N-isopropylpropan-2-amine (1.34 g, 10.4 mmol, 8.0 eq.) at 0° C. After stirring for 20 min at 0° C., methyl (1R,2R,3S,6S,7S)-10-oxo-4-azatricyclo[5.2.1.0^{2,6}]dec-8-ene-3-carboxylate (270 mg, 1.30 mmol, 1.0 eq.) was added. The mixture was stirred for 1 h at rt. The reaction was quenched with water (20 mL). The mixture was extracted with EtOAc (3×20 mL). The organic layers were combined, washed with brine (2×20 mL), dried over anhydrous sodium sulfate, filtered and concentrated under reduced pressure to afford the crude product. The crude product was chromatographed on a silica gel column with EA:PE (3:10) to provide methyl (1R,2R,3S,6S,7S)-4-[(2S)-2-[(tert-butoxycarbonyl)amino]-3,3-dimethylbutanoyl]-10-oxo-4-azatricyclo[5.2.1.0^{2,6}]dec-8-ene-3-carboxylate (330 mg, 57%) as a white solid. $^1$H NMR (400 MHz, CDCl$_3$-d) δ 6.33-6.69 (m, 2H), 5.11-5.26 (m, 1H), 4.43-4.56 (m, 1H), 4.15-4.30 (m, 1H), 3.85-3.94 (m, 1H), 3.69-3.83 (m, 4H), 3.27-3.38 (m, 1H), 3.16-3.25 (m, 1H), 3.04-3.13 (m, 2H), 1.37-1.55 (m, 9H), 0.90-1.07 (m, 9H). LC-MS (ESI, m/z): 421 [M+H]$^+$.

To a stirred methyl methyl (1R,2R,3S,6S,7S)-4-[(2S)-2-[(tert-butoxycarbonyl)amino]-3,3-dimethylbutanoyl]-10-oxo-4-azatricyclo[5.2.1.0^{2,6}]dec-8-ene-3-carboxylate (300 mg, 0.713 mmol, 1.0 eq.) in THF (3 mL)/water (3 mL) was added lithium hydroxide (85.4 mg, 3.56 mmol, 5.0 eq.) at rt. The mixture was stirred for 2 h at rt. The mixture was acidified to pH=6 with hydrochloric acid (2M) and extracted with EA (3×30 mL). The organic layers were combined, washed with brine (2×30 mL), dried over anhydrous sodium sulfate and concentrated under reduced pressure to afford (1R,2R,3S,6S,7S)-4-[(2S)-2-[(tert-butoxycarbonyl)amino]-3,3-dimethylbutanoyl]-10-oxo-4-azatricyclo[5.2.1.0^{2,6}]dec-8-ene-3-carboxylic acid (250 mg, crude) as an off-white solid. LC-MS (ESI, m/z): 407 [M+H]$^+$.

To a stirred mixture of (1R,2R,3S,6S,7S)-4-[(2S)-2-[(tert-butoxycarbonyl)amino]-3,3-dimethylbutanoyl]-10-oxo-4-azatricyclo[5.2.1.0^{2,6}]dec-8-ene-3-carboxylic acid (250 mg, 0.615 mmol, 1.0 eq.) in DCM (6 mL) was added trifluoroacetic acid (2 mL) at rt. The mixture was stirred for 1 h at rt and then concentrated under reduced pressure to provide (1R,2R,3S,6S,7S)-4-[(2S)-2-amino-3,3-dimethylbutanoyl]-10-oxo-4-azatricyclo[5.2.1.0^{2,6}]dec-8-ene-3-carboxylic acid (188 mg, crude) as a brown oil. LC-MS (ESI, m/z): 307 [M+H]$^+$.

To a stirred mixture of (1R,2R,3S,6S,7S)-4-[(2S)-2-amino-3,3-dimethylbutanoyl]-10-oxo-4-azatricyclo[5.2.1.0^{2,6}]dec-8-ene-3-carboxylic acid (188 mg, 0.614 mmol, 1 eq.) in MeOH (2 mL) was added trimethylamine (745 mg, 7.37 mmol, 12.0 eq.) and ethyl 2,2,2-trifluoroacetate (872 mg, 6.14 mmol, 10.0 eq.). The mixture was stirred for 2 days at rt and then acidified to pH=6 with hydrochloric acid (2M). The reaction was quenched with water (15 mL). The mixture was extracted with EtOAc (3×15 mL). The organic layers were combined, washed with brine (2×15 mL), dried over anhydrous sodium sulfate, filtered and concentrated under reduced pressure to afford (1R,2R,3S,6S,7S)-4-[(2S)-3,3-dimethyl-2-(2,2,2-trifluoroacetamido)butanoyl]-10-oxo-4-azatricyclo[5.2.1.0^{2,6}]dec-8-ene-3-carboxylic acid (166 mg, 67%, crude) as a yellow solid. LC-MS (ESI, m/z): 403 [M+H]$^+$.

To a stirred mixture of (2S)-2-amino-3-[(3S)-2-oxopyrrolidin-3-yl]propanamide (68.1 mg, 0.398 mmol, 1.0 eq.) and o-(7-azabenzotriazol-1-yl)-N,N,N',N'-te-tramethyluronium hexafluorophosphate (196 mg, 0.517 mmol, 1.3 eq.) in DMF (2 mL) was added N-ethyl-N-isopropylpropan-2-amine (411 mg, 3.18 mmol, 8.0 eq.). After stirring for min at 0° C., (1R,2R,3S,6S,7S)-4-[(2S)-3,3-dimethyl-2-(2,2,2-trifluoroacetamido)butanoyl]-10-oxo-4-azatricyclo[5.2.1.0^{2,6}]dec-8-ene-3-carboxylic acid (160 mg, 0.398 mmol, 1.0 eq.) was added. The mixture was stirred for 2 h at rt. The crude product was purified by C18 column with CH$_3$CN/Water (0.05% TFA). The desired fraction was concentrated under reduced pressure to provide (2S)-2-{[(1R,2R,3S,6S,7S)-4-[(2S)-3,3-dimethyl-2-(2,2,2-trifluoroacetamido)butanoyl]-10-oxo-4-azatricyclo[5.2.1.0^{2,6}]dec-8-en-3-yl]formamido}-3-[(3S)-2-oxopyrrolidin-3-yl]propanamide (90 mg, crude) as a yellow solid. LC-MS (ESI, m/z): 556 [M+H]$^+$.

To a stirred mixture of (2S)-2-{[(1R,2R,3S,6S,7S)-4-[(2S)-3,3-dimethyl-2-(2,2,2-trifluoroacetamido)butanoyl]-10-oxo-4-azatricyclo[5.2.1.0^{2,6}]dec-8-en-3-yl]formamido}-3-[(3S)-2-oxopyrrolidin-3-yl]propanamide (90.0 mg, 0.162 mmol, 1.0 eq.) in DCM (2 mL) was added pyridine (51.2 mg, 0.648 mmol, 4.0 eq.) and trifluoroacetic anhydride (51.0 mg, 0.243 mmol, 1.5 eq.). The mixture was stirred for 2 h at rt. The reaction was quenched with water (10 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was purified by prep-HPLC (Column: XSelect CSH Prep C18 OBD Column, 19*250 mm, 5 m; Mobile Phase A: Water (0.1% FA), Mobile Phase B: ACN; Flow rate: 25 mL/min; Gradient: 30% B to 60% B in 7 min, 60% B; Wave Length: 254 nm; RT1 (min): 6) to provide (1R,2R,3S,6S,7S)—N-[(1S)-1-cyano-2-[(3S)-2-oxopyrrolidin-3-yl]ethyl]-4-[(2S)-3,3-dimethyl-2-(2,2,2-trifluoroacetamido)butanoyl]-10-oxo-4-azatricyclo[5.2.1.0^{2,6}]dec-8-ene-3-carboxamide (6.9 mg, 7%) as a white solid. $^1$H NMR (400 MHz, DMSO-d$_6$) δ 8.75-9.08 (m, 2H), 7.32-7.50 (m, 1H), 6.35-6.65 (m, 2H), 4.82-5.00 (m, 1H), 4.30-4.75 (m, 1H), 4.10-4.28 (m, 1H), 3.72-3.90 (m, 1H), 3.56-3.70 (m, 1H), 3.20-3.30 (m, 1H), 3.10-3.19 (m, 4H), 2.81-2.92 (m, 1H), 2.30-2.40 (m, 1H), 2.10-2.20 (m, 2H), 1.62-1.90 (m, 2H), 0.81-1.10 (m, 9H). LC-MS (ESI, m/z): 538 [M+H]$^+$.

Example 90

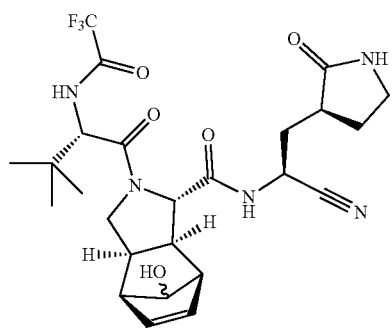

Compound 90

Compound 90 was prepared similarly as described for compound 88, using the TFA salt of methyl (1S,3aS,4S,7R,7aR,8R)-8-hydroxy-2,3,3a,4,7,7a-hexahydro-1H-4,7-methanoisoindole-1-carboxylate in place of methyl rac-(3aR,4R,4aR,5aS,6S,6aS)-1,2,3,3a,4,4a,5,5a,6,6a-decahydro-4,6-ethenocyclopropa[f]isoindole-1-carboxylate hydrochloride to provide (1R,2R,3S,6S,7S)—N-[(1S)-1-cyano-2-[(3S)-2-oxopyrrolidin-3-yl]ethyl]-4-[(2S)-3,3-dimethyl-2-(2,2,2-trifluoroacetamido)butanoyl]-10-hydroxy-4-azatricyclo[5.2.1.0^{2,6}]dec-8-ene-3-carboxamide as a diastereomeric mixture. $^1$H NMR (400 MHz, 80° C., DMSO-d$_6$) δ 8.60-9.10 (m, 2H), 7.30-7.60 (m, 1H), 5.80-6.20 (m, 2H), 5.00-5.30 (m, 1H), 4.80-5.00 (m, 1H), 4.40-4.75 (m, 1H), 4.05-4.30 (m, 1H), 3.70-3.90 (m, 1H), 3.40-3.68 (m, 2H), 3.10-3.58 (m, 2H), 2.85-3.05 (m, 2H), 2.25-2.85 (m, 2H), 2.30-2.50 (m, 1H), 2.10-2.21 (m, 2H), 1.60-1.90 (m, 2H), 0.80-1.10 (m, 9H). LC-MS (ESI, m/z): 540 [M+H]$^+$.

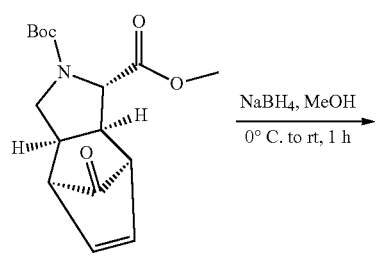

NaBH$_4$, MeOH
0° C. to rt, 1 h

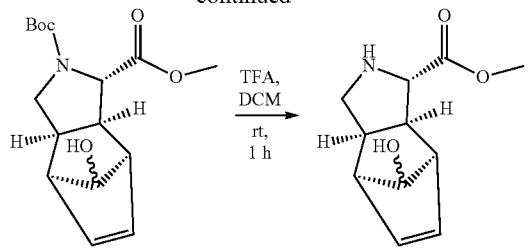

TFA, DCM
rt, 1 h

To a solution of 2-(tert-butyl) 1-methyl (1S,3aS,4S,7R,7aR)-8-oxo-1,3,3a,4,7,7a-hexahydro-2H-4,7-methanoisoindole-1,2-dicarboxylate (950 mg, 3.09 mmol, 1.0 eq.) in methanol (10 mL) was added sodium borohydride (114 mg, 3.09 mmol, 1.0 eq.) at 0° C. The mixture was stirred for 1 h at rt. The reaction was quenched with sat. ammonium chloride (aq.). The mixture was extracted with EA (3×80 mL). The organic layers were combined, washed with brine (2×50 mL), dried over anhydrous sodium sulfate, filtered and concentrated under reduced pressure to afford 2-(tert-butyl) 1-methyl (1S,3aS,4S,7R,7aR,8R)-8-hydroxy-1,3,3a,4,7,7a-hexahydro-2H-4,7-methanoisoindole-1,2-dicarboxylate (700 mg, crude) as a yellow oil. LC-MS (ESI, m/z): 210 [M−Boc+H]$^+$.

To a stirred mixture of 2-(tert-butyl) 1-methyl (1S,3aS,4S,7R,7aR)-8-hydroxy-1,3,3a,4,7,7a-hexahydro-2H-4,7-methanoisoindole-1,2-dicarboxylate (450 mg, 1.45 mmol, 1.0 eq.) in DCM (4.5 mL) was added trifluoroacetic acid (1.5 mL) at rt. The mixture was stirred for 1 h at rt and then concentrated under reduced pressure to afford methyl (1S,3aS,4S,7R,7aR,8R)-8-hydroxy-2,3,3a,4,7,7a-hexahydro-1H-4,7-methanoisoindole-1-carboxylate (305 mg, crude) as a yellow oil. LC-MS (ESI, m/z): 210 [M+H]$^+$.

Example 91

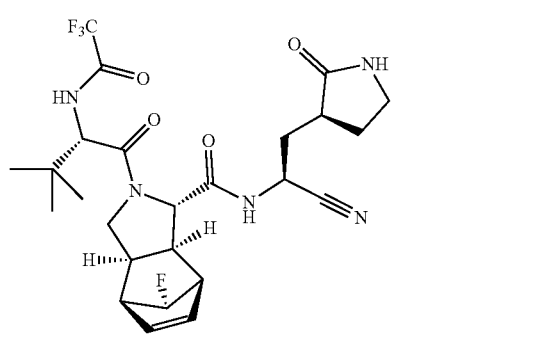

Compound 91

Compound 91 was prepared as described for compound 89, using methyl (1S,3aS,4S,7R,7aR,8*S)-8-fluoro-2,3,3a,4,7,7a-hexahydro-1H-4,7-methanoisoindole-1-carboxylate instead of methyl (1R,2R,3S,6S,7S)-10-oxo-4-azatricyclo[5.2.1.0^{2,6}]dec-8-ene-3-carboxylate to provide (1S,3aS,4S,7R,7aR,8S)—N—((S)-1-cyano-2-((S)-2-oxopyrrolidin-3-yl)ethyl)-2-((S)-3,3-dimethyl-2-(2,2,2-trifluoroacetamido)butanoyl)-8-fluoro-2,3,3a,4,7,7a-hexahydro-1H-4,7-methanoisoindole-1-carboxamide. $^1$H NMR (400 MHz, 80° C., DMSO-d6) δ 8.85-9.05 (m, 1H), 8.40-8.85 (m, 1H), 7.30-7.60 (m, 1H), 5.80-6.20 (m, 2H), 4.60-5.05 (m, 1H), 4.40-4.58 (m, 1H), 4.30-4.38 (m, 1H), 4.05-4.25 (m, 1H), 3.70-3.90 (m, 1H), 3.40-3.68 (m, 1H), 3.12-3.40 (m, 3H), 3.00-3.10 (m, 1H), 2.90-3.00 (m, 1H), 2.70-2.90 (m, 1H), 2.30-2.45 (m, 1H), 2.05-2.30 (m, 2H), 1.60-1.95 (m, 2H), 0.80-1.10 (m, 9H). LC-MS (ESI, m/z): 542 [M+H]⁺.

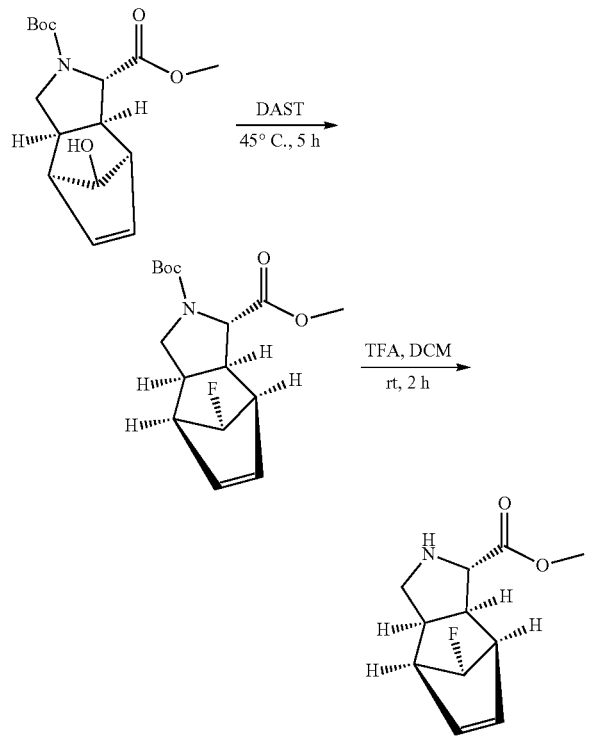

A mixture of 2-(tert-butyl) 1-methyl (1S,3aS,4S,7R,7aR,8R)-8-hydroxy-1,3,3a,4,7,7a-hexahydro-2H-4,7-methanoisoindole-1,2-dicarboxylate (1.0 g, 3.23 mmol, 1.0 eq.) in diethylaminosulfur trifluoride (20 mL) was stirred for 5 h at 45° C. The mixture was diluted with dichloromethane (100 mL). The reaction was quenched with sat. sodium bicarbonate (80 mL) at 0° C. The mixture was extracted with dichloromethane (3×80 mL). The organic layers were combined, washed with brine (2×50 mL), dried over anhydrous sodium sulfate, filtered and concentrated under reduced pressure. The crude product was purified by prep-HPLC (Column: XSelect CSH Prep C18 OBD Column, 19*150 mm, 5 m; Mobile Phase A: Water (0.05% TFA), Mobile Phase B: ACN; Flow rate: 25 mL/min; Gradient: 32% B to 52% B in 10 min, 52% B; Wave Length: 254 nm; RT1 (min): 8.78/9.3) to provide 2-(tert-butyl) 1-methyl (1S,3aS,4S,7R,7aR,8S)-8-fluoro-1,3,3a,4,7,7a-hexahydro-2H-4,7-methanoisoindole-1,2-dicarboxylate (350 mg, 35%) as a white oil. ¹H NMR (400 MHz, DMSO-d₆) δ 6.05-6.24 (m, 2H), 4.25-4.57 (m, 1H), 3.81-4.03 (m, 1H), 3.56-3.76 (m, 3H), 3.34-3.48 (m, 1H), 3.10-3.26 (m, 1H), 2.83-3.09 (m, 4H), 1.19-1.51 (m, 9H). LC-MS (ESI, m/z): 256 [M−56+H]⁺.

To a stirred mixture of 2-(tert-butyl) 1-methyl (1S,3aS,4S,7R,7aR,8*S)-8-fluoro-1,3,3a,4,7,7a-hexahydro-2H-4,7-methanoisoindole-1,2-dicarboxylate (350 mg, 1.12 mmol, 1.0 eq.) in dichloromethane (3 mL) was added trifluoroacetic acid (1 mL) at rt. The mixture was stirred for 2 h at rt. The mixture was concentrated under reduced pressure to provide methyl (1S,3aS,4S,7R,7aR,8*S)-8-fluoro-2,3,3a,4,7,7a-hexahydro-1H-4,7-methanoisoindole-1-carboxylate (240 mg, crude) as a yellow oil. LC-MS (ESI, m/z): 212 [M+H]⁺.

Example 92

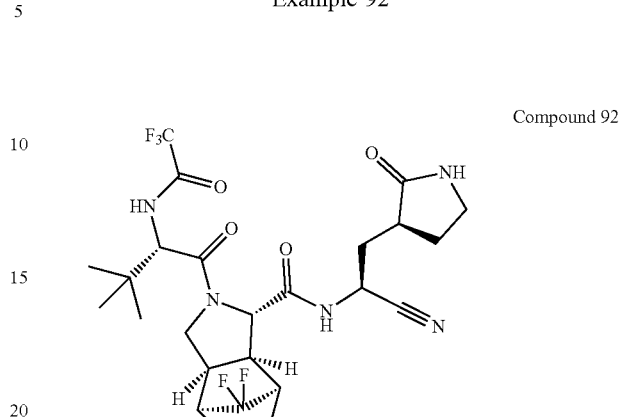

Compound 92

To a mixture of compound 82 (30.0 mg, 0.054 mmol, 1.0 eq.) in (2 mL) was added 10% palladium on activated carbon (15 mg) under hydrogen. The resulting mixture was stirred for 2 days at rt. The mixture was filtered through a celite pad. The filtrate was concentrated under reduced pressure to afford the crude product. The crude product was purified by prep-HPLC (Column: Kinetex EVO C18, 21.2*250 mm, 5 m; Mobile Phase A: Water (0.1% FA), Mobile Phase B: ACN; Flow rate: 25 mL/min; Gradient: 35% B to 65% B in 7 min, 65% B; Wave Length: 254 nm; RT1 (min): 5) to provide (1S,3aS,4S,7R,7aR)—N—((S)-1-cyano-2-((S)-2-oxopyrrolidin-3-yl)ethyl)-2-((S)-3,3-dimethyl-2-(2,2,2-trifluoroacetamido)butanoyl)-8,8-difluorooctahydro-1H-4,7-methanoisoindole-1-carboxamide (2.1 mg, 6%) as a white solid. ¹H NMR (400 MHz, 80° C., DMSO-d6) δ 8.95-9.20 (m, 1H), 8.70-8.90 (m, 1H), 7.35-7.55 (m, 1H), 4.85-5.00 (m, 1H), 4.65-4.75 (m, 1H), 4.55-4.65 (m, 1H), 3.90-4.05 (m, 1H), 3.70-3.85 (m, 1H), 3.10-3.20 (m, 2H), 2.90-3.00 (m, 1H), 2.60-2.80 (m, 1H), 2.30-2.45 (m, 2H), 2.20-2.30 (m, 1H), 2.10-2.20 (m, 2H), 1.50-1.90 (m, 5H), 1.20-1.35 (m, 1H), 0.90-1.10 (m, 9H). LC-MS (ESI, m/z): 562 [M+H]⁺.

Example 93

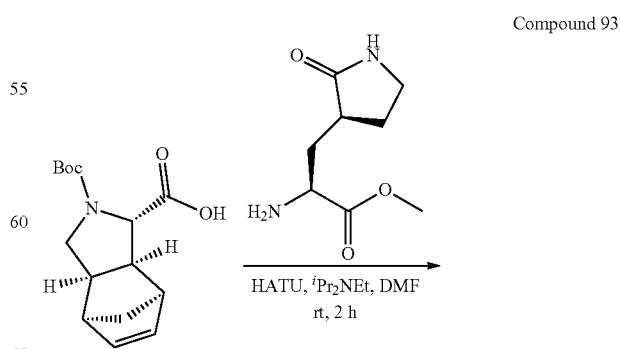

Compound 93

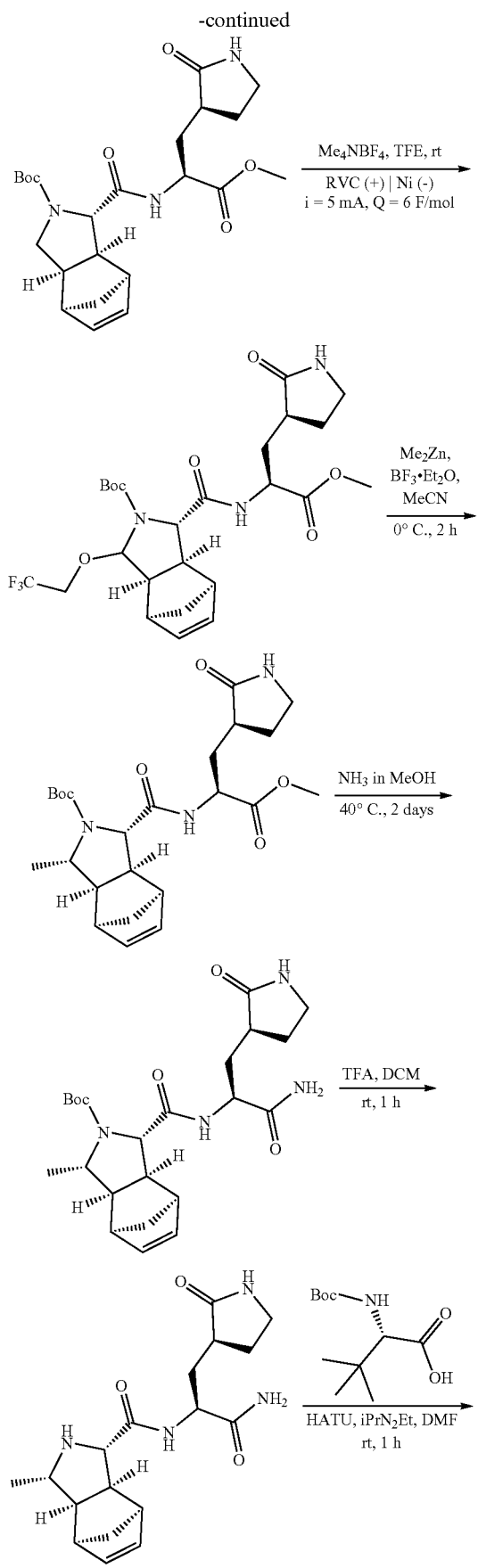
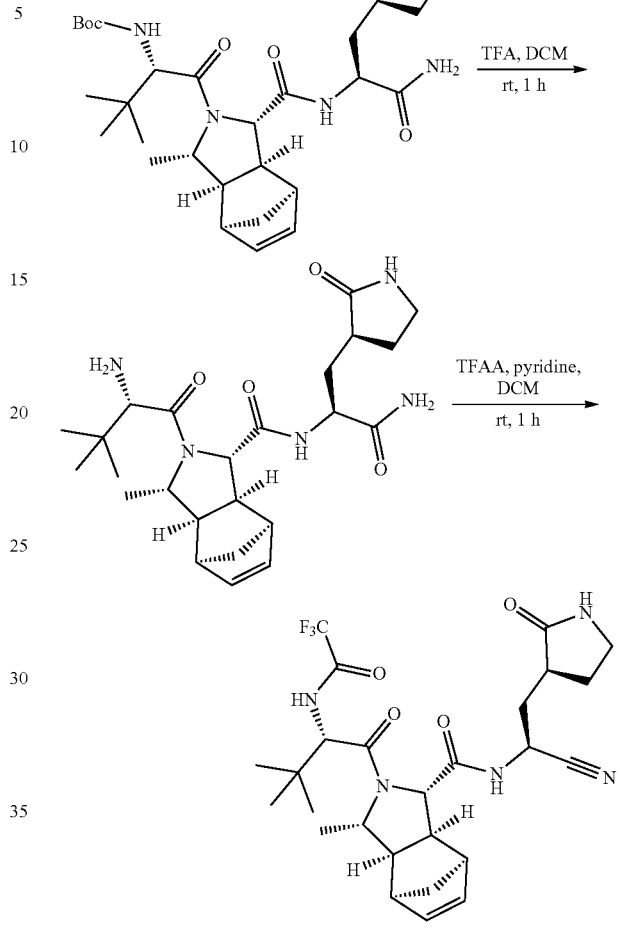

To a solution of (1R,2S,3S,6R,7S)-4-(tert-butoxycarbonyl)-4-azatricyclo[5.2.1.0^{2,6}]dec-8-ene-3-carboxylic acid (3.5 g, 12.5 mmol, 1.0 eq.) in DMF (40 mL) was added N,N,N',N'-tetramethyl-O-(7-azabenzotriazol-1-yl)uronium hexafluorophospate (6.19 g, 16.3 mmol, 1.3 eq.), N-ethyl-N-isopropylpropan-2-amine (11.3 g, 87.7 mmol, 7.0 eq.). The mixture was stirred at 0° C. for 30 min and methyl (2S)-2-amino-3-[(3S)-2-oxopyrrolidin-3-yl]propanoate (2.57 g, 13.8 mmol, 1.1 eq.) was added. The mixture was stirred for 2 h at rt. The mixture was purified by C18 column with CH$_3$CN/Water (0.05% TFA). The fraction was concentrated under reduced pressure to provide tert-butyl (1R,2S,3S,6R,7S)-3-{[(2S)-1-methoxy-1-oxo-3-[(3S)-2-oxopyrrolidin-3-yl]propan-2-yl]carbamoyl}-4-azatricyclo[5.2.1.0^{2,6}]dec-8-ene-4-carboxylate (5.00 g, 89%) as a brown-yellow solid. LC-MS (ESI, m/z): 448 [M+H]$^+$.

A 5 mL ElectraSyn vial was charged with tert-butyl (1R,2S,3S,6R,7S)-3-{[(2S)-1-methoxy-1-oxo-3-[(3S)-2-oxopyrrolidin-3-yl]propan-2-yl]carbamoyl}-4-azatricyclo[5.2.1.0^{2,6}]dec-8-ene-4-carboxylate (370 mg, 0.825 mmol, 1.0 eq.), tetramethylammonium ion (1.40 g, 20.0 mmol, 2.3 eq.) and TFE (110 mL). The cap containing an RVC anode and Ni plate cathode was assembled, and electrolysis was carried out at constant current (5 mA) for 6 F/mol. Another 9 reactions were carried out in parallel. The reaction contents were transferred to a round-bottom flask, both electrodes were vigorously rinsed with DCM, and the obtained solution was concentrated in vacuo. The crude product was purified by silica gel column chromatography with DCM:MeOH (32:1) to afford tert-butyl (1S,3aR,4S,7R,7aS)-1-(((S)-1-methoxy-1-oxo-3-((S)-2-oxopyrrolidin-3-yl)propan-2-yl)carbamoyl)-3-(2,2,2-trifluoroethoxy)-1,3,3a,4,7,7a-hexahydro-2H-4,7-methanoisoindole-2-carboxylate (2.5 g, crude) as an off-white solid. LC-MS (ESI, m/z): 546 [M+H]+.

To a solution of tert-butyl (1R,2S,3S,6R,7S)-3-{[(2S)-1-methoxy-1-oxo-3-[(3S)-2-oxopyrrolidin-3-yl]propan-2-yl]carbamoyl}-5-(2,2,2-trifluoroethoxy)-4-azatricyclo[5.2.1.0^{2,6}]dec-8-ene-4-carboxylate (2.50 g, 4.58 mmol, 1.0 eq.) in MeCN (30 mL) was added dimethylzinc (13.7 mL, 13.7 mmol, 3.0 eq.) at 0° C. under nitrogen. The mixture was stirred at 0° C. for 5 min and then BF$_3$•Et$_2$O (3.5 mL, 27.5 mmol, 6.0 eq.) was added. The mixture was stirred for 2 h at the same temperature. The reaction was quenched with saturated ammonium chloride solution (50 mL). The solution was extracted with DCM (3×60 mL). The organic layers were combined, washed with brine (80 mL), dried over anhydrous sodium sulfate, filtered and concentrated under reduced pressure. The residue was purified by C18 column with CH$_3$CN/Water (0.05% TFA). The desired fraction was concentrated under reduced pressure to provide tert-butyl (1R,2S,3S,5S,6R,7S)-3-{[(2S)-1-methoxy-1-oxo-3-[(3S)-2-oxopyrrolidin-3-yl]propan-2-yl]carbamoyl}-5-methyl-4-azatricyclo[5.2.1.0^{2,6}]dec-8-ene-4-carboxylate (380 mg, two steps yield 2%) as a yellow oil. LC-MS (ESI, m/z): 462 [M+H]+.

A mixture of tert-butyl (1R,2S,3S,5S,6R,7S)-3-{[(2S)-1-methoxy-1-oxo-3-[(3S)-2-oxopyrrolidin-3-yl]propan-2-yl]carbamoyl}-5-methyl-4-azatricyclo[5.2.1.0^{2,6}]dec-8-ene-4-carboxylate (380 mg, 0.820 mmol, 1.0 eq.) in ammonia (7 M in MeOH, 6 mL) was stirred for 2 days at 40° C. The mixture was concentrated under reduced pressure to afford tert-butyl (1R,2S,3S,5S,6R,7S)-3-{[(1S)-1-carbamoyl-2-[(3S)-2-oxopyrrolidin-3-yl]ethyl]carbamoyl}-5-methyl-4-azatricyclo[5.2.1.0^{2,6}]dec-8-ene-4-carboxylate (340 mg, crude) as a brown-yellow solid. LC-MS (ESI, m/z): 447 [M+H]+.

To a solution of tert-butyl (1R,2S,3S,5S,6R,7S)-3-{[(1S)-1-carbamoyl-2-[(3S)-2-oxopyrrolidin-3-yl]ethyl]carbamoyl}-5-methyl-4-azatricyclo[5.2.1.0^{2,6}]dec-8-ene-4-carboxylate (200 mg, 0.448 mmol, 1.0 eq.) in DCM (3 mL) was added trifluoroacetic acid (1 mL). The mixture was stirred for 1 h at rt and then concentrated under reduced pressure to afford (2S)-2-{[(1R,2S,3S,5S,6R,7S)-5-methyl-4-azatricyclo[5.2.1.0^{2,6}]dec-8-en-3-yl]formamido}-3-[(3S)-2-oxopyrrolidin-3-yl]propanamide (155 mg, crude) as a brown semi-solid. LC-MS (ESI, m/z): 347 [M+H]+.

To a mixture of (2S)-2-[(tert-butoxycarbonyl)amino]-3,3-dimethylbutanoic acid (103 mg, 0.447 mmol, 1.0 eq.) and o-(7-azabenzotriazol-1-yl)-N,N,N',N'-te-tramethyluronium hexafluorophosphate (204 mg, 0.536 mmol, 1.2 eq.) in DMF (3 mL) was added N-ethyl-N-isopropylpropan-2-amine (347 mg, 2.68 mmol, 6.0 eq.) at 0° C. After stirring for 15 min at 0° C., (2S)-2-{[(1R,2S,3S,5S,6R,7S)-5-methyl-4-azatricyclo[5.2.1.0^{2,6}]dec-8-en-3-yl]formamido}-3-[(3S)-2-oxopyrrolidin-3-yl]propanamide (155 mg, 0.447 mmol, 1.0 eq.) was added. The mixture was stirred for 1 h at rt and then purified by C18 column with CH$_3$CN/Water (0.05% TFA). The desired fraction was concentrated under reduced pressure to provide tert-butyl N-[(2S)-1-[(1R,2S,3S,5S,6R,7S)-3-{[(1S)-1-carbamoyl-2-[(3S)-2-oxopyrrolidin-3-yl]ethyl]carbamoyl}-5-methyl-4-azatricyclo[5.2.1.0^{2,6}]dec-8-en-4-yl]-3,3-dimethyl-1-oxobutan-2-yl]carbamate (140 mg, 53%) as a brown solid. LC-MS (ESI, m/z): 560 [M+H]+.

To a mixture of tert-butyl N-[(2S)-1-[(1R,2S,3S,5S,6R,7S)-3-{[(1S)-1-carbamoyl-2-[(3S)-2-oxopyrrolidin-3-yl]ethyl]carbamoyl}-5-methyl-4-azatricyclo[5.2.1.0^{2,6}]dec-8-en-4-yl]-3,3-dimethyl-1-oxobutan-2-yl]carbamate (70.0 mg, 0.125 mmol, 1.0 eq.) in DCM (1.5 mL) was added trifluoroacetic acid (0.5 mL). The mixture was stirred for 1 h at rt. The mixture was concentrated under reduced pressure to afford (2S)-2-{[(1R,2S,3S,5S,6R,7S)-4-[(2S)-2-amino-3,3-dimethylbutanoyl]-5-methyl-4-azatricyclo[5.2.1.0^{2,6}]dec-8-en-3-yl]formamido}-3-[(3S)-2-oxopyrrolidin-3-yl]propanamide (57.0 mg, crude) as a brown semi-solid. LC-MS (ESI, m/z): 460 [M+H]+.

To a mixture of (2S)-2-{[(1R,2S,3S,5S,6R,7S)-4-[(2S)-2-amino-3,3-dimethylbutanoyl]-5-methyl-4-azatricyclo[5.2.1.0^{2,6}]dec-8-en-3-yl]formamido}-3-[(3S)-2-oxopyrrolidin-3-yl]propanamide (57.0 mg, 0.124 mmol, 1.0 eq.) in DCM (2 mL) was added pyridine (39.0 mg, 0.496 mmol, 4.0 eq.) and trifluoroacetic anhydride (47.0 mg, 0.223 mmol, 1.8 eq.). The mixture was stirred for 1 h at rt. The reaction was quenched with water (5 mL). The mixture was extracted with DCM (3×5 mL). The organic layers were combined, washed with brine (2×5 mL), dried over anhydrous sodium sulfate, filtered and concentrated under reduced pressure to afford the crude product. The crude product was purified by prep-HPLC (Column: XSelect CSH Prep C18 OBD Column, 19×150 mm, 5 m; Mobile Phase A: Water (0.05% FA), Mobile Phase B: ACN; Flow rate: 25 mL/min; Gradient: 35% B to 65% B in 7 min, 65% B; Wave Length: 254 nm; RT1 (min): 5.97) to provide (1R,2S,3S,5S,6R,7S)—N-[(1S)-1-cyano-2-[(3S)-2-oxopyrrolidin-3-yl]ethyl]-4-[(2S)-3,3-dimethyl-2-(2,2,2-trifluoroacetamido)butanoyl]-5-methyl-4-azatricyclo[5.2.1.0^{2,6}]dec-8-ene-3-carboxamide (12.0 mg, 17%) as a white solid. $^1$H NMR (400 MHz, 80° C., DMSO-d$_6$) δ 8.70-9.50 (m, 1H), 8.55-8.65 (m, 1H), 7.35-7.60 (m, 1H), 5.80-6.20 (m, 2H), 4.60-5.02 (m, 1H), 4.40-4.58 (m, 1H), 4.00-4.19 (m, 1H), 3.64-3.80 (m, 1H), 3.10-3.30 (m, 3H), 2.90-3.01 (m, 1H), 2.76-2.89 (m, 1H), 2.48-2.70 (m, 1H), 2.06-2.46 (m, 3H), 1.60-1.95 (m, 2H), 1.30-1.50 (m, 4H), 1.16-1.29 (m, 1H), 0.84-1.05 (m, 9H). LC-MS (ESI, m/z): 538 [M+H]+.

Example 94

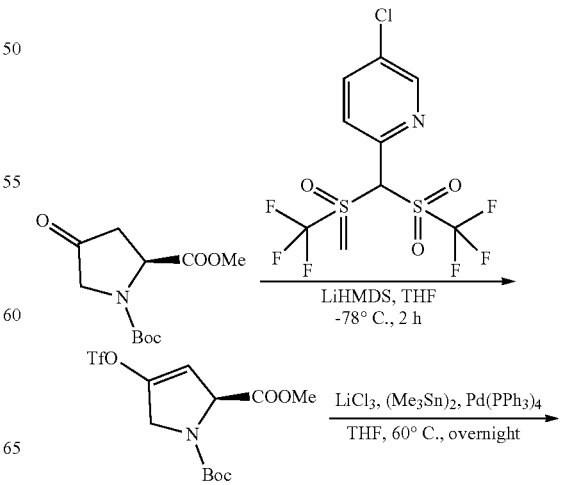

Compound 94

387

-continued

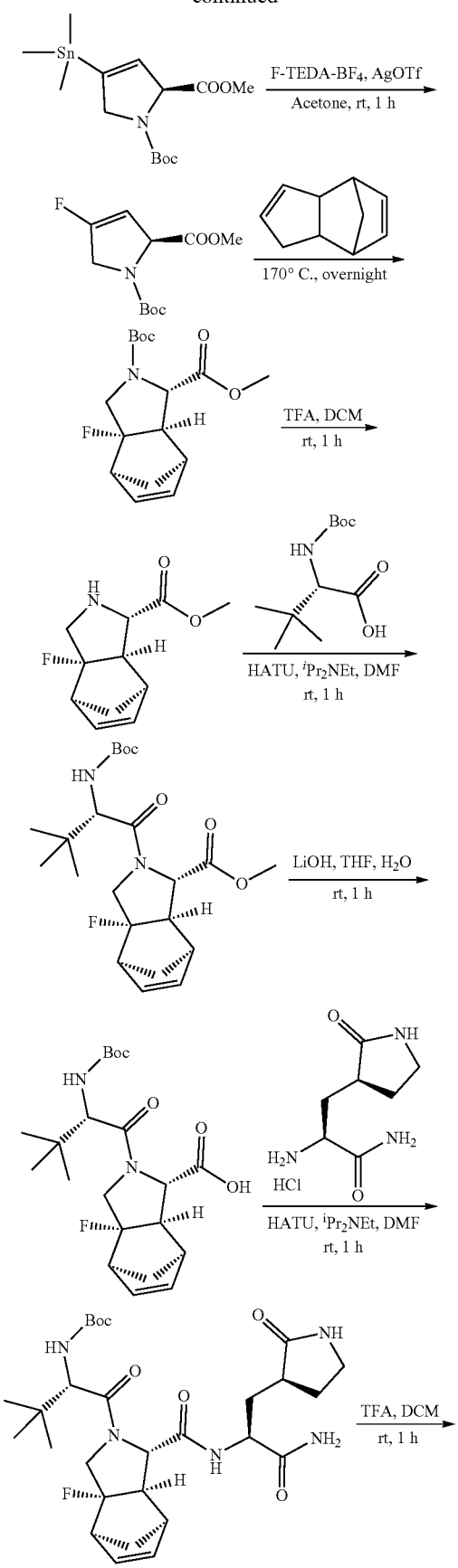

388

-continued

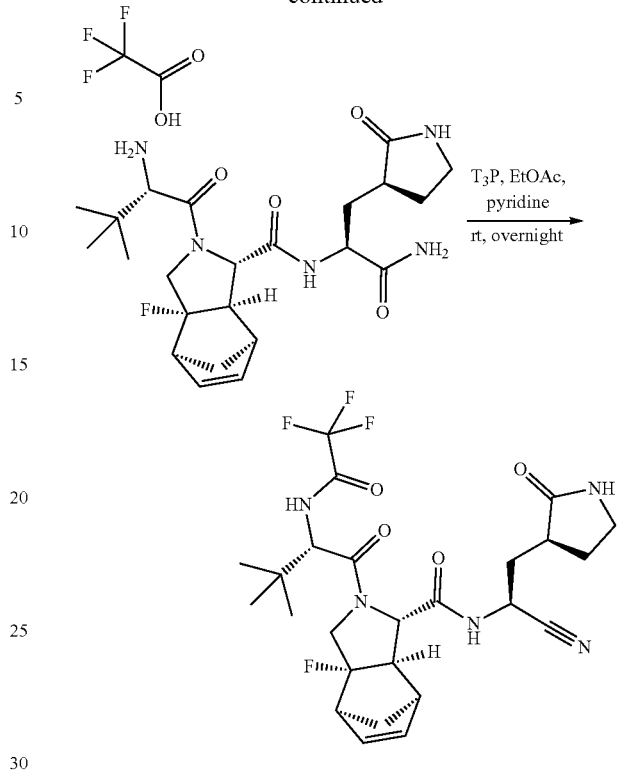

To a solution of 1-tert-butyl 2-methyl (2S)-4-oxopyrrolidine-1,2-dicarboxylate (15.0 g, 61.7 mmol, 1.0 eq.) in THF (240 mL) was added lithium bis(trimethylsilyl)amide (74 mL, 74.0 mmol, 1.2 eq., 1M in THF) at −78° C. under nitrogen. After stirring for 1 h at −78° C., a solution of comins' reagent (29.0 g, 74.0 mmol, 1.2 eq.) in THF (60 mL) was added dropwise. The mixture was stirred for 1 h at −78° C. under nitrogen. The reaction was quenched with water (600 mL). The mixture was extracted with EtOAc (3×500 mL). The organic layers were combined, washed with brine (2×500 mL), dried over anhydrous sodium sulfate, filtered and concentrated under reduced pressure to afford the crude product. The crude product was chromatographed on a silica gel column with EtOAc:PE (1:9) to provide the desired product 1-tert-butyl 2-methyl (2S)-4-(trifluoromethanesulfonyloxy)-2,5-dihydropyrrole-1,2-dicarboxylate (12.3 g, 48%) as a colorless oil. $^1$H NMR (400 MHz, Chloroform-d) δ 5.70-5.80 (m, 1H), 5.00-5.12 (m, 1H), 4.24-4.47 (m, 2H), 3.79 (s, 3H), 1.42-1.53 (m, 9H). LC-MS (ESI, m/z): 320 [M−56+H]$^+$.

To a mixture of 1-tert-butyl 2-methyl (2S)-4-(trifluoromethanesulfonyloxy)-2,5-dihydropyrrole-1,2-dicarboxylate (10.0 g, 26.6 mmol, 1.0 eq.), lithium chloride (3.95 g, 93.2 mmol, 3.5 eq.) and tetrakis(triphenylphosphine)platinum(0) (4.62 g, 4.00 mmol, 0.15 eq.) in THF (120 mL) was added hexamethyldistannane (13.1 g, 40.0 mmol, 1.5 eq.). The mixture was stirred overnight at 60° C. under nitrogen. The reaction was quenched with water (300 mL). The mixture was extracted with EtOAc (3×300 mL). The organic layers were combined, washed with brine (2×200 mL), dried over anhydrous sodium sulfate, filtered and concentrated under reduced pressure to afford the crude product. The crude product was chromatographed on a silica gel column with EtOAc:PE (6:94) to provide 1-tert-butyl 2-methyl (2S)-4-(trimethylstannyl)-2,5-dihydropyrrole-1,2-dicarboxylate (5.45 g, 49%) as a colorless oil. $^1$H NMR (400

MHz, Chloroform-d) δ 5.70-5.82 (m, 1H), 4.93-5.09 (m, 1H), 4.19-4.41 (m, 2H), 3.74-3.79 (m, 3H), 1.42-1.53 (m, 9H), 0.14-0.31 (m, 9H). LC-MS (ESI, m/z): 336 [M−56+H]$^+$.

To a mixture of silver trifluoromethanesulfonate (4.67 g, 18.2 mmol, 1.3 eq.) and 1-chloromethyl-4-fluoro-1,4-diazoniabicyclo[2.2.2]octane bis(tetrafluoroborate) (9.90 g, 27.9 mmol, 2.0 eq.) in dry acetone (165 mL) was added dropwise a solution of 1-tert-butyl 2-methyl (2S)-4-(trimethylstannyl)-2,5-dihydropyrrole-1,2-dicarboxylate (5.45 g, 14.0 mmol, 1.0 eq.) in dry acetone (55 mL) under nitrogen. The mixture was stirred for 1 h at rt. The reaction was quenched with saturated aqueous ammonium chloride (300 mL). The mixture was extracted with MTBE (3×300 mL). The organic layers were combined, washed with brine (2×200 mL), dried over anhydrous sodium sulfate, filtered and concentrated under reduced pressure to afford the crude product. The crude product was chromatographed on a silica gel column with EtOAc/PE (5:95) to provide 1-tert-butyl 2-methyl (2S)-4-fluoro-2,5-dihydropyrrole-1,2-dicarboxylate (780 mg, 20%) as a light yellow oil. $^1$H NMR (400 MHz, Chloroform-d) δ 5.11-5.22 (m, 1H), 4.87-4.99 (m, 1H), 4.24-4.36 (m, 1H), 4.12-4.23 (m, 1H), 3.75-3.80 (m, 3H), 1.42-1.53 (m, 9H). LC-MS (ESI, m/z): 190 [M−56+H]$^+$.

A mixture of 1-tert-butyl 2-methyl (2S)-4-fluoro-2,5-dihydropyrrole-1,2-dicarboxylate (400 mg, 1.63 mmol, 1.0 eq.) in dicyclopentadiene (10 mL) was stirred overnight at 170° C. The mixture was chromatographed on a silica gel column with EtOAc:PE (3:7) to provide the crude product. The crude product was purified by C18 column with CH$_3$CN/Water (0.05% TFA). The desired fraction was concentrated under reduced pressure to provide 2-(tert-butyl) 1-methyl (1S,3aS,4S,7R,7aR)-3a-fluoro-1,3,3a,4,7,7a-hexahydro-2H-4,7-methanoisoindole-1,2-dicarboxylate (140 mg, crude) as a brown oil. LC-MS (ESI, m/z): 212 [M−Boc+H]$^+$.

To a solution of 2-(tert-butyl) 1-methyl (1S,3aS,4S,7R,7aR)-3a-fluoro-1,3,3a,4,7,7a-hexahydro-2H-4,7-methanoisoindole-1,2-dicarboxylate (140 mg, 0.450 mmol, 1.0 eq.) in DCM (1.5 mL) was added trifluoroacetic acid (0.5 mL). The mixture was stirred for 1 h at rt and then concentrated under reduced pressure to afford the methyl (1S,3aS,4S,7R,7aR)-3a-fluoro-2,3,3a,4,7,7a-hexahydro-1H-4,7-methanoisoindole-1-carboxylate (95 mg, crude) as a brown oil. LC-MS (ESI, m/z): 212 [M+H]$^+$.

To a mixture of (2S)-2-[(tert-butoxycarbonyl)amino]-3,3-dimethylbutanoic acid (104 mg, 0.450 mmol, 1.0 eq.) and o-(7-azabenzotriazol-1-yl)-N,N,N',N'-te-tramethyluronium hexafluorophosphate (205 mg, 0.540 mmol, 1.2 eq.) in DMF (3 mL) was added N-ethyl-N-isopropylpropan-2-amine (349 mg, 2.70 mmol, 6.0 eq.) at 0° C. After stirring for 15 min, methyl (1S,3aS,4S,7R,7aR)-3a-fluoro-2,3,3a,4,7,7a-hexahydro-1H-4,7-methanoisoindole-1-carboxylate (95.0 mg, 0.450 mmol, 1.0 eq.) was added. The mixture was stirred for 1 h at rt. The reaction was quenched with water (10 mL). The mixture was extracted with EtOAc (3×10 mL). The organic layers were combined, washed with brine (2×10 mL), dried over anhydrous sodium sulfate, filtered and concentrated under reduced pressure to afford the crude product. The crude product was chromatographed on a silica gel column with EtOAc:PE (15:85) to provide methyl (1S,3aS,4S,7R,7aR)-2-((S)-2-((tert-butoxycarbonyl)amino)-3,3-dimethylbutanoyl)-3a-fluoro-2,3,3a,4,7,7a-hexahydro-1H-4,7-methanoisoindole-1-carboxylate (65.0 mg, 24%) as a light yellow semi-solid. LC-MS (ESI, m/z): 425 [M+H]$^+$.

To a mixture of methyl (1S,3aS,4S,7R,7aR)-2-((S)-2-((tert-butoxycarbonyl)amino)-3,3-dimethylbutanoyl)-3a-fluoro-2,3,3a,4,7,7a-hexahydro-1H-4,7-methanoisoindole-1-carboxylate (65.0 mg, 0.153 mmol, 1.0 eq.) in THF (0.5 mL)/water (0.5 mL) was added lithium hydroxide (11.0 mg, 0.459 mmol, 3.0 eq.). The mixture was stirred for 1 h at rt. The mixture was diluted with water (2 mL) and adjusted to pH=6 with hydrochloric acid (1 M). The mixture was extracted with EtOAc (3×2 mL). The organic layers were combined, washed with brine (2×1 mL), dried over anhydrous sodium sulfate, filtered and concentrated under reduced pressure to afford (1S,3aS,4S,7R,7aR)-2-((S)-2-((tert-butoxycarbonyl)amino)-3,3-dimethylbutanoyl)-3a-fluoro-2,3,3a,4,7,7a-hexahydro-1H-4,7-methanoisoindole-1-carboxylic acid (60.0 mg, crude) as a light yellow solid. LC-MS (ESI, m/z): 411 [M+H]$^+$.

To a mixture of (1S,3aS,4S,7R,7aR)-2-((S)-2-((tert-butoxycarbonyl)amino)-3,3-dimethylbutanoyl)-3a-fluoro-2,3,3a,4,7,7a-hexahydro-1H-4,7-methanoisoindole-1-carboxylic acid (61.0 mg, 0.149 mmol, 1.0 eq.) and o-(7-azabenzotriazol-1-yl)-N,N,N',N'-te-tramethyluronium hexafluorophosphate (68.0 mg, 0.179 mmol, 1.2 eq.) in DMF (2 mL) was added N-ethyl-N-isopropylpropan-2-amine (116 mg, 0.894 mmol, 6.0 eq.) at 0° C. After stirred for 15 min at same temperature, (2S)-2-amino-3-[(3S)-2-oxopyrrolidin-3-yl]propanamide hydrochloride (31.0 mg, 0.149 mmol, 1.0 eq.) was added. The mixture was stirred for 1 h at rt. The crude product was purified by C18 column with CH$_3$CN/Water (0.05% NH$_4$HCO$_3$+NH$_3$·H$_2$O, pH~10). The desired fraction was concentrated under reduced pressure to provide tert-butyl ((S)-1-((1S,3aS,4S,7R,7aR)-1-(((S)-1-amino-1-oxo-3-((S)-2-oxopyrrolidin-3-yl)propan-2-yl)carbamoyl)-3a-fluoro-1,3,3a,4,7,7a-hexahydro-2H-4,7-methanoisoindol-2-yl)-3,3-dimethyl-1-oxobutan-2-yl)carbamate (50.0 mg, 47%) as an off-white solid. LC-MS (ESI, m/z): 564 [M+H]$^+$.

To a mixture of tert-butyl ((S)-1-((1S,3aS,4S,7R,7aR)-1-(((S)-1-amino-1-oxo-3-((S)-2-oxopyrrolidin-3-yl)propan-2-yl)carbamoyl)-3a-fluoro-1,3,3a,4,7,7a-hexahydro-2H-4,7-methanoisoindol-2-yl)-3,3-dimethyl-1-oxobutan-2-yl)carbamate (50.0 mg, 0.089 mmol, 1.0 eq.) in DCM (1.5 mL) was added trifluoroacetic acid (0.5 mL). The mixture was stirred for 1 h at rt and then concentrated under reduced pressure to afford (2S)-2-{[(1R,2R,3S,6S,7S)-4-[(2S)-2-amino-3,3-dimethylbutanoyl]-6-fluoro-4-azatricyclo[5.2.1.0ˆ{2,6}]dec-8-en-3-yl]formamido}-3-[(3S)-2-oxopyrrolidin-3-yl]propanamide; trifluoroacetic acid (51.0 mg, crude) as a brown semi-solid. LC-MS (ESI, m/z): 464 [M+H]$^+$.

To a mixture of (2S)-2-{[(1R,2R,3S,6S,7S)-4-[(2S)-2-amino-3,3-dimethylbutanoyl]-6-fluoro-4-azatricyclo[5.2.1.0ˆ{2,6}]dec-8-en-3-yl]formamido}-3-[(3S)-2-oxopyrrolidin-3-yl]propanamide; trifluoroacetic acid (51.0 mg, 0.088 mmol, 1.0 eq.) in 2,4,6-tripropyl-1,3,5,2,4,6-trioxatriphosphorinane-2,4,6-trioxide (562 mg, 0.880 mmol, 10.0 eq., 50% in EtOAc) was added pyridine (35.0 mg, 0.440 mmol, 5.0 eq.). The mixture was stirred overnight at rt. The reaction was quenched with water (2 mL). The mixture was extracted with EtOAc (3×2 mL). The organic layers were combined, washed with brine (2×2 mL), dried over anhydrous sodium sulfate, filtered and concentrated under reduced pressure to afford the crude product. The crude product was purified by prep-HPLC (Column: XSelect CSH Prep C18 OBD Column, 19×250 mm, 5 m; Mobile Phase A: Water (0.1% FA), Mobile Phase B: ACN; Flow rate: 25 mL/min; Gradient: 37% B to 67% B in 7 min, 67% B; Wave Length: 254 nm; RT1 (min): 6.45) to provide (1R,2R,3S,6S,7S)—N-[(1S)-1-cyano-2-[(3S)-2-oxopyrrolidin-3-yl]ethyl]-4-[(2S)-3,3-dimethyl-2-(2,2,2-trifluoroacetamido)butanoyl]-6-fluoro-4-azatricyclo[5.2.1.0^{2,6}]dec-8-ene-3-carboxamide (12.6 mg, 26%) as a white solid. $^1$H NMR (400 MHz, DMSO-d$_6$) δ 8.70-9.05 (m, 2H), 7.30-7.60 (m, 1H), 5.90-6.60 (m, 2H), 4.84-5.03 (m, 1H), 4.30-4.55 (m, 1H), 3.75-4.29 (m, 3H), 2.93-3.12 (m, 4H), 2.55-2.70 (m, 1H), 2.30-2.45 (m, 1H), 2.08-2.22 (m, 2H), 1.45-2.07 (m, 4H), 0.82-1.10 (m, 9H). LC-MS (ESI, m/z): 542 [M+H]$^+$.

Example 95

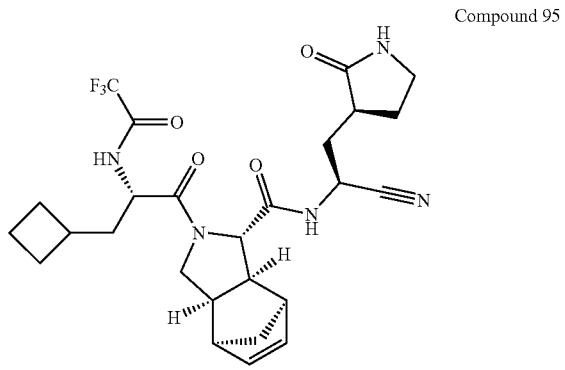 [SMILES: N#C[C@H](C[C@@H]1CCNC1=O)NC(=O)[C@@H]1[C@@H]2[C@H](CN1C(=O)[C@H](CC1CCC1)NC(=O)C(F)(F)F)[C@@H]1C=C[C@H]2C1]

Compound 95

Compound 95 was prepared similarly as described for Compound 3 using (S)-2-amino-3-cyclobutylpropanoic acid in place of (2S,3R)-2-amino-3-(tert-butoxy)butanoic acid. $^1$H NMR (500 MHz, 363K, DMSO-d$_6$) δ 8.40-9.00 (m, 2H), 7.28-7.45 (m, 1H), 5.98-6.26 (m, 2H), 4.78-5.00 (m, 1H), 4.08-4.40 (m, 1H), 3.90-4.00 (m, 1H), 3.52-3.70 (m, 1H), 3.33-3.45 (m, 1H), 3.08-3.22 (m, 3H), 3.00-3.08 (m, 1H), 2.90-2.98 (m, 1H), 2.74 (m, 1H), 2.22-2.40 (m, 2H), 2.09-2.21 (m, 2H), 1.86-2.05 (m, 2H), 1.55-1.85 (m, 8H), 1.34-1.48 (m, 2H). LCMS (ESI, m/z): 536 [M+H]$^+$.

Example 96

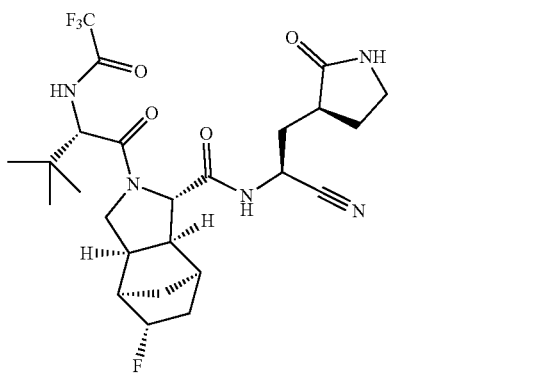

Compound 96

(1S,3aS,4R,5S,7R,7aS)-2-((S)-3,3-dimethyl-2-(2,2,2-trifluoroacetamido)butanoyl)-5-fluorooctahydro-1H-4,7-methanoisoindole-1-carboxylic acid was prepared from 2-(tert-butyl) 1-methyl (1S,3aR,4S,7R,7aS)-1,3,3a,4,7,7a-hexahydro-2H-4,7-methanoisoindole-1,2-dicarboxylate, similar as described for (1S,3aR,4S,6R,7S,7aR)-2-((S)-3,3-dimethyl-2-(2,2,2-trifluoroacetamido)butanoyl)-6-fluorooctahydro-1H-4,7-methanoisoindole-1-carboxylic acid, using R-MOP instead of S-MOP. Compound 96 was prepared from (1S,3aS,4R,5S,7R,7aS)-2-((S)-3,3-dimethyl-2-(2,2,2-trifluoroacetamido)butanoyl)-5-fluorooctahydro-1H-4,7-methanoisoindole-1-carboxylic acid, similarly as described for compound 86 from (1S,3aR,4S,6R,7S,7aR)-2-((S)-3,3-dimethyl-2-(2,2,2-trifluoroacetamido)butanoyl)-6-fluorooctahydro-1H-4,7-methanoisoindole-1-carboxylic acid. $^1$H NMR (400 MHz, 80° C., DMSO-d$_6$) δ 8.55-9.10 (m, 2H), 7.25-7.50 (m, 1H), 4.82-5.00 (m, 1H), 4.65-4.80 (m, 1H), 4.55-4.65 (m, 1H), 4.30-4.50 (m, 1H), 3.85-4.00 (m, 1H), 3.55-3.80 (m, 1H), 3.05-3.25 (m, 2H), 2.60-2.90 (m, 1H), 2.50-2.55 (m, 1H), 2.40-2.50 (m, 2H), 2.25-2.40 (m, 1H), 2.05-2.25 (m, 2H), 1.75-1.90 (m, 2H), 1.65-1.75 (m, 2H), 1.30-1.60 (m, 2H), 0.90-1.10 (m, 9H). LC-MS (ESI, m/z): 544 [M+H]$^+$.

Example 97

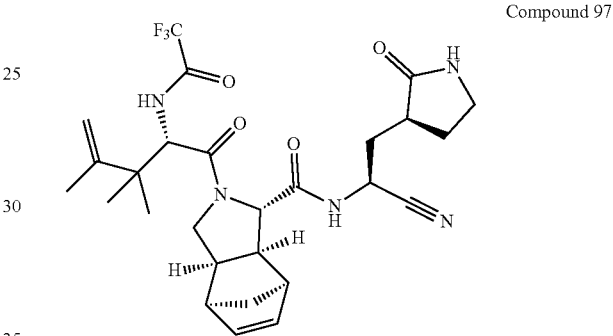

Compound 97

Compound 97 was prepared similarly as described for compound 69, using (S)-2-((tert-butoxycarbonyl)amino)-3,3,4-trimethylpent-4-enoic acid in place of (2S)-2-[(tert-butoxycarbonyl)amino]-3-cyclopropyl-3-methylbutanoic acid. $^1$H NMR (400 MHz, 80° C., DMSO-d$_6$) δ 8.23-9.00 (m, 2H), 7.44-7.65 (m, 1H), 5.91-6.23 (m, 2H), 4.86-4.95 (m, 1H), 4.54-4.82 (m, 3H), 3.88-4.33 (m, 1H), 3.60-3.75 (m, 1H), 3.33-3.45 (m, 1H), 3.05-3.30 (m, 3H), 3.01-3.04 (m, 1H), 2.86-3.00 (m, 1H), 2.61-2.72 (m, 1H), 2.06-2.41 (m, 3H), 1.54-1.93 (m, 5H), 1.27-1.45 (m, 2H), 0.82-1.24 (m, 6H). LC-MS (ESI, m/z): 550 [M+H]$^+$.

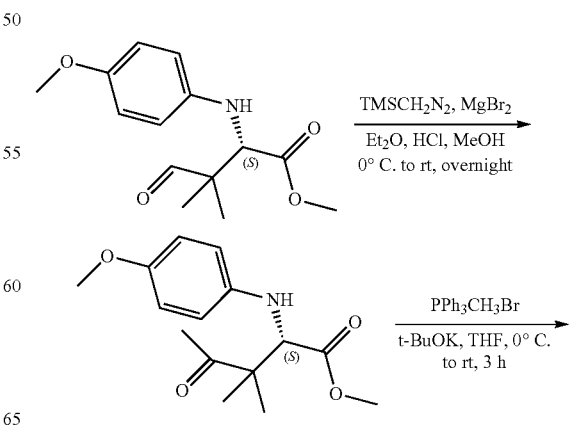

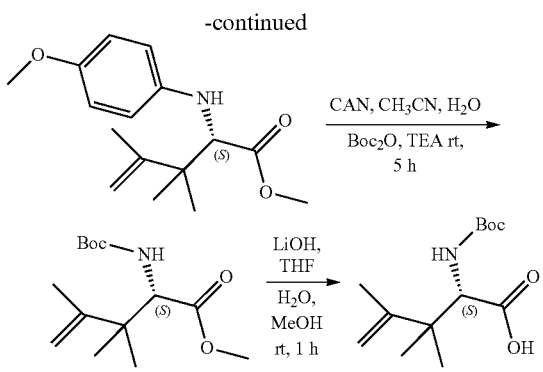

To a solution of methyl (S)-2-((4-methoxyphenyl)amino)-3,3-dimethyl-4-oxobutanoate (12.0 g, 45.2 mmol, 1.0 eq.) and magnesium bromide (29.2 g, 113 mmol, 2.5 eq.) in Et$_2$O (200 mL) was added (trimethylsilyl)diazomethane (11.4 g, 99.5 mmol, 2.2 eq.) at 0° C. The mixture was stirred for 0.5 h at 0° C. and then stirred overnight at rt. MeOH (60 mL) and hydrochloric acid (40 mL, 2 M) were added at 0° C. The mixture was stirred for 1 h at rt. The mixture was extracted with EA (3×100 mL). The organic layers were combined, washed with brine (2×50 mL), dried over anhydrous sodium sulfate, filtered and concentrated under reduced pressure to afford the crude product. The crude product was chromatographed on a silica gel column with EA:PE (17%) to provide methyl (S)-2-((4-methoxyphenyl)amino)-3,3-dimethyl-4-oxopentanoate (3.2 g, 22%) as a yellow solid. $^1$H NMR (400 MHz, DMSO-d$_6$) δ 6.68-6.75 (m, 4H), 5.26-5.31 (m, 1H), 4.38-4.67 (m, 1H), 3.64 (s, 3H), 3.59 (s, 3H), 2.16 (s, 3H), 1.06-1.15 (m, 6H). LC-MS (ESI, m/z): 280 [M+H]$^+$.

To a stirred mixture of methyltriphenylphosphanium bromide (7.37 g, 20.6 mmol, 1.8 eq.) in THF (50 mL) was added potassium tert-butoxide (2.31 g, 20.6 mmol, 1.8 eq.) at 0° C. under nitrogen. After stirring for 1 h, methyl (S)-2-((4-methoxyphenyl)amino)-3,3-dimethyl-4-oxopentanoate (3.2 g, 11.456 mmol, 1.0 eq.) was added. The mixture was stirred for 3 h at rt. The reaction was quenched with water (50 mL). The mixture was extracted with EA (3×100 mL). The organic layers were combined, washed with brine (2×50 mL), dried over anhydrous sodium sulfate, filtered and concentrated under reduced pressure to afford the crude product. The crude product was chromatographed on a silica gel column with EA:PE (5%) to provide methyl (S)-2-((4-methoxyphenyl)amino)-3,3,4-trimethylpent-4-enoate (820 mg, 25%) as a yellow solid. $^1$H NMR (400 MHz, DMSO-d$_6$) δ 6.69-6.73 (m, 2H), 6.59-6.64 (m, 2H), 5.01-5.10 (m, 1H), 4.78-4.81 (m, 2H), 3.99-4.02 (m, 1H), 3.63 (s, 3H), 2.56 (s, 3H), 1.76 (s, 3H), 1.11-1.16 (m, 6H). LC-MS (ESI, m/z): 278 [M+H]$^+$.

To a stirred mixture of methyl (S)-2-((4-methoxyphenyl)amino)-3,3,4-trimethylpent-4-enoate (800 mg, 2.88 mmol, 1.0 eq.) in CH$_3$CN (20 mL) and H$_2$O (5 mL) was added ceric ammonium nitrate (7.94 g, 14.4 mmol, 5.0 eq.). The mixture was stirred for 1 h at rt. To the mixture was added THF (5 mL). The mixture was basified to pH=8 with triethylamine. Di-tert-butyl dicarbonate (3.78 g, 17.3 mmol, 6.0 eq.) was added. The mixture was stirred for 5 h at rt and then diluted with H$_2$O (30 mL). The mixture was extracted with EA (3×50 mL). The organic layers were combined, washed with brine (2×20 mL), dried over anhydrous sodium sulfate, filtered and concentrated under reduced pressure to afford the crude product. The crude product was chromatographed on a silica gel column with EA:PE (9%-13%) to provide methyl (S)-2-((tert-butoxycarbonyl)amino)-3,3,4-trimethylpent-4-enoate (160 mg, 20%) as a yellow oil. $^1$H NMR (400 MHz, Chloroform-d) δ 5.01-5.11 (m, 1H), 4.77-4.86 (m, 2H), 4.37-4.39 (m, 1H), 3.67-3.71 (m, 3H), 1.82 (s, 3H), 1.45 (s, 9H), 1.10-1.12 (m, 6H). LC-MS (ESI, m/z): 272 [M+H]$^+$.

To a mixture of methyl (S)-2-((tert-butoxycarbonyl)amino)-3,3,4-trimethylpent-4-enoate (160 mg, 0.590 mmol, 1.0 eq.) in THF (2 mL), H$_2$O (1 mL) and MeOH (0.5 mL) was added lithium hydroxide (70.6 mg, 2.95 mmol, 5.0 eq.). The mixture was stirred for 1 h at rt and then concentrated under reduced pressure to remove MeOH and THF. The mixture was acidified to pH=5 with hydrochloric acid (1 M). The mixture was extracted with EA (3×50 mL). The organic layers were combined, dried over anhydrous sodium sulfate, filtered and concentrated under reduced pressure to provide the desired product (S)-2-((tert-butoxycarbonyl)amino)-3,3,4-trimethylpent-4-enoic acid (130 mg, crude) as an off-white solid. LC-MS (ESI, m/z): 258 [M+H]$^+$.

Example 98

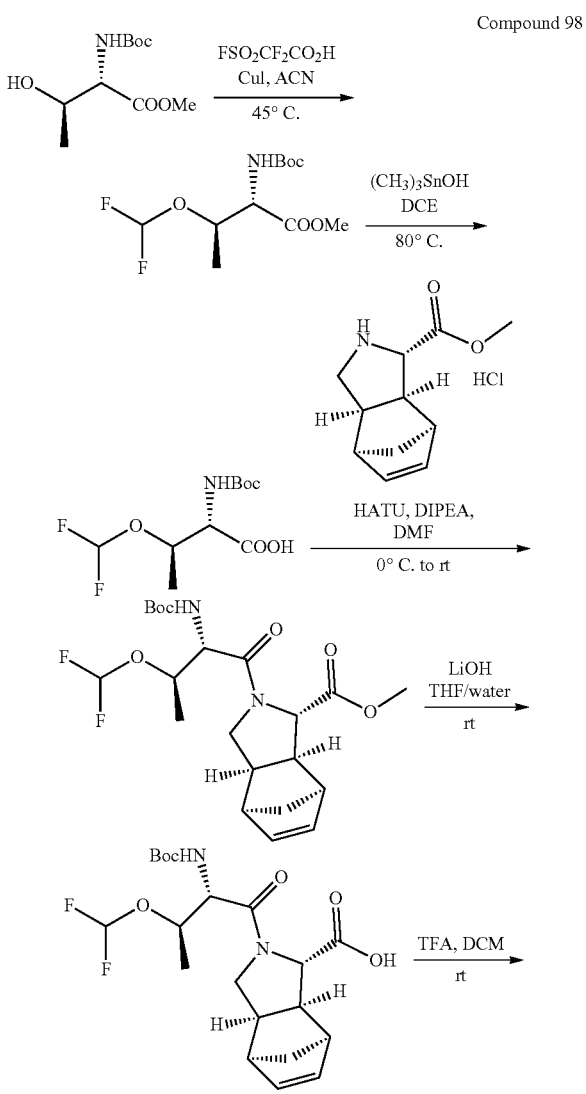

Compound 98

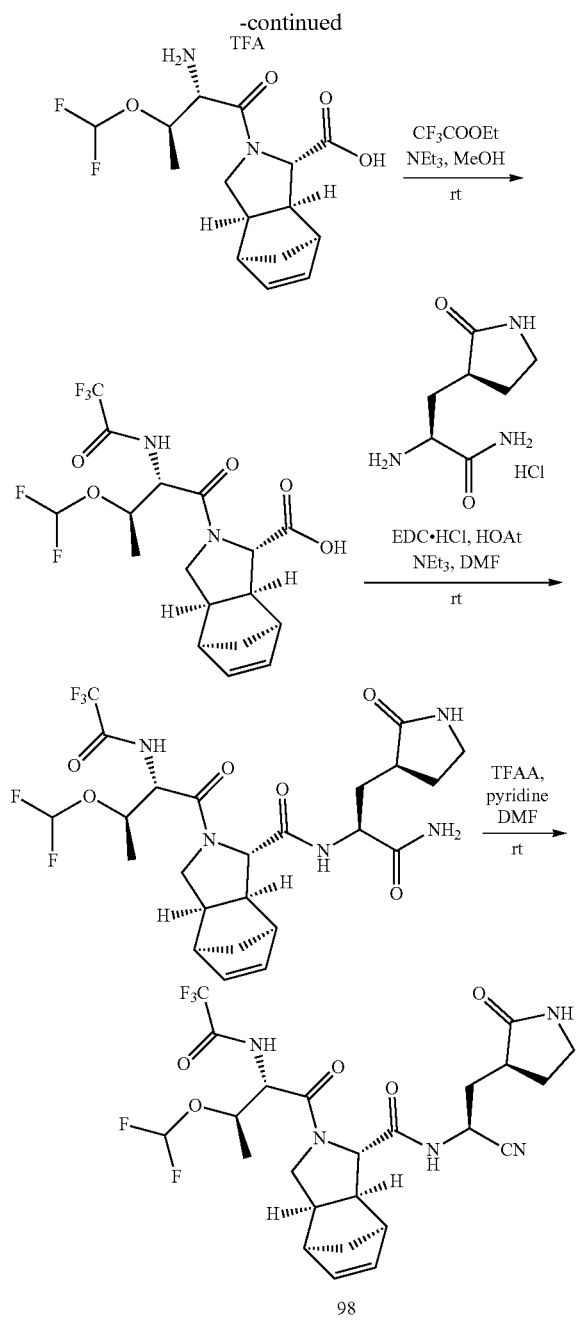

98

To a solution of methyl (tert-butoxycarbonyl)-L-threoninate (2.5 g, 10.7 mmol, 1.0 eq.) in ACN (20 mL) was added CuI (0.38 g, 2.00 mmol, 0.2 eq.). The mixture was heated at 45° C. and a solution of 2,2-difluoro-2-(fluorosulfonyl) acetic acid (2.5 mL, 21.4 mmol, 2.0 eq.) in ACN (10 mL) was added over 30 min. The mixture was concentrated under reduced pressure. The residue was partitioned between water and EA (20 mL). The phases were separated, and the aqueous phase was extracted with EA (2×20 mL). The organic phases were combined, washed with brine (20 mL), dried over Na$_2$SO$_4$, filtered and concentrated under reduced pressure. The residue was purified by flash chromatography on silica gel using a gradient of EA (10 to 15%) in hexane to afford methyl N-(tert-butoxycarbonyl)-O-(difluoromethyl)-L-threoninate (0.8 g, 26%) as a yellow oil.

To a solution of methyl N-(tert-butoxycarbonyl)-O-(difluoromethyl)-L-threoninate (0.8 g, 2.83 mmol, 1.0 eq.) in DCE (10 mL) was added trimethyl tinhydroxide (2.54 g, 14.1 mmol, 5.0 eq.). The mixture was heated at 80° C. for 5 h and then concentrated under reduced pressure. The residue was taken up with 2N HCl and extracted with EA (5×15 mL). The organic phases were combined, dried over Na$_2$SO$_4$, filtered and concentrated under reduced pressure. The residue was purified by flash chromatography on silica gel using a gradient of EA (30 to 40%) in hexane to afford N-(tert-butoxycarbonyl)-O-(difluoromethyl)-L-threonine (0.55 g, 72%) as a brown solid.

To a solution of methyl (1S,3aR,4S,7R,7aS)-2,3,3a,4,7,7a-hexahydro-1H-4,7-methanoisoindole-1-carboxylate hydrochloride (115 mg, 0.502 mmol, 1.0 eq.) and N-(tert-butoxycarbonyl)-O-(difluoromethyl)-L-threonine (169 mg, 0.628 mmol, 1.2 eq.) in DMF (1.1 mL) cooled at 0° C. was added DIPEA (0.26 mL, 1.50 mmol, 3.0 eq.). After 5 min at 0° C., HATU (286 mg, 0.752 mmol, 1.5 eq.) was added. The mixture was stirred at rt for 3 h. The mixture was diluted with water (5 mL) and extracted with EA (3×10 mL). The organic phases were combined, dried over Na$_2$SO$_4$, filtered and concentrated under reduced pressure. The residue was purified by flash chromatography on silica gel using a gradient of EA (30 to 40%) in hexane to afford methyl (1S,3aR,4S,7R,7aS)-2-(N-(tert-butoxycarbonyl)-O-(difluoromethyl)-L-threonyl)-2,3,3a,4,7,7a-hexahydro-1H-4,7-methanoisoindole-1-carboxylate (170 mg, 76%) as a white solid.

To a solution of methyl (1S,3aR,4S,7R,7aS)-2-(N-(tert-butoxycarbonyl)-O-(difluoromethyl)-L-threonyl)-2,3,3a,4,7,7a-hexahydro-1H-4,7-methanoisoindole-1-carboxylate (100 mg, 0.225 mmol, 1.0 eq.) in THF (1 mL) and water (1 mL) cooled at 0° C. was added LiOH (14 mg, 0.334 mmol, 1.5 eq.). The mixture was stirred at rt for 4 h. The mixture was acidified with 1N HCl and extracted with EA (10×10 mL). The organic phases were combined, dried over Na$_2$SO$_4$, filtered and concentrated under reduced pressure to afford ((1S,3aR,4S,7R,7aS)-2-(N-(tert-butoxycarbonyl)-O-(difluoromethyl)-L-threonyl)-2,3,3a,4,7,7a-hexahydro-1H-4,7-methanoisoindole-1-carboxylic acid (65 mg, 67%).

To a solution of ((1S,3aR,4S,7R,7aS)-2-(N-(tert-butoxycarbonyl)-O-(difluoromethyl)-L-threonyl)-2,3,3a,4,7,7a-hexahydro-1H-4,7-methanoisoindole-1-carboxylic acid (110 mg, 0.256 mmol, 1.0 eq.) in DCM (1.1 mL) cooled at 0° C. was added TFA (0.020 mL, 1.25 mmol, 5.0 eq.). The mixture was stirred at rt for 2 h and then concentrated under reduced pressure to afford (1S,3aR,4S,7R,7aS)-2-(O-(difluoromethyl)-L-threonyl)-2,3,3a,4,7,7a-hexahydro-1H-4,7-methanoisoindole-1-carboxylic acid under its TFA salt form (100 mg, 91%) as a white solid.

To a solution of (1S,3aR,4S,7R,7aS)-2-(O-(difluoromethyl)-L-threonyl)-2,3,3a,4,7,7a-hexahydro-1H-4,7-methanoisoindole-1-carboxylic acid trifluoroacetic acid salt (100 mg, 0.233 mmol, 1.0 eq.) in MeOH (1 mL) cooled at 0° C. were added ethyl 2,2,2-trifluoroacetate (0.14 mL, 1.06 mmol, 5.0 eq.) and NEt$_3$ (0.16 mL, 1.06 mmol, 5.0 eq.). The mixture was stirred at rt for 48 h and then concentrated under reduced pressure. The residue was purified by flash chromatography on C18 using a gradient of ACN (30 to 40%) in 0.01% FA in water to afford (1S,3aR,4S,7R,7aS)-2-(O-(difluoromethyl)-N-(2,2,2-trifluoroacetyl)-L-threonyl)-2,3,3a,4,7,7a-hexahydro-1H-4,7-methanoisoindole-1-carboxylic acid (60 mg, 60%) as a white solid.

To a solution of (1S,3aR,4S,7R,7aS)-2-(O-(difluoromethyl)-N-(2,2,2-trifluoroacetyl)-L-threonyl)-2,3,3a,4,7,7a-hexahydro-1H-4,7-methanoisoindole-1-carboxylic acid (60 mg, 0.141 mmol, 1.0 eq.) and (S)-2-amino-3-((S)-2-oxopyrrolidin-3-yl)propanamide hydrochloride (35 mg, 0.169 mmol, 1.2 eq.) in DMF (1 mL) were added EDC•HCl (53 mg, 0.261 mmol, 2.0 eq.), HOAt (19 mg, 0.140 mmol, 1.0 eq.) and NEt$_3$ (0.06 mL, 0.433 mmol, 3.0 eq.). The mixture was stirred at rt for 4 h. The mixture was diluted with water (5 mL) and extracted with EA (3×10 mL). The organic phases were combined, dried over Na$_2$SO$_4$, filtered and concentrated under reduced pressure. The residue was purified by flash chromatography on silica gel using a gradient of MeOH (1 to 10%) in DCM to afford (1S,3aR,4S,7R,7aS)—N—((S)-1-amino-1-oxo-3-((S)-2-oxopyrrolidin-3-yl)propan-2-yl)-2-(O-(difluoromethyl)-N-(2,2,2-trifluoroacetyl)-L-threonyl)-2,3,3a,4,7,7a-hexahydro-1H-4,7-methanoisoindole-1-carboxamide (60 mg, 74%) as a white solid.

To a solution of (1S,3aR,4S,7R,7aS)—N—((S)-1-amino-1-oxo-3-((S)-2-oxopyrrolidin-3-yl)propan-2-yl)-2-(O-(difluoromethyl)-N-(2,2,2-trifluoroacetyl)-L-threonyl)-2,3,3a,4,7,7a-hexahydro-1H-4,7-methanoisoindole-1-carboxamide (60 mg, 0.104 mmol, 1.0 eq.) in DMF (1 mL) cooled at 0° C. were added pyridine (0.03 mL, 0.372 mmol, 3.6 eq.) and TFAA (0.03 mL, 0.216 mmol, 2.1 eq.). The mixture was stirred at rt for 1 h. The mixture was diluted with water (10 mL) and extracted with EA (3×10 mL). The organic phases were combined, washed with brine (2×10 mL), dried over Na$_2$SO$_4$, filtered and concentrated under reduced pressure. The residue was purified by prep-HPLC (Column: Sunfire-C18 Column, 19*150 mm, 5 m; Mobile Phase A: 10 mM NH$_4$HCO$_3$ in water, Mobile Phase B: ACN; Flow rate: 17 mL/min; Gradient: 20% B to 60% B in 8 min) to afford (1S,3aR,4S,7R,7aS)—N—((S)-1-cyano-2-((S)-2-oxopyrrolidin-3-yl)ethyl)-2-(O-(difluoromethyl)-N-(2,2,2-trifluoroacetyl)-L-threonyl)-2,3,3a,4,7,7a-hexahydro-1H-4,7-methanoisoindole-1-carboxamide (12 mg, 21%) as a white solid. $^1$H NMR (500 MHz, 363K, DMSO-d$_6$) δ 9.50 (br. s., 1H), 8.64 (d, 1H), 7.36 (s, 1H), 6.37-6.74 (m, 1H), 5.98-6.22 (m, 2H), 4.89 (m, 1H), 4.52-4.77 (m, 1H), 4.41 (m, 1H), 3.94-4.25 (m, 1H), 3.71 (m, 1H), 3.29-3.49 (m, 1H), 3.04-3.22 (m, 3H), 2.80-2.97 (m, 2H), 2.75 (m, 1H), 2.25-2.39 (m, 1H), 2.08-2.22 (m, 2H), 1.61-1.89 (m, 2H), 1.41 (m, 2H), 1.19-1.28 (m, 3H). LCMS (ESI, m/z): 562 [M+H]$^+$.

Example 99

Compound 99

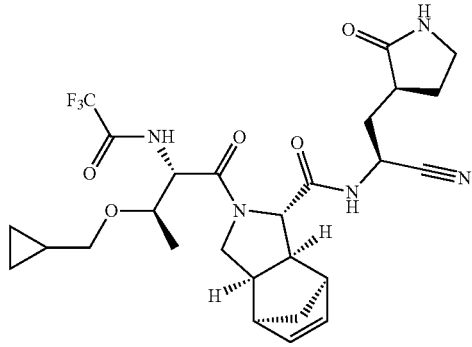

Compound 99 was prepared similarly as described for Compound 98 using N-(tert-butoxycarbonyl)-O-(cyclopropylmethyl)-L-threonine in place of N-(tert-butoxycarbonyl)-O-(difluoromethyl)-L-threonine. $^1$H NMR (500 MHz, 363K, DMSO-d6) δ 8.90-9.20 (br. s., 1H), 8.51-8.79 (m, 1H), 7.29-7.50 (m, 1H), 5.99-6.25 (m, 2H), 4.75-4.95 (m, 1H), 4.21-4.52 (m, 1H), 3.96-4.04 (m, 1H), 3.60-3.78 (m, 2H), 3.50 (m, 1H), 3.21-3.39 (m, 2H), 3.07-3.20 (m, 2H), 3.00-3.06 (m, 1H), 2.79-2.98 (m, 2H), 2.74 (m, 1H), 2.36 (m, 1H), 2.08-2.31 (m, 2H), 1.65-1.88 (m, 2H), 1.35-1.46 (m, 2H), 1.03-1.12 (m, 3H), 0.91 (m, 1H), 0.35-0.46 (m, 2H), 0.08-0.18 (m, 2H). LCMS (ESI, m/z): 566 [M+H]$^+$.

N-(tert-butoxycarbonyl)-O-(cyclopropylmethyl)-L-threonine: To a solution of methyl (tert-butoxycarbonyl)-L-threoninate (2 g, 8.57 mmol, 1.0 eq.) in THF (72 mL) were added allyl methyl carbonate (1.27 mL, 11.2 mmol, 1.3 eq.) and Pd(PPh$_3$)$_4$ (198 mg, 0.171 mmol, 0.02 eq.). The mixture was heated at 60° C. for 3 h and then concentrated under reduced pressure. The residue was purified by flash chromatography on silica gel using 10% EA in PE as the eluent to afford methyl O-allyl-N-(tert-butoxycarbonyl)-L-threoninate (1.8 g, 76%) as a colorless oil.

To a solution of methyl O-allyl-N-(tert-butoxycarbonyl)-L-threoninate (1.0 g, 3.66 mmol, 1.0 eq.) in Et$_2$O (10 mL) cooled at 0° C. were added a solution of diazomethane in Et$_2$O (100 mL) and Pd(OAc)$_2$ (164 mg, 0.732 mmol, 0.2 eq.). The mixture was stirred at rt for 16 h. The reaction mixture was filtered through celite, and the filtrate was concentrated under reduced pressure. The residue was purified by flash chromatography on silica gel using a gradient of EA (10 to 20%) in PE to afford methyl N-(tert-butoxycarbonyl)-O-(cyclopropylmethyl)-L-threoninate (900 mg, 85%) as a colorless oil.

The diazomethane solution in Et$_2$O was generated from N-methyl N-nitrosourea (10 g) in 40% KOH (30 mL) and diethyl ether (100 mL) at 0° C. The phases were separated. The organic phase was used directly for the reaction.

To a solution of methyl N-(tert-butoxycarbonyl)-O-(cyclopropylmethyl)-L-threoninate (900 mg, 3.13 mmol, 1.0 eq.) in THF (6 mL) and water (3 mL) cooled at 0° C. was added LiOH (197 mg, 4.70 mmol, 1.5 eq.). The mixture was stirred at rt for 12 h. After cooling to 0° C., the mixture was acidified with 1M HCl and extracted with EA (4×5 mL). The organic phases were combined, washed with brine (5 mL), dried over Na$_2$SO$_4$, filtered and concentrated under reduced pressure to afford N-(tert-butoxycarbonyl)-O-(cyclopropylmethyl)-L-threonine (800 mg, 93%) as a brown oil. $^1$H NMR (500 MHz, DMSO-d$_6$) δ 12.65 (br.s., 1H), 6.26 (d, 1H), 4.00 (m, 1H), 3.89 (m, 1H), 3.29 (m, 1H), 3.17 (m, 1H), 1.38 (s, 9H), 1.08 (d, 3H), 0.92 (m, 1H), 0.42 (m, 2H), 0.14 (m, 2H). LCMS (ESI, m/z): 274 [M+H]$^+$.

Example 100
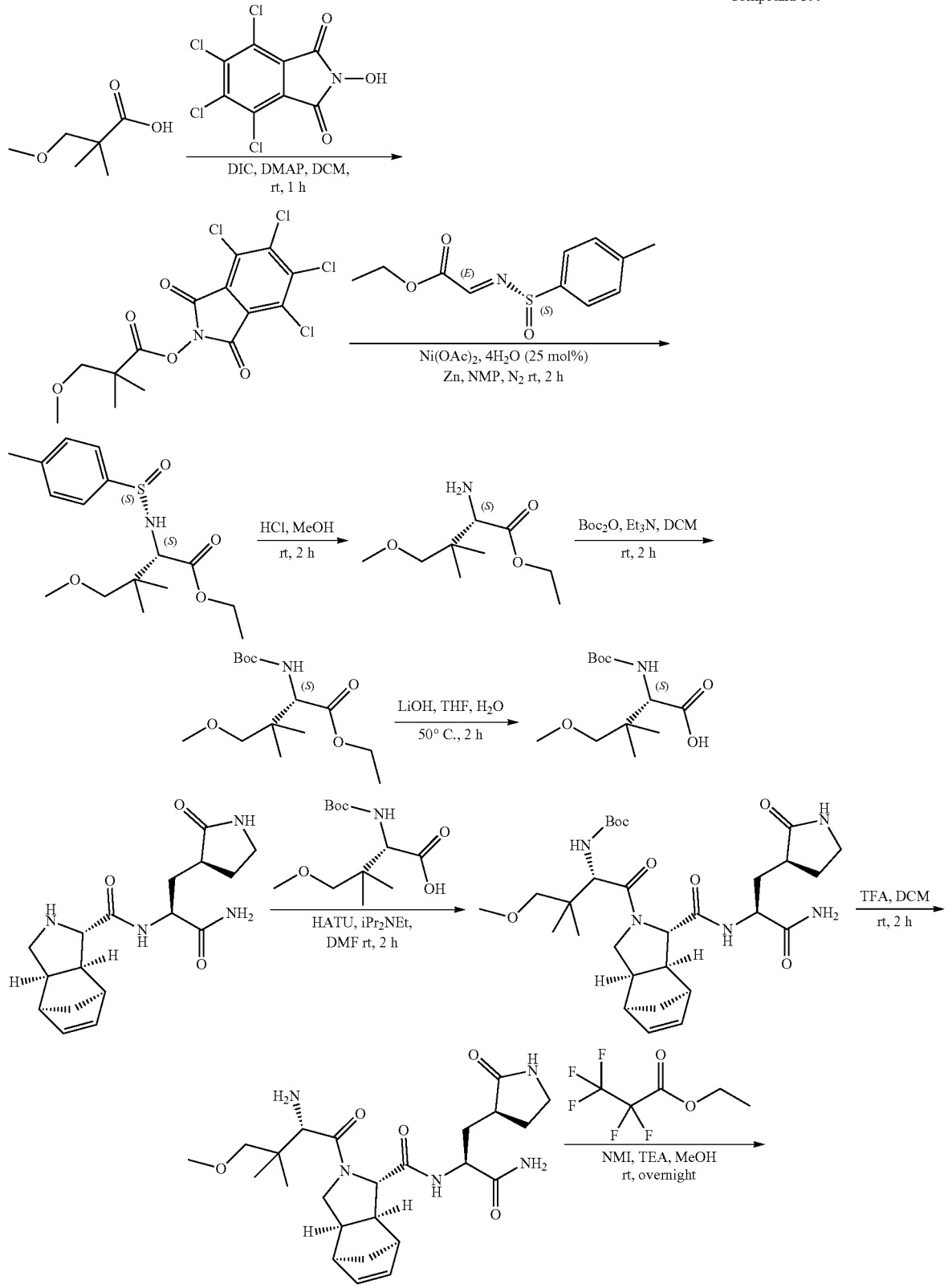
Compound 100

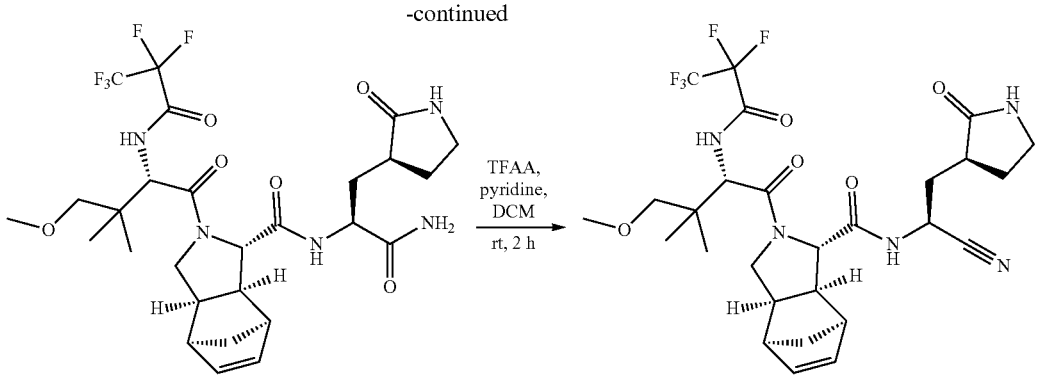

To a mixture of 3-methoxy-2,2-dimethylpropanoic acid (3.0 g, 22.7 mmol, 1.0 eq.), 4,5,6,7-tetrachloro-2-hydroxyisoindoline-1,3-dione (6.81 g, 22.7 mmol, 1.0 eq.) and N,N-dimethylpyridin-4-amine (0.277 g, 2.27 mmol, 0.1 eq.) in DCM (30 mL) was added N,N'-diisopropylcarbodiimide (3.15 g, 25.0 mmol, 1.1 eq.). The mixture was stirred for 1 h at rt. The mixture was chromatographed on a silica gel column with EA:PE (1:9) to provide 4,5,6,7-tetrachloro-1,3-dioxoisoindolin-2-yl 3-methoxy-2,2-dimethylpropanoate (2.8 g, 30%) as a light yellow solid. LC-MS (ESI, m/z): 416 [M+H]⁺.

To a mixture of 4,5,6,7-tetrachloro-1,3-dioxoisoindolin-2-yl 3-methoxy-2,2-dimethylpropanoate (2.8 g, 6.75 mmol, 1.0 eq.), ethyl (S,E)-2-((p-tolylsulfinyl)imino)acetate (2.58 g, 10.8 mmol, 1.6 eq.) and nickel(II) acetate tetrahydrate (0.419 g, 1.69 mmol, 0.25 eq.) in 1-methyl-2-pyrrolidinone (50 mL) was added zinc (1.32 g, 20.3 mmol, 3.0 eq.). The mixture was stirred overnight at rt under nitrogen. The reaction was quenched with water (150 mL). The mixture was extracted with EtOAc (3×200 mL). The organic layers were combined, washed with brine (2×80 mL), dried over anhydrous sodium sulfate, filtered and concentrated under reduced pressure to afford the crude product. The crude product was chromatographed on a silica gel column with EA:PE (1:4) to provide the desired the crude product. The crude product was purified by C18 column with CH₃CN/Water (0.05% NH₄HCO₃). The desired fraction was concentrated under reduced pressure to provide ethyl (S)-4-methoxy-3,3-dimethyl-2-(((S)-p-tolylsulfinyl)amino) butanoate (1.27 g, 58%) as a light yellow oil. LC-MS (ESI, m/z): 328 [M+H]⁺.

To a mixture of ethyl (S)-4-methoxy-3,3-dimethyl-2-(((S)-p-tolylsulfinyl)amino)butanoate (770 mg, 2.35 mmol, 1.0 eq.) in MeOH (8 mL) was added hydrogen chloride (338 mg, 9.40 mmol, 4.0 eq., 4 M in EtOH). The mixture was stirred for 2 h at rt and then concentrated under reduced pressure to afford ethyl (S)-2-amino-4-methoxy-3,3-dimethylbutanoate (444 mg, crude) as a yellow oil. LC-MS (ESI, m/z): 190 [M+H]⁺.

To a mixture of ethyl (S)-2-amino-4-methoxy-3,3-dimethylbutanoate (444 mg, 2.35 mmol, 1.0 eq.) in DCM (4 mL) were added trimethylamine (1.19 g, 11.8 mmol, 5.0 eq.) and di-tert-butyl dicarbonate (615 mg, 2.82 mmol, 1.2 eq.). The mixture was stirred for 2 h at rt. The reaction was quenched with water (50 mL). The mixture was extracted with dichloromethane (3×100 mL). The organic layers were combined, washed with brine (2×50 mL), dried over anhydrous sodium sulfate, filtered and concentrated under reduced pressure to afford the crude product. The crude product was chromatographed on a silica gel column with EA:PE (1:9) to provide ethyl (S)-2-((tert-butoxycarbonyl)amino)-4-methoxy-3,3-dimethylbutanoate (370 mg, crude) as a yellow oil. LC-MS (ESI, m/z): 290 [M+H]⁺.

To a mixture of ethyl (S)-2-((tert-butoxycarbonyl)amino)-4-methoxy-3,3-dimethylbutanoate (370 mg, 1.28 mmol, 1.0 eq.) in THF (4 mL)/water (4 mL) was added lithium hydroxide (147 mg, 6.40 mmol, 5.0 eq.). The mixture was stirred for 2 h at 50° C. The mixture was concentrated under reduced pressure to remove THF and adjusted to pH=5 with hydrochloric acid (2 M). The mixture was extracted with EtOAc (3×80 mL). The organic layers were combined, washed with brine (2×30 mL), dried over anhydrous sodium sulfate, filtered and concentrated under reduced pressure to afford (S)-2-((tert-butoxycarbonyl)amino)-4-methoxy-3,3-dimethylbutanoic acid (205 mg, crude) as a yellow oil. LC-MS (ESI, m/z): 206 [M−56+H]⁺.

To a mixture of (S)-2-((tert-butoxycarbonyl)amino)-4-methoxy-3,3-dimethylbutanoic acid (205 mg, 0.785 mmol, 1.0 eq.) in DMF (2 mL) were added o-(7-azabenzotriazol-1-yl)-N,N,N',N'-te-tramethyluronium hexafluorophosphate (358 mg, 0.942 mmol, 1.2 eq.) and N-ethyl-N-isopropylpropan-2-amine (608 mg, 4.71 mmol, 6.0 eq.) at 0° C. The mixture was stirred for 20 min, and then (1S,3aR,4S,7R,7aS)—N—((S)-1-amino-1-oxo-3-((S)-2-oxopyrrolidin-3-yl)propan-2-yl)-2,3,3a,4,7,7a-hexahydro-1H-4,7-methanoisoindole-1-carboxamide (260 mg, 0.783 mmol, 1.0 eq.) was added 0° C. The mixture was stirred for 2 h at rt. The mixture was purified by C18 column with CH₃CN/Water (0.05% FA). The desired fraction was concentrated under reduced pressure to provide tert-butyl ((S)-1-((1S,3aR,4S,7R,7aS)-1-(((S)-1-amino-1-oxo-3-((S)-2-oxopyrrolidin-3-yl)propan-2-yl)carbamoyl)-1,3,3a,4,7,7a-hexahydro-2H-4,7-methanoisoindol-2-yl)-4-methoxy-3,3-dimethyl-1-oxobutan-2-yl) carbamate (110 mg, 24%) as a light yellow solid. The product (110 mg) was purified by Achiral to afford tert-butyl ((S)-1-((1S,3aR,4S,7R,7aS)-1-(((S)-1-amino-1-oxo-3-((S)-2-oxopyrrolidin-3-yl)propan-2-yl)carbamoyl)-1,3,3a,4,7,7a-hexahydro-2H-4,7-methanoisoindol-2-yl)-4-methoxy-3,3-dimethyl-1-oxobutan-2-yl)carbamate (65 mg, 2nd peak) as a white solid. LC-MS (ESI, m/z): 576 [M+H]⁻.

To a stirred mixture of tert-butyl ((S)-1-((1S,3aR,4S,7R,7aS)-1-(((S)-1-amino-1-oxo-3-((S)-2-oxopyrrolidin-3-yl)propan-2-yl)carbamoyl)-1,3,3a,4,7,7a-hexahydro-2H-4,7-methanoisoindol-2-yl)-4-methoxy-3,3-dimethyl-1-oxobutan-2-yl)carbamate (50 mg, 0.087 mmol, 1.0 eq.) in dichloromethane (0.6 mL) was added trifluoroacetic acid (0.3 mL) rt. The mixture was stirred for 2 h at rt and then concentrated under reduced pressure to afford (1S,3aR,4S,7R,7aS)—N—((S)-1-amino-1-oxo-3-((S)-2-oxopyrrolidin-3-yl)propan-2-yl)-2-((S)-2-amino-4-methoxy-3,3-dimethylbutanoyl)-2,3,3a,4,7,7a-hexahydro-1H-4,7-methanoisoindole-1-carboxamide (41 mg, crude) as a yellow oil. LC-MS (ESI, m/z): 476 [M+H]⁺.

To a mixture of (1S,3aR,4S,7R,7aS)—N—((S)-1-amino-1-oxo-3-((S)-2-oxopyrrolidin-3-yl)propan-2-yl)-2-((S)-2-amino-4-methoxy-3,3-dimethylbutanoyl)-2,3,3a,4,7,7a-hexahydro-1H-4,7-methanoisoindole-1-carboxamide (41 mg, 0.086 mmol, 1.0 eq.) in MeOH (0.5 mL) were added triethylamine (60.8 mg, 0.602 mmol, 7.0 eq.), N-methylimidazole (21.1 mg, 0.258 mmol, 3.0 eq.) and ethyl pentafluoropropionate. The mixture was stirred for overnight at rt. The reaction was quenched with water (10 mL). The mixture was extracted with EtOAc (3×30 mL). The organic layers were combined, washed with brine (2×10 mL), dried over anhydrous sodium sulfate, filtered and concentrated under reduced pressure to afford the crude product. The crude product was purified by silica gel column chromatography with methanol:dichloromethane (6:94) to afford of (1S,3aR, 4S,7R,7aS)—N—((S)-1-amino-1-oxo-3-((S)-2-oxopyrrolidin-3-yl)propan-2-yl)-2-((S)-4-methoxy-3,3-dimethyl-2-(2, 2,3,3,3-pentafluoropropanamido)butanoyl)-2,3,3a,4,7,7a-hexahydro-1H-4,7-methanoisoindole-1-carboxamide (60 mg, crude) as a yellow oil. LC-MS (ESI, m/z): 622 [M+H]⁺.

To a mixture of N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-4-methoxy-3,3-dimethyl-1-oxobutan-2-yl]-2,2,3,3,3-pentafluoropropanamide (60 mg, 0.097 mmol, 1.0 eq.) in DCM (0.5 mL) were added pyridine (26.7 mg, 0.340 mmol, 3.5 eq.) and trifluoroacetic anhydride (24.3 mg, 0.116 mmol, 1.2 eq.). The mixture was stirred for 2 h at rt. The reaction was quenched with water (10 mL). The mixture was extracted with DCM (3×50 mL). The organic layers were combined, washed with brine (2×10 mL), dried over anhydrous sodium sulfate, filtered and concentrated under reduced pressure to afford the crude product. The crude product was purified by prep-HPLC (Column: XSelect CSH Prep C18 OBD Column, 19*150 mm, 5 m; Mobile Phase A: Water (0.1% FA), Mobile Phase B: ACN; Flow rate: 25 mL/min; Gradient: 37% B to 67% B in 7 min, 67% B; Wave Length: 220 nm; RT1 (min): 6.12) to provide (1S,3aR,4S, 7R,7aS)—N—((S)-1-cyano-2-((S)-2-oxopyrrolidin-3-yl)ethyl)-2-((S)-4-methoxy-3,3-dimethyl-2-(2,2,3,3,3-pentafluoropropanamido)butanoyl)-2,3,3a,4,7,7a-hexahydro-1H-4,7-methanoisoindole-1-carboxamide (11.6 mg, 19%) as an off-white solid. ¹H NMR (400 MHz, 80° C., DMSO-d₆) δ 8.60-9.00 (m, 2H), 7.35-7.60 (m, 1H), 5.90-6.30 (m, 2H), 4.85-5.05 (m, 1H), 4.50-4.70 (m, 1H), 3.95-4.20 (m, 1H), 3.60-3.75 (m, 1H), 3.40-3.60 (m, 1H), 3.25-3.35 (m, 1H), 3.00-3.20 (m, 7H), 2.80-3.00 (m, 2H), 2.65-2.80 (m, 1H), 2.25-2.45 (m, 1H), 2.08-2.25 (m, 2H), 1.60-1.90 (m, 2H), 1.30-1.50 (m, 2H), 0.85-1.10 (m, 6H). LC-MS (ESI, m/z): 604 [M+H]⁺.

Example 101

Compound 101

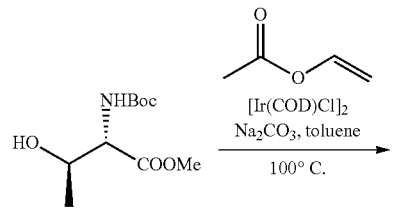

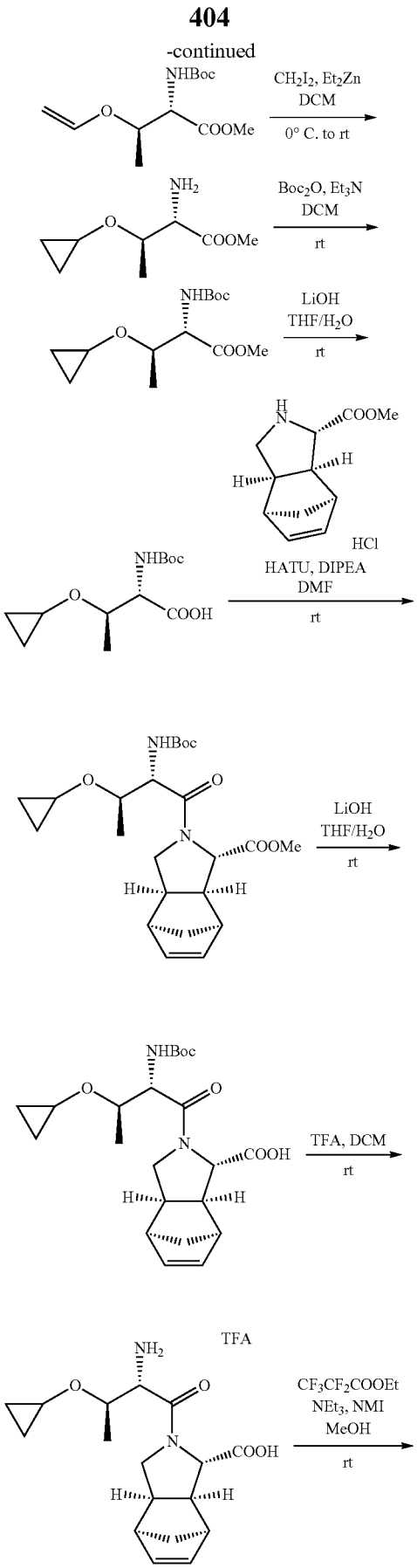

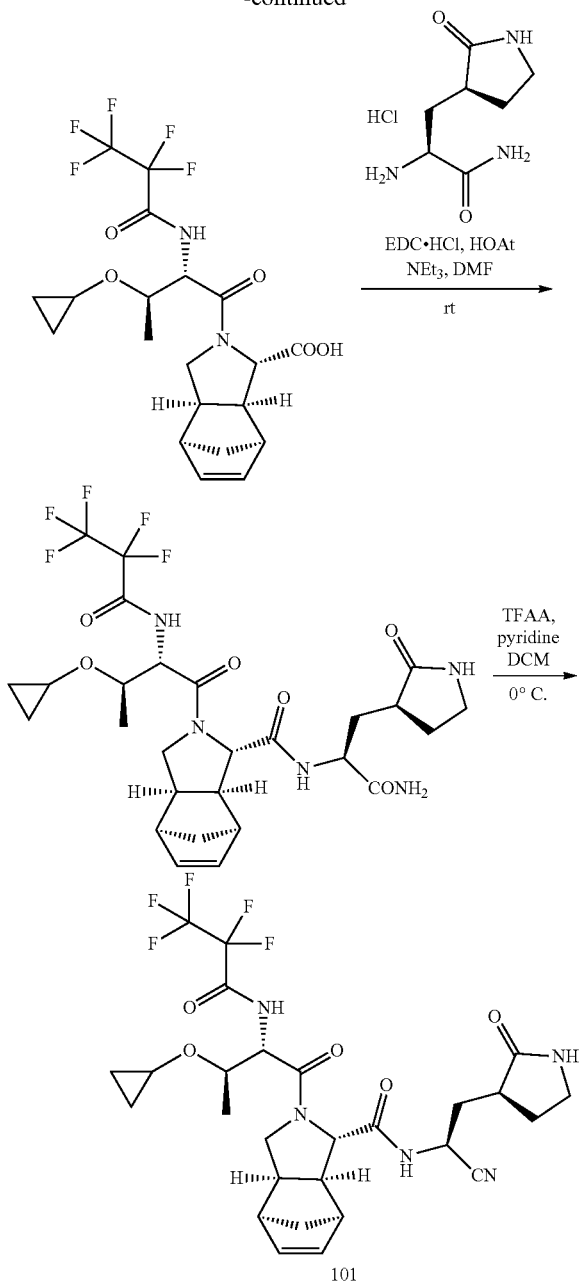

To a mixture of methyl (tert-butoxycarbonyl)-L-threoninate (1 g, 4.29 mmol, 1.0 eq.), vinyl acetate (1.58 mL, 17.1 mmol, 4.0 eq.) and Na$_2$CO$_3$ (273 mg, 2.57 mmol, 0.6 eq.) in toluene (10 mL) was added bis(1,5 cyclooctadiene)diiridium (I) dichloride (144 mg, 0.214 mmol, 0.05 eq.). The mixture was stirred at 100° C. in a sealed tube for 4 h. After cooling to rt, the mixture was diluted with EA (50 mL) and washed with water (20 mL). The phases were separated. The organic phase was washed with brine (20 mL), dried over Na$_2$SO$_4$, filtered and concentrated under reduced pressure. The residue was purified by flash chromatography on silica gel using a gradient of EA (10 to 20%) in PE to afford methyl N-(tert-butoxycarbonyl)-O-vinyl-L-threoninate (600 mg, 54%) as a brown oil.

To a solution of methyl N-(tert-butoxycarbonyl)-O-vinyl-L-threoninate (600 mg, 2.32 mmol, 1.0 eq.) in DCM (6 mL) cooled at 0° C. were added 0.9M Et$_2$Zn in hexane (6 mL, 5.79 mmol, 2.5 eq.) and CH$_2$I$_2$ (0.93 mL, 11.6 mmol, 5.0 eq.). The mixture was stirred at rt for 16 h. Ice/water (5 mL) was added and the phases were separated. The aqueous phase was extracted with EA (3×5 mL). The organic phases were combined, washed with water (5 mL), dried over Na$_2$SO$_4$, filtered and concentrated under reduced pressure to afford methyl O-cyclopropyl-L-threoninate (600 mg) as a brown oil.

To a solution of methyl O-cyclopropyl-L-threoninate (600 mg, 3.46 mmol, 1.0 eq.) in DCM (6 mL) cooled at 0° C. were added NEt$_3$ (0.96 mL, 6.93 mmol, 2.0 eq.) and Boc$_2$O (1.2 mL, 5.20 mmol, 1.5 eq.). The mixture was stirred at rt for 3 h. The mixture was diluted with DCM (50 mL) and washed with water. The phases were separated. The organic phase was washed with brine, dried over Na$_2$SO$_4$, filtered and concentrated under reduced pressure. The residue was purified by flash chromatography on silica gel using a gradient of EA (10 to 20%) in PE to afford methyl N-(tert-butoxycarbonyl)-O-cyclopropyl-L-threoninate (500 mg, 79% over two steps) as a yellow liquid. $^1$H NMR (400 MHz, CDCl$_3$) δ 5.16 (d, 1H), 4.27 (m, 1H), 4.14 (m, 1H), 3.73 (s, 3H), 3.27 (m, 1H), 1.45 (s, 9H), 1.26 (d, 3H), 0.51 (m, 2H), 0.38 (m, 2H). LCMS (ESI, m/z): 274 [M+H]$^+$.

To a solution of methyl N-(tert-butoxycarbonyl)-O-cyclopropyl-L-threoninate (500 mg, 1.83 mmol, 1.0 eq.) in THF (3.5 mL) and water (1.5 mL) cooled at 0° C. was added LiOH (115 mg, 2.74 mmol, 1.5 eq.). The mixture was stirred at rt for 6 h. After cooling to 0° C., the mixture was acidified with 1M HCl to pH=2 and extracted with EA (4×10 mL). The organic phases were combined, washed with brine (5 mL), dried over Na$_2$SO$_4$, filtered and concentrated under reduced pressure. The residue was purified by flash chromatography on C18 using a gradient of ACN (50 to 60%) in 0.1% FA in water to afford N-(tert-butoxycarbonyl)-O-cyclopropyl-L-threonine (350 mg, 74%) as a colorless oil.

To a solution of N-(tert-butoxycarbonyl)-O-cyclopropyl-L-threonine (150 mg, 0.578 mmol, 1.0 eq.) and methyl (1S,3aR,4S,7R,7aS)-2,3,3a,4,7,7a-hexahydro-1H-4,7-methanoisoindole-1-carboxylate hydrochloride (133 mg, 0.578 mmol, 1.0 eq.) in DMF (1.5 mL) cooled at 0° C. were added HATU (286 mg, 0.752 mmol, 1.3 eq.) and DIPEA (0.26 mL, 1.45 mmol, 2.5 eq.). The mixture was stirred at rt for 7 h. The mixture was diluted with water (5 mL) and extracted with EA (4×5 mL). The organic phases were combined, dried over Na$_2$SO$_4$, filtered and concentrated under reduced pressure. The residue was purified by flash chromatography on silica gel using a gradient of EA (20 to 30%) in PE to afford methyl (1S,3aR,4S,7R,7aS)-2-(N-(tert-butoxycarbonyl)-O-cyclopropyl-L-threonyl)-2,3,3a,4,7,7a-hexahydro-1H-4,7-methanoisoindole-1-carboxylate (180 mg, 71%) as a colorless solid.

To a solution of methyl (1S,3aR,4S,7R,7aS)-2-(N-(tert-butoxycarbonyl)-O-cyclopropyl-L-threonyl)-2,3,3a,4,7,7a-hexahydro-1H-4,7-methanoisoindole-1-carboxylate (195 mg, 0.449 mmol, 1.0 eq.) in THF (1.3 mL) and water (0.7 mL) cooled at 0° C. was added LiOH (28.2 mg, 0.673 mmol, 1.5 eq.). reaction mixture was stirred at rt for 4 h. After cooling to 0° C., the mixture was acidified with 1M HCl until pH ~2 and then extracted with EA (4×5 mL). The organic phases were combined, washed with brine (5 mL), dried over Na$_2$SO$_4$, filtered and concentrated under reduced pressure to afford (1S,3aR,4S,7R,7aS)-2-(N-(tert-butoxycarbonyl)-O-cyclopropyl-L-threonyl)-2,3,3a,4,7,7a-hexahydro-1H-4,7-methanoisoindole-1-carboxylic acid (180 mg, 95%) as an off-white solid.

To a solution of (1S,3aR,4S,7R,7aS)-2-(N-(tert-butoxycarbonyl)-O-cyclopropyl-L-threonyl)-2,3,3a,4,7,7a-hexahydro-1H-4,7-methanoisoindole-1-carboxylic acid (180 mg, 0.428 mmol, 1.0 eq.) in DCM (3 mL) cooled at 0° C. was added TFA (0.13 mL, 1.71 mmol, 4.0 eq.). The mixture was stirred at rt for 3 h and then concentrated under reduced pressure to afford quantitatively (1S,3aR,4S,7R,7aS)-2-(O-cyclopropyl-L-threonyl)-2,3,3a,4,7,7a-hexahydro-1H-4,7-methanoisoindole-1-carboxylic acid under its trifluoroacetic acid salt form (180 mg) as a brown solid.

To a solution of (1S,3aR,4S,7R,7aS)-2-(O-cyclopropyl-L-threonyl)-2,3,3a,4,7,7a-hexahydro-1H-4,7-methanoisoindole-1-carboxylic acid trifluoroacetic acid salt (180 mg, 0.414 mmol, 1.0 eq.) in MeOH (2 mL) cooled at 0° C. were added ethyl 2,2,3,3,3-pentafluoropropanoate (398 mg, 2.07 mmol, 5.0 eq.), NEt₃ (0.3 mL, 2.07 mmol, 5.0 eq.) and 1-methylimidazole (0.07 mL, 0.829 mmol, 2.0 eq.). The mixture was stirred at rt for 18 h. The mixture was concentrated under reduced pressure. The residue was taken up with water (5 mL), cooled at 0° C. and acidified with 1N HCl to pH ~2. The precipitate was filtered, washed with cold water and hexane and purified by flash chromatography on C18 using a gradient of ACN (30 to 40%) in 0.1% FA in water to afford (1S,3aR,4S,7R,7aS)-2-(O-cyclopropyl-N-(2,2,3,3,3-pentafluoropropanoyl)-L-threonyl)-2,3,3a,4,7,7a-hexahydro-1H-4,7-methanoisoindole-1-carboxylic acid (125 mg, 62%) as an off-white solid.

To a solution of (1S,3aR,4S,7R,7aS)-2-(O-cyclopropyl-N-(2,2,3,3,3-pentafluoropropanoyl)-L-threonyl)-2,3,3a,4,7,7a-hexahydro-1H-4,7-methanoisoindole-1-carboxylic acid (115 mg, 0.247 mmol, 1.0 eq.) in DMF (1.2 mL) cooled at 0° C. were added (S)-2-amino-3-((S)-2-oxopyrrolidin-3-yl)propanamide hydrochloride (61 mg, 0.296 mmol, 1.2 eq.), EDC•HCl (95 mg, 0.493 mmol, 2.0 eq.), HOAt (33 mg, 0.247 mmol, 1.0 eq.), and NEt₃ (0.10 mL, 0.714 mmol, 3.0 eq.). The mixture was stirred at rt for 18 h. The mixture was diluted with water (3 mL) and extracted with EA (4×5 mL). The organic phases were combined, dried over Na₂SO₄, filtered and concentrated under reduced pressure. The residue was purified by flash chromatography on C18 using a gradient of ACN (40 to 50%) in 0.1% FA in water to afford (1S,3aR,4S,7R,7aS)—N—((S)-1-amino-1-oxo-3-((S)-2-oxopyrrolidin-3-yl)propan-2-yl)-2-(O-cyclopropyl-N-(2,2,3,3,3-pentafluoropropanoyl)-L-threonyl)-2,3,3a,4,7,7a-hexahydro-1H-4,7-methanoisoindole-1-carboxamide (90 mg, 59%) as an off-white solid.

To a solution of (1S,3aR,4S,7R,7aS)—N—((S)-1-amino-1-oxo-3-((S)-2-oxopyrrolidin-3-yl)propan-2-yl)-2-(O-cyclopropyl-N-(2,2,3,3,3-pentafluoropropanoyl)-L-threonyl)-2,3,3a,4,7,7a-hexahydro-1H-4,7-methanoisoindole-1-carboxamide (85 mg, 0.137 mmol, 1.0 eq.) in DCM (1 mL) cooled at 0° C. were added pyridine (0.024 mL, 0.302 mmol, 2.2 eq.) and TFAA (0.021 mL, 0.151 mmol, 1.1 eq.). The mixture was stirred at 0° C. for 1 h. The mixture was diluted with water (3 mL), stirred for 5 min and extracted with EA (5×5 mL). The organic phases were combined, washed with sat. NaHCO₃ (2 mL), dried over Na₂SO₄, filtered and concentrated under reduced pressure. The residue was purified by preparative HPLC (Column: YMC-TRIART-C18 Column, 25*150 mm, 10 m; Mobile Phase A: 10 mM NH₄HCO₃ in water, Mobile Phase B: ACN; Flow rate: 17 mL/min; Gradient: 30% B to 70% B in 8 min) to afford (1S,3aR,4S,7R,7aS)—N—((S)-1-cyano-2-((S)-2-oxopyrrolidin-3-yl)ethyl)-2-(O-cyclopropyl-N-(2,2,3,3,3-pentafluoropropanoyl)-L-threonyl)-2,3,3a,4,7,7a-hexahydro-1H-4,7-methanoisoindole-1-carboxamide (32 mg, 39%) as a white solid. ¹H NMR (400 MHz, 362K, DMSO-d₆) δ 9.23 (m, 1H), 8.39-8.79 (m, 1H), 7.19-7.44 (m, 1H), 5.95-6.23 (m, 2H), 4.71-4.96 (m, 1H), 4.22-4.52 (m, 1H), 3.96-4.20 (m, 1H), 3.76-3.91 (m, 1H), 3.67 (m, 1H), 3.45-3.56 (m, 1H), 3.27-3.41 (m, 1H), 3.03-3.24 (m, 3H), 2.82-2.98 (m, 2H), 2.73 (m, 1H), 2.29-2.41 (m, 1H), 2.08-2.25 (m, 2H), 1.65-1.88 (m, 2H), 1.36-1.46 (m, 2H), 1.06-1.17 (m, 3H), 0.26-0.55 (m, 4H). LCMS (ESI, m/z): 602 [M+H]⁺.

Example 102

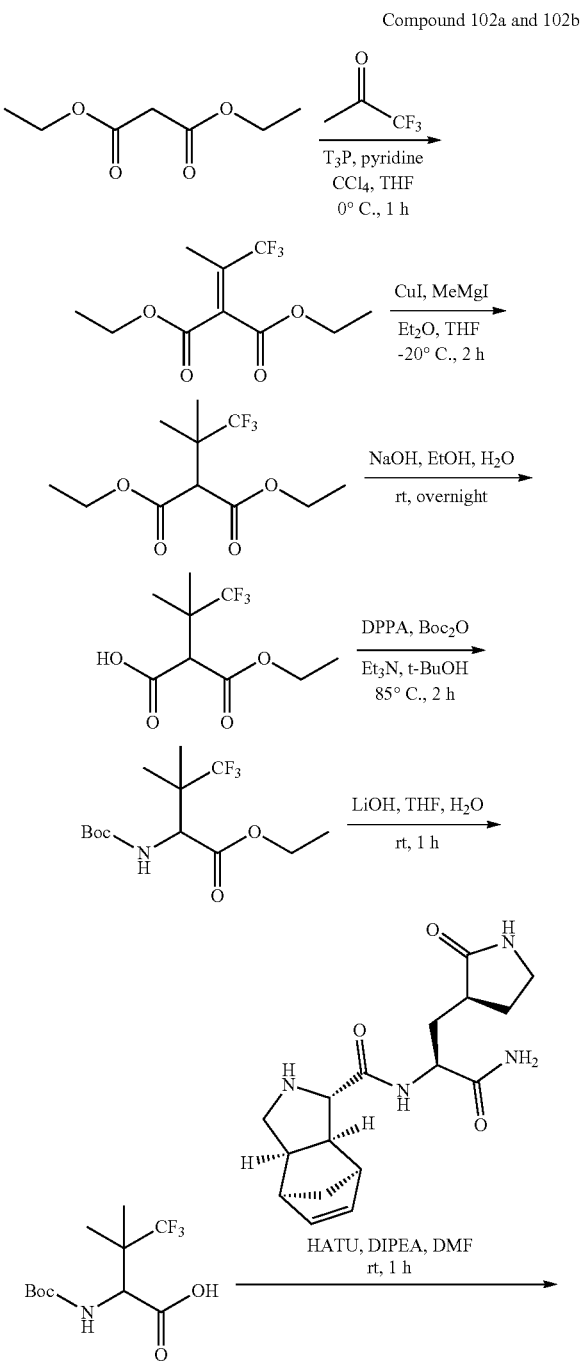

Compound 102a and 102b

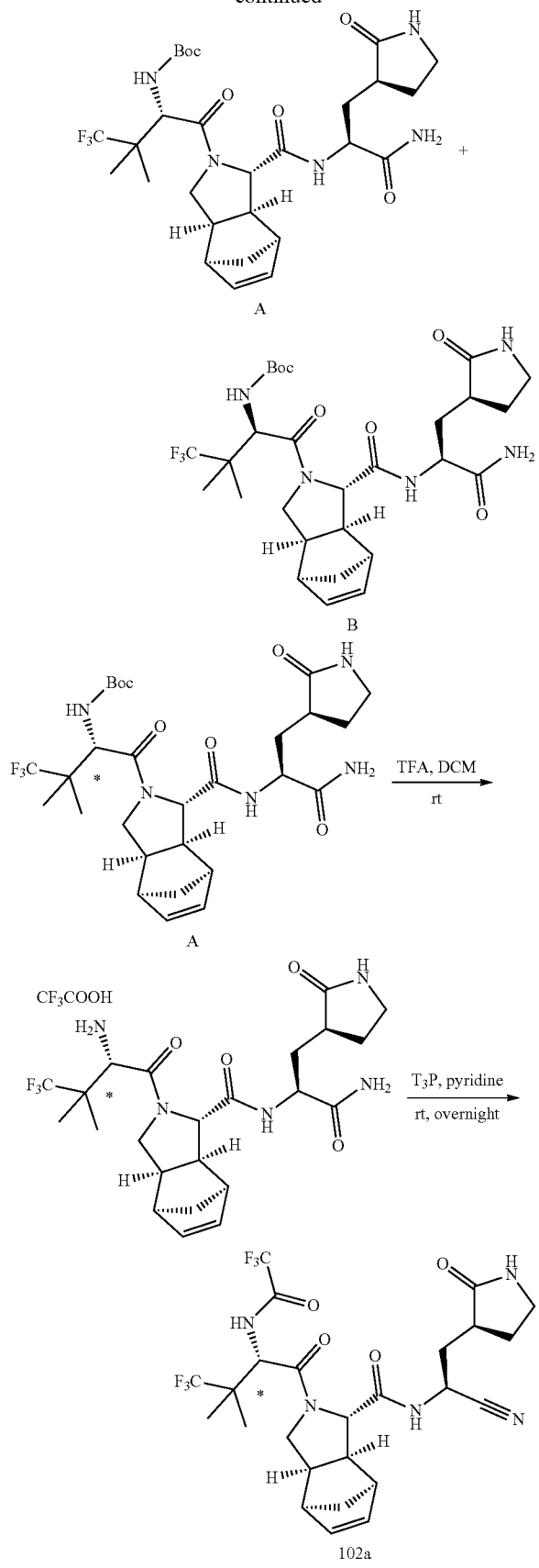

To a solution of titanium tetrachloride (35.5 g, 187 mmol, 1.0 eq.) in THF (750 mL) and carbon tetrachloride (90 mL) were added 1,1,1-trifluoroacetone (21.0 g, 187 mmol, 1.0 eq.) and diethyl malonatediethyl malonate (30 g, 187 mmol, 1.0 eq.) stirred under nitrogen at 0° C. After stirring for 0.5 h at 0° C., a solution of pyridine (60 mL) in THF (75 mL) was added and then stirred for 1 h at 0° C. The mixture was stirred overnight at rrt. The reaction was quenched with water (300 mL). The mixture was extracted with EA (3×500 mL). The organic layers were combined, washed with brine (2×300 mL) and saturated sodium bicarbonate (2×300 mL), dried over anhydrous sodium sulfate, filtered and concentrated under reduced pressure to afford the crude product. The crude product was chromatographed on a silica gel column with EA:PE (4%-10%) to provide diethyl 2-(1,1,1-trifluoropropan-2-ylidene)malonate (26 g, 54%) as a pale yellow oil. $^1$H NMR (400 MHz, Chloroform-d) δ 4.20-4.36 (m, 4H), 2.24 (s, 3H), 1.26-1.36 (m, 6H).

To a solution of diethyl 2-(1,1,1-trifluoropropan-2-ylidene)malonate (20.0 g, 78.7 mmol, 1.0 eq.) and cuprous iodide (7.49 g, 39.3 mmol, 0.5 eq.) in THF:DCM (250 mL, 1:5) was added dropwise methylmagnesium iodide (39.3 mL, 118 mmol, 1.5 eq., 3 M in Et$_2$O) over 1 h under nitrogen at −20° C. The mixture was stirred 1 h at −20° C. The mixture was poured into ice water (200 mL) and saturated aqueous ammonium chloride solution (200 mL) was added. The mixture stirred for 30 min. The mixture was extracted with EA (3×500 mL). The organic layers were combined, washed with brine (2×300 mL), dried over anhydrous sodium sulfate, filtered and concentrated under reduced pressure to afford diethyl 2-(1,1,1-trifluoro-2-methylpropan-2-yl)malonate (10.0 g, 47%, crude) as a colorless oil. $^1$H NMR (400 MHz, Chloroform-d) δ 4.11-4.23 (m, 4H), 3.66 (s, 1H), 1.30-1.41 (m, 6H), 1.26-1.29 (m, 6H). LCMS (ESI, m/z): 271 [M+H]$^+$.

To a solution of diethyl 2-(1,1,1-trifluoro-2-methylpropan-2-yl)malonate (10 g, 37.0 mmol, 1.0 eq.) in EtOH (100 mL) was added sodium hydroxide (1.48 g, 37.0 mmol, 1.0 eq., in 100 mL H$_2$O) stirred at rt. The mixture was stirred overnight at rt. The mixture was concentrated under reduced pressure to remove EtOH and extracted with EA (2×300 mL). The aqueous layer was acidified by 2 M aqueous hydrochloric acid to pH=3. The mixture was extracted with EA (3×300 mL). The organic layers were combined, dried over anhydrous sodium sulfate, filtered and concentrated under reduced pressure to afford 2-(ethoxycarbonyl)-4,4,4-trifluoro-3,3-dimethylbutanoic acid (6.5 g, 72%) as a yellow oil. $^1$H NMR (400 MHz, DMSO-d$_6$) δ 13.11 (br, 1H), 4.10-4.16 (m, 2H), 3.60 (s, 1H), 1.34-1.35 (m, 6H), 1.16-1.21 (m, 3H). LCMS (ESI, m/z): 243[M+H]$^+$.

To a mixture of 2-(ethoxycarbonyl)-4,4,4-trifluoro-3,3-dimethylbutanoic acid (6.50 g, 26.8 mmol, 1.0 eq.) in 2-methyl-2-propanol (100 mL) were added di-tert-butyl dicarbonate (23.4 g, 107 mmol, 4.0 eq.), triethylamine (3.53 g, 34.9 mmol, 1.3 eq.) and diphenylphosphoryl azide (8.86 g, 32.2 mmol, 1.2 eq.) stirred under nitrogen at rt. The mixture was stirred for 2 h at 85° C. The reaction was quenched with water (100 mL). The mixture was extracted with EA (3×300 mL). The organic layers were combined, washed with brine (2×150 mL), dried over anhydrous sodium sulfate, filtered and concentrated under reduced pressure to afford the crude product. The crude product was chromatographed on a silica gel column with EA:PE (5%) to provide ethyl 2-((tert-butoxycarbonyl)amino)-4,4,4-trifluoro-3,3-dimethylbutanoate (4.2 g, crude) as an off-white solid. LCMS (ESI, m/z): 214 [M−Boc+H]$^+$.

To a solution of ethyl 2-((tert-butoxycarbonyl)amino)-4,4,4-trifluoro-3,3-dimethylbutanoate (4.2 g, 13.4 mmol, 1.0 eq.) in THF (40 mL), H₂O (20 mL) and EtOH (20 mL) was added lithium hydroxide (1.61 g, 67.0 mmol, 5.0 eq.) at 0° C. The mixture was stirred for 1 h at rt and then concentrated under reduced pressure to remove THF and EtOH. The mixture was diluted with water (30 mL) and extracted with EA (2×100 mL). The aqueous layer was acidified by 2 M aqueous hydrochloric acid to pH=5. The mixture was extracted with EA (3×100 mL). The organic layers were combined, dried over anhydrous sodium sulfate, filtered and concentrated under reduced pressure to afford the crude product. The crude product was purified by C18 column with CH₃CN/Water (0.05% TFA). The desired fraction was concentrated under reduced pressure to provide 2-((tert-butoxycarbonyl)amino)-4,4,4-trifluoro-3,3-dimethylbutanoic acid (1.0 g, crude) as a yellow solid. LCMS (ESI, m/z): 186 [M−Boc+H]⁺.

To a mixture of 2-((tert-butoxycarbonyl)amino)-4,4,4-trifluoro-3,3-dimethylbutanoic acid (350 mg, 1.23 mmol, 1.0 eq.) in dimethylformamide (5 mL) were added o-(7-azabenzotriazol-1-yl)-N,N,N',N'-tetramethyluronium hexafluorophosphate (560 mg, 1.47 mmol, 1.2 eq.) and N-ethyl-N-isopropylpropan-2-amine (793 mg, 6.14 mmol, 5.0 eq.) at 0° C. After stirring for 20 min, (2S)-2-[(1R,2S,3S,6R,7S)-4-azatricyclo[5.2.1.0^{2,6}]dec-8-en-3-ylformamido]-3-[(3S)-2-oxopyrrolidin-3-yl]propanamide (408 mg, 1.23 mmol, 1.0 eq.) was added. The mixture was stirred for 1 h at rt. The reaction was quenched with water (5 mL). The crude product was purified by C18 column with CH₃CN/Water (0.05% FA), (42%). The desired fraction was concentrated under reduced pressure to provide tert-butyl N-[(2S)-1-[(1R,2S,3S,6R,7S)-3-{[(1S)-1-carbamoyl-2-[(3S)-2-oxopyrrolidin-3-yl]ethyl]carbamoyl}-4-azatricyclo[5.2.1.0^{2,6}]dec-8-en-4-yl]-4,4,4-trifluoro-3,3-dimethyl-1-oxobutan-2-yl]carbamate (400 mg, 54%) as a yellow solid. The product was separated by prep-SFC-HPLC (Column: CHIRALPAK IH, 3*25 cm, 5 μm; Mobile Phase A: CO₂, Mobile Phase B: MeOH (0.1% 2M NH₃-MeOH); Flow rate: 100 mL/min; Gradient: isocratic 25% B; Column Temperature (° C.): 35; Back Pressure (bar): 100; Wavelength: 220 nm; RT1 (min): 2.93; RT2 (min): 7.78;). Purification resulted in isomer 1, (130 mg, 17%, compound B) as a white solid and isomer 2 (165 mg, 22%, compound A) as white solids. LCMS (ESI, m/z): 600 [M+H]⁺.

To a mixture of tert-butyl ((S)-1-((1S,3aR,4S,7R,7aS)-1-(((S)-1-amino-1-oxo-3-((S)-2-oxopyrrolidin-3-yl)propan-2-yl)carbamoyl)-1,3,3a,4,7,7a-hexahydro-2H-4,7-methanoisoindol-2-yl)-4,4,4-trifluoro-1-oxobutan-2-yl) carbamate (160 mg, 0.267 mmol, 1.0 eq.) in dichloromethane (3 mL) was added trifluoroacetic acid (1 mL). The mixture was stirred for 2 h at rt and then concentrated under reduced pressure to afford (1S,3aR,4S,7R,7aS)—N—((S)-1-amino-1-oxo-3-((S)-2-oxopyrrolidin-3-yl)propan-2-yl)-2-((S)-2-amino-4,4,4-trifluoro-3,3-dimethylbutanoyl)-2,3,3a,4,7,7a-hexahydro-1H-4,7-methanoisoindole-1-carboxamide 2,2,2-trifluoroacetate (133 mg, crude) as a yellow oil. LC-MS (ESI, m/z): 500 [M+H]⁺.

To a stirred mixture of (1S,3aR,4S,7R,7aS)—N—((S)-1-amino-1-oxo-3-((S)-2-oxopyrrolidin-3-yl)propan-2-yl)-2-((S)-2-amino-4,4,4-trifluoro-3,3-dimethylbutanoyl)-2,3,3a,4,7,7a-hexahydro-1H-4,7-methanoisoindole-1-carboxamide 2,2,2-trifluoroacetate (133 mg, 0.266 mmol, 1.0 eq.) and propylphosphonic anhydride (1.69 g, 2.66 mmol, 10.0 eq., 50% in EtOAc) was added pyridine (105 mg, 1.33 mmol, 5.0 eq.) at rt. The mixture was stirred for overnight at rt. The reaction was quenched with water (20 mL). The mixture was extracted with EtOAc (3×50 mL). The organic layers were combined, washed with brine (2×10 mL), dried over anhydrous sodium sulfate, filtered and concentrated under reduced pressure to afford the crude product. The crude product was purified by prep-HPLC (Column: Sunfire Prep C18 OBD Column, 19*250 mm, 10 m; Mobile Phase A: Water (0.1% FA), Mobile Phase B: ACN; Flow rate: 25 mL/min; Gradient: 42% B to 72% B in 7 min, 72% B; Wave Length: 220 nm; RT1 (min): 6.55) to provide (1S,3aR,4S,7R,7aS)—N—((S)-1-cyano-2-((S)-2-oxopyrrolidin-3-yl)ethyl)-2-((S)-4,4,4-trifluoro-3,3-dimethyl-2-(2,2,2-trifluoroacetamido)butanoyl)-2,3,3a,4,7,7a-hexahydro-1H-4,7-methanoisoindole-1-carboxamide (47.9 mg, 31%, compound 102a) as a white solid. ¹H NMR (400 MHz, 80° C., DMSO-d₆) δ 9.45-9.80 (m, 1H), 8.60-9.20 (m, 1H), 7.20-7.70 (m, 1H), 5.85-6.30 (m, 2H), 5.00-5.30 (m, 1H), 4.50-5.00 (m, 1H), 3.90-4.20 (m, 1H), 3.60-3.90 (m, 1H), 3.35-3.60 (m, 1H), 3.15-3.35 (m, 2H), 2.90-3.10 (m, 3H), 2.60-2.89 (m, 1H), 2.05-2.45 (m, 3H), 1.65-1.90 (m, 2H), 0.90-1.50 (m, 8H). LC-MS (ESI, m/z): 578 [M+H]⁺.

Compound 120b was obtained similarly as described for compound 120a, using Intermediate B instead of intermediate A. LC-MS (ESI, m/z): 578 [M+H]⁺.

Example 103

Compound 103

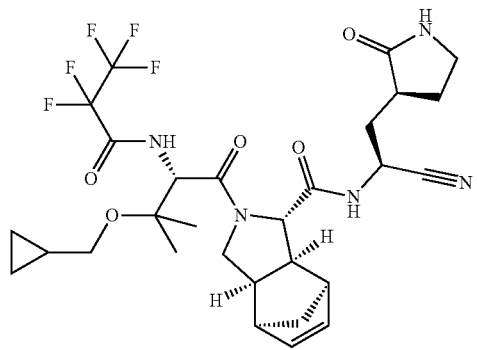

Compound 103 was prepared similarly as described for Compound 101 using methyl (S)-2-((tert-butoxycarbonyl)amino)-3-(cyclopropylmethoxy)-3-methylbutanoate in place of methyl N-(tert-butoxycarbonyl)-O-cyclopropyl-L-threoninate. ¹H NMR (400 MHz, 363K, DMSO-d₆) δ 8.32-8.84 (m, 2H), 7.35 (br. s., 1H), 5.92-6.25 (m, 2H), 4.90 (m, 1H), 4.63-4.80 (m, 1H), 3.99-4.29 (m, 1H), 3.75 (m, 1H), 3.34-3.54 (m, 1H), 3.02-3.25 (m, 5H), 2.81-2.96 (m, 2H), 2.75 (m, 1H), 2.22-2.41 (m, 1H), 2.14 (m, 2H), 1.62-1.91 (m, 2H), 1.34-1.47 (m, 2H), 1.10-1.24 (m, 6H), 0.87 (m, 1H), 0.39 (m, 2H), 0.13 (m, 2H). LCMS (ESI, m/z): 630 [M+H]⁺.

Methyl (S)-2-((tert-butoxycarbonyl)amino)-3-(cyclopropylmethoxy)-3-methylbutanoate: To a solution of methyl (S)-2-((tert-butoxycarbonyl)amino)-3-hydroxy-3-methylbutanoate (2.0 g, 8.10 mmol, 1.0 eq.) in THF (20 mL) were added allyl methyl carbonate (1.1 mL, 9.71 mmol, 1.2 eq.) and Pd(PPh₃)₄ (467 mg, 0.404 mmol, 0.05 eq.). The mixture was stirred at 70° C. for 16 h. The mixture was concentrated under reduced pressure. The residue was purified by flash chromatography on silica gel using a gradient of EA (5 to 20%) in PE to afford methyl (S)-3-(allyloxy)-2-((tert-butoxycarbonyl)amino)-3-methylbutanoate (1.5 g, 65%) as a yellow oil.

To a solution of methyl (S)-3-(allyloxy)-2-((tert-butoxycarbonyl)amino)-3-methylbutanoate (1.0 g, 3.48 mmol, 1.0 eq.) in Et$_2$O (5 mL) cooled at −30° C. were added a diazomethane solution in Et$_2$O (100 mL) and Pd(OAc)$_2$ (468 mg, 0.696 mmol, 0.2 eq.). The mixture was stirred at rt for 16 h. The mixture was filtered through celite. The filtrate was concentrated under reduced pressure. The residue was purified by flash chromatography on silica gel using a gradient of EA (5 to 20%) in PE to afford methyl (S)-2-((tert-butoxycarbonyl)amino)-3-(cyclopropylmethoxy)-3-methylbutanoate (950 mg, 91%) as an off-white solid. $^1$H NMR (500 MHz, CDCl$_3$) δ 5.33 (d, 1H), 4.29 (m, 1H), 3.73 (s, 3H), 3.15-3.27 (m, 2H), 1.44 (s, 9H), 1.30-1.40 (m, 6H), 0.95 (m, 1H), 0.48 (m, 2H), 0.16 (m, 2H). LCMS (ESI, m/z): 302 [M+H]$^+$.

The diazomethane solution in Et$_2$O was generated from N-methyl N-nitrosourea (10 g) in 40% KOH (30 mL) and diethyl ether (100 mL) at 0° C. The phases were separated. The organic phase was used directly for the reaction.

Example 104

Compound 104

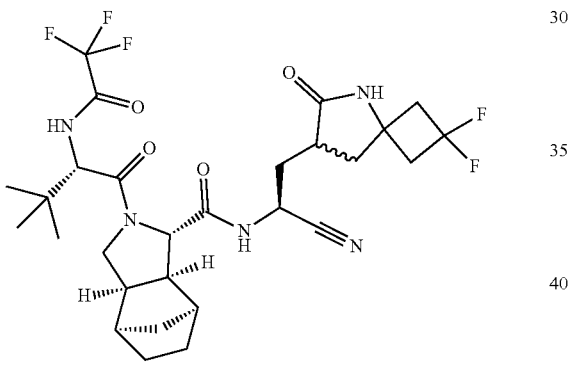

To a mixture of (1R,2S,3S,6R,7S)—N-[(1S)-1-cyano-2-{2,2-difluoro-6-oxo-5-azaspiro[3.4]octan-7-yl}ethyl]-4-[(2S)-3,3-dimethyl-2-(2,2,2-trifluoroacetamido)butanoyl]-4-azatricyclo[5.2.1.0^{2,6}]dec-8-ene-3-carboxamide (50.0 mg, 0.083 mmol, 1.0 eq.) in EtOAc (2 mL) was added 10% Palladium on activated carbon (25.0 mg). The mixture was stirred for 1 h at rt under hydrogen. The mixture was filtered through a celite pad, and the filtrate was concentrated under reduced pressure to afford the crude product. The crude product was purified by prepa-HPLC (Column: Kinetex EVO C18, 21.2×250 mm, 5 m; Mobile Phase A: Water (0.1% FA), Mobile Phase B: ACN; Flow rate: 25 mL/min; Gradient: 42% B to 72% B in 7 min, 72% B; Wave Length: 220 nm; RT: 5 min) to provide (1S,2S,3S,6R,7R)—N-[(1S)-1-cyano-2-{2,2-difluoro-6-oxo-5-azaspiro[3.4]octan-7-yl}ethyl]-4-[(2S)-3,3-dimethyl-2-(2,2,2-trifluoroacetamido) butanoyl]-4-azatricyclo[5.2.1.0^{2,6}]decane-3-carboxamide (13.6 mg, 27%) as a white solid. $^1$H NMR (400 MHz, 80° C., DMSO-d$_6$) δ 8.85-9.05 (m, 1H), 8.55-8.84 (m, 1H), 7.95-8.18 (m, 1H), 4.80-4.95 (m, 1H), 4.60-4.75 (m, 1H), 4.25-4.59 (m, 1H), 3.75-3.86 (m, 1H), 3.52-3.74 (m, 1H), 2.58-3.00 (m, 5H), 2.50-2.57 (m, 1H), 2.30-2.45 (m, 3H), 2.02-2.29 (m, 2H), 1.86-2.00 (m, 1H), 1.68-1.85 (m, 1H), 1.40-1.56 (m, 2H), 1.20-1.39 (m, 3H), 1.05-1.19 (m, 1H), 0.78-1.04 (m, 9H). LC-MS (ESI, m/z): 602 [M+H]$^+$.

Example 105

Compound 105

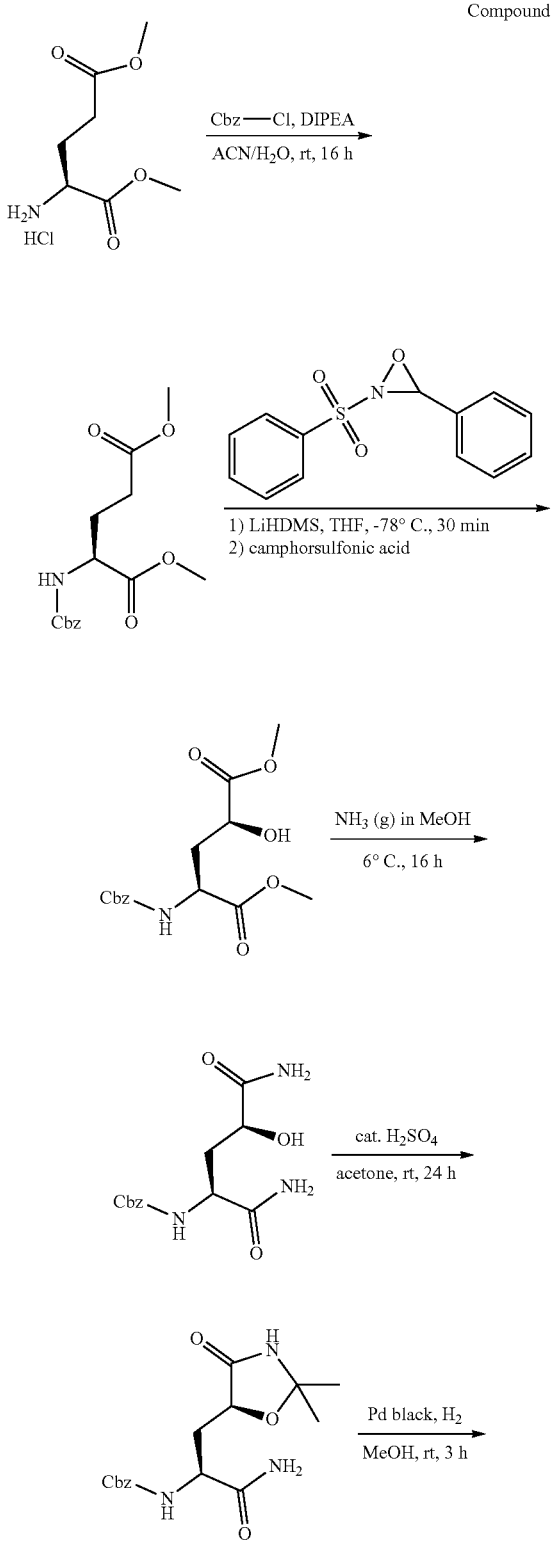

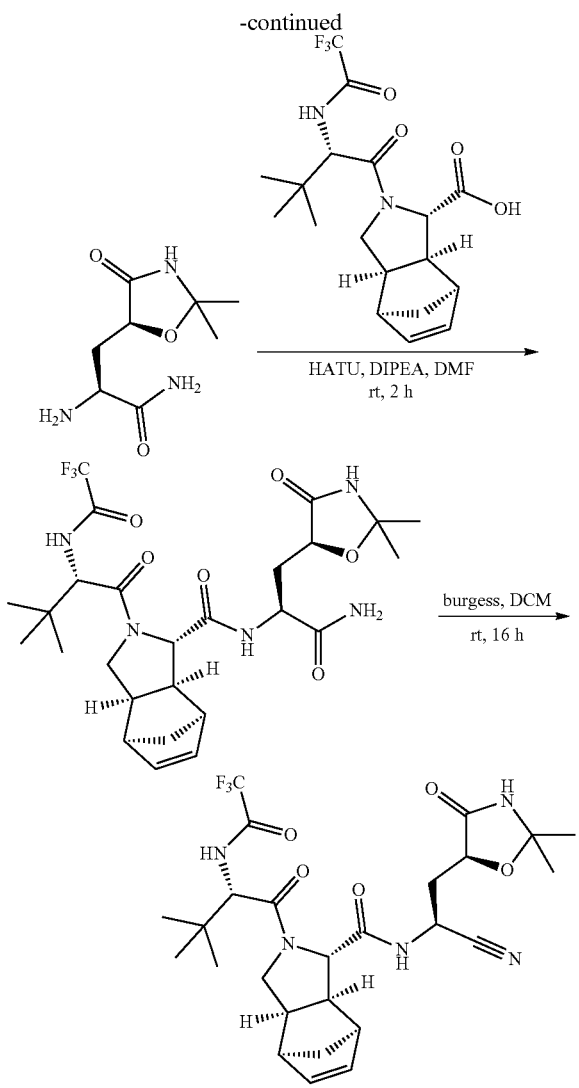

To a solution of dimethyl L-glutamate hydrogen chloride (5.00 g, 23.63 mmol, 1.0 eq.) in acetonitrile (200 mL) and water (30 mL) were added benzyl chloroformate (3.70 mL, 26.00 mmol, 1.1 eq.) and N,N-diisopropylethylamine (10.1 mL, 59.20 mmol, 2.5 eq.) under nitrogen. The mixture was stirred for 1 hour at rt and then concentrated under reduced pressure. The residue was purified by silica gel column chromatography, eluting with 0-50% tert-butyl methyl ether in dichloromethane to afford dimethyl ((benzyloxy)carbonyl)-L-glutamate (4.99 g, 68% yield) as colorless oil. $^1$H NMR (400 MHz, DMSO-$d_6$) δ 7.77 (d, J=7.8 Hz, 1H), 7.24-7.45 (m, 5H), 5.04 (s, 2H), 4.06-4.09 (m, 1H), 3.63 (s, 2H), 3.58 (s, 3H), 2.31-2.48 (m, 2H), 1.93-2.06 (m, 1H), 1.82-1.90 (m, 1H). LC-MS (ESI, m/z): 310 [M+H]$^+$.

To a solution of dimethyl N-benzyloxycarbonyl-L-glutamate (1.40 g, 4.76 mmol, 1.0 eq.) and 3-phenyl-N-phenylsulfonyl oxaziridine (1.87 g, 7.14 mmol, 1.5 eq.) in tetrahydrofuran (50 mL) was added lithium bis(trimethylsilyl) amide (1M solution in THF, 14.3 mL, 14.3 mmol, 3.0 eq.) dropwise at −78° C. under nitrogen. After stirred for 30 mins at −78° C., the reaction was quenched by the addition of a solution of camphorsulfonic acid (4.76 g, 20.94 mmol, 4.4 eq.) in THF (21 mL). The mixture was diluted with EA (100 mL), then aqueous HCl solution (conc. aq HCl solution:water, v:v=1:4, 100 mL). The mixture was warmed to rt and then stirred for 16 h. The mixture was extracted with EA (3×100 mL). The combined organic layer was washed with brine (100 mL), dried over anhydrous sodium sulfate and filtered. The filtrate was concentrated under reduced pressure to afford dimethyl (2S,4S)-2-(((benzyloxy)carbonyl) amino)-4-hydroxypentanedioate (2.00 g, crude) as light brown semi-solid, which was used in the next step directly without any further purification. LC-MS (ESI, m/z): 326 [M+H]$^+$.

A suspension of dimethyl (2S,4S)-2-(((benzyloxy)carbonyl)amino)-4-hydroxypentanedioate (2.00 g crude, 1.00 eq.) in NH$_3$ (g) in MeOH (7M solution, 40 mL) was stirred for 16 h at 60° C. The mixture was cooled to rt. The precipitated white solid was collected by filtration, washed with MeOH (2×10 mL) and dried in high vacuo to afford benzyl ((2S, 4S)-1,5-diamino-4-hydroxy-1,5-dioxopentan-2-yl)carbamate (902 mg, 67% yield for two steps) as a white solid. LC-MS (ESI, m/z): 296 [M+H]$^+$.

To a suspension of benzyl ((2S,4S)-1,5-diamino-4-hydroxy-1,5-dioxopentan-2-yl)carbamate (300 mg, 1.02 mmol, 1.0 eq.) in acetone (10 mL) was added conc. H$_2$SO$_4$ (0.1 mL). The mixture was stirred for 24 h at rt. The mixture was concentrated under reduced pressure. The residue was dissolved in DMSO and purified by reverse phase chromatography (Column: Agela C18 Column, 120 g; Mobile Phase A: Water (10 mM NH$_4$HCO$_3$+0.1% NH$_3$·H$_2$O), Mobile Phase B: ACN; Flow rate: 50 mL/min; Gradient: 0% B to 100% B in 60 min; Wavelength: 200 nm). The collected fraction was lyophilized directly to afford benzyl ((S)-1-amino-3-((S)-2,2-dimethyl-4-oxooxazolidin-5-yl)-1-oxopropan-2-yl)carbamate (144 mg, 42% yield) as a white solid. LC-MS (ESI, m/z): 336 [M+H]$^+$.

A mixture of benzyl ((S)-1-amino-3-((S)-2,2-dimethyl-4-oxooxazolidin-5-yl)-1-oxopropan-2-yl)carbamate (120 mg, 0.36 mmol, 1.0 eq.) and Pd black (67 mg, 0.63 mmol, 1.75 eq.) in methanol (20 mL) was degassed and refilled with hydrogen (3×). The mixture was stirred for 3 h at rt under hydrogen (hydrogen bag, 1-2 atm.). The mixture was filtered through a celite pad. The filtrate was concentrated under reduced pressure to afford (S)-2-amino-3-((S)-2,2-dimethyl-4-oxooxazolidin-5-yl)propanamide (70.0 mg, crude) as light yellow oil, which was used in the next step directly without any further purification. LC-MS (ESI, m/z): 20 2[M+H]$^+$.

To a mixture of (S)-2-amino-3-((S)-2,2-dimethyl-4-oxooxazolidin-5-yl)propanamide (70.0 mg, 0.35 mmol, 1.0 eq.) and (1S,3aR,4S,7R,7aS)-2-((S)-3,3-dimethyl-2-(2,2,2-trifluoroacetamido)butanoyl)-2,3,3a,4,7,7a-hexahydro-1H-4,7-methanoisoindole-1-carboxylic acid (163 mg, 0.42 mmol, 1.2 eq.) in DMF (5 mL) were added N,N-diisopropylethylamine (0.60 mL, 3.50 mmol, 10.0 eq.) and 2-(7-Azabenzotriazol-1-yl)-N,N,N',N'-tetramethyluronium hexafluorophosphate (330 mg, 0.87 mmol, 2.5 eq.). The mixture was stirred for 2 h at rt. The mixture was filtered with nylon syringe filter (13 mm*0.45 um). The filtrate was purified by reverse phase chromatography (Column: Agela C18 Column, 120 g; Mobile Phase A: Water (10 mM NH$_4$HCO$_3$+0.1% NH$_3$·H$_2$O), Mobile Phase B: ACN; Flow rate: 40 mL/min; Gradient: 0% B to 100% B in 60 min; Wavelength: 210 nm). The collected fraction was concentrated under reduced pressure to afford (1S,3aR,4S,7R, 7aS)—N—((S)-1-amino-3-((S)-2,2-dimethyl-4-oxooxazolidin-5-yl)-1-oxopropan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (157 mg, 79%) as a light orange solid. LC-MS (ESI, m/z): 572 [M+H]$^+$.

To a solution of (1S,3aR,4S,7R,7aS)—N—((S)-1-amino-3-((S)-2,2-dimethyl-4-oxooxazolidin-5-yl)-1-oxopropan-2-yl)-2-((S)-3,3-dimethyl-2-(2,2,2-trifluoroacetamido)bu-tanoyl)-2,3,3a,4,7,7a-hexahydro-1H-4,7-methanoisoindole-1-carboxamide (140 mg, 0.24 mmol, 1.0 rt) in dichloromethane (10 mL) was added Burgess reagent (300 mg, 1.26 mmol, 5.0 rt). The mixture was stirred for 16 h at rt and then concentrated. The residue was purified by reverse phase chromatography (Column: Agela Cis Column, 120 g; Mobile Phase A: Water (0.05% TFA), Mobile Phase B: ACN; Flow rate: 40 mL/min; Gradient: 0% B to 100% B in 60 min; Wavelength: 210 nm). The collected fraction was lyophilized directly to afford (1S,3aR,4S,7R,7aS)—N—((S)-1-cyano-2-((S)-2,2-dimethyl-4-oxooxazolidin-5-yl)ethyl)-2-((S)-3,3-dimethyl-2-(2,2,2-trifluoroacetamido)bu-tanoyl)-2,3,3a,4,7,7a-hexahydro-1H-4,7-methanoisoindole-1-carboxamide (43.4 mg, 32% yield) as a light orange solid. $^1$H NMR (400 MHz, 80° C., DMSO-$d_6$) δ 8.70-8.85 (m, 2H), 8.61-8.63 (m, 1H), 5.99-6.20 (m, 2H), 4.70-4.83 (m, 1H), 4.35-4.50 (m, 1H), 4.10-4.30 (m, 1H), 4.04 (d, J=2.4 Hz, 1H), 3.60-3.65 (m, 1H), 3.44-3.46 (m, 1H), 3.00-3.20 (m, 1H), 2.92-3.05 (m, 2H), 2.70-2.85 (m, 1H), 2.03-2.22 (m, 2H), 1.31-1.40 (m, 8H), 0.78-0.94 (m, 9H). LC-MS (ESI, m/z): 554 [M+H]$^+$.

Example 106

Compound 106

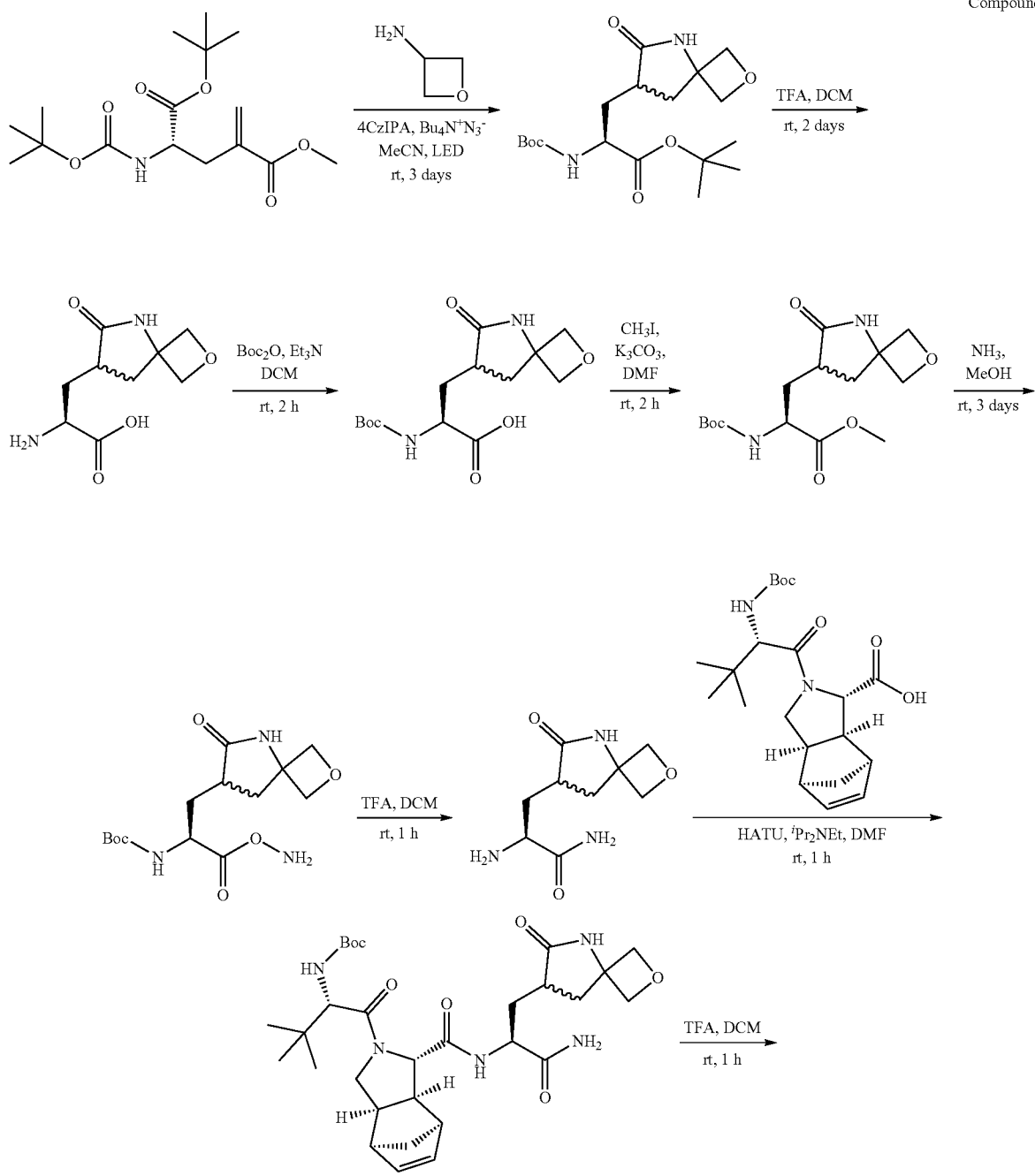

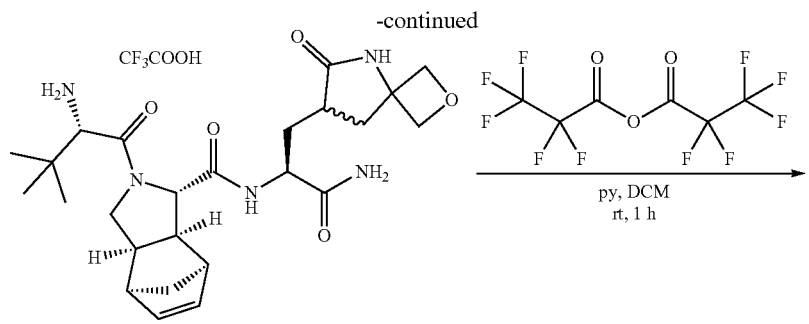

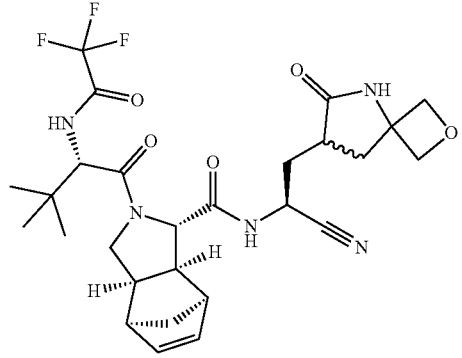

To a mixture of 1-tert-butyl 5-methyl (2S)-2-[(tert-butoxycarbonyl)amino]-4-methylidenepentanedioate (3.00 g, 9.11 mmol, 1.0 eq.), 2,4,5,6-tetra-9H-carbazol-9-yl-1,3-benzenedicarbonitrile (72.0 mg, 0.091 mmol, 0.01 eq.) and tetrabutylammonium azide (259 mg, 0.911 mmol, 0.1 eq.) in MeCN (40 mL) was added oxetan-3-amine (666 mg, 9.11 mmol, 1.0 eq.) under nitrogen. The mixture was stirred for 3 days at rt under nitrogen under 450 nm LED lamp. The mixture was concentrated under reduced pressure to afford the crude product. The crude product was chromatographed on a silica gel column with MeOH:DCM (1:12) to provide tert-butyl (2S)-2-[(tert-butoxycarbonyl)amino]-3-{6-oxo-2-oxa-5-azaspiro[3.4]octan-7-yl}propanoate (1.08 g, 32%) as a light yellow solid. ¹H NMR (400 MHz, DMSO-d₆) δ 8.52-8.62 (m, 1H), 6.70-7.40 (m, 1H), 4.60-4.70 (m, 1H), 4.40-4.59 (m, 3H), 3.75-4.10 (m, 1H), 2.54-2.65 (m, 1H), 2.27-2.39 (m, 1H), 1.80-2.10 (m, 2H), 1.48-1.60 (m, 1H), 1.32-1.47 (m, 18H). LC-MS (ESI, m/z): 371 [M+H]⁺.

To a mixture of tert-butyl (2S)-2-[(tert-butoxycarbonyl)amino]-3-{6-oxo-2-oxa-5-azaspiro[3.4]octan-7-yl}propanoate (1.08 g, 2.70 mmol, 1.0 eq.) in DCM (30 mL) was added trifluoroacetic acid (15 mL). The mixture was stirred for 2 days at rt and then concentrated under reduced pressure to afford (2S)-2-amino-3-{6-oxo-2-oxa-5-azaspiro[3.4]octan-7-yl}propanoic acid (578 mg, crude) as a brown oil. LC-MS (ESI, m/z): 215 [M+H]⁺.

To a mixture of (2S)-2-amino-3-{6-oxo-2-oxa-5-azaspiro[3.4]octan-7-yl}propanoic acid (578 mg, 2.70 mmol, 1.0 eq.) in DCM (10 mL) were added triethylamine (1.10 g, 10.9 mmol, 4.03 eq.) and di-tert-butyl dicarbonate (707 mg, 3.24 mmol, 1.2 eq.). The mixture was stirred for 2 h at rt and then concentrated under reduced pressure to afford (2S)-2-[(tert-butoxycarbonyl)amino]-3-{6-oxo-2-oxa-5-azaspiro[3.4]octan-7-yl}propanoic acid (850 mg, crude) as a brown oil. LC-MS (ESI, m/z): 315 [M+H]⁺.

To a mixture of (2S)-2-[(tert-butoxycarbonyl)amino]-3-{6-oxo-2-oxa-5-azaspiro[3.4]octan-7-yl}propanoic acid (847 mg, 2.70 mmol, 1.0 eq.) in DMF (15 mL) were added potassium carbonate (1.2 g, 8.08 mmol, 3.0 eq.) and methyl iodide (459 mg, 3.23 mmol, 1.2 eq.). The mixture was stirred for 2 h at rt. The reaction was quenched with water (30 mL). The mixture was extracted with EtOAc (3×30 mL). The organic layers were combined, washed with brine (2×30 mL), dried over anhydrous sodium sulfate, filtered and concentrated under reduced pressure to afford methyl (2S)-2-[(tert-butoxycarbonyl)amino]-3-{6-oxo-2-oxa-5-azaspiro[3.4]octan-7-yl}propanoate (438 mg, crude) as a yellow oil. LC-MS (ESI, m/z): 329 [M+H]⁺.

A mixture of methyl (2S)-2-[(tert-butoxycarbonyl)amino]-3-{6-oxo-2-oxa-5-azaspiro[3.4]octan-7-yl}propanoate (438 mg, 1.33 mmol, 1.0 eq.) in ammonia (15 mL, 7 M in MeOH) was stirred for 3 days at rt. The mixture was concentrated under reduced pressure to afford the crude product. The crude product was chromatographed on a silica gel column with MeOH:DCM (8:92) to provide tert-butyl N-[(1S)-1-carbamoyl-2-{6-oxo-2-oxa-5-azaspiro[3.4]octan-7-yl}ethyl]carbamate (180 mg, 40%) as a white solid. ¹H NMR (400 MHz, DMSO-d₆) δ 8.51-8.59 (m, 1H), 7.24-7.32 (m, 1H), 6.96-7.05 (s, 1H), 6.86-6.94 (m, 1H), 4.61-4.70 (m, 1H), 4.41-4.57 (m, 3H), 3.74-4.15 (m, 1H), 2.54-2.69 (m, 1H), 2.29-2.39 (m, 1H), 1.70-2.05 (m, 2H), 1.33-1.55 (m, 10H). LC-MS (ESI, m/z): 314 [M+H]⁺.

To a mixture of tert-butyl N-[(1S)-1-carbamoyl-2-{6-oxo-2-oxa-5-azaspiro[3.4]octan-7-yl}ethyl]carbamate (100 mg, 0.319 mmol, 1.0 eq.) in DCM (3 mL) was added trifluoroacetic acid (1 mL). The mixture was stirred for 1 h at rt and then concentrated under reduced pressure to afford (2S)-2-amino-3-{2-oxa-5-azaspiro[3.4]octan-7-yl}propanamide (68 mg, crude) as a brown oil. LC-MS (ESI, m/z): 214 [M+H]⁺.

To a mixture of (1R,2S,3S,6R,7S)-4-[(2S)-2-[(tert-butoxycarbonyl)amino]-3,3-dimethylbutanoyl]-4-azatricyclo[5.2.1.0^{2,6}]dec-8-ene-3-carboxylic acid (126 mg, 0.321 mmol, 1.0 eq.) and o-(7-azabenzotriazol-1-yl)-N,N,N',N'-tetramethyluronium hexafluorophosphate (145 mg, 0.381 mmol, 1.2 eq.) in DMF (3 mL) was added N-ethyl-N-isopropylpropan-2-amine (248 mg, 1.919 mmol, 6.00 eq.) at 0° C. After stirring for 15 min at 0° C., (2S)-2-amino-3-{6- oxo-2-oxa-5-azaspiro[3.4]octan-7-yl}propanamide (68.0 mg, 0.319 mmol, 1.0 eq.) was added. The mixture was stirred for 1 h at 0° C. The mixture was purified by C18 column with CH$_3$CN/Water (0.05% NH$_4$HCO$_3$+NH$_3$·H$_2$O, pH-13). The desired fraction was concentrated under reduced pressure to provide tert-butyl N-[(2S)-1-[(1R,2S, 3S,6R,7S)-3-{[(1S)-1-carbamoyl-2-{6-oxo-2-oxa-5-azaspiro[3.4]octan-7-yl}ethyl]carbamoyl}-4-azatricyclo [5.2.1.0^{2,6}]dec-8-en-4-yl]-3,3-dimethyl-1-oxobutan-2-yl]carbamate (100 mg, 52%) as a white solid. LC-MS (ESI, m/z): 588 [M+H]$^+$.

To a mixture of tert-butyl N-[(2S)-1-[(1R,2S,3S,6R,7S)-3-{[(1S)-1-carbamoyl-2-{6-oxo-2-oxa-5-azaspiro[3.4]octan-7-yl}ethyl]carbamoyl}-4-azatricyclo[5.2.1.0^{2,6}]dec-8-en-4-yl]-3,3-dimethyl-1-oxobutan-2-yl]carbamate (40.0 mg, 0.068 mmol, 1.0 eq.) in DCM (0.9 mL) was added trifluoroacetic acid (0.3 mL). The mixture was stirred at rt for 1 h and then concentrated under reduced pressure to afford (2S)-2-{[(1R,2S,3S,6R,7S)-4-[(2S)-2-amino-3,3-dimethylbutanoyl]-4-azatricyclo[5.2.1.0^{2,6}]dec-8-en-3-yl]formamido}-3-{6-oxo-2-oxa-5-azaspiro[3.4]octan-7-yl}propanamide (34.0 mg, crude) as a brown oil. LC-MS (ESI, m/z): 488 [M+H]$^+$.

To a mixture of (2S)-2-{[(1R,2S,3S,6R,7S)-4-[(2S)-2-amino-3,3-dimethylbutanoyl]-4-azatricyclo[5.2.1.0^{2,6}]dec-8-en-3-yl]formamido}-3-{6-oxo-2-oxa-5-azaspiro[3.4]octan-7-yl}propanamide (34.0 mg, 0.068 mmol, 1.0 eq.) in DCM (1 mL) were added pyridine (22.0 mg, 0.272 mmol, 4.0 eq.) and 2,2,3,3,3-pentafluoropropanoic anhydride (38.0 mg, 0.123 mmol, 1.8 eq.). The mixture was stirred for 1 h at rt. The reaction was quenched with water (2 mL). The mixture was extracted with DCM (3×2 mL). The organic layers were combined, washed with brine (2×2 mL), dried over anhydrous sodium sulfate, filtered and concentrated under reduced pressure to afford (1R,2S,3S,6R,7S)—N-[(1S)-1-cyano-2-{6-oxo-2-oxa-5-azaspiro[3.4]octan-7-yl}ethyl]-4-[(2S)-3,3-dimethyl-2-(2,2,2-trifluoroacetamido)butanoyl]-4-azatricyclo[5.2.1.0^{2,6}]dec-8-ene-3-carboxamide (30.0 mg, crude) as a brown oil. LC-MS (ESI, m/z): 566 [M+H]$^+$.

Crude (1R,2S,3S,6R,7S)—N-[(1S)-1-cyano-2-{6-oxo-2-oxa-5-azaspiro[3.4]octan-7-yl}ethyl]-4-[(2S)-3,3-dimethyl-2-(2,2,2-trifluoroacetamido)butanoyl]-4-azatricyclo[5.2.1.0^{2,6}]dec-8-ene-3-carboxamide (30.0 mg) was purified by prep-HPLC (Column: XSelect CSH Prep C18 OBD Column, 19×150 mm, 5 m; Mobile Phase A: Water (0.1% FA), Mobile Phase B: ACN; Flow rate: 25 mL/min; Gradient: 31% B to 61% B in 7 min, 61% B; Wave Length: 220 nm; RT1 (min): 5.6;) to provide (1R,2S,3S,6R,7S)—N-[(1S)-1-cyano-2-{6-oxo-2-oxa-5-azaspiro[3.4]octan-7-yl}ethyl]-4-[(2S)-3,3-dimethyl-2-(2,2,2-trifluoroacetamido)butanoyl]-4-azatricyclo[5.2.1.0^{2,6}]dec-8-ene-3-carboxamide (9.8 mg, 19%) as a white solid. $^1$H NMR (400 MHz, 80° C., DMSO-d6) δ 8.78-8.98 (m, 1H), 8.62-8.75 (m, 1H), 8.36-8.58 (m, 1H), 5.94-6.20 (m, 2H), 4.89-4.99 (m, 1H), 4.61-4.70 (m, 1H), 4.37-4.60 (m, 4H), 3.98-4.15 (m, 1H), 3.58-3.72 (m, 1H), 3.32-3.51 m, 1H), 3.11-3.21 (m, 1H), 2.67-2.99 (m, 4H), 2.51-2.62 (m, 1H), 2.39-2.47 (m, 1H), 1.92-2.33 (m, 1H), 1.67-1.89 (m, 1H), 1.34-1.48 (m, 2H), 0.84-1.06 (m, 9H). LC-MS (ESI, m/z): 566 [M+H]$^+$.

Example 107

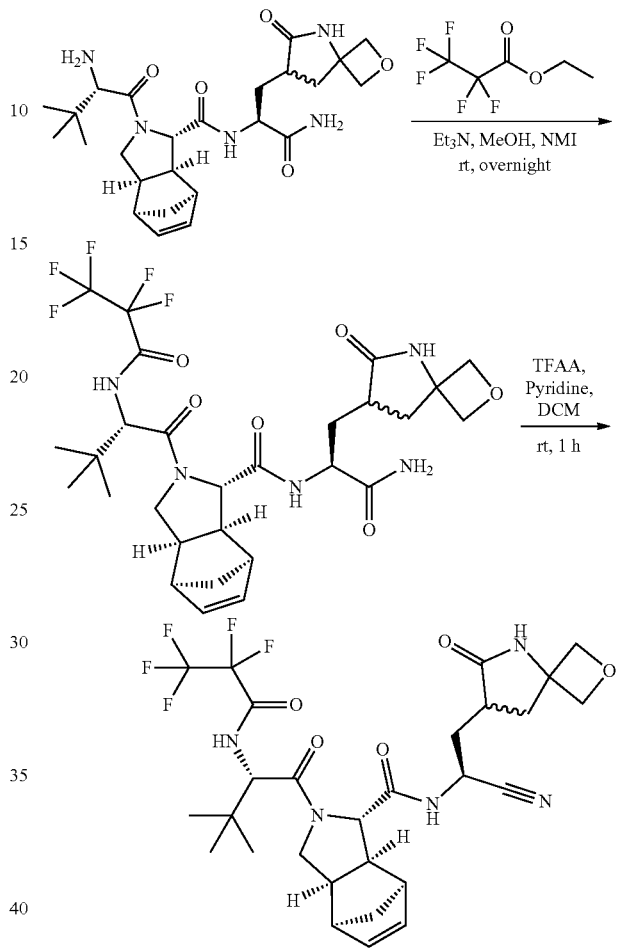

Compound 107

To a mixture of (2S)-2-{[(1R,2S,3S,6R,7S)-4-[(2S)-2-amino-3,3-dimethylbutanoyl]-4-azatricyclo[5.2.1.0^{2,6}]dec-8-en-3-yl]formamido}-3-{6-oxo-2-oxa-5-azaspiro[3.4]octan-7-yl}propanamide (66.0 mg, 0.136 mmol, 1.0 eq.) in MeOH (4 mL) were added triethylamine (69.0 mg, 0.680 mmol, 5.0 eq.), N-methylimidazole (22.0 mg, 0.272 mmol, 2.0 eq.) and ethyl pentafluoropropionate (261 mg, 1.36 mmol, 10.0 eq.). The mixture was stirred overnight at rt. The reaction was quenched with water (10 mL). The mixture was extracted with EtOAc (3×10 mL). The organic layers were combined, dried over anhydrous sodium sulfate, filtered and concentrated under reduced pressure to afford the crude product. The crude product was chromatographed on a silica gel column with MeOH:DCM (7:93) and then concentrated under reduced pressure to provide N-[(2S)-1-[(1R,2S,3S,6R,7S)-3-{[(1S)-1-carbamoyl-2-{6-oxo-2-oxa-5-azaspiro[3.4]octan-7-yl}ethyl]carbamoyl}-4-azatricyclo[5.2.1.0^{2,6}]dec-8-en-4-yl]-3,3-dimethyl-1-oxobutan-2-yl]-2,2,3,3,3-pentafluoropropanamide (60.0 mg, 66%) as an off-white solid. LC-MS (ESI, m/z): 634 [M+H]$^+$.

To a mixture of N-[(2S)-1-[(1R,2S,3S,6R,7S)-3-{[(1S)-1-carbamoyl-2-{6-oxo-2-oxa-5-azaspiro[3.4]octan-7-yl}ethyl]carbamoyl}-4-azatricyclo[5.2.1.0^{2,6}]dec-8-en-4-yl]-3,3-dimethyl-1-oxobutan-2-yl]-2,2,3,3,3- pentafluoropropanamide (60.0 mg, 0.095 mmol, 1.0 eq.) in DCM (1 mL) were added pyridine (27.0 mg, 0.333 mmol, 3.5 eq.) and trifluoroacetic anhydride (28.0 mg, 0.133 mmol, 1.4 eq.). The mixture was stirred for 1 h at rt. The reaction was quenched with water (3 mL). The mixture was extracted with DCM (3×3 mL). The organic layers were combined, washed with brine (2×3 mL), dried over anhydrous sodium sulfate, filtered and concentrated under reduced pressure to afford the crude product. The crude product was purified by prep-HPLC (Column: XSelect CSH Prep C18 OBD Column, 19×150 mm, 5 m; Mobile Phase A: Water (0.1% FA), Mobile Phase B: ACN; Flow rate: 25 mL/min; Gradient: 34% B to 64% B in 7 min, 64% B; Wave Length: 220 nm; RT1 (min): 6.25) to provide (1R,2S,3S,6R,7S)—N-[(1S)-1-cyano-2-{6-oxo-2-oxa-5-azaspiro[3.4]octan-7-yl}ethyl]-4-[(2S)-3,3-dimethyl-2-(2,2,3,3,3-pentafluoropropanamido)butanoyl]-4-azatricyclo[5.2.1.0^{2,6}]dec-8-ene-3-carboxamide (9.8 mg, 16%) as a white solid. $^1$H NMR (400 MHz, 80° C., DMSO-d$_6$) δ 8.60-8.96 (m, 2H), 8.08-8.59 (m, 1H), 5.91-6.25 (m, 2H), 4.80-5.03 (m, 1H), 4.60-4.75 (m, 1H), 4.33-4.59 (m, 4H), 3.95-4.20 (m, 1H), 3.60-3.75 (m, 1H), 3.35-3.59 (m, 1H), 2.80-3.00 (m, 2H), 2.60-2.79 (m, 2H), 2.50-2.59 (m, 1H), 2.35-2.40 (m, 1H), 1.90-2.34 (m, 2H), 1.65-1.86 (m, 1H), 1.32-1.46 (m, 2H), 0.80-1.02 (m, 9H). LC-MS (ESI, m/z): 616 [M+H]$^+$.

Example 108

Compound 108

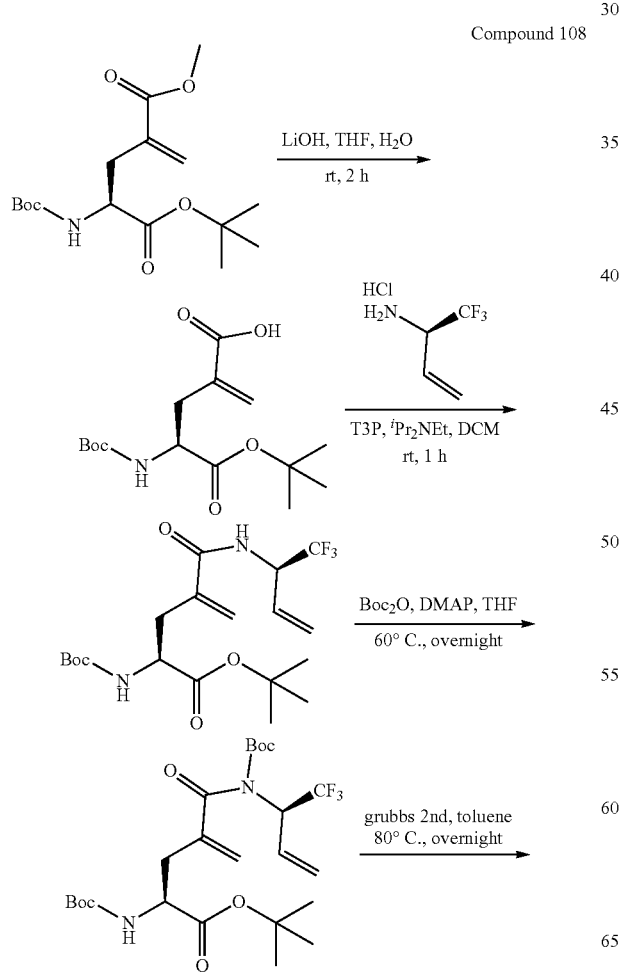

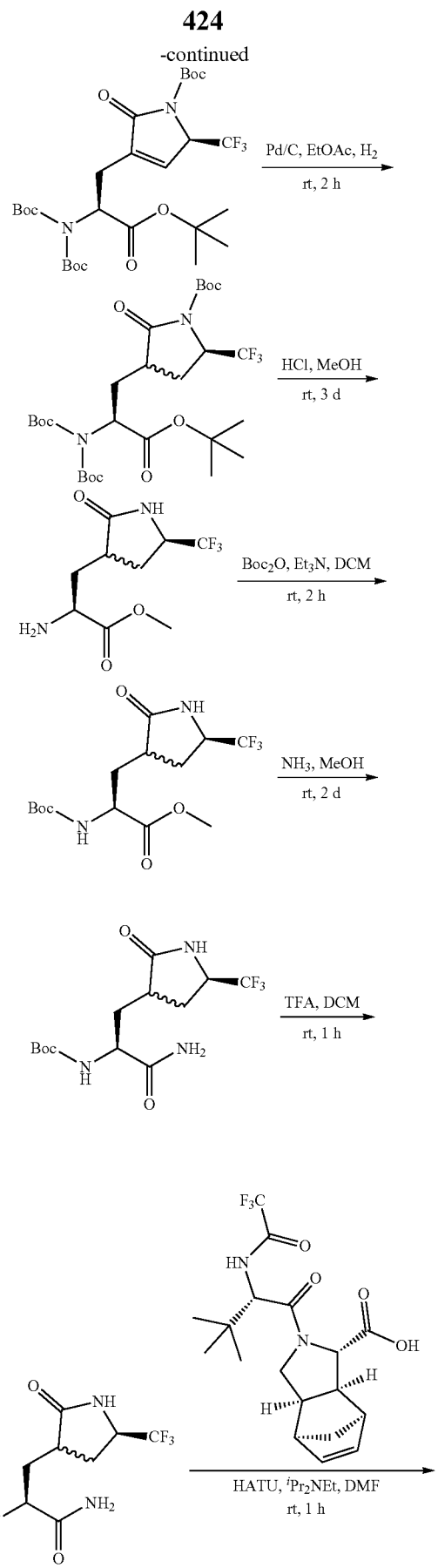

-continued

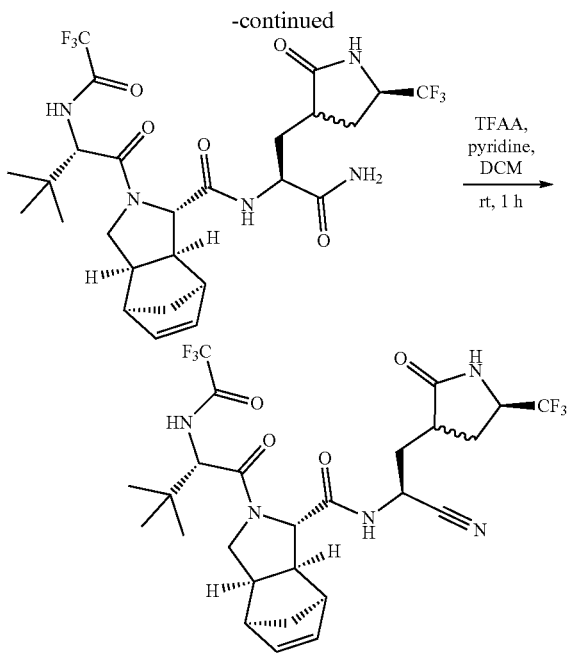

To a mixture of 1-tert-butyl 5-methyl (2S)-2-[(tert-butoxycarbonyl)amino]-4-methylidenepentanedioate (5.00 g, 15.2 mmol, 1.0 eq.) in THF (50 mL)/water (50 mL) was added lithium hydroxide (1.09 g, 45.5 mmol, 3.0 eq.). The mixture was stirred for 2 h at rt. Water (50 mL) was added, and the mixture was adjusted to pH=6 with hydrochloric acid (1 M). The mixture was extracted with EtOAc (3×100 mL). The organic layers were combined, dried over anhydrous sodium sulfate, filtered and concentrated under reduced pressure to afford the crude product. The crude product was purified by C18 column with CH$_3$CN/Water (0.05% TFA). The desired fraction was concentrated under reduced pressure to provide (4S)-5-(tert-butoxy)-4-[(tert-butoxycarbonyl)amino]-2-methylidene-5-oxopentanoic acid (2.56 g, 51%) as a light yellow semi-solid. $^1$H NMR (400 MHz, DMSO-d$_6$) δ 12.57 (s, 1H), 6.64-7.14 (m, 1H), 6.06-6.13 (m, 1H), 5.60-5.74 (m, 1H), 3.92-4.14 (m, 1H), 2.55-2.67 (m, 1H), 2.37-2.48 (m, 1H), 1.30-1.45 (m, 18H). LC-MS (ESI, m/z): 316 [M+H]$^+$.

To a mixture of (2R)-1,1,1-trifluorobut-3-en-2-amine hydrochloride (1.33 g, 8.23 mmol, 1.0 eq.) and (4S)-5-(tert-butoxy)-4-[(tert-butoxycarbonyl)amino]-2-methylidene-5-oxopentanoic acid (2.60 g, 8.23 mmol, 1.0 eq.) in DCM (40 mL) were added N-ethyl-N-isopropylpropan-2-amine (4.26 g, 32.9 mmol, 4.0 eq.) and 2,4,6-tripropyl-1,3,5,2,4,6-trioxatriphosphorinane-2,4,6-trioxide (5.24 g, 8.23 mmol, 1.0 eq., 50% in EtOAc). The mixture was stirred for 1 h at rt. The reaction was quenched with water (50 mL). The mixture was extracted with DCM (3×30 mL). The organic layers were combined, washed with brine (2×30 mL), dried over anhydrous sodium sulfate, filtered and concentrated under reduced pressure to afford the crude product. The crude product was chromatographed on a silica gel column with EtOAc:PE (13:87) to provide tert-butyl (2S)-2-[(tert-butoxycarbonyl)amino]-4-{[(2R)-1,1,1-trifluorobut-3-en-2-yl]carbamoyl}pent-4-enoate (1.66 g, 45%) as a light yellow semi-solid. LC-MS (ESI, m/z): 423 [M+H]$^+$.

To a mixture of tert-butyl (2S)-2-[(tert-butoxycarbonyl)amino]-4-{[(2R)-1,1,1-trifluorobut-3-en-2-yl]carbamoyl}pent-4-enoate (1.66 g, 3.93 mmol, 1.0 eq.) in THF (40 mL) were added di-tert-butyl dicarbonate (3.43 g, 15.7 mmol, 4.0 eq.) and N,N-dimethylpyridin-4-amine (240 mg, 1.96 mmol, 0.5 eq.). The mixture was stirred overnight at 60° C. The reaction was quenched with water (80 mL). The mixture was extracted with DCM (3×80 mL). The organic layers were combined, washed with brine (2×80 mL), dried over anhydrous sodium sulfate, filtered and concentrated under reduced pressure to afford the crude product. The crude product was chromatographed on a silica gel column with EtOAc:PE (7:93) to provide tert-butyl (2S)-2-[bis(tert-butoxycarbonyl)amino]-4-{[(tert-butoxycarbonyl)[(2R)-1,1,1-trifluorobut-3-en-2-yl]amino]carbonyl}pent-4-enoate (1.68 g, 67%) as a light yellow oil. LC-MS (ESI, m/z): 423 [M−200+H]$^+$.

To a mixture of tert-butyl (2S)-2-[bis(tert-butoxycarbonyl)amino]-4-{[(tert-butoxycarbonyl)[(2R)-1,1,1-trifluorobut-3-en-2-yl]amino]carbonyl}pent-4-enoate (1.0 g, 1.61 mmol, 1.0 eq.) in toluene (100 mL) was added Grubbs 2$^{nd}$ (409 mg, 0.482 mmol, 0.3 eq.) under nitrogen. The mixture was stirred overnight at 80° C. The reaction was quenched with water (200 mL). The mixture was extracted with EtOAc (3×200 mL). The organic layers were combined, washed with brine (2×200 mL), dried over anhydrous sodium sulfate, filtered and concentrated under reduced pressure to afford the crude product. The crude product was chromatographed on a silica gel column with EtOAc:PE (11:89) to provide tert-butyl (5R)-3-[(2S)-2-[bis(tert-butoxycarbonyl)amino]-3-(tert-butoxy)-3-oxopropyl]-2-oxo-5-(trifluoromethyl)-5H-pyrrole-1-carboxylate (580 mg, 56%) as a light yellow semi-solid. LC-MS (ESI, m/z): 395 [M−200+H]$^+$.

To a mixture of tert-butyl (5R)-3-[(2S)-2-[bis(tert-butoxycarbonyl)amino]-3-(tert-butoxy)-3-oxopropyl]-2-oxo-5-(trifluoromethyl)-5H-pyrrole-1-carboxylate (1.00 g, 1.68 mmol, 1.0 eq.) in EtOAc (20 mL) was added 10% Palladium on activated carbon (500 mg). The mixture was stirred for 2 h at rt under hydrogen. The mixture was filtered through a celite pad, and the filtrate was concentrated under reduced pressure to tert-butyl (5R)-3-[(2S)-2-[bis(tert-butoxycarbonyl)amino]-3-(tert-butoxy)-3-oxopropyl]-2-oxo-5-(trifluoromethyl)pyrrolidine-1-carboxylate (980 mg, 96%) as a yellow oil. LC-MS (ESI, m/z): 397 [M−200+H]$^+$.

To a solution of tert-butyl (5R)-3-[(2S)-2-[bis(tert-butoxycarbonyl)amino]-3-(tert-butoxy)-3-oxopropyl]-2-oxo-5-(trifluoromethyl)pyrrolidine-1-carboxylate (200 mg, 0.335 mmol, 1.0 eq.) in MeOH (5 mL) was added hydrochloric acid (5 mL, 9 M in water). The mixture was stirred for 3 days at rt and then concentrated under reduced pressure to afford methyl (2S)-2-amino-3-[(5R)-2-oxo-5-(trifluoromethyl)pyrrolidin-3-yl]propanoate (85.0 mg, crude) as a light brown semi-solid. LC-MS (ESI, m/z): 255 [M+H]$^+$.

To a mixture of methyl (2S)-2-amino-3-[(5R)-2-oxo-5-(trifluoromethyl)pyrrolidin-3-yl]propanoate (85.0 mg, 0.334 mmol, 1.0 eq.) in DCM (5 mL) were added di-tert-butyl dicarbonate (88.0 mg, 0.401 mmol, 1.2 eq.) and triethylamine (102 mg, 1.00 mmol, 3.0 eq.). The mixture was stirred for 2 h at rt. The reaction was quenched with water (10 mL). The mixture was extracted with DCM (3×10 mL). The organic layers were combined, washed with brine (2×10 mL), dried over anhydrous sodium sulfate, filtered and concentrated under reduced pressure to provide methyl (2S)-2-[(tert-butoxycarbonyl)amino]-3-[(5R)-2-oxo-5-(trifluoromethyl)pyrrolidin-3-yl]propanoate (100 mg, 75%) as a light brown oil. LC-MS (ESI, m/z): 255 [M−Boc+H]$^+$.

A mixture of methyl (2S)-2-[(tert-butoxycarbonyl)amino]-3-[(5R)-2-oxo-5-(trifluoromethyl)pyrrolidin-3-yl]propanoate (100 mg, 0.282 mmol, 1.0 eq.) in ammonia (3 mL, 7 M in MeOH) was stirred for 2 days at rt. The mixture was concentrated under reduced pressure to afford the crude product. The crude product was chromatographed on a silica gel column with MeOH:DCM (6:94) to provide tert-butyl N-[(1S)-1-carbamoyl-2-[(5R)-2-oxo-5-(trifluoromethyl) pyrrolidin-3-yl]ethyl]carbamate (40.0 mg, 39%) as an off-white solid. LC-MS (ESI, m/z): 240 [M−Boc+H]⁺.

To a mixture of tert-butyl N-[(1S)-1-carbamoyl-2-[(5R)-2-oxo-5-(trifluoromethyl)pyrrolidin-3-yl]ethyl]carbamate (40 mg, 0.118 mmol, 1.0 eq.) in DCM (1.5 mL) was added trifluoroacetic acid (0.5 mL). The resulting mixture was stirred for 1 h at rt and then concentrated under reduced pressure to afford (2S)-2-amino-3-[(5R)-2-oxo-5-(trifluoromethyl)pyrrolidin-3-yl]propanamide (28 mg, crude) as a brown oil. LC-MS (ESI, m/z): 240 [M+H]⁺.

To a mixture of (1R,2S,3S,6R,7S)-4-[(2S)-3,3-dimethyl-2-(2,2,2-trifluoroacetamido)butanoyl]-4-azatricyclo [5.2.1.0ˆ{2,6}]dec-8-ene-3-carboxylic acid (45.0 mg, 0.117 mmol, 1.0 eq.) and o-(7-azabenzotriazol-1-yl)-N,N,N',N'-tetramethyluronium hexafluorophosphate (53.0 mg, 0.140 mmol, 1.2 eq.) in DMF (1 mL) was added N-ethyl-N-isopropylpropan-2-amine (91.0 mg, 0.702 mmol, 6.0 eq.) at 0° C. After stirring for 15 min at 0° C., (2S)-2-amino-3-[(5R)-2-oxo-5-(trifluoromethyl)pyrrolidin-3-yl]propanamide (28.0 mg, 0.117 mmol, 1.0 eq.) was added. The mixture was stirred for 1 h at rt. The crude product was purified by C18 column with CH₃CN/Water (0.05% TFA). The desired fraction was concentrated under reduced pressure to provide (2S)-2-{[(1R,2S,3S,6R,7S)-4-[(2S)-3,3-dimethyl-2-(2,2,2-trifluoroacetamido)butanoyl]-4-azatricyclo [5.2.1.0ˆ{2,6}]dec-8-en-3-yl]formamido}-3-[(5R)-2-oxo-5-(trifluoromethyl)pyrrolidin-3-yl]propanamide (50.0 mg, 58%) as a light brown solid. LC-MS (ESI, m/z): 610 [M+H]⁺.

To a mixture of (2S)-2-{[(1R,2S,3S,6R,7S)-4-[(2S)-3,3-dimethyl-2-(2,2,2-trifluoroacetamido)butanoyl]-4-azatricyclo[5.2.1.0ˆ{2,6}]dec-8-en-3-yl]formamido}-3-[(5R)-2-oxo-5-(trifluoromethyl)pyrrolidin-3-yl]propanamide (50.0 mg, 0.082 mmol, 1.0 eq.) in DCM (2 mL) were added pyridine (23.0 mg, 0.287 mmol, 3.5 eq.) and trifluoroacetic anhydride (26.0 mg, 0.123 mmol, 1.5 eq.). The mixture was stirred for 1 h at rt. The reaction was quenched with water (5 mL). The mixture was extracted with DCM (3×5 mL). The organic layers were combined, washed with brine (2×5 mL), dried over anhydrous sodium sulfate, filtered and concentrated under reduced pressure to afford the crude product. The crude product was purified by prep-HPLC (Column: XSelect CSH Prep C18 OBD Column, 19×150 mm, 5 m; Mobile Phase A: Water (0.1% FA), Mobile Phase B: ACN; Flow rate: 25 mL/min; Gradient: 37% B to 67% B in 7 min, 67% B; Wave Length: 254 nm; RT (min): 6.2) to provide (1R,2S,3S,6R,7S)—N-[(1S)-1-cyano-2-[(5R)-2-oxo-5-(trifluoromethyl)pyrrolidin-3-yl]ethyl]-4-[(2S)-3,3-dimethyl-2-(2,2,2-trifluoroacetamido)butanoyl]-4-azatricyclo[5.2.1.0ˆ{2,6}]dec-8-ene-3-carboxamide (12.6 mg, 25%) as a white solid. LC-MS (ESI, m/z): 592 [M+H]⁺.

Example 109

Compound 109

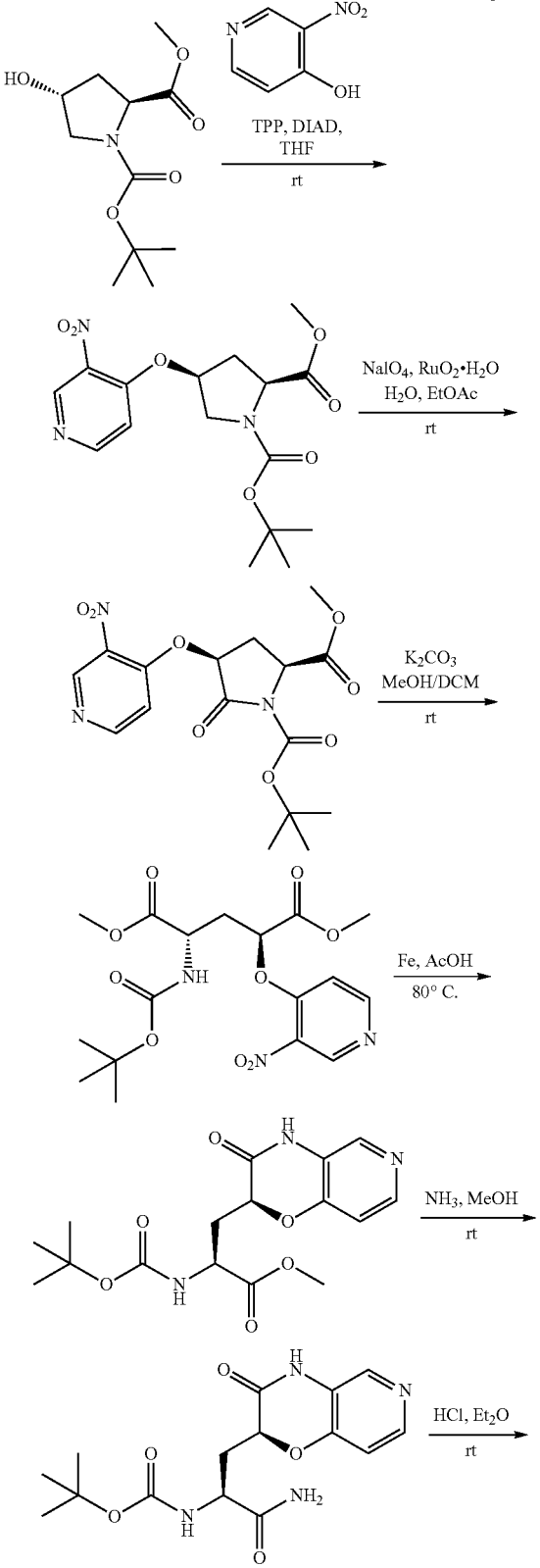

-continued

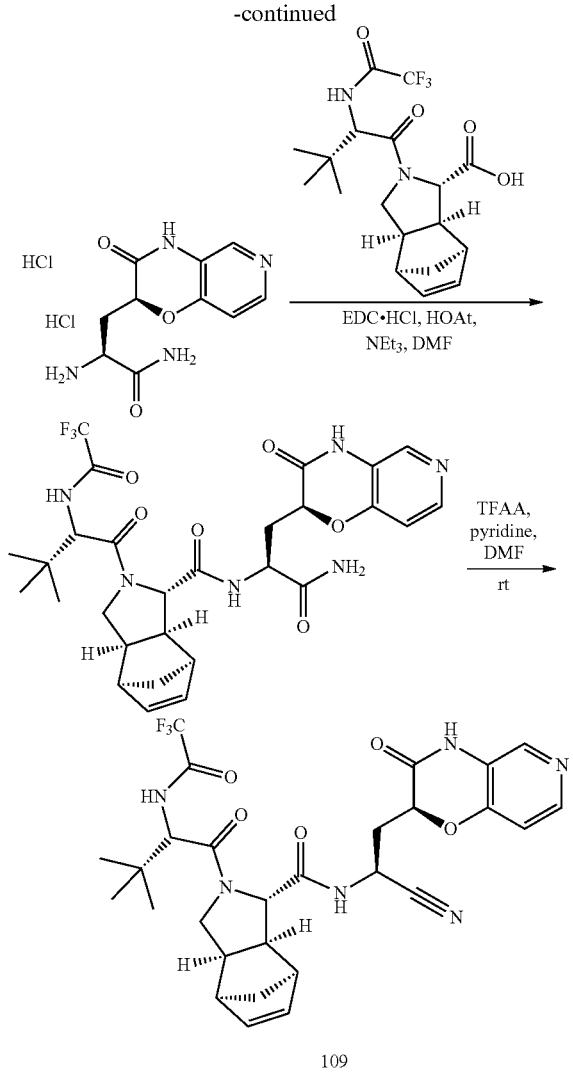

109

To a solution of 1-(tert-butyl) 2-methyl (2S,4R)-4-hydroxypyrrolidine-1,2-dicarboxylate (2.0 g, 8.16 mmol, 1.0 eq.) in THF (20 mL) cooled at 0° C. were added 3-nitropyridin-4-ol (1.7 g, 12.2 mmol, 1.5 eq.), triphenylphosphine (3.2 g, 12.2 mmol, 1.5 eq.) and DIAD (2.47 mL, 12.2 mmol, 1.5 eq.). The mixture was stirred at rt for 5 h and then concentrated under reduced pressure. The residue was purified by flash chromatography on silica gel using a gradient of EA (60 to 100%) in PE to afford 1-(tert-butyl) 2-methyl (2S,4S)-4-((3-nitropyridin-4-yl)oxy)pyrrolidine-1,2-dicarboxylate (2.5 g, 86%) as a yellow oil.

To a solution of NaIO$_4$ (7.2 g, 34.1 mmol, 5.0 eq.) in water (15 mL) was added Ru$_2$O·H$_2$O (135 g, 1.02 mmol, 0.15 eq.). The mixture was stirred at rt for 10 min. A solution of 1-(tert-butyl) 2-methyl (2S,4S)-4-((3-nitropyridin-4-yl)oxy)pyrrolidine-1,2-dicarboxylate (2.5 g, 6.81 mmol, 1.0 eq.) in EA (15 mL) was added. The mixture was stirred at rt for 16 h. The mixture was diluted with water (20 mL) and extracted with EA (2×20 mL). The organic phases were combined, diluted with IPA (50 mL), stirred for 10 min and filtered through celite. The filtrate was concentrated under reduced pressure. The residue was purified by flash chromatography on silica gel using a gradient of EA (60 to 100%) in PE to afford 1-(tert-butyl) 2-methyl (2S,4S)-4-((3-nitropyridin-4-yl)oxy)-5-oxopyrrolidine-1,2-dicarboxylate (2.3 g, 88%) as a pale yellow solid.

To a solution of 1-(tert-butyl) 2-methyl (2S,4S)-4-((3-nitropyridin-4-yl)oxy)-5-oxopyrrolidine-1,2-dicarboxylate (2.3 g, 6.04 mmol, 1.0 eq.) in MeOH (11.5 mL) and DCM (11.5 mL) cooled at 0° C. was added K$_2$CO$_3$ (83 mg, 0.603 mmol, 1.0 eq.). The mixture was stirred at rt for 1 h. The mixture was diluted with water (20 mL) and extracted with DCM (2×20 mL). The organic phases were combined, dried over Na$_2$SO$_4$, filtered and concentrated under reduced pressure. The residue was purified by flash chromatography on silica gel using a gradient of MeOH (1 to 10%) in DCM to afford dimethyl (2S,4S)-2-((tert-butoxycarbonyl)amino)-4-((3-nitropyridin-4-yl)oxy)pentanedioate (2.0 g, 80%) as a white solid.

To a solution of dimethyl (2S,4S)-2-((tert-butoxycarbonyl)amino)-4-((3-nitropyridin-4-yl)oxy)pentanedioate (2.0 g, 4.84 mmol, 1.0 eq.) in acetic acid (20 mL) was added Fe (1.35 g, 24.2 mmol, 5.0 eq.). The mixture was heated at 80° C. for 2 h and then concentrated under reduced pressure. The residue was basified with sat. NaHCO$_3$ and extracted with EA (2×20 mL). The organic phases were combined, dried over Na$_2$SO$_4$, filtered and concentrated under reduced pressure. The residue was purified by flash chromatography on silica gel using a gradient of MeOH (1 to 10%) in DCM to afford methyl (S)-2-((tert-butoxycarbonyl)amino)-3-((S)-3-oxo-3,4-dihydro-2H-pyrido[4,3-b][1,4]oxazin-2-yl)propanoate (1.4 g, 82%) as a white solid.

A solution of methyl (S)-2-((tert-butoxycarbonyl)amino)-3-((S)-3-oxo-3,4-dihydro-2H-pyrido[4,3-b][1,4]oxazin-2-yl)propanoate (500 mg, 1.42 mmol, 1.0 eq.) in 7M NH$_3$ in MeOH (5 mL) was stirred at rt for 48 h in a sealed tube. The mixture was concentrated under reduced pressure. The residue was purified by prep-HPLC (Column: X-SELECT-C18 Column, 19*250 mm, 5 m; Mobile Phase A: 10 mM NH$_4$HCO$_3$ in water, Mobile Phase B: ACN; Flow rate: 17 mL/min; Gradient: 2% B to 40% B in 8 min) to afford tert-butyl ((S)-1-amino-1-oxo-3-((S)-3-oxo-3,4-dihydro-2H-pyrido[4,3-b][1,4]oxazin-2-yl)propan-2-yl)carbamate (300 mg, 63%) as an off-white solid.

A solution of tert-butyl ((S)-1-amino-1-oxo-3-((S)-3-oxo-3,4-dihydro-2H-pyrido[4,3-b][1,4]oxazin-2-yl)propan-2-yl)carbamate (200 mg, 0.595 mmol, 1.0 eq.) in 2M HCl in Et$_2$O (5 mL) was stirred at rt for 2 h. The mixture was concentrated under reduced pressure to afford (S)-2-amino-3-((S)-3-oxo-3,4-dihydro-2H-pyrido[4,3-b][1,4]oxazin-2-yl)propenamide dihydrochloride (150 mg, 82%) as a white solid.

To a solution of (1S,3aR,4S,7R,7aS)-2-((S)-3,3-dimethyl-2-(2,2,2-trifluoroacetamido)butanoyl)-2,3,3a,4,7,7a-hexahydro-1H-4,7-methanoisoindole-1-carboxylic acid (150 mg, 0.386 mmol, 1.0 eq.) in DMF (1.5 mL) cooled at 0° C. were added (S)-2-amino-3-((S)-3-oxo-3,4-dihydro-2H-pyrido[4,3-b][1,4]oxazin-2-yl)propanamide dihydrochloride (104 mg, 0.364 mmol, 0.9 eq.), EDC•HCl (147 mg, 0.772 mmol, 2.0 eq.), HOAt (52 mg, 0.386 mmol, 1.0 eq.) and NEt$_3$ (0.16 mL, 1.16 mmol, 3.0 eq.). The mixture was stirred at rt for 16 h. The mixture was diluted with water (5 mL) and extracted with EA (2×10 mL). The organic phases were combined, washed with brine (2×5 mL), dried over Na$_2$SO$_4$, filtered and concentrated under reduced pressure. The residue was purified by flash chromatography on C18 using a gradient of ACN (20 to 40%) in 0.01% TFA in water to afford (1S,3aR,4S,7R,7aS)—N—((S)-1-amino-1-oxo-3-((S)-3-oxo-3,4-dihydro-2H-pyrido[4,3-b][1,4]oxazin-2-yl)propan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (150 mg, 64%) as a white solid.

To a solution of (1S,3aR,4S,7R,7aS)—N—((S)-1-amino-1-oxo-3-((S)-3-oxo-3,4-dihydro-2H-pyrido[4,3-b][1,4]

oxazin-2-yl)propan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (150 mg, 0.247 mmol, 1.0 eq.) in DMF (1.5 mL) were added pyridine (0.05 mL, 0.742 mmol, 3.0 eq.) and TFAA (0.06 mL, 0.495 mmol, 2.0 eq.). The mixture was stirred at rt for 30 min. The mixture was diluted with water (5 mL) and extracted with EA (2×5 mL). The organic phases were combined, washed with brine (2×5 mL), dried over Na₂SO₄, filtered and concentrated under reduced pressure. The residue was purified by prep-HPLC (Column: KROMOSIL-C18 Column, 25*250 mm, 7 m; Mobile Phase A: 10 mM NH₄HCO₃ in water, Mobile Phase B: ACN; Flow rate: 22 mL/min; Gradient: 20% B to 70% B in 8 min) to afford (1S,3aR,4S,7R,7aS)—N—((S)-1-cyano-2-((S)-3-oxo-3,4-dihydro-2H-pyrido[4,3-b][1,4]oxazin-2-yl)ethyl)-2-((S)-3,3-dimethyl-2-(2,2,2-trifluoroacetamido)butanoyl)-2,3,3a,4,7,7a-hexahydro-1H-4,7-methanoisoindole-1-carboxamide (70 mg, 48%) as a white solid. $^1$H NMR (500 MHz, 363K, DMSO-d₆) δ 8.50-9.10 (m, 3H), 8.09 (s, 1H), 8.07 (d, 1H), 6.87-6.93 (m, 1H), 5.97-6.20 (m, 2H), 4.90-5.08 (m, 1H), 4.70-4.82 (m, 1H), 4.43-4.48 (m, 1H), 3.99-4.16 (m, 1H), 3.65 (m, 1H), 3.37-3.47 (m, 1H), 3.01-3.22 (m, 1H), 2.88-2.96 (m, 2H), 2.73-2.85 (m, 1H), 2.50-2.57 (m, 1H), 2.32-2.40 (m, 1H), 1.37-1.44 (m, 2H), 0.82-0.91 (m, 9H). LCMS (ESI, m/z): 589 [M+H]⁺.

Example 110

Compound 110

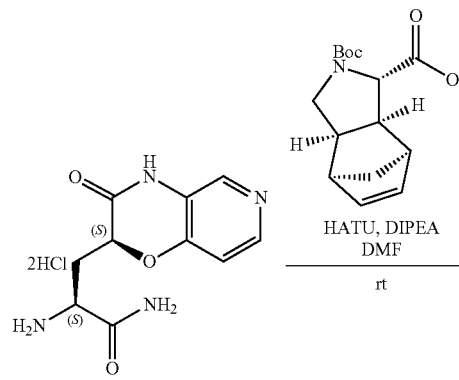

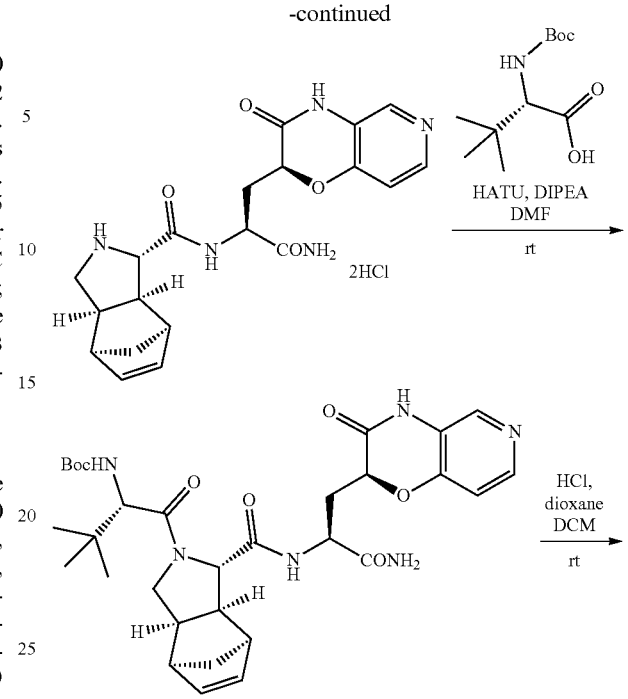

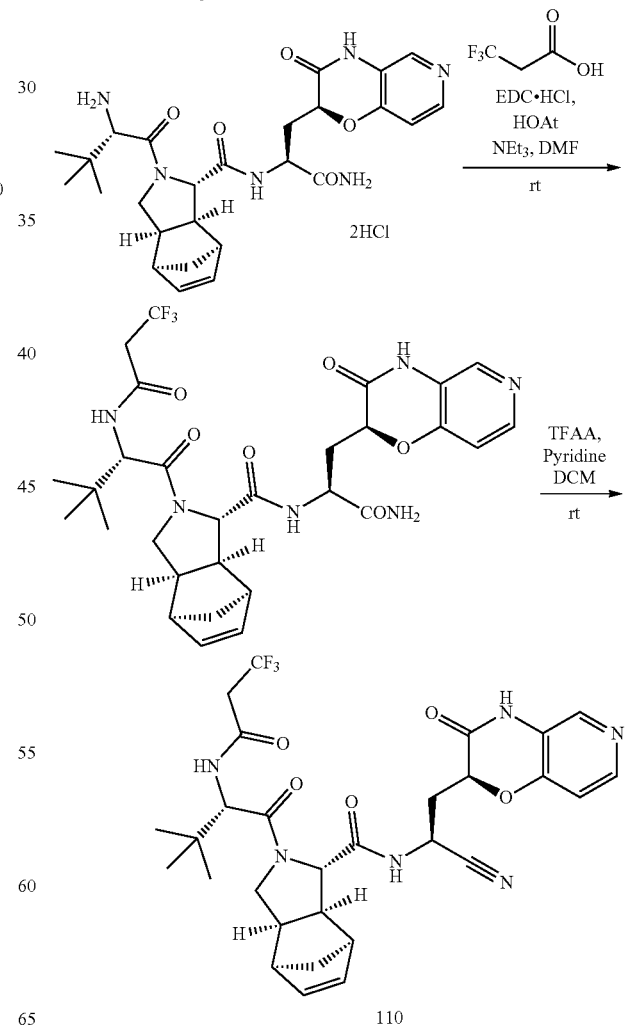

110

To a solution of (1S,3aR,4S,7R,7aS)-2-(tert-butoxycarbonyl)-2,3,3a,4,7,7a-hexahydro-1H-4,7-methanoisoindole-1-carboxylic acid (150 mg, 0.537 mmol, 1.0 eq.) in DMF (1.5 mL) cooled at 0° C. were added (S)-2-amino-3-((S)-3-oxo-3,4-dihydro-2H-pyrido[4,3-b][1,4]oxazin-2-yl)propanamide dihydrochloride (152 mg, 0.645 mmol, 1.2 eq.), DIPEA (0.22 mL, 1.34 mmol, 2.5 eq.) and HATU (306 mg, 0.805 mmol, 1.5 eq.). The mixture was stirred at rt for 2.5 h. The mixture was diluted with water (5 mL) and extracted with EA (2×10 mL). The organic phases were combined, washed with brine (2×5 mL), dried over Na₂SO₄, filtered and concentrated under reduced pressure. The residue was purified by flash chromatography on silica gel using a gradient of MeOH (1 to 10%) in DCM to afford tert-butyl (1S,3aR,4S,7R,7aS)-1-(((S)-1-amino-1-oxo-3-((S)-3-oxo-3,4-dihydro-2H-pyrido[4,3-b][1,4]oxazin-2-yl)propan-2-yl)carbamoyl)-1,3,3a,4,7,7a-hexahydro-2H-4,7-methanoisoindole-2-carboxylate (150 mg, 56%) as a white solid.

A solution of tert-butyl (1S,3aR,4S,7R,7aS)-1-(((S)-1-amino-1-oxo-3-((S)-3-oxo-3,4-dihydro-2H-pyrido[4,3-b][1,4]oxazin-2-yl)propan-2-yl)carbamoyl)-1,3,3a,4,7,7a-hexahydro-2H-4,7-methanoisoindole-2-carboxylate (150 mg, 0.301 mmol, 1.0 eq.) in 2M HCl in Et₂O (2.0 mL) was stirred at rt for 2 h. The mixture was concentrated under reduced pressure to afford quantitatively (1S,3aR,4S,7R,7aS)—N—((S)-1-amino-1-oxo-3-((S)-3-oxo-3,4-dihydro-2H-pyrido[4,3-b][1,4]oxazin-2-yl)propan-2-yl)-2,3,3a,4,7,7a-hexahydro-1H-4,7-methanoisoindole-1-carboxamide dihydrochloride as a white solid.

To a solution of (1S,3aR,4S,7R,7aS)—N—((S)-1-amino-1-oxo-3-((S)-3-oxo-3,4-dihydro-2H-pyrido[4,3-b][1,4]oxazin-2-yl)propan-2-yl)-2,3,3a,4,7,7a-hexahydro-1H-4,7-methanoisoindole-1-carboxamide dihydrochoride (150 mg, 0.393 mmol, 1.0 eq.) in DMF (1.5 mL) cooled at 0° C. were added (S)-2-((tert-butoxycarbonyl)amino)-3,3-dimethylbutanoic acid (109 mg, 0.471 mmol, 1.2 eq.), DIPEA (0.17 mL, 0.982 mmol, 2.5 eq.) and HATU (223 mg, 0.589 mmol, 1.5 eq.). The mixture was stirred at rt for 2.5 h. The mixture was diluted with water (5 mL) and extracted with EA (2×10 mL). The organic phases were combined, washed with brine (2×5 mL), dried over Na₂SO₄, filtered and concentrated under reduced pressure. The residue was purified by flash chromatography on silica gel using a gradient of MeOH (1 to 10%) in DCM to afford tert-butyl ((S)-1-((1S,3aR,4S,7R,7aS)-1-(((S)-1-amino-1-oxo-3-((S)-3-oxo-3,4-dihydro-2H-pyrido[4,3-b][1,4]oxazin-2-yl)propan-2-yl)carbamoyl)-1,3,3a,4,7,7a-hexahydro-2H-4,7-methanoisoindol-2-yl)-3,3-dimethyl-1-oxobutan-2-yl)carbamate (60 mg, 33%) as a white solid.

To a solution of tert-butyl ((S)-1-((1S,3aR,4S,7R,7aS)-1-(((S)-1-amino-1-oxo-3-((S)-3-oxo-3,4-dihydro-2H-pyrido[4,3-b][1,4]oxazin-2-yl)propan-2-yl)carbamoyl)-1,3,3a,4,7,7a-hexahydro-2H-4,7-methanoisoindol-2-yl)-3,3-dimethyl-1-oxobutan-2-yl)carbamate (60 mg, 0.098 mmol, 1.0 eq.) in DCM (0.6 mL) cooled at 0° C. was added 4N HCl in dioxane (0.09 mL, 0.393 mmol, 4.0 eq.). The mixture was stirred at rt for 2 h. The mixture was concentrated under reduced pressure to afford quantitatively (1S,3aR,4S,7R,7aS)—N—((S)-1-amino-1-oxo-3-((S)-3-oxo-3,4-dihydro-2H-pyrido[4,3-b][1,4]oxazin-2-yl)propan-2-yl)-2-((S)-2-amino-3,3-dimethylbutanoyl)-2,3,3a,4,7,7a-hexahydro-1H-4,7-methanoisoindole-1-carboxamide dihydrochloride as a white solid.

To a solution of (1S,3aR,4S,7R,7aS)—N—((S)-1-amino-1-oxo-3-((S)-3-oxo-3,4-dihydro-2H-pyrido[4,3-b][1,4]oxazin-2-yl)propan-2-yl)-2-((S)-2-amino-3,3-dimethylbutanoyl)-2,3,3a,4,7,7a-hexahydro-1H-4,7-methanoisoindole-1-carboxamide dihydrochloride (60 mg, 0.110 mmol, 1.0 eq.) in DMF (0.6 mL) cooled at 0° C. were added 3,3,3-trifluoropropanoic acid (21 mg, 0.165 mmol, 1.5 eq.), EDC•HCl (42 mg, 0.220 mmol, 2.0 eq.), HOAt (15 mg, 0.110 mmol, 1.0 eq.) and NEt₃ (0.04 mL, 0.330 mmol, 3.0 eq.). The mixture was stirred at rt for 16 h. The mixture was diluted with water (5 mL) and extracted with EA (2×10 mL). The organic phases were combined, washed with brine (2×5 mL), dried over Na₂SO₄, filtered and concentrated under reduced pressure. The residue was purified by flash chromatography on silica gel using a gradient of MeOH (1 to 10%) in DCM to afford (1S,3aR,4S,7R,7aS)—N—((S)-1-amino-1-oxo-3-((S)-3-oxo-3,4-dihydro-2H-pyrido[4,3-b][1,4]oxazin-2-yl)propan-2-yl)-2-((S)-3,3-dimethyl-2-(3,3,3-trifluoropropan amido)butanoyl)-2,3,3a,4,7,7a-hexahydro-1H-4,7-methanoisoindole-1-carboxamide (30 mg, 50%) as a white solid.

To a solution of (1S,3aR,4S,7R,7aS)—N—((S)-1-amino-1-oxo-3-((S)-3-oxo-3,4-dihydro-2H-pyrido[4,3-b][1,4]oxazin-2-yl)propan-2-yl)-2-((S)-3,3-dimethyl-2-(3,3,3-trifluoropropanamido)butanoyl)-2,3,3a,4,7,7a-hexahydro-1H-4,7-methanoisoindole-1-carboxamide (30 mg, 0.048 mmol, 1.0 eq.) in DCM (0.3 mL) cooled at 0° C. were added pyridine (0.008 mL, 0.105 mmol, 2.2 eq.) and TFAA (0.007 mL, 0.052 mmol, 1.1 eq.). The mixture was stirred at rt for 30 min. The mixture was diluted with water (5 mL) and extracted with EA (2×5 mL). The organic phases were combined, washed with brine (2×5 mL), dried over Na₂SO₄, filtered and concentrated under reduced pressure. The residue was purified by prep-HPLC (Column: X-SELECT-C18 Column, 19*150 mm, 5 m; Mobile Phase A: 10 mM NH₄HCO₃ in water, Mobile Phase B: ACN; Flow rate: 17 mL/min; Gradient: 20% B to 70% B in 8 min) to afford (1S,3aR,4S,7R,7aS)—N—((S)-1-cyano-2-((S)-3-oxo-3,4-dihydro-2H-pyrido[4,3-b][1,4]oxazin-2-yl)ethyl)-2-((S)-3,3-dimethyl-2-(3,3,3-trifluoropropanamido)butanoyl)-2,3,3a,4,7,7a-hexahydro-1H-4,7-methanoisoindole-1-carboxamide (15 mg, 52%) as a white solid. ¹H NMR (500 MHz, 363K, DMSO-d₆) δ 10.67-10.77 (br. s., 1H), 8.65 (d, 1H), 8.14-8.07 (m, 2H), 7.79-8.00 (m, 1H), 6.86-6.97 (m, 1H), 5.93-6.21 (m, 2H), 4.96-5.12 (m, 1H), 4.73-4.99 (m, 1H), 4.19-4.47 (m, 1H), 3.96-4.16 (m, 1H), 3.63 (m, 1H), 3.51 (m, 1H), 3.16-3.38 (m, 2H), 3.03 (m, 1H), 2.89-2.98 (m, 2H), 2.78 (m, 1H), 2.52-2.60 (m, 1H), 2.33-2.41 (m, 1H), 1.37-1.46 (m, 2H), 0.73-0.90 (m, 9H). LCMS (ESI, m/z): 603 [M+H]⁺.

Example 111

Compound 111

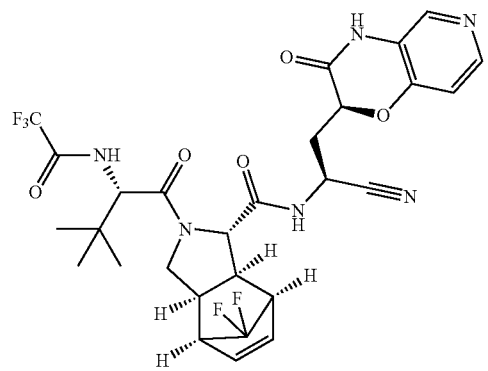

Compound 111 was prepared similarly as described for Compound 82 using (S)-2-amino-3-((S)-3-oxo-3,4-dihydro-2H-pyrido[4,3-b][1,4]oxazin-2-yl)propanamide dihydrochloride in place of (2S)-2-amino-3-[(3S)-2-oxopyrrolidin-3-yl]propanamide. $^{1}$H NMR (500 MHz, 364K, DMSO-d$_6$) δ 10.70 (br. s., 1H), 8.58-8.86 (m, 2H), 8.03-8.15 (m, 2H), 6.82-7.05 (m, 1H), 6.04-6.37 (m, 2H), 4.87-5.09 (m, 1H), 4.67-4.89 (m, 1H), 4.28-4.53 (m, 1H), 4.11-4.26 (m, 1H), 3.72 (m, 1H), 3.42-3.64 (m, 1H), 3.22-3.41 (m, 1H), 3.09-3.21 (m, 2H), 2.88-2.96 (m, 1H), 2.42-2.59 (m, 1H), 2.32-2.43 (m, 1H), 0.76-1.01 (m, 9H). LCMS (ESI, m/z): 625 [M+H]$^+$.

Example 112

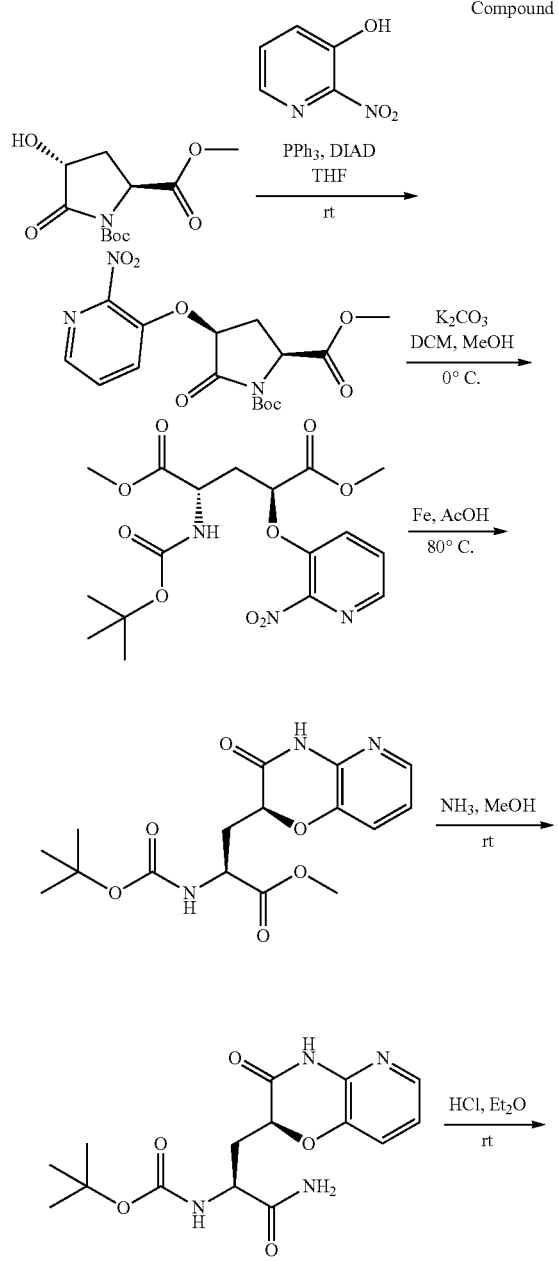

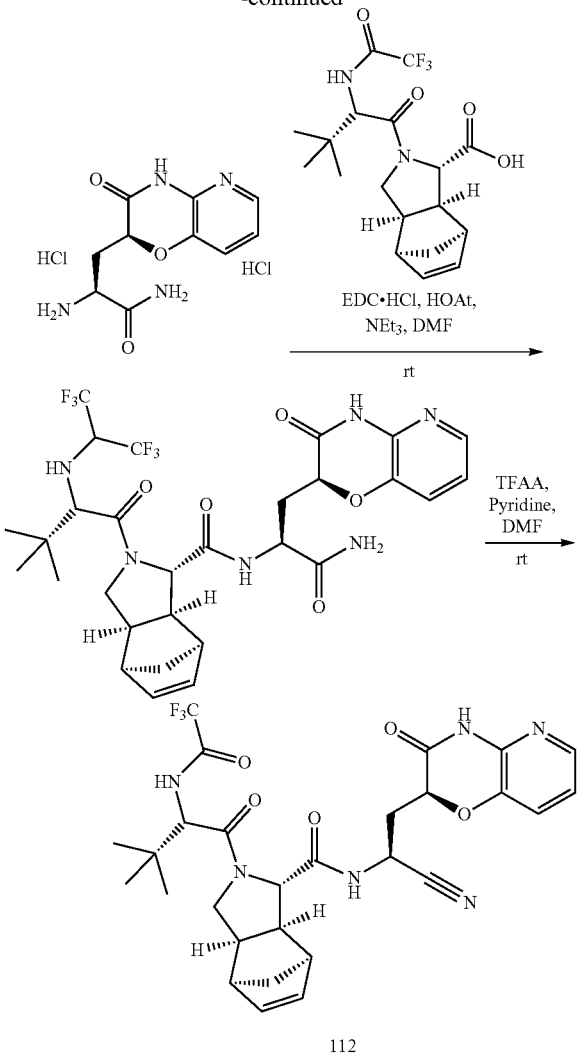

To a solution of 1-(tert-butyl) 2-methyl (2S,4R)-4-hydroxy-5-oxopyrrolidine-1,2-dicarboxylate (1.2 g, 4.63 mmol, 1.0 eq.) in THF (20 mL) cooled at 0° C. were added 2-nitropyridin-3-ol (648 mg, 4.63 mmol, 1.0 eq.), triphenylphosphine (1.8 g, 6.95 mmol, 1.5 eq.) and DIAD (1.36 mL, 6.95 mmol, 1.5 eq.). The mixture was stirred at rt for 16 h. The mixture was concentrated under reduced pressure. The residue was purified by flash chromatography on silica gel using a gradient of EA (60 to 100%) in PE to afford 1-(tert-butyl) 2-methyl (2S,4S)-4-((2-nitropyridin-3-yl)oxy)-5-oxopyrrolidine-1,2-dicarboxylate (1 g, 56%) as a yellow oil.

To a solution of 1-(tert-butyl) 2-methyl (2S,4S)-4-((2-nitropyridin-3-yl)oxy)-5-oxopyrrolidine-1,2-dicarboxylate (950 mg, 2.49 mmol, 1.0 eq.) in MeOH (10 mL) and DCM (10 mL) cooled at 0° C. was added K$_2$CO$_3$ (34 mg, 0.249 mmol, 0.1 eq.). The mixture was stirred at 0° C. for 1 h. Water (20 mL) was added, and the phases were separated. The aqueous phase was extracted with DCM (2×20 mL). The organic phases were combined, dried over Na$_2$SO$_4$, filtered and concentrated under reduced pressure. The residue was purified by flash chromatography on silica gel using a gradient of MeOH (1 to 10%) in DCM to afford dimethyl (2S,4S)-2-((tert-butoxycarbonyl)amino)-4-((2-nitropyridin-3-yl)oxy)pentanedioate (900 mg, 80%) as a white solid.

To a solution of dimethyl (2S,4S)-2-((tert-butoxycarbonyl)amino)-4-((2-nitropyridin-3-yl)oxy)pentanedioate (850 mg, 2.06 mmol, 1.0 eq.) in acetic acid (10 mL) was added Fe (576 mg, 10.3 mmol, 5.0 eq.). The mixture was heated at 80° C. for 2 h. The mixture was concentrated under reduced pressure. The residue was taken up with sat. NaHCO$_3$ and extracted with EA (2×20 mL). The organic phases were combined, dried over Na$_2$SO$_4$, filtered and concentrated under reduced pressure. The residue was purified by flash chromatography on silica gel using a gradient of MeOH (1 to 10%) in DCM to afford methyl (S)-2-((tert-butoxycarbonyl)amino)-3-((S)-3-oxo-3,4-dihydro-2H-pyrido[3,2-b][1,4]oxazin-2-yl)propanoate (550 mg, 76%) as a white solid.

A solution of methyl (S)-2-((tert-butoxycarbonyl)amino)-3-((S)-3-oxo-3,4-dihydro-2H-pyrido[3,2-b][1,4]oxazin-2-yl)propanoate (500 mg, 1.42 mmol, 1.0 eq.) in 7M NH$_3$ in MeOH (5 mL) was stirred at rt for 48 h in a sealed tube. The mixture was concentrated under reduced pressure. The residue was purified by prep-HPLC (Column: Sunfire-C18 Column, 19*150 mm, 5 m; Mobile Phase A: 10 mM NH$_4$HCO$_3$ in water, Mobile Phase B: ACN; Flow rate: 17 mL/min; Gradient: 20% B to 55% B in 8 min) to afford tert-butyl ((S)-1-amino-1-oxo-3-((S)-3-oxo-3,4-dihydro-2H-pyrido[3,2-b][1,4]oxazin-2-yl)propan-2-yl)carbamate (300 mg, 63%) as an off-white solid. $^1$H NMR (400 MHz, DMSO-d6) δ 11.25 (s, 1H), 7.91 (dd, 1H), 7.34 (d, 1H), 7.06-7.25 (d, 2H), 7.00 (m, 2H), 4.55 (m, 1H), 4.17 (m, 1H), 2.05-2.10 (m, 2H), 1.37 (s, 9H). LCMS (ESI, m/z): 337 [M+H]$^+$.

A solution of tert-butyl ((S)-1-amino-1-oxo-3-((S)-3-oxo-3,4-dihydro-2H-pyrido[3,2-b][1,4]oxazin-2-yl)propan-2-yl)carbamate (250 mg, 0.744 mmol, 1.0 eq.) in 2M HCl in Et$_2$O (5 mL) was stirred at rt for 2 h. The mixture was concentrated under reduced pressure to afford (S)-2-amino-3-((S)-3-oxo-3,4-dihydro-2H-pyrido[3,2-b][1,4]oxazin-2-yl)propenamide dihydrochloride (150 mg, 85%) as a white solid.

To a solution of (1S,3aR,4S,7R,7aS)-2-((S)-3,3-dimethyl-2-(2,2,2-trifluoroacetamido)butanoyl)-2,3,3a,4,7,7a-hexahydro-1H-4,7-methanoisoindole-1-carboxylic acid (120 mg, 0.309 mmol, 1.0 eq.) in DMF (1.2 mL) cooled at 0° C. were added (S)-2-amino-3-((S)-3-oxo-3,4-dihydro-2H-pyrido[3,2-b][1,4]oxazin-2-yl)propanamide dihydrochloride (87.5 mg, 0.371 mmol, 1.2 eq.), EDC•HCl (141 mg, 0.741 mmol, 2.0 eq.), HOAt (42 mg, 0.309 mmol, 1.0 eq.) and NEt$_3$ (0.17 mL, 1.236 mmol, 4.0 eq.). The mixture was stirred at rt for 16 h. The mixture was diluted with water (5 mL) and extracted with EA (2×10 mL). The organic phases were combined, washed with brine (2×5 mL), dried over Na$_2$SO$_4$, filtered and concentrated under reduced pressure. The residue was purified by flash chromatography on C18 using a gradient of ACN (20 to 40%) in 0.01% FA in water to afford (1S,3aR,4S,7R,7aS)—N—((S)-1-amino-1-oxo-3-((S)-3-oxo-3,4-dihydro-2H-pyrido[3,2-b][1,4]oxazin-2-yl)propan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (140 mg, 64%) as a white solid.

To a solution of (1S,3aR,4S,7R,7aS)—N—((S)-1-amino-1-oxo-3-((S)-3-oxo-3,4-dihydro-2H-pyrido[3,2-b][1,4]oxazin-2-yl)propan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (140 mg, 0.231 mmol, 1.0 eq.) in DMF (1.4 mL) were added pyridine (0.06 mL, 0.693 mmol, 3.0 eq.) and TFAA (0.1 mL, 0.462 mmol, 2.0 eq.). The mixture was stirred at rt for 30 min. The mixture was diluted with water (5 mL) and extracted with EA (2×5 mL). The organic phases were combined, washed with brine (2×5 mL), dried over Na$_2$SO$_4$, filtered and concentrated under reduced pressure. The residue was purified by prep-HPLC (Column: X-SELECT-C18 Column, 19*150 mm, 5 m; Mobile Phase A: 10 mM NH$_4$HCO$_3$ in water, Mobile Phase B: ACN; Flow rate: 17 mL/min; Gradient: 10% B to 70% B in 8 min) to afford (1S,3aR,4S,7R,7aS)—N—((S)-1-cyano-2-((S)-3-oxo-3,4-dihydro-2H-pyrido[3,2-b][1,4]oxazin-2-yl)ethyl)-2-((S)-3,3-dimethyl-2-(2,2,2-trifluoroacetamido)butanoyl)-2,3,3a,4,7,7a-hexahydro-1H-4,7-methanoisoindole-1-carboxamide (45 mg, 46%) as a white solid. $^1$H NMR (500 MHz, 363K, DMSO-d$_6$) δ 11.0 (br. s., 1H), 8.57-8.80 (m, 2H), 7.90 (d, 1H), 7.22-7.32 (m, 1H), 6.96 (m, 1H), 5.96-6.20 (m, 2H), 4.76-5.11 (m, 1H), 4.63 (m, 1H), 4.43 (m, 1H), 3.98-4.18 (m, 1H), 3.65 (t, 1H), 3.37-3.47 (m, 1H), 3.02-3.23 (m, 1H), 2.80-2.96 (m, 2H), 2.76 (m, 1H), 2.49-2.56 (m, 1H), 2.28-2.36 (m, 1H), 1.37-1.48 (m, 2H), 0.77-0.90 (m, 9H). LCMS (ESI, m/z): 589 [M+H]$^+$.

Example 113

Compound 113

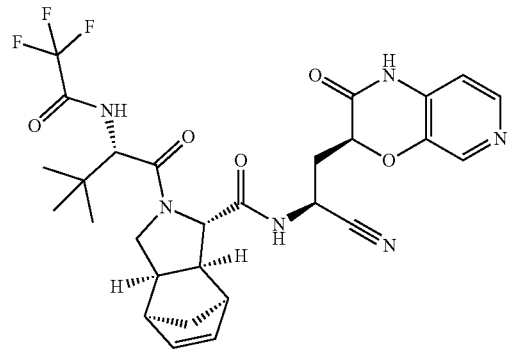

Compound 113 was prepared similarly as described for Compound 112 using 4-nitropyridin-3-ol in place of 2-nitropyridin-3-ol. $^1$H NMR (400 MHz, 363K, DMSO-d6) δ 10.95 (br. s., 1H), 8.63-8.82 (m, 2H), 8.06-8.25 (m, 2H), 6.90 (m, 1H), 5.95-6.21 (m, 2H), 4.87-5.13 (m, 1H), 4.65-4.85 (m, 1H), 4.39-4.52 (m, 1H), 3.97-4.20 (m, 1H), 3.65 (m, 1H), 3.36-3.50 (m, 1H), 3.02-3.23 (m, 1H), 2.81-2.96 (m, 2H), 2.77 (m, 1H), 2.44-2.60 (m, 1H), 2.23-2.41 (m, 1H), 1.36-1.47 (m, 2H), 0.76-0.93 (m, 9H). LCMS (ESI, m/z): 589 [M+H]$^+$.

Example 114

Compound 114

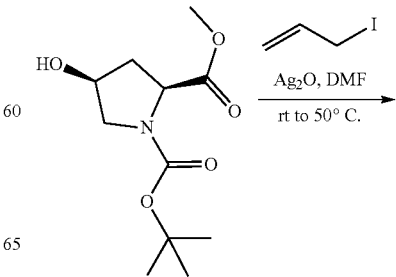

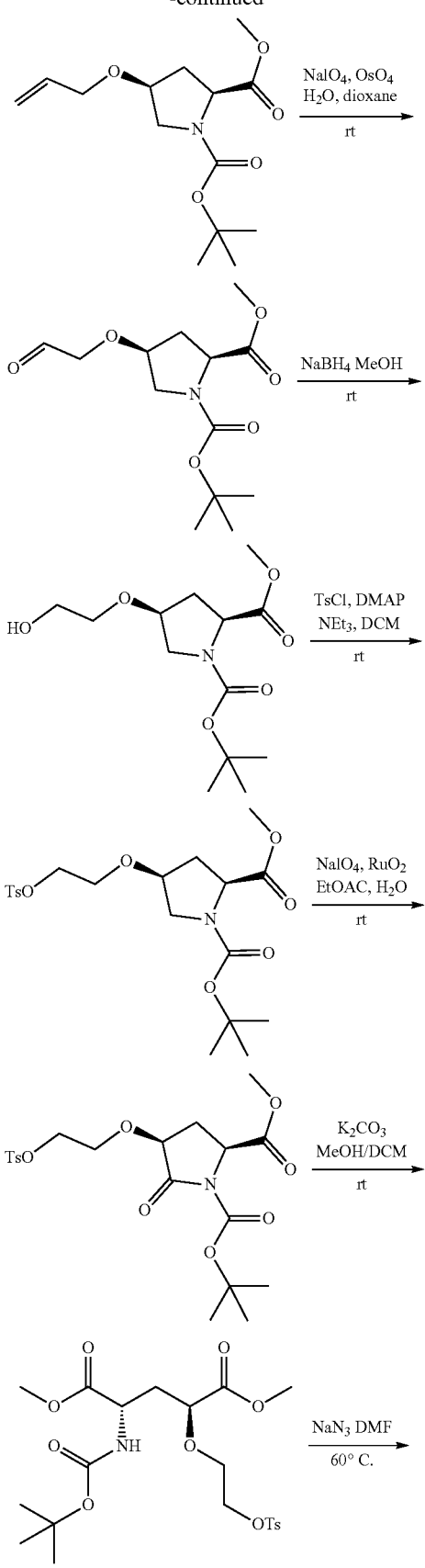
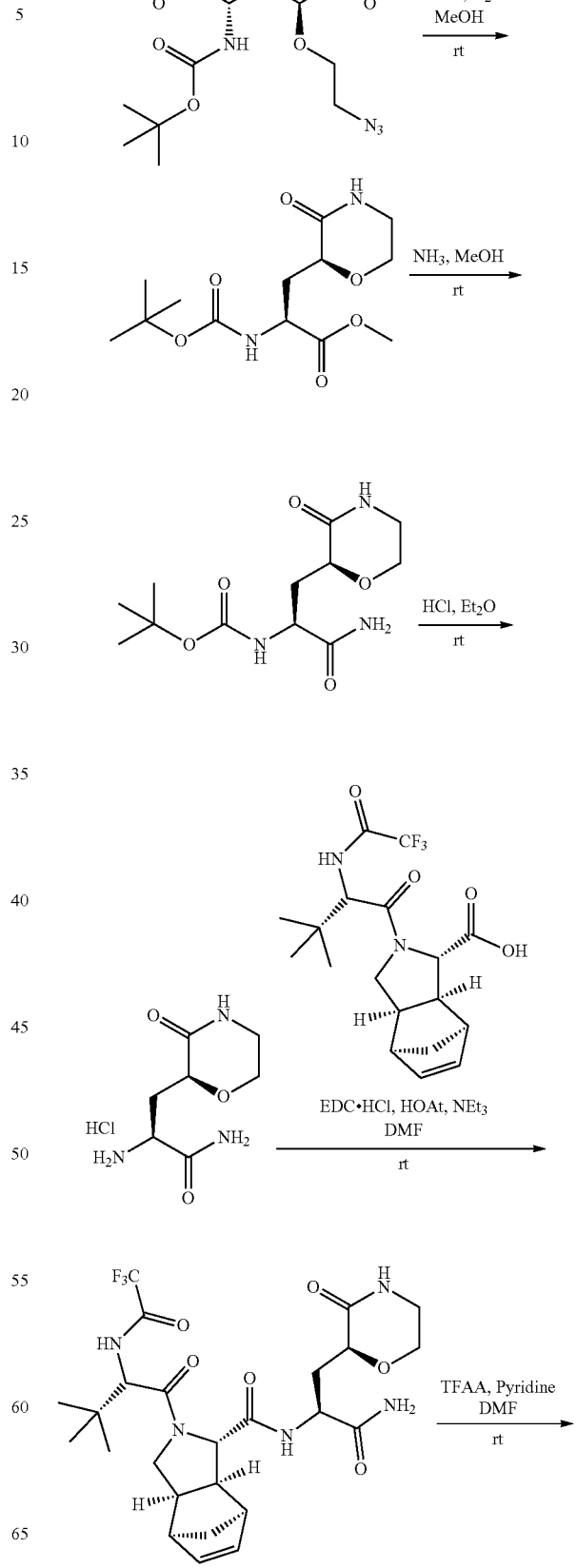

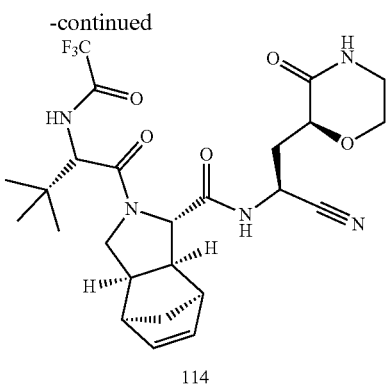

114

To a solution of 1-(tert-butyl) 2-methyl (2S,4S)-4-hydroxypyrrolidine-1,2-dicarboxylate (2.0 g, 8.16 mmol, 1.0 eq.) in DMF (20 mL) were added Ag$_2$O (5.6 g, 24.5 mmol, 3.0 eq.) and allyl iodide (2.24 mL, 24.5 mmol, 3.0 eq.). The mixture was stirred at rt for 12 h and heated at 50° C. for 5 h. After cooling to rt, the mixture was filtered through celite. The filtrate was diluted with water (50 mL) and extracted with EA (3×50 mL). The organic phases were combined, washed with brine (3×50 mL), dried over Na$_2$SO$_4$, filtered and concentrated under reduced pressure. The residue was purified by flash chromatography on silica gel using a gradient of EA (10 to 15%) in PE to afford 1-(tert-butyl) 2-methyl (2S,4S)-4-(allyloxy)pyrrolidine-1,2-dicarboxylate (2.1 g, 91%) as a colorless oil.

To a solution of 1-(tert-butyl) 2-methyl (2S,4S)-4-(allyloxy)pyrrolidine-1,2-dicarboxylate (2.1 g, 7.39 mmol, 1.0 eq.) in dioxane (20 mL) were added 2.5% OsO$_4$ in tBuOH (0.2 mL) and a solution of NaIO$_4$ (3.16 g, 14.8 mmol, 2.0 eq.) in water (20 mL) over 10 min. The mixture was vigorously stirred at rt for 1 h. The mixture was diluted with water (50 mL) and extracted with EA (3×50 mL). The organic phases were combined, dried over Na$_2$SO$_4$, filtered and concentrated under reduced pressure. The residue was purified by flash chromatography on silica gel using a gradient of EA (40 to 50%) in PE to afford 1-(tert-butyl) 2-methyl (2S,4S)-4-(2-oxoethoxy)pyrrolidine-1,2-dicarboxylate (1.25 g, 60%) as a colorless oil.

To a solution of (1-(tert-butyl) 2-methyl (2S,4S)-4-(2-oxoethoxy)pyrrolidine-1,2-dicarboxylate (1.2 g, 4.21 mmol, 1.0 eq.) in methanol (12 mL) cooled at 0° C. was added portionwise NaBH$_4$ (160 mg, 4.21 mmol, 1.0 eq.). The mixture was stirred at rt for 1 h. The mixture was diluted with ice-cold water (10 mL) and extracted with DCM (2×20 mL). The organic phases were combined, washed with brine (2×10 mL), dried over Na$_2$SO$_4$, filtered and concentrated under reduced pressure. The residue was purified by flash chromatography on silica gel using a gradient of MeOH (5 to 10%) in DCM to afford 1-(tert-butyl) 2-methyl (2S,4S)-4-(2-hydroxyethoxy)pyrrolidine-1,2-dicarboxylate (1.1 g, 91%) as a colorless oil.

To a solution of 1-(tert-butyl) 2-methyl (2S,4S)-4-(2-hydroxyethoxy)pyrrolidine-1,2-dicarboxylate (1.1 g, 3.80 mmol, 1.0 eq.) in DCM (22 mL) cooled at 0° C. were added NEt$_3$ (1.6 mL, 11.4 mmol, 3.0 eq.), DMAP (46 mg, 0.376 mmol, 0.1 eq.) and TsCl (1.45 g, 7.61 mmol, 2.0 eq.). The mixture was stirred at rt overnight. The mixture was washed with ice-cold water (10 mL). The phases were separated. The aqueous phase was extracted with DCM (2×20 mL). The organic phases were combined, washed with brine (2×10 mL), dried over Na$_2$SO$_4$, filtered and concentrated under reduced pressure. The residue was purified by flash chromatography on silica gel using a gradient of EA (40 to 45%) in PE to afford 1-(tert-butyl) 2-methyl (2S,4S)-4-(2-(tosyloxy)ethoxy)pyrrolidine-1,2-dicarboxylate (1.4 g, 83%) as a colorless oil.

To a solution of NaIO$_4$ (10.1 g, 47.4 mmol, 15.0 eq.) in water (20 mL) was added RuO$_2$·H$_2$O (84 mg, 0.632 mmol, 0.2 eq.). The mixture was stirred at rt for 10 min. A solution of 1-(tert-butyl) 2-methyl (2S,4S)-4-(2-(tosyloxy)ethoxy) pyrrolidine-1,2-dicarboxylate (1.4 g, 3.16 mmol, 1.0 eq.) in EA (20 mL) was added. The mixture was stirred at rt for 16 h. The mixture was diluted with ice-cold water (20 mL). The phases were separated. The aqueous phase was extracted with EA (2×30 mL). The organic phases were combined, washed with brine (2×10 mL), dried over Na$_2$SO$_4$, filtered and concentrated under reduced pressure. The residue was purified by flash chromatography on silica gel using a gradient of EA (40 to 45%) in PE to afford 1-(tert-butyl) 2-methyl (2S,4S)-5-oxo-4-(2-(tosyloxy)ethoxy)pyrrolidine-1,2-dicarboxylate (770 mg, 55%) as a colorless oil.

To a solution of 1-(tert-butyl) 2-methyl (2S,4S)-5-oxo-4-(2-(tosyloxy)ethoxy)pyrrolidine-1,2-dicarboxylate (550 mg, 1.20 mmol, 1.0 eq.) in MeOH (2.75 mL) and DCM (2.75 mL) cooled at 0° C. was added K$_2$CO$_3$ (33 mg, 0.239 mmol, 0.2 eq.). The mixture was stirred at rt for 1 h. Water (10 mL) was added and the phases were separated. The aqueous phase was extracted with DCM (2×20 mL). The organic phases were combined, dried over Na$_2$SO$_4$, filtered and concentrated under reduced pressure to afford dimethyl (2S,4S)-2-((tert-butoxycarbonyl)amino)-4-(2-tosyloxy) ethoxy)pentanedioate (570 mg) as an oil.

To a solution of dimethyl (2S,4S)-2-((tert-butoxycarbonyl)amino)-4-(2-tosyloxy)ethoxy)pentanedioate (570 mg, 1.16 mmol, 1.0 eq.) in DMF (5 mL) was added NaN$_3$ (151 mg, 2.33 mmol, 2.0 eq.). The mixture was heated at 60° C. for 2 h. After cooling to rt, the mixture was diluted with ice-cold water (10 mL) and extracted with EA (2×10 mL). The organic phases were combined, washed with brine (2×10 mL), dried over Na$_2$SO$_4$, filtered and concentrated under reduced pressure. The residue was purified by flash chromatography on silica gel using a gradient of EA (25 to 30%) in PE to afford dimethyl (2S,4S)-2-(2-azidoethoxy)-4-((tert-butoxycarbonyl)amino)pentanedioate (360 mg, 85%) as a colorless oil.

To a solution of dimethyl (2S,4S)-2-(2-azidoethoxy)-4-((tert-butoxycarbonyl)amino)pentanedioate (360 mg, 0.999 mmol, 1.0 eq.) in MeOH (10 mL) was added 10% Pd/C (70 mg, 50% wet). The mixture was stirred at rt under H$_2$ atmosphere for 2 h. The mixture was filtered through celite. The solid was washed with DCM (10 mL). The filtrate was concentrated under reduced pressure. The residue was purified by flash chromatography on silica gel using a gradient of MeOH (2 to 5%) in DCM to afford methyl (S)-2-((tert-butoxycarbonyl)amino)-3-((S)-3-oxomorpholin-2-yl)propanoate (225 mg, 74%) as a colorless oil. $^1$H NMR (400 MHz, CDCl$_3$) δ 6.05 (bs, 1H), 5.37 (m, 1H), 4.50 (m, 1H), 4.17 (dd, 1H), 4.04 (m, 1H), 3.74 (m, 4H), 3.61 (m, 1H), 3.30 (m, 1H), 2.36-2.42 (m, 1H), 2.21-2.26 (m, 1H), 1.44 (s, 9H). LCMS (ESI, m/z): 303 [M+H]$^+$.

A solution of methyl (S)-2-((tert-butoxycarbonyl)amino)-3-((S)-3-oxomorpholin-2-yl)propanoate (225 mg, 0.733 mmol, 1.0 eq.) in 7M NH$_3$ in methanol (5 mL) was stirred at rt for 24 h in a sealed tube. The mixture was concentrated under reduced pressure to afford tert-butyl ((S)-1-amino-1-oxo-3-((S)-3-oxomorpholin-2-yl)propan-2-yl)carbamate (200 mg, 93%) as an off-white solid.

A solution of tert-butyl ((S)-1-amino-1-oxo-3-((S)-3-oxomorpholin-2-yl)propan-2-yl)carbamate (100 mg, 0.595 mmol, 1.0 eq.) in 2M HCl in Et₂O (5 mL) was stirred at rt for 2 h. The mixture was concentrated under reduced pressure to afford (S)-2-amino-3-((S)-3-oxomorpholin-2-yl)propanamide hydrochloride (62 mg, 95%) as a white solid.

To a solution of (1S,3aR,4S,7R,7aS)-2-((S)-3,3-dimethyl-2-(2,2,2-trifluoroacetamido)butanoyl)-2,3,3a,4,7,7a-hexahydro-1H-4,7-methanoisoindole-1-carboxylic acid (130 mg, 0.335 mmol, 1.0 eq.) in DMF (1.3 mL) cooled at 0° C. were added (S)-2-amino-3-((S)-3-oxomorpholin-2-yl)propanamide hydrochloride (64 mg, 0.335 mmol, 1.0 eq.), EDC•HCl (130 mg, 0.678 mmol, 2.0 eq.), HOAt (44 mg, 0.335 mmol, 1.0 eq.) and NEt₃ (0.22 mL, 1.67 mmol, 5.0 eq.). The mixture was stirred at rt for 16 h. The mixture was diluted with water (10 mL) and extracted with EA (3×10 mL). The organic phases were combined, washed with brine (2×10 mL), dried over Na₂SO₄, filtered and concentrated under reduced pressure. The residue was purified by flash chromatography on silica gel using a gradient of MeOH (5 to 6%) in DCM to afford (1S,3aR,4S,7R,7aS)—N—((S)-1-amino-1-oxo-3-((S)-3-oxomorpholin-2-yl)propan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (120 mg, 65%) as a white solid.

To a solution of (1S,3aR,4S,7R,7aS)—N—((S)-1-amino-1-oxo-3-((S)-3-oxomorpholin-2-yl)propan-2-yl)-2-((S)-3,3-dimethyl-2-(2,2,2-trifluoroacetamido)butanoyl)-2,3,3a,4,7,7a-hexahydro-1H-4,7-methanoisoindole-1-carboxamide (100 mg, 0.179 mmol, 1.0 eq.) in DMF (1 mL) were added pyridine (0.04 mL, 0.537 mmol, 3.0 eq.) and TFAA (0.028 mL, 0.359 mmol, 2.0 eq.). The mixture was stirred at rt for 2 h. The mixture was diluted with water (5 mL) and extracted with EA (3×10 mL). The organic phases were combined, washed with brine (2×5 mL), dried over Na₂SO₄, filtered and concentrated under reduced pressure. The residue was purified by prep-HPLC (Column: SUNFIRE-C18 Column, 19*150 mm, 5 m; Mobile Phase A: 10 mM NH₄HCO₃ in water, Mobile Phase B: ACN; Flow rate: 18 mL/min; Gradient: 10% B to 60% B in 8 min) to afford (1S,3aR,4S,7R,7aS)—N—((S)-1-cyano-2-((S)-3-oxomorpholin-2-yl)ethyl)-2-((S)-3,3-dimethyl-2-(2,2,2-trifluoroacetamido)butanoyl)-2,3,3a,4,7,7a-hexahydro-1H-4,7-methanoisoindole-1-carboxamide (65 mg, 67%) as a white solid. ¹H NMR (500 MHz, 364K, DMSO-d₆) δ 8.09-8.80 (m, 2H), 7.70 (s, 1H), 5.94-6.22 (m, 2H), 4.86 (m, 1H), 4.44-4.74 (m, 1H), 4.01-4.24 (m, 2H), 3.88 (m, 1H), 3.57-3.77 (m, 2H), 3.45 (m, 1H), 3.33 (m, 1H), 3.12-3.24 (m, 1H), 3.05 (m, 1H), 2.80-2.95 (m, 2H), 2.75 (m, 1H), 2.38 (m, 1H), 2.07-2.21 (m, 1H), 1.36-1.46 (m, 2H), 0.88-0.97 (m, 9H). LCMS (ESI, m/z): 540 [M+H]⁺.

Example 115

Compound 115

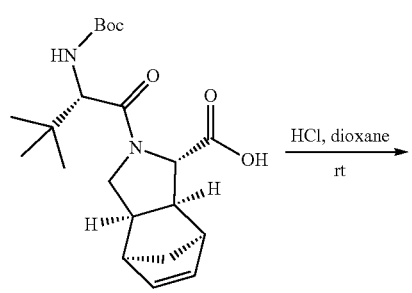

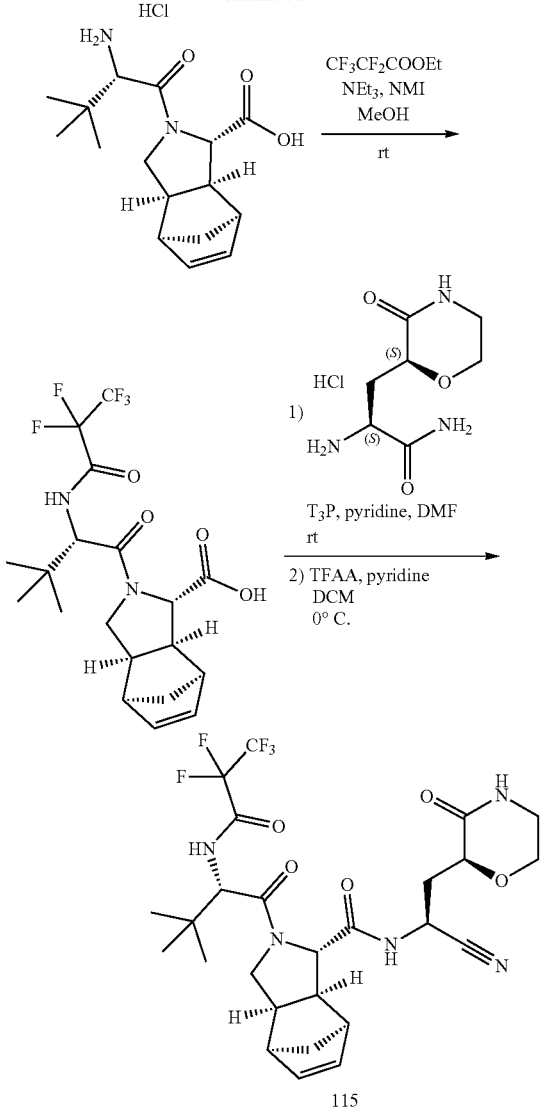

115

A mixture of (1S,3aR,4S,7R,7aS)-2-((S)-2-((tert-butoxycarbonyl)amino)-3,3-dimethylbutanoyl)-2,3,3a,4,7,7a-hexahydro-1H-4,7-methanoisoindole-1-carboxylic acid (770 mg, 1.96 mmol, 1.0 eq.) in 4N HCl in dioxane (4 mL) was stirred at rt for 4 h. The mixture was concentrated under reduced pressure to afford quantitatively (1S,3aR,4S,7R,7aS)-2-((S)-2-amino-3,3-dimethylbutanoyl)-2,3,3a,4,7,7a-hexahydro-1H-4,7-methanoisoindole-1-carboxylic acid hydrochloride as an off-white solid.

To a solution of (1S,3aR,4S,7R,7aS)-2-((S)-2-amino-3,3-dimethylbutanoyl)-2,3,3a,4,7,7a-hexahydro-1H-4,7-methanoisoindole-1-carboxylic acid hydrochloride (100 mg, 0.304 mmol, 1.0 eq.) in MeOH (1 mL) cooled at 0° C. were added ethyl 2,2,3,3,3-pentafluoropropanoate (292 mg, 1.52 mmol, 5.0 eq.), NEt₃ (0.21 mL, 1.52 mmol, 5.0 eq.) and 1-methylimidazole (0.05 mL, 1.03 mmol, 2.0 eq.). The mixture was stirred at rt for 18 h. After cooling to 0° C., the mixture was acidified by addition of 1N HCl until pH=2, diluted with water (0.5 mL) and aged at 0° C. overnight. The precipitate was filtered, washed with cold water and dried under reduced pressure to afford (1S,3aR,4S,7R,7aS)-2-((S)-3,3-dimethyl-2-(2,2,3,3,3-pentafluoropropanamido)butanoyl)-

2,3,3a,4,7,7a-hexahydro-1H-4,7-methanoisoindole-1-carboxylic acid (60 mg, 45%) as an off-white solid.

To a solution of (1S,3aR,4S,7R,7aS)-2-((S)-3,3-dimethyl-2-(2,2,3,3,3-pentafluoropropanamido)butanoyl)-2,3,3a,4,7,7a-hexahydro-1H-4,7-methanoisoindole-1-carboxylic acid (100 mg, 0.228 mmol, 1.0 eq.) in DMF (1.0 mL) cooled at 0° C. were added (S)-2-amino-3-((S)-3-oxomorpholin-2-yl)propanamide hydrochloride (66 mg, 0.297 mmol, 1.3 eq.), pyridine (0.18 mL, 2.28 mmol, 10.0 eq.) and 50% T$_3$P in EA (0.54 mL, 0.912 mmol, 4.0 eq.). The mixture was stirred at rt for 7 h. Cold water (5 mL) was added, and the phases were separated. The aqueous phase was extracted with EA (4×10 mL). The organic phases were combined, washed with brine and sat. NaHCO$_3$, dried over Na$_2$SO$_4$, filtered and concentrated under reduced pressure. The residue was dissolved in DCM (1 mL) and cooled to 0° C. After addition of pyridine (0.035 mL, 0.435 mmol, 2.2 eq.) and TFAA (0.030 mL, 0.217 mmol, 1.1 eq.), the mixture was stirred at 0° C. for 1 h. Water (3 mL) was added. The mixture was stirred at rt for 5 min, and the phases were separated. The aqueous phase was extracted with EA (5×5 mL). The organic phases were combined, washed with sat. NaHCO$_3$ (2 mL), dried over Na$_2$SO$_4$, filtered and concentrated under reduced pressure. The residue was purified by prep-HPLC (Column: SUNFIRE-C18 Column, 19*150 mm, 5 m; Mobile Phase A: 10 mM NH$_4$HCO$_3$ in water, Mobile Phase B: ACN; Flow rate: 17 mL/min; Gradient: 20% B to 55% B in 9 min) to afford (1S,3aR,4S,7R,7aS)—N—((S)-1-cyano-2-((S)-3-oxomorpholin-2-yl)ethyl)-2-((S)-3,3-dimethyl-2-(2,2,3,3,3 pentafluoropropanamido)butanoyl)-2,3,3a,4,7,7a-hexahydro-1H-4,7-methanoisoindole-1-carboxamide (40 mg, 30%) as a white solid. $^1$H NMR (500 MHz, 363K, DMSO-d$_6$) δ 8.38-8.68 (m, 2H), 7.72 (br. s., 1H), 5.92-6.22 (m, 2H), 4.63-4.91 (m, 1H), 4.55 (s, 1H), 3.99-4.21 (m, 2H), 3.88 (m, 1H), 3.58-3.76 (m, 2H), 3.47 (m, 1H), 3.29-3.40 (m, 1H), 3.11-3.24 (m, 1H), 3.00-3.10 (m, 1H), 2.81-2.96 (m, 2H), 2.75 (m, 1H), 2.31-2.42 (m, 1H), 2.08-2.23 (m, 1H), 1.36-1.46 (m, 2H), 0.87-1.02 (m, 9H). LCMS (ESI, m/z): 590 [M+H]$^+$.

Example 116

Compound 116

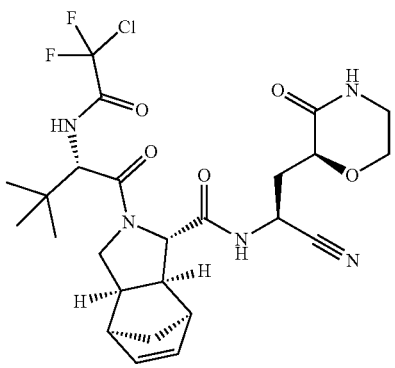

Compound 116 was prepared similarly as described for Compound 115 using methyl 2-chloro-2,2-difluoroacetate in place ethyl 2,2,3,3,3-pentafluoropropanoate. $^1$H NMR (500 MHz, 363K, DMSO-d$_6$) δ 8.19-8.71 (m, 2H), 7.61-7.85 (br. s., 1H), 5.92-6.23 (m, 2H), 4.65-4.94 (m, 1H), 4.37-4.61 (m, 1H), 3.97-4.24 (m, 2H), 3.87 (m, 1H), 3.57-3.74 (m, 2H), 3.41-3.56 (m, 1H), 3.33 (m, 1H), 3.12-3.24 (m, 1H), 3.00-3.10 (m, 1H), 2.65-2.95 (m, 3H), 2.38 (m, 1H), 2.13 (m, 1H), 1.30-1.48 (m, 2H), 0.77-1.09 (m, 9H). LCMS (ESI, m/z): 556 [M+H]$^+$.

Example 117

Compound 117

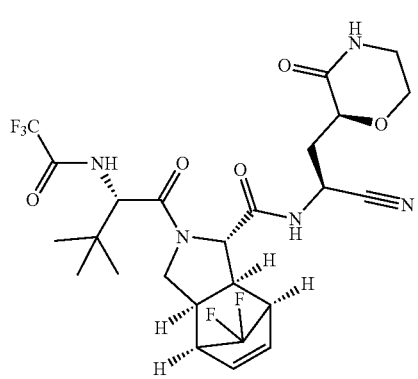

Compound 117 was prepared similarly as described for Compound 82 using (S)-2-amino-3-((S)-3-oxomorpholin-2-yl)propanamide hydrochloride in place of (2S)-2-amino-3-[(3S)-2-oxopyrrolidin-3-yl]propanamide. $^1$H NMR (500 MHz, 363K, DMSO-d$_6$) δ 8.22-8.82 (m, 2H), 7.72 (br. s., 1H), 6.07-6.33 (m, 2H), 4.66-4.91 (m, 1H), 4.32-4.52 (m, 1H), 4.13-4.25 (m, 1H), 4.05 (m, 1H), 3.88 (m, 1H), 3.57-3.77 (m 3H), 3.39-3.51 (m, 2H), 3.08-3.31 (m, 3H), 2.86-2.94 (m, 1H), 2.33-2.46 (m, 1H), 2.09-2.22 (m, 1H), 0.86-1.01 (m, 9H). LCMS (ESI, m/z): 576 [M+H]$^+$.

Example 118

Compound 118

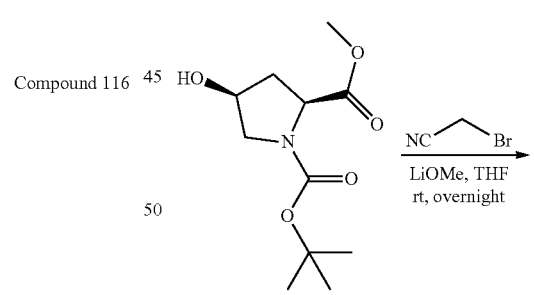

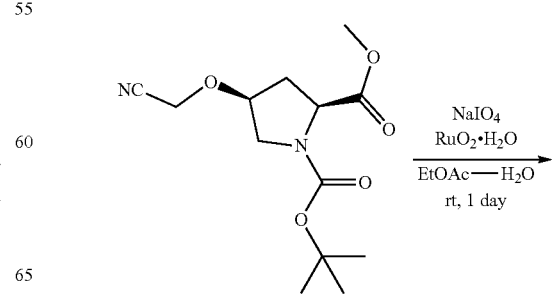

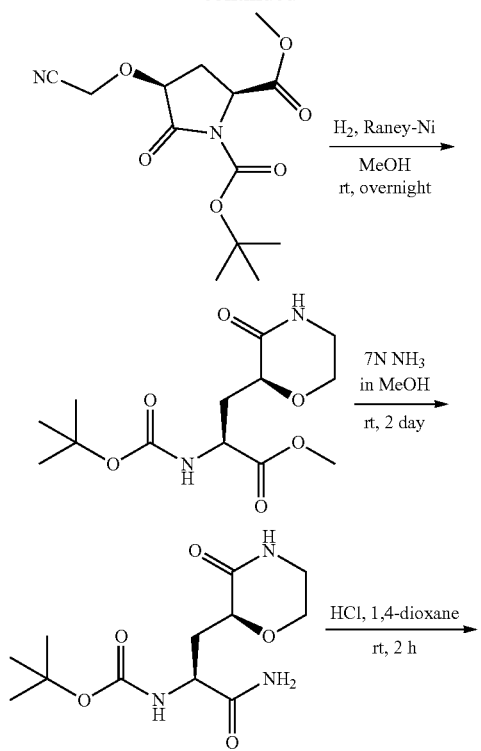
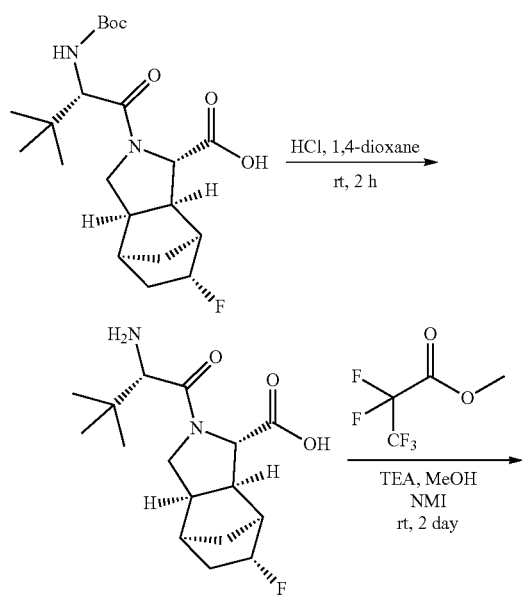
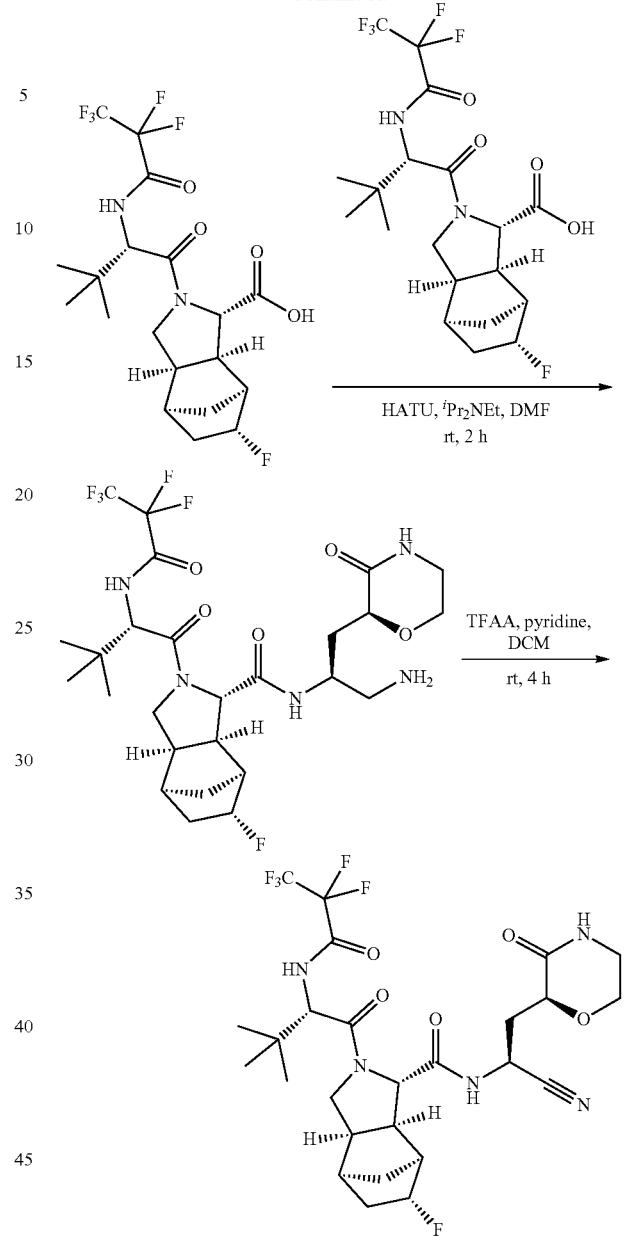

To a mixture of 1-(tert-butyl) 2-methyl (2S,4S)-4-hydroxypyrrolidine-1,2-dicarboxylate (10.0 g, 40.8 mmol, 1.0 eq.) in dry THF (100 mL) were added bromo acetonitrile (17.0 g, 143 mmol, 3.5 eq.) and lithium methanolate (5.29 g, 143 mmol, 3.5 eq.). The mixture was stirred for overnight at rt. The reaction was monitored by LC-MS, some 1-(tert-butyl) 2-methyl (2S,4S)-4-hydroxypyrrolidine-1,2-dicarboxylate (<15% (PDA)) remained. Another batch of lithium methanolate (2.26 g, 61.2 mmol, 1.5 eq.) and bromo acetonitrile (7.28 g, 61.2 mmol, 1.5 eq.) was added. The mixture was stirred for 3 h. The reaction was quenched with ice-water (200 mL) and extracted with EtOAc (3×400 mL). The organic layers were combined, washed with brine (2×80 mL), dried over anhydrous sodium sulfate, filtered and concentrated under reduced pressure to afford the crude product. The crude product was chromatographed on a silica gel column with EA:PE (50%-75%) to provide 1-(tert-butyl) 2-methyl (2S,4S)-4-(cyanomethoxy)pyrrolidine-1,2-dicarboxylate (6.0 g, 52%) as a light yellow oil (turned to solid upon storage). $^1$H NMR (400 MHz, CDCl$_3$): δ 4.17-4.53 (m, 4H), 3.46-3.83 (m, 5H), 2.24-2.51 (m, 2H), 1.31-1.55 (m, 9H). LC-MS (ESI, m/z): 185 [M−Boc+H]$^+$.

To a stirred solution of sodium periodate (13.4 g, 63.3 mmol, 3.0 eq) in water (15 mL) at rt was added ruthenium (IV) oxide hydrated (1.43 g, 9.50 mmol, 0.15 eq). The mixture was stirred for 10 min and then 1-(tert-butyl) 2-methyl (2S,4S)-4-(cyanomethoxy)pyrrolidine-1,2-dicarboxylate (6.0 g, 21.1 mmol, 1.0 eq) in ea (60 mL) was added at rt. The mixture was stirred for 1 day at rt. The mixture was filtered and extracted with EtOAc (3×200 mL). The organic layers were combined, washed with brine (2×50 mL), dried over anhydrous sodium sulfate, filtered and concentrated under reduced pressure to afford the crude product. The crude product was chromatographed on a silica gel column with EA:PE (70%) to provide 1-(tert-butyl) 2-methyl (2S,4S)-4-(cyanomethoxy)-5-oxopyrrolidine-1,2-dicarboxylate (5.0 g, 79%) as a yellow oil. $^1$H NMR (400 MHz, CDCl$_3$): δ 4.73-4.86 (m, 1H), 4.50-4.62 (m, 2H), 4.18-4.28 (m, 1H), 3.77-3.86 (m, 3H), 2.64-2.81 (m, 1H), 2.07-2.14 (m, 1H), 1.46-1.55 (m, 9H). LC-MS (ESI, m/z): 199 [M−Boc+H]$^+$.

To a mixture of 1-(tert-butyl) 2-methyl (2S,4S)-4-(cyanomethoxy)-5-oxopyrrolidine-1,2-dicarboxylate (5.0 g, 16.8 mmol, 1.0 eq.) in MeOH (50 mL) was added Raney-Ni (2.0 g) at rt under hydrogen. The mixture was stirred for overnight at rt. The supernatant was transferred, and the residue Raney-Ni was washed with DCM (5×). The mixture filtered and concentrated under reduced pressure to afford the crude product. The crude product was chromatographed on a silica gel column with MeOH:DCM (6%) to provide methyl (S)-2-((tert-butoxycarbonyl)amino)-3-((S)-3-oxomorpholin-2-yl)propanoate (3.5 g, 70%) as a yellow oil. LC-MS (ESI, m/z): 203 [M−Boc+H]$^+$ A mixture of methyl (S)-2-((tert-butoxycarbonyl)amino)-3-((S)-3-oxomorpholin-2-yl)propanoate (3.5 g, 11.6 mmol, 1.0 eq.) in ammonia (100 mL, 7M in MeOH) was stirred 2 days at rt. The mixture was concentrated under reduced pressure to afford the crude product. The crude product was purified by silica gel column chromatography with methanol:dichloromethane (15:85) to afford tert-butyl ((S)-1-amino-1-oxo-3-((S)-3-oxomorpholin-2-yl)propan-2-yl)carbamate (2.1 g, 64%) as a yellow solid. LC-MS (ESI, m/z): 288 [M+H]$^+$ The mixture of tert-butyl ((S)-1-amino-1-oxo-3-((S)-3-oxomorpholin-2-yl)propan-2-yl)carbamate (100 mg, 0.348 mmol, 1.0 eq.) and hydrogen chloride (5 mL, 4M in 1,4-dioxane) was stirred for 2 h at rt. The mixture was concentrated under reduced pressure to afford (S)-2-amino-3-((S)-3-oxomorpholin-2-yl)propanamide (70 mg, crude) as an off-white solid. LC-MS (ESI, m/z): 188 [M+H]$^+$.

The mixture of (1S,3aR,4S,6R,7S,7aR)-2-((S)-2-((tert-butoxycarbonyl)amino)-3,3-dimethylbutanoyl)-6-fluorooctahydro-1H-4,7-methanoisoindole-1-carboxylic acid (400 mg, 0.970 mmol, 1.0 eq.) and hydrogen chloride (10 mL, 4M in 1,4-dioxane) was stirred for 2 h at rt. The mixture was concentrated under reduced pressure to afford (1S,3aR,4S,6R,7S,7aR)-2-((S)-2-amino-3,3-dimethylbutanoyl)-6-fluorooctahydro-1H-4,7-methanoisoindole-1-carboxylic acid (303 mg, crude) as a yellow solid. LC-MS (ESI, m/z): 313 [M+H]$^+$.

To a mixture of (1S,3aR,4S,6R,7S,7aR)-2-((S)-2-amino-3,3-dimethylbutanoyl)-6-fluorooctahydro-1H-4,7-methanoisoindole-1-carboxylic acid (303 mg, 0.970 mmol, 1.0 eq.) in MeOH (3 mL) were added triethylamine (490 mg, 4.85 mmol, 5.0 eq.), N-methylimidazole (159 mg, 1.94 mmol, 2.0 eq.) and methyl 2,2,3,3,3-pentafluoropropanoate (863 mg, 4.850 mmol, 5.0 eq.). The mixture was stirred for 2 days at rt. The crude product was purified by C18 column with CH$_3$CN/Water (0.05% FA). The desired fraction was concentrated under reduced pressure to provide (1S,3aR,4S,6R,7S,7aR)-2-((S)-3,3-dimethyl-2-(2,2,3,3,3-pentafluoropropanamido)butanoyl)-6-fluorooctahydro-1H-4,7-methanoisoindole-1-carboxylic acid (350 mg, 78%) as a yellow solid. LC-MS (ESI, m/z): 459 [M+H]$^+$.

To a mixture of (1S,3aR,4S,6R,7S,7aR)-2-((S)-3,3-dimethyl-2-(2,2,3,3,3-pentafluoropropanamido)butanoyl)-6-fluorooctahydro-1H-4,7-methanoisoindole-1-carboxylic acid (150 mg, 0.327 mmol, 1.0 eq.) in N,N-dimethylformamide (2 mL) were added o-(7-azabenzotriazol-1-yl)-N,N,N',N'-te-tramethyluronium hexafluorophosphate (149 mg, 0.392 mmol, 1.2 eq.) and N-ethyl-N-isopropylpropan-2-amine (254 mg, 1.96 mmol, 6.0 eq.) at 0° C. The mixture was stirred for 20 min at 0° C., and then (S)-2-amino-3-((S)-3-oxomorpholin-2-yl)propanamide (61.2 mg, 0.327 mmol, 1.0 eq.) was added at 0° C. The mixture was stirred for 2 h at rt. The mixture was purified by C18 column with CH$_3$CN/Water (0.05% TFA). The desired fraction was concentrated under reduced pressure to provide (1S,3aR,4S,6R,7S,7aR)—N—((S)-1-amino-1-oxo-3-((S)-3-oxomorpholin-2-yl)propan-2-yl)-2-((S)-3,3-dimethyl-2-(2,2,3,3,3-pentafluoropropanamido)butanoyl)-6-fluorooctahydro-1H-4,7-methanoisoindole-1-carboxamide (100 mg, 48%) as a yellow solid. LC-MS (ESI, m/z): 628 [M+H]$^+$.

To a mixture of (1S,3aR,4S,6R,7S,7aR)—N—((S)-1-amino-1-oxo-3-((S)-3-oxomorpholin-2-yl)propan-2-yl)-2-((S)-3,3-dimethyl-2-(2,2,3,3,3-pentafluoropropanamido)butanoyl)-6-fluorooctahydro-1H-4,7-methanoisoindole-1-carboxamide (100 mg, 0.159 mmol, 1.0 eq.) in DCM (1 mL) were added pyridine (50.4 mg, 0.636 mmol, 4.0 eq.) and trifluoroacetic anhydride (56.9 mg, 0.270 mmol, 1.7 eq.). The mixture was stirred for 4 h at rt. The reaction was quenched with water (10 mL). The mixture was extracted with dichloromethane (3×30 mL). The organic layers were combined, washed with brine (2×10 mL), dried over anhydrous sodium sulfate, filtered and concentrated under reduced pressure to afford the crude product. The crude product was purified by prep-HPLC (Column: XSelect CSH Prep C18 OBD Column, 19*250 mm, 5 m; Mobile Phase A: Water (0.1% FA), Mobile Phase B: ACN; Flow rate: 25 mL/min; Gradient: 42% B to 72% B in 7 min, 72% B; Wave Length: 220 nm; RT1 (min): 6.3) to provide (1S,2R,3S,6R,7S,9R)—N-[(1S)-1-cyano-2-[(2S)-3-oxomorpholin-2-yl]ethyl]-4-[(2S)-3,3-dimethyl-2-(2,2,3,3,3-pentafluoropropanamido)butanoyl]-9-fluoro-4-azatricyclo[5.2.1.0ˆ{2,6}]decane-3-carboxamide (41.4 mg, 42%) as a white solid. $^1$H NMR (400 MHz, 80° C., DMSO-d$_6$) δ 8.80-9.00 (m, 1H), 8.60-8.80 (m, 1H), 7.70-7.95 (m, 1H), 4.80-5.00 (m, 1H), 4.65-4.80 (m, 1H), 4.53-4.65 (m, 1H), 4.20-4.50 (m, 1H), 4.00-4.18 (m, 1H), 3.80-4.00 (m, 1H), 3.70-3.80 (m, 1H), 3.50-3.70 (m, 2H), 3.25-3.45 (m, 1H), 3.10-3.20 (m, 1H), 2.60-2.70 (m, 2H), 2.50-2.60 (m, 1H), 2.25-2.45 (m, 2H), 2.05-2.20 (m, 1H), 1.80-2.00 (m, 1H), 1.45-1.75 (m, 2H), 1.20-1.45 (m, 1H), 0.90-1.10 (m, 9H). LC-MS (ESI, m/z): 610 [M+H]$^+$.

Example 119

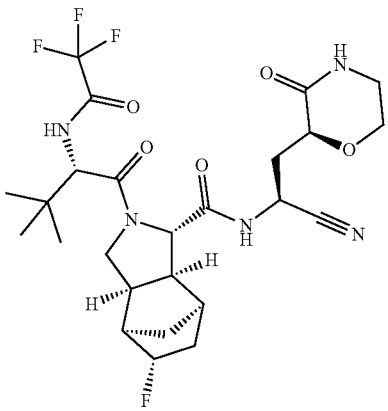

Compound 119

Compound 119 was prepared from (1S,3aS,4R,5S,7R,7aS)-2-((S)-3,3-dimethyl-2-(2,2,2-trifluoroacetamido)butanoyl)-5-fluorooctahydro-1H-4,7-methanoisoindole-1-carboxylic acid, similarly as described for compound 118 from (1S,3aR,4S,6R,7S,7aR)-2-((S)-3,3-dimethyl-2-(2,2,3,3,3-pentafluoropropanamido)butanoyl)-6-fluorooctahydro-1H-4,7-methanoisoindole-1-carboxylic acid. $^1$H NMR (400 MHz, 80° C., DMSO-d6) δ 8.50-9.20 (m, 2H), 7.70-7.90 (m, 1H), 4.55-4.95 (m, 3H), 4.30-4.50 (m, 1H), 4.00-4.15 (m, 1H), 3.80-4.00 (m, 2H), 3.50-3.70 (m, 2H), 3.25-3.40 (m, 1H), 3.10-3.20 (m, 1H), 2.55-2.90 (m, 1H), 2.40-2.53 (m, 1H), 2.25-2.40 (m, 3H), 2.05-2.23 (m, 1H), 1.55-1.80 (m, 2H), 1.30-1.55 (m, 2H), 0.85-1.10 (m, 9H). LC-MS (ESI, m/z): 560 [M+H]$^+$.

Example 120

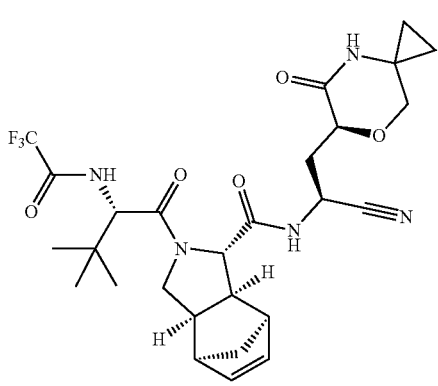

Compound 120

Compound 120 was prepared similarly as described for Compound 114 using methyl (S)-2-((tert-butoxycarbonyl)amino)-3-((S)-5-oxo-7-oxa-4-azaspiro[2.5]octan-6-yl)propanoate in place of methyl (S)-2-((tert-butoxycarbonyl)amino)-3-((S)-3-oxomorpholin-2-yl)propanoate. $^1$H NMR (500 MHz, 364K, DMSO-d$_6$) δ 8.14-8.74 (m, 2H), 7.75-7.95 (br. s., 1H), 5.93-6.23 (m, 1H), 4.69-4.93 (m, 1H), 4.49 (m, 1H), 4.02-4.26 (m, 2H), 3.71-3.91 (m, 1H), 3.65 (m, 1H), 3.35-3.57 (m, 2H), 3.00-3.24 (m, 1H), 2.79-2.94 (m, 2H), 2.76 (m, 1H), 2.37-2.50 (m, 1H), 2.10-2.27 (m, 1H), 1.32-1.48 (m, 2H), 0.86-1.03 (m, 9H), 0.57-0.81 (m, 4H). LCMS (ESI, m/z): 566 [M+H]$^+$.

Methyl (S)-2-((tert-butoxycarbonyl)amino)-3-((S)-5-oxo-7-oxa-4-azaspiro[2.5]octan-6-yl)propanoate: To a solution of 1-(tert-butyl) 2-methyl (2S,4S)-4-hydroxypyrrolidine-1,2-dicarboxylate (5.0 g, 20.4 mmol, 1.0 eq.) in THF (50 mL) were added LiOMe (3.8 g, 102 mmol, 5.0 eq.) and bromoacetonitrile (7.11 mL, 102 mmol, 5.0 eq.). The mixture was stirred at rt for 4 h. The mixture was poured into ice-cold water (20 mL) and extracted with EA (3×50 mL). The organic phases were combined, washed with brine (2×30 mL), dried over Na$_2$SO$_4$, filtered and concentrated under reduced pressure. The residue was purified by flash chromatography on silica gel using a gradient of EA (40 to 50%) in PE to afford 1-(tert-butyl) 2-methyl (2S,4S)-4-(cyanomethoxy)pyrrolidine-1,2-dicarboxylate (1.5 g, 26%) as a brown oil.

To a solution of sodium periodate (1.6 g, 7.38 mmol, 3.0 eq.) in water (10 mL) was added RuO$_2$•H$_2$O (49 mg, 0.369 mmol, 0.15 eq.). The mixture was stirred at rt for 10 min. After the addition of a solution of 1-(tert-butyl) 2-methyl (2S,4S)-4-(cyanomethoxy)pyrrolidine-1,2-dicarboxylate (700 mg, 2.46 mmol, 1.0 eq.) in EA (10 mL), the mixture was stirred at rt for 16 h. The mixture was diluted with water (20 mL). The phases were separated. The aqueous phase was extracted with EA (2×30 mL). The organic phases were combined and iPrOH (5 mL) was added. After stirring for 10 min, brine (10 mL) was added. The phases were separated. The organic phase was washed with brine (10 mL), dried over Na$_2$SO$_4$, filtered and concentrated under reduced pressure. The residue was purified by flash chromatography on silica gel using a gradient of EA (45 to 50%) in PE to afford 1-(tert-butyl) 2-methyl (2S,4S)-4-(cyanomethoxy)-5-oxopyrrolidine-1,2-dicarboxylate (650 mg, 88%) as a colorless oil.

To a solution of 1-(tert-butyl) 2-methyl (2S,4S)-4-(cyanomethoxy)-5-oxopyrrolidine-1,2-dicarboxylate (600 mg, 2.01 mmol, 1.0 eq.) in DCM (6 mL) and methanol (6 mL) cooled at 0° C. was added K$_2$CO$_3$ (56 mg, 0.402 mmol, 0.2 eq.). The mixture was stirred at rt for 1 h. Ice-cold water (10 mL) was added, and the phases were separated. The aqueous phase was extracted with DCM (2×30 mL). The organic phases were combined, dried over Na$_2$SO$_4$, filtered and concentrated under reduced pressure. The residue was purified by flash chromatography on silica gel using a gradient of EA (35 to 40%) in PE to afford dimethyl (2S,4S)-2-((tert-butoxycarbonyl)amino)-4-(cyanomethoxy)pentanedioate (550 mg, 82%) as a colorless oil.

To a solution of dimethyl (2S,4S)-2-((tert-butoxycarbonyl)amino)-4-(cyanomethoxy)pentanedioate (200 mg, 0.606 mmol, 1.0 eq.) in THF (2 mL) cooled at −78° C. were added Ti(OiPr)$_4$ (0.45 mL, 1.33 mmol, 2.2 eq.) and 3M EtMgBr solution in Et$_2$O (1.61 mL, 4.84 mmol, 8.0 eq.). The mixture was stirred at rt for 1 h. BF$_3$•Et$_2$O (0.37 mL, 2.66 mmol, 4.4 eq.) was added. After 1 h at rt, the mixture was poured into 28% NH$_4$OH (5 mL) and was extracted with EA (3×20 mL). The organic phases were combined, washed with brine (2×5 mL), dried over Na$_2$SO$_4$, filtered and concentrated under reduced pressure. The residue was purified by flash chromatography on silica gel using a gradient of EA (80 to 100%) in PE to afford methyl (S)-2-((tert-butoxycarbonyl)amino)-3-((S)-5-oxo-7-oxa-4-azaspiro[2.5]octan-6-yl)propanoate (33 mg, 16%) as a yellow oil. $^1$H NMR (400 MHz, CDCl$_3$) δ 5.67 (br. s., 1H), 5.41 (m, 1H), 4.54 (m, 1H), 4.24 (m, 1H), 3.96 (m, 1H), 3.74 (s, 3H), 3.51 (m, 1H), 2.33-2.41 (m, 1H), 2.27-2.31 (m, 1H), 1.44 (s, 9H), 0.79-0.89 (m, 3H), 0.71 (m, 1H). LCMS (ESI, m/z): 329 [M+H]$^+$.

Example 121

Compound 121

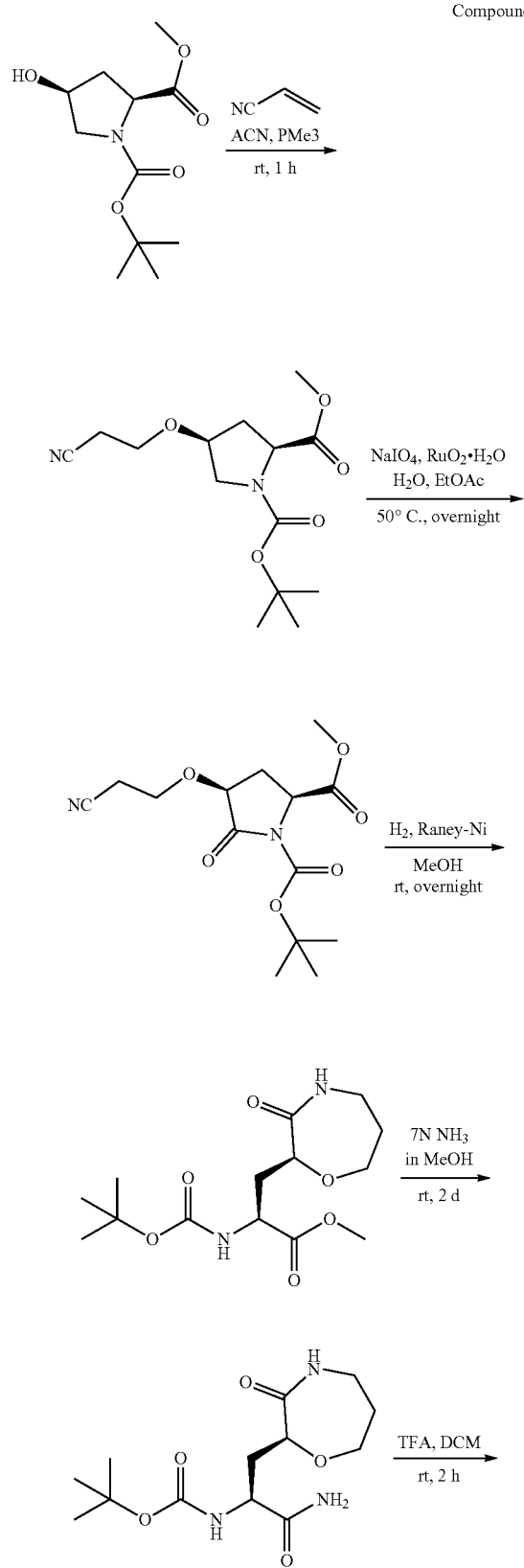

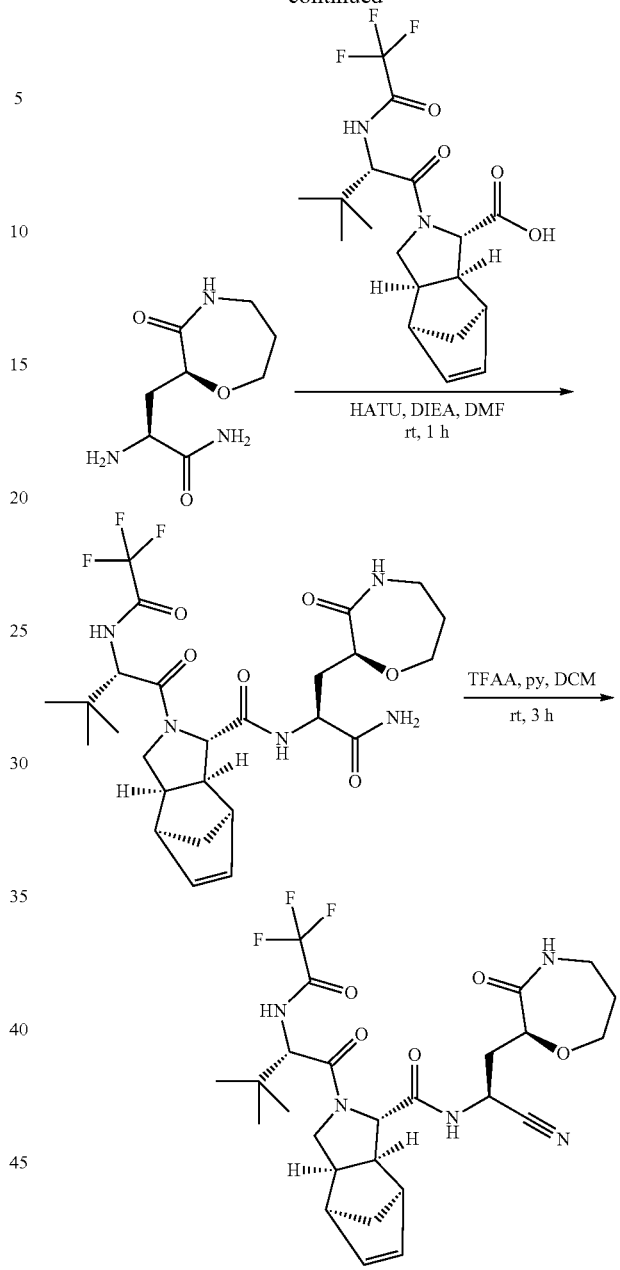

To a stirred mixture of 1-tert-butyl 2-methyl (2S,4S)-4-hydroxypyrrolidine-1,2-dicarboxylate (5.00 g, 20.3 mmol, 1.0 eq.) and trimethylphosphine (2.04 mL, 2.03 mmol, 0.1 eq.) in ACN (20 mL) was added acrylonitrile (10.8 g, 203 mmol, 10.0 eq.). The mixture was stirred for 1 h at rt. The crude product was purified by C18 column with $CH_3CN$/Water (0.05% TFA). The desired fraction was concentrated under reduced pressure to provide 1-tert-butyl 2-methyl (2S,4S)-4-(2-cyanoethoxy)pyrrolidine-1,2-dicarboxylate (3.9 g, 60%) as a yellow oil. $^1$H NMR (400 MHz, DMSO-$d_6$) δ 4.24-4.40 (m, 1H), 4.10-4.23 (m, 1H), 3.60-3.70 (m, 3H), 3.50-3.59 (m, 3H), 2.20-2.30 (m, 1H), 2.63-2.70 (m, 2H), 2.25-2.48 (m, 1H), 2.00-2.10 (m, 1H), 1.25-1.48 (m, 9H). LC-MS (ESI, m/z): 199 [M−Boc+H]$^+$.

To a stirred mixture of 1-tert-butyl 2-methyl (2S,4S)-4-(2-cyanoethoxy)pyrrolidine-1,2-dicarboxylate (7.00 g, 23.4 mmol, 1.0 eq.) in EA (50 mL) were added sodium periodate (25.0 g, 116 mmol, 4.98 eq.) and ruthenium(IV) oxide hydrated (1.56 g, 11.7 mmol, 0.5 eq.) in water (50 mL). The mixture was stirred for overnight at 50° C. The mixture was diluted with EA (500 mL) and then filtered through a celite pad. The organic layer was washed with brine (500 mL), dried over anhydrous sodium sulfate, filtered and concentrated under reduced pressure to afford the crude product. The crude product was chromatographed on a silica gel column with EA:PE (80%) to provide 1-tert-butyl 2-methyl (2S,4S)-4-(2-cyanoethoxy)-5-oxopyrrolidine-1,2-dicarboxylate (5.4 g, crude) as a yellow oil LC-MS (ESI, m/z): 213 [M−Boc+H]$^+$.

A mixture of 1-tert-butyl 2-methyl (2S,4S)-4-(2-cyanoethoxy)-5-oxopyrrolidine-1,2-dicarboxylate (4.40 g, 14.1 mmol, 1.0 eq.) and Raney nickel (2.30 g) in MeOH (20 mL) was stirred for overnight at rt under hydrogen. The mixture was filtered through a celite pad and washed with methanol (3×10 mL). The crude product was chromatographed on a silica gel column with MeOH:DCM (8:100) to provide methyl (2S)-2-[(tert-butoxycarbonyl)amino]-3-[(2S)-3-oxo-1,4-oxazepan-2-yl]propanoate (1.9 g, 40%) as a white solid. $^1$H NMR (400 MHz, DMSO-d$_6$) δ 7.60-7.85 (m, 1H), 7.10-7.31 (m, 1H), 3.90-4.25 (m, 3H), 3.60-3.70 (m, 3H), 3.40-3.59 (m, 1H), 3.10-3.30 (m, 2H), 1.75-1.95 (m, 2H), 1.60-1.70 (m, 2H), 1.30-1.48 (m, 9H). LC-MS (ESI, m/z): 482 [M+H]$^+$.

A mixture of methyl (2S)-2-[(tert-butoxycarbonyl)amino]-3-[(2S)-3-oxo-1,4-oxazepan-2-yl]propanoate (1.90 g, 6.01 mmol, 1.0 eq.) in NH$_3$ (g) (20.0 mL, 7M in MeOH) was stirred for 2 d at rt and then concentrated under reduced pressure to afford tert-butyl N-[(1S)-1-carbamoyl-2-[(2S)-3-oxo-1,4-oxazepan-2-yl]ethyl]carbamate (1.4 g, 73%, crude) as a white solid. $^1$H NMR (400 MHz, DMSO-d$_6$) δ 7.60-7.85 (m, 1H), 7.25-7.41 (m, 1H), 6.90-7.10 (m, 1H), 6.70-6.88 (m, 1H), 4.00-4.20 (m, 2H), 3.85-3.95 (m, 1H), 3.45-3.60 (m, 1H), 3.10-3.26 (m, 2H), 1.70-1.93 (m, 2H), 1.55-1.68 (m, 2H), 1.26-1.48 (m, 9H). LC-MS (ESI, m/z): 302 [M+H]$^+$.

To a stirred mixture of tert-butyl N-[(1S)-1-carbamoyl-2-[(2S)-3-oxo-1,4-oxazepan-2-yl]ethyl]carbamate (154 mg, 0.511 mmol, 1.0 eq.) in DCM (3 mL) was added trifluoroacetic acid (1 mL). The mixture was stirred for 2 h at rt and then concentrated under reduced pressure to afford (2S)-2-amino-3-[(2S)-3-oxo-1,4-oxazepan-2-yl]propanamide (103 mg, crude) as a brown oil. LC-MS (ESI, m/z): 202 [M+H]$^+$.

To a stirred mixture of (1R,2S,3S,6R,7S)-4-[(2S)-3,3-dimethyl-2-(2,2,2-trifluoroacetamido)butanoyl]-4-azatricyclo[5.2.1.0^{2,6}]dec-8-ene-3-carboxylic acid (386 mg, 0.994 mmol, 1.0 eq.) and o-(7-azabenzotriazol-1-yl)-N,N,N',N'-tetramethyluronium hexafluorophosphate (491 mg, 1.29 mmol, 1.3 eq.) in DMF (2 mL) was added N-ethyl-N-isopropylpropan-2-amine (1.02 g, 7.95 mmol, 8.0 eq.) at 0° C. After stirring for 20 min at 0° C., tert-butyl N-[(1S)-1-carbamoyl-2-[(2S)-3-oxo-1,4-oxazepan-2-yl]ethyl]carbamate (200 mg, 0.664 mmol, 1.0 eq.) was added. The mixture was stirred for 1 h at rt. The crude product was purified by C18 column with CH$_3$CN/Water (0.05% TFA). The desired fraction was concentrated under reduced pressure to provide (2S)-2-{[(1R,2S,3S,6R,7S)-4-[(2S)-3,3-dimethyl-2-(2,2,2-trifluoroacetamido)butanoyl]-4-azatricyclo[5.2.1.0^{2,6}] dec-8-en-3-yl]formamido}-3-[(2S)-3-oxo-1,4-oxazepan-2-yl]propanamide (220 mg, 36%) as a white solid. LC-MS (ESI, m/z): 572 [M+H]$^+$.

To a stirred mixture of (2S)-2-{[(1R,2S,3S,6R,7S)-4-[(2S)-3,3-dimethyl-2-(2,2,2-trifluoroacetamido)butanoyl]-4-azatricyclo[5.2.1.0^{2,6}]dec-8-en-3-yl]formamido}-3-[(2S)-3-oxo-1,4-oxazepan-2-yl]propanamide (210 mg, 0.367 mmol, 1.0 eq.) in DCM (2 mL) were added pyridine (116 mg, 1.46 mmol, 4.0 eq.) and trifluoroacetic anhydride (46.3 mg, 0.477 mmol, 1.3 eq.). The mixture was stirred for 3 h at rt. The reaction was quenched with water (30 mL). The mixture was extracted with EtOAc (3×30 mL). The organic layers were combined, washed with brine (2×30 mL), dried over anhydrous sodium sulfate, filtered and concentrated under reduced pressure to afford the crude product. The crude product was purified by prep-HPLC (Column: Xselect CSH F-Phenyl OBD column, 19*250 mm, 5 m; Mobile Phase A: Water (0.1% FA), Mobile Phase B: ACN; Flow rate: 25 mL/min; Gradient: 30% B to 60% B in 7 min, 60% B; Wave Length: 254 nm; RT1 (min): 6) to provide (1R,2S,3S,6R,7S)—N-[(1S)-1-cyano-2-[(2S)-3-oxo-1,4-oxazepan-2-yl]ethyl]-4-[(2S)-3,3-dimethyl-2-(2,2,2-trifluoroacetamido)butanoyl]-4-azatricyclo[5.2.1.0^{2,6}]dec-8-ene-3-carboxamide (115 mg, 56%) as a white solid. $^1$H NMR (400 MHz, 80° C., DMSO-d$_6$) δ 8.70-9.00 (m, 1H), 8.20-8.69 (m, 1H), 7.40-7.70 (m, 1H), 5.85-6.25 (m, 2H), 4.80-5.00 (m, 1H), 4.40-4.65 (m, 1H), 3.95-4.10 (m, 2H), 3.80-3.94 (m, 1H), 3.50-3.79 (m, 2H), 3.38-3.49 (m, 1H), 2.80-3.37 (m, 5H), 2.68-2.79 (m, 1H), 2.10-2.30 (m, 1H), 1.80-2.09 (m, 1H), 1.50-1.79 (m, 2H), 1.30-1.49 (m, 2H), 0.85-1.00 (m, 9H). LC-MS (ESI, m/z): 554 [M+H]$^+$.

Example 122

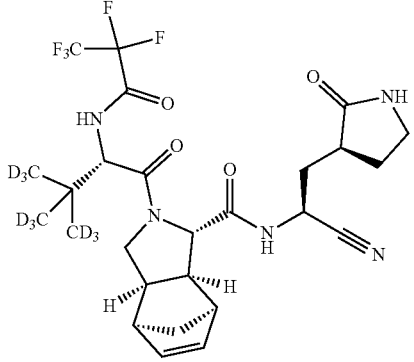

Compound 122

Compound 122 was prepared similarly as described for compound 124, using CF$_3$CF$_2$CO$_2$Me in place of CF$_3$CO$_2$Me and additionally adding N-methyl imidazole (2 eq.) in the same reaction. $^1$H NMR (400 MHz, DMSO-d$_6$) δ 99.38-9.29 (1H, m), 9.00-8.80 (1H, m), 7.77-7.65 (1H, m), 6.21-5.94 (2H, m), 4.99-4.88 (1H, m), 4.60-4.53 (1H, m), 4.20-3.93 (1H, m), 3.70-3.60 (1H, m), 3.50-3.40 (1H, m), 3.18-2.90 (5H, m), 2.72-2.62 (1H, m), 2.41-2.30 (1H, m), 2.21-2.00 (2H, m), 1.80-1.61 (2H, m), 1.42-1.34 (2H, m). LC-MS (ESI, m/z): 1188 ["2M+Na"]$^+$.

Example 123

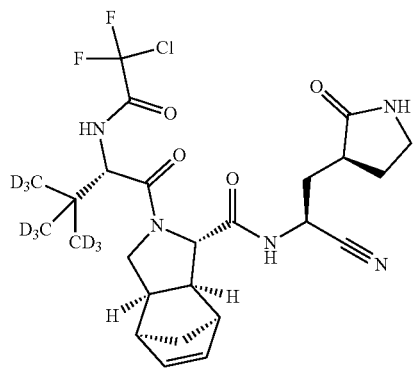

Compound 123

Compound 123 was prepared similarly as described for compound 124, using $ClCF_2CO_2Me$ in place of $CF_3CO_2Me$ and additionally adding NMI (2 eq.) in the same reaction. $^1H$ NMR (400 MHz, DMSO-$d_6$) δ 9.18-9.09 (1H, d), 8.99-8.90 (1H, m), 7.76-7.66 (1H, m), 6.21-5.97 (2H, m), 4.99-4.88 (1H, m), 4.68-4.45 (1H, d), 4.17-3.94 (1H, m), 3.71-3.61 (1H, t), 3.48-3.38 (1H, m), 3.18-2.90 (5H, m), 2.74-2.64 (1H, m), 2.42-2.30 (1H, m), 2.21-2.00 (2H, m), 1.80-1.62 (2H, m), 1.42-1.34 (2H, m). LC-MS (ESI, m/z): 1119/1121 ["2M+Na"]$^+$.

Example 124

Compound 124

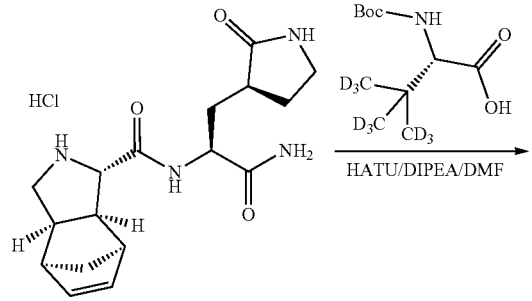

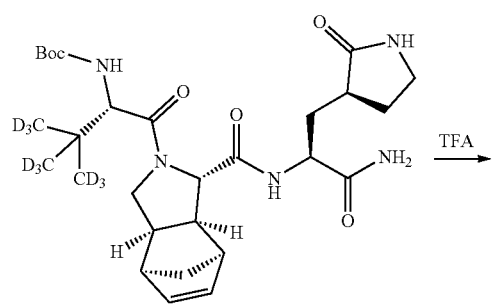

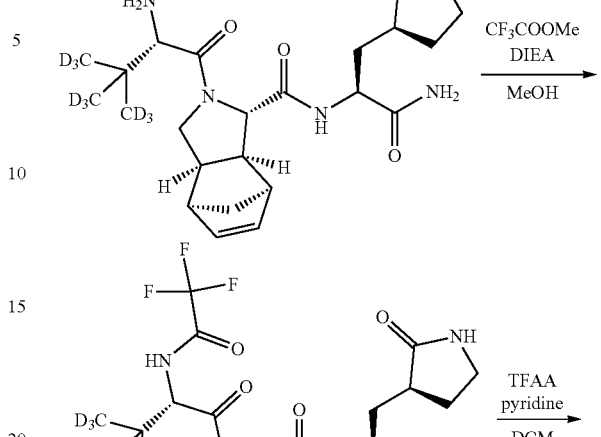

124

(1S,3aR,4S,7R,7aS)—N—((S)-1-amino-1-oxo-3-((S)-2-oxopyrrolidin-3-yl)propan-2-yl)-2,3,3a,4,7,7a-hexahydro-1H-4,7-methanoisoindole-1-carboxamide hydrochloride (312 mg) and N-Boc-L-tert-leucine-d9 (203 mg) were combined in a reactor under Ar. Diisopropylethylamine (0.6 mL) was added, and then anhydrous DMF (15 mL). The mixture was cooled to −30° C., and then HATU (386 mg) was added. The mixture was allowed to warm to 0° C. over 1 h and the temperature was maintained for another 45 mins. A solution of citric acid in (914 mg in 4 mL water) was added. The mixture extracted with dichloromethane (2×15-mL). The extracts were combined and then filtered through sodium sulfate. The mixture was concentrated, and then finished with a 50° C.-water bath on a rotary evaporator to obtain a yellow oil (1.05 g). The mixture was dissolved in dichloromethane (10 mL) and then loaded onto a 50 g normal phase silica gel cartridge. A linear gradient of 0-to-15% methanol in dichloromethane was applied and TLC in combination with ninhydrin stain with heating was used to find the product fractions, which were then concentrated to obtain tert-butyl ((S)-1-(((1S,3aR,4S,7R,7aS)-1-(((S)-1-amino-1-oxo-3-((S)-2-oxopyrrolidin-3-yl)propan-2-yl)carbamoyl)-1,3,3a,4,7,7a-hexahydro-2H-4,7-methanoisoindol-2-yl)-3,3-bis(methyl-d3)-1-oxobutan-2-yl-4,4,4-d3) carbamate (363 mg) as a white solid. LC-MS (ESI, m/z): 555 [M+H]$^+$.

Tert-butyl ((S)-1-((1S,3aR,4S,7R,7aS)-1-(((S)-1-amino-1-oxo-3-((S)-2-oxopyrrolidin-3-yl)propan-2-yl)carbamoyl)-1,3,3a,4,7,7a-hexahydro-2H-4,7-methanoisoindol-2-yl)-3,3-bis(methyl-d3)-1-oxobutan-2-yl-4,4,4-d3)carbamate (155 mg) was mixed with trifluoroacetic acid (10 mL/g starting material). The mixture was stirred for 30 mins and then concentrated. DIEA (10 eq.) was added, followed by methanol (20 mL/g starting material), and CF$_3$COOMe (5 eq.). The mixture was capped and stirred to completion, as determined by LC-MS. The mixture was concentrated, diluted with dichloromethane, washed with aq. citric acid solution, filtered through sodium sulfate and purified by normal-phase silica gel chromatography using a 0-to-15% methanol-dichloromethane linear gradient, to obtain (1S,3aR,4S,7R,7aS)—N—((S)-1-amino-1-oxo-3-((S)-2-oxopyrrolidin-3-yl)propan-2-yl)-2-((S)-3,3-bis(methyl-d3)-2-(2,2,2-trifluoroacetamido)butanoyl-4,4,4-d3)-2,3,3a,4,7,7a-hexahydro-1H-4,7-methanoisoindole-1-carboxamide (137 mg).

(1S,3aR,4S,7R,7aS)—N—((S)-1-amino-1-oxo-3-((S)-2-oxopyrrolidin-3-yl)propan-2-yl)-2-((S)-3,3-bis(methyl-d3)-2-(2,2,2-trifluoroacetamido)butanoyl-4,4,4-d3)-2,3,3a,4,7,7a-hexahydro-1H-4,7-methanoisoindole-1-carboxamide (137 mg) was mixed with pyridine (5.0 eq.) and dichloromethane (20 mL/g), and then cooled in an ice-bath. Portions of TFAA (1 eq.) were successively added to finish the reaction: After each addition, the mixture was stirred for 30 mins while maintaining cooling. Upon completion, the mixture was stirred with water and then extracted with dichloromethane. The extracts were filtered through sodium sulfate, concentrated, purified by reversed-phase chromatography and concentrated to obtain compound 124 (47.2 mg). $^1$H NMR (400 MHz, DMSO-d$_6$) δ 9.45-9.37 (1H, d), 9.08-8.91 (1H, m), 7.77-7.67 (1H, m), 6.20-5.99 (2H, m), 5.00-4.88 (1H, m), 4.65-4.4.45 (1H, m), 4.20-3.93 (1H, m), 3.70-3.60 (1H, m), 3.50-3.40 (1H, m), 3.18-2.90 (5H, m), 2.72-2.62 (1H, m), 2.40-2.30 (1H, m), 2.20-2.00 (2H, m), 1.80-1.61 (2H, m), 1.45-1.36 (2H, m). LC-MS (ESI, m/z): 1087 ["2M+Na"].

Example 125

Compound 125

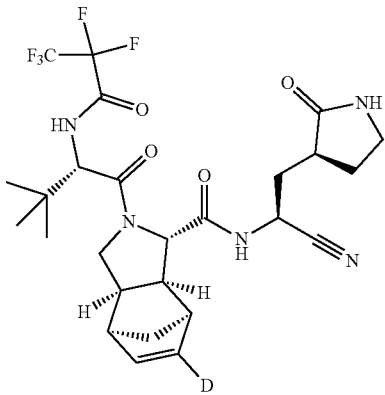

Compound 125 was prepared similarly as described for compound 76, starting from 2-(tert-butyl) 1-methyl (1S,3aR,4S,7R,7aS)-1,3,3a,4,7,7a-hexahydro-2H-4,7-methanoisoindole-1,2-dicarboxylate-6-d in place of 2-(tert-butyl) 1-methyl (1S,3aR,4S,7R,7aS)-1,3,3a,4,7,7a-hexahydro-2H-4,7-methanoisoindole-1,2-dicarboxylate. $^1$H NMR (400 MHz, DMSO-d$_6$) δ 8.65-8.85 (m, 1H), 7.30-7.55 (m, 1H), 5.85-6.25 (m, 1H), 4.82-4.98 (m, 1H), 4.50-4.69 (m, 1H), 3.98-4.18 (m, 1H), 3.57-3.70 (m, 1H), 3.35-3.48 (m, 1H), 3.10-3.22 (m, 3H), 2.80-2.98 (m, 2H), 2.68-2.78 (m, 1H), 2.32-2.40 (m, 1H), 2.02-2.18 (m, 2H), 1.63-1.88 (m, 2H), 1.32-1.45 (m, 2H), 0.80-1.05 (m, 9H). LC-MS (ESI, m/z): 575 [M+H]$^+$.

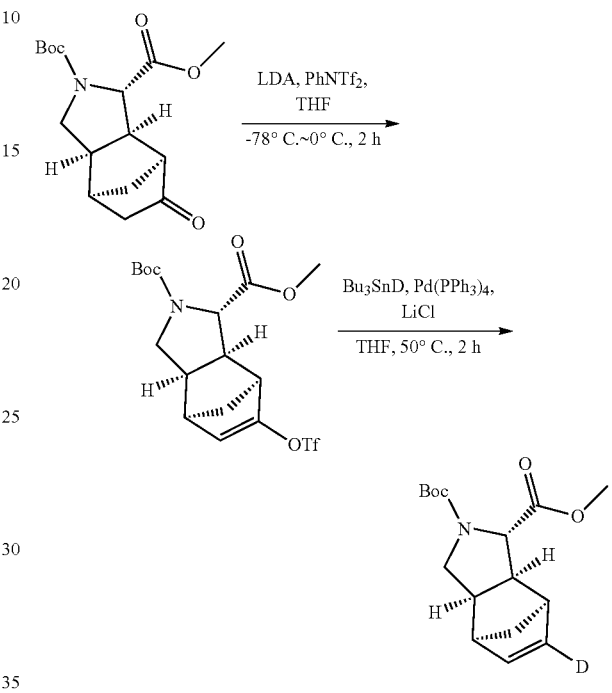

To a stirred mixture of 4-tert-butyl 3-methyl (1S,2R,3S,6R,7S)-9-oxo-4-azatricyclo[5.2.1.0^{2,6}]decane-3,4-dicarboxylate (600 mg, 1.93 mmol, 1.0 eq.) in THF (6 mL) was added lithium diisopropylamide (1.94 mL, 3.87 mmol, 2.0 eq.) dropwise at −78° C. under nitrogen. The mixture was stirred for 1 h at 0° C. and then 1,1,1-trifluoro-N-phenyl-N-((trifluoromethyl)sulfonyl)methanesulfonamide (1.03 g, 2.90 mmol, 1.5 eq.) was added slowly at −78° C. The mixture was stirred for 2 h at 0° C. The reaction was quenched with water (20 mL). The mixture was extracted with EtOAc (3×30 mL). The organic layers were combined, washed with brine (2×20 mL), dried over anhydrous sodium sulfate, filtered and concentrated under reduced pressure to afford the crude product. The crude product was chromatographed on a silica gel column with EA:PE (3:7) to provide the crude product. The crude product was purified by Cis column with CH$_3$CN/Water (0.05% FA). The desired fraction was concentrated under reduced pressure to provide 4-tert-butyl 3-methyl (1S,2R,3S,6R,7R)-9-(trifluoromethanesulfonyloxy)-4-azatricyclo[5.2.1.0^{2,6}]dec-8-ene-3,4-dicarboxylate (400 mg, 44%) as a light yellow oil. LC-MS (ESI, m/z): 342 [M-Boc+H]$^+$.

To a mixture of 4-tert-butyl 3-methyl (1S,2R,3S,6R,7R)-9-(trifluoromethanesulfonyloxy)-4-azatricyclo[5.2.1.0^{2,6}]dec-8-ene-3,4-dicarboxylate (180 mg, 0.408 mmol, 1.0 eq.), lithium chloride (138 mg, 3.26 mmol, 8.0 eq.) and tetrakis(triphenylphosphine)platinum(0) (80.0 mg, 0.069 mmol, 0.17 eq.) in THF (2 mL) was added tributylstannane-d (834 mg, 2.86 mmol, 7.0 eq.) under nitrogen. The mixture was stirred for 2 h at 50° C. The reaction was quenched with water (10 mL). The mixture was extracted with EtOAc (3×20 mL). The organic layers were combined, washed with brine (2×10 mL), dried over anhydrous sodium sulfate, filtered and concentrated under reduced pressure to afford the crude product. The crude product was purified by C18 column with CH$_3$CN/Water (0.05% NH$_4$HCO$_3$+ NH$_3$·H$_2$O, pH-13). The desired fraction was concentrated under reduced pressure to provide 2-(tert-butyl) 1-methyl (1S,3aR,4S,7R,7aS)-1,3,3a,4,7,7a-hexahydro-2H-4,7-methanoisoindole-1,2-dicarboxylate-6-d (60.0 mg, 44%) as a light yellow semi-solid. $^1$H NMR (400 MHz, CDCl$_3$-d) δ 6.14-6.30 (m, 1H), 3.82-3.98 (m, 1H), 3.61-3.77 (m, 3H), 3.35-3.53 (m, 1H), 3.01-3.24 (m, 2H), 2.73-2.98 (m, 3H), 1.50-1.58 (m, 1H), 1.32-1.49 (m, 10H). LC-MS (ESI, m/z): 195 [M−Boc+H]$^+$.

Example 126

Compound 126

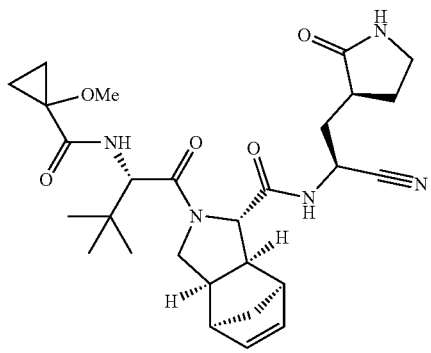

Compound 126 was prepared similarly as described for Compound 72 using 1-methoxycyclopropane-1-carboxylic acid in place of 2,2-difluoroacetic acid. $^1$H NMR (500 MHz, 363K, DMSO-d$_6$) δ 8.54-8.77 (m, 1H), 7.28-7.44 (m, 1H), 6.85-7.07 (m, 1H), 5.89-6.20 (m, 2H), 4.67-4.94 (m, 1H), 4.47 (d, 1H), 4.01-4.12 (m, 1H), 3.63 (m, 1H), 3.38-3.51 (m, 1H), 3.21-3.31 (m, 3H), 3.06-3.21 (m, 2H), 3.03 (m, 1H), 2.87-2.95 (m, 2H), 2.74 (m, 1H), 2.21-2.40 (m, 1H), 2.11-2.20 (m, 2H), 1.66-1.88 (m, 2H), 1.35-1.46 (m, 2H), 0.97-1.12 (m, 4H), 0.86-0.95 (m, 9H). LCMS (ESI, m/z): 526 [M+H]$^+$.

Example 127

Compound 127

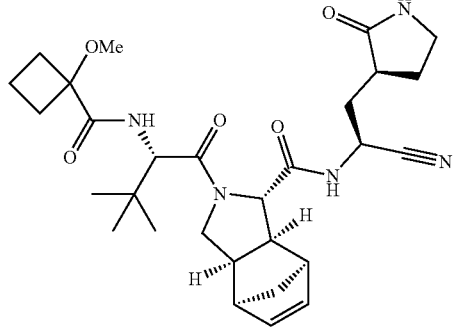

Compound 127 was prepared similarly as described for Compound 72 using 1-methoxycyclobutane-1-carboxylic acid in place of 2,2-difluoroacetic acid. $^1$H NMR (500 MHz, 363K, DMSO-d6) δ 8.36-8.82 (m, 1H), 7.29-7.47 (m, 1H), 6.54-6.83 (m, 1H), 5.85-6.22 (m, 2H), 4.72-4.99 (m, 1H), 4.39-4.50 (m, 1H), 4.03-4.10 (m, 1H), 3.35-3.76 (m, 3H), 3.00-3.24 (m, 5H), 2.87-2.98 (m, 2H), 2.68-2.86 (m, 1H), 2.22-2.41 (m, 3H), 2.00-2.19 (m, 3H), 1.65-1.83 (m, 3H), 1.33-1.46 (m, 3H), 0.82-0.94 (d, 10H). LCMS (ESI, m/z): 540 [M+H]$^+$.

Example 128

Compound 128

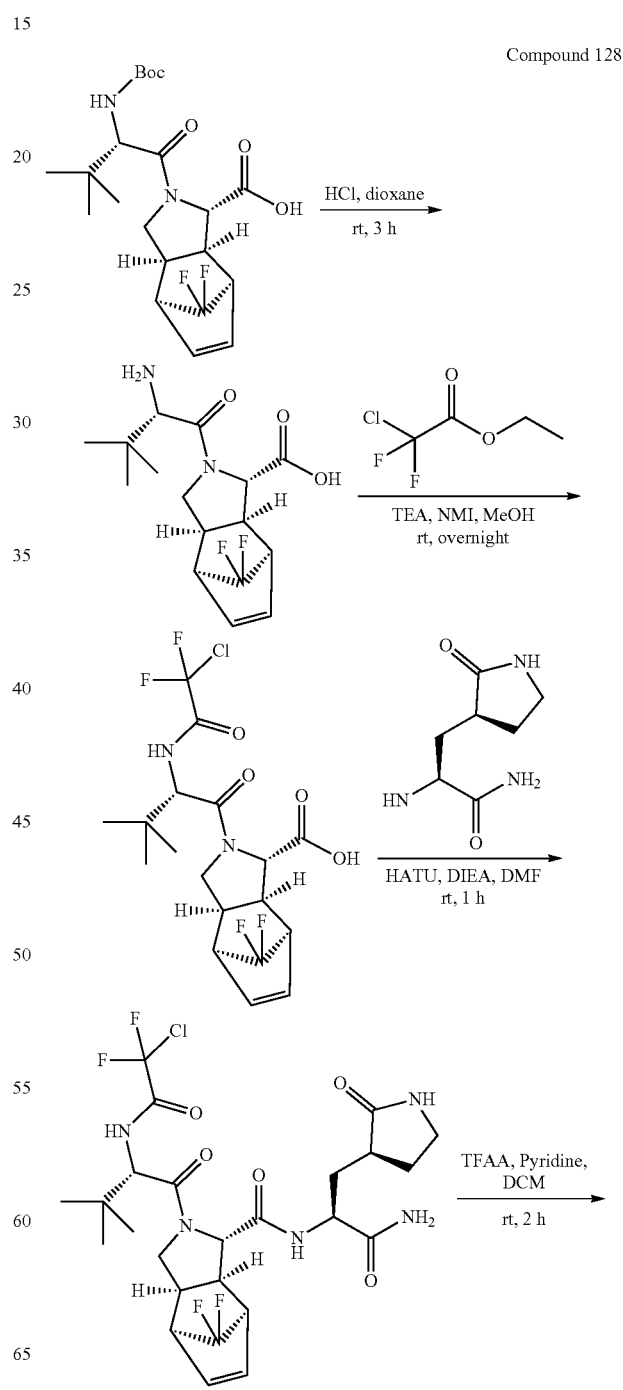

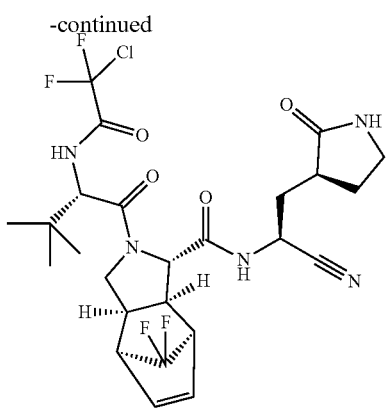

To a stirred mixture of (1R,2R,3S,6S,7S)-4-[(2S)-2-[(tert-butoxycarbonyl)amino]-3,3-dimethylbutanoyl]-10,10-difluoro-4-azatricyclo[5.2.1.0^{2,6}]dec-8-ene-3-carboxylic acid (400 mg, 0.934 mmol, 1.0 eq.) in 1,4-dioxane (1 mL) was added hydrochloric acid (10 mL, 4M in 1,4-dioxane). The mixture was stirred for 3 h at rt and then concentrated under reduced pressure to afford (1R,2R,3S,6S,7S)-4-[(2S)-2-amino-3,3-dimethylbutanoyl]-10,10-difluoro-4-azatricyclo[5.2.1.0^{2,6}]dec-8-ene-3-carboxylic acid (306 mg, crude) as a white solid. LC-MS (ESI, m/z): 329 [M+H]$^+$.

To a stirred mixture of (1R,2R,3S,6S,7S)-4-[(2S)-2-amino-3,3-dimethylbutanoyl]-10,10-difluoro-4-azatricyclo[5.2.1.0^{2,6}]dec-8-ene-3-carboxylic acid (306 mg, 0.932 mmol, 1.0 eq.) in methanol (5 mL) were added ethyl 2-chloro-2,2-difluoroacetate (738 mg, 4.66 mmol, 5.0 eq.), triethylamine (471 mg, 4.66 mmol, 5.0 eq.) and N-methylimidazole (153 mg, 1.86 mmol, 2.0 eq.). The mixture was stirred for overnight at rt. The mixture was adjusted to pH=6 with hydrochloric acid (2 M) and extracted with EtOAc (3×50 mL). The organic layers were combined, washed with brine (2×50 mL), dried over anhydrous sodium sulfate, filtered and concentrated under reduced pressure to afford c (1R,2R,3S,6S,7S)-4-[(2S)-2-(2-chloro-2,2-difluoroacetamido)-3,3-dimethylbutanoyl]-10,10-difluoro-4-azatricyclo[5.2.1.0^{2,6}]dec-8-ene-3-carboxylic acid (350 mg, 80%, crude) as a white solid. $^1$H NMR (400 MHz, DMSO-d$_6$) δ 12.43-13.25 (m, 1H), 8.96-9.31 (m, 1H), 6.02-6.33 (m, 2H), 4.47-4.55 (m, 1H), 4.16-4.32 (m, 1H), 3.60-3.66 (m, 1H), 3.09-3.36 (m, 4H), 2.93-3.04 (m, 1H), 0.86-1.05 (m, 9H). LC-MS (ESI, m/z): 441 [M+H]$^+$.

To a stirred mixture of (1R,2R,3S,6S,7S)-4-[(2S)-2-(2-chloro-2,2-difluoroacetamido)-3,3-dimethylbutanoyl]-10,10-difluoro-4-azatricyclo[5.2.1.0^{2,6}]dec-8-ene-3-carboxylic acid (350 mg, 0.794 mmol, 1.0 eq.) and o-(7-azabenzotriazol-1-yl)-N,N,N',N'-tetramethyluronium hexafluorophosphate (392 mg, 1.03 mmol, 1.3 eq.) in DMF (5 mL) was added N-ethyl-N-isopropylpropan-2-amine (820 mg, 6.35 mmol, 8.0 eq.) at 0° C. After stirring for 20 min at 0° C., (2S)-2-amino-3-[(3S)-2-oxopyrrolidin-3-yl]propanamide (135 mg, 0.794 mmol, 1.0 eq.) was added. The mixture was stirred for 1 h at rt. The reaction was quenched with water (30 mL). The mixture was extracted with EtOAc (3×30 mL). The organic layers were combined, washed with brine (2×30 mL), dried over anhydrous sodium sulfate, filtered and concentrated under reduced pressure to afford the crude product. The crude product was purified by C18 column with CH$_3$CN/Water (0.05% TFA). The desired fraction was concentrated under reduced pressure to provide (2S)-2-{[(1R,2R,3S,6S,7S)-4-[(2S)-2-(2-chloro-2,2-difluoroacetamido)-3,3-dimethylbutanoyl]-10,10-difluoro-4-azatricyclo[5.2.1.0^{2,6}]dec-8-en-3-yl]formamido}-3-[(3S)-2-oxopyrrolidin-3-yl]propanamide (250 mg, 50%) as a yellow solid. LC-MS (ESI, m/z): 59 4[M+H]$^+$.

To a stirred mixture of (2S)-2-{[(1R,2R,3S,6S,7S)-4-[(2S)-2-(2-chloro-2,2-difluoroacetamido)-3,3-dimethylbutanoyl]-10,10-difluoro-4-azatricyclo[5.2.1.0^{2,6}]dec-8-en-3-yl]formamido}-3-[(3S)-2-oxopyrrolidin-3-yl]propanamide (250 mg, 0.421 mmol, 1.0 eq.) in DCM (3 mL) were added pyridine (116 mg, 1.47 mmol, 3.5 eq.) and trifluoroacetic anhydride (123 mg, 0.589 mmol, 1.4 eq.). The mixture was stirred for 2 h at rt. The reaction was quenched with water (30 mL). The mixture was extracted with EtOAc (3×30 mL). The organic layers were combined, washed with brine (2×30 mL), dried over anhydrous sodium sulfate, filtered and concentrated under reduced pressure to afford the crude product. The crude product was purified by prep-HPLC (Column: XSelect CSH Prep C18 OBD Column, 19*150 mm, 5 m; Mobile Phase A: Water (0.1% FA), Mobile Phase B: ACN; Flow rate: 25 mL/min; Gradient: 36% B to 66% B in 7 min, 66% B; Wave Length: 220 nm; RT1 (min): 5) to provide (1R,2R,3S,6S,7S)-4-[(2S)-2-(2-chloro-2,2-difluoroacetamido)-3,3-dimethylbutanoyl]-N-[(1S)-1-cyano-2-[(3S)-2-oxopyrrolidin-3-yl]ethyl]-10,10-difluoro-4-azatricyclo[5.2.1.0^{2,6}]dec-8-ene-3-carboxamide (93 mg, 38%) as a white solid. $^1$H NMR (400 MHz, 80° C., DMSO-d$_6$) δ 8.70-8.88 (m, 1H), 8.50-8.69 (m, 1H), 7.32-7.54 (m, 1H), 6.06-6.40 (m, 2H), 4.63-5.00 (m, 1H), 4.30-4.54 (m, 1H), 4.05-4.23 (m, 1H), 3.65-3.85 (m, 1H), 3.55-3.64 (m, 1H), 3.23-3.50 (m, 1H), 3.10-3.22 (m, 4H), 2.80-2.92 (m, 1H), 2.08-2.45 (m, 3H), 1.62-1.92 (m, 2H), 0.81-1.10 (m, 9H). LC-MS (ESI, m/z): 576 [M+H]$^+$.

Example 129

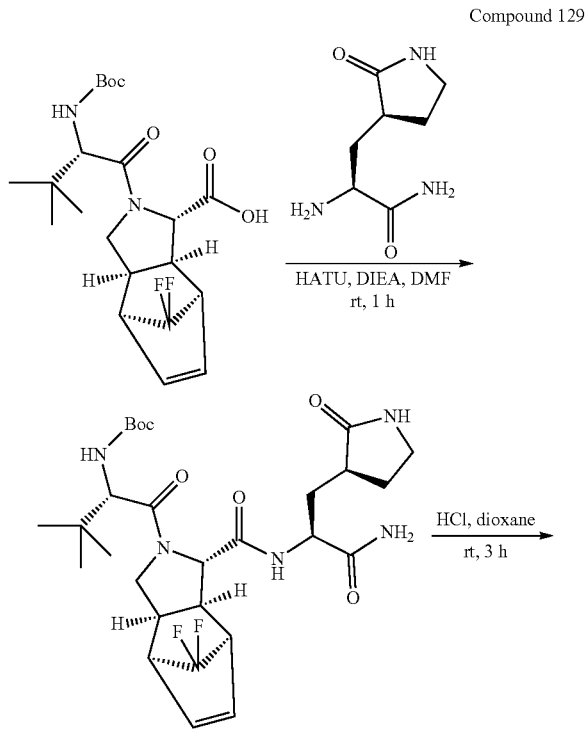

Compound 129

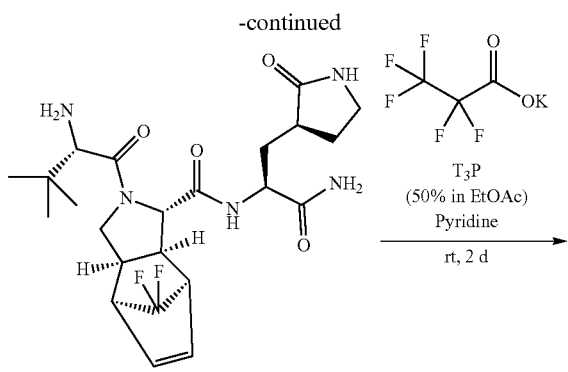

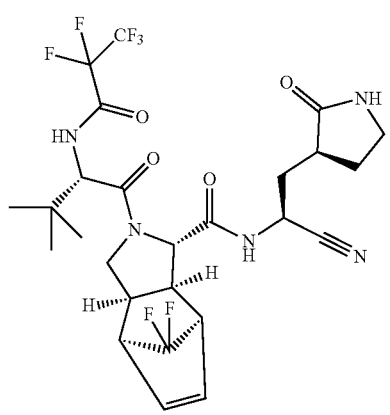

To a stirred mixture of (2S)-2-amino-3-[(3S)-2-oxopyrrolidin-3-yl]propanamide (159 mg, 0.934 mmol, 1.0 eq.) and o-(7-azabenzotriazol-1-yl)-N,N,N',N'-te-tramethyluronium hexafluorophosphate (461 mg, 1.21 mmol, 1.3 eq.) in DMF (6 mL) was added N-ethyl-N-isopropylpropan-2-amine (965 mg, 7.47 mmol, 8.0 eq.) at 0° C. After stirring for 20 min at 0° C., (1R,2R,3S,6S,7S)-4-[(2S)-2-[(tert-butoxycarbonyl)amino]-3,3-dimethylbutanoyl]-10,10-difluoro-4-azatricyclo[5.2.1.0^{2,6}]dec-8-ene-3-carboxylic acid (400 mg, 0.934 mmol, 1.0 eq.) was added. The mixture was stirred for 1 h at rt. The reaction was quenched with water (50 mL). The mixture was extracted with EtOAc (3×50 mL). The organic layers were combined, washed with brine (2×50 mL), dried over anhydrous sodium sulfate, filtered and concentrated under reduced pressure to afford the crude product. The crude product was chromatographed on a silica gel column with MeOH:DCM (7:100) to provide tert-butyl N-[(2S)-1-[(1R,2R,3S,6S,7S)-3-{[(1S)-1-carbamoyl-2-[(3S)-2-oxopyrrolidin-3-yl]ethyl]carbamoyl}-10,10-difluoro-4-azatricyclo[5.2.1.0^{2,6}]dec-8-en-4-yl]-3,3-dimethyl-1-oxobutan-2-yl]carbamate (350 mg, 61%) as a yellow solid. LC-MS (ESI, m/z): 58 2[M+H]+.

To a stirred mixture of tert-butyl N-[(2S)-1-[(1R,2R,3S,6S,7S)-3-{[(1S)-1-carbamoyl-2-[(3S)-2-oxopyrrolidin-3-yl]ethyl]carbamoyl}-10,10-difluoro-4-azatricyclo[5.2.1.0^{2,6}]dec-8-en-4-yl]-3,3-dimethyl-1-oxobutan-2-yl]carbamate (350 mg, 0.602 mmol, 1.0 eq.) in 1,4-dioxane (1 mL) was added hydrochloric acid (15 mL, 4M in 1,4-dioxane). The mixture was stirred for 3 h at rt and then concentrated under reduced pressure to afford (2S)-2-{[(1R,2R,3S,6S,7S)-4-[(2S)-2-amino-3,3-dimethylbutanoyl]-10,10-difluoro-4-azatricyclo[5.2.1.0^{2,6}]dec-8-en-3-yl]formamido}-3-[(3S)-2-oxopyrrolidin-3-yl]propanamide (289 mg, crude) as a white solid. LC-MS (ESI, m/z): 482 [M+H]+.

To a stirred mixture of (2S)-2-{[(1R,2R,3S,6S,7S)-4-[(2S)-2-amino-3,3-dimethylbutanoyl]-10,10-difluoro-4-azatricyclo[5.2.1.0^{2,6}]dec-8-en-3-yl]formamido}-3-[(3S)-2-oxopyrrolidin-3-yl]propanamide (289 mg, 0.600 mmol, 1.0 eq.) and potassium 2,2,3,3,3-pentafluoropropanoate (121 mg, 0.600 mmol, 1.0 eq.) in tripropyl-1,3,5,2l^[5],4l^[5],6l^[5]-trioxatriphosphinane-2,4,6-trione (1.91 g, 6.00 mmol, 10 eq.) was added pyridine (237 mg, 3.00 mmol, 5.0 eq.). The mixture was stirred for 2 d at rt. The reaction was quenched with water (50 mL). The mixture was extracted with EtOAc (3×50 mL). The organic layers were combined, washed with brine (2×50 mL), dried over anhydrous sodium sulfate, filtered and concentrated under reduced pressure to afford the crude product. The crude product was purified by prep-HPLC (Column: XSelect CSH Prep C18 OBD Column, 19*150 mm, 5 m; Mobile Phase A: Water (0.1% FA), Mobile Phase B: ACN; Flow rate: 25 mL/min; Gradient: 30% B to 60% B in 10 min, 60% B; Wave Length: 220 nm; RT1 (min): 8.73) to provide (1R,2R,3S,6S,7S)—N-[(1S)-1-cyano-2-[(3S)-2-oxopyrrolidin-3-yl]ethyl]-4-[(2S)-3,3-dimethyl-2-(2,2,3,3,3-pentafluoropropanamido)butanoyl]-10,10-difluoro-4-azatricyclo[5.2.1.0^{2,6}]dec-8-ene-3-carboxamide (45.7 mg, 12%) as a white solid. $^1$H NMR (400 MHz, 80° C., DMSO-d6) δ 8.70-8.91 (m, 2H), 7.32-7.54 (m, 1H), 6.00-6.40 (m, 2H), 4.83-5.00 (m, 1H), 4.50-4.70 (m, 1H), 4.10-4.40 (m, 1H), 3.65-3.85 (m, 1H), 3.55-3.64 (m, 1H), 3.23-3.50 (m, 1H), 3.10-3.22 (m, 4H), 2.80-2.92 (m, 1H), 2.08-2.45 (m, 3H), 1.62-1.92 (m, 2H), 0.81-1.10 (m, 9H). LC-MS (ESI, m/z): 610 [M+H]+.

Example 130

Compound 131

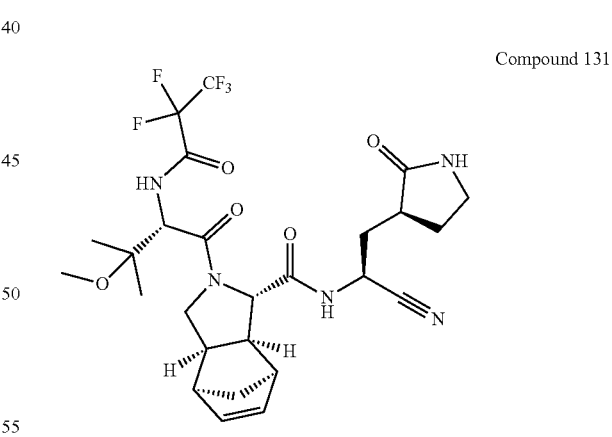

Compound 131 was prepared similarly as described for Compound 101 using methyl (S)-2-((tert-butoxycarbonyl)amino)-3-methoxy-3-methylbutanoate in place of methyl N-(tert-butoxycarbonyl)-O-cyclopropyl-L-threoninate. $^1$H NMR (400 MHz, 363K, DMSO-d$_6$) δ 8.09-8.89 (m, 2H), 7.29-7.43 (br. s., 1H), 5.93-6.24 (m, 2H), 4.91 (m, 1H), 4.65-4.81 (m, 1H), 4.00-4.23 (m, 1H), 3.62-3.75 (m, 1H), 3.34-3.54 (m, 1H), 3.02-3.24 (m, 6H), 2.80-2.98 (m, 2H), 2.74 (m, 1H), 2.22-2.41 (m, 1H), 2.04-2.20 (m, 2H), 1.63-1.91 (m, 2H), 1.30-1.48 (m, 2H), 1.05-1.22 (m, 6H). LCMS (ESI, m/z): 590 [M+H]+.

Example 131

Compound 132

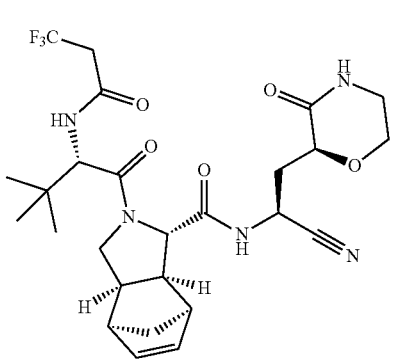

Compound 131 was prepared similarly as described for Compound 101 using methyl (S)-2-((tert-butoxycarbonyl)amino)-3-methoxy-3-methylbutanoate in place of methyl N-(tert-butoxycarbonyl)-O-cyclopropyl-L-threoninate. $^1$H NMR (400 MHz, 363K, DMSO-$d_6$) δ 8.09-8.89 (m, 2H), 7.29-7.43 (br. s., 1H), 5.93-6.24 (m, 2H), 4.91 (m, 1H), 4.65-4.81 (m, 1H), 4.00-4.23 (m, 1H), 3.62-3.75 (m, 1H), 3.34-3.54 (m, 1H), 3.02-3.24 (m, 6H), 2.80-2.98 (m, 2H), 2.74 (m, 1H), 2.22-2.41 (m, 1H), 2.04-2.20 (m, 2H), 1.63-1.91 (m, 2H), 1.30-1.48 (m, 2H), 1.05-1.22 (m, 6H). LCMS (ESI, m/z): 590 [M+H]$^+$.

Example 132

Compound 133

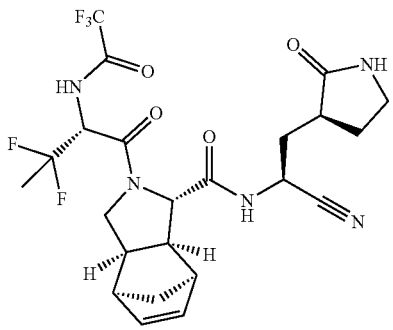

Compound 131 was prepared similarly as described for Compound 101 using methyl (S)-2-((tert-butoxycarbonyl)amino)-3-methoxy-3-methylbutanoate in place of methyl N-(tert-butoxycarbonyl)-O-cyclopropyl-L-threoninate. $^1$H NMR (400 MHz, 363K, DMSO-$d_6$) δ 8.09-8.89 (m, 2H), 7.29-7.43 (br. s., 1H), 5.93-6.24 (m, 2H), 4.91 (m, 1H), 4.65-4.81 (m, 1H), 4.00-4.23 (m, 1H), 3.62-3.75 (m, 1H), 3.34-3.54 (m, 1H), 3.02-3.24 (m, 6H), 2.80-2.98 (m, 2H), 2.74 (m, 1H), 2.22-2.41 (m, 1H), 2.04-2.20 (m, 2H), 1.63-1.91 (m, 2H), 1.30-1.48 (m, 2H), 1.05-1.22 (m, 6H). LCMS (ESI, m/z): 590 [M+H]$^+$.

Example 133

Compound 134

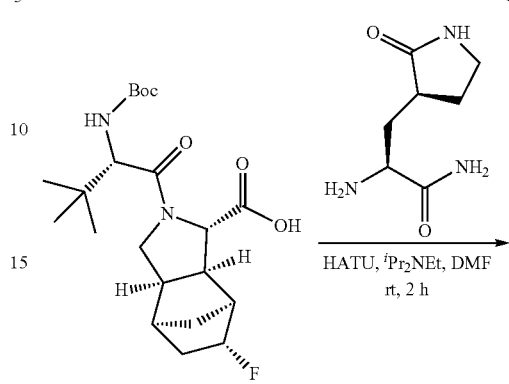

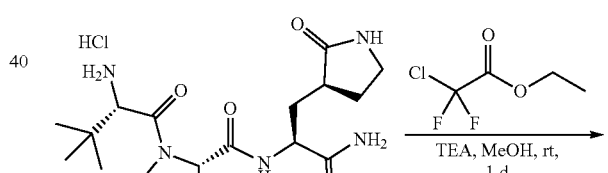

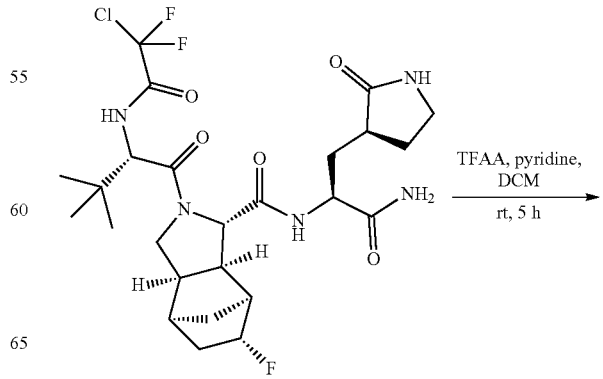

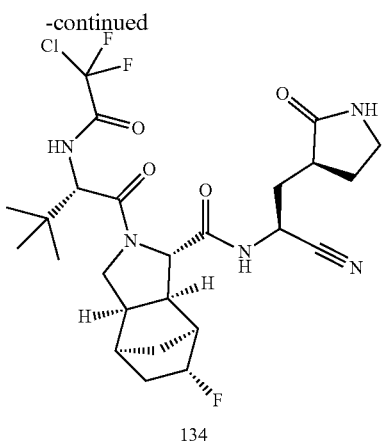

134

To a mixture of (1S,3aR,4S,6R,7S,7aR)-2-((S)-2-((tert-butoxycarbonyl)amino)-3,3-dimethylbutanoyl)-6-fluorooctahydro-1H-4,7-methanoisoindole-1-carboxylic acid (180 mg, 0.437 mmol, 1.0 eq.) in N,N-dimethylformamide (3 mL) were added o-(7-azabenzotriazol-1-yl)-N,N,N',N'-tetramethyluronium hexafluorophosphate (199 mg, 0.524 mmol, 1.2 eq.) and N-ethyl-N-isopropylpropan-2-amine (338 mg, 2.62 mmol, 6.0 eq.) at 0° C. The mixture was stirred for 20 min at 0° C., and then (S)-2-amino-3-((S)-2-oxopyrrolidin-3-yl)propanamide (75.0 mg, 0.437 mmol, 1.0 eq.) was added at 0° C. The mixture was stirred for 2 h at rt. The mixture was purified by C18 column with CH₃CN/Water (0.05% TFA). The desired fraction was concentrated under reduced pressure to provide tert-butyl ((S)-1-((1S,3aR,4S,6R,7S,7aR)-1-(((S)-1-amino-1-oxo-3-((S)-2-oxopyrrolidin-3-yl)propan-2-yl)carbamoyl)-6-fluorooctahydro-2H-4,7-methanoisoindol-2-yl)-3,3-dimethyl-1-oxobutan-2-yl)carbamate (190 mg, 78%) as a yellow solid. LC-MS (ESI, m/z): 566 [M+H]⁺.

A mixture of tert-butyl ((S)-1-((1S,3aR,4S,6R,7S,7aR)-1-(((S)-1-amino-1-oxo-3-((S)-2-oxopyrrolidin-3-yl)propan-2-yl)carbamoyl)-6-fluorooctahydro-2H-4,7-methanoisoindol-2-yl)-3,3-dimethyl-1-oxobutan-2-yl)carbamate (190 mg, 0.336 mmol, 1.0 eq.) in hydrogen chloride (5 mL, 4M in 1,4-dioxane) was stirred for 2 h at rt. The mixture was concentrated under reduced pressure to (1S,3aR,4S,6R,7S,7aR)—N—((S)-1-amino-1-oxo-3-((S)-2-oxopyrrolidin-3-yl)propan-2-yl)-2-((S)-2-amino-3,3-dimethylbutanoyl)-6-fluorooctahydro-1H-4,7-methanoisoindole-1-carboxamide hydrochloride (156 mg, crude) as a yellow oil. LC-MS (ESI, m/z): 466 [M+H]⁺.

To a mixture of (1S,3aR,4S,6R,7S,7aR)—N—((S)-1-amino-1-oxo-3-((S)-2-oxopyrrolidin-3-yl)propan-2-yl)-2-((S)-2-amino-3,3-dimethylbutanoyl)-6-fluorooctahydro-1H-4,7-methanoisoindole-1-carboxamide hydrochloride (156 mg, 0.336 mmol, 1.0 eq.) in MeOH (3 mL) were added ethyl 2-chloro-2,2-difluoroacetate (530 mg, 3.36 mmol, 10.0 eq.) and trimethylamine (407 mg, 4.03 mmol, 12.0 eq.). The mixture was stirred overnight at rt and then acidified to pH=3 with hydrochloric acid (2M). The aqueous layer was extracted with EA (3×60 mL). The organic layers were combined, washed with brine (2×20 mL) and dried over anhydrous sodium sulfate. The mixture was concentrated under reduced pressure to afford the crude product. The crude was purified by C18 column with CH₃CN/Water (0.05% TFA). The desired fraction was concentrated under reduced pressure to provide (1S,3aR,4S,6R,7S,7aR)—N—((S)-1-amino-1-oxo-3-((S)-2-oxopyrrolidin-3-yl)propan-2-yl)-2-((S)-2-(2-chloro-2,2-difluoroacetamido)-3,3-dimethylbutanoyl)-6-fluorooctahydro-1H-4,7-methanoisoindole-1-carboxamide (80 mg, 41%) as a yellow oil. LC-MS (ESI, m/z): 578[M+H]⁺.

To a mixture of (1S,3aR,4S,6R,7S,7aR)—N—((S)-1-amino-1-oxo-3-((S)-2-oxopyrrolidin-3-yl)propan-2-yl)-2-((S)-2-(2-chloro-2,2-difluoroacetamido)-3,3-dimethylbutanoyl)-6-fluorooctahydro-1H-4,7-methanoisoindole-1-carboxamide (80.0 mg, 0.138 mmol, 1.0 eq.) in DCM (1 mL) were added pyridine (49.1 mg, 0.621 mmol, 4.5 eq.) and trifluoroacetic anhydride (60.9 mg, 0.290 mmol, 2.1 eq.). The mixture was stirred for 5 h at rt. The reaction was quenched with water (5 mL). The mixture was extracted with dichloromethane (3×30 mL). The organic layers were combined, washed with brine (2×10 mL), dried over anhydrous sodium sulfate, filtered and concentrated under reduced pressure to afford the crude product. The crude product was purified by prep-HPLC (Column: XSelect CSH Prep C18 OBD Column, 19*150 mm, 5 m; Mobile Phase A: Water (0.1% FA), Mobile Phase B: ACN; Flow rate: 25 mL/min; Gradient: 33% B to 63% B in 7 min, 63% B; Wave Length: 220 nm; RT1 (min): 5.87) to provide (1S,3aR,4S,6R,7S,7aR)-2-((S)-2-(2-chloro-2,2-difluoroacetamido)-3,3-dimethylbutanoyl)-N—((S)-1-cyano-2-((S)-2-oxopyrrolidin-3-yl)ethyl)-6-fluorooctahydro-1H-4,7-methanoisoindole-1-carboxamide (29.6 mg, 38%) as a white solid. ¹H NMR (400 MHz, 100° C., DMSO-d₆) δ 9.65-8.80 (m, 1H), 8.50-8.65 (m, 1H), 7.35 (br, 1H), 4.80-4.95 (m, 1H), 4.55-4.70 (m, 1H), 4.45-4.55 (m, 1H), 4.30-4.45 (m, 1H), 4.70-4.80 (m, 1H), 4.60-4.70 (m, 1H), 3.15-3.25 (m, 1H), 3.05-3.15 (m, 1H), 2.60-2.70 (m, 2H), 2.50-2.60 (m, 1H), 2.30-2.40 (m, 2H), 2.10-2.20 (m, 2H), 1.90-2.05 (m, 1H), 1.85-1.95 (m, 1H), 1.75-1.85 (m, 1H), 1.65-1.75 (m, 1H), 1.40-1.60 (m, 1H), 1.20-1.40 (m, 1H), 0.90-1.10 (m, 9H). LC-MS (ESI, m/z): 560 [M+H]⁺.

Example 134

Compound 135

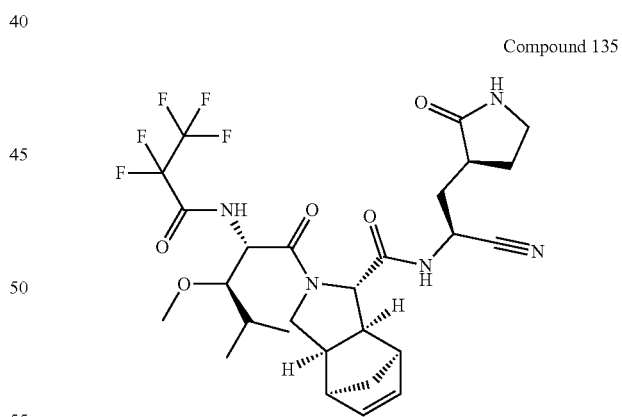

Compound 135 was prepared similarly as described for Compound 101 using (2S,3R)-2-((tert-butoxycarbonyl)amino)-3-methoxy-4-methylpentanoic acid in place of N-(tert-butoxycarbonyl)-O-cyclopropyl-L-threonine. ¹H NMR (500 MHz, 363K, DMSO-d6) δ 8.57-8.89 (m, 2H), 7.29-7.42 (m, 1H), 5.96-6.28 (m, 2H), 4.76-4.94 (m, 1H), 4.26-4.67 (m, 1H), 3.95-4.10 (m, 1H), 3.67 (t, 1H), 3.34-3.46 (m, 2H), 3.30-3.33 (m, 3H), 3.03-3.37 (m, 3H), 2.84-2.96 (m, 2H), 2.73 (m, 1H), 2.30-2.40 (m, 1H), 2.08-2.19 (m, 2H), 1.65-1.87 (m, 3H), 1.36-1.47 (m, 2H), 0.82-0.96 (m, 6H). LCMS (ESI, m/z): 604 [M+H]⁺.

(2S,3R)-2-((tert-Butoxycarbonyl)amino)-3-methoxy-4-methylpentanoic acid: A solution of tert-butyl (R)-4-((R)-1-hydroxy-2-methylpropyl)-2,2-dimethyloxazolidine-3-carboxylate (1.7 g, 6.23 mmol, 1.0 eq.) in DMF (17 mL) cooled at 0° C. was added NaH (373 mg, 9.34 mmol, 1.5 eq.). The mixture was stirred at 0° C. for 1 h. Methyl iodide (0.46 mL, 7.47 mmol, 1.2 eq.) was added. The mixture was stirred at rt for 16 h. The mixture was diluted with water (30 mL) and then extracted with EA (2×20 mL). The organic phases were combined, washed with brine (20 mL), dried over $Na_2SO_4$, filtered and concentrated under reduced pressure. The residue was purified by flash chromatography on silica gel using a gradient of EA (1 to 5%) in PE to afford tert-butyl (R)-4-((R)-1-methoxy-2-methylpropyl)-2,2-dimethyloxazolidine-3-carboxylate (1.5 g, 88%) as a colorless oil.

To a solution of tert-butyl (R)-4-((R)-1-methoxy-2-methylpropyl)-2,2-dimethyloxazolidine-3-carboxylate (580 mg, 2.02 mmol, 1.0 eq.) in acetone (6 mL) cooled at 0° C. was added Jones reagent (2.5 mL, 5.00 mmol, 2.5 eq.). The mixture was stirred at rt for 5 h and then concentrated under reduced pressure. The residue was taken up with iPrOH (5 mL), neutralized by addition of $NaHCO_3$ until pH=7 and extracted with EA (2×10 mL). The organic phases were combined, washed with brine (20 mL), dried over $Na_2SO_4$, filtered and concentrated under reduced pressure to afford (2S,3R)-2-((tert-butoxycarbonyl)amino)-3-methoxy-4-methylpentanoic acid (450 mg, 85%) as a colorless oil. $^1$H NMR (400 MHz, DMSO-$d_6$) δ 12.7 (br. s., 1H), 6.23 (d, 1H), 4.14 (dd, 1H), 3.25-3.35 (m, 4H), 1.70 (m, 1H), 1.38 (s, 9H), 1.03 (d, 2H), 0.93 (d, 3H), 0.84 (d, 3H). LCMS (ESI, m/z): 262 $[M+H]^+$.

Example 135

LC-MS Methods

| Compound No. | Rt (min) | $[M + H]^+$ or $[M - H]^-$ | LCMS Method |
|---|---|---|---|
| 1 | 1.119 | $[M + H]^+$ = 524 | 48 |
| 2 | 1.234 | $[M + H]^+$ = 538 | 48 |
| 3 | 1.244 | $[M + H - 56]^+$ = 512 | 48 |
| 4 | 1.633 | $[M + H]^+$ = 537 | 57 |
| 5 | 1.071 | $[M + H]^+$ = 533 | 48 |
| 6 | 1.062 | $[M + H]^+$ = 534 | 23 |
| 7 | 1.153 | $[M + H]^+$ = 534 | 23 |
| 8 | 1.291 | $[M + H]^+$ = 499 | 48 |
| 9 | 0.820, 0.856 | $[M + H]^+$ = 576 | 41 |
| 10 | 1.035, 1.096 | $[M + H]^+$ = 610 | 48 |
| 11 | 1.167, 1.236 | $[M + H]^+$ = 585 | 48 |
| 12 | 1.503 | $[M + H]^+$ = 526 | 59 |
| 13 | 1.195 | $[M + H]^+$ = 536 | 48 |
| 14 | 0.997 | $[M + H]^+$ = 550 | 11 |
| 15 | 1.016 | $[M + H]^+$ = 552 | 11 |
| 16 | 0.959 | $[M + H]^+$ = 538 | 11 |
| 17a | 1.456 | $[M + H]^+$ = 578 | 62 |
| 17b | 1.451 | $[M + H]^+$ = 578 | 62 |
| 18 | 1.632 | $[M + H]^+$ = 552 | 59 |
| 19 | 1.330 | $[M + H]^+$ = 522 | 27 |
| 20 | 0.955 | $[M + H]^+$ = 564 | 11 |
| 21 | 1.282 | $[M + H]^+$ = 496 | 27 |
| 22 | 0.826 | $[M + H]^+$ = 526 | 27 |
| 23 | 1.426 | $[M + H]^+$ = 574 | 61 |
| 24 | 1.378 | $[M + H]^+$ = 522 | 58 |
| 25 | 0.937 | $[M + H]^+$ = 550 | 60 |
| 26 | 0.917 | $[M + H]^+$ = 550 | 60 |
| 27 | 0.937, 0.947 | $[M + H]^+$ = 534 | 11 |
| 28 | 0.966 | $[M + H]^+$ = 536 | 11 |
| 29 | 1.063, 1.073 | $[M + H]^+$ = 586 | 11 |
| 30 | 0.893 | $[M + H]^+$ = 514 | 11 |
| 31 | 1.385, 1.428 | $[M + H]^+$ = 588 | 37 |
| 32 | 0.966 | $[M + H]^+$ = 528 | 11 |
| 33 | 0.893 | $[M + H]^+$ = 532 | 11 |
| 34 | 0.928 | $[M + H]^+$ = 522 | 11 |
| 35 | 0.944 | $[M + H]^+$ = 536 | 11 |
| 36 | 0.770 | $[M + H]^+$ = 512 | 11 |
| 37 | 0.955, 0.970 | $[M + H]^+$ = 548 | 11 |
| 38 | 2.092 | $[M + H]^+$ = 485 | A |
| 39 | 0.965 | $[M + H]^+$ = 540 | 11 |
| 40 | 0.989 | $[M + H]^+$ = 542 | 11 |
| 41 | 0.997, 1.026 | $[M + H]^+$ = 532 | 64 |
| 42 | 2.187 | $[M - H]^-$ = 546 | A |
| 43 | 1.940 | $[M - H]^-$ = 508 | A |
| 44 | 1.402 | $[M + H]+$ = 526 | 48 |
| 45 | 0.924 | $[M + H]+$ = 613 | 47 |
| 46 | 1.212, 1.331 | $[M + H]+$ = 612 | 48 |
| 47 | 0.893 | $[M + H]+$ = 510 | 11 |
| 48 | 0.982 | $[M + H]+$ = 556 | 11 |
| 49 | 0.907 | $[M + H]+$ = 539 | 11 |
| 50 | 1.441 | $[M + H]+$ = 526 | 58 |
| 51 | 1.104, 1.128 | $[M + H]+$ = 577 | 64 |
| 52 | 1.078 | $[M + H]+$ = 588 | 11 |
| 53 | 1.992 | $[M - H]^-$ = 492 | A |
| 54 | 2.159 | $[M - H]^-$ = 497 | A |
| 55 | 2.103 | $[M + H]^+$ = 501 | A |
| 56 | 2.221 | $[M + H]^+$ = 483 | A |
| 57 | 2.128 | $[M - H]^-$ = 532 | A |
| 58 | 2.016 | $[M + H]^+$ = 528 | A |
| 58a | 2.040 | $[M + H]^+$ = 528 | A |
| 58b | 2.037 | $[M + H]^+$ = 528 | A |
| 59 | 2.191 | $[M + H]^+$ = 538 | A |
| 59a | 2.181 | $[M - H]^-$ = 536 | A |
| 59b | 2.231 | $[M - H]^-$ = 536 | A |
| 60 | 1.021 | $[M + H]+$ = 552 | 11 |
| 61 | 0.968 | $[M + H]+$ = 562 | 11 |
| 62 | 1.003, 1.015 | $[M + H]+$ = 538 | 11 |
| 63 | 0.923 | $[M + H]+$ = 524 | 11 |
| 64 | 0.934 | $[M + H]+$ = 516 | 11 |
| 65 | 1.275 | $[M + H]+$ = 528 | 64 |
| 66 | 0.926 | $[M + H]+$ = 522 | 11 |
| 67 | 1.037 | $[M + H]+$ = 558 | 11 |
| 68 | 0.983 | $[M + H]+$ = 548 | 11 |
| 69 | 0.989 | $[M + H]+$ = 550 | 11 |
| 70 | 1.984 | $[M + H]^+$ = 496 | A |
| 71 | 2.218 | $[M + H]^+$ = 540 | A |
| 71a | 2.199 | $[M - H]^-$ = 538 | A |
| 71b | 2.203 | $[M + H]^+$ = 540 | A |
| 72 | 2.056 | $[M + H]^+$ = 506 | A |
| 73 | 2.114 | $[M + H]^+$ = 520 | A |
| 74 | 2.095 | $[M + H]^+$ = 516 | A |
| 75 | 2.200 | $[M + H]^+$ = 566 | A |
| 76 | 2.252 | $[M + H]^+$ = 574 | A |
| 77 | 2.084 | $[M + H]^+$ = 528 | A |
| 78 | 2.213 | $[M - H]^-$ = 580 | A |
| 79 | 2.175 | $[M - H]^-$ = 580 | A |
| 80 | 2.026 | $[M - H]^-$ = 524 | A |
| 81 | 2.057 | $[M + H]^+$ = 538 | A |
| 82 | 0.936 | $[M + H]+$ = 560 | 11 |
| 83 | 0.998-1.028 | $[M + H]+$ = 600 | 11 |
| 83a | 1.015, 1.047 | $[M + H]+$ = 600 | 11 |
| 83b | 1.040, 1.075 | $[M + H]+$ = 600 | 11 |
| 84 | 2.062-2.076 | $[M + H]^+$ = 479 | A |
| 85 | 0.857 | $[M + H]+$ = 542 | 11 |
| 86 | 0.955 | $[M + H]+$ = 544 | 11 |
| 87 | 0.905 | $[M + H]+$ = 594 | 11 |
| 88 | 0.965 | $[M + H]+$ = 550 | 11 |
| 89 | 0.874 | $[M + H]+$ = 538 | 11 |
| 90 | 1.135 | $[M + H]+$ = 540 | 66 |
| 91 | 0.931 | $[M + H]+$ = 542 | 11 |
| 92 | 0.955 | $[M + H]+$ = 562 | 11 |
| 93 | 1.015 | $[M + H]+$ = 538 | 11 |
| 94 | 1.393, 1.412 | $[M + H]+$ = 542 | 62 |
| 95 | 2.155 | $[M + H]^+$ = 536 | A |
| 96 | 1.277 | $[M + H]+$ = 544 | 62 |
| 97 | 0.994 | $[M + H]+$ = 550 | 11 |

LC-MS Methods

| Compound No. | Rt (min) | [M + H]⁺ or [M − H]⁻ | LCMS Method |
|---|---|---|---|
| 98 | 2.091 | [M + H]⁺ = 562 | A |
| 99 | 2.124 | [M + H]⁺ = 566 | A |
| 100 | 0.928 | [M + H]+ = 604 | 11 |
| 101 | 2.176 | [M + H]⁺ = 602 | A |
| 102a | 0.867, 0.875 | [M + H]+ = 578 | 11 |
| 102b | 0.879 | [M + H]+ = 578 | 11 |
| 103 | 2.264 | [M + H]⁺ = 630 | A |
| 104 | 1.045 | [M + H]+ = 602 | 11 |
| 105 | 0.989 | [M + H]+ = 554 | 11 |
| 106 | 0.950 | [M + H]+ = 566 | 11 |
| 107 | 1.070 | [M + H]+ = 616 | 11 |
| 108 | 1.034, 1.048 | [M + H]+ = 592 | 11 |
| 109 | 2.008 | [M + H]⁺ = 589 | A |
| 110 | 1.963 | [M + H]⁺ = 603 | A |
| 111 | 2.005 | [M + H]⁺ = 625 | A |
| 112 | 2.228 | [M + H]⁺ = 589 | A |
| 113 | 1.984 | [M + H]⁺ = 589 | A |
| 114 | 2.169 | [M + H]⁺ = 540 | A |
| 115 | 2.208 | [M + H]⁺ = 590 | A |
| 116 | 2.139 | [M + H]⁺ = 556 | A |
| 117 | 2.109 | [M + H]⁺ = 576 | A |
| 118 | 1.495 | [M + H]+ = 610 | 58 |
| 119 | 1.259 | [M + H]+ = 560 | 62 |
| 120 | 2.177 | [M + H]⁺ = 566 | A |
| 121 | 0.869 | [M + H]+ = 554 | 11 |
| 122 | 2.75 | [2M + Na]+:1188 | B |
| 123 | 2.60 | [2M + Na]+: 1119 | B |
| 124 | 2.25 | [2M + Na]+: 1087 | C |
| 125 | 1.594 | [M + H]+ = 575 | 62 |
| 126 | 2.065 | [M + H]⁺ = 526 | A |
| 127 | 2.127 | [M + H]⁺ = 540 | A |
| 128 | 1.025 | [M + H]+ = 576 | 11 |
| 129 | 1.070 | [M + H]+ = 610 | 11 |
| 131 | 2.150 | [M + H]⁺ = 590 | A |
| 132 | 2.041 | [M + H]⁺ = 554 | A |
| 133 | 2.037 | [M + H]⁺ = 532 | A |
| 134 | 1.341 | [M + H]+ = 560 | 62 |
| 135 | 2.217 | [M + H]⁺ = 604 | A |

Final compounds can be obtained in some cases as a mixture with a corresponding stereoisomer. Retention times of the main isomers are depicted in the table above.

Description of LC-MS Methods

| LC Method | Instrument | Column | Mobile Phase | Gradient | Flow | Col T | Run Time |
|---|---|---|---|---|---|---|---|
| 11 | Shimadzu LCMS-2020 | HALO 2.0 μm C18 90A (2.0 μm, 3.0*30 mm) | A: Water/0.1% FA B: Acetonitrile/0.1% FA | From 95% A to 0% A in 1.09 min, held for 0.6 min, to 95% A in 0.05 min, held for 0.10 min | 1.5 mL/min | 40 | 1.85 min |
| 23 | Shimadzu LCMS-2020 | Shim-pack Scepter SP-C18 (3 μm, 3.0*33 mm) | A: Water/6.5 mM NH₄HCO₃ + Ammonia Hydroxide (pH = 10) B: Acetonitrile | From 90% A to 5% A in 1.19 min, held for 0.6 min, to 90% A in 0.02 min, held for 0.18 min | 1.2 mL/min | 40 | 2 min |
| 27 | Shimadzu LCMS-2020 | HALO 2.0 μm C18 90A (2.0 μm, 3.0*30 mm) | A: Water/0.1% FA B: ACN/0.1% FA | From 95% A to 35% A in 1.69 min, to 0% A in 0.6 min, held for 0.5 min, to 95% A in 0.03 min, held for 0.17 min | 1.5 mL/min | 40 | 3 min |
| 41 | Shimadzu LCMS-2020 | HALO C18 (2.0 μm, 3.0*30 mm) | A: Water + 0.05% TFA B: ACN + 0.05% TFA | From 95% A to 0% A in 1.19 min, held for 0.5 min, to 95% A in 0.05 min, held for 0.25 min | 1.5 mL/min | 40 | 2 min |
| 47 | Shimadzu LCMS-2020 | Shim-pack Scepter SP-C18 (3 μm, 3.0*33 mm) | A: Water/6.5 mM NH₄HCO₃ + Ammonia Hydroxide (pH = 10) B: Acetonitrile | From 80% A to 5% A in 1.99 min, held for 0.7 min, to 90% A in 0.05 min, held for 0.25 min | 1.2 mL/min | 40 | 3 min |
| 48 | Shimadzu LCMS-2020 | Shim-pack Scepter SP-C18 (3 μm, 3.0*33 mm) | A: Water/6.5 mM NH₄HCO₃ + Ammonia | From 70% A to 5% A in 1.99 min, held for 0.7 min, to | 1.2 mL/min | 40 | 3 min |

-continued

| LC Method | Instrument | Column | Mobile Phase | Gradient | Flow | Col T | Run Time |
|---|---|---|---|---|---|---|---|
| | | | Hydroxide (pH = 10) B: Acetonitrile | 90% A in 0.05 min, held for 0.25 min | | | |
| 57 | Shimadzu LCMS-2020 | Shim-Pack C18 (3 μm, 3.0*33 mm) | A: Water/ 6.5 mM NH$_4$HCO$_3$ + Ammonia Hydroxide (pH = 10) B: Acetonitrile | From 90% A to 30% A in 1.69 min, to 5% A in 0.6 min, held for 0.5 min, to 90% A in 0.03 min, held for 0.17 min | 1.2 mL/min | 40 | 3 min |
| 58 | Shimadzu LCMS-2020 | HALO 2.0 μm C18 90A (2.0 μm, 3.0*30 mm) | A: Water/ 0.1% FA B: ACN/ 0.1% FA | From 95% A to 30% A in 1.69 min, to 0% A in 0.6 min, held for 0.5 min, to 95% A in 0.03 min, held for 0.17 min | 1.5 mL/min | 40 | 3 min |
| 59 | Shimadzu LCMS-2020 | HALO C18 (2.0 μm, 3.0*30 mm) | A: Water + 0.05% TFA B: ACN + 0.05% TFA | From 95% A to 35% A in 1.69 min, to 5% A in 0.6 min, held for 0.5 min, to 95% A in 0.03 min, held for 0.17 min | 1.5 mL/min | 40 | 3 min |
| 60 | Shimadzu LCMS-2020 | HALO 90A C18 (2.0 μm, 3.0*30 mm) | A: Water + 0.05% TFA B: ACN + 0.05% TFA | From 95% A to 0% A in 1.19 min, held for 0.6 min, to 95% A in 0.05 min, held for 0.15 min | 1.2 mL/min | 40 | 1.9 min |
| 61 | Shimadzu LCMS-2020 | HALO 2.0 μm C18 90A (2.0 μm, 3.0*30 mm) | A: Water/ 0.1% FA B: ACN/ 0.1% FA | From 95% A to 0% A in 2.19 min, held for 0.5 min, to 95% A in 0.05 min, held for 0.45 min | 1.5 mL/min | 40 | 3.2 min |
| 62 | Shimadzu LCMS-2020 | HALO 2.0 μm C18 90A (2.0 μm, 3.0*30 mm) | A: Water/ 0.1% FA B: ACN/ 0.1% FA | From 95% A to 5% A in 2.19 min, held for 0.6 min, to 95% A in 0.05 min, held for 0.25 min | 1.5 mL/min | 40 | 3 min |
| 64 | Shimadzu LCMS-2020 | HALO 2.0 μm C18 90A (2.0 μm, 3.0*30 mm) | A: Water/ 0.1% FA B: ACN/ 0.1% FA | From 80% A to 30% A in 1.69 min, to 100% A in 0.6 min, held for 0.5 min, to 95% A in 0.03 min, held for 0.17 min | 1.5 mL/min | 40 | 3 min |
| 66 | Shimadzu LCMS-2020 | HALO 2.0 μm C18 90A (2.0 μm, 3.0*30 mm) | A: Water/ 0.1% FA B: ACN/ 0.1% FA | From 95% A to 5% A in 2.19 min, held for 0.6 min, to 95% A in 0.05 min, held for 0.25 min | 1.5 mL/min | 60 | 3 min |
| A | Agilent 6150 SQ Mass Spectrometer coupled to an Agilent 1290 | Acquity UPLC BEH C18 (1.7 μm, 2.1*50 mm) | A: 0.1% FA in Water, B: 0.1% FA in Acetonitrile | 98% A held for 0.2 min, to 2% A in 1.3 min, held for 1.8 min, to 98% A in 0.1 min, held | 0.6 mL/min | 70 | 3.8 min |

| LC Method | Instrument | Column | Mobile Phase | Gradient | Flow | Col T | Run Time |
|---|---|---|---|---|---|---|---|
| | Infinity LC System | | | for 0.4 min | | | |
| B | Shimadzu LCMS-2020 | Waters Cortecs C18 2.7u 3.0 × 75 mm | A: Water/ 0.1% FA B: Acetonitrile/ 0.1% FA | From 5% B to 95% B in 2.5 min, held for 0.5 min, to 5% B in 0.05 min, held for 0.95 min | 0.4 mL/ min | 40 | 4 min |
| C | Shimadzu LCMS-2020 | Waters Cortecs C18 2.7u 3.0 × 75 mm | A: Water/ 0.1% FA B: Acetonitrile/ 0.1% FA | From 25% B to 95% B in 2.5 min, held for 0.5 min, to 5% B in 0.05 min, held for 0.95 min | 0.4 mL/ min | 40 | 4 min |

Example 139

Additional Compounds

Additional compounds of Formula (I) can be prepared using similar materials and methods described herein, such as those described herein.

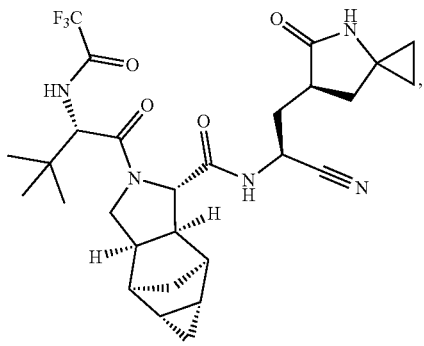

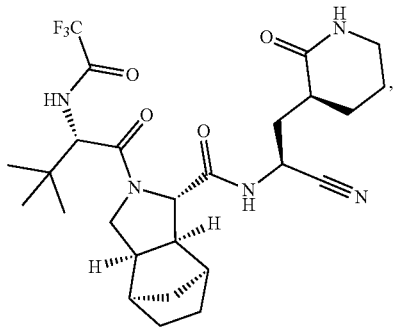

-continued

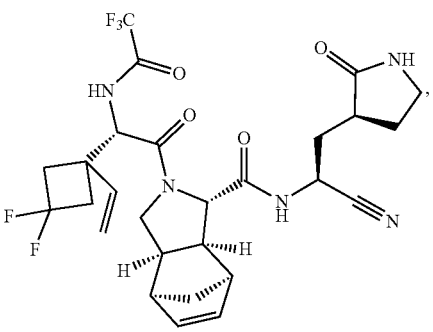

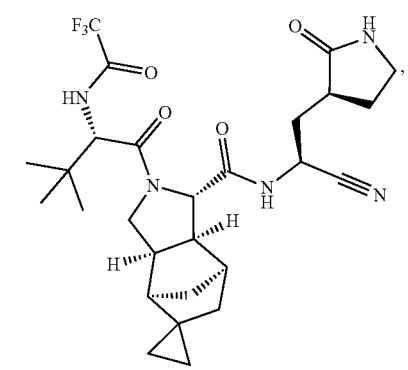

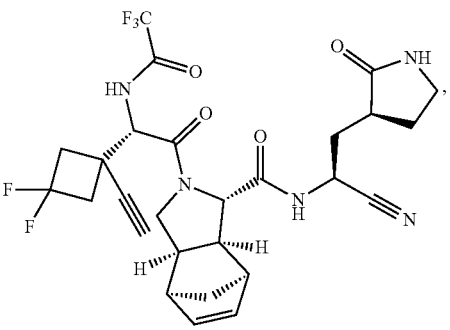

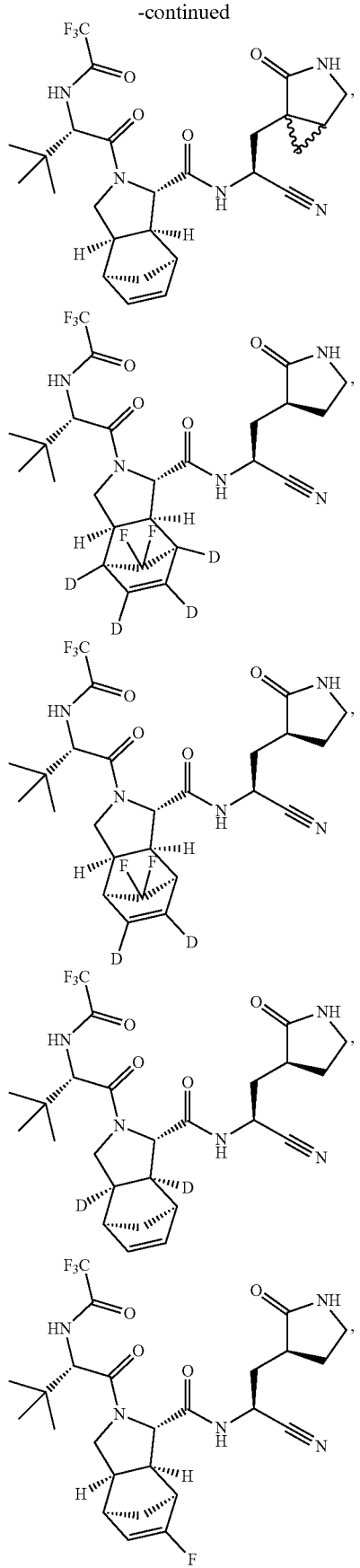
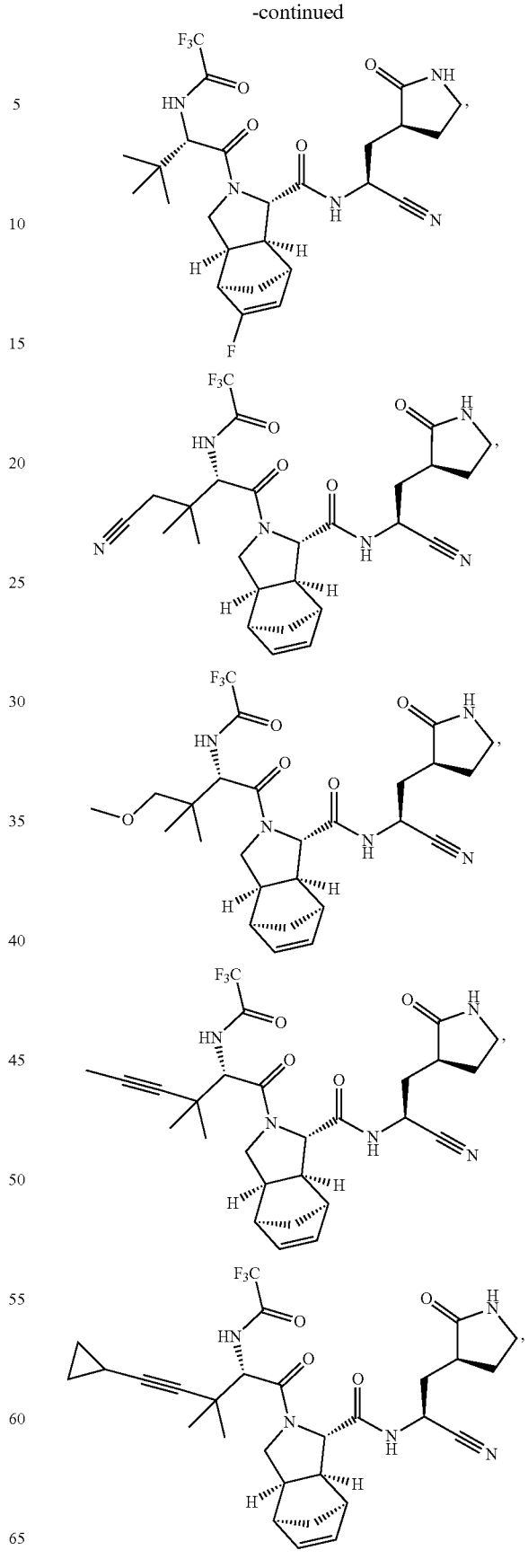

481
-continued
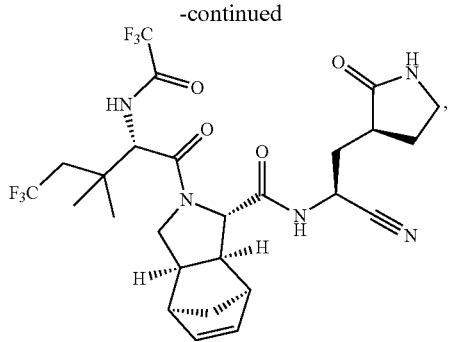
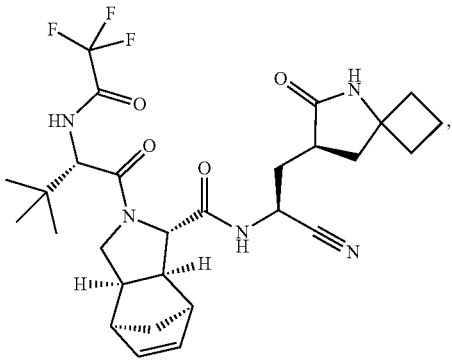
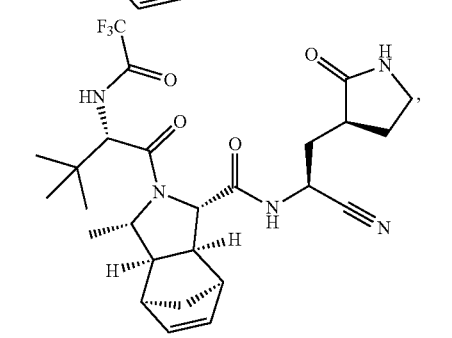
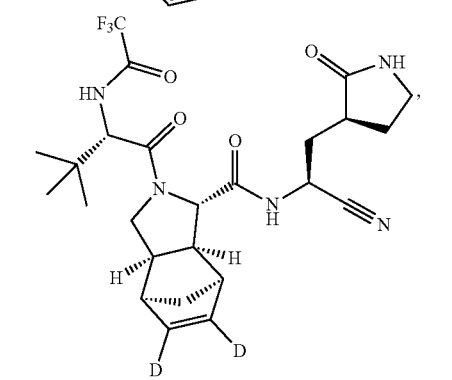
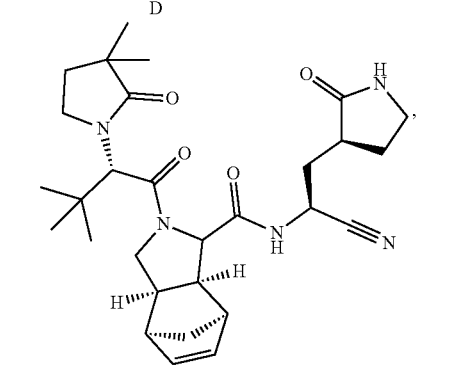
482
-continued
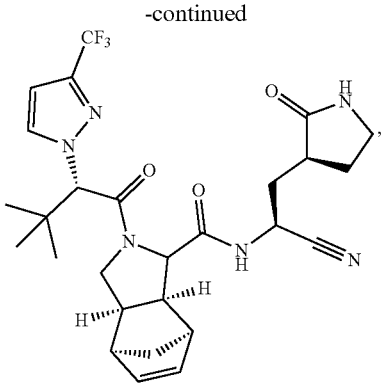
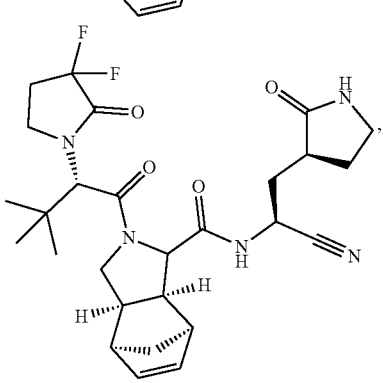
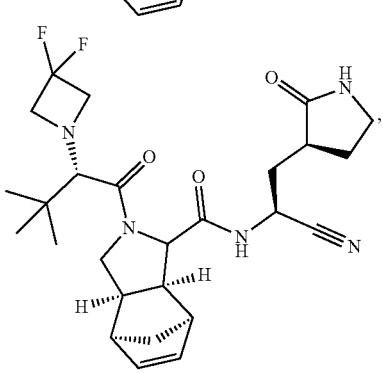
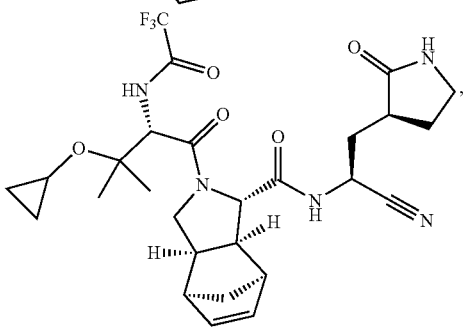
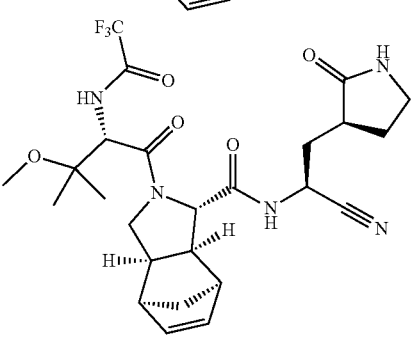

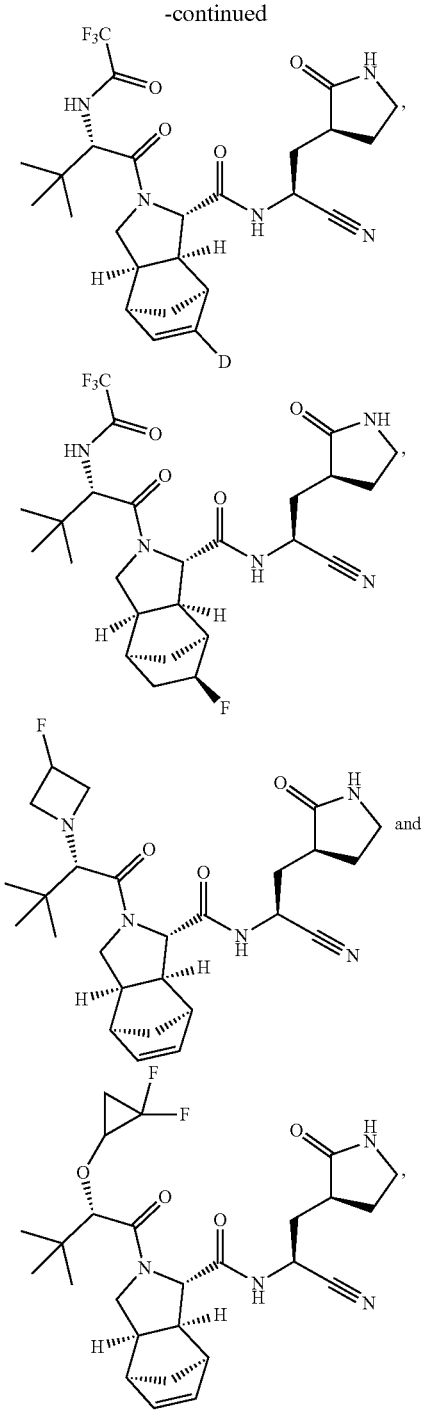

including pharmaceutically acceptable salts thereof.

Example A

SARS-Cov-2 3CLpro and HRV3C Duplex Assay

Protease assays were performed in 384-well low volume polypropylene microtiter plates at ambient temperature. For the duplex assay, 3CLpro and HRV3C was added using a Multidrop Combi (Thermo Scientific; Waltham, MA) and preincubated for 30 mins with small molecules. The reactions were initiated by the addition of the two peptide substrates. The reactions were incubated for 30 mins and quenched by the addition of 0.5% formic acid (final) with subsequent neutralization using 1% sodium bicarbonate (final). Internal standard peptides were added in 20 mM Hepes pH 8.0 for quantitation of the protease products. For SAMDI-MS analysis, 2 μL of each reaction mixture was transferred using a 384-channel automated liquid handler to SAMDI biochip arrays functionalized with a neutravidin-presenting self-assembled monolayer. The SAMDI arrays were incubated for 1 h in a humidified chamber to allow the specific immobilization of the biotinylated peptide substrates, cleaved products and internal standards. The samples were purified by washing the SAMDI arrays with deionized ultrafiltered water and dried with compressed air. A matrix comprising alpha-cyano cinnamic acid in 80% acetonitrile: 20% aqueous ammonium citrate was applied in an automated format by dispensing 50 nL to each spot in the array. SAMDI-MS was performed using reflector-positive mode on an AB Sciex TOF-TOF 5800 System (AB Sciex, Framingham, MA) with 400 shots/spot analyzed in a random raster sampling. For data analysis, area under the curves (peaks) (AUCs) for the product and internal standard were calculated using the TOF/TOF Series Explorer (AB Sciex), and the amount of product formed was calculated using the equation (AUC product/AUC internal standard). The amount of product generated was calculated using the ratio of product area under the curve (AUC) divided by the AUC of the internal standard. Negative controls were pre-quenched with 0.5% formic acid final. Assay robustness was determined by Z-Factor. The $IC_{50}$s were determined by fitting the curves using a four-parameter equation in Graphpad Prism 8.

Table 1 indicates related $IC_{50}$ values for the tested compounds where 'A' indicates an $EC_{50}$<20 nM, 'B' indicates an $IC_{50}$ of ≥20 nM and <200 nM, 'C' indicates an $IC_{50}$≥200 nM and <2000 nM, 'D' indicates an $IC_{50}$≥2000 nM and <20000 nM and 'E' indicates an $IC_{50}$≥20000 nM and <100000 nM. As shown by the data in Table 1, compounds described herein (including pharmaceutically acceptable salts thereof) can effectively inhibit and be used to treat a coronavirus and rhinovirus.

TABLE 1

| Compound | SARS-Cov-2 | HRV |
|---|---|---|
| 1 | A | >10 μM |
| 2 | B | >10 μM |
| 3 | A | >10 μM |
| 4 | B | >10 μM |
| 5 | C | >10 μM |
| 6 | B | >10 μM |
| 7 | A | >10 μM |
| 8 | B | >10 μM |
| 9 | A | >10 μM |
| 10 | A | B |
| 11 | A | C |
| 12 | A | >10 μM |
| 13 | B | >10 μM |
| 14 | A | >10 μM |
| 15 | A | >10 μM |
| 16 | A | >10 μM |
| 17a | A | >10 μM |
| 17b | A | >10 μM |
| 18 | A | >10 μM |
| 19 | B | >10 μM |
| 20 | A | >10 μM |
| 21 | A | >10 μM |
| 22 | C | >10 μM |
| 23 | B | >10 μM |
| 24 | A | >10 μM |

TABLE 1-continued

| Compound | SARS-Cov-2 | HRV |
|---|---|---|
| 25 | A | >10 μM |
| 26 | B | >10 μM |
| 27 | A | >10 μM |
| 28 | A | >10 μM |
| 29 | A | >10 μM |
| 30 | A | >10 μM |
| 31 | A | >10 μM |
| 32 | A | >10 μM |
| 33 | A | >10 μM |
| 34 | A | >10 μM |
| 35 | B | >10 μM |
| 36 | A | >10 μM |
| 37 | B | >10 μM |
| 38 | B | >10 μM |
| 39 | A | >10 μM |
| 40 | A | >10 μM |
| 41 | A | >10 μM |
| 42 | B | >10 μM |
| 43 | A | >10 μM |
| 44 | B | >10 μM |
| 45 | B | D |
| 46 | A | C |
| 47 | B | >10 μM |
| 48 | A | >10 μM |
| 49 | A | >10 μM |
| 50 | A | >10 μM |
| 51 | A | >10 μM |
| 52 | A | >10 μM |
| 53 | B | >10 μM |
| 54 | C | >10 μM |
| 55 | B | >10 μM |
| 56 | C | >10 μM |
| 57 | B | >10 μM |
| 58 | C | >10 μM |
| 58a | >10 μM | >10 μM |
| 58b | C | >10 μM |
| 59 | A | >10 μM |
| 59a | C | >10 μM |
| 59b | A | >10 μM |
| 60 | B | >10 μM |
| 61 | A | >10 μM |
| 62 | A | >10 μM |
| 63 | A | >10 μM |
| 64 | A | >10 μM |
| 65 | A | >10 μM |
| 66 | A | >10 μM |
| 67 | A | >10 μM |
| 68 | A | >10 μM |
| 69 | A | >10 μM |
| 70 | D | >10 μM |
| 71 | A | >10 μM |
| 71a | D | >10 μM |
| 71b | A | >10 μM |
| 72 | A | >10 μM |
| 73 | A | >10 μM |
| 74 | A | >10 μM |
| 75 | A | >10 μM |
| 76 | A | >10 μM |
| 77 | B | >10 μM |
| 78 | B | >10 μM |
| 79 | A | >10 μM |
| 80 | A | >10 μM |
| 81 | A | D |
| 82 | A | >10 μM |
| 83 | A | >10 μM |
| 83a | A | >0.5 μM |
| 83b | A | >0.5 μM |
| 84 | D | >10 μM |
| 85 | C | >10 μM |
| 86 | A | >0.5 μM |
| 87 | A | >0.5 μM |
| 88 | A | >10 μM |
| 89 | A | >10 μM |
| 90 | B | >10 μM |
| 91 | A | >0.5 μM |
| 92 | B | >0.5 μM |
| 93 | A | >0.5 μM |
| 94 | A | >0.5 μM |
| 95 | A | >10 μM |
| 96 | B | >0.5 μM |
| 97 | A | >10 μM |
| 98 | A | >0.5 μM |
| 99 | A | >0.5 μM |
| 100 | A | >0.5 μM |
| 101 | A | >0.5 μM |
| 102a | A | >0.5 μM |
| 102b | >0.5 μM | >0.5 μM |
| 103 | A | >0.5 μM |
| 104 | A | >0.5 μM |
| 105 | B | >0.5 μM |
| 106 | A | >0.5 μM |
| 107 | A | >0.5 μM |
| 108 | A | >0.5 μM |
| 109 | A | >0.5 μM |
| 110 | A | >0.5 μM |
| 111 | A | >0.5 μM |
| 112 | A | >0.5 μM |
| 113 | A | >0.5 μM |
| 114 | A | >0.5 μM |
| 115 | A | >0.5 μM |
| 116 | A | >0.5 μM |
| 117 | A | >0.5 μM |
| 118 | A | >0.5 μM |
| 119 | B | >0.5 μM |
| 120 | A | >0.5 μM |
| 121 | A | >0.5 μM |
| 124 | A | >0.5 μM |
| 125 | A | >0.5 μM |
| 126 | B | >0.5 μM |
| 127 | B | >0.5 μM |
| 128 | A | >0.5 μM |
| 129 | A | >0.5 μM |
| 131 | A | >0.5 μM |
| 132 | A | >0.5 μM |
| 133 | A | >0.5 μM |
| 134 | A | >0.5 μM |
| 135 | A | >0.5 μM |

Example B

Coronavirus Assay

OC43 Coronavirus Assay in HeLa Cells

The human beta-coronavirus OC43 was purchased from ATCC (Manassas, VA) and propagated using HCT-8 human colorectal epithelial cells (ATCC). HeLa human cervical epithelial cells (ATCC) were used as susceptible host cell lines and were cultured using EMEM media, supplemented with 10% fetal bovine serum (FBS), 1% (v/v) penicillin/streptomycin (P/S), 1% (v/v) HEPES and 1% (v/v) cellgro Glutagro™ supplement (all Corning, Manassas, VA) at 37° C. For the OC43 antiviral assay, $1.5 \times 10^4$ HeLa cells per well were plated in 100 μL complete media in white 96-well plates with clear bottoms at 37° C. for up to 24 h to facilitate attachment and allow cells to recover from seeding stresses. Next day, the cell culture medium was removed. Serially diluted compounds in 100 μL assay media (EMEM, 2% FBS, 1% P/S, 1% cellgro Glutagro™ supplement, 1% HEPES) were added to the cells and incubated for 4 H at 37° C. in a humidified 5% $CO_2$ incubator. 100 μL of OC43 virus stock was diluted to a concentration known to produce optimal cytopathic effect, inducing 80-90% reduction in cell viability. 96-well plates were incubated for 6 (HeLa) days at 33° C.; each plate contains uninfected control wells as well as virus-infected wells that were not treated with compound. Cytotoxicity plates without the addition of OC43 virus were carried out in parallel. At the end of the incubation period, 100 μL cell culture supernatant was replaced with 100 μL cell-titer-glo reagent (Promega, Madison, WI) and incubated for at least 10 min at rt prior to measuring luminescence. Luminescence was measured on a Perkin Elmer (Waltham, MA) Envision plate reader. Antiviral % inhibition was calculated as follows: [(Compound treated cells infected sample)−(no compound infected control)]/[(Uninfected control)−(no compound infected control)]*100; Using GraphPad (San Diego, CA) prism software version 8.3.1, the antiviral dose-response plot was generated as a sigmoidal fit, log(inhibitor) vs response-variable slope (four parameters) model and the $EC_{50}$ was calculated which is the predicted compound concentration corresponding to a 50% inhibition of the viral cytopathic effect.

Table 2 indicates related $EC_{50}$ and $CC_{50}$ values for the tested compounds 'A' indicates an $EC_{50}$<100 nM, 'B' indicates an $EC_{50}$ of ≥100 nM and <1000 nM, 'C' indicates an $EC_{50}$≥1000 nM and <10000 nM and 'D' indicates an $EC_{50}$≥10000 nM and <100000 nM. For $CC_{50}$, the values are reported in micromolar (μm), 'A' indicates a $CC_{50}$≥10000 nM and 'B' indicates a $CC_{50}$≥1 μM and <10 μM.

TABLE 2

| Compound | $EC_{50}$ | $CC_{50}$ |
|---|---|---|
| 1 | A | >100 |
| 2 | B | >100 |
| 3 | A | >100 |
| 4 | A | >100 |
| 5 | B | >100 |
| 6 | A | >100 |
| 7 | A | >100 |
| 8 | B | >100 |
| 9 | A | >100 |
| 10 | B | A |
| 11 | B | >100 |
| 12 | A | >100 |
| 13 | B | >100 |
| 14 | A | >100 |
| 16 | A | >100 |
| 17a | A | >100 |
| 17b | B | >100 |
| 18 | A | >100 |
| 19 | A | >100 |
| 20 | A | >100 |
| 21 | A | >100 |
| 22 | C | >100 |
| 23 | C | >100 |
| 24 | A | >100 |
| 25 | A | >100 |
| 26 | B | >100 |
| 27 | A | >100 |
| 28 | A | >100 |
| 29 | A | A |
| 30 | A | >100 |
| 31 | B | A |
| 32 | A | >100 |
| 33 | A | >100 |
| 34 | A | >100 |
| 35 | B | >100 |
| 36 | B | >100 |
| 37 | >10 μM | >100 |
| 38 | C | >100 |
| 39 | A | >100 |
| 40 | A | >100 |
| 41 | A | >100 |
| 42 | B | >100 |
| 43 | B | >100 |
| 44 | B | B |
| 45 | C | >100 |
| 46 | B | A |
| 47 | B | >100 |
| 48 | A | >100 |
| 49 | B | >100 |
| 50 | A | >100 |
| 51 | B | >100 |
| 52 | B | >100 |

TABLE 2-continued

| Compound | $EC_{50}$ | $CC_{50}$ |
|---|---|---|
| 53 | C | A |
| 54 | >10 μM | >100 |
| 55 | C | >100 |
| 56 | >10 μM | >100 |
| 57 | B | >100 |
| 58 | C | >100 |
| 58a | >10 μM | >100 |
| 58b | C | >100 |
| 59 | A | >100 |
| 59a | >10 μM | >100 |
| 59b | A | >100 |
| 60 | C | >100 |
| 61 | B | >100 |
| 62 | A | >100 |
| 63 | A | >100 |
| 64 | A | >100 |
| 65 | A | >100 |
| 66 | B | >100 |
| 67 | A | >100 |
| 68 | A | >100 |
| 69 | A | >100 |
| 70 | >10 μM | >100 |
| 71 | B | >100 |
| 71a | >10 μM | >100 |
| 71b | A | >100 |
| 72 | A | >100 |
| 73 | A | >100 |
| 74 | A | >100 |
| 75 | B | >100 |
| 76 | A | >100 |
| 77 | C | >100 |
| 78 | C | >100 |
| 79 | B | >100 |
| 80 | A | >100 |
| 81 | A | >100 |
| 82 | A | >100 |
| 83 | A | >100 |
| 83a | A | >100 |
| 83b | A | >100 |
| 84 | >1 μM | >100 |
| 85 | >10 μM | >100 |
| 86 | A | >100 |
| 87 | A | >100 |
| 88 | B | >100 |
| 89 | B | >100 |
| 90 | #N/A | >100 |
| 91 | A | >100 |
| 92 | B | >100 |
| 93 | A | >100 |
| 94 | A | >100 |
| 95 | A | >100 |
| 96 | B | >100 |
| 97 | A | >100 |
| 98 | A | >100 |
| 99 | A | >100 |
| 100 | A | >100 |
| 101 | A | >100 |
| 102a | A | >100 |
| 102b | >1 μM | >100 |
| 103 | A | >100 |
| 104 | B | >100 |
| 105 | B | >100 |
| 106 | A | >100 |
| 107 | A | >100 |
| 108 | A | >100 |
| 109 | A | >100 |
| 110 | A | >100 |
| 111 | A | >100 |
| 112 | B | >100 |
| 113 | A | >100 |
| 114 | A | >100 |
| 115 | A | >100 |
| 116 | A | >100 |
| 117 | A | >100 |
| 118 | A | >100 |
| 119 | B | >100 |
| 120 | A | >100 |
| 121 | A | >100 |

TABLE 2-continued

| Compound | EC$_{50}$ | CC$_{50}$ |
|---|---|---|
| 125 | A | >100 |
| 126 | B | >100 |
| 127 | B | >100 |
| 128 | A | >100 |
| 129 | A | >100 |
| 131 | A | >100 |
| 132 | A | >100 |
| 133 | A | >100 |
| 134 | A | >100 |

SARS-CoV-2 Infection Model in VeroE6 Cells

The SARS-CoV-2 antiviral assay is derived from the previously established SARS-CoV assay (PMID: 15961169). In this assay, fluorescence of Vero E6-eGFP cells declines after infection with SARS-CoV-2 due to the cytopathogenic effect of the virus. In the presence of an antiviral compound, the cytopathogenicity is inhibited and the fluorescent signal rescued. On day −1, the test compounds were serially diluted in assay medium (DMEM supplemented with 2% v/v FCS). The plates were incubated (37° C., 5% CO$_2$ and 95% relative humidity) overnight. On day 0, the diluted compounds were mixed with Vero E6-eGFP cells (25,000 cells/well), SARS-CoV-2-GHB-03021/2020 (20 TCID$_{50}$/well) and the MDR1-inhibitor CP-100356 (final concentration 0.5 µM) in 96-well blackview plates (Greiner Bio-One, Vilvoorde, Belgium). The plates were incubated in a humidified incubator at 37° C. and 5% CO$_2$. At 4 days p.i., the wells were examined for eGFP expression using an argon laser-scanning microscope. The microscope settings were excitation at 488 nm and emission at 510 nm and the fluorescence images of the wells were converted into signal values. The results were expressed as EC$_{50}$ values defined as the concentration of compound achieving 50% rescue from the virus-reduced eGFP signals as compared to the untreated virus-infected control cells. Toxicity of compounds in the absence of virus was evaluated in a standard MTS-assay as described previously (PMID: 22575574).

Table 3 indicates related EC$_{50}$ and CC$_{50}$ values for the tested compounds 'A' indicates an EC$_{50}$<100 nM, 'B' indicates an EC$_{50}$ of >100 nM, <1000 nM, 'C' indicates an EC$_{50}$≥1000 nM and <10000 nM and 'D' indicates an EC$_{50}$≥10000 nM and <50000 nM. For CC$_{50}$, the values are reported in micromolar (m). 'A' indicates a CC$_{50}$≥10 m. 'B' indicates a CC$_{50}$≥1 m and <10 m.

TABLE 3

| Compound | VeroE6 + CP (EC$_{50}$) | VeroE6 + CP (CC$_{50}$) |
|---|---|---|
| 1 | A | >50 |
| 2 | A | >50 |
| 3 | A | >50 |
| 4 | B | >50 |
| 5 | C | >50 |
| 6 | C | >50 |
| 7 | A | >50 |
| 8 | B | >50 |
| 9 | A | >50 |
| 10 | B | >50 |
| 11 | B | >50 |
| 12 | A | >50 |
| 13 | A | >50 |
| 14 | A | >10 |
| 15 | A | >50 |
| 16 | A | >50 |
| 17a | A | >50 |
| 17b | B | >50 |
| 18 | A | >50 |
| 19 | B | >50 |
| 20 | A | >50 |
| 21 | A | >50 |
| 22 | C | >50 |
| 23 | B | >50 |
| 24 | B | >50 |
| 25 | B | >50 |
| 26 | B | >50 |
| 27 | A | >10 |
| 28 | A | >10 |
| 29 | A | >10 |
| 30 | A | >10 |
| 31 | B | >50 |
| 32 | A | >50 |
| 33 | A | >50 |
| 34 | A | >50 |
| 35 | B | >50 |
| 36 | B | >50 |
| 37 | C | >50 |
| 38 | B | >50 |
| 39 | A | >50 |
| 40 | A | >50 |
| 41 | A | >50 |
| 42 | B | >50 |
| 43 | B | >50 |
| 44 | C | A |
| 45 | C | >100 |
| 46 | B | A |
| 47 | B | >50 |
| 48 | A | >50 |
| 49 | B | >50 |
| 50 | A | >50 |
| 51 | B | >50 |
| 53 | B | >50 |
| 54 | C | >50 |
| 55 | B | >50 |
| 56 | C | >50 |
| 57 | B | >50 |
| 58 | C | >50 |
| 59 | A | >50 |
| 70 | D | >50 |
| 85 | D | >50 |

B.1.1.7 Infection Model in A549-dual_ACE2_TMPRSS2 Cells

The A549-dual_ACE2_TMPRSS2 cells (InvivoGen Cat #a549-cov2r) were propagated in the growth medium which was prepared by supplementing DMEM (gibco cat no 41965-039) with 10% v/v heat-inactivated FCS and 10 ag/mL blasticidin (InvivoGen ant-bl-05), 100 µg/mL hygromycin (InvivoGen ant-hg-1), 0.5 µg/mL puromycin (InvivoGen ant-pr-1) and 100 µg/mL zeocin (InvivoGen ant-zn-05) in a humidified 5% CO$_2$ incubator at 37° C. The assay medium was prepared by supplementing DMEM (gibco cat no 41965-039) with 2% v/v heat-inactivated FCS.

The virus isolate used is from the B.1.1.7 lineage (derived from hCoV-19/Belgium/rega-12211513/2020; EPI-_ISL_791333,2020-12-21; see Abdelnabi et al., "Comparing infectivity and virulence of emerging SARS-CoV-2 variants in Syrian hamsters" EBioMedicine (2021) June; 68:103403. doi: 10.1016/j.ebiom.2021.103403).

For antiviral testing, cells were seeded in 96-well plates (Falcon) at a density of 15,000 cells per well in assay medium. After overnight growth, cells were treated with the indicated compound concentrations and infected with a MOI of 0.001 TCID50/cell (final volume 200 µL/well in assay medium). On day 4 p.i. differences in cell viability caused by virus-induced CPE or by compound-specific side effects are analyzed using MTS as described previously (PMID: 22575574).

For toxicity testing, the same experimental setup was used except that assay medium without virus was added to the cells and that an additional control of well without cells was added to the plate.

Table 4 indicates related $EC_{50}$ and $CC_{50}$ values for the tested compounds 'A' indicates an $EC_{50}$<100 nM, 'B' indicates an $EC_{50}$ of ≥100 nM and <1000 nM, 'C' indicates an $EC_{50}$≥1000 nM and <10000 nM. For $CC_{50}$, the values are reported in micromolar (M). 'A' indicates a $CC_{50}$≥10 μM. 'B' indicates a $CC_{50}$≥1 μM and <10 μM.

TABLE 4

| Compound | A549-dual_ ACE2_TMPRSS2 ($EC_{50}$) | A549-dual_ ACE2_TMPRSS2 ($CC_{50}$) |
| --- | --- | --- |
| 1 | A | >50 |
| 2 | A | >10 |
| 3 | A | >10 |
| 4 | B | >10 |
| 5 | C | >10 |
| 6 | C | >10 |
| 7 | A | >10 |
| 8 | A | >10 |
| 9 | B | >10 |
| 10 | B | >10 |
| 11 | B | >10 |
| 12 | A | >10 |
| 13 | A | >10 |
| 14 | A | >10 |
| 15 | A | >10 |
| 16 | A | >10 |
| 17a | B | >10 |
| 17b | B | >10 |
| 18 | B | >10 |
| 19 | B | >10 |
| 20 | B | >10 |
| 21 | A | >10 |
| 22 | C | >10 |
| 23 | B | >10 |
| 24 | B | >10 |
| 25 | B | >10 |
| 26 | B | >10 |
| 27 | B | >10 |
| 28 | A | >10 |
| 29 | A | >10 |
| 30 | A | >10 |
| 31 | A | >10 |
| 32 | A | >10 |
| 33 | B | >10 |
| 34 | B | >10 |
| 35 | C | >10 |
| 36 | C | >10 |
| 37 | C | >10 |
| 38 | C | >10 |
| 39 | A | >10 |
| 40 | A | >10 |
| 41 | A | >10 |
| 42 | B | >10 |
| 43 | B | >10 |
| 44 | C | A |
| 45 | C | >50 |
| 46 | B | >50 |
| 47 | B | >10 |
| 48 | A | >10 |
| 49 | B | >10 |
| 50 | A | >10 |
| 51 | C | >10 |
| 52 | B | >10 |
| 53 | C | >10 |
| 54 | >10 | >10 |
| 55 | B | >10 |
| 56 | C | >10 |
| 57 | B | >10 |
| 58 | C | >10 |
| 58a | >10 | >10 |
| 58b | C | >10 |
| 59 | A | >10 |
| 59a | C | >10 |
| 59b | A | >10 |
| 60 | B | >10 |
| 61 | B | >10 |
| 62 | A | >10 |
| 63 | A | >10 |
| 64 | A | >10 |
| 65 | A | >10 |
| 66 | B | >10 |
| 67 | A | >10 |
| 68 | A | >10 |
| 69 | A | >10 |
| 70 | >10 | >10 |
| 71 | A | >10 |
| 71a | >10 | >10 |
| 71b | A | >10 |
| 72 | A | >10 |
| 73 | A | >10 |
| 74 | A | >10 |
| 75 | A | >10 |
| 76 | A | >10 |
| 77 | B | >10 |
| 78 | B | >10 |
| 79 | B | >10 |
| 80 | B | >10 |
| 81 | A | >10 |
| 82 | A | >10 |
| 83 | A | >10 |
| 83a | A | >10 |
| 83b | A | >1 |
| 84 | C | >10 |
| 85 | >10 | >10 |
| 86 | A | >10 |
| 87 | A | >1 |
| 88 | B | >10 |
| 89 | B | >10 |
| 90 | C | >10 |
| 91 | A | >10 |
| 92 | B | >10 |
| 93 | A | >10 |
| 94 | A | >1 |
| 95 | A | >10 |
| 96 | B | >1 |
| 97 | A | >10 |
| 98 | A | >10 |
| 99 | A | >1 |
| 100 | A | >1 |
| 101 | A | >1 |
| 102a | A | >1 |
| 102b | >1 | >1 |
| 103 | A | >1 |
| 104 | A | >10 |
| 105 | A | >10 |
| 106 | A | >10 |
| 107 | A | >1 |
| 108 | A | >10 |
| 109 | A | >10 |
| 110 | A | >1 |
| 111 | B | >1 |
| 112 | A | >10 |
| 113 | A | >1 |
| 114 | A | >10 |
| 115 | A | >1 |
| 116 | A | >1 |
| 117 | A | >1 |
| 118 | A | >1 |
| 119 | B | >1 |
| 120 | A | >1 |
| 121 | A | >1 |
| 126 | B | >10 |
| 127 | A | >10 |
| 128 | A | >1 |
| 129 | A | >1 |
| 131 | A | >1 |
| 132 | A | >1 |

TABLE 4-continued

| Compound | A549-dual_ ACE2_TMPRSS2 (EC$_{50}$) | A549-dual_ ACE2_TMPRSS2 (CC$_{50}$) |
|---|---|---|
| 133 | B | >1 |
| 135 | A | >1 |

Tables 2, 3 and 4 demonstrate that compounds described herein (including pharmaceutically acceptable salts thereof) can effectively inhibit and treat a coronavirus.

Example C

Picornavirus & Norovirus Assays

Compounds of Formula (I), including pharmaceutically acceptable salts thereof, are tested following a protocol similar to the protocol described in one of the following articles: Kim et al., Journal of Virology (2012) 86(21): 11754-11762, Zhang et al, JACS (2020) (https://dx.doi.org/10.1021/acs.jmedchem.9b01828), and U.S. Pat. No. 9,603,864.

The protocols of Kim et al., and Zhang et al., can be used to test for activity against a picornavirus and norovirus.

Example D

For the cathepsin L assay, 10 pM of human cathepsin L (R&D Systems; Minneapolis, MN) was preincubated for 30 mins with test compounds. Reactions were initiated by the addition of a peptide substrate Z-FR-AMC (final concentration 2 µM, Anaspec; Fremont, CA). Fluorescence was measured at 2-minute intervals for 30 mins using a 355/460 excitation/emission filter module on an Envision plate reader (Perkin Elmer; Waltham, MA). The IC$_{50}$ values were calculated for each assay by fitting the curves using a four-parameter equation in GraphPad Prism.

Table 5 indicates related IC$_{50}$ values for the tested compounds where 'A' indicates an IC$_{50}$≥10000 nM, 'B' indicates an IC$_{50}$ of ≥1000 nM and <10000 nM, 'C' indicates an IC$_{50}$≥100 nM and <1000 nM, 'D' indicates an IC$_{50}$<100 nM.

TABLE 5

| Compound | Cathepsin L IC$_{50}$ |
|---|---|
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | A |
| 16 | A |
| 17a | A |
| 17b | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | A |
| 40 | A |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 58a | A |
| 58b | A |
| 59 | A |
| 59a | A |
| 59b | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 71a | A |
| 72 | A |
| 73 | A |
| 74 | A |
| 75 | A |
| 76 | A |
| 77 | A |
| 78 | A |
| 79 | A |
| 80 | A |
| 82 | A |
| 83 | A |
| 85 | A |
| 86 | A |
| 91 | A |
| 99 | A |
| 100 | A |
| 109 | A |
| 114 | A |
| 128 | A |
| 129 | A |
| 131 | A |
| 132 | A |
| 133 | A |

TABLE 5-continued

| Compound | Cathepsin L IC$_{50}$ |
|---|---|
| 134 | A |
| 135 | A |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the present disclosure.

What is claimed is:

1. A compound of Formula (I), or a pharmaceutically acceptable salt thereof, having the structure:

wherein:

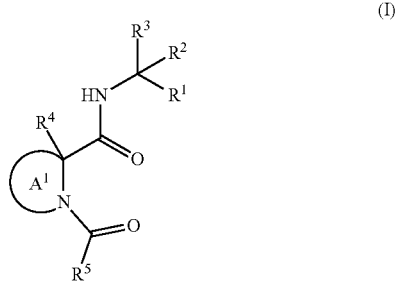

(I)

Ring $A^1$ is selected from the group consisting of

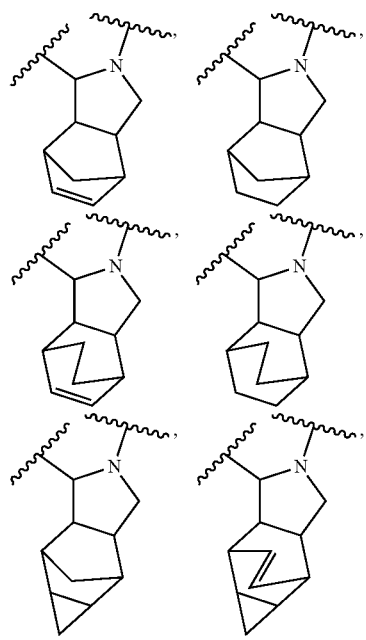

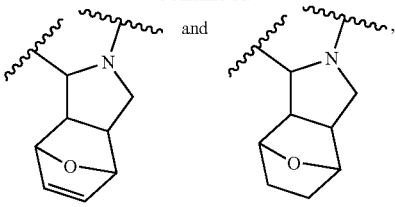

and wherein Ring $A^1$ is optionally substituted with one or more moieties independently selected from the group consisting of =O, =CH$_2$, deuterium, halogen, hydroxy, an unsubstituted C$_{1-4}$ alkyl, an unsubstituted C$_{1-4}$ haloalkyl, an unsubstituted C$_{2-4}$ alkenyl and an unsubstituted or a substituted C$_{3-6}$ monocyclic cycloalkyl, wherein the C$_{3-6}$ monocyclic cycloalkyl is connected in a spiro-fashion;

$R^1$ is selected from the group consisting of cyano, an unsubstituted or a substituted C$_{2-5}$ alkynyl, an unsubstituted or a substituted acyl, an unsubstituted or a substituted ketoamide, —CH(OH)((P=O)(OR$^6$)$_2$) and —C(=O)CH$_2$—O—((P=O)(OR$^7$)$_2$);

each $R^6$ and each $R^7$ re independently hydrogen, an unsubstituted C$_{1-6}$ alkyl, an unsubstituted C$_{2-6}$ alkenyl, an unsubstituted C$_{1-6}$ haloalkyl, an unsubstituted or a substituted aryl or an unsubstituted or a substituted aryl(C$_{1-4}$ alkyl);

$R^2$ is hydrogen, deuterium or halogen;

$R^3$ is an unsubstituted or a substituted monocyclic nitrogen-containing heterocyclyl(C$_{1-4}$ alkyl), an unsubstituted or a substituted bicyclic nitrogen-containing heterocyclyl(C$_{1-4}$ alkyl) or an unsubstituted or a substituted monocyclic nitrogen-containing heteroaryl (C$_{1-4}$ alkyl);

$R^4$ is hydrogen, deuterium or halogen;

$R^5$ is

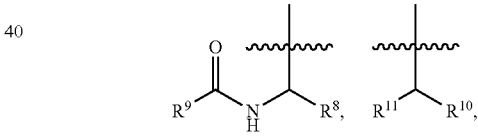

a substituted monocyclic C$_{3-6}$ cycloalkyl or a substituted 4- to 6-membered monocyclic heterocyclyl, wherein the monocyclic C$_{3-6}$ cycloalkyl and the 4- to 6-membered monocyclic heterocyclyl are independently substituted 1, 2 or 3 times with a moiety selected from the group consisting of deuterium, halogen, an unsubstituted C$_{1-6}$ alkyl, an unsubstituted C$_{1-6}$ haloalkyl and an unsubstituted C$_{1-6}$ alkoxy, or independently substituted in a spiro-fashion by an unsubstituted or a substituted bicyclic cycloalkenyl or an unsubstituted or a substituted bicyclic heterocyclyl;

$R^8$ and $R^{10}$ are independently selected from the group consisting of an unsubstituted or a substituted C$_{2-6}$ alkyl, an unsubstituted or a substituted C$_{2-6}$ alkenyl, an unsubstituted or a substituted C$_{2-6}$ alkynyl, an unsubstituted or a substituted monocyclic C$_{3-6}$ cycloalkyl, an unsubstituted or a substituted bicyclic C$_{5-8}$ cycloalkyl, an unsubstituted or a substituted monocyclic 4- to 6-membered heterocyclyl and an unsubstituted monocyclic C$_{3-6}$ cycloalkyl(CH$_2$)—, wherein when the C$_{2-6}$ alkyl is substituted, the C$_{2-6}$ alkyl is substituted 1, 2, 3 or 4 times with a substituent independently selected from the group consisting of halogen, cyano, an unsubstituted or a substituted monocyclic $C_{3-6}$ cycloalkyl, an unsubstituted $C_{1-4}$ alkoxy and an unsubstituted $C_{1-4}$ haloalkoxy, or the $C_{2-6}$ alkyl is substituted 1 to 13 times with deuterium;

wherein when the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl are substituted, the $C_{2-6}$ alkenyl, the $C_{2-6}$ alkynyl, the monocyclic $C_{3-6}$ cycloalkyl, the bicyclic $C_{5-8}$ cycloalkyl and the monocyclic 4- to 6-membered heterocyclyl are substituted 1, 2, 3 or 4 times with a substituent independently selected from the group consisting of halogen, an unsubstituted $C_{1-4}$ alkyl, an unsubstituted $C_{2-4}$ alkenyl, an unsubstituted $C_{2-4}$ alkynyl, an unsubstituted $C_{1-4}$ haloalkyl, an unsubstituted or a substituted monocyclic $C_{3-6}$ cycloalkyl and an unsubstituted $C_{1-4}$ alkoxy; and $R^9$ is selected from the group consisting of an unsubstituted or a substituted $C_{1-6}$ alkyl, an unsubstituted or a substituted $C_{1-6}$ haloalkyl, a substituted monocyclic $C_{3-6}$ cycloalkyl, an unsubstituted or a substituted bicyclic $C_{5-6}$ cycloalkyl, an unsubstituted or a substituted monocyclic heteroaryl and an unsubstituted or a substituted monocyclic heterocyclyl, wherein the substituted $C_{1-6}$ alkyl is substituted 1 or 2 times with an unsubstituted $C_{1-4}$ alkoxy, wherein the substituted monocyclic $C_{3-6}$ cycloalkyl is substituted 1, 2, 3 or 4 times with a substituent independently selected from the group consisting of halogen, an unsubstituted $C_{1-4}$ alkyl, an unsubstituted $C_{1-4}$ alkoxy, an unsubstituted $C_{1-4}$ haloalkyl and an unsubstituted monocyclic $C_{3-6}$ cycloalkyl, and wherein the substituted $C_{1-6}$ haloalkyl is substituted 1 or 2 times with an unsubstituted $C_{1-4}$ alkoxy; and $R^{11}$ is selected from the group consisting of an optionally substituted monocyclic 4- to 6-membered heterocyclyl, —(NH)$_m$-an optionally substituted 5- to 6-membered monocyclic heteroaryl, —O-an optionally substituted $C_{1-6}$ alkyl, —O-an optionally substituted $C_{3-8}$ cycloalkyl and —O-an optionally substituted $C_{3-8}$ cycloalkyl ($C_{1-4}$ alkyl), wherein m is 0 or 1.

2. The compound of claim 1, wherein $R^1$ is cyano.

3. The compound of claim 1, wherein Ring $A^1$ is an unsubstituted

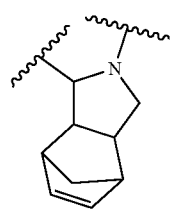 [SMILES: *C1C2C3C=CC(C3)C2CN1*]

or a substituted

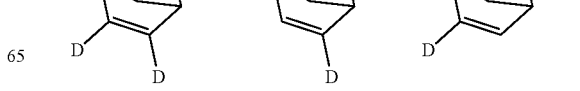

substituted with one or more moieties independently selected from the group consisting of =O, =CH$_2$, deuterium, halogen, hydroxy, an unsubstituted $C_{1-4}$ alkyl, an unsubstituted $C_{1-4}$ haloalkyl, an unsubstituted $C_{2-4}$ alkenyl and an unsubstituted or a substituted $C_{3-6}$ monocyclic cycloalkyl.

4. The compound of claim 1, wherein Ring $A^1$ is selected from the group consisting of:

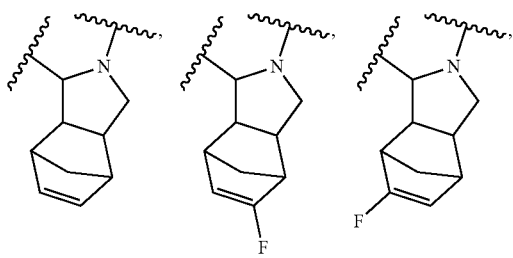
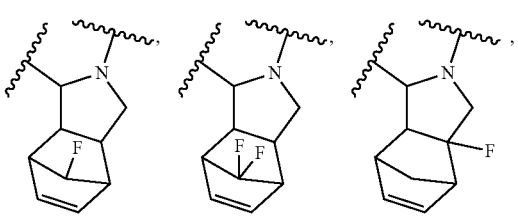
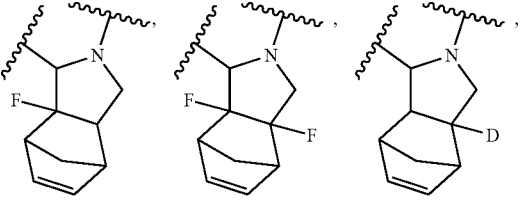
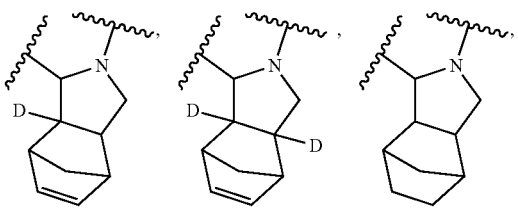
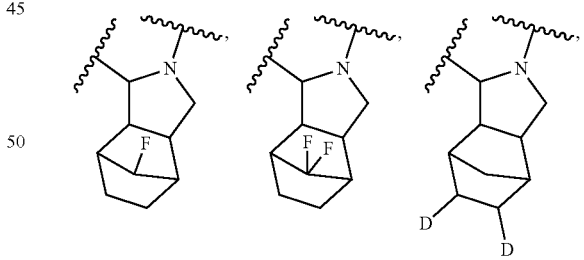
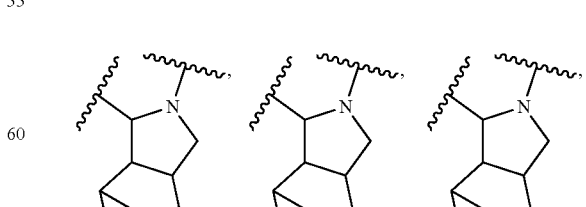

-continued

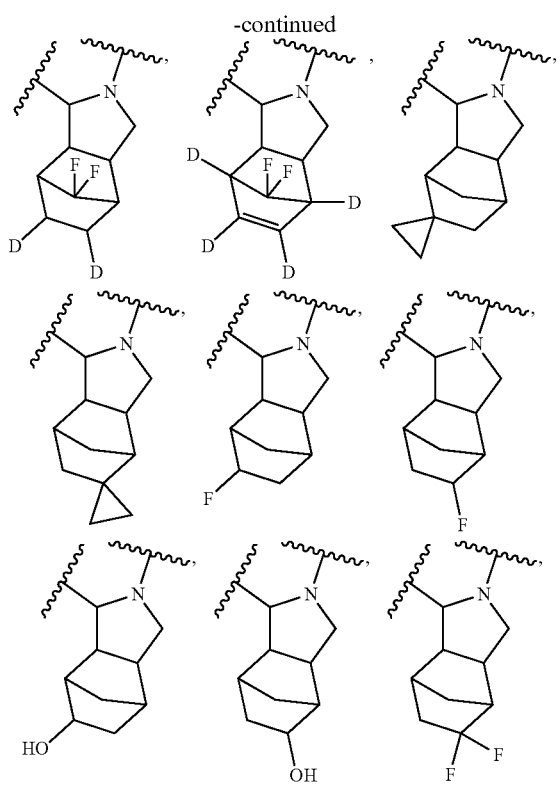

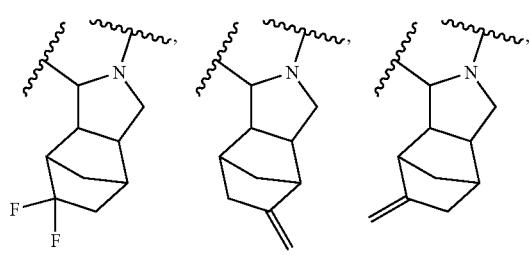

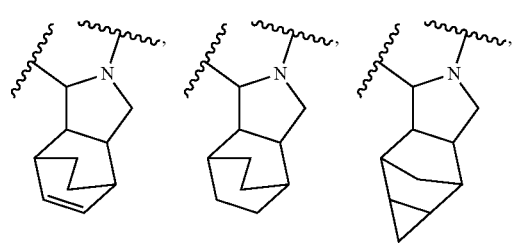

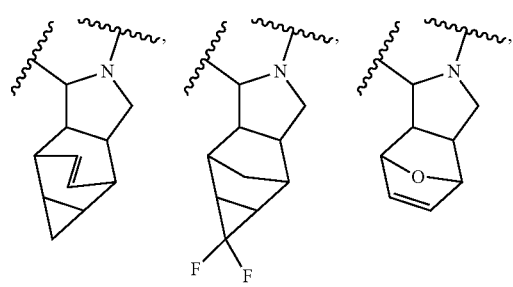

-continued

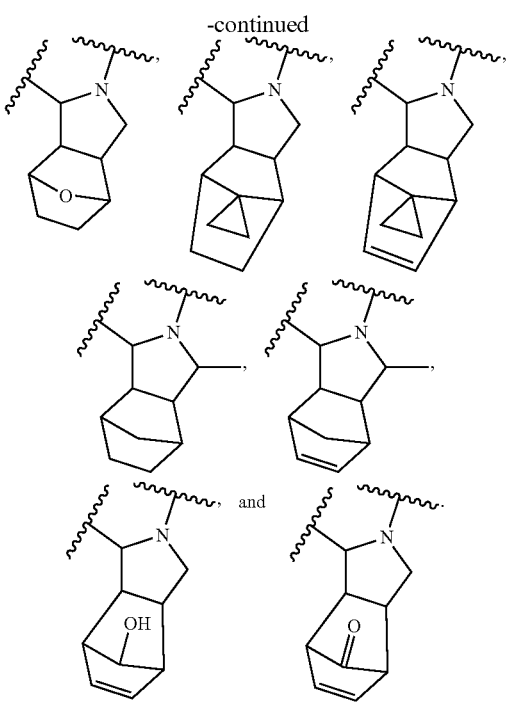

5. The compound of claim 1, wherein R⁵ is

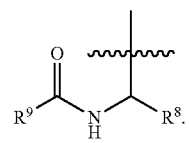

6. The compound of claim 5, wherein $R^8$ is an unsubstituted or a substituted $C_{2-6}$ alkyl.

7. The compound of claim 5, wherein $R^9$ is an unsubstituted or a substituted $C_{1-6}$ alkyl.

8. The compound of claim 5, wherein $R^9$ is an unsubstituted $C_{1-6}$ haloalkyl.

9. The compound of claim 5, wherein $R^9$ is an unsubstituted or substituted monocyclic $C_{3-6}$ cycloalkyl, an unsubstituted or a substituted bicyclic $C_{5-6}$ cycloalkyl, an unsubstituted or a substituted monocyclic heteroaryl or an unsubstituted or a substituted monocyclic heterocyclyl.

10. The compound of claim 5, wherein R⁵ is selected from the group consisting of:

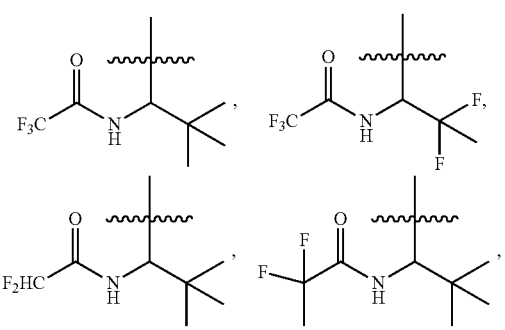

501
-continued
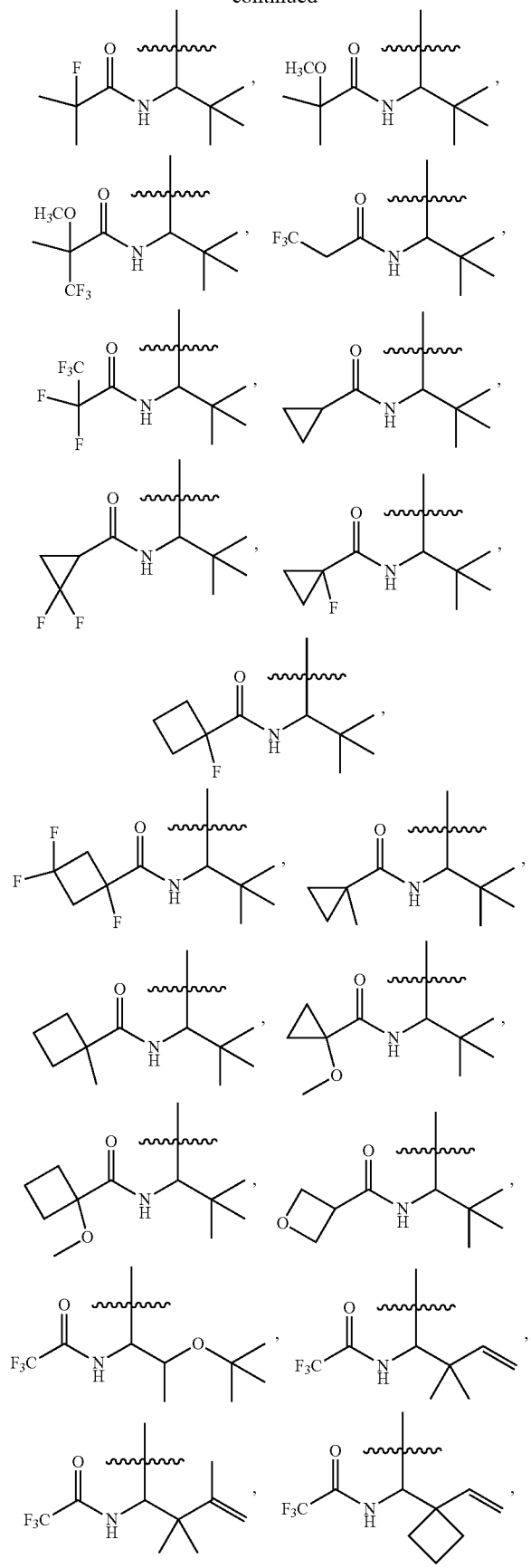
502
-continued
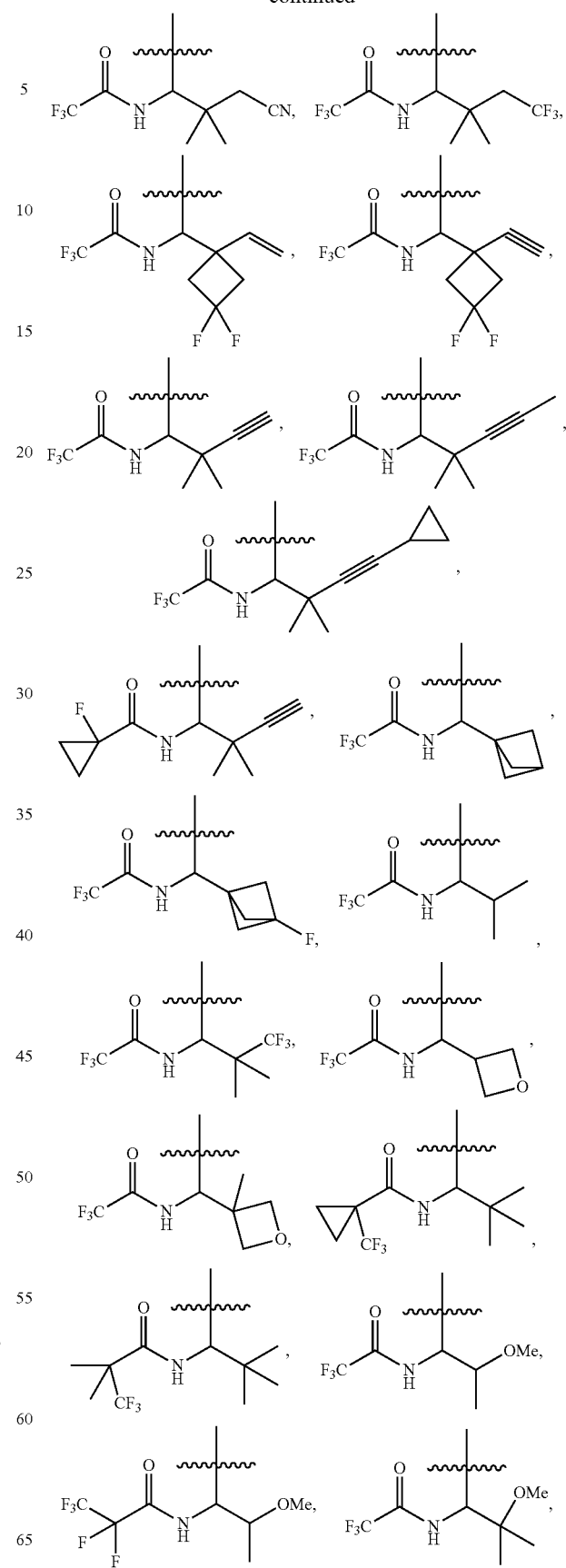

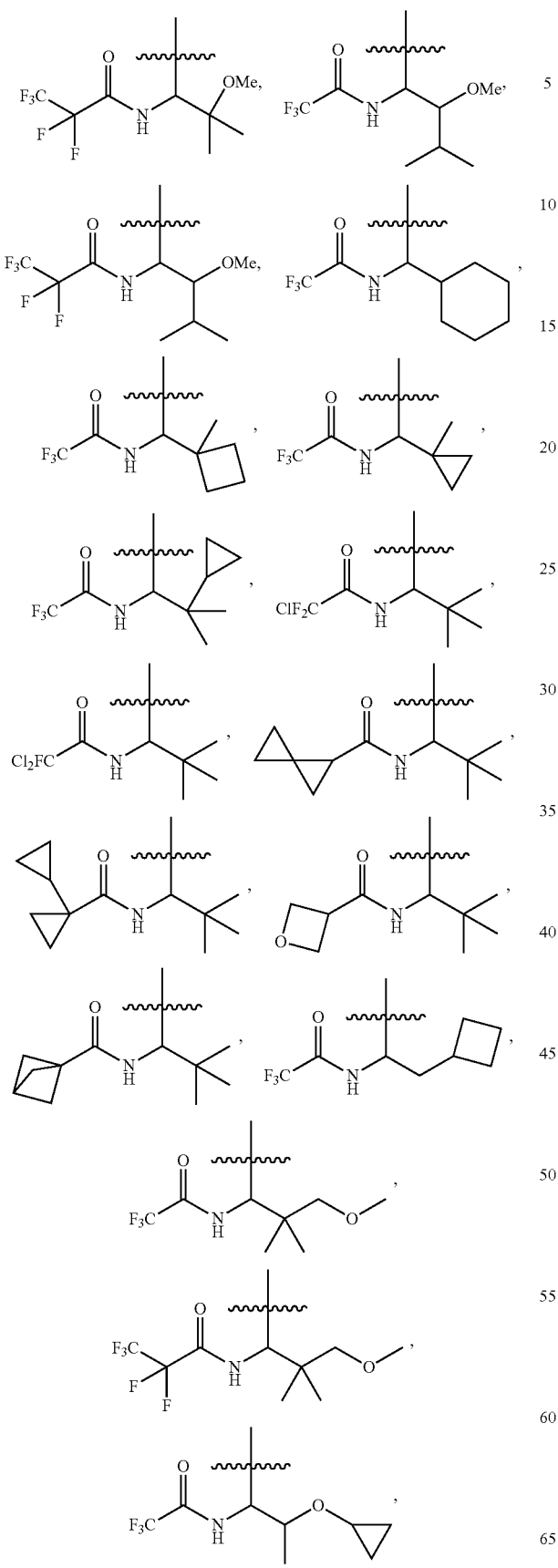
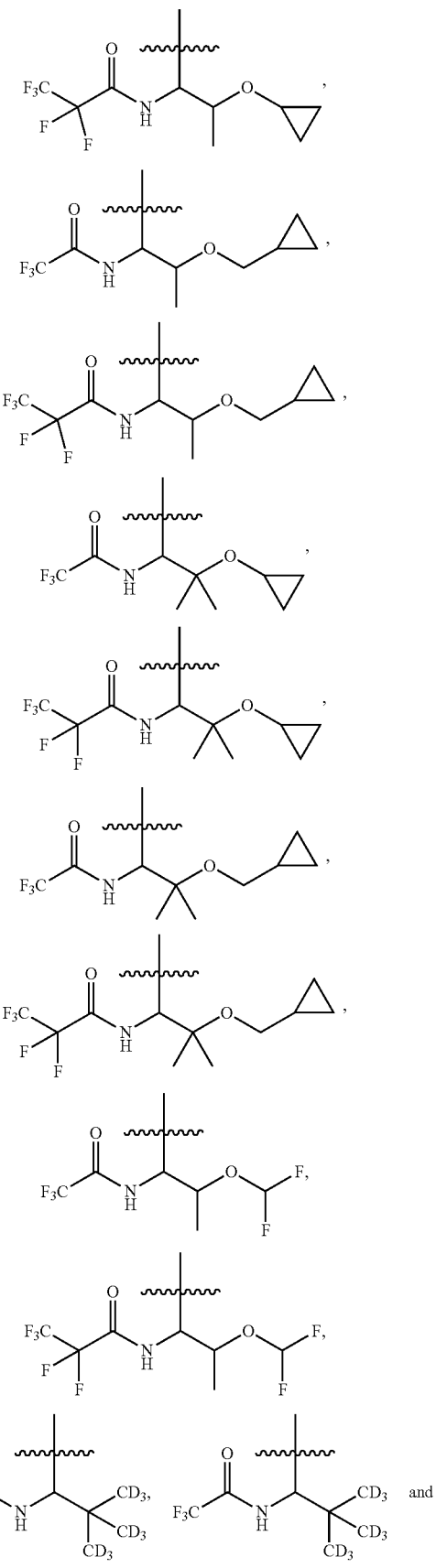

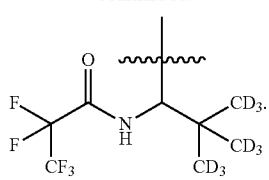

11. The compound of claim 1, wherein $R^3$ is an unsubstituted or a substituted monocyclic nitrogen-containing heterocyclyl($C_{1-4}$ alkyl).

12. The compound of claim 11, wherein the monocyclic nitrogen-containing heterocyclyl($C_{1-4}$ alkyl) is a 5-membered monocyclic nitrogen-containing heterocyclyl($C_1$-4 alkyl) or a 6-membered monocyclic nitrogen-containing heterocyclyl($C_1$-4 alkyl).

13. The compound of claim 11, wherein the monocyclic nitrogen-containing heterocyclyl($C_{1-4}$ alkyl) is azepan-2-one($C_{1-4}$ alkyl), imidazolidin-2-one($C_{1-4}$ alkyl), tetrahydropyrimidin-2-one($C_{1-4}$ alkyl), pyrrolidin-2-one($C_{1-4}$ alkyl), piperidin-2-one($C_{1-4}$ alkyl), pyrazolidin-3-one ($C_{1-4}$ alkyl), morpholin-3-one($C_{1-4}$ alkyl), oxazolidin-4-one($C_{1-4}$ alkyl) 1,4-oxazepan-3-one($C_{1-4}$ alkyl) or morpholin-3-one($C_{1-4}$ alkyl).

14. The compound of claim 1, wherein $R^3$ is

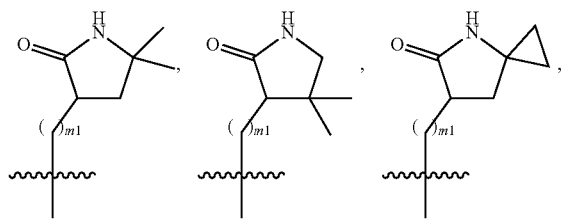

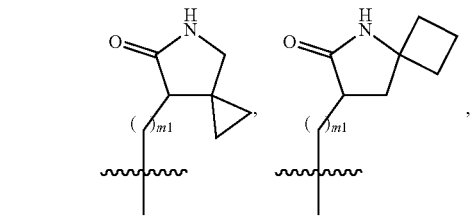

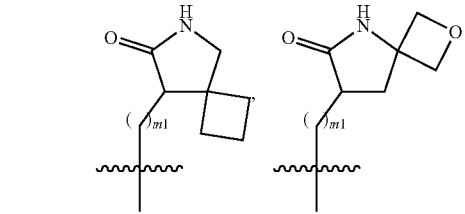

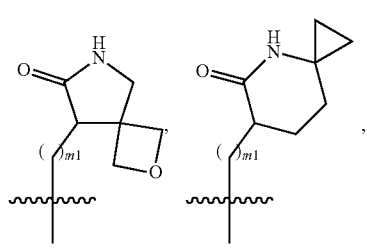

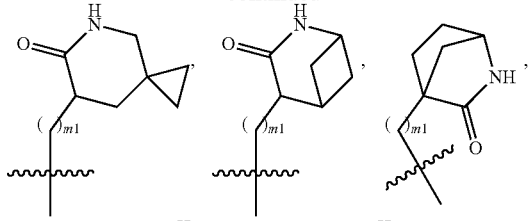

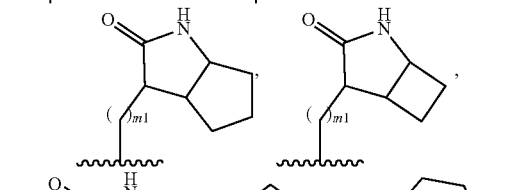

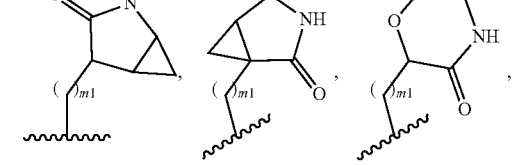

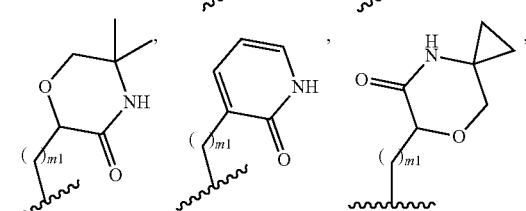

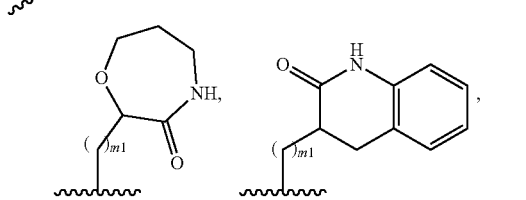

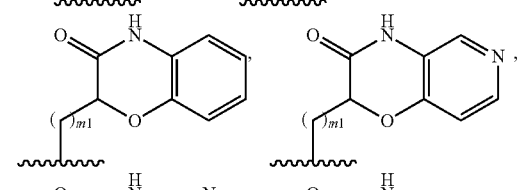

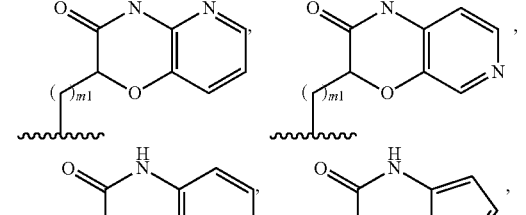

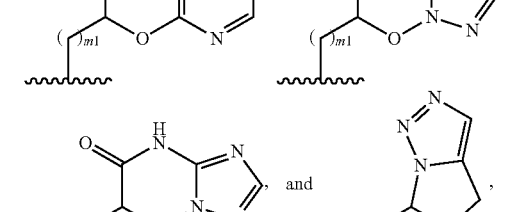

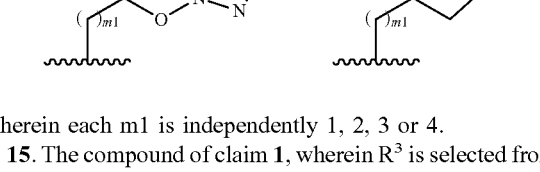

wherein each m1 is independently 1, 2, 3 or 4.

15. The compound of claim 1, wherein $R^3$ is selected from the group consisting of:

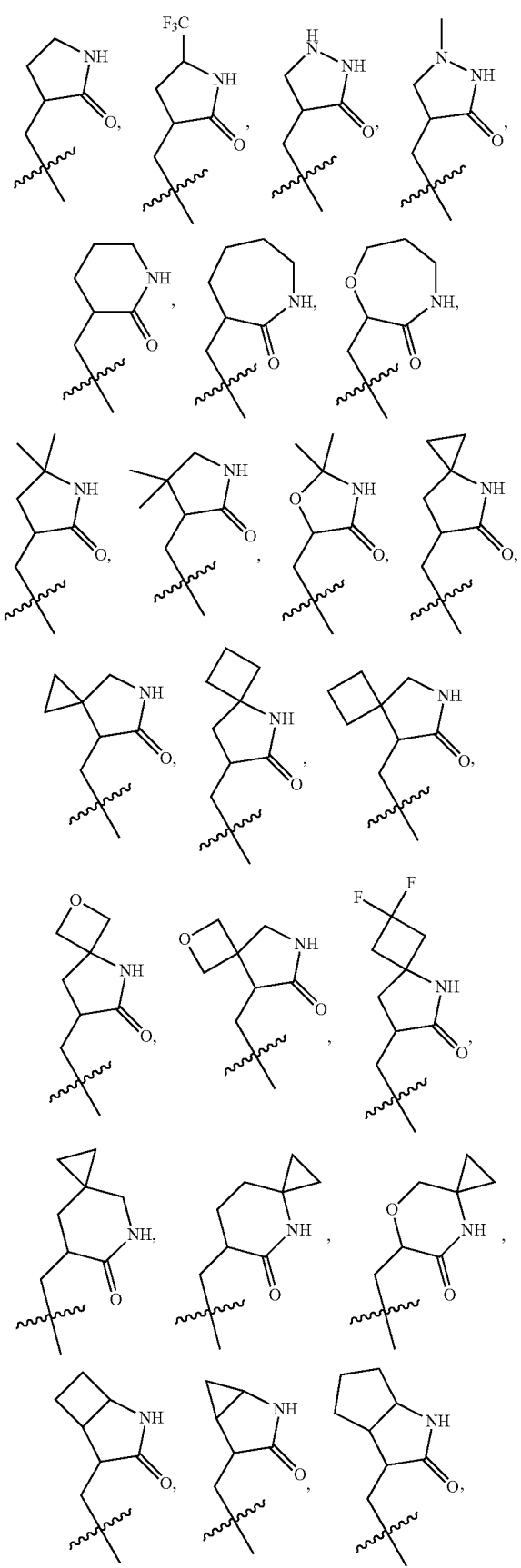
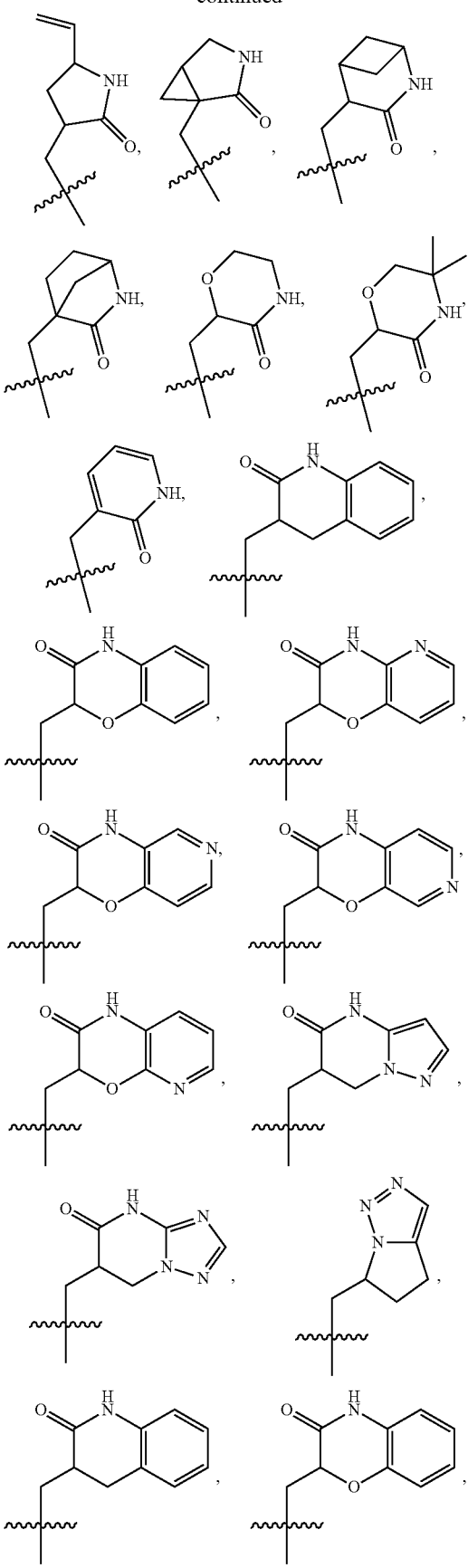

509
-continued
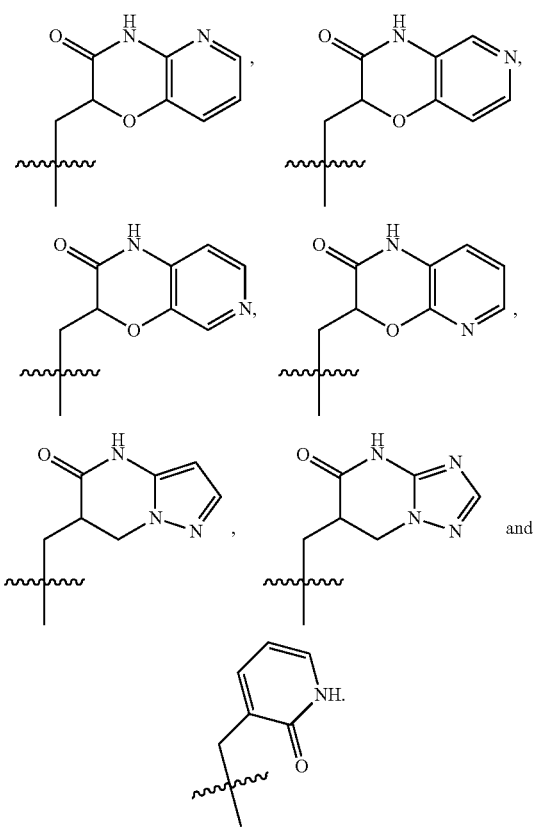
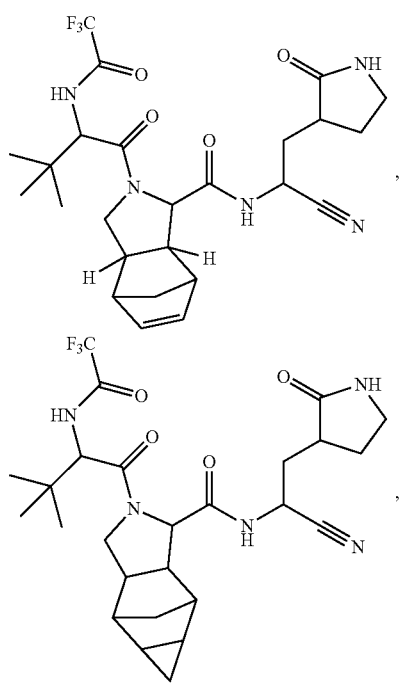
16. The compound of claim 1, wherein $R^2$ is hydrogen; and $R^4$ is hydrogen.
17. The compound of claim 1, wherein the compound is selected from the group consisting of:
510
-continued
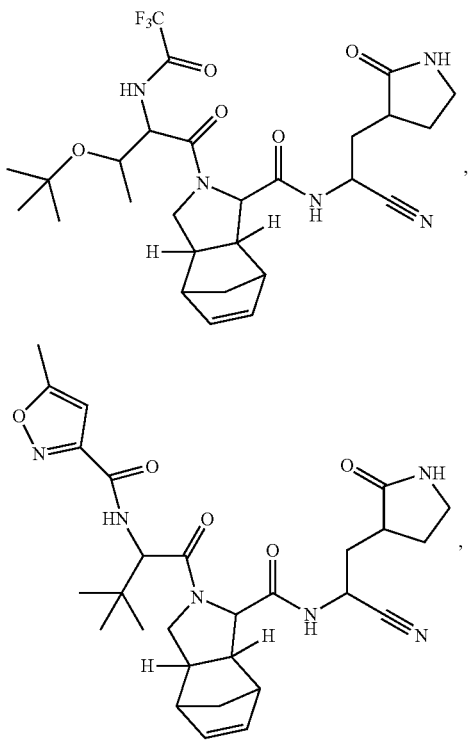
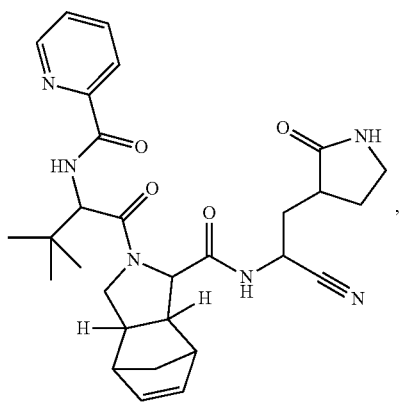
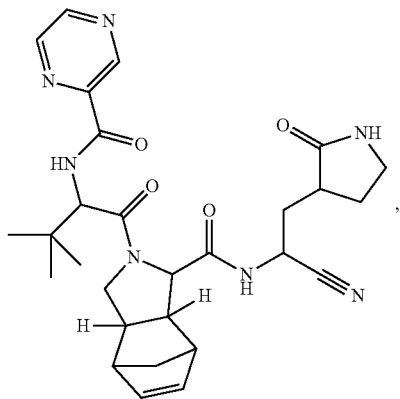

511
-continued
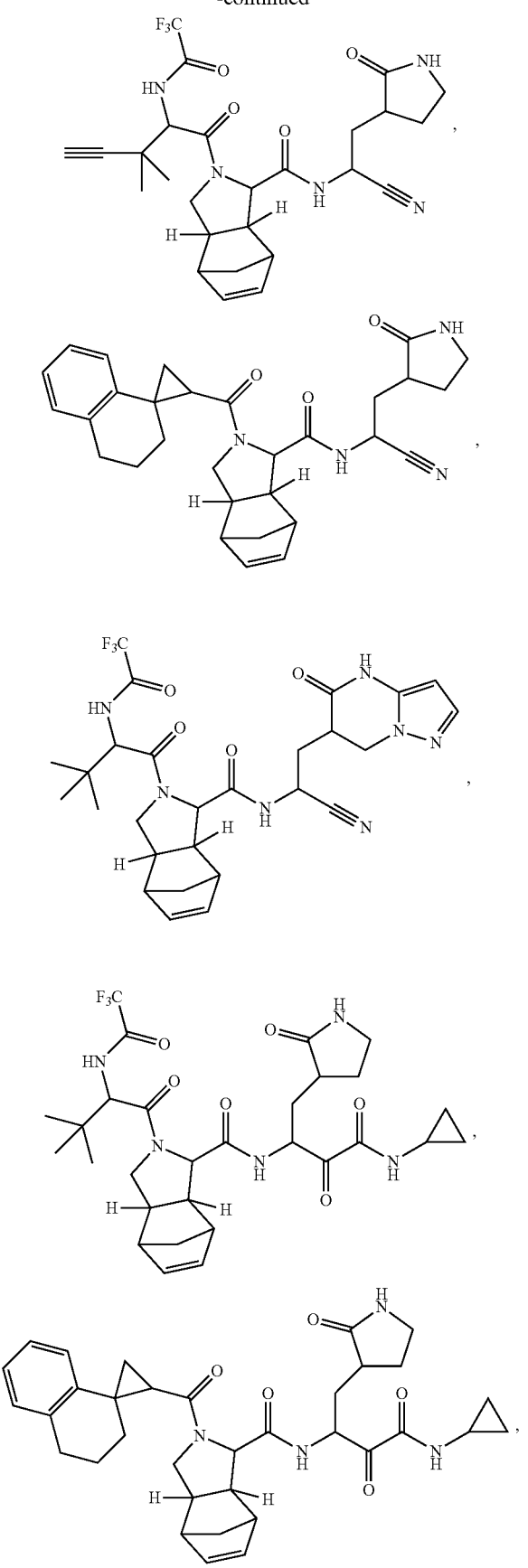
512
-continued
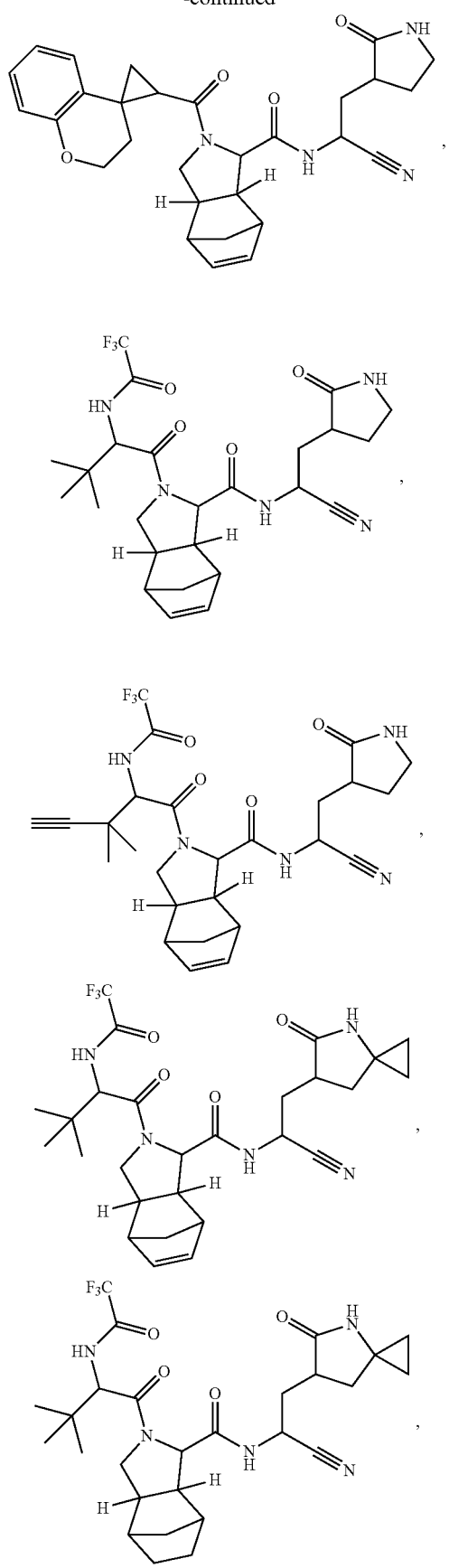

513
-continued
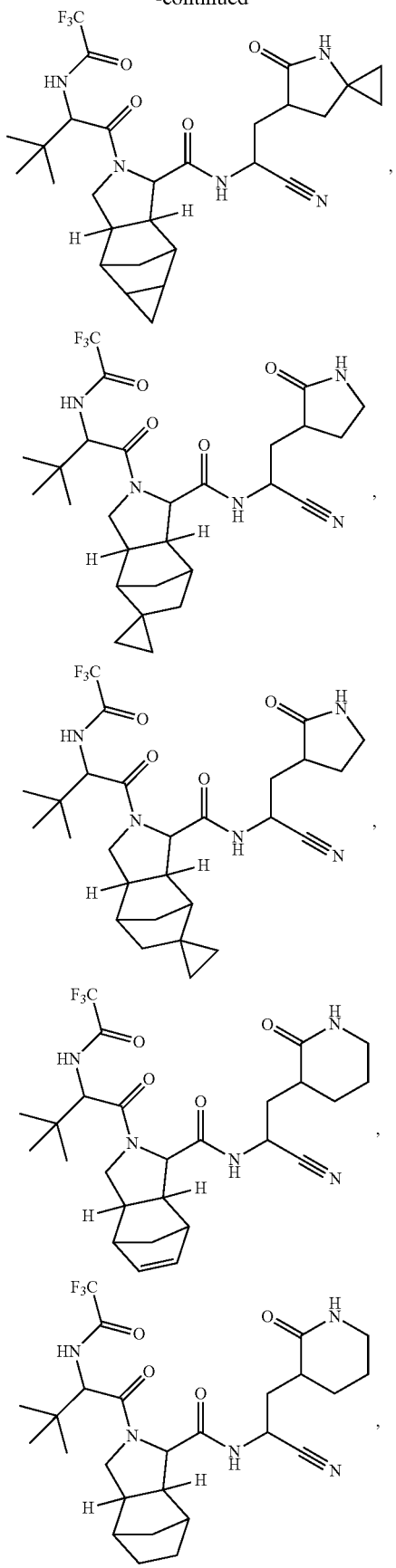
514
-continued
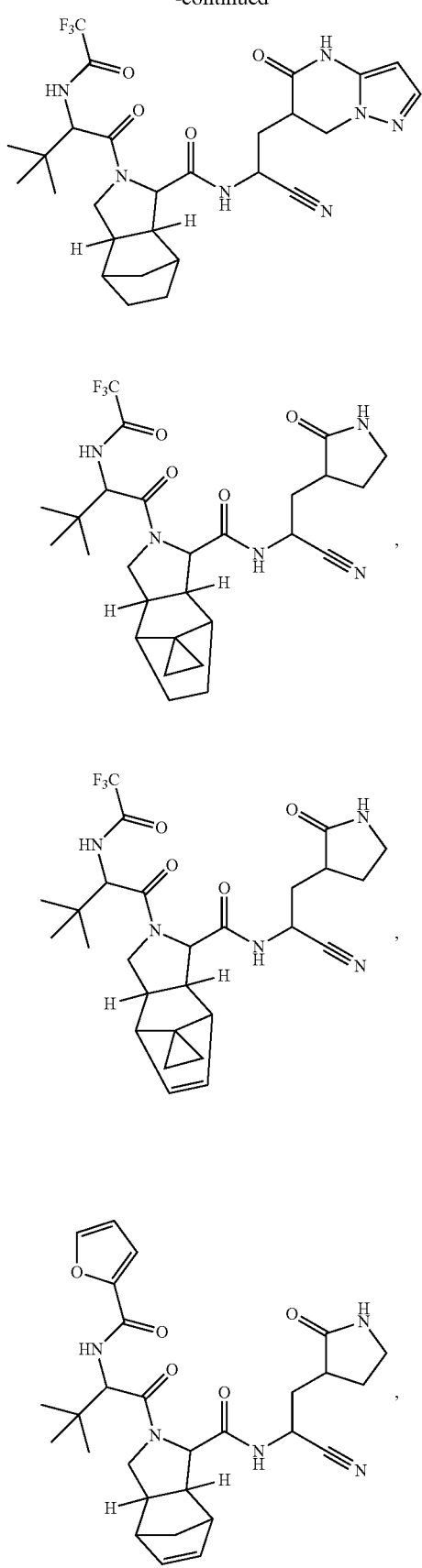

515
-continued
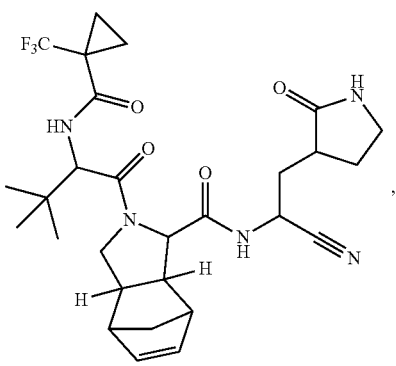
,
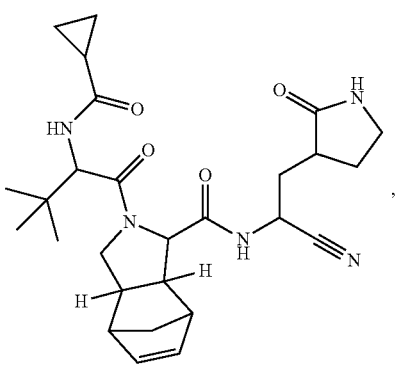
,
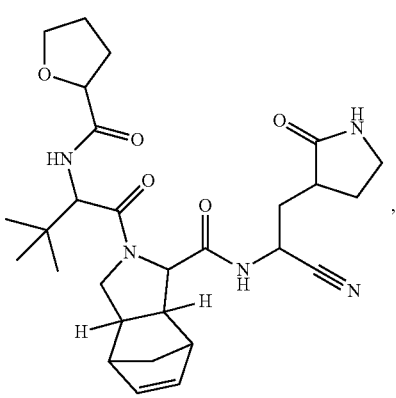
,
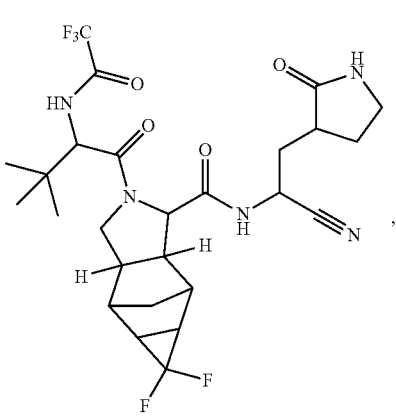
,
516
-continued
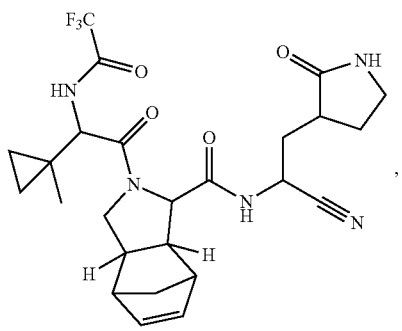
,
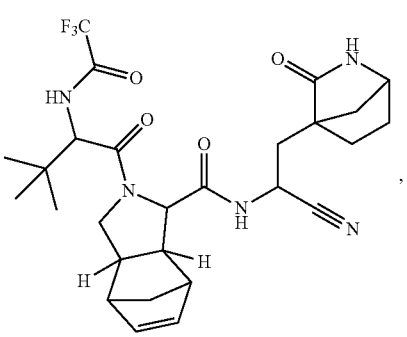
,
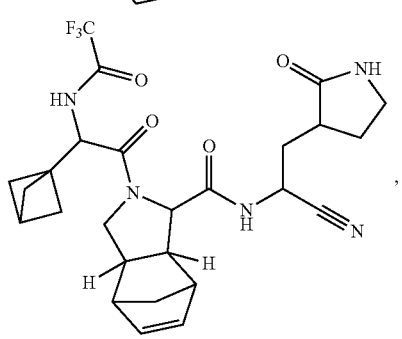
,
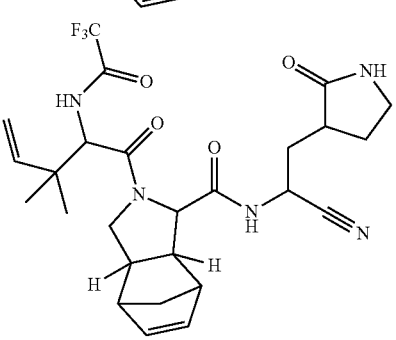
,
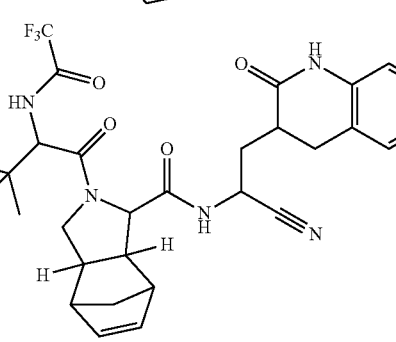
,

517
-continued
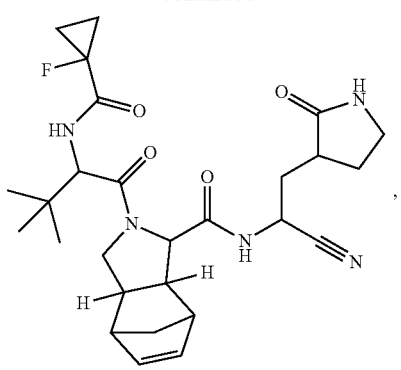
,
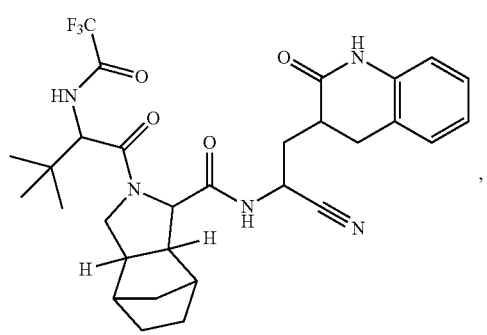
,
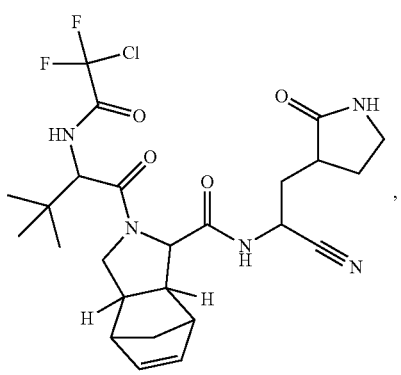
,
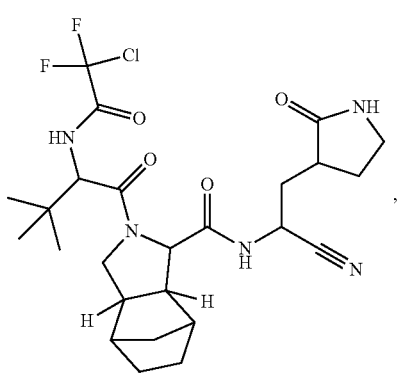
,
518
-continued
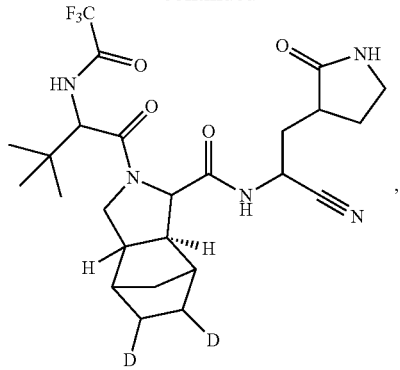
,
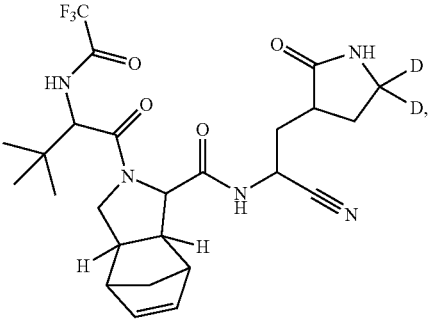
,
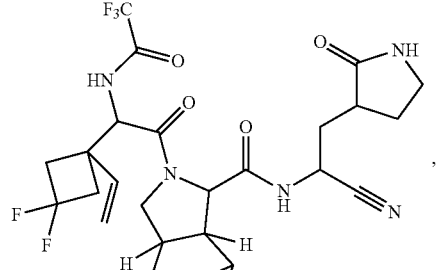
,
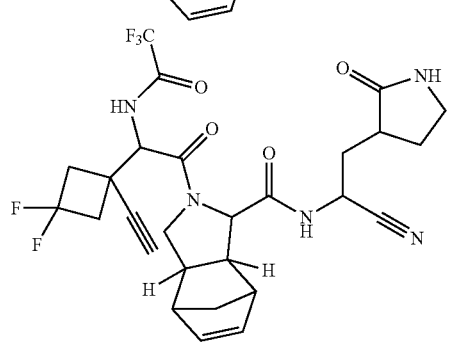
,
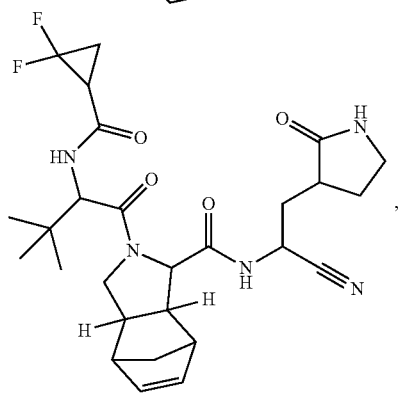
, 519
-continued
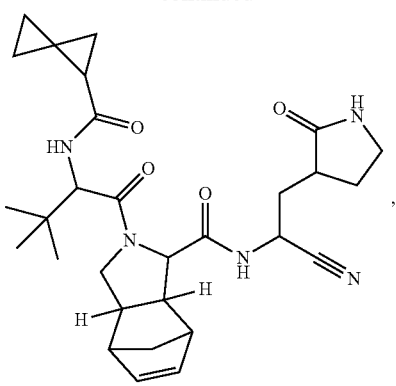
,
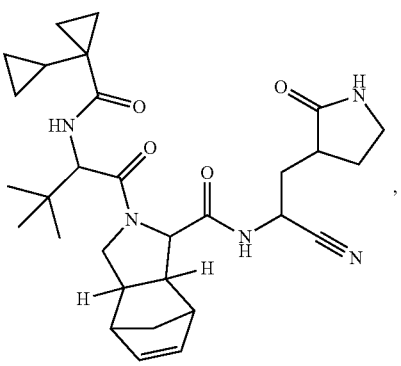
,
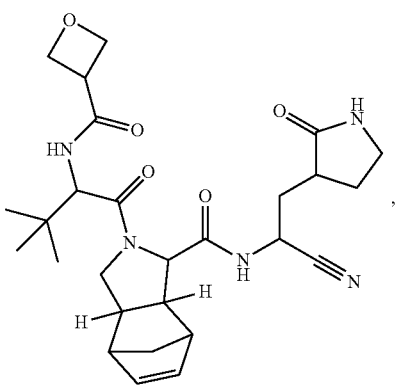
,
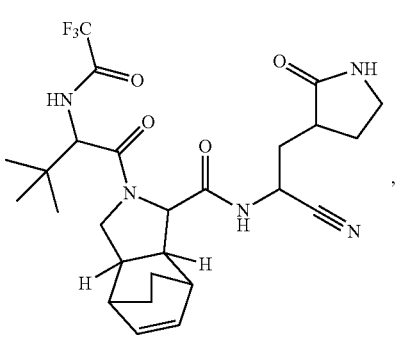
,
520
-continued
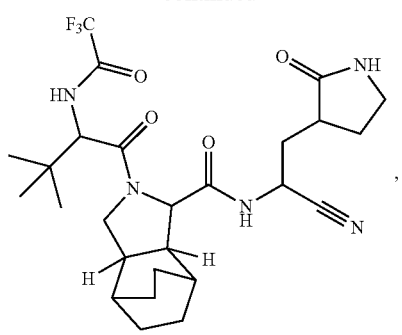
,
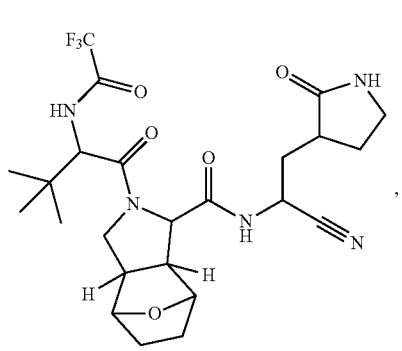
,
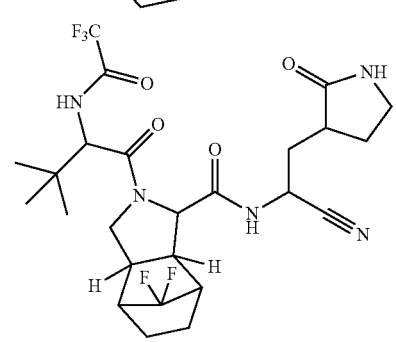
,
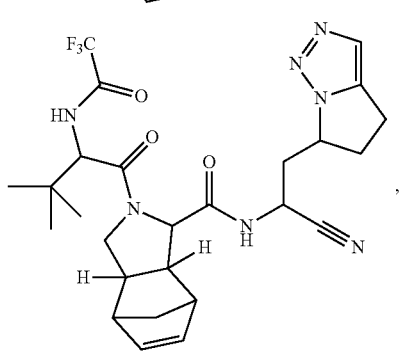
,
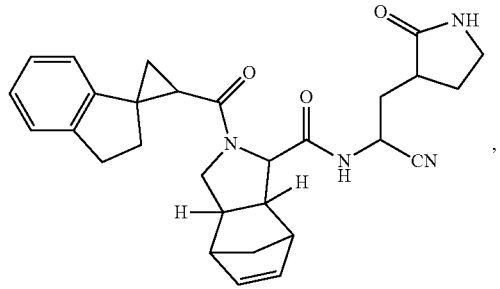
, 521
-continued
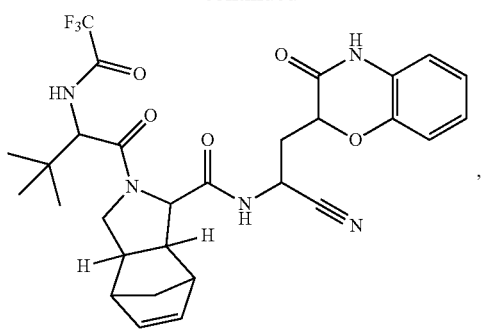
,
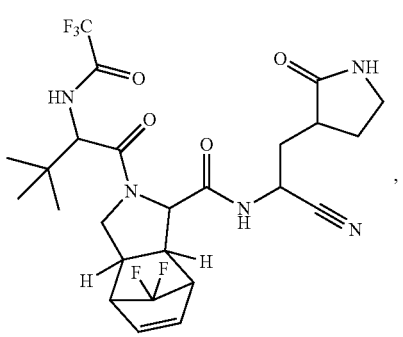
,
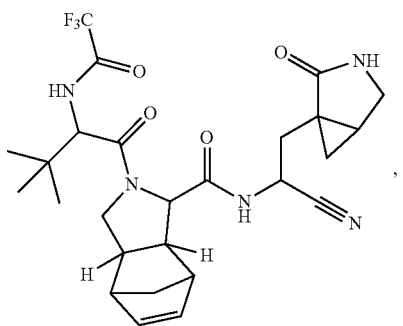
,
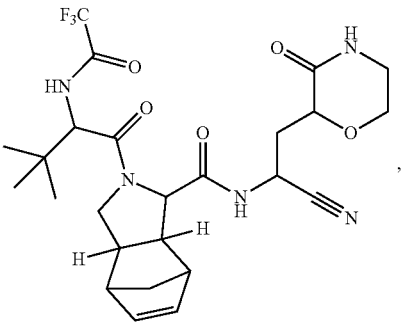
,
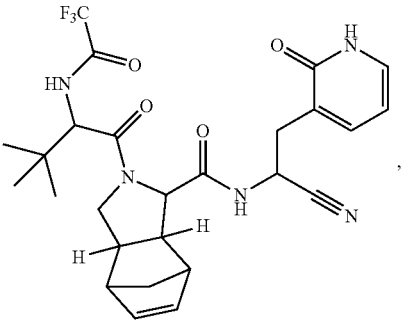
,
522
-continued
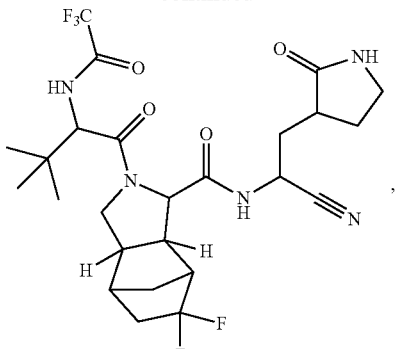
,
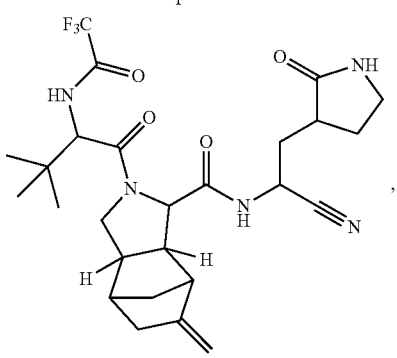
,
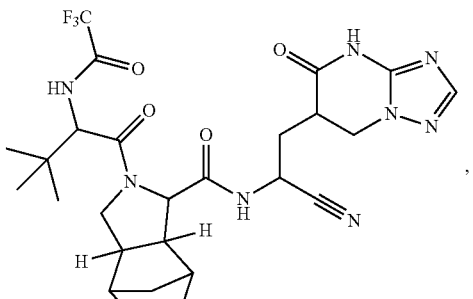
,
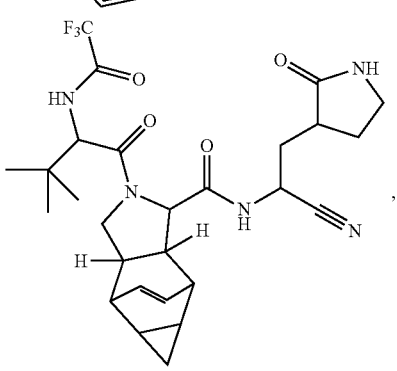
,
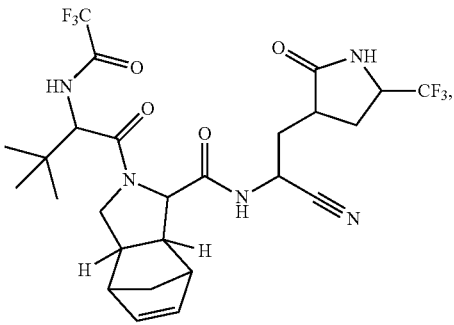
, 523
-continued
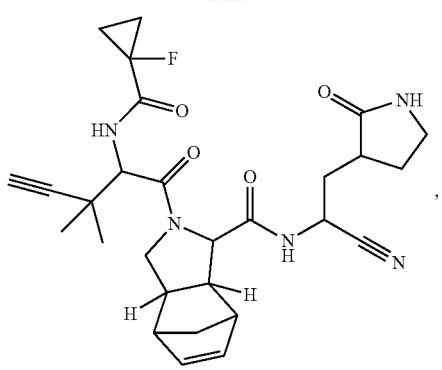
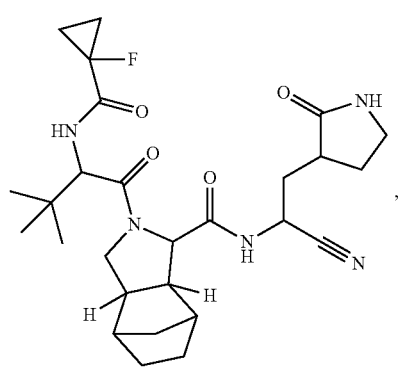
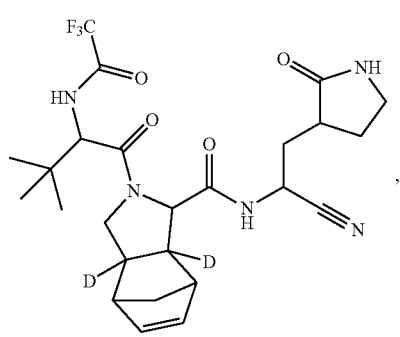
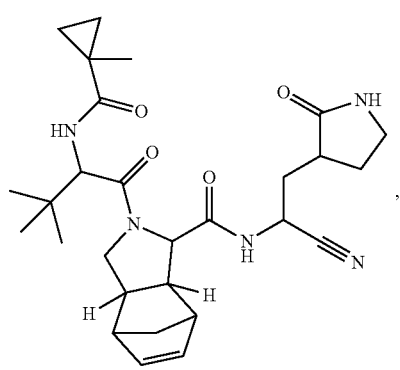
524
-continued
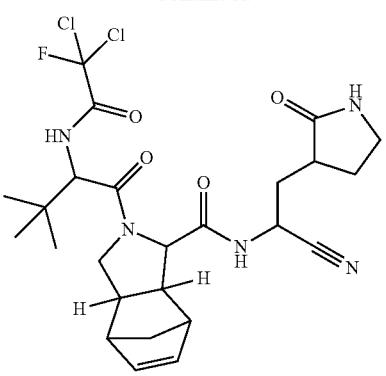
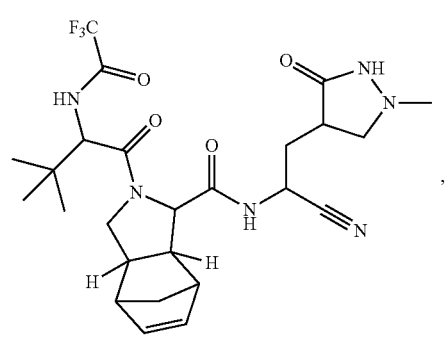
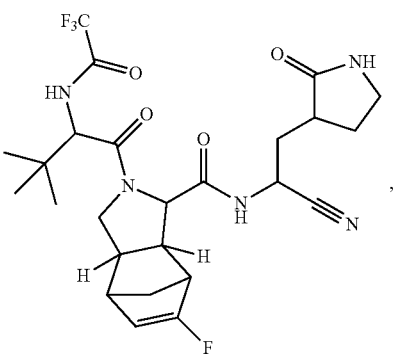
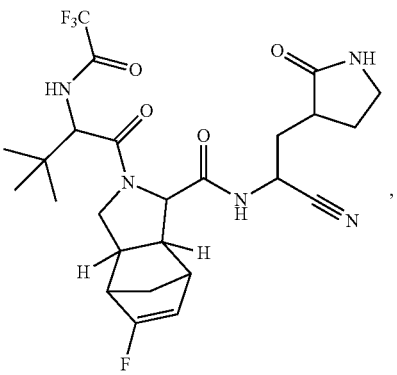

525
-continued
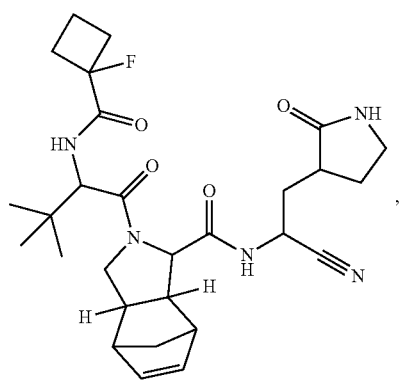
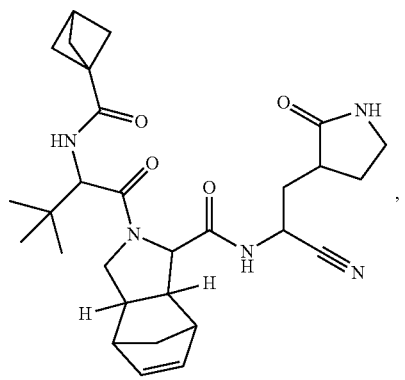
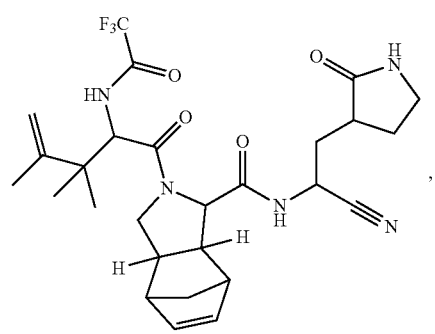
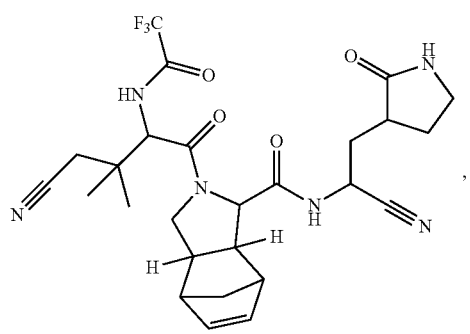
526
-continued
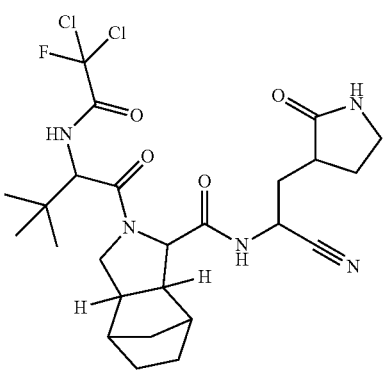
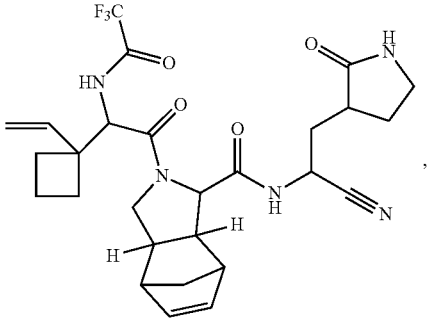
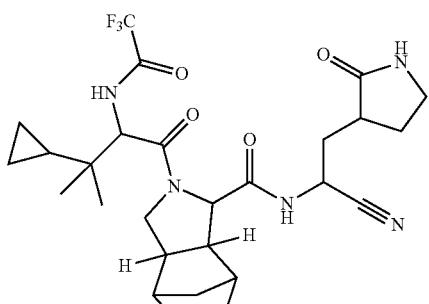
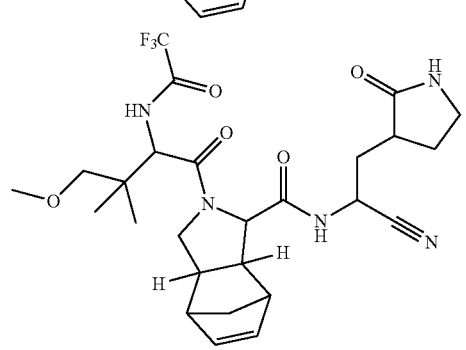
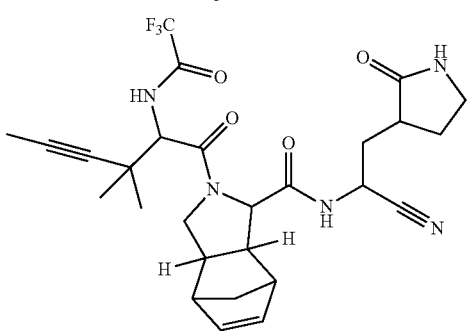

527
-continued
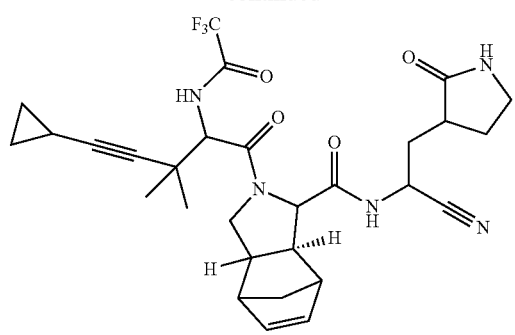
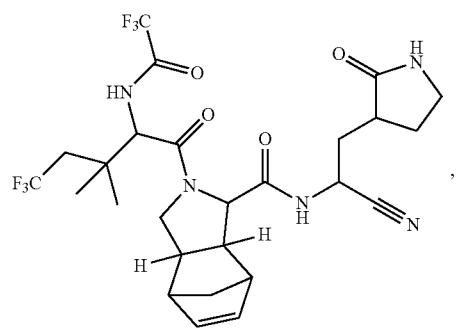
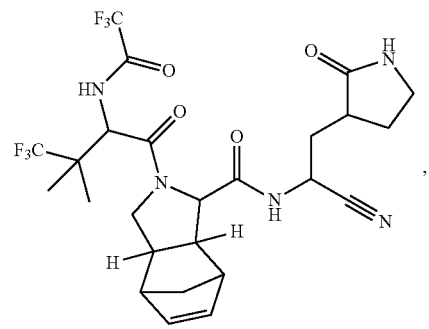
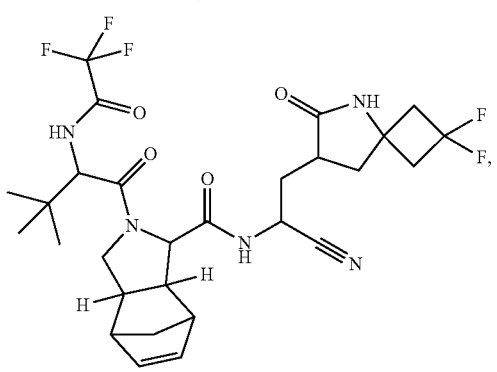
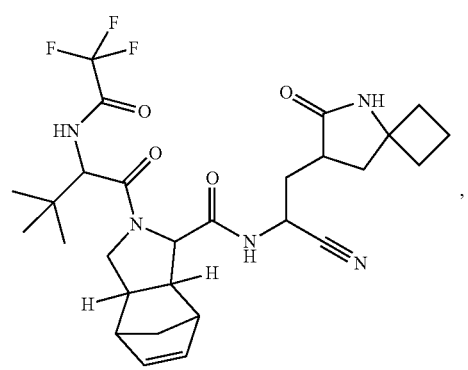
528
-continued
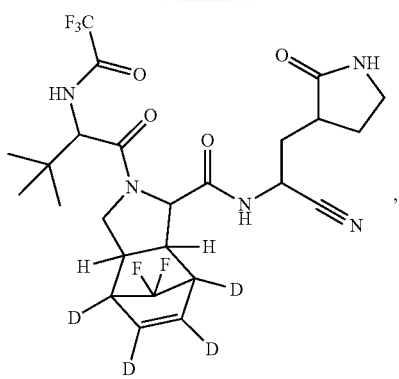
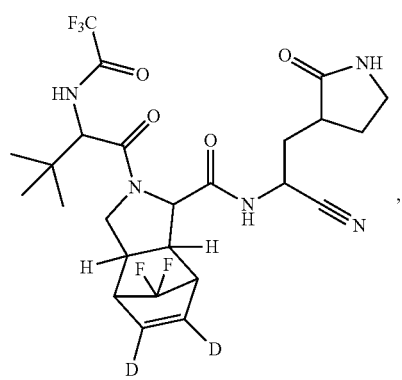
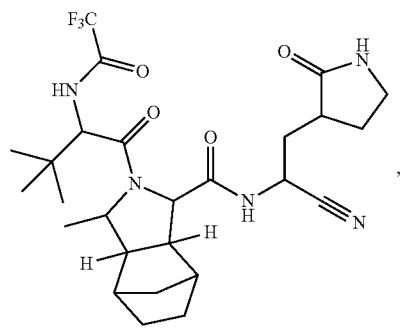
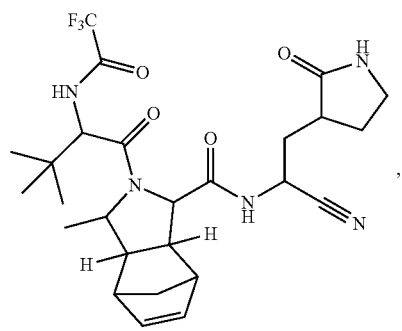

529
-continued
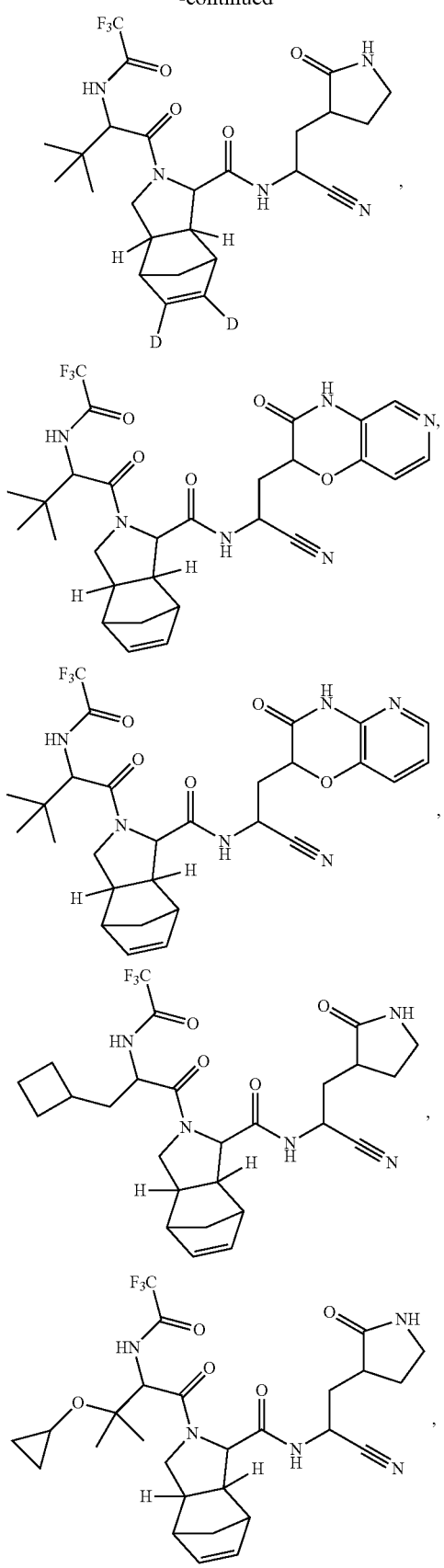
530
-continued
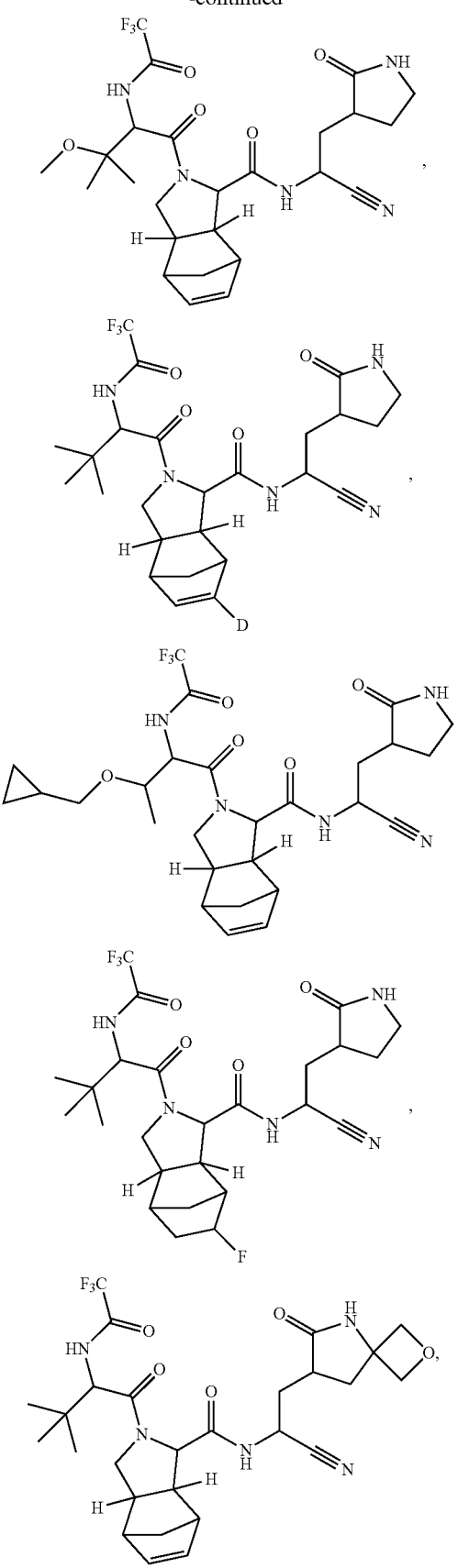

531
-continued
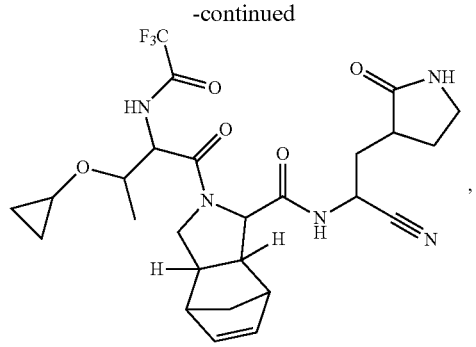
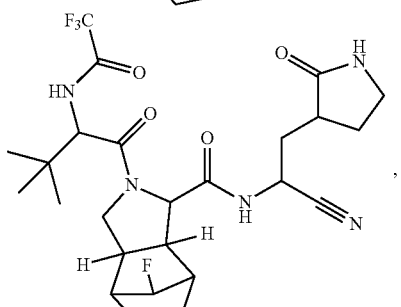
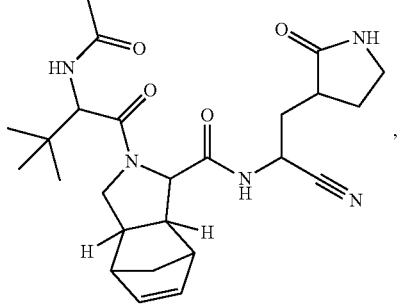
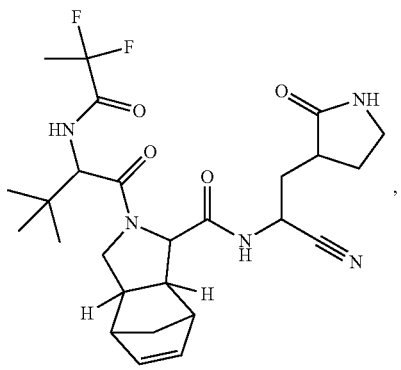
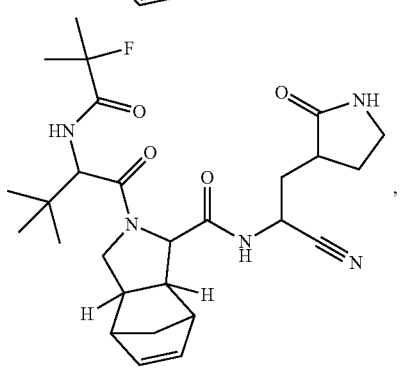
532
-continued
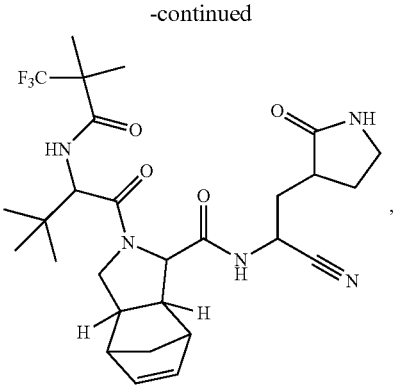
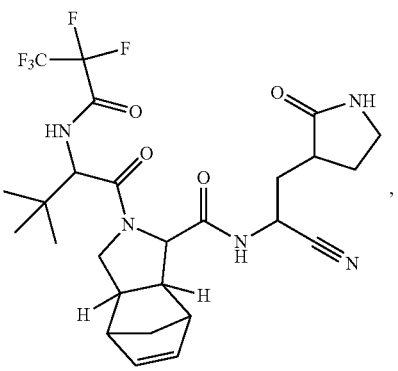
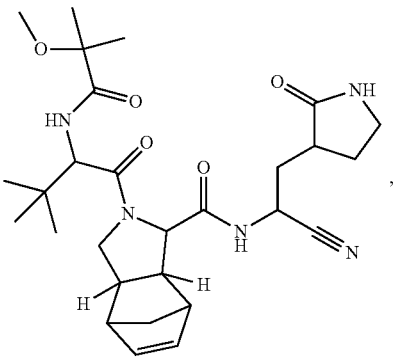
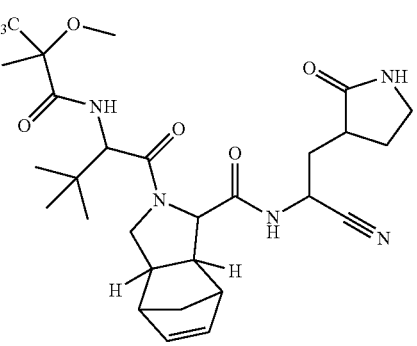

533
-continued
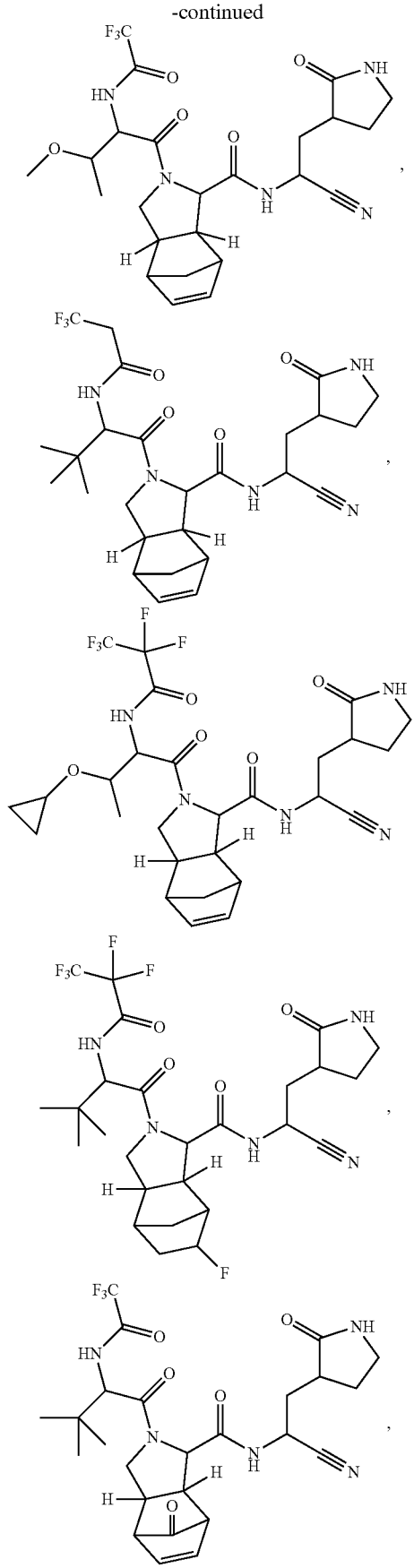
534
-continued
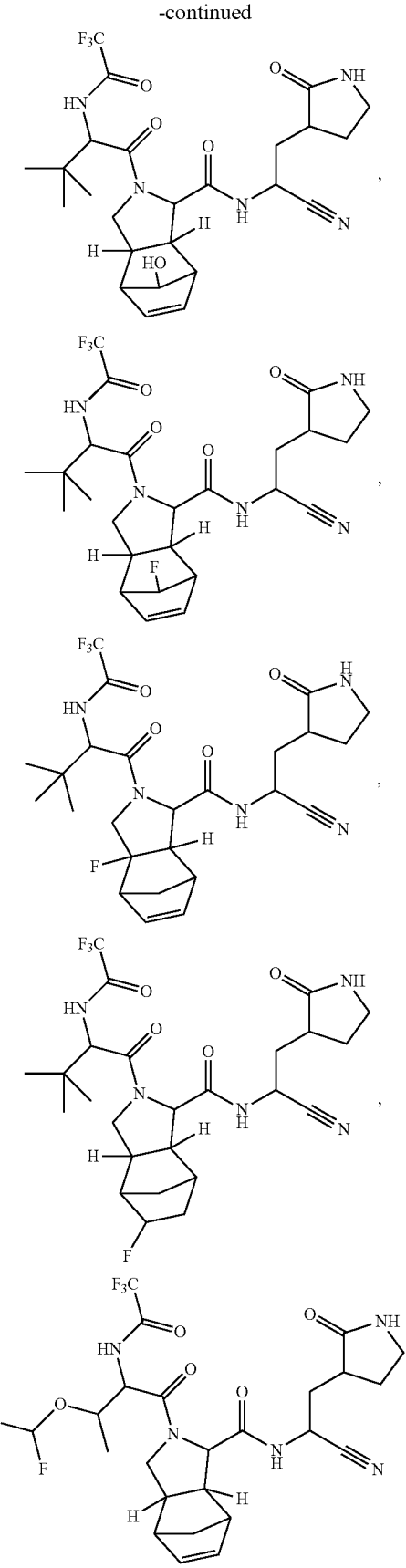

535
-continued
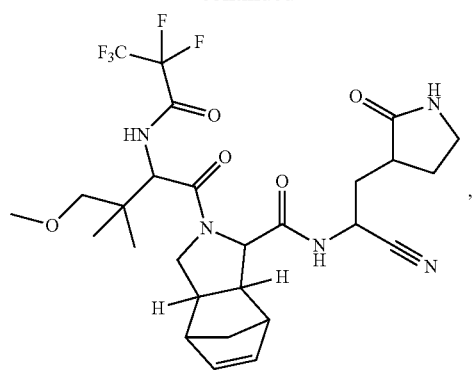
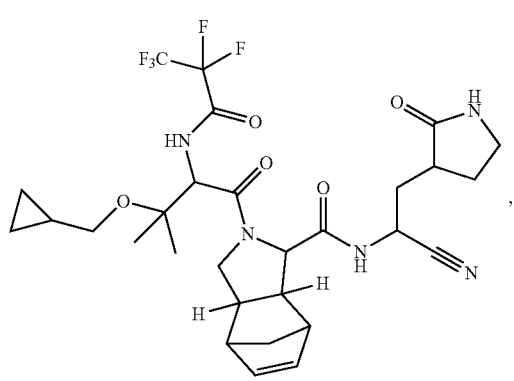
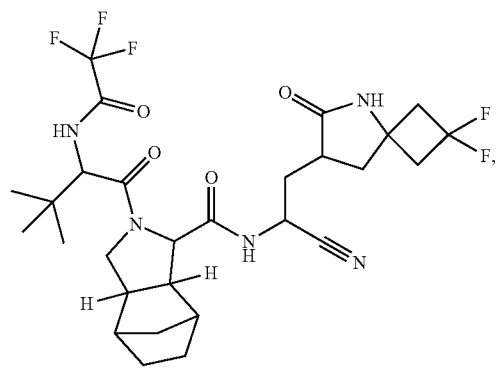
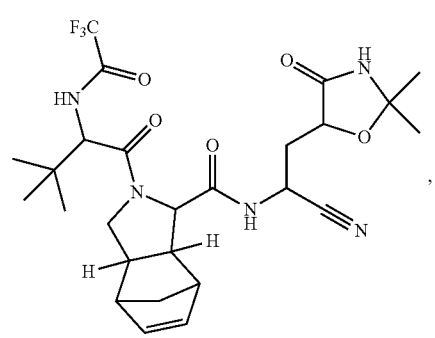
536
-continued
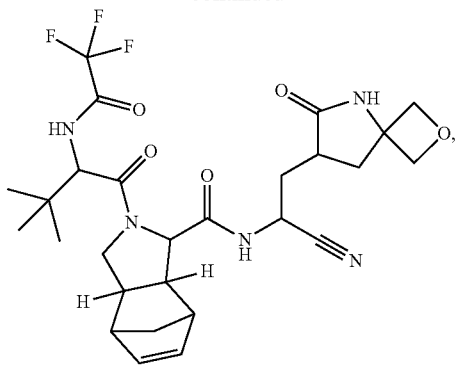
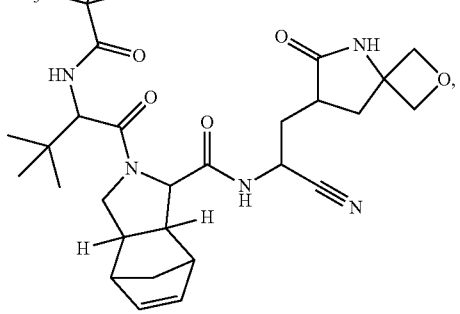
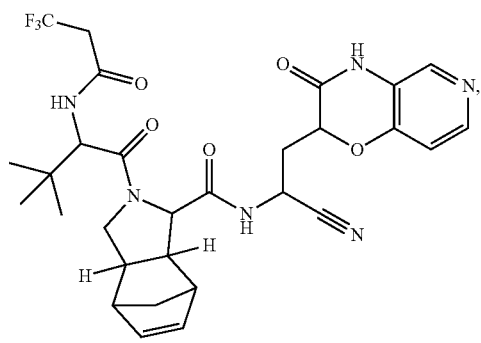
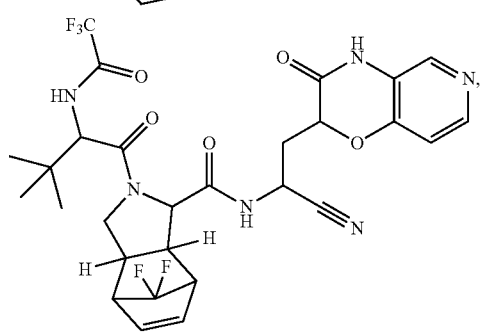
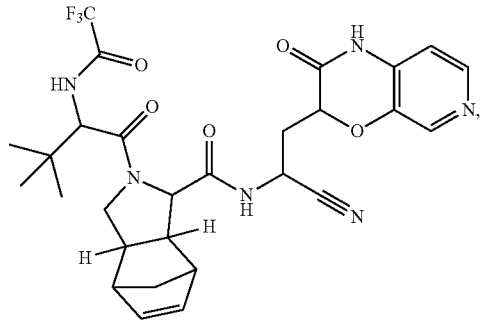

-continued
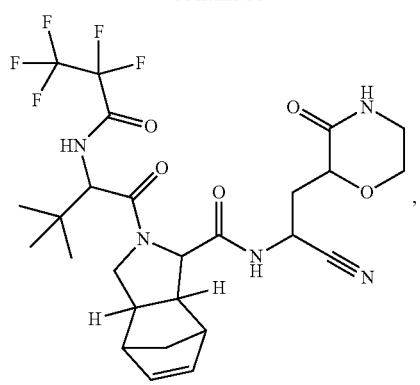
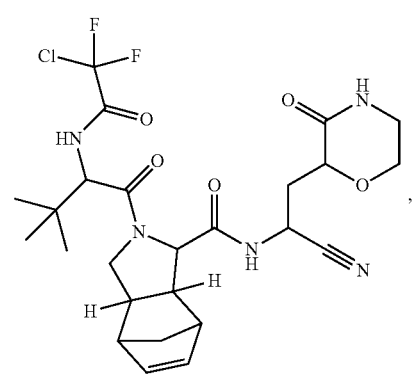
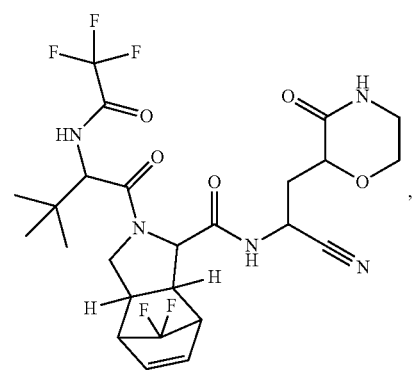
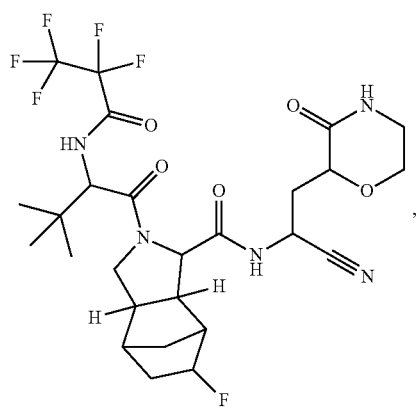
-continued
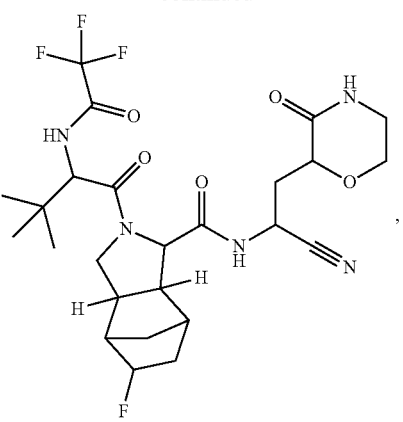
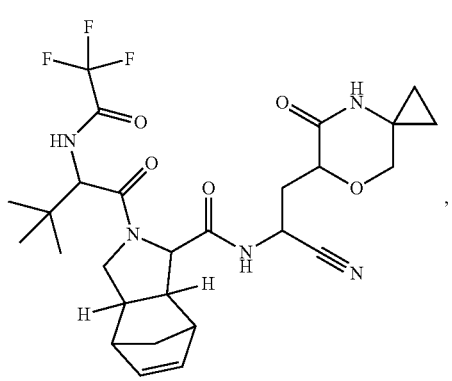
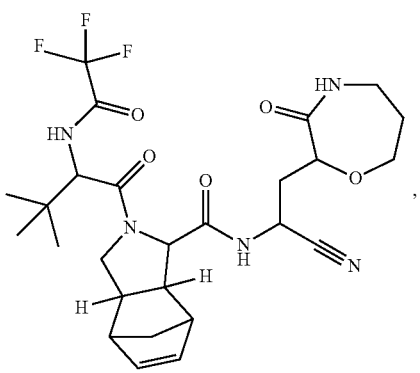
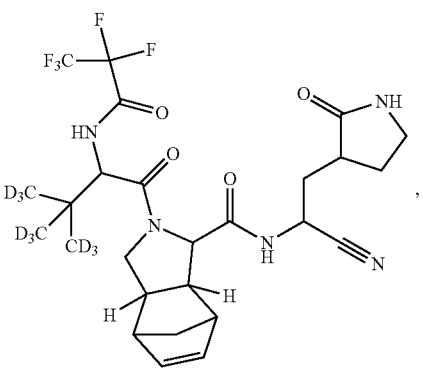

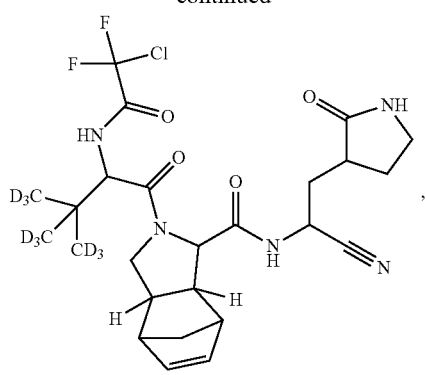
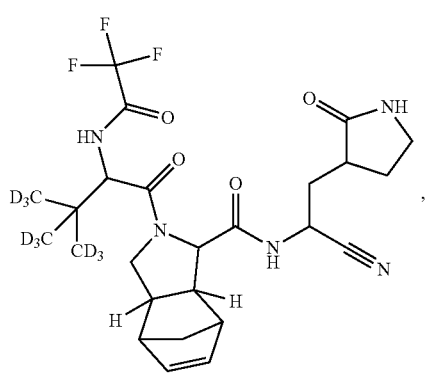
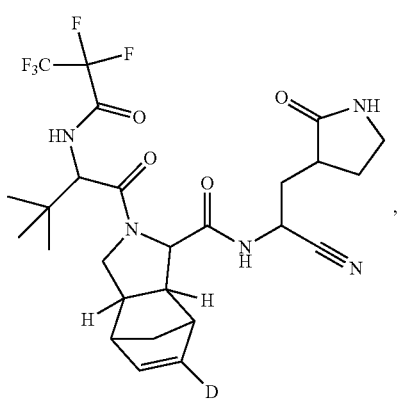
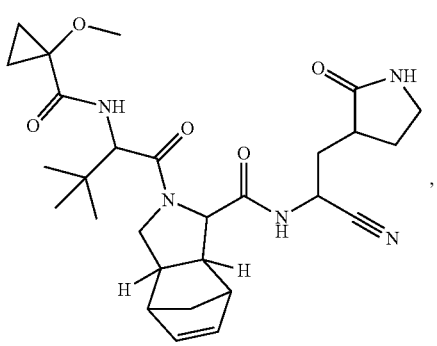
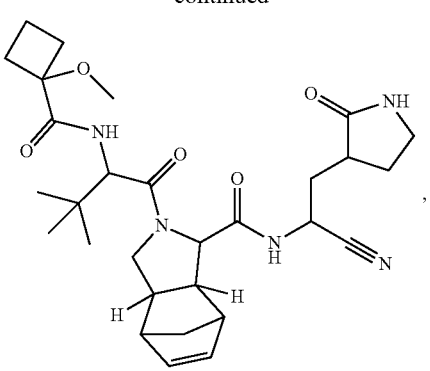
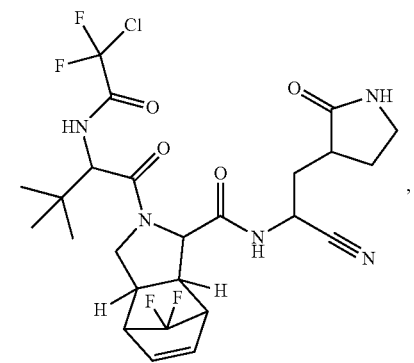
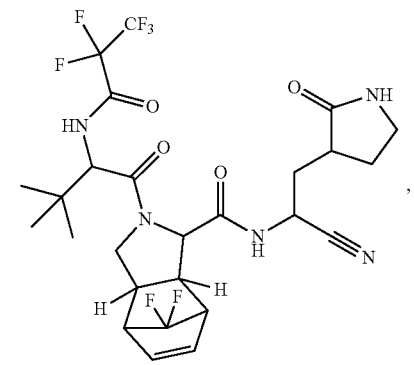
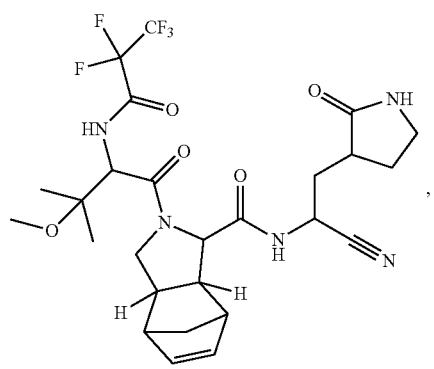

541
-continued
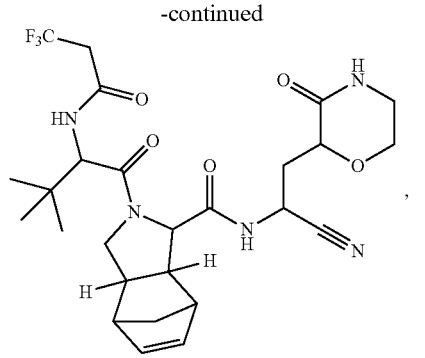
,
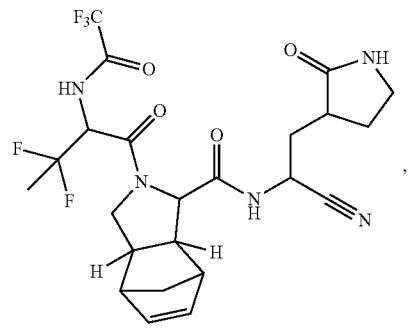
,
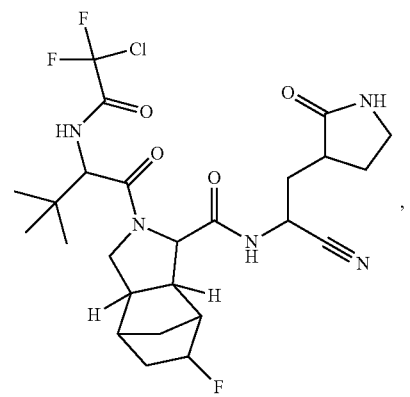
,
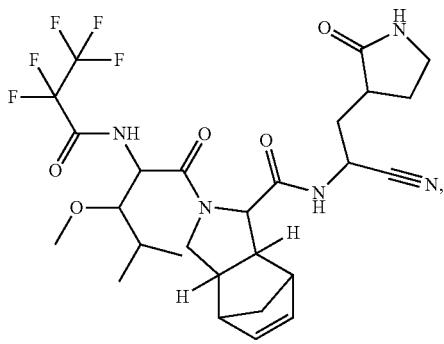
,
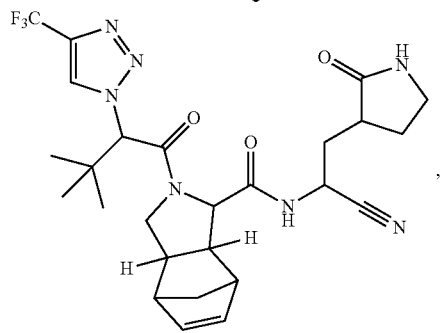
,
542
-continued
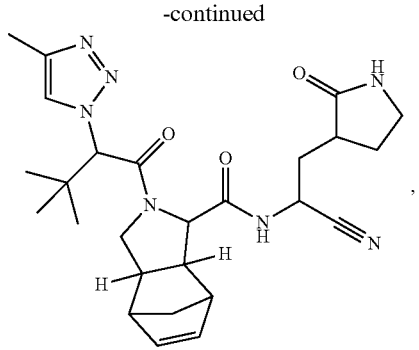
,
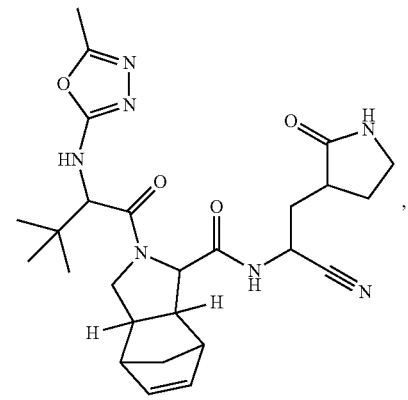
,
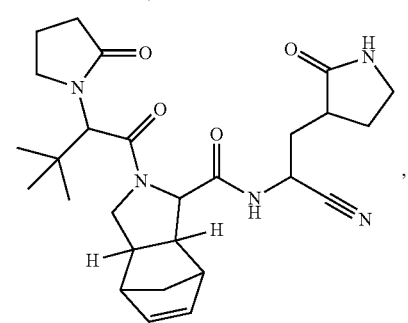
,
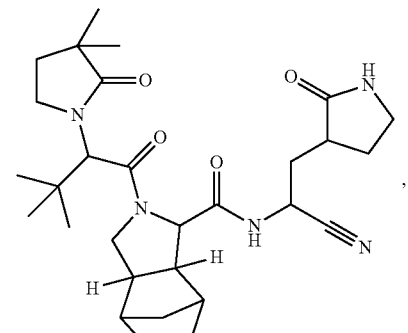
,
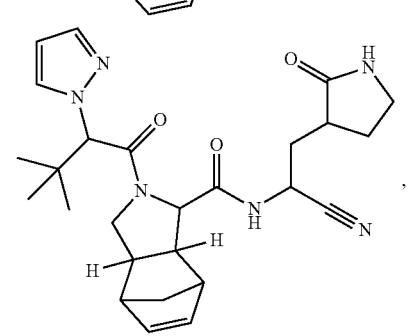
, 543
-continued
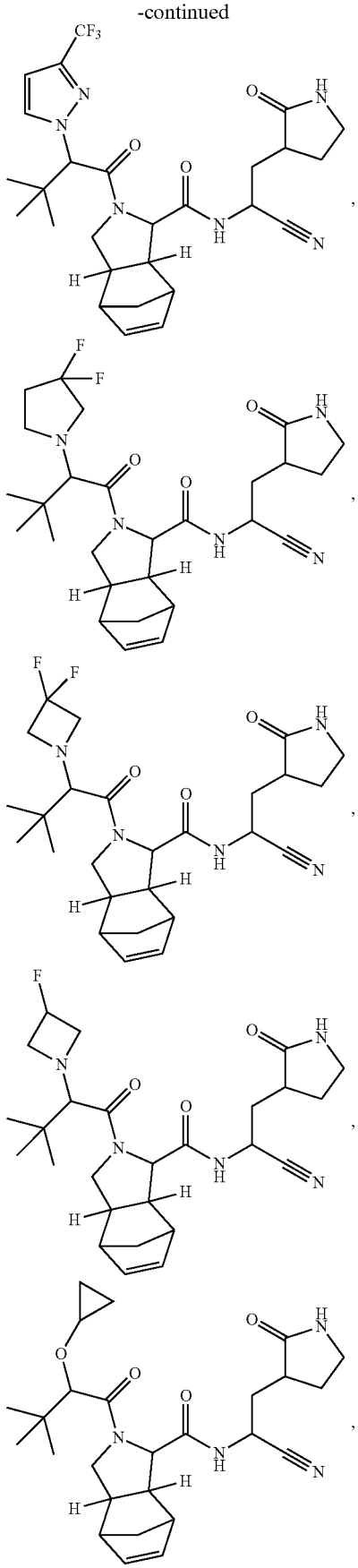
544
-continued
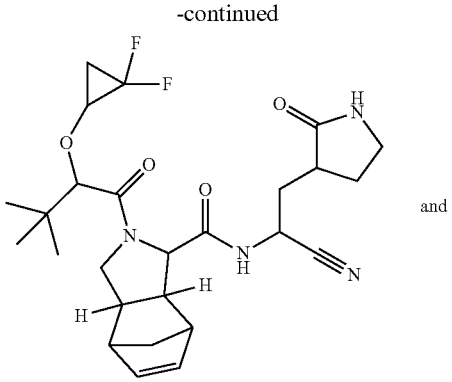
and
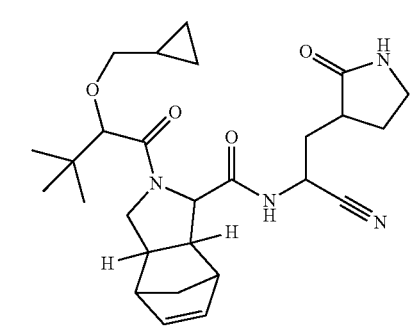
or a pharmaceutically acceptable salt of any of the foregoing.
18. The compound of claim 1, wherein the compound is selected from the group consisting of:
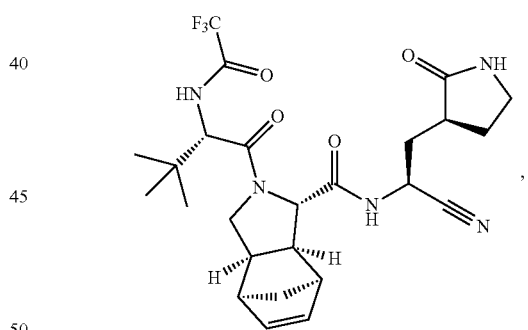
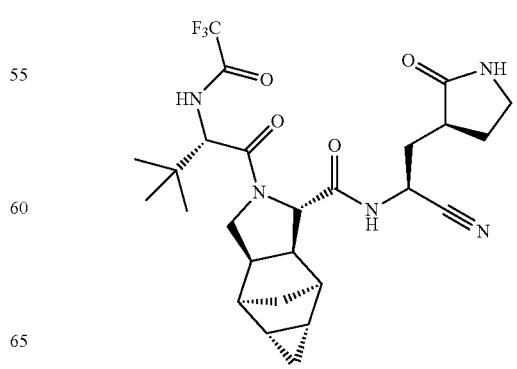

545
-continued
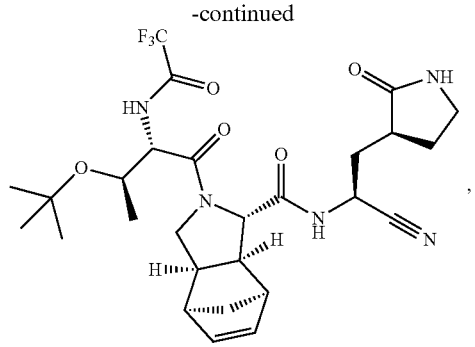
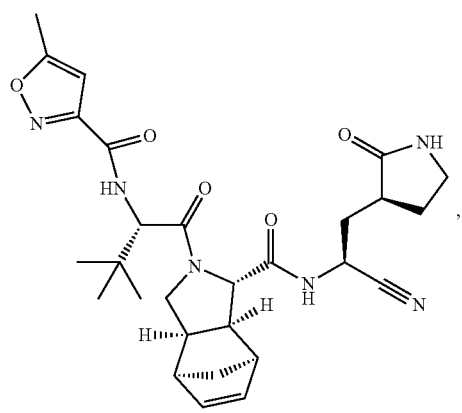
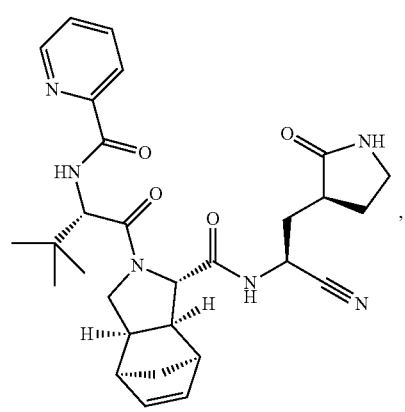
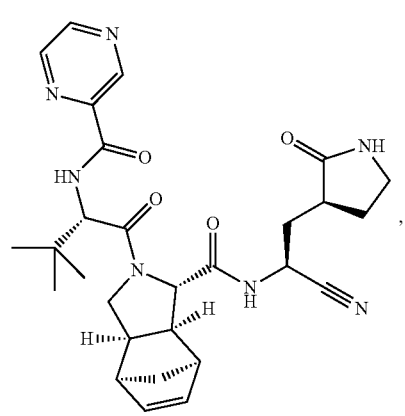
546
-continued
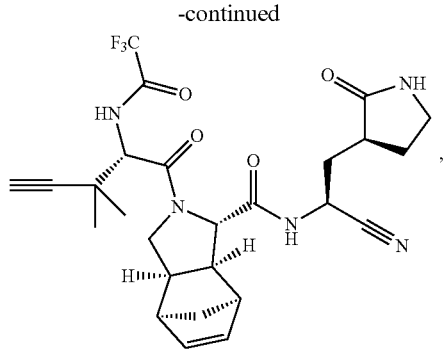
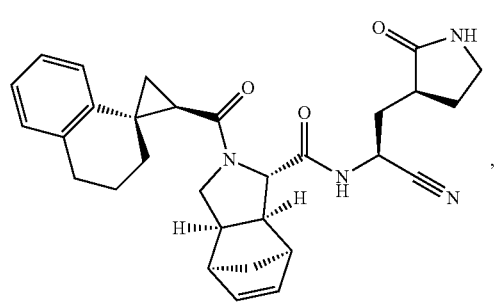
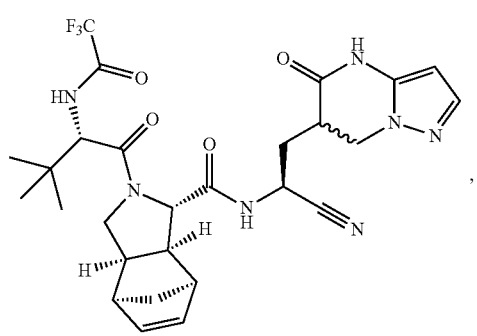
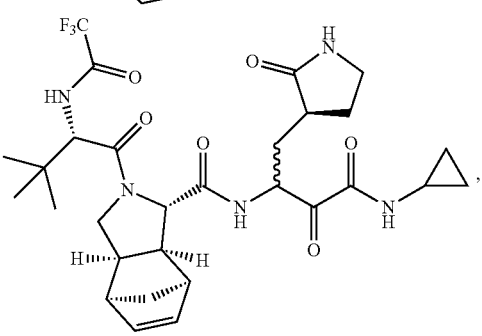
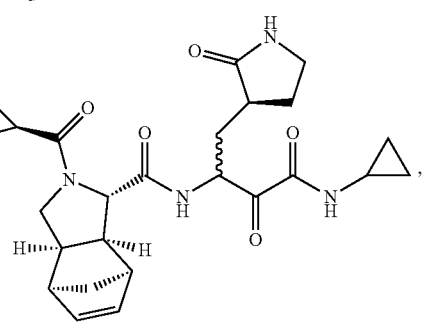

547
-continued
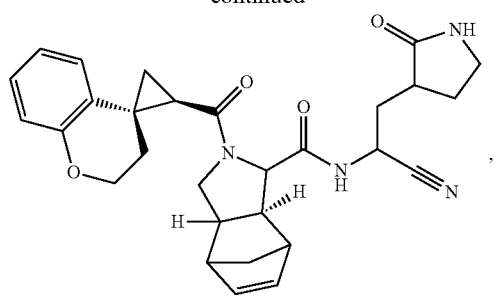
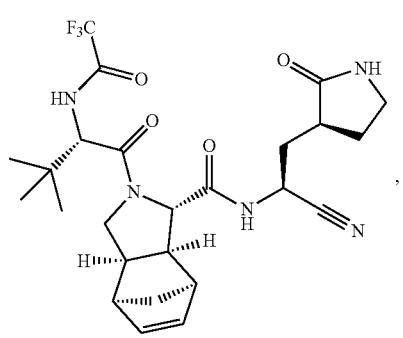
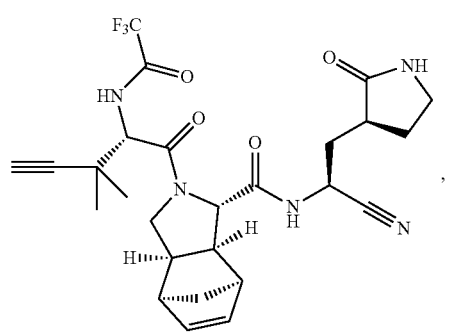
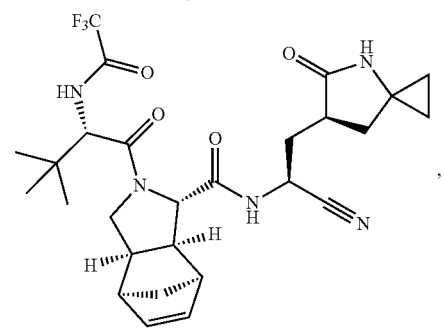
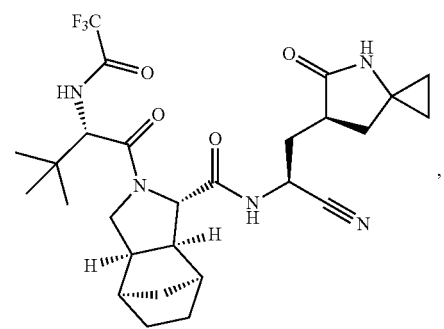
548
-continued
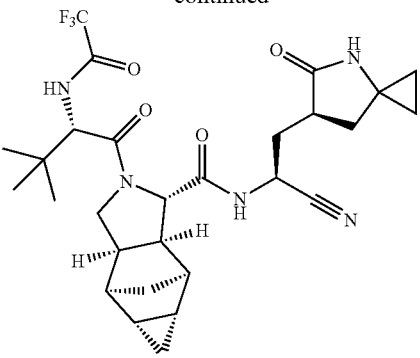
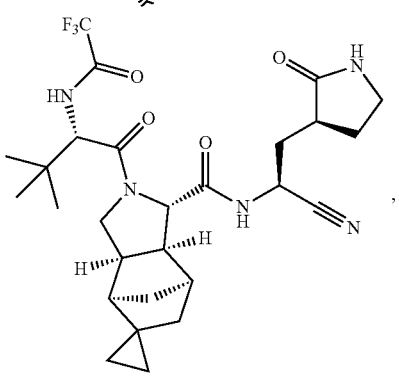
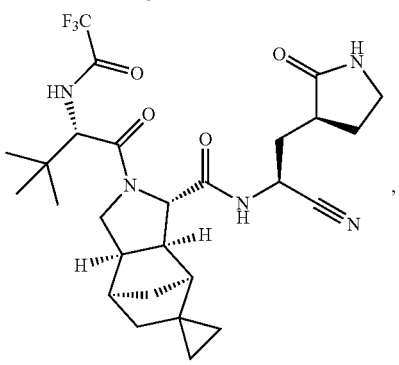
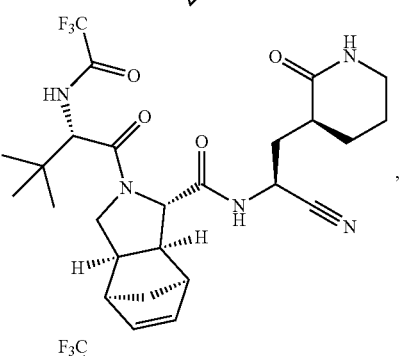
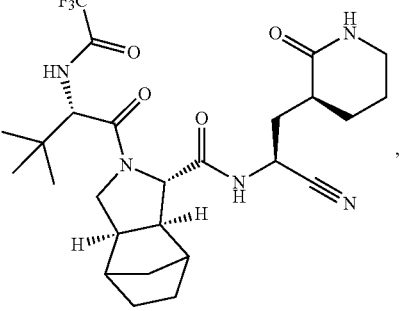

549
-continued
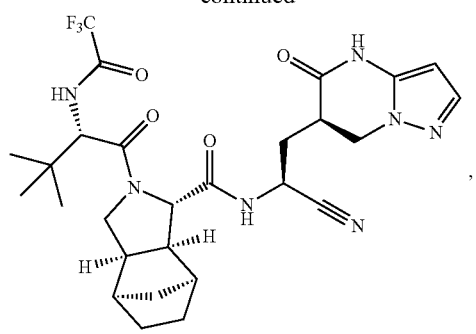
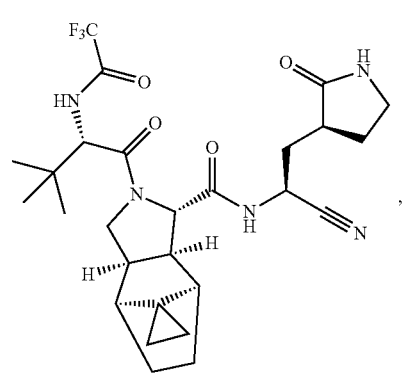
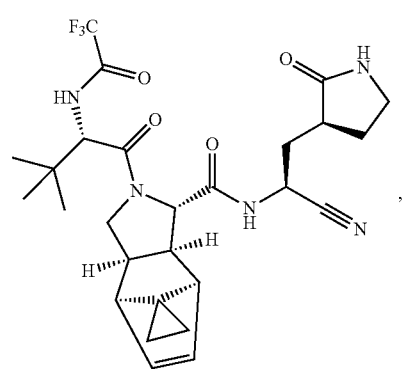
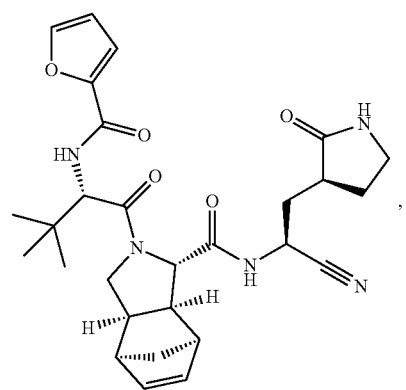
550
-continued
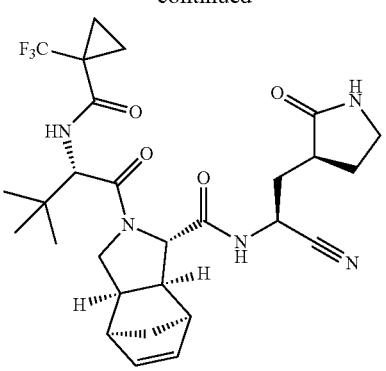
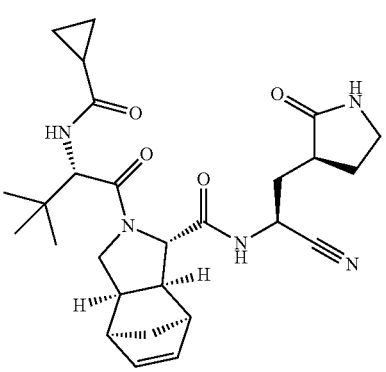
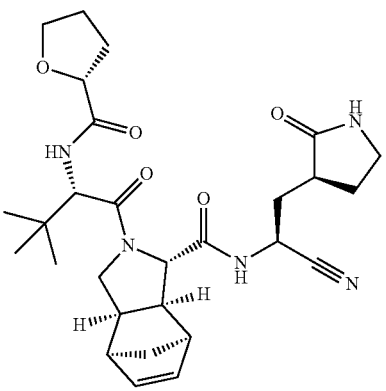
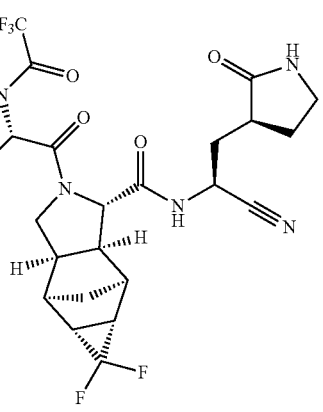

551
-continued
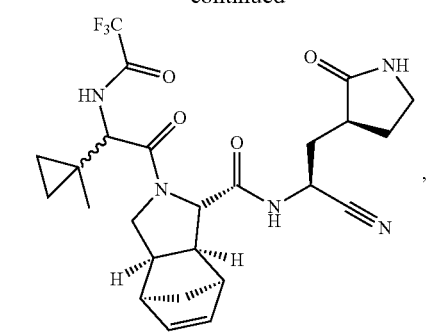
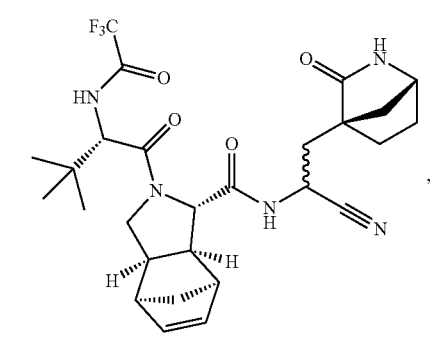
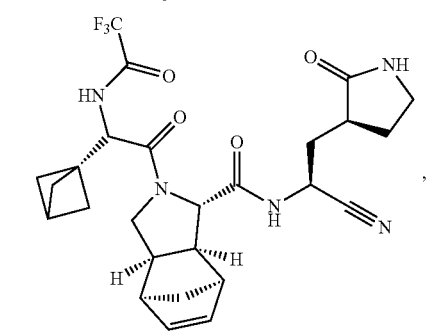
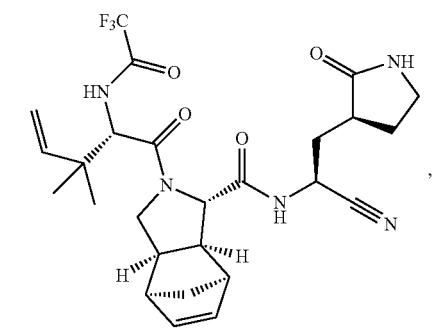
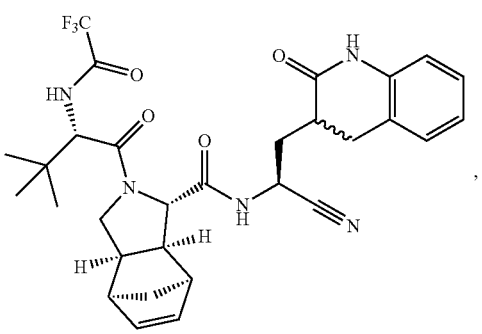
552
-continued
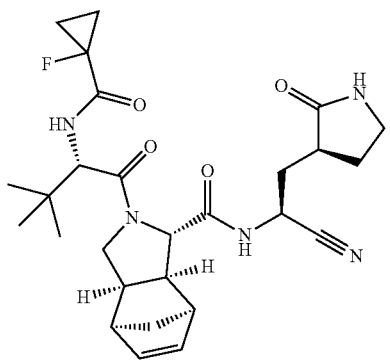
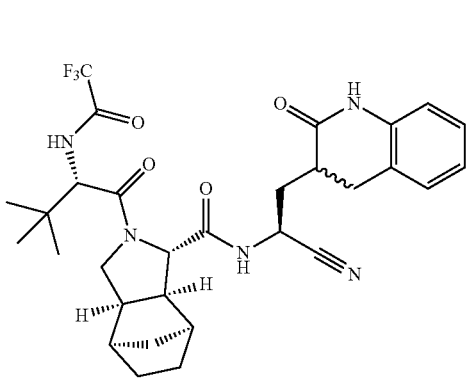
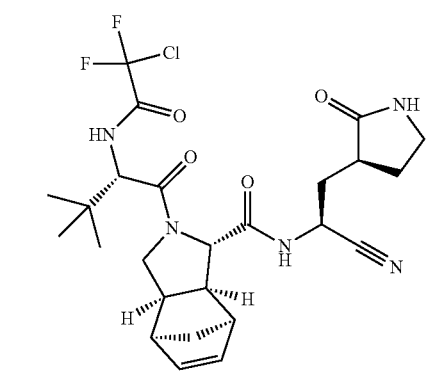
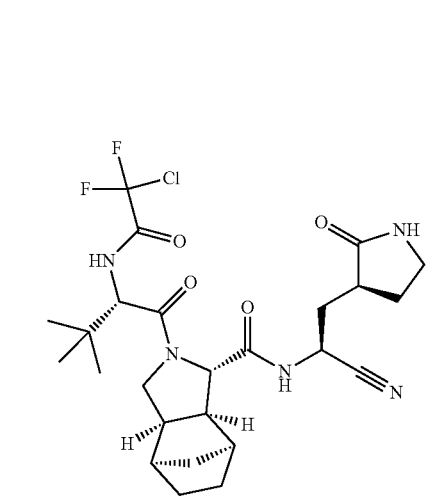

553
-continued
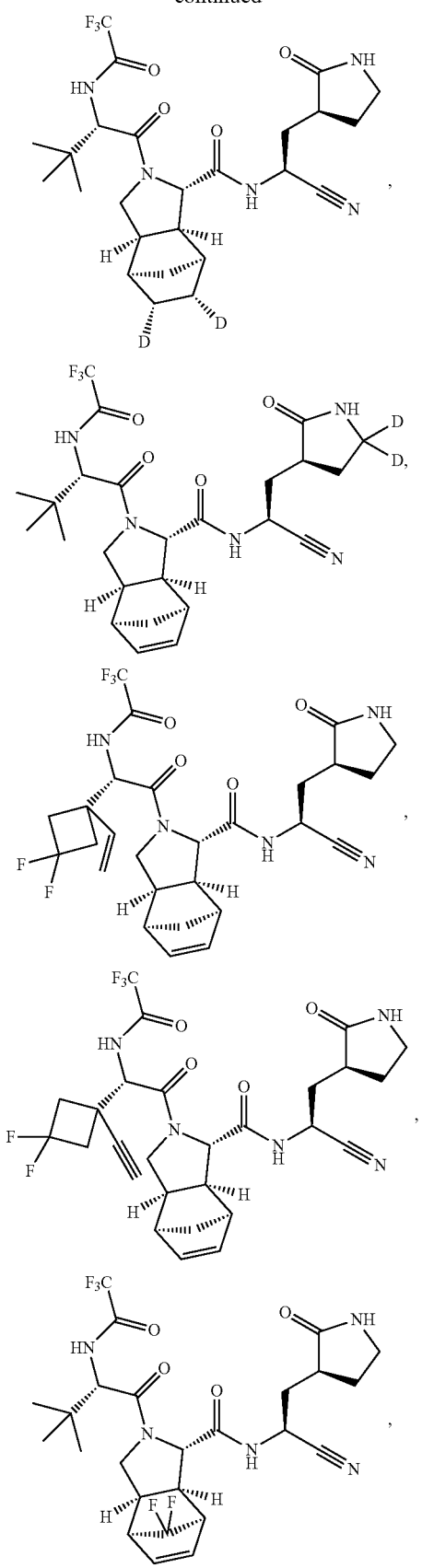
554
-continued
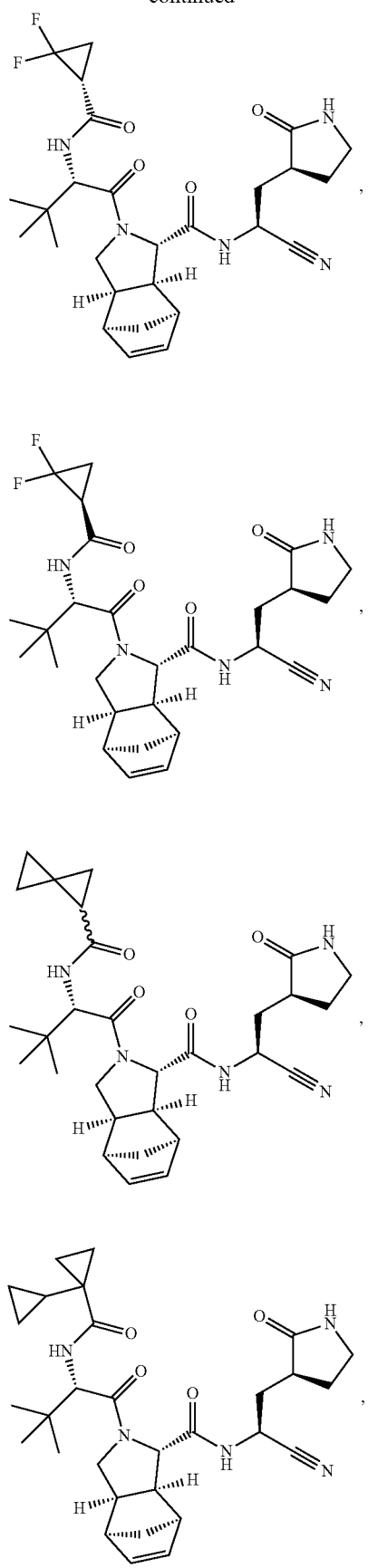

555
-continued
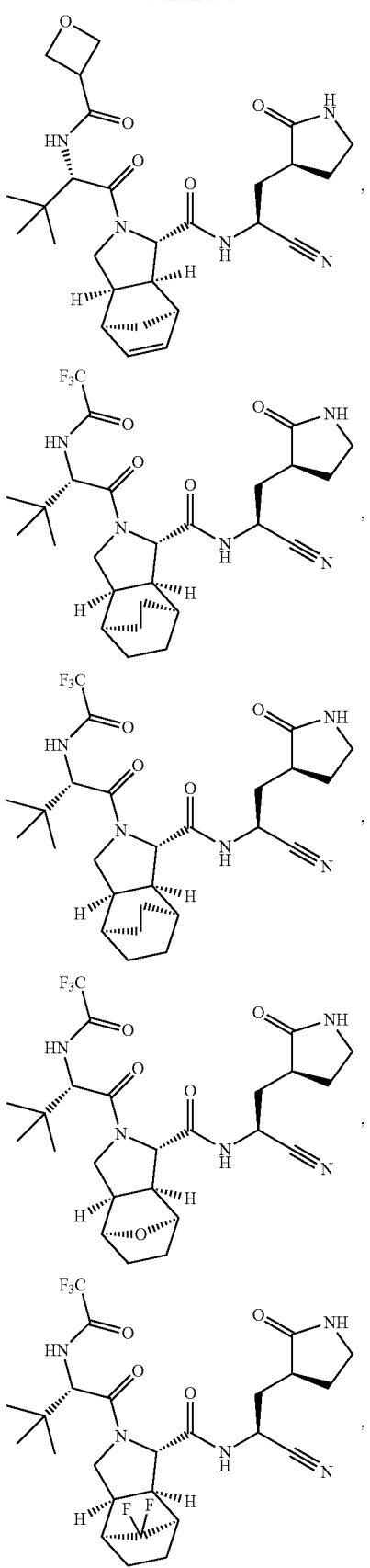
556
-continued
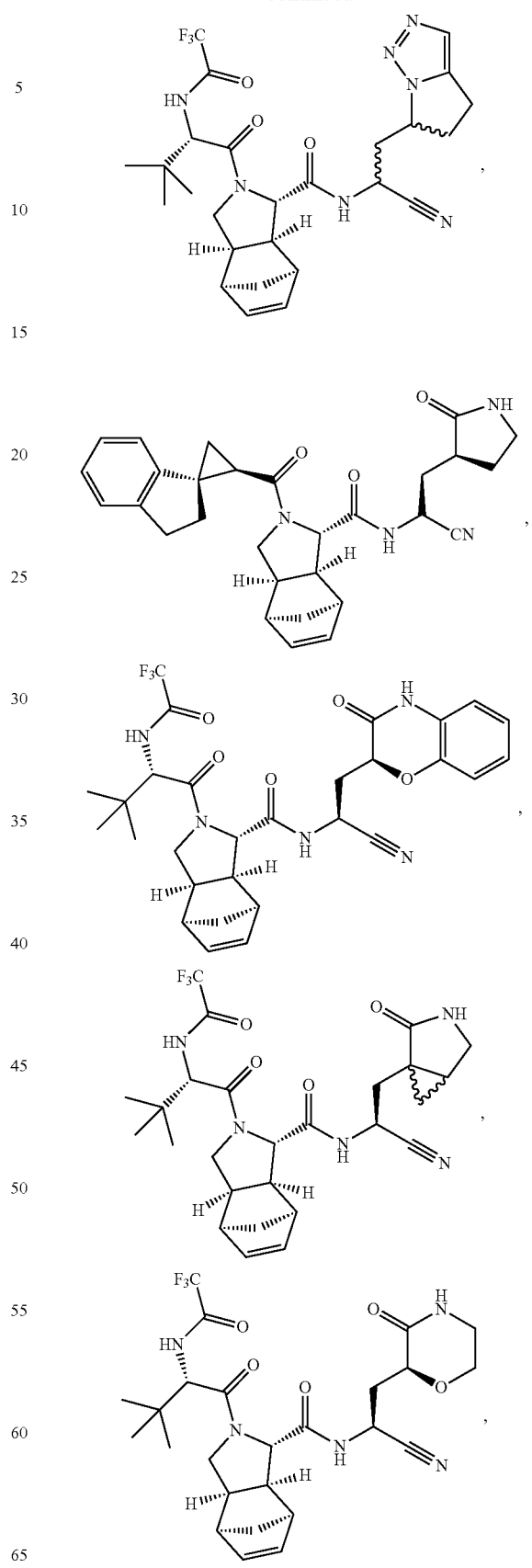

557
-continued
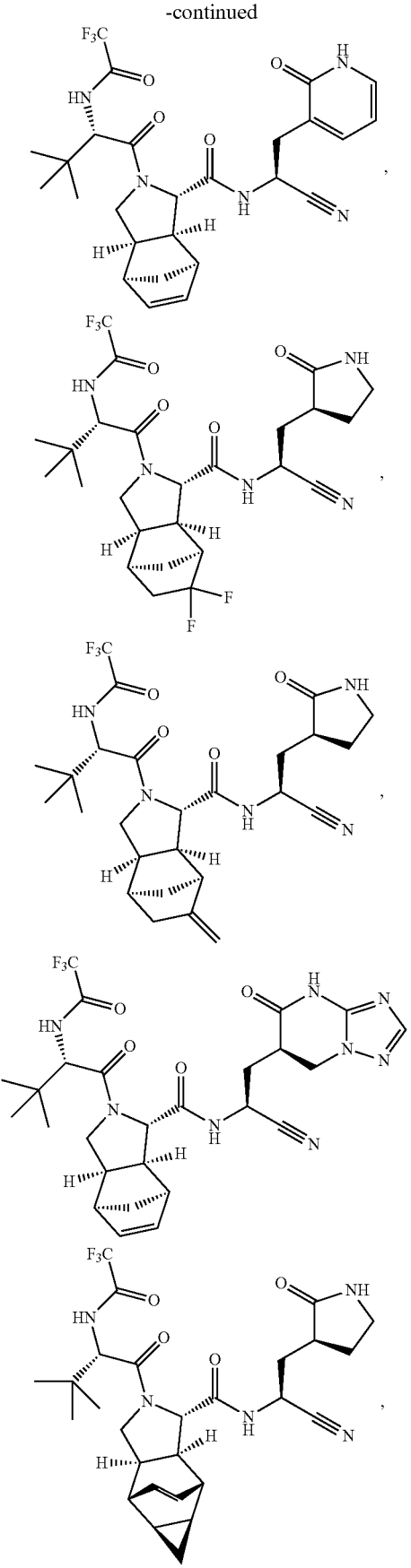
558
-continued
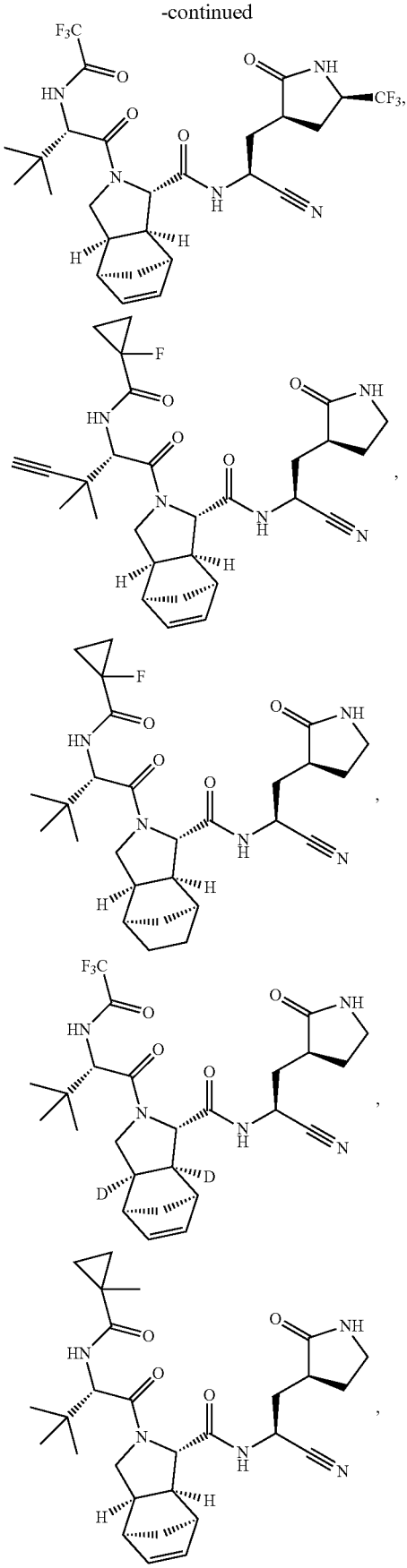

559
-continued
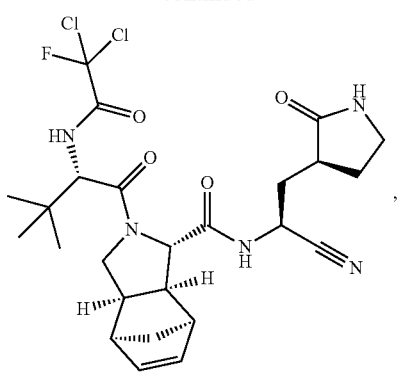
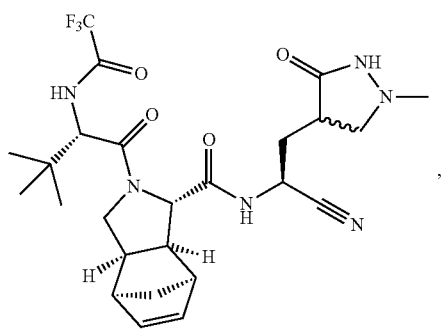
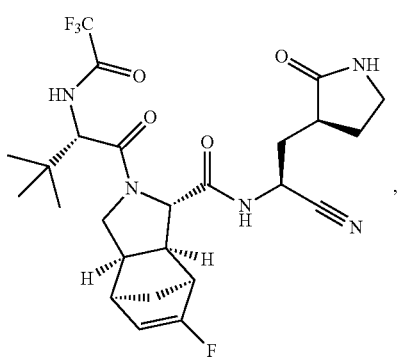
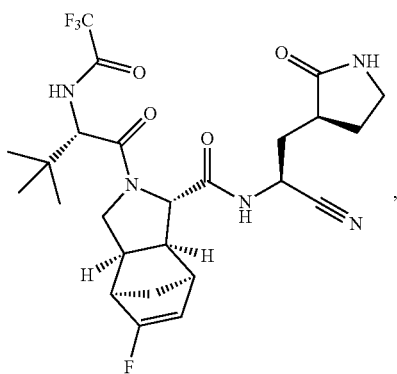
560
-continued
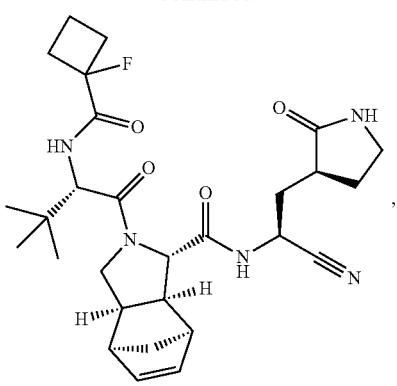
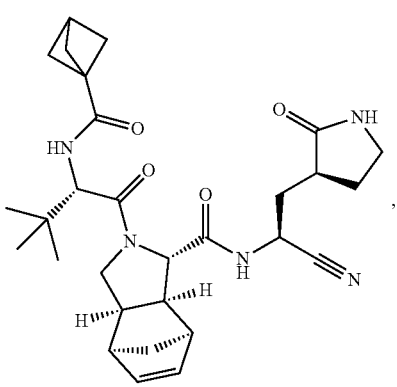
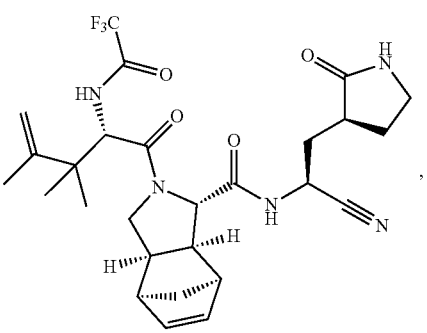
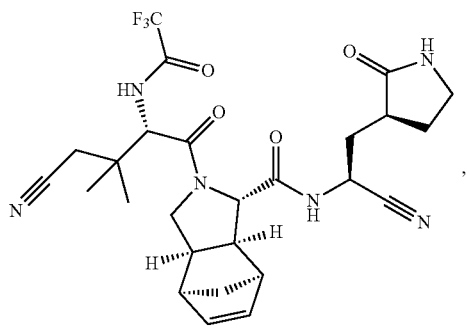

561
-continued
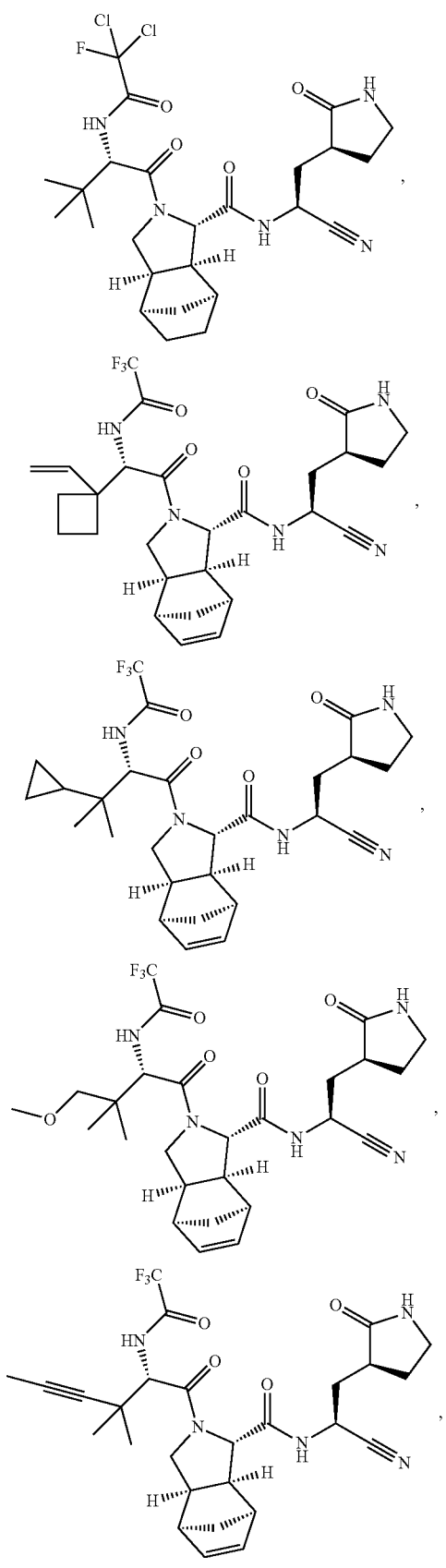
562
-continued
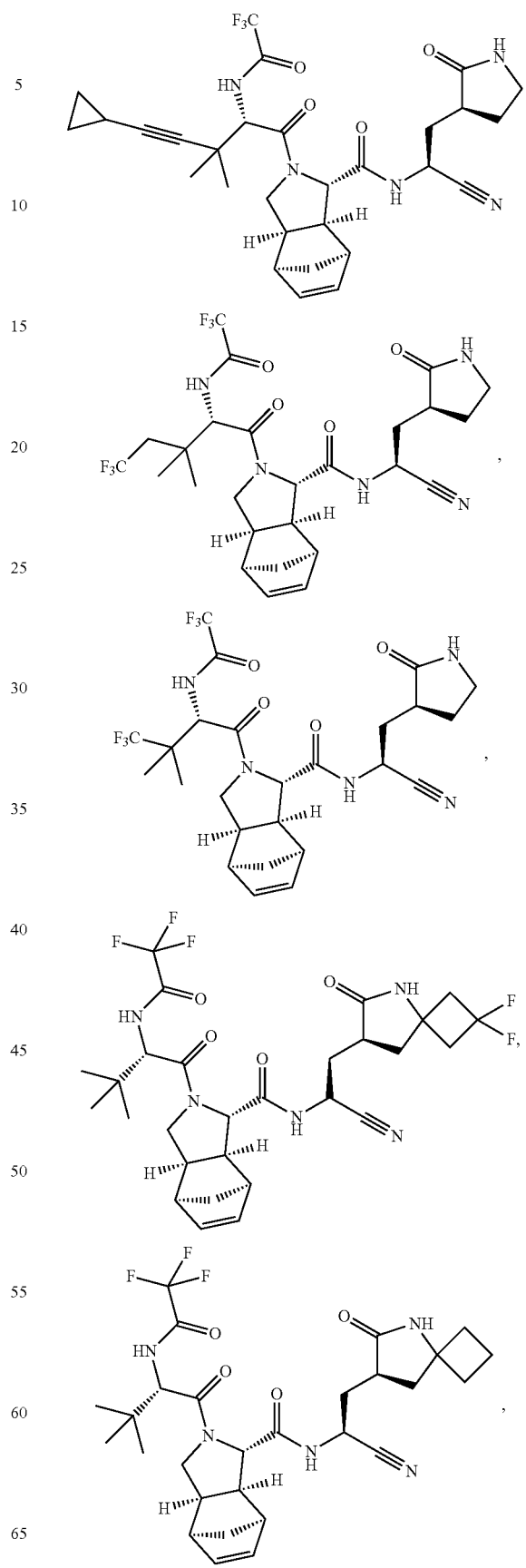

563
-continued
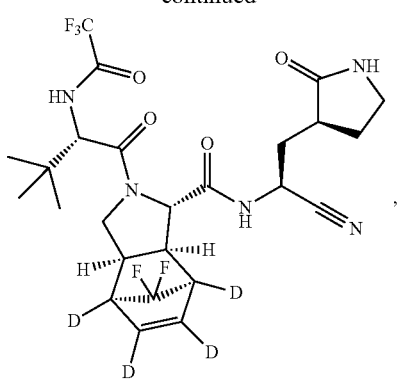
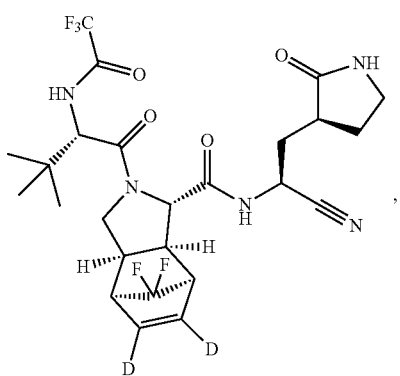
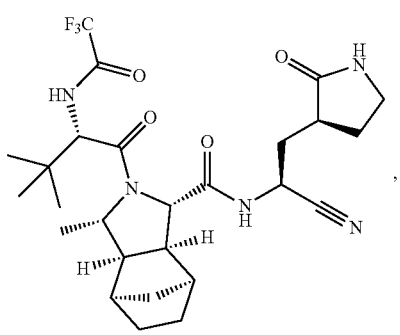
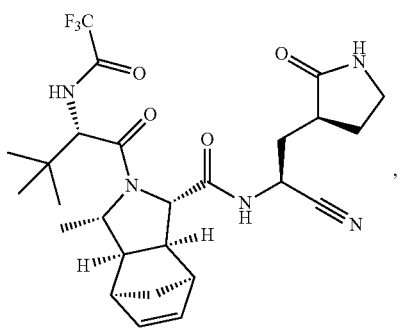
564
-continued
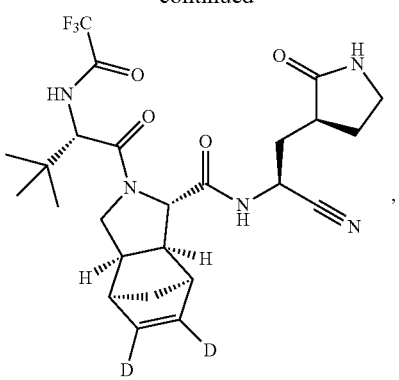
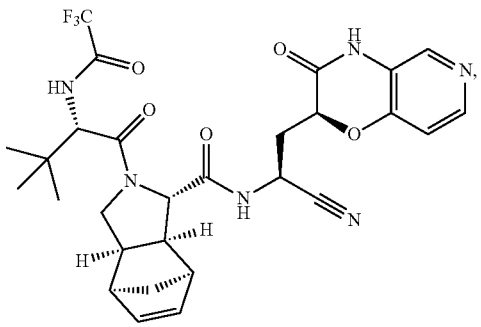
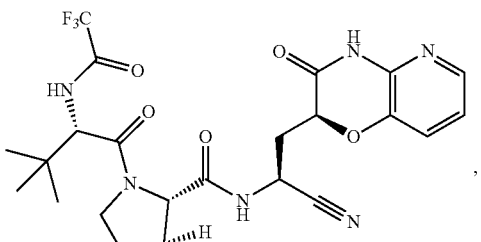
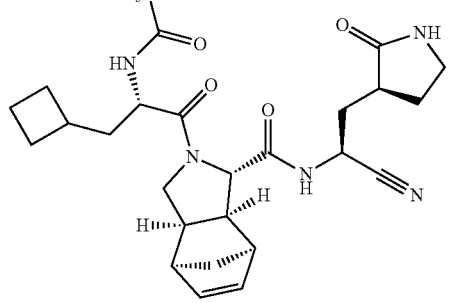
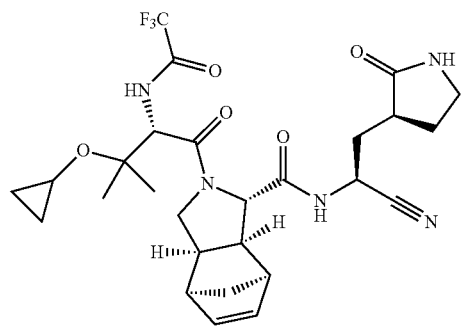

565
-continued
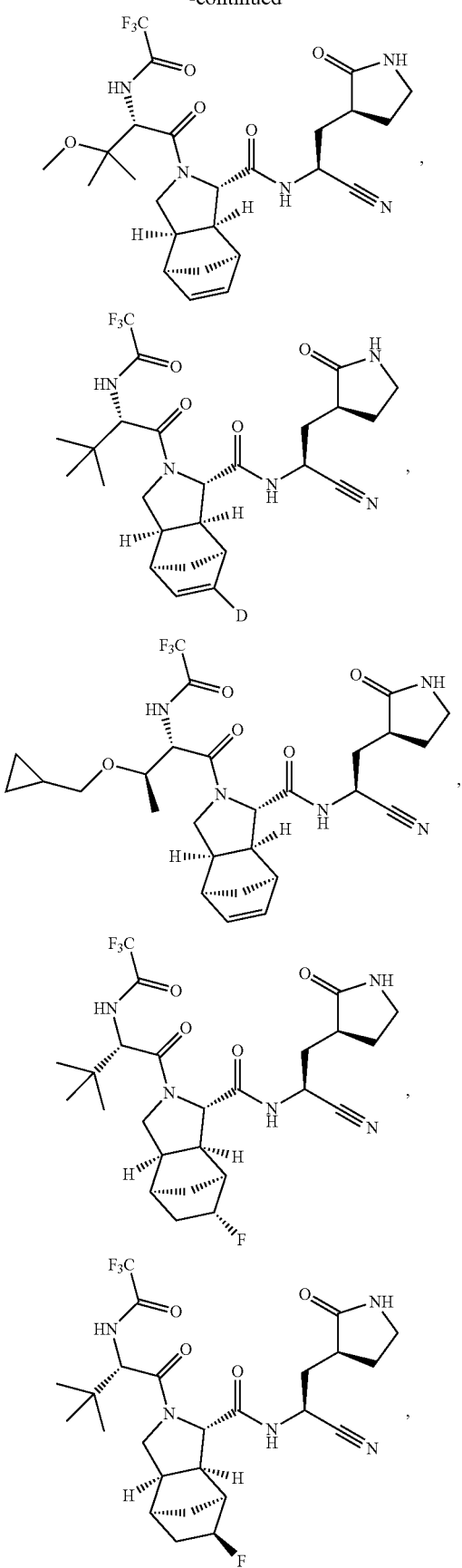
566
-continued
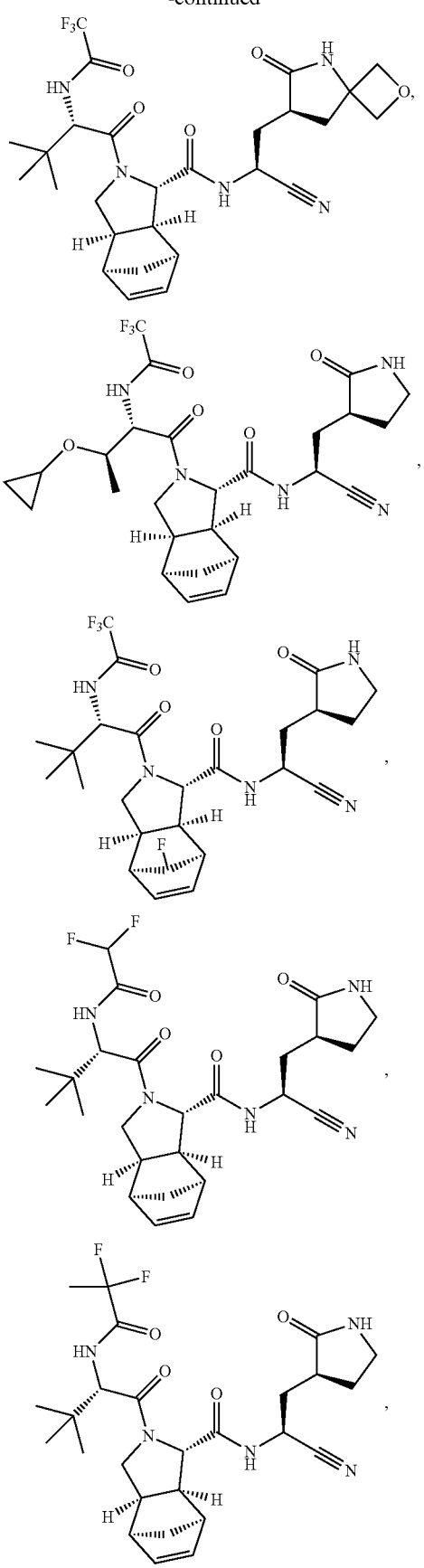

567
-continued
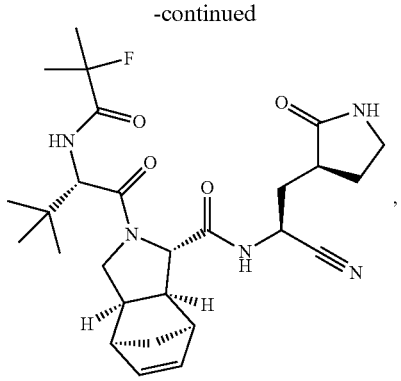
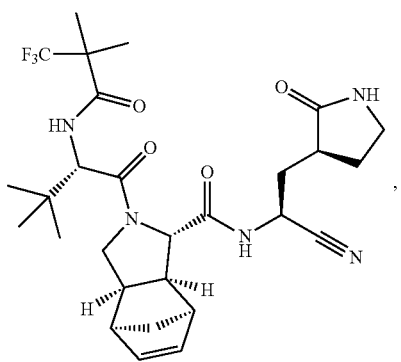
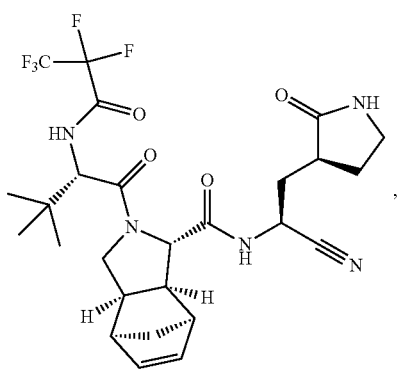
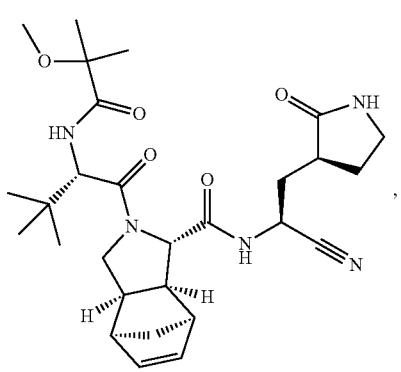
568
-continued
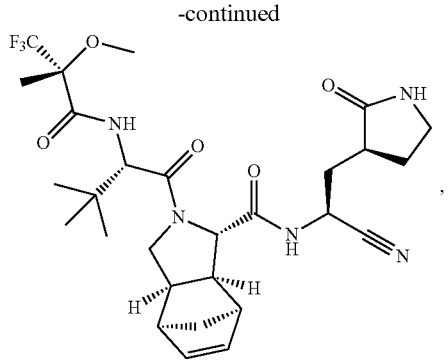
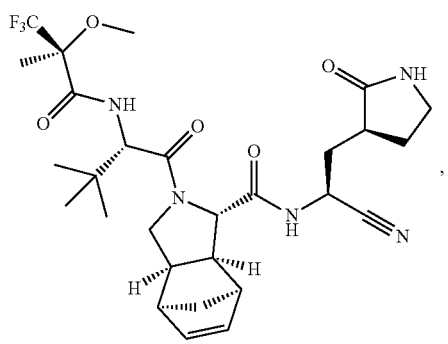
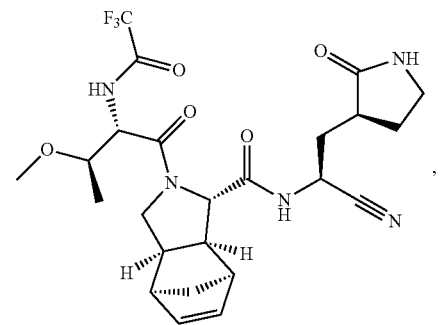
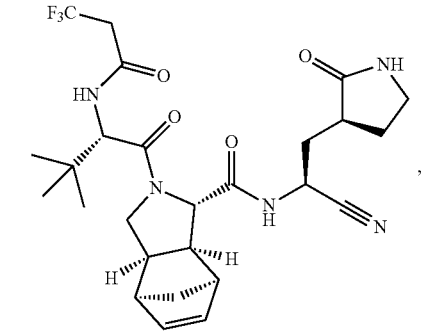
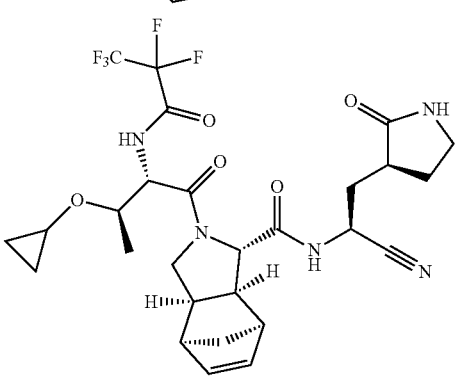

569
-continued
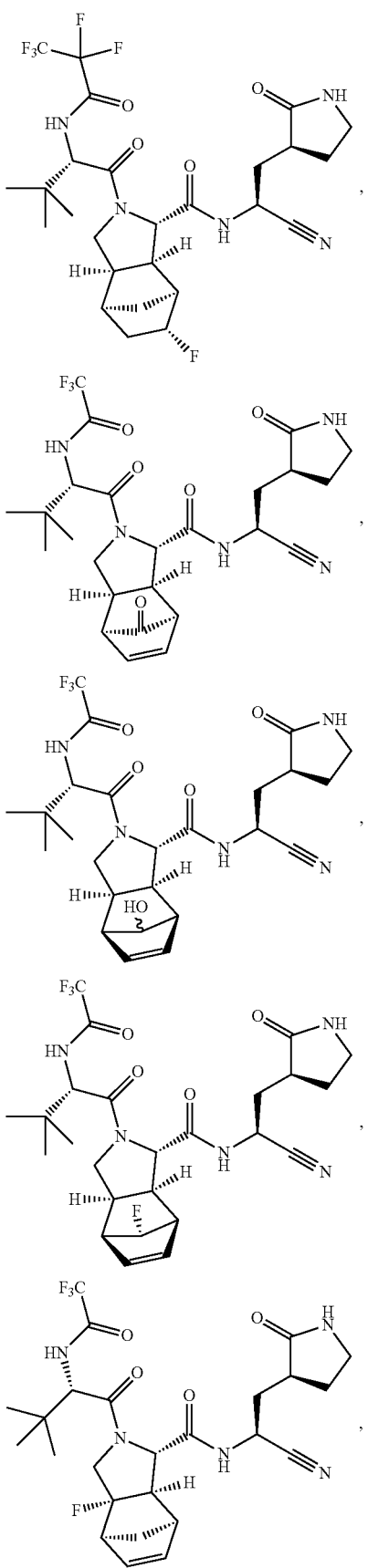
570
-continued
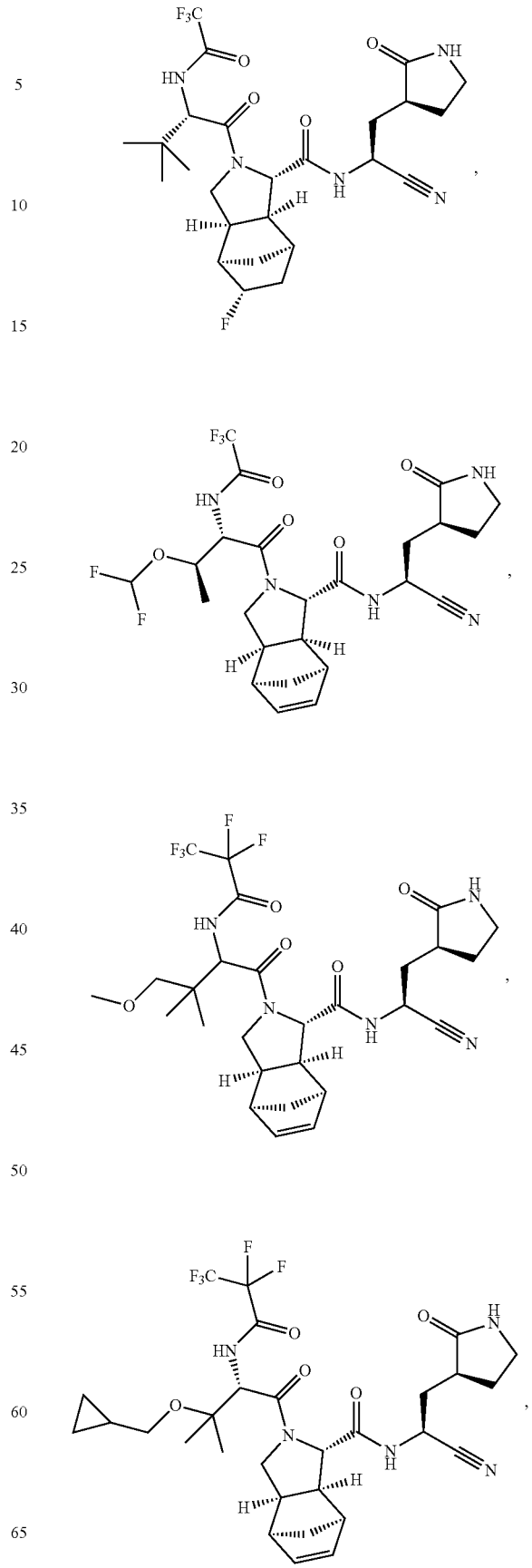

571
-continued
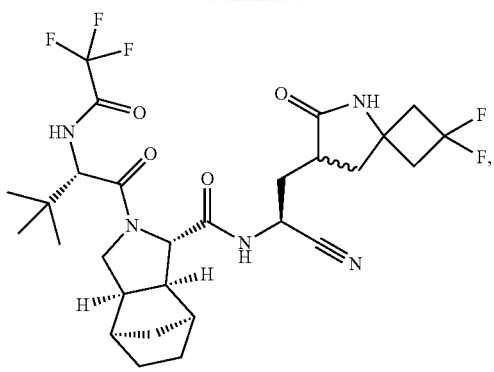
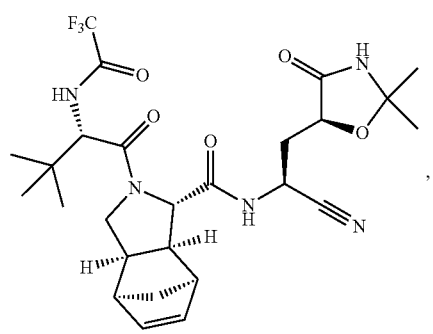
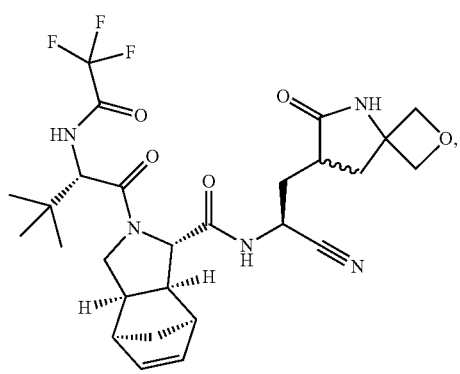
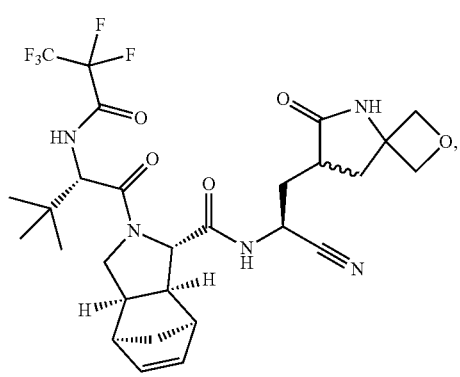
572
-continued
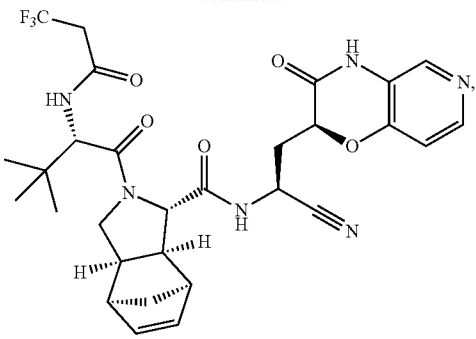
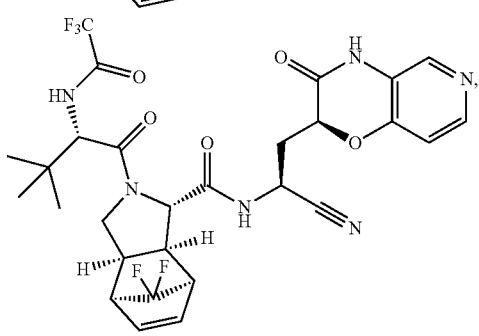
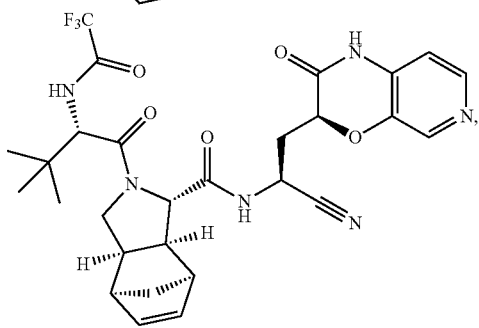
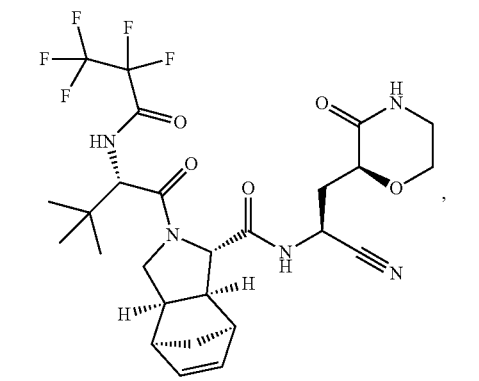
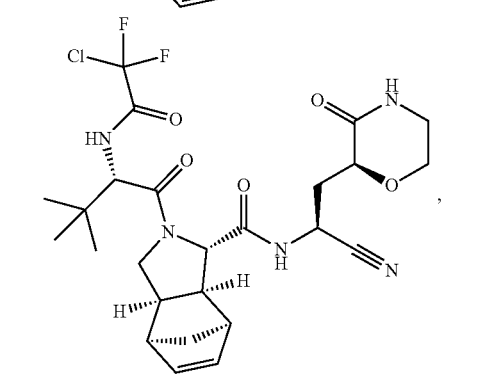

573
-continued
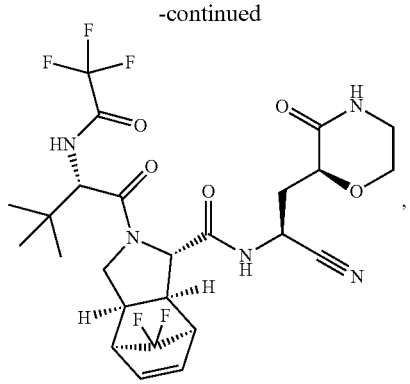
,
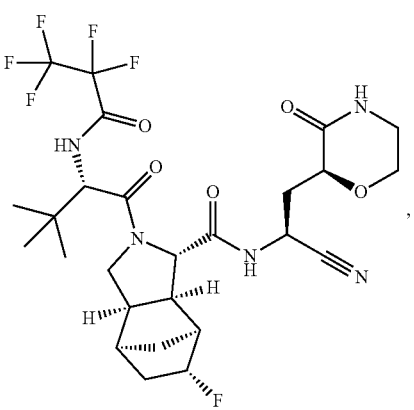
,
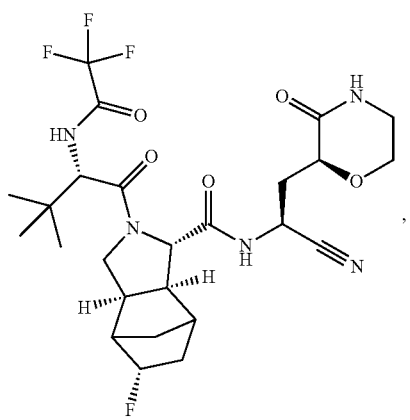
,
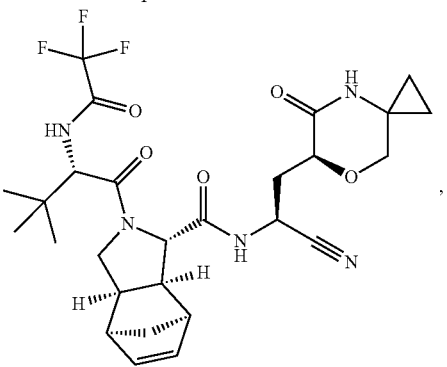
,
574
-continued
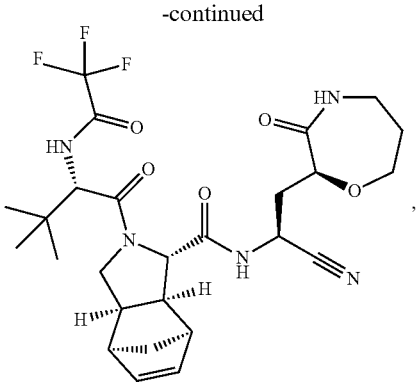
,
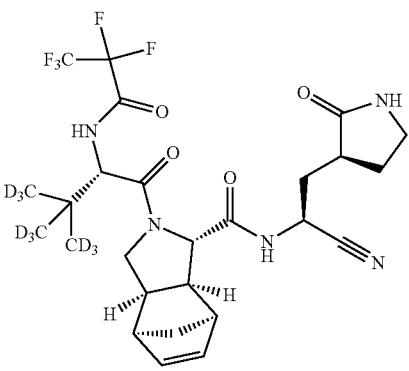
,
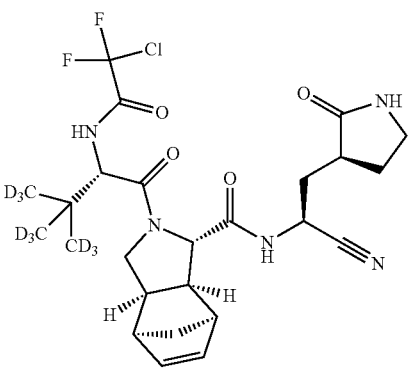
,
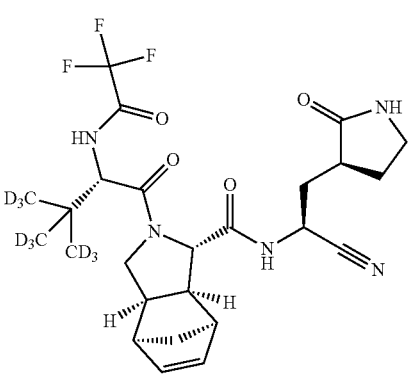
, 575
-continued
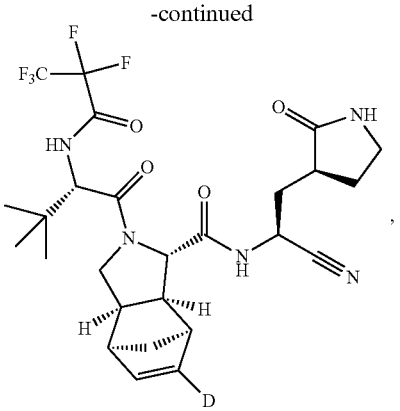
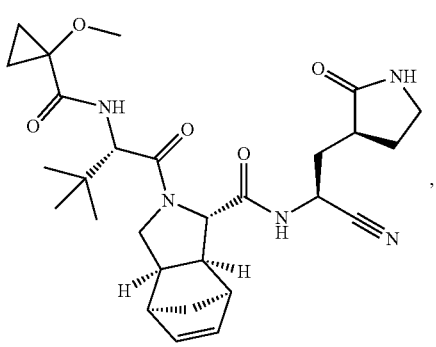
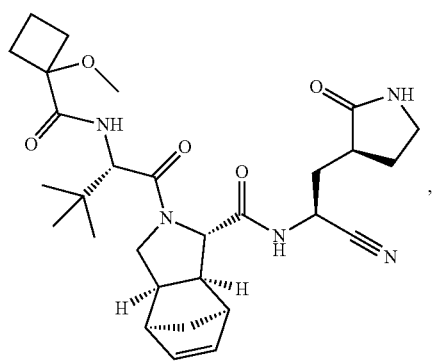
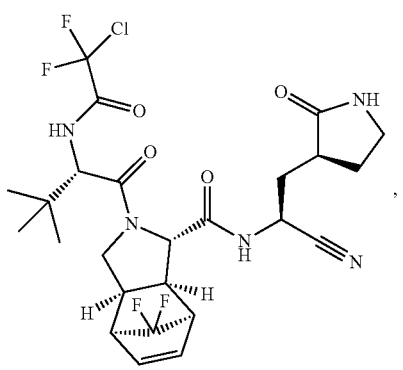
576
-continued
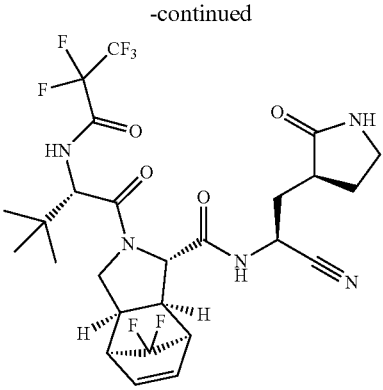
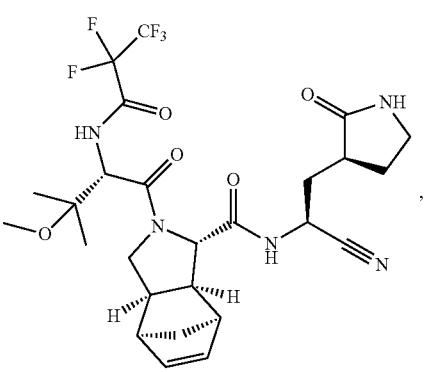
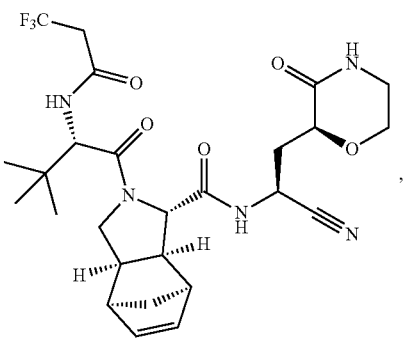
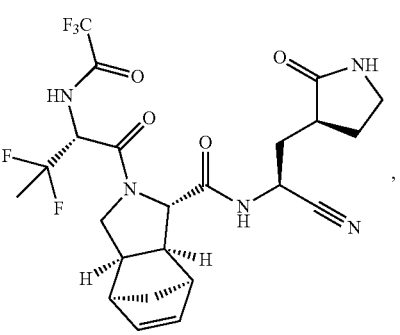

577
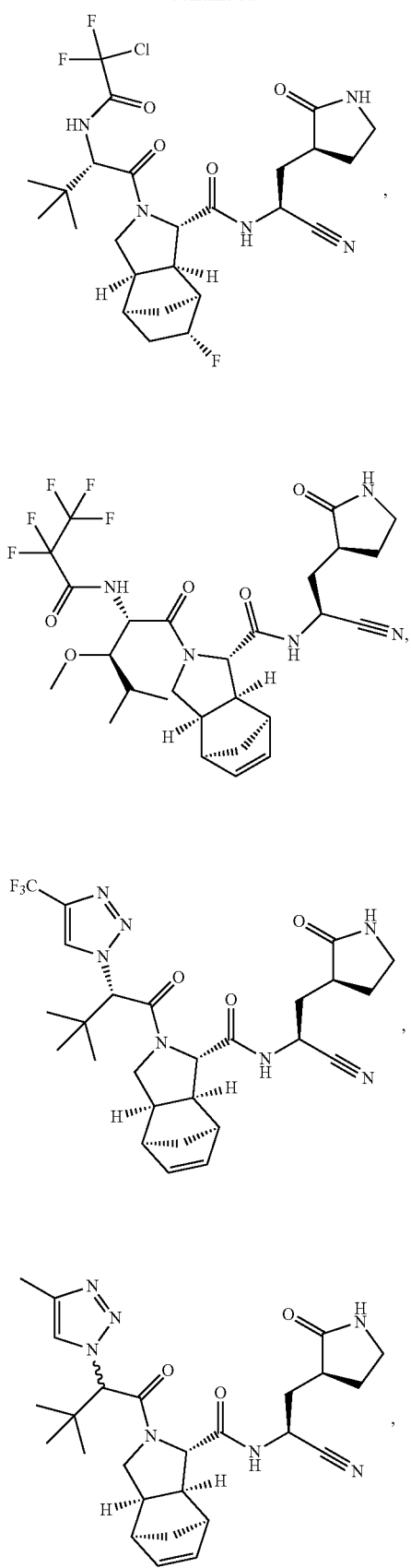
578
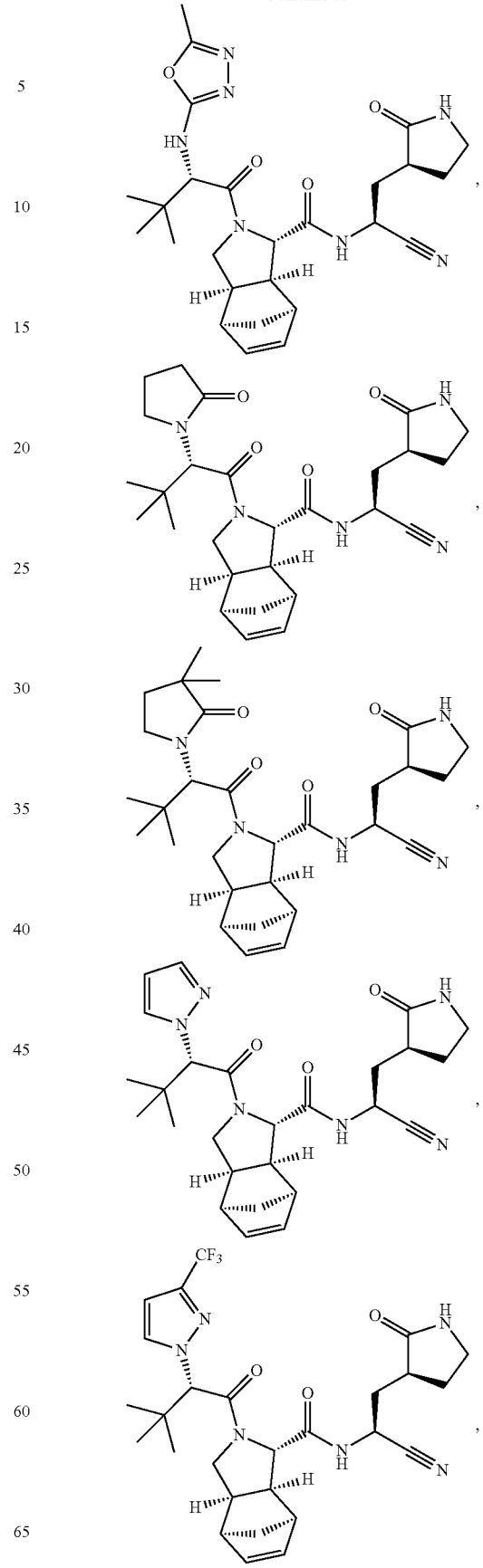

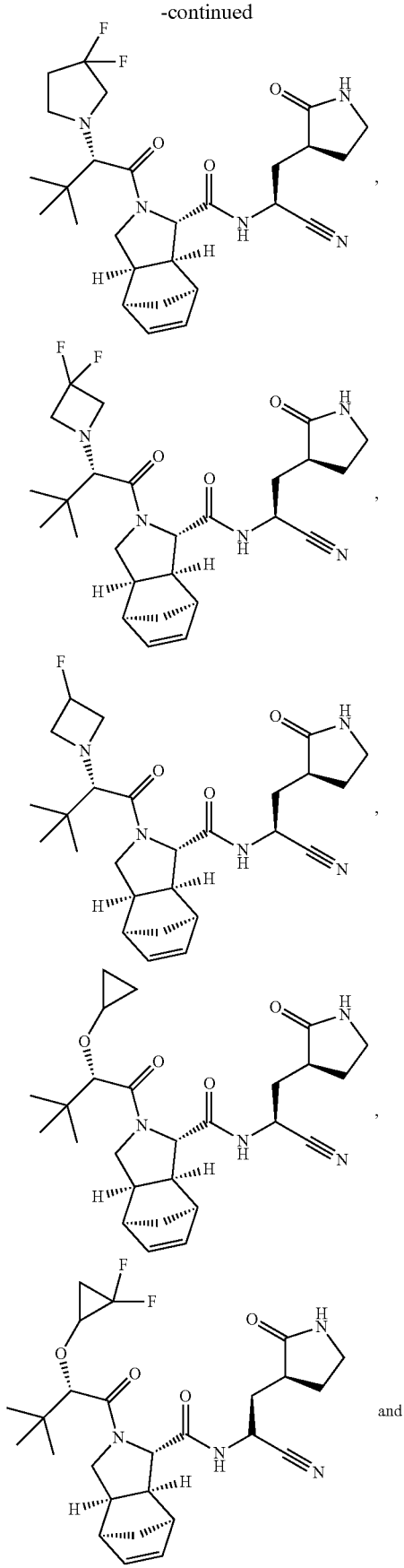

,

,

,

, and

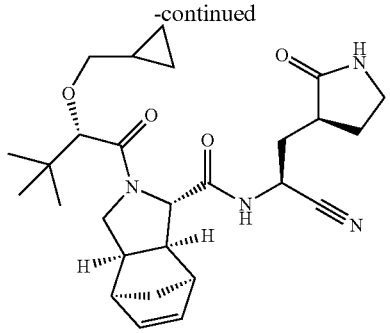

or a pharmaceutically acceptable salt of any of the foregoing.

19. A pharmaceutical composition comprising an effective amount of a compound of claim 1, or a pharmaceutically acceptable salt thereof, and excipient.

20. A method for treating a coronavirus infection in a subject comprising administering to the subject in need thereof an effective amount of a compound of claim 1, or a pharmaceutically acceptable salt thereof.

21. A method for inhibiting a coronavirus protease comprising contacting a cell infected with a coronavirus with an effective amount of a compound of claim 1, or a pharmaceutically acceptable salt thereof, wherein the compound, or a pharmaceutically acceptable salt thereof, selectively inhibits the coronavirus protease of the coronavirus compared to Cathepsin L.

22. The compound of claim 1 having the structure

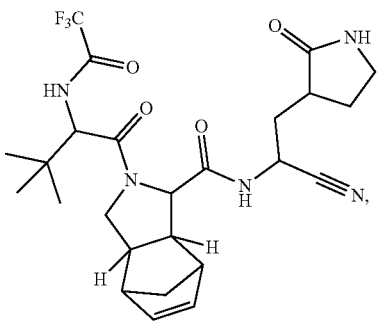 [SMILES: CC(C)(C)C(NC(=O)C(F)(F)F)C(=O)N1CC2C3C=CC(C3)C2C1C(=O)NC(C#N)CC1CCNC1=O]

or a pharmaceutically acceptable salt thereof.

23. The compound of claim 1 having the structure

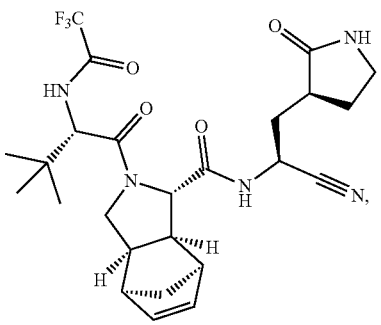 [SMILES: CC(C)(C)[C@H](NC(=O)C(F)(F)F)C(=O)N1C[C@H]2[C@@H]([C@H]1C(=O)N[C@H](C#N)C[C@@H]1CCNC1=O)[C@H]1C=C[C@@H]2C1]

or a pharmaceutically acceptable salt thereof.

24. The compound of claim 1 having the structure

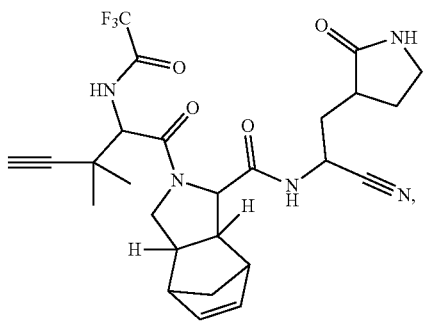 [SMILES: C#CC(C)(C)C(NC(=O)C(F)(F)F)C(=O)N1CC2C3C=CC(C3)C2C1C(=O)NC(C#N)CC1CCNC1=O]

or a pharmaceutically acceptable salt thereof.

25. The compound of claim 1 having the structure

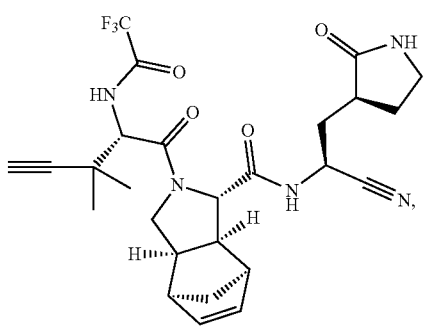 [SMILES: C#CC(C)(C)[C@H](NC(=O)C(F)(F)F)C(=O)N1C[C@H]2[C@@H]([C@H]1C(=O)N[C@H](C#N)C[C@@H]1CCNC1=O)[C@H]1C=C[C@@H]2C1]

or a pharmaceutically acceptable salt thereof.

26. The compound of claim 1 having the structure

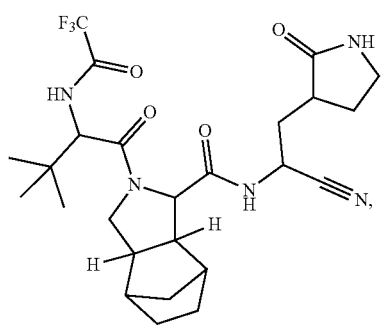 [SMILES: CC(C)(C)C(NC(=O)C(F)(F)F)C(=O)N1CC2C3CCC(C3)C2C1C(=O)NC(C#N)CC1CCNC1=O]

or a pharmaceutically acceptable salt thereof.

27. The compound of claim 1 having the structure

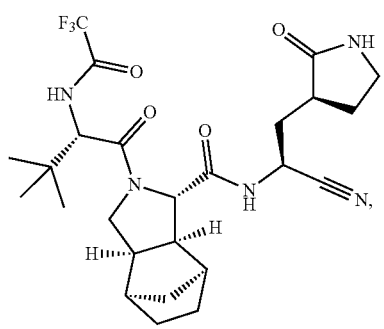 [SMILES: CC(C)(C)[C@H](NC(=O)C(F)(F)F)C(=O)N1C[C@@H]2[C@@H]3CC[C@@H](C3)[C@@H]2[C@H]1C(=O)N[C@H](C#N)C[C@@H]1CCNC1=O]

or a pharmaceutically acceptable salt thereof.

28. The compound of claim 1 having the structure

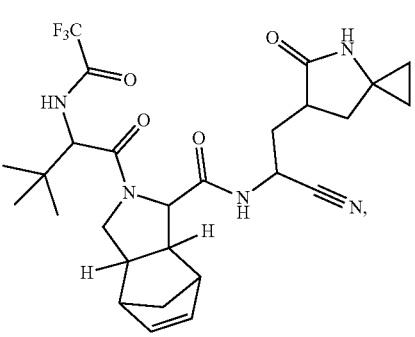 [SMILES: CC(C)(C)C(NC(=O)C(F)(F)F)C(=O)N1CC2C3C=CC(C3)C2C1C(=O)NC(C#N)CC1CC2(CC2)NC1=O]

or a pharmaceutically acceptable salt thereof.

29. The compound of claim 1 having the structure

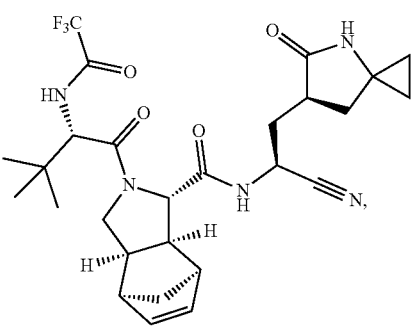 [SMILES: CC(C)(C)[C@H](NC(=O)C(F)(F)F)C(=O)N1C[C@H]2[C@@H]([C@H]1C(=O)N[C@H](C#N)C[C@@H]1CC3(CC3)NC1=O)[C@H]1C=C[C@@H]2C1]

or a pharmaceutically acceptable salt thereof.

30. The compound of claim 1 having the structure

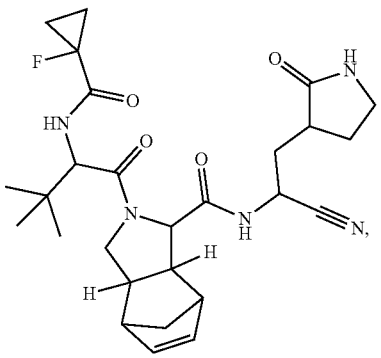 [SMILES: CC(C)(C)C(NC(=O)C1(F)CC1)C(=O)N1CC2C3C=CC(C3)C2C1C(=O)NC(C#N)CC1CCNC1=O]

or a pharmaceutically acceptable salt thereof.

31. The compound of claim 1 having the structure

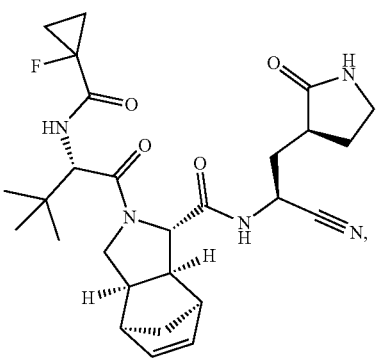 [SMILES: CC(C)(C)[C@H](NC(=O)C1(F)CC1)C(=O)N1C[C@H]2[C@@H]([C@H]1C(=O)N[C@H](C#N)C[C@@H]1CCNC1=O)[C@H]1C=C[C@@H]2C1]

or a pharmaceutically acceptable salt thereof.

32. The compound of claim 1 having the structure

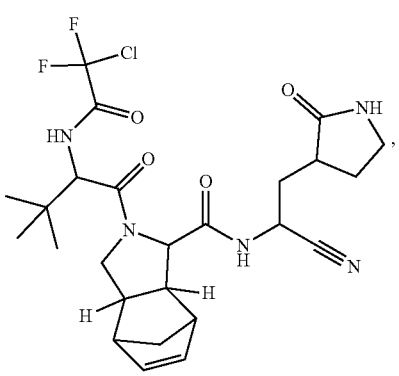 [SMILES: CC(C)(C)C(NC(=O)C(F)(F)Cl)C(=O)N1CC2C3C=CC(C3)C2C1C(=O)NC(C#N)CC1CCNC1=O]

or a pharmaceutically acceptable salt thereof.

33. The compound of claim 1 having the structure

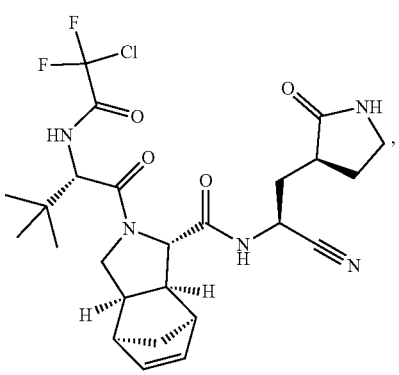 [SMILES: CC(C)(C)[C@H](NC(=O)C(F)(F)Cl)C(=O)N1C[C@H]2[C@@H]([C@H]1C(=O)N[C@H](C#N)C[C@@H]1CCNC1=O)[C@H]1C=C[C@@H]2C1]

or a pharmaceutically acceptable salt thereof.

34. The compound of claim 1 having the structure

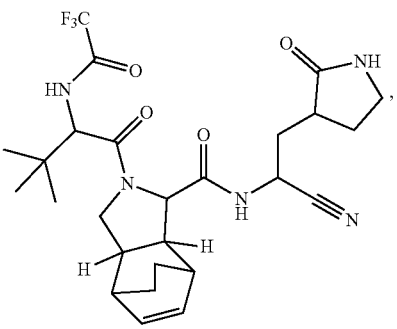 [SMILES: CC(C)(C)C(NC(=O)C(F)(F)F)C(=O)N1CC2C3C=CC(CC3)C2C1C(=O)NC(C#N)CC1CCNC1=O]

or a pharmaceutically acceptable salt thereof.

35. The compound of claim 1 having the structure

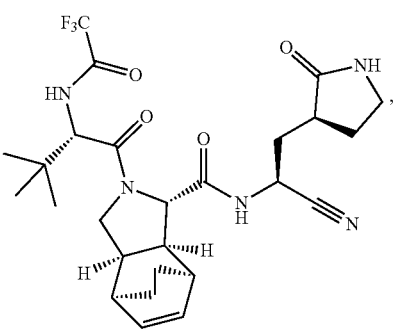 [SMILES: CC(C)(C)[C@H](NC(=O)C(F)(F)F)C(=O)N1C[C@H]2[C@@H]([C@H]1C(=O)N[C@H](C#N)C[C@@H]1CCNC1=O)[C@H]1C=C[C@@H]2CC1]

or a pharmaceutically acceptable salt thereof.

36. The compound of claim 1 having the structure

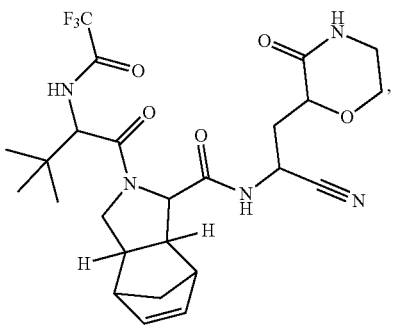 [SMILES: CC(C)(C)C(NC(=O)C(F)(F)F)C(=O)N1CC2C3C=CC(C3)C2C1C(=O)NC(C#N)CC1OCCNC1=O]

or a pharmaceutically acceptable salt thereof.

37. The compound of claim 1 having the structure

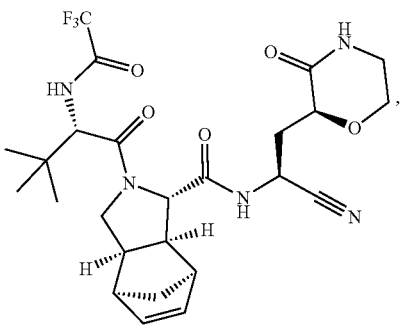 [SMILES: CC(C)(C)[C@H](NC(=O)C(F)(F)F)C(=O)N1C[C@H]2[C@@H]([C@H]1C(=O)N[C@H](C#N)C[C@@H]1OCCNC1=O)[C@H]1C=C[C@@H]2C1]

or a pharmaceutically acceptable salt thereof.

38. The compound of claim 1 having the structure

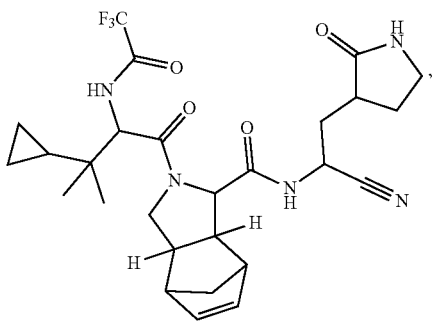 [SMILES: CC(C)(C1CC1)C(NC(=O)C(F)(F)F)C(=O)N1CC2C3C=CC(C3)C2C1C(=O)NC(C#N)CC1CCNC1=O]

or a pharmaceutically acceptable salt thereof.

39. The compound of claim 1 having the structure

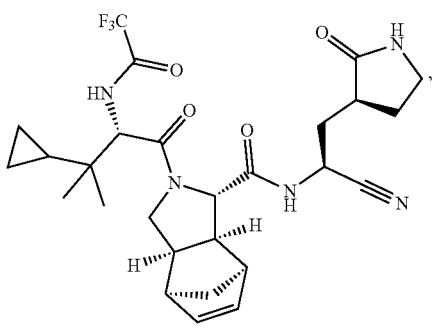 [SMILES: CC(C)(C1CC1)[C@H](NC(=O)C(F)(F)F)C(=O)N1C[C@H]2[C@@H]([C@H]1C(=O)N[C@H](C#N)C[C@@H]1CCNC1=O)[C@H]1C=C[C@@H]2C1]

or a pharmaceutically acceptable salt thereof.

40. The compound of claim 1 having the structure

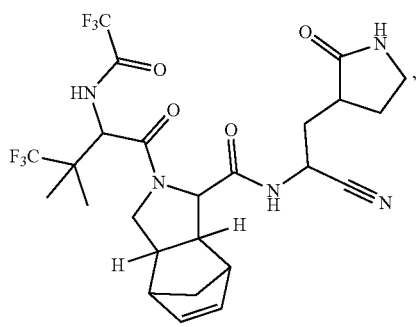 [SMILES: CC(C)(C(NC(=O)C(F)(F)F)C(=O)N1CC2C3C=CC(C3)C2C1C(=O)NC(C#N)CC1CCNC1=O)C(F)(F)F]

or a pharmaceutically acceptable salt thereof.

41. The compound of claim 1 having the structure

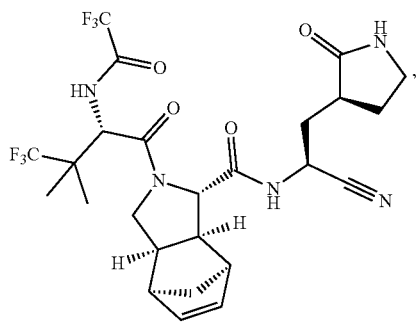 [SMILES: CC(C)([C@H](NC(=O)C(F)(F)F)C(=O)N1C[C@H]2[C@@H]([C@H]1C(=O)N[C@H](C#N)C[C@@H]1CCNC1=O)[C@H]1C=C[C@@H]2C1)C(F)(F)F]

or a pharmaceutically acceptable salt thereof.

42. The compound of claim 1 having the structure

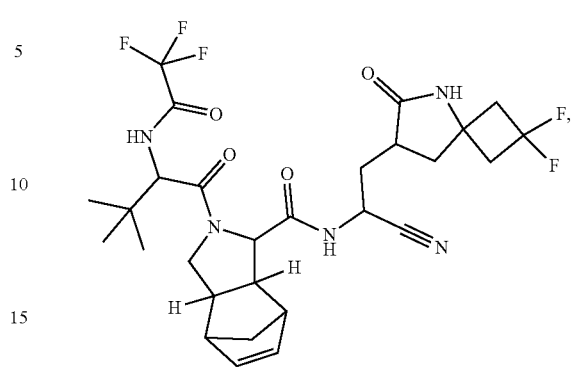

or a pharmaceutically acceptable salt thereof.

43. The compound of claim 1 having the structure

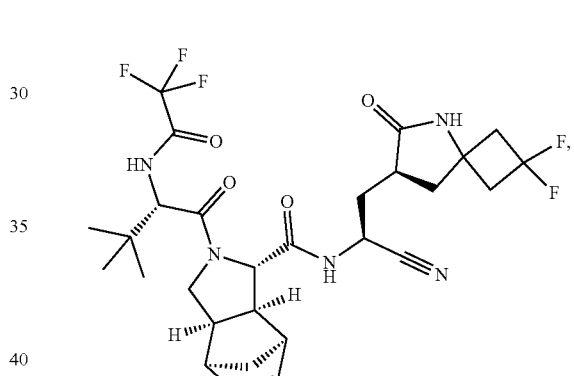

or a pharmaceutically acceptable salt thereof.

44. The compound of claim 1 having the structure

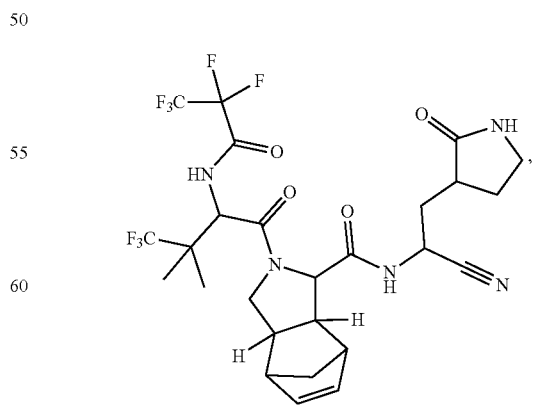

or a pharmaceutically acceptable salt thereof.

45. The compound of claim 1 having the structure

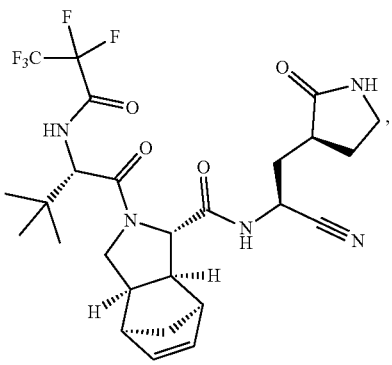 [SMILES: CC(C)(C)[C@H](NC(=O)C(F)(F)C(F)(F)F)C(=O)N1C[C@H]2[C@@H]([C@H]1C(=O)N[C@H](C#N)C[C@@H]1CCNC1=O)[C@H]1C=C[C@@H]2C1]

or a pharmaceutically acceptable salt thereof.

46. The compound of claim 1 having the structure

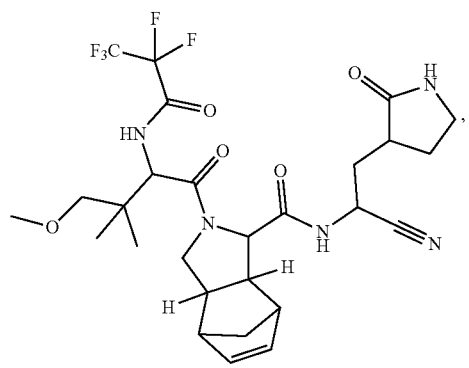 [SMILES: COCC(C)(C)C(NC(=O)C(F)(F)C(F)(F)F)C(=O)N1CC2C3C=CC(C3)C2C1C(=O)NC(C#N)CC1CCNC1=O]

or a pharmaceutically acceptable salt thereof.

47. The compound of claim 1 having the structure

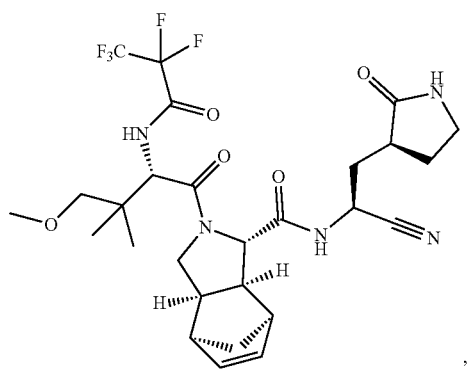

or a pharmaceutically acceptable salt thereof.

48. The compound of claim 1 having the structure

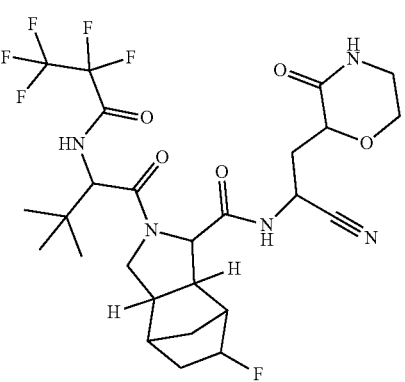

or a pharmaceutically acceptable salt thereof.

49. The compound of claim 1 having the structure

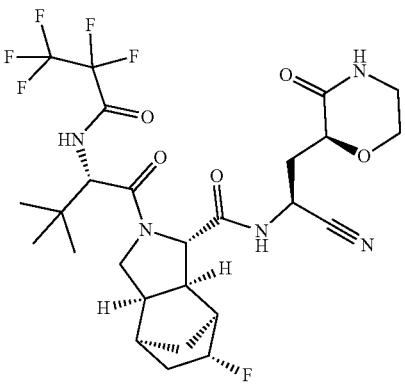

or a pharmaceutically acceptable salt thereof.

50. The compound of claim 1 having the structure

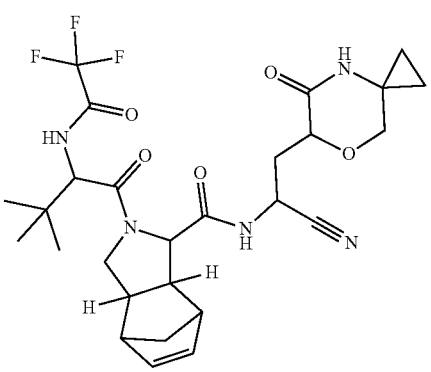

or a pharmaceutically acceptable salt thereof.

51. The compound of claim 1 having the structure

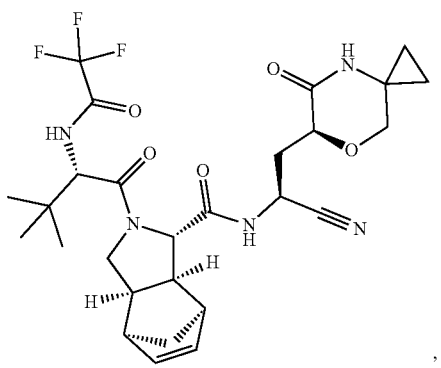

, or a pharmaceutically acceptable salt thereof.

52. The compound of claim 1 having the structure

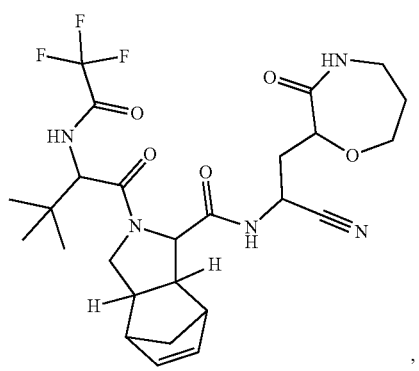 [SMILES: CC(C)(C)C(NC(=O)C(F)(F)F)C(=O)N1CC2C3C=CC(C3)C2C1C(=O)NC(C#N)CC1OCCCNC1=O]

, or a pharmaceutically acceptable salt thereof.

53. The compound of claim 1 having the structure

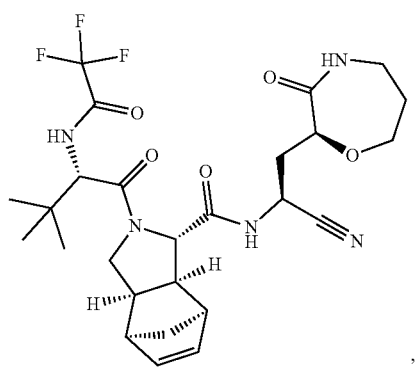 [SMILES: CC(C)(C)[C@H](NC(=O)C(F)(F)F)C(=O)N1C[C@H]2[C@@H]([C@H]1C(=O)N[C@H](C#N)C[C@@H]1OCCCNC1=O)[C@H]1C=C[C@@H]2C1]

, or a pharmaceutically acceptable salt thereof.

54. The compound of claim 1 having the structure

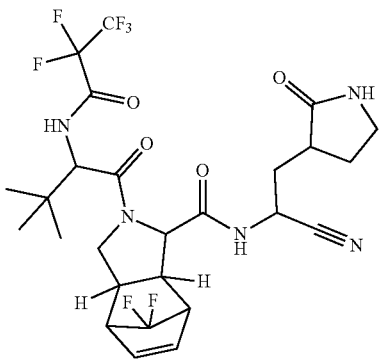

, or a pharmaceutically acceptable salt thereof.

55. The compound of claim 1 having the structure

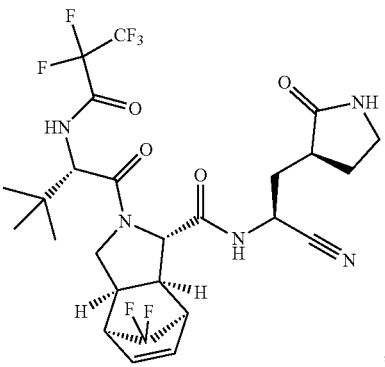

, or a pharmaceutically acceptable salt thereof.

56. The compound of claim 1 having the structure

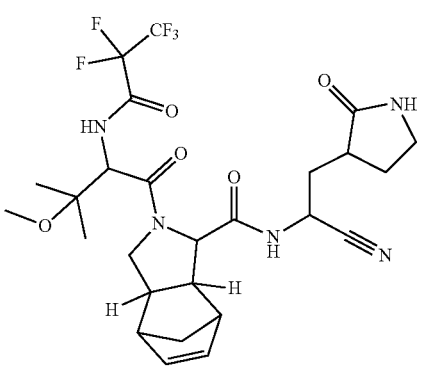

, or a pharmaceutically acceptable salt thereof.

57. The compound of claim 1 having the structure

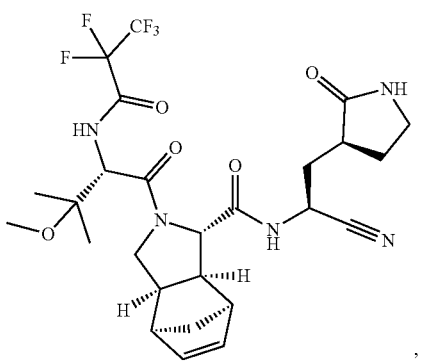 [SMILES: COC(C)(C)[C@H](NC(=O)C(F)(F)C(F)(F)F)C(=O)N1C[C@H]2[C@@H]([C@H]1C(=O)N[C@H](C#N)C[C@@H]1CCNC1=O)[C@H]1C=C[C@@H]2C1]

or a pharmaceutically acceptable salt thereof.

58. The compound of claim 1 having the structure

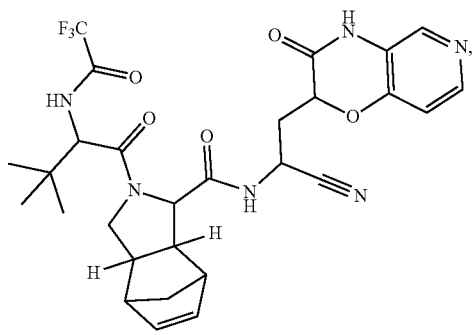 [SMILES: CC(C)(C)C(NC(=O)C(F)(F)F)C(=O)N1CC2C3C=CC(C3)C2C1C(=O)NC(C#N)CC1Oc2ccncc2NC1=O]

or a pharmaceutically acceptable salt thereof.

59. The compound of claim 1 having the structure

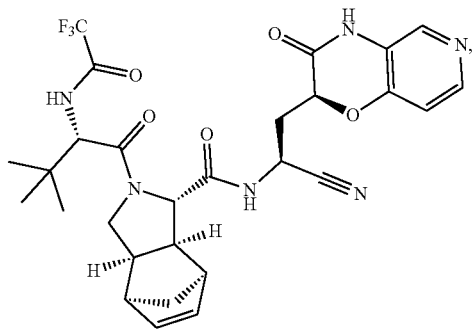

or a pharmaceutically acceptable salt thereof.

60. The compound of claim 1 having the structure

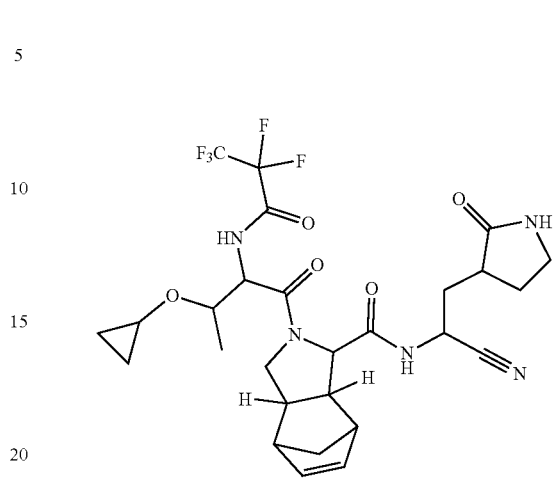

or a pharmaceutically acceptable salt thereof.

61. The compound of claim 1 having the structure

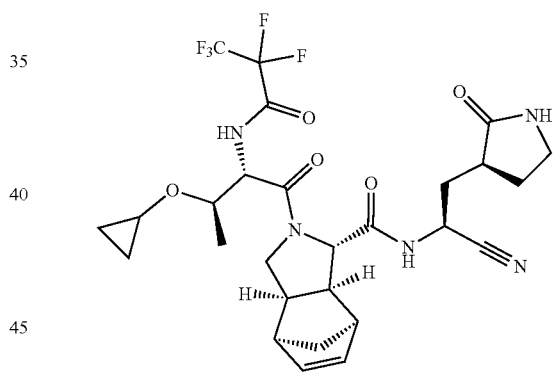

or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 11,851,422 B2 | |
| APPLICATION NO. | : 17/811008 | |
| DATED | : December 26, 2023 | |
| INVENTOR(S) | : Koen Vandyck | |

It is certified that error appears in the above-identified patent and that said Letters Patent is hereby corrected as shown below:

On the Title Page

Column 1, Line 1, under Assignees, delete "Inc.;" and insert --Inc., South San Francisco, CA (US);--.

On Page 3, Column 2, Line 14, item (56) under Other Publications, delete "SARA" and insert --SARS--.

On Page 3, Column 2, Line 17, item (56) under Other Publications, delete ""SARA" and insert --"SARS--.

On Page 3, Column 2, Line 37, item (56) under Other Publications, delete "alkylglumates" and insert --alkylglutamates--.

On Page 3, Column 2, Line 60, item (56) under Other Publications, delete "beceprevir" and insert --boceprevir--.

On Page 3, Column 2, Line 61, item (56) under Other Publications, delete "inhibitos" and insert --inhibitors--.

On Page 4, Column 1, Line 1, item (56) under Other Publications, delete "dihdropyrid" and insert --dihydropyrid--.

On Page 4, Column 1, Line 2, item (56) under Other Publications, delete "Anaalogues" and insert --Analogues--.

In the Specification

In Column 1, Line 36, delete "Norviruses" and insert --Noroviruses--.

In Column 13, Line 22, delete "—O-(an" and insert -- —O— (an--.

Signed and Sealed this
Second Day of July, 2024

Katherine Kelly Vidal
*Director of the United States Patent and Trademark Office*

CERTIFICATE OF CORRECTION (continued)
U.S. Pat. No. 11,851,422 B2

In Column 13, Line 23, delete "—O-(an" and insert -- —O— (an--.

In Column 14, Line 55, delete "A1" and insert --$A^1$--.

In Column 15, Lines 30-39, delete " 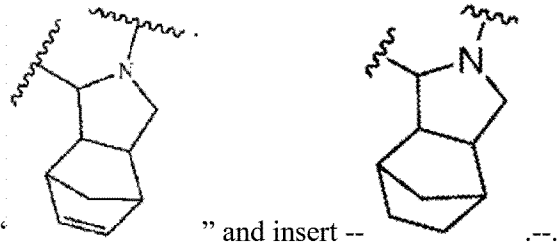 " and insert -- --.

In Column 19, Lines 22-32, delete " 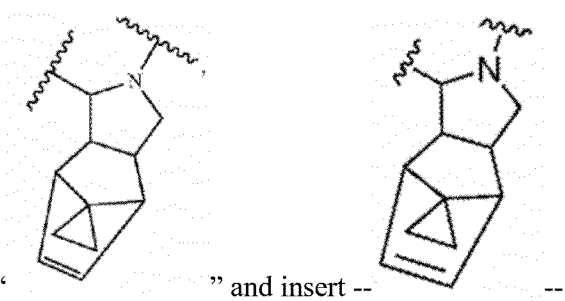 " and insert -- --.

In Column 19, Lines 22-32, delete " 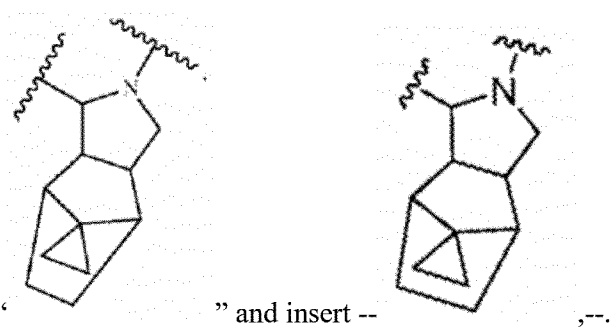 " and insert -- ,--.

In Column 31, Line 35, delete "$C_1$" and insert --Cl--.

In Column 42, Line 22 (Approx.), delete "$C_{1-8}$" and insert --$C_{1-6}$--.

In Column 42, Line 23 (Approx.), delete "$C_{1-8}$" and insert --$C_{1-6}$--.

In Column 47, Lines 30-54, delete " 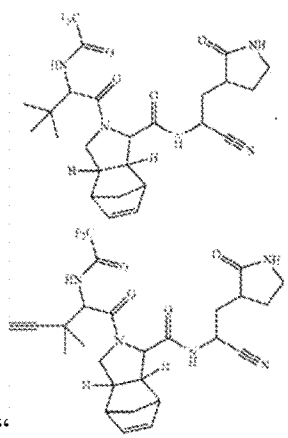 " and insert
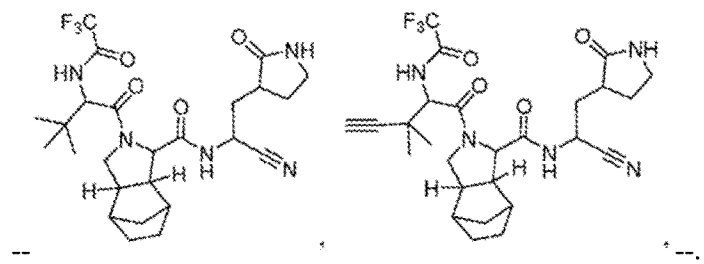
-- --.
In Column 56, Lines 41-54, delete " 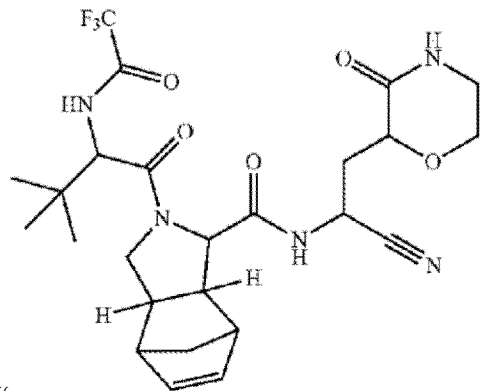 " and insert
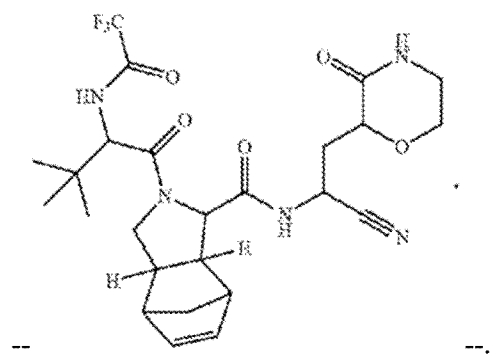
-- --.

In Column 76, Lines 18-31, delete " 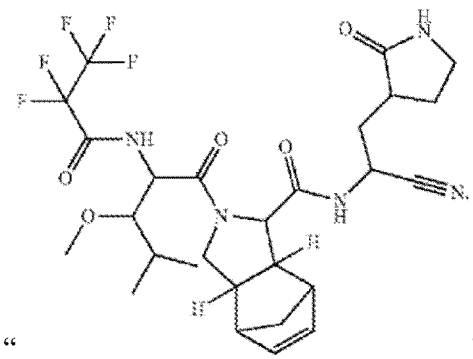 " and insert
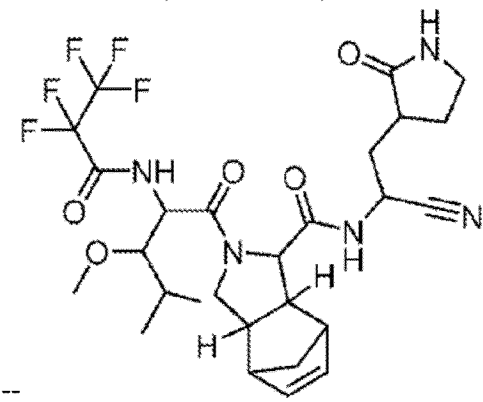 ,--.
In Column 79, Lines 15-41, delete " 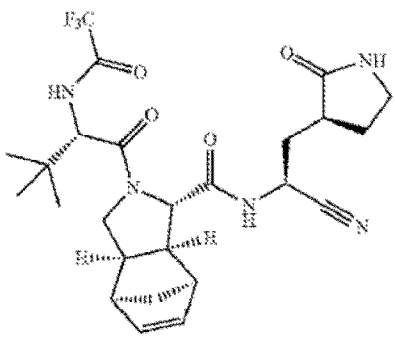 " and insert
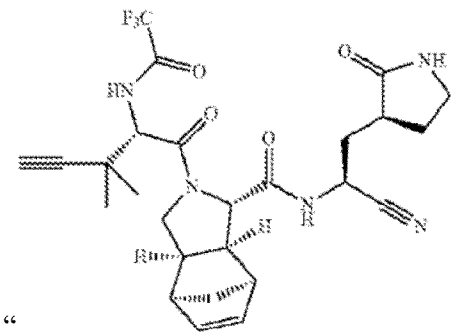

CERTIFICATE OF CORRECTION (continued)
U.S. Pat. No. 11,851,422 B2

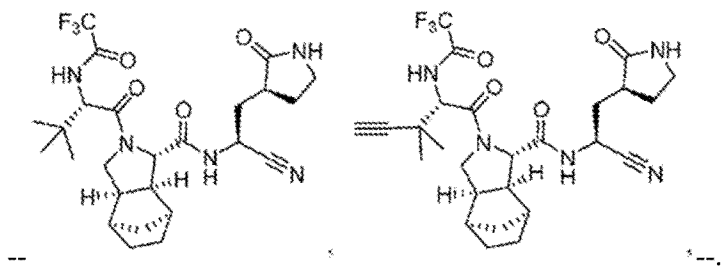

In Column 80, Lines 55-66, delete " 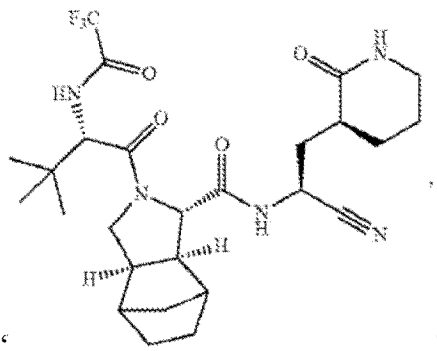 " and insert

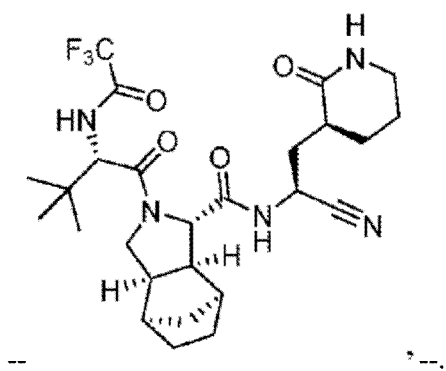

-- .

In Column 87, Lines 16-27, delete " 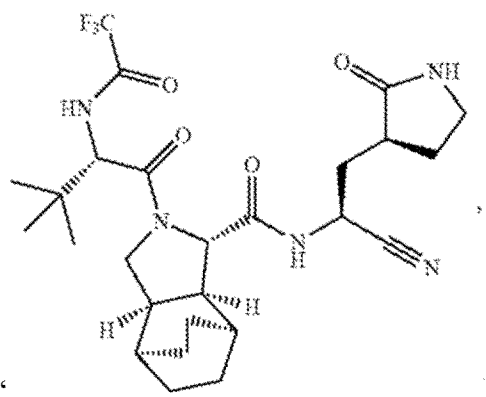 " and insert

CERTIFICATE OF CORRECTION (continued)

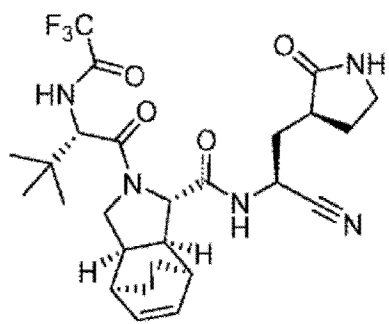

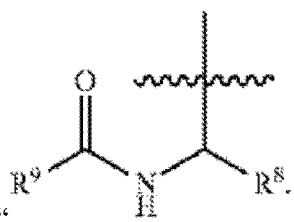 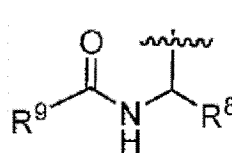

In Column 117, Lines 1-6, delete " 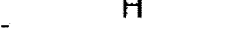 " and insert -- ;--.

In Column 117, Line 11, delete "A1" and insert --$A^1$--.

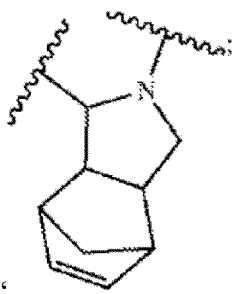 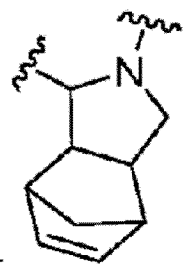

In Column 117, Lines 25-33, delete "  " and insert -- .--.

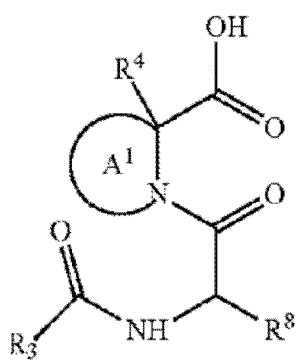 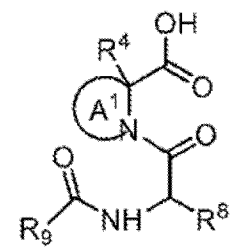

In Column 118, Lines 56-67, delete " A1-6 " and insert -- A1-6 --.

In Column 123, Line 2, delete "—O-(an" and insert -- —O— (an--.

In Column 123, Line 2, delete "—O-(an" and insert -- —O— (an--.

In Column 126, Line 12 (Approx.), delete "NEtO)." and insert --NEt$_3$).--.

CERTIFICATE OF CORRECTION (continued)
U.S. Pat. No. 11,851,422 B2

In Column 126, Line 22 (Approx.), delete "PG$^B$" and insert --PG$^{B1}$--.

In Column 127, Lines 9-15, delete " " and insert -- 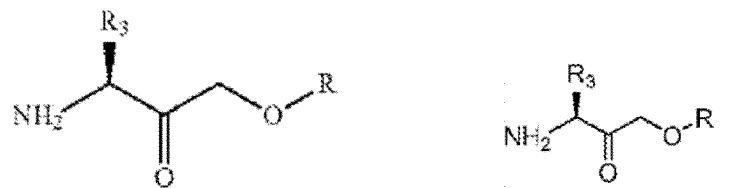 --.

In Columns 129-130, Lines 2-40 (Approx.), delete

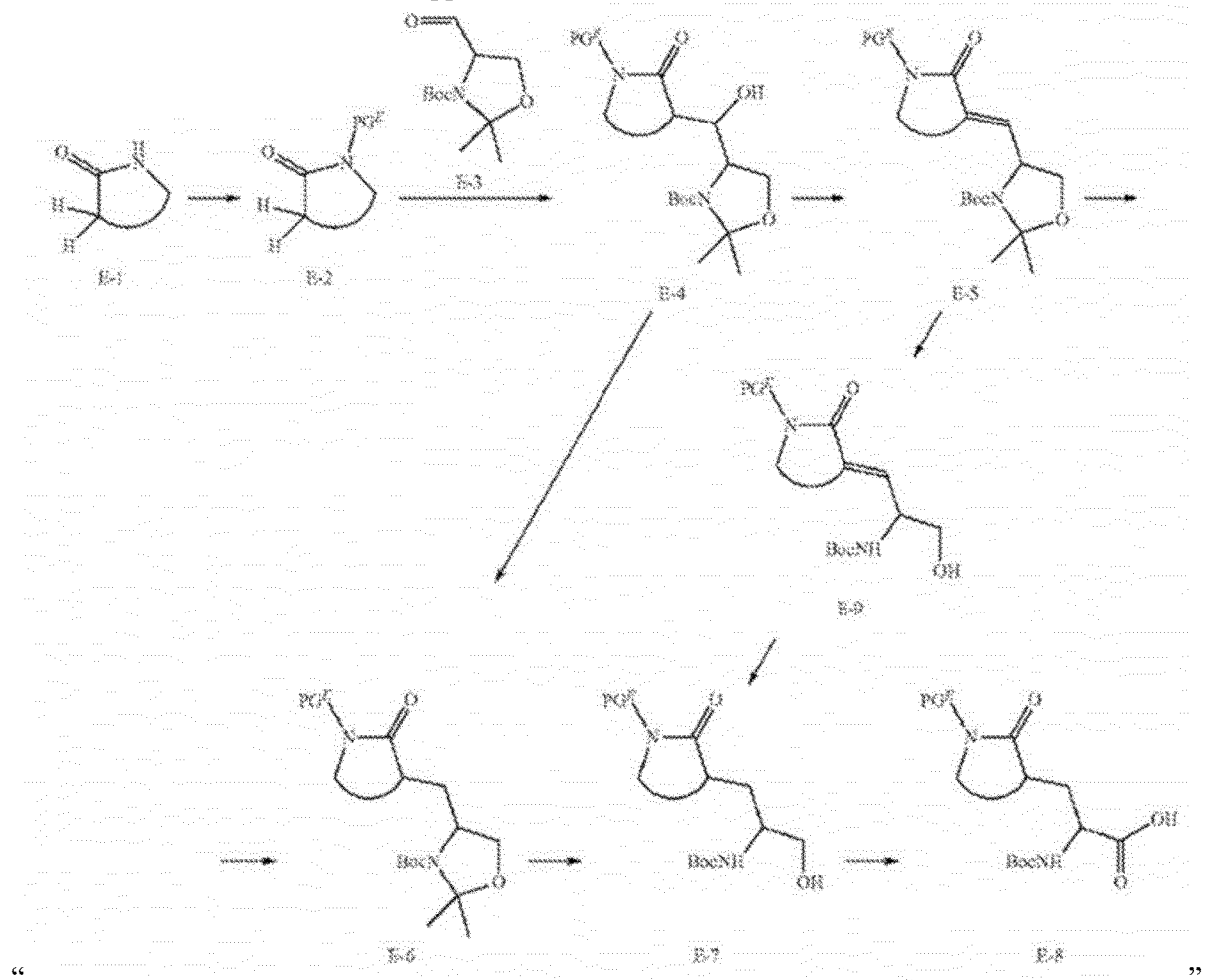

"

and insert

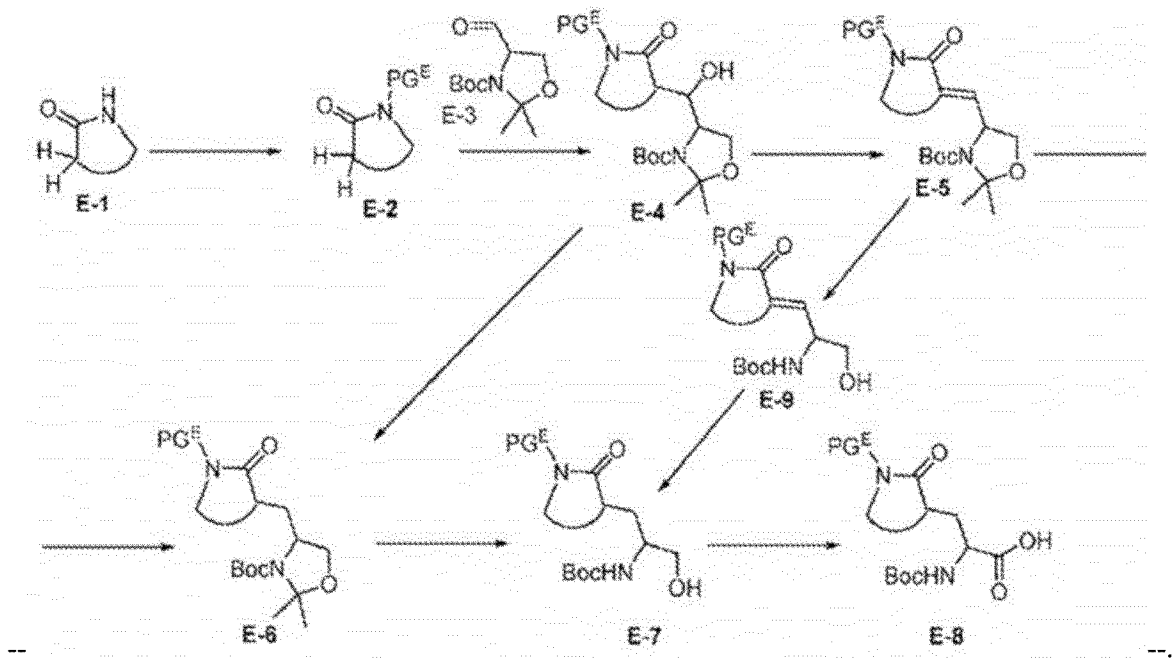
In Column 137, Lines 28-36, delete " 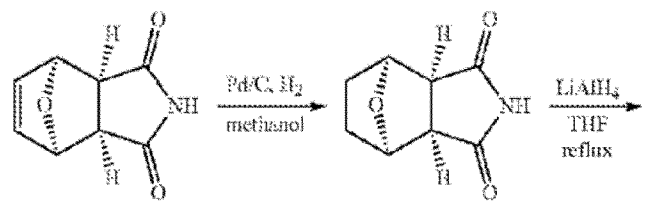 " and
insert -- 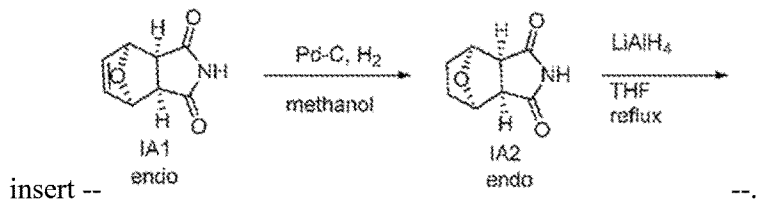 --.

In Columns 137-138, Lines 40-50 (Approx.), delete " 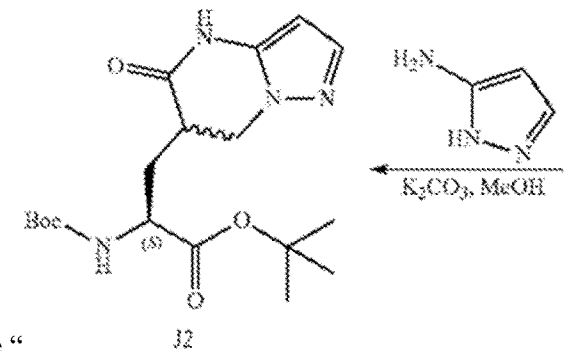 "

and insert -- 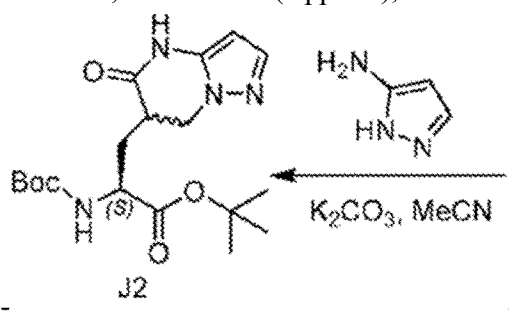 --.

In Column 145, Line 59, delete "20)" and insert --20).--.

In Column 146, Lines 30-35, delete " 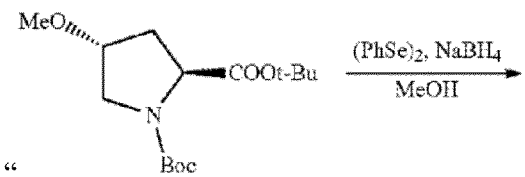 " and insert

-- 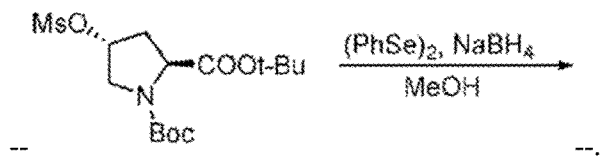 --.

In Column 147, Line 57, delete "i-tert-butyl" and insert --di-tert-butyl--.

In Column 151, Line 32 (Approx.), delete "2 h" and insert --3 h--.

In Column 156, Line 5, delete "5 m;" and insert --5 μm;--.

In Column 156, Line 10 (Approx.), delete "RT2(min):" and insert --RT2 (min):--.

In Column 156, Line 15 (Approx.), delete "Celloluse-2" and insert --Cellulose-2--.

In Column 156, Line 15 (Approx.), delete "3 m," and insert --3 μm,--.

In Column 156, Line 20, delete "Celloluse-2" and insert --Cellulose-2--.

In Column 156, Line 20, delete "3 m," and insert --3 µm,--.

In Column 157, Lines 10-20, delete " 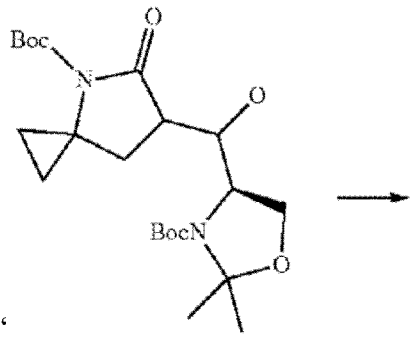 " and insert 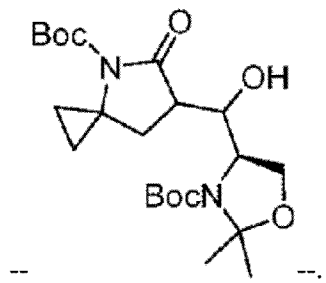 --.

In Column 160, Line 1, delete "RT2(min):" and insert --RT2 (min):--.

In Column 162, Line 38 (Approx.), delete "12 h" and insert --2 h--.

In Column 162, Line 65, delete "hexafluorophospate" and insert --hexafluorophosphate--.

In Column 163, Line 64, delete "hexafluorophospate" and insert --hexafluorophosphate--.

In Column 164, Line 30 (Approx.), delete "5 m;" and insert --5 µm;--.

In Column 167, Line 50, delete "Xselect" and insert --XSelect--.

In Column 167, Line 51, delete "5 m," and insert --5 µm,--.

In Column 169, Line 23, delete "5-6" and insert --5~6--.

In Column 170, Line 10 (Approx.), delete "5 m;" and insert --5 µm;--.

In Column 170, Line 19, delete "[M-56+H]$^{+}$" and insert --[M+H-56]$^{+}$--.

In Column 172, Line 46 (Approx.), delete "10 m;" and insert --10 µm;--.

In Column 174, Line 59, delete "5 m;" and insert --5 µm;--.

In Column 175, Lines 5-15, delete " 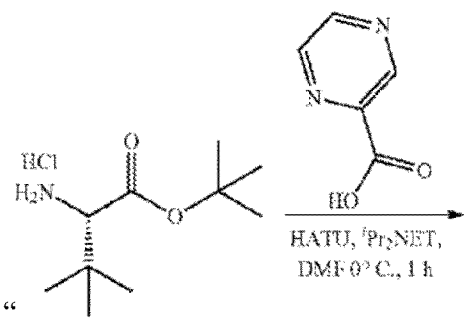 " and insert
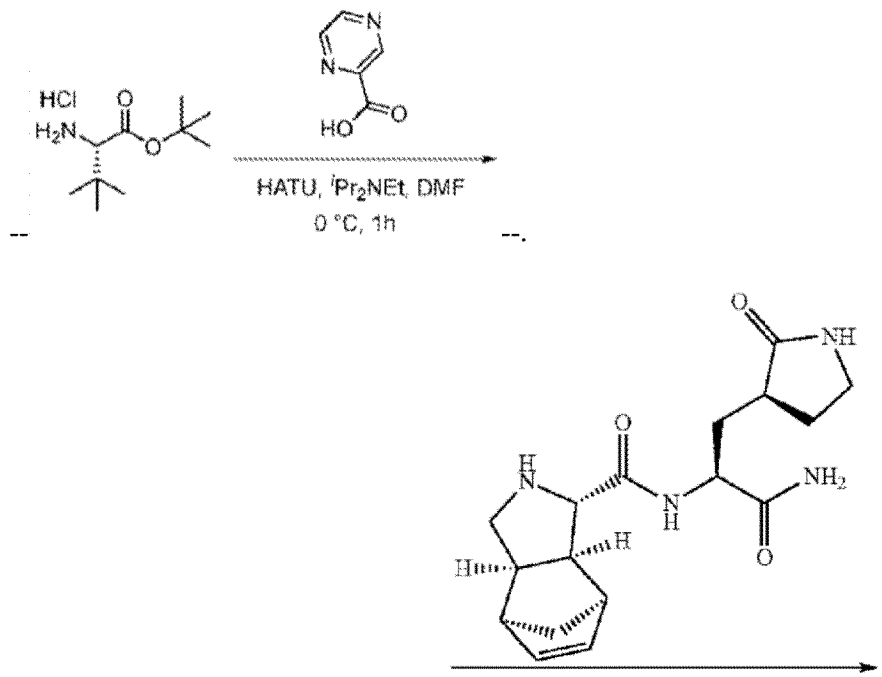
--.
In Column 175, Lines 33-48, delete " " and insert
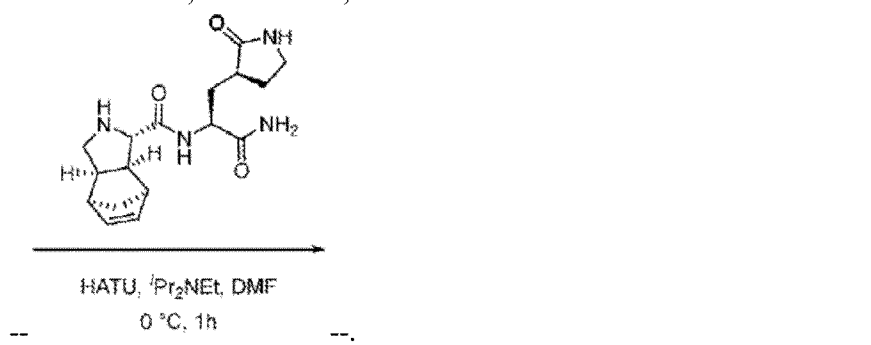
--.
In Column 176, Line 21, delete "N, N, N',N'-" and insert --N,N,N',N'--.
In Column 177, Line 19, delete "5 m;" and insert --5 µm;--.
In Column 179, Line 28, delete "Å," and insert --A,--.
In Column 181, Line 15 (Approx.), delete "10 m;" and insert --10 µm;--.

In Column 183, Line 51, delete "[M+H]+" and insert --[M+H]$^+$--.

In Column 183, Line 66, delete "5 m;" and insert --5 μm;--.

In Column 184, Lines 20-28, delete " " and insert -- 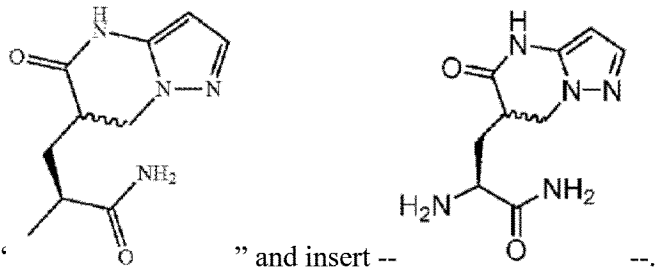 --.

In Column 185, Line 19, delete "5 m;" and insert --5 μm;--.

In Column 193, Line 10 (Approx.), delete "5 m;" and insert --5 μm;--.

In Column 193, Lines 55-66, delete " 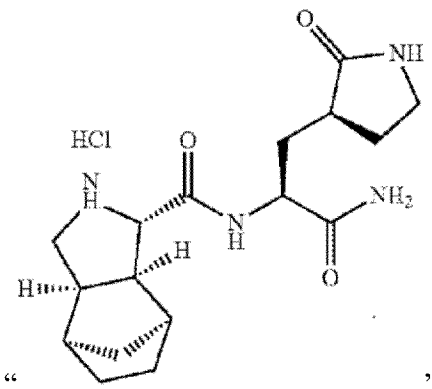 " and insert -- 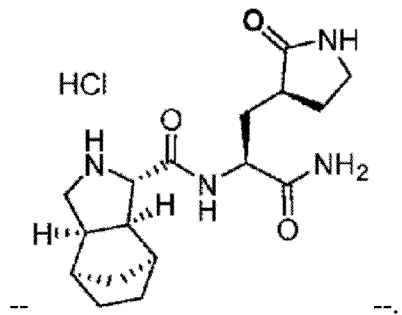 --.

In Column 195, Line 22, delete "5 m;" and insert --5 μm;--.

In Column 197, Line 52, delete "10 m;" and insert --10 μm;--.

In Column 202, Line 28 (Approx.), delete "10 m;" and insert --10 μm;--.

In Column 203, Line 59, delete "5 m;" and insert --5 μm;--.

In Column 203, Lines 63-64, delete "RT2(min):" and insert --RT2 (min):--.

CERTIFICATE OF CORRECTION (continued)
U.S. Pat. No. 11,851,422 B2

In Column 204, Line 2, delete "Sum" and insert --5 um--.

In Column 204, Line 3, delete "5 m;" and insert --5 µm;--.

In Column 204, Line 7, delete "RT2(min):" and insert --RT2 (min):--.

In Column 204, Line 61, delete "5 m;" and insert --5 µm;--.

In Column 206, Lines 61-62, delete "5 m;" and insert --5 µm;--.

In Column 208, Line 40, delete "5 m;" and insert --5 µm;--.

In Column 209, Line 65, delete "5 m;" and insert --5 µm;--.

In Column 210, Lines 33-38, delete " [TFFA, pyridine / DCM / rt, 2h] " and insert -- [TFAA, pyridine / DCM / rt, 2h] --.

In Column 211, Line 25, delete "5 m;" and insert --5 µm;--.

In Column 213, Line 66, delete "10 m;" and insert --10 µm;--.

In Column 215, Line 67, delete "[M-56+H]⁺" and insert --[M+H-56]⁺--.

In Column 217, Line 10 (Approx.), delete "5 m;" and insert --5 µm;--.

In Column 218, Line 65, delete "5 m;" and insert --5 µm;--.

In Column 220, Line 67, delete "ional" and insert --BHT--.

In Column 222, Line 51, delete "5 m;" and insert --5 µm;--.

In Column 226, Line 27, delete "zyankali" and insert --KCN--.

In Column 226, Line 53, delete "10 m;" and insert --10 µm;--.

In Column 227, Line 2 (Approx.), delete " " and insert -- --.

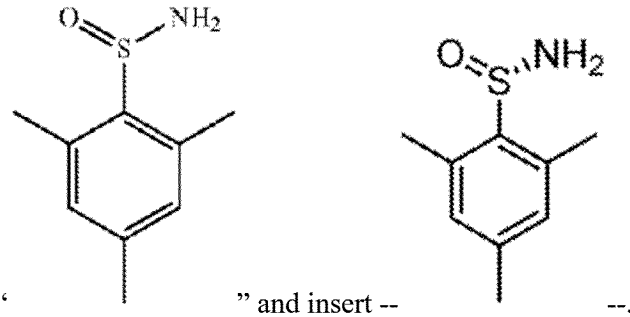

In Column 230, Line 59, delete "[M-56+H]⁺" and insert --[M+H-56]⁺--.
In Column 231, Line 5, delete "[M-56+H]⁺" and insert --[M+H-56]⁺--.
In Column 231, Line 61, delete "10 m;" and insert --10 μm;--.
In Column 232, Lines 8-50, delete " 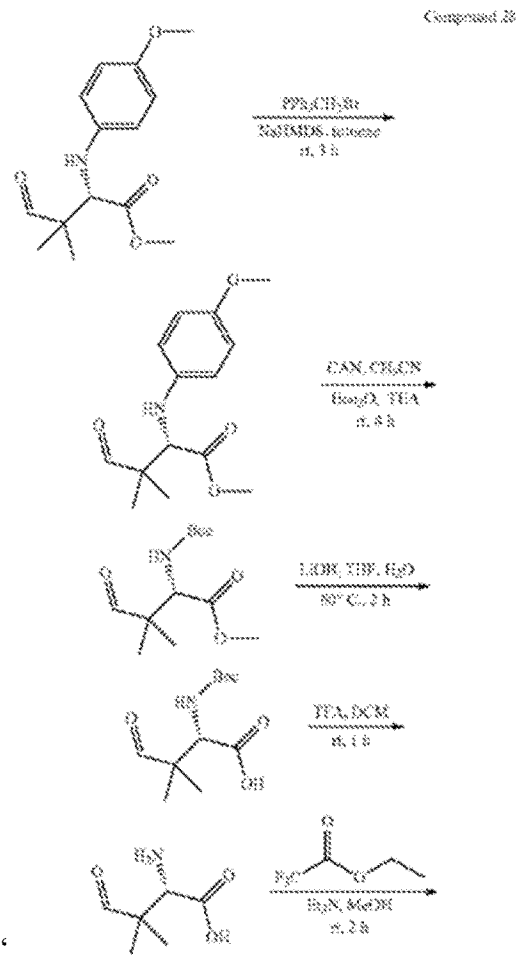 " and insert 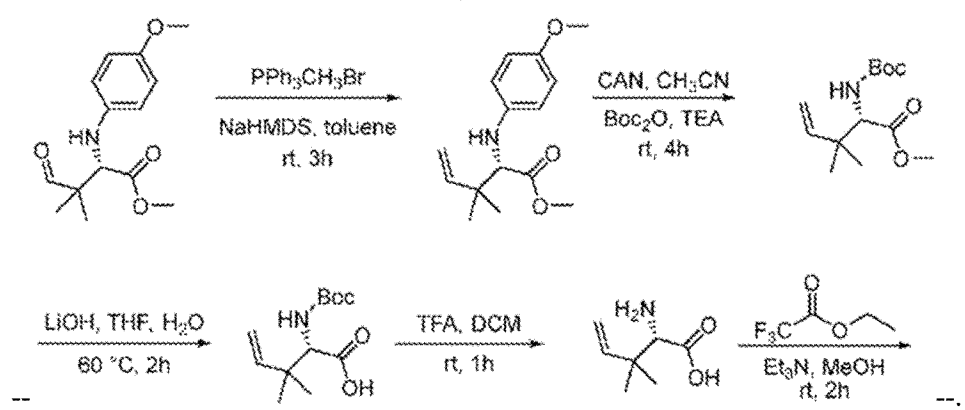 --.

In Column 233, Lines 13-27, delete " 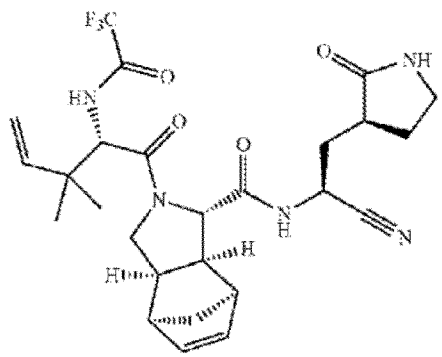 " and insert

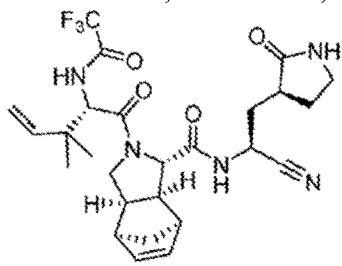

--.

In Column 234, Line 5, delete "[M-56+H]$^+$" and insert --[M+H-56]$^+$--.

In Column 234, Line 18, delete "[M-56+H]$^+$" and insert --[M+H-56]$^+$--.

In Column 235, Line 8 (Approx.), delete "10 m;" and insert --10 μm;--.

In Column 238, Line 6, delete "5 m;" and insert --5 μm;--.

In Column 239, Line 34 (Approx.), delete "10 m;" and insert --10 μm;--.

In Column 240, Line 56, delete "10 m;" and insert --10 μm;--.

In Column 242, Line 67, delete "5 m;" and insert --5 μm;--.

In Column 244, Line 54, delete "5 m;" and insert --5 μm;--.

In Column 246, Line 33 (Approx.), delete "[M+H]$^+$" and insert --[M+H]$^+$.--.

In Column 246, Lines 50-51 (Approx.), delete "5 m;" and insert --5 μm;--.

In Column 248, Lines 12-13 (Approx.), delete "5 m;" and insert --5 μm;--.

In Column 249, Line 52, delete "5 m;" and insert --5 μm;--.

In Column 252, Line 40, delete "(0%-5%" and insert --(0%~5%--.

In Column 253, Line 15, delete "(0%-10%" and insert --(0%~10%--.

In Column 253, Line 66, delete "Xselect" and insert --XSelect--.

In Column 253, Line 67, delete "5 m, n;" and insert --5 μm,--.

In Column 256, Line 4, delete "5 m;" and insert --5 μm;--.

In Column 256, Line 16, delete "5 m," and insert --5 μm,--.

In Column 256, Line 23, delete "5 m," and insert --5 μm,--.

In Column 258, Line 14 (Approx.), delete "10 m;" and insert --10 μm;--.

In Column 261, Line 13 (Approx.), delete "10 m;" and insert --10 μm;--.

In Column 261, Line 57 (Approx.), after "Compound" insert --41--.

In Column 261, Line 57 (Approx.), delete "prepare" and insert --prepared--.

In Column 261, Line 57 (Approx.), delete "or" and insert --for--.

In Column 264, Line 18, delete "X-SELECT" and insert --XSelect--.

In Column 264, Line 18, delete "19×150mm Sum;" and insert --19×150mm, 5 μm;--.

In Column 266, Line 62, delete "X-SELECT" and insert --XSelect--.

In Column 266, Line 62, delete "19×150mm Sum;" and insert --19×150mm, 5 μm;--.

In Column 267, Line 55, delete "hexafluorophospate" and insert --hexafluorophosphate--.

In Column 268, Line 19, delete "5 m;" and insert --5 μm;--.

In Column 269, Line 42, delete "hexafluorophospate" and insert --hexafluorophosphate--.

In Column 270, Line 56, delete "hexafluorophospate" and insert --hexafluorophosphate--.

In Column 272, Line 52, delete "5 m;" and insert --5 μm;--.

In Column 273, Lines 5-15, delete " 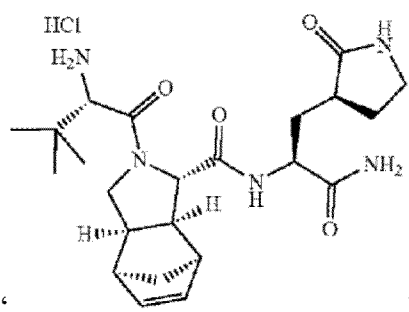 " and insert
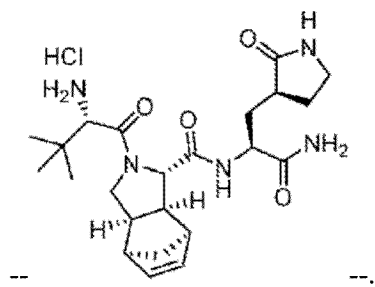 --.
In Column 275, Lines 37-58, delete " 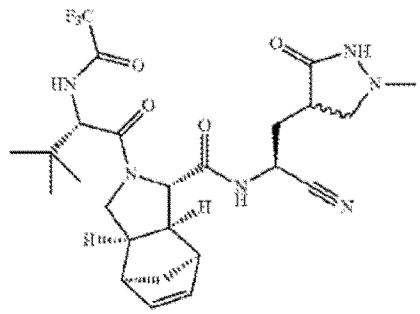 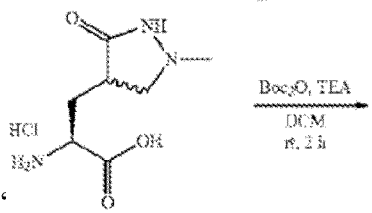 " and insert
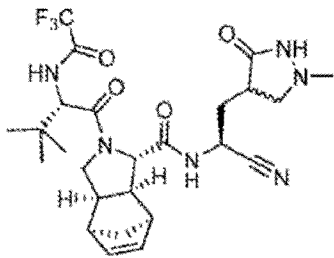 --.
In Column 276, Line 4, delete "5 m;" and insert --5 μm;--.
In Column 276, Line 8 (Approx.), delete "RT2(min):" and insert --RT2 (min):--.

In Column 277, Line 33 (Approx.), delete "5 m;" and insert --5 μm;--.

In Column 280, Line 5, delete "5 m;" and insert --5 μm;--.

In Column 281, Lines 5-7, delete " 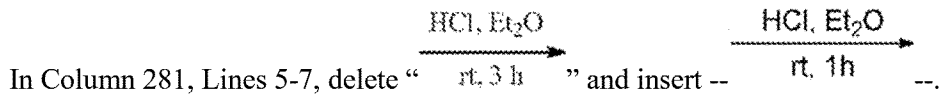 " and insert --   --.

In Column 282, Line 27, delete "[M-56+H]$^+$" and insert --[M+H-56]$^+$--.

In Column 282, Line 49, delete "[M-56+H]$^+$" and insert --[M+H-56]$^+$--.

In Column 283, Line 23, delete "5 m;" and insert --5 μm;--.

In Column 286, Line 52 (Approx.), delete "5 m;" and insert --5 μm;--.

In Column 289, Lines 31-44, delete " 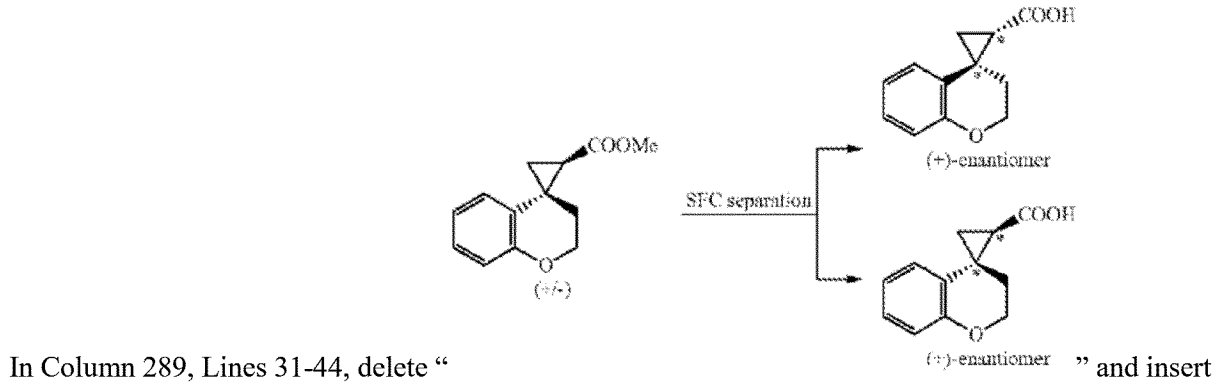 " and insert -- 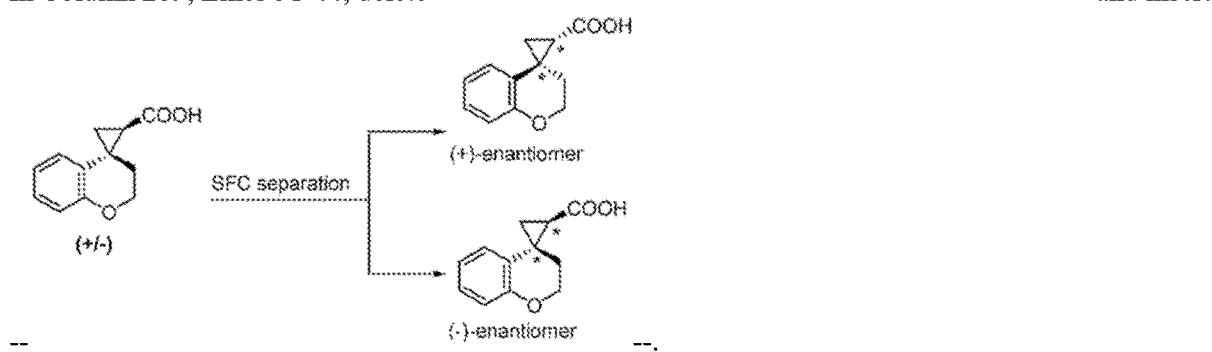 --.

In Column 290, Line 38, delete "X-SELECT" and insert --XSelect--.

In Column 290, Line 39, delete "Sum;" and insert --5 μm;--.

In Column 290, Line 59, delete "trans" and insert --Trans--.

In Column 290, Line 61, delete "m;" and insert --5 μm;--.

In Column 291, Line 5, delete "[α]$_{25}^D$:" and insert --[α]$^{25}_D$:--.

In Column 291, Line 6, delete "3 m," and insert --3 μm,--.
In Column 291, Line 14, delete "3 m," and insert --3 μm,--.
In Column 293, Lines 43-67, delete " 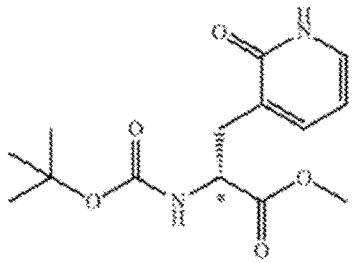 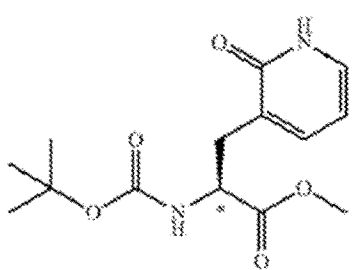 " and insert -- 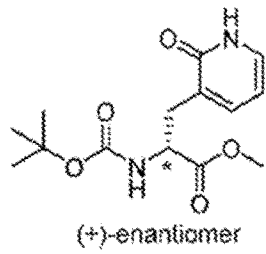 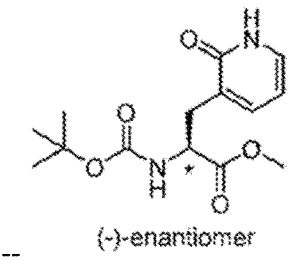 --.
In Column 295, Line 25, delete "5 m;" and insert --5 μm;--.
In Column 295, Line 36, delete "[α]$_{25}^{D}$:" and insert --[α]$^{25}_{D}$:--.
In Column 295, Line 37, delete "3 m," and insert --3 μm,--.
In Column 295, Line 44, delete "3 m," and insert --3 μm,--.

In Column 300, Line 19, delete "X-SELECT" and insert --XSelect--.

In Column 300, Line 20, delete "Sum;" and insert --5 μm;--.

In Column 301, Line 17, delete "5 m;" and insert --5 μm;--.

In Column 301, Line 30, delete "3 m," and insert --3 μm,--.

In Column 301, Line 39 (Approx.), delete "3 m," and insert --3 μm,--.

In Column 304, Lines 35-50, delete " 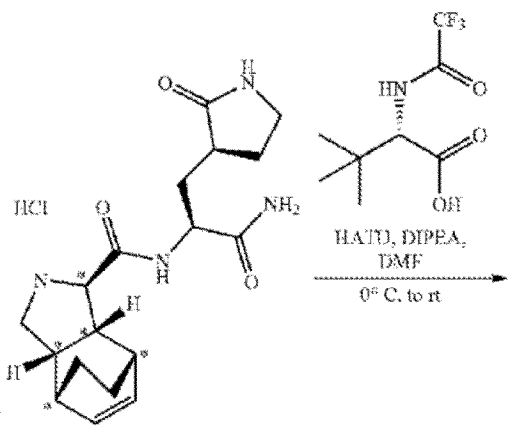 " and insert " 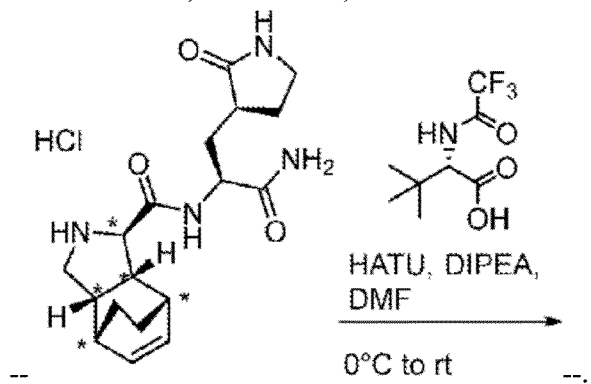 --.

In Column 305, Line 40, delete "5 m;" and insert --5 μm;--.

In Column 305, Line 55, delete "3 m," and insert --3 μm,--.

In Column 305, Line 66, delete "3 m," and insert --3 μm,--.

In Column 307, Lines 9-10, delete "X-SELECT" and insert --XSelect--.

In Column 307, Line 10, delete "5 m;" and insert --5 μm;--.

In Column 308, Lines 25-35, delete " 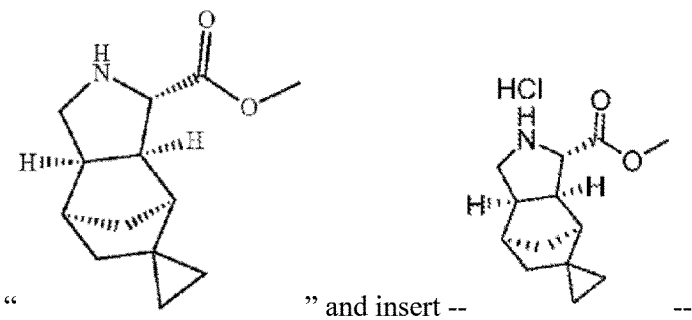 " and insert -- --.
In Column 311, Line 52, delete "5 m;" and insert --5 μm;--.
In Column 313, Line 30 (Approx.), below " 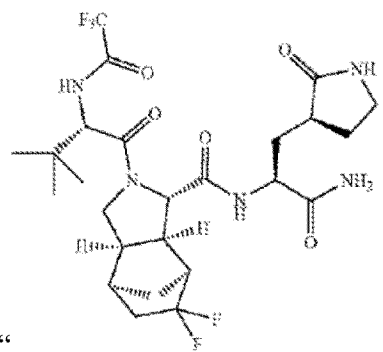 " insert
-- 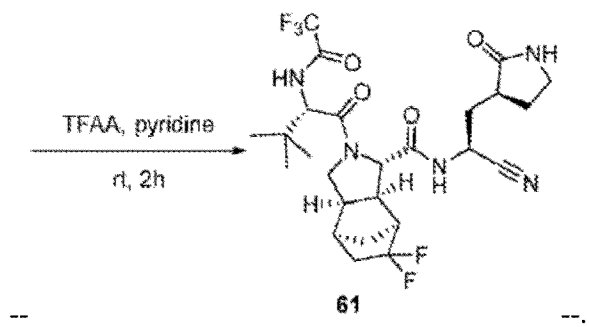 --.
In Column 313, Line 54, delete "[M-56+H]$^+$" and insert --[M+H-56]$^+$--.
In Column 315, Line 21, delete "Xselect" and insert --XSelect--.
In Column 315, Line 22, delete "30*150 mm 5m, n;" and insert --30*150 mm, 5 μm;--.

In Column 317, Lines 2-15, delete " 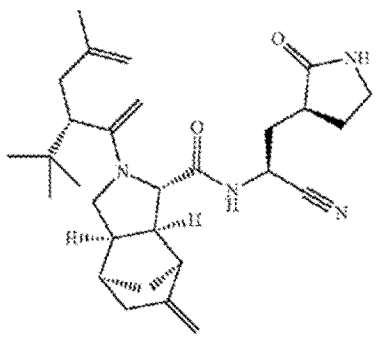 " and insert 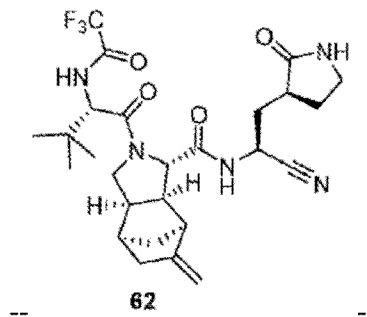 --.

In Column 318, Line 51, delete "5 m;" and insert --5 µm;--.

In Column 321, Line 22, delete "Xselect" and insert --XSelect--.

In Column 321, Line 23, delete "5 m;" and insert --5 µm;--.

In Column 323, Lines 49-50 (Approx.), delete "5 m;" and insert --5 µm;--.

In Column 325, Line 26 (Approx.), delete "5 m;" and insert --5 µm;--.

In Column 327, Line 5, delete "5 m;" and insert --5 µm;--.

In Column 329, Line 24 (Approx.), delete "10 m;" and insert --10 µm;--.

In Column 334, Line 3, delete "[M+H]+" and insert --[M+H]$^{+}$--.

In Column 334, Line 18, delete "Xselect" and insert --XSelect--.

In Column 334, Line 19, delete "30*150 mm 5m, n;" and insert --30*150 mm, 5µm;--.

In Column 335, Lines 9-16, delete " 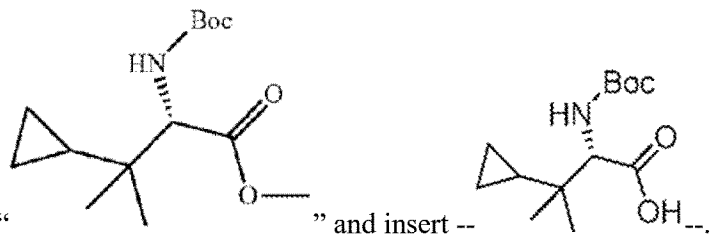 " and insert -- 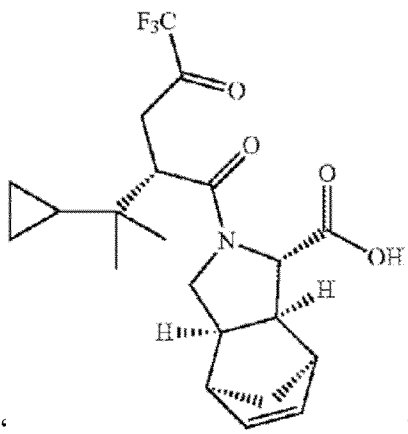 --.

In Column 336, Lines 40-54, delete " 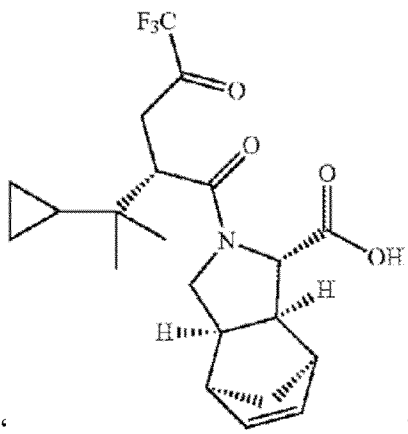 " and insert -- 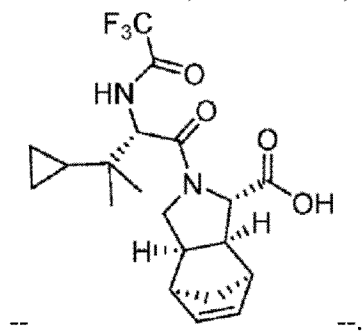 --.

In Column 338, Lines 54-55, delete "eq eq.)" and insert --eq.)--.

In Column 339, Line 30, delete "30*150, Sum;" and insert --30*150 mm, 5 μm;--.

In Column 342, Line 64, delete "5 m," and insert --5 μm,--.

In Column 343, Line 6, delete "5 m," and insert --5 μm,--.

In Column 344, Lines 59-60 (Approx.), delete "X-SELECT" and insert --XSelect--.

In Column 344, Line 60 (Approx.), delete "5 m;" and insert --5 μm;--.

In Column 347, Lines 50-51 (Approx.), delete "10 m;" and insert --10 μm;--.

CERTIFICATE OF CORRECTION (continued)
U.S. Pat. No. 11,851,422 B2

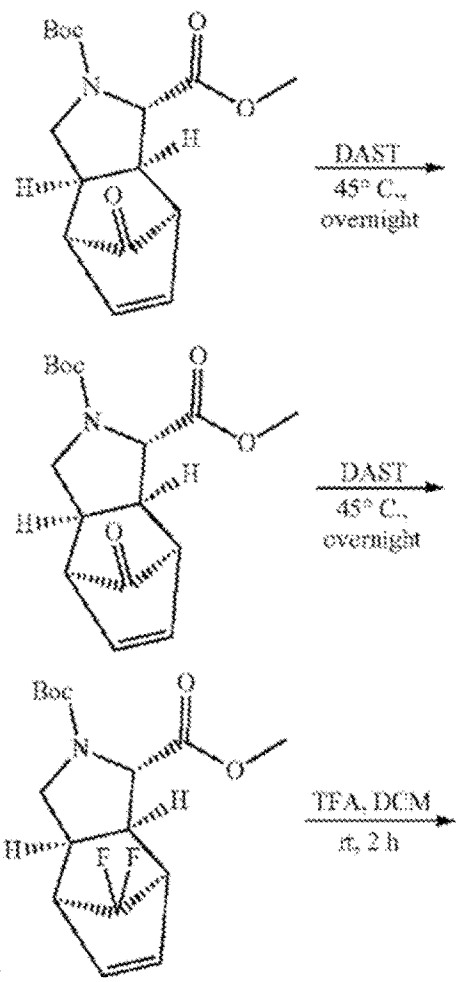

In Column 351, Lines 40-65, delete "

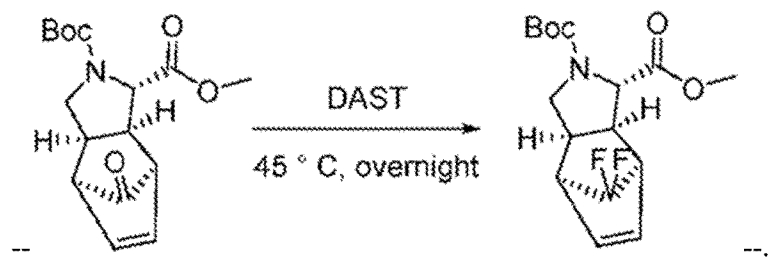

" and insert

--                                                         --.

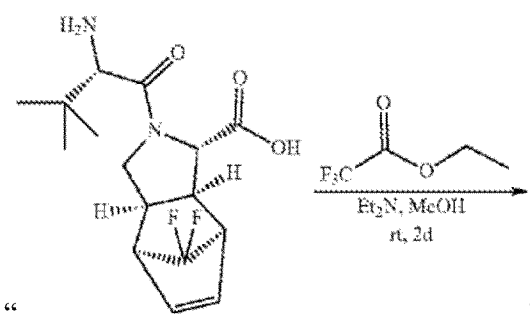

In Column 352, Lines 40-51, delete "                                                        " and insert

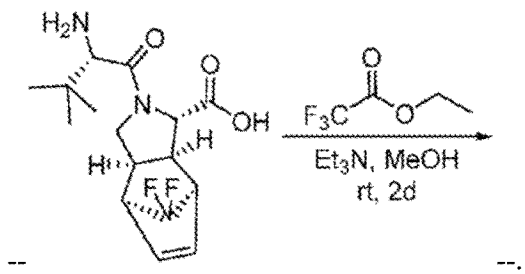

In Column 356, Line 56, delete "5 m;" and insert --5 µm;--.

In Column 360, Line 6, delete "5 m;" and insert --5 µm;--.

In Column 360, Line 53, delete "Sum" and insert --5 µm--.

In Column 360, Line 53, delete "Celluloes-3," and insert --Cellulose-3,--.

In Column 360, Line 53, delete "5 m;" and insert --5 µm;--.

In Column 360, Line 57, delete "RT2(min):" and insert --RT2 (min):--.

In Column 363, Line 33, delete "lithiumol" and insert --LiOH--.

In Column 364, Line 55, delete "5 m;" and insert --5 µm;--.

In Column 367, Line 3, delete "[M-56+H]$^{+}$" and insert --[M+H-56]$^{+}$--.

In Column 368, Lines 19-20, delete "te-tramethyluronium" and insert --tetramethyluronium--.

In Column 368, Line 51, delete "5 m;" and insert --5 µm;--.

In Column 369, Line 55, delete "Xselect" and insert --XSelect--.

In Column 369, Line 56, delete "5 m;" and insert --5 µm;--.

In Column 370, Lines 7-46, delete " 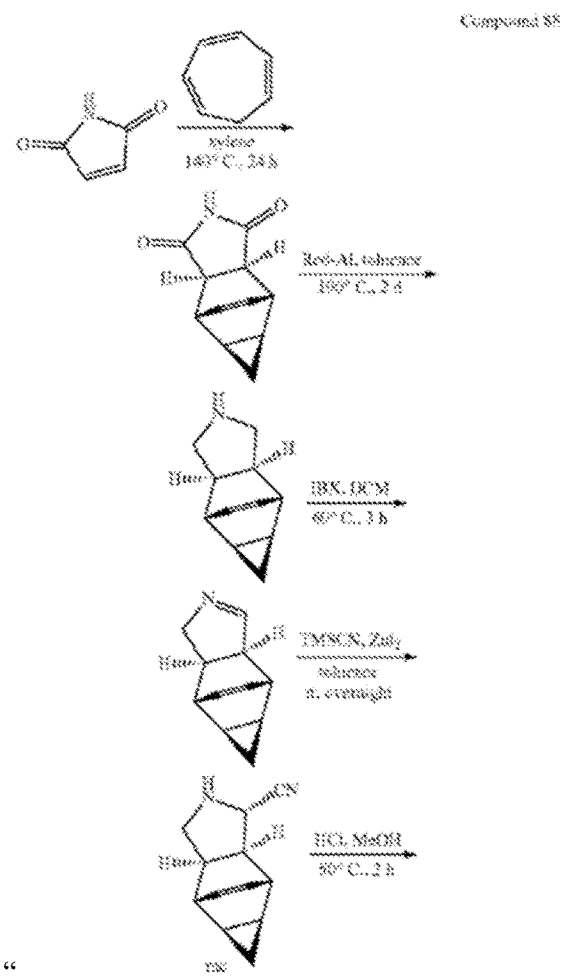 " and insert
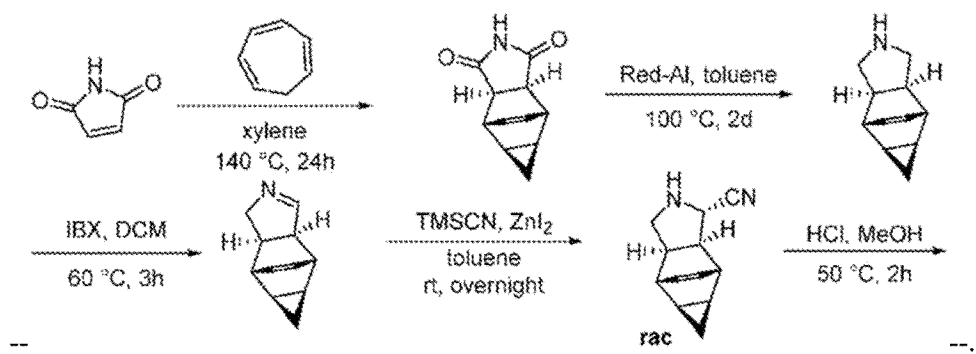
--.
In Column 374, Line 3, delete "te-tramethyluronium" and insert --tetramethyluronium--.
In Column 375, Line 9 (Approx.), delete "te-tramethyluronium" and insert --tetramethyluronium--.
In Column 375, Line 37 (Approx.), delete "5 m;" and insert --5 µm;--.
In Column 377, Lines 41-42, delete "te-tramethyluronium" and insert --tetramethyluronium--.

In Column 377, Line 63, delete "methyl methyl" and insert --mixture of methyl--.

In Column 378, Lines 38-39, delete "te-tramethyluronium" and insert --tetramethyluronium--.

In Column 378, Line 41, after "for" insert --20--.

In Column 378, Line 67, delete "5 m;" and insert --5 μm;--.

In Column 381, Line 50, delete "5 m;" and insert --5 μm;--.

In Column 381, Line 60, delete "[M-56+H]⁺" and insert --[M+H-56]⁺--.

In Column 382, Lines 30-31, delete "5 m;" and insert --5 μm;--.

In Column 383, Lines 54-62, delete " 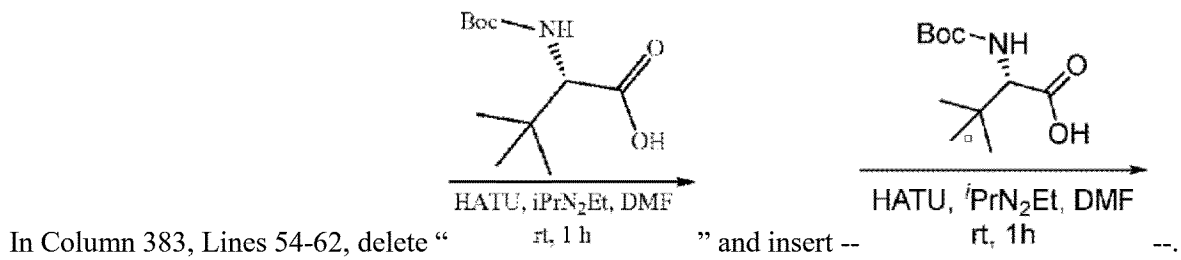 " and insert -- --.

In Column 384, Line 46 (Approx.), delete "hexafluorophospate" and insert --hexafluorophosphate--.

In Column 384, Line 57, delete "brown-yellow" and insert --brown yellow--.

In Column 385, Line 41, delete "brown-yellow" and insert --brown yellow--.

In Column 385, Line 55, delete "te-tramethyluronium" and insert --tetramethyluronium--.

In Column 386, Line 28 (Approx.), delete "5 m;" and insert --5 μm;--.

In Column 386, Lines 48-61, delete " 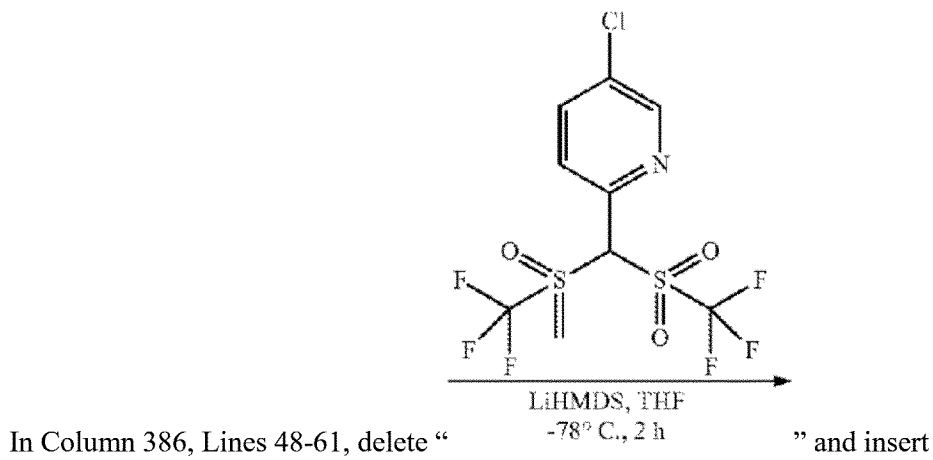 " and insert

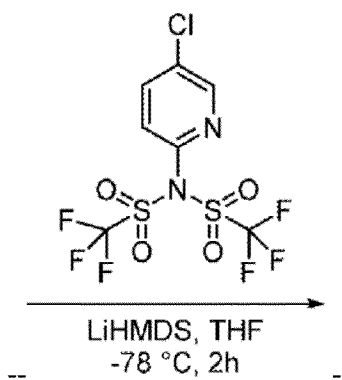

In Column 388, Line 51, delete "[M-56+H]⁺" and insert --[M+H-56]⁺--.

In Column 389, Lines 3-4, delete "[M-56+H]⁺" and insert --[M+H-56]⁺--.

In Column 389, Line 24, delete "[M-56+H]⁺" and insert --[M+H-56]⁺--.

In Column 389, Line 48, delete "te-tramethyluronium" and insert --tetramethyluronium--.

In Column 390, Line 19, delete "te-tramethyluronium" and insert --tetramethyluronium--.

In Column 390, Line 62, delete "5 m;" and insert --5 µm;--.

In Column 396, Line 3, delete "tinhydroxide" and insert --tin hydroxide--.

In Column 397, Line 30 (Approx.), delete "5 m;" and insert --5 µm;--.

In Columns 399-400, Line 3 (Approx.), delete " 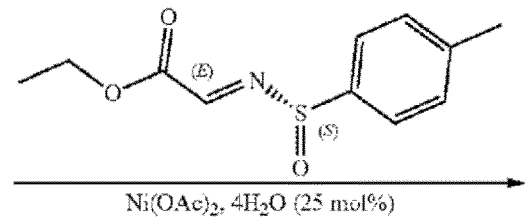 " and insert -- 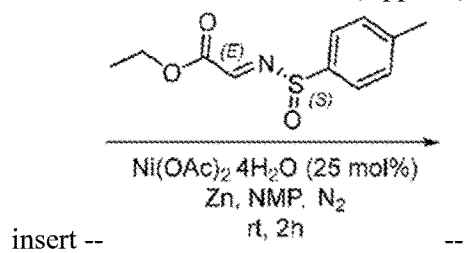 --.

In Columns 399-400, Line 6 (Approx.), delete " 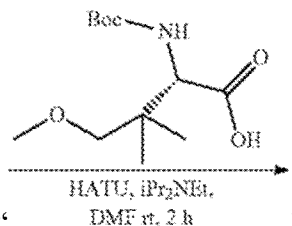 " and insert
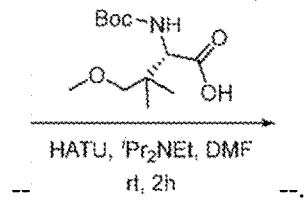 --.
In Column 402, Line 33, delete "[M-56+H]$^+$" and insert --[M+H-56]$^+$--.
In Column 402, Line 37, delete "te-tramethyluronium" and insert --tetramethyluronium--.
In Column 402, Line 57, delete "[M+H]$^-$" and insert --[M+H]$^+$--.
In Column 403, Line 37 (Approx.), delete "5 m;" and insert --5 μm;--.
In Column 407, Line 60, delete "10 m;" and insert --10 μm;--.
In Column 408, Lines 16-22, delete " 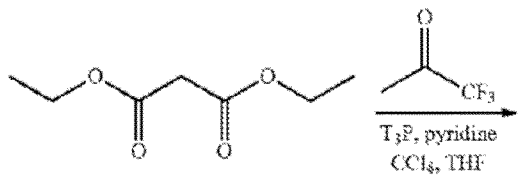 " and insert 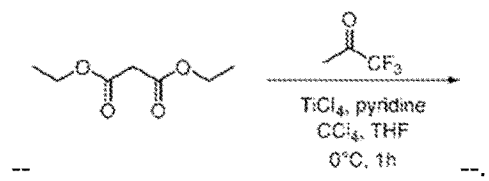 --.

In Column 408, Lines 49-64, delete " 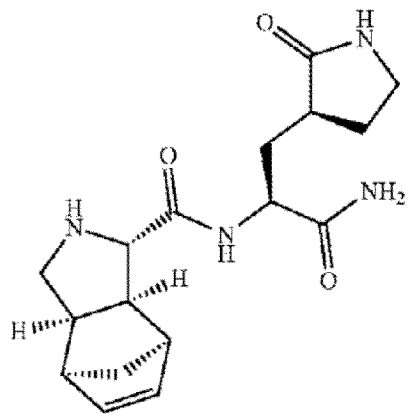 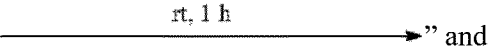 " and insert 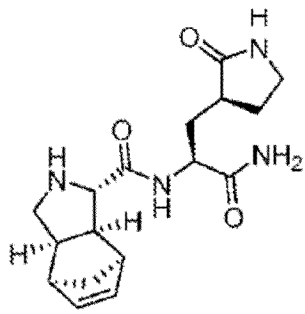 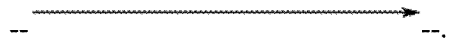 --.
In Column 409, Lines 28-40, delete " 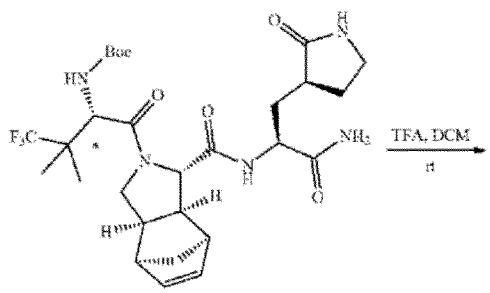  " and insert 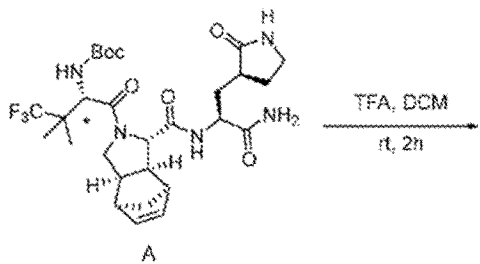  --.
In Column 410, Line 8, delete "rrt." and insert --rt.--.

In Column 411, Line 22, delete "te-tramethyluronium" and insert --tetramethyluronium--.
In Column 412, Line 7, delete "10 m;" and insert --10 μm;--.
In Column 413, Line 54, delete "prepa-HPLC" and insert --prep-HPLC--.
In Column 413, Line 55, delete "5 m;" and insert --5 μm;--.
In Column 414, Lines 22-30, delete " 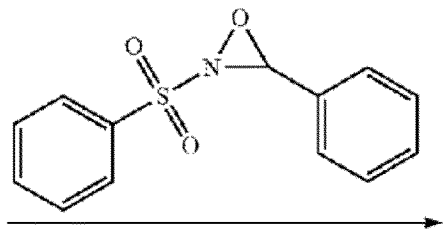 " and insert
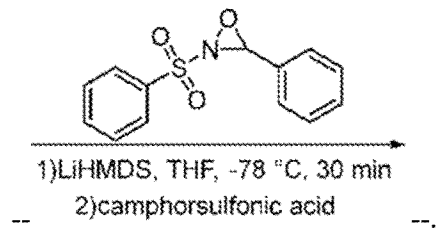 --.
In Column 415, Lines 2-15, delete " 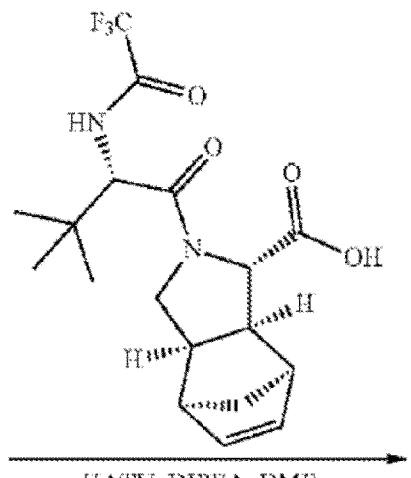 " and insert

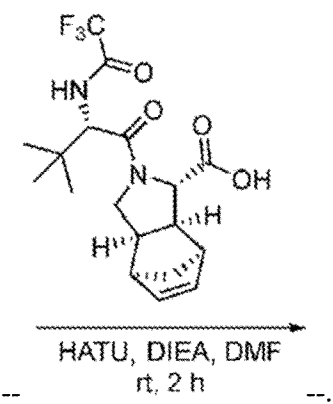
In Column 416, Line 27, delete "C18" and insert --$C_{18}$--.
In Column 416, Line 58, delete "C18" and insert --$C_{18}$--.
In Column 417, Line 9 (Approx.), delete "Cis" and insert --$C_{18}$--.
In Columns 417-418, Line 16 (Approx.), delete " 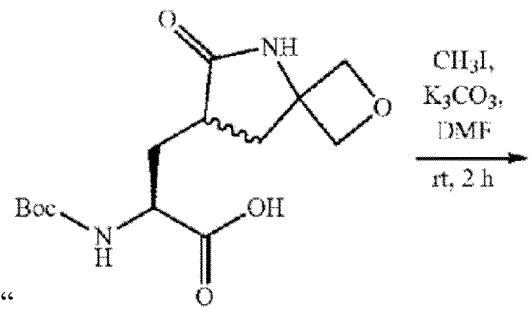 " and insert -- 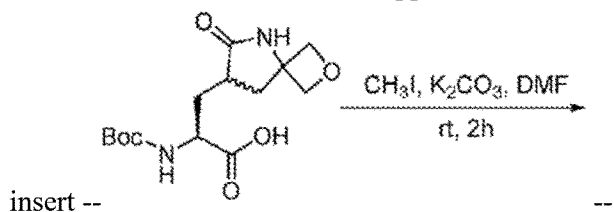 --.
In Columns 417-418, Line 17 (Approx.), delete " 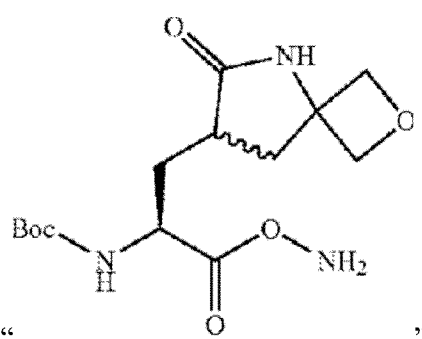 " and insert

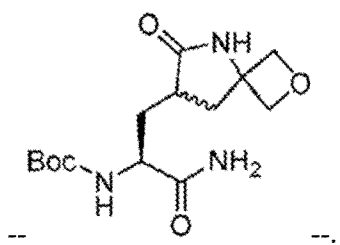
-- --.
In Column 420, Lines 63-64, delete "te-tramethyluronium" and insert --tetramethyluronium--.
In Column 421, Line 51 (Approx.), delete "5 m;" and insert --5 μm;--.
In Column 423, Line 11, delete "5 m;" and insert --5 μm;--.
In Column 423, Lines 57-66, delete " 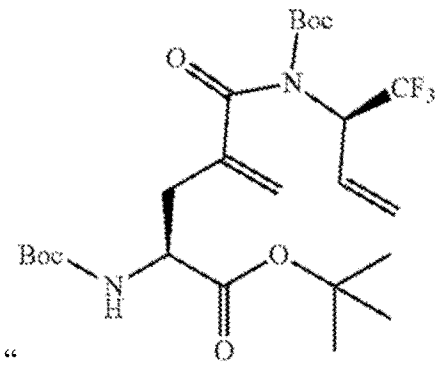 " and insert 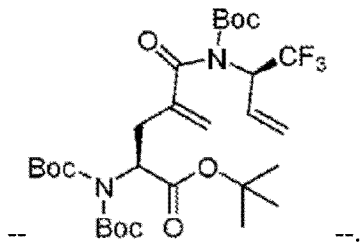 -- --.
In Column 427, Lines 22-23, delete "te-tramethyluronium" and insert --tetramethyluronium--.
In Column 427, Line 59, delete "5 m;" and insert --5 μm;--.

In Column 429, Lines 2-14, delete " 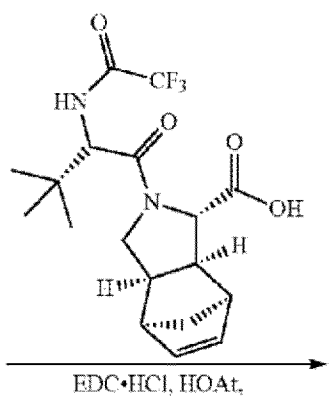 " and insert

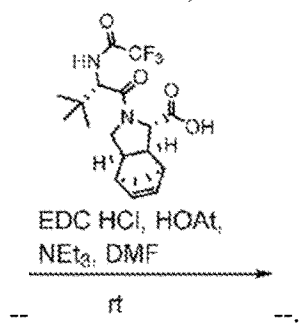 --.

In Column 430, Line 32, delete "X-SELECT" and insert --XSelect--.

In Column 430, Line 33, delete "5 m;" and insert --5 μm;--.

In Column 431, Line 11 (Approx.), delete "7 m;" and insert --7 μm;--.

In Column 433, Line 33, delete "dihydrochoride" and insert --dihydrochloride--.

In Column 434, Line 29, delete "X-SELECT" and insert --XSelect--.

In Column 434, Line 30, delete "5 m;" and insert --5 μm;--.

In Column 435, Lines 35-44, delete " 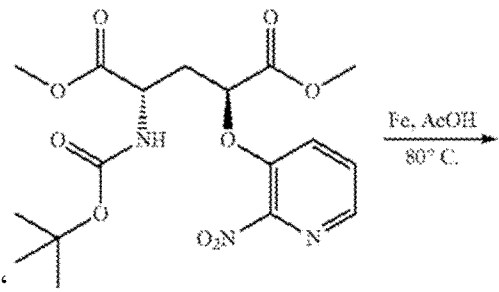 " and insert

In Column 436, Lines 16-26, delete " 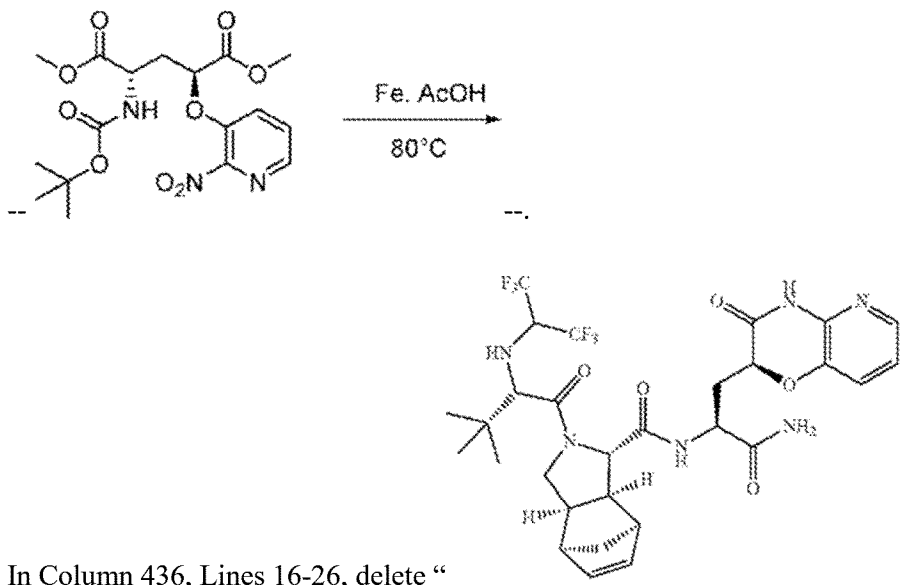 " and insert  -- 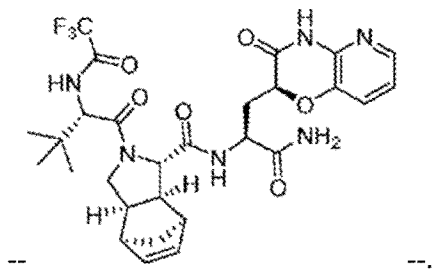 --.

In Column 437, Line 20, delete "5 m;" and insert --5 μm;--.

In Column 438, Line 2, delete "X-SELECT" and insert --XSelect--.

In Column 438, Line 2, delete "5 m;" and insert --5 μm;--.

In Column 443, Line 37, delete "5 m;" and insert --5 μm;--.

In Column 445, Line 25, delete "5 m;" and insert --5 μm;--.

In Column 449, Line 11, delete "ea" and insert --EA--.

In Column 450, Line 22 (Approx.), delete "te-tramethyluronium" and insert --tetramethyluronium--.

In Column 450, Line 51, delete "5 m;" and insert --5 μm;--.

In Column 455, Line 56 (Approx.), delete "te-tramethyluronium" and insert --tetramethyluronium--.

In Column 456, Line 18 (Approx.), delete "Xselect" and insert --XSelect--.

In Column 456, Line 19 (Approx.), delete "5 m;" and insert --5 μm;--.

In Column 457, Lines 38-46, delete " 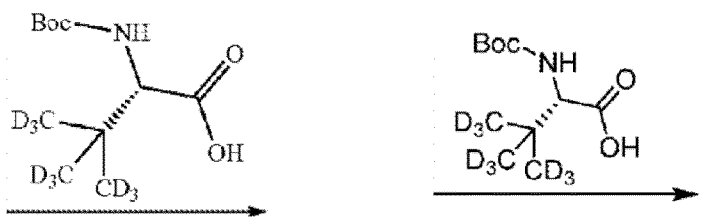 " and insert -- --.

In Column 460, Line 52, delete "Cis" and insert --$C_{18}$--.

In Column 462, Lines 38-49, delete " 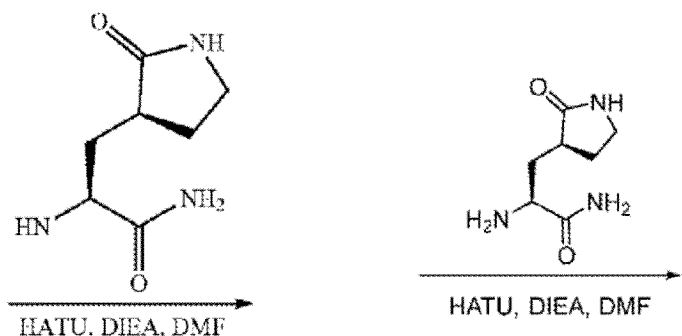 " and insert -- --.

In Column 463, Line 52, delete "te-tramethyluronium" and insert --tetramethyluronium--.

In Column 464, Line 19, delete "5 m;" and insert --5 μm;--.

In Column 465, Line 40, delete "te-tramethyluronium" and insert --tetramethyluronium--.

In Column 466, Line 22, delete "5 m;" and insert --5 μm;--.

In Column 470, Line 19, delete "5 m;" and insert --5 μm;--.

In Column 472, Lines 16-23, 32-39, 52-54, 56-63, and 65-66 (Approx.), delete "[M+H]+" and insert --[M+H]$^+$--.

In Column 473, Lines 8, 10-11, and 13-17 (Approx.), delete "[M+H]+" and insert --[M+H]$^+$--.

In Column 474, Lines 7, 9, 12, 14, 15, and 18 (Approx.), delete "[M+H]+" and insert --[M+H]$^+$--.

In Column 474, Lines 9-11 (Approx.), delete "[2M+Na]+" and insert --[2M+Na]$^+$--.

CERTIFICATE OF CORRECTION (continued)
U.S. Pat. No. 11,851,422 B2

In Column 481, Lines 14-39, delete " 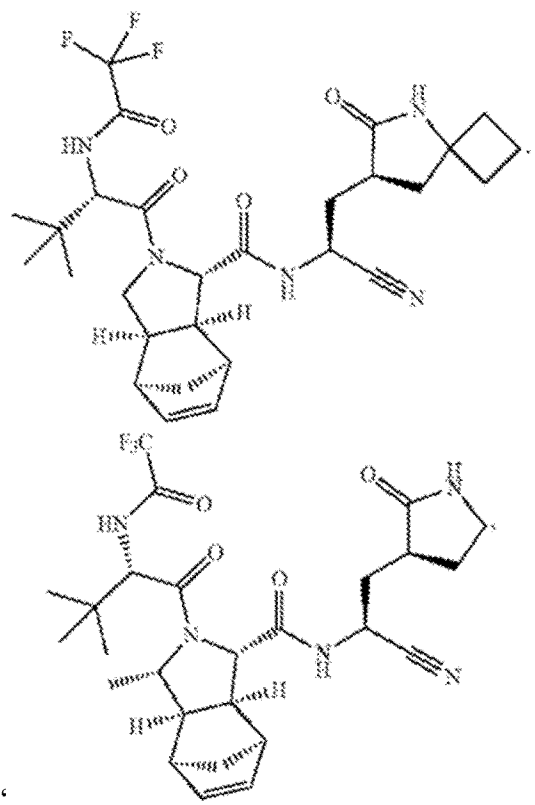 " and insert

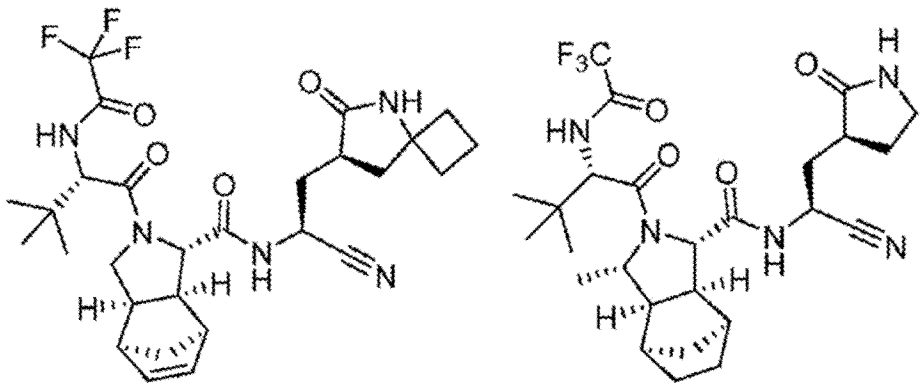

--.

In Column 482, Lines 16-29, delete " 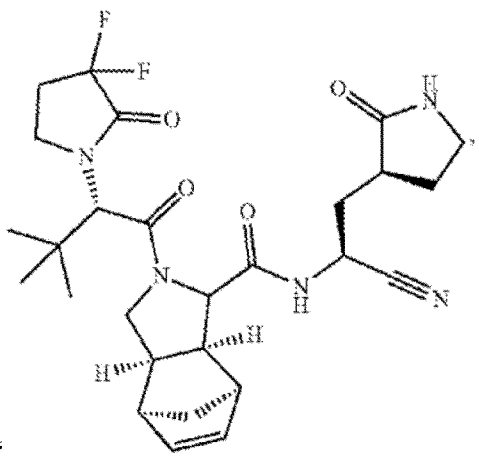 " and insert

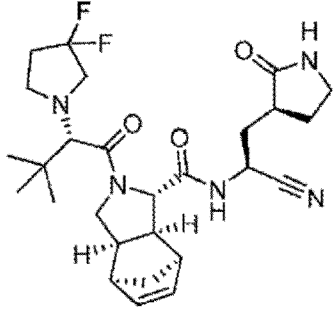

-- 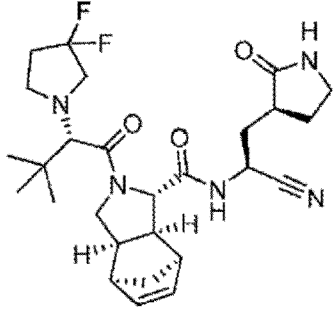 ,--.

In Column 489, Line 46, delete "(m)." and insert --(μM).--.

In Column 489, Line 46, delete "10 m." and insert --10 μM.--.

In Column 489, Line 47, delete "1 m" and insert --1 μM--.

In Column 489, Line 47, delete "10 m." and insert --10 μM.--.

In Column 490, Line 48 (Approx.), delete "ag/mL" and insert --μg/mL--.

In Column 491, Line 9, delete "(M)." and insert --(μM).--.

In the Claims

In Column 495, Claim 1, Line 25 (Approx.), below "acceptable salt thereof, having the structure:", delete "wherein:".

In Column 495, Claim 1, Line 40, before "Ring" insert --wherein:--.

In Column 496, Claim 1, Line 24 (Approx.), delete "re" and insert --are--.

In Column 497, Claim 1, Line 37 (Approx.), delete "—(NH)$_m$-an" and insert -- —(NH)$_m$— an--.

CERTIFICATE OF CORRECTION (continued)
U.S. Pat. No. 11,851,422 B2

In Column 497, Claim 1, Line 38 (Approx.), delete "—O-an" and insert -- —O— an--.

In Column 497, Claim 1, Line 39 (Approx.), delete "—O-an" and insert -- —O— an--.

In Column 497, Claim 1, Line 40 (Approx.), delete "—O-an" and insert -- —O— an--.

In Column 499, Claim 4, Lines 2-10, delete " " and insert -- 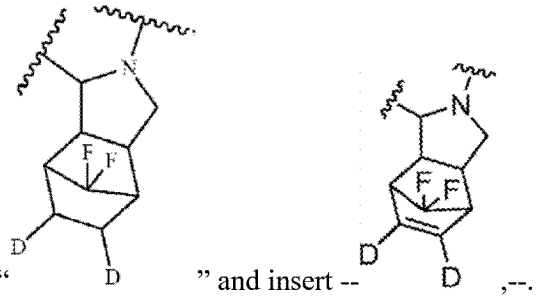 ,--.

In Column 500, Claim 4, Lines 19-27, delete " " and insert -- 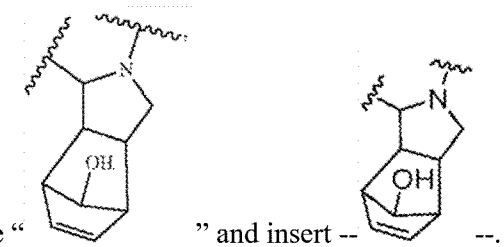 --.

In Column 505, Claim 12, Line 16, delete "(C$_1$-4" and insert --(C$_{1-4}$--.

In Column 505, Claim 12, Line 18, delete "(C$_1$-4" and insert --(C$_{1-4}$--.

In Column 505, Claim 13, Line 25, delete "(C$_{1-4}$ alkyl)" and insert --(C$_{1-4}$alkyl),--.

In Column 506, Claim 14, Lines 56-63, delete " " and insert 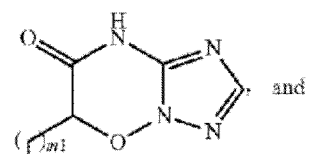

-- 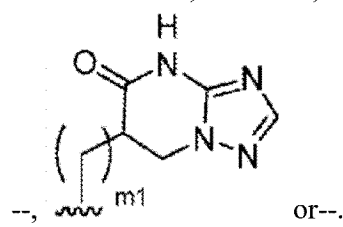 or--.

CERTIFICATE OF CORRECTION (continued)
U.S. Pat. No. 11,851,422 B2

In Column 512, Claim 17, Lines 15-41, delete " 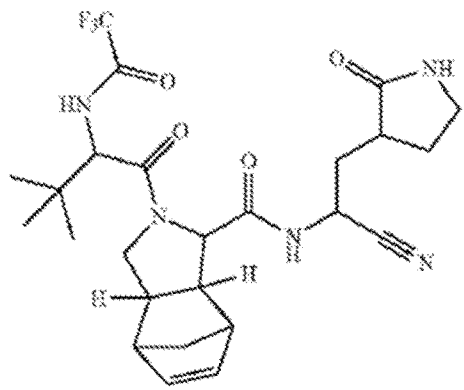 " and insert -- 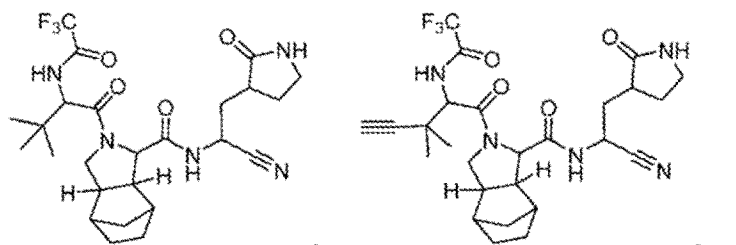 --.

In Column 544, Claim 17, Lines 17-29, delete " 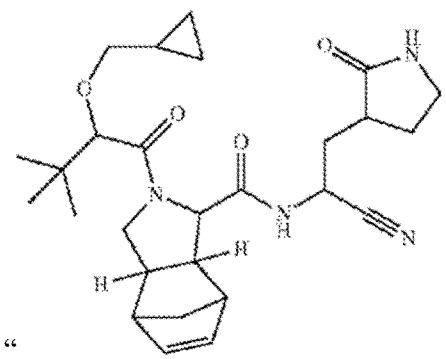 " and insert

In Column 555, Claim 18, Lines 16-27, delete " 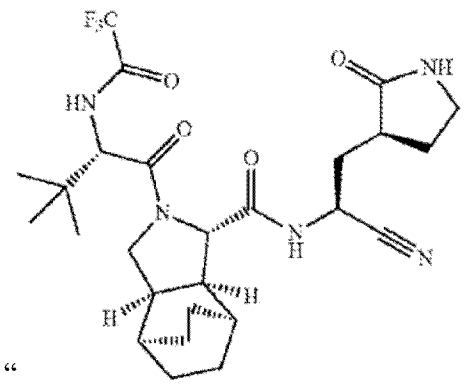 " and insert -- 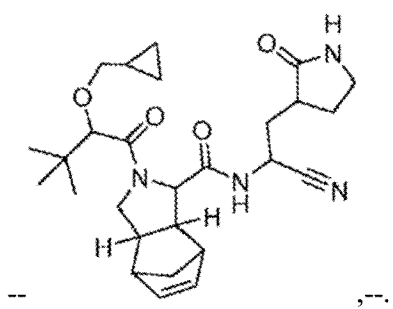 ,--.
In Column 580, Claim 18, Lines 2-14, delete " 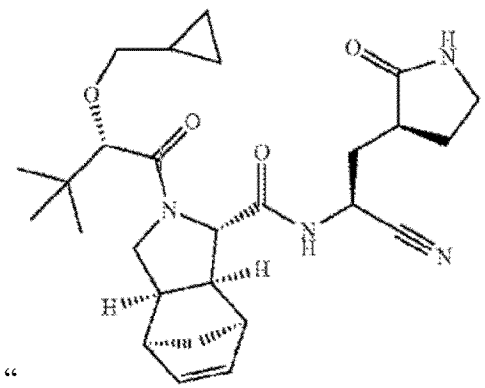 " and insert -- 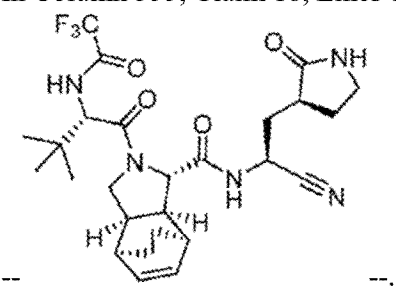 --.

CERTIFICATE OF CORRECTION (continued)
U.S. Pat. No. 11,851,422 B2

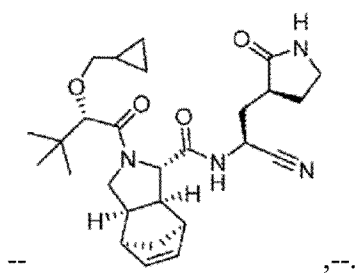

In Column 586, Claim 44, Lines 51-64, delete " 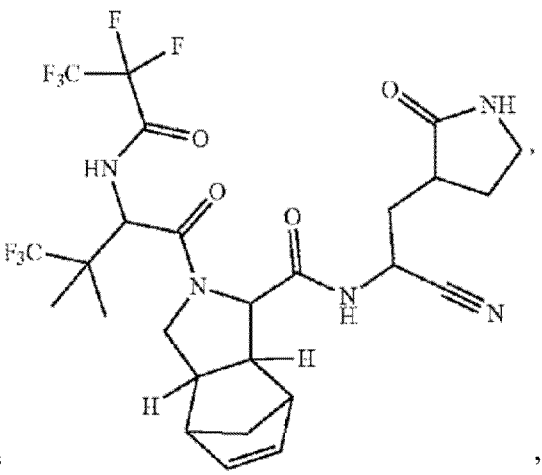 " and insert -- 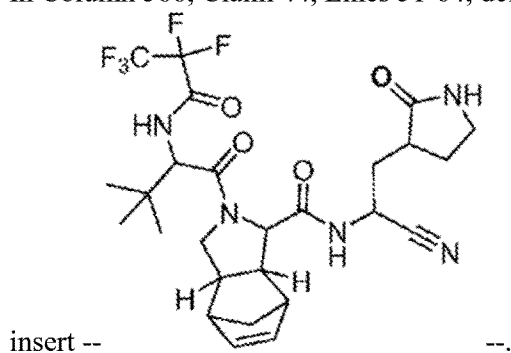 --.